(12) United States Patent
Bacon et al.

(10) Patent No.: US 11,078,208 B1
(45) Date of Patent: *Aug. 3, 2021

(54) HIV INHIBITOR COMPOUNDS

(71) Applicant: Gilead Sciences, Inc., Foster City, CA (US)

(72) Inventors: Elizabeth M. Bacon, Burlingame, CA (US); Elbert Chin, San Mateo, CA (US); Jeromy J. Cottell, Redwood City, CA (US); Ashley Anne Katana, North Olmstead, OH (US); Darryl Kato, San Francisco, CA (US); John O. Link, San Francisco, CA (US); Nathan Shapiro, Belmont, CA (US); Teresa Alejandra Trejo Martin, Belmont, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/805,933

(22) Filed: Mar. 2, 2020

Related U.S. Application Data

(63) Continuation of application No. 16/364,487, filed on Mar. 26, 2019, which is a continuation of application No. 15/888,749, filed on Feb. 5, 2018, now Pat. No. 10,294,234.

(60) Provisional application No. 62/455,348, filed on Feb. 6, 2017.

(51) Int. Cl.

| | | |
|---|---|---|
| *C07D 405/14* | (2006.01) | |
| *C07D 487/08* | (2006.01) | |
| *C07D 491/04* | (2006.01) | |
| *A61P 31/18* | (2006.01) | |
| *A61K 45/06* | (2006.01) | |
| *C07C 275/16* | (2006.01) | |
| *C07D 401/12* | (2006.01) | |
| *C07D 471/08* | (2006.01) | |
| *C07D 487/10* | (2006.01) | |
| *C07C 243/28* | (2006.01) | |
| *A61K 31/52* | (2006.01) | |
| *A61K 31/55* | (2006.01) | |
| *A61K 31/553* | (2006.01) | |
| *A61K 31/685* | (2006.01) | |
| *A61K 31/688* | (2006.01) | |
| *C07D 403/12* | (2006.01) | |

(52) U.S. Cl.
CPC ........... *C07D 487/08* (2013.01); *A61K 31/52* (2013.01); *A61K 31/55* (2013.01); *A61K 31/553* (2013.01); *A61K 31/685* (2013.01); *A61K 31/688* (2013.01); *A61K 45/06* (2013.01); *A61P 31/18* (2018.01); *C07C 243/28* (2013.01); *C07C 275/16* (2013.01); *C07D 401/12* (2013.01); *C07D 403/12* (2013.01); *C07D 405/14* (2013.01); *C07D 471/08* (2013.01); *C07D 487/10* (2013.01); *C07D 491/04* (2013.01)

(58) Field of Classification Search
CPC ... C07D 487/08; C07D 491/04; C07D 405/14
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,902,514 A | 2/1990 | Barclay et al. |

(Continued)

FOREIGN PATENT DOCUMENTS

| | | |
|---|---|---|
| AU | 2003200066 | 4/2003 |
| EP | 521827 | 1/1993 |

(Continued)

OTHER PUBLICATIONS

"Transporter Certified Hepatocytes" Qualyst Transporter Solutions, 2012, LLC:1-2.

(Continued)

*Primary Examiner* — Emily A Bernhardt
(74) *Attorney, Agent, or Firm* — Fish & Richardson P.C.

(57) ABSTRACT

The invention provides a compound of Formula I:

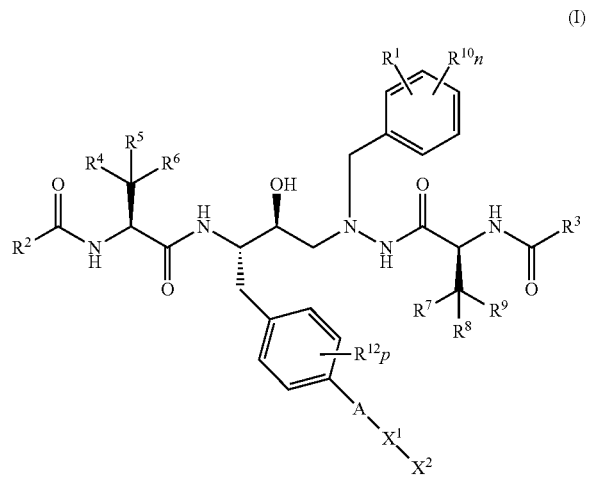

(I)

or a pharmaceutically acceptable salt thereof as described herein. The invention also provides pharmaceutical compositions comprising a compound of Formula I, processes for preparing compounds of Formula I, therapeutic methods for treating the proliferation of the HIV virus, treating AIDS or delaying the onset of AIDS symptoms in a mammal using compounds of Formula I.

23 Claims, 5 Drawing Sheets

(56) References Cited

U.S. PATENT DOCUMENTS

| | | | |
|---|---|---|---|
| 4,992,445 | A | 2/1991 | Lawter et al. |
| 5,001,139 | A | 3/1991 | Lawter et al. |
| 5,023,252 | A | 6/1991 | Hseih |
| 5,461,067 | A | 10/1995 | Norbeck et al. |
| 5,616,345 | A | 4/1997 | Geoghegan et al. |
| 5,679,688 | A | 10/1997 | Grobelny |
| 5,753,652 | A | 5/1998 | Fassler et al. |
| 5,849,911 | A | 12/1998 | Fassler et al. |
| 10,294,234 | B2 | 5/2019 | Bacon et al. |
| 10,752,636 | B2 | 8/2020 | Bacon et al. |
| 2005/0159469 | A1 | 7/2005 | Randolph et al. |
| 2009/0076097 | A1 | 3/2009 | Czarnik |
| 2010/0143301 | A1 | 6/2010 | Desai et al. |
| 2013/0165489 | A1 | 6/2013 | Cocklin et al. |
| 2013/0289067 | A1 | 10/2013 | Ghosh et al. |
| 2014/0221356 | A1 | 8/2014 | Jin et al. |
| 2014/0221378 | A1 | 8/2014 | Miyazaki et al. |
| 2014/0221380 | A1 | 8/2014 | Miyazaki et al. |
| 2018/0258097 | A1 | 9/2018 | Bacon et al. |
| 2019/0308983 | A1 | 10/2019 | Bacon et al. |
| 2020/0030327 | A1 | 1/2020 | Chin et al. |

FOREIGN PATENT DOCUMENTS

| | | |
|---|---|---|
| EP | 604368 | 6/1994 |
| EP | 2003120 | 12/2008 |
| IN | 2008CH01037 | 4/2016 |
| WO | WO9318006 | 9/1993 |
| WO | WO9419332 | 9/1994 |
| WO | WO9719055 | 5/1997 |
| WO | WO9740029 | 10/1997 |
| WO | WO9746514 | 12/1997 |
| WO | WO9803476 | 1/1998 |
| WO | WO200104120 | 1/2001 |
| WO | WO200146120 | 6/2001 |
| WO | WO2002094768 | 11/2002 |
| WO | WO2003020370 | 3/2003 |
| WO | WO2003078438 | 9/2003 |
| WO | WO2004096286 | 11/2004 |
| WO | WO2005061487 | 7/2005 |
| WO | WO2006014282 | 2/2006 |
| WO | WO2006015261 | 2/2006 |
| WO | WO2006110157 | 10/2006 |
| WO | WO2007002172 | 1/2007 |
| WO | WO2008011116 | 1/2008 |
| WO | WO2008011117 | 1/2008 |
| WO | WO2008118849 | 10/2008 |
| WO | WO2008156632 | 12/2008 |
| WO | WO2009062285 | 5/2009 |
| WO | WO2009114151 | 9/2009 |
| WO | WO2009136365 | 11/2009 |
| WO | WO2010032852 | 3/2010 |
| WO | WO2010077317 | 7/2010 |
| WO | WO2010130034 | 10/2010 |
| WO | WO2011026781 | 3/2011 |
| WO | WO2011080562 | 7/2011 |
| WO | WO2012003497 | 1/2012 |
| WO | WO2012003498 | 1/2012 |
| WO | WO2012031237 | 3/2012 |
| WO | WO2012092168 | 7/2012 |
| WO | WO2012092188 | 7/2012 |
| WO | WO2012145728 | 10/2012 |
| WO | WO2012170792 | 12/2012 |
| WO | WO2013006738 | 1/2013 |
| WO | WO2013006792 | 1/2013 |
| WO | WO2013091096 | 6/2013 |
| WO | WO2013159064 | 10/2013 |
| WO | WO2014100323 | 6/2014 |
| WO | WO2015097667 | 7/2015 |
| WO | WO2015175994 | 11/2015 |
| WO | WO2016033243 | 3/2016 |
| WO | WO2018145021 | 8/2018 |

OTHER PUBLICATIONS

Australian Office Action in AU Appln. No. 2018215546, dated Dec. 19, 2019, 3 pages.

Berge et al., "Pharmaceutical salts," J. Pharma Sci., 1977, 66(1):1-19.

Choiu et al., "In Vitro OATP1 B1 and OATP1 B3 Inhibition is Associated With Observations of Benign Clinical Unconjugated Hyperbilirubinemia," Xenobiotica, Informa Healthcare, 2014, 44(3):276-282.

Chu et al. "Species Differences in Drug Transporters and Implications for Translating Preclinical Findings to Humans," Expert Opinion Drug Metabolism Toxicology, 2013, 9(3):237-252.

Cihlar et al., "Suppression of HIV-1 Protease Inhibitor Resistance by Phosphonemediated Solvent Anchoring," Journal of Molecular Biology, 2006, 363:635-647.

Colombian Notice of Opposition in CO Appln. No. NC2019/0008531, dated Feb. 11, 2020, 14 pages (with English translation).

Croom et al., "Atazanavir—a review of its use in the management of HIV-1 infection," Drugs, 2009, 69(8):1107-1140.

European Office Action in European Application No. 18706072, dated Sep. 25, 2019, 13 pages.

Foster, "Deuterium Isotope Effects in Studies of Drug Metabolism," Trends Pharmacol. Sci., 5(12):524-527 (1984).

Giacomini et al., "Membrane Transporters in Drug Development," Nature Reviews Drug Development, 2010, 9:215-236.

Gillis, E. et al., "Applications of Fluorine in Medicinal Chemistry", Journal of Medicinal Chemistry, Feb. 2013, 58(21):8315-8359.

Indian Office Action in IN Appln. No. 201917032272, dated Mar. 4, 2020, 4 pages (with English translation).

International Search Report and Written Opinion in International Application No. PCT/US2018/016893, dated Apr. 24, 2018, 12 pages.

Link et al., "Novel HIV P1 With High Resistance Barrier and Potential for Unboosted OD Oral dosing", Abstract, CROI—Conference on Retroviruses and Opportunistic Infections, Seattle, WA: 1-3, 2017.

Link et al., "Novel HIV P1 With High Resistance Barrier and Potential for Unboosted OD Oral Dosing," CROI—Conference on the Retroviruses and Opportunistic Infections, Poster:1-3, 2017.

Link et al., "Novel HIV P1 with High Resistance Barrier and Potential for Unboosted OD Oral Dosing," Poster; CROI—Conference on Retroviruses and Opportunistic Infections; Poster, 2017, 433: 1-6.

Lv et al., "HIV protease inhibitors: a review of molecular selectivity and toxicity," HIV/AIDS—Research and Palliative Care, 2015, 7:95-104.

Poonam Shah and Andrew D. Westwell, "The role of fluorine in medicinal chemistry", Journal of Enzyme Inhibition and Medicinal Chemistry, Oct. 2007; 22(5): 527-540.

Swift et al., "Sandwich-Cultered Hepatocytes: An In Vitro Model to Evaluate Hepatobiliary Transporter-Based Drug Interactions and Hepatotoxicity," Drug Metabolism Review, 2010, 42(3):1-45.

Taiwanese Office Action in TW Application No. 107103968, dated Dec. 3, 2019. 7 pages (with English translation).

Taiwanese Office Action in TW Application No. 107103968, dated Jan. 29, 2019, 9 pages.

Taiwanese Office Action in TW Appln. No. 108124043, dated May 11, 2020, 7 pages (with English translation).

Third Party Observation in International Application No. PCT/US2018/016893, dated Jun. 7, 2019, 10 pages.

Chilean Office Action in CL Appln. No. 201902204, dated Jun. 15, 2020, 24 pages (with English translation).

Eurasian Office Action in EA Appln. No. 201991684/28, dated Oct. 1, 2020, 5 pages (with English tmnslation).

Gulf Coop Council Office Action in GC Appln. No. 2019-37997, dated Jul. 28, 2020, 4 pages.

Japanese Office Action in JP Appln. No. 2019-542392, dated Oct. 6, 2020, 6 pages (with English translation).

Ukrainian Office Action in UA Appln. No. a2019 09440, dated Sep. 21, 2020, 5 pages (with English translation).

Chilean Office Action in CL Appln. No. 201902204, dated Nov. 16, 2020, 25 pages.

(56) References Cited

OTHER PUBLICATIONS

Gulf Coop Council Office Action in GC Appln. No. 2019-37997, dated Nov. 29, 2020, 3 pages.
New Zealand Office Action in NZ Appln. No. 755929, dated Nov. 13, 2020, 5 pages.
PCT International Preliminary Report on Patentability in International Appln. No. PCT/US2019-043965, dated Feb. 2, 2021, 7 pages.
PCT Third Party Observation in International Appln. No. PCT/US2019/043965, dated Nov. 30, 2020, 9 pages.
Rouquayrol et al., "Transepithelial transport of prodrugs of the HIV protease inhibitors Sanquinavir, Indinavir, and Nelfinavir across CaCo-2 cell monolayers," Pharmaceutical Research, 2002, 19(11):1704-1712.
Stella et al., "Prodrugs: Challenges and Rewards Part 1," Biotechnology: Pharmaceutical Aspects, 2007, 5:33-52.
Subbaiah et al., "Design strategies in the prodrugs of HIV-1 protease inhibitors to improve pharmaceutical properties," European Journal of Medicinal Chemistry, 2017, 139:865-883.
Korean Office Action in KR Appln. No. 10-2019-7025847, dated Feb. 26, 2021, 10 pages (with English translation).
Eurasian Office Action in EA Application No. 201991684, dated Mar. 18, 2021, 2 pages (with English translation).
Canadian Office Action in CA Application No. 3,051,588, dated Apr. 30, 2021, 3 pages.

HIV INHIBITOR COMPOUNDS

CROSS REFERENCE TO RELATED APPLICATIONS

This application is a continuation of U.S. application Ser. No. 16/364,487, filed Mar. 26, 2019, which is a continuation of U.S. application Ser. No. 15/888,749, filed Feb. 5, 2018, now issued U.S. Pat. No. 10,294,234, which claims benefit of priority U.S. Provisional Patent Application Ser. No. 62/455,348, filed Feb. 6, 2017. The contents of these applications are incorporated herein by reference in their entireties.

FIELD

The present disclosure relates to novel compounds for use in the treatment of a Retroviridae viral infection including an infection caused by the HIV virus. The present disclosure also relates to intermediates for its preparation and to pharmaceutical compositions containing those compounds.

BACKGROUND

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Several protease inhibitors (PI) are presently approved for use in AIDS or HIV. Yet many PI inhibitors suffer from high rates of hepatic metabolism, which may require co-administration of a booster or more frequent dosing. Furthermore, viral resistance remains a problem. Accordingly, there is a need for new agents that inhibit the replication of HIV.

SUMMARY

The present disclosure provides compounds and methods for the treatment of an HIV infection. Accordingly, in one embodiment, the invention provides a compound of Formula I:

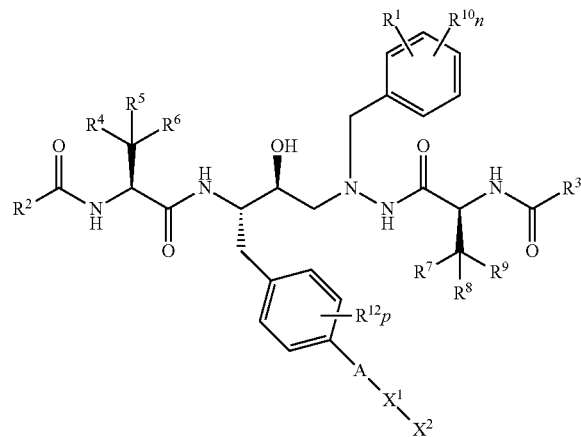

(I)

or a pharmaceutically acceptable salt thereof, wherein:

$R^1$ is a 5 to 10-membered heterocycle having 1 to 5 heteroatoms selected from N, O, and S, or a 5 to 10-membered heteroaryl having 1 to 5 heteroatoms selected from N, O, and S, wherein the 5 to 10-membered heterocycle or 5 to 10-membered heteroaryl is optionally substituted with 1 to 5 $R^a$ groups;

$R^2$ and $R^3$ are each independently $C_{1-4}$alkyl, $C_{3-6}$cycloalkyl, O—$R^{2A}$, $C_{1-2}$alkyl-O—$R^{2A}$, N—$(R^{3A})_2$, or $C_{1-2}$alkyl-N—$(R^{3A})_2$, wherein each $R^{2A}$ is independently $C_{1-4}$alkyl, $C_{3-6}$cycloalkyl, or a 4 to 10-membered heterocyclyl having 1 to 5 heteroatoms selected from N, O, and S, wherein each $R^{3A}$ is independently hydrogen, $C_{1-4}$alkyl, $C_{3-6}$cycloalkyl, or COO($R^e$), and wherein each $C_{3-6}$cycloalkyl or 4 to 10-membered heterocyclyl is optionally substituted by 1 to 3 $R^f$ groups, wherein each $R^f$ is independently $C_{1-2}$alkyl or halogen;

$R^4$ is hydrogen, halo, $C_{1-4}$alkyl, $C_{1-4}$haloalkyl, $C_{3-6}$cycloalkyl, $C_{1-4}$alkoxy, or $C_{1-4}$haloalkoxy;

$R^7$ is hydrogen, halo, $C_{1-4}$alkyl, $C_{1-4}$haloalkyl, $C_{3-6}$cycloalkyl, $C_{1-4}$alkoxy, or $C_{1-4}$haloalkoxy;

$R^5$, $R^6$, $R^8$, and $R^9$ are each independently hydrogen, halo, $C_{1-2}$alkyl, $C_{1-2}$haloalkyl, or $C_{3-6}$cycloalkyl;

and wherein two or more of $R^4$, $R^5$ and $R^6$ or two or more of $R^7$, $R^8$, and $R^9$ optionally join together to form one or more $C_{3-6}$cycloalkyl groups that are optionally substituted with 1 to 4 groups selected from halogen, $C_{1-2}$alkyl, and $C_{1-2}$haloalkyl;

each $R^{10}$ is independently halogen, cyano, $C_{1-4}$alkoxy, $C_{1-6}$alkyl, or $C_{3-6}$cycloalkyl;

n is 0 to 4;

each $R^a$ is independently halogen, $C_{1-4}$alkyl, $C_{1-4}$alkyl with 1 to 2 groups selected from hydroxyl and $C_{1-4}$ alkoxy, $C_{1-4}$haloalkyl, $C_{1-4}$alkoxy, $C_{3-6}$ cycloalkyl, 4 to 10-membered heterocyclyl having 1 to 5 heteroatoms selected from N, O, and S which is optionally substituted with $R^{a1}$, or O—$R^{3B}$, wherein $R^{3B}$ is $C_{3-6}$cycloalkyl optionally substituted with $R^{a1}$ or a 4 to 10-membered heterocyclyl having 1 to 5 heteroatoms selected from N, O, and S optionally substituted with $R^{a1}$, wherein each $R^{a1}$ is independently $C_{1-4}$alkyl, $C_{3-6}$cycloalkyl, $C_{1-4}$haloalkyl, or 4 to 8-membered heterocyclyl having 1 to 3 heteroatoms selected from N, O, and S;

A is ethynyl or a bond;

$X^1$ is a 6 to 10-membered aryl or a 5 to 10-membered heteroaryl having 1 to 3 heteroatoms selected from N, O, and S, wherein each 6 to 10-membered aryl or 5 to 10-membered heteroaryl is optionally substituted with 1 to 4 $R^b$ groups;

$X^2$ is hydrogen or a 4 to 10-membered heterocyclyl having 1 to 5 heteroatoms selected from N, O, and S, wherein the 4 to 10-membered heterocyclyl is optionally substituted with one $R^{11}$ and optionally substituted with 1 to 5 $R^b$ groups;

$R^{11}$ is C=O($R^c$), $CH_2(R^d)$, S(O)$_{1-2}$($C_{1-4}$alkyl), S(O)$_{1-2}$$C_{3-6}$cycloalkyl, a 4 to 10-membered heterocyclyl having 1 to 5 heteroatoms selected from N, O, and S, or a 5 to 9-membered heteroaryl having 1 to 5 heteroatoms selected from N, O, and S, wherein each 4 to 10-membered heterocyclyl or 5 to 9-membered heteroaryl is optionally substituted with 1 to 5 $R^b$ groups;

each $R^b$ is independently halogen, oxo, $C_{1-4}$alkyl, $C_{1-4}$alkyl with 1 to 2 groups selected from hydroxyl and $C_{1-4}$ alkoxy, $C_{1-4}$haloalkyl, $C_{1-4}$ alkoxy, or COO($R^e$);

$R^c$ is $C_{1-4}$alkyl, $C_{1-4}$ haloalkyl, $C_{1-4}$alkoxy, N($R^e$)$_2$, $C_{3-6}$cycloalkyl, or a 4 to 6-membered heterocyclyl having 1 to 3 heteroatoms selected from N, O, and S, wherein the $C_{3-6}$ cycloalkyl and the 4 to 6-membered heterocyclyl are optionally substituted by 1 to 5 $R^b$ groups;

$R^d$ is COO($R^e$), N($R^e$)$_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl is optionally substituted by 1 to 5 $R^b$ groups;

each $R^{12}$ is $C_{1-2}$alkyl, halo, —O$C_{1-2}$alkyl, or cyano;

each p is 0 to 4;

and each $R^e$ is independently hydrogen or $C_{1-4}$alkyl.

Also provided is a pharmaceutical composition comprising a therapeutically effective amount of a compound disclosed herein, or a pharmaceutically acceptable salt thereof, and a pharmaceutically acceptable excipient. In certain embodiments, the pharmaceutical composition further comprising one, two, three, or four additional therapeutic agents.

Also provided is method of treating or preventing a human immunodeficiency virus (HIV) infection comprising administering a therapeutically effective amount of a compound disclosed herein, or a pharmaceutically acceptable salt thereof, to a subject in need thereof.

In certain embodiments, the current disclosure relates to an article of manufacture comprising a unit dosage of a compound disclosed herein, or a pharmaceutically acceptable salt thereof.

Also provided is a compound disclosed herein, or a pharmaceutically acceptable salt thereof, for use in therapy.

A compound disclosed herein, or a pharmaceutically acceptable salt thereof, for use in a method of treating or preventing a human immunodeficiency virus (HIV) infection comprising administering a therapeutically effective amount of said compound to a subject in need thereof, is also provided.

DETAILED DESCRIPTION

Figure 1:
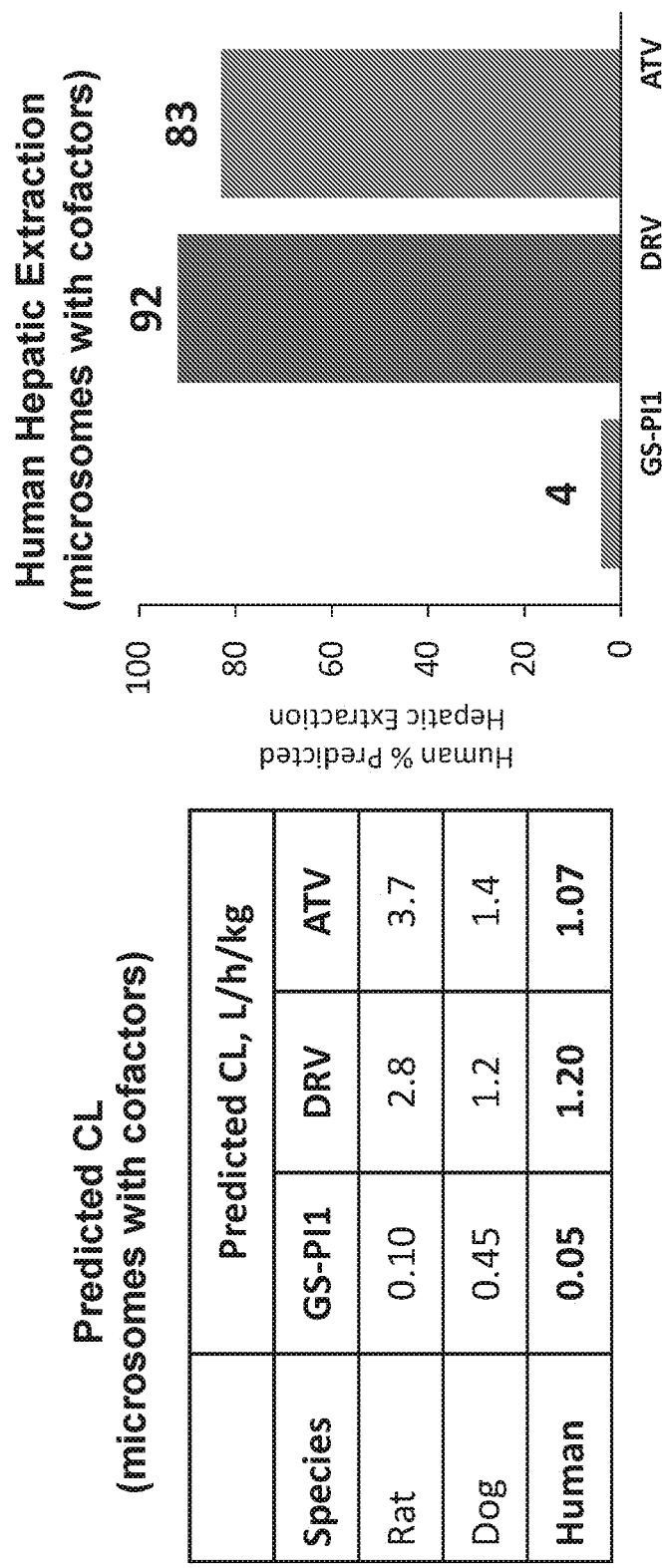
FIG. 1 describes the hepatic predicted clearance for certain compounds and reference compounds as more fully described in the biological examples herein.

The following is a list of abbreviations and acronyms used throughout the application:

Abbreviation Meaning

° C. Degree Celsius
ATP Adenosine-5′-triphosphate
AcOH Acetic acid
d Doublet
dd Doublet of doublets
DCE 1,2-dichloroethane
DCM Dichloromethane
DIPEA N,N-diisopropylethylamine
DME 1,2-dimethoxyethane
DMF Dimethylformamide
DMSO Dimethylsulfoxide
dppf 1,1′-Bis(diphenylphosphino)ferrocene
EGTA Ethylene glycol tetraacetic acid
ETOAC Ethyl acetate
equiv/eq Equivalents
ESI Electrosprayionization
Ac Acetate
Et Ethyl
g Grams
HATU 2-(7-Aza-1H-Benzotriazole-1-yl)-1,1,3,3-tetramethyluronium hexafluorophosphate
hERG human Ether-à-go-go Related Gene
HPLC High-performance liquid chromatography
h/hr Hours
Hz Hertz
IC$_{50}$ The half maximal inhibitory concentration
J Coupling constant
Kg Kilogram
M Molar
m multiplet
m/z mass-to-charge ratio
M+ Mass peak
M+H Mass peak plus hydrogen
Me Methyl
MeOH Methyl alcohol/methanol
mg Milligram
MHz Megahertz
min/m Minute
ml/mL Milliliter
mM Millimolar
mmol Millimole
MS Mass spectroscopy
mw Microwave
N Normal
mol Mole
NMP N-methylpyrrolidinone
NMR Nuclear magnetic resonance
Ph Phenyl
ppm Parts per million
prep Preparative
Rf Retention factor
RP Reverse phase
RT/rt Room temperature
s Second
s Singlet
t Triplet
TEA Triethylamine
TFA Trifluoroacetic acid
TLC Thin layer chromatography
TMS trimethylsilyl
WT Wild type
δ Chemical shift
μg Microgram
μL/μl Microliter
μM Micromolar
μm Micrometer
μmol Micromole Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash at the front or end of a chemical group is a matter of convenience; chemical groups may be depicted with or without one or more dashes without losing their ordinary meaning. A wavy line drawn through a line in a structure indicates a point of attachment of a group, e.g.:

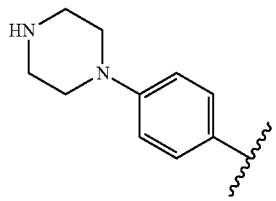 [SMILES: *c1ccc(N2CCNCC2)cc1]

A dashed line indicates an optional bond. Where multiple substituent groups are identified the point of attachment is at the terminal substituent (e.g. for "alkylaminocarbonyl" the point of attachment is at the carbonyl substituent).

The prefix "$C_{x-y}$" indicates that the following group has from x (e.g. 1) to y (e.g. 6) carbon atoms, one or more of which, in certain groups (e.g. heteroalkyl, heteroaryl, heteroarylalkyl, etc), may be replaced with one or more heteroatoms or heteroatomic groups. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g. 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" refers to the compounds of Formula (I), (Ia), (Ib), (Ic), (Id), and/or (Ie). Also included are the specific compounds of Examples 1-245.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡C—), propargyl (—CH$_2$C≡C—), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH$_2$. Amino groups may also be substituted as described herein, such as with alkyl, carbonyl or other amino groups. The term "alkylamino" refers to an amino group substituted with one or two alkyl substituents (e.g. dimethylamino or propylamino).

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1, 2, 3, 4-tetrahydronaphthyl. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Non-limiting examples of aryl groups include, but are not limited to, phenyl, indenyl, naphthyl, 1, 2, 3, 4-tetrahydronaphthyl, anthracenyl, and the like.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo [3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, spiro [3.3]heptane, and 1-cyclohex-3-enyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Alkoxy" or "alkoxyl" refers to a moiety of the formula —O-alkyl, wherein the alkyl portion is as defined above. For example, C$_{1-4}$ alkoxy refers to a moiety having 1-4 carbon alkyl group attached to the oxygen. "Haloalkoxy" or "haloalkoxyl" refers to a moiety of the formula —O-haloalkyl, wherein the haloalkyl portion is as defined above. For example, C$_{1-4}$ alkoxy refers to a moiety having 1-4 carbon halo alkyl group attached to the oxygen.

"Heteroalkyl" refers to an alkyl in which one or more of the carbon atoms (and any associated hydrogen atoms) are each independently replaced with the same or different heteroatom or heteroatomic ngroup. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl, each of which may be optionally substituted. A heteroalkyl group comprises from 1 to 10 carbon and up to four three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-12 members, 5-10 members, or 5-6 members.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 5 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1]octanyl, 2,5-diazabicyclo[2.2.1]heptanyl, 3,6-diazabicyclo[3.1.1]heptanyl, 3-oxa-7,9-diazabicyclo[3.3.1]nonanyl, and hexahydropyrazino[2,1-c][1,4]oxazinyl, for example.

"Hydroxyl" and "hydroxy" are used interchangeably and refer to —OH. "Oxo" refers to

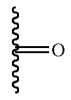

or

Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: C$_{1-6}$ alkylamiocarbonyl (e.g. CH$_3$CH$_2$NHC(O)—) C$_{1-6}$ alkoxycarbonyl (e.g. CH$_3$O—C(O)—), 5-7 membered heterocyclyl-C$_{1-6}$ alkyl (e.g. piperazinyl-CH$_2$—), C$_{1-6}$ alkylsulfonyl-5-7 membered heterocyclyl (e.g. CH$_3$S(O)$_2$-morpholinyl-), 5-7 membered heterocyclyl C$_{1-6}$ alkoxy 5-7 membered heterocyclyloxy, (4-7 membered heterocyclyl)-4-7 membered heterocyclyl (e.g. oxetanyl-pyrrolidinyl-), C$_{3-6}$ cycloalkylaminocarbonyl (e.g. cyclopropyl-NH—C(O)—), 5-7 membered heterocyclyl-C$_{2-6}$ alkynyl (e.g. N-piperazinyl-CH$_2$C≡CCH$_2$—), and C$_{6-10}$ arylaminocarbonyl (e.g. phenyl-NH—C(O)—).

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents (R-groups) join together (e.g. when R$^7$ and R$^8$ join together) they may be taken from the same point of attachment to form a spiro ring.

The phrase "meta (3) position with respect to the point of attachment of the A ring", refers to the position on the ring where the substituent (e.g. —CN) is adjoined and is shown below with an arrow, wherein z represents a carbon atom or nitrogen:

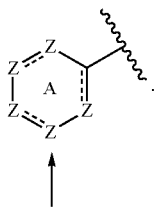

Similarly, para (4) position substitution refers to attachment of a substituent at the position indicated below, with respect to the point of attachment (e.g. of the B ring):

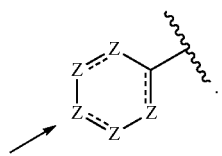

Similarly, ortho or 2-position refers to attachment of a substituent at the position indicated below, with respect to the point of attachment:

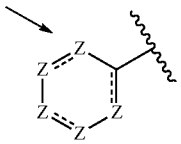

The compounds described herein include isomers, stereoisomers and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

The term "fused" refers to a ring which is bound to an adjacent ring.

"Enantiomers" are a pair of stereoisomers that are non-superimposable mirror images of each other. A 1:1 mixture of a pair of enantiomers is a "racemic" mixture.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"$IC_{95}$" or "$EC_{95}$" refers to the inhibitory concentration required to achieve 95% of the maximum desired effect, which in many cases here is the inhibition of the HIV virus. This term is obtained using an in vitro assay evaluating the concentration-dependent inhibition of wild type HIV virus.

"$IC_{50}$" or "$EC_{50}$" refers to the inhibitory concentration required to achieve 50% of the maximum desired effect, which in many cases here is the inhibition of the HIV virus. This term is obtained using an in vitro assay evaluating the concentration-dependent inhibition of wild type HIV virus.

"IQ" or "inhibitory quotient" refers to the ratio between the trough drug concentration ($C_{tau}$) and level of drug resistance of the HIV isolate as determined by the $IC_{95}$ (i.e. $C_{tau}/IC_{95}$).

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

The present disclosure also provides for prodrugs of the compounds disclosed herein. A "prodrug" is defined in the pharmaceutical field as a biologically inactive derivative of a drug that upon administration to the human body is converted to the biologically active parent drug according to some chemical or enzymatic pathway.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated. As is evident to one skilled in the art, a sufficient or significant delay can, in effect, encompass prevention, in that the subject does not develop the disease or condition. For example, a method that "delays" development of AIDS is a method that reduces the probability of disease development in a given time frame and/or reduces extent of the disease in a given time frame, when compared to not using the method. Such comparisons may be based on clinical studies, using a statistically significant number of subjects. For example, the development of AIDS can be detected using known methods, such as confirming a subject's HIV$^+$ status and assessing the subject's T-cell count or other indication of AIDS development, such as extreme fatigue, weight loss, persistent diarrhea, high fever, swollen lymph nodes in the neck, armpits or groin, or presence of an opportunistic condition that is known to be associated with AIDS (e.g., a condition that is generally not present in subjects with functioning immune systems but does occur in AIDS patients). Development may also refer to disease progression that may be initially undetectable and includes occurrence, recurrence and onset.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, the term "preventing HIV infection" refers to administering to a subject who does not have a detectable HIV infection an anti-HIV therapeutic substance. It is understood that the subject for anti-HIV preventative therapy may be an individual at risk of contracting the HIV virus. Further, it is understood that prevention may not result in complete protection against onset of the disease or disorder. In some instances, prevention includes reducing the risk of developing the disease or disorder. The reduction of the risk may not result in complete elimination of the risk of developing the disease or disorder.

As used herein, an "at risk" individual is an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, individuals at risk for AIDS are those having HIV.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

The compounds of the invention include solvates, hydrates, tautomers, stereoisomers and salt forms thereof.

Provided are also compounds in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I and $^{125}$I, respectively. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (Ia) or (Ib), can generally be prepared by conventional techniques known to those skilled in the art or by processes analogous to those described in the Examples as set out below using an appropriate isotopically-labeled reagent in place of the non-labeled reagent previously employed.

As referenced herein, darunavir is a HIV protease inhibitor having the structure:

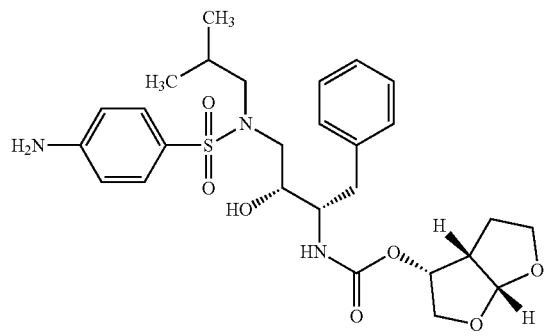 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

and having the IUPAC name [(3aS,4R,6aR)-2,3,3a,4,5,6a-hexahydrofuro[2,3-b]furan-4-yl] N-[(2S,3R)-4-[(4-aminophenyl)sulfonyl-(2-methylpropyl)amino]-3-hydroxy-1-phenylbutan-2-yl]carbamate. Darunavir (DRV) is marketed under the brand name PREZISTA®.

As referenced herein, atazanavir is a HIV protease inhibitor having the structure:

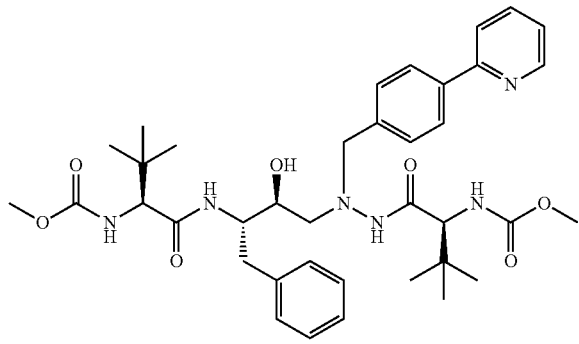

and having the IUPAC name methyl N-[(2S)-1-[2-[(2S,3S)-2-hydroxy-3-[[(2S)-2-(methoxycarbonylamino)-3,3-dimethylbutanoyl]amino]-4-phenylbutyl]-2-[(4-pyridin-2-ylphenyl)methyl]hydrazinyl]-3,3-dimethyl-1-oxobutan-2-yl]carbamate. Atazanavir (ATV) is marked under the brand name REYATAZ®.

Compounds

In certain embodiments, a compound of Formula I is provided:

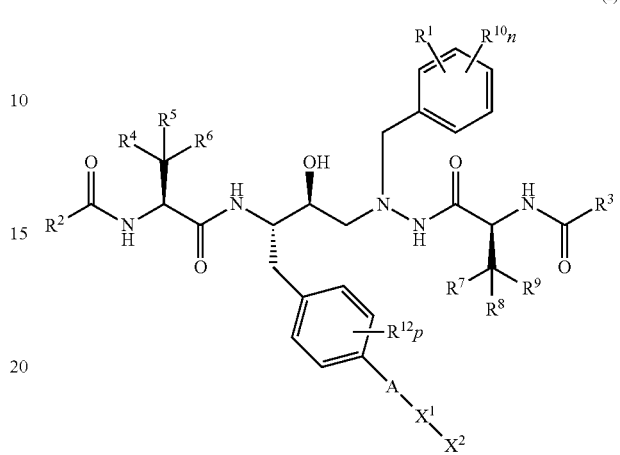

or a pharmaceutically acceptable salt thereof, wherein:

$R^{1}$ is a 5 to 10-membered heterocycle having 1 to 5 heteroatoms selected from N, O, and S, or a 5 to 10-membered heteroaryl having 1 to 5 heteroatoms selected from N, O, and S, wherein the 5 to 10-membered heterocycle or 5 to 10-membered heteroaryl is optionally substituted with 1 to 5 $R^{a}$ groups;

$R^{2}$ and $R^{3}$ are each independently $C_{1-4}$alkyl, $C_{3-6}$cycloalkyl, O—$R^{2A}$, $C_{1-2}$alkyl-O—$R^{2A}$, N—$(R^{3A})_{2}$, or $C_{1-2}$alkyl-N—$(R^{3A})_{2}$, wherein each $R^{2A}$ is independently $C_{1-4}$alkyl, $C_{3-6}$cycloalkyl, or a 4 to 10-membered heterocyclyl having 1 to 5 heteroatoms selected from N, O, and S, wherein each $R^{3A}$ is independently hydrogen, $C_{1-4}$alkyl, $C_{3-6}$cycloalkyl, or COO($R^{e}$), and wherein each $C_{3-6}$cycloalkyl or 4 to 10-membered heterocyclyl is optionally substituted by 1 to 3 $R^{f}$ groups, wherein each $R^{f}$ is independently $C_{1-2}$alkyl or halogen;

$R^{4}$ is hydrogen, halo, $C_{1-4}$alkyl, $C_{1-4}$haloalkyl, $C_{3-6}$cycloalkyl, $C_{1-4}$alkoxy, or $C_{1-4}$haloalkoxy;

$R^{7}$ is hydrogen, halo, $C_{1-4}$alkyl, $C_{1-4}$haloalkyl, $C_{3-6}$cycloalkyl, $C_{1-4}$alkoxy, or $C_{1-4}$haloalkoxy;

$R^{5}$, $R^{6}$, $R^{8}$, and $R^{9}$ are each independently hydrogen, halo, $C_{1-2}$alkyl, $C_{1-2}$haloalkyl, or $C_{3-6}$cycloalkyl;

and wherein two or more of $R^{4}$, $R^{5}$ and $R^{6}$ or two or more of $R^{7}$, $R^{8}$, and $R^{9}$ optionally join together to form one or more $C_{3-6}$cycloalkyl groups that are optionally substituted with 1 to 4 groups selected from halogen, $C_{1-2}$alkyl, and $C_{1-2}$haloalkyl;

each $R^{10}$ is independently halogen, cyano, $C_{1-4}$alkoxy, $C_{1-6}$alkyl, or $C_{3-6}$cycloalkyl;

n is 0 to 4;

each $R^{a}$ is independently halogen, $C_{1-4}$alkyl, $C_{1-4}$alkyl with 1 to 2 groups selected from hydroxyl and $C_{1-4}$ alkoxy, $C_{1-4}$haloalkyl, $C_{1-4}$alkoxy, $C_{3-6}$ cycloalkyl, 4 to 10-membered heterocyclyl having 1 to 5 heteroatoms selected from N, O, and S which is optionally substituted with $R^{a1}$, or O—$R^{3B}$, wherein $R^{3B}$ is $C_{3-6}$cycloalkyl optionally substituted with $R^{a1}$ or a 4 to 10-membered heterocyclyl having 1 to 5 heteroatoms selected from N, O, and S optionally substituted with $R^{a1}$, wherein each $R^{a1}$ is independently $C_{1-4}$alkyl, $C_{3-6}$cycloalkyl, $C_{1-4}$haloalkyl, or 4 to 8-membered heterocyclyl having 1 to 3 heteroatoms selected from N, O, and S;

A is ethynyl or a bond;

$X^1$ is a 6 to 10-membered aryl or a 5 to 10-membered heteroaryl having 1 to 3 heteroatoms selected from N, O, and S, wherein each 6 to 10-membered aryl or 5 to 10-membered heteroaryl is optionally substituted with 1 to 4 $R^b$ groups;

$X^2$ is hydrogen or a 4 to 10-membered heterocyclyl having 1 to 5 heteroatoms selected from N, O, and S, wherein the 4 to 10-membered heterocyclyl is optionally substituted with one $R^{11}$ and optionally substituted with 1 to 5 $R^b$ groups;

$R^{11}$ is C=O($R^c$), CH$_2$($R^d$), S(O)$_{1-2}$(C$_{1-4}$alkyl), S(O)$_{1-2}$C$_{3-6}$cycloalkyl, a 4 to 10-membered heterocyclyl having 1 to 5 heteroatoms selected from N, O, and S, or a 5 to 9-membered heteroaryl having 1 to 5 heteroatoms selected from N, O, and S, wherein each 4 to 10-membered heterocyclyl or 5 to 9-membered heteroaryl is optionally substituted with 1 to 5 $R^b$ groups;

each $R^b$ is independently halogen, oxo, $C_{1-4}$alkyl, $C_{1-4}$alkyl with 1 to 2 groups selected from hydroxyl and $C_{1-4}$ alkoxy, $C_{1-4}$haloalkyl, $C_{1-4}$ alkoxy, or COO($R^e$);

$R^c$ is $C_{1-4}$alkyl, $C_{1-4}$ haloalkyl, $C_{1-4}$alkoxy, N($R^e$)$_2$, $C_{3-6}$cycloalkyl, or a 4 to 6-membered heterocyclyl having 1 to 3 heteroatoms selected from N, O, and S, wherein the $C_{3-6}$cycloalkyl and the 4 to 6-membered heterocyclyl are optionally substituted by 1 to 5 $R^b$ groups;

$R^d$ is COO($R^e$), N($R^e$)$_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl is optionally substituted by 1 to 5 $R^b$ groups;

each $R^{12}$ is $C_{1-2}$alkyl, halo, —O$C_{1-2}$alkyl, or cyano;

each p is 0 to 4;

and each $R^e$ is independently hydrogen or $C_{1-4}$alkyl.

In certain embodiments, the compound of Formula I is a compound of Formula (Ia):

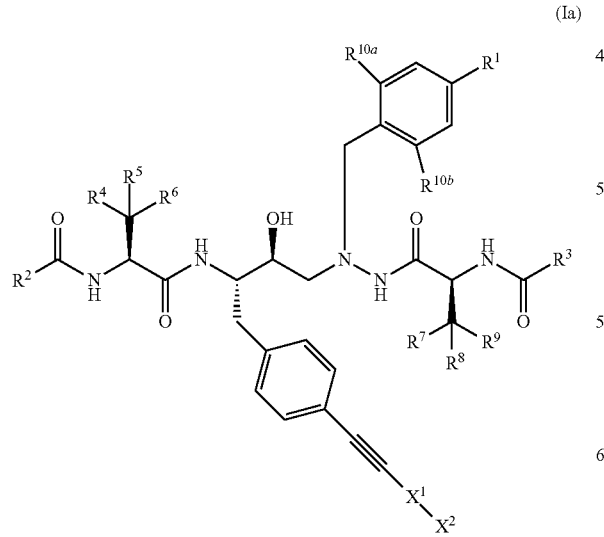

(Ia)

wherein $R^1$, $R^2$, $R^3$, $R^4$, $R^5$, $R^6$, $R^7$, $R^8$, $R^9$, $X^1$, and $X^2$ are as defined herein and $R^{10a}$ and $R^{10b}$ are independently halogen, cyano, $C_{1-4}$alkoxy, $C_{1-6}$alkyl, or $C_{3-6}$cycloalkyl.

In certain embodiments, the compound of Formula I or Formula (Ia) is a compound of Formula (Ib)

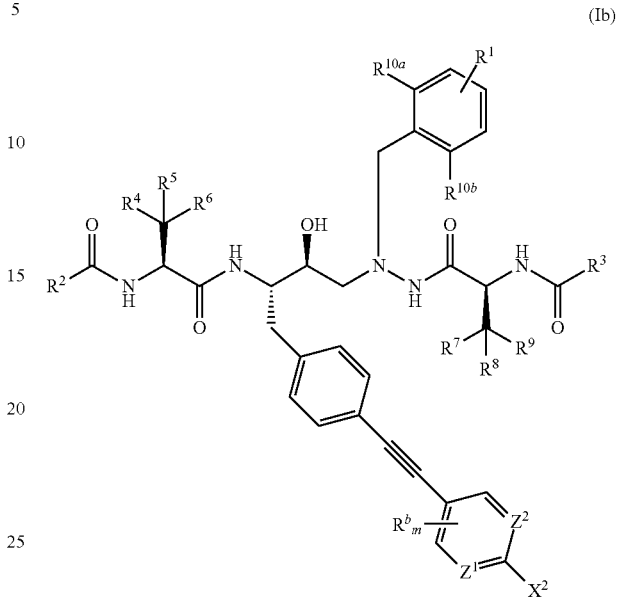

(Ib)

wherein: $Z^1$ and $Z^2$ are independently N or CH; m is 0 to 2, $R^{10a}$ and $R^{10b}$ are independently halogen, cyano, $C_{1-4}$alkoxy, $C_{1-6}$alkyl, or $C_{3-6}$cycloalkyl, and $R^1$, $R^2$, $R^3$, $R^4$, $R^5$, $R^6$, $R^7$, $R^8$, $R^9$, and $X^2$ are as defined herein.

In certain embodiments, the compound of Formula I, (Ia), or (Ib), is a compound of Formula (Ic):

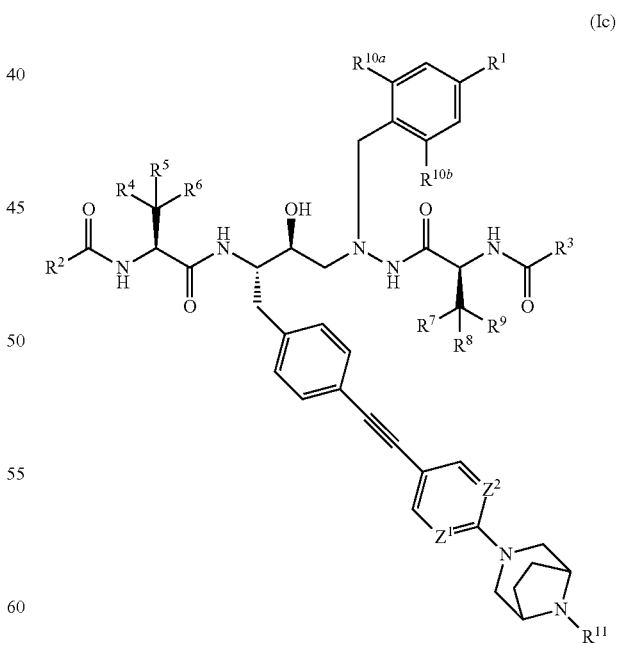

(Ic)

wherein $Z^1$ and $Z^2$ are independently N or CH, $R^{10a}$ and $R^{10b}$ are independently halogen, cyano, $C_{1-4}$alkoxy, $C_{1-6}$alkyl, or $C_{3-6}$cycloalkyl, and $R^1$, $R^2$, $R^3$, $R^4$, $R^5$, $R^6$, $R^7$, $R^8$, and $R^9$, are as defined herein.

In certain embodiments, the compound of Formula I or (Ia) is a compound of Formula (Id):

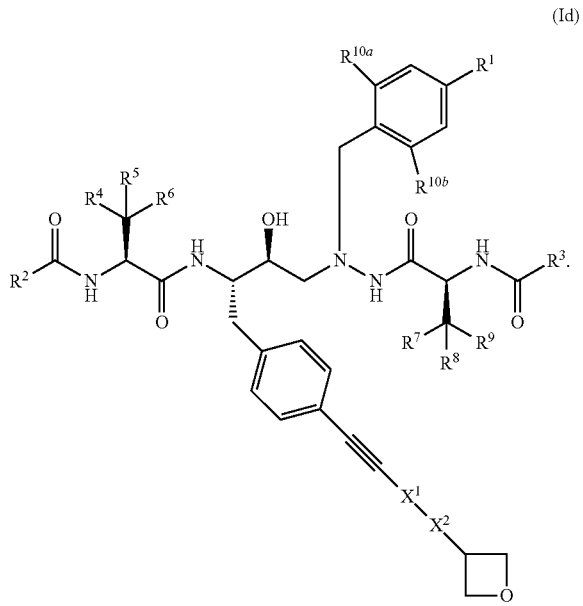

(Id)

wherein $R^{10a}$ and $R^{10b}$ are independently halogen, cyano, $C_{1-4}$alkoxy, $C_{1-6}$alkyl, or $C_{3-6}$cycloalkyl, and $R^1$, $R^2$, $R^3$, $R^4$, $R^5$, $R^6$, $R^7$, $R^8$, $R^9$, $X^1$ and $X^2$ are as defined herein.

In certain embodiments, the compound of Formula I or (Ia) is a compound of Formula (Ie):

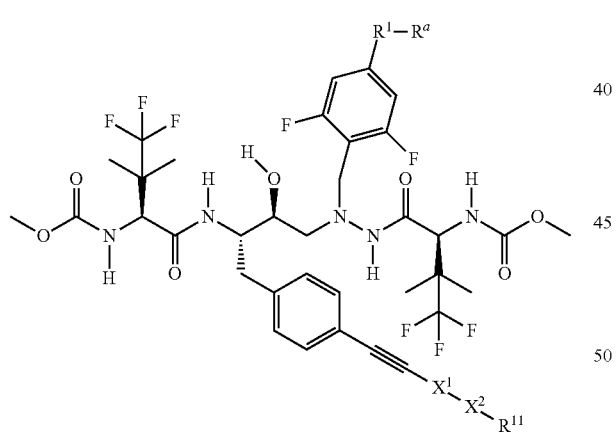

(Ie)

wherein $R^1$, $R^a$, $R^1$, $X^1$ and $X^2$ are as defined herein.

In certain embodiments of a compound of Formula (I), (Ia), (Ib), (Ic) or (Id), $R^4$ and $R^7$ may be the same or different. In certain embodiments of a compound of Formula (I), (Ia), (Ib), (Ic) or (Id), $R^4$ is hydrogen, $C_{1-4}$alkyl, or $C_{1-4}$haloalkyl. In certain embodiments, $R^4$ is $C_{1-4}$haloalkyl. In certain embodiments of a compound of Formula (I), (Ia), (Ib), (Ic) or (Id), $R^4$ is $CF_3$. In certain embodiments of a compound of Formula (I), (Ia), (Ib), (Ic) or (Id), $R^7$ is hydrogen, $C_{1-4}$alkyl, or $C_{1-4}$haloalkyl. In certain embodiments of a compound of Formula (I), (Ia), (Ib), (Ic) or (Id), $R^7$ is $C_{1-4}$haloalkyl. In certain embodiments, $R^7$ is $CF_3$. In certain embodiments of a compound of Formula (I), (Ia), (Ib), (Ic) or (Id), $R^4$ and $R^7$ are $CF_3$ or methyl. In certain embodiments of a compound of Formula (I), (Ia), (Ib), (Ic) or (Id), $R^5$, $R^6$, $R^8$, and $R^9$ may be the same or different. In certain embodiments of a compound of Formula (I), (Ia), (Ib), (Ic) or (Id), $R^5$, $R^6$, $R^8$, and $R^9$ are each independently hydrogen, halo, $C_{1-2}$alkyl, $C_{1-2}$haloalkyl, or $C_{3-6}$cycloalkyl. In certain embodiments of a compound of Formula (I), (Ia), (Ib), (Ic) or (Id), $R^5$, $R^6$, $R^8$, and $R^9$ are hydrogen, methyl, or fluoro. In certain embodiments of a compound of Formula (I), (Ia), (Ib), (Ic) or (Id), $R^5$ and $R^6$ are $C_{1-2}$alkyl. In certain embodiments of a compound of Formula (I), (Ia), (Ib), (Ic) or (Id), $R^5$ and $R^6$ are methyl. In certain embodiments of a compound of Formula (I), (Ia), (Ib), (Ic) or (Id), $R^8$ and $R^9$ are $C_{1-2}$alkyl. In certain embodiments of a compound of Formula (I), (Ia), (Ib), (Ic) or (Id), $R^8$ and $R^9$ are methyl. In certain embodiments of a compound of Formula (I), (Ia), (Ib), (Ic) or (Id), two or more of $R^4$, $R^5$, and $R^6$ or $R^7$, $R^8$, and $R^9$ may join together to form one or more $C_{3-6}$cycloalkyl groups that are optionally substituted with halogen.

In certain embodiments of a compound of Formula (I), (Ia), (Ib), (Ic), (Id) or (Ie), $R^1$ is a 5 to 6-membered heterocycle having 1 to 3 heteroatoms selected from N, O, and S, or a 5 to 6-membered heteroaryl having 1 to 3 heteroatoms selected from N, O, and S, wherein the 5 to 6-membered heterocycle or 5 to 6-membered heteroaryl is optionally substituted with 1 to 3 $R^a$ groups. In certain embodiments of a compound of Formula (I), (Ia), (Ib), (Ic), (Id) or (Ie), $R^1$ is a 5 to 6-membered heterocycle having 1 to 3 heteroatoms selected from N, O, and S and is optionally substituted with 1 to 3 $R^a$ groups. In certain embodiments of a compound of Formula (I), (Ia), (Ib), (Ic), (Id) or (Ie), $R^1$ is:

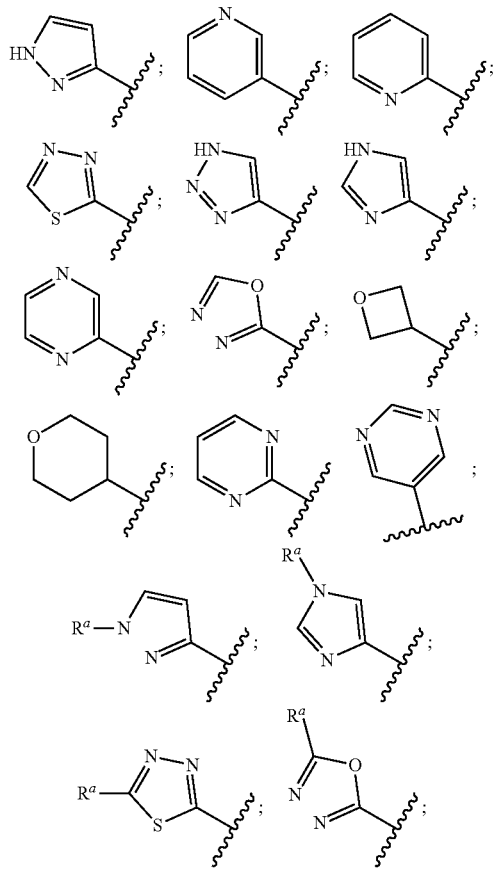

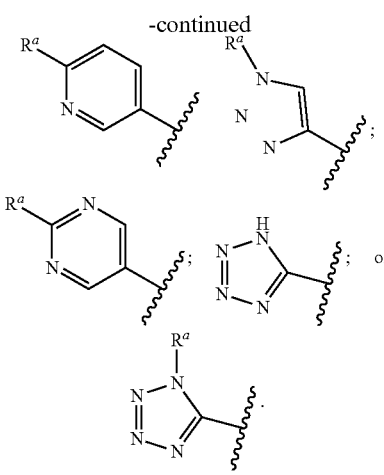
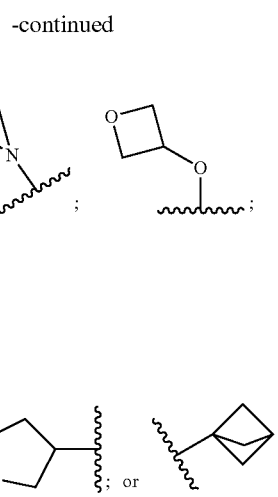

In certain embodiments, $R^1$ is

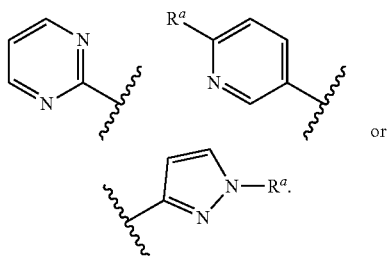

or

In certain embodiments, $R^1$ is:

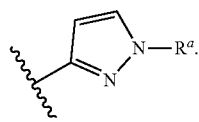

In certain embodiments of a compound of Formula (I), (Ia), (Ib), (Ic), (Id) or (Ie), $R^a$ is independently $C_{1-4}$alkyl, $C_{1-4}$alkyl with 1 to 2 groups selected from hydroxyl and $C_{1-4}$ alkoxy, $C_{1-4}$ haloalkyl, or a 4 to 8-membered heterocyclyl having 1 to 3 heteroatoms selected from N, O, and S optionally substituted with $R^{a1}$. In certain embodiments of a compound of Formula (I), (Ia), (Ib), (Ic), (Id) or (Ie), $R^a$ is independently $C_{1-4}$alkyl, $C_{1-4}$alkyl with 1 to 2 groups selected from hydroxyl and $C_{1-4}$ alkoxy, $C_{1-4}$ haloalkyl, furanyl, oxetanyl, or 3,8-diazabicyclo[3.2.1]octanyl optionally substituted with $R^{a1}$. In certain embodiments of a compound of Formula (I), (Ia), (Ib), (Ic), (Id) or (Ie), $R^a$ is independently $C_{1-4}$alkyl, $C_{1-4}$alkyl with 1 to 2 groups selected from hydroxyl and $C_{1-4}$ alkoxy, or $C_{1-4}$ haloalkyl. In certain embodiments of a compound of Formula (I), (Ia), (Ib), (Ic), (Id) or (Ie), $R^a$ is:

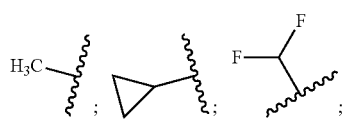

In certain embodiments of a compound of Formula (I), (Ia), (Ib), (Ic), (Id) or (Ie), $R^a$ is $C_{1-4}$haloalkyl. In certain embodiments of a compound of Formula (I), (Ia), (Ib), (Ic), (Id) or (Ie), $R^a$ is:

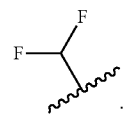

In certain embodiments of a compound of Formula (I), (Ia), (Ib), (Ic), (Id) or (Ie) $R^a$ may be substituted by $R^{a1}$. In certain embodiments of a compound of Formula (I), (Ia), (Ib), (Ic), (Id) or (Ie), $R^a$ is substituted with one $R^{a1}$ group. In certain embodiments of a compound of Formula (I), (Ia), (Ib), (Ic), (Id) or (Ie), $R^{a1}$ is $C_{1-4}$alkyl, $C_{3-6}$ cycloalkyl, $C_{1-4}$haloalkyl, or 4 to 8-membered heterocyclyl having 1 to 3 heteroatoms selected from N, O, and S. In certain embodiments of a compound of Formula (I), (Ia), (Ib), (Ic), (Id) or (Ie), the 4 to 8-membered heterocyclyl contains 1 to 2 nitrogen heteroatoms or 1 to 2 oxygen atoms.

In certain embodiments of a compound of Formula (I), (Ia), or (Ie), $X^1$ is a 6-membered aryl or a 5 to 6-membered heteroaryl having 1 to 3 heteroatoms selected from N, O, and S, wherein each 6-membered aryl or 5 to 6-membered heteroaryl is optionally substituted with 1 to 4 $R^b$ groups. In certain embodiments of a compound of Formula (I), (Ia), or (Ie), $X^1$ is pyrimidine or pyridine optionally substituted with 1 to 4 $R^b$ groups. In certain embodiments of a compound of Formula (I), (Ia), or (Ie), $X^1$ is pyrimidine or pyridine. In certain embodiments of a compound of Formula (I), (Ia), or (Ie), $X^1$ is:

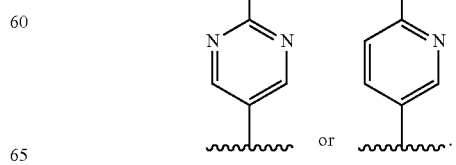

In certain embodiments of a compound of Formula (I), (Ia), or (Ie), $X^1$ is

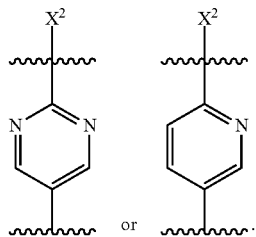

In certain embodiments of a compound of Formula (I), (Ia), or (Ie), $X^1$ is

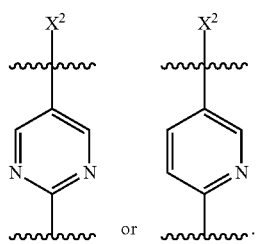

In certain embodiments of a compound of Formula (I), (Ia), (Ib), (Id) or (Ie), $X^2$ is a 4 to 10-membered heterocyclyl having 1 to 3 heteroatoms selected from N, O, and S and is optionally substituted with one $R^{11}$ and optionally substituted with 1 to 5 $R^b$ groups. In certain embodiments, $X^2$ may be substituted by $R^{11}$ and $R^b$. In certain embodiments of a compound of Formula (I), (Ia), (Ib), (Id) or (Ie) $X^2$ is:

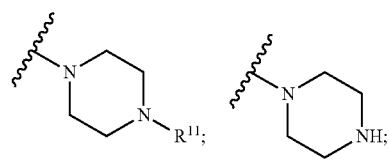

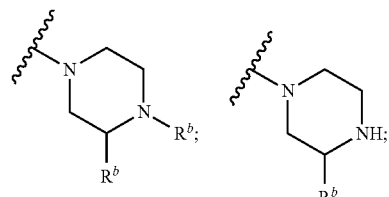

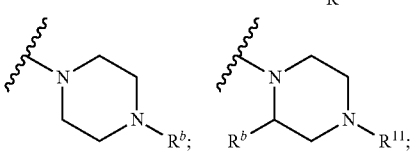

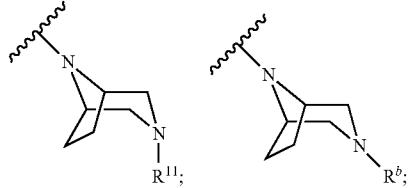

-continued

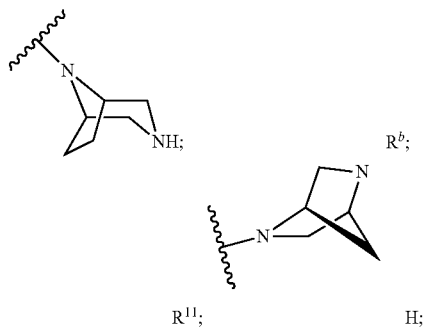

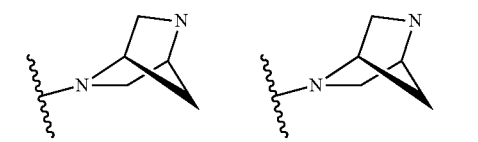

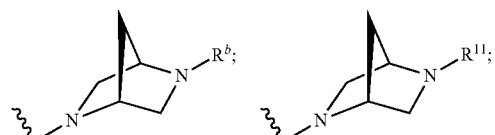

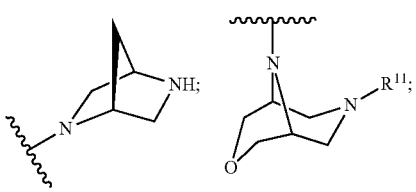

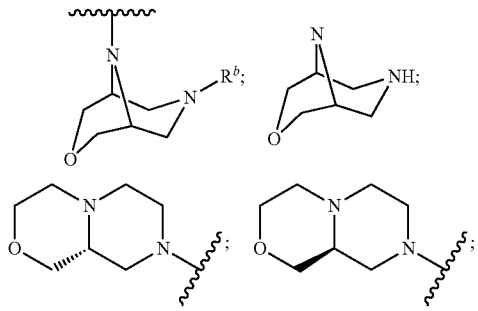

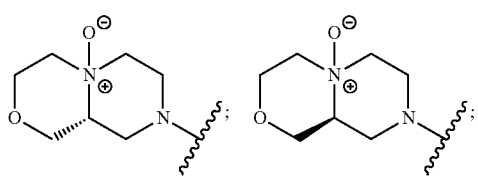

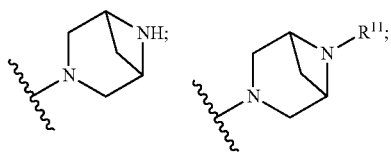

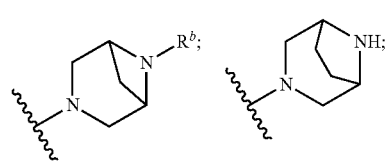

-continued

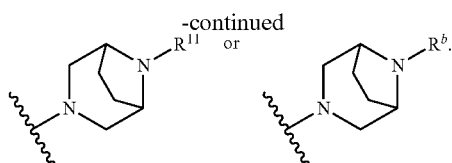

or

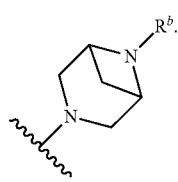

In certain embodiments of a compound of Formula (I), (Ia), (Ib), (Id) or (Ie), $X^2$ is:

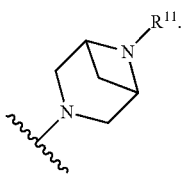

In certain embodiments of a compound of Formula (I), (Ia), (Ib), (Id) or (Ie), $X^2$ is:

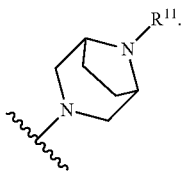

In certain embodiments of a compound of Formula (I), (Ia), (Ib), (Id) or (Ie) $X^2$ is

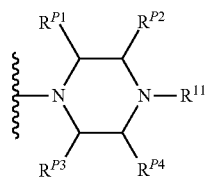

wherein:
a) $R^{P1}$, $R^{P2}$, $R^{P3}$, and $R^{P4}$ are each hydrogen;

b) $R^{P1}$ and $R^{P3}$ are taken together to form a —CH$_2$— or —CH$_2$CH$_2$— group and $R^{P2}$ and $R^{P4}$ are each hydrogen;

c) $R^{P2}$ and $R^{P4}$ are taken together to form a —CH$_2$— or —CH$_2$CH$_2$— group and $R^{P1}$ and $R^{P3}$ are each hydrogen.

d) $R^{P1}$ and $R^{P4}$ are taken together to form a —CH$_2$— group and $R^{P2}$ and $R^{P3}$ are each hydrogen; or e) $R^{P2}$ and $R^{P3}$ are taken together to form a —CH$_2$— group and $R^{P1}$ and $R^{P4}$ are each hydrogen.

In certain embodiments of a compound of Formula (I), (Ia), (Ib), (Id) or (Ie) $X^2$ is

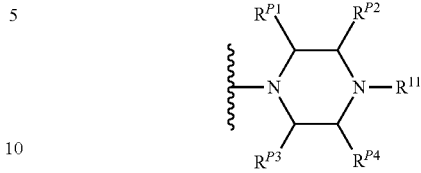

wherein:
$R^{P1}$ and $R^{P3}$ are taken together to form a —CH$_2$— or —CH$_2$CH$_2$— group and $R^{P2}$ and $R^{P4}$ are each hydrogen; or
$R^{P2}$ and $R^{P4}$ are taken together to form a —CH$_2$— or —CH$_2$CH$_2$— group and $R^{P1}$ and $R^{P3}$ are each hydrogen.

In certain embodiments of a compound of Formula (I), (Ia), (Ib), (Ic), (Id) or (Ie), $X^2$ is optionally substituted by $R^{11}$. In certain embodiments of a compound of Formula (I), (Ia), (Ib), (Ic), (Id) or (Ie), $R^{11}$ is 4 to 10-membered heterocyclyl having 1 to 3 heteroatoms selected from N, O, and S. In certain embodiments of a compound of Formula (I), (Ia), (Ib), (Ic), (Id) or (Ie), $R^{11}$ is a 4 to 6-membered heterocycle having one oxygen. In certain embodiments of a compound of Formula (I), (Ia), (Ib), (Ic), (Id) or (Ie), $R^{11}$ is oxetanyl, tetrahydrofuranyl, or tetrahydropyranyl. In certain embodiments of a compound of Formula (I), (Ia), (Ib), (Ic), (Id) or (Ie), $R^{11}$ is oxetan-3-yl, tetrahydrofuran-3-yl, or tetrahydropyran-4-yl.

In certain embodiments of a compound of Formula (I), (Ia), (Ib), (Ic), or (Id), $R^2$ and $R^3$ may be the same or different. In certain embodiments of a compound of Formula (I), (Ia), (Ib), (Ic), or (Id), $R^2$ and $R^3$ are each independently $C_{1-4}$alkyl, $C_{3-6}$cycloalkyl, or O—$R^{2A}$, wherein $R^{2A}$ is $C_{1-4}$alkyl, $C_{3-6}$cycloalkyl, or a 4 to 10-membered heterocyclyl having 1 to 5 heteroatoms selected from N, O, and S. In certain embodiments of a compound of Formula (I), (Ia), (Ib), (Ic), or (Id), $R^2$ and $R^3$ are each independently

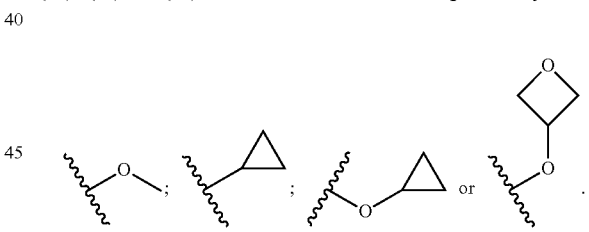

In certain embodiments of a compound of Formula (I), (Ia), (Ib), (Ic), or (Id), $R^2$ and $R^3$ are each methoxy.

In certain embodiments of a compound of Formula (I), each $R^{10}$ may be the same or different when n is greater than one. In some embodiments of a compound of Formula (I), (Ia), (Ib), (Ic), or (Id), n=0, 1, or 2. In certain embodiments of a compound of Formula (I), (Ia), (Ib), (Ic), or (Id), each $R^{10}$ is, halogen. In certain embodiments, each $R^{10}$ is, chloro or fluoro.

In certain embodiments of a compound of Formula (Ia), (Ib), (Ic), or (Id), $R^{10a}$ and $R^{10b}$ may be the same or different. In certain embodiments of a compound of Formula (Ia), (Ib), (Ic), or (Id), $R^{10a}$ and $R^{10b}$ are each halogen. In certain of a compound of Formula (Ia), (Ib), (Ic), or (Id), $R^{10a}$ and $R^{10b}$ are each chloro or fluoro.

In certain embodiments of compound of Formula I, A is ethynyl. In certain embodiments of a compound of Formula I, A is a bond.

In certain embodiments, whenever present, each of $X^1$ and $X^2$ may be substituted by one or more $R^b$ groups. In certain embodiments, each $R^b$ is independently halogen, oxo, $C_{1-4}$alkyl, $C_{1-4}$alkyl with 1 to 2 groups selected from hydroxyl and $C_{1-4}$ alkoxy, $C_{1-4}$ haloalkyl, $C_{1-4}$ alkoxy, or $COO(R^e)$. In certain embodiments, each $R^b$ is independently oxo or halo.

In certain embodiments of a compound of Formula I, each $R^{12}$ is $C_{1-2}$alkyl, halo, $-OC_{1-2}$alkyl or cyano. In certain embodiments of a compound of Formula I, $R^{12}$ is fluoro, chloro, or methyl.

In certain embodiments of a compound of Formula (Ib) or (Ic), one of $Z^1$ and $Z^2$ is N and the other is CH. In certain embodiments of a compound of Formula (Ib) or (Ic), both of $Z^1$ and $Z^2$ are N.

As disclosed above, any of the definitions for the variables provided (e.g. A, $R^1$, $R^2$, $R^3$, $R^4$, $R^5$, $R^6$, $R^7$, $R^8$, $R^9$, $R^{10}$, $R^{10a}$, $R^{10b}$, $Z^1$, $Z^2$, $X^1$, and $X^2$) may be combined and grouped with other variables, whether or not specifically recited together.

In certain embodiments of a compound of Formula (Ia), $R^1$ is

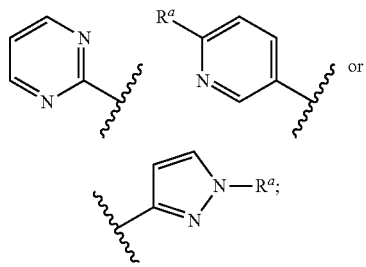

$R^a$ is $C_{1-4}$ haloalkyl; $X^1$ is pyrimidine or pyridine, $R^2$ and $R^3$ are each methoxy, $R^4$ is $CH_3$ or $CF_3$, $R^7$ is $CH_3$ or $CF_3$, $R^5$, $R^6$, $R^8$, and $R^9$ are each methyl, $X^2$ is:

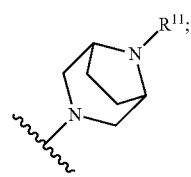

$R^{10a}$ and $R^{10b}$ are each halogen; and $R^{11}$ is a 4 to 6-membered heterocycle having one oxygen.

In certain embodiments of a compound of Formula (Ib), $R^1$ is

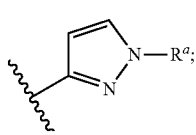

$R^a$ is $C_{1-4}$haloalkyl; m is 0, $Z^1$ and $Z^2$ are independently N or CH, $R^2$ and $R^3$ are each methoxy, $R^4$ is $CH_3$ or $CF_3$, $R^7$ is $CH_3$ or $CF_3$, $R^5$, $R^6$, $R^8$, and $R^9$ are each methyl; $X^2$ is:

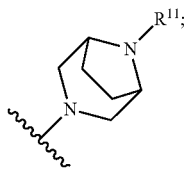

$R^{10a}$ and $R^{10b}$ are each halogen; and $R^{11}$ is a 4 to 6-membered heterocycle having one oxygen.

In certain embodiments of a compound of Formula (Ic), $R^1$

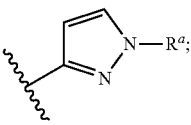

$R^a$ is $C_{1-4}$haloalkyl; $Z^1$ and $Z^2$ are independently N or CH, $R^2$ and $R^3$ are each methoxy, $R^4$ is $CH_3$ or $CF_3$, $R^7$ is $CH_3$ or $CF_3$, $R^5$, $R^6$, $R^8$, and $R^9$ are each methyl; $R^{10a}$ and $R^{10b}$ are each halogen; and $R^{11}$ is oxetanyl, tetrahydrofuranyl, or tetrahydropyranyl.

In certain embodiments of a compound of Formula (Id), $R^1$ is

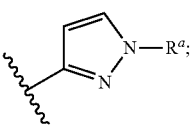

$R^a$ is $-CHF_2$; $X^1$ is pyrimidine or pyridine, $R^2$ and $R^3$ are each methoxy, $R^4$ is $CH_3$ or $CF_3$, $R^7$ is $CH_3$ or $CF_3$, $R^5$, $R^6$, $R^8$, and $R^9$ are each methyl, $X^2$ is:

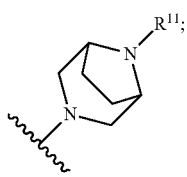

and $R^{10a}$ and $R^{10b}$ are each halogen, and $R^{11}$ is oxetanyl, tetrahydrofuranyl, or tetrahydropyranyl.

In certain embodiments, the compound is:
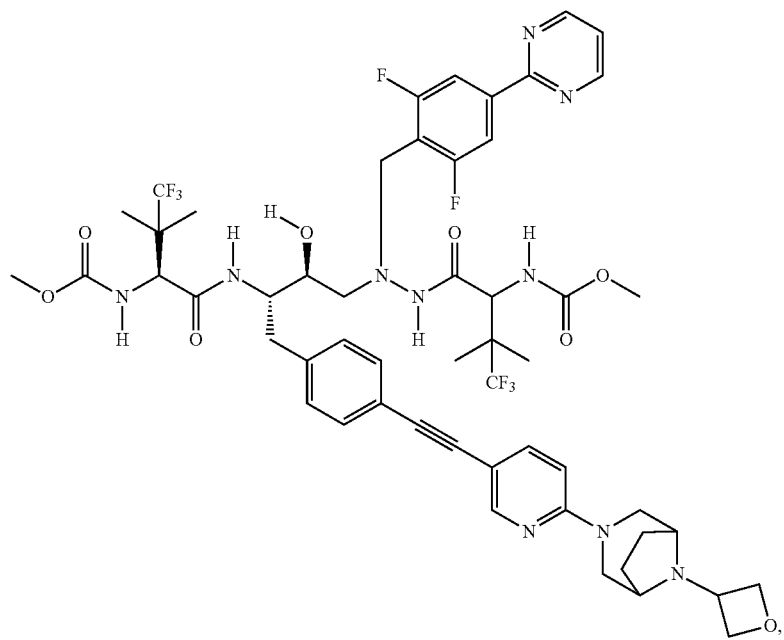
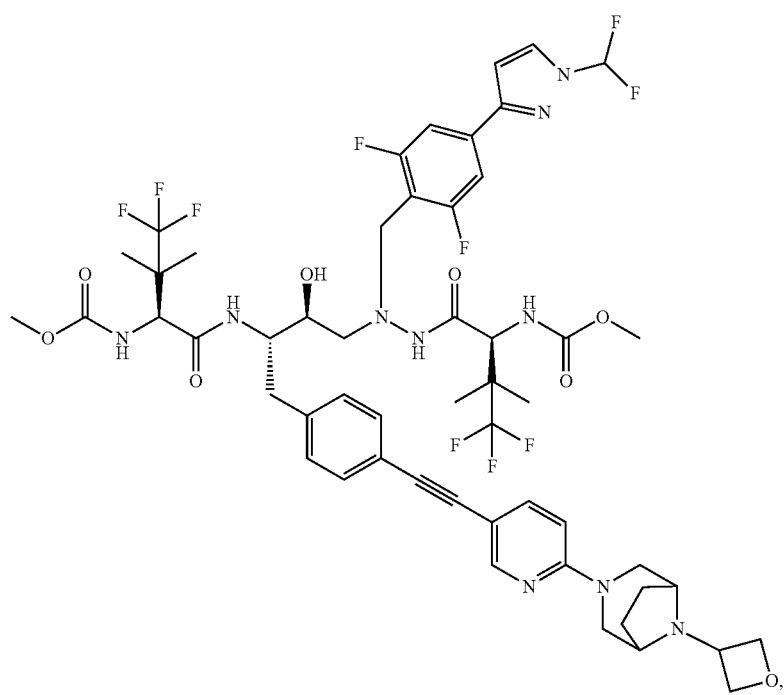

-continued
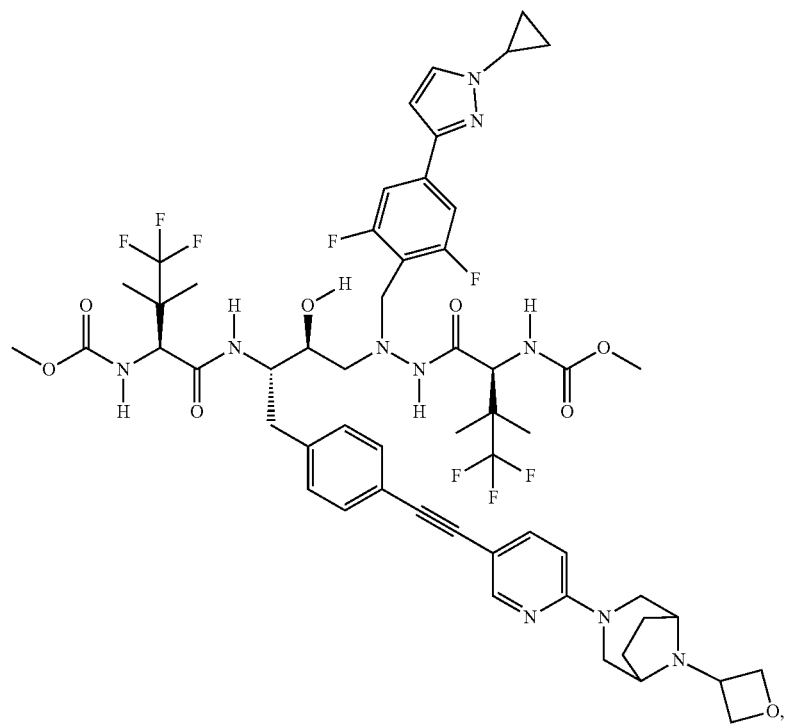
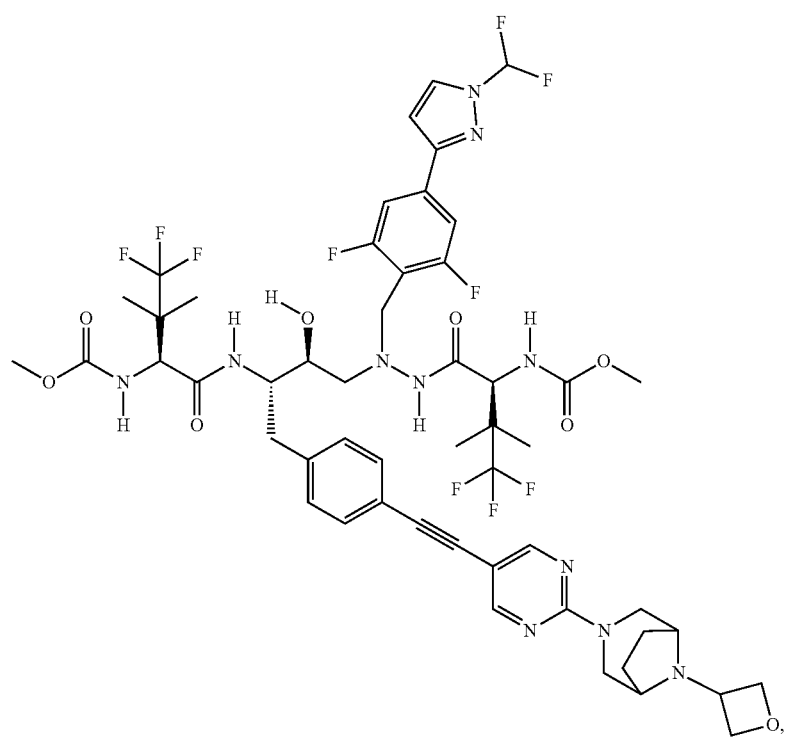

-continued
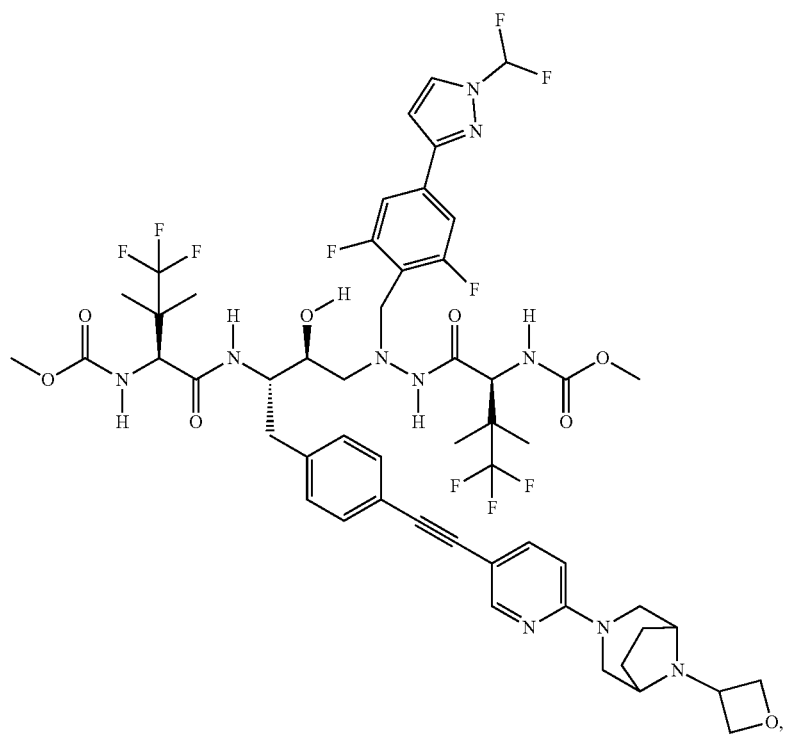
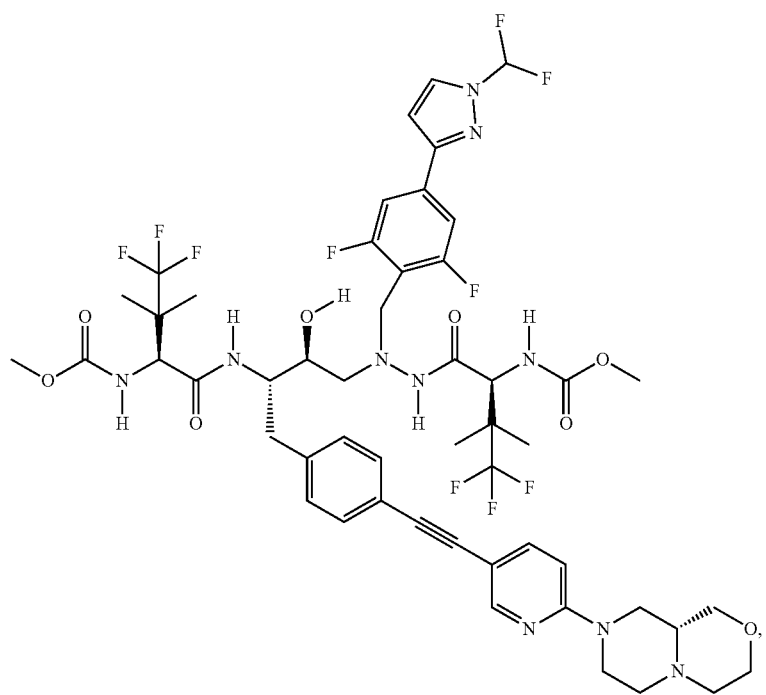

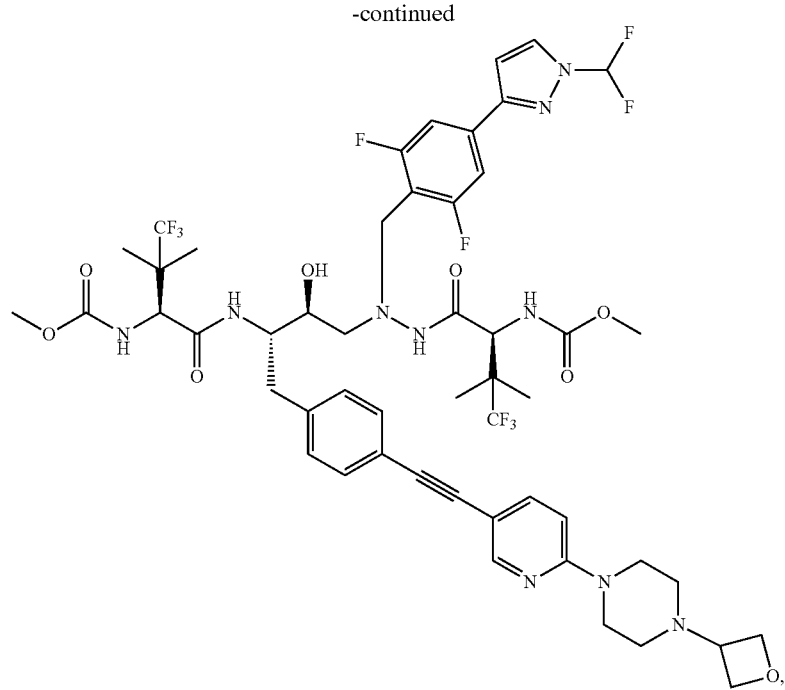
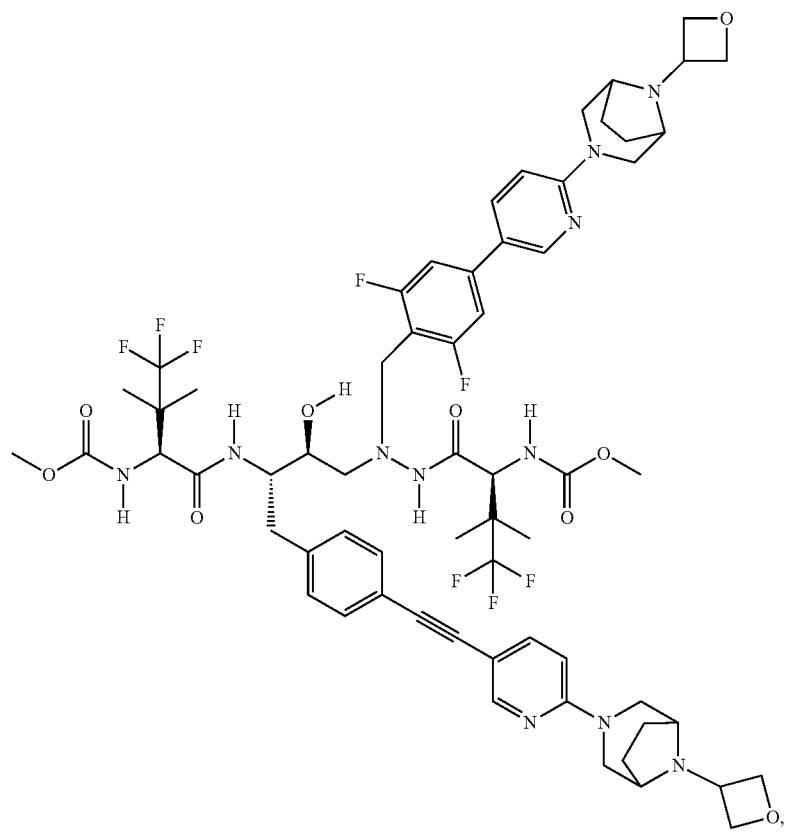

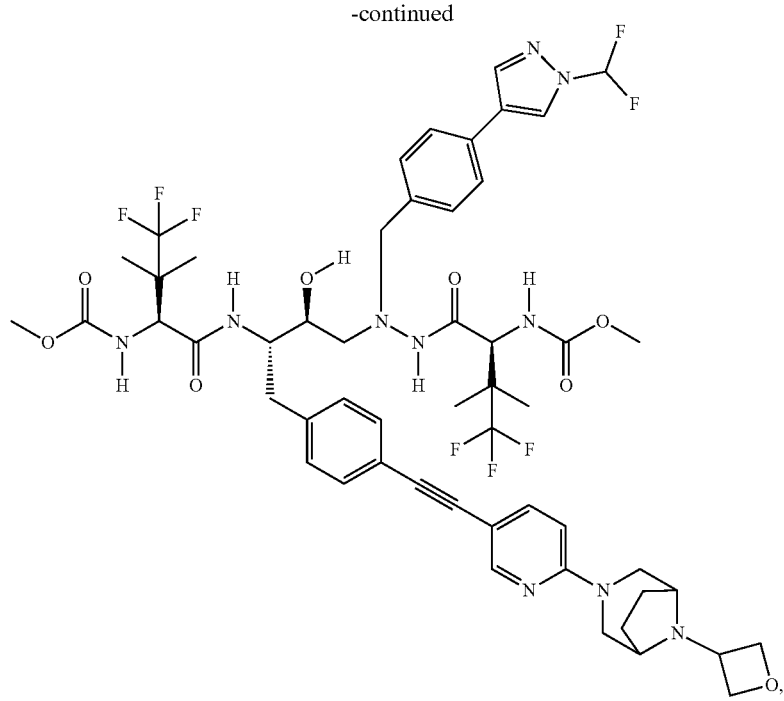
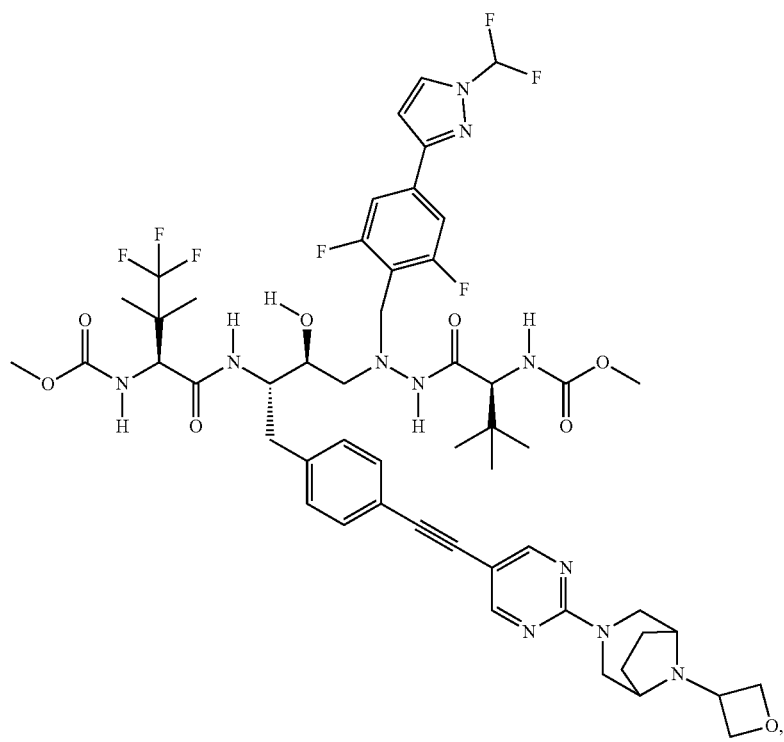

or

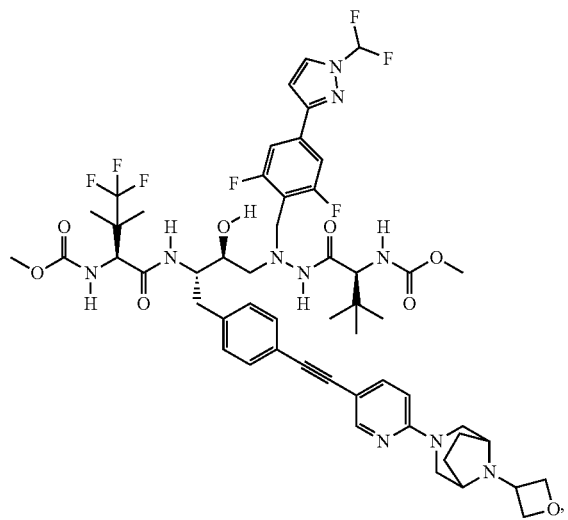 [SMILES: COC(=O)N[C@H](C(=O)NN(Cc1c(F)cc(-c2ccn(C(F)F)n2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

or a pharmaceutically acceptable salt thereof.

In certain embodiments, the compounds is a compound of any of Examples 1-245, or a pharmaceutically acceptable salt thereof.

In certain embodiments, the compound is

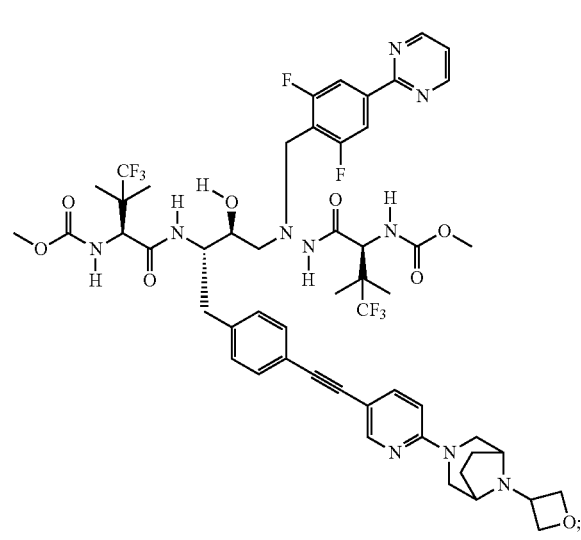

or a pharmaceutically acceptable salt thereof.

In certain embodiments, the compound is

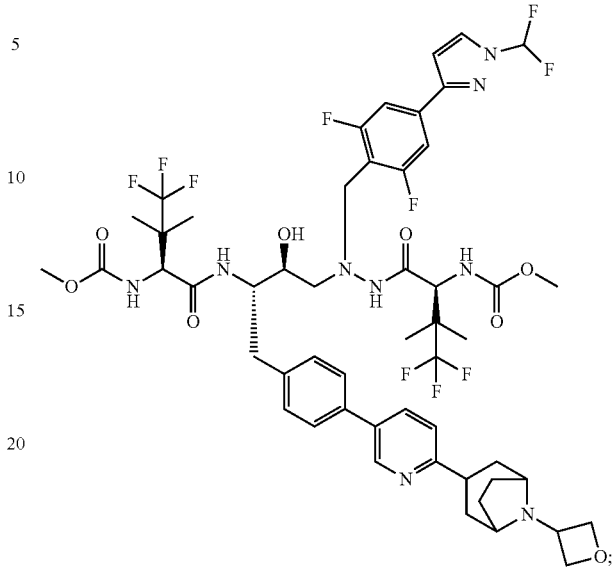

or a pharmaceutically acceptable salt thereof.

In certain embodiments, the compound is or a pharmaceutically acceptable salt thereof.

In certain embodiments, the compound is
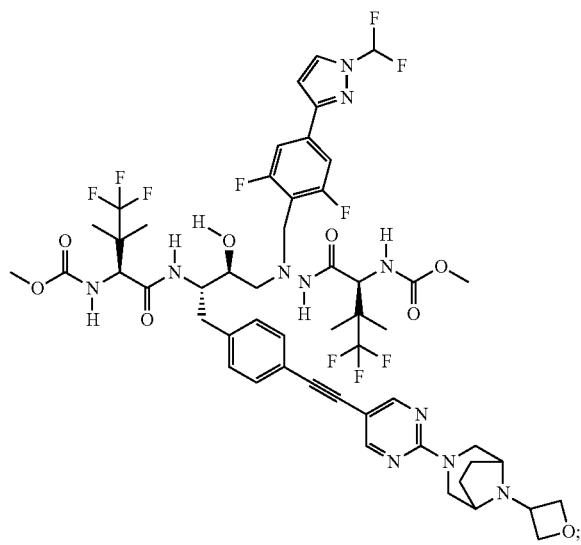
or a pharmaceutically acceptable salt thereof.
In certain embodiments, the compound is
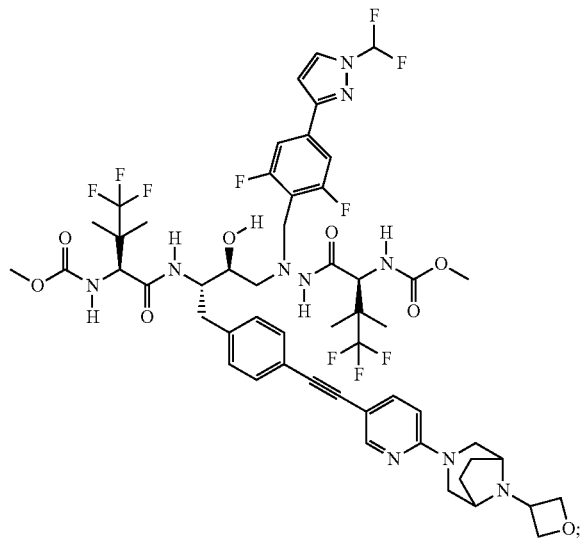
or a pharmaceutically acceptable salt thereof.
In certain embodiments, the compound is
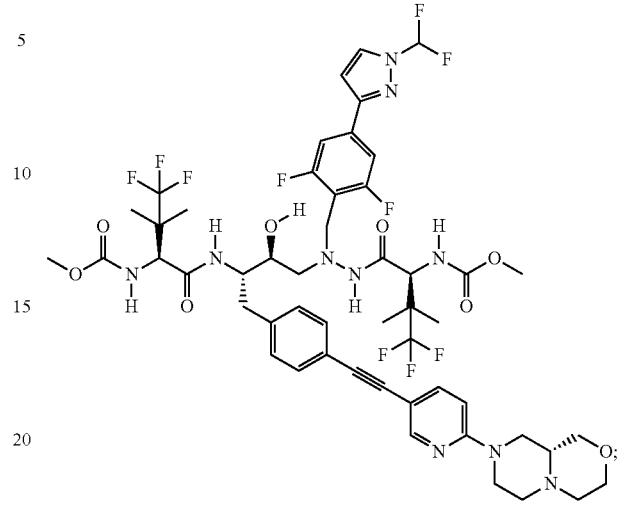
or a pharmaceutically acceptable salt thereof.
In certain embodiments, the compound is
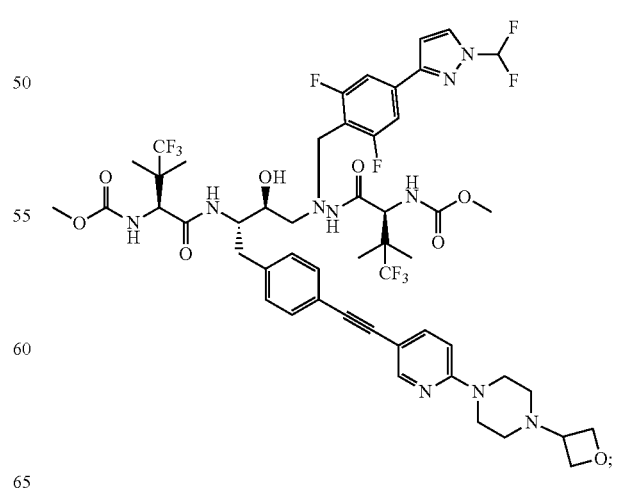
or a pharmaceutically acceptable salt thereof.

In certain embodiments, the compound is

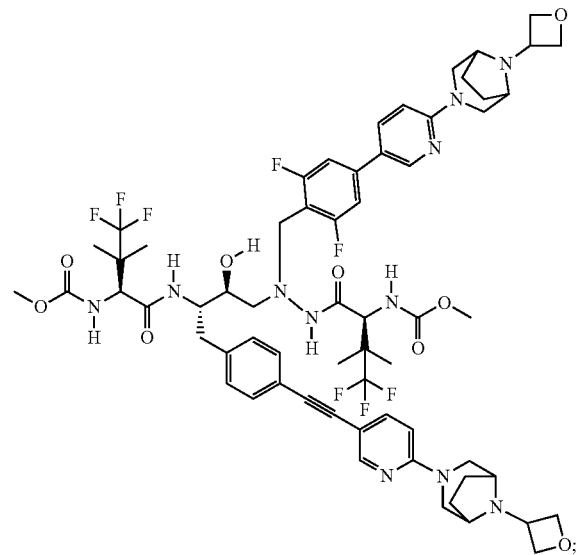 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(N3CC4CCC(C3)N4C3COC3)nc2)cc1F)NC(=O)[C@@H](NC(=O)OC)C(C)(C)C(F)(F)F)C(C)(C)C(F)(F)F]

or a pharmaceutically acceptable salt thereof.

In certain embodiments, the compound is

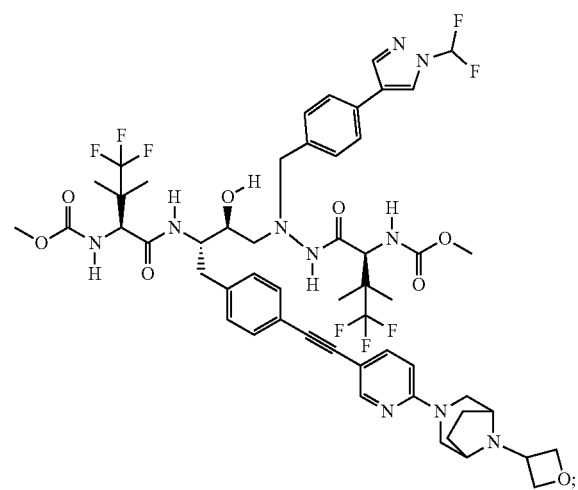 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(/C(C=N)=C/NC(F)F)cc1)NC(=O)[C@@H](NC(=O)OC)C(C)(C)C(F)(F)F)C(C)(C)C(F)(F)F]

or a pharmaceutically acceptable salt thereof.

In certain embodiments, the compound is

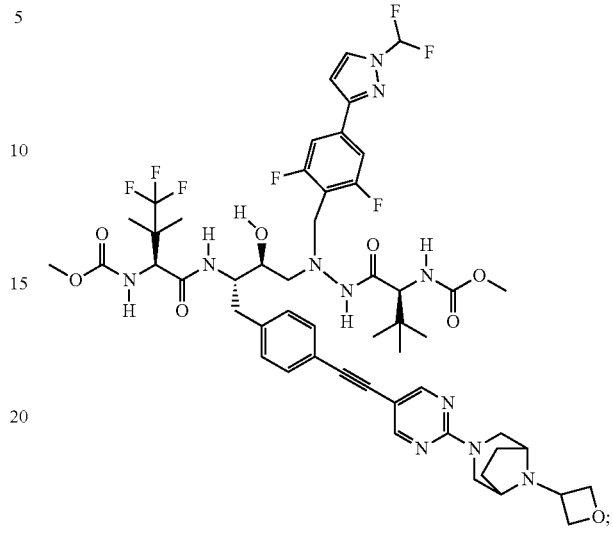

or a pharmaceutically acceptable salt thereof.
In certain embodiments, the compound is

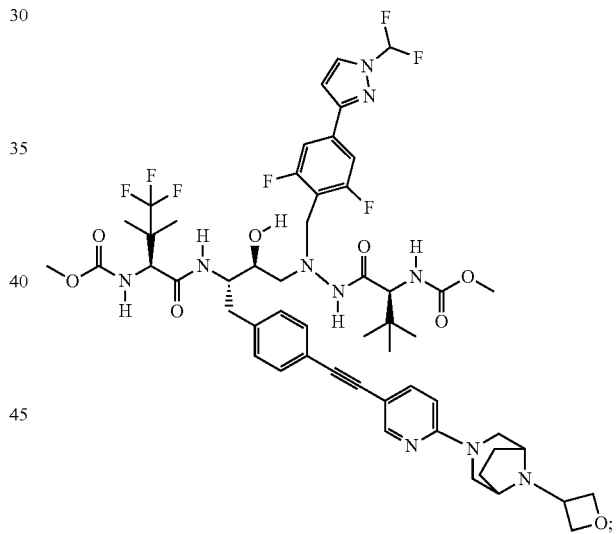

or a pharmaceutically acceptable salt thereof.

Methods of Treatment

The pharmaceutical compositions of compounds of Formula (I) (including compounds of Formulae (Ia)-(Ie) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I), or a pharmaceutically acceptable salt, can be formulated so as to provide quick, sustained or delayed release of the active ingredient after administration to the subject by employing procedures known in the art. Controlled-release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009.

In some embodiments, the compounds described herein, or a pharmaceutically acceptable salt thereof, may be administered with a syringe. In some embodiments, the syringe is disposable. In some embodiments, the syringe is reusable. In some embodiments, the syringe is pre-filled with a compound described herein, or a pharmaceutically acceptable salt thereof.

In some embodiments, the compounds described herein, or a pharmaceutically acceptable salt thereof, may be administered with an auto-injector comprising a syringe. In some embodiments, the syringe is disposable. In some embodiments, the syringe is reusable. In some embodiments, the syringe is pre-filled with a compound described herein, or a pharmaceutically acceptable salt thereof.

In certain embodiments, a method of treating or preventing a human immunodeficiency virus (HIV) infection comprising administering a therapeutically effective amount of a compound disclosed herein, or a pharmaceutically acceptable salt thereof, to a subject in need thereof, is provided. In certain embodiments, a method of treating a human immunodeficiency virus (HIV) infection comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one, two, three, or four additional therapeutic agents. In certain embodiments, the subject is at risk of contracting the HIV virus, such as a subject who has one or more risk factors known to be associated with contracting the HIV virus. In certain embodiments, the subject may have not previously received antiviral treatment (treatment naïve). In certain embodiments, the subject may have previously received antiviral treatment (treatment experienced). In certain embodiments, the subject may have previously received antiviral treatment and developed resistance to the previously received antiviral treatment.

In certain embodiments, a method of treating or preventing a human immunodeficiency virus (HIV) infection comprising administering a therapeutically effective amount of a compound disclosed herein, or a pharmaceutically acceptable salt thereof, to a subject in need thereof, in combination with a therapeutically effective amount of one or more (e.g., one, two, three, or four; or one or two; or one to three; or one to four) additional therapeutic agents selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof, is provided. In certain embodiments, the one or more (e.g., one, two, three, or four; or one or two; or one to three; or one to four) additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof. In certain embodiments, the one or more additional therapeutic agent does not include a pharmacokinetic enhancer.

In certain embodiments, a method for inhibiting the replication of the HIV virus, treating AIDS or delaying the onset of AIDS in a subject (e.g., a human), comprising administering a compound disclosed herein, or a pharmaceutically acceptable salt thereof, to the subject is disclosed.

In certain embodiments, a compound of disclosed herein, or a pharmaceutically acceptable salt thereof for use in medical therapy of an HIV infection (e.g. HIV-1 or the replication of the HIV virus (e.g. HIV-1) or AIDS or delaying the onset of AIDS in a subject (e.g., a human)) is disclosed.

In certain embodiments, a compound disclosed herein, or a pharmaceutically acceptable salt thereof for use in the manufacture of a medicament for treating an HIV infection or the replication of the HIV virus or AIDS or delaying the onset of AIDS in a subject (e.g., a human) is disclosed. One embodiment relates to a compound disclosed herein, or a pharmaceutically acceptable salt thereof, for use in the prophylactic or therapeutic treatment of an HIV infection or AIDS or for use in the therapeutic treatment or delaying the onset of AIDS.

In certain embodiments, the use of a compound disclosed herein, or a pharmaceutically acceptable salt thereof, for the manufacture of a medicament for an HIV infection in a subject (e.g., a human) is disclosed. In certain embodiments, a compound disclosed herein, or a pharmaceutically acceptable salt thereof, for use in the prophylactic or therapeutic treatment of an HIV infection is disclosed.

In certain embodiments, in the methods of use, the administration is to a subject (e.g., a human) in need of the treatment. In certain embodiments, in the methods of use, the administration is to a subject (e.g., a human) who is at risk of developing AIDS.

The compounds disclosed herein, or a pharmaceutically acceptable salt thereof, for use in therapy is provided. In one embodiment, a compound disclosed herein, or a pharmaceutically acceptable salt thereof, is for use in a method of treating an HIV infection or the replication of the HIV virus or AIDS or delaying the onset of AIDS in a subject (e.g., a human).

The compounds disclosed herein, or a pharmaceutically acceptable salt thereof, for use in a method of treating or preventing HIV infection in a subject in need thereof is provided. In certain embodiments, a compound disclosed herein, or a pharmaceutically acceptable salt thereof, for use in a method of treating HIV infection in a subject in need thereof is provided. In certain embodiments, the subject in need thereof is a human who has been infected with HIV. In certain embodiments, the subject in need thereof is a human who has been infected with HIV but who has not developed AIDS. In certain embodiments, the subject in need thereof is a subject at risk for developing AIDS. In certain embodiments, the subject in need thereof is a human who has been infected with HIV and who has developed AIDS.

In one embodiment, a compound disclosed herein, or a pharmaceutically acceptable salt thereof, in combination with one or more (e.g. one, two, three, or four; or one or two; or one to three; or one to four) additional therapeutic agents as described herein for use in a method of treating or preventing HIV infection in a subject in need thereof is provided. In one embodiment, said additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof. In certain embodiments, said additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or any combinations thereof.

In one embodiment, a compound disclosed herein, or a pharmaceutically acceptable salt thereof, in combination with a first additional therapeutic agent selected from the group consisting of tenofovir alafenamide fumarate, tenofovir alafenamide, and tenofovir alafenamide hemifumarate, and a second additional therapeutic agent, wherein the second additional therapeutic agent is emtricitabine, is provided for use in a method of treating or preventing HIV infection in a subject in need thereof. In a particular embodiment, a compound disclosed herein, or a pharmaceutically acceptable salt thereof, in combination with a first additional therapeutic agent selected from the group consisting of tenofovir disoproxil fumarate, tenofovir disoproxil, and tenofovir disoproxil hemifumarate, and a second additional therapeutic agent, wherein the second additional therapeutic agent is emtricitabine, is provided for use in a method of treating or preventing HIV infection in a subject in need thereof.

In a particular embodiment, a compound disclosed herein or a pharmaceutically acceptable salt thereof, are provided for use to prevent HIV infection from taking hold if the individual is exposed to the virus and/or to keep the virus from establishing a permanent infection and/or to prevent the appearance of symptoms of the disease and/or to prevent the virus from reaching detectable levels in the blood, for example for pre-exposure prophylaxis (PrEP) or post-exposure prophylaxis (PEP). Accordingly, in certain embodiments, methods for reducing the risk of acquiring HIV (e.g., HIV-1 and/or HIV-2) are provided. For example, methods for reducing the risk of acquiring HIV (e.g., HIV-1 and/or HIV-2) comprise administration of a compound disclosed herein, or a pharmaceutically acceptable salt thereof. In certain embodiments, methods for reducing the risk of acquiring HIV (e.g., HIV-1 and/or HIV-2) comprise administration of a compound disclosed herein, or a pharmaceutically acceptable salt thereof, in combination with one or more additional therapeutic agents. In certain embodiments, methods for reducing the risk of acquiring HIV (e.g., HIV-1 and/or HIV-2) comprise administration of a pharmaceutical composition comprising a therapeutically effective amount of the compound disclosed herein, or pharmaceutically acceptable salt thereof, and a pharmaceutically acceptable excipient.

In certain embodiments, methods for reducing the risk of acquiring HIV (e.g., HIV-1 and/or HIV-2) comprise administration of a compound of disclosed herein, or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In certain embodiments, the reduction in risk of acquiring HIV is at least about 40%, 50%, 60%, 70%, 80%, 90%, or 95%. In certain embodiments, the reduction in risk of acquiring HIV is at least about 75%. In certain embodiments, the reduction in risk of acquiring HIV is about 80%, 85%, or 90%.

In another embodiment, the use of a compound disclosed herein, or a pharmaceutically acceptable salt thereof, for the manufacture of a medicament for the treatment of an HIV infection in a human being having or at risk of having the infection is disclosed.

Also disclosed herein is a compound disclosed herein, or a pharmaceutically acceptable salt thereof, for use in the therapeutic treatment or delaying the onset of AIDS.

Also disclosed herein is a compound disclosed herein, or a pharmaceutically acceptable salt thereof, for use in the prophylactic or therapeutic treatment of an HIV infection.

In certain embodiments, a compound disclosed herein, or a pharmaceutically acceptable salt thereof can be used as a research tool (e.g. to study the inhibition of HIV reverse transcriptase in a subject or in vitro).

Kits that include a compound of Formula (I), or a pharmaceutically acceptable salt, thereof, and suitable packaging are provided. In one embodiment, a kit further includes instructions for use. In one aspect, a kit includes a compound of Formula (I), or a pharmaceutically acceptable salt thereof, and instructions for use of the compounds in the treatment of the diseases or conditions described herein.

Articles of manufacture that include a compound of Formula (I), or a pharmaceutically acceptable salt thereof, in a suitable container are provided. The container may be a vial, jar, ampoule, preloaded syringe, and intravenous bag.

Administration of HIV Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I) is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In some embodiments, a compound of Formula (I) is formulated as a tablet, which may optionally contain one or more other compounds useful for treating HIV. In certain embodiments, the tablet can contain another active ingredient for treating HIV, such as compounds that target the HIV capsid, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In some embodiments, the compounds that target the HIV capsid are selected from the group consisting of:

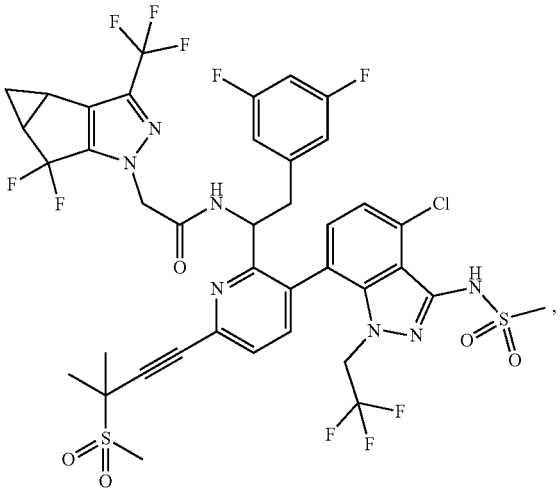

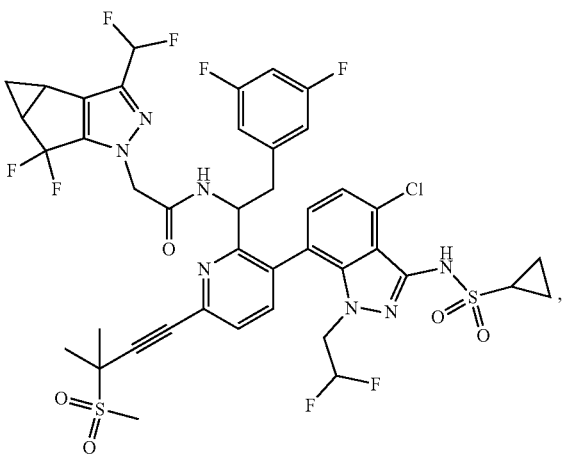

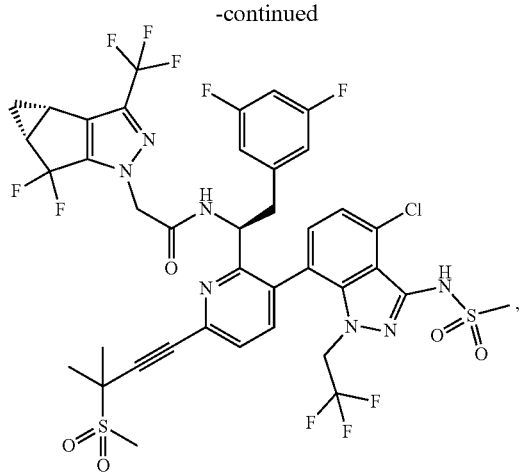

and

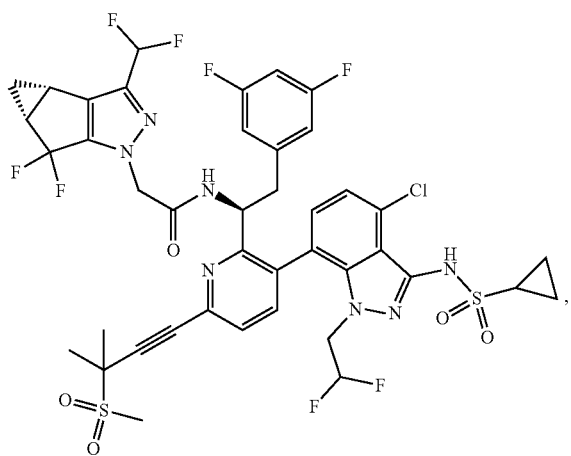 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

In certain embodiments, such tablets are suitable for once daily dosing.

HIV Combination Therapy

In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent is selected from immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies such as chimeric antigen receptor T-cell, CAR-T (e.g., YESCARTA® (axicabtagene ciloleucel)), and engineered T cell receptors, TCR-T.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, H1 viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, and VM-1500.

In some embodiments, examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, BET-bromodomain 4 (BRD4) inhibitors, ionomycin, PMA, SAHA (suberanilohydroxamic acid, or suberoyl, anilide, and hydroxamic acid), IL-15, JQ1, disulfram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series;

In some embodiments, examples of capsid inhibitors include:

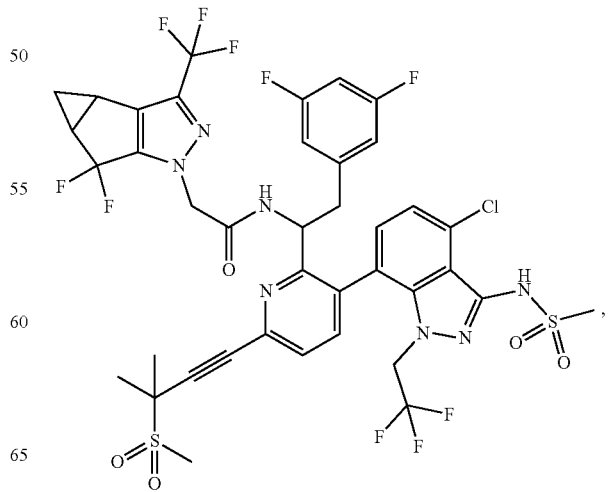

-continued
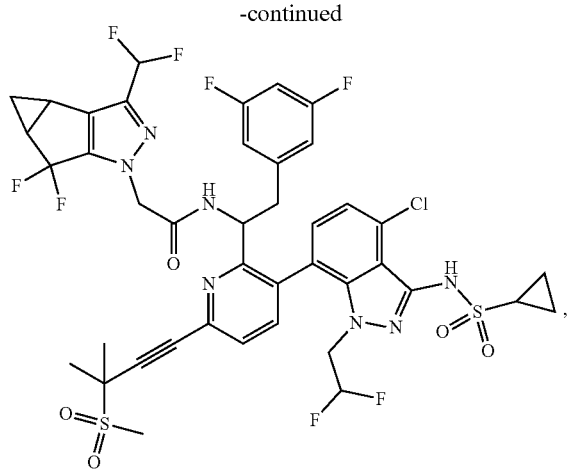
and
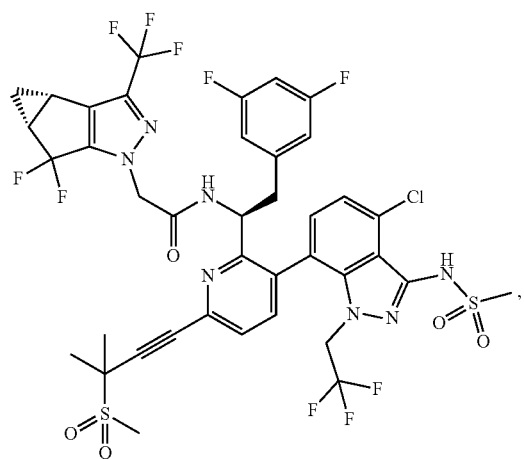
and
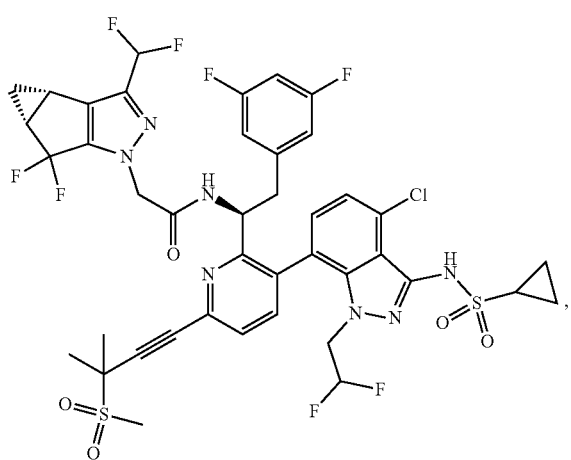 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]
or a pharmaceutically acceptable salt thereof.
In some embodiments, the capsid inhibitor is selected from:
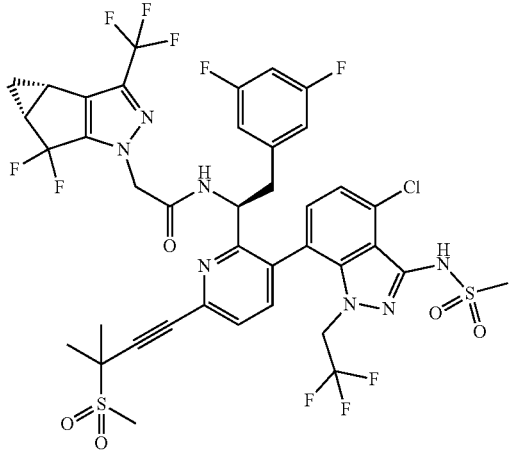 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]
and
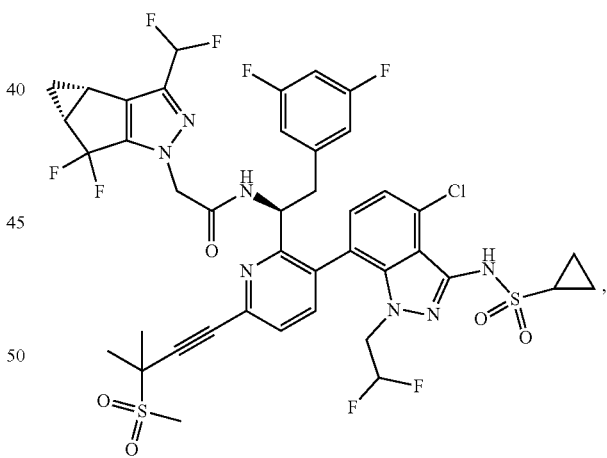
or a pharmaceutically acceptable salt thereof.

In some embodiments, the capsid inhibitor is:

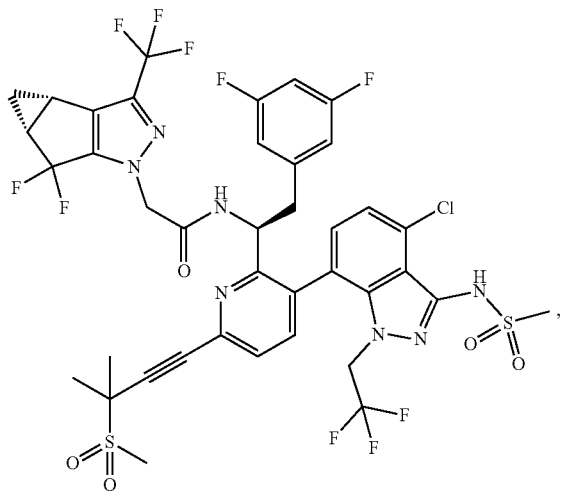

or a pharmaceutically acceptable salt thereof.

In some embodiments, the capsid inhibitor is:

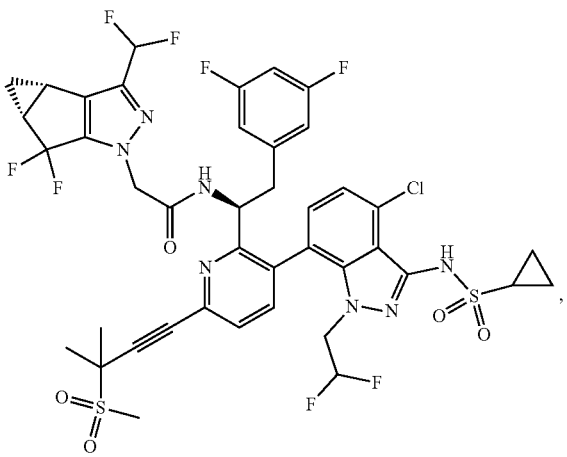 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

Immune-Based Therapies

Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103.

In some embodiments, examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 ago-nists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, MB-66

Examples of those targeting HIV in such a manner include bavituximab, UB-421, C2F5, C2G12, C4E10, C2F5+C2G12+C4E10, 3-BNC-117, PGT145, PGT121, MDX010 (ipilimumab), VRC01, A32, 7B2, 10E8, VRC-07-523, VRC-HIVMAB080-00-AB, MGD-014 and VRC07.

In some embodiments, examples of those targeting HIV in such a manner include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07. Example of HIV bispecific antibodies include MGD014.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/

100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+ Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine.

In some embodiments, examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

HIV Combination Therapy

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with abacavir sulfate, bictegravir, tenofovir, tenofovir disoproxil, tenofovir disoproxil fumarate, tenofovir disoproxil hemifumarate, tenofovir alafenamide, or tenofovir alafenamide hemifumarate.

In a particular embodiment, a compound disclosed herein, or a pharmaceutically acceptable salt thereof, is combined with tenofovir, tenofovir disoproxil, tenofovir disoproxil fumarate, tenofovir alafenamide, or tenofovir alafenamide hemifumarate.

In a particular embodiment, a compound disclosed herein, or a pharmaceutically acceptable salt thereof, is combined with a first additional therapeutic agent selected from the group consisting of abacavir sulfate, bictegravir, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In some embodiments, a compound disclosed herein, or a pharmaceutically acceptable salt thereof, is combined with a capsid inhibitor(s) (e.g., capsid polymerization inhibitors and/or capsid disrupting compounds).

In some embodiments, a compound disclosed herein, or a pharmaceutically acceptable salt thereof, is combined with (about 10 to about 1000 mg) of a capsid inhibitor selected from:

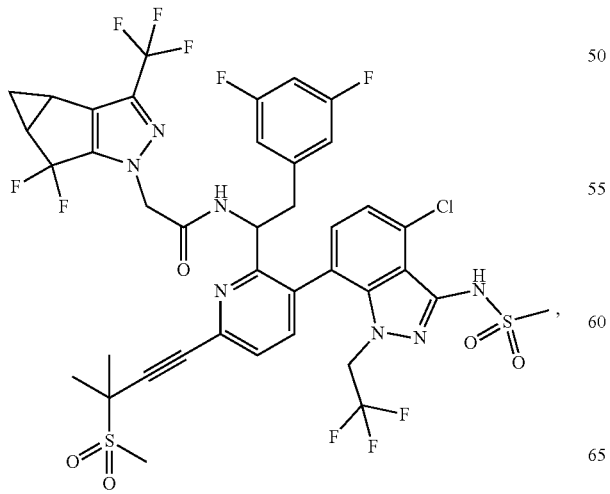

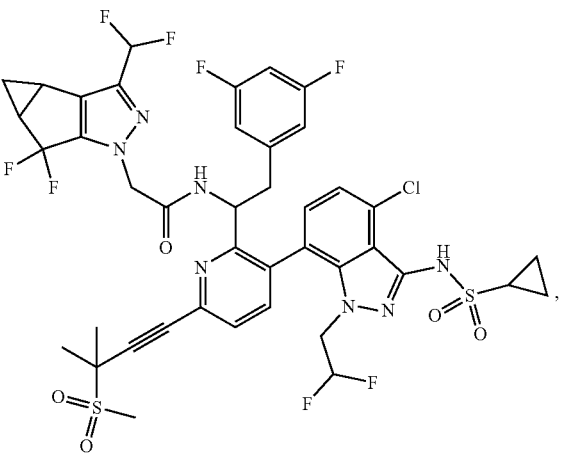

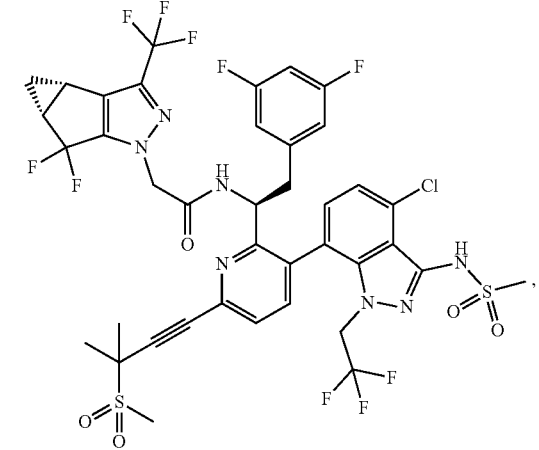 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

and

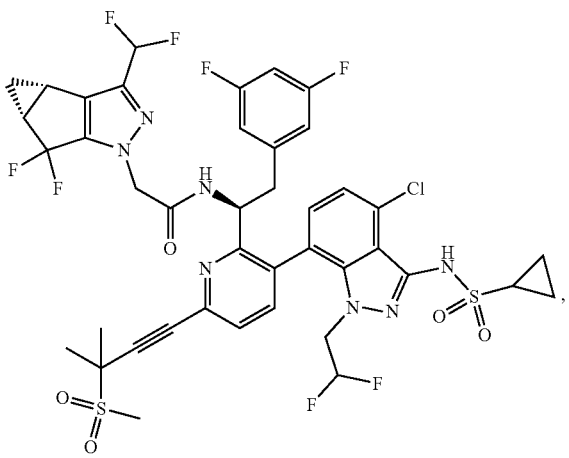 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

In some embodiments, a compound disclosed herein, or a pharmaceutically acceptable salt thereof, is combined with a capsid inhibitor selected from:

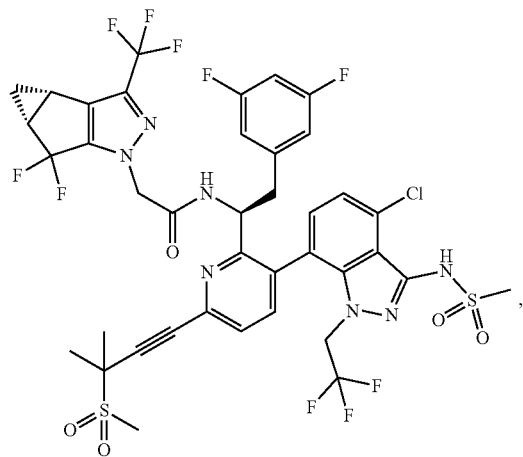 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

and

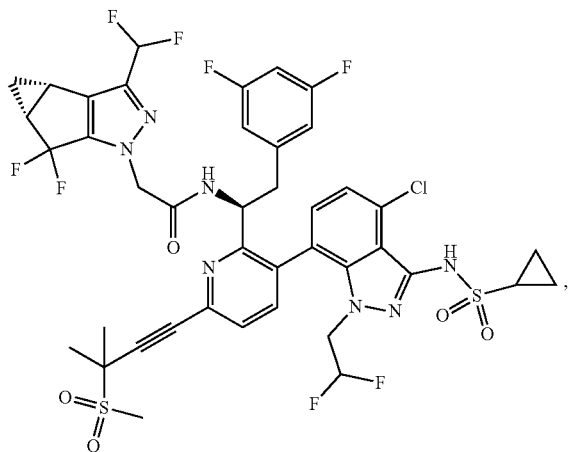 [SMILES: CC(C)(C#Cc1ccc(-c2ccc(Cl)c3c(NS(=O)(=O)C4CC4)nn(CC(F)F)c23)c([C@H](Cc2cc(F)cc(F)c2)NC(=O)Cn2nc(C(F)F)c3c2C(F)(F)[C@@H]2C[C@H]32)n1)S(C)(=O)=O]

or a pharmaceutically acceptable salt thereof.

In some embodiments, a compound disclosed herein, or a pharmaceutically acceptable salt thereof, is combined with:

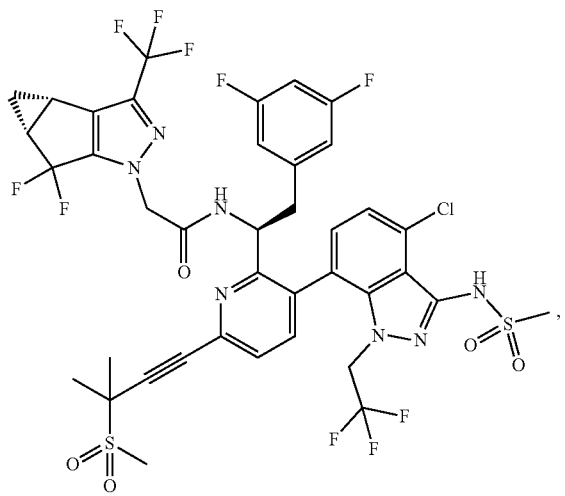 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a pharmaceutically acceptable salt thereof.

In some embodiments, a compound disclosed herein, or a pharmaceutically acceptable salt thereof, is combined with:

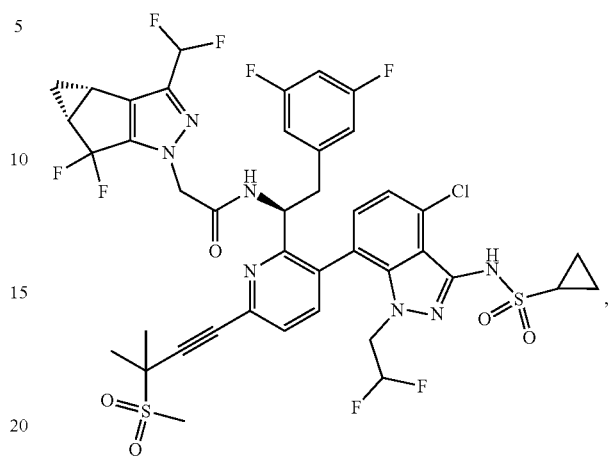

or a pharmaceutically acceptable salt thereof.

A compound as disclosed herein (e.g., any compound of Formula (I)) may be combined with one or more additional therapeutic agents in any dosage amount of the compound of Formula (I) (e.g., from 1 mg to 1000 mg of compound).

In certain embodiments, a compound disclosed herein, or a pharmaceutically acceptable salt thereof, is combined with 5-30 mg tenofovir alafenamide, in the form of tenofovir alafenamide fumarate, tenofovir alafenamide hemifumarate, or tenofovir alafenamide, or any salt of solvate form of tenofovir alafenamide. In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula (I)) may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula (I)) may be combined with the agents provided herein in any dosage amount of the compound (e.g., from 1 mg to 1000 mg of compound) the same as if each combination of dosages were specifically and individually listed.

In certain embodiments, a compound disclosed herein, or a pharmaceutically acceptable salt thereof, is combined with a HIV nucleoside or nucleotide inhibitor and an integrase inhibitor. In certain embodiments, a compound disclosed herein, or a pharmaceutically acceptable salt thereof, is combined with GS-9131 and bictegravir.

In one embodiment, kits comprising a compound disclosed herein, or a pharmaceutically acceptable salt thereof, in combination with one or more (e.g., one, two, three, one or two, or one to three) additional therapeutic agents are provided.

Birth Control (Contraceptive) Combination Therapy

Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Examples of dendritic cell therapy include AGS-004.

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof.

Examples of HIV CAR-T include VC-CAR-T.

TCR-T Cell Therapy

TCR-T cells are engineered to target HIV derived peptides present on the surface of virus-infected cells.

Certain embodiments of the methods disclosed herein exclude the administration of a pharmacokinetic enhancer. For example, in certain methods disclosed herein, the subject is not administered a pharmacokinetic enhancer, such as cobicistat or ritonavir, during the treatment with a compound disclosed herein, or a pharmaceutically acceptable salt thereof. Thus, in certain embodiments, a method of treating or preventing a human immunodeficiency virus (HIV) infection is provided, comprising administering a therapeutically effective amount of a compound disclosed herein, or a pharmaceutically acceptable salt thereof, to a subject in need thereof, wherein the treatment does not comprise administration of a pharmacokinetic enhancer. In certain embodiments, a method of treating or preventing a human immunodeficiency virus (HIV) infection is provided, comprising administering a therapeutically effective amount of a compound disclosed herein, or a pharmaceutically acceptable salt thereof, once daily to a subject in need thereof, wherein the treatment does not comprise administration of a pharmacokinetic enhancer.

The present disclosure also provides all of the P, S, A and I intermediates described in the Examples section below.

EXAMPLES

Methods for preparing the novel compounds described herein will be apparent to those of skill in the art with suitable procedures being described, for example, in the reaction schemes and examples below.

Sections 1.1-1.8 provide exemplary synthetic schemes for assembling compounds of Formula I. Sections 2.1-2.4 show preparation of Intermediate I, Intermediate P, Intermediate S, and Intermediate A, as used herein. Section 3 provides example syntheses and compounds. Section 4 shows biological activity.

1. General Schemes

SCHEME 1.1

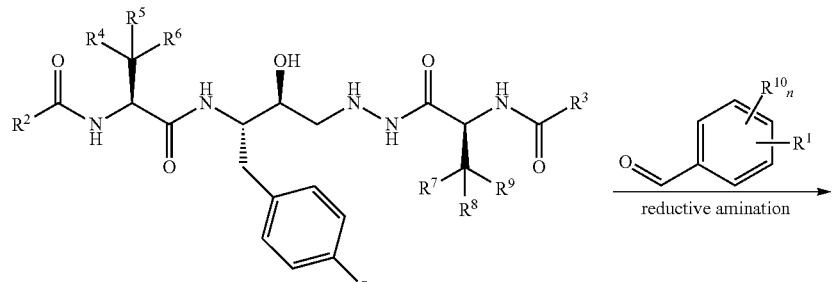

1.1a

-continued

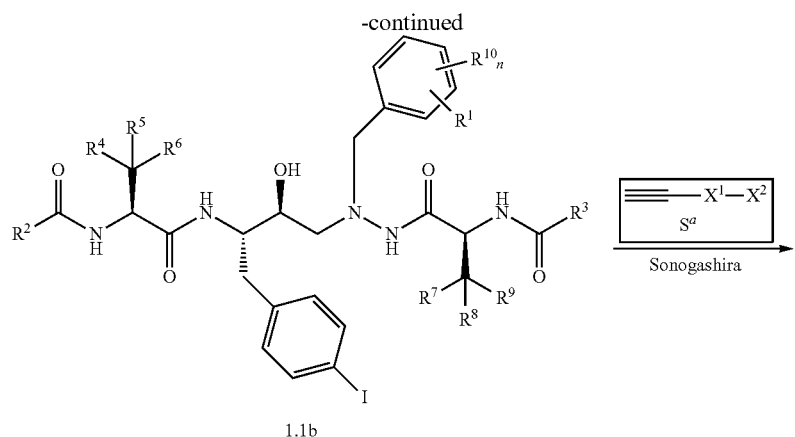

1.1b

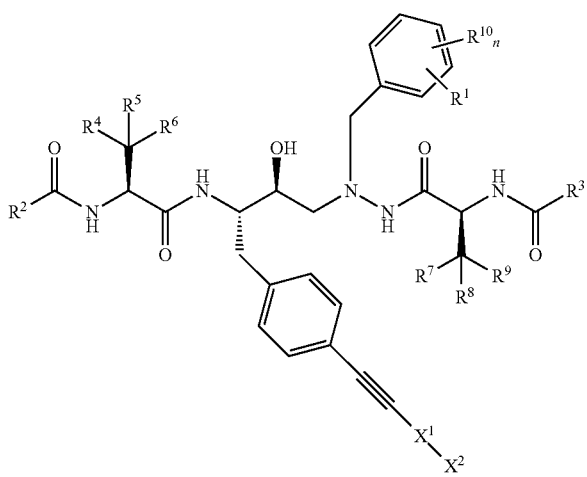

Scheme 1.1 shows a general synthesis of a compound within the scope of Formula I beginning with reductive amination of compound 1.1a with a substituted benzaldehyde (Intermediate P). Reductive amination may be accomplished, for example, with a cyanoborohydride reagent such as sodium cyanoborohydride. Subsequent metal-catalyzed coupling such as Sonogashira- or Suzuki-couplings. Sonogashira coupling of compound 1.1b with an alkynyl Intermediate $S^a$ gives a compound of Formula I.

Examples 1-130, 219, and 224-245 were prepared by this general strategy (by reductive amination of the appropriate Intermediate P with the corresponding organohalide peptide Intermediate I, followed by Sonogashira coupling with the appropriate Intermediate S). Example 1 provides exemplary reaction conditions and reagents appropriate for preparing a compound of Formula I according to Scheme 1.1.

SCHEME 1.2

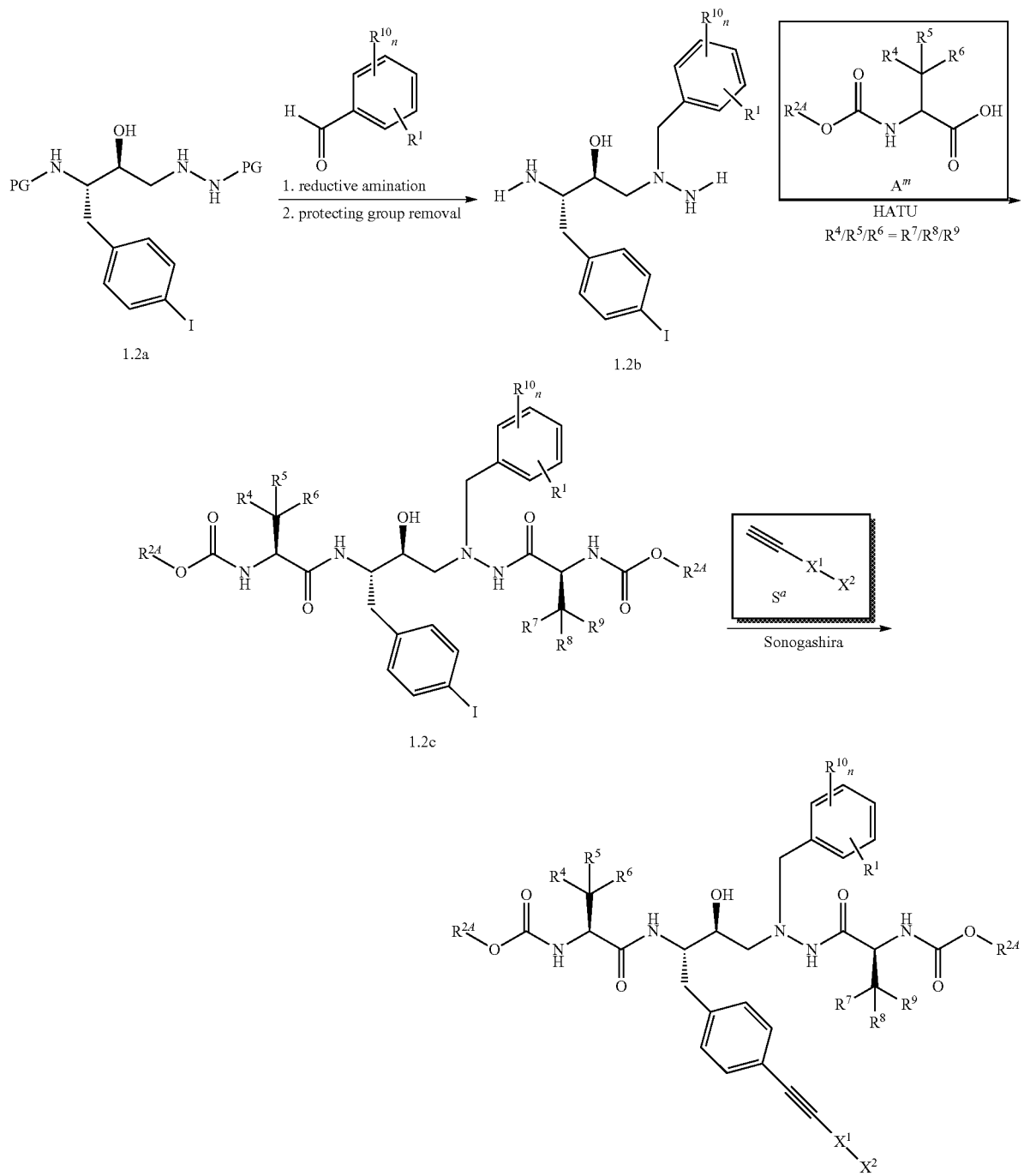

Scheme 1.2 shows a general synthesis of a compound within the scope of Formula I with reductive amination of a protected amino hydrazinyl iodophenyl butanol, compound 1.2a. Exemplary protecting groups (PG) for compound 1.2a include t-butylcarbonyl (BOC) protecting group and fluuorenylmethyloxy carbonyl (FMOC). Reductive amination of compound 1.2a with a substituted benzaldehyde Intermediate P gives compound 1.2b after removal of the protecting groups. Reductive amination may be accomplished, by way of non-limiting example, with sodium cyanoborohydride. HATU coupling of compound 1.2b with an amino acid Intermediate $A^m$ gives a compound 1.2c. Sonogashira coupling of compound 1.2c with an alkyne Intermediate $S^a$ gives a compound of Formula I.

Examples 133-180 and 220 were prepared by this general strategy (reductive amination of the appropriate P with an amino hydrazinyl iodophenyl butanol followed by HATU coupling $A^m$, which is then followed by Sonogashira coupling with an alkynyl Intermediate $S^a$). Example 133 provides exemplary reaction conditions and reagents appropriate for preparing a compound of Formula I according to Scheme 1.2.

SCHEME 1.3
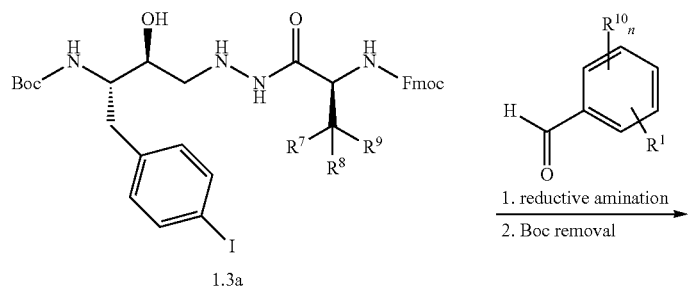
1.3a
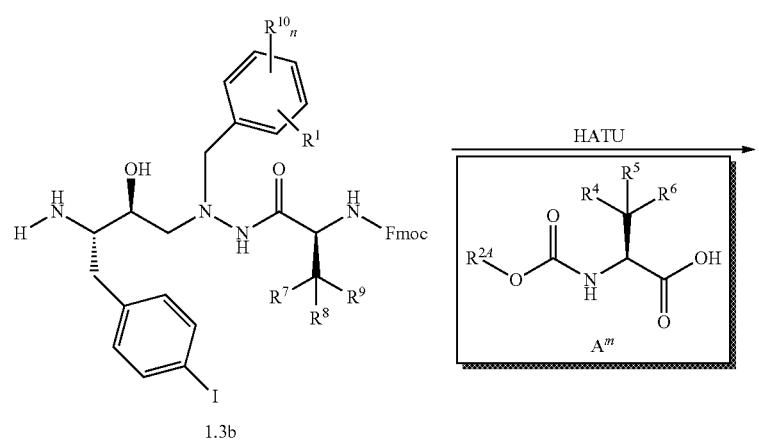
1.3b
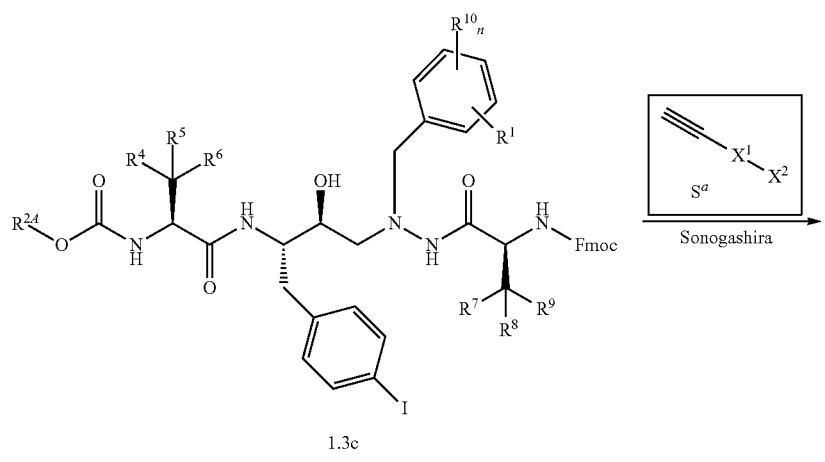
1.3c

-continued

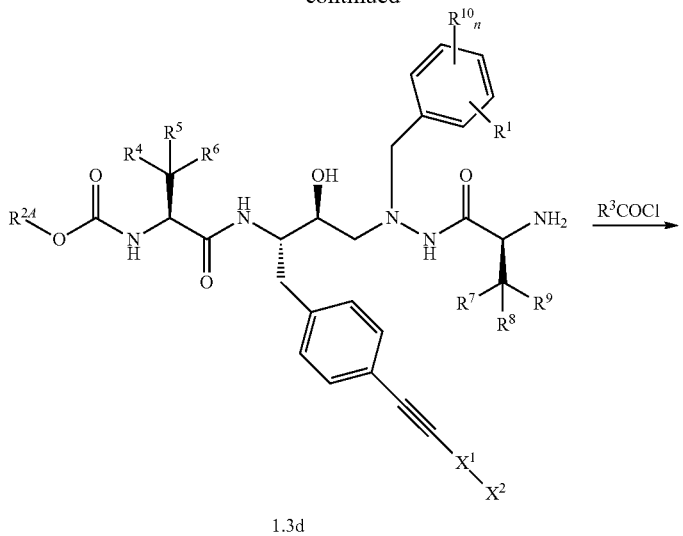

1.3d

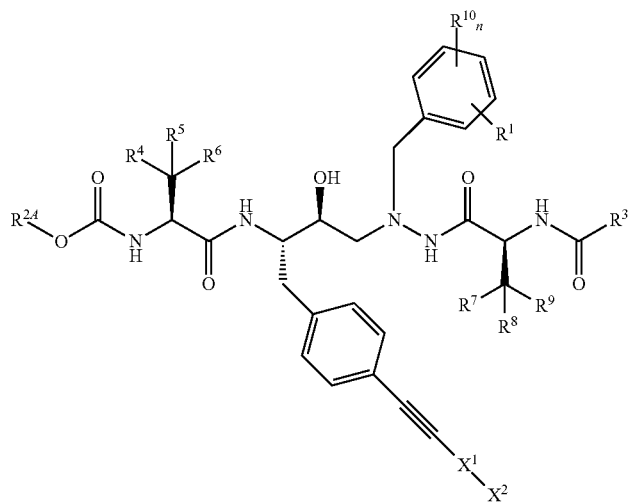

Scheme 1.3 shows a general synthesis of a compound within the scope of Formula I beginning with reductive amination of a protected organohalide compound 1.3a with a benzaldehyde Intermediate P and Boc removal to give compound 1.3b. Reductive amination may be accomplished, by way of non-limiting example, with sodium cyanoborohydride. Boc removal may be accomplished, by way of non-limiting examples, with trifluoroacetic acid or hydrochloric acid. HATU coupling of compound 1.3b with an amino acid Intermediate A''' gives the intermediate peptide 1.3c. Sonogashira coupling of the intermediate peptide 1.3c and an alkynyl Intermediate S gives intermediate 1.3d. Subsequent reaction of compound 1.3d with an acyl chloride gives a compound of Formula I.

Examples 183-186 were prepared by this general strategy. Example 183 provides exemplary reaction conditions and reagents appropriate for preparing a compound of the invention according to Scheme 1.3.

SCHEME 1.4
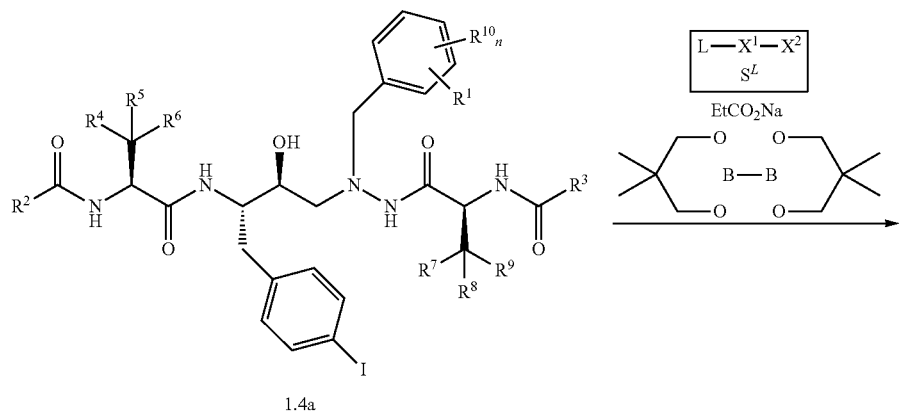
1.4a
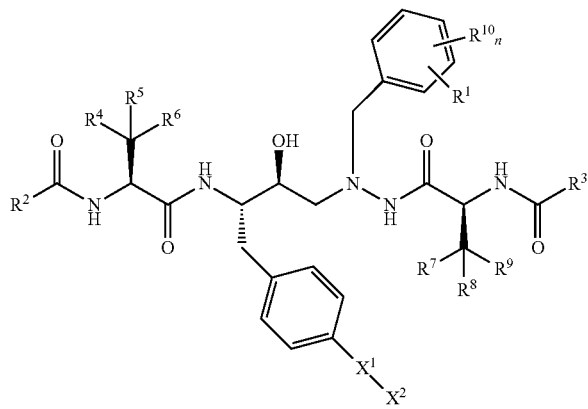
X[1] may be installed directly on the halophenyl as exemplified in Scheme 1.4. In this example, an organohalide Intermediate $S^L$ (shown above where L is iodo, bromo, or chloro) is coupled with compound 1.4a by Borylation-Suzuki reaction. Examples 188-201 were prepared using the methodology shown in Scheme 1.4. Exemplary reaction conditions are found in Example 188.
Scheme 1.5
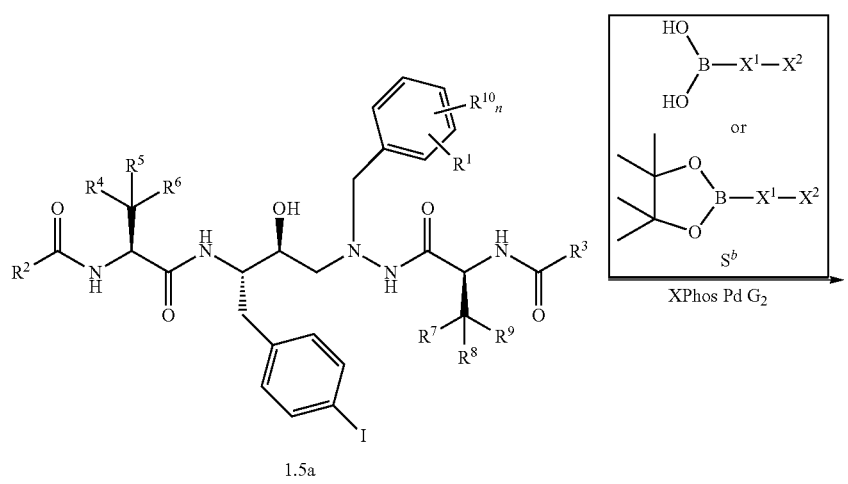
1.5a -continued

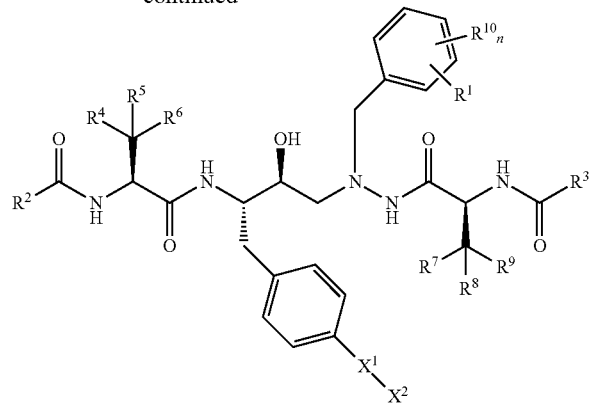

Alternatively, $X^1$ may be installed by metal catalyzed coupling of a boronic acid or boronic ester (Intermediate $S^b$) with compound 1.5a. The reaction is conducted with XPhos Pd $G_2$. Xphos is also known as XPhos is 2-Dicyclohexylphosphino-2',4',6'-triisopropylbiphenyl. Pd $G_2$ is chloro(2-dicyclohexylphosphino-2',4',6'-triisopropyl-1,1'-biphenyl)[2-(2'-amino-1,1'-biphenyl)]palladium(II). Examples 202-211 and 218 were prepared according to Scheme 1.5. Example 202 provides exemplary reaction conditions for this transformation.

SCHEME 1.6

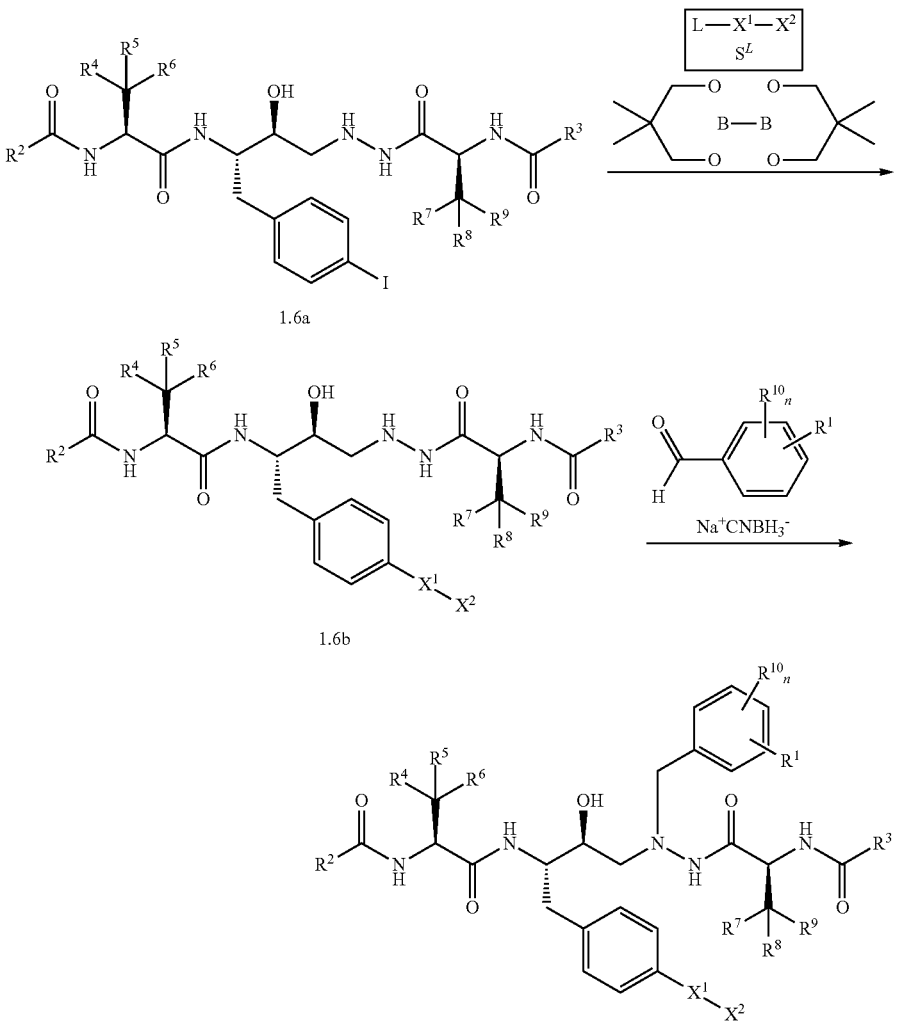

Example 212 was made in according to Scheme 1.6. Example 212 provides exemplary reaction conditions for transformations according to Scheme 1.6.
SCHEME 1.7
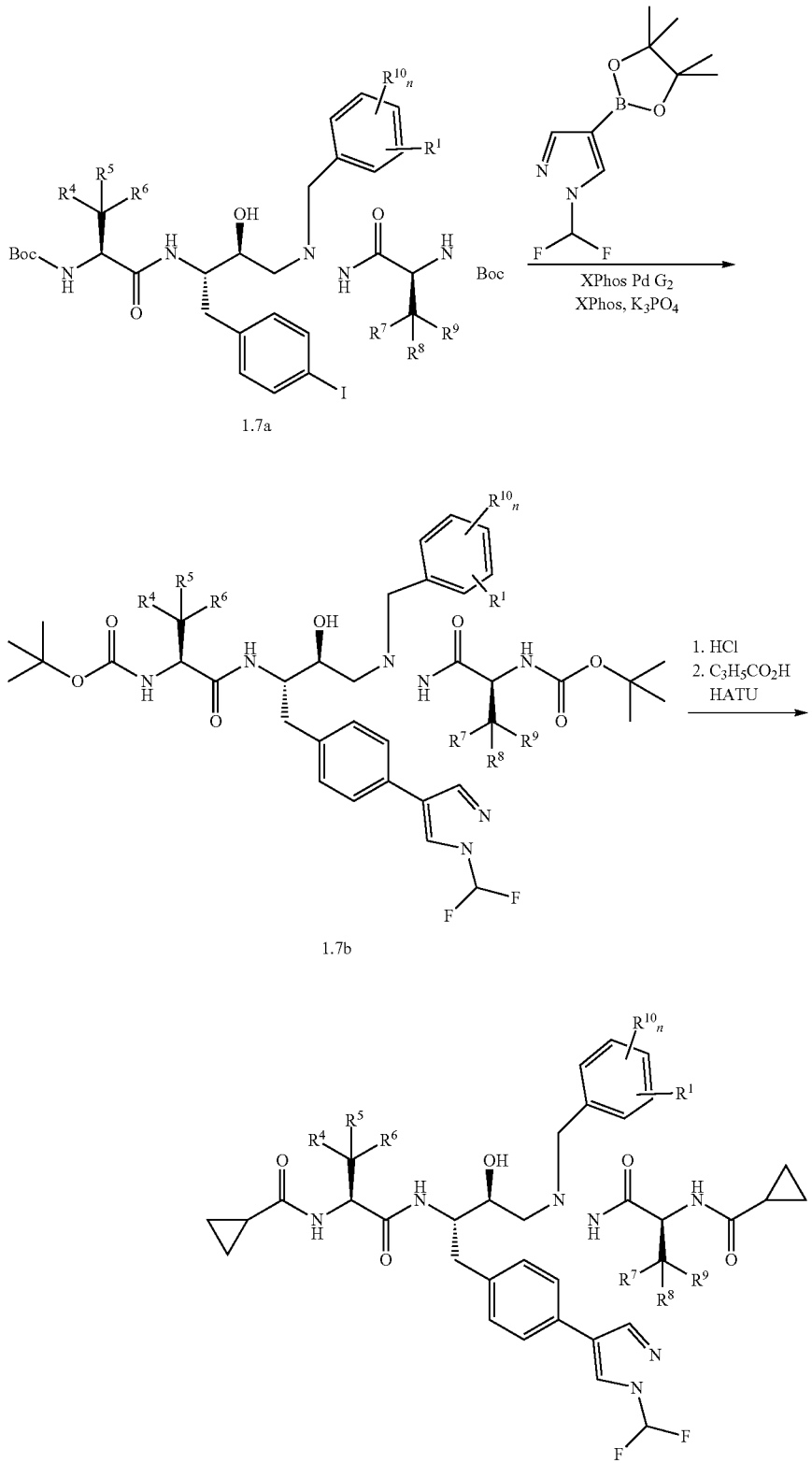

Scheme 1.7 shows an example of a Suzuki cross coupling, followed by Boc-deprotection and amide bond formation. Exemplary reaction conditions can be found in Example 213. Examples 214-217 show installation of different $R^2$ and $R^3$ groups using the same general strategy and the appropriate acid chloride.
SCHEME 1.8
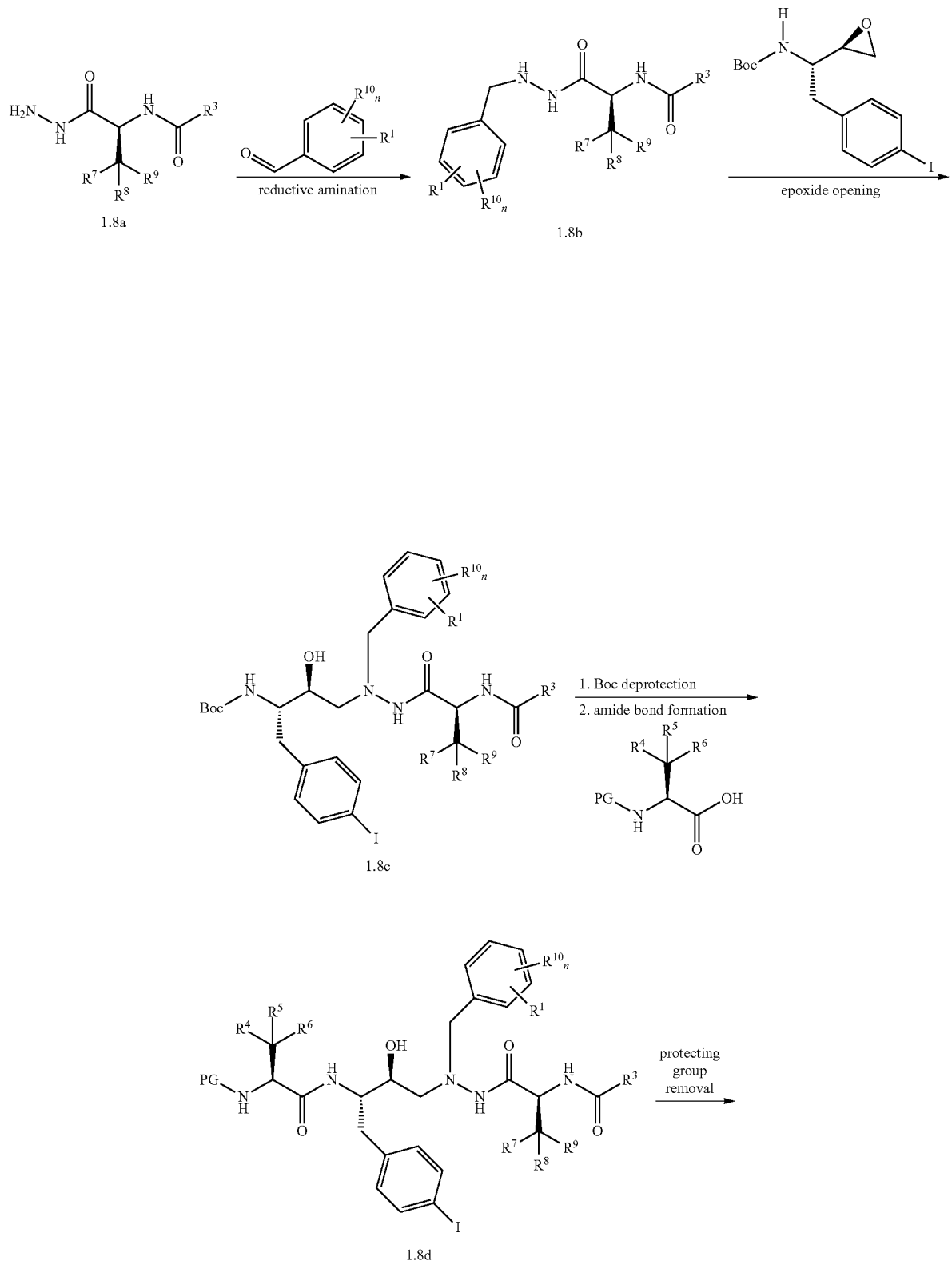

-continued
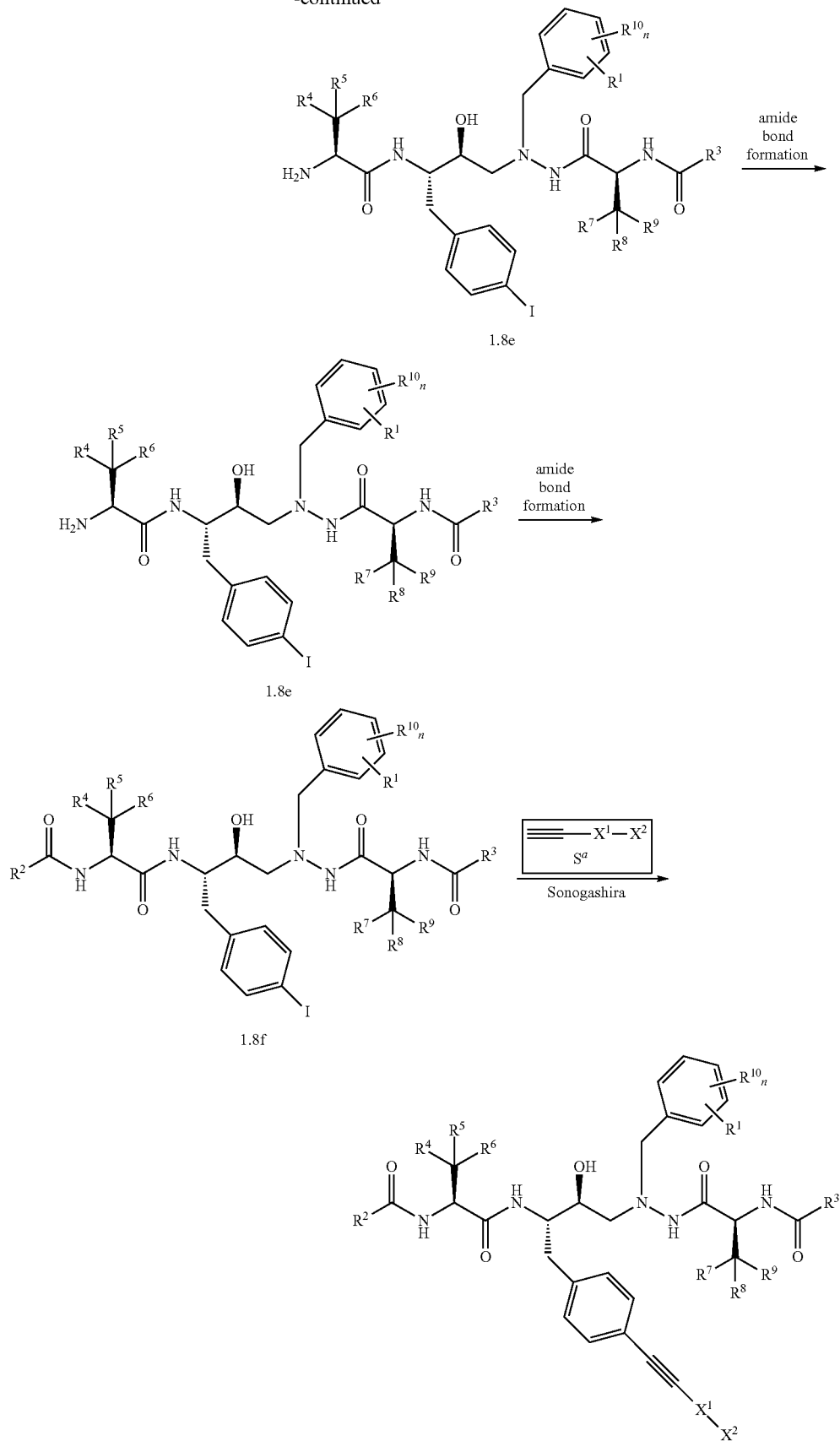
1.8e
1.8e
1.8f

Scheme 1.8 shows a general synthesis of a compound within the scope of Formula I beginning with reductive amination of compound 1.8a with a substituted benzaldehyde (Intermediate P). Reductive amination of compound 1.8a with a substituted benzaldehyde Intermediate P gives compound 1.8b. Reductive amination may be accomplished, by way of non-limiting example, with sodium cyanoborohydride. Subsequent epoxide opening of tert-butyl ((S)-2-(4-iodophenyl)-1-((R)-oxiran-2-yl)ethyl)carbamate give compound 1.8c. Subsequent Boc removal followed by Subsequent amide bond formation gives compound 1.8d. Boc removal may be accomplished, by way of non-limiting examples, with trifluoroacetic acid or hydrochloric acid. Amide bond formation may be accomplished, by way of non-limiting example, with a carboxylic acid and a reagent, such as HATU. Subsequent protecting group removal gives compound 1.8e. Subsequent amide bond formation gives compound 1.8f. Amide bond formation may be accomplished, by way of non-limiting example, with a carboxylic acid and a reagent, such as HATU. Subsequently metal-catalyzed coupling such as Sonogashira- or Suzuki-couplings may be performed. Sonogashira coupling of compound 1.8d with an alkynyl Intermediate S$^a$ gives a compound of Formula I.

Examples 221-223 were prepared by this general strategy.

2. Synthesis of Intermediates 2.1 Synthesis of P Intermediates

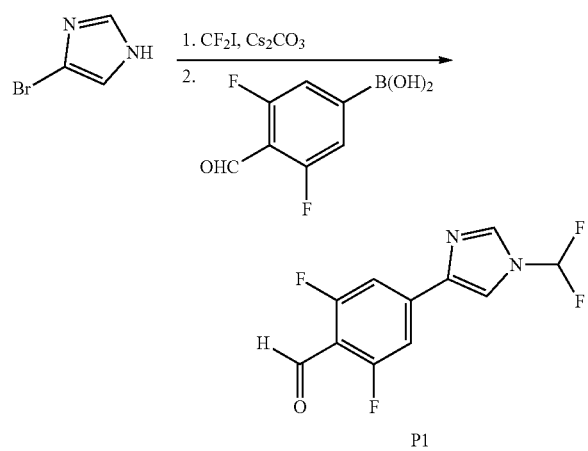

P1

4-(1-(difluoromethyl)-1H-imidazol-4-yl)-2,6-difluorobenzaldehyde (P1)

A suspension of 4-bromo-1H-imidazole (1 g, 6.8 mmol) cesium carbonate (44430 mg, 136.36 mmol), and difluoroiodomethane (10% wt. in THF, 20 ml, 10.62 mmol) in a 75 mL sealed vessel was heated at 50° C. overnight. The reaction mixture was cooled to room temperature and then filtered through Celite. The filter cake was washed with EtOAc. The filtrate was washed with brine, dried over sodium sulfate and carefully concentrated. The residue was purified by silica column chromatography (17% to 47% EtOAc/Hex) to give 1.3 g of a mixture of regioisomers. This mixture was combined with 3,5-Difluoro-4-formylphenylboronic acid (1.6 g, 8.58 mmol), XPhos Pd G2 (0.4 g, 0.26 mmol), 2-(Dicyclohexylphosphino)-2',4',6'-triisopropylbiphenyl (0.12 g, 0.26 mmol), Potassium phosphate tribasic (2 M, 3.3 ml) in dioxane (11 ml) and degassed for 10 min with argon, then heated at 100° C. overnight. The reaction mixture was cooled to room temperature, concentrated under reduce pressure, the residue was diluted with EtOAc and washed with brine 2× then dried over Na$_2$SO$_4$, filtered and concentrated under reduced pressure. The crude residue was purified by silica column chromatography (23% to 92% EtOAc/Hex) to give the desired isomer P1. MS (ESI) m/z 259.2 [M+H]$^+$. $^1$H NMR (400 MHz, Chloroform-d) δ 10.32 (d, J=1.1 Hz, 1H), 7.91 (d, J=1.3 Hz, 1H), 7.63 (d, J=1.3 Hz, 1H), 7.48-7.36 (m, 2H), 7.16 (t, J=60.8 Hz, 1H).

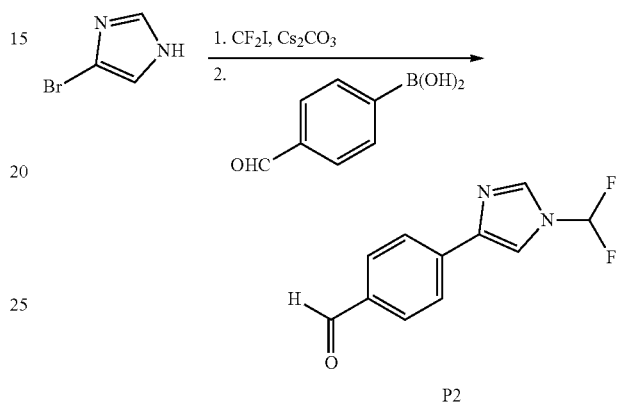

P2

4-(1-(difluoromethyl)-1H-imidazol-4-yl)benzaldehyde (P2)

The title compound P2 was prepared according to the method presented for the synthesis of intermediate P1 but instead utilizing (4-formylphenyl)boronic acid. MS (ESI) m/z 223.2 [M+H]$^+$. $^1$H NMR (400 MHz, Chloroform-d) δ 10.02 (s, 1H), 8.01-7.89 (m, 5H), 7.62 (d, J=1.3 Hz, 1H), 7.15 (t, J=60.9 Hz, 1H).

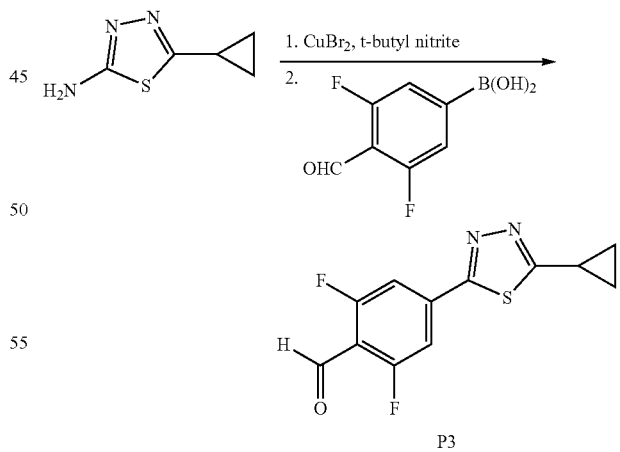

P3

4-(5-cyclopropyl-1,3,4-thiadiazol-2-yl)-2,6-difluorobenzaldehyde (P3)

To a heterogeneous solution of Cupric bromide (3.8 g, 17 mmol) and tert-Butyl nitrite (2.53 ml, 21.25 mmol) in MeCN (78 mL) in a 3 neck flask charged with a stir bar, side arm inlet, under argon, was added 5-cyclopropyl-1,3,4-thiadiazol-2-amine (2 g, 14.16 mmol) slowly due to exothermic reaction, and stirred at room temperature under argon overnight. The reaction mixture was quenched with 78 mL of saturated NH4Cl (aq) and extracted with diethyl ether and the organic layer was dried over MgSO4, filtered and concentrated in vacuo. The crude residue was purified by silica column chromatography (10% to 50% EtOAc/Hex). The product (0.28 g, 1.34 mmol) was combined with 3,5-Difluoro-4-formylphenylboronic acid (0.5 g, 2.69 mmol), XPhos Pd G2 (0.15 g, 0.09 mmol), 2-(Dicyclohexylphosphino)-2',4',6'-triisopropylbiphenyl (45.06 mg, 0.09 mmol), potassium phosphate tribasic (2 M, 1.34 ml) in dioxane (4.9 ml) and degassed for 10 min with argon, then heated at 100° C. overnight. The reaction mixture was cooled to room temperature, concentrated under reduce pressure, the residue was diluted with EtOAc and washed with brine 2× then dried over Na2SO4, filtered and concentrated under reduced pressure. The crude residue was purified by silica column chromatography (21% to 100% EtOAc/Hex) to give the desired isomer P3. MS (ESI) m/z 267.1 [M+H]+. 1H NMR (400 MHz, Chloroform-d) δ 10.37 (s, 1H), 7.56 (d, J=9.0 Hz, 2H), 5.30 (d, J=0.7 Hz, 0H), 2.47 (dt, J=8.1, 3.7 Hz, 1H), 1.55 (s, 5H), 1.33 (dd, J=8.3, 4.1 Hz, 2H), 1.26 (d, J=4.4 Hz, 5H), 0.92-0.79 (m, 2H).

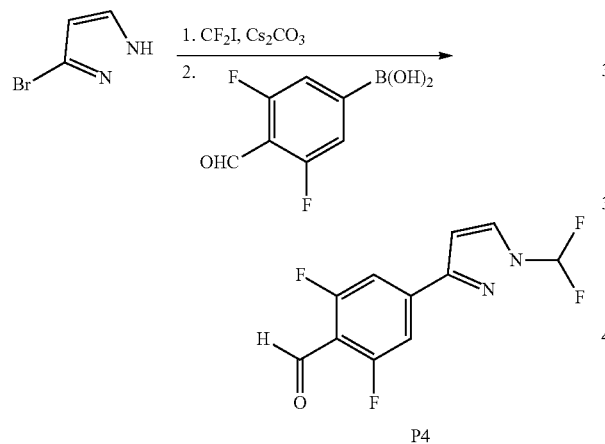

Synthesis of 4-(1-(difluoromethyl)-1H-pyrazol-3-yl)-2, 6-difluorobenzaldehyde (P4)

In a 150 mL pressure vessel, a suspension of 3-bromo-1H-pyrazole (8 g, 54.43 mmol) cesium carbonate (53.2 g, 163.29 mmol), and difluoroiodomethane (10% wt. in THF, 200 ml, 106.23 mmol) was heated at 45° C. overnight. The reaction mixture was cooled to room temperature and then filtered through Celite. The filter cake was washed with Et2O (3×150 mL). The filtrate was washed with brine, dried over sodium sulfate and carefully concentrated (20° C. bath, 100 mb vacuum) to give ~17 g of a 1.5:1 ratio of regioisomers and solvent still present. This crude material was combined with 3,5-Difluoro-4-formylphenylboronic acid (12.65 g, 68.03 mmol), Palladium acetate (0.31 g, 1.381 mmol), butyldi-1-adamantylphosphine (1.171 g, 3.265 mmol) and Potassium carbonate (22.80 g, 164.96 mmol) in dioxane (150 mL) and water (50 mL) the mixture was degassed for 10 min with argon, then heated at 100° C. overnight. The reaction mixture was cooled to room temperature, concentrated under reduce pressure, the residue was diluted with EtOAc and washed with brine 2× then dried over Na2SO4, filtered and concentrated under reduced pressure. The crude residue was purified by silica column chromatography (5% to 15% EtOAc/Hex). Mixed fractions were recrystallized (5:1 Hex/EtOAc) combined pure product afforded P4. 1H NMR (400 MHz, Chloroform-d) δ 10.35 (d, J=1.0 Hz, 1H), 7.92 (d, J=2.8 Hz, 1H), 7.46 (d, J=9.6 Hz, 2H), 7.24 (t, J=60.5 Hz, 1H), 6.80 (d, J=2.8 Hz, 1H).

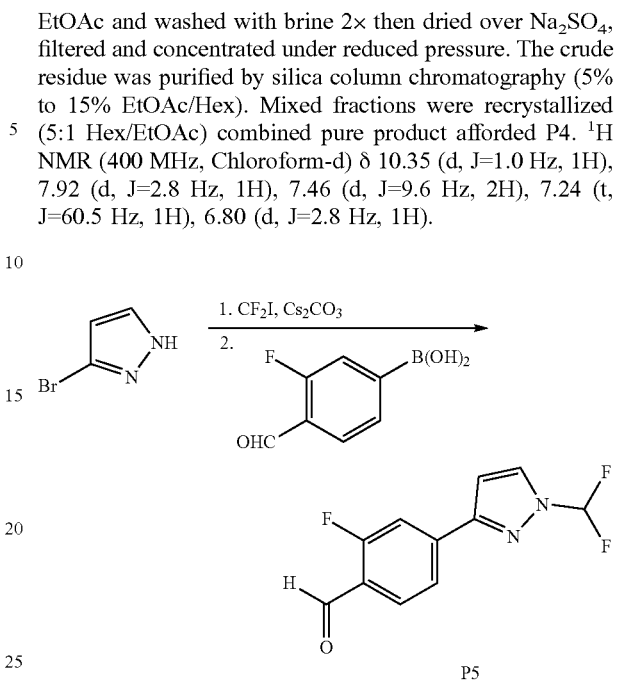

Synthesis of 4-(1-(difluoromethyl)-1H-pyrazol-3-yl)-2-fluorobenzaldehyde (P5)

The title compound P5 was prepared according to the method presented for the synthesis of intermediate P4 but instead utilizing (3-fluoro-4-formylphenyl)boronic acid. 1H NMR (400 MHz, Chloroform-d) δ 10.41 (s, 1H), 7.97 (dd, J=8.0, 7.1 Hz, 1H), 7.71 (d, J=1.7 Hz, 1H), 7.50-7.34 (m, 2H), 6.55 (d, J=1.7 Hz, 1H).

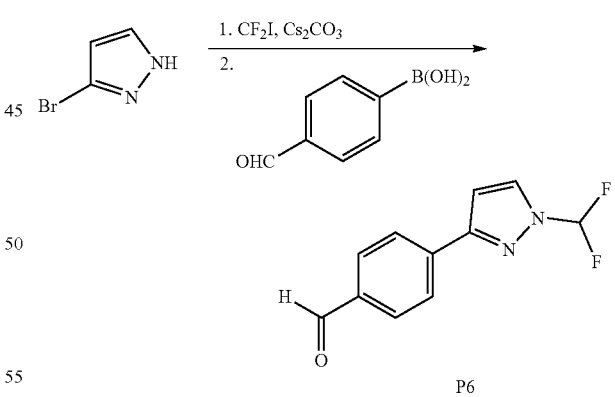

Synthesis of 4-(1-(difluoromethyl)-1H-pyrazol-3-yl)benzaldehyde (P6)

The title compound P6 was prepared according to the method presented for the synthesis of intermediate P4 but instead utilizing (4-formylphenyl)boronic acid. 1H NMR (400 MHz, Chloroform-d) δ 10.05 (s, 1H), 8.03-7.93 (m, 4H), 7.90 (d, J=2.7 Hz, 1H), 6.85 (d, J=2.7 Hz, 1H).

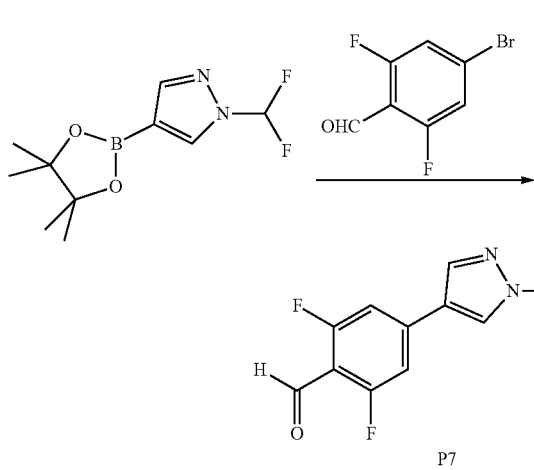

P7

Synthesis of 4-(1-(difluoromethyl)-1H-pyrazol-4-yl)-2,6-difluorobenzaldehyde (P7)

A suspension of 1-Difluoromethyl-4-(4,4,5,5-tetramethyl-[1,3,2]dioxaborolan-2-yl)-1H-pyrazole (1.47 g, 6.03 mmol), 4-bromo-2,6-difluorobenzaldehyde (1.1 g, 4.98 mmol), palladium acetate (0.03 g, 0.12 mmol), butyldi-1-adamantylphosphine (0.11 g, 0.3 mmol), and potassium carbonate (2.06 g, 14.93 mmol) in water (7 ml) and 1,4-dioxane (22 ml) in a tube was degassed for 10 min with argon, then the tube was sealed and heated at 100° C. overnight. The reaction mixture was cooled to room temperature, concentrated under reduce pressure, the residue was diluted with EtOAc and washed with brine 2× then dried over Na$_2$SO$_4$, filtered and concentrated under reduced pressure. The crude residue was purified by silica column chromatography (10% to 25% EtOAc/Hex) to afford P7. $^1$H NMR (400 MHz, Chloroform-d) δ 10.32 (s, 1H), 8.16 (s, 1H), 7.96 (s, 1H), 7.23 (t, J=60.4 Hz, 1H), 7.14 (d, J=9.5 Hz, 2H).

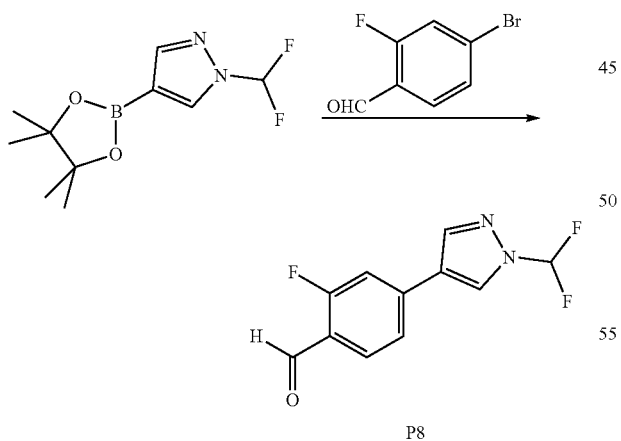

P8

Synthesis of 4-(1-(difluoromethyl)-1H-pyrazol-4-yl)-2-fluorobenzaldehyde (P8)

The title compound P8 was prepared according to the method presented for the synthesis of intermediate P7 but instead utilizing 4-bromo-2-fluorobenzaldehyde. $^1$H NMR (400 MHz, Chloroform-d) δ 10.35 (d, J=0.7 Hz, 1H), 8.15 (d, J=0.7 Hz, 1H), 7.98 (q, J=0.8 Hz, 1H), 7.91 (dd, J=8.1, 7.3 Hz, 1H), 7.42 (ddd, J=8.1, 1.7, 0.8 Hz, 1H), 7.31 (dd, J=11.3, 1.6 Hz, 1H), 7.23 (s, 1H).

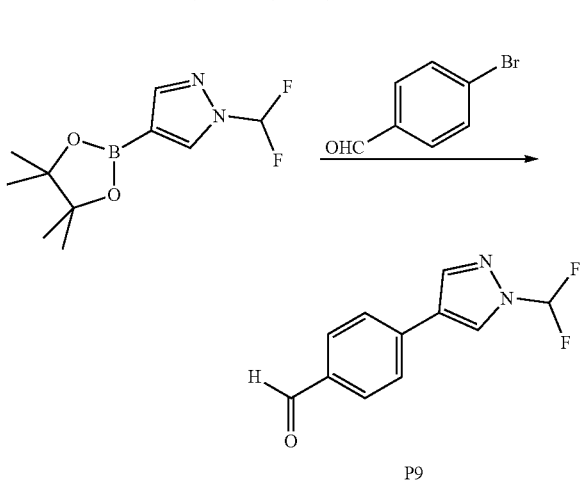

P9

Synthesis of 4-(1-(difluoromethyl)-1H-pyrazol-4-yl)benzaldehyde (P9)

The title compound P9 was prepared according to the method presented for the synthesis of intermediate P7 but instead utilizing 4-bromobenzaldehyde. $^1$H NMR (400 MHz, Chloroform-d) δ 10.02 (s, 1H), 8.16 (s, 1H), 8.01 (d, J=0.8 Hz, 1H), 7.96-7.90 (m, 2H), 7.71-7.66 (m, 2H), 7.24 (t, J=0.14 Hz, 1H).

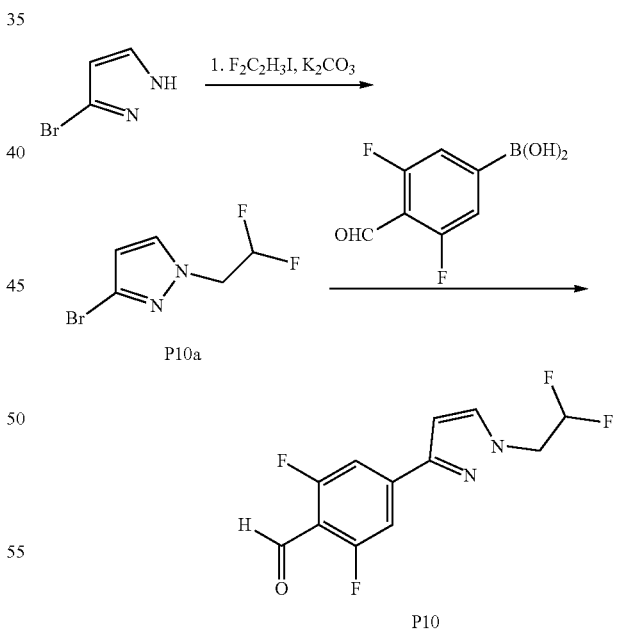

P10

Synthesis of 3-bromo-1-(2,2-difluoroethyl)-1H-pyrazole (P10a)

To a solution of 3-bromo-1H-pyrazole (6 g, 42.86 mmol) and Potassium carbonate (20.73 g, 150.03 mmol) in DMF (20 mL) at 35° C., was added a solution of 1,1-difluoro-2-iodoethane (24.68 g, 128.59 mmol) dropwise via an addition funnel. The reaction was stirred overnight then cooled to room temperature, diluted with ether/hexanes and washed with brine and NH₄Cl solution. The organic layer was separated dried over Na₂SO₄, filtered and concentrated under reduced pressure. The crude residue was purified by silica column chromatography (7% to 25% EtOAc/Hex) to afford P10a (5.4 g 63.6%). MS (ESI) m/z 211.0 [M+H]⁺. 1H NMR (400 MHz, Chloroform-d) δ 7.36 (d, J=2.4 Hz, 1H), 6.32 (d, J=2.4 Hz, 1H), 6.06 (tt, J=55.4, 4.3 Hz, 1H), 4.41 (td, J=13.3, 4.3 Hz, 2H).

Synthesis of 4-(1-(2,2-difluoroethyl)-1H-pyrazol-3-yl)-2,6-difluorobenzaldehyde (P10)

P10a (4.31 g, 0.02 mol) was combined with 3,5-Difluoro-4-formylphenylboronic acid (4.96 g, 24.49 mmol), PdCl₂(tBu₂PPh)₂ (570 mg, 0.92 mmol), and potassium phosphate tribasic monohydrate (1.0 M, 40.82 ml) in 2-methyltetrahydrofuran (20 mL) and water (20 mL) the mixture was degassed for 10 min with argon, then heated at 75° C. overnight. The reaction was cooled to room temperature, the organic layer was separated and the aqueous layer was extracted into EtOAc. The combined organic layers were washed with 1M HCl, then brine, filter concentrated under reduce pressure, the residue was diluted with EtOAc and washed with brine 2× then dried over Na₂SO₄, filtered and concentrated under reduced pressure, recrystallized (1:3 EtOAc/hexanes). The separated solids contained a mixture of desired isomer and unreacted boronic acid. This mixture was purified by silica column chromatography (70% to 100% DCM/Hex) to afford P10 (2.3 g, 41%) MS (ESI) m/z 273.1 [M+H]⁺. ¹H NMR (400 MHz, Chloroform-d) δ 10.34 (d, J=1.0 Hz, 1H), 7.55 (d, J=2.4 Hz, 1H), 7.47-7.38 (m, 2H), 6.67 (d, J=2.4 Hz, 1H), 6.15 (tt, J=55.3, 4.3 Hz, 1H), 4.52 (td, J=13.5, 4.3 Hz, 2H).

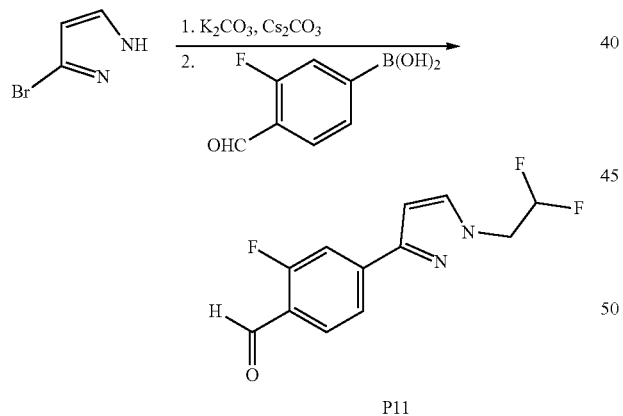

P11

Synthesis of 4-(1-(2,2-difluoroethyl)-1H-pyrazol-3-yl)-2-fluorobenzaldehyde (P11)

The title compound P11 was prepared according to the method presented for the synthesis of intermediate P10 but instead utilizing (3-fluoro-4-formylphenyl)boronic acid. ¹H NMR (400 MHz, Chloroform-d) δ 10.34 (d, J=0.8 Hz, 1H), 7.89 (dd, J=8.1, 7.2 Hz, 1H), 7.70-7.58 (m, 2H), 7.54 (d, J=2.4 Hz, 1H), 7.33 (dt, J=8.0, 1.0 Hz, 0H), 7.26 (dd, J=10.7, 1.5 Hz, 0H), 6.68 (d, J=2.4 Hz, 1H), 6.42 (d, J=1.9 Hz, 0H), 6.15 (tt, J=55.4, 4.3 Hz, 1H), 4.52 (td, J=13.5, 4.3 Hz, 2H).

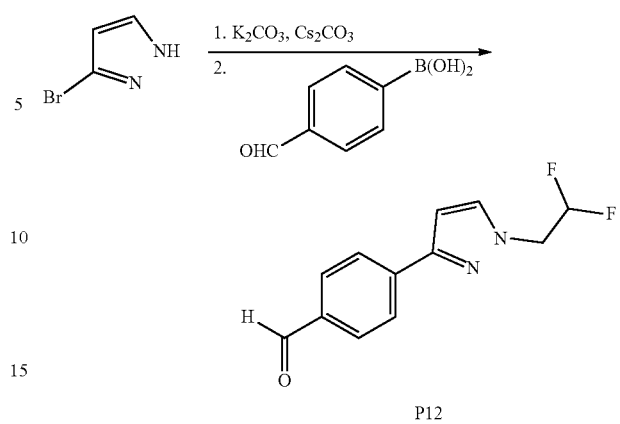

P12

Synthesis of 4-(1-(2,2-difluoroethyl)-1H-pyrazol-3-yl)benzaldehyde (P12)

The title compound P12 was prepared according to the method presented for the synthesis of compound P10 but instead utilizing (4-formylphenyl)boronic acid. MS (ESI) m/z 273.1 [M+H]⁺. ¹H NMR (400 MHz, Chloroform-d) δ 10.34 (d, J=1.0 Hz, 1H), 7.55 (d, J=2.4 Hz, 1H), 7.47-7.38 (m, 2H), 6.67 (d, J=2.4 Hz, 1H), 6.15 (tt, J=55.3, 4.3 Hz, 1H), 4.52 (td, J=13.5, 4.3 Hz, 2H).

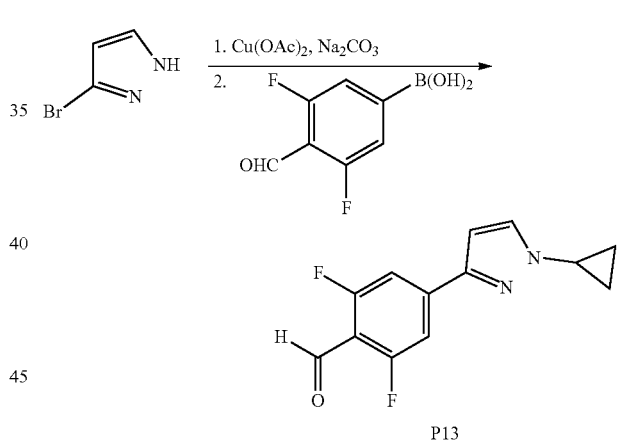

P13

Synthesis of 4-(1-cyclopropyl-1H-pyrazol-3-yl)-2,6-difluorobenzaldehyde (P13)

A suspension of copper(II) acetate anhydrous (3.7 g, 20.41 mmol), and 2,2'-bipyridyl (3.2 g, 20.41 mmol) in DCE (40 mL) was degassed, warmed to 50° C., and stirred for 10 minutes, before addition to 3-bromo-1H-Pyrazole (3 g, 20.41 mmol), cyclopropylboronic acid (5.3 g, 20.41) and sodium carbonate (4.8 g, 44.91 mmol) in DCE (60 mL). The reaction was stirred at 65° C. for 48 h. The reaction mixture was cool to room temperature, filtered through a Celite frit, and rinsed with EtOAc. The filtrate was concentrated under reduced pressure, the residue was partitioned between EtOAc and NH₄Cl solution, the organic layer was washed with NH₄Cl, Na₂CO₃ soln. brine, dried over Na₂SO₄ and purified by silica column chromatography (10% to 35% EtOAc/Hex) to afford 3-bromo-1-cyclopropyl-1H-pyrazole.

3-bromo-1-cyclopropyl-1H-pyrazole (1.5 g, 8.18 mmol) was combined with 3,5-Difluoro-4-formylphenylboronic acid (1.8 g, 9.8 mmol), PdCl$_2$(tBu$_2$PPh)$_2$ (0.29 g, 0.41 mmol), and potassium phosphate tribasic monohydrate (4.71 g, 20.45 mmol) in 2-methyltetrahydrofuran (60 mL) and water (60 mL) was degassed for 10 min with argon, then heated to reflux for 3 h. The reaction mixture was cooled to room temperature, the organic layer was separated and the aqueous layer was extracted into EtOAc. The combined organic layers were washed with 1M HCl, then brine, filtered and concentrated under reduce pressure, the residue was diluted with EtOAc and washed with brine 2× then dried over Na$_2$SO$_4$, filtered and concentrated under reduced pressure. This mixture was purified by silica column chromatography (50% to 100% DCM/Hex-10% EtOAc/DCM) to afford P13 (1.2 g, 49%) MS (ESI) m/z 249.2 [M+H]$^+$. $^1$H NMR (400 MHz, Chloroform-d) δ 10.33 (s, 1H), 7.52 (d, J=2.4 Hz, 1H), 7.42 (d, J=10.1 Hz, 2H), 6.57 (d, J=2.4 Hz, 1H), 3.66 (tt, J=7.4, 3.9 Hz, 1H), 1.26-1.15 (m, 2H), 1.09 (qd, J=5.7, 2.4 Hz, 2H).

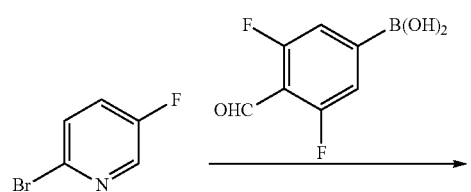

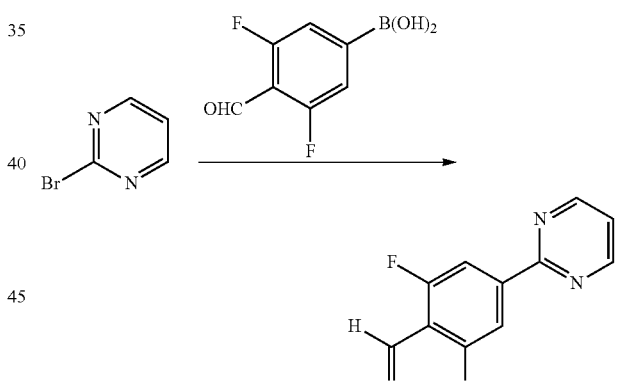

Synthesis of 2,6-difluoro-4-(4-fluoropyridin-2-yl)benzaldehyde (P15)

The title compound P15 was prepared according to the method presented for the synthesis of compound P14 but instead utilizing 2-bromo-4-fluoropyridine. MS (ESI) m/z 238.2 [M+H]$^+$. $^1$H NMR (400 MHz, Chloroform-d) δ 10.39 (s, 1H), 8.70 (dd, J=8.6, 5.5 Hz, 1H), 7.67 (d, J=9.9 Hz, 3H), 7.48 (dd, J=9.8, 2.3 Hz, 1H), 7.11 (ddd, J=7.9, 5.5, 2.3 Hz, 1H).

P14

Synthesis of 2,6-difluoro-4-(4-fluoropyridin-2-yl)benzaldehyde (P14)

A suspension of 2-bromo-5-fluoropyridine (0.95 g, 5.39 mmol), 3,5-Difluoro-4-formylphenylboronic acid (0.8 g, 4.3 mmol), bis(triphenylphosphine) palladium (II) dichloride (302 mg, 0.43 mmol), and potassium carbonate (1.49 g, 10.76 mmol) in a mixture of DME (10 ml) and water (5 ml) was degassed for 10 min with argon, then heated at 85° C. overnight. The reaction mixture was cooled to room temperature, concentrated under reduce pressure, the residue was diluted with EtOAc and washed with brine 2× then dried over Na$_2$SO$_4$, filtered and concentrated under reduced pressure. The crude residue was purified by silica column chromatography (10% to 20% EtOAc/Hex) to afford P14 (122 mg, 12%). MS (ESI) m/z 238.1 [M+H]$^+$. $^1$H NMR (400 MHz, Chloroform-d) δ 10.38 (d, J=1.2 Hz, 1H), 8.59 (d, J=2.8 Hz, 1H), 7.78 (ddd, J=8.8, 4.2, 0.6 Hz, 1H), 7.68-7.60 (m, 2H), 7.55 (ddd, J=8.8, 7.8, 2.9 Hz, 1H).

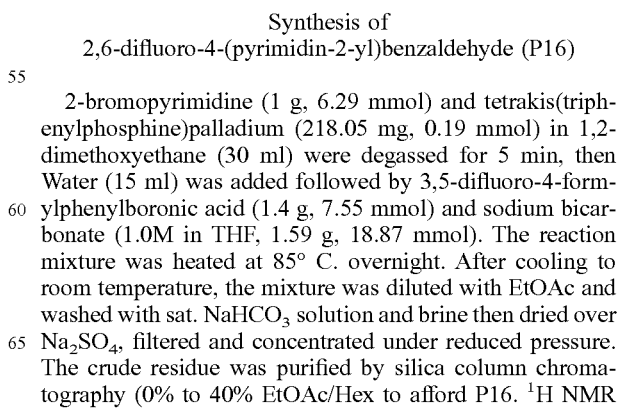

Synthesis of 2,6-difluoro-4-(pyrimidin-2-yl)benzaldehyde (P16)

2-bromopyrimidine (1 g, 6.29 mmol) and tetrakis(triphenylphosphine)palladium (218.05 mg, 0.19 mmol) in 1,2-dimethoxyethane (30 ml) were degassed for 5 min, then Water (15 ml) was added followed by 3,5-difluoro-4-formylphenylboronic acid (1.4 g, 7.55 mmol) and sodium bicarbonate (1.0M in THF, 1.59 g, 18.87 mmol). The reaction mixture was heated at 85° C. overnight. After cooling to room temperature, the mixture was diluted with EtOAc and washed with sat. NaHCO$_3$ solution and brine then dried over Na$_2$SO$_4$, filtered and concentrated under reduced pressure. The crude residue was purified by silica column chromatography (0% to 40% EtOAc/Hex to afford P16. $^1$H NMR (400 MHz, Chloroform-d) δ 10.42 (d, J=1.0 Hz, 1H), 8.87 (d, J=4.9 Hz, 2H), 8.16-8.03 (m, 2H), 7.32 (t, J=4.8 Hz, 1H).

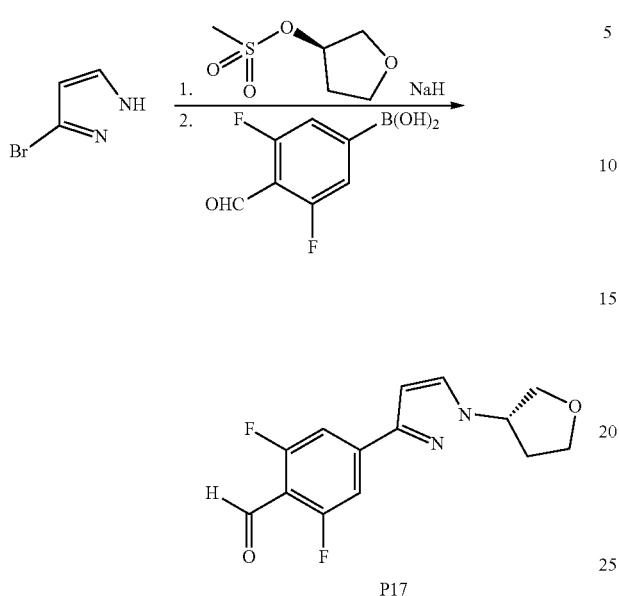

P17

(S)-2,6-difluoro-4-(1-(tetrahydrofuran-3-yl)-1H-pyrazol-3-yl)benzaldehyde (P17)

To a solution of 3-bromo-1H-pyrazole (583 mg, 3.97 mmol) in DMF (15 mL) cooled in an ice bath was added sodium hydride (60% oil dispersion, 241 mg, 6.03 mmol). After stirring for 1.5 h, a solution of (R)-tetrahydrofuran-3-yl methanesulfonate (Reference: PCT Int Appl 2013068458) (998 mg, 6.01 mmol) in DMF (5 mL) was added and the reaction mixture was heated to 100° C. overnight. The reaction mixture was cooled to room temperature, diluted with EtOAc and washed with brine. The organic layer was separated, dried over Na$_2$SO$_4$, concentrated under vacuum and the crude residue was purified by silica column chromatography (20% to 40% EtOAc/Hex to afford (S)-3-bromo-1-(tetrahydrofuran-3-yl)-1H-pyrazole (0.17 g, 0.78 mmol), this material was combined in a 20 mL microwave vial with 3,5-Difluoro-4-formylphenylboronic acid (0.19 g, 1 mmol), palladium acetate (6.5 mg, 0.03 mmol), butyldi-1-adamantylphosphine (21.4 mg, 0.06 mmol), and potassium carbonate (0.33 g, 2.4 mmol) in a mixture of water (2 ml) and 1,4-dioxane (6 ml), the mixture was degassed with argon for 5 min. The reaction was microwaved at 100° C. for 1.5 h, then cooled to room temperature, concentrated under vacuum, then diluted with EtOAc and washed with water and brine. The organic extract was dried over Na$_2$SO$_4$, filtered and concentrated under reduced pressure. This mixture was purified by silica column chromatography (20% to 40% EtOAc/hex) to afford P17. MS (ESI) m/z 279.1 [M+H]$^+$. $^1$H NMR (400 MHz, Chloroform-d) δ 10.32 (d, J=1.0 Hz, 1H), 7.55 (d, J=2.4 Hz, 1H), 7.48-7.34 (m, 2H), 6.62 (d, J=2.4 Hz, 1H), 5.03 (ddt, J=8.2, 5.8, 3.4 Hz, 1H), 4.31-4.03 (m, 4H), 3.98 (td, J=8.6, 5.5 Hz, 1H), 2.51 (dtd, J=13.4, 8.3, 7.1 Hz, 1H), 2.43-2.28 (m, 1H).

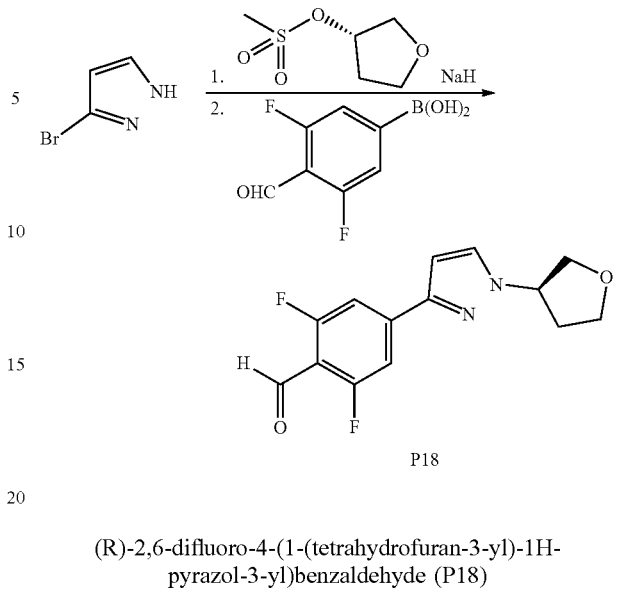

P18

(R)-2,6-difluoro-4-(1-(tetrahydrofuran-3-yl)-1H-pyrazol-3-yl)benzaldehyde (P18)

The title compound P18 was prepared according to the method presented for the synthesis of compound P17 but instead utilizing (S)-tetrahydrofuran-3-yl methanesulfonate (Reference: PCT Int Appl 2013068458). MS (ESI) m/z 279.1 [M+H]$^+$. $^1$H NMR (400 MHz, Chloroform-d) δ 10.34 (d, J=1.1 Hz, 1H), 7.56 (d, J=2.4 Hz, 1H), 7.50-7.33 (m, 2H), 6.63 (d, J=2.4 Hz, 1H), 5.04 (ddt, J=9.0, 6.6, 3.5 Hz, 1H), 4.27-4.04 (m, 4H), 3.99 (td, J=8.6, 5.5 Hz, 1H), 2.52 (dtd, J=13.3, 8.2, 7.1 Hz, 1H), 2.38 (dddd, J=13.3, 8.0, 5.5, 3.4 Hz, 1H).

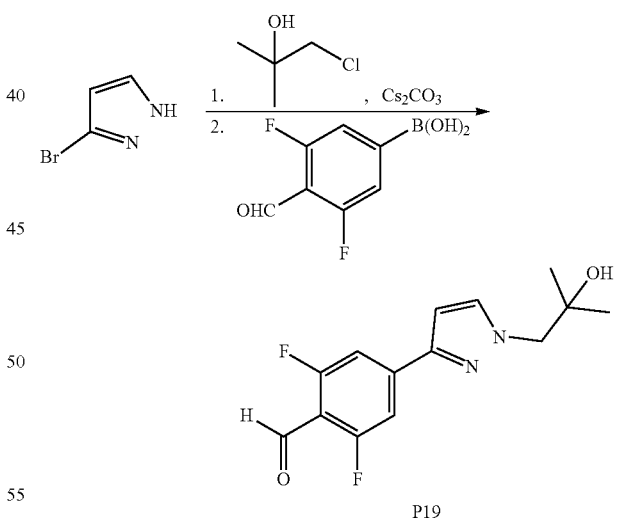

P19

2,6-difluoro-4-(1-(2-hydroxy-2-methylpropyl)-1H-pyrazol-3-yl)benzaldehyde (P19)

The title compound P19 was prepared according to the method presented for the synthesis of compound P4 but instead utilizing 1-chloro-2-methylpropan-2-ol. MS (ESI) m/z 281.0 [M+H]$^+$. $^1$H NMR (400 MHz, Chloroform-d) δ 10.33 (s, 1H), 7.52 (d, J=2.3 Hz, 1H), 7.47-7.35 (m, 2H), 6.64 (d, J=2.4 Hz, 1H), 4.13 (s, 2H), 1.22 (s, 7H).

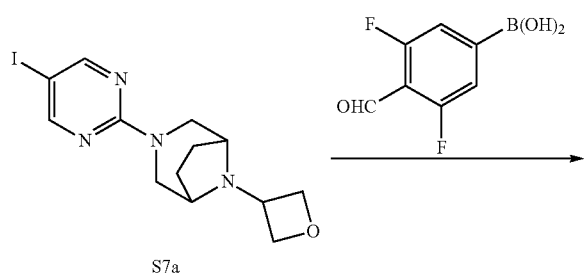

Synthesis of 2,6-difluoro-4-(2-(8-(oxetan-3-yl)-3,8-diazabicyclo[3.2.1]octan-3-yl)pyrimidin-5-yl)benzaldehyde (P20)

A suspension of S7a (0.14 g, 3.7 mol), (3,5-difluoro-4-formylphenyl)boronic acid (110.29 mg, 5.9 mol), potassium carbonate (0.15 g, 1 mmol), and tetrakis(triphenylphosphine)palladium (20 mg, 0.19 mmol) in a mixture of dioxane (15 ml) and water (15 ml) was degassed for 10 min. The reaction mixture was heated at 85° C. for 3 h. After cooling to room temperature, the mixture was diluted with EtOAc and washed with sat. NaHCO$_3$ solution and brine then dried over Na$_2$SO$_4$, filtered and concentrated under reduced pressure. The crude residue was purified by silica column chromatography (0% to 40% EtOAc/Hex to afford P20 (99 mg, 62%). MS (ESI) m/z 387.2 [M+H]$^+$. $^1$H NMR (400 MHz, Chloroform-d) δ 10.33 (s, 1H), 8.55 (s, 1H), 7.11 (d, J=9.8 Hz, 1H), 4.74 (t, J=6.3 Hz, 1H), 4.61 (s, 1H), 4.40 (d, J=12.8 Hz, 1H), 3.69 (s, 1H), 3.33-3.02 (m, 3H), 1.86 (s, 1H), 1.65 (d, J=8.1 Hz, 1H), 1.55 (s, 2H).

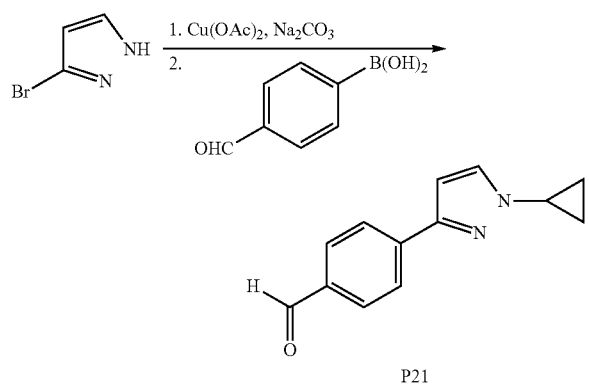

Synthesis of 4-(1-cyclopropyl-1H-pyrazol-3-yl)benzaldehyde (P21)

The title compound P21 was prepared according to the method presented for the synthesis of compound P13 but instead utilizing (4-formylphenyl)boronic acid. MS (ESI) m/z 213.2 [M+H]$^+$. $^1$H NMR (400 MHz, Chloroform-d) δ 10.01 (s, 1H), 7.97 (d, J=8.3 Hz, 2H), 7.92-7.86 (m, 2H), 7.50 (d, J=2.3 Hz, 1H), 6.61 (d, J=2.3 Hz, 1H), 3.66 (tt, J=7.4, 3.8 Hz, 1H), 1.22-1.15 (m, 2H), 1.11-1.03 (m, 2H).

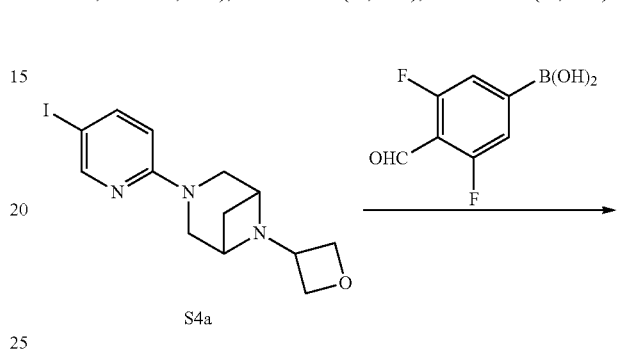

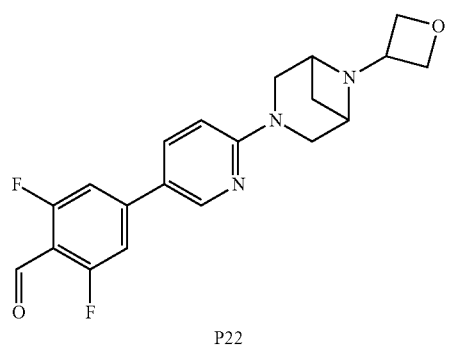

Synthesis of 2,6-difluoro-4-(6-(6-(oxetan-3-yl)-3,6-diazabicyclo[3.1.1]heptan-3-yl)pyridin-3-yl)benzaldehyde (P22)

A suspension of S4a (0.53 g, 1 mmol), by (3,5-difluoro-4-formylphenyl)boronic acid (413.8 mg, 2.0 mmol), and potassium carbonate (0.16 g, 4 mmol), and Cl$_2$Pd(tBu$_2$PPh)$_2$ (0.02 g, 0.37 mmol) in a mixture of dioxane (15 ml) and water (15 ml) were degassed for 10 min. The reaction mixture was heated at 60° C. for 3 h. After cooling to room temperature, the mixture was diluted with EtOAc and washed with sat. NaHCO$_3$ solution and brine then dried over Na$_2$SO$_4$, filtered and concentrated under reduced pressure. The crude residue was purified by silica column chromatography (1% to 15% (MeOH/(1% E$_3$N in EtOAc) to afford P22 (470 mg, 85%). MS (ESI) m/z 372.2 [M+H]$^+$. $^1$H NMR (400 MHz, Chloroform-d) δ 10.34 (s, 1H), 8.52 (d, J=2.5 Hz, 1H), 7.76 (dd, J=8.9, 2.5 Hz, 1H), 7.16 (d, J=10.4 Hz, 2H), 6.61 (d, J=8.8 Hz, 1H), 4.71 (t, J=6.2 Hz, 2H), 4.50 (s, 2H), 3.87 (t, J=6.2 Hz, 3H), 3.57 (s, 4H), 2.78 (d, J=7.3 Hz, 1H), 1.64 (d, J=8.9 Hz, 1H).

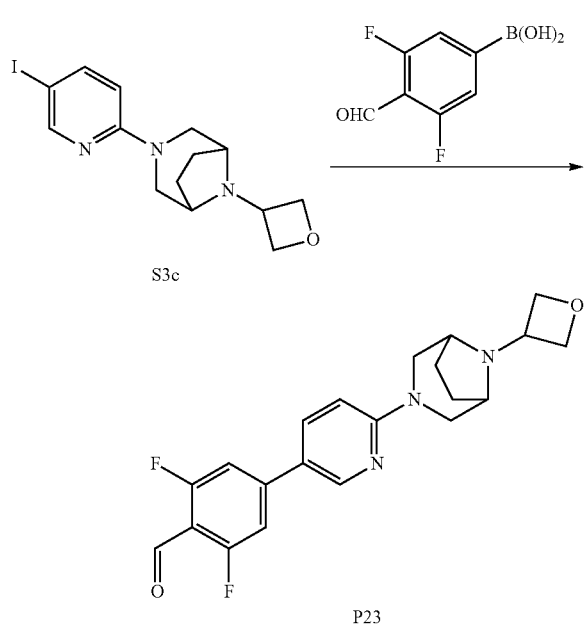

Synthesis of 2,6-difluoro-4-(6-(8-(oxetan-3-yl)-3,8-diazabicyclo[3.2.1]octan-3-yl)pyridin-3-yl)benzaldehyde (P23)

The title compound P23 was prepared according to the method presented for the synthesis of compound P20 but instead utilizing S3c. MS (ESI) m/z 386.1 [M+H]⁺.

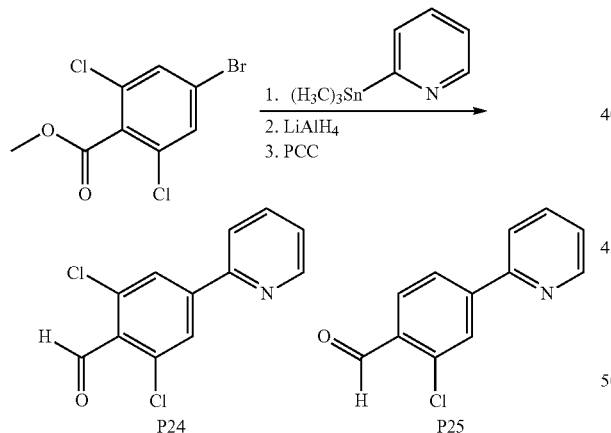

Synthesis of 2,6-dichloro-4-(pyridin-2-yl)benzaldehyde (P24) and 2-chloro-4-(pyridin-2-yl)benzaldehyde (P25)

In a sealed tube, methyl 4-bromo-2,6-dichlorobenzoate both (3.18 g, 11.2 mmol) and 2-(trimethylstannyl)pyridine (1.94 ml, 11.2 mmol) and tetrakis(triphenyl phosphine) palladium (647.1 mg, 0.56 mmol) are suspended in DMF (25 mL). The mixture was degassed with argon for 10 min heated to 100° C. for 18 hours, and then at room temperature. After 48 h the reaction was diluted with EtOAc and washed with KF (3 g in 50 mL water) and brine (3×) and dried over Na₂SO₄, filtered and concentrated under reduced pressure. The crude residue was purified by silica column chromatography (0% to 20% EtOAc/hexanes) to afford methyl 2,6-dichloro-4-(pyridin-2-yl)benzoate (1.5 g, 47.5%). This material was dissolved in THF (25 mL), cooled to 0° C., then lithium aluminum hydride (0.4 g, 10.63 mmol) was added slowly, after the addition was completed, the reaction mixture was warmed up slowly to room temperature and stirred for 1 h, then cooled back to 0° C. added water (500 uL) slowly (vigorous gas evolution), followed by NaOH (2 M, 500 uL) then water (1500 uL). The slurry was stirred at room temperature. After 1 h, Na₂SO₄ was added, and then the mixture was filtered through Celite. The solid was rinsed with Et₂O (~200 mL), and the filtrate was concentrated under reduced pressure, the residue was diluted with EtOAc and washed with water then dried over Na₂SO₄, filtered and concentrated under reduced pressure. The crude residue (1.5 g, 5.9 mmol) was combined with pyridinium chlorochromate (1.91 g, 8.85 mmol) and Celite (700 mg, 7 mmol), DCM (10 mL) was added and the reaction mixture was stirred at room temperature for 48 h. The reaction was filtered through a Celite frit with a small plug of silica, and rinsed several times with DCM/EtOAc, and then the filtrate was dried over Na₂SO₄, filtered and concentrated under reduced pressure. The crude residue was purified by silica column chromatography to afford P24 (392 mg, 26.3%). MS (ESI) m/z 252.0 [M+H]⁺. 1H NMR (400 MHz, Chloroform-d) δ 10.54 (s, 1H), 8.74 (ddd, J=4.8, 1.8, 0.9 Hz, 1H), 8.06 (s, 2H), 7.83 (ddd, J=8.0, 7.4, 1.8 Hz, 1H), 7.77 (dt, J=8.0, 1.1 Hz, 1H), 7.36 (ddd, J=7.4, 4.8, 1.2 Hz, 1H) and P25 (195 mg, 15.2%). MS (ESI) m/z 218.1 [M+H]⁺. 1H NMR (400 MHz, Chloroform-d) δ 10.52 (d, J=0.8 Hz, 1H), 8.74 (ddd, J=4.8, 1.7, 1.0 Hz, 1H), 8.17 (dd, J=1.6, 0.5 Hz, 1H), 8.07-7.95 (m, 2H), 7.91-7.75 (m, 2H), 7.39-7.29 (m, 1H).

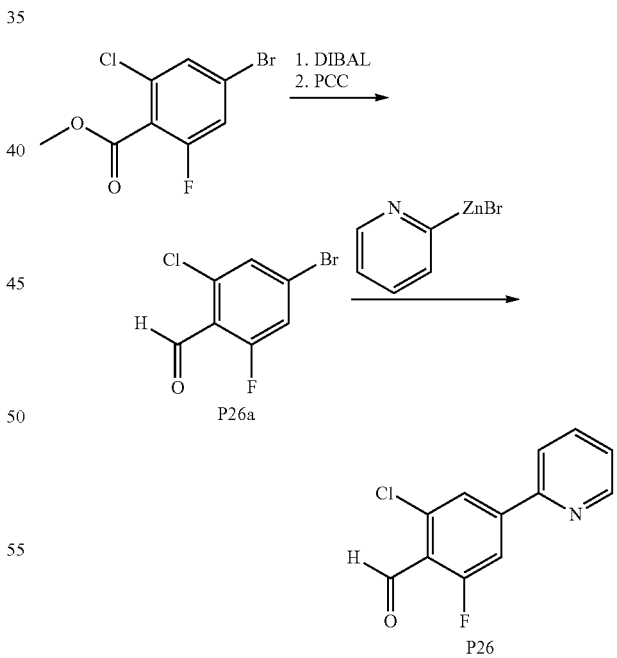

Synthesis 4-bromo-2,6-difluorobenzaldehyde (P26a)

To a solution of methyl 4-bromo-2-chloro-6-fluorobenzoate (5.6 g, 20.94 mmol) in DCM (100 mL) at −78° C., was added dropwise diisobutylaluminum hydride (1.0M in toluene, 60 ml). After 4.5 h the reaction mixture was quenched with MeOH (2.4 mL), then NaOH (6.0 M, 2.4 mL) followed by water (5 mL). The reaction was stirred for 1 h, and then Na$_2$SO$_4$ was added, filtered, and concentrated under vacuum, the residue (4.96 g, 20.71 mmol) was dissolved in DCM (100 mL) and cooled to 5° C., then pyridinium chlorochromate (6.27 g, 0.03 mol) was added and the mixture was stirred overnight, allowing to slowly warm to room temperature. Silica gel (10 g) was added, the mixture was filtered through a 1.5 inch plug of silica gel eluting with 5:1 DCM/EtOAc to give P26a (4.67 g, 92%). $^1$H NMR (400 MHz, Chloroform-d) δ 10.38 (s, 1H), 7.54-7.41 (m, 1H), 7.31 (dd, J=9.7, 1.8 Hz, 1H). $^{19}$F NMR (377 MHz, Chloroform-d) δ -113.31 (d, J=9.7 Hz).

Synthesis of 2-chloro-6-fluoro-4-(pyridin-2-yl)benzaldehyde (P26)

To a solution of P26a (2.5 g, 10.53 mmol) and Pd(tBu$_2$PPh)$_2$Cl$_2$ (213 mg, 0.34 mmol) in methyl tetrahydrofuran (7 mL) at room temperature, was added 2-pyridylzinc bromide (0.5M in THF, 28.43 ml). The reaction was degassed with Ar for 10 min, and then warmed to 60° C. After 3 h the mixture was cooled to room temperature, diluted with EtOAc and washed with saturated solution of NH$_4$Cl. The organic extract was dried over Na$_2$SO$_4$, filtered and concentrated under reduced pressure. The crude residue was purified by silica column chromatography (3%-35% EtOAc in 1:1 DCM/hexane) to afford P26 (1.09 g, 41%) MS (ESI) m/z 236.1 [M+H]$^+$. $^1$H NMR (400 MHz, Chloroform-d) δ 10.49 (d, J=1.1 Hz, 1H), 8.74 (ddd, J=4.8, 1.8, 1.0 Hz, 1H), 7.96 (t, J=1.4 Hz, 1H), 7.86 (d, J=1.8 Hz, 0H), 7.85-7.80 (m, 1H), 7.78 (q, J=1.1 Hz, 1H), 7.77-7.74 (m, 1H), 7.36 (ddd, J=7.4, 4.8, 1.2 Hz, 1H). $^{19}$F NMR (377 MHz, Chloroform-d) δ -114.35 (d, J=11.6 Hz).

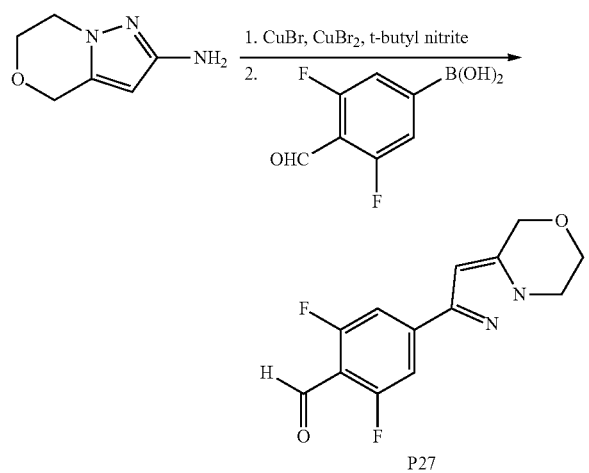

Synthesis of 4-(6,7-dihydro-4H-pyrazolo[5,1-c][1,4]oxazin-2-yl)-2,6-difluorobenzaldehyde (P27)

6,7-dihydro-4H-pyrazolo[5,1-c][1,4]oxazin-2-amine (1 g, 0.01 mol) in CH$_3$CN (5 mL) at 15° C. was combined with cuprous bromide (1.24 g, 0.01 mol) and Cupric bromide (16.05 mg, 0.07 mmol), then tert-Butyl nitrite (1.11 ml, 0.01 mol) was added very slowly and the reaction was stirred overnight. The mixture was quenched with aqueous NH4Cl, diluted with DCM, the layers were splitted, and the organic layer was dried over Na$_2$SO$_4$, filtered and concentrated under reduced pressure. The crude residue was purified by silica column chromatography (7%-40% EtOAc/hexanes), the product (0.59 g, 2.91 mmol) was combined with 3,5-Difluoro-4-formylphenylboronic acid (0.81 g, 4.36 mmol), PdCl$_2$(tBu$_2$PPh)$_2$ (0.08 g, 0.12 mmol), and potassium phosphate tribasic monohydrate (1.67 g, 7.27 mmol) in 2-methyltetrahydrofuran (25 mL) and water (60 mL) was degassed for 10 min with argon, then heated to reflux for 3 h. The reaction mixture was cooled to room temperature, diluted with EtOAc, washed with water, 5% citric acid solution, and brine. The separated organic layer was dried over Na$_2$SO$_4$, filtered and concentrated under reduced pressure. The residue was crystallized from EtOAc/ether to afford P27 (486 mg, 63%) MS (ESI) m/z 265.1 [M+H]$^+$.

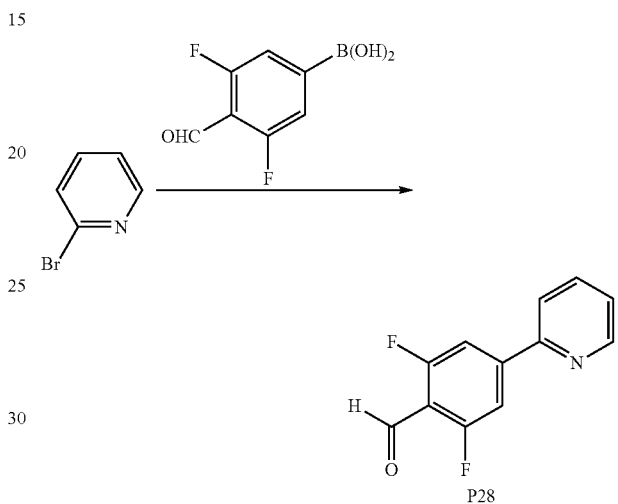

Synthesis of 2,6-difluoro-4-(pyridin-2-yl)benzaldehyde (P28)

The title compound P28 was prepared according to the method presented for the synthesis of compound P20 but instead utilizing 2-bromopyridine. MS (ESI) m/z 202.2 [M+H]$^+$.

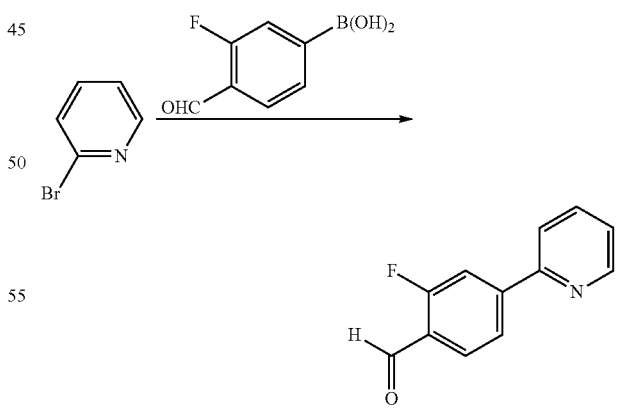

Synthesis of 2,6-difluoro-4-(pyridin-2-yl)benzaldehyde (P29)

The title compound P29 was prepared according to the method presented for the synthesis of compound P20 but instead utilizing 2-bromopyridine and (3-fluoro-4-form-ylphenyl)boronic acid. MS (ESI) m/z 220.2 [M+H]+.

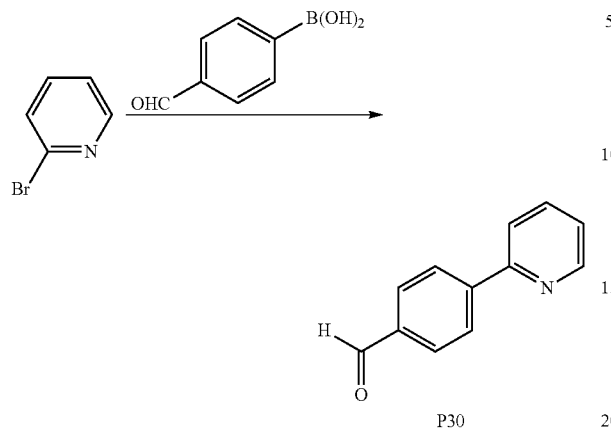

P30

Synthesis of 4-(pyridin-2-yl)benzaldehyde (P30)

The title compound P30 was prepared according to the method presented for the synthesis of compound P20 but instead utilizing 2-bromopyridine and (4-formylphenyl)boronic acid. MS (ESI) m/z 184.1 [M+H]+.

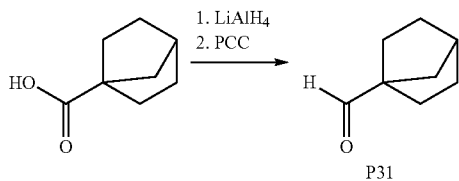

P31

Synthesis of bicyclo[2.2.1]heptane-1-carbaldehyde (P31)

Bicyclo[2.2.1]heptane-1-carboxylic acid (1000 mg, 0.01 mol) was dissolved in methyl tetrahydrofurane (3 mL), cooled to 0° C., then lithium aluminum hydride (0.5 g, 14 mmol) was added slowly, after the addition was completed, the reaction mixture was warmed up slowly to room temperature and stirred for 2 h, the mixture was cooled back to 0° C. added water (540 uL) slowly (vigorous gas evolution), followed by NaOH (2 M, 540 uL) then water (1500 uL). The slurry was stirred at room temperature. After 1 h Na$_2$SO$_4$ was added then the mixture was filtered through Celite. The solid was rinsed with DCM (~200 mL), and the filtrate was concentrated under reduced pressure. The crude residue (900 mg, 7.13 mmol) was dissolved in DCM (10 mL) cooled in an ice bath and combined with pyridinium chlorochromate (2.61 g, 12.12 mmol) and Celite (700 mg, 7 mmol), the reaction was allowed to war up to room temperature slowly and stirred for 48 h. The reaction was filtered through a Celite frit with a small plug of silica, and rinsed several times with DCM, and then the filtrate was concentrated under reduced pressure at 5° C. to afford P31 (1.7 g, 95%). $^1$H NMR (400 MHz, Chloroform-d) δ 9.85 (s, 1H), 2.41 (td, J=4.2, 2.1 Hz, 1H), 2.04-1.27 (m, 10H).

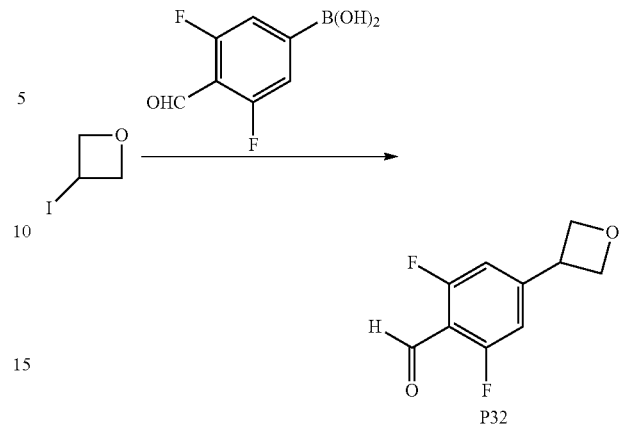

P32

Synthesis of 2,6-difluoro-4-(oxetan-3-yl)benzaldehyde (P32)

In a sealed tube, 3-Iodo-oxetane (0.24 ml, 3 mmol), (3,5-difluoro-4-formylphenyl)boronic acid (250 mg, 1.34 mmol), 4,4'-Di-tert-butyl-2,2'-dipyridyl (18.05 mg, 0.07 mmol) Ni(NO3)2-6H2O (19.55 mg, 0.07 mmol) and Potassium carbonate (557.51 mg, 4.03 mmol) in 1,4-Dioxane (5 ml) were combined. The mixture was degassed with argon for 10 min heated to 80° C. for 12 hours, and then cooled to room temperature. After 48 h the reaction was diluted with EtOAc and washed with brine (2x) and dried over Na$_2$SO$_4$, filtered and concentrated under reduced pressure. The crude residue was purified by silica column chromatography (10% to 30% EtOAc/hexanes) to afford P32 (49 mg, 18%). 1H NMR (400 MHz, Chloroform-d) δ 10.26 (d, J=1.2 Hz, 1H), 6.99 (d, J=9.5 Hz, 2H), 5.04 (dd, J=8.2, 6.3 Hz, 2H), 4.62 (t, J=6.3 Hz, 2H), 4.14 (tt, J=8.2, 6.2 Hz, 1H).

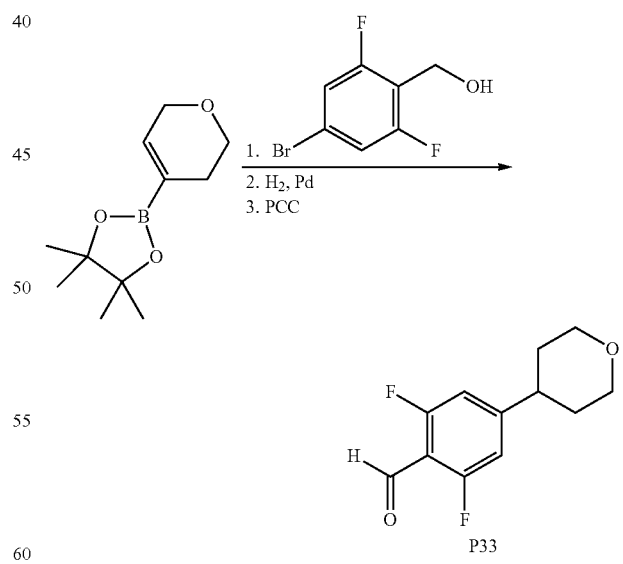

P33

Synthesis of 2,6-difluoro-4-(tetrahydro-2H-pyran-4-yl)benzaldehyde (P33)

3,6-Dihydro-2H-pyran-4-boronic acid pinacol ester (414.48 mg, 1.97 mmol), 4-Bromo-2,6-difluorobenzyl alcohol (0.4 g, 2 mmol), tetrakis(triphenylphosphine)palladium (103.63 mg, 0.09 mmol), and sodium carbonate (2M, 2.24 mL) in 1,4-dioxane (6 ml) were combined. The mixture was degassed with argon for 10 min heated to 80° C. for 12 hours, and then cooled to room temperature. The reaction was diluted with EtOAc and washed with brine (2×) and dried over $Na_2SO_4$, filtered and concentrated under reduced pressure. The crude residue was purified by silica column chromatography (20% to 50% EtOAc/hexanes), the product (405 mg, 1.79 mmol) was dissolved in EtOAc (8 mL), Palladium (10% on C, 38.1 mg, 0.36 mmol) was added and the mixture was stirred at room temperature under hydrogen for 18 h. The mixture was filtered through Celite, and rinsed several times with EtOAc, the filtrate was concentrated under reduced pressure.

The crude residue (450 mg, 1.97 mmol) was dissolved in DCM (10 mL) and combined with pyridinium chlorochromate (637.49 mg, 2.96 mmol), the reaction was stirred at room temperature for 48 h. The reaction was then filtered through a Celite and rinsed several times with DCM, the filtrate was concentrated under reduced pressure to afford P33. 1H NMR (400 MHz, Chloroform-d) δ 10.28 (d, J=1.2 Hz, 1H), 6.85 (d, J=10.0 Hz, 2H), 4.08 (dt, J=11.5, 3.2 Hz, 2H), 3.60-3.33 (m, 2H), 2.90-2.71 (m, 1H), 1.83-1.70 (m, 4H).

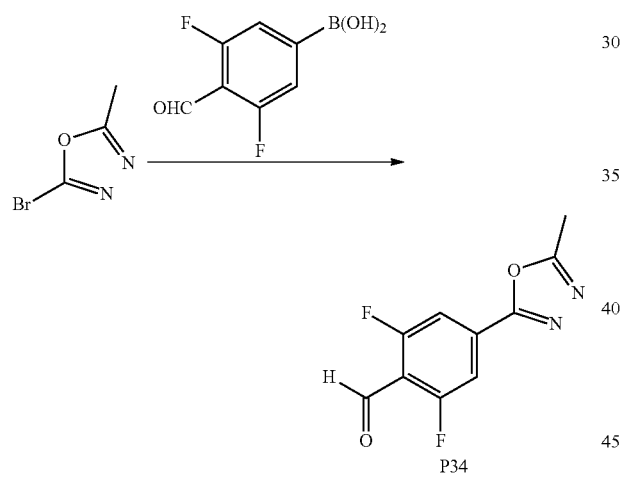

P34

Synthesis of 2,6-difluoro-4-(5-methyl-1,3,4-oxadiazol-2-yl)benzaldehyde (P34)

The title compound P34 was prepared according to the method presented for the synthesis of compound P1 but instead utilizing 2-bromo-5-methyl-1,3,4-oxadiazole. MS (ESI) m/z 225.1 $[M+H]^+$.

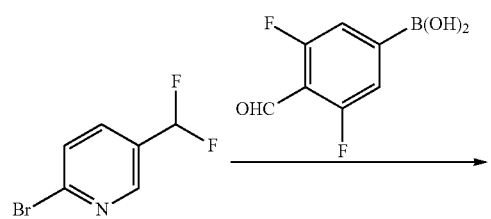

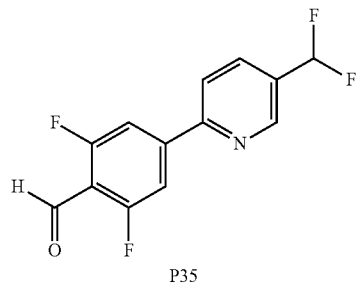

P35

Synthesis of 4-(5-(difluoromethyl) pyridin-2-yl)-2,6-difluorobenzaldehyde (P35)

The title compound P35 was prepared according to the method presented for the synthesis of compound P1 but instead utilizing 2-bromo-5-(difluoromethyl)pyridine. MS (ESI) m/z 270.1$[M+H]^+$.

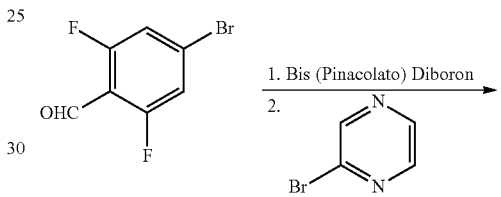

P36

Synthesis of 2,6-difluoro-4-(pyrazin-2-yl)benzaldehyde (P36)

A mixture of 4-bromo-2,6-difluorobenzaldehyde (2 g, 9.05 mmol), bis (pinacolato) diboron (3.22 g, 12.67 mmol), dichloro 1,1'-bis(diphenylphosphino)ferrocene palladium (II) dichloromethane (739.04 mg, 0.9 mmol) and potassium acetate (1776.34 mg, 18.1 mmol) in 1, 4-dioxane (18 mL) were heated to 90° C. for 12 hours. After cooling to room temperature 2-bromopyrazine (1.64 ml, 18.1 mmol), tetrakis (triphenylphosphine)palladium (1.05 g, 0.9 mmol) and potassium carbonate (2 M, 11.31 ml) were added. The mixture was degassed by pulling vacuum and back-filling with Ar (3×), then the reaction was heated to 90° C. for 12 hours, cooled to room temperature, diluted with EtOAc and washed with saturated solution of brine. The organic extract was dried over $Na_2SO_4$, filtered and concentrated under reduced pressure. The crude residue was purified by silica column chromatography (0%-100% EtOAc/DCM) to afford P36 MS (ESI) m/z 221.1 $[M+H]^+$.

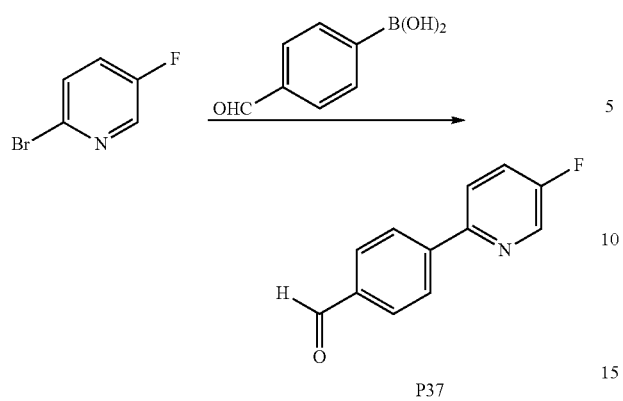

Synthesis of 4-(5-fluoropyridin-2-yl)benzaldehyde (P37)

The title compound P37 was prepared according to the method presented for the synthesis of compound P14 of but instead utilizing (4-formylphenyl)boronic acid. MS (ESI) m/z 202.14 [M+H]⁺.

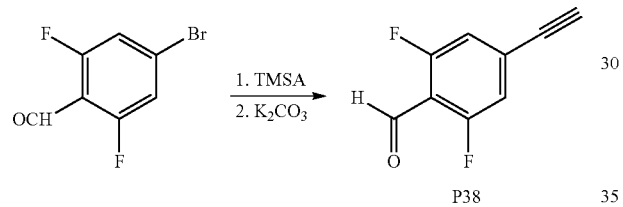

Synthesis of 4-ethynyl-2,6-difluorobenzaldehyde (P38)

A solution of 4-bromo-2,6-difluorobenzaldehyde Reactant 2 (6 g, 27.15 mmol), CuI (517.06 mg, 2.71 mmol) PdCl$_2$(tBu$_2$PPh)$_2$ (955.53 mg, 1.36 mmol) trimethylsilylacetylene (7.67 ml, 54.3 mmol) in a 3:1 mixture of CH$_3$CN (50 mL)/Et$_3$N (10 mL) was degassed with Argon for 10 min. The reaction mixture was heated to 70° C. for 18 h. After cooling to room temperature the mixture was filtered through silica, the filtrate was concentrated and purified by silica column chromatography (1%-15% EtOAc/Hex) The product was dissolved in MeOH (5 ml) and Potassium carbonate (1876.01 mg, 13.57 mmol) were added, the mixture was stirred at room temperature. After 20 min the reaction was concentrated to dryness, then diluted with DCM and washed with brine. The organic extract was dried over Na$_2$SO$_4$ to give p38 (2.99 g, 66%). ¹H NMR (400 MHz, Chloroform-d) δ 10.30 (d, J=1.1 Hz, 1H), 7.04 (d, J=9.1 Hz, 2H), 0.26 (s, 9H).

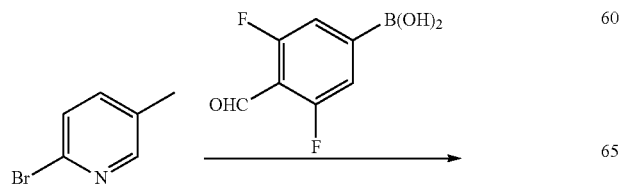

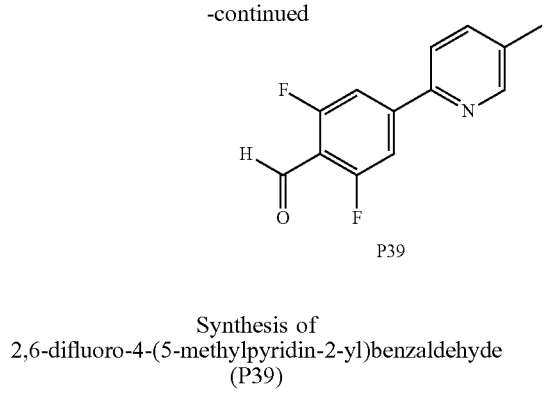

Synthesis of 2,6-difluoro-4-(5-methylpyridin-2-yl)benzaldehyde (P39)

The title compound P39 was prepared according to the method presented for the synthesis of compound P16 but instead utilizing 2-bromo-5-methylpyridine.

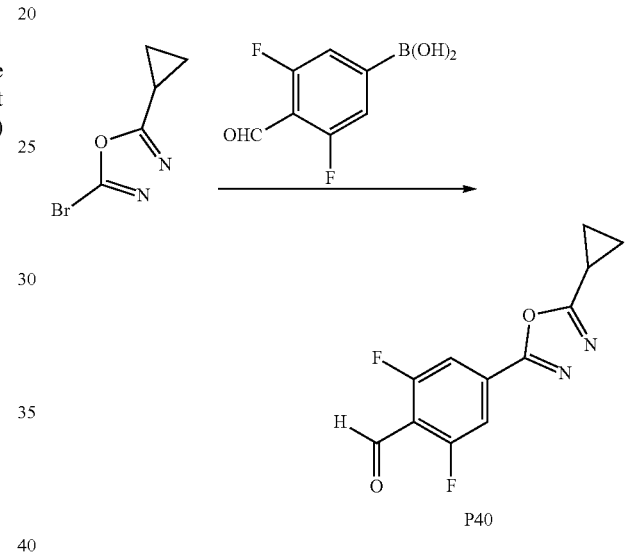

Synthesis of 4-(5-cyclopropyl-1,3,4-oxadiazol-2-yl)-2,6-difluorobenzaldehyde (P40)

The title compound P40 was prepared according to the method presented for the synthesis of compound P1 but instead utilizing 2-bromo-5-cyclopropyl-1,3,4-oxadiazole. MS (ESI) m/z 251.1 [M+H]⁺.

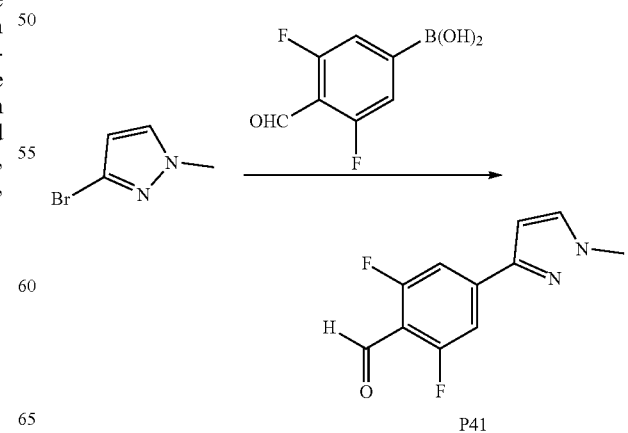

Synthesis of 2,6-difluoro-4-(1-methyl-1H-pyrazol-3-yl)benzaldehyde (P41)

A solution of 3-bromo-1-methyl-1H-pyrazole (0.14 g, 3.7 mol), (3,5-difluoro-4-formylphenyl)boronic acid (9.19 g, 49.43 mmol), sodium carbonate (8.72 g, 82.27 mmol), and tetrakis(triphenylphosphine)palladium (1.9 g, 1.64 mmol) in a mixture of 1,2-Dimethoxyethane (84 ml) and water (36 ml) was degassed for 10 min. The reaction mixture was heated at 100° C. for 18 h. After cooling to room temperature, the mixture was diluted concentrated in vacuo then diluted with EtOAc and washed with brine then dried over $Na_2SO_4$, filtered and concentrated under reduced pressure. The crude residue was purified by silica column chromatography (20% to 40% EtOAc/Hex to afford P41. MS (ESI) m/z 223.3 $[M+H]^+$.

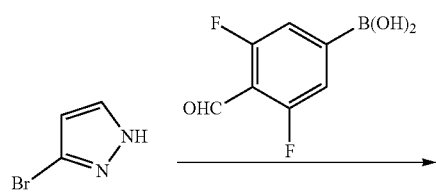

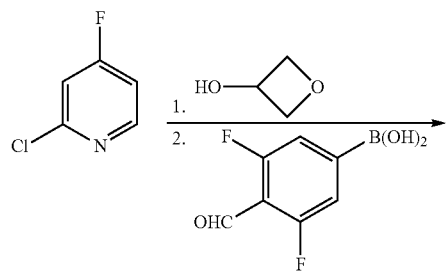

P42

Synthesis of 2,6-difluoro-4-(1H-pyrazol-3-yl)benzaldehyde (P42)

The title compound P42 was prepared according to the method presented for the synthesis of compound P1 but instead utilizing 3-bromo-1H-pyrazole. MS (ESI) m/z 209.1 $[M+H]^+$.

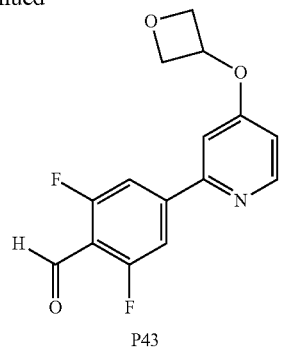

P43

Synthesis of 2,6-difluoro-4-(4-(oxetan-3-yloxy)pyridin-2-yl)benzaldehyde (P43)

To a suspension of NaH (60%, 310.79 mg, 7.77 mmol) in THF (11 mL) was added oxetan-3-ol (0.42 ml, 6.66 mmol) dropwise, the mixture was stirred for 30 minutes followed by addition of 2-chloro-4-fluoropyridine (0.5 ml, 5.55 mmol). The reaction mixture was stirred overnight, diluted with EtOAc and washed with water and brine then dried over $Na_2SO_4$, filtered and concentrated under reduced pressure. The crude residue was purified by silica column chromatography (30% to 60% EtOAc/Hex) the product (849 mg, 4.57 mmol) was combined with (3,5-difluoro-4-formylphenyl)boronic acid (1020.52 mg, 5.49 mmol) potassium carbonate (2M, 5.49 ml) and Pd(dppf)Cl2 (279.29 mg, 0.46 mmol) in DME (23 ml), the mixture was degassed by pulling vacuum and back-filling with Ar (5×) heated to reflux for 3 h. After cooling to room temperature, the mixture was diluted with EtOAc and washed with water and brine then dried over $Na_2SO_4$, filtered and concentrated under reduced pressure. The crude residue was purified by silica column chromatography (30% to 60% EtOAc/Hex) to afford P43 (1.22 g, 80%). MS (ESI) m/z 292.1 $[M+H]^+$.

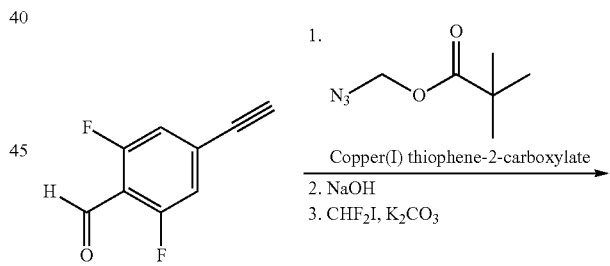

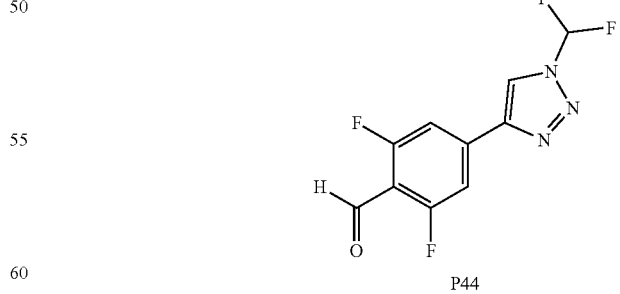

P44

Synthesis of 4-(1-(difluoromethyl)-1H-1,2,3-triazol-4-yl)-2,6-difluorobenzaldehyde (P44)

4-ethynyl-2,6-difluorobenzaldehyde (1.5 g, 9.0 mmol) was dissolved in THF (10 mL). Copper(I) thiophene-2- carboxylate (115.71 mg, 0.9 mmol) was added followed by azidomethyl pivalate (2.1 mL, 13.5 mmol) over 5 minutes. After 15 minutes, complete conversion was observed by LCMS analysis. The reaction was quenched with aqueous NaHCO₃, and the intermediate product was extracted into ethyl acetate, dried over sodium sulfate, filtered, and concentrated in vacuo. The crude mixture was slurried in 40 mL 1:1 MeOH:EtOH, and aqueous NaOH solution was added (2M, 9.9 mL, 19.9 mmol). After 30 minutes aqueous NaHCO₃ was added, and the intermediate product was extracted into ethyl acetate, dried over sodium sulfate, filtered, and concentrated in vacuo. The crude product was transferred using THF (20 mL) to a 500 mL pressure vessel containing potassium carbonate (4.4 g, 32 mmol) and a magnetic stir bar. A solution of difluoroiodomethane (10% in THF, 68 mL, 36 mmol) was added and the vessel was sealed. The mixture was stirred overnight at 50° C. overnight. The crude mixture was filtered, concentrated in vacuo and purified by flash column chromatography (0→25% EtOAc in 1:1 hexanes:DCM). The desired regioisomer was major and was isolated in the middle fractions. 1H NMR (400 MHz, Chloroform-d) δ 10.36 (s, 1H), 8.31 (s, 1H), 7.62 (t, J=58.8 Hz, 1H), 7.59-7.51 (m, 2H). 19F NMR (377 MHz, Chloroform-d) δ −95.78 (d, J=58.9 Hz), −113.68 (d, J=9.2 Hz).

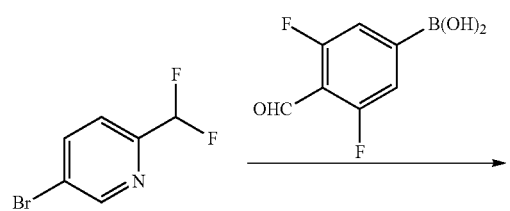

Synthesis of 4-(6-(difluoromethyl)pyridin-3-yl)-2,6-difluorobenzaldehyde (P45)

The title compound P45 was prepared according to the method presented for the synthesis of compound P16 but instead utilizing 5-bromo-2-(difluoromethyl)pyridine. ¹H NMR (400 MHz, Chloroform-d) δ 10.40 (s, 1H), 8.94-8.79 (m, 1H), 8.04 (dd, J=8.2, 2.3 Hz, 1H), 7.79 (d, J=8.2 Hz, 1H), 7.25 (d, J=9.3 Hz, 2H), 6.70 (t, J=55.2 Hz, 1H). ¹⁹F NMR (377 MHz, Chloroform-d) δ −113.37 (d, J=9.3 Hz), −116.56 (d, J=55.5 Hz).

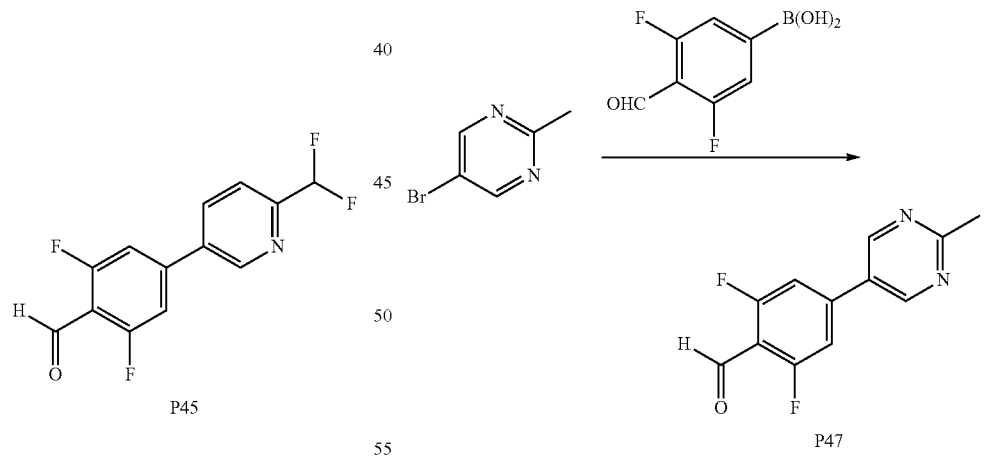

Synthesis of 4-(1-cyclopropyl-1H-pyrazol-4-yl)benzaldehyde (P46)

The title compound P46 was prepared according to the method presented for the synthesis of compound P7 but instead utilizing (4-formylphenyl)boronic acid and 4-bromo-1-cyclopropyl-1H-pyrazole. MS (ESI) m/z 213.2 [M+H]⁺.

Synthesis of 2,6-difluoro-4-(2-methylpyrimidin-5-yl)benzaldehyde (P47)

The title compound P47 was prepared according to the method presented for the synthesis of compound P16 but instead utilizing 5-bromo-2-methylpyrimidine. MS (ESI) m/z 235.2 [M+H]⁺. 1H NMR (400 MHz, Chloroform-d) δ 10.38 (t, J=1.0 Hz, 1H), 8.86 (s, 2H), 7.30-7.14 (m, 3H), 2.82 (s, 3H).

2.2 Synthesis of S Intermediates

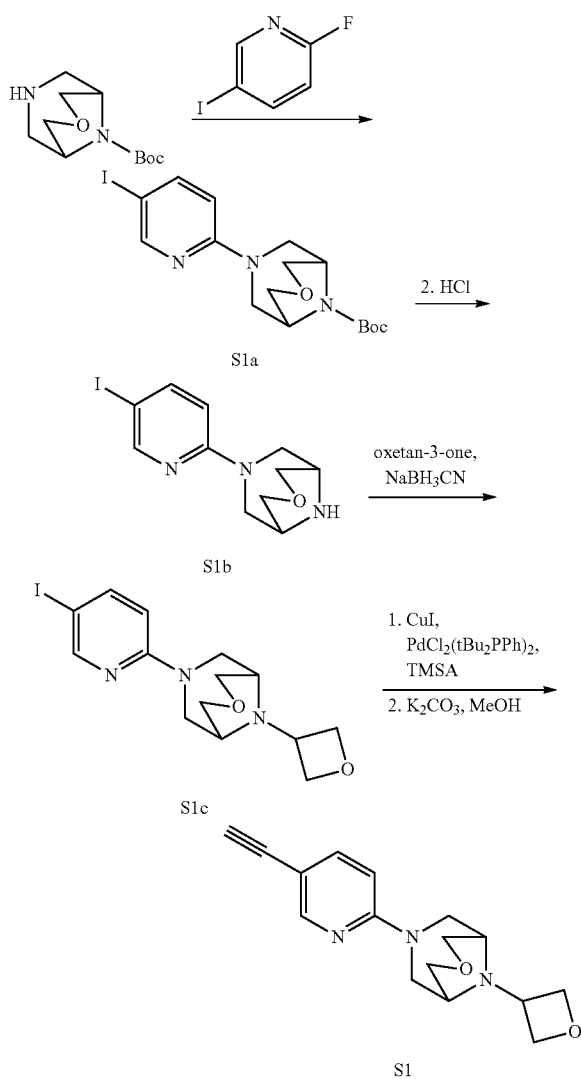

Synthesis of tert-butyl 7-(5-iodopyridin-2-yl)-3-oxa-7,9-diazabicyclo[3.3.1]nonane-9-carboxylate (S1a)

A solution of tert-butyl 3-oxa-7,9-diazabicyclo[3.3.1]nonane-9-carboxylate (1 g, 4.38 mmol) 2-fluoro-5-iodopyridine (1.12 g, 5.04 mmol), and sodium carbonate (0.84 g, 7.88 mmol) in 1-Methyl-2-pyrrolidinone (4 ml) was heated at 85° C. overnight. The mixture was cooled to room temperature, diluted with water and extracted into DCM. The organic extract was dried over Na$_2$SO$_4$ filtered and concentrated under reduced pressure. The residue was purified by silica chromatography to yield S1a (1.57 g, 62.3%). MS (ESI) m/z 431.9 [M+H]$^+$. $^1$H NMR (400 MHz, Chloroform-d) δ 8.30 (dd, J=2.4, 0.7 Hz, 1H), 7.66 (dd, J=9.0, 2.3 Hz, 1H), 6.44 (d, J=9.0 Hz, 1H), 4.25 (d, J=12.7 Hz, 1H), 4.21-4.00 (m, 3H), 3.97-3.86 (m, 2H), 3.80 (t, J=11.9 Hz, 2H), 3.26 (t, J=15.1 Hz, 2H), 1.48 (s, 9H).

Synthesis of 7-(5-iodopyridin-2-yl)-3-oxa-7,9-diazabicyclo[3.3.1]nonane (S1b)

To a solution of S1a (1.57 g, 0.004 mol) in DCM (15 mL) in a water bath at room temperature was added was added HCl (4.0M in dioxane, 4.6 mL). The reaction was stirred at room temperature overnight. The reaction was concentrated to dryness. MS (ESI) m/z 332.0 [M+H]$^+$. $^1$H NMR (400 MHz, Methanol-d4) δ 8.26 (dd, J=2.2, 0.7 Hz, 1H), 8.22 (ddd, J=9.5, 2.2, 1.0 Hz, 1H), 7.27 (d, J=9.7 Hz, 1H), 4.60 (d, J=14.4 Hz, 2H), 4.21 (dt, J=13.5, 0.9 Hz, 2H), 4.08 (dt, J=13.3, 2.4 Hz, 2H), 3.88 (d, J=14.6 Hz, 2H), 3.81 (s, 2H).

Synthesis of 7-(5-iodopyridin-2-yl)-9-(oxetan-3-yl)-3-oxa-7,9-diazabicyclo[3.3.1]nonane (S1c)

To S1b (0.62 g, 8.62 mmol) suspended in NMP (6 mL), was added Et$_3$N (0.12 ml, 0.8 mmol), oxetan-3-one (0.51 ml, 8.5 mmol), and sodium cyanoborohydride (2.62 g, 41.72 mmol) was added and the reaction mixture was stirred for 5 min then more Et$_3$N (0.18 ml, 0.1 mmol), stirred at room temperature for 4 h, then warmed up to 30° C. After 2 h the reaction was cooled to room temperature, diluted with EtOAc and washed with brine. The organic extract was dried over Na$_2$SO$_4$ filtered and concentrated under reduced pressure to afford S1c (0.84 g, 95%). MS (ESI) m/z 388.1 [M+H]$^+$.

Synthesis of 7-(5-ethynylpyridin-2-yl)-9-(oxetan-3-yl)-3-oxa-7,9-diazabicyclo[3.3.1]nonane (S1)

A solution of S1c (0.84 g, 0 mol), CuI (24.73 mg, 0.13 mmol) PdCl$_2$(tBu$_2$PPh)$_2$ (45.7 mg, 0.06 mmol), trimethylsilylacetylene (0.92 ml, 0.01 mol), in a 3:1 mixture of CH$_3$CN (9 mL)/Et$_3$N (3 mL) was degassed with Argon for 10 min. The reaction mixture was heated to 40° C. for 90 min. The reaction was diluted with EtOAc and washed with NaHCO$_3$ solution and dried over Na$_2$SO$_4$, filtered and concentrated under reduced pressure. The crude residue was dissolved in MeOH (5 ml) and Potassium carbonate (0.45 g, 3.0 mmol) were added, the mixture was stirred at room temperature. After 15 min the reaction was concentrated to dryness, then diluted with DCM and washed with brine. The organic extract was dried over Na$_2$SO$_4$ to give S1 (300 mg 48%). MS (ESI) m/z 286.2 [M+H]$^+$. $^1$H NMR (400 MHz, Chloroform-d) δ 8.17 (dd, J=2.3, 0.8 Hz, 1H), 7.40 (dd, J=8.9, 2.3 Hz, 1H), 6.35 (dd, J=8.9, 0.8 Hz, 1H), 4.55 (t, J=6.2 Hz, 2H), 4.42 (t, J=5.9 Hz, 2H), 4.25 (p, J=6.2 Hz, 1H), 3.84 (dt, J=11.3, 2.2 Hz, 2H), 3.78 (d, J=12.9 Hz, 2H), 3.71 (dt, J=11.5, 0.9 Hz, 2H), 3.24 (ddd, J=12.9, 4.9, 2.0 Hz, 2H), 2.92 (s, 1H), 2.65-2.52 (m, 2H).

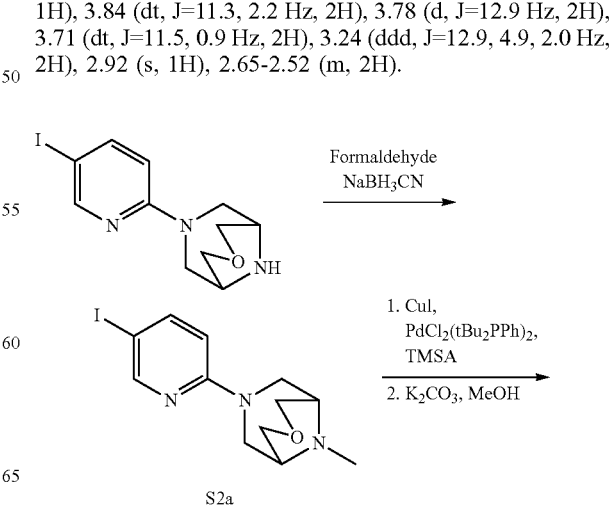

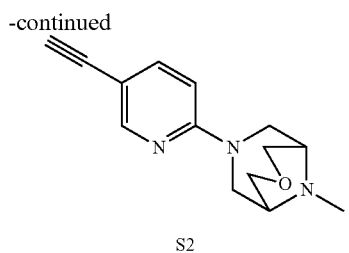

Synthesis of 7-(5-ethynylpyridin-2-yl)-9-methyl-3-oxa-7,9-diazabicyclo[3.3.1]nonane The title compound S2 was prepared according to the method presented for the synthesis of compound S1 but instead utilizing formaldehyde. MS (ESI) m/z 244.2 [M+H]$^+$. $^1$H NMR (400 MHz, Chloroform-d) δ 8.33 (d, J=2.3 Hz, 1H), 7.55 (dd, J=8.9, 2.3 Hz, 1H), 6.52 (d, J=8.9 Hz, 1H), 4.01 (d, J=11.2 Hz, 2H), 3.91 (d, J=12.9 Hz, 2H), 3.85 (d, J=11.2 Hz, 2H), 3.53 (ddd, J=13.0, 4.8, 2.0 Hz, 2H), 3.07 (s, 1H), 2.86-2.75 (m, 2H), 2.62 (s, 3H).

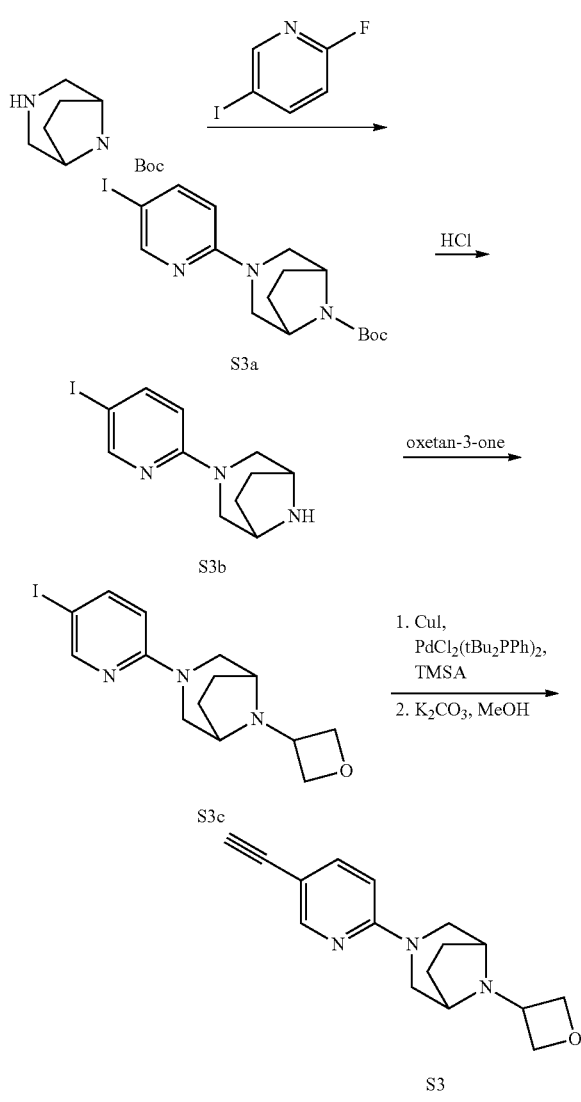

Synthesis of tert-butyl 3-(5-iodopyridin-2-yl)-3,8-diazabicyclo[3.2.1]octane-8-carboxylate (S3a)

The title compound S3a was prepared according to the method presented for the synthesis of compound S1a but instead utilizing tert-butyl 3,8-diazabicyclo[3.2.1]octane-8-carboxylate. MS (ESI) m/z 415.8 [M+H]$^+$. $^1$H NMR (400 MHz, Chloroform-d) δ 8.36-8.26 (m, 1H), 7.65 (dd, J=9.0, 2.4 Hz, 1H), 6.40 (d, J=9.0 Hz, 1H), 4.33 (s, 2H), 3.82 (d, J=40.5 Hz, 2H), 3.05 (s, 2H), 1.94 (dd, J=8.7, 4.6 Hz, 2H), 1.73 (d, J=7.3 Hz, 2H), 1.47 (s, 9H).

Synthesis of 3-(5-iodopyridin-2-yl)-3,8-diazabicyclo[3.2.1]octane hydrochloride (S3b)

The title compound S3b was prepared according to the method presented for the synthesis of compound S1b but instead utilizing S3a. MS (ESI) m/z 316.1 [M+H]$^+$.

Synthesis of 3-(5-iodopyridin-2-yl)-8-(oxetan-3-yl)-3,8 diazabicyclo[3.2.1]octane (S3c)

The title compound S3c was prepared according to the method presented for the synthesis of compound S1c but instead utilizing S3b. MS (ESI) m/z 372.1 [M+H]$^+$. $^1$H NMR (400 MHz, Chloroform-d) δ 8.22 (d, J=2.3 Hz, 1H), 7.57 (dd, J=8.9, 2.4 Hz, 1H), 6.30 (d, J=9.0 Hz, 1H), 4.65 (t, J=6.3 Hz, 2H), 4.52 (t, J=5.8 Hz, 2H), 3.70 (dd, J=11.8, 2.4 Hz, 2H), 3.23-3.08 (m, 2H), 3.04 (dd, J=11.7, 2.2 Hz, 2H), 1.87-1.70 (m, 2H), 1.63 (d, J=7.5 Hz, 2H).

Synthesis of 3-(5-ethynylpyridin-2-yl)-8-(oxetan-3-yl)-3,8-diazabicyclo[3.2.1]octane (S3)

The title compound S3 was prepared according to the method presented for the synthesis of compound S1c but instead utilizing S3c. MS (ESI) m/z 244.0 [M+H]$^+$. $^1$H NMR (400 MHz, Methanol-d4) δ 8.16 (d, J=2.3 Hz, 1H), 7.55 (dd, J=8.9, 2.3 Hz, 1H), 6.66 (d, J=8.9 Hz, 1H), 4.76 (t, J=6.4 Hz, 3H), 4.57 (t, J=5.8 Hz, 3H), 3.88 (dd, J=12.2, 2.4 Hz, 3H), 3.78 (ddd, J=11.9, 6.5, 5.4 Hz, 1H), 3.43 (s, 1H), 3.29 (dd, J=6.9, 1.7 Hz, 4H), 3.10 (dd, J=11.9, 2.2 Hz, 3H), 1.93 (dd, J=8.7, 4.4 Hz, 2H), 1.68 (t, J=6.9 Hz, 2H).

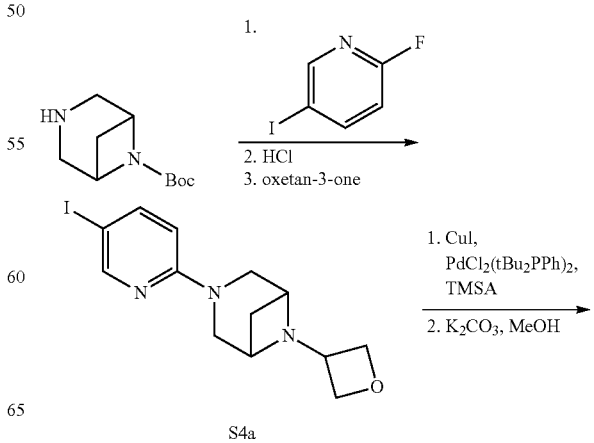

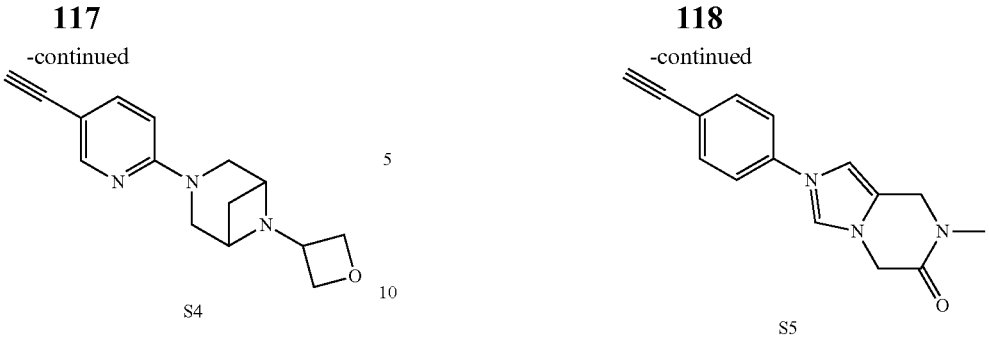

S4

Synthesis of 3-(5-iodopyridin-2-yl)-6-(oxetan-3-yl)-3,6-diazabicyclo[3.1.1]heptane (S4a)

The title compound S4a was prepared according to the method presented for the synthesis of compound S1c but instead utilizing tert-butyl 3,6-diazabicyclo[3.1.1]heptane-6-carboxylate. MS (ESI) m/z 358.0 [M+H]$^+$.

Synthesis of 3-(5-ethynylpyridin-2-yl)-6-(oxetan-3-yl)-3,6-diazabicyclo[3.1.1]heptane (S4)

The title compound S4 was prepared according to the method presented for the synthesis of compound S1 but instead utilizing S4a. MS (ESI) m/z 256.2 [M+H]$^+$. $^1$H NMR (400 MHz, Methanol-d4) δ 8.13 (d, J=2.3 Hz, 1H), 7.53 (dd, J=8.9, 2.3 Hz, 1H), 6.55 (d, J=8.9 Hz, 1H), 4.65 (t, J=6.3 Hz, 2H), 4.36 (dd, J=6.3, 4.7 Hz, 2H), 3.77 (dd, J=19.2, 5.7 Hz, 3H), 3.44 (s, 4H), 3.37 (s, 1H), 2.61 (dt, J=9.1, 6.2 Hz, 1H), 1.54 (d, J=9.1 Hz, 1H).

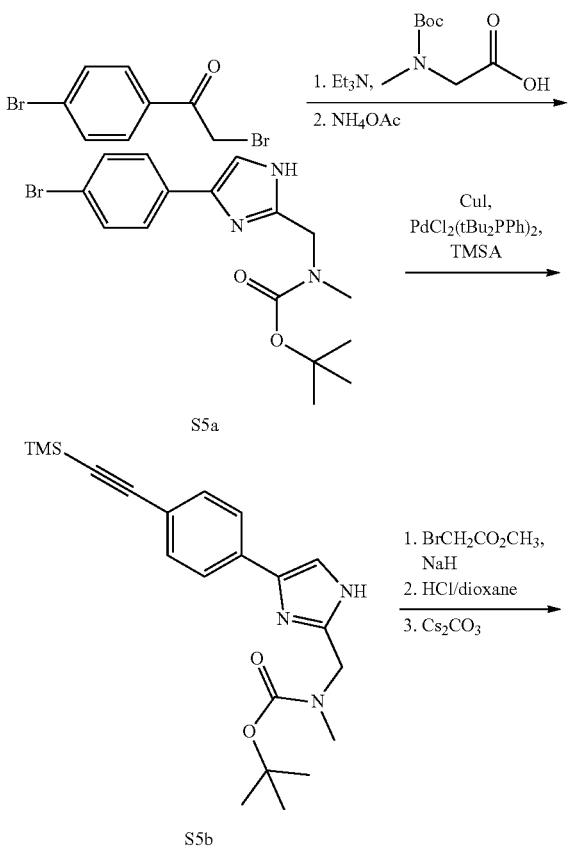

S5

Synthesis of tert-butyl ((4-(4-bromophenyl)-1H-imidazol-2-yl)methyl)(methyl)carbamate (S5a)

To a solution of N-(tert-butoxycarbonyl)-N-methylglycine (4.81 g, 25.41 mmol) and 2,4'-dibromoacetophenone (6.42 g, 23.1 mmol) in MeCN (50 ml) was added Et$_3$N 9 (3.84 ml, 0.03 mol), the mixture was stirred for 5 min (small exotherm), then warmed to 30° C. The mixture was cooled to room temperature, diluted with EtOAc and washed saturated NH4Cl, saturated NaHCO$_3$, and brine, then dried over Na$_2$SO$_4$, filtered and concentrated under reduced pressure. The residue was suspended in a mixture of isopropanol (10 ml) and toluene (100 ml) and ammonium acetate (37 g, 0.48 mol) was added, the reaction was refluxed for 4 h. Cooled to room temperature diluted with isopropyl acetate, washed with water, dried over Na$_2$SO$_4$, filtered, concentrated under reduced pressure and the residue was purified by column chromatography (50% to 100% EtOAc/Hexanes) to afford S5a (8.0 g, 90%) MS (ESI) m/z 368 [M+H]$^+$. 1H NMR (400 MHz, Methanol-d4) δ 7.61 (d, J=8.1 Hz, 2H), 7.54-7.45 (m, 2H), 7.40 (s, 1H), 4.50 (s, 2H), 2.91 (s, 3H), 1.45 (d, J=21.0 Hz, 9H).

Synthesis of tert-butyl methyl((4-(4-((trimethylsilyl)ethynyl)phenyl)-1H-imidazol-2-yl)methyl)carbamate (S5b)

A solution of S5a (8 g, 0.02 mol), CuI (0.249 g, 1.0 mmol), PdCl$_2$(tBu$_2$PPh)$_2$ (0.408 g, 0.655 mmol), trimethylsilylacetylene (12.44 ml, 0.09 mol) in a mixture of CH$_3$CN/Et$_3$N 3:1 (50 mL) was degassed with Argon for 10 min. The reaction mixture was heated to 65° C. overnight. The reaction was diluted with EtOAc and washed with NaHCO3 solution and dried over Na$_2$SO$_4$, filtered and concentrated under reduced pressure. The crude residue was used for the next step without purification (5.85 g, 70%). MS (ESI) m/z 384.3 [M+H]$^+$. $^1$H NMR (400 MHz, Methanol-d4) δ 7.66 (d, J=8.0 Hz, 2H), 7.45-7.31 (m, 3H), 4.84 (s, 2H), 2.91 (s, 4H), 1.46 (s, 9H), 0.23 (s, 9H).

Synthesis of 2-(4-ethynylphenyl)-7-methyl-7,8-dihydroimidazo[1,2-a]pyrazin-6(5H)-one (S5)

To an ice cooled solution of S5b (1450 mg, 0 mol) in 2-methyl tetrahydrofuran (3 ml) was added sodium hydride (60%, 0.21 g, 0.01 mol). After 10 min, methyl bromoacetate (0.72 ml, 0.01 mol) was added; the mixture was stirred for 5 min then warmed up to room temperature. After 30 min the reaction was diluted with EtOAc, rinsed with brine, dried over Na$_2$SO$_4$, filtered, concentrated under reduced pressure and the residue was purified by column chromatography (20% to 55% EtOAc/Hexanes). The product was dissolved in DCE (10 ml) and HCl (4.0M in dioxane, 11.69 ml)

warmed to 25 C. After 2 h the reaction was concentrated under vacuo. The residue was dissolved in DMF (10 ml), Cesium carbonate (3.05 g, 0.01 mol) was added, warmed up 65 C for 45 min, cooled to room temperature added MeOH (10 mL), stir 25 min. Slowly dilute with ~40 mL water, stir 20 min. Filter off precipitated solids, rinsing with 30% MeOH in water. Concentrated under reduce pressure and the crude material was carried on without further purification (0.479 g, 62%) MS (ESI) m/z 252.1 [M+H]⁺. ¹H NMR (400 MHz, DMSO-d6) δ 7.69 (d, J=8.0 Hz, 2H), 7.59 (s, 1H), 7.40 (d, J=8.0 Hz, 2H), 4.65 (s, 2H), 4.56 (s, 2H), 4.11 (s, 1H), 2.95 (s, 3H).

Hz, 1H), 3.90-3.75 (m, 1H), 3.31-3.10 (m, 2H), 2.93 (s, 1H), 2.82 (dd, J=9.5, 2.0 Hz, 1H), 2.73-2.60 (m, 1H), 1.82 (ddt, J=9.7, 2.4, 1.2 Hz, 1H), 1.73 (ddt, J=9.8, 2.5, 1.2 Hz, 1H).

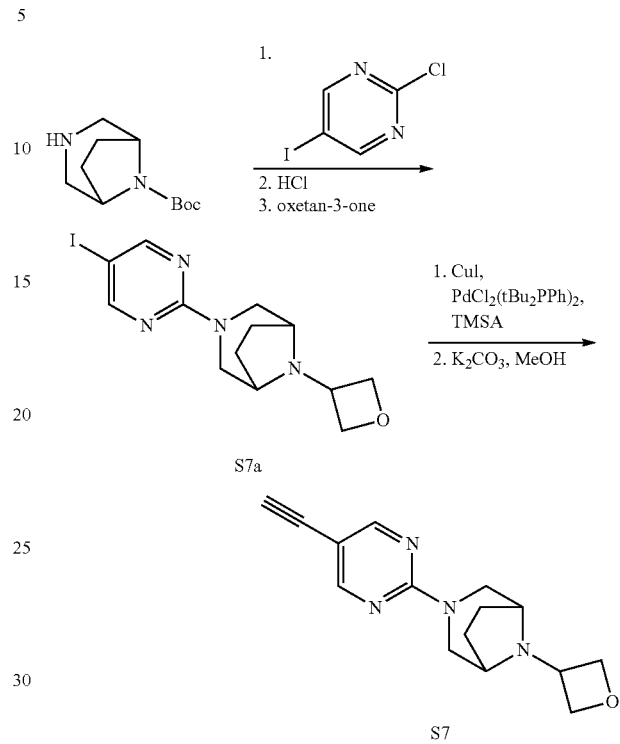

S7a

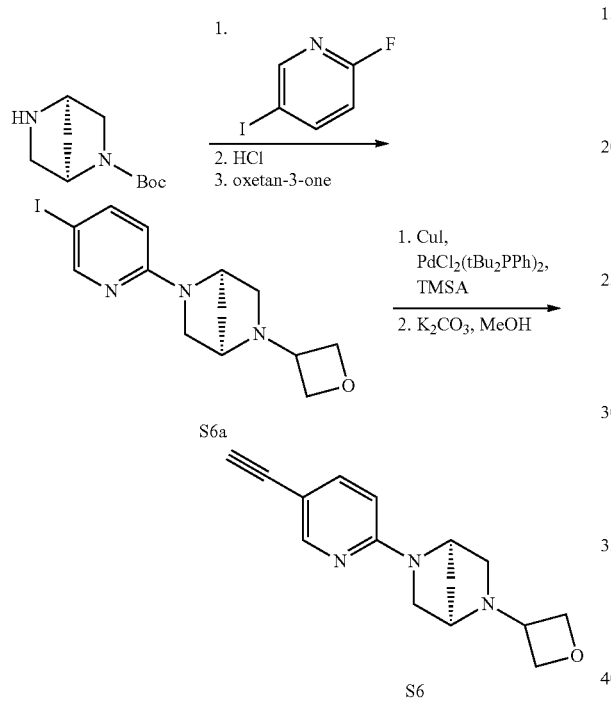

S6a

S6

Synthesis of (1R,4R)-2-(5-iodopyridin-2-yl)-5-(oxetan-3-yl)-2,5-diazabicyclo[2.2.1]heptane (S6a)

The title compound S6a was prepared according to the method presented for the synthesis of compound S1c but instead utilizing tert-butyl (1R,4R)-2,5-diazabicyclo[2.2.1]heptane-2-carboxylate. MS (ESI) m/z 358.0 [M+H]⁺. ¹H NMR (400 MHz, Chloroform-d) δ 8.25 (dd, J=2.3, 0.8 Hz, 1H), 7.61 (ddd, J=8.8, 2.3, 0.6 Hz, 1H), 6.18 (dd, J=8.8, 0.8 Hz, 1H), 4.71-4.58 (m, 3H), 4.52 (t, J=6.1 Hz, 1H), 4.45 (t, J=5.9 Hz, 1H), 4.05-3.85 (m, 1H), 3.55 (d, J=2.4 Hz, 1H), 3.43-3.18 (m, 2H), 2.94 (dd, J=9.5, 2.0 Hz, 1H), 2.83 (dd, J=9.4, 1.4 Hz, 1H), 2.00-1.89 (m, 1H), 1.89-1.80 (m, 1H), 1.39 (t, J=7.3 Hz, 1H).

Synthesis of (1R,4R)-2-(5-ethynylpyridin-2-yl)-5-(oxetan-3-yl)-2,5-diazabicyclo[2.2.1]heptane (S6)

The title compound S6 was prepared according to the method presented for the synthesis of compound S1 but instead utilizing S6a. MS (ESI) m/z 256.1 [M+H]⁺. ¹H NMR (400 MHz, Chloroform-d) δ 8.13 (dd, J=2.2, 0.9 Hz, 1H), 7.37 (dd, J=8.7, 2.3 Hz, 1H), 6.23-5.98 (m, 1H), 4.54 (dt, J=12.8, 6.5 Hz, 3H), 4.39 (t, J=6.1 Hz, 1H), 4.32 (t, J=5.9

Synthesis of 3-(5-iodopyrimidin-2-yl)-8-(oxetan-3-yl)-3,8-diazabicyclo[3.2.1]octane (S7a)

The title compound S7a was prepared according to the method presented for the synthesis of compound S1c but instead utilizing 2-chloro-5-iodopyrimidine. MS (ESI) m/z 373.0 [M+H]⁺. ¹H NMR (400 MHz, Chloroform-d) δ 8.37 (s, 2H), 4.71 (t, J=6.3 Hz, 2H), 4.59 (s, 2H), 4.21 (d, J=12.4 Hz, 2H), 3.68 (s, 1H), 3.15 (s, 4H), 1.83 (s, 2H), 1.62 (s, 2H).

Synthesis of 3-(5-ethynylpyrimidin-2-yl)-8-(oxetan-3-yl)-3,8-diazabicyclo[3.2.1]octane (S7)

The title compound S7 was prepared according to the method presented for the synthesis of compound S1 but instead utilizing S7a. MS (ESI) m/z 271.1[M+H]⁺. ¹H NMR (400 MHz, Chloroform-d) δ 8.38 (s, 1H), 4.71 (t, J=6.2 Hz, 2H), 4.67-4.46 (m, 2H), 4.40-4.24 (m, 2H), 3.69 (p, J=6.1 Hz, 1H), 3.29-3.10 (m, 4H), 1.89-1.73 (m, 2H), 1.74-1.47 (m, 2H).

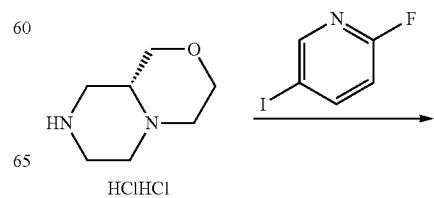

121

-continued

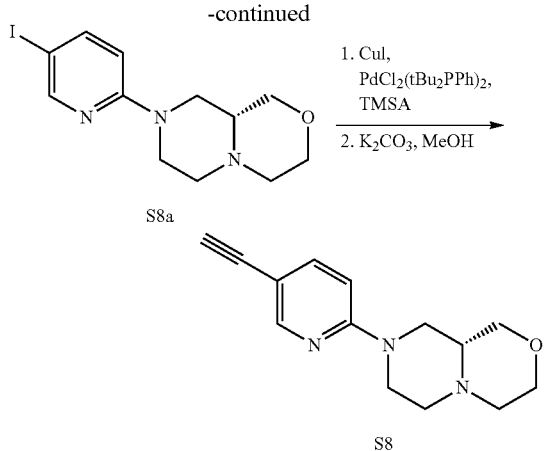

Synthesis of (R)-8-(5-iodopyridin-2-yl)octahydropyrazino[2,1-c][1,4]oxazine (S8a)

The title compound S8a was prepared according to the method presented for the synthesis of compound S1a but instead utilizing (R)-octahydropyrazino[2,1-c][1,4]oxazine dihydrochloride. MS (ESI) m/z 346.1 [M+H]+.

Synthesis of (R)-8-(5-ethynylpyridin-2-yl) octahydropyrazino[2,1-c][1,4]oxazine (S8)

The title compound S8 was prepared according to the method presented for the synthesis of compound S1 but instead utilizing S8a. MS (ESI) m/z 244.2 [M+H]+. $^1$H NMR (400 MHz, Chloroform-d) δ 8.30 (dd, J=2.3, 0.8 Hz, 1H), 7.54 (dd, J=8.8, 2.3 Hz, 1H), 6.56 (dd, J=8.9, 0.8 Hz, 1H), 4.23-4.04 (m, 2H), 3.88 (dd, J=11.4, 3.4 Hz, 1H), 3.81 (dd, J=11.1, 3.1 Hz, 1H), 3.73 (t, J=11.5 Hz, 1H), 3.32 (t, J=10.6 Hz, 1H), 3.13-3.01 (m, 2H), 2.86 (d, J=11.4 Hz, 1H), 2.72 (d, J=11.5 Hz, 1H), 2.54 (t, J=11.7 Hz, 1H), 2.49-2.25 (m, 2H).

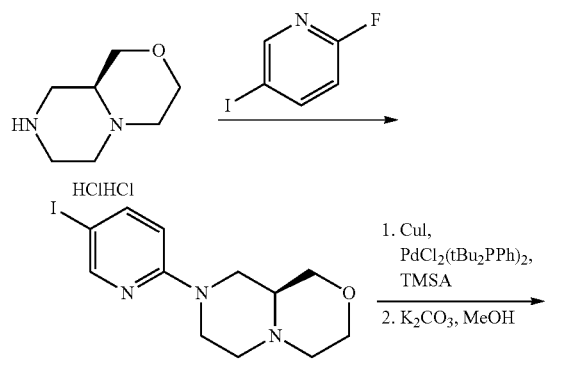

122

Synthesis of (S)-8-(5-iodopyridin-2-yl)octahydropyrazino[2,1-c][1,4]oxazine (S9a)

The title compound S9a was prepared according to the method presented for the synthesis of compound S1a but instead utilizing (R)-octahydropyrazino[2,1-c][1,4]oxazine dihydrochloride. MS (ESI) m/z 346.1 [M+H]+.

Synthesis of (S)-8-(5-ethynylpyridin-2-yl) octahydropyrazino[2,1-c][1,4]oxazine (S9)

The title compound S9 was prepared according to the method presented for the synthesis of compound S1 but instead utilizing S9a. MS (ESI) m/z 244.2 [M+H]+. $^1$H NMR (400 MHz, Chloroform-d) δ 8.30 (dd, J=2.3, 0.8 Hz, 1H), 7.54 (dd, J=8.8, 2.3 Hz, 1H), 6.56 (dd, J=8.9, 0.8 Hz, 1H), 4.23-4.04 (m, 2H), 3.88 (dd, J=11.4, 3.4 Hz, 1H), 3.81 (dd, J=11.1, 3.1 Hz, 1H), 3.73 (t, J=11.5 Hz, 1H), 3.32 (t, J=10.6 Hz, 1H), 3.13-3.01 (m, 2H), 2.86 (d, J=11.4 Hz, 1H), 2.72 (d, J=11.5 Hz, 1H), 2.54 (t, J=11.7 Hz, 1H), 2.49-2.25 (m, 2H).

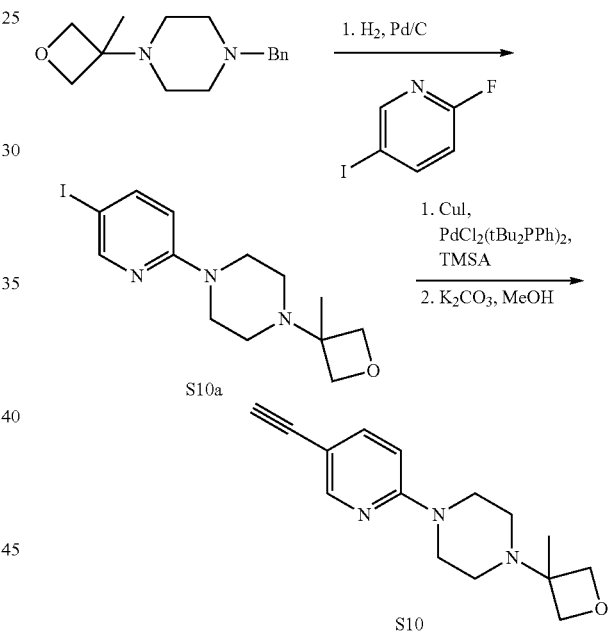

1-(5-iodopyridin-2-yl)-4-(3-methyloxetan-3-yl)piperazine (S10a)

1-benzyl-4-(3-methyloxetan-3-yl)piperazine (6.75 g, 27.4 mmol), palladium (10% on carbon, 1.46 g, 1.37 mmol) in EtOH (55 ml) were combined in a PARR flask and shaken on the hydrogenator overnight at 45 PSI. The reaction was filtered over Celite, the filter cake was washed with 25% MeOH/DCM and the filtrate was concentrated under reduced pressure. The residue was combined 2-fluoro-5-iodopyridine to prepare the title compound S10a according to the method presented for the synthesis of compound S1a. MS (ESI) m/z 360.0 [M+H]+. $^1$H NMR (400 MHz, Chloroform-d) δ 8.31 (d, J=2.3 Hz, 1H), 7.66 (d, J=9.0 Hz, 1H), 6.48 (d, J=9.0 Hz, 1H), 4.62 (d, J=5.5 Hz, 2H), 4.26 (d, J=5.5 Hz, 2H), 3.54 (s, 4H), 2.44 (s, 5H), 1.37 (s, 3H).

1-(5-ethynylpyridin-2-yl)-4-(3-methyloxetan-3-yl)piperazine (S10)

The title compound S10 was prepared according to the method presented for the synthesis of compound S1 but instead utilizing S10a. MS (ESI) m/z 258.0 [M+H]+. 1H NMR (400 MHz, Methanol-d4) δ 8.18 (dd, J=2.3, 0.8 Hz, 1H), 7.56 (dd, J=8.9, 2.3 Hz, 1H), 6.76 (dd, J=9.0, 0.8 Hz, 1H), 4.78-4.52 (m, 2H), 4.28 (d, J=5.9 Hz, 2H), 3.65-3.48 (m, 4H), 3.43 (s, 1H), 2.59-2.39 (m, 4H), 1.38 (d, J=0.7 Hz, 3H).

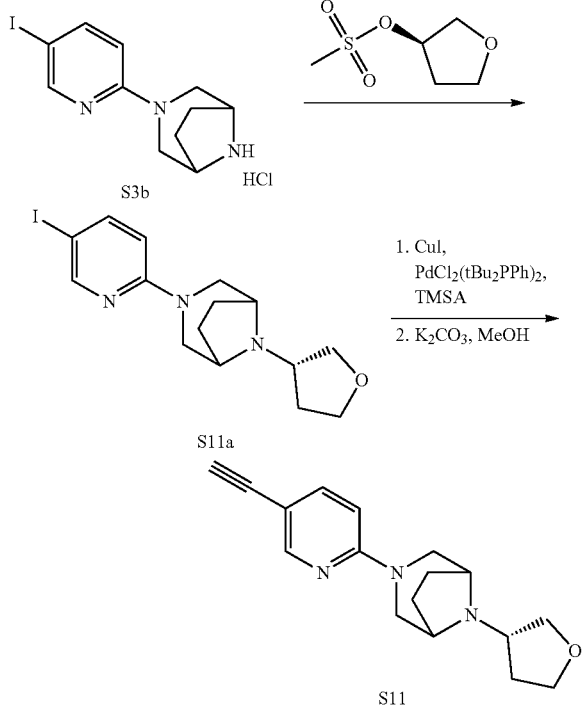

Synthesis of 3-(5-iodopyridin-2-yl)-8-((S)-tetrahydrofuran-3-yl)-3,8-diazabicyclo [3.2.1]octane (S11a)

A solution of S3b (1.0 g, 3.173 mmol), (R)-tetrahydrofuran-3-yl methanesulfonate (965 mg, 5.807 mmol), and potassium carbonate (1754 mg, 12.69 mmol) in CH₃CN (15 mL) was heated at reflux for 48 h. The reaction mixture cooled to room temperature, diluted with EtOAc and washed with brine. The organic extract was dried over Na₂SO₄, filtered and concentrated under reduced pressure. The residue was purified by column chromatography (0% to 5% MeOH/EtOAc) to afford S11a (355.2 mg, 29%) MS (ESI) m/z 386.1 [M+H]+. 1H NMR (400 MHz, Chloroform-d) δ 8.22 (dd, J=2.3, 0.7 Hz, 1H), 7.56 (dd, J=8.9, 2.4 Hz, 1H), 6.29 (dd, J=9.0, 0.7 Hz, 1H), 3.96-3.84 (m, 2H), 3.76 (dt, J=8.6, 7.6 Hz, 1H), 3.62 (ddd, J=11.5, 8.9, 2.5 Hz, 2H), 3.55 (dd, J=8.2, 6.9 Hz, 1H), 3.33 (d, J=4.7 Hz, 1H), 3.20 (d, J=3.4 Hz, 1H), 3.11-2.97 (m, 3H), 2.02 (dtd, J=12.1, 7.4, 4.7 Hz, 1H), 1.95-1.87 (m, 2H), 1.87-1.72 (m, 1H), 1.67-1.56 (m, 2H).

Synthesis of 3-(5-ethynylpyridin-2-yl)-8-((S)-tetrahydrofuran-3-yl)-3,8-diazabicyclo[3.2.1]octane (S11)

The title compound S11 was prepared according to the method presented for the synthesis of compound S1 but instead utilizing S11a. MS (ESI) m/z 284.1 [M+H]+. 1H NMR (400 MHz, Methanol-d4) δ 8.22-8.10 (m, 1H), 7.55 (dd, J=8.9, 2.3 Hz, 1H), 6.65 (dd, J=9.1, 0.8 Hz, 1H), 3.97 (td, J=8.1, 4.5 Hz, 2H), 3.89-3.74 (m, 3H), 3.63 (dd, J=8.4, 6.6 Hz, 1H), 3.48 (d, J=4.4 Hz, 1H), 3.42 (s, 1H), 3.35 (s, 1H), 3.26-3.19 (m, 1H), 3.12 (dt, J=12.2, 3.5 Hz, 2H), 2.15 (ddd, J=11.8, 8.2, 4.5 Hz, 1H), 2.03 (dd, J=14.4, 7.3 Hz, 2H), 1.85 (dq, J=12.0, 7.8 Hz, 1H), 1.69 (d, J=9.1 Hz, 2H).

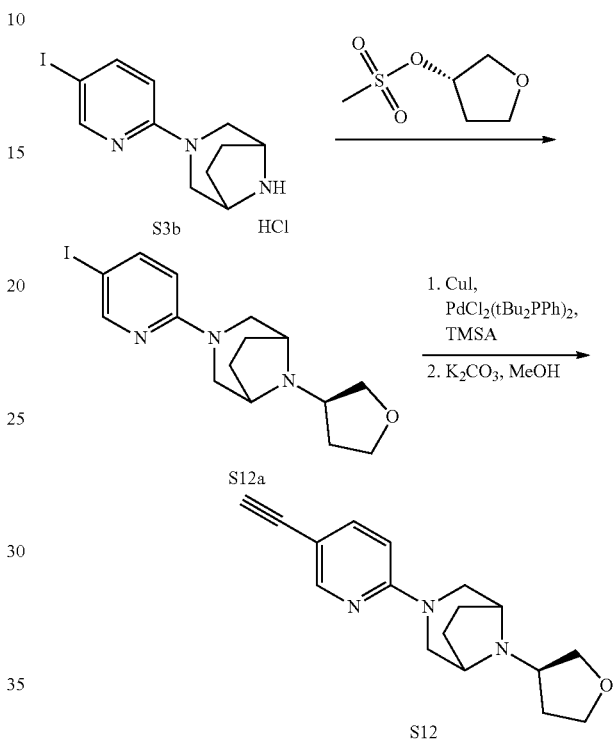

Synthesis of 3-(5-iodopyridin-2-yl)-8-((R)-tetrahydrofuran-3-yl)-3,8-diazabicyclo[3.2.1] octane (S12a)

The title compound S12a was prepared according to the method presented for the synthesis of compound S11a but instead utilizing (S)-tetrahydrofuran-3-yl methanesulfonate. MS (ESI) m/z 386.1 [M+H]+. 1H NMR (400 MHz, Chloroform-d) δ 8.28 (d, J=2.3 Hz, 1H), 7.62 (dd, J=9.0, 2.4 Hz, 1H), 6.36 (d, J=9.0 Hz, 1H), 4.04-3.91 (m, 2H), 3.90-3.75 (m, 1H), 3.68 (ddd, J=11.6, 8.8, 2.5 Hz, 2H), 3.61 (dd, J=8.2, 6.9 Hz, 1H), 3.39 (q, J=2.7 Hz, 1H), 3.26 (dt, J=5.0, 2.1 Hz, 1H), 3.18-3.04 (m, 3H), 2.17-2.01 (m, 1H), 1.97 (dd, J=9.4, 5.6 Hz, 2H), 1.90-1.77 (m, 1H), 1.74-1.63 (m, 2H).

Synthesis of 3-(5-ethynylpyridin-2-yl)-8-((R)-tetrahydrofuran-3-yl)-3,8diazabicyclo[3.2.1] octane (S12)

The title compound S12 was prepared according to the method presented for the synthesis of compound S1 but instead utilizing S12a. MS (ESI) m/z 284.1 [M+H]+. 1H NMR (400 MHz, Methanol-d4) δ 8.22-8.07 (m, 1H), 7.55 (dd, J=8.9, 2.3 Hz, 1H), 6.65 (dd, J=8.8, 0.9 Hz, 1H), 3.96 (td, J=8.1, 4.5 Hz, 2H), 3.88-3.74 (m, 3H), 3.63 (dd, J=8.4, 6.6 Hz, 1H), 3.48 (d, J=4.4 Hz, 1H), 3.42 (s, 1H), 3.35 (s, 1H), 3.24 (t, J=7.0 Hz, 1H), 3.12 (dt, J=12.1, 3.4 Hz, 2H), 2.26-2.09 (m, 1H), 2.03 (dd, J=14.1, 7.5 Hz, 2H), 1.85 (dq, J=12.0, 8.0 Hz, 1H), 1.69 (d, J=9.1 Hz, 2H).

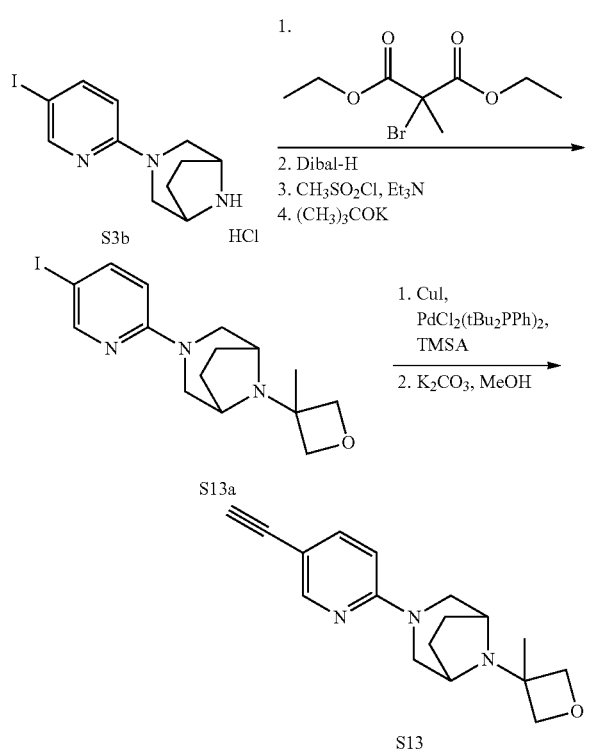

Synthesis of 3-(5-iodopyridin-2-yl)-8-(3-methyl-oxetan-3-yl)-3,8-diazabicyclo[3.2.1]octane (S13a)

A suspension of S3b (3 g, 9.519 mmol), diethyl 2-bromo-2-methylmalonate (2.25 ml, 11.78 mmol), and sodium carbonate (1.19 g, 19.19 mmol) in NMP (30 mL) in a 100 ml sealed tube was stirred at 70° C. for 48 h. The reaction mixture was cooled to room temperature, diluted with EtOAc and washed with brine 2×. The organic extract was dried over $Na_2SO_4$ filtered, and the crude residue was purified by silica column chromatography (10%-20% EtOAc/hexanes) to afford diethyl 2-(3-(5-iodopyridin-2-yl)-3,8-diazabicyclo[3.2.1]octan-8-yl)-2-methylmalonate (2.32 g, 50%). MS (ESI) m/z 488.0 [M+H]$^+$. $^1$H NMR (400 MHz, Chloroform-d) δ 8.27 (dd, J=2.4, 0.7 Hz, 1H), 7.61 (dd, J=9.0, 2.4 Hz, 1H), 6.51-6.27 (m, 1H), 4.37-4.07 (m, 4H), 3.84 (s, 2H), 3.79-3.72 (m, 2H), 3.29-3.07 (m, 2H), 1.77-1.63 (m, 4H), 1.62 (s, 3H), 1.27 (t, J=7.2 Hz, 6H).

To a solution of diethyl 2-(3-(5-iodopyridin-2-yl)-3,8-diazabicyclo[3.2.1]octan-8-yl)-2-methylmalonate (907.9 mg, 1.863 mmol) in DCM (40 mL) at −78° C. was added Dibal-H (1.0 M in toluene, 93 ml). The reaction was gradually warmed to room temperature and stirred overnight. Dibal-H (1.0 M in DCM, 16 ml) was added, stirred for 1 h, and then cooled to 0° C. diluted with $Et_2O$. Slowly added water (4.4 mL), 15% NaOH (4.4 mL), followed by water (10.9 mL), warmed to room temperature and stirred for 15 min. Added $Na_2SO_4$, stirred for 15 min, then filtered off salts to give 2-(3-(5-iodopyridin-2-yl)-3,8-diazabicyclo[3.2.1]octan-8-yl)-2-methylpropane-1,3-diol (2.059 g, 65%). MS (ESI) m/z 404.0 [M+H]$^+$. $^1$H NMR (400 MHz, Methanol-d4) δ 8.18 (dd, J=2.4, 0.7 Hz, 1H), 7.69 (dd, J=9.0, 2.4 Hz, 1H), 6.54 (d, J=9.1 Hz, 1H), 3.91-3.66 (m, 4H), 3.49 (s, 4H), 3.10-2.88 (m, 2H), 1.83 (d, J=8.8 Hz, 2H), 1.72 (t, J=6.6 Hz, 2H), 1.00 (s, 3H). To a solution of 2-(3-(5-iodopyridin-2-yl)-3,8-diazabicyclo[3.2.1]octan-8-yl)-2-methylpropane-1,3-diol (2.06 g, 5.106 mmol) and triethylamine (1.5 ml, 10.76 mmol) in THF (25 mL) at 0° C. was added methanesulfonyl chloride (0.40 ml, 5.169 mmol). The reaction was gradually warmed to room temperature and stirred overnight. The reaction mixture was diluted with EtOAc and washed with brine. The organic extract was dried over $Na_2SO_4$, filtered, and the crude residue was purified by silica column chromatography (25%-50% EtOAc/hexanes) to afford 3-chloro-2-(3-(5-iodopyridin-2-yl)-3,8-diazabicyclo[3.2.1]octan-8-yl)-2-methylpropan-1-ol (441.6 mg, 20.5%). MS (ESI) m/z 422.2 [M+H]$^+$. $^1$H NMR (400 MHz, Chloroform-d) δ 8.27 (dd, J=2.4, 0.7 Hz, 1H), 7.62 (dd, J=8.9, 2.4 Hz, 1H), 6.35 (dd, J=9.0, 0.7 Hz, 1H), 4.63 (s, 1H), 3.90-3.63 (m, 4H), 3.56 (d, J=5.1 Hz, 1H), 3.35 (s, 1H), 3.06 (dt, J=11.8, 3.0 Hz, 2H), 2.87 (t, J=13.5 Hz, 1H), 2.66 (d, J=14.0 Hz, 1H), 1.88 (dt, J=9.9, 4.9 Hz, 2H), 1.76-1.63 (m, 2H), 1.57 (s, 3H).

To a solution of 3-chloro-2-(3-(5-iodopyridin-2-yl)-3,8-diazabicyclo[3.2.1]octan-8-yl)-2-methylpropan-1-ol (418.5 mg, 0.992 mmol) in THF (10 mL) at 0° C., was added potassium tert-butoxide (1.0 M THF, 3 ml). After 10 min the reaction mixture was quenched with water, diluted with EtOAc and washed with brine. The organic extract was dried over $Na_2SO_4$, filtered, and the crude residue was purified by silica column chromatography (50%-100% EtOAc/hexanes) to afford S13a (222.8 mg, 58% yield). MS (ESI) m/z 386.1 [M+H]$^+$. $^1$H NMR (400 MHz, Chloroform-d) δ 8.27 (dd, J=2.4, 0.7 Hz, 1H), 7.61 (dd, J=9.0, 2.4 Hz, 1H), 6.35 (dd, J=9.0, 0.7 Hz, 1H), 3.68 (ddd, J=11.5, 4.4, 2.6 Hz, 2H), 3.49-3.34 (m, 1H), 3.30 (q, J=2.7 Hz, 1H), 3.07 (dd, J=11.6, 2.5 Hz, 2H), 2.70 (dd, J=5.0, 0.7 Hz, 1H), 2.64-2.53 (m, 2H), 2.39 (d, J=13.2 Hz, 1H), 1.96-1.79 (m, 2H), 1.68-1.57 (m, 2H), 1.42 (d, J=0.6 Hz, 3H).

Synthesis of 3-(5-ethynylpyridin-2-yl)-8-(3-methyl-oxetan-3-yl)-3,8-diazabicyclo[3.2.1]octane (S13)

The title compound S13 was prepared according to the method presented for the synthesis of compound S1 but instead utilizing S13a. MS (ESI) m/z 284.2 [M+H]$^+$. $^1$H NMR (400 MHz, Methanol-d4) δ 8.15 (dd, J=2.3, 0.8 Hz, 1H), 7.53 (dd, J=8.9, 2.3 Hz, 1H), 6.64 (dd, J=9.0, 0.8 Hz, 1H), 3.91-3.74 (m, 3H), 3.50-3.43 (m, 1H), 3.42 (s, 1H), 3.39-3.32 (m, 1H), 3.08 (dt, J=11.7, 1.9 Hz, 3H), 2.72 (dd, J=4.9, 0.7 Hz, 2H), 2.66 (d, J=13.3 Hz, 1H), 2.60 (d, J=4.9 Hz, 1H), 2.43 (d, J=13.3 Hz, 1H), 1.94 (dd, J=9.4, 5.5 Hz, 3H), 1.69-1.57 (m, 2H), 1.42 (d, J=0.6 Hz, 4H).

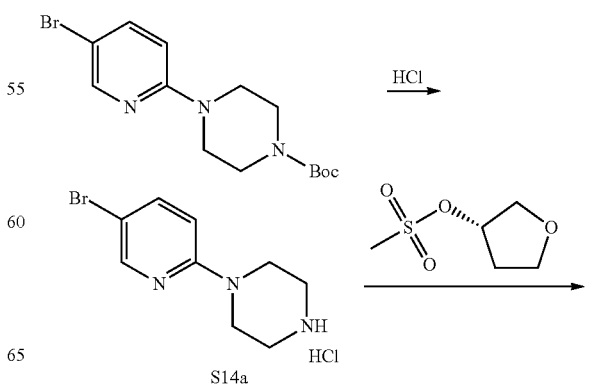

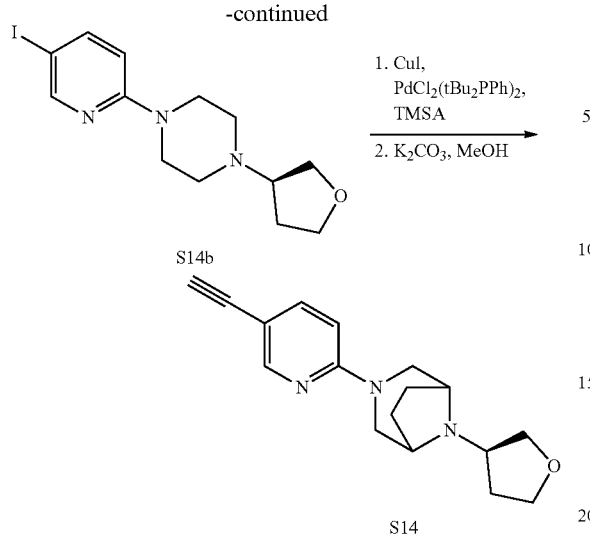

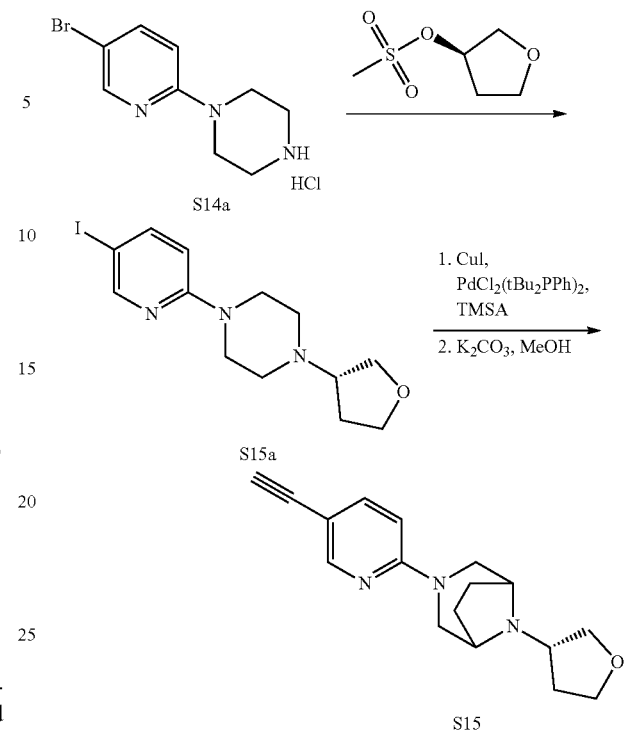

Synthesis of 1-(5-bromopyridin-2-yl)piperazine hydrochloride (S14a)

To a solution of tert-butyl 4-(5-bromopyridin-2-yl)piperazine-1-carboxylate (5 g, 14.61 mmol) in DCM (60 mL) and MeOH (18 mL), was added HCl (4.0 M in dioxanes, 18 mL, 72 mmol). The reaction mixture was stirred at room temperature overnight. The reaction was diluted with DCM and washed with 2N NaOH. The aqueous layer was extracted with DCM 2× and the combined organic layers were dried over $Na_2SO_4$, filtered and concentrated under reduce pressure to afford S14a (3.2 g, 90.4%). MS (ESI) m/z 242.1 ([M+H]$^+$. $^1$H NMR (400 MHz, Chloroform-d) δ 8.18 (dd, J=2.6, 0.7 Hz, 1H), 7.52 (dd, J=9.0, 2.6 Hz, 1H), 6.53 (dd, J=9.1, 0.7 Hz, 1H), 3.54-3.40 (m, 4H), 3.09-2.87 (m, 4H).

Synthesis of (R)-1-(5-bromopyridin-2-yl)-4-(tetrahydrofuran-3-yl)piperazine (S14b)

The title compound S14a was prepared according to the method presented for the synthesis of compound S11a but instead utilizing S14a and (S)-tetrahydrofuran-3-yl methanesulfonate. MS (ESI) m/z 312.1 [M+H]$^+$. $^1$H NMR (400 MHz, Chloroform-d) δ 8.19 (dd, J=2.6, 0.7 Hz, 1H), 7.53 (dd, J=9.0, 2.5 Hz, 1H), 6.54 (dd, J=9.0, 0.7 Hz, 1H), 3.96 (td, J=8.6, 4.4 Hz, 1H), 3.91 (dd, J=8.7, 6.8 Hz, 1H), 3.80 (td, J=8.4, 7.5 Hz, 1H), 3.69 (t, J=7.7 Hz, 1H), 3.52 (t, J=5.3 Hz, 4H), 3.01 (t, J=7.3 Hz, 1H), 2.63 (d, J=9.9 Hz, 2H), 2.57-2.46 (m, 2H), 2.07 (ddd, J=9.9, 7.1, 3.3 Hz, 1H), 1.90 (q, J=11.1, 9.5 Hz, 1H).

Synthesis of (R)-1-(5-ethynylpyridin-2-yl)-4-(tetrahydrofuran-3-yl)piperazine (S14)

The title compound S14 was prepared according to the method presented for the synthesis of compound S1 but instead utilizing S14b. MS (ESI) m/z 258.1 [M+H]$^+$. $^1$H NMR (400 MHz, Methanol-d4) δ 8.18 (d, J=2.3 Hz, 1H), 7.56 (dd, J=8.8, 2.3 Hz, 1H), 6.76 (d, J=8.8 Hz, 1H), 3.95 (dt, J=8.5, 4.3 Hz, 1H), 3.90 (dd, J=8.8, 7.0 Hz, 2H), 3.76 (q, J=8.2 Hz, 1H), 3.68 (dd, J=8.8, 6.6 Hz, 1H), 3.58 (t, J=5.2 Hz, 4H), 3.43 (s, 1H), 3.09-2.97 (m, 1H), 2.65 (dt, J=10.6, 5.2 Hz, 2H), 2.54 (dt, J=11.2, 5.2 Hz, 2H), 2.20-2.06 (m, 1H), 1.96-1.83 (m, 1H).

Synthesis of (S)-1-(5-bromopyridin-2-yl)-4-(tetrahydrofuran-3-yl)piperazine (S15a)

The title compound S15a was prepared according to the method presented for the synthesis of compound S11a but instead utilizing S14a. MS (ESI) m/z 312.2 [M+H]$^+$. $^1$H NMR (400 MHz, Chloroform-d) δ 8.18 (dd, J=2.6, 0.7 Hz, 1H), 7.52 (dd, J=9.0, 2.6 Hz, 1H), 6.53 (dd, J=9.1, 0.7 Hz, 1H), 3.96 (td, J=8.6, 4.4 Hz, 1H), 3.91 (dd, J=8.6, 6.8 Hz, 1H), 3.80 (td, J=8.4, 7.5 Hz, 1H), 3.68 (dd, J=8.7, 6.7 Hz, 1H), 3.52 (dd, J=5.9, 4.5 Hz, 4H), 3.00 (p, J=7.1 Hz, 1H), 2.63 (dt, J=10.7, 5.2 Hz, 2H), 2.50 (dt, J=10.8, 5.1 Hz, 2H), 2.17-1.99 (m, 1H), 1.99-1.79 (m, 1H).

Synthesis of (S)-1-(5-ethynylpyridin-2-yl)-4-(tetrahydrofuran-3-yl)piperazine (S15))

The title compound S15 was prepared according to the method presented for the synthesis of compound S1 but instead utilizing S15a. MS (ESI) m/z 258.1 [M+H]$^+$. $^1$H NMR (400 MHz, Methanol-d4) δ 8.09 (dd, J=2.4, 0.8 Hz, 1H), 7.47 (dd, J=8.9, 2.3 Hz, 1H), 6.66 (dd, J=9.0, 0.8 Hz, 1H), 3.86 (dt, J=8.6, 4.3 Hz, 1H), 3.80 (dd, J=8.9, 7.0 Hz, 2H), 3.67 (td, J=8.4, 7.2 Hz, 1H), 3.59 (dd, J=8.7, 6.6 Hz, 1H), 3.49 (t, J=5.2 Hz, 4H), 3.34 (s, 1H), 3.02-2.86 (m, 1H), 2.55 (dt, J=10.7, 5.2 Hz, 2H), 2.44 (dt, J=11.1, 5.2 Hz, 2H), 2.10-1.94 (m, 2H), 1.86-1.71 (m, 2H).

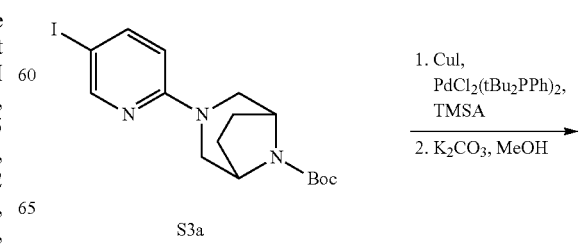

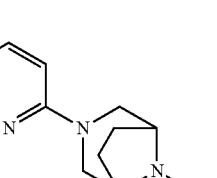

S16

Synthesis of tert-butyl 3-(5-ethynylpyridin-2-yl)-3,8-diazabicyclo[3.2.1]octane-8-carboxylate (S16)

The title compound S16 was prepared according to the method presented for the synthesis of compound S1 but instead utilizing S3a. MS (ESI) m/z 313.9 [M+H]+. $^1$H NMR (400 MHz, Methanol-d4) δ 8.18 (dd, J=2.3, 0.8 Hz, 1H), 7.56 (dd, J=8.9, 2.3 Hz, 1H), 6.69 (dd, J=8.9, 0.9 Hz, 1H), 4.45-4.30 (m, 2H), 4.04-3.95 (m, 2H), 3.43 (s, 1H), 3.02 (d, J=12.2 Hz, 2H), 1.94 (dd, J=8.7, 4.4 Hz, 2H), 1.75 (d, J=7.3 Hz, 2H), 1.48 (s, 9H).

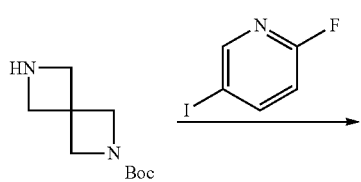

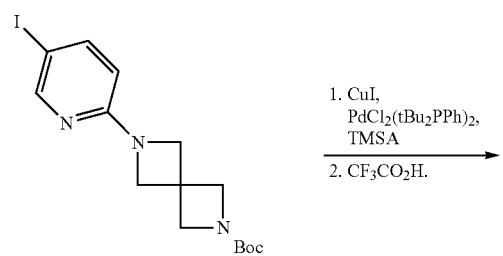

S17a

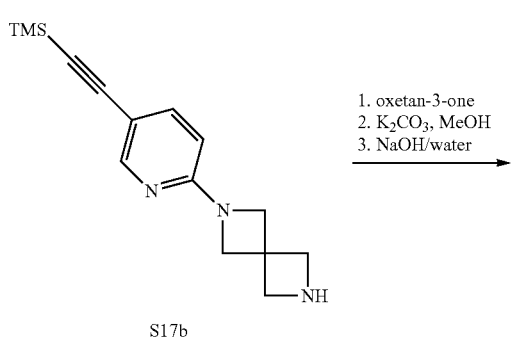

S17b

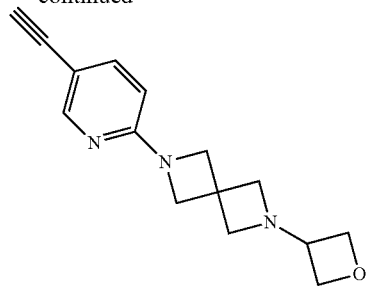

S17

Synthesis of tert-butyl 6-(5-iodopyridin-2-yl)-2-azaspiro[3.3]heptane-2-carboxylate (S17a)

The title compound S17a was prepared according to the method presented for the synthesis of compound S1a but instead utilizing tert-Butyl 2,6-diazaspiro[3.3]heptane-2-carboxylate. MS (ESI) m/z 401.9 [M+H]+. $^1$H NMR (400 MHz, Chloroform-d) δ 8.28 (d, J=2.2 Hz, 1H), 7.67 (d, J=8.7 Hz, 1H), 6.14 (d, J=8.7 Hz, 1H), 4.13 (s, 4H), 4.10 (s, 4H), 1.44 (s, 9H).

Synthesis of 6-(5-((trimethylsilyl)ethynyl)pyridin-2-yl)-2-azaspiro[3.3]heptane (S17b)

A solution of S17a (1.048 mg, 2.612 mmol), CuI (0.111 g, 0.583 mmol), PdCl$_2$(tBu$_2$PPh)$_2$ (0.163 g, 0.261 mmol), TMSA (2.1 ml, 14.75 mmol), Et$_3$N (2.7 ml, 19.48 mmol) in CH$_3$CN (20 mL) at 0° C. was degassed with Argon for 10 min. The reaction mixture stirred at reflux overnight, then cooled to room temperature, diluted with EtOAc, washed with NaHCO$_3$ solution and dried over Na$_2$SO$_4$, filtered, concentrated under reduced pressure and the residue was purified by silica column chromatography (20% to 40% EtOAc/Hex) to give (760 mg, 78%) of desired product. This product (0.4 g, 1076.58 μmol) was dissolved in DCM (5 mL) and trifluoroacetic acid (1000 μl, 13.07 mmol) was added, the mixture was stirred at 0° C. After 4 h, the reaction mixture was concentrated under reduced pressure, diluted with toluene (5 mL) and concentrated to afford S17b (0.54 g, 100.1%). MS (ESI) m/z 272.1 [M+H]+.

Synthesis of 6-(5-ethynylpyridin-2-yl)-2-(oxetan-3-yl)-2-azaspiro[3.3]heptane (S17)

A suspension of S17b (538 mg, 1.08 mmol) with triethylamine (0.3 ml, 2.154 mmol) in 2-Me THF (4 mL) and AcOH (0.2 mL), was added oxetan-3-one (234 mg, 3.247 mmol) in 2-Me-THF (1 mL) followed by sodium cyanoborohydride (209 mg, 3.326 mmol). The reaction was stirred at room temperature. After 18 h, the reaction mixture was quenched with NaHCO3 solution and partitioned with EtOAc. The organic extract was dried over Na$_2$SO$_4$, filtered, concentrated under reduced pressure and the residue was purified by silica column chromatography (50% to 75% EtOAc/Hex). The product was dissolved in MeOH (5 mL), Potassium carbonate (0.28 g, 2.05 mmol) was added and the mixture was stirred at room temperature. After 48 h the reaction mixture was concentrated under reduced pressure, diluted with EtOAc, washed with brine, dried over Na$_2$SO$_4$, filtered, and concentrated under reduced pressure. The residue was dissolved in methanol (2.0 mL) and sodium hydroxide solution (2M, 2 ml) was added, warmed up to 70° C. for 18 h. The reaction was cooled to room temperature concentrated under reduced pressure; the residue was diluted with EtOAc, washed with brine, dried over Na$_2$SO$_4$, filtered, and concentrated under reduced pressure to afford S17 MS (ESI) m/z 256.1 [M+H]$^+$. $^1$H NMR (400 MHz, Methanol-d4) δ 8.09 (dd, J=2.2, 0.8 Hz, 1H), 7.55 (dd, J=8.7, 2.2 Hz, 1H), 6.36 (dd, J=8.7, 0.8 Hz, 1H), 4.72 (td, J=6.7, 0.5 Hz, 3H), 4.45 (ddd, J=6.8, 4.9, 0.6 Hz, 3H), 4.13 (s, 5H), 3.76 (tt, J=6.5, 4.9 Hz, 1H), 3.50 (s, 5H), 3.44 (s, 1H).

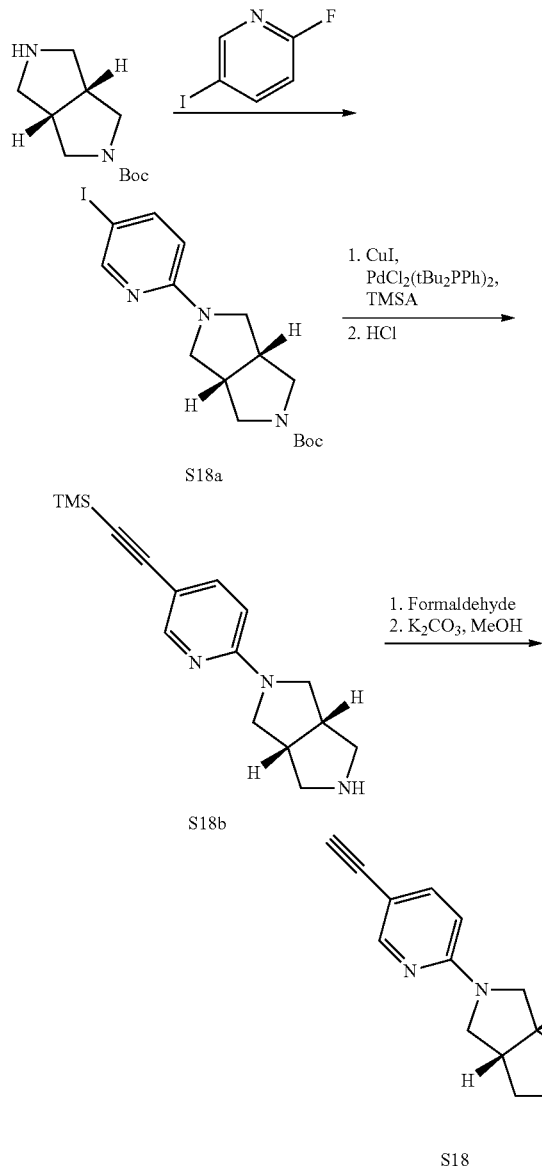

Synthesis of tert-butyl (3aR,6aS)-5-(5-iodopyridin-2-yl)hexahydropyrrolo[3,4-c]pyrrole-2(1H)-carboxylate (S18a)

The title compound S18a was prepared according to the method presented for the synthesis of compound S1a but instead utilizing tert-butyl (3aR,6aS)-hexahydropyrrolo[3,4-c]pyrrole-2(1H)-carboxylate. MS (ESI) m/z 415.8 [M+H]$^+$. $^1$H NMR (400 MHz, Chloroform-d) δ 8.28 (dd, J=2.4, 0.8 Hz, 1H), 7.63 (dd, J=8.9, 2.3 Hz, 1H), 6.19 (d, J=8.9 Hz, 1H), 3.66 (dd, J=10.7, 7.0 Hz, 4H), 3.51-3.17 (m, 4H), 2.99 (d, J=5.9 Hz, 2H), 1.45 (s, 9H).

Synthesis of (3aR,6aS)-2-(5-((trimethylsilyl)ethynyl)pyridin-2-yl)octahydropyrrolo[3,4-c]pyrrole (S18b)

A solution of S18a (0.986 g, 2.374 mmol), CuI (0.099 g, 0.522 mmol), PdCl$_2$(tBu$_2$PPh)$_2$ (0.148 g, 0.237 mmol), TMSA (1.9 ml, 13.35 mmol), Et$_3$N (2.5 ml, 18.04 mmol) in CH$_3$CN (8 mL) was degassed with Argon for 10 min. The reaction mixture was heated to 60° C. and stirred overnight. The reaction was diluted with EtOAc and washed with NaHCO3 solution, dried over Na$_2$SO$_4$, filtered, and concentrated under reduced pressure and the residue was purified by silica column chromatography (10% to 30% EtOAc/Hex), the product (0.68 g, 1.75 mmol) was dissolved in a mixture of DCM (8 mL) and MeOH (2 mL) and HCl (4.0 M in dioxanes, 2 ml) was added. The reaction was stirred for 18 h, diluted with DCM, washed with 2N NaOH solution. The aqueous layer was re-extracted with DCM and the combined organic extracts were dried over Na$_2$SO$_4$, filtered, and concentrated under reduced pressure to afford S18b (0.56 g, 112.7%). MS (ESI) m/z 286.2 [M+H]$^+$. $^1$H NMR (400 MHz, Methanol-d4) δ 7.82 (dd, J=2.1, 0.7 Hz, 1H), 7.73 (dd, J=9.5, 2.1 Hz, 1H), 6.88 (dd, J=9.5, 0.9 Hz, 1H), 3.78-3.63 (m, 2H), 3.59-3.48 (m, 2H), 3.46-3.34 (m, 3H), 3.25-3.10 (m, 3H), −0.00 (s, 9H).

Synthesis of (3aR,6aS)-2-(5-ethynylpyridin-2-yl)-5-methyloctahydropyrrolo[3,4-c]pyrrole (S18)

To a solution of S18b (0.25 g, 0.701 mmol) in DCE (6 mL) was added formaldehyde solution (0.30 ml, 8.143 mmol) and acetic acid (0.025 ml, 4.367 mmol). The reaction mixture was heated at 60° C. for 30 min. Cooled to room temperature and added sodium cyanoborohydride (165.1 mg, 2.63 mmol). The reaction was heated at 60° C. for 45 min, then cooled to room temperature, diluted with EtOAc, washed with brine, back-extracted the aqueous layer with EtOAc, dried over Na$_2$SO$_4$, filtered, and concentrated under reduced pressure the residue was dissolved in MeOH (5 mL) and Potassium carbonate (0.29 g, 2.1 mmol) was added, the reaction mixture was stirred at room temperature. After 18 h, the reaction was concentrated under reduced pressure and the residue was diluted with EtOAc, washed with brine dried over Na$_2$SO$_4$, filtered, and concentrated under reduced pressure to afford S18 (0.15 g, 87%). MS (ESI) m/z 228.1 [M+H]$^+$. $^1$H NMR (400 MHz, Methanol-d4) δ 8.19 (dd, J=2.3, 0.8 Hz, 1H), 7.60 (dd, J=8.8, 2.3 Hz, 1H), 6.58 (dd, J=8.9, 0.8 Hz, 1H), 3.70-3.59 (m, 1H), 3.54-3.45 (m, 3H), 3.10 (s, 3H), 2.97-2.84 (m, 2H), 2.54 (dd, J=9.7, 4.0 Hz, 2H), 2.39 (s, 3H).

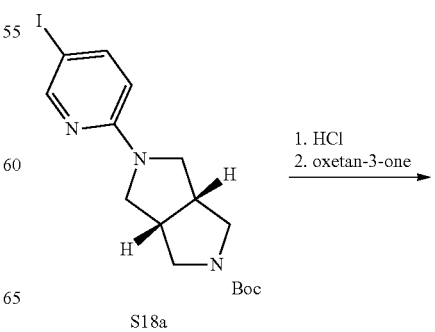

133

-continued

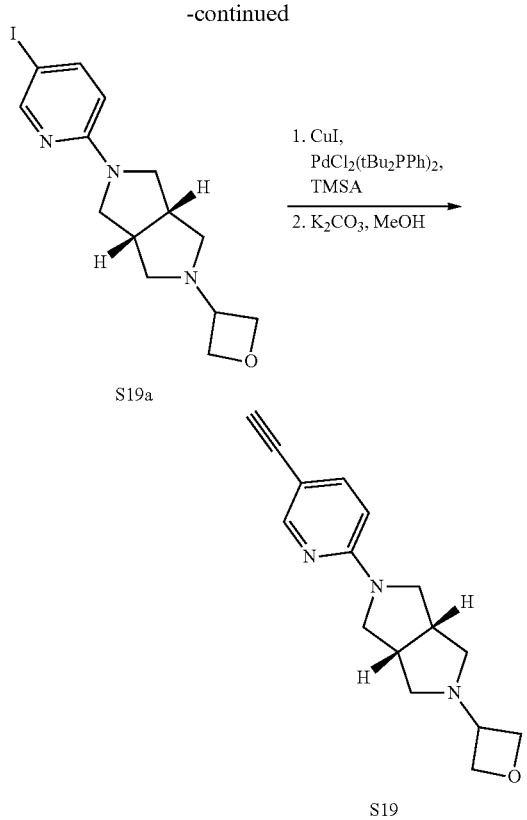

Synthesis of (3aR,6aS)-2-(5-iodopyridin-2-yl)-5-(oxetan-3-yl)octahydropyrrolo[3,4-c]pyrrole (S19a)

The title compound S19a was prepared according to the method presented for the synthesis of compound S1c but instead utilizing S18a. MS (ESI) m/z 372.1 [M+H]$^+$. $^1$H NMR (400 MHz, Methanol-d4) δ 8.17 (dd, J=2.3, 0.7 Hz, 1H), 7.71 (ddd, J=8.9, 2.3, 0.8 Hz, 1H), 6.43 (dd, J=9.0, 0.7 Hz, 1H), 4.69 (t, J=6.6 Hz, 2H), 4.64-4.55 (m, 2H), 3.70-3.60 (m, 1H), 3.59-3.49 (m, 2H), 3.38 (dd, J=10.8, 3.1 Hz, 2H), 3.02 (td, J=7.3, 3.7 Hz, 2H), 2.88-2.71 (m, 2H), 2.42 (dd, J=9.4, 4.0 Hz, 2H).

Synthesis of (3aR,6aS)-2-(5-ethynylpyridin-2-yl)-5-(oxetan-3-yl)octahydropyrrolo[3,4-c]pyrrole (S19)

The title compound S19 was prepared according to the method presented for the synthesis of compound S1 but instead utilizing S19a. MS (ESI) m/z 270.2 [M+H]$^+$. $^1$H NMR (400 MHz, Methanol-d4) δ 8.05 (dd, J=2.2, 0.8 Hz, 1H), 7.46 (dd, J=8.8, 2.3 Hz, 1H), 6.43 (dd, J=8.9, 0.8 Hz, 1H), 4.68-4.58 (m, 2H), 4.59-4.44 (m, 2H), 3.64-3.45 (m, 2H), 3.40-3.30 (m, 4H), 2.95 (dq, J=7.5, 3.9 Hz, 2H), 2.70 (dd, J=9.6, 7.1 Hz, 1H), 2.36 (dd, J=9.5, 4.0 Hz, 2H).

134

-continued

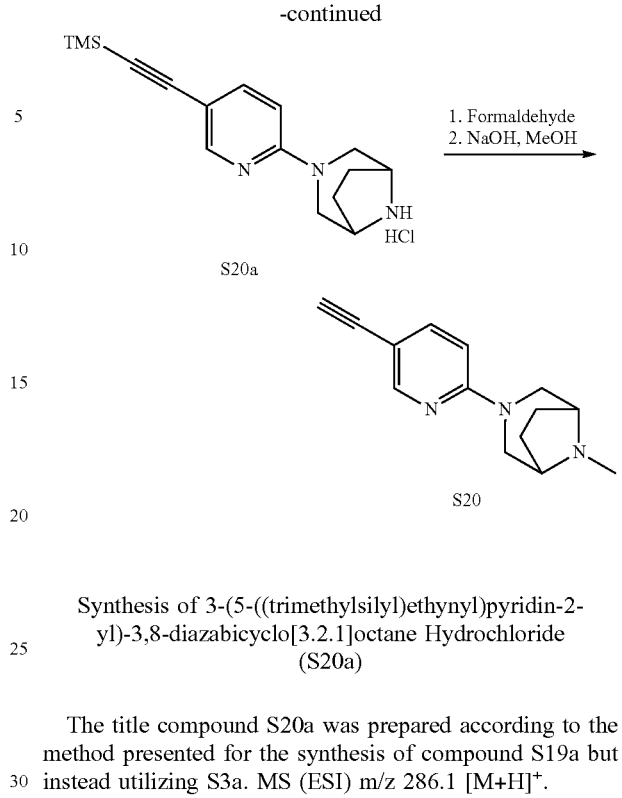

Synthesis of 3-(5-((trimethylsilyl)ethynyl)pyridin-2-yl)-3,8-diazabicyclo[3.2.1]octane Hydrochloride (S20a)

The title compound S20a was prepared according to the method presented for the synthesis of compound S19a but instead utilizing S3a. MS (ESI) m/z 286.1 [M+H]$^+$.

Synthesis of 3-(5-ethynylpyridin-2-yl)-8-methyl-3,8-diazabicyclo[3.2.1]octane (S20)

To a solution of S20a (0.2 g, 0.7 mmol) in THF (6 mL) was added formaldehyde solution (0.13 ml, 3.5 mmol) and acetic acid (0.03 ml, 0.51 mmol). The reaction mixture stirred at room temperature overnight. Sodium cyanoborohydride (132.09 mg, 2.1 mmol) was added. After 5 h, MeOH (2 mL) and NaOH (2 N, 2 mL) were added and the mixture was stirred for another 18 h. The reaction was concentrated under reduced pressure, diluted with EtOAc, washed with brine, back-extracted the aqueous layer with EtOAc, dried over Na$_2$SO$_4$, filtered, concentrated under reduced pressure and the residue was purified by silica column chromatography (100% EtOAc to 5%-10% MeOH/EtOAc) to give S20 (62.6 mg, 39.3%). MS (ESI) m/z 228.2 [M+H]$^+$. $^1$H NMR (400 MHz, Methanol-d4) δ 8.16 (dd, J=2.4, 0.8 Hz, 1H), 7.55 (dd, J=8.9, 2.3 Hz, 1H), 6.66 (dd, J=8.9, 0.9 Hz, 1H), 3.86 (dd, J=12.5, 2.4 Hz, 3H), 3.42 (s, 1H), 3.08 (dd, J=12.3, 2.3 Hz, 3H), 2.36 (d, J=2.4 Hz, 3H), 2.07 (dt, J=7.1, 3.2 Hz, 2H), 1.68 (t, J=6.8 Hz, 2H).

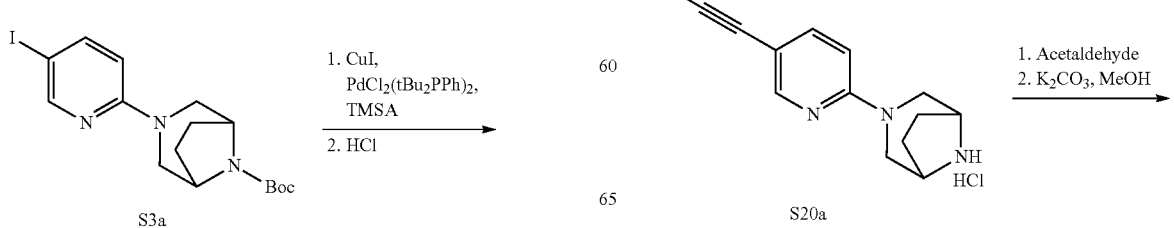

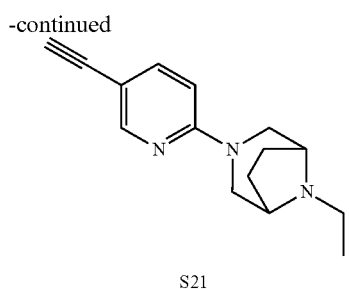

S21

Synthesis of 8-ethyl-3-(5-ethynylpyridin-2-yl)-3,8-diazabicyclo[3.2.1]octane (S21)

To a solution of S20a (0.24 g, 0.83 mmol) in THF (5 mL) and MeOH (2 mL) was added acetaldehyde (0.5 ml, 8.90 mmol) and acetic acid (0.04 ml, 0.7 mmol). After 18 h sodium cyanoborohydride (314 mg, 5.0 mmol) was added. Stirred overnight, diluted with EtOAc, washed with brine, back-extracted the aqueous layer with EtOAc, dried over $Na_2SO_4$, filtered, and concentrated under reduced pressure and the residue was purified by silica column chromatography (10%-20% MeOH/EtOAc) to give (0.12 g, 0.39 mmol) of product which was dissolved in MeOH (5 mL) and potassium carbonate (0.16 g, 1.17 mmol) was added, the reaction mixture was stirred at room temperature. After 3 h, the reaction was concentrated under reduced pressure and the residue was diluted with EtOAc, washed with brine dried over $Na_2SO_4$, filtered, and concentrated under reduced pressure to afford S21 (0.09 g, 44%). MS (ESI) m/z 242.2 [M+H]$^+$. $^1$H NMR (400 MHz, Methanol-d4) δ 8.16 (dd, J=2.3, 0.8 Hz, 1H), 7.55 (dd, J=8.9, 2.3 Hz, 1H), 6.65 (dd, J=8.9, 0.9 Hz, 1H), 3.85 (dd, J=12.5, 2.4 Hz, 2H), 3.44 (dd, J=4.6, 2.5 Hz, 2H), 3.41 (s, 1H), 3.09 (dd, J=12.2, 2.2 Hz, 2H), 2.52 (q, J=7.2 Hz, 2H), 2.00 (dt, J=7.0, 3.1 Hz, 2H), 1.67 (t, J=6.8 Hz, 2H), 1.15 (t, J=7.2 Hz, 3H).

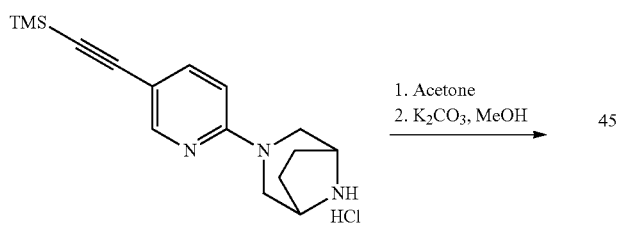

S20a

Synthesis of 3-(5-ethynylpyridin-2-yl)-8-isopropyl-3,8-diazabicyclo[3.2.1]octane (S22)

To a solution of S20a (0.1 g, 0.35 mmol) in Methanol (1.2 ml) was added sodium acetate (28.74 mg, 0.35 mmol), acetic acid (21.04 mg, 0.35 mmol) and acetone (20.35 mg, 0.35 mmol) the mixture was stirred at 40° C. After 1 h sodium cyanoborohydride (44.03 mg, 0.7 mmol) was added and the reaction was stirred at 40° C. After 12 h the mixture was cooled to room temperature, concentrated under reduce pressure and the residue was diluted with EtOAc, washed with saturated NaHCO3 solution, dried over $Na_2SO_4$, filtered, and concentrated under reduced pressure and purified by silica column chromatography (2% MeOH/EtOAc). The product was dissolved in Methanol (1 ml), potassium carbonate (0.05 g, 0.35 mmol) was added and after 1 h the mixture was concentrated diluted with EtOAc, washed with water, dried over Na2SO4, filtered concentrated to yield S22 (28 mg, 31.3%). MS (ESI) m/z 256.2 [M+H]$^+$. $^1$H NMR (400 MHz, Methanol-d$_4$) δ 8.18 (d, J=2.3 Hz, 1H), 7.57 (dd, J=8.9, 2.4 Hz, 1H), 6.68 (d, J=8.9 Hz, 1H), 3.93-3.68 (m, 6H), 3.43 (s, 1H), 3.23-3.12 (m, 3H), 2.86 (s, 2H), 2.07-1.92 (m, 3H), 1.75 (t, J=6.6 Hz, 3H), 1.20 (d, J=6.4 Hz, 8H).

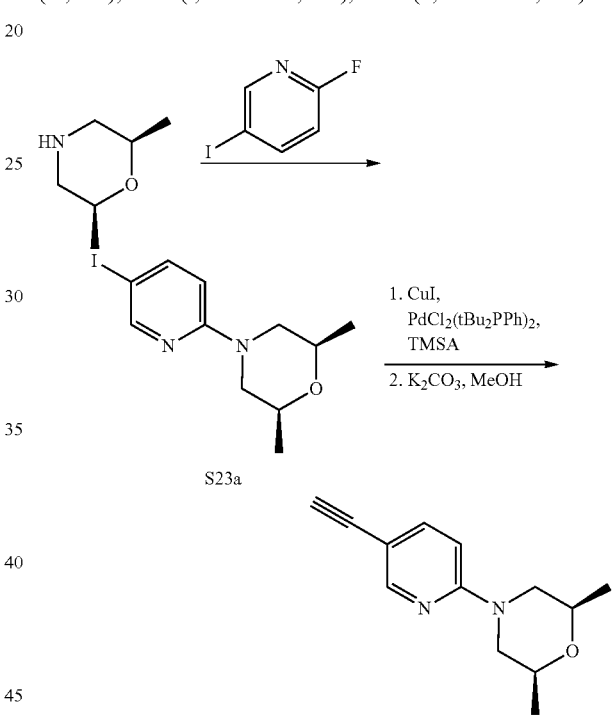

Synthesis of (2S,6R)-4-(5-iodopyridin-2-yl)-2,6-dimethylmorpholine (S23a)

The title compound S23a was prepared according to the method presented for the synthesis of compound S1a but instead utilizing (2S,6R)-2,6-dimethylmorpholine. MS (ESI) m/z 319.0 [M+H]$^+$. $^1$H NMR (400 MHz, Chloroform-d) δ 8.32 (d, J=2.3 Hz, 1H), 7.69 (d, J=8.9 Hz, 1H), 6.49 (d, J=9.0 Hz, 1H), 4.00 (d, J=12.6 Hz, 2H), 3.70 (ddd, J=10.6, 6.3, 2.6 Hz, 2H), 2.53 (t, J=11.6 Hz, 2H), 1.26 (d, J=6.2 Hz, 6H).

Synthesis of (2S,6R)-4-(5-ethynylpyridin-2-yl)-2,6-dimethylmorpholine (S23)

The title compound S23 was prepared according to the method presented for the synthesis of compound S1 but instead utilizing S23a. MS (ESI) m/z 217.1 [M+H]$^+$.

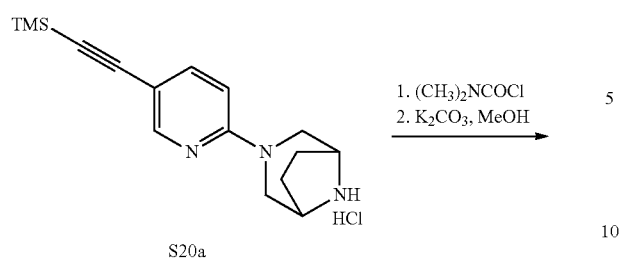

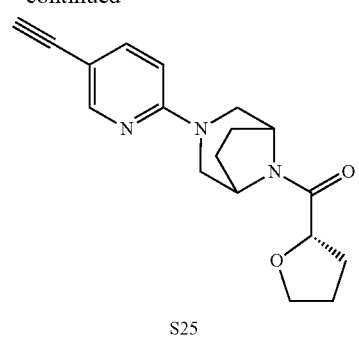

Synthesis of (3-(5-ethynylpyridin-2-yl)-3,8-diazabicyclo[3.2.1]octan-8-yl)((S)-tetrahydrofuran-2-yl)methanone (S25)

To S20a suspended in CH₂Cl₂ (10 mL) was added (S)-tetrahydrofuran-2-carboxylic acid (0.12 ml, 1 mmol), Et₃N (0.68 ml, 5 mmol) followed by HATU (0.48 g, 1 mmol). The mixture was stirred for 1.5 h. The mixture was diluted with DCM and washed with water. The organic layer was dried over Na₂SO₄, and concentrated in vacuo. The residue was dissolved in MeOH (20 mL), cooled to 5° C. and potassium carbonate (0.4 g, 3 mmol) was added. After 30 min, the reaction quenched with water and brine, extracted into DCM, dried over Na₂SO₄, filtered, concentrated under reduced pressure and the residue was purified by silica column chromatography (60%-100% EtOAc/hexanes to 5% MeOH/EtOAc) to give S25 (0.23 g, 74.3%). MS (ESI) m/z 312.2 [M+H]⁺. ¹H NMR (400 MHz, Chloroform-d) δ 8.29 (dd, J=2.3, 0.8 Hz, 1H), 7.54 (dt, J=8.9, 2.4 Hz, 1H), 6.48 (d, J=8.8 Hz, 1H), 4.84 (t, J=8.6 Hz, 1H), 4.66 (d, J=6.8 Hz, 1H), 4.56 (ddd, J=14.9, 7.4, 5.7 Hz, 2H), 4.12 (ddd, J=20.9, 12.7, 2.3 Hz, 1H), 3.99-3.73 (m, 4H), 3.21 (dd, J=12.1, 2.3 Hz, 1H), 3.14 (dd, J=12.0, 2.4 Hz, 1H), 3.07 (s, 1H), 3.06-3.02 (m, 0H), 2.41-2.21 (m, 1H), 2.15-1.70 (m, 5H).

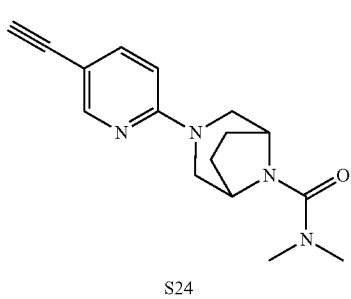

Synthesis of 3-(5-ethynylpyridin-2-yl)-N,N-dimethyl-3,8-diazabicyclo[3.2.1]octane-8-carboxamide (S24)

To a solution of S20a (200 mg, 0.558 mmol) and Et₃N (0.3 ml, 2.164 mmol) in DCM (5 mL) at 0° C., was added dimethylcarbamoyl chloride (0.055 ml, 0.601 mmol). The reaction was gradually warmed to room temperature and stirred overnight. The reaction was concentrated under reduced pressure. The residue was dissolved in MeOH (5 mL) and K₂CO₃ (313 mg, 2.236 mmol) was added. After stirring at room temperature for 48 h, the reaction was concentrated, then diluted with EtOAc and washed with brine. The organic extracts were dried over Na₂SO₄ to give S24 (123.9 mg, 78%). MS (ESI) m/z 276.2 [M+H]⁺. ¹H NMR (400 MHz, Methanol-d4) δ 8.17 (dd, J=2.3, 0.8 Hz, 1H), 7.55 (dd, J=8.9, 2.3 Hz, 1H), 6.69 (dd, J=9.0, 0.8 Hz, 1H), 4.19 (dd, J=4.5, 2.2 Hz, 3H), 3.98 (dd, J=12.4, 2.5 Hz, 3H), 3.42 (s, 1H), 3.11 (dd, J=12.2, 2.1 Hz, 3H), 2.94 (s, 8H), 1.88 (dd, J=8.5, 4.4 Hz, 3H), 1.71 (q, J=6.7 Hz, 2H).

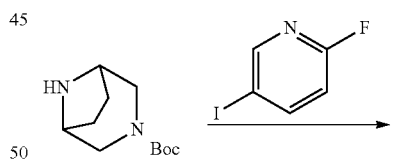

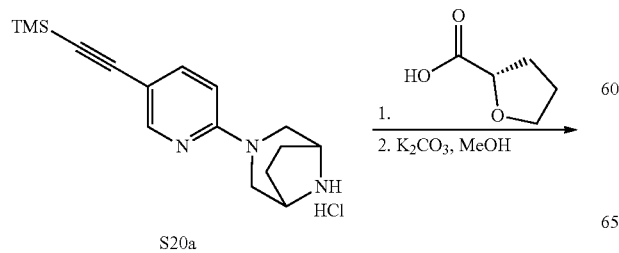

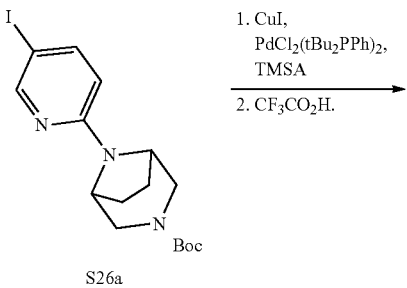

-continued

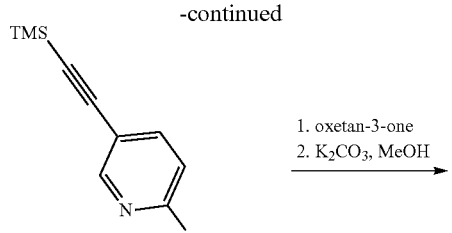

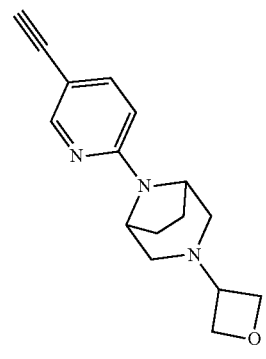

Synthesis of tert-butyl 8-(5-iodopyridin-2-yl)-3,8-diazabicyclo[3.2.1]octane-3-carboxylate (S26a)

The title compound S26a was prepared according to the method presented for the synthesis of compound S1a but instead utilizing tert-butyl 3,8-diazabicyclo[3.2.1]octane-3-carboxylate. MS (ESI) m/z 415.8 [M+H]$^+$. $^1$H NMR (400 MHz, Chloroform-d) δ 8.31 (d, J=2.2 Hz, 1H), 7.70 (s, 1H), 6.46 (s, 1H), 4.45 (s, 2H), 3.78 (d, J=52.7 Hz, 2H), 3.14 (dd, J=50.9, 12.9 Hz, 2H), 2.06-1.77 (m, 4H), 1.45 (s, 12H).

Synthesis of 8-(5-((trimethylsilyl)ethynyl)pyridin-2-yl)-3,8-diazabicyclo[3.2.1]octane (S26b)

The title compound S26b was prepared according to the method presented for the synthesis of compound S17b but instead utilizing S26a. MS (ESI) m/z 286.2 [M+H]$^+$.

Synthesis of 8-(5-ethynylpyridin-2-yl)-3-(oxetan-3-yl)-3,8-diazabicyclo[3.2.1]octane (S26)

The title compound S26 was prepared according to the method presented for the synthesis of compound S18 but instead utilizing oxetan-3-one. MS (ESI) m/z 270.2 [M+H]$^+$.
$^1$H NMR (400 MHz, Methanol-d4) δ 8.18 (d, J=2.3 Hz, 1H), 7.58 (dd, J=8.8, 2.3 Hz, 1H), 6.73 (d, J=8.8 Hz, 1H), 4.61 (dt, J=11.1, 5.5 Hz, 7H), 3.51-3.44 (m, 2H), 2.64 (dd, J=10.9, 2.6 Hz, 3H), 2.23 (d, J=10.7 Hz, 2H), 2.14 (t, J=6.2 Hz, 2H), 1.99 (dd, J=8.3, 4.2 Hz, 2H).

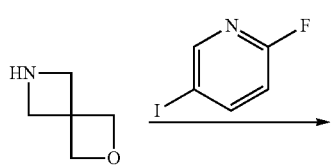

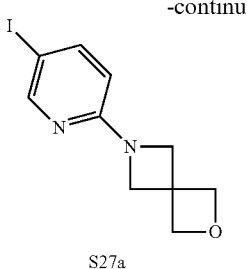
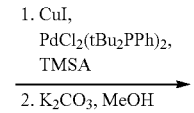
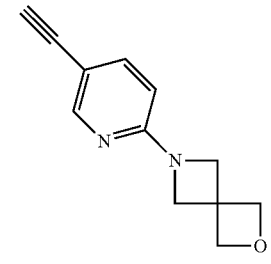

Synthesis of 5-iodo-2-(2-oxaspiro[3.3]heptan-6-yl)pyridine (S27a)

The title compound S27a was prepared according to the method presented for the synthesis of compound S1a but instead utilizing 2-oxa-6-azaspiro[3.3]heptane. $^1$H NMR (400 MHz, Chloroform-d) δ 8.16 (dd, J=2.4, 0.7 Hz, 1H), 7.52 (dd, J=8.8, 2.4 Hz, 1H), 6.20 (d, J=8.8 Hz, 1H), 4.84 (s, 4H), 4.17 (s, 5H).

Synthesis of 5-ethynyl-2-(2-oxaspiro[3.3]heptan-6-yl)pyridine (S27)

The title compound S27 was prepared according to the method presented for the synthesis of compound S1 but instead utilizing S27a. MS (ESI) m/z 201.1 [M+H]$^+$.

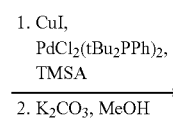
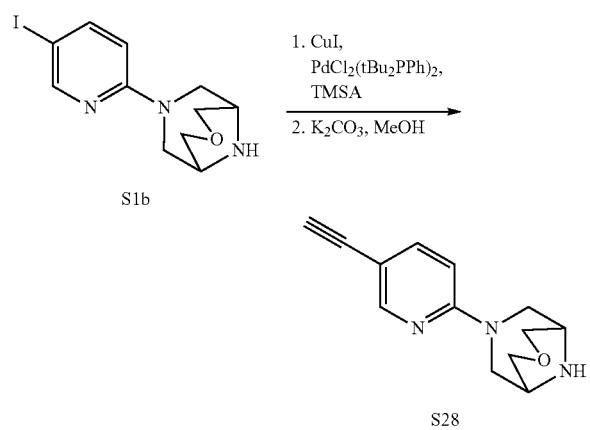

Synthesis of 7-(5-ethynylpyridin-2-yl)-3-oxa-7,9-diazabicyclo[3.3.1]nonane (S28)

The title compound S28 was prepared according to the method presented for the synthesis of compound S1 but instead utilizing S1b. MS (ESI) m/z 230.1 [M+H]$^+$. $^1$H NMR (400 MHz, Chloroform-d) δ 8.25 (s, 1H), 7.56-7.43

(m, 1H), 6.48 (d, J=8.9 Hz, 1H), 4.42 (d, J=13.5 Hz, 2H), 4.12 (d, J=12.1 Hz, 2H), 3.93 (d, J=12.2 Hz, 2H), 3.59 (d, J=13.6 Hz, 2H), 3.36 (s, 2H), 3.00 (d, J=1.1 Hz, 1H).

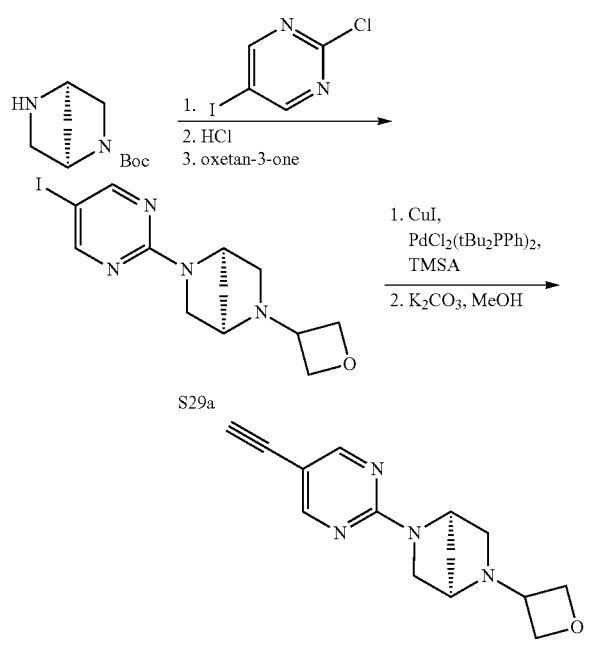

Synthesis of (1R,4R)-2-(5-iodopyrimidin-2-yl)-5-(oxetan-3-yl)-2,5-diazabicyclo[2.2.1] heptane (S29a)

The title compound S29a was prepared according to the method presented for the synthesis of compound S7a but instead utilizing tert-butyl (1R,4R)-2,5-diazabicyclo[2.2.1]heptane-2-carboxylate. MS (ESI) m/z 359.1 [M+H]⁺. 1H NMR (400 MHz, Chloroform-d) δ 8.37 (s, 2H), 4.79 (s, 1H), 4.69 (dt, J=10.0, 6.5 Hz, 2H), 4.55 (t, J=6.1 Hz, 1H), 4.48 (t, J=5.9 Hz, 1H), 3.98 (p, J=6.3 Hz, 1H), 3.57 (s, 1H), 3.46 (dd, J=11.0, 1.6 Hz, 1H), 3.36 (dd, J=10.8, 2.0 Hz, 1H), 2.98 (dd, J=9.6, 2.0 Hz, 1H), 2.82 (d, J=9.6 Hz, 1H), 1.97 (d, J=9.9 Hz, 1H), 1.86 (d, J=9.8 Hz, 1H).

Synthesis of (1R,4R)-2-(5-ethynylpyridin-2-yl)-5-(oxetan-3-yl)-2,5-diazabicyclo[2.2.1]heptane (S29)

The title compound S29 was prepared according to the method presented for the synthesis of compound S1 but instead utilizing S29a. MS (ESI) m/z 257.1 [M+H]⁺. 1H NMR (400 MHz, Chloroform-d) δ 8.39 (s, 2H), 4.88 (s, 1H), 4.70 (dt, J=9.5, 6.5 Hz, 2H), 4.52 (dt, J=26.3, 6.0 Hz, 2H), 3.99 (p, J=6.3 Hz, 1H), 3.58 (s, 1H), 3.52 (d, J=10.9 Hz, 1H), 3.41 (dd, J=11.0, 2.0 Hz, 1H), 3.18 (s, 1H), 2.99 (d, J=9.6 Hz, 1H), 2.83 (d, J=9.6 Hz, 1H), 1.98 (d, J=9.9 Hz, 1H), 1.87 (d, J=9.8 Hz, 1H).

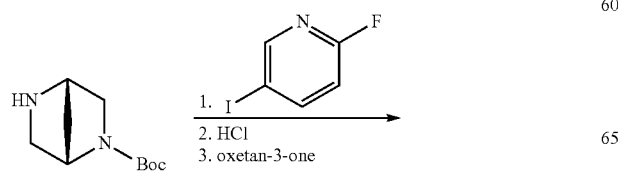

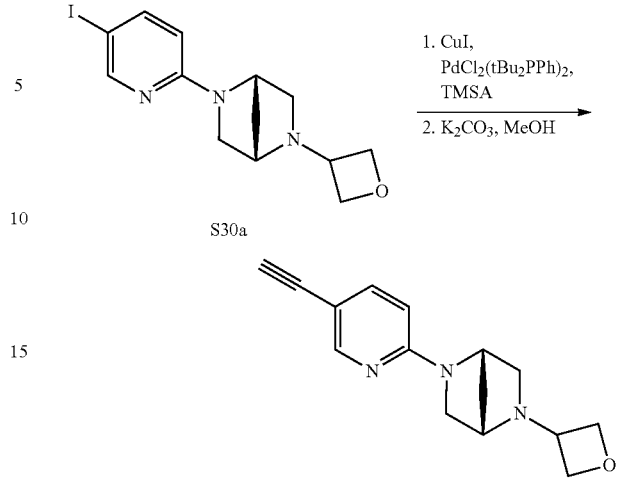

Synthesis of (1S,4S)-2-(5-iodopyridin-2-yl)-5-(oxetan-3-yl)-2,5-diazabicyclo[2.2.1]heptane (S30a)

The title compound S30a was prepared according to the method presented for the synthesis of compound S1c but instead utilizing tert-butyl (1S,4S)-2,5-diazabicyclo[2.2.1]heptane-2-carboxylate. MS (ESI) m/z 358.0 [M+H]⁺.

Synthesis of (1S,4S)-2-(5-ethynylpyridin-2-yl)-5-(oxetan-3-yl)-2,5-diazabicyclo[2.2.1] heptane (S30)

The title compound S30 was prepared according to the method presented for the synthesis of compound S1 but instead utilizing S30a. MS (ESI) m/z 256.2 ([M+H]⁺. 1H NMR (400 MHz, Chloroform-d) δ 8.12 (dd, J=2.3, 0.8 Hz, 1H), 7.36 (dd, J=8.7, 2.3 Hz, 1H), 6.11 (d, J=8.7 Hz, 1H), 4.59 (s, 1H), 4.53 (dt, J=12.9, 6.5 Hz, 2H), 4.36 (dt, J=31.2, 5.3 Hz, 2H), 3.82 (p, J=5.9 Hz, 1H), 3.44 (s, 1H), 3.17 (s, 1H), 2.91 (s, 1H), 2.87-2.73 (m, 1H), 2.75-2.64 (m, 1H), 1.94-1.78 (m, 1H), 1.73 (d, J=9.7 Hz, 1H).

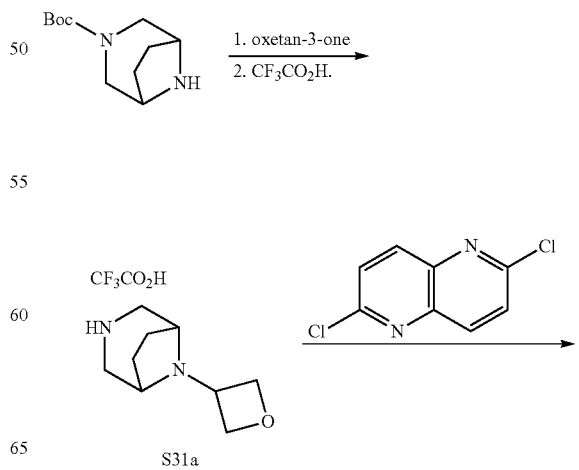

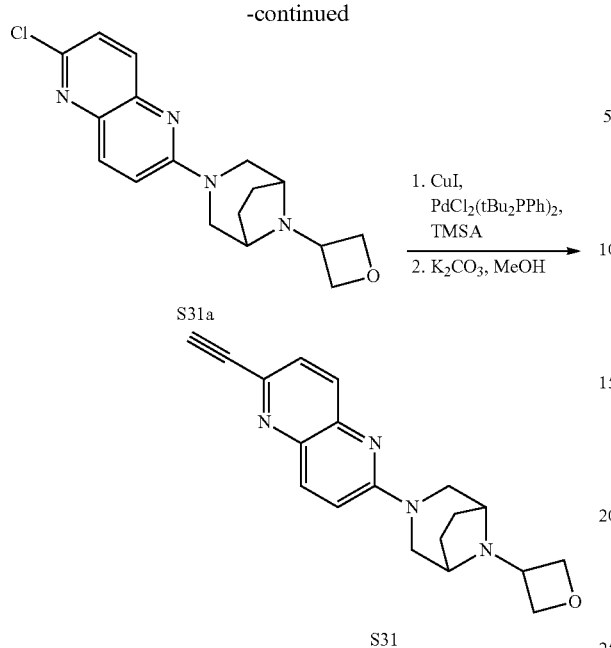

Synthesis of 8-(oxetan-3-yl)-3,8-diazabicyclo[3.2.1]octane 2,2,2-trifluoroacetate S31a)

The title compound S31a was prepared according to the method presented for the synthesis of compound S1c but instead utilizing tert-butyl 3,8-diazabicyclo[3.2.1]octane-3-carboxylate followed by Boc deprotection in the same manner as the synthesis of the compound S17b. MS (ESI) m/z 169.2 [M+H]$^+$. $^1$H NMR (400 MHz, Methanol-d4) δ 4.79 (t, J=6.9 Hz, 2H), 4.66 (dd, J=7.2, 5.2 Hz, 2H), 4.10 (tt, J=6.8, 5.2 Hz, 1H), 3.76 (dq, J=5.0, 2.3 Hz, 2H), 3.51 (dd, J=13.6, 2.0 Hz, 2H), 3.41-3.33 (m, 2H), 2.31-2.21 (m, 2H), 2.11-1.95 (m, 2H).

Synthesis of 2-chloro-6-(8-(oxetan-3-yl)-3,8-diazabicyclo[3.2.1]octan-3-yl)-1,5-naphthyridine (S31b)

The title compound S31b was prepared according to the method presented for the synthesis of compound S1a but instead utilizing 2,6-dichloro-1,5-naphthyridine. MS (ESI) m/z 330.7 [M+H]$^+$. $^1$H NMR (400 MHz, Chloroform-d) δ 7.95 (dd, J=9.5, 0.8 Hz, 1H), 7.86 (dd, J=8.8, 0.8 Hz, 1H), 7.38 (d, J=8.7 Hz, 1H), 7.07 (d, J=9.4 Hz, 1H), 4.71 (t, J=6.2 Hz, 2H), 4.58 (t, J=5.7 Hz, 2H), 4.05 (d, J=11.3 Hz, 2H), 3.74-3.63 (m, 1H), 3.28-3.20 (m, 5H), 1.86 (dd, J=9.1, 4.4 Hz, 2H).

Synthesis of 2-ethynyl-6-(8-(oxetan-3-yl)-3,8-diazabicyclo[3.2.1]octan-3-yl)-1,5-naphthyridine (S31)

The title compound S31 was prepared according to the method presented for the synthesis of compound S1 but instead utilizing S31b. MS (ESI) m/z 321.2 [M+H]$^+$. $^1$H NMR (400 MHz, Chloroform-d) δ 7.93 (d, J=9.5 Hz, 1H), 7.77 (d, J=8.6 Hz, 1H), 7.47 (d, J=8.6 Hz, 1H), 7.00 (d, J=9.5 Hz, 1H), 4.63 (t, J=6.2 Hz, 2H), 4.50 (t, J=5.8 Hz, 2H), 4.01 (d, J=11.8 Hz, 2H), 3.61 (p, J=6.0 Hz, 1H), 3.27-3.07 (m, 4H), 3.06 (s, 1H), 1.77 (dd, J=8.9, 4.3 Hz, 2H), 1.66-1.52 (m, 2H).

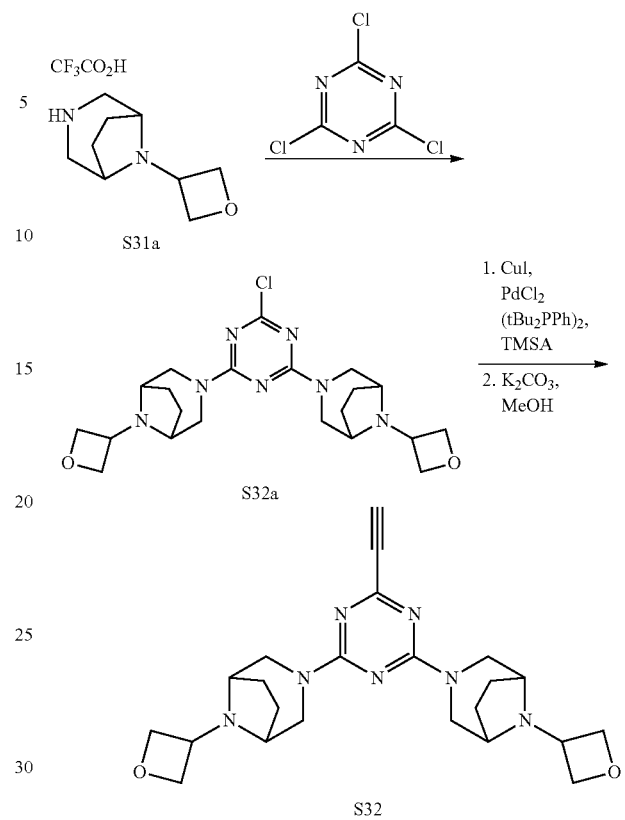

Synthesis of 3,3'-(6-chloro-1,3,5-triazine-2,4-diyl)bis(8-(oxetan-3-yl)-3,8-diazabicyclo [3.2.1]octane) (S32a)

The title compound S32a was prepared according to the method presented for the synthesis of compound S1a but instead utilizing S31a and 2,4,6-trichloro-1,3,5-triazine. MS (ESI) m/z 448.3 [M+H]$^+$. $^1$H NMR (400 MHz, Chloroform-d) δ 4.70 (t, J=6.2 Hz, 4H), 4.56 (s, 3H), 4.32 (d, J=13.0 Hz, 2H), 4.30-4.20 (m, 2H), 3.64 (h, J=5.8 Hz, 2H), 3.21-3.04 (m, 8H), 1.89-1.73 (m, 4H), 1.71-1.51 (m, 5H).

Synthesis of 3,3'-(6-ethynyl-1,3,5-triazine-2,4-diyl)bis(8-(oxetan-3-yl)-3,8-diazabicyclo [3.2.1]octane) (S32)

The title compound S32 was prepared according to the method presented for the synthesis of compound S1 but instead utilizing S32a. MS (ESI) m/z 438.3 [M+H]$^+$. $^1$H NMR (400 MHz, Chloroform-d) δ 4.55 (t, J=6.2 Hz, 4H), 4.48-4.33 (m, 4H), 4.23 (d, J=12.5 Hz, 2H), 4.12 (t, J=10.9 Hz, 2H), 3.49 (q, J=5.7 Hz, 2H), 3.05-2.85 (m, 8H), 2.78 (s, 1H), 1.71-1.57 (m, 4H), 1.52-1.34 (m, 4H).

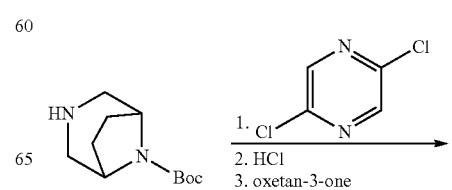

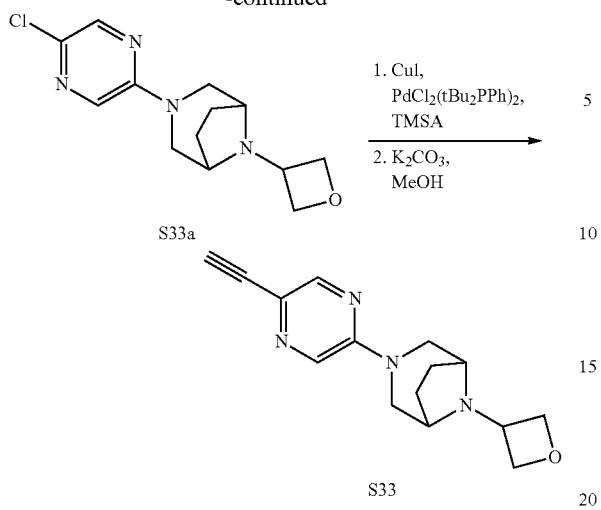

Synthesis of 3-(5-chloropyrazin-2-yl)-8-(oxetan-3-yl)-3,8-diazabicyclo[3.2.1]octane (S33a)

The title compound S33a was prepared according to the method presented for the synthesis of compound S1c but instead utilizing 2,5-dichloropyrazine MS (ESI) m/z 281.3 [M+H]+. 1H NMR (400 MHz, Chloroform-d) δ 8.04 (d, J=1.4 Hz, 1H), 7.74 (d, J=1.5 Hz, 1H), 4.72 (t, J=6.3 Hz, 2H), 4.58 (t, J=5.8 Hz, 2H), 3.77 (dd, J=11.6, 2.3 Hz, 2H), 3.69 (ddd, J=11.9, 6.5, 5.5 Hz, 1H), 3.23 (dd, J=4.8, 2.6 Hz, 2H), 3.18 (dd, J=11.5, 2.3 Hz, 2H), 1.92-1.83 (m, 2H), 1.73-1.65 (m, 2H).

Synthesis of 3-(5-ethynylpyrazin-2-yl)-8-(oxetan-3-yl)-3,8-diazabicyclo[3.2.1]octane (S33)

The title compound S33 was prepared according to the method presented for the synthesis of compound S1 but instead utilizing S33a. MS (ESI) m/z 271.2 [M+H]+. 1H NMR (400 MHz, Chloroform-d) δ 8.21 (d, J=1.5 Hz, 1H), 7.98 (d, J=1.5 Hz, 1H), 4.73 (dd, J=6.3 Hz, 2H), 4.59 (t, J=5.8 Hz, 2H), 3.90 (d, J=10.5 Hz, 1H), 3.70 (p, J=6.0 Hz, 1H), 3.27-3.18 (m, 4H), 3.17 (s, 1H), 1.94-1.83 (m, 2H), 1.74-1.64 (m, 2H), 1.57 (s, 1H).

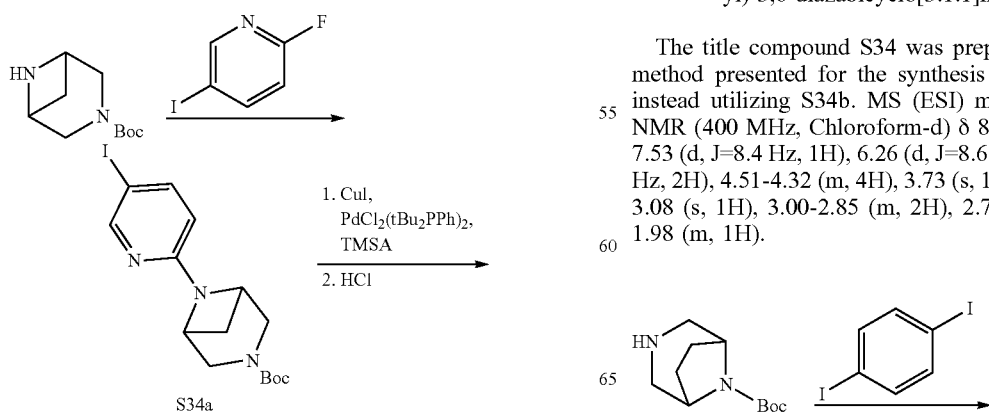

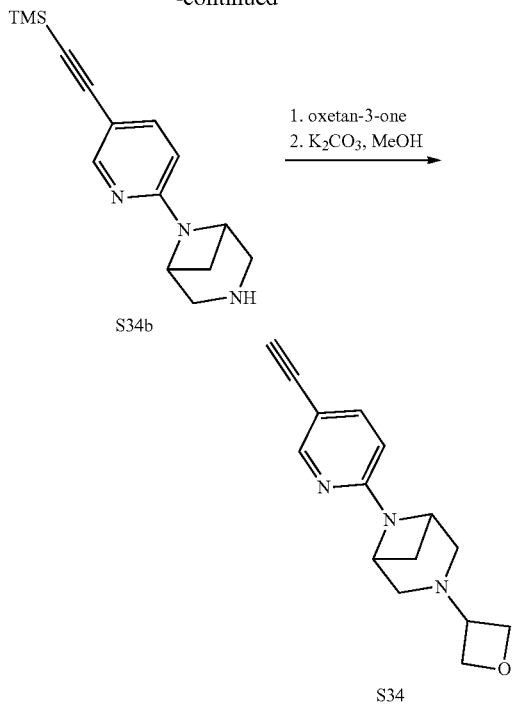

Synthesis of tert-butyl 6-(5-iodopyridin-2-yl)-3,6-diazabicyclo[3.1.1]heptane-3-carboxylate (S34a)

The title compound S34a was prepared according to the method presented for the synthesis of compound S1a but instead utilizing tert-butyl 3,6-diazabicyclo[3.1.1]heptane-3-carboxylate. MS (ESI) m/z 401.8 [M+H]+.

Synthesis of 6-(5-((trimethylsilyl)ethynyl)pyridin-2-yl)-3,6-diazabicyclo[3.1.1]heptane (S34b)

The title compound S34b was prepared according to the method presented for the synthesis of compound S1c but instead utilizing S34a. MS (ESI) m/z 272.2 [M+H]+. 1H NMR (400 MHz, Methanol-d4) δ 8.22-8.09 (m, 1H), 8.01 (d, J=1.9 Hz, 1H), 7.93 (d, J=1.6 Hz, 1H), 7.78 (d, J=8.7 Hz, 1H), 6.97 (d, J=9.2 Hz, 1H), 6.90 (d, J=9.1 Hz, 1H), 5.87 (d, J=2.8 Hz, 1H), 5.47 (d, J=2.7 Hz, 1H), 4.86-4.71 (m, 3H), 3.69-3.57 (m, 3H), 3.53-3.44 (m, 3H), 3.10-3.03 (m, 3H), 2.96 (d, J=9.0 Hz, 2H), 2.02-1.95 (m, 1H), 0.00 (s, 9H).

Synthesis of 6-(5-ethynylpyridin-2-yl)-3-(oxetan-3-yl)-3,6-diazabicyclo[3.1.1]heptane (S34)

The title compound S34 was prepared according to the method presented for the synthesis of compound S1 but instead utilizing S34b. MS (ESI) m/z 256.1 [M+H]+. 1H NMR (400 MHz, Chloroform-d) δ 8.32 (d, J=2.1 Hz, 1H), 7.53 (d, J=8.4 Hz, 1H), 6.26 (d, J=8.6 Hz, 1H), 4.56 (t, J=6.8 Hz, 2H), 4.51-4.32 (m, 4H), 3.73 (s, 1H), 3.26-3.11 (m, 2H), 3.08 (s, 1H), 3.00-2.85 (m, 2H), 2.71-2.58 (m, 1H), 2.21-1.98 (m, 1H).

1H), 3.18 (dd, J=11.0, 2.5 Hz, 2H), 3.00 (s, 2H), 2.84 (d, J=10.7 Hz, 2H), 2.75 (s, 1H), 1.72-1.47 (m, 4H).

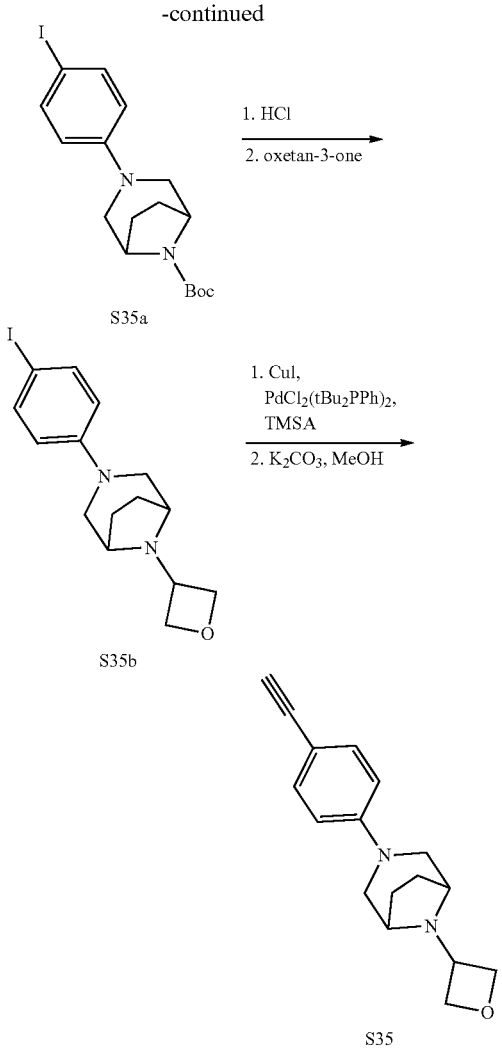

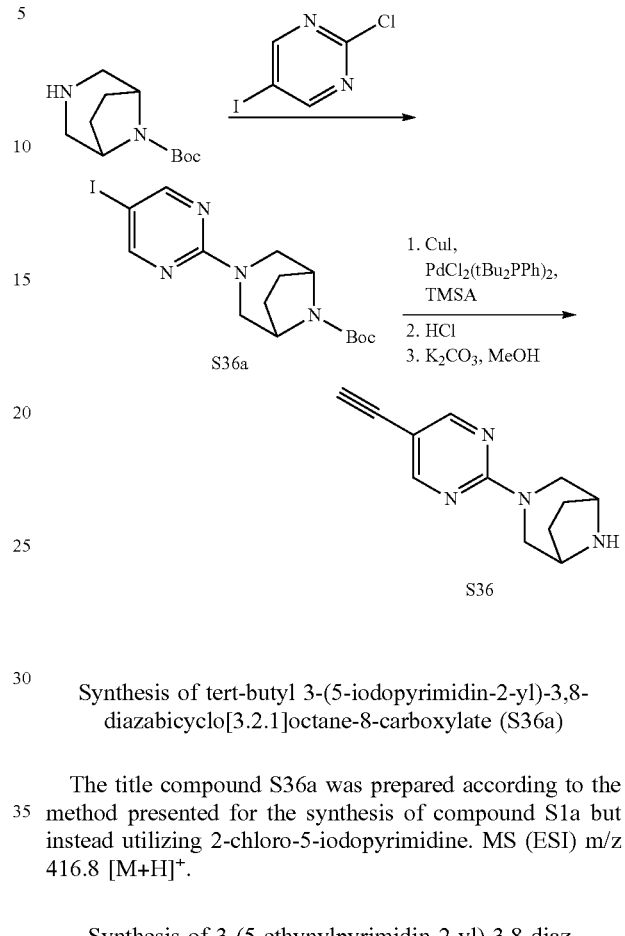

Synthesis of tert-butyl 3-(5-iodopyrimidin-2-yl)-3,8-diazabicyclo[3.2.1]octane-8-carboxylate (S36a)

The title compound S36a was prepared according to the method presented for the synthesis of compound S1a but instead utilizing 2-chloro-5-iodopyrimidine. MS (ESI) m/z 416.8 [M+H]$^+$.

Synthesis of 3-(5-ethynylpyrimidin-2-yl)-3,8-diazabicyclo[3.2.1]octane (S36)

The title compound S36 was prepared according to the method presented for the synthesis of compound S1 but instead utilizing S36a. MS (ESI) m/z 215.2 [M+H]$^+$.

Synthesis of tert-butyl 3-(4-iodophenyl)-3,8-diazabicyclo[3.2.1]octane-8-carboxylate (S35a)

The title compound S35aa was prepared according to the method presented for the synthesis of compound S1c but instead utilizing 1,4-diiodobenzene. MS (ESI) m/z 414.9 [M+H]$^+$. $^1$H NMR (400 MHz, Chloroform-d) δ 7.56-7.43 (m, 2H), 6.68-6.55 (m, 2H), 4.34 (s, 2H), 3.35 (dd, J=11.2, 2.4 Hz, 2H), 2.97 (s, 2H), 2.00-1.80 (m, 4H), 1.46 (s, 9H).

Synthesis of 3-(4-iodophenyl)-8-(oxetan-3-yl)-3,8-diazabicyclo[3.2.1]octane (S35b)

The title compound S35b was prepared according to the method presented for the synthesis of compound S1c but instead utilizing S35a. MS (ESI) m/z 371.2 [M+H]$^+$.

Synthesis of 3-(4-ethynylphenyl)-8-(oxetan-3-yl)-3,8-diazabicyclo[3.2.1]octane (S35)

The title compound S35 was prepared according to the method presented for the synthesis of compound S1 but instead utilizing S35b. MS (ESI) m/z 269.2 [M+H]$^+$. $^1$H NMR (400 MHz, Chloroform-d) δ 7.19-7.08 (m, 2H), 6.53-6.40 (m, 2H), 4.49 (t, J=6.3 Hz, 2H), 4.36 (s, 2H), 3.50 (s,

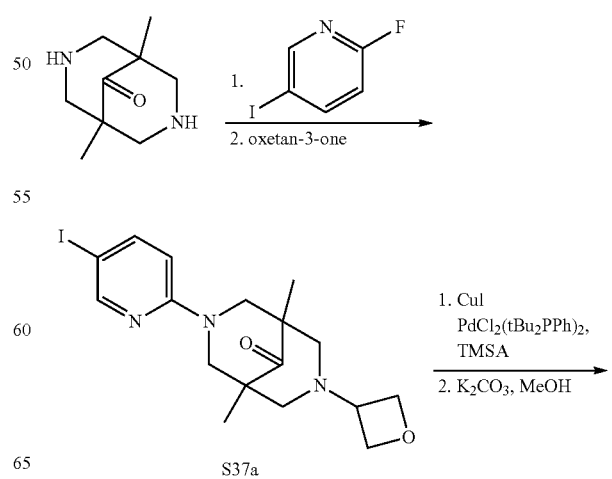

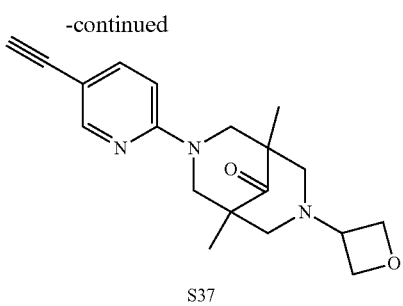

S37

Synthesis of 3-(5-iodopyridin-2-yl)-1,5-dimethyl-7-(oxetan-3-yl)-3,7-diazabicyclo[3.3.1] nonan-9-one (S37a)

The title compound S37a was prepared according to the method presented for the synthesis of compound S1c but instead utilizing 1,5-dimethyl-3,7-diazabicyclo[3.3.1] nonan-9-one. MS (ESI) m/z 428.1 [M+H]$^+$. $^1$H NMR (400 MHz, Chloroform-d) δ 8.34 (s, 1H), 7.71 (s, 1H), 6.62 (s, 1H), 4.70 (s, 2H), 4.37 (t, J=6.5 Hz, 2H), 4.15 (t, J=6.4 Hz, 3H), 3.29-3.05 (m, 3H), 3.02-2.80 (m, 1H), 2.17 (dd, J=11.2, 2.3 Hz, 2H), 1.55 (s, 2H), 1.03 (s, 6H).

Synthesis of 3-(5-ethynylpyridin-2-yl)-1,5-dimethyl-7-(oxetan-3-yl)-3,7-diazabicyclo[3.3.1] nonan-9-one (S37)

The title compound S37 was prepared according to the method presented for the synthesis of compound S1 but instead utilizing S37a. MS (ESI) m/z 326.3 [M+H]$^+$. $^1$H NMR (400 MHz, Chloroform-d) δ 8.34 (d, J=2.2 Hz, 1H), 7.59 (d, J=8.8 Hz, 1H), 6.69 (d, J=8.9 Hz, 1H), 4.80 (d, J=13.4 Hz, 2H), 4.34 (t, J=6.4 Hz, 2H), 4.12 (t, J=6.2 Hz, 2H), 3.24-2.99 (m, 3H), 2.91 (d, J=10.9 Hz, 2H), 2.17 (dd, J=11.3, 2.3 Hz, 2H), 1.55 (s, 1H), 1.03 (s, 6H).

Synthesis of 3-(5-ethynylpyridin-2-yl)-8-(methylsulfonyl)-3,8-diazabicyclo[3.2.1]octane (S38)

To a solution of S20a (630 mg, 1.76 mmol) in DCM (10 mL) was added N,N-diisopropylethylamine (1.22 ml, 0.01 mol), the mixture was cooled to 5° C., and then methanesulfonyl chloride (0.2 ml, 3.0 mmol) was added. After 3 min the reaction was quenched with NaHCO3 saturated solution, the organic layer was separated, dried over Na2SO4, filtered, concentrated and the residue was dissolved in MeOH (15 mL), the solution was cooled to 10° C., then added K2CO3 (0.44 g, 0.01 mol). After 15 min the precipitate was filtered off, rinsed with 10% MeOH in water and dried under vacuum to give S38 (477 mg, 93.1%) MS (ESI) m/z 292.2 [M+H]$^+$. $^1$H NMR (400 MHz, Chloroform-d) δ 8.07 (dd, J=2.3, 0.8 Hz, 1H), 7.32 (dd, J=8.8, 2.3 Hz, 1H), 6.26 (d, J=8.8 Hz, 1H), 4.12 (dd, J=4.7, 2.4 Hz, 2H), 3.83 (dd, J=12.3, 2.5 Hz, 2H), 2.92 (dd, J=12.1, 2.1 Hz, 2H), 2.84 (s, 1H), 2.75 (s, 3H), 1.89-1.76 (m, 2H), 1.65-1.56 (m, 2H).

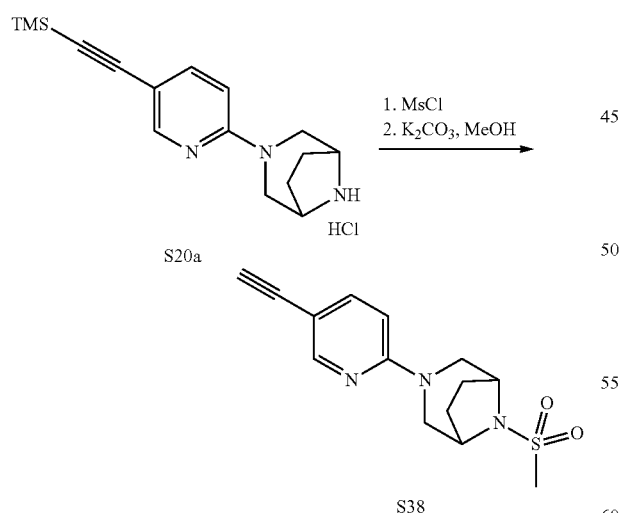

Synthesis of tert-butyl 7-(5-iodopyridin-2-yl)-3,7-diazabicyclo[3.3.1]nonane-3-carboxylate (S39a)

The title compound S39a was prepared according to the method presented for the synthesis of compound S1a but instead utilizing tert-butyl 3,7-diazabicyclo[3.3.1]nonane-3-carboxylate. MS (ESI) m/z 430.2 [M+H]$^+$.

Synthesis of 3-(5-((trimethylsilyl)ethynyl)pyridin-2-yl)-3,7-diazabicyclo[3.3.1]nonane Dihydrochloride (S39b)

The title compound S39b was prepared according to the method presented for the synthesis of compound S1 but instead utilizing S39a. MS (ESI) m/z 300.2 [M+H]$^+$. $^1$H NMR (400 MHz, Methanol-d4) δ 7.97 (d, J=2.2 Hz, 1H), 7.74 (dd, J=9.4, 2.2 Hz, 1H), 7.10 (d, J=9.3 Hz, 1H), 4.00 (d, J=12.6 Hz, 2H), 3.30 (d, J=13.0 Hz, 2H), 3.21 (t, J=11.5 Hz, 2H), 3.12 (d, J=13.0 Hz, 2H), 2.21 (s, 2H), 1.87 (d, J=13.8 Hz, 1H), 1.78 (d, J=13.7 Hz, 1H), 0.00 (s, 9H).

Synthesis of 1-(7-(5-ethynylpyridin-2-yl)-3,7-diazabicyclo[3.3.1]nonan-3-yl)ethan-1-one (S39)

To a mixture of S39b (0.39 g, 1 mmol) and Et₃N (0.73 ml, 0.01 mol) in DCM (10 mL), acetic anhydride (0.14 ml, 1 mmol) was added. After 5 min, the reaction was quenched with 1M NaOH, the layers were separated and the organic layer was dried over Na₂SO₄, filtered, concentrated and the residue was dissolved in MeOH (20 mL), then added K₂CO₃ (0.44 g, 3 mmol). After 20 min the reaction was diluted with DCM, washed with water, the organic layer was dried over Na₂SO₄, filtered, concentrated under reduced pressure and the residue was purified by silica column chromatography (60%-100% EtOAc/hexanes to 5% MeOH/EtOAc) to give S39 (111 mg, 39%) MS (ESI) m/z 270.2 [M+H]⁺. ¹H NMR (400 MHz, Methanol-d4) δ 8.12 (dd, J=2.3, 0.8 Hz, 1H), 7.48 (dd, J=9.0, 2.4 Hz, 1H), 6.69 (dd, J=9.0, 0.8 Hz, 1H), 4.74-4.59 (m, 2H), 4.33-4.20 (m, 1H), 4.04 (d, J=13.4 Hz, 1H), 3.42 (dt, J=13.5, 2.7 Hz, 1H), 3.39 (s, 1H), 3.11 (dddd, J=11.1, 8.0, 3.2, 2.2 Hz, 2H), 2.87 (dt, J=13.5, 2.6 Hz, 1H), 2.06 (q, J=3.0 Hz, 2H), 2.01-1.94 (m, 2H), 1.84 (s, 3H).

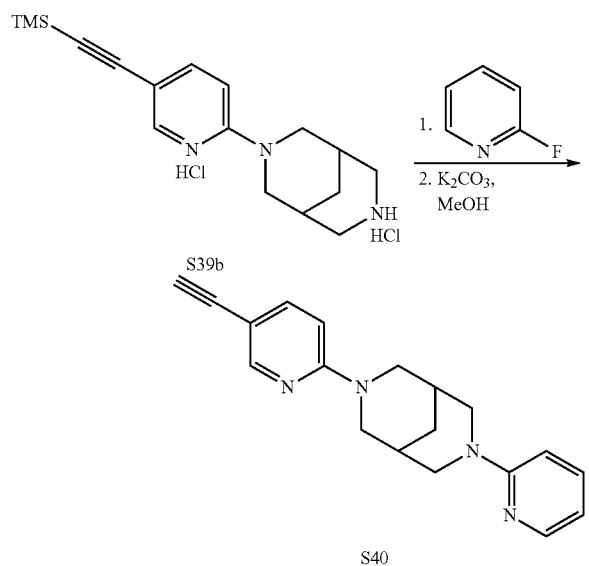

S39b

S40

Synthesis of 3-(5-ethynylpyridin-2-yl)-7-(pyridin-2-yl)-3,7-diazabicyclo[3.3.1]nonane (S40)

In a microwave tube a mixture of S39b (0.21 g, 0.6 mmol), 2-Fluoropyridine (0.1 ml, 1 mmol), sodium bicarbonate (0.24 g, 3 mol) in NMP (1 mL) were microwaved at 130° C. for 20 min, then at 150° C. for 20 min, the reaction was diluted with DCM, washed with water, the organic layer was dried over Na₂SO₄, filtered, concentrated under reduced pressure and the residue was purified by silica column chromatography to give S40 (9 mg, 5%) MS (ESI) m/z 305.2 [M+H]⁺. ¹H NMR (400 MHz, Chloroform-d) δ 8.06 (d, J=2.3 Hz, 1H), 7.93 (dd, J=5.1, 2.0 Hz, 1H), 7.25 (dd, J=9.0, 2.4 Hz, 1H), 7.25-7.16 (m, 1H), 6.39 (d, J=8.7 Hz, 1H), 6.36-6.30 (m, 2H), 4.39-4.17 (m, 4H), 3.15-3.02 (m, 5H), 2.93 (s, 1H), 2.18-2.07 (m, 2H), 1.89 (d, J=3.4 Hz, 2H).

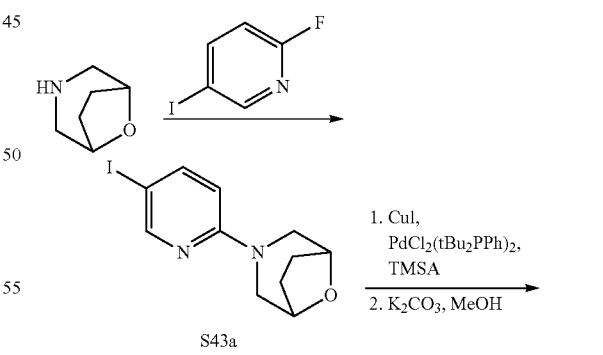

S39b

S41

Synthesis of 3-(5-ethynylpyridin-2-yl)-7-(oxetan-3-yl)-3,7-diazabicyclo[3.3.1]nonane (S41)

The title compound S41 was prepared according to the method presented for the synthesis of compound S1c but instead utilizing S39b. MS (ESI) m/z 284.3 [M+H]⁺. ¹H NMR (400 MHz, Methanol-d4) δ 8.17-7.96 (m, 1H), 7.46 (dd, J=9.0, 2.4 Hz, 1H), 6.77-6.49 (m, 1H), 4.41 (t, J=6.4 Hz, 2H), 4.26 (t, J=6.2 Hz, 2H), 4.19 (d, J=12.9 Hz, 2H), 3.31 (s, 1H), 3.23-3.12 (m, 3H), 2.80-2.65 (m, 2H), 2.13-1.91 (m, 4H), 1.91-1.76 (m, 1H), 1.73-1.61 (m, 1H).z

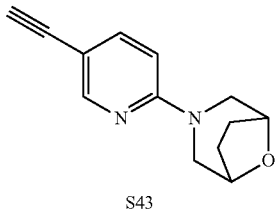

S43a

S43

Synthesis of 3-(5-iodopyridin-2-yl)-8-oxa-3-azabicyclo[3.2.1]octane (S43a)

The title compound S43a was prepared according to the method presented for the synthesis of compound S1a but instead utilizing 8-oxa-3-azabicyclo[3.2.1]octane. MS (ESI) m/z 317.1 [M+H]⁺.

Synthesis of 3-(5-ethynylpyridin-2-yl)-8-oxa-3-azabicyclo[3.2.1]octane (S43b)

The title compound S43 was prepared according to the method presented for the synthesis of compound S1 but instead utilizing S43a. MS (ESI) m/z 215.2 [M+H]⁺. ¹H NMR (400 MHz, Methanol-d4) δ 8.17 (dd, J=2.3, 0.8 Hz, 1H), 7.56 (dd, J=8.9, 2.3 Hz, 1H), 6.67 (dd, J=8.9, 0.8 Hz, 1H), 4.46 (dq, J=4.4, 2.3 Hz, 2H), 3.86 (dt, J=12.8, 1.1 Hz, 2H), 3.43 (s, 1H), 3.07 (d, J=2.6 Hz, 1H), 3.03 (d, J=2.6 Hz, 1H), 2.02-1.74 (m, 4H).

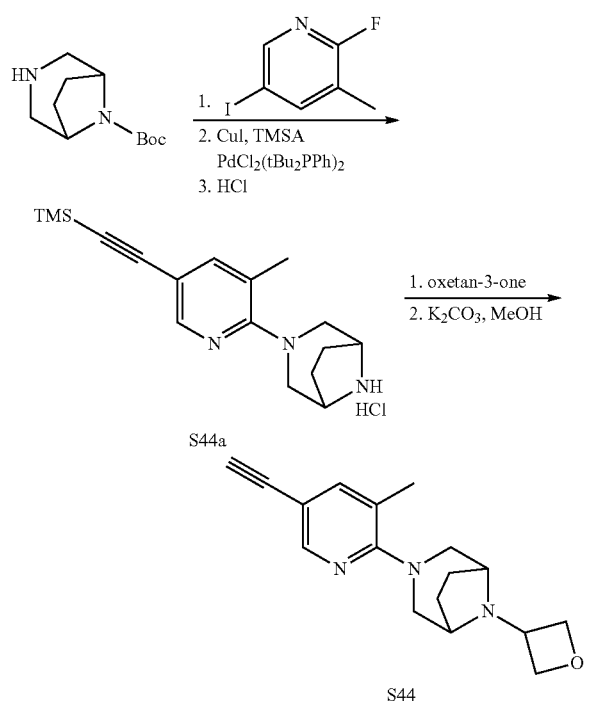

S44a

S44

Synthesis of 3-(3-methyl-5-((trimethylsilyl)ethynyl)pyridin-2-yl)-3,8-diazabicyclo[3.2.1] octane (S44a)

The title compound S44a was prepared according to the methods presented for the synthesis of compound S3 but instead utilizing 2-fluoro-5-iodo-3-methylpyridine. MS (ESI) m/z 300.3 [M+H]⁺.

Synthesis of 3-(5-ethynyl-3-methylpyridin-2-yl)-8-(oxetan-3-yl)-3,8-diazabicyclo[3.2.1] octane (S44)

The title compound S44 was prepared according to the methods presented for the synthesis of compound S3 but instead utilizing S44a. MS (ESI) m/z 284.2 [M+H]⁺. ¹H NMR (400 MHz, Chloroform-d) δ 8.24 (d, J=2.2 Hz, 1H), 8.05 (d, J=2.3 Hz, 0H), 7.43 (dd, J=2.1, 0.9 Hz, 1H), 7.30 (d, J=1.9 Hz, 0H), 7.19 (d, J=15.2 Hz, 0H), 5.80 (d, J=15.1 Hz, 0H), 5.30 (s, 0H), 4.70 (t, J=6.2 Hz, 3H), 4.59 (s, 2H), 3.76 (s, 1H), 3.35-3.26 (m, 2H), 3.18 (d, J=30.6 Hz, 5H), 3.09 (s, 1H), 2.27 (s, 0H), 2.24 (s, 3H), 1.96-1.79 (m, 5H), 0.24 (d, J=7.3 Hz, 0H), 0.15 (d, J=6.0 Hz, 0H), 0.08 (s, 0H).

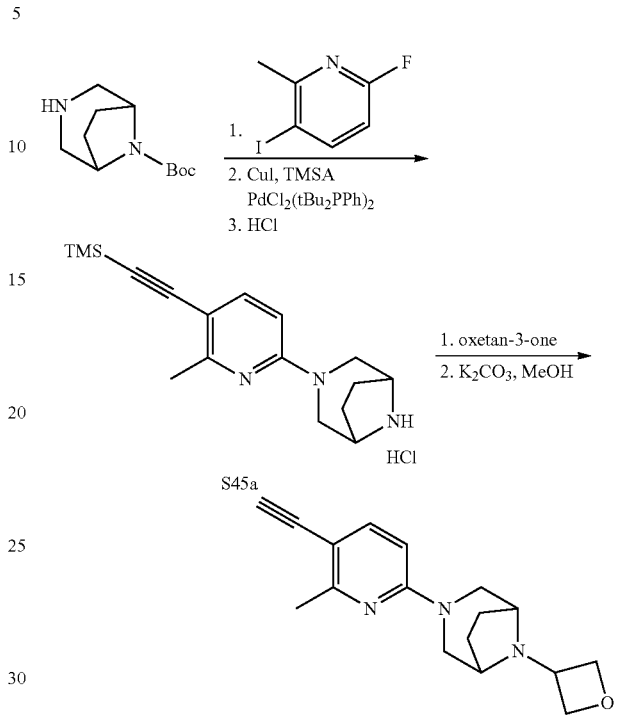

S45a

S45

Synthesis of 3-(6-methyl-5-((trimethylsilyl)ethynyl)pyridin-2-yl)-3,8-diazabicyclo[3.2.1] octane (S45a)

The title compound S45a was prepared according to the methods presented for the synthesis of compound S3 but instead utilizing 6-fluoro-3-iodo-2-methylpyridine. MS (ESI) m/z 300.3 [M+H]⁺.

Synthesis of 3-(5-ethynyl-6-methylpyridin-2-yl)-8-(oxetan-3-yl)-3,8-diazabicyclo[3.2.1]octane (S45)

The title compound S45 was prepared according to the methods presented for the synthesis of compound S3 but instead utilizing S45a. MS (ESI) m/z 284.2 [M+H]⁺. ¹H NMR (400 MHz, Chloroform-d) δ 7.46 (d, J=8.7 Hz, 1H), 6.28 (d, J=8.7 Hz, 1H), 5.30 (s, 0H), 4.72 (t, J=6.3 Hz, 2H), 4.59 (t, J=5.8 Hz, 2H), 4.07 (d, J=12.6 Hz, 0H), 3.89 (d, J=11.0 Hz, 2H), 3.71 (p, J=6.0 Hz, 1H), 3.26 (d, J=13.4 Hz, 1H), 3.24 (s, 0H), 3.23 (s, 1H), 3.19 (s, 2H), 3.14-3.07 (m, 2H), 2.51 (s, 3H), 1.85 (dd, J=11.5, 6.7 Hz, 2H), 1.70 (t, J=6.7 Hz, 1H).

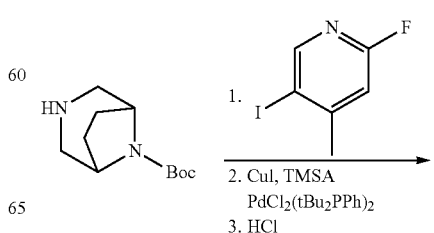

-continued

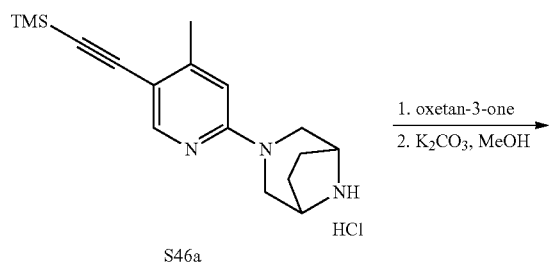

S46a 1. oxetan-3-one
2. K$_2$CO$_3$, MeOH

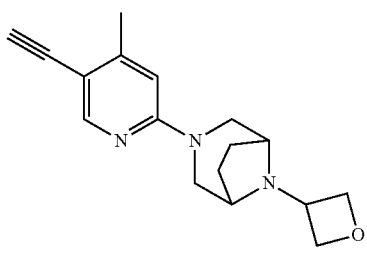

S46

Synthesis of 3-(4-methyl-5-((trimethylsilyl)ethynyl)pyridin-2-yl)-3,8-diazabicyclo[3.2.1] octane (S46a)

The title compound S46a was prepared according to the methods presented for the synthesis of compound S3 but instead utilizing 2-fluoro-5-iodo-4-methylpyridine. MS (ESI) m/z 300.4 [M+H]$^+$.

Synthesis of 3-(5-ethynyl-4-methylpyridin-2-yl)-8-(oxetan-3-yl)-3,8-diazabicyclo[3.2.1] octane (S46)

The title compound S46 was prepared according to the methods presented for the synthesis of compound S3 but instead utilizing S46a. MS (ESI) m/z 284.2 [M+H]$^+$. $^1$H NMR (400 MHz, Chloroform-d) δ 8.22 (s, 1H), 6.33 (s, 1H), 5.30 (s, 0H), 4.72 (t, J=6.3 Hz, 2H), 4.59 (t, J=5.8 Hz, 2H), 3.85 (dd, J=11.8, 2.4 Hz, 2H), 3.70 (p, J=6.0 Hz, 1H), 3.24 (s, 0H), 3.23 (s, 1H), 3.22-3.09 (m, 4H), 2.34 (d, J=0.7 Hz, 3H), 1.85 (dd, J=8.9, 4.3 Hz, 2H), 1.72-1.66 (m, 2H).

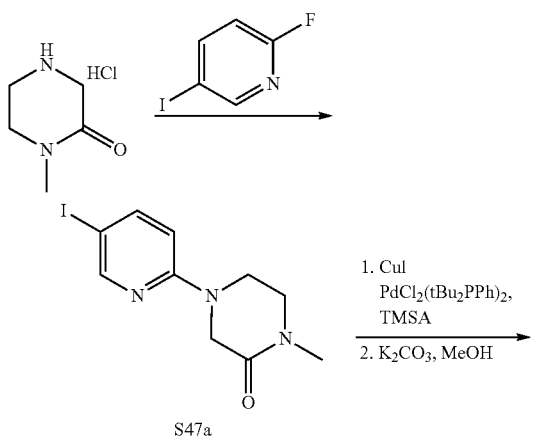

S47a

1. CuI
PdCl$_2$(tBu$_2$PPh)$_2$,
TMSA
2. K$_2$CO$_3$, MeOH

-continued

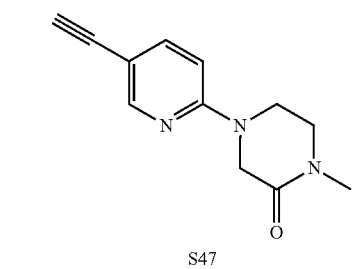

S47

Synthesis of 4-(5-iodopyridin-2-yl)-1-methylpiperazin-2-one (S47a)

The title compound S47a was prepared according to the methods presented for the synthesis of compound S1a but instead utilizing 1-Methylpiperazin-2-one hydrochloride. MS (ESI) m/z 318.0 [M+H]$^+$.

Synthesis of 3-(5-ethynyl-4-methylpyridin-2-yl)-8-(oxetan-3-yl)-3,8-diazabicyclo[3.2.1] octane 4-(5-ethynylpyridin-2-yl)-1-methylpiperazin-2-one (S47)

The title compound S47 was prepared according to the methods presented for the synthesis of compound S3 but instead utilizing S47a. MS (ESI) m/z 216.1 [M+H]$^+$.

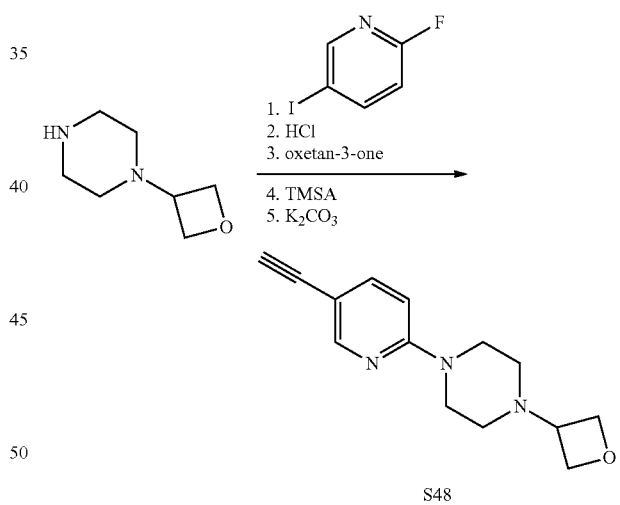

S48

Synthesis of 1-(5-ethynylpyridin-2-yl)-4-(oxetan-3-yl)piperazine (S48)

The title compound S48 was prepared according to the methods presented for the synthesis of compound S1 but instead utilizing 1-(oxetan-3-yl) piperazine. MS (ESI) m/z 244.16 [M+H]$^+$. $^1$H NMR (400 MHz, Methanol-d4) δ 8.18 (d, J=2.2 Hz, 1H), 7.56 (dd, J=8.9, 2.3 Hz, 1H), 6.75 (d, J=8.9 Hz, 1H), 4.70 (t, J=6.6 Hz, 3H), 4.63 (t, J=6.2 Hz, 3H), 3.68-3.56 (m, 6H), 3.55-3.47 (m, 1H), 3.42 (s, 1H), 2.52-2.37 (m, 6H), 1.27 (d, J=13.9 Hz, 0H).

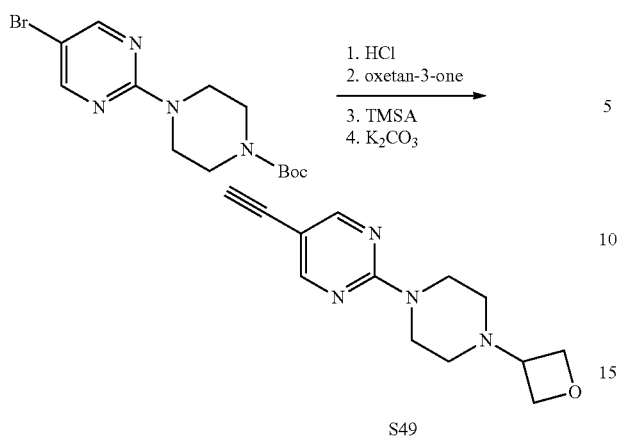

Synthesis of 5-ethynyl-2-(4-(oxetan-3-yl)piperazin-1-yl)pyrimidine (S49)

The title compound S49 was prepared according to the methods presented for the synthesis of compound S1 but instead utilizing tert-butyl 4-(5-bromopyrimidin-2-yl)piperazine-1-carboxylate. MS (ESI) m/z 245.2 [M+H]$^+$.

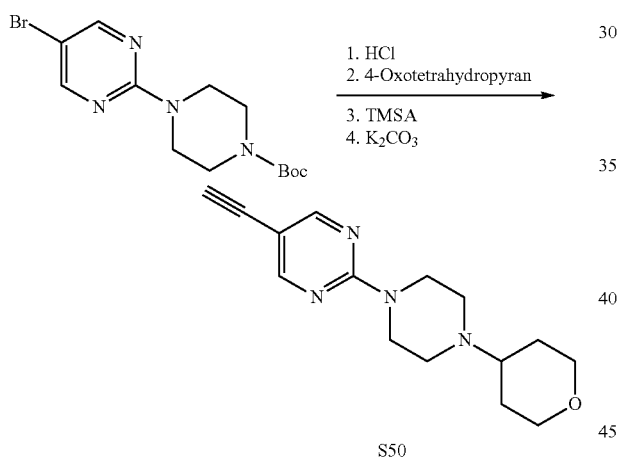

Synthesis of 5-ethynyl-2-(4-(tetrahydro-2H-pyran-4-yl)piperazin-1-yl)pyrimidine (S50)

The title compound S50 was prepared according to the methods presented for the synthesis of compound S1 but instead utilizing tert-butyl 4-(5-bromopyrimidin-2-yl)piperazine-1-carboxylate and 4-Oxotetrahydropyran. MS (ESI) m/z 272.70 [M+H]$^+$.

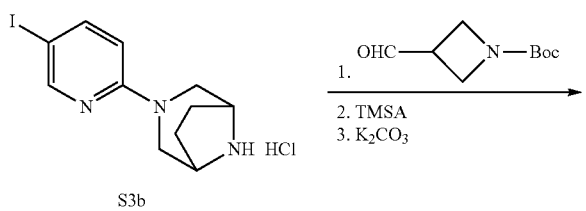

Synthesis of tert-butyl 3-((3-(5-ethynylpyridin-2-yl)-3,8-diazabicyclo[3.2.1]octan-8-yl)methyl)azetidine-1-carboxylate (S51)

The title compound S51 was prepared according to the methods presented for the synthesis of compound S1 but instead utilizing S3b and tert-butyl 3-formylazetidine-1-carboxylate. MS (ESI) m/z 383.05 [M+H]$^+$.

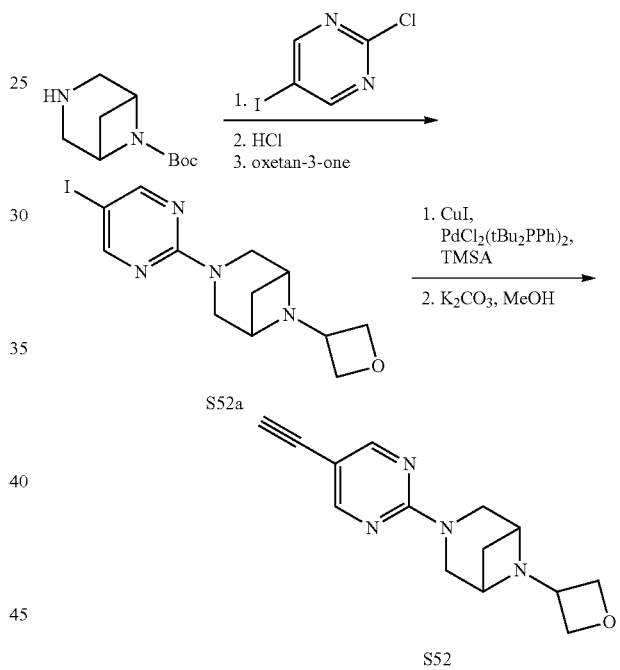

Synthesis of 3-(5-iodopyrimidin-2-yl)-6-(oxetan-3-yl)-3,6-diazabicyclo[3.1.1]heptane (S52a)

The title compound S52a was prepared according to the method presented for the synthesis of compound S1c but instead utilizing tert-butyl 3,6-diazabicyclo[3.1.1]heptane-6-carboxylate and 2-chloro-5-iodopyrimidine. MS (ESI) m/z 359.1 [M+H]$^+$. $^1$H NMR (400 MHz, Chloroform-d) δ 8.47 (s, 2H), 4.70 (t, J=6.2 Hz, 2H), 4.48 (t, J=5.5 Hz, 2H), 3.87 (p, J=5.5 Hz, 1H), 3.81 (d, J=6.1 Hz, 2H), 3.56 (q, J=13.2 Hz, 4H), 2.74 (q, J=7.8 Hz, 1H), 1.58 (d, J=8.9 Hz, 1H).

Synthesis of 3-(5-ethynylpyrimidin-2-yl)-6-(oxetan-3-yl)-3,6-diazabicyclo[3.1.1]heptane (S52)

The title compound S52 was prepared according to the method presented for the synthesis of compound S1 but instead utilizing S52a. MS (ESI) m/z 257.1 [M+H]⁺. ¹H NMR (400 MHz, Chloroform-d) δ 8.32 (s, 2H), 4.55 (t, J=6.1 Hz, 2H), 4.32 (dd, J=6.0, 4.8 Hz, 2H), 3.72 (ddd, J=11.1, 6.2, 4.9 Hz, 1H), 3.65 (d, J=6.0 Hz, 2H), 3.50 (d, J=13.3 Hz, 2H), 3.43 (d, J=13.3 Hz, 2H), 3.06 (s, 1H), 2.58 (dt, J=8.1, 6.1 Hz, 1H), 1.44 (d, J=8.8 Hz, 1H).

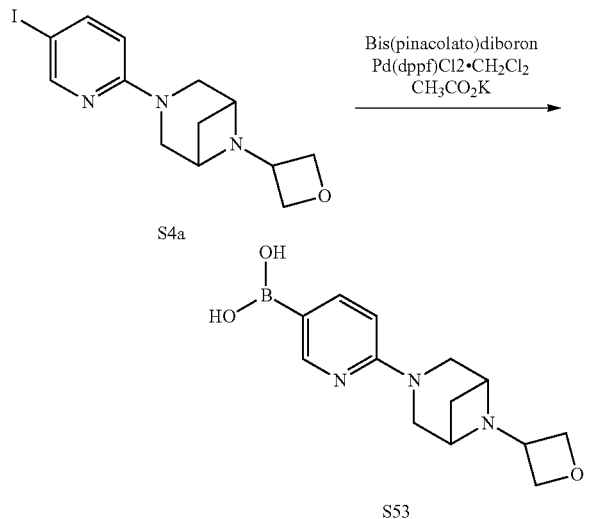

Synthesis of (6-(6-(oxetan-3-yl)-3,6-diazabicyclo [3.1.1]heptan-3-yl)pyridin-3-yl)boronic Acid (S53)

A suspension of S4a (0.17 g, 0.47 mmol) Bis (Pinacolato) Diboron (0.18 g, 0.72 mmol), potassium acetate (0.17 g, 1.68 mmol) and [1,1' bis(diphenylphosphino)ferrocene] dichloropalladium (II) (0.04 g, 0.05 mmol) in DMF (4.5 mL) was degassed with argon for 5 min, then heated at 90° C. for 1 h. Cooled to room temperature, Diluted with EtOAc and washed with 5% LiCL solution 2x. The separated organic layer was dried over Na₂SO₄ and concentrated under vacuum, the residue was purified by HPLC and the product was lyophilized to afford S53. MS (ESI) m/z 276.2 [M+H]⁺. ¹H NMR (400 MHz, Methanol-d4) δ 8.35 (d, J=1.7 Hz, 1H), 8.31 (dd, J=9.0, 1.8 Hz, 1H), 7.18 (d, J=9.0 Hz, 1H), 4.74-4.58 (m, 4H), 4.27-3.99 (m, 4H), 3.28-3.16 (m, 1H), 2.21-2.06 (m, 2H).

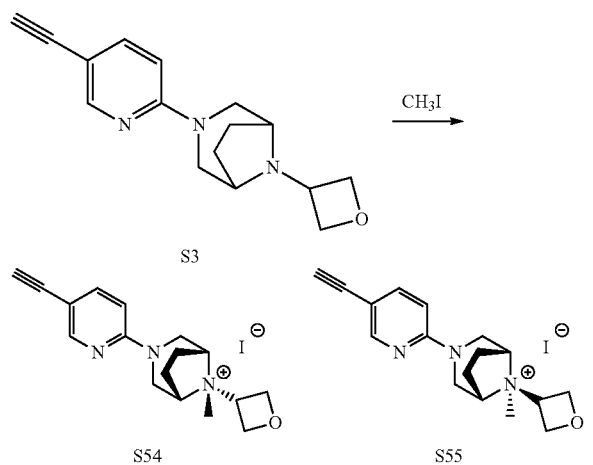

Synthesis of 3-(5-ethynylpyridin-2-yl)-8-methyl-8-(oxetan-3-yl)-3,8-diazabicyclo[3.2.1]octan-8-ium Iodide (S54 and S55)

To a solution of S3 in acetone (1 mL) in a vial at 30° C. was added Iodomethane (0.06 ml, 1.0 mmol), warmed up to 70° C. and the mixture was stirred overnight. After cooling to room temperature the reaction was diluted with ether, stirred for 5 min, the solids were filtered and dried in vacuum to afford a 3:1 mixture of isomers (S54:S55) where the major product (S4) has the methyl syn to the bridge. MS (ESI) m/z 284.0 [M+H]⁺. ¹H NMR (400 MHz, Methanol-d4) δ 8.08-8.02 (m, 1H), 7.50-7.40 (m, 1H), 6.58 (d, J=9.0 Hz, 0H), 6.54 (dd, J=8.8, 0.9 Hz, 1H), 5.37 (t, J=8.1 Hz, 1H), 4.86-4.70 (m, 5H), 4.05-3.94 (m, 3H), 3.88 (d, J=14.3 Hz, 3H), 3.54 (d, J=14.7 Hz, 1H), 3.45 (s, 1H), 3.37 (d, J=2.1 Hz, 1H), 3.34 (s, 4H), 3.30 (s, 1H), 2.37-2.27 (m, 2H), 2.21-2.11 (m, 1H), 2.07-1.94 (m, 2H), 1.94 (s, 1H).

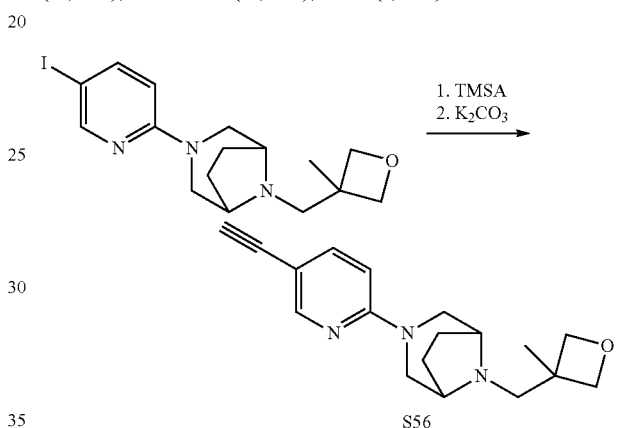

Synthesis of 3-(5-ethynylpyridin-2-yl)-8-((3-methyl-oxetan-3-yl)methyl)-3,8-diazabicyclo[3.2.1]octane (S56)

The title compound S56 was prepared according to the methods presented for the synthesis of compound S1 but instead utilizing 3-(5-iodopyridin-2-yl)-8-((3-methyloxetan-3-yl)methyl)-3,8-diazabicyclo[3.2.1]octane. MS (ESI) m/z 298.19 [M+H]⁺.

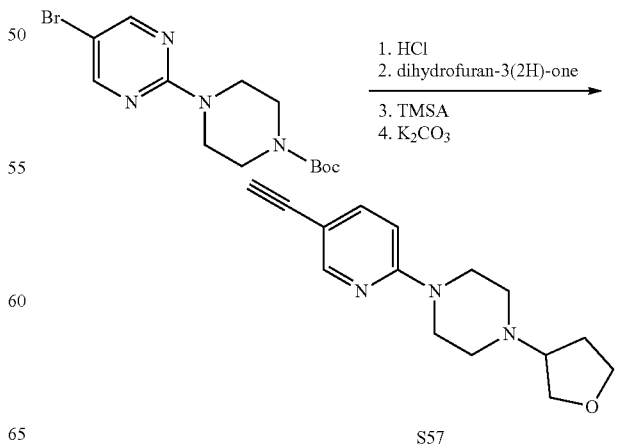

161

Synthesis of 1-(5-ethynylpyridin-2-yl)-4-(tetrahydrofuran-3-yl)piperazine (S57)

The title compound S57 was prepared according to the methods presented for the synthesis of compound S50 but instead utilizing dihydrofuran-3(2H)-one. ¹H-NMR and MS data identical to S14.

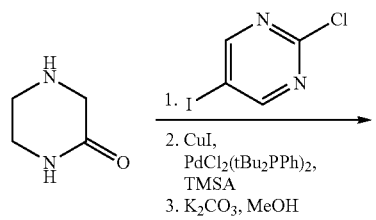

162

Synthesis of 4-(5-ethynylpyrimidin-2-yl)piperazin-2-one (S58a)

The title compound S58a was prepared according to the methods presented for the synthesis of compound S47 but instead utilizing piperazin-2-one and 2-chloro-5-iodopyrimidine MS (ESI) m/z 303.0 [M+H]$^+$. ¹H NMR (400 MHz, Chloroform-d) δ 8.44 (s, 2H), 6.11 (s, 1H), 4.46 (s, 2H), 4.16-3.91 (m, 2H), 3.47 (td, J=5.4, 2.7 Hz, 2H), 3.19 (s, 1H).

Synthesis of 4-(5-ethynylpyrimidin-2-yl)-1-methylpiperazin-2-one (S58)

To a solution of S58a (115 mg, 0.57 mmol) in THF (5 mL) and DMF (1 mL) at 0° C. was added sodium hydride, (60% oil dispersion, 59 mg, 1.475 mmol). After 15 min, added iodomethane (0.15 ml, 2.409 mmol). The reaction mixture was warmed up to room temperature and stirred for 2 h, then quenched with water and partitioned with EtOAc. The separated organic layer was dried over Na$_2$SO$_4$ and concentrated under vacuum to afford S58 (124.9 mg, 100%). MS (ESI) m/z 217.1 [M+H]$^+$. ¹H NMR (400 MHz, Methanol-d4) δ 8.45 (s, 2H), 4.37 (s, 2H), 4.18-4.03 (m, 2H), 3.65 (s, 1H), 3.57-3.43 (m, 2H), 3.01 (s, 3H).

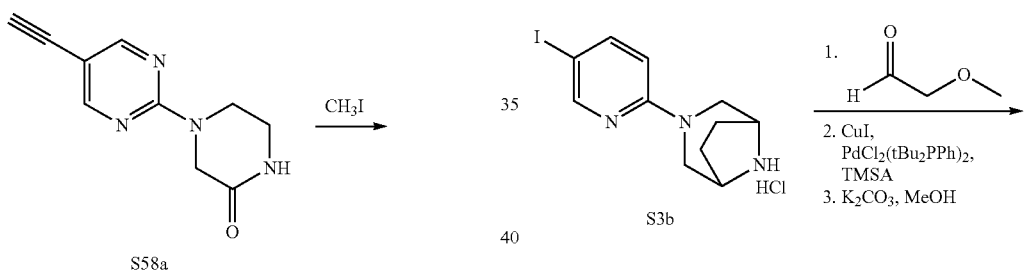

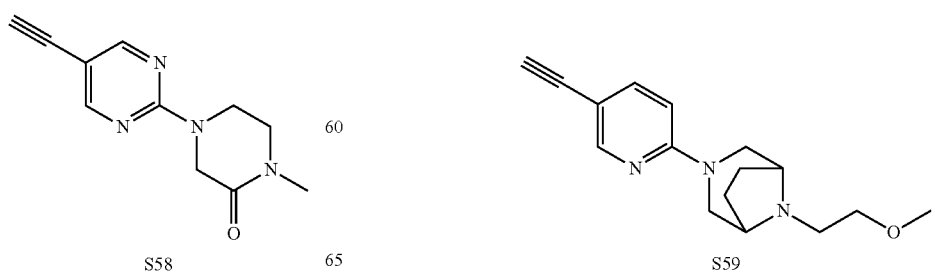

Synthesis of 3-(5-ethynylpyridin-2-yl)-8-(2-methoxyethyl)-3,8-diazabicyclo[3.2.1]octane (S59)

The title compound S59 was prepared according to the methods presented for the synthesis of compound S3 but instead utilizing 2-methoxyacetaldehyde. MS (ESI) m/z 303.02 [M+H]$^+$.

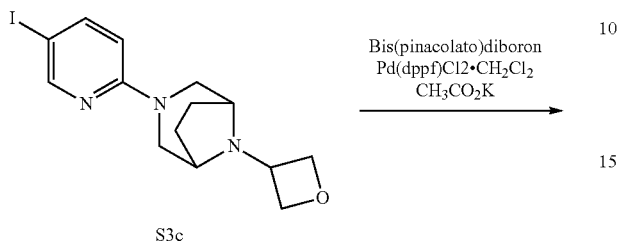

Synthesis of (6-(8-(oxetan-3-yl)-3,8-diazabicyclo[3.2.1]octan-3-yl)pyridin-3-yl)boronic Acid (S60)

The title compound S60 was prepared according to the methods presented for the synthesis of compound S53 but instead utilizing S3c. MS (ESI) m/z 290.2 [M+H]$^+$. $^1$H NMR (400 MHz, Methanol-d4) δ 8.33 (s, 1H), 8.08 (d, J=9.2 Hz, 1H), 7.04 (d, J=8.9 Hz, 1H), 4.91 (t, J=7.3 Hz, 3H), 4.76 (dd, J=7.7, 5.2 Hz, 2H), 4.36 (s, 1H), 4.17 (d, J=13.4 Hz, 3H), 4.00 (s, 2H), 3.46 (d, J=13.2 Hz, 2H), 2.28-2.10 (m, 2H), 2.01 (d, J=8.4 Hz, 2H).

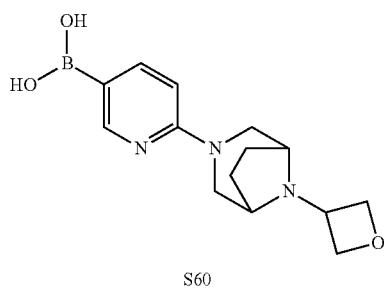

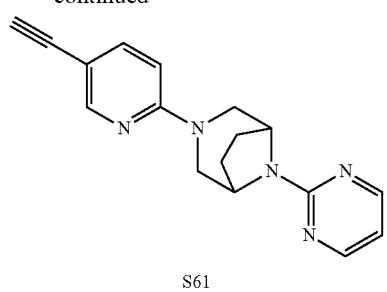

Synthesis of 3-(5-ethynylpyridin-2-yl)-8-(pyrimidin-2-yl)-3,8-diazabicyclo[3.2.1]octane (S61)

A suspension of S20a (0.15 g, 0.42 mmol), sodium bicarbonate (250 mg, 2.9 mmol), and 2-Chloropyrimidine (0.17 g, 1.5 mmol) in isopropanol (1.5 mL) was stirred at 65° C. overnight. The reaction mixture was then cooled to room temperature, diluted with ethyl acetate and filtered through celite. The crude mixture was concentrated in vacuo and redissolved in methanol (5 mL). Potassium carbonate (0.29 g, 2.1 mmol) was added and the mixture was stirred for 30 minutes. The reaction was quenched with water and the crude product was extracted into DCM, dried over sodium sulfate, filtered, concentrated in vacuo, and purified by column chromatography (30%→70% EtOAc→hexanes). MS (ESI) m/z 292.2 [M+H]$^+$. 1H NMR (400 MHz, Methanol-d4) δ 8.35 (d, J=4.8 Hz, 2H), 8.17 (dd, J=2.4, 0.8 Hz, 1H), 7.55 (dd, J=8.9, 2.3 Hz, 1H), 6.69 (dd, J=9.0, 0.8 Hz, 1H), 6.64 (t, J=4.8 Hz, 1H), 4.89 (dq, J=4.6, 2.3 Hz, 3H), 4.02 (dd, J=12.4, 2.3 Hz, 3H), 3.42 (s, 1H), 3.13 (dd, J=12.3, 2.3 Hz, 3H), 2.08-1.96 (m, 3H), 1.96-1.82 (m, 3H).

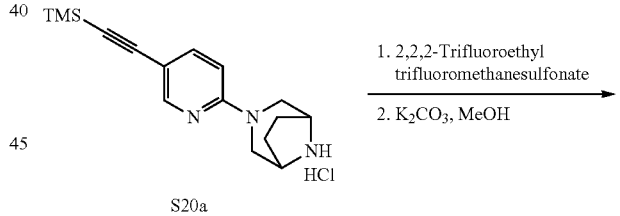

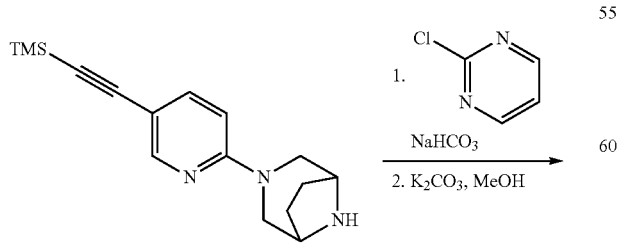

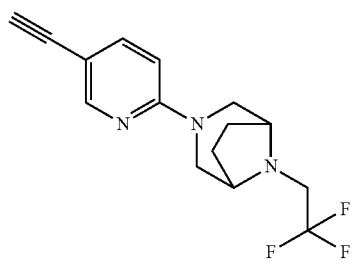

3-(5-ethynylpyridin-2-yl)-8-(2,2,2-trifluoroethyl)-3,8-diazabicyclo[3.2.1]octane (S62)

The title compound S62 was prepared according to the methods presented for the synthesis of compound S63 but instead utilizing 2,2,2-Trifluoroethyl trifluoromethanesulfonate. MS (ESI) m/z 296.20 [M+H]+.

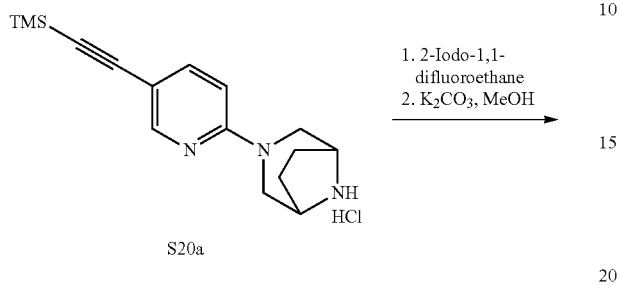

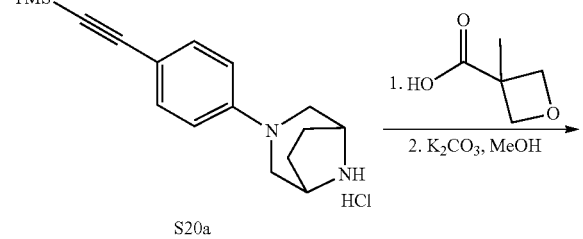

Synthesis of 8-(2,2-difluoroethyl)-3-(5-ethynylpyridin-2-yl)-3,8-diazabicyclo[3.2.1]octane (S63)

To a suspension of Reactant 1 (0.2 g, 0.56 mmol) and 2-Iodo-1,1-difluoroethane (0.15 g, 0.78 mmol) in 1,4-Dioxane (3 ml) were added Cesium carbonate 99.95% (0.21 g, 3.35 mmol). The mixture was stirred at 60° C. overnight. Cooled to room temperature and 2,2-Difluoroethyl trifluoromethane sulfonate (98% min) (0.17 g, 0.78 mmol) was added. The mixture was warmed up to 60° C. for 8 h. Quenched with brine, extracted with EtOAc. The organic layer was dried over Na2SO4, filtered, concentrated and purified by silica column chromatography (10% EtOAc/Hex). The product was dissolved in Methanol (3 ml), potassium carbonate (0.11 g, 0.82 mmol) was added and after 1 h the mixture was concentrated diluted with EtOAc, washed with water, dried over Na2SO4, filtered concentrated to yield S63 (76 mg, 99.7%). MS (ESI) m/z 278.2 [M+H]+

Synthesis (3-(5-ethynylpyridin-2-yl)-3,8-diazabicyclo[3.2.1]octan-8-yl)(3-methyloxetan-3-yl)methanone (S64)

To S20a suspended in CH2Cl2 (10 mL) was added 3-methyloxetane-3-carboxylic acid (0.12 g, 1 mmol), Et3N (0.68 ml, 5 mmol) followed by HATU (0.48 g, 1 mmol). The mixture was stirred for 1.5 h. The mixture was diluted with DCM and washed with water. The organic layer was dried over Na2SO4, and concentrated in vacuo. The residue was dissolved in MeOH (20 mL), cooled to 5° C. and potassium carbonate (0.4 g, 3 mmol) was added. After 30 min, the reaction quenched with water and brine, extracted into DCM, dried over Na2SO4, filtered, concentrated under reduced pressure and the residue was purified by silica column chromatography (60%-100% EtOAc/hexanes to 5% MeOH/EtOAc) to give S64.

MS (ESI) m/z 312.22 [M+H].

2.3 SYNTHESIS OF A INTERMEDIATES

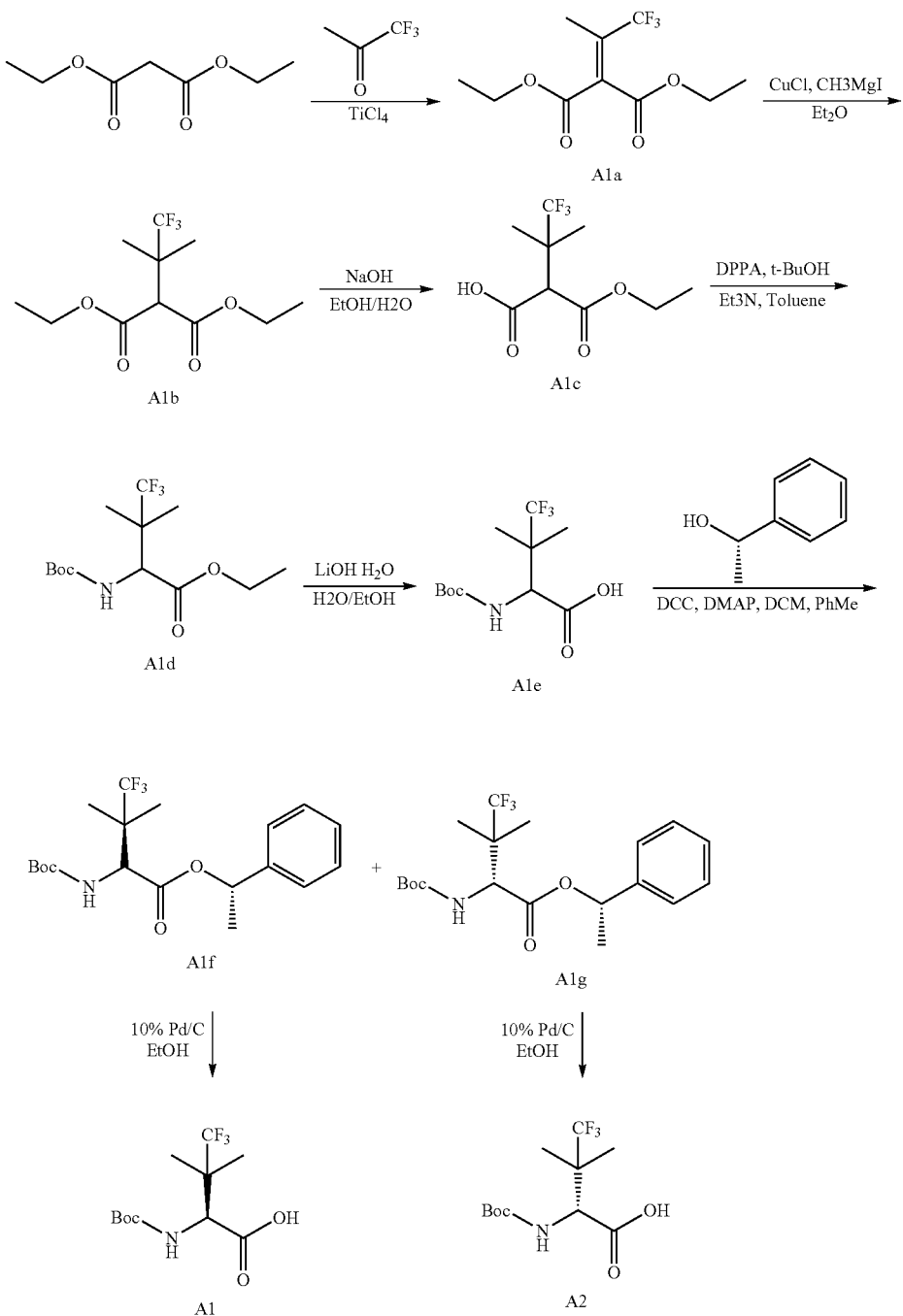

Synthesis of ethyl 2-(1,1,1-trifluoropropan-2-ylidene)malonate (A1a)

A mixture of dry THF (5000 mL) and dry CCl$_4$ (600 mL) was cooled to 0° C. and treated with TiCl$_4$ (275 mL, 2.50 mol). The resulting yellow suspension was stirred at 0° C. for 5 min, treated sequentially with 1,1,1-trifluoropropan-2-one (140 g, 1.25 mol) and freshly distilled diethyl malonate (200 g, 1.25 mol), and then stirred at 0° C. for 0.5 hour. The reaction mixture was then treated with a solution of dry pyridine (400 mL) in dry THF (500 mL) and stirred at 0° C. for 1 hour and then at room temperature overnight. The reaction mixture was quenched with water and extracted with EtOAc (1 L×3). The combined organic extracts were washed with brine and saturated NaHCO$_3$, dried (MgSO$_4$), filtered and concentrated under reduced pressure. The residue was purified by column chromatography on silica gel (EtOAc:PE=1:50) to give the title compound A1a (298 g, 94%).

$^1$H NMR (CDCl$_3$, 300 MHz): δ 4.32-4.23 (m, 4H), 2.20 (s, 3H), 1.33-1.24 (m, 6H).

Synthesis of diethyl 2-(1,1,1-trifluoro-2-methylpropan-2-yl)malonate (A1b)

A mixture of methylmagnesium iodide (3.0 mol/L in ether, 10 L, 30 mol) and cuprous chloride (3.5 g, 35 mmol) was stirred at 0° C., treated with a solution of compound A1a (178 g, 700 mmol) in dry Et$_2$O (1000 mL) over 30 min, and stirred at rt for 30 min and then quenched with the dropwise addition of ice-water (1.5 L) followed by HCl aq (3 mol/L, 350 mL). The mixture was then extracted with Et$_2$O (1 L×3). The combined organic extracts were washed with NaOH aq (1 N), water and brine, dried (MgSO$_4$), filtered and evaporated. The residue crude compound A1b (90 g, 47%) was used directly in next step without further purification. MS (ESI) m/z 271 [M+H]$^+$. $^1$H NMR (CDCl$_3$, 300 MHz): δ 4.22-4.15 (m, 4H), 3.64 (s, 1H), 1.38 (s, 6H), 1.30-1.24 (m, 6H).

Synthesis of 2-(ethoxycarbonyl)-4,4,4-trifluoro-3,3-dimethylbutanoic Acid (A1c)

A solution of compound A1b (144 g, 0.53 mol) in a mixture of EtOH (500 mL) and water (500 mL) was treated with NaOH (19 g, 0.48 mmol) in portions at 0° C., and stirred at room temperature for 5 hours. The reaction mixture was evaporated to syrup, dissolved in water (1 L), and extracted with Et$_2$O (2 L). The aqueous phase was acidified with 1 M HCl to pH=2.0 and extracted with EtOAc (1 L×3). The combined organic extracts were washed with brine, dried (MgSO$_4$), filtered and evaporated to give the title compound A1c (107 g, 84%) which was used directly in next step without further purification. MS (ESI) m/z 241 [M+H]$^+$. $^1$H NMR (CDCl$_3$, 300 MHz): δ 4.23 (q, J=5.4 Hz, 2H), 3.69 (s, 1H), 1.40 (s, 6H), 1.27 (t, J=5.1 Hz, 3H).

Synthesis of ethyl 2-((tert-butoxycarbonyl)amino)-4,4,4-trifluoro-3,3-dimethylbutanoate (A1d)

A solution of compound A1c (110 g, 454 mmol) in dry toluene (600 mL) was treated with triethylamine (45.4 g, 454 mmol) and diphenylphosphoryl azide (125 g, 454 mmol), the reaction mixture was refluxed for 1 hour, then t-BuOH (46.7 g, 630 mmol) was added in. The mixture was refluxed overnight. Cooled to rt, the solvent was evaporated and the residue was dissolved in EtOAc (1 L), washed with 5% NaHCO$_3$ solution, dried (MgSO$_4$), filtered and evaporated. The remainder was purified by column chromatography on silica gel (EtOAc:PE=1:9) to give crude compound A1d (60 g, 46%), which was used directly in next step without further purification. MS (ESI) m/z 313 [M+H]$^+$. $^1$H NMR (CDCl$_3$, 300 MHz): δ 5.20 (d, J=5.7 Hz, 1H), 4.44 (d, J=10.8 Hz, 1H), 4.25-4.16 (m, 2H), 1.44 (s, 9H), 1.39-1.26 (m, 6H), 1.19 (m, 3H).

Synthesis of 2-((tert-butoxycarbonyl)amino)-4,4,4-trifluoro-3,3-dimethylbutanoic Acid (A1e)

To a solution of compound A1d (380 g, 1214 mmol) in water (2000 mL) and ethanol (2000 mL) was added LiOH.H$_2$O (134 g, 3166 mmol). The mixture was stirred overnight. Diluted with EtOAc, acidify to pH=2, extracted with EtOAc (2000 mL×3). The organic layer was washed with brine, dried over MgSO$_4$, and concentrated to afford compound A1e (300 g, 86%) as a white solid. $^1$H NMR (CDCl$_3$, 300 MHz): δ 5.20 (d, J=10.2 Hz, 1H), 4.48 (d, J=10.2 Hz, 1H), 1.45 (s, 9H), 1.30 (s, 3H), 1.25 (s, 3H).

Synthesis of (S)—(S)-1-phenylethyl 2-((tert-butoxycarbonyl)amino)-4,4,4-trifluoro-3,3-dimethylbutanoate (A1g)

The acid A1e (300 g, 1052 mmol) and (N,N'-Dicyclohexylcarbodiimide (325 g, 1578 mmol) were combined in DCM (250 mL) and PhMe (4000 mL). The solution was cooled to 0° C., and then 4-(Dimethylamino)pyridine (128 g, 1052 mmol) and (S)-(−)-1-Phenylethanol (128 g, 1052 mmol) were added and the mixture was allowed to warm to room temperature and stirred overnight. The mixture was concentrated, and then the residue was taken up in EtOAc/water, and extracted with EtOAc (2000 mL×3). The combined organic layers were washed with brine, dried over MgSO$_4$ and concentrated. The crude was purified by column chromatography on silica gel (0-8% EtOAc/PE) to get two compounds. The mixture of diastereomers was separated by chiral column (IA; Heptane; IPA (70:30)). First peak was collected to get the compound A1f (105 g, 25%) and the second peak was collected to get the compound A1g (80 g, 19%). $^1$H NMR of compound A1f (CDCl$_3$, 300 MHz): δ 7.38-7.31 (m, 5H), 5.90 (q, J=6.3 Hz, 1H), 5.18 (d, J=9.6 Hz, 1H), 4.48 (d, J=9.6 Hz, 1H), 1.56 (d, J=6.9 Hz, 3H), 1.44 (s, 9H), 1.31 (s, 3H), 1.21 (s, 3H). $^1$H NMR of compound A1g (CDCl$_3$, 300 MHz): δ 7.34-7.30 (m, 5H), 5.92 (q, J=6.3 Hz, 1H), 5.20 (d, J=9.6 Hz, 1H), 4.44 (d, J=9.6 Hz, 1H), 1.58 (d, J=6.9 Hz, 3H), 1.45 (s, 9H), 1.21 (s, 3H), 1.11 (s, 3H).

Synthesis of (S)-2-((tert-butoxycarbonyl)amino)-4,4,4-trifluoro-3,3-dimethylbutanoic Acid (A1)

The compound A1f (83 g, 214 mmol) was diluted with ethanol (1000 mL). Pd/C (10%, wet, 17 g) was added and the atmosphere was replaced with hydrogen. After stirring for 5 hours, the mixture was filtered over celite, washing with EtOAc and the filtrate was concentrated to get product A1 (50 g, 82%). MS (ESI) m/z 186 [M-Boc+1]$^+$. $^1$H NMR (300 MHz, DMSO-d$_6$): δ 12.98 (br s, 1H), 7.18 (d, J=9.6 Hz, 1H), 4.27 (d, J=9.9 Hz, 1H), 1.36 (s, 9H), 1.14 (s, 6H).

Synthesis of (R)-2-((tert-butoxycarbonyl)amino)-4,4,4-trifluoro-3,3-dimethylbutanoic Acid (A2)

The compound A1g (80 g, 205 mmol) was diluted with ethanol (800 mL). Pd/C (10%, wet, 15 g) was added and the atmosphere was replaced with hydrogen. After stirring for 5 hours, the mixture was filtered over celite, washing with EtOAc and the filtrate was concentrated to get product A2 (45 g, 77%). MS (ESI) m/z 186 [M-Boc+1]$^+$. $^1$H NMR (300 MHz, DMSO-d$_6$): δ7.18 (d, J=9.6 Hz, 1H), 4.25 (d, J=9.9 Hz, 1H), 1.36 (s, 9H), 1.14 (s, 6H).

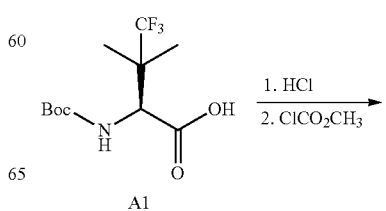

A1

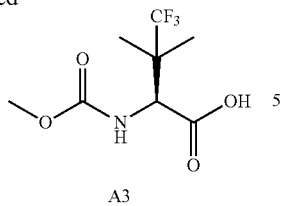

A3

Synthesis of (S)-4, 4, 4-trifluoro-2-((methoxycarbonyl) amino)-3, 3-dimethylbutanoic Acid (A3)

To a solution of A1 (10 g, 35.06 mmol) in DCM (160 mL) and MeOH (40 mL), was added HCl (4.0M in dioxane, 40 mL). The reaction was stirred at room temperature overnight. The reaction was concentrated to dryness (foamy). The residue was dissolved in a mixture of dioxane and 2M NaOH (90 mL), stirred for 5 min, and then add methyl chloroformate (5.7 mL, 73.33 mmol). After 4 h the reaction was extracted with 2×100 mL DCM (discard organics) and the aqueous layer was adjusted to pH ~2 with 4M HCl (~50 mL). The aqueous layer was extracted with 2×150 mL EtOAc, the combined EtOAc layers were dried over sodium sulfate, filtered, and concentrated to give A3 (8.54 g, 100%). MS (ESI) m/z 244.0 [M+H]$^+$. $^1$H NMR (400 MHz, Methanol-d4) δ 4.57-4.41 (m, 1H), 3.66 (d, J=2.1 Hz, 5H), 1.25 (d, J=10.0 Hz, 7H).

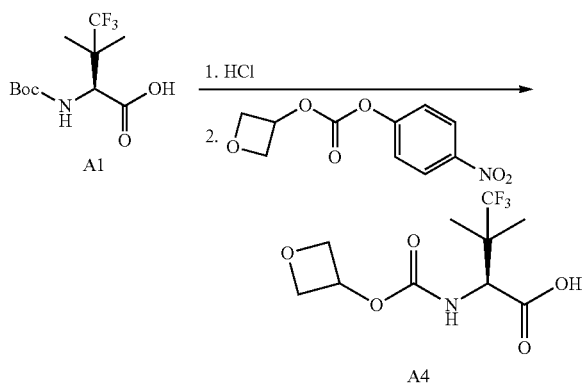

A4

Synthesis of (S)-4,4,4-trifluoro-3,3-dimethyl-2-(((oxetan-3-yloxy)carbonyl)amino)butanoic Acid (A4)

The title compound A4 was prepared according to the method presented for the synthesis of compound A3 but instead utilizing 4-nitrophenyl oxetan-3-yl carbonate. MS (ESI) m/z 285.5 [M+H]$^+$. $^1$H NMR (400 MHz, Methanol-d4) δ 7.66 (d, J=9.9 Hz, 1H), 5.37 (tt, J=6.3, 5.1 Hz, 1H), 4.87-4.82 (m, 2H), 4.62 (tdd, J=7.5, 5.1, 0.9 Hz, 2H), 4.49-4.41 (m, 1H), 1.28 (s, 3H), 1.25 (s, 3H).

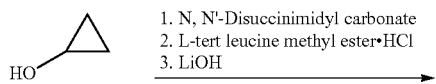

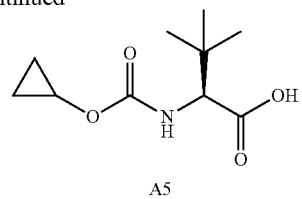

A5

Synthesis of (S)-2-((cyclopropoxycarbonyl) amino)-3, 3-dimethylbutanoic Acid (A5)

To a solution of cyclopropanol (0.4 ml, 6.37 mmol) in CH$_3$CN (18 mL) at 0° C., was added bis(2,5-dioxopyrrolidin-1-yl) carbonate (DSC) (3.26 g, 12.74 mmol) followed by Et$_3$N (2.66 ml, 19.11 mmol). The reaction mixture was warmed up to 40° C. and stirred overnight. After cooling to room temperature, the reaction was concentrated under reduced pressure and the residue triturated with DCM, the solid filtered, and the filtrated was purified by silica column chromatography (10%-100% EtOAc/hexanes). The product (663 mg, 3.33 mmol) was dissolved in THF (5 mL) and L-tert-leucine methyl ester hydrochloride (0.91 g, 5 mmol) and Et$_3$N (1.39 ml, 0.01 mol) were added, the reaction was warmed up to 40° C. for 18 h, then at room temperature for 48 h, diluted with EtOAc, washed with water. The organic layer was dried over Na$_2$SO$_4$, filtered and concentrated under reduced pressure and the residue (760 mg, 3.31 mmol) was dissolved in a mixture of Methanol (4 mL)/water (2 mL), lithium hydroxide, monohydrate (0.56 g, 0.01 mol) was added. After 16 h, the mixture was concentrated, diluted with EtOAc, washed with brine, the organic layer was dried over Na2SO4, filtered, and concentrated under reduced pressure to afford A5 $^1$H NMR (400 MHz, Chloroform-d) δ 4.19 (d, J=9.6 Hz, 1H), 1.02 (s, 11H), 0.68 (d, J=4.8 Hz, 5H).

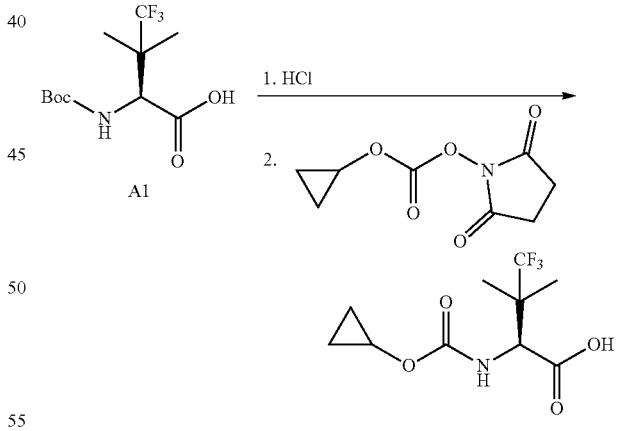

A6

Synthesis of (S)-2-((cyclopropoxycarbonyl)amino)-4,4,4-trifluoro-3,3-dimethylbutanoic Acid (A6)

The title compound A6 was prepared according to the method presented for the synthesis of compound A3 but instead utilizing cyclopropyl (2,5-dioxopyrrolidin-1-yl) carbonate. 1H NMR (400 MHz, Chloroform-d) δ 5.33 (d, J=9.8 Hz, 1H), 4.53 (d, J=9.9 Hz, 1H), 4.08-4.01 (m, 1H), 1.35 (s, 3H), 1.26 (s, 3H), 0.81-0.52 (m, 4H).

2.4 Synthesis of I Intermediates

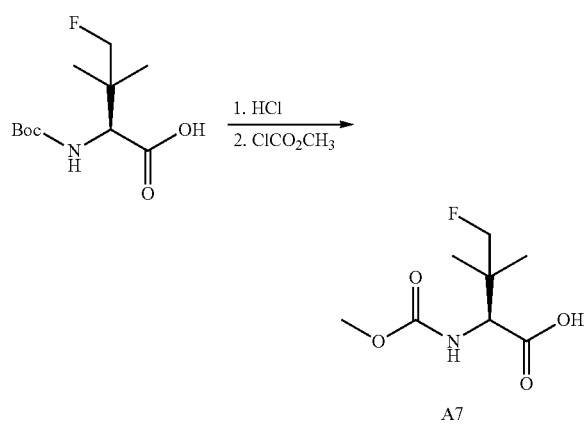

Synthesis of (S)-4-fluoro-2-((methoxycarbonyl)amino)-3,3-dimethylbutanoic Acid (A7)

The title compound A7 was prepared according to the method presented for the synthesis of compound A3 but instead utilizing (S)-2-((tert-butoxycarbonyl)amino)-4-fluoro-3,3-dimethylbutanoic acid (US 2013/0183629 A1 (pp. 178-179))

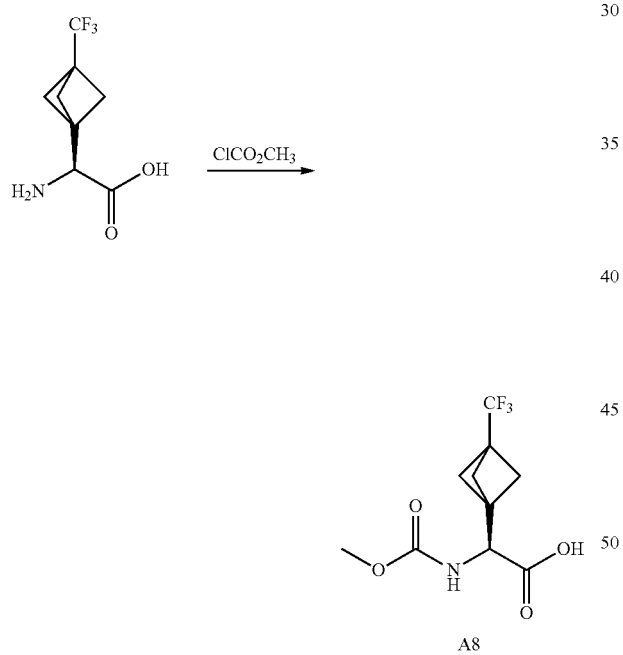

Synthesis of (S)-2-((methoxycarbonyl)amino)-2-(3-(trifluoromethyl)bicyclo[1.1.1]pentan-1-yl)acetic Acid (A8)

The title compound A8 was prepared according to the method presented for the synthesis of compound A3 but instead utilizing (S)-2-amino-2-(3-(trifluoromethyl)bicyclo[1.1.1]pentan-1-yl)acetic acid. MS (ESI) m/z 267.0 [M+H]$^+$. $^1$H NMR (400 MHz, Methanol-d4) δ 4.35-4.26 (m, 1H), 3.65 (s, 3H), 1.97 (qd, J=9.6, 1.7 Hz, 6H).

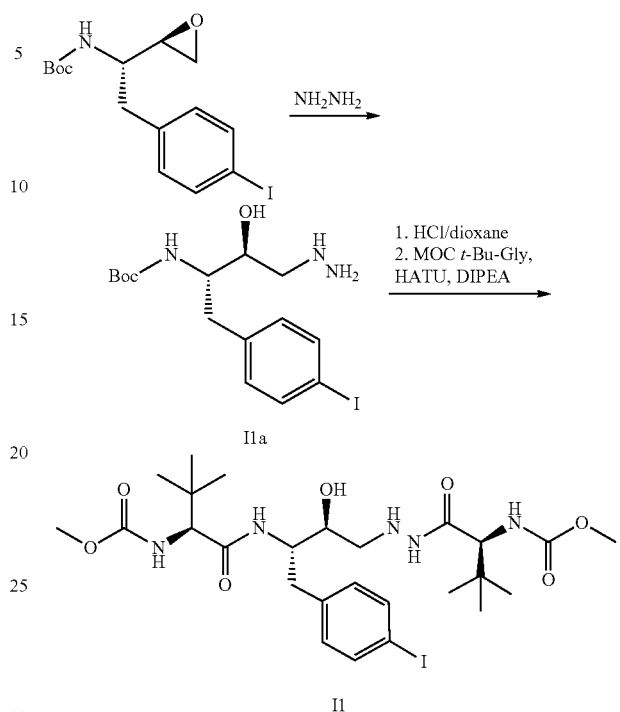

Synthesis of tert-butyl ((2S,3S)-4-hydrazinyl-3-hydroxy-1-(4-iodophenyl)butan-2-yl) carbamate (I1a)

To a solution of the NH$_2$NH$_2$ (48.3 g, 0.82 mol) in iPrOH (157 mL) was added tert-butyl ((S)-2-(4-iodophenyl)-1-((R)-oxiran-2-yl)ethyl)carbamate (16.1 g, 41.4 mmol) dissolved in DCM (79 mL) dropwise over 1 h at 0° C. The ice bath was removed and the reaction mixture was stirred at rt for 16 h. The mixture was evaporated solvents, diluted with water, filtrated, washed with water and dried to give compound I1a (17.0 g, 97%). $^1$H NMR (300 MHz, CDCl$_3$): δ 7.59 (d, J=7.8 Hz, 2H), 7.02-6.96 (m, 2H), 5.03 (d, J=9.9 Hz, 1H), 3.78-3.66 (m, 2H), 2.85-2.67 (m, 4H), 2.04 (s, 3H), 1.38 (s, 9H).

Synthesis of ((S)-1-{(1S,2S)-2-hydroxy-1-(4-iodobenzyl)-3-[N'—((S)-2-methoxy carbonylamino-3,3-dimethyl-butyryl)-hydrazino]-propylcarbamoyl}-2,2-dimethyl-propyl)-carbamic Acid Methyl Ester (I1)

To a solution of the I1a (34.0 g, 80.7 mmol) in CH$_2$Cl$_2$ (990 mL) at room temperature was added 4 M hydrochloric acid (198 mL). After stirring for 2 h at 45° C., LC/MS indicated completion of the reaction and the mixture was concentrated in vacuo. To this crude residue suspended in CH$_2$Cl$_2$ (700 mL) and cooled to −20° C. was added DIPEA (48.2 g, 373.9 mmol), Moc-tBu-Gly (25.53 g, 135.1 mmol) followed by HATU (53.4 g, 140.5 mmol). The mixture was warmed up to room temperature slowly and stirred for 1 h. The mixture was diluted with DCM (1 L) and washed with aqueous 1N HCl solution (400 mL), aqueous saturated NaHCO$_3$ solution (400 mL), water (600 mL×2), and brine (600 mL) in sequence. The organic layer was dried over Na$_2$SO$_4$, and concentrated in vacuo to give the residue which was purified by column chromatography on silica gel eluted with EtOAc:petroleum ether=2:1 to 100% of EtOAc to EtOAc:MeOH=50:1 to give product I1 (8.2 g, 19.4%). MS (ESI) m/z 664.0 [M+H]+. 1H NMR (300 MHz, CD3OD): δ 7.53 (d, J=8.1 Hz, 2H), 7.01 (d, J=8.4 Hz, 2H), 4.10-4.21 (m, 1H), 3.90 (s, 1H), 3.82 (s, 1H), 3.69-3.64 (m, 7H), 2.78-2.76 (m, 4H), 0.95 (s, 9H), 0.91 (s, 9H);

concentrated under reduced pressure. The crude residue was purified by silica column chromatography (2% to 5% MeOH/DCM) to afford 12 (7.39 g, 60%) MS (ESI) m/z 773.0 [M+H]+. 1H NMR (400 MHz, Methanol-d4) δ 7.52 (d, J=8.1 Hz, 2H), 6.99 (d, J=8.2 Hz, 2H), 3.71 (q, J=6.9 Hz, 7H), 3.65 (s, 3H), 1.37 (dd, J=7.0, 1.7 Hz, 32H), 1.19-1.07 (m, 10H).

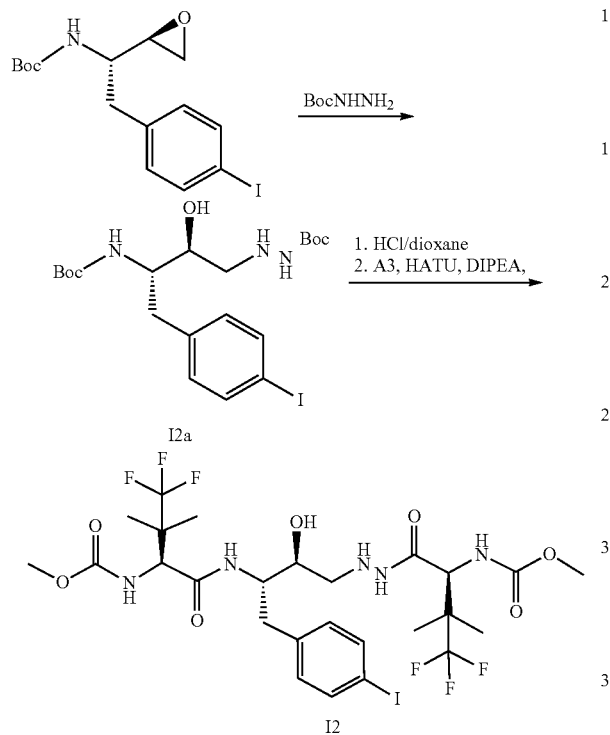

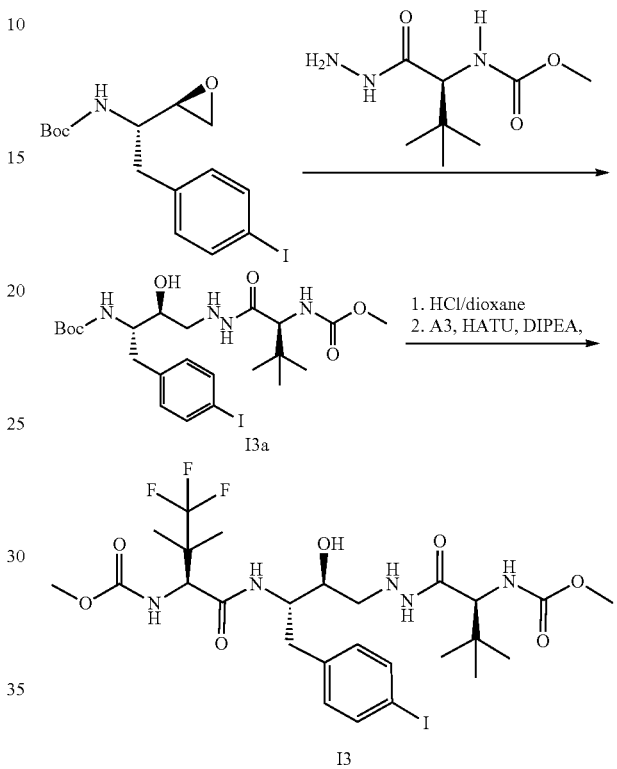

Synthesis of tert-butyl 2-((2S,3S)-3-((tert-butoxycarbonyl)amino)-2-hydroxy-4-(4 iodophenyl)butyl)hydrazine-1-carboxylate (I2a)

A mixture of tert-butyl ((S)-2-(4-iodophenyl)-1-((R)-oxiran-2-yl)ethyl)carbamate (5 g, 12.85 mmol) and tert-butylhydrazinecarboxylate (3.4 g, 25.69 mmol) in isopropanol (60 mL) was heated to 80° C. for 48 h, then cooled to room temperature and concentrated under reduced pressure. The residue was purified by silica column chromatography (0% to 40% EtOAc/DCM) to afford I2a (4.86 g, 72.6%) MS (ESI) m/z 522.19 [M+H]+

Synthesis of methyl ((5S,10S,11S,14S)-16,16,16-trifluoro-10-hydroxy-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (I2)

I2a (5.0 g, 10 mmol) was dissolved in DCM (15 mL) and HCl (4.0M in dioxane, 36 mL). The reaction was stirred overnight then concentrated under reduce pressure. To the residue was added A3 (4.96 g, 20 mmol) and HATU (8.02 g, 21 mmol) in DCM (100 mL), followed by N, N-diisopropylethylamine (16.7 ml, 96 mmol). The reaction was stirred at room temperature overnight. The reaction mixture was diluted with DCM and washed with saturated NaHCO3, and brine then dried over Na2SO4, filtered and Synthesis of tert-butyl ((2S,3S)-3-hydroxy-1-(4-iodophenyl)-4-(2-((S)-2-((methoxycarbonyl)amino)-3,3-dimethylbutanoyl)hydrazinyl)butan-2-yl)carbamate (I3a)

The title compound I3a was prepared according to the method presented for the synthesis of compound I1 but instead utilizing methyl (S)-(1-hydrazinyl-3,3-dimethyl-1-oxobutan-2-yl)carbamate. MS (ESI) m/z 593.1 [M+H]+.

Synthesis of methyl ((5S,10S,11S,14S)-5-(tert-butyl)-16,16,16-trifluoro-10-hydroxy-11-(4-iodobenzyl)-15,15-dimethyl-3,6,13-trioxo-2-oxa-4,7,8,12-tetraazahexadecan-14-yl)carbamate The title compound I3 was prepared according to the method presented for the synthesis of compound I2 but instead utilizing I3a and A3. MS (ESI) m/z 718.7 [M+H]+.

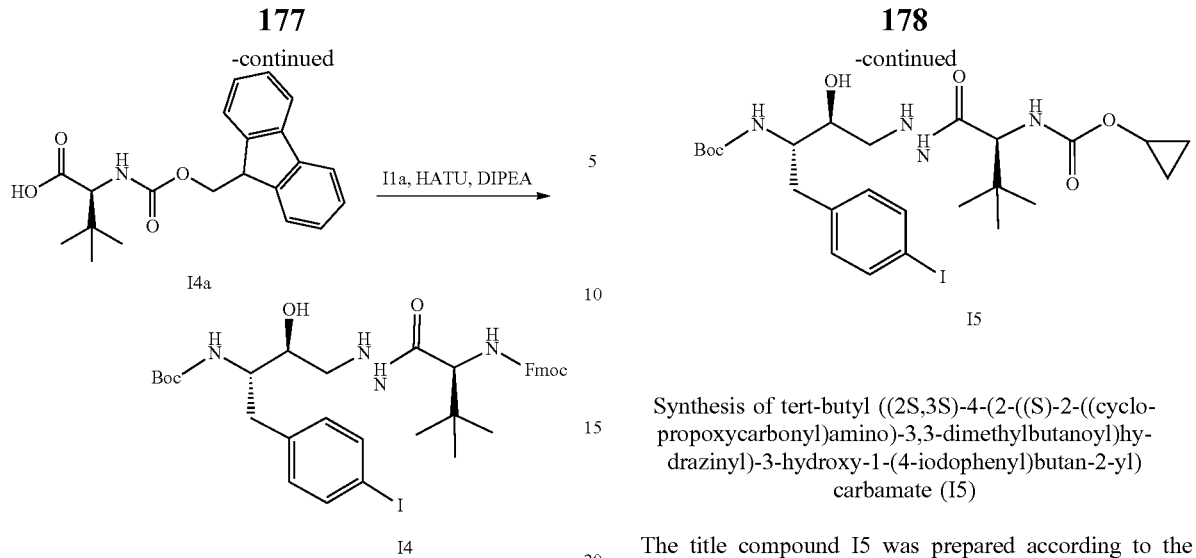

Synthesis of (S)-2-((((9H-fluoren-9-yl)methoxy) carbonyl)amino)-3,3-dimethylbutanoic Acid (I4a)

L-tert-Leucine (2 g, 15.25 mmol) was dissolved in 10% Na₂CO₃ solution (80 ml), the solution was cooled to 0° C., then added 9-Fluorenylmethyl chloroformate (4.77 g, 18.44 mmol) in dioxane (31 mL). After 2 h, the reaction mixture was diluted with water, washed with ether and the aqueous layer was adjusted to pH ~2 with 6N HCl and extracted with EtOAc. The combined EtOAc layers were dried over Na₂SO₄, filtered, and concentrated to give I4a. MS (ESI) m/z 353.8 [M+H]⁺.

Synthesis of (9H-fluoren-9-yl)methyl ((S)-1-(2-((2S,3S)-3-((tert-butoxycarbonyl)amino)-2-hydroxy-4-(4-iodophenyl)butyl)hydrazinyl)-3,3-dimethyl-1-oxobutan-2-yl)carbamate (I4)

To I4a (2.55 g, 7.22 mmol) was added I1a (3 g, 7.12 mmol), HATU (2.7 g, 7.1 mmol) and a mixture of CH₂Cl₂/DMF (2:1) (75 ml) followed by N,N-diisopropylethylamine (3 ml, 17.22 mmol). The reaction was stirred at stirred at room temperature for 4 h. The reaction mixture was diluted with EtOAc and washed with saturated NH₄Cl, and brine then dried over Na₂SO₄, filtered and concentrated under reduced pressure. The crude residue was purified by silica column chromatography (2% to 5% MeOH/DCM) to afford I4 (2.38 g, 44%) MS (ESI) m/z 757.1 [M+H]⁺. ¹H NMR (400 MHz, Chloroform-d) δ 8.01 (s, 1H), 7.75 (t, J=7.5 Hz, 5H), 7.66-7.46 (m, 6H), 7.38 (q, J=7.5 Hz, 4H), 7.34-7.27 (m, 1H), 6.95 (dd, J=16.8, 8.0 Hz, 4H), 5.52 (d, J=47.2 Hz, 2H), 5.01 (dd, J=19.2, 10.0 Hz, 1H), 4.48 (dd, J=10.5, 6.5 Hz, 1H), 4.34 (dt, J=28.9, 9.8 Hz, 2H), 4.19 (t, J=6.8 Hz, 2H), 3.91 (dd, J=45.4, 14.8 Hz, 2H), 3.60 (d, J=31.0 Hz, 2H), 1.39 (d, J=16.0 Hz, 13H).

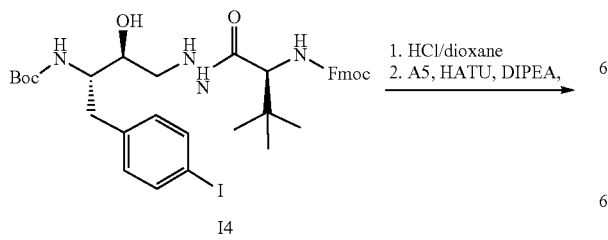

Synthesis of tert-butyl ((2S,3S)-4-(2-((S)-2-((cyclopropoxycarbonyl)amino)-3,3-dimethylbutanoyl)hydrazinyl)-3-hydroxy-1-(4-iodophenyl)butan-2-yl)carbamate (I5)

The title compound I5 was prepared according to the method presented for the synthesis of compound I2 but instead utilizing I4 and A5. MS (ESI) m/z 619.4 [M+H]⁺. ¹H NMR (400 MHz, Chloroform-d) δ 8.02 (s, 0H), 7.59 (d, J=8.0 Hz, 2H), 7.00 (d, J=7.9 Hz, 2H), 5.37 (s, 1H), 5.04 (s, 1H), 4.02 (s, 1H), 3.83 (s, 1H), 3.74-3.58 (m, 1H), 2.95 (s, 1H), 2.88 (d, J=0.7 Hz, 1H), 2.85 (d, J=7.7 Hz, 1H), 2.80 (s, 6H), 1.38 (s, 8H), 1.01 (d, J=10.5 Hz, 1H), 0.90 (s, 8H), 0.66 (d, J=4.7 Hz, 4H).

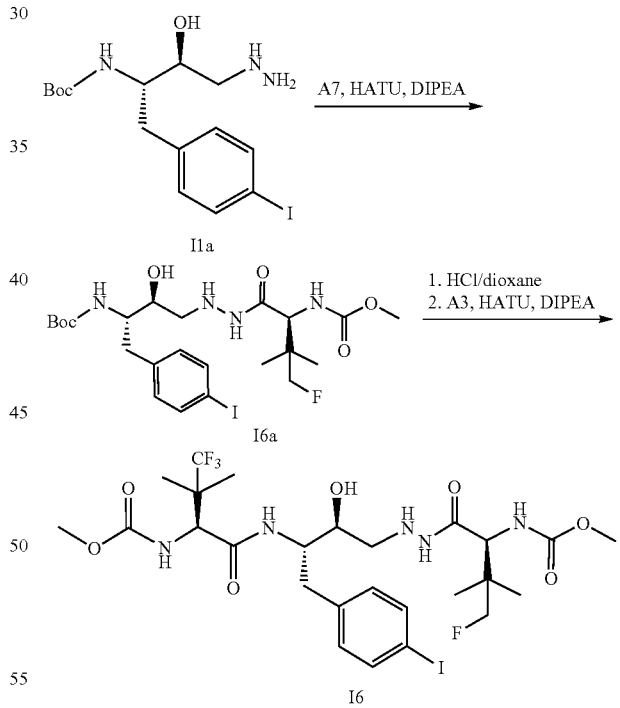

Synthesis of tert-butyl ((2S,3S)-4-(2-((S)-4-fluoro-2-((methoxycarbonyl)amino)-3,3-dimethylbutanoyl) hydrazinyl)-3-hydroxy-1-(4-iodophenyl)butan-2-yl) carbamate (I6a)

The title compound I6a was prepared according to the method presented for the synthesis of compound I4 but instead utilizing A7. MS (ESI) m/z 611.5 [M+H]⁺. ¹H NMR (400 MHz, Chloroform-d) δ 7.57 (d, J=8.0 Hz, 2H), 6.98 (d, J=8.1 Hz, 2H), 5.50 (s, 1H), 4.97 (d, J=9.8 Hz, 1H), 4.37-4.17 (m, 1H), 4.03 (td, J=25.3, 23.8, 9.4 Hz, 2H), 3.68 (s, 4H), 3.50 (s, 0H), 3.17 (qd, J=7.4, 4.4 Hz, 1H), 2.94 (s, 1H), 2.82 (dt, J=15.8, 5.5 Hz, 4H), 1.50 (t, J=7.4 Hz, 1H), 1.46 (dd, J=17.4, 6.7 Hz, 3H), 1.39 (s, 9H), 0.96 (s, 5H).

Synthesis of methyl ((5S,8S,9S,14S)-16-fluoro-9-hydroxy-8-(4-iodobenzyl)-15,15-dimethyl-3,6,13-trioxo-5-(1,1,1-trifluoro-2-methylpropan-2-yl)-2-oxa-4,7,11,12-tetraazahexadecan-14-yl)carbamate (I6)

The title compound I6 was prepared according to the method presented for the synthesis of compound I2 but instead utilizing I6a. MS (ESI) m/z 736.1 [M+H]$^+$.

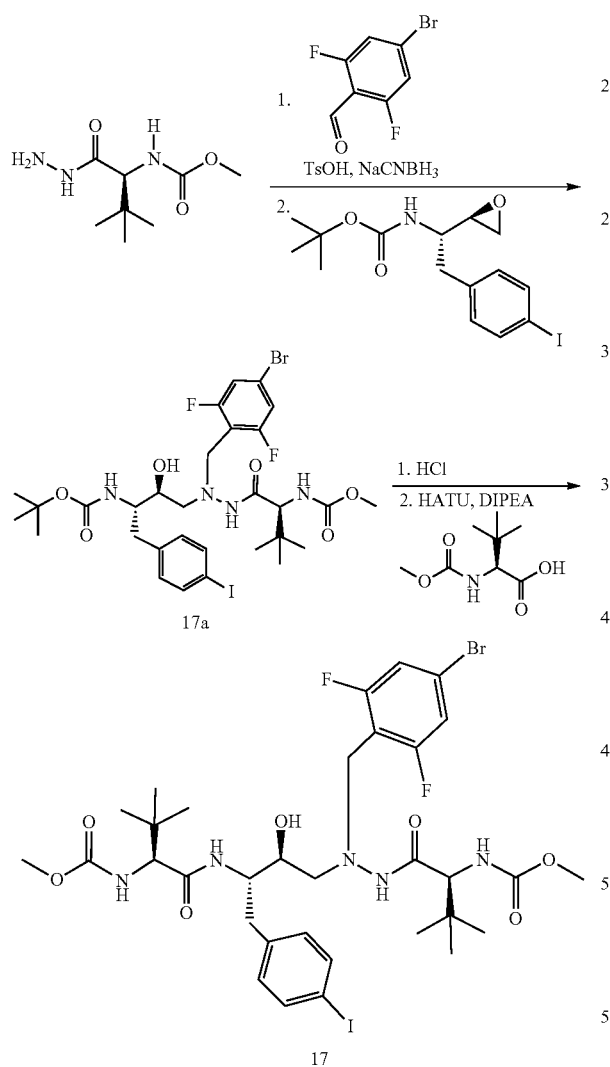

17a

17

Synthesis of methyl ((5S,8S,9S,14S)-11-(4-bromo-2,6-difluorobenzyl)-5-(tert-butyl)-9-hydroxy-8-(4-iodobenzyl)-15,15-dimethyl-3,6,13-trioxo-2-oxa-4,7,11,12-tetraazahexadecan-14-yl)carbamate (I7)

Methyl (S)-1-hydrazinyl-3,3-dimethyl-1-oxobutan-2-yl)carbamate (9.2 g, 45 mmol) and 4-bromo-2,6-difluorobenzaldehyde (10 g, 45 mmol) were stirred in THF at room temperature for 60 minutes. 4-methylbenzenesulfonic acid monohydrate (9.0 g, 48 mmol) was added and the mixture was stirred for an addition 75 minutes. The mixture was cooled to 8° C., followed by addition of NaCNBH$_3$ (3.8 g, 61 mmol). The reaction was observed to exotherm to 30° C. The mixture was stirred for 4 hours at room followed by dilution with DCM (200 mL) and quenching with 1M K$_3$PO$_4$ to pH 12. The organic layer was separated, dried over Na$_2$SO$_4$, filtered, and concentrated in vacuo. The crude product was combined with tert-butyl ((S)-2-(4-iodophenyl)-1-((R)-oxiran-2-yl)ethyl)carbamate (8.5 g, 22 mmol) in isopropanol (30 mL) and heptanes (40 mL). The mixture was stirred at reflux for 40 hours, after which time it was cooled to room temperature and diluted with 15 mL hexanes. The product (I7a) was collected by filtration and the solids rinsed with 20% IPA in hexanes. MS (ESI) m/z 797.8 [M+H]$^+$.

The title compound I7 was prepared according to the method presented for the synthesis of compound I1 but instead utilizing methyl (S)-(1-(2-(4-bromo-2,6-difluorobenzyl)hydrazinyl)-3,3-dimethyl-1-oxobutan-2-yl)carbamate (I7a) MS (ESI) m/z 869.72 [M+H]. $^1$H NMR (400 MHz, Methanol-d$_4$) δ 7.53 (d, J=7.9 Hz, 2H), 7.16 (d, J=6.9 Hz, 2H), 7.00 (d, J=8.2 Hz, 2H), 4.16-4.03 (m, 2H), 3.95-3.83 (m, 2H), 3.76-3.57 (m, 11H), 2.90-2.72 (m, 6H), 0.86 (d, J=23.1 Hz, 18H).

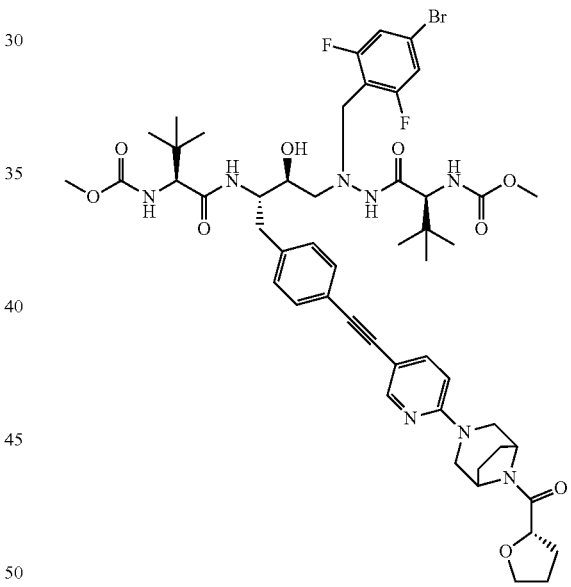

18

Synthesis of methyl ((5S,8S,9S,14S)-11-(4-bromo-2,6-difluorobenzyl)-5-(tert-butyl)-9-hydroxy-15,15-dimethyl-3,6,13-trioxo-8-(4-((6-(8-((S)-tetrahydrofuran-2-carbonyl)-3,8-diazabicyclo[3.2.1]octan-3-yl)pyridin-3-yl)ethynyl)benzyl)-2-oxa-4,7,11,12-tetraazahexadecan-14-yl)carbamate (I8)

Intermediates: I7, and S25. MS (ESI) m/z 1052.92 [M+H]. $^1$H NMR (400 MHz, Methanol-d$_4$) δ 8.19 (s, 1H), 7.79 (d, J=8.8 Hz, 2H), 7.35 (d, J=7.8 Hz, 2H), 7.23 (d, J=8.1 Hz, 2H), 7.17 (d, J=6.9 Hz, 2H), 6.98 (t, J=10.5 Hz, 1H), 4.69 (t, J=6.8 Hz, 2H), 4.21-4.00 (m, 4H), 3.98-3.81 (m, 5H), 3.80-3.62 (m, 9H), 3.25-3.09 (m, 2H), 2.98-2.85 (m, 2H), 2.79 (d, J=6.6 Hz, 2H), 2.30-2.08 (m, 1H), 2.02-1.72 (m, 6H), 0.87 (d, J=21.7 Hz, 22H).

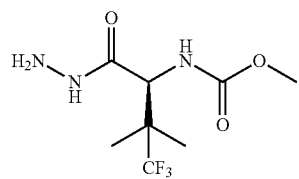
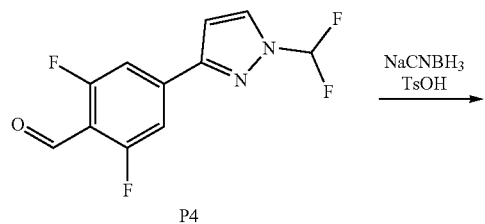
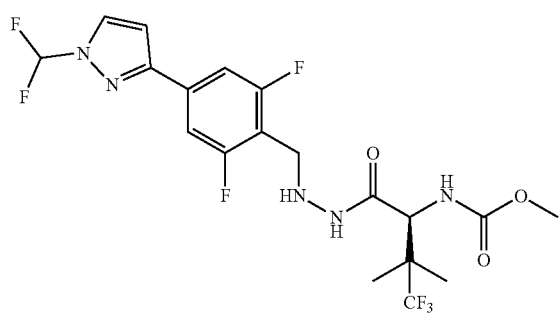
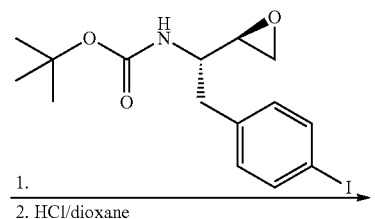
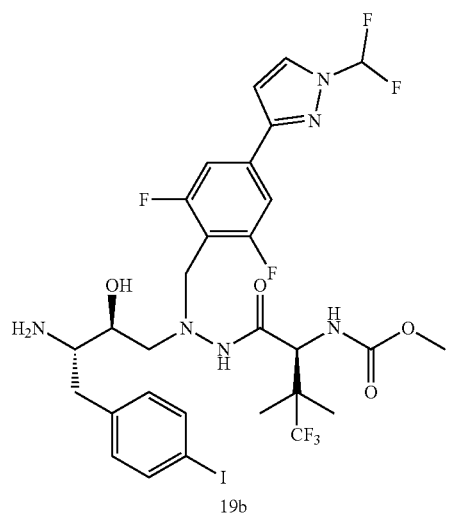
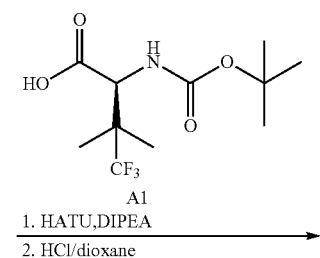

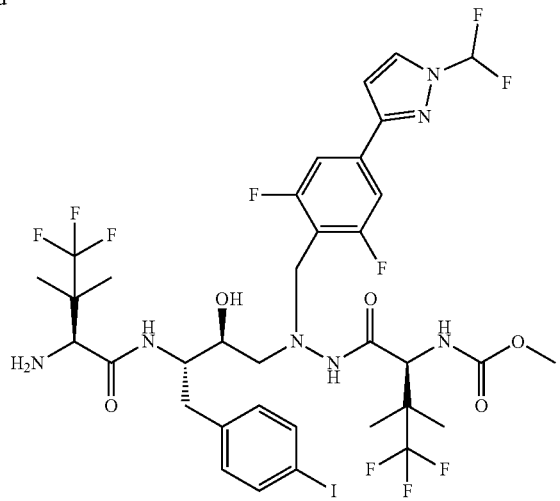

19

Methyl ((S)-1-(2-((2S,3S)-3-((S)-2-amino-4,4,4-trifluoro-3,3-dimethylbutanamido)-2-hydroxy-4-(4-iodophenyl)butyl)-2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate (I9)

A solution of methyl (S)-(4,4,4-trifluoro-1-hydrazinyl-3,3-dimethyl-1-oxobutan-2-yl)carbamate HCl salt (200 mg, 0.68 mmol) and 4-(1-(difluoromethyl)-1H-pyrazol-3-yl)-2,6-difluorobenzaldehyde (P4) (190 mg, 0.75 mmol) in ethanol (5 mL) and acetic acid (0.5 mL) was stirred at 50° C. for 1 hour. The reaction was then cooled to room temperature, diluted with EtOAc, rinsed with aq NaHCO₃, dried over Na2SO4, filtered, and concentrated in vacuo. The crude mixture was redissolved in MeTHF (10 mL) and cooled to 5° C. SODIUM CYANOBOROHYDRIDE (64 mg, 1.0 mmol) was added followed by 4-methylbenzenesulfonic acid monohydrate (155 mg, 0.82 mmol). After 1 hour, the reaction was warmed to room temperature and additional SODIUM CYANOBOROHYDRIDE (64 mg, 1.0 mmol) and 4-methylbenzenesulfonic acid monohydrate (155 mg, 0.82 mmol) were added. After an additional 30 minutes, the reaction was quenched with 2M NaOH to pH 14. The mixture was then stirred at 40° C. for 30 minutes. The mixture was cooled to room temperature, diluted with EtOAc, and the aqueous layer was removed. The organic layer was dried over Na2SO4, filtered, concentrated in vacuo, and purified by column chromatography (30%→70% EtOAc in hexanes) to provide methyl (S)-(1-(2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate (I9a). 1H NMR (400 MHz, Chloroform-d) δ 7.87 (d, J=2.8 Hz, 1H), 7.35 (d, J=7.9 Hz, 2H), 7.22 (t, J=60.7 Hz, 1H), 6.72 (d, J=2.8 Hz, 1H), 5.34 (d, J=9.7 Hz, 1H), 4.30 (d, J=9.7 Hz, 1H), 4.17 (d, J=12.9 Hz, 1H), 4.06 (d, J=13.0 Hz, 1H), 3.67 (s, 3H), 1.23 (s, 3H), 1.16 (s, 3H). MS (ESI) m/z 499.2 [M+H].

Methyl (S)-(1-(2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate (I9a) (0.25 g, 0.50 mmol) was combined with tert-butyl ((S)-2-(4-iodophenyl)-1-((R)-oxiran-2-yl)ethyl)carbamate (0.21 g, 0.55 mmol) in heptanes (4 mL) and IPA (2 mL). The mixture was stirred at 90° C. in a sealed tube overnight. The crude mixture was cooled to room temperature, concentrated in vacuo, and redissolved in DCM (10 mL), and cooled to 5° C. 4M Hydrochloric acid (4.0M in dioxane, 0.89 ml) was added and the mixture was stirred overnight, allowing to slowly warm to room temperature. Concentration in vacuo provided methyl ((S)-1-(2-((2S,3S)-3-amino-2-hydroxy-4-(4-iodophenyl)butyl)-2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate (I9b) as an HCl salt. MS (ESI) m/z 787.9 [M+H]. This crude salt (I9b) was combined in DCM (5 mL) with (S)-2-((tert-butoxycarbonyl)amino)-4,4,4-trifluoro-3,3-dimethylbutanoic acid (A1) (0.11 g, 0.38 mmol) and DIPEA (0.27 ml, 2 mmol). HATU (0.14 g, 0.36 mmol) was added. After 20 minutes the reaction was quenched with aq NaOH, the organic layer was separated, dried over Na2SO4, filtered, and concentrated in vacuo, The resulting mixture was redissolved in DCM and 4M HCl in dioxane (0.76 ml) was added. After 3.5 hours, the mixture was concentrated in vacuo to provide methyl ((S)-1-(2-((2S,3S)-3-((S)-2-amino-4,4,4-trifluoro-3,3-dimethylbutanamido)-2-hydroxy-4-(4-iodophenyl)butyl)-2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate as an HCl salt that was used without further purification. MS (ESI) m/z 956.2 [M+H].

3. Example Compounds, Synthesis, and Characterization
EXAMPLE 1
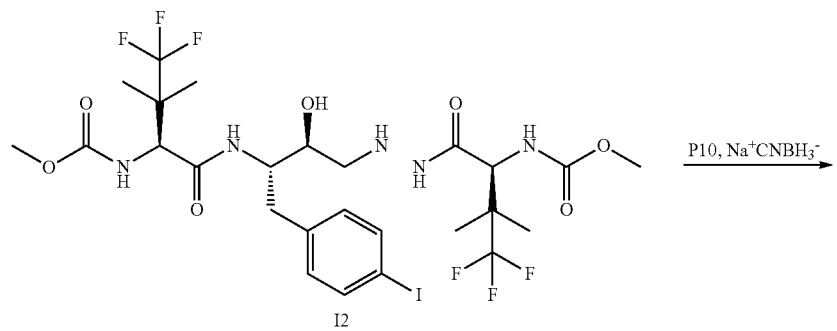
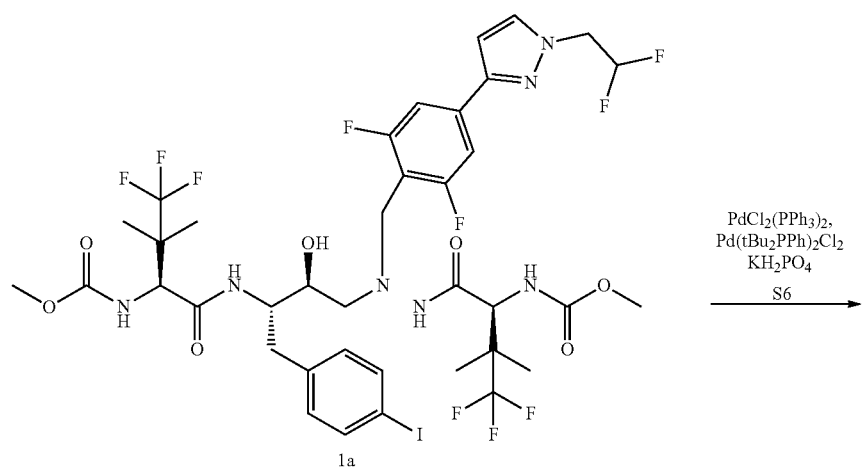
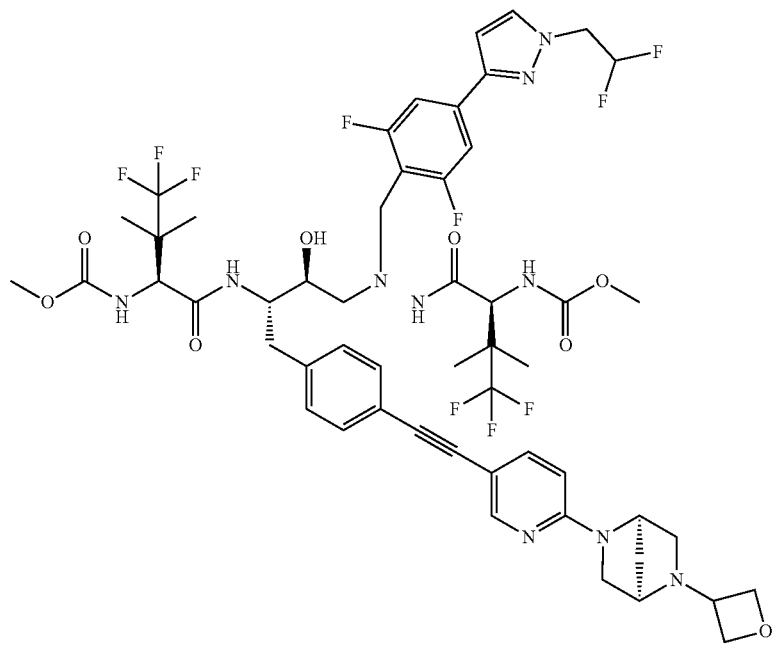

Synthesis of methyl ((5S,10S,11S,14S)-8-(4-(1-(2,2-difluoroethyl)-1H-pyrazol-3-yl)-2,6-difluorobenzyl)-16,16,16-trifluoro-10-hydroxy-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (1a)

Combined P10 (289.23 mg, 0.88 mmol) and I2 (486 mg, 0.63 mmol) were stirred in a 3:1 mixture of THF/AcOH (7.0 mL) at 55° C. for 1 h. The mixture was cooled to room temperature and polymer supported sodium cyanoborohydride (2.49 mmol/g, 780.02 mg, 1.94 mmol) was added and the reaction mixture was stirred at room temperature for 2 h, and then at 28° C. overnight and 35° C. for 3 h. The mixture was cooled to room temperature, filtered, concentrated under reduced pressure and the residue was purified by column chromatography (45% to 75% EtOAc/Hexanes) to afford 1a MS (ESI) m/z 1028.3 [M+H]$^+$.

Synthesis of methyl ((5S,10S,11S,14S)-8-(4-(1-(2,2-difluoroethyl)-1H-pyrazol-3-yl)-2,6-difluorobenzyl)-16,16,16-trifluoro-10-hydroxy-15,15-dimethyl-11-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (1)

In a vial, a solution of 1a (28 mg, 0.027 mmol), S6 (10.4 mg, 0.041 mmol), copper (I) iodide (0.52 mg, 0.002 mmol), trans-Dichlorobis(triphenylphosphine)palladium (II) (99%, 0.87 mg, 0.004 mmol) in a mixture of and MeCN:Et$_3$N 3:1 (1 mL) was degassed and then heated to 25° C. for 25 min. Concentrated under reduced pressure. The residue was purified by HPLC and Lyophilized to give 1. MS (ESI) m/z 1131.2 [M+H]$^+$. $^1$H NMR (400 MHz, Methanol-d4) δ 8.19 (s, 1H), 8.10 (d, J=9.3 Hz, 1H), 7.92 (d, J=8.8 Hz, 1H), 7.64 (d, J=2.5 Hz, 1H), 7.28 (d, J=8.4 Hz, 2H), 7.22 (d, J=7.9 Hz, 2H), 7.05 (d, J=9.9 Hz, 1H), 6.82 (d, J=9.0 Hz, 1H), 6.76 (d, J=9.8 Hz, 1H), 6.65 (d, J=2.5 Hz, 1H), 6.32-5.96 (m, 1H), 4.96 (s, 1H), 4.61 (dd, J=8.2, 4.7 Hz, 1H), 4.58-4.49 (m, 3H), 4.45 (dd, J=14.2, 4.8 Hz, 1H), 4.37 (s, 1H), 4.21 (d, J=9.9 Hz, 1H), 4.04 (d, J=13.0 Hz, 2H), 3.84 (d, J=13.2 Hz, 1H), 3.74 (d, J=11.9 Hz, 1H), 3.67 (d, J=11.5 Hz, 2H), 3.54 (s, 4H), 3.47 (s, 3H), 2.92-2.73 (m, 4H), 2.73-2.62 (m, 1H), 2.24 (s, 2H), 1.05 (d, J=4.5 Hz, 7H), 1.01 (s, 3H), 0.92 (s, 3H).

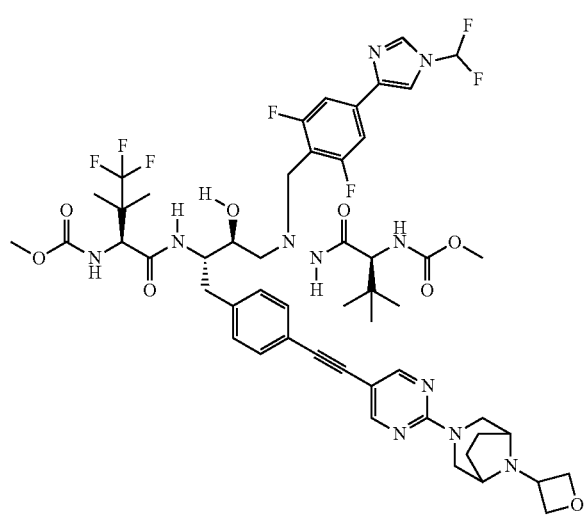

EXAMPLE 2

Methyl ((5S,8S,9S,14S)-11-(4-(1-(difluoromethyl)-1H-imidazol-4-yl)-2,6-difluorobenzyl)-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (2)

Intermediates: I3, P1, and S7. MS (ESI) m/z 1102.2 [M+H]$^+$. $^1$H NMR (400 MHz, Methanol-d4) δ 8.53 (d, J=0.8 Hz, 2H), 8.21 (d, J=9.3 Hz, 1H), 8.17 (d, J=1.2 Hz, 1H), 8.02 (d, J=1.3 Hz, 1H), 7.59 (t, J=59.9 Hz, 1H), 7.37 (dd, J=19.9, 8.1 Hz, 5H), 7.23 (d, J=7.9 Hz, 3H), 6.83 (d, J=9.9 Hz, 1H), 4.96 (t, J=7.6 Hz, 3H), 4.81 (dd, J=8.2, 5.0 Hz, 3H), 4.44 (d, J=9.9 Hz, 1H), 4.12 (d, J=19.4 Hz, 6H), 3.95 (d, J=13.2 Hz, 1H), 3.75 (d, J=10.1 Hz, 3H), 3.69 (d, J=0.8 Hz, 4H), 3.65 (s, 4H), 3.46 (d, J=14.4 Hz, 3H), 2.90 (d, J=8.9 Hz, 2H), 2.79 (d, J=8.9 Hz, 2H), 2.25-2.12 (m, 3H), 1.99 (d, J=8.8 Hz, 2H), 1.14 (s, 4H), 1.10 (s, 4H), 0.86 (s, 12H).

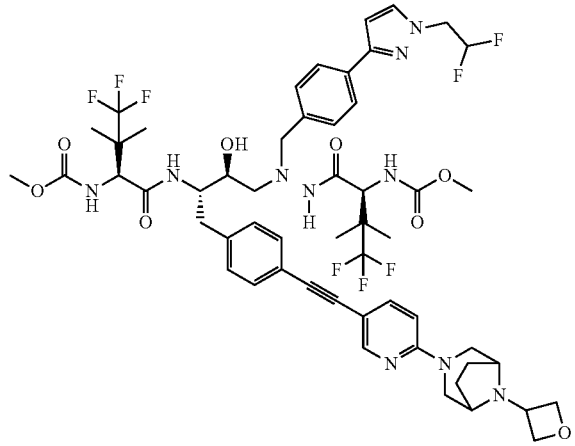

EXAMPLE 3

Methyl ((5S,10S,11S,14S)-8-(4-(1-(2,2-difluoroethyl)-1H-pyrazol-3-yl)benzyl)-16,16,16-trifluoro-10-hydroxy-15,15-dimethyl-11-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (3)

Intermediates: I2, P12, and S3. MS (ESI) m/z 1133.6 [M+H]$^+$. $^1$H NMR (400 MHz, Methanol-d4) δ 8.29 (d, J=2.2 Hz, 1H), 8.10 (d, J=9.5 Hz, 1H), 7.69 (dd, J=8.8, 2.3 Hz, 1H), 7.60 (d, J=1.9 Hz, 1H), 7.53 (d, J=7.9 Hz, 2H), 7.36 (d, J=8.0 Hz, 2H), 7.33 (d, J=7.8 Hz, 2H), 7.22 (d, J=8.0 Hz, 2H), 7.15 (d, J=9.7 Hz, 1H), 6.85 (d, J=8.8 Hz, 1H), 6.78 (d, J=10.0 Hz, 1H), 6.35 (d, J=1.9 Hz, 1H), 4.96 (t, J=7.6 Hz, 2H), 4.81-4.76 (m, 2H), 4.47 (td, J=13.6, 4.3 Hz, 2H), 4.37 (dd, J=19.3, 11.6 Hz, 2H), 4.25 (d, J=9.7 Hz, 1H), 4.15 (s, 2H), 3.99 (d, J=9.2 Hz, 2H), 3.74 (s, 1H), 3.68 (s, 3H), 3.60 (s, 3H), 3.39 (s, 1H), 3.36 (s, 1H), 2.90 (d, J=9.0 Hz, 2H), 2.86-2.72 (m, 1H), 2.22 (d, J=8.5 Hz, 2H), 2.07 (d, J=8.6 Hz, 1H), 1.11 (s, 6H), 1.06 (s, 3H), 0.81 (s, 3H).

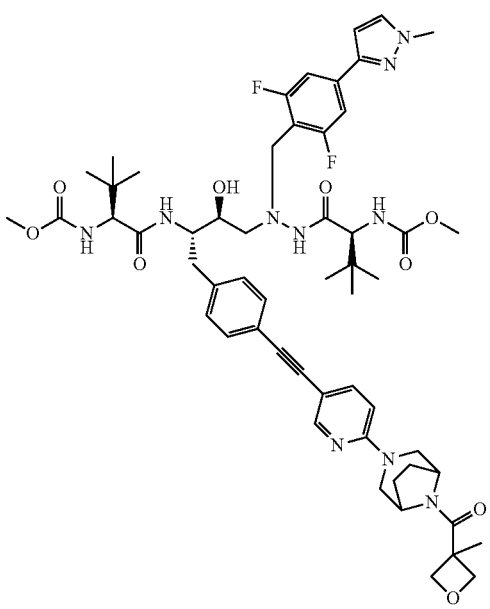

EXAMPLE 4 methyl ((5S,8S,9S,14S)-5-(tert-butyl)-11-(2,6-difluoro-4-(1-methyl-1H-pyrazol-3-yl)benzyl)-9-hydroxy-15,15-dimethyl-8-(4-((6-(8-(3-methyloxetane-3-carbonyl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate (4)

Intermediates: 11, P41, and S64. MS (ESI) m/z 1053.33 [M+H]⁺. ¹H NMR (400 MHz, Methanol-d₄) δ 8.21 (dd, J=2.2, 0.7 Hz, 1H), 7.90-7.69 (m, 2H), 7.61 (d, J=2.3 Hz, 1H), 7.33 (t, J=8.4 Hz, 5H), 7.24 (d, J=8.0 Hz, 2H), 6.98 (d, J=9.2 Hz, 1H), 6.65 (d, J=2.3 Hz, 1H), 5.06 (s, 1H), 4.93 (s, 1H), 4.41 (d, J=6.0 Hz, 2H), 4.22-4.02 (m, 4H), 3.91 (d, J=13.2 Hz, 6H), 3.79-3.54 (m, 9H), 3.20 (d, J=12.0 Hz, 2H), 2.92 (h, J=5.7, 4.9 Hz, 2H), 2.81 (d, J=7.9 Hz, 2H), 2.08-1.80 (m, 6H), 1.69 (s, 3H), 0.87 (d, J=20.1 Hz, 21H).

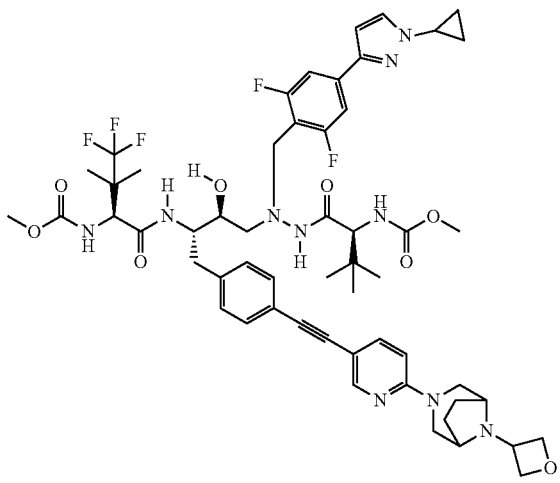 [SMILES: COC(=O)N[C@H](C(=O)NN(Cc1c(F)cc(C(=N)/C=C\NC2CC2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 5 methyl ((5S,8S,9S,14S)-11-(4-(1-cyclopropyl-1H-pyrazol-3-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (5)

Intermediates: I3, P13, and S3. MS (ESI) m/z 1091.3 [M+H]⁺. ¹H NMR (400 MHz, Methanol-d4) δ 8.20 (d, J=2.3 Hz, 1H), 8.10 (d, J=9.4 Hz, 1H), 7.60 (dt, J=5.5, 2.7 Hz, 2H), 7.24 (t, J=7.8 Hz, 4H), 7.12 (d, J=8.1 Hz, 2H), 6.77 (d, J=8.9 Hz, 1H), 6.71 (d, J=9.9 Hz, 1H), 6.54 (d, J=2.4 Hz, 1H), 4.95-4.85 (m, 2H), 4.71 (dd, J=8.3, 5.0 Hz, 2H), 4.34 (d, J=10.0 Hz, 1H), 4.26 (d, J=14.3 Hz, 2H), 4.11-3.94 (m, 4H), 3.87 (s, 1H), 3.84 (s, 0H), 3.67 (s, 1H), 3.59 (s, 4H), 3.56 (s, 3H), 3.28 (d, J=13.9 Hz, 2H), 2.80 (d, J=9.1 Hz, 2H), 2.69 (d, J=8.9 Hz, 2H), 2.21-2.04 (m, 2H), 1.98 (d, J=8.6 Hz, 2H), 1.04 (s, 4H), 1.00 (s, 3H), 0.99-0.94 (m, 1H), 0.77 (s, 9H).

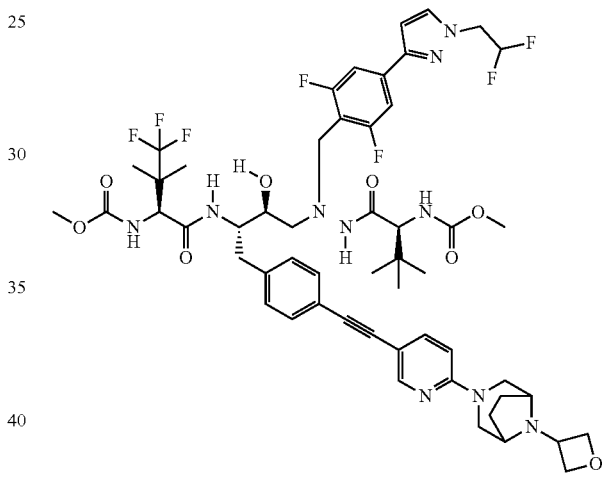

EXAMPLE 6 methyl ((5S,8S,9S,14S)-11-(4-(1-(2,2-difluoroethyl)-1H-pyrazol-3-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (6)

Intermediates: I3, P10, and S3. MS (ESI) m/z 1115.3 [M+H]⁺. ¹H NMR (400 MHz, Methanol-d4) δ 8.20 (d, J=2.2 Hz, 1H), 8.10 (d, J=9.3 Hz, 1H), 7.64 (d, J=2.4 Hz, 1H), 7.61 (dd, J=8.8, 2.3 Hz, 1H), 7.28 (d, J=8.4 Hz, 2H), 7.23 (d, J=8.0 Hz, 2H), 7.12 (d, J=8.1 Hz, 2H), 6.77 (d, J=9.0 Hz, 1H), 6.72 (d, J=9.9 Hz, 0H), 6.65 (d, J=2.4 Hz, 1H), 6.12 (tt, J=55.3, 4.0 Hz, 1H), 4.87 (dd, J=8.3, 7.0 Hz, 2H), 4.71 (dd, J=8.3, 5.0 Hz, 2H), 4.54-4.42 (m, 2H), 4.38-4.31 (m, 1H), 4.26 (d, J=13.8 Hz, 2H), 4.13-3.97 (m, 4H), 3.85 (s, 0H), 3.67 (s, 1H), 3.59 (s, 2H), 3.55 (s, 3H), 3.30 (s, 1H), 3.26 (s, 1H), 2.81 (d, J=9.3 Hz, 2H), 2.70 (d, J=9.4 Hz, 2H), 2.17-2.06 (m, 2H), 1.98 (d, J=8.6 Hz, 2H), 1.05 (s, 3H), 1.01 (s, 3H), 0.77 (s, 9H).

191

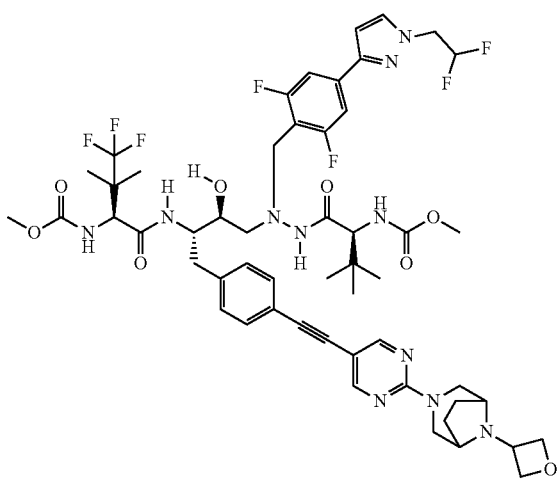 [SMILES: COC(=O)N[C@H](C(=O)NN(Cc1c(F)cc(C(=N)/C=C\NCC(F)F)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C]

EXAMPLE 7 methyl ((5S,8S,9S,14S)-11-(4-(1-(2,2-difluoro-ethyl)-1H-pyrazol-3-yl)-2,6-difluorobenzyl)-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (7)

Intermediates: I3, P10, and S7. MS (ESI) m/z 1117.4 [M+H]⁺. ¹H NMR (400 MHz, Methanol-d4) δ 8.44 (s, 2H), 8.11 (d, J=9.4 Hz, 1H), 7.64 (d, J=2.4 Hz, 1H), 7.26 (dd, J=14.0, 8.2 Hz, 4H), 7.14 (d, J=8.1 Hz, 2H), 6.73 (d, J=10.0 Hz, 1H), 6.65 (d, J=2.5 Hz, 1H), 6.12 (tt, J=55.3, 4.0 Hz, 1H), 4.95-4.82 (m, 2H), 4.74-4.62 (m, 3H), 4.51 (td, J=14.3, 4.0 Hz, 2H), 4.35 (d, J=9.9 Hz, 1H), 4.02 (d, J=19.0 Hz, 4H), 3.86 (d, J=13.2 Hz, 1H), 3.67 (s, 1H), 3.59 (s, 3H), 3.55 (s, 3H), 3.37 (d, J=14.5 Hz, 2H), 2.81 (d, J=8.9 Hz, 2H), 2.70 (d, J=9.3 Hz, 2H), 2.23-2.02 (m, 2H), 1.98-1.83 (m, 2H), 1.04 (s, 3H), 1.01 (s, 3H), 0.77 (s, 9H).

192

EXAMPLE 8 methyl ((5S,8S,9S,14S)-11-(4-(1-(2,2-difluoro-ethyl)-1H-pyrazol-3-yl)-2,6-difluorobenzyl)-9-hydroxy-15,15-dimethyl-8-(4-((6-(((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (8)

Intermediates: I3, P10, and S6. MS (ESI) m/z 1101.6 [M+H]⁺. ¹H NMR (400 MHz, Methanol-d4) δ 8.16 (d, J=2.2 Hz, 1H), 8.08 (d, J=9.4 Hz, 1H), 7.64 (d, J=2.4 Hz, 1H), 7.61 (dd, J=8.8, 2.2 Hz, 1H), 7.25 (dd, J=21.0, 8.1 Hz, 3H), 7.12 (d, J=8.0 Hz, 2H), 6.70 (d, J=10.3 Hz, 0H), 6.64 (d, J=2.4 Hz, 1H), 6.58 (d, J=8.8 Hz, 1H), 6.12 (tt, J=55.2, 3.9 Hz, 1H), 4.96 (s, 1H), 4.91-4.82 (m, 1H), 4.61 (dd, J=8.4, 4.6 Hz, 1H), 4.57-4.42 (m, 3H), 4.41 (s, 1H), 4.35 (d, J=6.5 Hz, 1H), 4.02 (d, J=13.2 Hz, 2H), 3.87 (d, J=13.2 Hz, 1H), 3.72-3.61 (m, 3H), 3.59 (s, 3H), 3.55 (s, 2H), 2.80 (d, J=8.7 Hz, 1H), 2.70 (d, J=9.5 Hz, 2H), 2.24 (s, 2H), 1.05 (s, 3H), 1.01 (s, 3H), 0.77 (s, 8H).

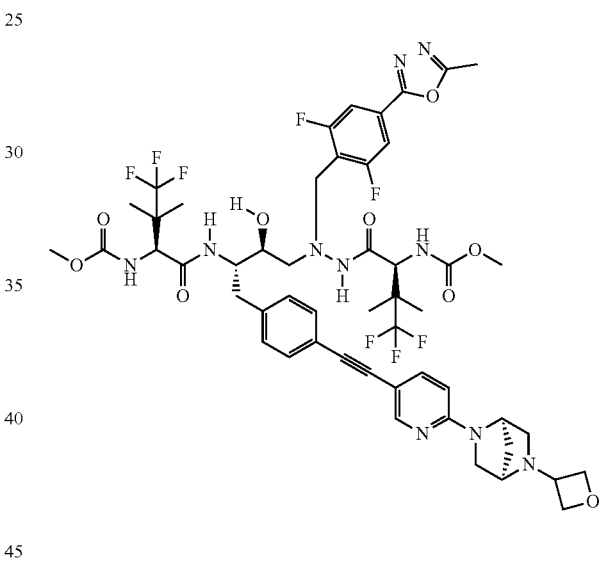

EXAMPLE 9 methyl ((5S,8S,9S,14S)-11-(2,6-difluoro-4-(5-methyl-1,3,4-oxadiazol-2-yl)benzyl)-16,16,16-trifluoro-9-hydroxy-15,15-dimethyl-8-(4-((6-(((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (9)

Intermediates: I2, P34, and S6. MS (ESI) m/z 1101.6 [M+H]⁺. ¹H NMR (400 MHz, Methanol-d4) δ 8.16 (d, J=2.1 Hz, 1H), 8.10 (d, J=9.4 Hz, 1H), 7.60 (d, J=8.3 Hz, 1H), 7.48 (d, J=7.1 Hz, 2H), 7.23 (d, J=7.9 Hz, 2H), 7.13 (d, J=8.0 Hz, 2H), 6.76 (d, J=10.1 Hz, 1H), 6.57 (d, J=8.8 Hz, 1H), 4.96 (s, 1H), 4.61 (s, 1H), 4.49 (t, J=8.9 Hz, 1H), 4.41 (s, 1H), 4.35 (d, J=9.7 Hz, 1H), 4.18 (d, J=9.9 Hz, 1H), 4.09 (d, J=13.1 Hz, 1H), 3.87 (d, J=13.1 Hz, 1H), 3.77-3.55 (m, 8H), 2.82 (d, J=8.5 Hz, 3H), 2.71 (d, J=10.1 Hz, 1H), 2.54 (s, 3H), 2.23 (s, 2H), 1.05 (d, J=7.7 Hz, 9H), 0.92 (s, 3H).

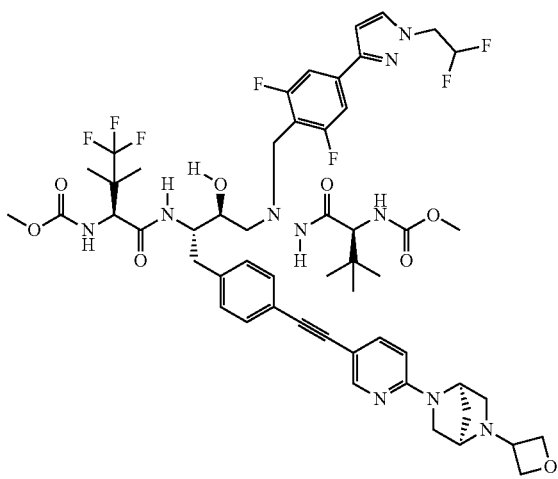

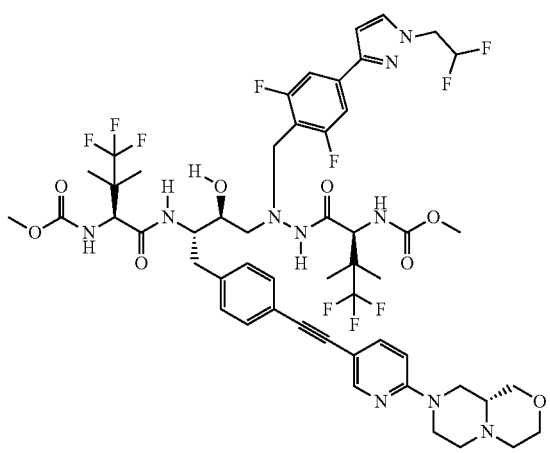 [SMILES: COC(=O)N[C@H](C(=O)N[C@@H](Cc1ccc(C#Cc2ccc(N3CCN4CCOC[C@H]4C3)nc2)cc1)[C@@H](O)CN(Cc1c(F)cc(C(=N)/C=C\NCC(F)F)cc1F)NC(=O)[C@@H](NC(=O)OC)C(C)(C)C(F)(F)F)C(C)(C)C(F)(F)F]

EXAMPLE 10

Methyl ((5S,8S,9S,14S)-11-(4-(1-(2,2-difluoro-ethyl)-1H-pyrazol-3-yl)-2,6-difluorobenzyl)-16,16,16-trifluoro-8-(4-(((6-((R)-hexahydropyrazino[2,1-c][1,4]oxazin-8(1H)-yl)pyridin-3-yl)ethynyl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (10)

Intermediates: I2, P10, and S8. MS (ESI) m/z 1143.6 [M+H]$^+$. $^1$H NMR (400 MHz, Methanol-d4) δ 8.26-8.19 (m, 1H), 8.10 (d, J=9.4 Hz, 1H), 7.65 (d, J=2.5 Hz, 1H), 7.61 (dd, J=8.9, 2.3 Hz, 1H), 7.29 (d, J=8.5 Hz, 2H), 7.24 (d, J=7.9 Hz, 2H), 7.13 (d, J=8.1 Hz, 2H), 6.86 (d, J=8.9 Hz, 1H), 6.72 (d, J=10.0 Hz, 1H), 6.66 (d, J=2.4 Hz, 1H), 6.30-5.97 (m, 1H), 4.51 (td, J=14.2, 3.9 Hz, 3H), 4.35 (d, J=9.7 Hz, 1H), 4.22 (d, J=10.0 Hz, 1H), 4.04 (d, J=12.4 Hz, 4H), 3.60 (s, 3H), 3.57 (s, 3H), 3.48 (d, J=11.0 Hz, 1H), 2.89-2.61 (m, 5H), 1.08 (s, 4H), 1.05 (s, 3H), 1.02 (s, 3H), 0.94 (s, 3H).

EXAMPLE 11

Methyl ((5S,8S,9S,14S)-11-(2,6-difluoro-4-(5-methyl-1,3,4-oxadiazol-2-yl)benzyl)-16,16,16-trifluoro-9-hydroxy-15,15-dimethyl-8-(4-(((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (11)

Intermediates: I2, P34, and S3. MS (ESI) m/z 1121.3 [M+H]$^+$. $^1$H NMR (400 MHz, Methanol-d4) δ 8.20 (d, J=2.3 Hz, 1H), 8.08 (d, J=9.4 Hz, 1H), 7.60 (dd, J=8.9, 2.3 Hz, 1H), 7.48 (d, J=7.1 Hz, 2H), 7.24 (d, J=7.9 Hz, 2H), 7.13 (d, J=8.1 Hz, 2H), 7.08 (d, J=10.5 Hz, 1H), 6.77 (d, J=9.0 Hz, 1H), 6.73 (d, J=9.9 Hz, 1H), 4.93-4.82 (m, 2H), 4.74-4.63 (m, 2H), 4.34 (d, J=9.9 Hz, 1H), 4.26 (d, J=13.5 Hz, 1H), 4.18 (d, J=10.0 Hz, 1H), 4.09 (d, J=17.9 Hz, 4H), 3.88 (d, J=13.1 Hz, 1H), 3.64 (s, 1H), 3.60 (d, J=2.9 Hz, 6H), 3.28 (d, J=13.8 Hz, 2H), 2.82 (d, J=8.6 Hz, 3H), 2.75-2.62 (m, 1H), 2.54 (s, 3H), 2.22-2.06 (m, 2H), 1.98 (d, J=8.6 Hz, 2H), 1.06 (s, 6H), 1.04 (s, 3H), 0.93 (s, 3H).

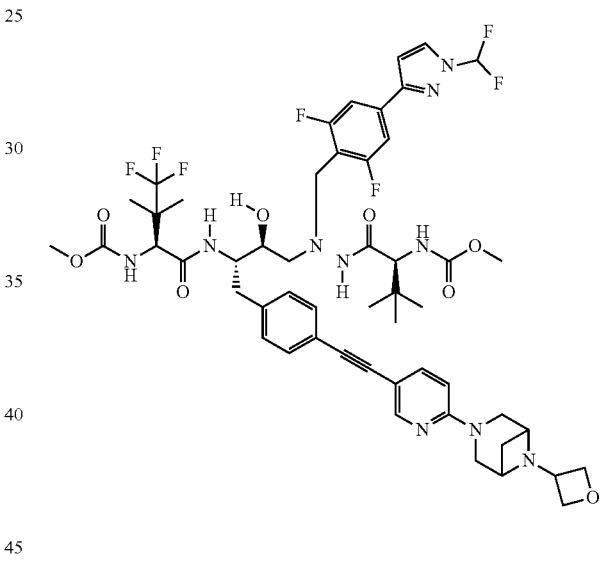

EXAMPLE 12

Methyl ((5S,8S,9S,14S)-11-(4-(1-(difluoromethyl)-1H-pyrazol-3-yl)-2,6-difluorobenzyl)-9-hydroxy-15,15-dimethyl-8-(4-(((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (12)

Intermediates: I3, P4, and S4. MS (ESI) m/z 1087.8 [M+H]$^+$. $^1$H NMR (400 MHz, Methanol-d4) δ 8.33 (s, 1H), 8.15 (d, J=9.4 Hz, 1H), 8.10 (d, J=2.8 Hz, 1H), 7.78-7.71 (m, 1H), 7.52 (t, J=59.9 Hz, 1H), 7.45 (d, J=8.2 Hz, 2H), 7.33 (d, J=7.8 Hz, 3H), 7.22 (d, J=7.9 Hz, 3H), 6.93 (d, J=2.7 Hz, 1H), 6.78 (d, J=9.2 Hz, 2H), 4.70-4.57 (m, 2H), 4.44 (d, J=9.7 Hz, 1H), 4.13 (d, J=12.4 Hz, 3H), 3.97 (d, J=13.0 Hz, 1H), 3.76 (s, 1H), 3.69 (s, 4H), 3.65 (s, 3H), 2.90 (d, J=8.7 Hz, 2H), 2.80 (d, J=11.1 Hz, 2H), 2.11 (d, J=10.6 Hz, 1H), 1.39-1.23 (m, 2H), 1.15 (s, 4H), 1.11 (s, 4H), 0.86 (s, 11H).

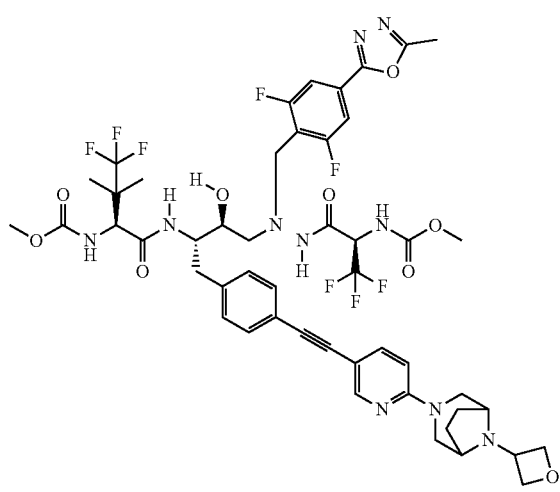

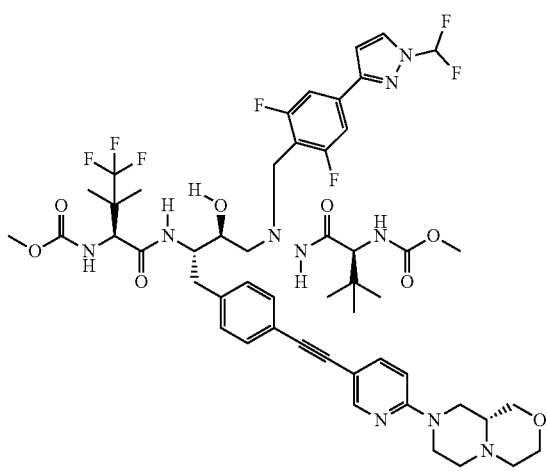

EXAMPLE 13

Methyl ((5S,8S,9S,14S)-11-(4-(1-(difluoromethyl)-1H-pyrazol-3-yl)-2,6-difluorobenzyl)-8-(4-((6-((R)-hexahydropyrazino[2,1-c][1,4]oxazin-8(1H)-yl)pyridin-3-yl)ethynyl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (13)

Intermediates: I3, P4, and S8. MS (ESI) m/z 1073.9 [M+H]+. 1H NMR (400 MHz, Methanol-d4) δ 8.30 (d, J=2.2 Hz, 1H), 8.19 (d, J=9.3 Hz, 1H), 8.10 (d, J=2.7 Hz, 1H), 7.75-7.59 (m, 2H), 7.56 (dd, J=7.4, 3.4 Hz, 1H), 7.53 (t, J=59.8 Hz, 2H), 7.45 (d, J=8.2 Hz, 3H), 7.32 (d, J=7.9 Hz, 3H), 7.22 (d, J=8.1 Hz, 3H), 7.03-6.88 (m, 3H), 6.82 (d, J=10.0 Hz, 1H), 4.62 (dd, J=22.7, 13.0 Hz, 2H), 4.44 (d, J=9.7 Hz, 1H), 4.12 (d, J=12.2 Hz, 6H), 3.97 (d, J=13.1 Hz, 2H), 3.85 (t, J=12.6 Hz, 1H), 3.76 (s, 2H), 3.69 (s, 4H), 3.59 (d, J=10.8 Hz, 2H), 3.01-2.70 (m, 6H), 1.14 (s, 4H), 1.11 (s, 4H), 0.86 (s, 12H).

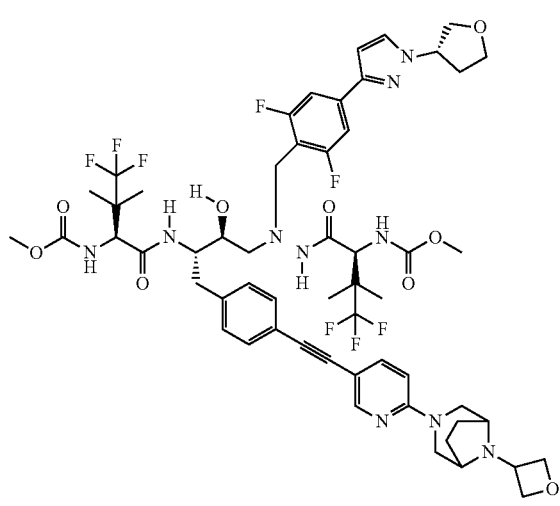

EXAMPLE 14

Methyl ((5S,8S,9S,14S)-11-(2,6-difluoro-4-(1-((S)-tetrahydrofuran-3-yl)-1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (14)

Intermediates: I2, P17, and S3. MS (ESI) m/z 1176.1 [M+H]+. 1H NMR (400 MHz, Methanol-d4) δ 8.20 (d, J=2.3 Hz, 1H), 8.11 (d, J=9.3 Hz, 1H), 7.68-7.58 (m, 2H), 7.25 (dd, J=13.9, 8.3 Hz, 4H), 7.12 (d, J=8.0 Hz, 2H), 6.75 (dd, J=17.1, 9.4 Hz, 2H), 6.59 (d, J=2.4 Hz, 1H), 4.97 (dq, J=8.2, 3.8 Hz, 1H), 4.87 (t, J=7.6 Hz, 3H), 4.71 (dd, J=8.3, 5.0 Hz, 3H), 4.52-4.32 (m, 1H), 4.32-4.18 (m, 3H), 4.17-3.99 (m, 6H), 3.97 (d, J=4.7 Hz, 2H), 3.84 (td, J=8.3, 5.4 Hz, 2H), 3.58 (d, J=9.5 Hz, 8H), 3.27 (d, J=13.9 Hz, 3H), 2.80-2.52 (m, 4H), 2.45-2.33 (m, 1H), 2.33-2.23 (m, 1H), 2.13 (d, J=10.7 Hz, 2H), 2.03-1.92 (m, 2H), 1.07 (s, 4H), 1.05 (s, 3H), 1.00 (s, 3H), 0.94 (s, 3H).

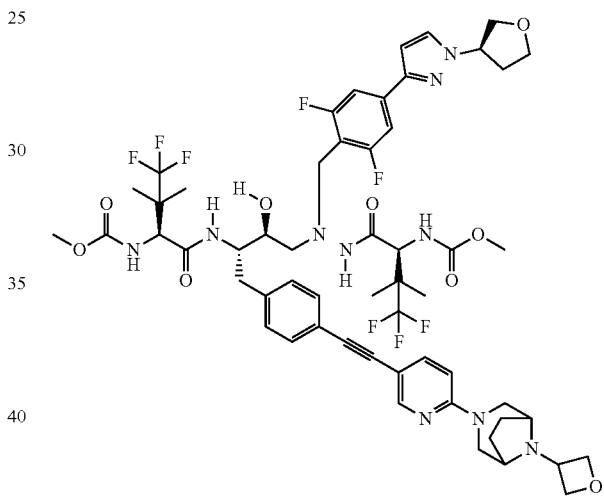

EXAMPLE 15

Methyl ((5S,8S,9S,14S)-11-(2,6-difluoro-4-(1-((R)-tetrahydrofuran-3-yl)-1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (15)

Intermediates: I2, P18, and S3. MS (ESI) m/z 1176.1 [M+H]+. 1H NMR (400 MHz, Methanol-d4) δ 8.19 (s, 1H), 8.11 (d, J=9.4 Hz, 1H), 7.63 (d, J=2.4 Hz, 1H), 7.60 (d, J=8.8 Hz, 1H), 7.25 (dd, J=14.4, 8.2 Hz, 4H), 7.12 (d, J=8.0 Hz, 2H), 6.74 (t, J=10.2 Hz, 2H), 6.59 (d, J=2.4 Hz, 1H), 4.98 (dd, J=8.3, 3.9 Hz, 1H), 4.69 (t, J=6.7 Hz, 2H), 4.35 (d, J=9.9 Hz, 1H), 4.22 (d, J=10.0 Hz, 1H), 4.03 (dd, J=14.5, 7.1 Hz, 3H), 3.97 (d, J=4.7 Hz, 2H), 3.90-3.79 (m, 2H), 3.63 (s, 1H), 3.58 (d, J=9.2 Hz, 6H), 2.81 (d, J=7.8 Hz, 2H), 2.68 (d, J=10.0 Hz, 1H), 2.49-2.33 (m, 1H), 2.33-2.21 (m, 1H), 2.10 (s, 1H), 1.94 (s, 0H), 1.07 (s, 3H), 1.05 (s, 3H), 1.00 (s, 3H), 0.94 (s, 3H).

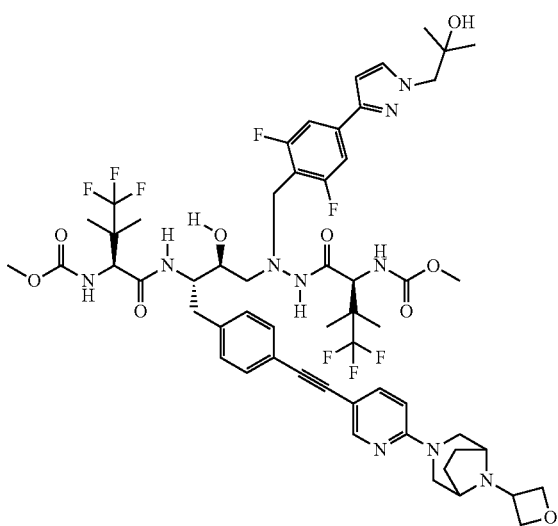 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(C(=N)/C=C\NCC(C)(C)O)cc1F)NC(=O)[C@@H](NC(=O)OC)C(C)(C)C(F)(F)F)C(C)(C)C(F)(F)F]

EXAMPLE 16

Methyl ((5S,8S,9S,14S)-11-(2,6-difluoro-4-(1-(2-hydroxy-2-methylpropyl)-1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (16)

Intermediates: I2, P19, and S3. MS (ESI) m/z 1177.2 [M+H]$^+$. $^1$H NMR (400 MHz, Methanol-d4) δ 8.20 (s, 1H), 8.10 (d, J=9.2 Hz, 1H), 7.61 (s, 1H), 7.59 (d, J=2.3 Hz, 2H), 7.25 (dd, J=12.2, 8.1 Hz, 4H), 7.12 (d, J=8.0 Hz, 2H), 6.77 (d, J=9.0 Hz, 1H), 6.72 (d, J=10.2 Hz, 1H), 6.60 (d, J=2.4 Hz, 1H), 4.87 (t, J=7.6 Hz, 3H), 4.71 (dd, J=8.3, 5.0 Hz, 2H), 4.35 (d, J=9.9 Hz, 1H), 4.30-4.13 (m, 2H), 4.03 (d, J=12.6 Hz, 3H), 3.84 (d, J=13.3 Hz, 1H), 3.58 (d, J=8.2 Hz, 5H), 3.28 (d, J=13.9 Hz, 2H), 2.81 (d, J=7.8 Hz, 2H), 2.72 (d, J=15.2 Hz, 1H), 2.12 (s, 1H), 1.98 (d, J=8.6 Hz, 2H), 1.10 (s, 6H), 1.07 (s, 3H), 1.05 (s, 3H), 1.01 (s, 3H), 0.93 (s, 3H).

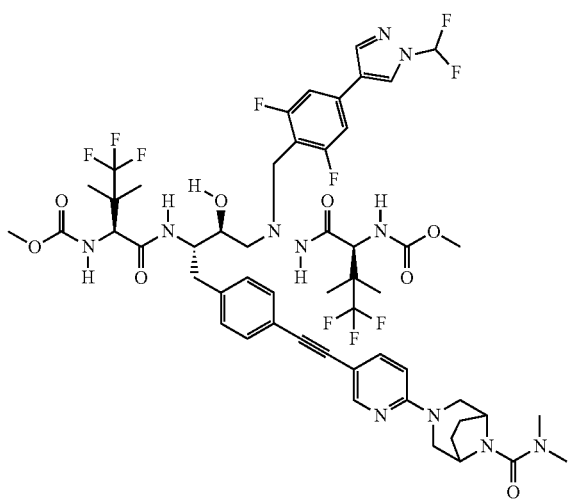

EXAMPLE 17

Methyl ((5S,8S,9S,14S)-11-(4-(1-(difluoromethyl)-1H-pyrazol-4-yl)-2,6-difluorobenzyl)-8-(4-((6-(8-(dimethylcarbamoyl)-3,8-diazabicyclo[3.2.1]octan-3-yl)pyridin-3-yl)ethynyl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (17)

Intermediates: I2, P7, and S24. MS (ESI) m/z 1177.2 [M+H]$^+$. 1H NMR (400 MHz, Methanol-d4) δ 8.53 (d, J=0.7 Hz, 1H), 8.22-8.13 (m, 2H), 8.11 (s, 1H), 7.86 (dd, J=9.3, 2.2 Hz, 1H), 7.50 (s, 1H), 7.40-7.30 (m, 2H), 7.23 (dd, J=8.2, 5.7 Hz, 4H), 7.17 (d, J=9.9 Hz, 1H), 7.10 (d, J=9.3 Hz, 1H), 6.81 (d, J=9.9 Hz, 1H), 4.50-4.37 (m, 1H), 4.35-4.23 (m, 3H), 4.12 (t, J=11.1 Hz, 2H), 4.00-3.87 (m, 3H), 3.66 (d, J=10.3 Hz, 7H), 3.43-3.33 (m, 2H), 2.96 (s, 6H), 2.94-2.69 (m, 2H), 1.96 (t, J=5.3 Hz, 2H), 1.78 (t, J=6.9 Hz, 2H), 1.26-1.07 (m, 9H), 1.02 (s, 3H).

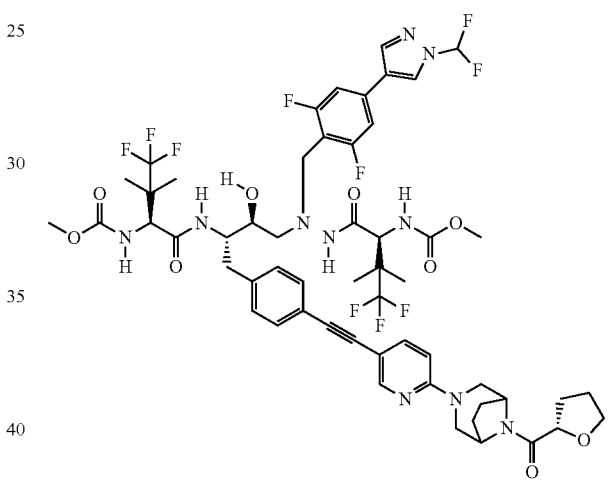

EXAMPLE 18

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-8-(4-((6-(8-((S)-tetrahydrofuran-2-carbonyl)-3,8-diazabicyclo[3.2.1]octan-3-yl)pyridin-3-yl)ethynyl)benzyl)-5-(1,1,1-trifluoro-2-methylpropan-2-yl)-2-oxa-4,7,11,12-tetraazahexadecan-14-yl)carbamate (18)

Intermediates: I2, P7, and S25. MS (ESI) m/z 1177.2 [M+H]$^+$. $^1$H NMR (400 MHz, Methanol-d4) δ 8.44 (s, 1H), 8.13-8.05 (m, 2H), 8.03 (s, 1H), 7.68 (t, J=8.5 Hz, 1H), 7.41 (s, 1H), 7.31-7.22 (m, 2H), 7.20-7.05 (m, 5H), 6.96-6.84 (m, 1H), 6.72 (d, J=10.0 Hz, 1H), 4.75-4.65 (m, 5H), 4.60 (dd, J=7.6, 6.2 Hz, 2H), 4.40-4.26 (m, 1H), 4.25-4.12 (m, 1H), 4.10-3.87 (m, 4H), 3.87-3.71 (m, 3H), 3.58 (d, J=10.7 Hz, 6H), 3.17-2.96 (m, 2H), 2.89-2.59 (m, 4H), 2.19-1.93 (m, 2H), 1.93-1.67 (m, 4H), 1.15-0.96 (m, 9H), 0.94 (s, 3H).

EXAMPLE 20 methyl ((5S,8S,9S,14S)-8-(4-((6-(2-oxa-6-azaspiro [3.3]heptan-6-yl)pyridin-3-yl)ethynyl)benzyl)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (20)

Intermediates: I2, P7, and S27. MS (ESI) m/z 1086.3 [M+H]+. 1H NMR (400 MHz, Methanol-d4) δ 8.54 (s, 1H), 8.17 (d, J=9.2 Hz, 1H), 8.12 (s, 1H), 8.08 (d, J=1.9 Hz, 1H), 7.93 (dd, J=9.4, 2.0 Hz, 1H), 7.69-7.60 (m, 1H), 7.56 (dd, J=7.2, 3.3 Hz, 0H), 7.51 (s, 0H), 7.40-7.33 (m, 2H), 7.25 (d, J=8.0 Hz, 4H), 7.17 (d, J=9.9 Hz, 1H), 6.83 (d, J=9.3 Hz, 1H), 4.86 (s, 4H), 4.49 (s, 4H), 4.43 (d, J=3.7 Hz, 1H), 4.36-4.25 (m, 1H), 4.24-4.05 (m, 2H), 3.92 (d, J=13.1 Hz, 1H), 3.67 (d, J=7.6 Hz, 7H), 2.99-2.70 (m, 4H), 1.23-1.06 (m, 9H), 1.03 (s, 3H).

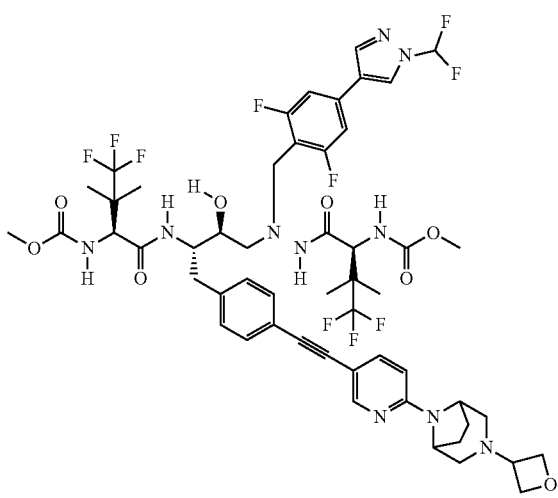

EXAMPLE 19 methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(3-(oxetan-3-yl)-3,8-diazabicyclo[3.2.1]octan-8-yl) pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (19)

Intermediates: I2, P7, and S26. MS (ESI) m/z 1177.2 [M+H]+. 1H NMR (400 MHz, Methanol-d4) δ 8.54 (d, J=0.7 Hz, 1H), 8.26-8.22 (m, 1H), 8.17 (d, J=9.4 Hz, 1H), 8.12 (s, 1H), 7.78 (d, J=8.9 Hz, 1H), 7.51 (s, 1H), 7.39-7.32 (m, 2H), 7.24 (t, J=8.3 Hz, 4H), 7.17 (d, J=9.8 Hz, 1H), 7.01 (d, J=9.0 Hz, 1H), 6.81 (d, J=9.9 Hz, 1H), 4.80 (ddtd, J=4.5, 2.0, 1.0, 0.5 Hz, 1H), 4.76-4.69 (m, 4H), 4.50-4.37 (m, 1H), 4.36-4.25 (m, 1H), 4.13 (t, J=10.7 Hz, 3H), 3.93 (d, J=13.2 Hz, 1H), 3.68 (d, J=10.5 Hz, 6H), 2.97-2.66 (m, 6H), 2.33-2.10 (m, 3H), 1.26-1.08 (m, 9H), 1.03 (s, 3H).

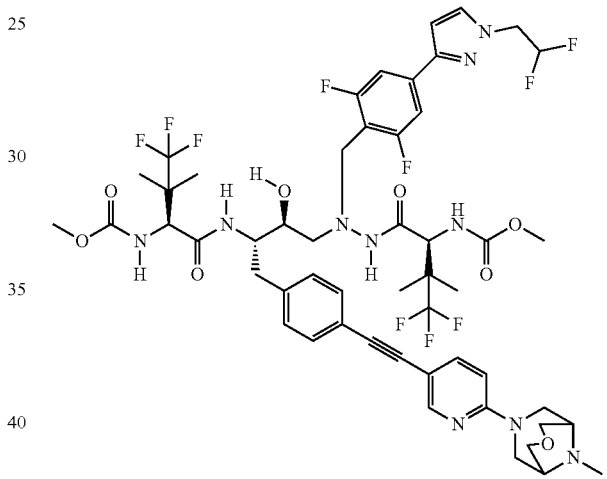

EXAMPLE 21 methyl ((5S,8S,9S,14S)-11-(4-(1-(2,2-difluoroethyl)-1H-pyrazol-3-yl)-2,6-difluorobenzyl)-16,16,16-trifluoro-9-hydroxy-15,15-dimethyl-8-(4-((6-(9-methyl-3-oxa-7,9-diazabicyclo[3.3.1]nonan-7-yl) pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (21)

Intermediates: I2, P10, and S2. MS (ESI) m/z 1143.2 [M+H]+. 1H NMR (400 MHz, Methanol-d4) δ 8.18 (d, J=2.3 Hz, 1H), 8.06 (d, J=9.3 Hz, 1H), 7.64 (d, J=2.5 Hz, 1H), 7.58 (dd, J=8.9, 2.3 Hz, 1H), 7.28 (d, J=8.5 Hz, 2H), 7.23 (d, J=8.0 Hz, 2H), 7.12 (d, J=8.1 Hz, 2H), 7.02 (d, J=9.7 Hz, 1H), 6.77 (d, J=9.0 Hz, 1H), 6.71-6.61 (m, 2H), 6.12 (tt, J=55.4, 4.0 Hz, 1H), 4.50 (td, J=14.3, 3.9 Hz, 2H), 4.34 (d, J=9.6 Hz, 1H), 4.29-4.18 (m, 1H), 4.04 (d, J=13.0 Hz, 6H), 3.84 (d, J=13.2 Hz, 1H), 3.63 (s, 3H), 3.56 (s, 3H), 3.50 (s, 2H), 3.10 (s, 3H), 2.81 (d, J=8.1 Hz, 2H), 2.69 (d, J=9.4 Hz, 1H), 1.07 (s, 3H), 1.05 (s, 3H), 1.02 (s, 3H), 0.94 (s, 3H).

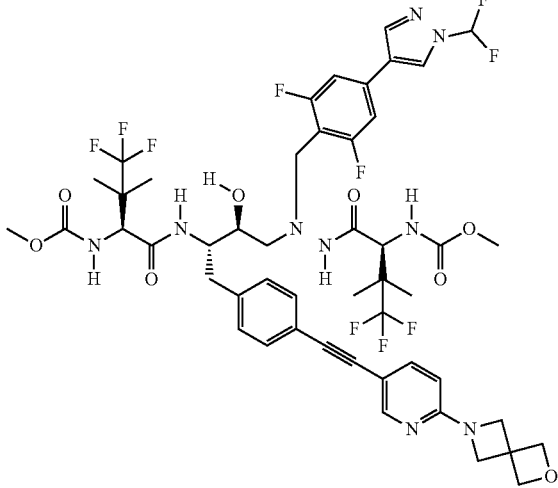

201

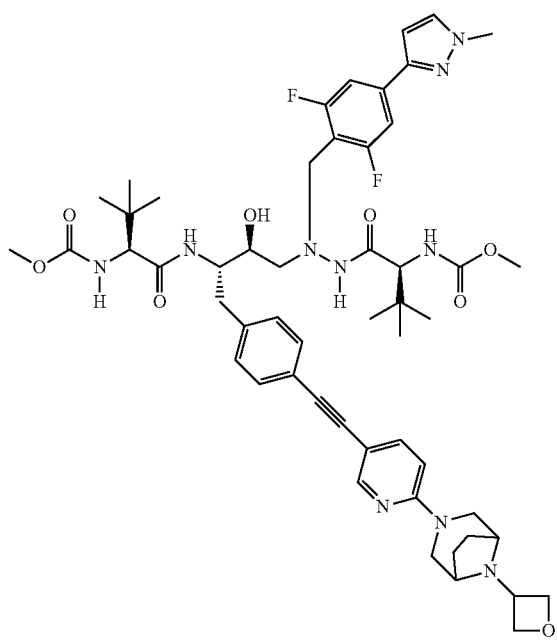 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccn(C)n2)cc1F)NC(=O)[C@@H](NC(=O)OC)C(C)(C)C)C(C)(C)C]

202

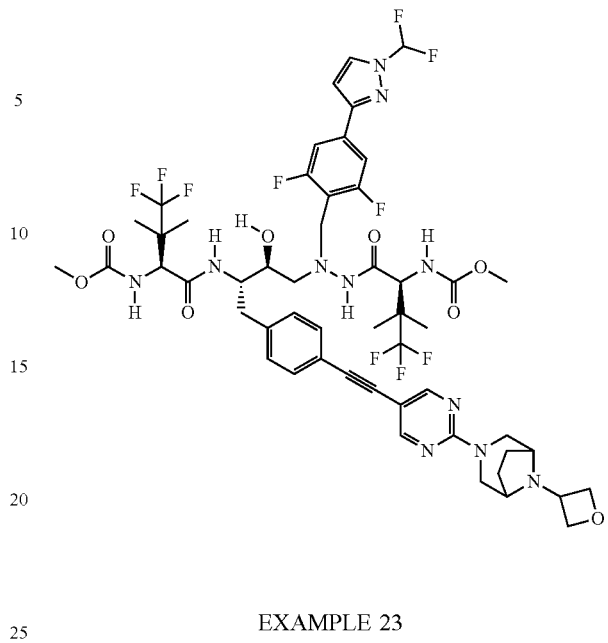

EXAMPLE 23

Methyl ((5S,8S,9S,14S)-11-(4-(1-(difluoromethyl)-1H-pyrazol-3-yl)-2,6-difluorobenzyl)-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (23)

Intermediates: I3, P4, and S7. MS (ESI) m/z 1102.5 [M+H]$^+$. $^1$H NMR (400 MHz, Methanol-d4) δ 8.53 (s, 2H), 8.20 (d, J=9.4 Hz, 1H), 8.11 (d, J=2.7 Hz, 1H), 7.53 (t, J=59.9, 59.4 Hz, 1H), 7.45 (d, J=8.2 Hz, 2H), 7.34 (d, J=8.0 Hz, 2H), 7.23 (d, J=8.2 Hz, 2H), 6.94 (d, J=2.8 Hz, 1H), 6.83 (d, J=9.9 Hz, 1H), 5.03-4.92 (m, 2H), 4.83-4.76 (m, 2H), 4.44 (d, J=10.0 Hz, 1H), 4.16-4.05 (m, 2H), 3.97 (d, J=13.2 Hz, 1H), 3.85-3.71 (m, 1H), 3.69 (s, 3H), 3.65 (s, 3H), 3.54-3.39 (m, 2H), 2.96-2.72 (m, 3H), 2.27-2.13 (m, 2H), 2.04-1.91 (m, 2H), 1.14 (s, 3H), 1.11 (s, 3H), 0.86 (s, 9H).

EXAMPLE 22

Methyl ((5S,8S,9S,14S)-5-(tert-butyl)-11-(2,6-difluoro-4-(1-methyl-1H-pyrazol-3-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate (22)

Intermediates 11, P41, and S3. MS (ESI) m/z 1011.29 [M+H]$^+$. $^1$H NMR (400 MHz, Methanol-d$_4$)) δ 8.30 (d, J=2.2 Hz, 1H), 7.70 (dd, J=8.8, 2.3 Hz, 1H), 7.61 (d, J=2.3 Hz, 1H), 7.33 (d, J=7.7 Hz, 5H), 7.23 (d, J=7.8 Hz, 2H), 6.86 (d, J=8.9 Hz, 1H), 6.65 (d, J=2.3 Hz, 1H), 4.96 (t, J=7.6 Hz, 2H), 4.82-4.77 (m, 2H), 4.35 (d, J=13.8 Hz, 2H), 4.13 (d, J=13.4 Hz, 4H), 3.93 (s, 6H), 3.67 (d, J=6.4 Hz, 8H), 3.38 (d, J=13.9 Hz, 2H), 3.00-2.77 (m, 5H), 2.31-2.20 (m, 2H), 2.14-2.04 (m, 2H), 0.87 (d, J=20.7 Hz, 21H).

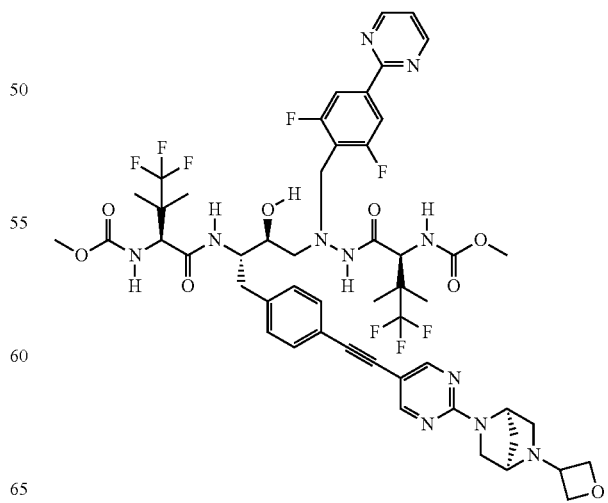

EXAMPLE 24

Methyl ((5S,8S,9S,14S)-11-(2,6-difluoro-4-(pyrimidin-2-yl)benzyl)-16,16,16-trifluoro-9-hydroxy-15,15-dimethyl-8-(4-((2-((1R,4R)-5-(oxetan-3-yl)-2,5-diazabicyclo[2.2.1]heptan-2-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (24)

Intermediates: I2, P16, and S29. MS (ESI) m/z 1104.3 [M+H]⁺. ¹H NMR (400 MHz, Methanol-d4) δ 8.87 (d, J=4.9 Hz, 2H), 8.52 (s, 2H), 8.19 (d, J=9.5 Hz, 1H), 7.98 (d, J=8.5 Hz, 2H), 7.41 (t, J=4.9 Hz, 1H), 7.35 (d, J=8.0 Hz, 2H), 7.24 (d, J=8.1 Hz, 2H), 7.12 (d, J=10.1 Hz, 1H), 6.82 (d, J=10.1 Hz, 1H), 5.18 (s, 1H), 4.99-4.90 (m, 2H), 4.64-4.55 (m, 1H), 4.44 (d, J=10.0 Hz, 1H), 4.30 (d, J=10.0 Hz, 1H), 4.24-4.10 (m, 2H), 3.98 (d, J=13.0 Hz, 1H), 3.90 (d, J=12.5 Hz, 1H), 3.85-3.72 (m, 3H), 3.69 (s, 3H), 3.67 (s, 3H), 2.96-2.74 (m, 4H), 2.33 (s, 2H), 1.15 (s, 6H), 1.11 (s, 3H), 1.02 (s, 3H).

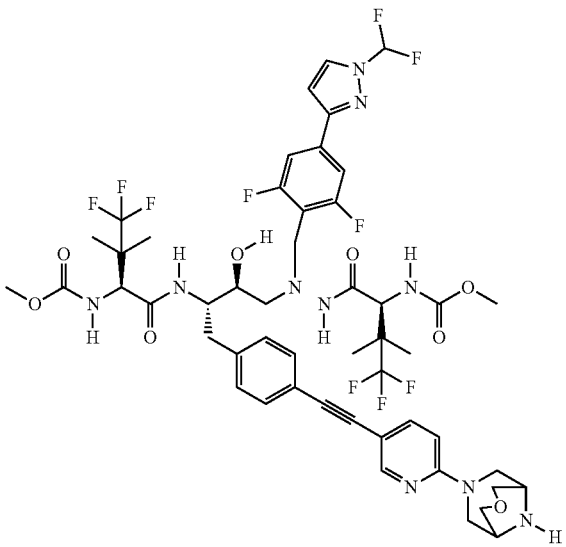

EXAMPLE 25

Methyl ((5S,8S,9S,14S)-11-(4-(1-(2,2-difluoroethyl)-1H-pyrazol-3-yl)-2,6-difluorobenzyl)-16,16,16-trifluoro-9-hydroxy-15,15-dimethyl-8-(4-((2-((1R,4R)-5-(oxetan-3-yl)-2,5-diazabicyclo[2.2.1]heptan-2-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (25)

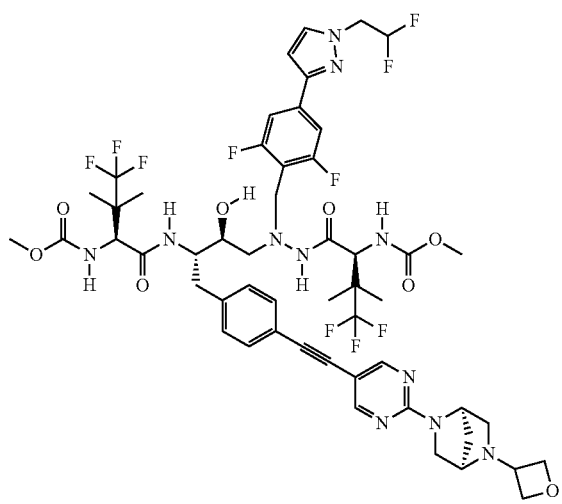 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1c(F)cc(-c2ccn(CC(F)F)n2)cc1F)NC(=O)[C@@H](NC(=O)OC)C(C)(C)C(F)(F)F)C(C)(C)C(F)(F)F]

Intermediates: I2, P10, and S29. MS (ESI) m/z 1156.4 [M+H]⁺. ¹H NMR (400 MHz, Methanol-d4) δ 8.52 (s, 2H), 8.18 (d, J=9.3 Hz, 1H), 7.37 (d, J=8.5 Hz, 2H), 7.34 (d, J=8.1 Hz, 1H), 7.23 (d, J=8.0 Hz, 2H), 7.14 (d, J=8.8 Hz, 1H), 6.81 (d, J=9.9 Hz, 1H), 6.74 (d, J=2.4 Hz, 1H), 6.22 (tt, J=55.5, 4.0 Hz, 1H), 5.18 (s, 1H), 5.01-4.90 (m, 2H), 4.72 (s, 1H), 4.60 (td, J=14.1, 3.7 Hz, 4H), 4.52 (s, 0H), 4.44 (d, J=9.9 Hz, 1H), 4.31 (d, J=10.0 Hz, 1H), 4.20-4.07 (m, 2H), 3.98-3.86 (m, 2H), 3.81 (d, J=12.8 Hz, 1H), 3.76-3.71 (m, 2H), 3.69 (s, 3H), 3.66 (s, 3H), 3.00-2.71 (m, 4H), 2.34 (s, 2H), 1.16 (s, 3H), 1.14 (s, 3H), 1.11 (s, 3H), 1.03 (s, 3H).

EXAMPLE 26

Methyl ((5S,8S,9S,14S)-8-(4-((6-(3-oxa-7,9-diazabicyclo[3.3.1]nonan-7-yl)pyridin-3-yl)ethynyl)benzyl)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (26)

Intermediates: I2, P4, and S28. MS (ESI) m/z 1115.4 [M+H]⁺. ¹H NMR (400 MHz, Methanol-d4) δ 8.17 (d, J=2.3 Hz, 1H), 8.07 (d, J=9.4 Hz, 1H), 8.01 (d, J=2.8 Hz, 1H), 7.56 (dd, J=8.8, 2.4 Hz, 1H), 7.44 (t, J=59.9 Hz, 1H), 7.36 (d, J=8.3 Hz, 2H), 7.23 (d, J=7.9 Hz, 2H), 7.12 (d, J=8.1 Hz, 2H), 6.84 (d, J=2.7 Hz, 1H), 6.78 (d, J=9.1 Hz, 1H), 6.69 (d, J=10.0 Hz, 1H), 4.70-4.61 (m, 2H), 4.34 (d, J=9.8 Hz, 1H), 4.21 (d, J=10.0 Hz, 1H), 4.08-4.00 (m, 4H), 3.94 (d, J=13.0 Hz, 2H), 3.85 (d, J=13.1 Hz, 1H), 3.64 (s, 1H), 3.60 (s, 3H), 3.58-3.54 (m, 4H), 3.42 (d, J=14.4 Hz, 3H), 2.85-2.62 (m, 4H), 1.07 (s, 3H), 1.05 (s, 3H), 1.02 (s, 3H), 0.94 (s, 3H).

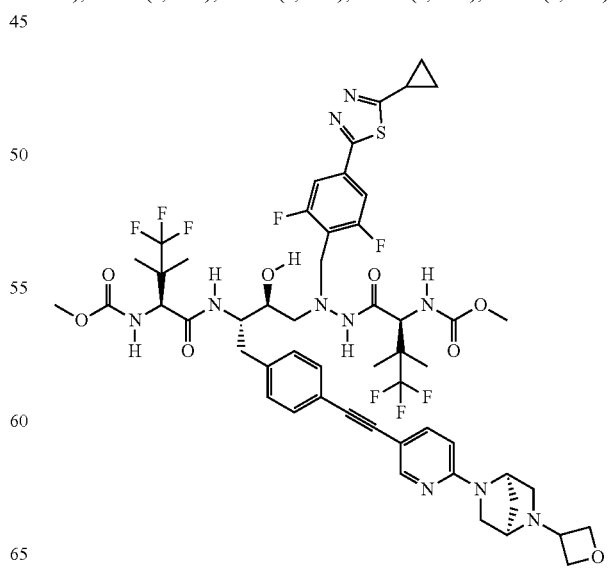

EXAMPLE 27

Methyl ((5S,8S,9S,14S)-11-(4-(5-cyclopropyl-1,3,4-thiadiazol-2-yl)-2,6-difluorobenzyl)-16,16,16-trifluoro-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (27)

Intermediates: I2, P3, and S6. MS (ESI) m/z 1149.3 [M+H]+. 1H NMR (400 MHz, Methanol-d4) δ 8.16 (d, J=2.2 Hz, 1H), 8.06 (d, J=9.4 Hz, 1H), 7.60 (dd, J=8.8, 2.3 Hz, 1H), 7.42 (d, J=7.5 Hz, 2H), 7.23 (d, J=7.9 Hz, 2H), 7.13 (d, J=8.1 Hz, 2H), 7.06 (d, J=10.1 Hz, 1H), 6.71 (d, J=10.0 Hz, 1H), 6.56 (d, J=8.8 Hz, 1H), 4.96 (s, 1H), 4.92-4.78 (m, 2H), 4.61 (s, 1H), 4.55-4.44 (m, 1H), 4.41 (s, 1H), 4.34 (d, J=9.8 Hz, 1H), 4.19 (d, J=10.0 Hz, 1H), 4.12-4.01 (m, 2H), 3.87 (d, J=13.1 Hz, 1H), 3.72-3.61 (m, 2H), 3.60 (s, 3H), 3.58 (s, 3H), 2.89-2.75 (m, 3H), 2.73-2.61 (m, 1H), 2.43 (ddd, J=13.1, 8.5, 4.9 Hz, 1H), 2.23 (s, 2H), 1.27-1.18 (m, 2H), 1.10-1.01 (m, 11H), 0.93 (s, 3H).

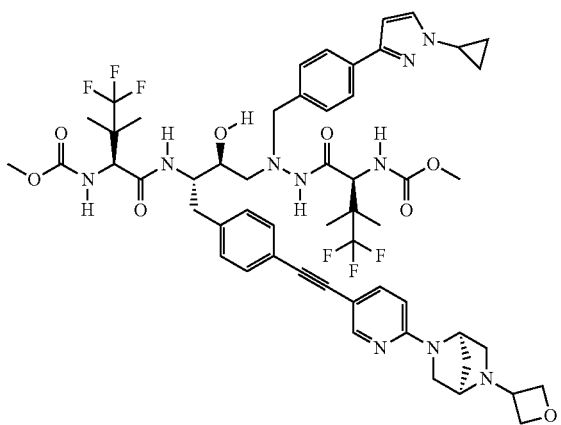 [SMILES: COC(=O)N[C@H](C(=O)N[C@@H](Cc1ccc(C#Cc2ccc(N3C[C@H]4C[C@@H]3CN4C3COC3)nc2)cc1)[C@@H](O)CN(Cc1ccc(C(=N)/C=C\NC2CC2)cc1)NC(=O)[C@@H](NC(=O)OC)C(C)(C)C(F)(F)F)C(C)(C)C(F)(F)F]

EXAMPLE 28

Methyl ((5S,8S,9S,14S)-11-(4-(1-cyclopropyl-1H-pyrazol-3-yl)benzyl)-16,16,16-trifluoro-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (28)

Intermediates: I2, P21, and S6. MS (ESI) m/z 1095.8 [M+H]+. 1H NMR (400 MHz, Methanol-d4) δ 8.16 (d, J=2.2 Hz, 1H), 8.02 (d, J=9.5 Hz, 1H), 7.62-7.57 (m, 3H), 7.56 (d, J=2.4 Hz, 1H), 7.31 (d, J=8.0 Hz, 2H), 7.23 (d, J=7.9 Hz, 2H), 7.12 (d, J=8.1 Hz, 2H), 7.04 (s, 1H), 6.67 (d, J=9.7 Hz, 1H), 6.56 (d, J=8.8 Hz, 1H), 6.47 (d, J=2.4 Hz, 1H), 4.96 (s, 1H), 4.89-4.83 (m, 1H), 4.84-4.78 (m, 1H), 4.65-4.54 (m, 1H), 4.54-4.44 (m, 2H), 4.41 (s, 1H), 4.30 (d, J=9.9 Hz, 1H), 4.16 (d, J=9.7 Hz, 1H), 4.12-4.00 (m, 1H), 3.88 (d, J=13.2 Hz, 1H), 3.78 (d, J=13.5 Hz, 1H), 3.73-3.60 (m, 2H), 3.60-3.53 (m, 4H), 3.51 (s, 3H), 2.87-2.76 (m, 2H), 2.76-2.59 (m, 2H), 2.23 (s, 2H), 1.07-0.94 (m, 10H), 0.92 (s, 3H), 0.72 (s, 3H).

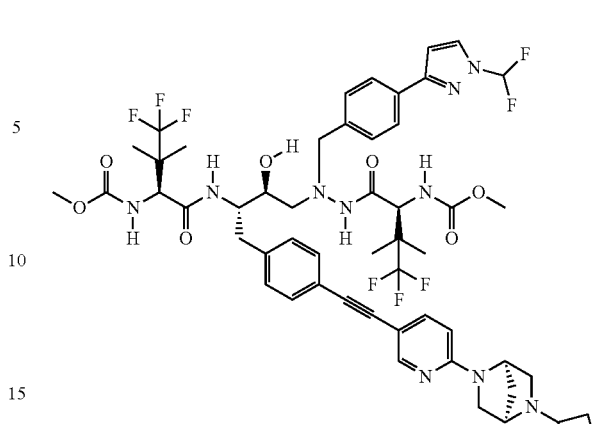

EXAMPLE 29

Methyl ((5S,8S,9S,14S)-11-(4-(1-(difluoromethyl)-1H-pyrazol-3-yl)benzyl)-16,16,16-trifluoro-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (29)

Intermediates: I2, P6, and S6. MS (ESI) m/z 1105.9 [M+H]+. 1H NMR (400 MHz, Methanol-d4) δ 8.25 (d, J=2.2 Hz, 1H), 8.11 (d, J=9.3 Hz, 1H), 8.05 (d, J=2.7 Hz, 1H), 7.78 (d, J=8.1 Hz, 2H), 7.69 (dd, J=8.8, 2.3 Hz, 1H), 7.49 (t, J=59.7 Hz, 1H), 7.45 (d, J=8.1 Hz, 2H), 7.32 (d, J=7.9 Hz, 2H), 7.22 (d, J=8.1 Hz, 2H), 7.12 (d, J=9.4 Hz, 1H), 6.86 (d, J=2.7 Hz, 1H), 6.77 (d, J=9.9 Hz, 1H), 6.66 (d, J=8.7 Hz, 1H), 5.05 (s, 1H), 4.95 (dd, J=8.4, 6.5 Hz, 1H), 4.93-4.87 (m, 1H), 4.70 (dd, J=8.5, 4.6 Hz, 1H), 4.66-4.53 (m, 2H), 4.50 (s, 1H), 4.40 (d, J=9.9 Hz, 1H), 4.24 (d, J=9.8 Hz, 1H), 4.21-4.12 (m, 1H), 4.01 (d, J=13.2 Hz, 1H), 3.88 (d, J=13.2 Hz, 1H), 3.82-3.69 (m, 2H), 3.68 (s, 3H), 3.59 (s, 3H), 2.96-2.66 (m, 4H), 2.33 (s, 2H), 1.12 (s, 3H), 1.10 (s, 3H), 1.02 (s, 3H), 0.83 (s, 3H).

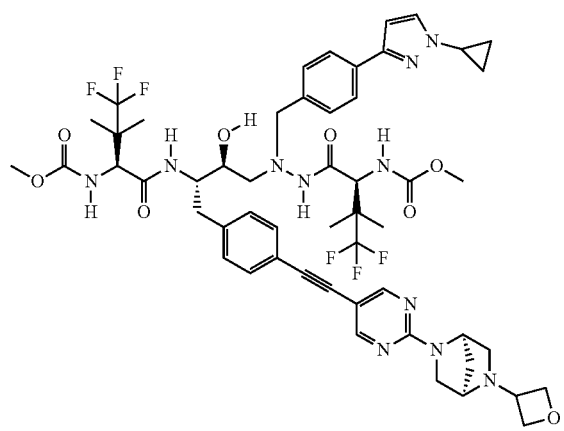 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1ccc(C(=N)/C=C\NC2CC2)cc1)NC(=O)[C@@H](NC(=O)OC)C(C)(C)C(F)(F)F)C(C)(C)C(F)(F)F]

EXAMPLE 30 methyl ((5S,8S,9S,14S)-11-(4-(1-cyclopropyl-1H-pyrazol-3-yl)benzyl)-16,16,16-trifluoro-9-hydroxy-15,15-dimethyl-8-(4-((2-((1R,4R)-5-(oxetan-3-yl)-2,5-diazabicyclo[2.2.1]heptan-2-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (30)

Intermediates: I2, P21, and S29. MS (ESI) m/z 1096.7 [M+H]+. 1H NMR (400 MHz, Methanol-d4) δ 8.51 (s, 2H), 8.10 (d, J=9.0 Hz, 1H), 7.68 (d, J=8.0 Hz, 2H), 7.65 (d, J=2.4 Hz, 1H), 7.40 (d, J=7.9 Hz, 2H), 7.34 (d, J=7.8 Hz, 2H), 7.22 (d, J=7.9 Hz, 2H), 6.76 (d, J=10.1 Hz, 1H), 6.56 (d, J=2.4 Hz, 1H), 5.18 (s, 1H), 4.93 (dt, J=20.6, 7.3 Hz, 1H), 4.72 (s, 1H), 4.65-4.55 (m, 1H), 4.51 (s, 0H), 4.40 (d, J=7.8 Hz, 1H), 4.25 (d, J=7.8 Hz, 1H), 4.15 (s, 1H), 4.02-3.78 (m, 3H), 3.67 (s, 3H), 3.66 (d, J=3.8 Hz, 1H), 3.59 (s, 3H), 2.94-2.67 (m, 4H), 2.41-2.30 (m, 2H), 2.05-1.99 (m, 1H), 1.93 (s, 1H), 1.15-1.04 (m, 10H), 1.01 (s, 3H), 0.81 (s, 3H).

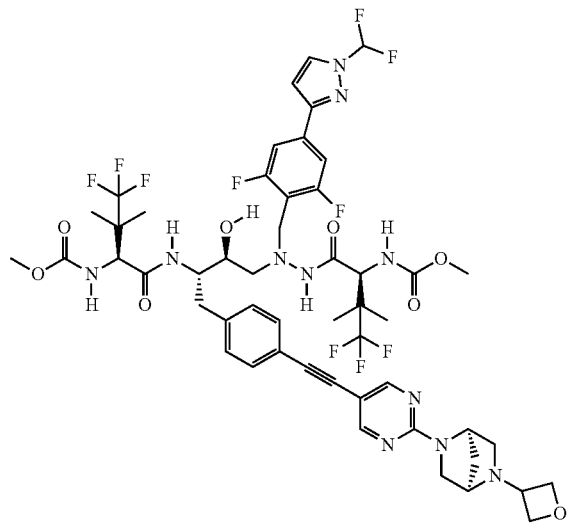

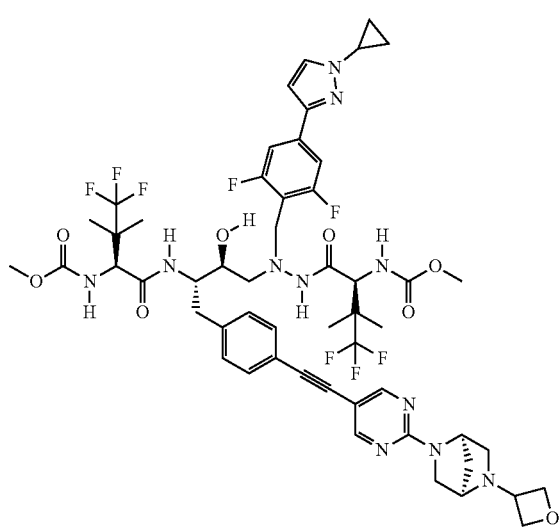 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 31

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((2-((1R,4R)-5-(oxetan-3-yl)-2,5-diazabicyclo[2.2.1]heptan-2-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (31)

Intermediates: I2, P13, and S29. MS (ESI) m/z 1132.3 [M+H]+. 1H NMR (400 MHz, Methanol-d4) δ 8.51 (s, 2H), 8.15 (d, J=9.4 Hz, 1H), 7.69 (d, J=2.4 Hz, 1H), 7.38-7.27 (m, 4H), 7.23 (d, J=8.0 Hz, 2H), 7.10 (d, J=10.0 Hz, 1H), 6.77 (d, J=9.8 Hz, 1H), 6.63 (d, J=2.4 Hz, 1H), 5.18 (s, 1H), 4.93 (dt, J=20.5, 7.3 Hz, 2H), 4.72 (s, 1H), 4.60 (td, J=12.1, 11.2, 5.5 Hz, 1H), 4.51 (s, 1H), 4.46-4.39 (m, 1H), 4.36-4.24 (m, 1H), 4.18-4.07 (m, 2H), 3.93 (d, J=11.4 Hz, 1H), 3.89 (s, 1H), 3.80 (d, J=12.7 Hz, 1H), 3.76-3.67 (m, 5H), 3.66 (s, 2H), 2.96-2.70 (m, 4H), 2.33 (s, 2H), 1.22-1.04 (m, 12H), 1.02 (s, 3H).

EXAMPLE 32

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-((1R,4R)-5-(oxetan-3-yl)-2,5-diazabicyclo[2.2.1]heptan-2-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (32)

Intermediates: I2, P4, and S29. MS (ESI) m/z 1142.4 [M+H]+. 1H NMR (400 MHz, Methanol-d4) δ 8.51 (s, 2H), 8.14 (d, J=9.3 Hz, 1H), 8.10 (d, J=2.7 Hz, 1H), 7.52 (t, J=59.9 Hz, 1H), 7.44 (d, J=8.2 Hz, 2H), 7.34 (d, J=7.9 Hz, 2H), 7.23 (d, J=8.0 Hz, 2H), 7.09 (d, J=9.6 Hz, 1H), 6.93 (d, J=2.7 Hz, 1H), 6.78 (d, J=9.9 Hz, 1H), 5.18 (s, 1H), 4.93 (dt, J=20.5, 7.3 Hz, 2H), 4.71 (s, 1H), 4.60 (dq, J=11.6, 6.2, 5.6 Hz, 2H), 4.51 (s, 1H), 4.44 (d, J=9.8 Hz, 1H), 4.30 (d, J=9.9 Hz, 1H), 4.21-4.05 (m, 2H), 3.94 (d, J=13.5 Hz, 1H), 3.90 (d, J=12.9 Hz, 1H), 3.80 (d, J=12.6 Hz, 1H), 3.77-3.70 (m, 2H), 3.68 (s, 3H), 3.66 (s, 3H), 2.96-2.72 (m, 4H), 2.44-2.24 (m, 2H), 1.16 (s, 3H), 1.14 (s, 3H), 1.11 (s, 3H), 1.02 (s, 3H).

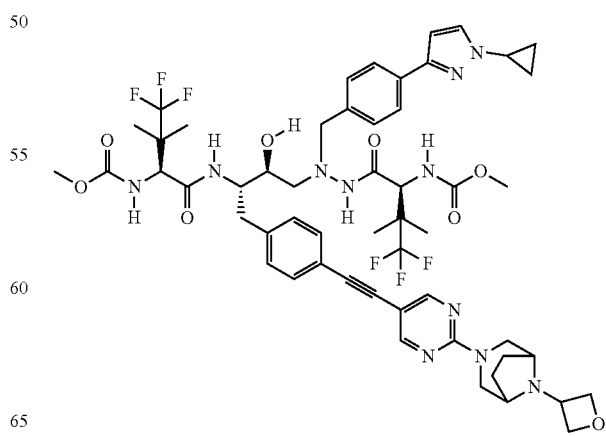

EXAMPLE 33

Methyl ((5S,8S,9S,14S)-11-(4-(1-cyclopropyl-1H-pyrazol-3-yl)benzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (33)

Intermediates: I2, P21, and S7. MS (ESI) m/z 1142.4 [M+H]⁺. 1H NMR (400 MHz, Methanol-d4) δ 8.52 (s, 2H), 8.10 (d, J=9.5 Hz, 1H), 7.68 (d, J=8.1 Hz, 2H), 7.64 (d, J=2.3 Hz, 1H), 7.40 (d, J=8.0 Hz, 2H), 7.34 (d, J=7.9 Hz, 2H), 7.22 (d, J=8.0 Hz, 2H), 7.11 (d, J=9.5 Hz, 1H), 6.75 (d, J=9.7 Hz, 1H), 6.56 (d, J=2.4 Hz, 1H), 4.96 (t, J=7.6 Hz, 2H), 4.82-4.71 (m, 3H), 4.39 (d, J=9.9 Hz, 1H), 4.24 (d, J=9.7 Hz, 1H), 4.20-4.06 (m, 2H), 3.97 (d, J=13.2 Hz, 1H), 3.87 (d, J=13.4 Hz, 1H), 3.77-3.71 (m, 1H), 3.67 (s, 4H), 3.59 (s, 3H), 3.45 (d, J=14.6 Hz, 2H), 2.93-2.86 (m, 2H), 2.85-2.67 (m, 1H), 2.31-2.15 (m, 2H), 2.06-1.93 (m, 2H), 1.15-1.03 (m, 10H), 1.01 (s, 3H), 0.82 (s, 3H).

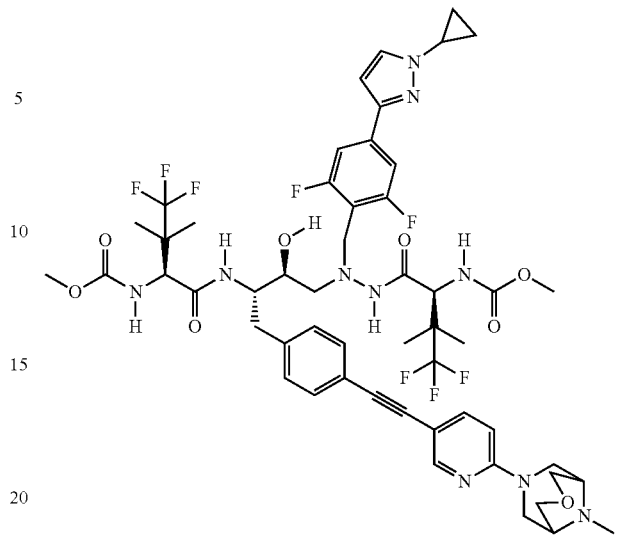

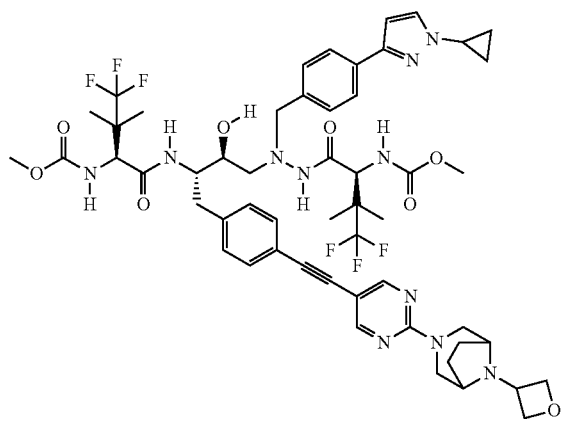 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1ccc(C(=N)/C=C\NC2CC2)cc1)NC(=O)[C@@H](NC(=O)OC)C(C)(C)C(F)(F)F)C(C)(C)C(F)(F)F]

EXAMPLE 34

Methyl ((5S,8S,9S,14S)-11-(4-(1-cyclopropyl-1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (34)

Intermediates: I2, P21, and S3. MS (ESI) m/z 1109.5 [M+H]⁺. ¹H NMR (400 MHz, Methanol-d4) δ 8.20 (d, J=2.3 Hz, 1H), 8.03 (d, J=9.5 Hz, 1H), 7.66-7.58 (m, 3H), 7.56 (d, J=2.4 Hz, 1H), 7.31 (d, J=8.0 Hz, 2H), 7.23 (d, J=7.9 Hz, 2H), 7.12 (d, J=8.1 Hz, 2H), 7.07 (d, J=9.5 Hz, 1H), 6.76 (d, J=8.9 Hz, 1H), 6.68 (d, J=10.0 Hz, 1H), 6.47 (d, J=2.4 Hz, 1H), 4.92-4.82 (m, 2H), 4.74-4.66 (m, 2H), 4.34-4.21 (m, 3H), 4.18-4.12 (m, 1H), 4.11-3.99 (m, 3H), 3.88 (d, J=13.1 Hz, 1H), 3.78 (d, J=13.3 Hz, 1H), 3.65 (d, J=9.0 Hz, 1H), 3.60-3.53 (m, 4H), 3.51 (s, 3H), 3.28 (d, J=13.8 Hz, 2H), 2.86-2.76 (m, 2H), 2.76-2.56 (m, 2H), 2.17-2.08 (m, 2H), 2.03-1.92 (m, 2H), 1.07-0.89 (m, 13H), 0.72 (s, 3H).

EXAMPLE 35

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((6-(9-methyl-3-oxa-7,9-diazabicyclo[3.3.1]nonan-7-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (35)

Intermediates: I2, P13, and S2. MS (ESI) m/z 1119.5 [M+H]⁺. 1H NMR (400 MHz, Methanol-d4) δ 8.27 (dd, J=2.3, 0.7 Hz, 1H), 8.16 (d, J=9.4 Hz, 1H), 7.73 (dd, J=9.0, 2.3 Hz, 1H), 7.69 (d, J=2.4 Hz, 1H), 7.41-7.26 (m, 4H), 7.21 (d, J=8.2 Hz, 2H), 7.13 (d, J=9.8 Hz, 1H), 6.96 (d, J=9.0 Hz, 1H), 6.79 (d, J=9.9 Hz, 1H), 6.63 (d, J=2.4 Hz, 1H), 4.64 (d, J=14.7 Hz, 2H), 4.53-4.41 (m, 1H), 4.35-4.25 (m, 1H), 4.22-4.06 (m, 7H), 3.93 (d, J=13.2 Hz, 1H), 3.78 (dt, J=14.9, 3.0 Hz, 2H), 3.73-3.67 (m, 4H), 3.66 (s, 3H), 3.63 (s, 2H), 3.19 (s, 3H), 2.94-2.72 (m, 4H), 1.21-0.99 (m, 16H).

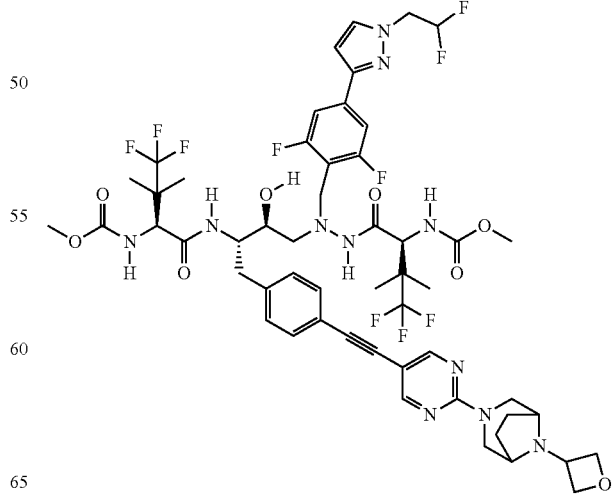

EXAMPLE 36

Methyl ((5S,8S,9S,14S)-11-(4-(1-(2,2-difluoro-ethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (36)

Intermediates: I2, P10, and S7. MS (ESI) m/z 1170.9 [M+H]+. $^1$H NMR (400 MHz, Methanol-d4) δ 8.53 (s, 2H), 8.19 (d, J=9.3 Hz, 1H), 7.74 (d, J=2.4 Hz, 1H), 7.37 (d, J=8.5 Hz, 2H), 7.34 (d, J=8.1 Hz, 2H), 7.23 (d, J=8.1 Hz, 2H), 7.15 (d, J=10.0 Hz, 1H), 6.81 (d, J=9.9 Hz, 1H), 6.74 (d, J=2.4 Hz, 1H), 6.22 (tt, J=55.3, 4.0 Hz, 1H), 5.02-4.93 (m, 2H), 4.83-4.78 (m, 2H), 4.77 (s, 1H), 4.60 (td, J=14.3, 3.9 Hz, 2H), 4.44 (d, J=10.0 Hz, 1H), 4.31 (d, J=10.0 Hz, 1H), 4.22-4.03 (m, 4H), 3.93 (d, J=13.2 Hz, 1H), 3.72 (s, 2H), 3.69 (s, 3H), 3.66 (s, 3H), 3.51-3.40 (m, 2H), 2.96-2.81 (m, 3H), 2.81-2.72 (m, 1H), 2.27-2.12 (m, 2H), 2.04-1.94 (m, 2H), 1.16 (s, 3H), 1.14 (s, 3H), 1.11 (s, 3H), 1.03 (s, 3H).

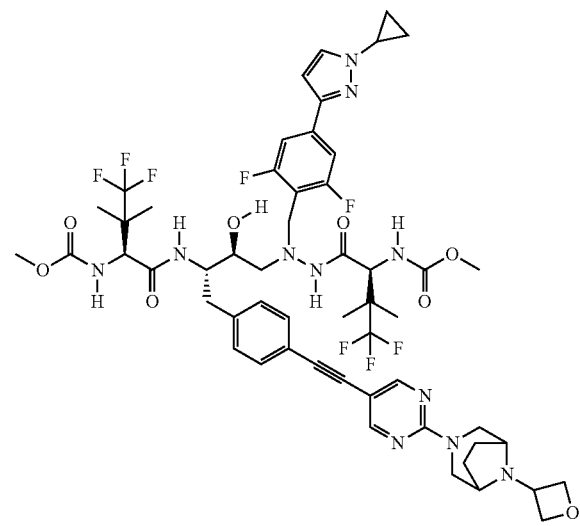 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 37

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (37)

Intermediates: I2, P13, and S7. MS (ESI) m/z 1146.9 [M+H]+. $^1$H NMR (400 MHz, Methanol-d4) δ 8.43 (s, 2H), 8.10 (d, J=9.3 Hz, 1H), 7.60 (d, J=2.4 Hz, 1H), 7.25 (d, J=8.0 Hz, 4H), 7.14 (d, J=8.1 Hz, 2H), 7.07 (d, J=10.1 Hz, 1H), 6.72 (d, J=10.0 Hz, 1H), 6.55 (d, J=2.4 Hz, 1H), 4.93-4.82 (m, 2H), 4.75-4.57 (m, 4H), 4.45-4.28 (m, 1H), 4.22 (d, J=10.0 Hz, 1H), 4.14-3.97 (m, 4H), 3.83 (d, J=13.2 Hz, 1H), 3.71-3.61 (m, 1H), 3.59 (s, 3H), 3.57 (s, 3H), 3.42-3.32 (m, 2H), 2.86-2.63 (m, 4H), 2.17-2.05 (m, 2H), 1.94-1.82 (m, 2H), 1.12-1.06 (m, 3H), 1.06-0.95 (m, 10H), 0.93 (s, 3H).

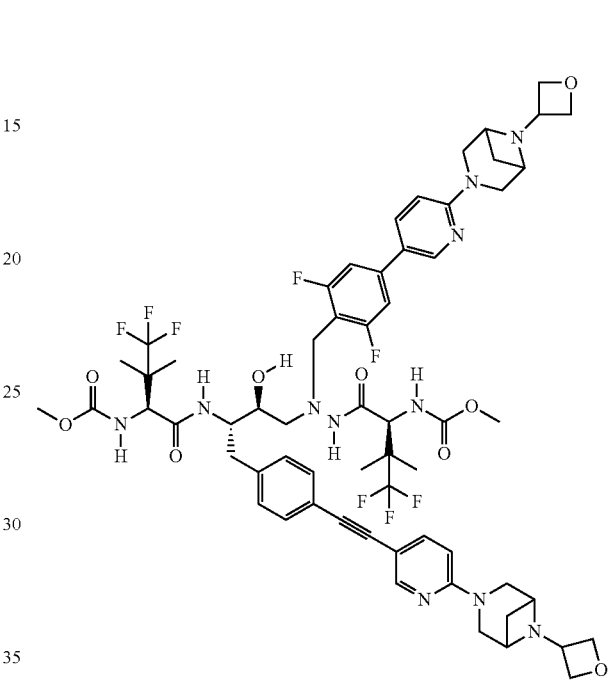

EXAMPLE 38

Methyl ((5S,8S,9S,14S)-11-(2,6-difluoro-4-(6-(6-(oxetan-3-yl)-3,6-diazabicyclo[3.1.1]heptan-3-yl)pyridin-3-yl)benzyl)-16,16,16-trifluoro-9-hydroxy-15,15-dimethyl-8-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (38)

Intermediates: I2, P22, and S4. MS (ESI) m/z 1254.4 [M+H]+. $^1$H NMR (400 MHz, Methanol-d4) δ 8.31 (d, J=2.4 Hz, 1H), 8.15 (d, J=2.1 Hz, 1H), 7.80 (d, J=9.0 Hz, 1H), 7.62-7.51 (m, 1H), 7.23 (d, J=7.8 Hz, 2H), 7.12 (d, J=8.0 Hz, 2H), 7.08 (d, J=8.7 Hz, 2H), 6.69 (d, J=9.0 Hz, 1H), 6.60 (d, J=8.9 Hz, 1H), 4.66 (t, J=6.5 Hz, 4H), 4.40-4.31 (m, 6H), 4.04 (d, J=12.6 Hz, 2H), 3.89-3.80 (m, 3H), 3.77 (t, J=6.3 Hz, 4H), 3.61 (d, J=1.2 Hz, 3H), 3.57 (s, 3H), 3.48 (d, J=13.4 Hz, 8H), 2.89-2.55 (m, 6H), 1.57 (t, J=8.8 Hz, 2H), 1.24-1.13 (m, 3H), 1.08 (s, 3H), 1.06 (s, 3H), 1.03 (s, 3H), 0.95 (s, 3H).

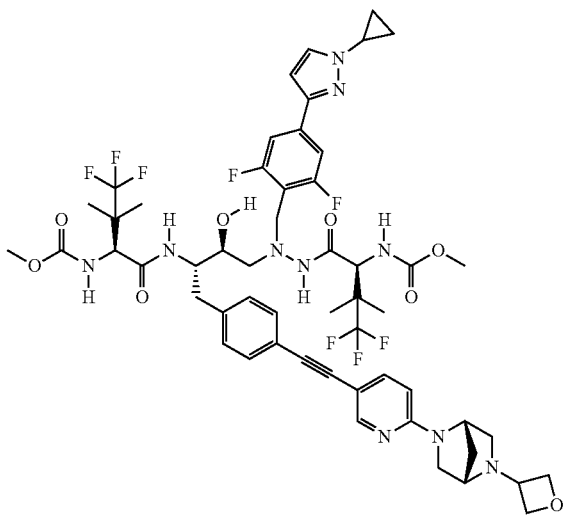 [SMILES: COC(=O)N[C@H](C(=O)N[C@@H](Cc1ccc(C#Cc2ccc(N3C[C@@H]4C[C@H]3CN4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 39

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((6-((1S,4S)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (39)

Intermediates: I2, P13, and S30. MS (ESI) m/z 1131.5 [M+H]+. ¹H NMR (400 MHz, Methanol-d4) δ 8.16 (d, J=2.2 Hz, 1H), 8.10 (d, J=9.2 Hz, 1H), 7.61 (d, J=2.4 Hz, 2H), 7.59 (d, J=2.2 Hz, 1H), 7.29-7.19 (m, 5H), 7.12 (d, J=8.0 Hz, 2H), 6.73 (d, J=10.0 Hz, 1H), 6.63-6.52 (m, 2H), 4.95 (s, 1H), 4.89-4.83 (m, 1H), 4.65-4.56 (m, 1H), 4.54-4.43 (m, 2H), 4.41 (s, 1H), 4.35 (d, J=9.9 Hz, 1H), 4.22 (d, J=9.9 Hz, 1H), 4.12-3.97 (m, 2H), 3.83 (d, J=13.2 Hz, 1H), 3.70 (d, J=11.8 Hz, 1H), 3.65-3.61 (m, 1H), 3.59 (s, 3H), 3.57 (s, 3H), 2.86-2.60 (m, 4H), 2.23 (s, 2H), 1.10-0.95 (m, 13H), 0.93 (s, 3H).

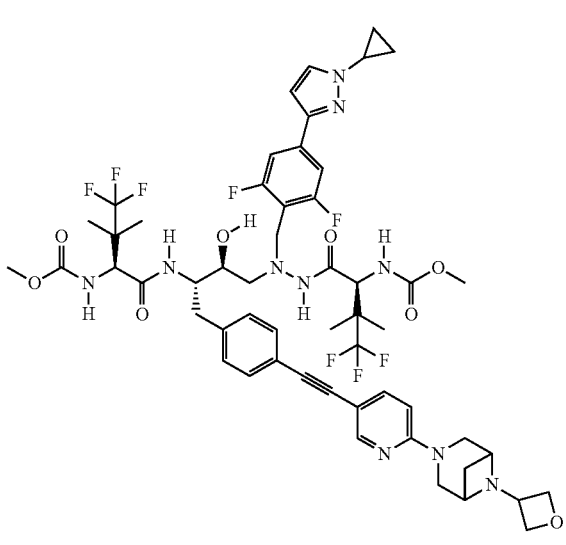 [SMILES: COC(=O)N[C@H](C(=O)N[C@@H](Cc1ccc(C#Cc2ccc(N3CC4CC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 40

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (40)

Intermediates: I2, P13, and S4. MS (ESI) m/z 1131.9 [M+H]+. ¹H NMR (400 MHz, Methanol-d4) δ 8.23 (d, J=2.3 Hz, 1H), 8.09 (d, J=9.5 Hz, 1H), 7.64 (dd, J=8.8, 2.3 Hz, 1H), 7.60 (d, J=2.4 Hz, 1H), 7.23 (dd, J=8.4, 3.3 Hz, 4H), 7.12 (d, J=8.1 Hz, 2H), 6.68 (d, J=8.9 Hz, 1H), 6.54 (d, J=2.4 Hz, 1H), 4.93-4.83 (m, 2H), 4.51 (dd, J=8.2, 4.0 Hz, 2H), 4.34 (s, 1H), 4.27-4.18 (m, 1H), 4.12-3.94 (m, 4H), 3.83 (d, J=13.2 Hz, 1H), 3.65-3.60 (m, 1H), 3.59 (s, 3H), 3.56 (s, 3H), 2.85-2.62 (m, 4H), 2.01 (d, J=11.0 Hz, 1H), 1.18 (d, J=13.9 Hz, 1H), 1.10-0.94 (m, 13H), 0.92 (s, 3H).

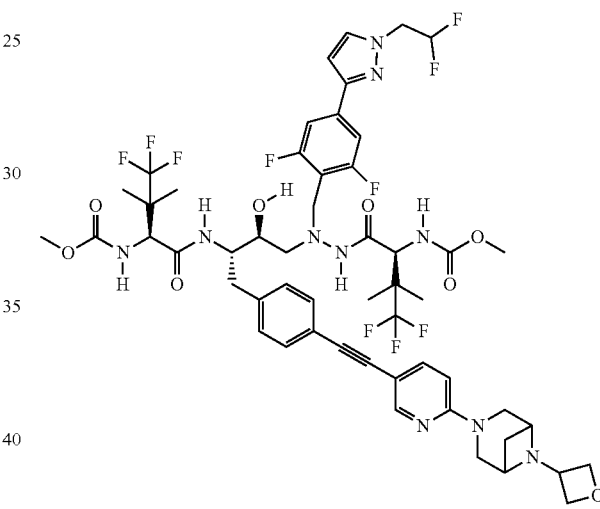

EXAMPLE 41

Methyl ((5S,8S,9S,14S)-11-(4-(1-(2,2-difluoroethyl)-1H-pyrazol-3-yl)-2,6-difluorobenzyl)-16,16,16-trifluoro-9-hydroxy-15,15-dimethyl-8-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (41)

Intermediates: I2, P10, and S4. MS (ESI) m/z 1155.6 [M+H]+. ¹H NMR (400 MHz, Methanol-d4) δ 8.24 (d, J=2.2 Hz, 1H), 8.10 (d, J=9.3 Hz, 1H), 7.69-7.60 (m, 2H), 7.28 (d, J=8.4 Hz, 2H), 7.24 (d, J=7.9 Hz, 2H), 7.13 (d, J=8.1 Hz, 2H), 6.69 (d, J=9.0 Hz, 1H), 6.65 (d, J=2.5 Hz, 1H), 6.13 (tt, J=55.3, 3.9 Hz, 1H), 4.58-4.42 (m, 4H), 4.35 (s, 1H), 4.27-4.18 (m, 1H), 4.16-3.95 (m, 4H), 3.84 (d, J=13.3 Hz, 1H), 3.63 (s, 2H), 3.60 (s, 3H), 3.57 (s, 3H), 2.86-2.72 (m, 3H), 2.72-2.58 (m, 1H), 2.02 (d, J=11.0 Hz, 1H), 1.19 (d, J=13.9 Hz, 1H), 1.07 (s, 3H), 1.05 (s, 3H), 1.02 (s, 3H), 0.93 (s, 3H).

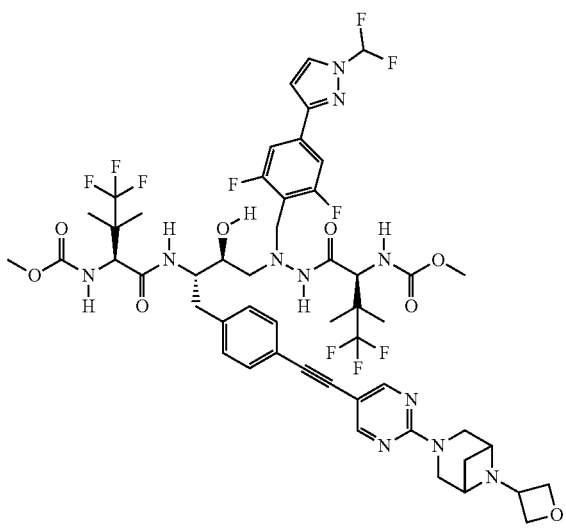 [SMILES: COC(=O)N[C@H](C(=O)N[C@@H](Cc1ccc(C#Cc2cnc(N3CC4CC(C3)N4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 42

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(6-(oxetan-3-yl)-3,6-diazabicyclo[3.1.1]heptan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (42)

Intermediates: I2, P4, and S52. MS (ESI) m/z 1143.8 [M+H]$^+$. $^1$H NMR (400 MHz, Methanol-d4) δ 8.57 (s, 2H), 8.19 (d, J=9.4 Hz, 0H), 8.11 (d, J=2.8 Hz, 1H), 7.70-7.51 (m, 4H), 7.44 (d, J=8.2 Hz, 2H), 7.36 (d, J=7.9 Hz, 2H), 7.28-7.20 (m, 2H), 6.93 (d, J=2.8 Hz, 1H), 4.65 (d, J=7.4 Hz, 2H), 4.49-4.41 (m, 2H), 4.37-4.28 (m, 2H), 4.27-4.11 (m, 4H), 3.91 (dd, J=25.4, 13.9 Hz, 2H), 3.73 (s, 2H), 3.70 (s, 3H), 3.67 (s, 3H), 2.94-2.83 (m, 3H), 2.83-2.70 (m, 1H), 2.09 (t, J=11.9 Hz, 1H), 1.18-1.13 (m, 6H), 1.12 (s, 3H), 1.02 (s, 3H).

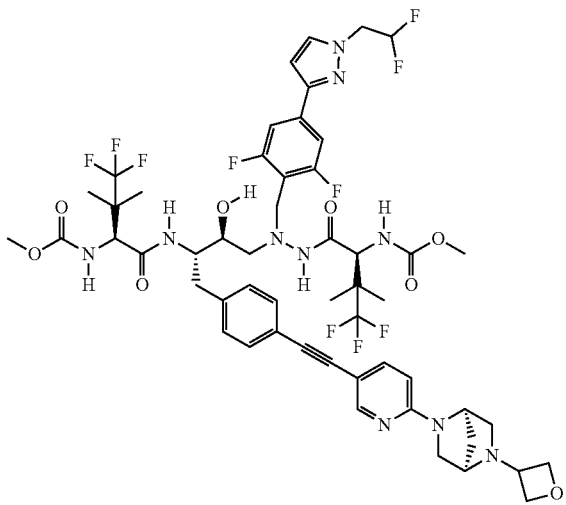 [SMILES: COC(=O)N[C@H](C(=O)N[C@@H](Cc1ccc(C#Cc2ccc(N3C[C@H]4C[C@@H]3CN4C3COC3)nc2)cc1)[C@@H](O)CN(Cc1c(F)cc(-c2ccn(CC(F)F)n2)cc1F)NC(=O)[C@@H](NC(=O)OC)C(C)(C)C(F)(F)F)C(C)(C)C(F)(F)F]

EXAMPLE 43

Methyl ((5S,8S,9S,14S)-11-(4-(1-(2,2-difluoroethyl)-1H-pyrazol-3-yl)-2,6-difluorobenzyl)-16,16,16-trifluoro-9-hydroxy-15,15-dimethyl-8-(4-(((6-(((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (43)

Intermediates: I2, P10, and S6. MS (ESI) m/z 1155.5 [M+H]$^+$. $^1$H NMR (400 MHz, Methanol-d4) δ 8.25 (d, J=1.9 Hz, 1H), 8.19 (d, J=9.4 Hz, 1H), 7.74 (d, J=2.5 Hz, 1H), 7.69 (dd, J=8.6, 2.3 Hz, 1H), 7.38 (d, J=8.4 Hz, 2H), 7.32 (d, J=7.8 Hz, 2H), 7.22 (d, J=8.0 Hz, 2H), 6.82 (d, J=9.9 Hz, 1H), 6.75 (d, J=2.4 Hz, 1H), 6.66 (d, J=8.8 Hz, 1H), 6.39-6.05 (m, 1H), 5.06-5.02 (m, 1H), 4.74-4.67 (m, 1H), 4.65-4.53 (m, 2H), 4.50 (s, 1H), 4.44 (d, J=9.9 Hz, 1H), 4.31 (d, J=10.0 Hz, 1H), 4.13 (d, J=13.4 Hz, 2H), 3.93 (d, J=13.3 Hz, 1H), 3.83-3.72 (m, 2H), 3.69 (s, 3H), 3.66 (s, 3H), 2.94-2.72 (m, 2H), 2.33 (s, 2H), 1.16 (s, 3H), 1.14 (s, 3H), 1.11 (s, 3H), 1.02 (s, 3H).

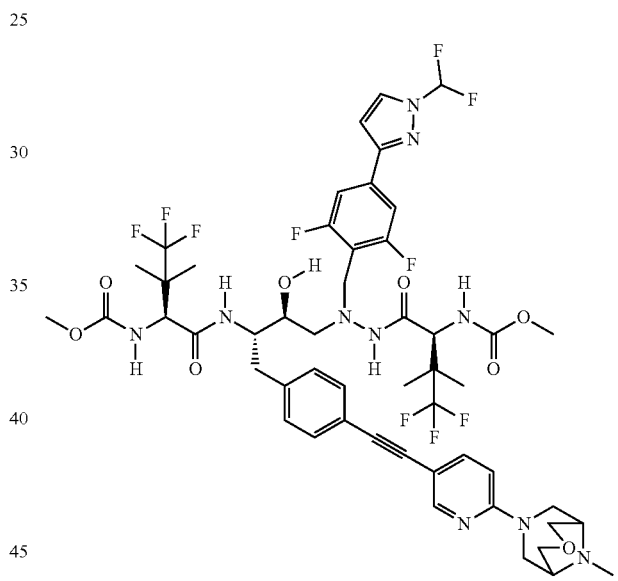

EXAMPLE 44

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(9-methyl-3-oxa-7,9-diazabicyclo[3.3.1]nonan-7-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (44)

Intermediates: I2, P4, and S2. MS (ESI) m/z 1130.0 [M+H]$^+$. $^1$H NMR (400 MHz, Methanol-d4) δ 8.18 (d, J=2.3 Hz, 1H), 8.10 (d, J=9.3 Hz, 1H), 8.01 (d, J=2.7 Hz, 1H), 7.58 (dd, J=9.2, 2.6 Hz, 1H), 7.44 (t, J=59.7 Hz, 1H), 7.36 (d, J=8.2 Hz, 2H), 7.23 (d, J=7.8 Hz, 2H), 7.12 (d, J=8.0 Hz, 2H), 7.09-7.00 (m, 1H), 6.85 (d, J=2.8 Hz, 1H), 6.78 (d, J=8.9 Hz, 1H), 6.72 (d, J=10.0 Hz, 1H), 4.35 (d, J=9.9 Hz, 1H), 4.21 (d, J=9.9 Hz, 1H), 4.13-3.94 (m, 5H), 3.85 (d, J=13.2 Hz, 1H), 3.71-3.63 (m, 3H), 3.60 (s, 3H), 3.57 (s, 3H), 3.51 (s, 2H), 3.10 (s, 3H), 2.88-2.73 (m, 3H), 2.73-2.64 (m, 1H), 1.07 (s, 3H), 1.05 (s, 3H), 1.02 (s, 3H), 0.93 (s, 3H).

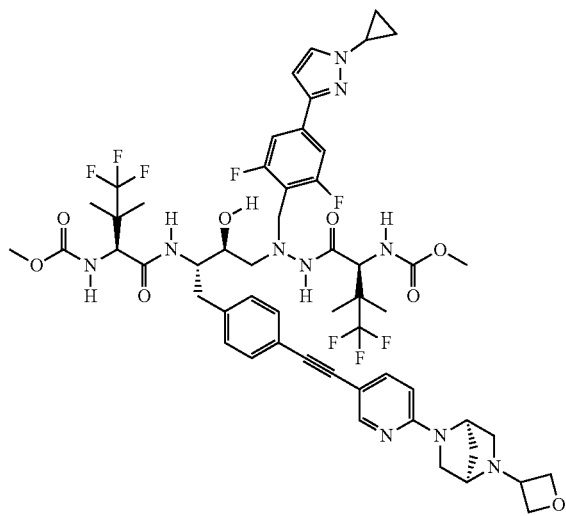 [SMILES: COC(=O)N[C@H](C(=O)N[C@@H](Cc1ccc(C#Cc2ccc(N3C[C@H]4C[C@@H]3CN4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 45

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (45)

Intermediates: I2, P13, and S6. MS (ESI) m/z 1130.0 [M+H]$^+$. $^1$H NMR (400 MHz, Methanol-d4) δ 8.16 (d, J=2.2 Hz, 1H), 8.10 (d, J=9.3 Hz, 1H), 7.65-7.55 (m, 2H), 7.30-7.19 (m, 4H), 7.12 (d, J=8.0 Hz, 2H), 7.08 (d, J=10.0 Hz, 1H), 6.72 (d, J=9.9 Hz, 1H), 6.58 (d, J=8.8 Hz, 1H), 6.55 (d, J=2.4 Hz, 1H), 4.96 (s, 1H), 4.86 (dd, J=8.3, 6.4 Hz, 1H), 4.61 (dd, J=8.5, 4.6 Hz, 1H), 4.56-4.44 (m, 2H), 4.42 (s, 1H), 4.35 (d, J=9.8 Hz, 1H), 4.22 (d, J=10.0 Hz, 1H), 4.08-3.98 (m, 2H), 3.83 (d, J=13.2 Hz, 1H), 3.73-3.61 (m, 4H), 3.59 (s, 3H), 3.57 (s, 3H), 2.85-2.72 (m, 2H), 2.72-2.62 (m, 1H), 2.24 (s, 2H), 1.07 (s, 3H), 1.06-0.94 (m, 10H), 0.93 (s, 3H).

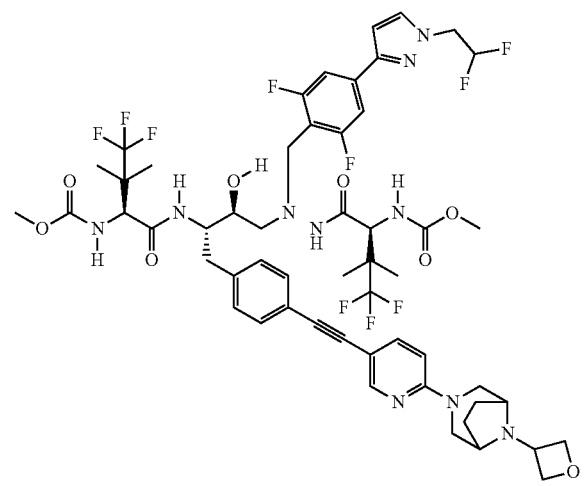

EXAMPLE 46

Methyl ((5S,10S,11S,14S)-8-(4-(1-(2,2-difluoroethyl)-1H-pyrazol-3-yl)-2,6-difluorobenzyl)-16,16,16-trifluoro-10-hydroxy-15,15-dimethyl-11-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (46)

Intermediates: I2, P10, and S3. MS (ESI) m/z 1169.4 [M+H]$^+$. $^1$H NMR (400 MHz, Methanol-d4) δ 8.30 (d, J=2.3 Hz, 1H), 8.19 (d, J=9.3 Hz, 1H), 7.74 (d, J=2.4 Hz, 1H), 7.70 (dd, J=8.9, 2.3 Hz, 1H), 7.38 (d, J=8.4 Hz, 2H), 7.33 (d, J=7.9 Hz, 2H), 7.22 (d, J=8.0 Hz, 2H), 7.19-7.12 (m, 1H), 6.86 (d, J=8.9 Hz, 1H), 6.81 (d, J=9.9 Hz, 1H), 6.74 (d, J=2.5 Hz, 1H), 6.22 (tt, J=55.5, 4.2 Hz, 1H), 4.97 (t, J=7.6 Hz, 3H), 4.80 (dd, J=8.2, 5.0 Hz, 2H), 4.60 (td, J=14.2, 3.9 Hz, 2H), 4.44 (d, J=9.9 Hz, 1H), 4.36 (d, J=13.6 Hz, 2H), 4.31 (d, J=10.0 Hz, 1H), 4.19-4.10 (m, 4H), 3.93 (d, J=13.2 Hz, 1H), 3.77-3.71 (m, 2H), 3.69 (s, 3H), 3.66 (s, 3H), 3.37 (d, J=13.8 Hz, 2H), 2.96-2.69 (m, 4H), 2.29-2.16 (m, 2H), 2.16-2.03 (m, 2H), 1.17 (s, 3H), 1.14 (s, 3H), 1.11 (s, 3H), 1.03 (s, 3H).

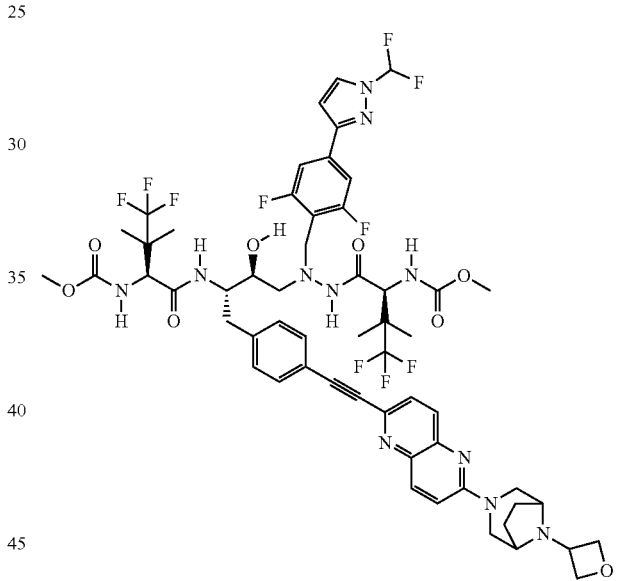

EXAMPLE 47

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)-1,5-naphthyridin-2-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (47)

Intermediates: I2, P4, and S31. MS (ESI) m/z 1206.3 [M+H]$^+$. $^1$H NMR (400 MHz, Methanol-d4) δ 8.23 (d, J=9.4 Hz, 1H), 8.16-8.10 (m, 2H), 8.09 (d, J=8.7 Hz, 1H), 7.77 (d, J=8.7 Hz, 1H), 7.54 (t, J=59.5 Hz, 1H), 7.52 (d, J=9.6 Hz, 1H), 7.50-7.43 (m, 4H), 7.30 (d, J=8.0 Hz, 2H), 7.22-7.13

(m, 1H), 6.95 (d, J=2.8 Hz, 1H), 6.85 (d, J=10.0 Hz, 1H), 4.99 (t, J=7.6 Hz, 2H), 4.84 (dd, J=8.3, 5.0 Hz, 2H), 4.65 (d, J=14.1 Hz, 2H), 4.45 (d, J=9.9 Hz, 1H), 4.31 (d, J=9.9 Hz, 1H), 4.27-4.11 (m, 4H), 3.95 (d, J=13.2 Hz, 1H), 3.84-3.74 (m, 1H), 3.71 (s, 3H), 3.67 (s, 3H), 2.99-2.83 (m, 3H), 2.83-2.74 (m, 1H), 2.30-2.19 (m, 2H), 2.17-2.06 (m, 2H), 1.17 (s, 3H), 1.15 (s, 3H), 1.12 (s, 3H), 1.04 (s, 3H).

1H), 3.71-3.62 (m, 2H), 3.59 (d, J=1.2 Hz, 3H), 3.57 (d, J=1.5 Hz, 3H), 3.50 (d, J=2.0 Hz, 1H), 3.46 (s, 3H), 2.88-2.73 (m, 3H), 2.73-2.63 (m, 1H), 2.49-2.38 (m, 1.5H), 2.28 (d, J=11.3 Hz, 0.5H), 2.20-2.05 (m, 2H), 1.06 (s, 3H), 1.05 (s, 3H), 1.02 (s, 3H), 0.93 (s, 3H).

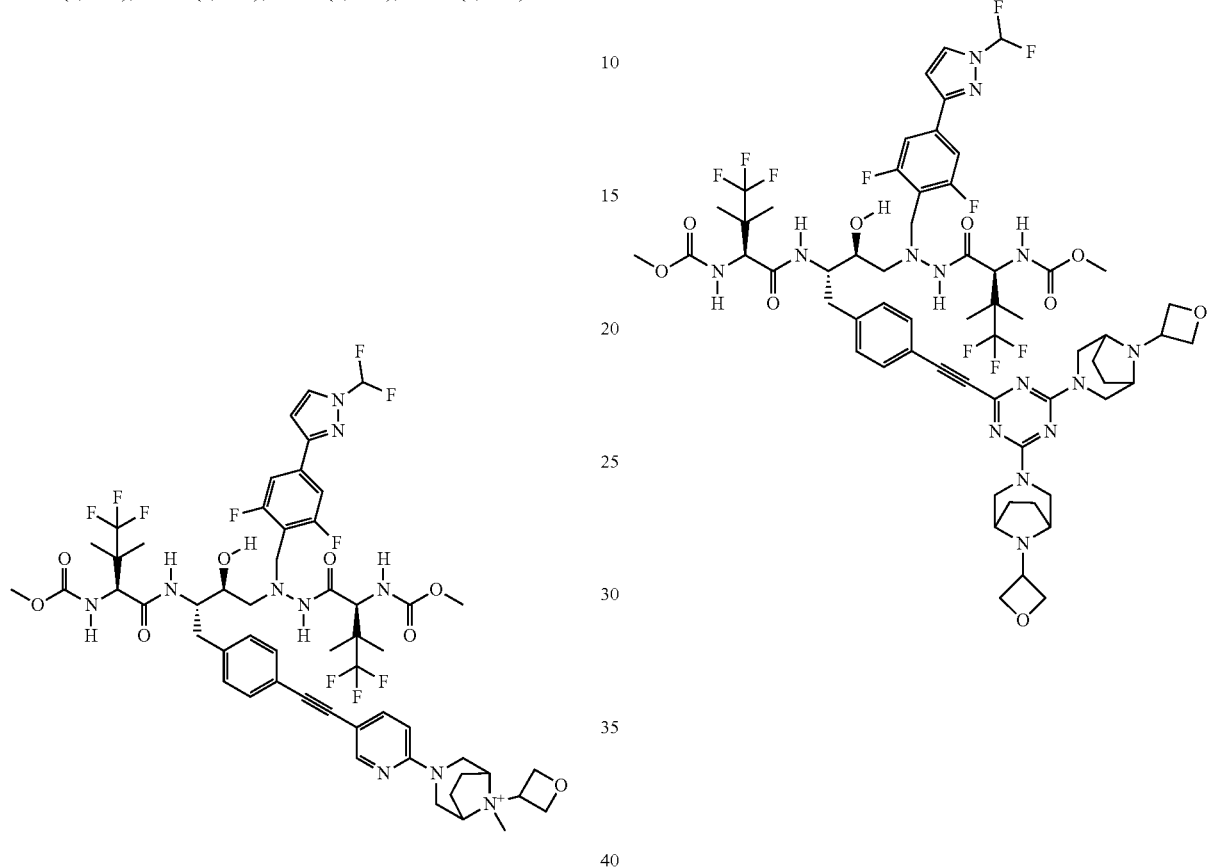

EXAMPLE 48

3-(5-((4-((2S,3S)-4-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-3-hydroxy-2-((S)-4,4,4-trifluoro-2-((methoxycarbonyl)amino)-3,3-dimethylbutanamido)butyl)phenyl) ethynyl)pyridin-2-yl)-8-methyl-8-(oxetan-3-yl)-3,8-diazabicyclo[3.2.1]octan-8-ium (48)

Intermediates: I2, P4, and S54 and S55. MS (ESI) m/z 1169.4 [M+H]+. 1H NMR (400 MHz, Methanol-d4) δ 8.21 (d, J=2.5 Hz, 1H), 8.10 (d, J=9.4 Hz, 1H), 8.01 (d, J=2.7 Hz, 1H), 7.64-7.57 (m, 1H), 7.44 (t, J=60.3 Hz, 1H), 7.36 (d, J=8.2 Hz, 2H), 7.23 (d, J=7.9 Hz, 2H), 7.13 (d, J=8.0 Hz, 2H), 7.07 (d, J=9.8 Hz, 1H), 6.85 (d, J=2.8 Hz, 1H), 6.73 (d, J=10.6 Hz, 1H), 6.70 (d, J=9.0 Hz, 1H), 5.55-5.45 (m, 1H), 5.00-4.83 (m, 4H), 4.35 (d, J=9.9 Hz, 1H), 4.21 (d, J=10.0 Hz, 1H), 4.14 (s, 2H), 4.12-3.94 (m, 4H), 3.85 (d, J=13.2 Hz,

EXAMPLE 49

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((4-((1R,5S)-8-(oxetan-3-yl)-3,8-diazabicyclo[3.2.1]octan-3-yl)-6-(8-(oxetan-3-yl)-3,8-diazabicyclo[3.2.1]octan-3-yl)-1,3,5-triazin-2-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (49)

Intermediates: I2, P4, and S32. MS (ESI) m/z 1323.4 [M+H]+. 1H NMR (400 MHz, Methanol-d4) δ 8.20 (d, J=9.4 Hz, 1H), 8.11 (d, J=2.7 Hz, 1H), 7.53 (t, J=59.6 Hz, 1H), 7.50-7.40 (m, 4H), 7.20-7.11 (m, 1H), 6.94 (d, J=2.8 Hz, 1H), 6.75 (d, J=9.7 Hz, 1H), 5.00-4.91 (m, 4H), 4.83-4.68 (m, 4H), 4.54-4.39 (m, 3H), 4.33-4.27 (m, 1H), 4.21-4.04 (m, 6H), 3.94 (d, J=13.1 Hz, 1H), 3.71 (s, 3H), 3.66 (s, 3H), 3.51-3.39 (m, 5H), 3.00-2.72 (m, 4H), 2.37-2.11 (m, 4H), 2.03-1.84 (m, 4H), 1.16 (s, 3H), 1.13 (s, 3H), 1.10 (s, 3H), 1.03 (s, 3H).

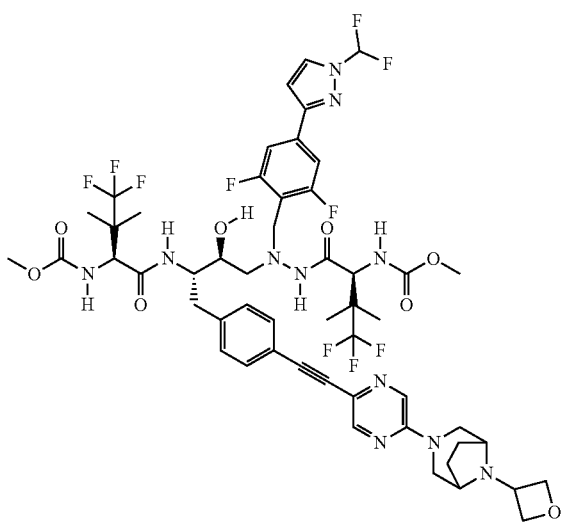 [SMILES: COC(=O)N[C@H](C(=O)N[C@@H](Cc1ccc(C#Cc2cnc(N3CC4CCC(C3)N4C3COC3)cn2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 50

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((5-(8-(oxetan-3-yl)-3,8-diazabicyclo[3.2.1]octan-3-yl)pyrazin-2-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (50)

Intermediates: I2, P4, and S33. MS (ESI) m/z 1156.5 [M+H]$^+$. $^1$H NMR (400 MHz, Methanol-d4) δ 8.34 (d, J=1.3 Hz, 1H), 8.25 (s, 1H), 8.16 (d, J=9.3 Hz, 1H), 8.10 (d, J=2.7 Hz, 1H), 7.53 (t, J=59.4 Hz, 1H), 7.45 (d, J=8.3 Hz, 2H), 7.40 (d, J=8.0 Hz, 2H), 7.26 (d, J=8.0 Hz, 2H), 6.93 (d, J=2.8 Hz, 1H), 4.97 (t, J=7.6 Hz, 2H), 4.82-4.76 (m, 2H), 4.47-4.36 (m, 3H), 4.30 (d, J=9.9 Hz, 1H), 4.23-4.10 (m, 4H), 3.95 (d, J=12.9 Hz, 1H), 3.78-3.72 (m, 1H), 3.69 (s, 3H), 3.66 (s, 3H), 3.46 (d, J=14.0 Hz, 3H), 2.96-2.71 (m, 4H), 2.27-2.20 (m, 1H), 2.14-2.02 (m, 2H), 1.16 (s, 3H), 1.14 (s, 3H), 1.11 (s, 3H), 1.03 (s, 3H).

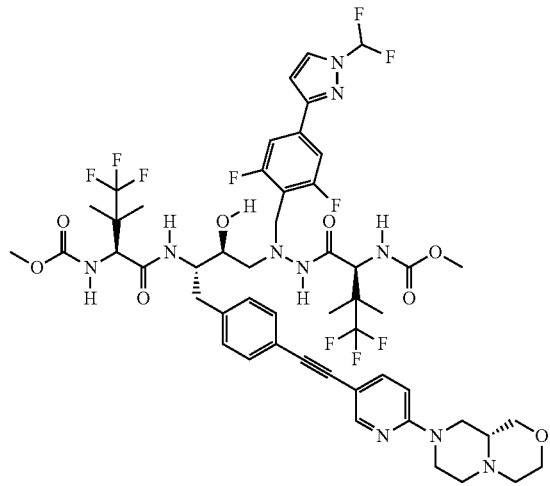 [SMILES: COC(=O)N[C@H](C(=O)N[C@@H](Cc1ccc(C#Cc2ccc(N3CCN4CCOC[C@H]4C3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 51 methyl ((5S,8S,9S,14S)-11-(4-(1-(difluoromethyl)-1H-pyrazol-3-yl)-2,6-difluorobenzyl)-16,16,16-trifluoro-8-(4-((6-((R)-hexahydropyrazino[2,1-c][1,4]oxazin-8(1H)-yl)pyridin-3-yl)ethynyl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (51)

Intermediates: I2, P4, and S8. MS (ESI) m/z 1129.4 [M+H]$^+$. $^1$H NMR (400 MHz, Methanol-d4) δ 8.24-8.15 (m, 1H), 8.08 (d, J=9.4 Hz, 1H), 8.01 (d, J=2.7 Hz, 1H), 7.61 (dd, J=8.8, 2.3 Hz, 1H), 7.44 (t, J=59.7 Hz, 1H), 7.36 (d, J=8.2 Hz, 2H), 7.24 (d, J=8.0 Hz, 2H), 7.13 (d, J=8.1 Hz, 2H), 6.89-6.79 (m, 2H), 4.60-4.44 (m, 1H), 4.34 (s, 1H), 4.25-4.18 (m, 1H), 4.11-3.98 (m, 4H), 3.85 (d, J=13.2 Hz, 1H), 3.76 (t, J=12.6 Hz, 1H), 3.68-3.62 (m, 1H), 3.60 (s, 3H), 3.57 (s, 3H), 3.54-3.35 (m, 2H), 2.85-2.74 (m, 4H), 2.73-2.64 (m, 1H), 1.07 (s, 3H), 1.05 (s, 3H), 1.02 (s, 3H), 0.93 (s, 3H).

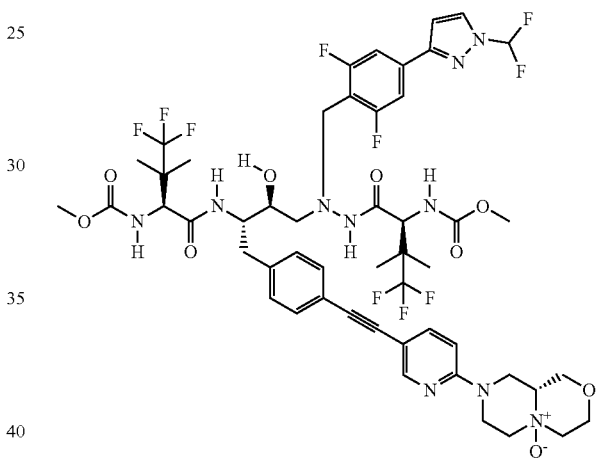

EXAMPLE 52

(9aR)-8-(5-((4-(((2S,3S)-4-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-3-hydroxy-2-((S)-4,4,4-trifluoro-2-((methoxycarbonyl)amino)-3,3-dimethylbutanamido)butyl)phenyl)ethynyl)pyridin-2-yl)octahydro-5H-pyrazino[2,1-c][1,4]oxazine 5-oxide (52)

To a solution of 51 (17 mg, 0.02 mmol) in CH$_3$CN (1 mL) was added 3-Chloroperoxybenzoic acid (77%, 3.9 mg, 0.02 mmol) the mixture was stirred for 5 min then purified by HPLC to afford 52. MS (ESI) m/z 1146.1 [M+H]$^+$. $^1$H NMR (400 MHz, Methanol-d4) δ 8.38-8.23 (m, 1H), 8.17-8.06 (m, 2H), 7.99-7.88 (m, 0H), 7.73-7.65 (m, 1H), 7.59-7.40 (m, 3H), 7.33 (d, J=7.9 Hz, 2H), 7.22 (d, J=8.0 Hz, 2H), 7.10 (d, J=10.2 Hz, 1H), 6.98-6.91 (m, 2H), 6.77 (d, J=10.1 Hz, 1H), 4.59 (d, J=14.5 Hz, 1H), 4.41 (dd, J=21.3, 12.0 Hz, 2H), 4.28 (dd, J=17.0, 11.1 Hz, 2H), 4.14 (d, J=12.9 Hz, 2H), 4.10-3.87 (m, 6H), 3.67 (d, J=10.5 Hz, 8H), 3.26-3.12 (m, 1H), 3.00-2.73 (m, 4H), 2.02 (s, 2H), 1.24-1.10 (m, 10H), 1.02 (s, 3H).

223

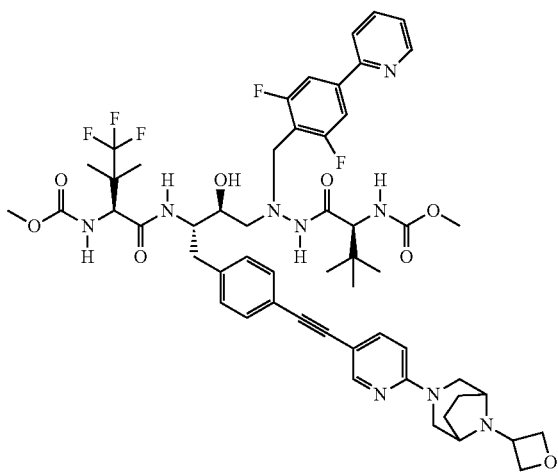 [SMILES: COC(=O)N[C@H](C(=O)NN(Cc1c(F)cc(-c2ccccn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 53

Methyl ((5S,8S,9S,14S)-11-(2,6-difluoro-4-(pyridin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (53)

Intermediates: I3, P28, and S3. MS (ESI) m/z 1062.4 [M+H]+. 1H NMR (400 MHz, Methanol-d4) δ 8.64 (d, J=4.9 Hz, 1H), 8.30 (d, J=2.2 Hz, 1H), 8.15 (d, J=9.3 Hz, 1H), 7.91 (s, 2H), 7.70 (dd, J=8.7, 2.3 Hz, 1H), 7.60 (d, J=8.5 Hz, 2H), 7.33 (d, J=7.8 Hz, 2H), 7.22 (d, J=8.0 Hz, 2H), 6.86 (d, J=8.9 Hz, 1H), 6.77 (d, J=10.5 Hz, 1H), 4.96 (t, J=7.6 Hz, 2H), 4.82-4.76 (m, 4H), 4.40 (dd, J=33.8, 12.0 Hz, 3H), 4.16 (d, J=12.1 Hz, 4H), 4.00 (d, J=13.3 Hz, 1H), 3.79-3.60 (m, 9H), 3.37 (d, J=14.0 Hz, 3H), 2.95-2.77 (m, 4H), 2.22 (s, 2H), 2.08 (d, J=8.7 Hz, 2H), 1.13 (d, J=11.3 Hz, 6H), 0.86 (s, 10H).

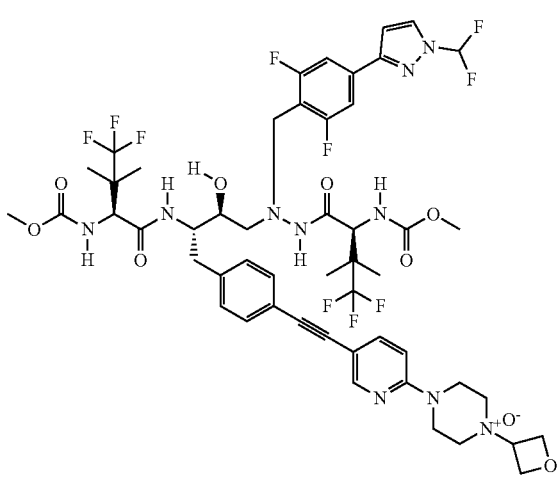

224

EXAMPLE 54

4-(5-((4-((2S,3S)-4-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl)hydrazinyl)-3-hydroxy-2-((S)-4,4,4-trifluoro-2-((methoxycarbonyl)amino)-3,3-dimethylbutanamido)butyl)phenyl)ethynyl)pyridin-2-yl)-1-(oxetan-3-yl)piperazine 1-oxide (54)

The title compound 54 was prepared according to the method presented for the synthesis of compound 52 but instead utilizing 112. MS (ESI) m/z 1145.9 [M+H]+. 1H NMR (400 MHz, Methanol-d4) δ 8.31 (d, J=2.2 Hz, 1H), 8.19-8.05 (m, 2H), 7.77-7.59 (m, 2H), 7.59-7.51 (m, 1H), 7.44 (d, J=8.2 Hz, 2H), 7.39-7.30 (m, 3H), 7.22 (d, J=8.0 Hz, 2H), 7.09 (d, J=10.0 Hz, 1H), 7.01-6.88 (m, 2H), 6.77 (d, J=9.9 Hz, 1H), 5.14-5.00 (m, 3H), 4.94 (dd, J=8.1, 6.7 Hz, 2H), 4.47 (dd, J=25.9, 10.4 Hz, 3H), 4.37-4.24 (m, 1H), 4.14 (d, J=13.0 Hz, 2H), 3.95 (d, J=13.2 Hz, 1H), 3.87-3.57 (m, 14H), 2.98-2.67 (m, 4H), 1.25-1.06 (m, 10H), 1.02 (s, 3H).

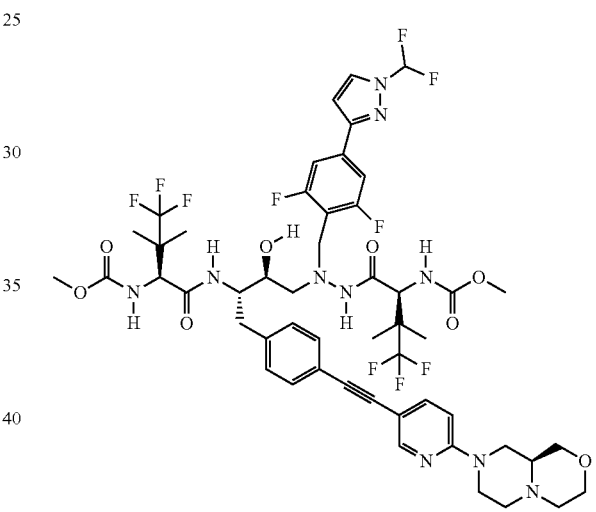

EXAMPLE 55

Methyl ((5S,8S,9S,14S)-11-(4-(1-(difluoromethyl)-1H-pyrazol-3-yl)-2,6-difluorobenzyl)-16,16,16-trifluoro-8-(4-((6-((S)-hexahydropyrazino[2,1-c][1,4]oxazin-8(1H)-yl)pyridin-3-yl)ethynyl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (55)

Intermediates: I2, P4, and S9. MS (ESI) m/z 1129.9 [M+H]+. 1H NMR (400 MHz, Methanol-d4) δ 8.21 (dd, J=2.2, 0.8 Hz, 1H), 8.01 (d, J=2.7 Hz, 1H), 7.61 (dd, J=8.9, 2.3 Hz, 1H), 7.44 (t, J=59.6 Hz, 1H), 7.36 (d, J=8.3 Hz, 2H), 7.24 (d, J=7.9 Hz, 2H), 7.13 (d, J=8.1 Hz, 2H), 6.90-6.83 (m, 2H), 4.60-4.44 (m, 1H), 4.34 (s, 1H), 4.21 (s, 1H), 4.14-3.98 (m, 4H), 3.85 (d, J=13.1 Hz, 1H), 3.76 (t, J=12.6 Hz, 1H), 3.67-3.62 (m, 1H), 3.60 (s, 3H), 3.57 (s, 3H), 3.54-3.35 (m, 2H), 2.88-2.73 (m, 4H), 2.73-2.66 (m, 1H), 1.07 (s, 3H), 1.05 (s, 3H), 1.02 (s, 3H), 0.93 (s, 3H).

EXAMPLE 56

Methyl ((5S,8S,9S,14S)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-11-(4-(pyridin-2-yl)benzyl)-5-(1,1,1-trifluoro-2-methylpropan-2-yl)-2-oxa-4,7,11,12-tetraazahexadecan-14-yl)carbamate (56)

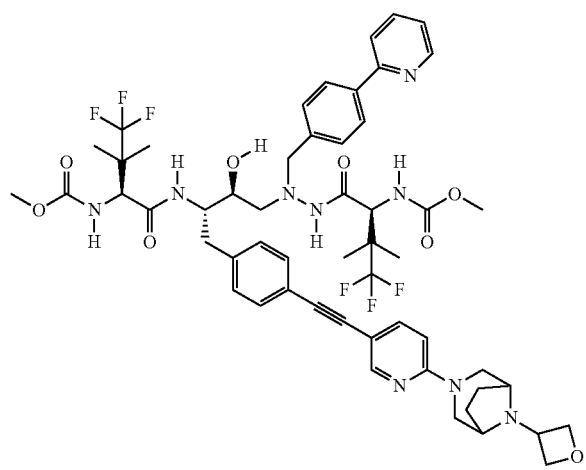 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(-c2ccccn2)cc1)NC(=O)[C@@H](NC(=O)OC)C(C)(C)C(F)(F)F)C(C)(C)C(F)(F)F]

Intermediates: I2, P30, and S3. MS (ESI) m/z 1081.3 [M+H]⁺. ¹H NMR (400 MHz, Methanol-d4) δ 8.75 (d, J=5.6 Hz, 1H), 8.41 (t, J=8.0 Hz, 1H), 8.36-8.25 (m, 1H), 8.20 (d, J=8.2 Hz, 1H), 8.09 (d, J=9.5 Hz, 1H), 7.88 (d, J=8.0 Hz, 2H), 7.81 (t, J=6.6 Hz, 1H), 7.74-7.63 (m, 3H), 7.33 (d, J=7.9 Hz, 2H), 7.23 (d, J=8.0 Hz, 2H), 7.18 (d, J=9.9 Hz, 1H), 6.86 (d, J=8.9 Hz, 1H), 6.81 (d, J=9.8 Hz, 1H), 4.96 (dd, J=8.1, 7.1 Hz, 2H), 4.81 (dd, J=8.2, 5.0 Hz, 2H), 4.44-4.30 (m, 3H), 4.24 (d, J=9.6 Hz, 1H), 4.16 (s, 2H), 4.08 (d, J=13.6 Hz, 1H), 3.99 (d, J=13.4 Hz, 1H), 3.76 (s, 1H), 3.68 (s, 3H), 3.56 (s, 3H), 3.38 (d, J=13.7 Hz, 2H), 2.98-2.72 (m, 3H), 2.27-2.16 (m, 2H), 2.12-2.03 (m, 2H), 1.12 (s, 3H), 1.10 (s, 3H), 1.04 (s, 3H), 0.84 (s, 3H). ¹⁹F NMR (377 MHz, Methanol-d4) δ -77.36, -77.68, -77.89.

EXAMPLE 57

Methyl ((5S,8S,9S,14S)-11-(4-(6,7-dihydro-4H-pyrazolo[5,1-c][1,4]oxazin-2-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (57)

Intermediates: I2, P27, and S3. MS (ESI) m/z 1161.4 [M+H]⁺. ¹H NMR (400 MHz, Methanol-d4) δ 8.29 (d, J=2.3 Hz, 1H), 8.18 (d, J=9.3 Hz, 1H), 7.70 (dd, J=8.9, 2.3 Hz, 1H), 7.42-7.31 (m, 4H), 7.22 (d, J=8.1 Hz, 2H), 7.17 (d, J=9.9 Hz, 1H), 6.86 (d, J=8.9 Hz, 1H), 6.81 (d, J=9.9 Hz, 1H), 6.48 (s, 1H), 4.96 (t, J=7.6 Hz, 2H), 4.85 (s, 2H), 4.81 (dd, J=8.3, 5.0 Hz, 2H), 4.47-4.39 (m, 1H), 4.35 (d, J=14.5 Hz, 2H), 4.33-4.26 (m, 1H), 4.22-4.07 (m, 9H), 3.93 (d, J=13.3 Hz, 1H), 3.69 (s, 3H), 3.67 (s, 3H), 3.44-3.35 (m, 2H), 2.96-2.71 (m, 4H), 2.27-2.17 (m, 2H), 2.08 (d, J=8.6 Hz, 2H), 1.17 (s, 3H), 1.15 (s, 3H), 1.11 (s, 3H), 1.02 (s, 3H). ¹⁹F NMR (377 MHz, Methanol-d4) δ -77.40, -77.74, -77.92, -115.37.

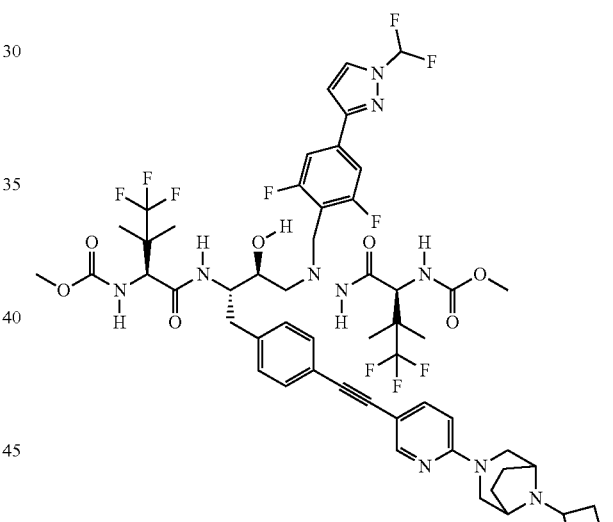

EXAMPLE 58

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (58) (GS-PI1)

Intermediates: I2, P4, and S3. MS (ESI) m/z 1155.6 [M+H]⁺. ¹H NMR (400 MHz, Methanol-d4) δ 8.29 (dd, J=2.3, 0.7 Hz, 1H), 8.18 (d, J=9.3 Hz, 1H), 8.11 (d, J=2.7 Hz, 1H), 7.72-7.68 (m, 1H), 7.54 (d, J=59.9 Hz, 1H), 7.45 (d,

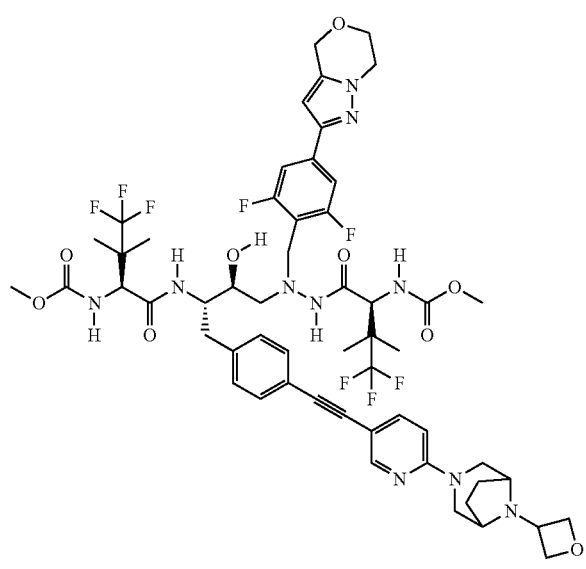 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2cc3n(n2)CCOC3)cc1F)NC(=O)[C@@H](NC(=O)OC)C(C)(C)C(F)(F)F)C(C)(C)C(F)(F)F]

J=8.2 Hz, 2H), 7.33 (d, J=8.0 Hz, 2H), 7.22 (d, J=8.2 Hz, 2H), 7.15 (d, J=10.0 Hz, 1H), 6.94 (d, J=2.7 Hz, 1H), 6.86 (d, J=8.9 Hz, 1H), 6.81 (d, J=9.9 Hz, 1H), 4.99-4.92 (m, 2H), 4.84-4.77 (m, 2H), 4.44 (d, J=9.9 Hz, 1H), 4.40-4.26 (m, 3H), 4.22-4.09 (m, 4H), 3.94 (d, J=13.2 Hz, 1H), 3.78-3.70 (m, 2H), 3.69 (s, 3H), 3.66 (s, 3H), 3.38 (d, J=13.9 Hz, 2H), 2.95-2.70 (m, 4H), 2.30-2.15 (m, 2H), 2.15-2.03 (m, 2H), 1.16 (s, 3H), 1.14 (s, 3H), 1.11 (s, 3H), 1.03 (s, 3H). $^{19}$F NMR (377 MHz, Methanol-d4) δ −77.40, −77.73, −77.90, −96.95 (dd, J=59.9, 19.6 Hz), −114.92.

(m, 3H), 3.93 (d, J=13.2 Hz, 1H), 3.69 (s, 3H), 3.68-3.61 (m, 4H), 3.00 (dt, J=10.2, 6.3 Hz, 1H), 2.94-2.72 (m, 4H), 2.09-1.98 (m, 1H), 1.17 (s, 3H), 1.15 (s, 3H), 1.12 (s, 3H), 1.03 (s, 3H). $^{19}$F NMR (377 MHz, Methanol-d4) δ −77.39, −77.71, −77.96, −96.87 (d, J=59.7 Hz), −115.01.

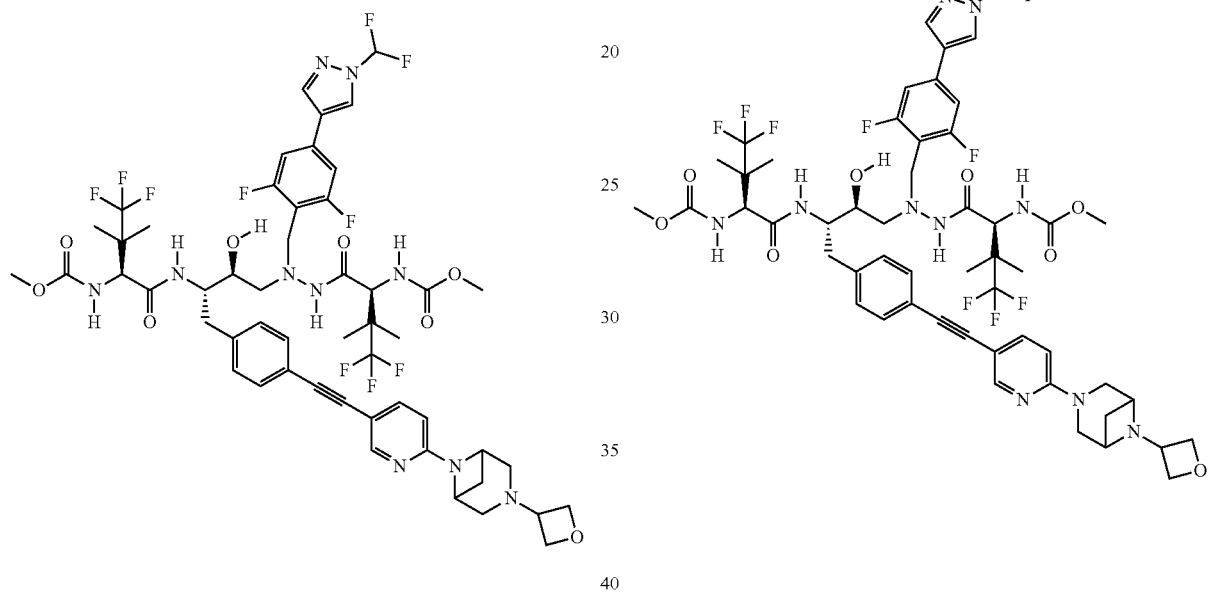

EXAMPLE 59

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(3-(oxetan-3-yl)-3,6-diazabicyclo[3.1.1]heptan-6-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (59)

Intermediates: I2, P7, and S34. MS (ESI) m/z 1141.6 [M+H]$^+$. $^1$H NMR (400 MHz, Methanol-d4) δ 8.54 (d, J=0.8 Hz, 1H), 8.37-8.24 (m, 1H), 8.18 (d, J=9.3 Hz, 1H), 8.13 (s, 1H), 7.79 (dd, J=8.6, 2.2 Hz, 1H), 7.51 (t, J=59.7 Hz, 1H), 7.34 (d, J=8.2 Hz, 2H), 7.29-7.20 (m, 4H), 7.18 (d, J=9.8 Hz, 1H), 6.82 (d, J=9.8 Hz, 1H), 6.73 (d, J=8.7 Hz, 1H), 4.77 (t, J=7.6 Hz, 2H), 4.62 (d, J=6.3 Hz, 1H), 4.53 (dd, J=8.3, 5.1 Hz, 2H), 4.49-4.41 (m, 1H), 4.37-4.29 (m, 1H), 4.27-4.07

EXAMPLE 60

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (60)

Intermediates: I2, P7, and S4. MS (ESI) m/z 1141.3 [M+H]$^+$. $^1$H NMR (400 MHz, Methanol-d4) δ 8.54 (d, J=0.7 Hz, 1H), 8.37-8.29 (m, 1H), 8.17 (d, J=9.4 Hz, 1H), 8.13 (s, 1H), 7.74 (dd, J=8.9, 2.3 Hz, 1H), 7.51 (t, J=59.7 Hz, 1H), 7.34 (d, J=7.9 Hz, 2H), 7.24 (dd, J=12.7, 8.2 Hz, 4H), 7.18 (d, J=10.1 Hz, 1H), 6.84-6.76 (m, 2H), 5.08-4.93 (m, 2H), 4.65-4.56 (m, 2H), 4.50-4.41 (m, 1H), 4.39-4.27 (m, 1H), 4.21-4.03 (m, 3H), 3.93 (d, J=13.2 Hz, 1H), 3.78-3.68 (m, 4H), 3.67 (s, 3H), 2.95-2.73 (m, 4H), 2.11 (d, J=11.1 Hz, 1H), 1.17 (s, 3H), 1.15 (s, 3H), 1.12 (s, 3H), 1.03 (s, 3H). $^{19}$F NMR (377 MHz, Methanol-d4) δ −77.39, −77.72, −77.93, −96.87 (d, J=59.7 Hz), −115.02

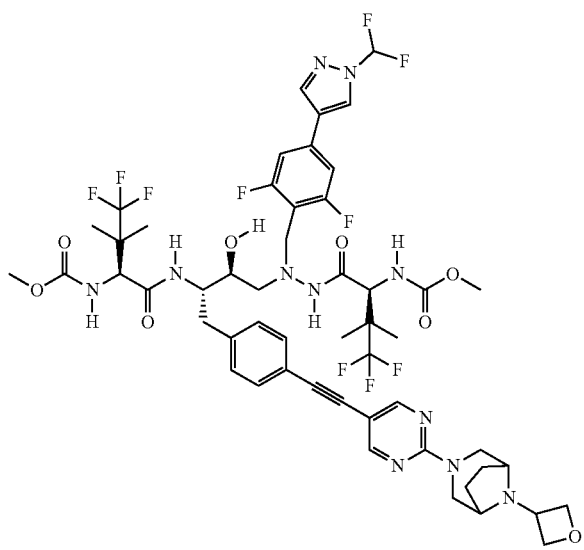 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

EXAMPLE 61

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (61)

Intermediates: I2, P7, and S7. MS (ESI) m/z 1156.9 [M+H]⁺. ¹H NMR (400 MHz, Methanol-d4) δ 8.54 (d, J=0.7 Hz, 1H), 8.53 (s, 2H), 8.18 (d, J=9.2 Hz, 1H), 8.13 (s, 1H), 7.51 (t, J=59.7 Hz, 1H), 7.34 (d, J=8.2 Hz, 2H), 7.24 (t, J=8.1 Hz, 4H), 7.18 (d, J=9.9 Hz, 1H), 6.82 (d, J=9.9 Hz, 1H), 5.00-4.92 (m, 2H), 4.84-4.77 (m, 2H), 4.44 (d, J=9.9 Hz, 1H), 4.31 (d, J=10.0 Hz, 1H), 4.21-4.07 (m, 3H), 3.79-3.70 (m, 1H), 3.69 (s, 3H), 3.66 (s, 3H), 3.52-3.41 (m, 2H), 2.96-2.66 (m, 4H), 2.21 (d, J=11.2 Hz, 2H), 1.99 (d, J=9.1 Hz, 2H), 1.17 (s, 3H), 1.14 (s, 3H), 1.11 (s, 3H), 1.03 (s, 3H). ¹⁹F NMR (377 MHz, Methanol-d4) δ -77.39, -77.72, -77.86, -96.87 (d, J=59.7 Hz), -115.03.

EXAMPLE 62

Methyl ((5S,8S,9S,14S)-11-(4-(1-(difluoromethyl)-1H-pyrazol-4-yl)-2,6-difluorobenzyl)-8-(4-((6-(1,5-dimethyl-7-(oxetan-3-yl)-9-oxo-3,7-diazabicyclo[3.3.1]nonan-3-yl)pyridin-3-yl)ethynyl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (62)

Intermediates: I2, P7, and S37. MS (ESI) m/z 1229.3 [M+H]⁺. ¹H NMR (400 MHz, Methanol-d4) δ 8.54 (d, J=0.8 Hz, 1H), 8.27 (d, J=2.2 Hz, 1H), 8.17 (d, J=9.3 Hz, 1H), 8.12 (s, 1H), 7.98-7.88 (m, 1H), 7.58 (t, J=59.7 Hz, 1H), 7.38-7.33 (m, 2H), 7.25 (dd, J=8.2, 5.8 Hz, 4H), 7.18 (d, J=9.9 Hz, 1H), 6.80 (d, J=9.9 Hz, 1H), 4.83-4.75 (m, 1H), 4.65 (d, J=13.5 Hz, 2H), 4.54 (t, J=6.8 Hz, 2H), 4.43 (d, J=9.7 Hz, 1H), 4.35-4.16 (m, 3H), 4.13 (t, J=11.3 Hz, 2H), 4.02 (d, J=12.4 Hz, 0H), 3.93 (d, J=13.1 Hz, 1H), 3.72 (d, J=10.4 Hz, 2H), 3.69 (d, J=2.1 Hz, 3H), 3.66 (s, 3H), 3.53-3.44 (m, 1H), 2.99-2.71 (m, 4H), 2.47 (d, J=11.6 Hz, 2H), 1.17 (s, 4H), 1.14 (s, 3H), 1.11 (s, 4H), 1.07 (s, 5H), 1.03 (s, 3H). ¹⁹F NMR (377 MHz, Methanol-d4) δ -77.38, -77.71 (d, J=5.6 Hz), -77.97, -96.87 (d, J=59.7 Hz), -115.02.

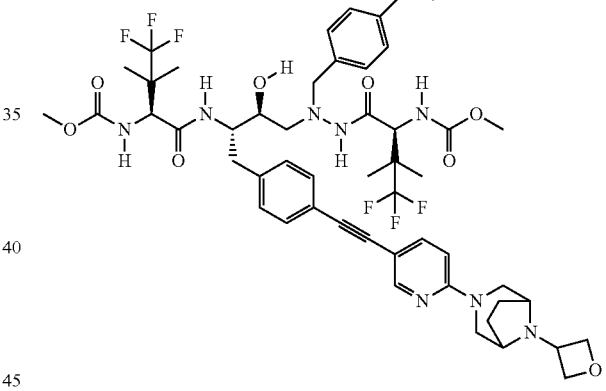

EXAMPLE 63

Methyl ((5S,8S,9S,14S)-11-(4-(1-(difluoromethyl)-1H-pyrazol-4-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (63)

Intermediates: I2, P9, and S3. MS (ESI) m/z 1119.9 [M+H]⁺. ¹H NMR (400 MHz, Methanol-d4) δ 8.38 (s, 1H), 8.29 (d, J=2.3 Hz, 1H), 8.09 (d, J=9.7 Hz, 1H), 8.06 (s, 1H), 7.69 (dd, J=8.9, 2.3 Hz, 1H), 7.54 (d, J=8.1 Hz, 2H), 7.48 (t, J=59.9 Hz, 1H), 7.41 (d, J=8.1 Hz, 2H), 7.33 (d, J=7.8 Hz, 2H), 7.21 (d, J=8.0 Hz, 2H), 7.14 (d, J=9.6 Hz, 1H), 6.86 (d, J=8.9 Hz, 1H), 6.76 (d, J=9.8 Hz, 1H), 4.96 (t, J=7.6 Hz, 2H), 4.81 (dd, J=8.3, 5.1 Hz, 2H), 4.45-4.31 (m, 3H), 4.25 (d, J=9.6 Hz, 1H), 4.15 (s, 3H), 3.98 (d, J=13.2 Hz, 1H), 3.86 (d, J=13.0 Hz, 1H), 3.74 (d, J=8.3 Hz, 1H), 3.68 (s, 3H), 3.60

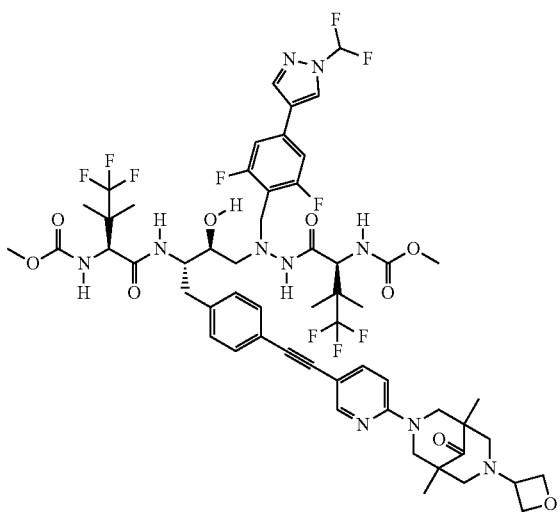 [SMILES: COC(=O)N[C@H](C(=O)N[C@@H](Cc1ccc(C#Cc2ccc(N3CC4(C)CN(C5COC5)CC(C)(C3)C4=O)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

(s, 3H), 3.37 (d, J=13.9 Hz, 2H), 2.95-2.67 (m, 4H), 2.30-2.19 (m, 2H), 2.07 (d, J=8.6 Hz, 2H), 1.12 (s, 3H), 1.09 (s, 3H), 1.01 (s, 3H), 0.85 (s, 3H). $^{19}$F NMR (376 MHz, Methanol-d4) δ −77.41, −77.66, −77.73, −96.57 (d, J=59.9 Hz).

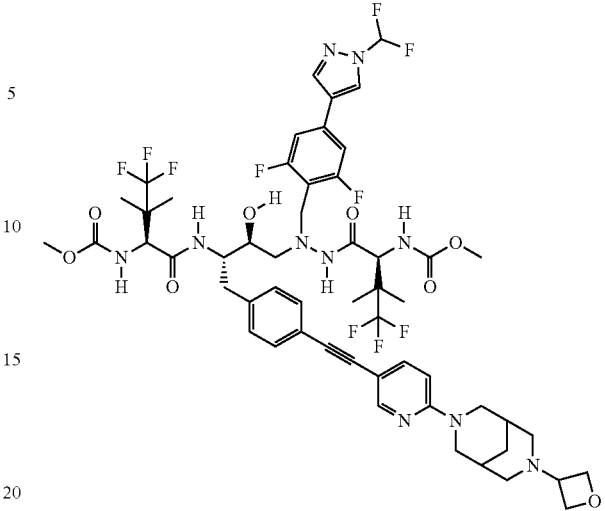

EXAMPLE 65

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(7-(oxetan-3-yl)-3,7-diazabicyclo[3.3.1]nonan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (65)

Intermediates: I2, P7, and S41. MS (ESI) m/z 1169.8 [M+H]$^+$. $^1$H NMR (400 MHz, Methanol-d4) δ 8.53 (s, 1H), 8.38 (s, 1H), 8.14 (d, J=9.5 Hz, 1H), 8.12 (s, 1H), 7.78 (d, J=9.5 Hz, 1H), 7.58 (t, J=59.7 Hz, 1H), 7.35 (d, J=7.2 Hz, 2H), 7.24 (t, J=7.8 Hz, 4H), 7.14 (d, J=9.8 Hz, 1H), 7.01 (d, J=8.9 Hz, 1H), 6.79 (d, J=10.0 Hz, 1H), 4.79 (t, J=7.8 Hz, 2H), 4.50-4.24 (m, 5H), 4.19-4.05 (m, 2H), 3.93 (d, J=13.2 Hz, 1H), 3.79-3.63 (m, 9H), 3.14 (d, J=12.3 Hz, 2H), 3.00-2.72 (m, 4H), 2.46 (s, 2H), 2.13-1.92 (m, 2H), 1.17 (s, 3H), 1.15 (s, 3H), 1.12 (s, 3H), 1.03 (s, 3H). $^{19}$F NMR (376 MHz, Methanol-d4) δ −77.36, −77.70, −77.78, −96.88 (d, J=59.8 Hz), −115.01.

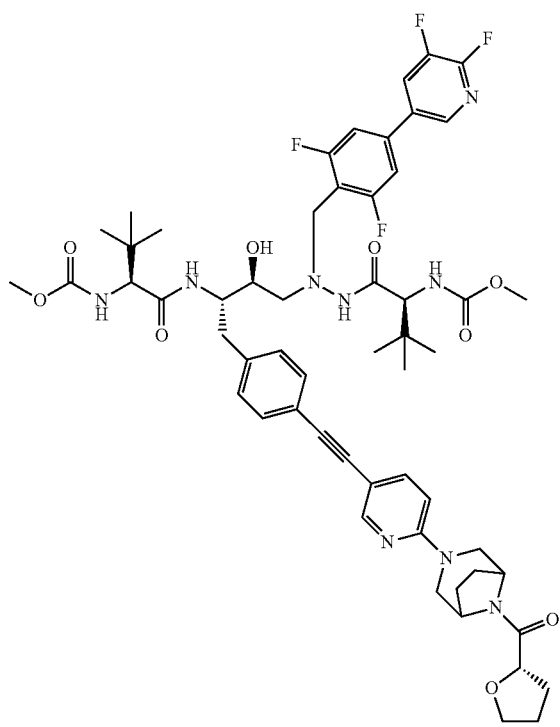 [SMILES: COC(=O)N[C@H](C(=O)N[C@@H](Cc1ccc(C#Cc2ccc(N3CC4CCC(C3)N4C(=O)[C@@H]3CCCO3)nc2)cc1)[C@@H](O)CN(CCc1c(F)cc(-c2cnc(F)c(F)c2)cc1F)NC(=O)[C@@H](NC(=O)OC)C(C)(C)C)C(C)(C)C]

EXAMPLE 64

Methyl ((5S,8S,9S,14S)-5-(tert-butyl)-11-(4-(5,6-difluoropyridin-3-yl)-2,6-difluorobenzyl)-9-hydroxy-15,15-dimethyl-3,6,13-trioxo-8-(4-((6-(8-((S)-tetrahydrofuran-2-carbonyl)-3,8-diazabicyclo[3.2.1]octan-3-yl)pyridin-3-yl)ethynyl)benzyl)-2-oxa-4,7,11,12-tetraazahexadecan-14-yl)carbamate (64)

Intermediates: I8, and 3-difluoro-5-(4,4,5,5-tetramethyl-1,3,2-dioxaborolan-2-yl)pyridine. MS (ESI) m/z 1086.21 [M+H]$^+$. $^1$H NMR (400 MHz, Methanol-d4) δ 8.28 (t, J=1.9 Hz, 1H), 8.24-8.06 (m, 2H), 7.79 (q, J=8.3 Hz, 2H), 7.42-7.14 (m, 7H), 6.99 (t, J=10.5 Hz, 1H), 4.80-4.65 (m, 3H), 4.25-3.84 (m, 10H), 3.77-3.58 (m, 9H), 3.19 (t, J=12.3 Hz, 1H), 3.02-2.75 (m, 6H), 2.31-1.76 (m, 4H), 0.87 (d, J=27.6 Hz, 20H).

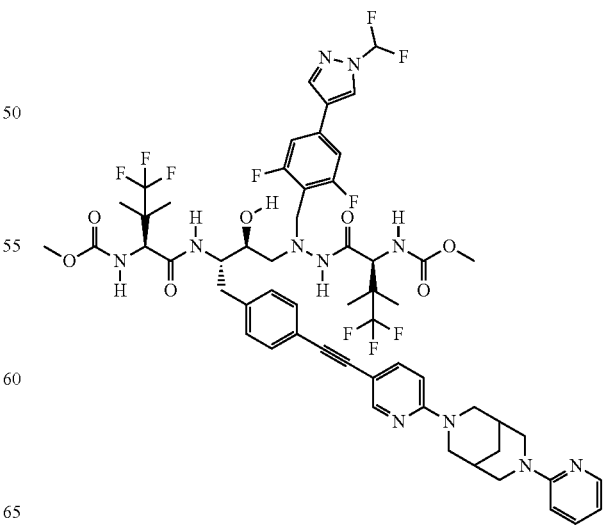

EXAMPLE 66

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-8-(4-((6-(7-(pyridin-2-yl)-3,7-diazabicyclo[3.3.1]nonan-3-yl)pyridin-3-yl)ethynyl)benzyl)-5-(1,1,1-trifluoro-2-methylpropan-2-yl)-2-oxa-4,7,11,12-tetraazahexadecan-14-yl)carbamate (66)

Intermediates: I2, P7, and S40. MS (ESI) m/z 1190.7 [M+H]$^+$. $^1$H NMR (400 MHz, Methanol-d4) δ 8.52 (d, J=0.7 Hz, 1H), 8.17-8.09 (m, 2H), 7.98 (d, J=2.2 Hz, 1H), 7.81 (ddd, J=9.1, 7.0, 1.8 Hz, 1H), 7.76 (ddd, J=6.4, 1.8, 0.7 Hz, 1H), 7.57 (dd, J=9.2, 2.3 Hz, 1H), 7.50 (t, J=59.7 Hz, 1H), 7.30 (d, J=7.9 Hz, 2H), 7.26-7.18 (m, 5H), 7.13 (d, J=9.9 Hz, 1H), 6.93 (d, J=9.3 Hz, 1H), 6.79 (t, J=6.7 Hz, 1H), 4.50 (d, J=13.3 Hz, 2H), 4.46-4.38 (m, 1H), 4.24 (d, J=13.1 Hz, 2H), 4.20-4.05 (m, 2H), 3.93 (d, J=13.1 Hz, 1H), 3.77-3.67 (m, 5H), 3.66 (s, 3H), 3.58-3.46 (m, 2H), 3.38 (d, J=13.3 Hz, 2H), 2.96-2.71 (m, 4H), 2.35 (s, 2H), 2.14 (t, J=3.2 Hz, 2H), 1.17 (s, 3H), 1.15 (s, 3H), 1.12 (s, 3H), 1.03 (s, 3H). $^{19}$F NMR (376 MHz, Methanol-d4) δ −77.34, −77.66, −77.97, −96.87 (d, J=59.6 Hz), −115.00 (d, J=8.7 Hz).

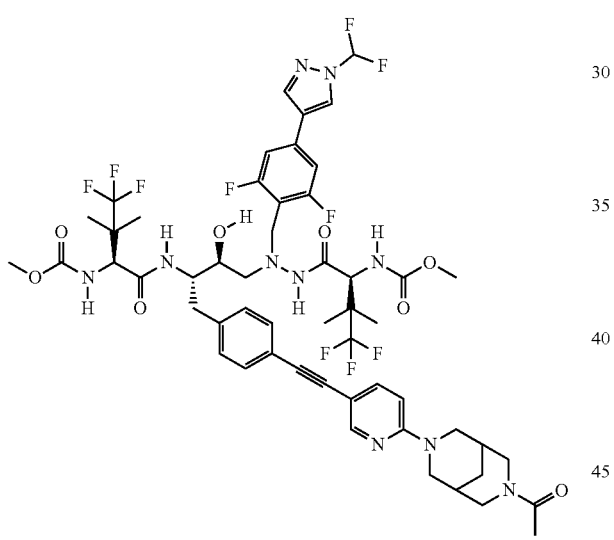

EXAMPLE 67

Methyl ((5S,8S,9S,14S)-8-(4-((6-(7-acetyl-3,7-diazabicyclo[3.3.1]nonan-3-yl)pyridin-3-yl)ethynyl)benzyl)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (67)

Intermediates: I2, P7, and S39. MS (ESI) m/z 1155.9 [M+H]$^+$. $^1$H NMR (400 MHz, Methanol-d4) δ 8.44 (s, 1H), 8.07 (d, J=9.5 Hz, 1H), 8.03 (s, 1H), 7.99 (d, J=2.3 Hz, 1H), 7.75 (d, J=9.4 Hz, 1H), 7.49 (t, J=59.7 Hz, 1H), 7.26 (d, J=7.9 Hz, 2H), 7.20-7.03 (m, 5H), 6.72 (d, J=10.2 Hz, 1H), 4.61 (d, J=13.5 Hz, 1H), 4.38-4.29 (m, 3H), 4.24-4.17 (m, 1H), 4.04 (dt, J=29.4, 13.9 Hz, 5H), 3.83 (d, J=13.1 Hz, 1H), 3.66-3.61 (m, 1H), 3.59 (s, 3H), 3.57 (s, 3H), 3.44-3.26 (m, 4H), 2.87-2.62 (m, 6H), 2.11 (s, 3H), 1.95 (s, 3H), 1.80 (s, 3H), 1.08 (s, 3H), 1.05 (s, 3H), 1.02 (s, 3H), 0.94 (s, 3H). $^{19}$F NMR (377 MHz, Methanol-d4) δ −77.38, −77.70, −77.88 (TFA peak), −96.88 (d, J=59.8 Hz), −115.02.

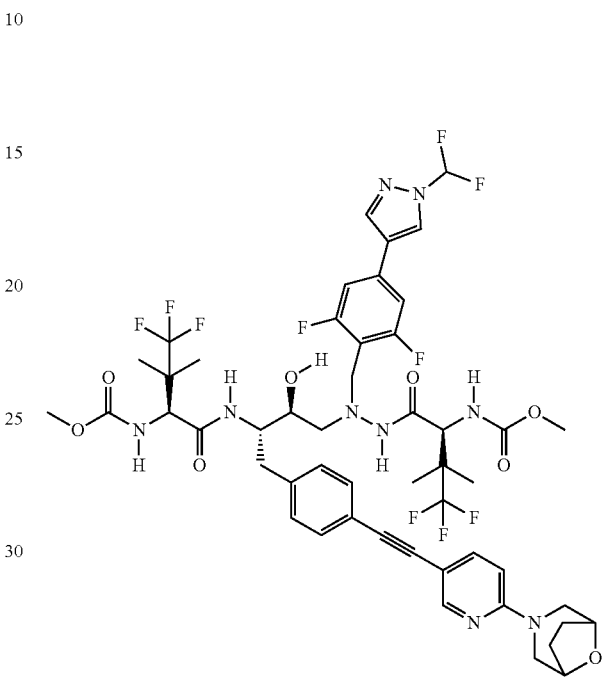

EXAMPLE 68

Methyl ((5S,8S,9S,14S)-8-(4-((6-(8-oxa-3-azabicyclo[3.2.1]octan-3-yl)pyridin-3-yl)ethynyl)benzyl)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (68)

Intermediates: I2, P7, and S43. MS (ESI) m/z 1100.8[M+H]$^+$. $^1$H NMR (400 MHz, Methanol-d4) δ 8.44 (s, 1H), 8.11-8.04 (m, 2H), 8.03 (s, 1H), 7.73 (d, J=9.4 Hz, 1H), 7.41 (t, J=59.8 Hz, 1H), 7.26 (d, J=7.2 Hz, 3H), 7.15 (t, J=7.6 Hz, 5H), 6.94 (d, J=9.2 Hz, 1H), 4.47-4.38 (m, 2H), 4.37-4.30 (m, 1H), 4.24-4.18 (m, 1H), 4.12-3.96 (m, 2H), 3.84 (d, J=13.1 Hz, 1H), 3.72 (d, J=12.2 Hz, 2H), 3.66-3.61 (m, 1H), 3.59 (s, 3H), 3.57 (s, 3H), 3.18-3.12 (m, 2H), 2.86-2.63 (m, 5H), 1.97-1.85 (m, 2H), 1.81-1.73 (m, 2H), 1.08 (s, 3H), 1.05 (s, 3H), 1.02 (s, 3H), 0.94 (s, 3H). $^{19}$F NMR (377 MHz, Methanol-d4) δ −77.38, −77.70, −77.94, −96.88 (d, J=59.7 Hz), −115.02.

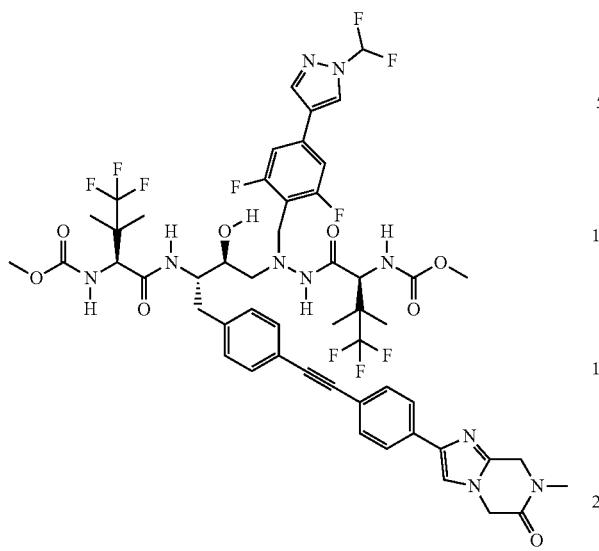

EXAMPLE 69

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((4-(7-methyl-6-oxo-5,6,7,8-tetrahydroimidazo[1,2-a]pyrazin-2-yl)phenyl)ethynyl)benzyl)-3,6,13-trioxo-5-(1,1,1-trifluoro-2-methylpropan-2-yl)-2-oxa-4,7,11,12-tetraazahexadecan-14-yl)carbamate (69)

Intermediates: I2, P7, and S5. MS (ESI) m/z 1137.9 [M+H]+. $^1$H NMR (400 MHz, Methanol-d4) δ 8.44 (s, 1H), 8.09 (d, J=9.4 Hz, 1H), 8.03 (s, 1H), 7.73 (s, 1H), 7.63 (d, J=8.3 Hz, 2H), 7.51 (d, J=8.3 Hz, 2H), 7.41 (d, J=59.7 Hz, 1H), 7.32-7.25 (m, 2H), 7.16 (dd, J=8.3, 3.3 Hz, 4H), 7.09 (d, J=9.9 Hz, 1H), 6.71 (d, J=10.0 Hz, 1H), 4.39-4.30 (m, 1H), 4.30-4.17 (m, 1H), 4.11-3.97 (m, 2H), 3.84 (d, J=13.2 Hz, 1H), 3.68-3.62 (m, 1H), 3.61 (s, 3H), 3.57 (s, 3H), 3.08 (s, 3H), 2.82 (d, J=7.9 Hz, 2H), 2.78-2.61 (m, 2H), 1.08 (s, 3H), 1.05 (s, 3H), 1.02 (s, 3H), 0.94 (s, 3H). $^{19}$F NMR (377 MHz, Methanol-d4) δ −77.39, −77.70, −77.82, −96.87 (d, J=59.7 Hz), −115.00.

EXAMPLE 70

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(8-(methylsulfonyl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (70)

Intermediates: I2, P7, and S38. MS (ESI) m/z 1177.4 [M+H]+. $^1$H NMR (400 MHz, Methanol-d4) δ 8.54 (s, 1H), 8.20 (d, J=2.2 Hz, 1H), 8.12 (s, 1H), 7.73 (d, J=9.4 Hz, 1H), 7.50 (d, J=59.7 Hz, 1H), 7.33 (d, J=7.9 Hz, 2H), 7.25 (d, J=8.4 Hz, 2H), 7.22 (d, J=8.0 Hz, 2H), 6.91 (d, J=9.1 Hz, 1H), 4.43 (s, 1H), 4.39 (s, 2H), 4.30 (s, 1H), 4.18-4.01 (m, 4H), 3.93 (d, J=13.1 Hz, 1H), 3.76-3.70 (m, 1H), 3.69 (s, 3H), 3.66 (s, 3H), 3.21 (d, J=11.9 Hz, 2H), 3.04 (s, 3H), 2.95-2.70 (m, 4H), 2.12-1.99 (m, 2H), 1.86 (t, J=7.0 Hz, 2H), 1.17 (s, 4H), 1.14 (s, 3H), 1.11 (s, 3H), 1.03 (s, 3H). $^{19}$F NMR (377 MHz, Methanol-d4) δ −77.40 (d, J=5.6 Hz), −77.71, −77.90, −96.88 (d, J=59.7 Hz), −115.01.

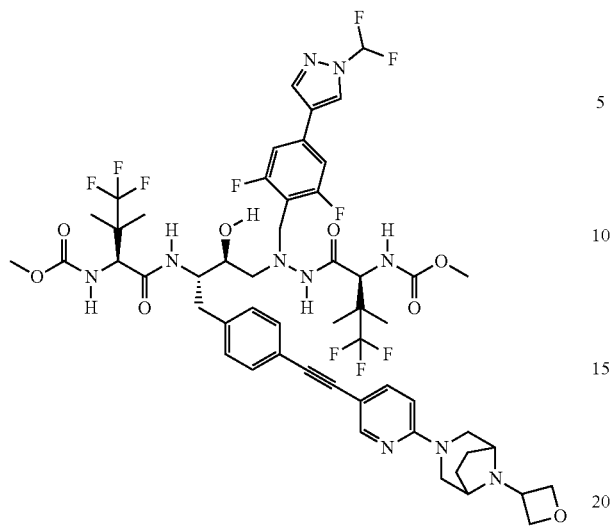
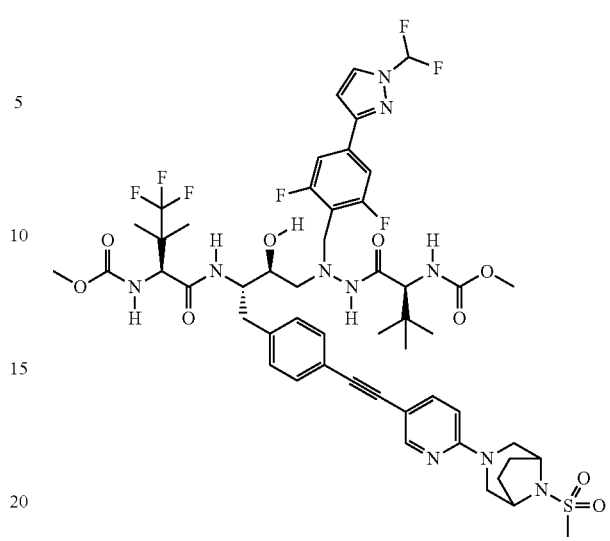

EXAMPLE 71

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (71)

Intermediates: I2, P7, and S3. MS (ESI) m/z 1155.6 [M+H]+. $^1$H NMR (400 MHz, Methanol-d4) δ 8.45 (s, 1H), 8.24-8.18 (m, 1H), 8.08 (d, J=9.3 Hz, 1H), 8.03 (d, J=0.7 Hz, 1H), 7.65-7.52 (m, 3H), 7.50-7.43 (m, 1H), 7.41 (d, J=59.7 Hz, 1H), 7.23 (d, J=7.9 Hz, 2H), 7.16 (d, J=8.4 Hz, 2H), 7.13 (d, J=8.1 Hz, 2H), 6.77 (d, J=8.9 Hz, 1H), 6.71 (d, J=10.0 Hz, 1H), 4.87 (t, J=7.6 Hz, 2H), 4.71 (dd, J=8.2, 5.0 Hz, 2H), 4.34 (d, J=9.9 Hz, 1H), 4.26 (d, J=13.8 Hz, 2H), 4.21 (d, J=10.0 Hz, 1H), 4.11-3.97 (m, 5H), 3.83 (d, J=13.2 Hz, 1H), 3.66-3.61 (m, 1H), 3.59 (s, 3H), 3.57 (s, 3H), 3.28 (d, J=13.9 Hz, 2H), 2.85-2.63 (m, 4H), 2.19-2.09 (m, 2H), 2.02-1.95 (m, 2H), 1.08 (s, 3H), 1.05 (s, 3H), 1.02 (s, 3H), 0.94 (s, 3H). $^{19}$F NMR (377 MHz, Methanol-d4) δ −77.40, −77.72, −96.87 (d, J=59.7 Hz), −115.02.

EXAMPLE 72

Methyl ((5S,8S,9S,14S)-11-(4-(1-(difluoromethyl)-1H-pyrazol-3-yl)-2,6-difluorobenzyl)-9-hydroxy-15,15-dimethyl-8-(4-((6-(8-(methylsulfonyl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (72)

Intermediates: I3, P4, and S38. MS (ESI) m/z 1123.8 [M+H]+. $^1$H NMR (400 MHz, Methanol-d4) δ 8.24-8.14 (m, 2H), 8.10 (d, J=2.7 Hz, 1H), 7.80 (dd, J=9.2, 2.3 Hz, 1H), 7.53 (t, J=59.9 Hz, 1H), 7.44 (d, J=8.2 Hz, 2H), 7.34 (d, J=8.0 Hz, 2H), 7.28-7.18 (m, 2H), 7.01 (d, J=9.2 Hz, 1H), 6.93 (d, J=2.7 Hz, 1H), 6.80 (d, J=9.9 Hz, 1H), 4.47-4.38 (m, 3H), 4.17-4.07 (m, 2H), 4.04 (dd, J=12.3, 2.4 Hz, 2H), 3.96 (d, J=13.1 Hz, 1H), 3.77-3.72 (m, 2H), 3.69 (s, 3H), 3.65 (s, 3H), 3.27 (dd, J=12.1, 2.5 Hz, 2H), 3.04 (s, 3H), 2.97-2.71 (m, 4H), 2.13-2.04 (m, 2H), 1.90-1.81 (m, 2H), 1.14 (s, 3H), 1.11 (s, 3H), 0.86 (s, 9H). $^{19}$F NMR (377 MHz, Methanol-d4) δ −77.32, −77.93, −96.91 (dd, J=59.9, 15.2 Hz), −114.77.

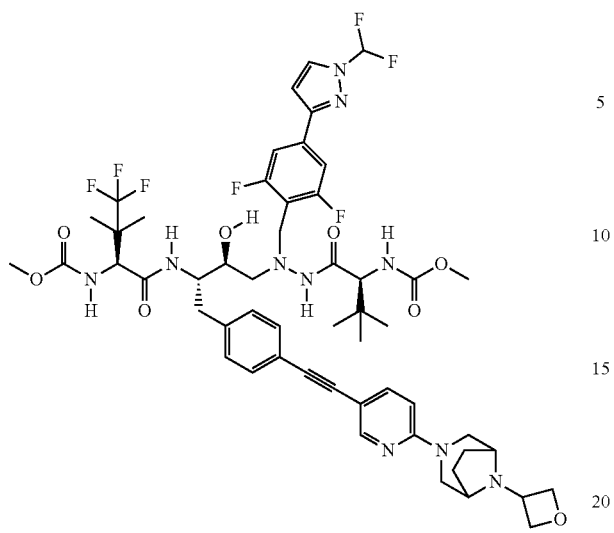

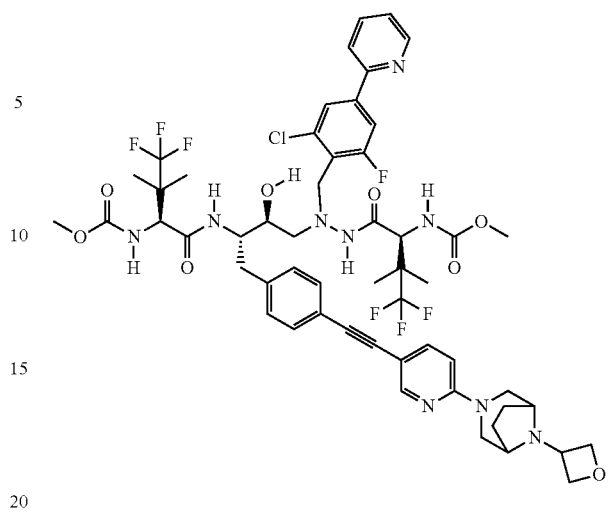

EXAMPLE 73

Methyl ((5S,8S,9S,14S)-11-(4-(1-(difluoromethyl)-1H-pyrazol-3-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (73)

Intermediates: I3, P4, and S3. MS (ESI) m/z 1102.2 [M+H]⁺. ¹H NMR (400 MHz, Methanol-d4) δ 8.29 (d, J=2.2 Hz, 1H), 8.17 (d, J=9.4 Hz, 1H), 8.10 (d, J=2.7 Hz, 1H), 7.71 (dd, J=8.8, 2.3 Hz, 1H), 7.53 (d, J=59.8 Hz, 1H), 7.44 (d, J=8.3 Hz, 2H), 7.33 (d, J=7.9 Hz, 2H), 7.22 (d, J=8.0 Hz, 2H), 6.93 (d, J=2.8 Hz, 1H), 6.91-6.84 (m, 1H), 4.96 (dd, J=8.2, 7.0 Hz, 2H), 4.83 (dd, J=8.2, 5.1 Hz, 2H), 4.61-4.49 (m, 1H), 4.43 (s, 1H), 4.40-4.29 (m, 2H), 4.19-4.04 (m, 4H), 3.97 (d, J=13.1 Hz, 1H), 3.81-3.72 (m, 2H), 3.69 (s, 3H), 3.65 (s, 3H), 3.41 (dd, J=14.2, 1.7 Hz, 2H), 2.99-2.70 (m, 4H), 2.32-2.18 (m, 2H), 2.13-1.99 (m, 2H), 1.14 (s, 3H), 1.11 (s, 3H), 0.86 (s, 9H). ¹⁹F NMR (377 MHz, Methanol-d4) δ -77.35, -78.05 (TFA peak), -96.93 (dd, J=59.7, 14.5 Hz), -114.79.

EXAMPLE 74

Methyl ((5S,8S,9S,14S)-11-(2-chloro-6-fluoro-4-(pyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (74)

Intermediates: I2, P26, and S3. MS (ESI) m/z 1133.4 [M+H]⁺. ¹H NMR (400 MHz, Methanol-d4) δ 8.71 (d, J=5.2 Hz, 1H), 8.35-8.27 (m, 1H), 8.19-8.11 (m, 2H), 8.03 (d, J=8.0 Hz, 1H), 7.88 (s, 1H), 7.70 (dd, J=8.9, 2.3 Hz, 1H), 7.69-7.64 (m, 1H), 7.63-7.57 (m, 1H), 7.33 (d, J=7.9 Hz, 2H), 7.23 (d, J=7.9 Hz, 2H), 6.87 (dd, J=9.0, 0.8 Hz, 1H), 4.96 (dd, J=8.2, 7.1 Hz, 2H), 4.82 (dd, J=8.2, 5.1 Hz, 2H), 4.59-4.51 (m, 1H), 4.45-4.41 (m, 1H), 4.39-4.24 (m, 5H), 4.20-4.11 (m, 4H), 4.05 (d, J=12.7 Hz, 1H), 3.82-3.73 (m, 2H), 3.69 (s, 3H), 3.63 (s, 3H), 3.44-3.36 (m, 2H), 2.92 (t, J=9.0 Hz, 3H), 2.81 (dd, J=12.6, 9.5 Hz, 1H), 2.30-2.18 (m, 2H), 2.12-2.04 (m, 2H), 1.14 (s, 6H), 1.12 (s, 3H), 1.00 (s, 3H). ¹⁹F NMR (377 MHz, Methanol-d4) δ -77.30, -77.68, -78.09 (TFA peak), -112.80.

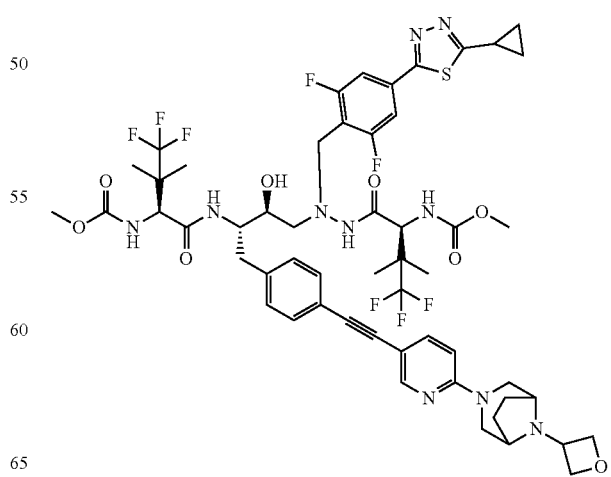

EXAMPLE 75

Methyl ((5S,8S,9S,14S)-11-(4-(5-cyclopropyl-1,3,4-thiadiazol-2-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (75)

Intermediates: I2, P3, and S3. MS (ESI) m/z 1163.9 [M+H]+. 1H NMR (400 MHz, Methanol-d4) δ 8.32-8.26 (m, 1H), 8.12 (d, J=9.4 Hz, 1H), 7.70 (dd, J=8.8, 2.3 Hz, 1H), 7.51 (d, J=7.5 Hz, 2H), 7.33 (d, J=8.0 Hz, 2H), 7.22 (d, J=8.0 Hz, 2H), 7.12 (d, J=9.8 Hz, 1H), 6.86 (d, J=8.9 Hz, 1H), 6.77 (d, J=9.9 Hz, 1H), 4.96 (t, J=7.6 Hz, 2H), 4.79 (s, 1H), 4.43 (d, J=9.8 Hz, 1H), 4.35 (d, J=14.0 Hz, 2H), 4.28 (d, J=10.0 Hz, 1H), 4.17 (s, 5H), 3.97 (d, J=13.2 Hz, 1H), 3.74 (d, J=13.6 Hz, 1H), 3.69 (s, 3H), 3.67 (s, 3H), 3.38 (d, J=13.9 Hz, 2H), 3.02-2.84 (m, 3H), 2.82-2.74 (m, 1H), 2.53 (td, J=8.6, 4.3 Hz, 1H), 2.27-2.18 (m, 2H), 2.08 (d, J=8.6 Hz, 2H), 1.35-1.30 (m, 2H), 1.27 (d, J=16.2 Hz, 0H), 1.20-1.13 (m, 9H), 1.12 (s, 3H), 1.03 (s, 3H). 19F NMR (376 MHz, Methanol-d4) δ -77.31, -77.67, -77.82, -113.25.

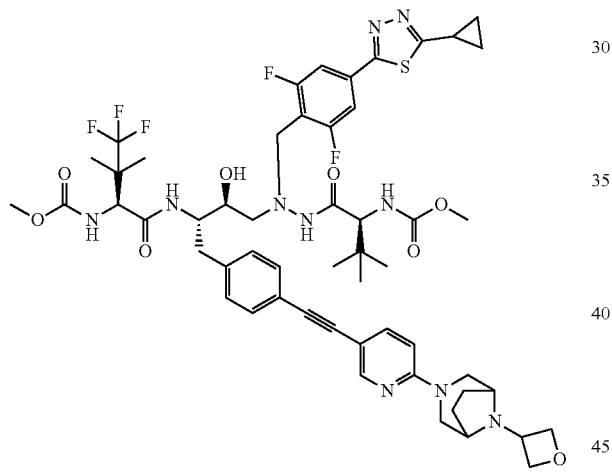

EXAMPLE 76

Methyl ((5S,8S,9S,14S)-11-(4-(5-cyclopropyl-1,3,4-thiadiazol-2-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (76)

Intermediates: I3, P3, and S3. MS (ESI) m/z 1110.1 [M+H]+. 1H NMR (400 MHz, Methanol-d4) δ 8.32-8.27 (m, 1H), 8.13 (d, J=9.2 Hz, 1H), 7.70 (dd, J=8.7, 2.3 Hz, 1H), 7.51 (d, J=7.5 Hz, 2H), 7.33 (d, J=7.9 Hz, 2H), 7.22 (d, J=8.0 Hz, 2H), 6.86 (d, J=8.9 Hz, 1H), 6.78 (s, 0H), 4.96 (t, J=7.6 Hz, 2H), 4.79 (s, 1H), 4.54 (s, 1H), 4.43 (d, J=6.3 Hz, 1H), 4.35 (d, J=13.9 Hz, 2H), 4.15 (s, 5H), 3.99 (d, J=13.1 Hz, 1H), 3.74 (s, 1H), 3.69 (s, 4H), 3.65 (s, 3H), 3.38 (d, J=13.9 Hz, 2H), 3.34 (s, 1H), 3.00-2.75 (m, 2H), 2.51 (dq, J=8.5, 4.9, 4.3 Hz, 1H), 2.27-2.18 (m, 2H), 2.08 (d, J=8.6 Hz, 2H), 1.36-1.30 (m, 2H), 1.19-1.13 (m, 6H), 1.12 (s, 3H), 0.85 (s, 10H). 19F NMR (376 MHz, Methanol-d4) δ -77.28, -77.92, -113.11.

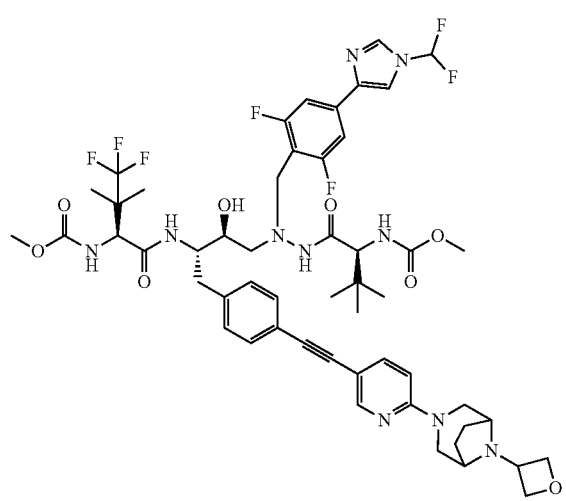 [SMILES: COC(=O)N[C@H](C(=O)NN(Cc1c(F)cc(-c2cn(C(F)F)cn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 77

Methyl ((5S,8S,9S,14S)-11-(4-(1-(difluoromethyl)-1H-imidazol-4-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (77)

Intermediates: I3, P1, and S3. MS (ESI) m/z 1102.0 [M+H]+. 1H NMR (400 MHz, Methanol-d4) δ 8.30 (d, J=2.1 Hz, 1H), 8.15 (s, 1H), 8.00 (s, 1H), 7.74-7.66 (m, 1H), 7.57 (s, 1H), 7.42 (s, 0H), 7.39 (d, J=8.4 Hz, 2H), 7.32 (d, J=7.8 Hz, 2H), 7.21 (d, J=8.0 Hz, 3H), 6.86 (d, J=8.9 Hz, 1H), 4.97 (t, J=7.6 Hz, 3H), 4.80 (d, J=5.2 Hz, 1H), 4.43 (d, J=9.8 Hz, 1H), 4.35 (d, J=14.1 Hz, 2H), 4.19-4.08 (m, 5H), 3.96 (d, J=13.2 Hz, 1H), 3.76 (s, 1H), 3.69 (s, 4H), 3.65 (s, 3H), 3.38 (d, J=13.9 Hz, 3H), 2.90 (d, J=8.1 Hz, 2H), 2.81 (s, 1H), 2.22 (s, 2H), 2.08 (d, J=8.7 Hz, 2H), 1.13 (d, J=14.1 Hz, 8H), 0.86 (s, 12H). 19F NMR (376 MHz, Methanol-d4) δ -77.36, -77.93, -94.99 (d, J=60.0 Hz), -115.00

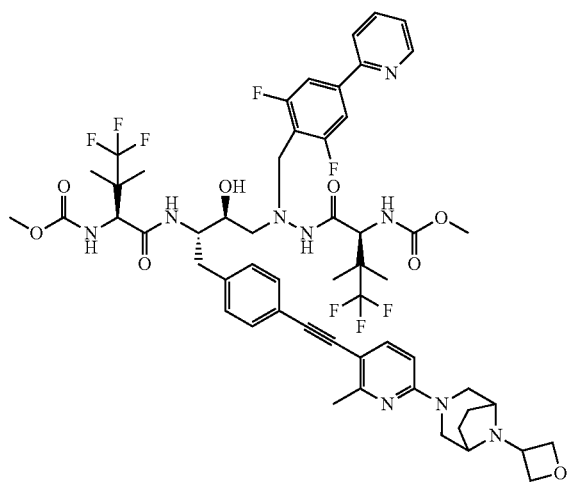 [SMILES: COC(=O)N[C@H](C(=O)N[C@@H](Cc1ccc(C#Cc2ccc(N3CC4CCC(C3)N4C3COC3)nc2C)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]

EXAMPLE 78

Methyl ((5S,8S,9S,14S)-11-(2,6-difluoro-4-(pyridin-2-yl)benzyl)-16,16,16-trifluoro-9-hydroxy-15,15-dimethyl-8-(4-((2-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (78)

Intermediates: I2, P28, and S45. MS (ESI) m/z 1131.0 [M+H]$^+$. $^1$H NMR (400 MHz, Methanol-d4) δ 8.65 (d, J=5.0 Hz, 1H), 8.14 (d, J=9.3 Hz, 1H), 7.98-7.85 (m, 2H), 7.61 (t, J=8.1 Hz, 3H), 7.47-7.38 (m, 1H), 7.33 (d, J=7.8 Hz, 3H), 7.22 (d, J=8.0 Hz, 2H), 7.09 (d, J=9.9 Hz, 1H), 6.77 (d, J=9.8 Hz, 1H), 6.67 (d, J=8.7 Hz, 1H), 4.96 (t, J=7.6 Hz, 2H), 4.42 (dd, J=25.4, 11.7 Hz, 2H), 4.33-4.27 (m, 1H), 4.22-4.10 (m, 4H), 3.98 (d, J=13.0 Hz, 1H), 3.73 (s, 1H), 3.68 (s, 4H), 3.63 (s, 3H), 3.35 (d, J=14.0 Hz, 2H), 2.97-2.86 (m, 3H), 2.84-2.75 (m, 1H), 2.56 (s, 4H), 2.25-2.16 (m, 2H), 2.13-2.01 (m, 2H), 1.28 (d, J=8.8 Hz, 0H), 1.16 (d, J=2.7 Hz, 7H), 1.13 (s, 4H), 1.03 (s, 3H). $^{19}$F NMR (376 MHz, Methanol-d4) δ −77.35, −77.68, −114.72.

EXAMPLE 79

Methyl ((5S,8S,9S,14S)-11-(4-(1-(difluoromethyl)-1H-imidazol-4-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (79)

Intermediates: I2, P1, and S3. MS (ESI) m/z 1156.0 [M+H]$^+$. $^1$H NMR (400 MHz, Methanol-d4) δ 8.32-8.28 (m, 1H), 8.15 (d, J=1.2 Hz, 1H), 8.13 (s, 0H), 8.00 (d, J=1.3 Hz, 1H), 7.73 (s, 0H), 7.70 (dd, J=8.8, 2.3 Hz, 1H), 7.58 (s, 1H), 7.43 (s, 0H), 7.39 (d, J=8.4 Hz, 2H), 7.33 (d, J=7.8 Hz, 2H), 7.22 (d, J=8.0 Hz, 2H), 7.12 (d, J=9.8 Hz, 1H), 6.86 (d, J=8.9 Hz, 1H), 6.77 (d, J=10.0 Hz, 0H), 4.97 (t, J=7.6 Hz, 2H), 4.82-4.78 (m, 2H), 4.53 (s, 1H), 4.44 (d, J=6.5 Hz, 1H), 4.39-4.28 (m, 3H), 4.13 (d, J=15.7 Hz, 4H), 3.94 (d, J=13.3 Hz, 1H), 3.69 (s, 3H), 3.67 (s, 3H), 3.38 (d, J=13.9 Hz, 2H), 2.97-2.72 (m, 6H), 2.27-2.19 (m, 2H), 2.08 (d, J=8.6 Hz, 2H), 1.21 (t, J=7.3 Hz, 4H), 1.16 (d, J=8.4 Hz, 6H), 1.11 (s, 3H), 1.03 (s, 3H). $^{19}$F NMR (376 MHz, Methanol-d4) δ −74.51, −76.39, −77.39, −77.71, −77.89, −94.98 (d, J=60.0 Hz), −97.37 (d, J=59.1 Hz), −115.13

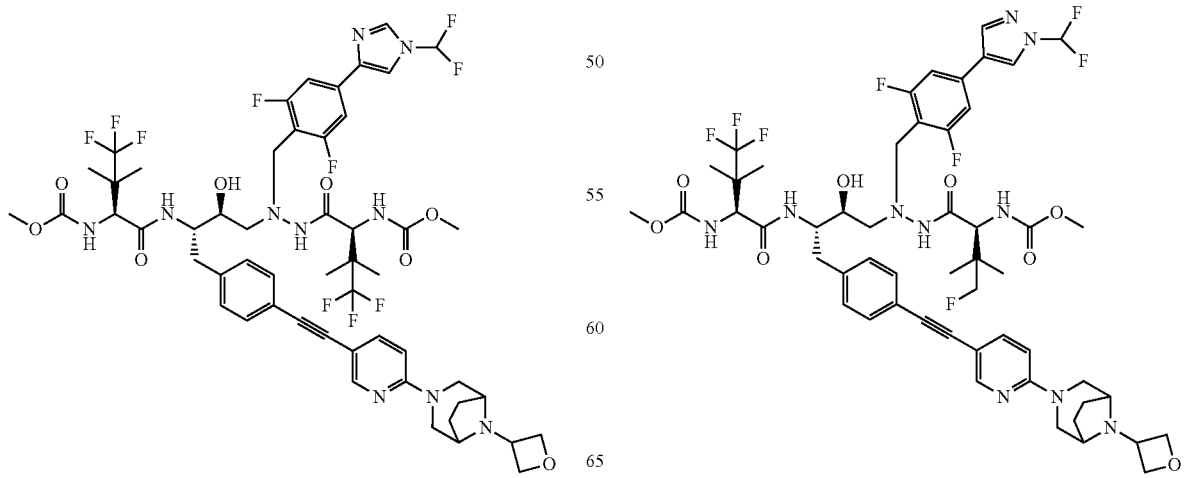

EXAMPLE 80

Methyl ((5S,8S,9S,14S)-11-(4-(1-(difluoromethyl)-1H-pyrazol-4-yl)-2,6-difluorobenzyl)-16-fluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (80)

Intermediates: I6, P7, and S3. MS (ESI) m/z 1119.5 [M+H]$^+$. $^1$H NMR (400 MHz, Methanol-d4) δ 8.54 (d, J=0.7 Hz, 1H), 8.32-8.27 (m, 1H), 8.17 (d, J=9.4 Hz, 1H), 8.12 (s, 1H), 7.88-7.73 (m, 0H), 7.70 (dd, J=8.8, 2.3 Hz, 1H), 7.65 (s, 0H), 7.51 (s, 1H), 7.38-7.30 (m, 2H), 7.24 (dd, J=16.7, 8.2 Hz, 4H), 6.86 (d, J=9.0 Hz, 1H), 6.81 (d, J=9.9 Hz, 1H), 4.96 (dd, J=8.1, 7.0 Hz, 2H), 4.84-4.77 (m, 2H), 4.47-4.41 (m, 1H), 4.36 (d, J=13.7 Hz, 2H), 4.22 (d, J=9.2 Hz, 1H), 4.18-4.03 (m, 5H), 4.00 (s, 1H), 3.98-3.91 (m, 2H), 3.71 (s, 0H), 3.69 (s, 3H), 3.66 (s, 3H), 3.37 (d, J=13.8 Hz, 2H), 3.04 (q, J=7.4 Hz, 1H), 2.99 (d, J=0.5 Hz, 0H), 2.90 (d, J=9.1 Hz, 2H), 2.86 (d, J=0.7 Hz, 0H), 2.79 (d, J=9.6 Hz, 2H), 2.28-2.19 (m, 2H), 2.11-2.02 (m, 2H), 1.29 (t, J=7.3 Hz, 1H), 1.13 (d, J=10.8 Hz, 6H), 1.02 (t, J=7.4 Hz, 0H), 0.93-0.84 (m, 6H). $^{19}$F NMR (377 MHz, Methanol-d4) δ -77.38, -77.88, -96.88 (d, J=59.7 Hz), -114.92

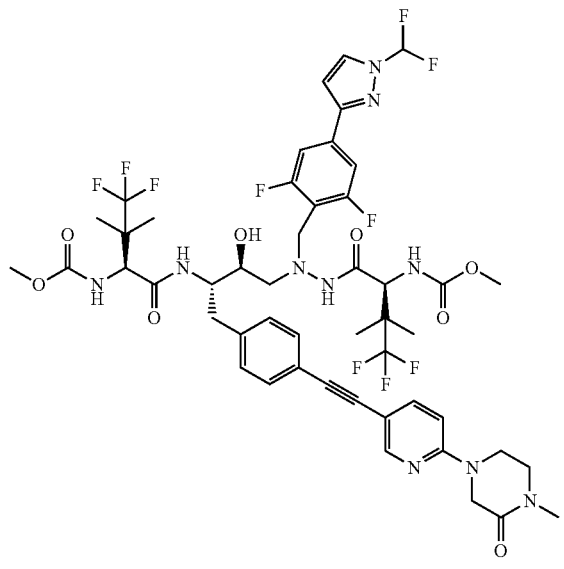

EXAMPLE 81

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(4-methyl-3-oxopiperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (81)

Intermediates: I2, P4, and S47. MS (ESI) m/z 1102.9 [M+H]$^+$. $^1$H NMR (400 MHz, Methanol-d4) δ 8.25-8.21 (m, 1H), 8.16 (d, J=9.3 Hz, 1H), 8.10 (d, J=2.8 Hz, 1H), 7.77 (dd, J=9.0, 2.3 Hz, 1H), 7.53 (s, 1H), 7.45 (d, J=8.2 Hz, 2H), 7.34 (d, J=8.0 Hz, 2H), 7.23 (d, J=8.0 Hz, 2H), 7.13 (d, J=9.9 Hz, 1H), 6.98-6.91 (m, 2H), 6.80 (d, J=9.9 Hz, 1H), 4.48-4.41 (m, 1H), 4.36-4.27 (m, 1H), 4.20 (s, 2H), 4.14 (d, J=13.0 Hz, 2H), 3.96 (s, 1H), 3.95-3.87 (m, 3H), 3.73 (s, 2H), 3.68 (d, J=11.7 Hz, 6H), 3.60-3.51 (m, 2H), 3.04 (s, 3H), 2.94-2.84 (m, 3H), 2.84-2.73 (m, 1H), 1.20-1.08 (m, 9H), 1.03 (s, 3H). $^{19}$F NMR (377 MHz, Methanol-d4) δ -77.38, -77.71, -96.96 (dd, J=59.8, 19.5 Hz), -114.92.

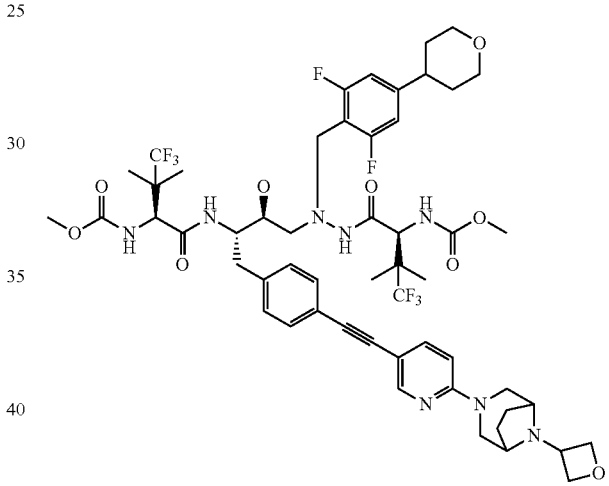

EXAMPLE 82

Methyl ((5S,8S,9S,14S)-11-(2,6-difluoro-4-(tetrahydro-2H-pyran-4-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (82)

Intermediates: I2, P33, and S3. MS (ESI) m/z 1123.1 [M+H]$^+$. $^1$H NMR (400 MHz, Methanol-d4) δ 8.30 (dd, J=2.4, 0.7 Hz, 1H), 8.16 (d, J=9.4 Hz, 1H), 7.70 (dd, J=8.8, 2.3 Hz, 1H), 7.33 (d, J=7.9 Hz, 2H), 7.21 (d, J=8.3 Hz, 2H), 6.92-6.71 (m, 3H), 4.97 (dd, J=8.1, 7.2 Hz, 2H), 4.83-4.74 (m, 2H), 4.58-4.23 (m, 4H), 4.17-3.96 (m, 8H), 3.90 (d, J=13.4 Hz, 1H), 3.74-3.58 (m, 8H), 3.54 (td, J=11.2, 3.9 Hz, 2H), 3.39 (d, J=13.8 Hz, 2H), 3.03-2.60 (m, 5H), 2.36-2.17 (m, 2H), 2.20-2.03 (m, 4H), 1.93-1.83 (m, 1H), 1.80-1.48 (m, 5H), 1.29 (d, J=3.8 Hz, 1H), 1.20-1.05 (m, 11H), 0.95 (d, J=41.7 Hz, 4H).

247

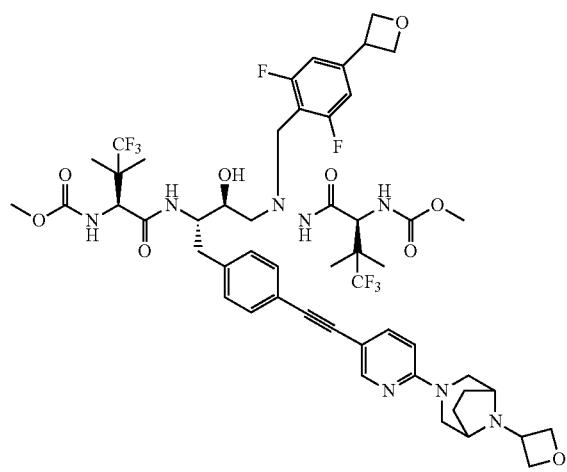

248

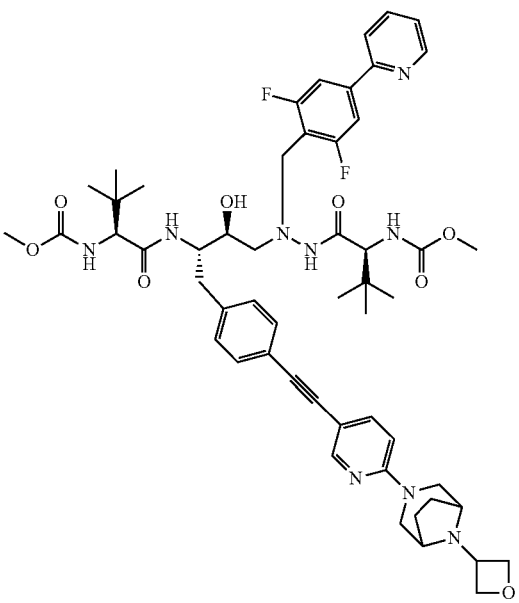 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccccn2)cc1F)NC(=O)[C@@H](NC(=O)OC)C(C)(C)C)C(C)(C)C]

EXAMPLE 83

Methyl ((5S,8S,9S,14S)-11-(2,6-difluoro-4-(oxetan-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (83)

Intermediates: I2, P32, and S3. MS (ESI) m/z 1095.5 [M+H]$^+$. $^1$H NMR (400 MHz, Methanol-d4) δ 8.28 (dd, J=2.3, 0.7 Hz, 1H), 8.15 (d, J=9.4 Hz, 1H), 7.69 (dd, J=8.8, 2.3 Hz, 1H), 7.32 (d, J=8.0 Hz, 2H), 7.20 (d, J=8.1 Hz, 2H), 6.99 (d, J=8.3 Hz, 2H), 6.92-6.70 (m, 2H), 5.05 (dd, J=8.3, 6.1 Hz, 3H), 4.95 (dd, J=8.2, 7.0 Hz, 3H), 4.80 (dd, J=8.0, 4.8 Hz, 3H), 4.67 (t, J=6.3 Hz, 2H), 4.50-4.17 (m, 4H), 4.14 (d, J=4.3 Hz, 3H), 3.68 (d, J=1.5 Hz, 7H), 3.38 (dd, J=14.2, 1.7 Hz, 3H), 3.00-2.68 (m, 2H), 2.06 (d, J=9.0 Hz, 1H), 1.73 (d, J=7.2 Hz, 0H), 1.64-1.49 (m, 1H), 1.42-1.25 (m, 25H), 1.17-1.05 (m, 11H), 1.01 (s, 3H), 0.96 (d, J=6.6 Hz, 2H), 0.92-0.80 (m, 24H).

EXAMPLE 84

Methyl ((5S,8S,9S,14S)-5-(tert-butyl)-11-(2,6-difluoro-4-(pyridin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate (84)

Intermediates: I1, P28, and S3. MS (ESI) m/z 1009.35 [M+H]$^+$. $^1$H NMR (400 MHz, Methanol-d$_4$) δ 8.65 (d, J=4.9 Hz, 1H), 8.34-8.25 (m, 1H), 8.01-7.87 (m, 2H), 7.83 (d, J=9.4 Hz, 1H), 7.70 (dd, J=8.8, 2.3 Hz, 1H), 7.59 (d, J=8.6 Hz, 2H), 7.44 (dd, J=7.0, 5.0 Hz, 1H), 7.33 (d, J=7.8 Hz, 2H), 7.24 (d, J=7.9 Hz, 2H), 6.86 (d, J=8.7 Hz, 1H), 4.96 (t, J=7.6 Hz, 2H), 4.84-4.79 (m, 1H), 4.53 (s, 1H), 4.35 (d, J=13.9 Hz, 2H), 4.15 (s, 6H), 4.00 (d, J=13.1 Hz, 1H), 3.90 (s, 1H), 3.80-3.58 (m, 9H), 3.40 (s, 1H), 3.03-2.80 (m, 5H), 2.34-2.20 (m, 3H), 2.07 (d, J=8.6 Hz, 2H), 0.87 (d, J=24.4 Hz, 19H).

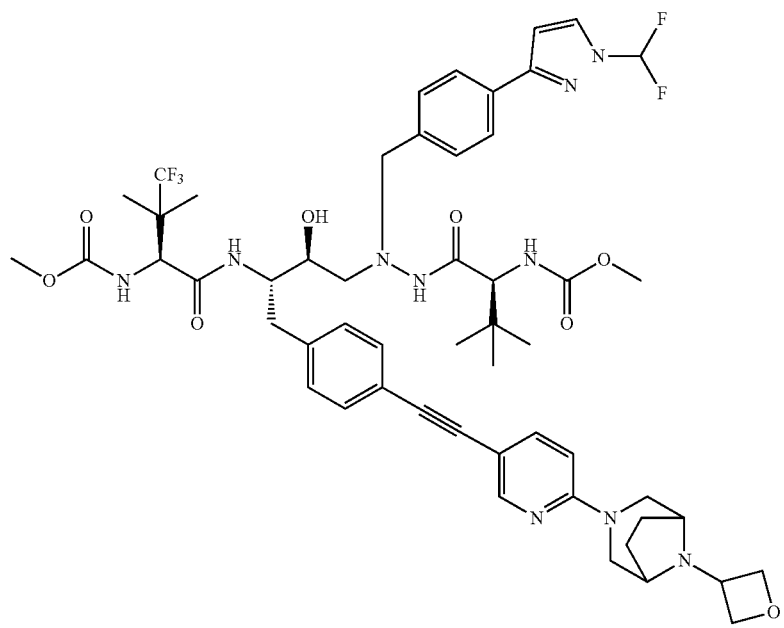 [SMILES: COC(=O)N[C@H](C(=O)NN(Cc1ccc(C(=N)/C=C\NC(F)F)cc1)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 85

Methyl ((5S,8S,9S,14S)-11-(4-(1-(difluoromethyl)-1H-pyrazol-3-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (85)

Intermediates: I3, P6, and S3. MS (ESI) m/z 1066.1 [M+H]$^+$. $^1$H NMR (400 MHz, Methanol-d$_4$) δ 8.25 (d, J=2.3 Hz, 1H), 8.13-8.04 (m, 2H), 7.83-7.74 (m, 4H), 7.47 (d, J=8.2 Hz, 3H), 7.35-7.30 (m, 3H), 7.23 (d, J=8.2 Hz, 3H), 6.99 (d, J=9.1 Hz, 2H), 6.86 (d, J=2.7 Hz, 1H), 4.58-4.49 (m, 2H), 4.35 (t, J=4.9 Hz, 1H), 4.31-4.23 (m, 3H), 4.17 (d, J=3.8 Hz, 3H), 4.03-3.89 (m, 2H), 3.81 (s, 1H), 3.67 (s, 5H), 3.62-3.49 (m, 6H), 2.95-2.74 (m, 3H), 2.30-2.23 (m, 2H), 2.07 (d, J=8.8 Hz, 2H), 1.02 (d, J=34.0 Hz, 6H), 0.74 (s, 10H). $^{19}$F NMR (377 MHz, Methanol-d$_4$) δ −77.58, −96.21 (d, J=59.7 Hz).

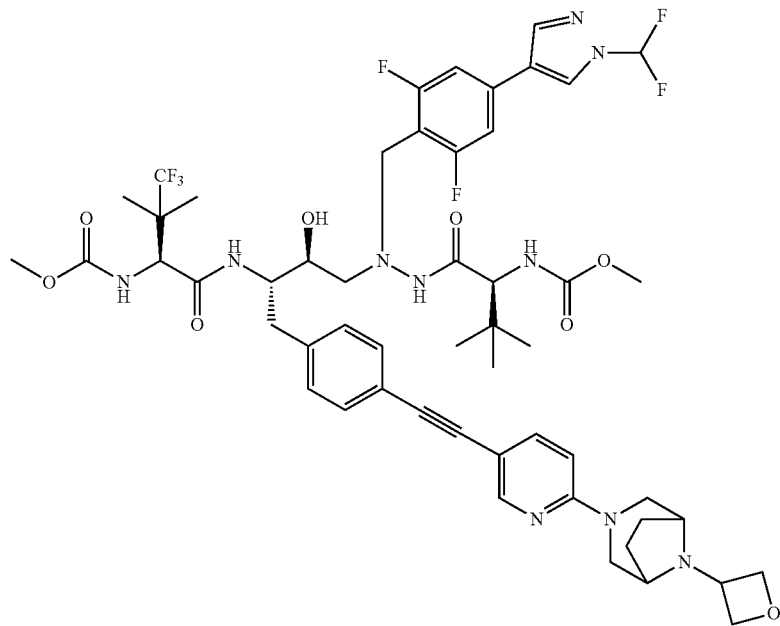 [SMILES: COC(=O)N[C@H](C(=O)NN(Cc1c(F)cc(/C(C=N)=C/NC(F)F)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 86

Methyl ((5S,8S,9S,14S)-11-(4-(1-(difluoromethyl)-1H-pyrazol-4-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (86)

Intermediates: I3, P7, and S3. MS (ESI) m/z 1066.1 [M+H]$^+$. $^1$H NMR (400 MHz, Methanol-$d_4$) δ 8.53 (d, J=0.7 Hz, 1H), 8.16 (d, J=9.3 Hz, 1H), 8.11 (d, J=0.6 Hz, 1H), 7.72-7.69 (m, 1H), 7.37-7.30 (m, 3H), 7.27-7.19 (m, 5H), 6.87 (dd, J=9.1, 0.8 Hz, 1H), 6.80 (d, J=9.9 Hz, 1H), 4.98-4.94 (m, 2H), 4.84-4.81 (m, 2H), 4.46-4.41 (m, 1H), 4.38-4.31 (m, 2H), 4.18-4.07 (m, 5H), 3.95 (d, J=13.2 Hz, 1H), 3.76 (s, 1H), 3.67 (d, J=15.6 Hz, 7H), 3.40 (dd, J=14.2, 1.8 Hz, 2H), 2.93-2.87 (m, 2H), 2.80 (s, 2H), 2.26-2.20 (m, 2H), 2.10-2.04 (m, 2H), 1.13 (d, J=11.9 Hz, 7H), 0.86 (s, 11H). $^{19}$F NMR (377 MHz, Methanol-$d_4$) δ −78.10, −96.87 (d, J=59.7 Hz), −114.89.

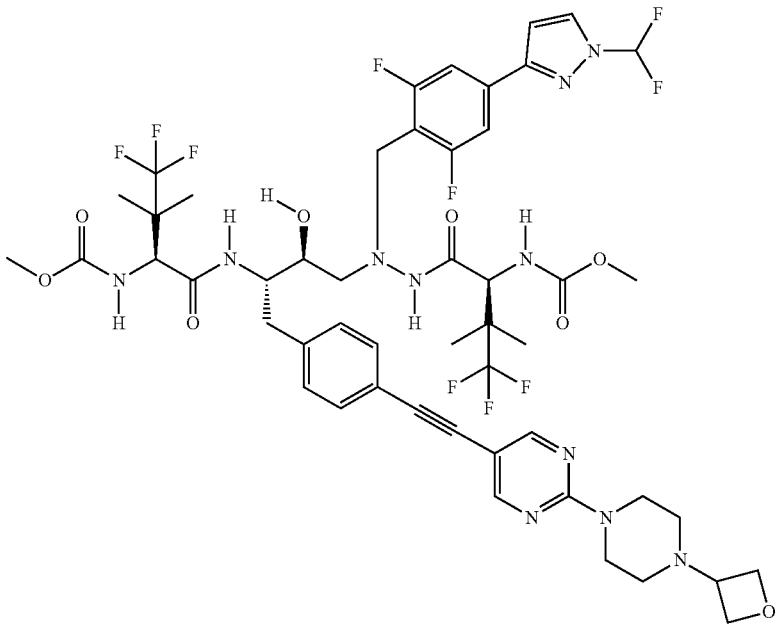 [SMILES: COC(=O)N[C@H](C(=O)N[C@@H](Cc1ccc(C#Cc2cnc(N3CCN(C4COC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 87 methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(4-(oxetan-3-yl)piperazin-1-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (87)

Intermediates: I2, P4, and S49. MS (ESI) m/z 1130.9 [M+H]$^+$. $^1$H NMR (400 MHz, Methanol-d4) δ 8.52 (s, 1H), 8.20-8.01 (m, 1H), 7.67 (s, 0H), 7.52 (s, 0H), 7.44 (d, J=8.2 Hz, 1H), 7.40-7.29 (m, 1H), 7.23 (d, J=8.2 Hz, 1H), 7.09 (d, J=9.9 Hz, 0H), 6.93 (d, J=2.8 Hz, 1H), 6.77 (d, J=9.9 Hz, 0H), 4.90 (t, J=7.7 Hz, 1H), 4.52-4.27 (m, 2H), 4.14 (d, J=13.5 Hz, 2H), 3.94 (d, J=13.1 Hz, 1H), 3.67 (d, J=10.3 Hz, 4H), 2.98-2.72 (m, 2H), 1.28-1.06 (m, 5H), 1.02 (s, 1H).

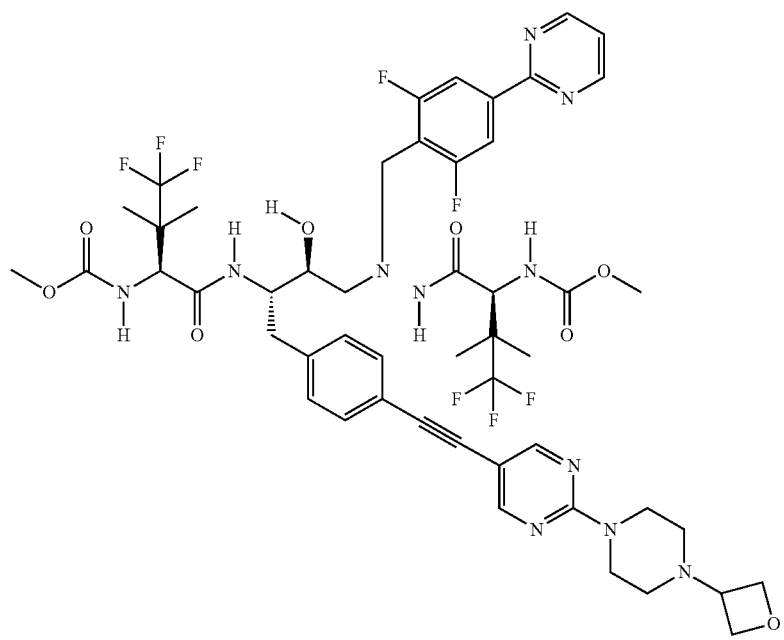

EXAMPLE 88

Methyl ((5S,8S,9S,14S)-11-(2,6-difluoro-4-(pyrimidin-2-yl)benzyl)-16,16,16-trifluoro-9-hydroxy-15,15-dimethyl-8-(4-((2-(4-(oxetan-3-yl)piperazin-1-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (88)

Intermediates: I2, P16, and S49. MS (ESI) m/z 1092.9 [M+H]$^+$. $^1$H NMR (400 MHz, Methanol-d4) δ 8.86 (d, J=4.8 Hz, 1H), 8.52 (s, 1H), 8.14 (d, J=9.3 Hz, 0H), 7.97 (d, J=8.6 Hz, 1H), 7.40 (t, J=4.9 Hz, 1H), 7.34 (d, J=7.9 Hz, 1H), 7.23 (d, J=8.2 Hz, 1H), 7.08 (d, J=10.0 Hz, 0H), 6.78 (d, J=9.9 Hz, 0H), 4.90 (t, J=7.7 Hz, 1H), 4.51-4.26 (m, 2H), 4.25-4.09 (m, 2H), 3.98 (d, J=13.2 Hz, 1H), 3.67 (d, J=8.1 Hz, 3H), 3.26 (s, 2H), 2.99-2.75 (m, 2H), 2.02 (s, 0H), 1.24-1.07 (m, 5H), 1.02 (s, 1H).

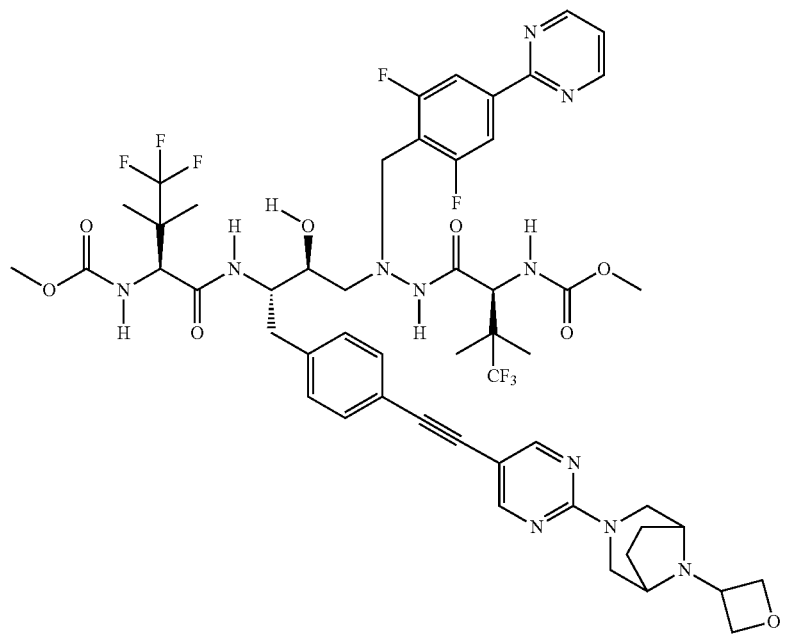 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ncccn2)cc1F)NC(=O)[C@@H](NC(=O)OC)C(C)(C)C(F)(F)F)C(C)(C)C(F)(F)F]

EXAMPLE 89

Methyl ((5S,8S,9S,14S)-11-(2,6-difluoro-4-(pyrimidin-2-yl)benzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl) carbamate (89)

Intermediates: I2, P16, and S7. MS (ESI) m/z 1119.3 [M+H]$^+$. $^1$H NMR (400 MHz, Methanol-d4) δ 8.86 (d, J=4.8 Hz, 1H), 8.52 (s, 1H), 8.15 (d, J=9.4 Hz, 1H), 7.97 (d, J=8.6 Hz, 1H), 7.40 (t, J=4.9 Hz, 1H), 7.34 (d, J=7.9 Hz, 1H), 7.23 (d, J=8.0 Hz, 1H), 7.09 (d, J=9.9 Hz, 0H), 6.78 (d, J=9.9 Hz, 0H), 4.96 (t, J=7.6 Hz, 1H), 4.82-4.70 (m, 2H), 4.43 (d, J=9.9 Hz, 0H), 4.30 (d, J=10.0 Hz, 1H), 4.24-4.06 (m, 2H), 3.98 (d, J=13.1 Hz, 1H), 3.68 (d, J=8.7 Hz, 4H), 3.46 (d, J=14.7 Hz, 1H), 2.99-2.70 (m, 2H), 2.27-2.10 (m, 1H), 1.99 (d, J=8.7 Hz, 1H), 1.19-1.05 (m, 5H), 1.02 (s, 2H).

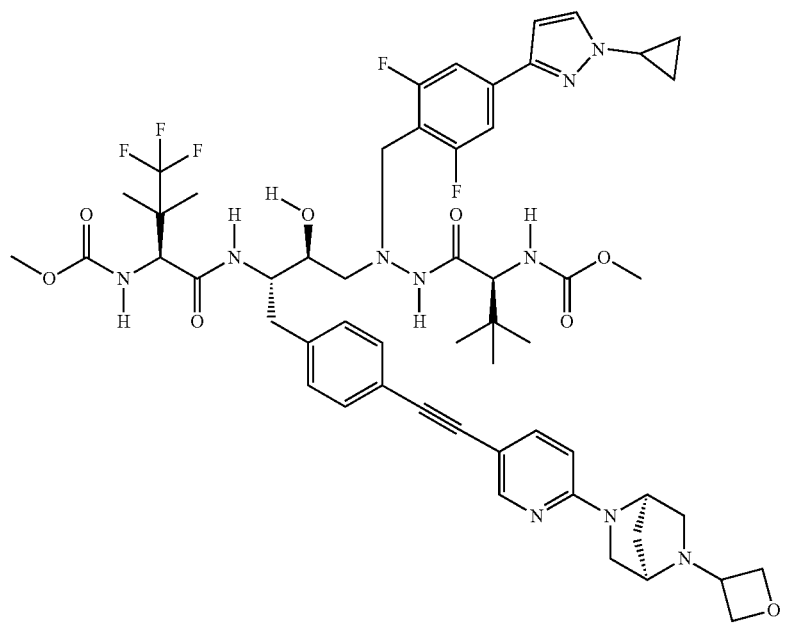 [SMILES: COC(=O)N[C@H](C(=O)NN(Cc1c(F)cc(-c2ccn(C3CC3)n2)cc1F)C[C@H](O)[C@H](Cc1ccc(C#Cc2ccc(N3C[C@H]4C[C@@H]3CN4C3COC3)nc2)cc1)NC(=O)[C@@H](NC(=O)OC)C(C)(C)C(F)(F)F)C(C)(C)C]

EXAMPLE 90

Methyl ((5S,8S,9S,14S)-11-(4-(1-cyclopropyl-1H-pyrazol-3-yl)-2,6-difluorobenzyl)-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (90)

Intermediates: I3, P13, and S6. MS (ESI) m/z 1078.1 [M+H]$^+$. 1H NMR (400 MHz, Methanol-d4) δ 8.25 (d, J=2.2 Hz, 1H), 8.15 (d, J=9.4 Hz, 1H), 7.70 (dd, J=11.1, 2.3 Hz, 2H), 7.43-7.27 (m, 4H), 7.21 (d, J=7.9 Hz, 2H), 6.77 (d, J=9.9 Hz, 0H), 6.73-6.58 (m, 2H), 5.05 (s, 1H), 5.00-4.88 (m, 2H), 4.71 (dd, J=8.4, 4.6 Hz, 1H), 4.64-4.54 (m, 2H), 4.47 (d, J=31.7 Hz, 2H), 4.10 (d, J=13.2 Hz, 2H), 3.95 (d, J=13.2 Hz, 1H), 3.82-3.56 (m, 13H), 3.33 (s, 1H), 2.89 (d, J=8.9 Hz, 2H), 2.33 (s, 2H), 1.21-0.99 (m, 11H), 0.86 (s, 10H).

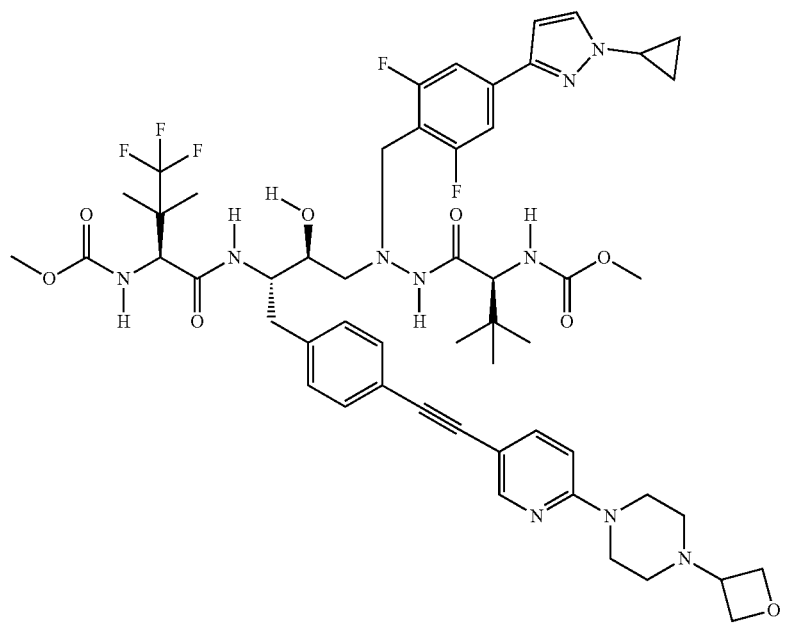 [SMILES: COC(=O)N[C@H](C(=O)NN(Cc1c(F)cc(-c2ccn(C3CC3)n2)cc1F)C[C@H](O)[C@H](Cc1ccc(C#Cc2ccc(N3CCN(C4COC4)CC3)nc2)cc1)NC(=O)[C@@H](NC(=O)OC)C(C)(C)C(F)(F)F)C(C)(C)C]
EXAMPLE 91
Methyl ((5S,8S,9S,14S)-11-(4-(1-cyclopropyl-1H-pyrazol-3-yl)-2,6-difluorobenzyl)-9-hydroxy-15,15-dimethyl-8-(4-((6-(4-(oxetan-3-yl)piperazin-1-yl)pyridin-3-yl)ethynyl) benzyl)-3,6,13-trioxo-5-(1,1,1-trifluoro-2-methylpropan-2-yl)-2-oxa-4,7,11,12-tetraazahexadecan-14-yl)carbamate (91)
Intermediates: I3, P13, and S48. MS (ESI) m/z 1066.6 [M+H]$^+$. $^1$H NMR (400 MHz, Methanol-d4) δ 8.30 (d, J=2.2 Hz, 1H), 8.15 (d, J=9.4 Hz, 1H), 7.79-7.63 (m, 2H), 7.33 (dd, J=8.2, 5.2 Hz, 4H), 7.21 (d, J=8.0 Hz, 2H), 6.95 (d, J=8.9 Hz, 1H), 6.77 (d, J=10.0 Hz, 1H), 6.63 (d, J=2.4 Hz, 1H), 4.91 (t, J=7.7 Hz, 2H), 4.54-4.33 (m, 2H), 4.18-4.02 (m, 2H), 4.03-3.85 (m, 5H), 3.83-3.58 (m, 10H), 2.89 (d, J=9.3 Hz, 2H), 1.27 (d, J=13.9 Hz, 1H), 1.21-1.00 (m, 12H), 0.86 (s, 10H).

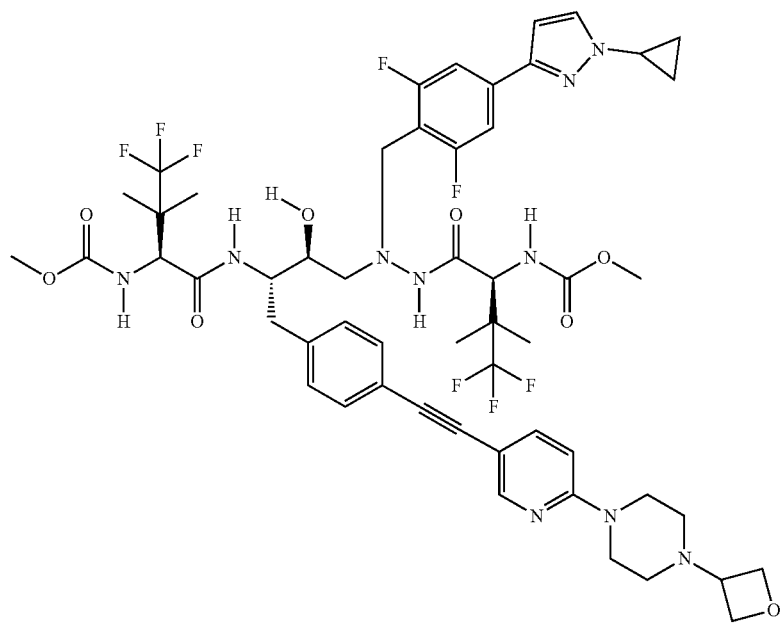 [SMILES: COC(=O)N[C@H](C(=O)N[C@@H](Cc1ccc(C#Cc2ccc(N3CCN(C4COC4)CC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 92

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (92)

Intermediates: I2, P13, and S48. MS (ESI) m/z 1119.3 [M+H]$^+$. $^1$H NMR (400 MHz, Methanol-d4) δ 8.29 (d, J=2.2 Hz, 1H), 8.14 (d, J=9.4 Hz, 1H), 7.70 (dd, J=9.2, 2.3 Hz, 2H), 7.64-7.51 (m, 0H), 7.33 (dd, J=8.4, 4.0 Hz, 5H), 7.21 (d, J=8.0 Hz, 2H), 7.11 (d, J=9.8 Hz, 1H), 6.94 (d, J=8.9 Hz, 1H), 6.76 (d, J=10.0 Hz, 1H), 6.63 (d, J=2.4 Hz, 1H), 5.48 (s, 1H), 4.91 (dd, J=8.3, 7.0 Hz, 3H), 4.51-4.38 (m, 2H), 4.31 (d, J=9.9 Hz, 1H), 4.13 (dd, J=15.3, 11.1 Hz, 3H), 3.93 (d, J=13.0 Hz, 2H), 3.79-3.62 (m, 10H), 3.58-3.43 (m, 0H), 2.99-2.66 (m, 5H), 1.27 (d, J=13.9 Hz, 1H), 1.21-0.97 (m, 19H).

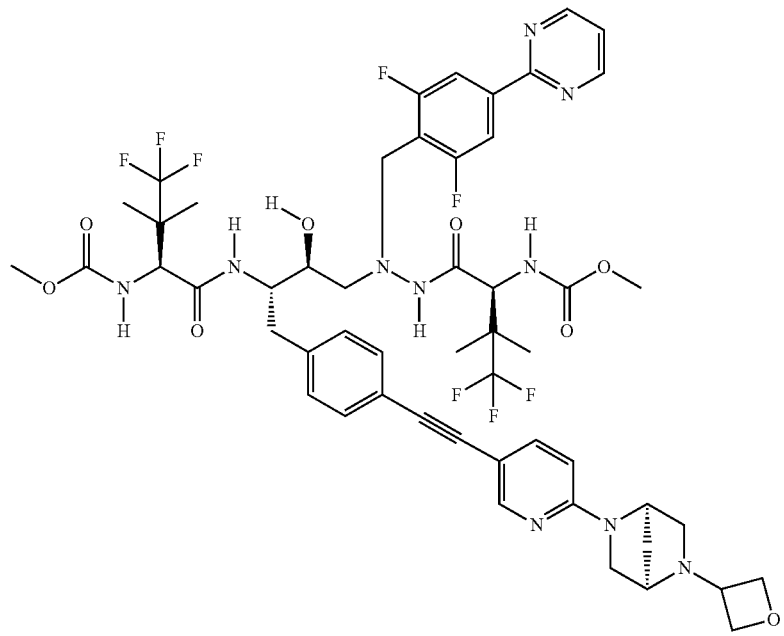 [SMILES: COC(=O)N[C@H](C(=O)N[C@@H](Cc1ccc(C#Cc2ccc(N3C[C@H]4C[C@@H]3CN4C3COC3)nc2)cc1)[C@@H](O)CN(Cc1c(F)cc(-c2ncccn2)cc1F)NC(=O)[C@@H](NC(=O)OC)C(C)(C)C(F)(F)F)C(C)(C)C(F)(F)F]

EXAMPLE 93

Methyl ((5S,8S,9S,14S)-11-(2,6-difluoro-4-(pyrimidin-2-yl)benzyl)-16,16,16-trifluoro-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (93)

Intermediates: I2, P16, and S6. MS (ESI) m/z 1103.1 [M+H]$^+$. $^1$H NMR (400 MHz, Methanol-d4) δ 8.86 (d, J=4.8 Hz, 1H), 8.28-8.20 (m, 0H), 8.14 (d, J=9.4 Hz, 0H), 7.96 (d, J=8.5 Hz, 1H), 7.71 (dd, J=8.8, 2.3 Hz, 1H), 7.40 (t, J=4.9 Hz, 1H), 7.32 (d, J=7.9 Hz, 1H), 7.22 (d, J=8.1 Hz, 1H), 6.74-6.65 (m, 1H), 5.05 (d, J=2.0 Hz, 1H), 5.01-4.90 (m, 1H), 4.72 (dd, J=8.4, 4.8 Hz, 1H), 4.58-4.49 (m, 1H), 4.43 (t, J=5.0 Hz, 0H), 4.40-4.26 (m, 1H), 4.18 (d, J=12.8 Hz, 1H), 3.98 (d, J=13.1 Hz, 1H), 3.87-3.63 (m, 5H), 3.34 (s, 0H), 3.03-2.75 (m, 2H), 2.33 (s, 1H), 1.13 (d, J=14.3 Hz, 5H), 1.02 (s, 2H).

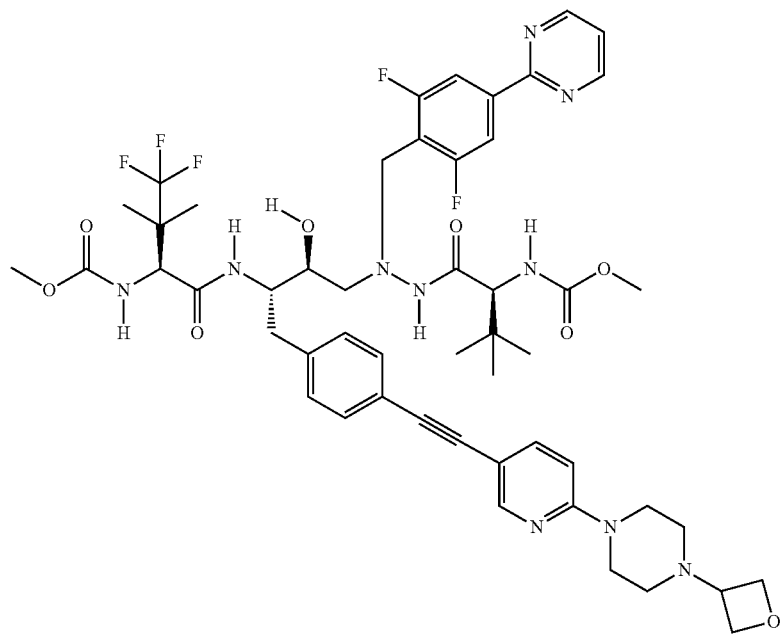 [SMILES: COC(=O)N[C@H](C(=O)NN(Cc1c(F)cc(-c2ncccn2)cc1F)C[C@H](O)[C@H](Cc1ccc(C#Cc2ccc(N3CCN(C4COC4)CC3)nc2)cc1)NC(=O)[C@@H](NC(=O)OC)C(C)(C)C(F)(F)F)C(C)(C)C]

EXAMPLE 94 methyl ((5S,8S,9S,14S)-11-(2,6-difluoro-4-(pyrimidin-2-yl)benzyl)-9-hydroxy-15,15-dimethyl-8-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (94)

Intermediates: I3, P16, and S48. MS (ESI) m/z 1037.6 [M+H]$^+$. $^1$H NMR (400 MHz, Methanol-d4) δ 8.86 (d, J=4.8 Hz, 1H), 8.29 (d, J=2.2 Hz, 0H), 7.97 (d, J=8.9 Hz, 1H), 7.70 (dd, J=8.8, 2.3 Hz, 1H), 7.39 (t, J=4.9 Hz, 1H), 7.32 (d, J=7.8 Hz, 1H), 7.21 (d, J=7.9 Hz, 1H), 6.95 (d, J=8.9 Hz, 1H), 6.77 (d, J=9.9 Hz, 0H), 4.84 (s, 15H), 4.57-4.31 (m, 1H), 4.16 (d, J=14.1 Hz, 1H), 3.98 (d, J=35.4 Hz, 2H), 3.76 (s, 1H), 3.67 (d, J=14.2 Hz, 4H), 3.04-2.69 (m, 2H), 2.02 (s, 1H), 1.27 (d, J=13.9 Hz, 1H), 1.12 (d, J=14.5 Hz, 3H), 0.85 (s, 5H).

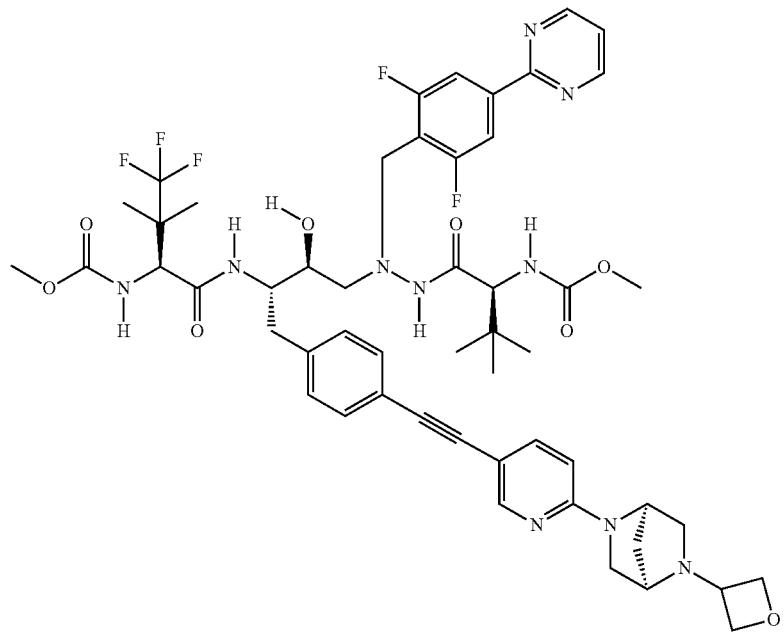 [SMILES: COC(=O)N[C@H](C(=O)NN(Cc1c(F)cc(-c2ncccn2)cc1F)C[C@H](O)[C@H](Cc1ccc(C#Cc2ccc(N3C[C@H]4C[C@@H]3CN4C3COC3)nc2)cc1)NC(=O)[C@@H](NC(=O)OC)C(C)(C)C(F)(F)F)C(C)(C)C]

EXAMPLE 95

Methyl ((5S,8S,9S,14S)-11-(2,6-difluoro-4-(pyrimidin-2-yl)benzyl)-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (95)

Intermediates: I3, P16, and S6. MS (ESI) m/z 1050.0 [M+H]+. $^1$H NMR (400 MHz, Methanol-d4) δ 8.86 (d, J=4.9 Hz, 1H), 8.24 (d, J=2.1 Hz, 0H), 8.15 (d, J=9.3 Hz, 0H), 7.97 (d, J=8.7 Hz, 1H), 7.70 (dd, J=8.8, 2.2 Hz, 1H), 7.39 (t, J=4.9 Hz, 1H), 7.32 (d, J=7.8 Hz, 1H), 7.21 (d, J=7.9 Hz, 1H), 6.78 (d, J=9.8 Hz, 0H), 6.67 (d, J=8.8 Hz, 1H), 5.05 (s, 0H), 4.98-4.85 (m, 1H), 4.71 (dd, J=8.4, 4.7 Hz, 1H), 4.66-4.55 (m, 1H), 4.53-4.41 (m, 1H), 4.16 (d, J=13.7 Hz, 1H), 4.00 (d, J=13.1 Hz, 1H), 3.87-3.61 (m, 6H), 3.30 (p, J=1.6 Hz, 4H), 3.00-2.74 (m, 2H), 2.33 (s, 1H), 1.12 (d, J=14.5 Hz, 3H), 0.85 (s, 5H).

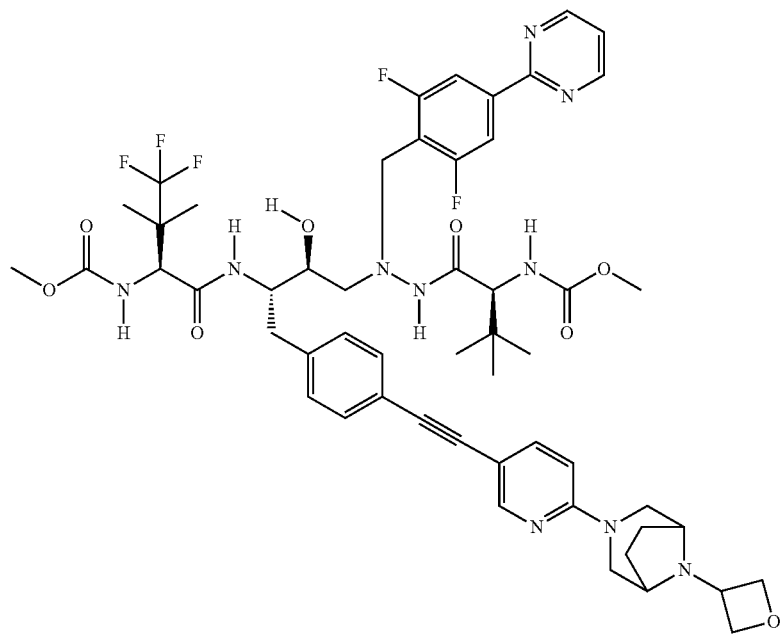 [SMILES: COC(=O)N[C@H](C(=O)NN(Cc1c(F)cc(-c2ncccn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 96

Methyl ((5S,8S,9S,14S)-11-(2,6-difluoro-4-(pyrimidin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (96)

Intermediates: I3, P16, and S3. MS (ESI) m/z 1063.5 [M+H]$^+$. $^1$H NMR (400 MHz, Methanol-d4) δ 8.86 (dd, J=4.9, 0.8 Hz, 1H), 8.29 (d, J=2.2 Hz, 0H), 8.15 (d, J=9.4 Hz, 0H), 7.97 (d, J=8.6 Hz, 1H), 7.69 (dd, J=8.9, 2.3 Hz, 1H), 7.40 (t, J=4.9 Hz, 1H), 7.32 (d, J=7.8 Hz, 1H), 7.21 (d, J=8.0 Hz, 1H), 6.85 (d, J=8.9 Hz, 1H), 6.77 (d, J=10.0 Hz, 0H), 4.96 (t, J=7.6 Hz, 1H), 4.83 (s, 20H), 4.39 (dd, J=34.8, 11.8 Hz, 2H), 4.16 (d, J=14.7 Hz, 2H), 4.01 (d, J=13.1 Hz, 1H), 3.84-3.60 (m, 4H), 3.37 (d, J=13.9 Hz, 1H), 3.01-2.73 (m, 2H), 2.33-2.17 (m, 1H), 2.07 (d, J=8.6 Hz, 1H), 1.12 (d, J=14.3 Hz, 3H), 0.85 (s, 5H).

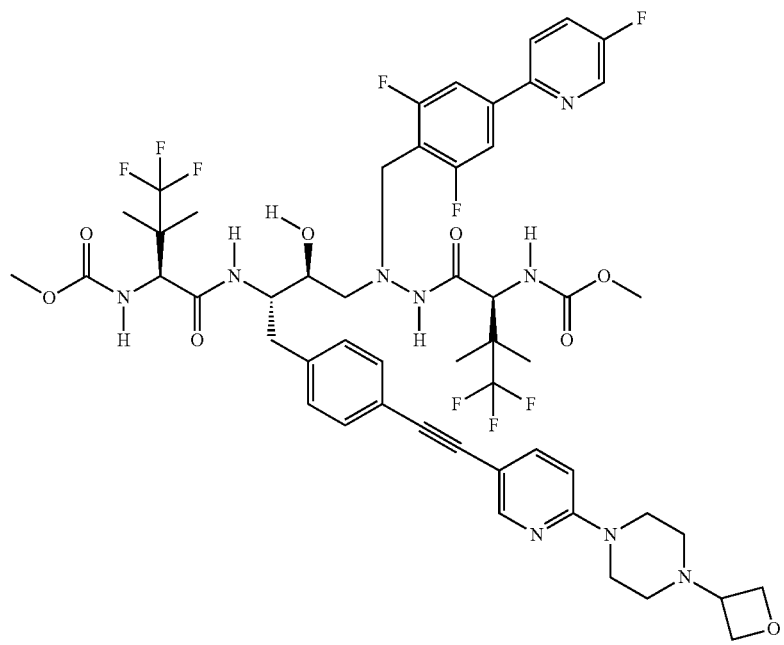 [SMILES: COC(=O)N[C@H](C(=O)N[C@@H](Cc1ccc(C#Cc2ccc(N3CCN(C4COC4)CC3)nc2)cc1)[C@@H](O)CN(Cc1c(F)cc(-c2ccc(F)cn2)cc1F)NC(=O)[C@@H](NC(=O)OC)C(C)(C)C(F)(F)F)C(C)(C)C(F)(F)F]

EXAMPLE 97

Methyl ((5S,8S,9S,14S)-11-(2,6-difluoro-4-(5-fluoropyridin-2-yl)benzyl)-16,16,16-trifluoro-9-hydroxy-15,15-dimethyl-8-(4-((6-(4-(oxetan-3-yl)piperazin-1-yl)pyridin-3-yl)ethynyl) benzyl)-3,6,13-trioxo-5-(1,1,1-trifluoro-2-methylpropan-2-yl)-2-oxa-4,7,11,12-tetraazahexadecan-14-yl)carbamate (97)

Intermediates: I2, P14, and S48. MS (ESI) m/z 1108.4 [M+H]⁺. 1H NMR (400 MHz, Methanol-d4) δ 8.54 (d, J=2.9 Hz, 1H), 8.29 (d, J=2.2 Hz, 1H), 8.14 (d, J=9.3 Hz, 1H), 7.95 (dd, J=8.9, 4.2 Hz, 1H), 7.78-7.51 (m, 4H), 7.32 (d, J=7.8 Hz, 2H), 7.22 (d, J=8.0 Hz, 2H), 7.11 (d, J=10.0 Hz, 1H), 6.94 (d, J=8.9 Hz, 1H), 6.77 (d, J=9.9 Hz, 1H), 4.83 (s, 46H), 4.52-4.25 (m, 3H), 4.16 (d, J=13.4 Hz, 2H), 3.96 (d, J=13.1 Hz, 1H), 3.67 (d, J=15.7 Hz, 7H), 3.26 (s, 5H), 2.97-2.72 (m, 4H), 2.02 (s, 2H), 1.28-1.08 (m, 10H), 1.02 (s, 3H).

EXAMPLE 98

Methyl ((5S,8S,9S,14S)-11-(2,6-difluoro-4-(4-fluoropyridin-2-yl)benzyl)-16,16,16-trifluoro-9-hydroxy-15,15-dimethyl-8-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (98)

Intermediates: I2, P15, and S48. MS (ESI) m/z 1109.1 [M+H]⁺. ¹H NMR (400 MHz, Methanol-d4) δ 8.66 (dd, J=8.6, 5.6 Hz, 1H), 8.34-8.27 (m, 1H), 8.16 (d, J=9.3 Hz, 1H), 7.86 (t, J=8.4 Hz, 1H), 7.80-7.61 (m, 4H), 7.61-7.48 (m, 1H), 7.33 (d, J=7.9 Hz, 2H), 7.28-7.17 (m, 3H), 7.14 (d, J=9.8 Hz, 1H), 6.99-6.92 (m, 1H), 6.79 (d, J=10.0 Hz, 1H), 4.86 (s, 32H), 4.54-4.39 (m, 2H), 4.35-4.26 (m, 1H), 4.17 (d, J=13.1 Hz, 2H), 3.95 (t, J=17.4 Hz, 4H), 3.67 (d, J=16.6 Hz, 7H), 2.98-2.73 (m, 4H), 1.28 (d, J=13.9 Hz, 5H), 1.20-1.08 (m, 10H), 1.03 (s, 3H).

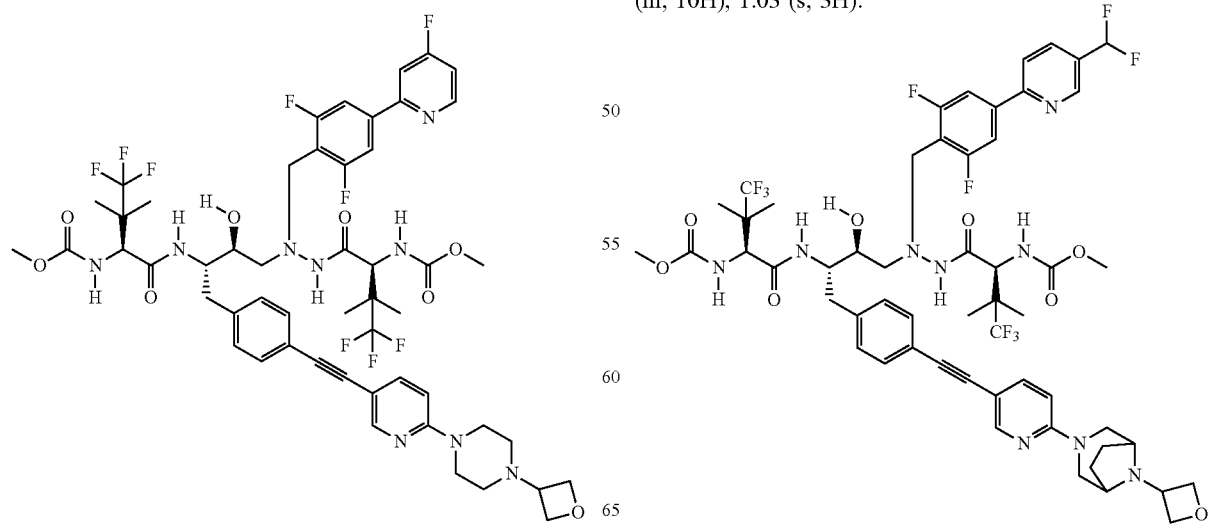

EXAMPLE 99

Methyl ((5S,8S,9S,14S)-11-(4-(5-(difluoromethyl)pyridin-2-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (99)

Intermediates: I2, P35, and S3. MS (ESI) m/z 1167.2 [M+H]⁺. ¹H NMR (400 MHz, Methanol-d₄) δ 8.15 (d, J=9.4 Hz, 1H), 8.10-8.00 (m, 3H), 7.72-7.60 (m, 4H), 7.33 (d, J=7.9 Hz, 2H), 7.22 (d, J=8.0 Hz, 2H), 7.11 (d, J=18.4 Hz, 1H), 6.88-6.75 (m, 3H), 4.96 (t, J=7.6 Hz, 2H), 4.80 (d, J=5.0 Hz, 1H), 4.54 (s, 1H), 4.47-4.42 (m, 1H), 4.33 (dd, J=16.8, 11.9 Hz, 4H), 4.20-4.12 (m, 4H), 3.98 (d, J=13.1 Hz, 1H), 3.67 (d, J=17.6 Hz, 8H), 3.39 (d, J=13.7 Hz, 2H), 2.90 (dd, J=10.5, 7.0 Hz, 3H), 2.84-2.77 (m, 1H), 2.27-2.19 (m, 2H), 2.11-2.04 (m, 2H), 1.18-1.11 (m, 9H), 1.03 (s, 3H).

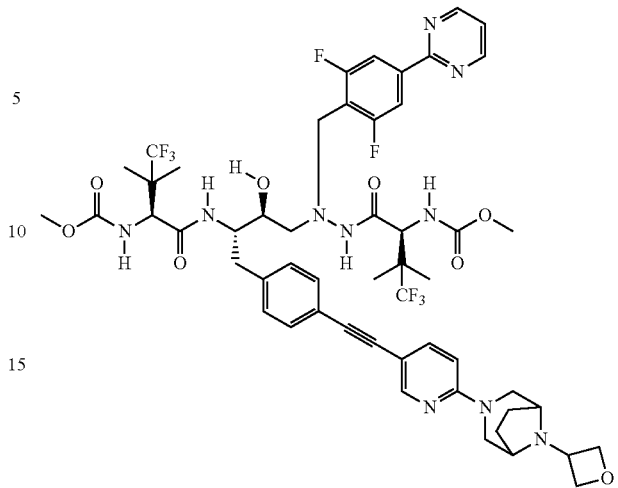

EXAMPLE 100

Methyl ((5S,8S,9S,14S)-11-(4-(6-(difluoromethyl)pyridin-3-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (100)

Intermediates: I2, P45, and S3. MS (ESI) m/z 1165.0 [M+H]⁺. ¹H NMR (400 MHz, Methanol-d₄) δ 8.91 (d, J=1.8 Hz, 1H), 8.31-8.22 (m, 2H), 7.79 (d, J=8.2 Hz, 1H), 7.73-7.61 (m, 2H), 7.34 (dd, J=8.2, 3.3 Hz, 4H), 7.25-7.15 (m, 3H), 6.93-6.84 (m, 2H), 6.77 (s, 1H), 4.96 (t, J=7.6 Hz, 2H), 4.82-4.79 (m, 2H), 4.54 (s, 1H), 4.38-4.28 (m, 4H), 4.16 (s, 4H), 3.98 (d, J=13.2 Hz, 1H), 3.67 (d, J=21.9 Hz, 7H), 3.39 (d, J=13.8 Hz, 2H), 2.96-2.76 (m, 5H), 2.28-2.20 (m, 2H), 2.12-2.04 (m, 2H), 1.23-1.12 (m, 9H), 1.04 (s, 3H).

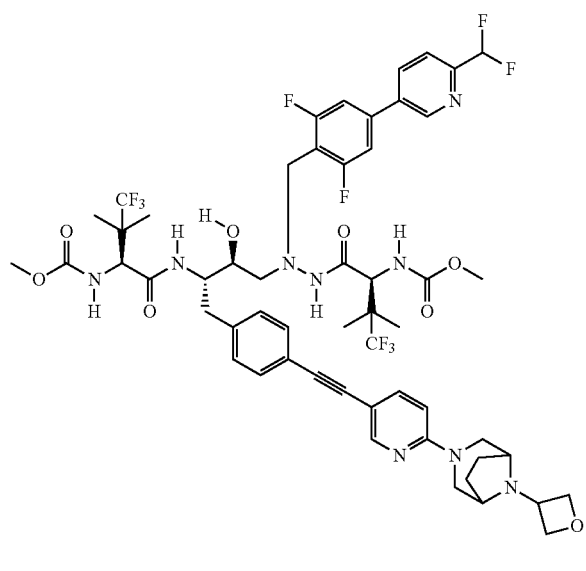 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(C(F)F)nc2)cc1F)NC(=O)[C@@H](NC(=O)OC)C(C)(C)C(F)(F)F)C(C)(C)C(F)(F)F]

EXAMPLE 101

Methyl ((5S,8S,9S,14S)-11-(2,6-difluoro-4-(pyrimidin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (101)

Intermediates: I2, P16, and S3. MS (ESI) m/z 1116.2 [M+H]⁺. ¹H NMR (400 MHz, Methanol-d₄) δ 8.87 (dd, J=4.9, 4.1 Hz, 2H), 8.32-8.27 (m, 1H), 8.15 (d, J=9.3 Hz, 1H), 7.97 (d, J=8.5 Hz, 2H), 7.70 (dd, J=8.8, 2.3 Hz, 1H), 7.44-7.29 (m, 4H), 7.24 (t, J=9.4 Hz, 2H), 7.07 (t, J=13.8 Hz, 1H), 6.81 (dd, J=34.9, 9.4 Hz, 2H), 4.96 (t, J=7.6 Hz, 2H), 4.82-4.78 (m, 2H), 4.61-4.41 (m, 3H), 4.33 (dd, J=18.6, 12.0 Hz, 4H), 4.16 (s, 4H), 3.99 (d, J=13.1 Hz, 1H), 3.68 (d, J=8.8 Hz, 6H), 3.41-3.35 (m, 2H), 2.95-2.76 (m, 4H), 2.27-2.20 (m, 2H), 2.08 (d, J=8.7 Hz, 2H), 1.15 (dd, J=14.6, 11.3 Hz, 9H), 1.03 (s, 3H).

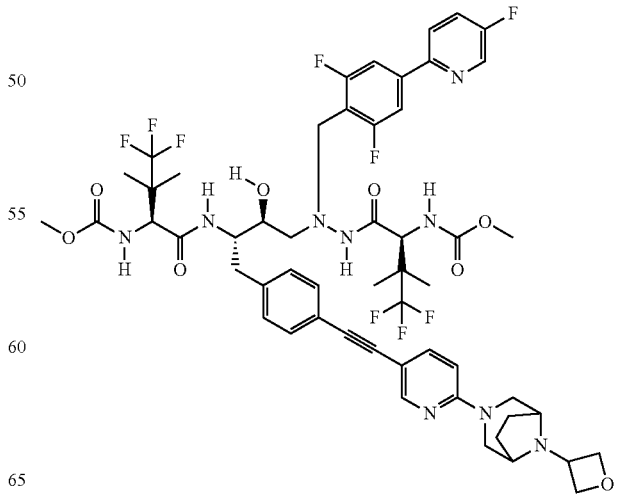

EXAMPLE 102

Methyl ((5S,8S,9S,14S)-11-(2,6-difluoro-4-(5-fluoropyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (102)

Intermediates: I2, P14, and S3. MS (ESI) m/z 1135.4 [M+H]$^+$. $^1$H NMR (400 MHz, Methanol-d$_4$) δ 8.54 (d, J=2.9 Hz, 1H), 7.97-7.94 (m, 1H), 7.70-7.53 (m, 12H), 7.33 (d, J=7.9 Hz, 2H), 7.22 (d, J=8.0 Hz, 2H), 6.86 (d, J=8.9 Hz, 1H), 4.96 (t, J=7.6 Hz, 2H), 4.84-4.81 (m, 1H), 4.54 (s, 1H), 4.44 (t, J=5.0 Hz, 1H), 4.38-4.29 (m, 3H), 4.15 (d, J=5.9 Hz, 4H), 3.98 (s, 1H), 3.67 (d, J=15.3 Hz, 8H), 3.44-3.37 (m, 2H), 2.92-2.74 (m, 4H), 2.23 (dd, J=9.6, 4.5 Hz, 2H), 2.12-2.03 (m, 2H), 1.18-1.10 (m, 8H), 1.03 (s, 3H).

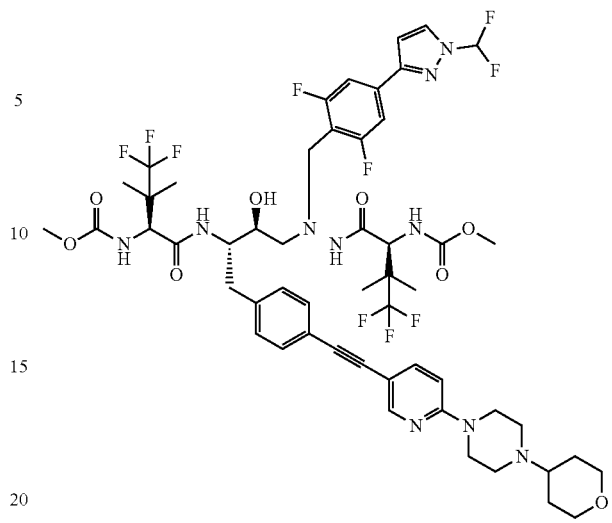

EXAMPLE 103

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((2-(4-(oxetan-3-yl)piperazin-1-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (103)

Intermediates: I2, P7, and S49. MS (ESI) m/z 1130.9 [M+H]$^+$. $^1$H NMR (400 MHz, Methanol-d$_4$) δ 8.53 (d, J=4.0 Hz, 3H), 8.19-8.11 (m, 3H), 7.38-7.32 (m, 3H), 7.24 (t, J=8.0 Hz, 5H), 7.16 (d, J=9.9 Hz, 1H), 4.90 (t, J=7.6 Hz, 3H), 4.83-4.78 (m, 1H), 4.48-4.36 (m, 3H), 4.31 (d, J=10.0 Hz, 1H), 4.17-4.08 (m, 4H), 3.93 (d, J=13.3 Hz, 1H), 3.67 (d, J=9.7 Hz, 9H), 2.93-2.72 (m, 6H), 1.19-1.09 (m, 11H), 1.03 (s, 3H).

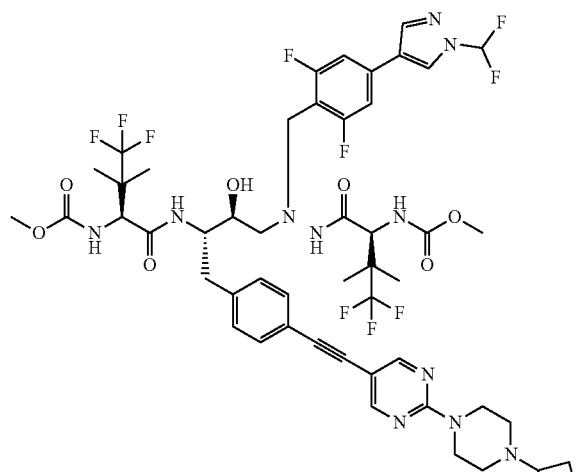

EXAMPLE 104

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-8-(4-((6-(4-(tetrahydro-2H-pyran-4-yl)piperazin-1-yl)pyridin-3-yl)ethynyl)benzyl)-5-(1,1,1-trifluoro-2-methylpropan-2-yl)-2-oxa-4,7,11,12-tetraazahexadecan-14-yl)carbamate (104)

Intermediates: I2, P4, and S50. MS (ESI) m/z 1158.2 [M+H]$^+$. $^1$H NMR (400 MHz, Methanol-d$_4$) δ 8.31-8.29 (m, 1H), 8.16 (d, J=9.4 Hz, 1H), 8.10 (d, J=2.7 Hz, 1H), 7.73-7.61 (m, 2H), 7.45 (d, J=8.3 Hz, 3H), 7.33 (d, J=7.8 Hz, 2H), 7.22 (d, J=8.0 Hz, 3H), 6.94 (dd, J=5.7, 3.0 Hz, 2H), 4.30 (d, J=9.9 Hz, 1H), 4.19-4.06 (m, 5H), 3.95 (d, J=13.2 Hz, 1H), 3.68 (d, J=11.0 Hz, 10H), 3.47 (ddd, J=24.1, 12.1, 9.2 Hz, 5H), 2.93-2.74 (m, 5H), 2.11 (d, J=10.4 Hz, 3H), 1.77 (qd, J=12.1, 4.6 Hz, 3H), 1.18-1.10 (m, 10H), 1.03 (s, 3H).

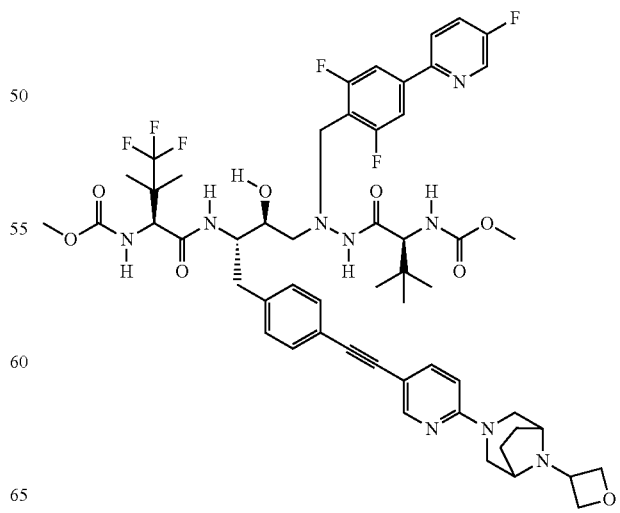

EXAMPLE 105

Methyl ((5S,8S,9S,14S)-11-(2,6-difluoro-4-(5-fluoropyridin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (105)

Intermediates: I3, P14, and S3. MS (ESI) m/z 1081.1 [M+H]⁺. ¹H NMR (400 MHz, Methanol-$d_4$) δ 8.54 (d, J=2.9 Hz, 1H), 8.29 (d, J=2.2 Hz, 1H), 8.15 (d, J=9.4 Hz, 1H), 7.95 (dd, J=8.9, 4.2 Hz, 1H), 7.76-7.64 (m, 2H), 7.60 (d, J=8.7 Hz, 2H), 7.32 (d, J=7.9 Hz, 2H), 7.21 (d, J=8.0 Hz, 2H), 6.94-6.80 (m, 1H), 4.96 (t, J=7.6 Hz, 2H), 4.85 (s, 14H), 4.54 (s, 1H), 4.43 (s, 1H), 4.39-4.28 (m, 2H), 4.18-4.09 (m, 4H), 3.99 (d, J=13.0 Hz, 1H), 3.82-3.58 (m, 8H), 3.41-3.33 (m, 2H), 3.00-2.71 (m, 4H), 2.23 (dd, J=9.8, 4.6 Hz, 2H), 2.14-2.01 (m, 2H), 1.13 (d, J=12.5 Hz, 6H), 0.86 (s, 9H).

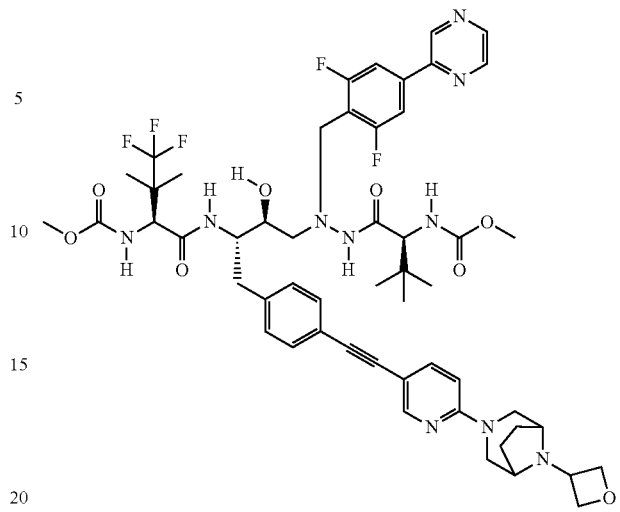

EXAMPLE 106

Methyl ((5S,8S,9S,14S)-11-(2,6-difluoro-4-(5-fluoropyridin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (106)

Intermediates: I3, P36, and S45. MS (ESI) m/z 1078.8 [M+H]⁺. ¹H NMR (400 MHz, Methanol-$d_4$) δ 8.71 (s, 1H), 8.16 (d, J=9.4 Hz, 1H), 7.72 (d, J=8.3 Hz, 2H), 7.62 (d, J=8.7 Hz, 1H), 7.32 (d, J=7.8 Hz, 2H), 7.24 (s, 0H), 6.81 (d, J=9.9 Hz, 1H), 6.67 (d, J=8.7 Hz, 1H), 4.96 (t, J=7.6 Hz, 2H), 4.54 (s, 1H), 4.50-4.30 (m, 3H), 4.15 (t, J=10.1 Hz, 4H), 4.01 (d, J=13.1 Hz, 1H), 3.81-3.55 (m, 7H), 3.37 (d, J=13.8 Hz, 2H), 3.00-2.74 (m, 4H), 2.56 (s, 3H), 2.22 (dd, J=9.6, 4.4 Hz, 2H), 2.13-1.97 (m, 2H), 1.14 (d, J=10.5 Hz, 6H), 0.85 (s, 9H).

EXAMPLE 107

Methyl ((5S,8S,9S,14S)-11-(2,6-difluoro-4-(pyrazin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (107)

Intermediates: I3, P36, and S3. MS (ESI) m/z 1064.3 [M+H]⁺. ¹H NMR (400 MHz, Methanol-$d_4$) δ 9.15 (s, 1H), 8.59 (s, 1H), 8.32-8.26 (m, 1H), 7.76-7.66 (m, 3H), 7.33 (d, J=7.8 Hz, 2H), 7.22 (d, J=8.0 Hz, 2H), 6.89-6.84 (m, 1H), 6.79 (d, J=9.8 Hz, 1H), 4.96 (t, J=7.6 Hz, 3H), 4.84-4.79 (m, 3H), 4.54 (s, 1H), 4.44 (d, J=6.5 Hz, 1H), 4.39-4.31 (m, 2H), 4.16 (d, J=4.9 Hz, 4H), 4.01 (d, J=13.1 Hz, 1H), 3.78-3.63 (m, 9H), 3.43-3.36 (m, 2H), 2.94-2.77 (m, 5H), 2.27-2.19 (m, 2H), 2.11-2.04 (m, 2H), 1.13 (d, J=10.7 Hz, 6H), 0.86 (s, 9H).

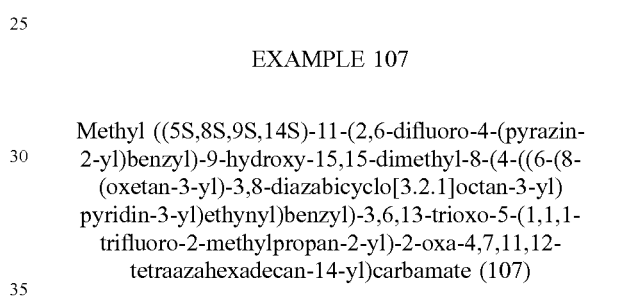

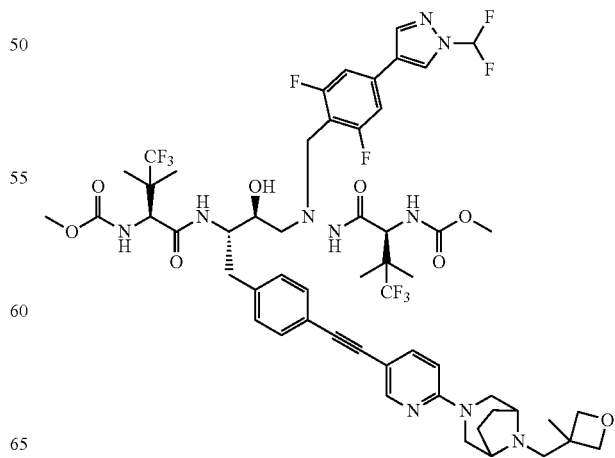

EXAMPLE 108

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(8-((3-methyloxetan-3-yl)methyl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (108)

Intermediates: I2, P7, and S56. $^1$H NMR (400 MHz, Methanol-d$_4$) δ 8.52 (d, J=0.7 Hz, 1H), 8.28 (d, J=2.4 Hz, 1H), 8.13 (d, J=8.4 Hz, 2H), 7.75-7.61 (m, 2H), 7.57-7.46 (m, 1H), 7.39-7.30 (m, 2H), 7.23 (dd, J=10.8, 8.2 Hz, 4H), 7.12 (d, J=9.9 Hz, 1H), 6.80 (dd, J=31.1, 9.4 Hz, 2H), 4.61 (d, J=6.3 Hz, 2H), 4.50-4.36 (m, 3H), 4.30-4.23 (m, 3H), 4.12 (d, J=12.2 Hz, 3H), 3.93 (d, J=13.2 Hz, 1H), 3.81 (d, J=11.0 Hz, 0H), 3.68 (d, J=10.0 Hz, 6H), 3.56 (s, 1H), 3.45 (d, J=14.1 Hz, 1H), 2.98-2.64 (m, 4H), 2.38 (d, J=11.2 Hz, 2H), 2.19-2.05 (m, 2H), 1.62 (s, 2H), 1.22-1.08 (m, 9H), 1.00 (d, J=26.6 Hz, 4H).

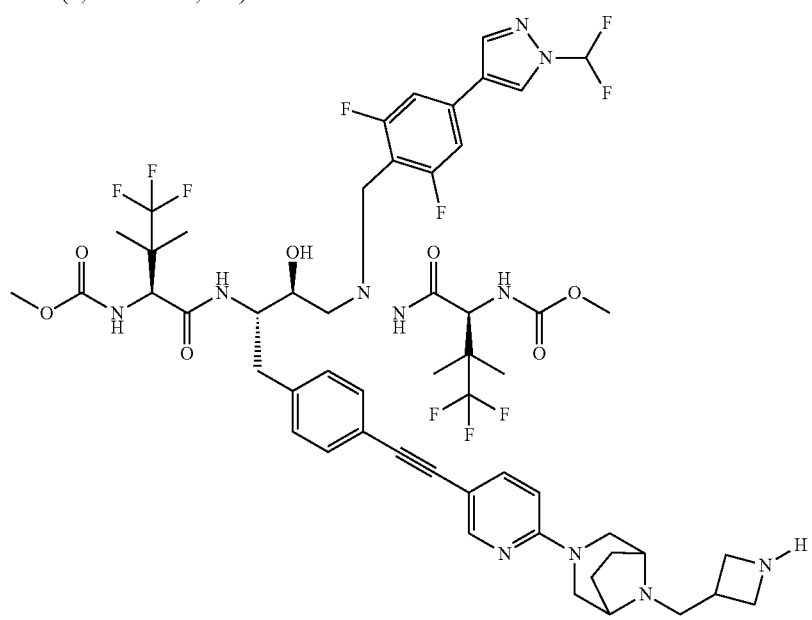

EXAMPLE 109

Methyl ((5S,8S,9S,14S)-8-(4-((6-(8-(azetidin-3-ylmethyl)-3,8-diazabicyclo[3.2.1]octan-3-yl)pyridin-3-yl)ethynyl)benzyl)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (109)

Intermediates: I2, P7, and S51 followed by treatment with trifluoroacetic acid to remove the Boc-group. MS (ESI) m/z 1169.0 [M+H]$^+$. $^1$H NMR (400 MHz, Methanol-d$_4$) δ 8.51 (d, J=0.7 Hz, 1H), 8.11 (s, 2H), 7.70 (dd, J=8.9, 2.3 Hz, 1H), 7.35-7.31 (m, 2H), 7.26-7.20 (m, 4H), 6.87-6.84 (m, 1H), 4.44 (d, J=6.5 Hz, 1H), 4.33-4.22 (m, 6H), 4.19-4.04 (m, 7H), 3.93 (d, J=13.2 Hz, 1H), 3.68 (d, J=9.4 Hz, 9H), 3.54 (s, 3H), 3.43 (d, J=13.7 Hz, 3H), 2.93-2.73 (m, 5H), 2.28 (dd, J=8.6, 3.7 Hz, 2H), 2.13-2.05 (m, 2H), 1.19-1.10 (m, 9H), 1.04 (s, 3H).

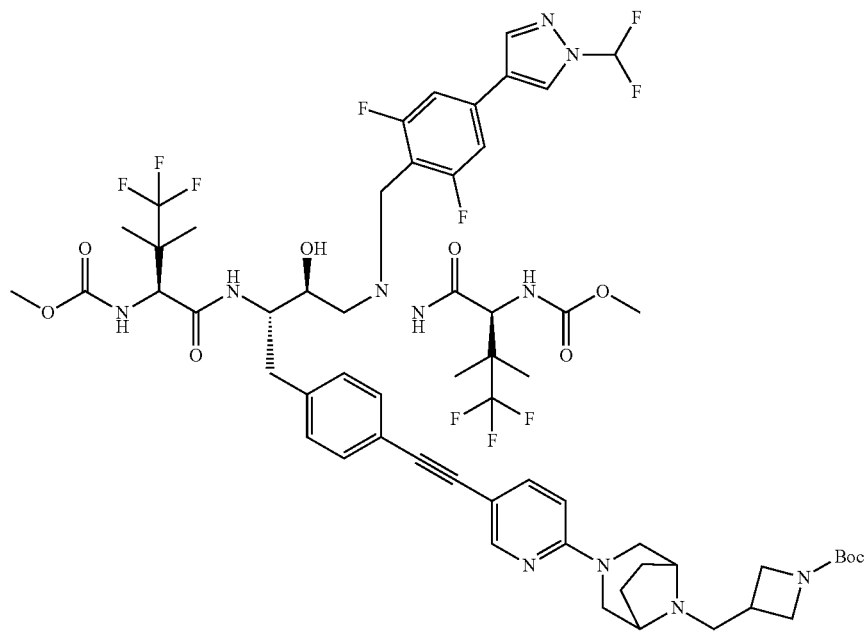

EXAMPLE 110 tert-butyl 3-((3-(5-((4-((2S,3S)-4-(1-(4-(1-(difluoromethyl)-1H-pyrazol-4-yl)-2,6-difluorobenzyl)-2-((S)-4,4,4-trifluoro-2-((methoxycarbonyl)amino)-3,3-dimethylbutanoyl)hydrazinyl)-3-hydroxy-2-((S)-4,4,4-trifluoro-2-((methoxycarbonyl) amino)-3,3-dimethylbutanamido)butyl)phenyl)ethynyl)pyridin-2-yl)-3,8-diazabicyclo[3.2.1]octan-8-yl)methyl) azetidine-1-carboxylate (110)

Intermediates: I2, P7, and S51. MS (ESI) m/z 1268.3 [M+H]⁺. ¹H NMR (400 MHz, Methanol-d₄) δ 8.51 (d, J=0.7 Hz, 1H), 8.11 (s, 2H), 7.70 (dd, J=8.9, 2.3 Hz, 1H), 7.35-7.31 (m, 2H), 7.26-7.19 (m, 4H), 6.88-6.84 (m, 1H), 4.44 (d, J=6.5 Hz, 1H), 4.33-4.22 (m, 6H), 4.19-4.05 (m, 7H), 3.93 (d, J=13.2 Hz, 2H), 3.68 (d, J=9.4 Hz, 16H), 3.54 (s, 3H), 3.43 (d, J=13.7 Hz, 2H), 2.94-2.74 (m, 6H), 2.28 (dd, J=8.6, 3.7 Hz, 2H), 2.12-2.06 (m, 2H), 1.18-1.10 (m, 9H), 1.04 (s, 3H).

EXAMPLE 111

Methyl ((5S,8S,9S,14S)-16,16,16-trifluoro-11-(4-(5-fluoropyridin-2-yl)benzyl)-9-hydroxy-15,15-dimethyl-8-(4-((6-(8-(oxetan-3-yl)-3,8-diazabicyclo [3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (111)

Intermediates: I2, P37, and S3. MS (ESI) m/z 1100.4 [M+H]⁺. ¹H NMR (400 MHz, Methanol-d₄) δ 8.50 (d, J=2.9 Hz, 1H), 7.88 (dd, J=8.7, 4.2 Hz, 3H), 7.72-7.63 (m, 3H), 7.49 (d, J=7.9 Hz, 2H), 7.33 (d, J=7.8 Hz, 2H), 7.22 (d, J=8.0 Hz, 2H), 6.86 (d, J=8.8 Hz, 1H), 4.96 (t, J=7.6 Hz, 2H), 4.84-4.80 (m, 3H), 4.54 (s, 1H), 4.42-4.32 (m, 4H), 4.25 (d, J=6.6 Hz, 1H), 4.15 (d, J=4.7 Hz, 3H), 4.05-4.00 (m, 1H), 3.92 (d, J=13.3 Hz, 1H), 3.75 (d, J=8.3 Hz, 1H), 3.68 (s, 3H), 3.58 (s, 3H), 3.39 (d, J=13.8 Hz, 3H), 2.93-2.71 (m, 5H), 2.28-2.19 (m, 2H), 2.07 (d, J=8.6 Hz, 2H), 1.11 (d, J=8.0 Hz, 7H), 1.02 (s, 3H), 0.83 (s, 3H).

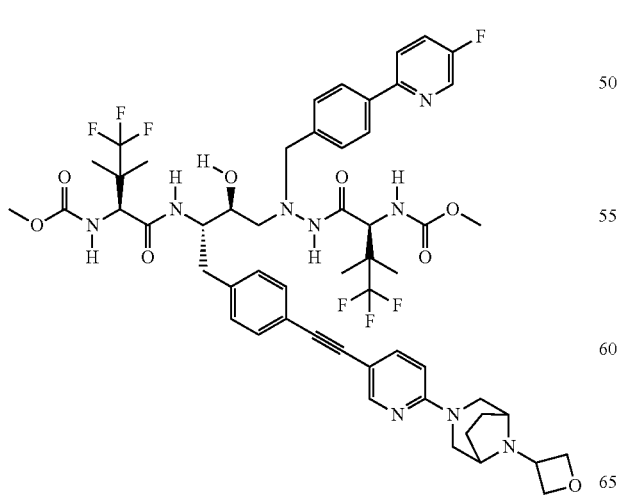

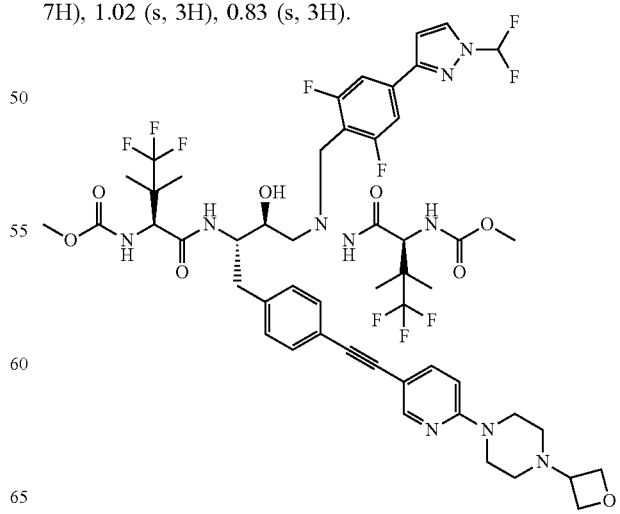

EXAMPLE 112

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (112)

Intermediates: I2, P4, and S48. MS (ESI) m/z 1129.9 [M+H]$^+$. $^1$H NMR (400 MHz, Methanol-d$_4$) δ 8.33-8.29 (m, 1H), 8.14 (d, J=9.4 Hz, 1H), 8.10 (d, J=2.7 Hz, 1H), 7.74-7.61 (m, 2H), 7.53 (s, 1H), 7.45 (t, J=6.9 Hz, 2H), 7.39-7.31 (m, 3H), 7.22 (d, J=8.2 Hz, 3H), 7.09 (d, J=9.9 Hz, 1H), 6.98-6.91 (m, 2H), 4.94-4.88 (m, 3H), 4.42 (td, J=7.9, 7.2, 4.1 Hz, 2H), 4.35-4.27 (m, 2H), 4.20-4.11 (m, 3H), 3.95 (d, J=13.2 Hz, 3H), 3.79-3.65 (m, 11H), 2.94-2.84 (m, 3H), 2.83-2.74 (m, 1H), 1.21-1.10 (m, 9H), 1.04 (d, J=7.2 Hz, 3H).

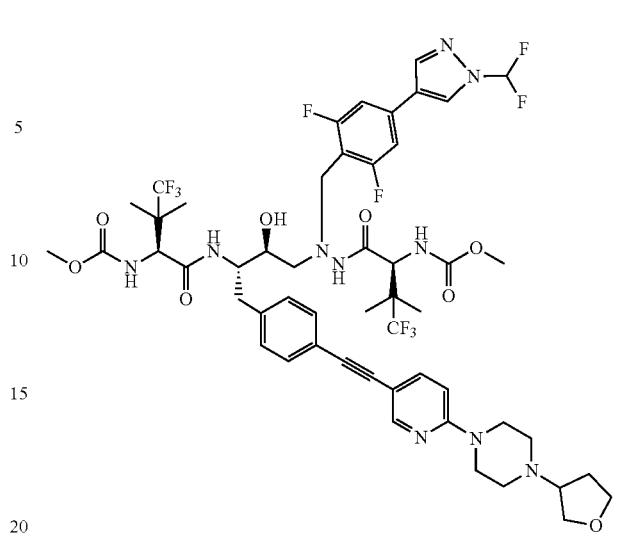

EXAMPLE 114

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-8-(4-((6-(4-(tetrahydrofuran-3-yl)piperazin-1-yl)pyridin-3-yl)ethynyl)benzyl)-5-(1,1,1-trifluoro-2-methylpropan-2-yl)-2-oxa-4,7,11,12-tetraazahexadecan-14-yl)carbamate (114)

Intermediates: I2, P7, and S57. MS (ESI) m/z 1144.4 [M+H]$^+$. $^1$H NMR (400 MHz, Methanol-d$_4$) δ 8.52 (s, 1H), 8.30 (d, J=2.2 Hz, 1H), 8.12 (s, 2H), 7.71-7.64 (m, 1H), 7.36-7.30 (m, 2H), 7.23 (dd, J=11.8, 8.2 Hz, 4H), 7.13 (d, J=9.8 Hz, 1H), 6.93 (d, J=8.9 Hz, 1H), 6.78 (d, J=9.9 Hz, 1H), 4.46-4.41 (m, 1H), 4.31 (d, J=9.5 Hz, 1H), 4.21-4.00 (m, 7H), 3.97-3.85 (m, 3H), 3.78-3.65 (m, 9H), 3.42 (s, 5H), 2.94-2.74 (m, 5H), 2.43 (dtd, J=12.8, 8.2, 4.3 Hz, 2H), 2.24 (ddd, J=13.7, 9.2, 5.0 Hz, 1H), 1.20-1.10 (m, 9H), 1.03 (s, 3H).

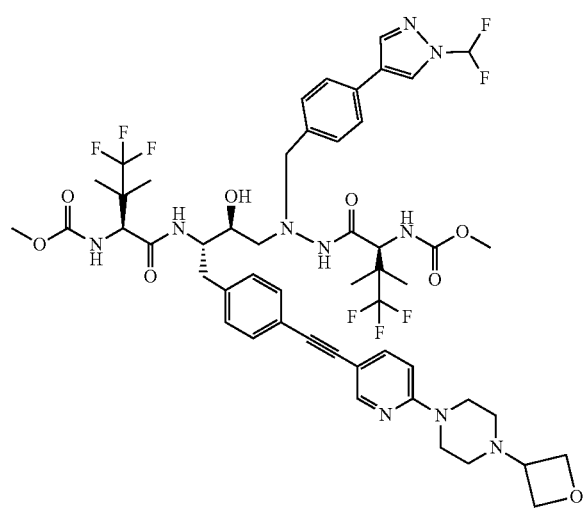 [SMILES: COC(=O)N[C@H](C(=O)N[C@@H](Cc1ccc(C#Cc2ccc(N3CCN(C4COC4)CC3)nc2)cc1)[C@@H](O)CN(Cc1ccc(-c2cnn(C(F)F)c2)cc1)NC(=O)[C@@H](NC(=O)OC)C(C)(C)C(F)(F)F)C(C)(C)C(F)(F)F]

EXAMPLE 113

Methyl ((5S,8S,9S,14S)-11-(4-(1-(difluoromethyl)-1H-pyrazol-4-yl)benzyl)-16,16,16-trifluoro-9-hydroxy-15,15-dimethyl-8-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (113)

Intermediates: I2, P9, and S48. MS (ESI) m/z 1093.9 [M+H]$^+$. $^1$H NMR (400 MHz, Methanol-d$_4$) δ 8.38 (s, 1H), 8.31-8.28 (m, 1H), 8.06 (s, 1H), 7.70 (dd, J=8.8, 2.3 Hz, 1H), 7.57-7.52 (m, 3H), 7.48 (s, 1H), 7.41 (d, J=8.0 Hz, 2H), 7.32 (d, J=7.4 Hz, 2H), 7.21 (d, J=8.1 Hz, 2H), 6.95 (d, J=8.9 Hz, 1H), 4.94-4.89 (m, 3H), 4.85-4.80 (m, 2H), 4.45-4.37 (m, 3H), 4.25 (s, 1H), 4.15 (s, 1H), 4.01-3.84 (m, 6H), 3.74 (d, J=8.9 Hz, 1H), 3.68 (s, 3H), 3.60 (s, 3H), 2.89 (d, J=8.9 Hz, 2H), 2.85-2.67 (m, 3H), 1.28 (d, J=13.9 Hz, 5H), 1.11 (d, J=12.5 Hz, 6H), 1.01 (s, 3H), 0.88-0.81 (m, 3H).

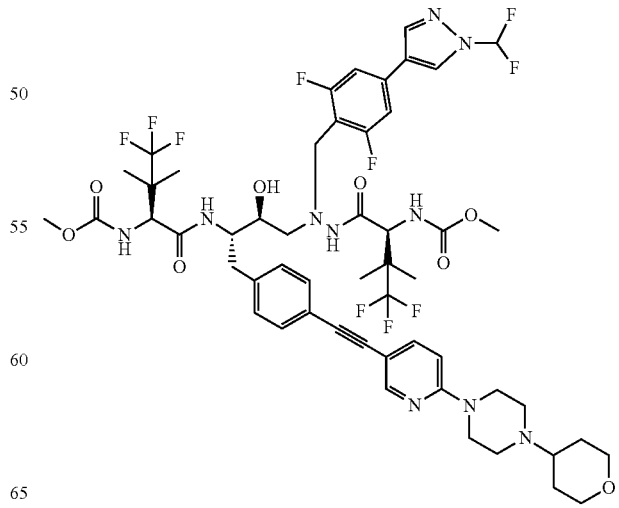

EXAMPLE 115

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-8-(4-((6-(4-(tetrahydro-2H-pyran-4-yl)piperazin-1-yl)pyridin-3-yl)ethynyl)benzyl)-5-(1,1,1-trifluoro-2-methylpropan-2-yl)-2-oxa-4,7,11,12-tetraazahexadecan-14-yl)carbamate (115)

Intermediates: I2, P7, and S50. MS (ESI) m/z 1158.0 [M+H]+. 1H NMR (400 MHz, Methanol-d4) δ 8.52 (d, J=0.8 Hz, 1H), 8.30 (dd, J=2.3, 0.8 Hz, 1H), 8.12 (d, J=6.0 Hz, 2H), 7.70 (dd, J=8.9, 2.3 Hz, 1H), 7.36-7.31 (m, 3H), 7.27-7.20 (m, 5H), 6.96-6.91 (m, 1H), 4.43 (d, J=9.7 Hz, 2H), 4.31 (d, J=9.9 Hz, 1H), 4.11 (dq, J=11.3, 6.3, 4.7 Hz, 5H), 3.93 (d, J=13.2 Hz, 2H), 3.68 (d, J=10.2 Hz, 9H), 3.56-3.40 (m, 5H), 2.93-2.73 (m, 5H), 2.14-2.06 (m, 3H), 1.77 (qd, J=12.1, 4.7 Hz, 3H), 1.18-1.11 (m, 10H), 1.03 (s, 3H).

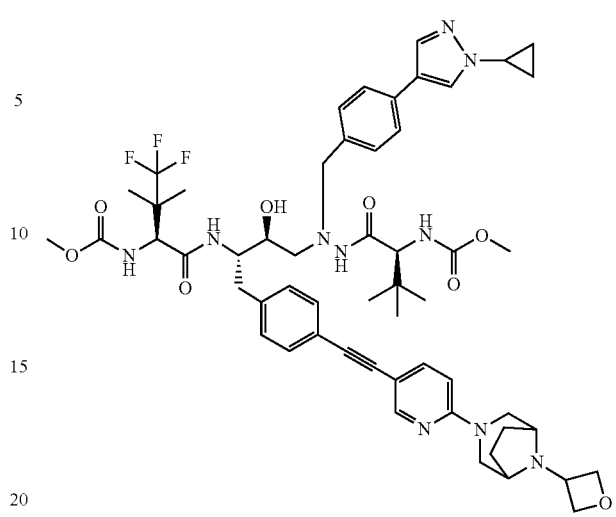

EXAMPLE 116

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(4-(oxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (116)

Intermediates: I2, P7, and S48. MS (ESI) m/z 1130.4 [M+H]+. 1H NMR (400 MHz, Methanol-d4) δ 8.53 (d, J=0.7 Hz, 1H), 8.31-8.28 (m, 1H), 8.13 (d, J=10.9 Hz, 2H), 7.70 (dd, J=8.9, 2.3 Hz, 1H), 7.36-7.30 (m, 3H), 7.23 (dd, J=11.5, 8.1 Hz, 5H), 7.13 (d, J=10.0 Hz, 1H), 6.95 (d, J=8.8 Hz, 1H), 4.90 (t, J=7.7 Hz, 3H), 4.82 (s, 2H), 4.42 (ddd, J=9.9, 7.1, 3.6 Hz, 2H), 4.31 (d, J=10.0 Hz, 1H), 4.20-4.09 (m, 3H), 3.93 (d, J=11.8 Hz, 5H), 3.68 (d, J=10.1 Hz, 8H), 2.95-2.73 (m, 5H), 1.21-1.10 (m, 10H), 1.03 (s, 4H).

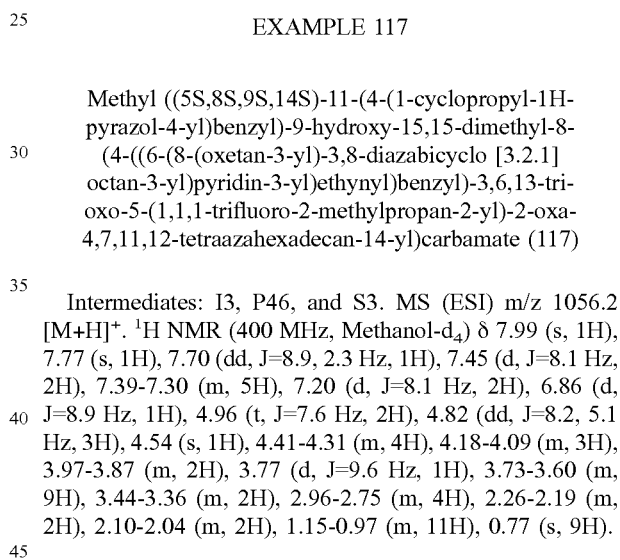

EXAMPLE 117

Methyl ((5S,8S,9S,14S)-11-(4-(1-cyclopropyl-1H-pyrazol-4-yl)benzyl)-9-hydroxy-15,15-dimethyl-8-(4-((6-(8-(oxetan-3-yl)-3,8-diazabicyclo [3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (117)

Intermediates: I3, P46, and S3. MS (ESI) m/z 1056.2 [M+H]+. 1H NMR (400 MHz, Methanol-d4) δ 7.99 (s, 1H), 7.77 (s, 1H), 7.70 (dd, J=8.9, 2.3 Hz, 1H), 7.45 (d, J=8.1 Hz, 2H), 7.39-7.30 (m, 5H), 7.20 (d, J=8.1 Hz, 2H), 6.86 (d, J=8.9 Hz, 1H), 4.96 (t, J=7.6 Hz, 2H), 4.82 (dd, J=8.2, 5.1 Hz, 3H), 4.54 (s, 1H), 4.41-4.31 (m, 4H), 4.18-4.09 (m, 3H), 3.97-3.87 (m, 2H), 3.77 (d, J=9.6 Hz, 1H), 3.73-3.60 (m, 9H), 3.44-3.36 (m, 2H), 2.96-2.75 (m, 4H), 2.26-2.19 (m, 2H), 2.10-2.04 (m, 2H), 1.15-0.97 (m, 11H), 0.77 (s, 9H).

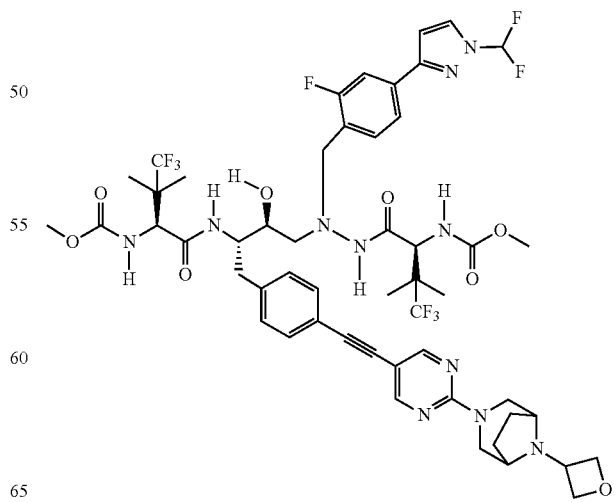

EXAMPLE 118

Methyl ((5S,8S,9S,14S)-11-(4-(1-(difluoromethyl)-1H-pyrazol-3-yl)-2-fluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (118)

Intermediates: I2, P5, and S7. MS (ESI) m/z 1138.2 [M+H]$^+$. $^1$H NMR (400 MHz, Methanol-d4) δ 8.52 (d, J=1.0 Hz, 2H), 8.10 (d, J=9.4 Hz, 1H), 7.76 (d, J=1.7 Hz, 1H), 7.67 (t, J=7.7 Hz, 1H), 7.45 (t, J=58.0 Hz, 1H), 7.34 (d, J=7.9 Hz, 2H), 7.26-7.18 (m, 4H), 7.16 (d, J=9.8 Hz, 1H), 6.79 (d, J=9.9 Hz, 1H), 6.56 (d, J=1.7 Hz, 1H), 4.96 (t, J=7.6 Hz, 2H), 4.76 (s, 1H), 4.48-4.36 (m, 1H), 4.28-4.18 (m, 2H), 4.14 (s, 3H), 4.08 (s, 1H), 3.98 (d, J=13.7 Hz, 1H), 3.75 (s, 1H), 3.58 (s, 3H), 3.47 (d, J=14.5 Hz, 2H), 2.91 (d, J=9.2 Hz, 2H), 2.83 (d, J=6.6 Hz, 2H), 2.27-2.15 (m, 2H), 1.99 (d, J=8.8 Hz, 2H), 1.14 (s, 3H), 1.13 (s, 3H), 1.09 (s, 3H), 0.95 (s, 3H).

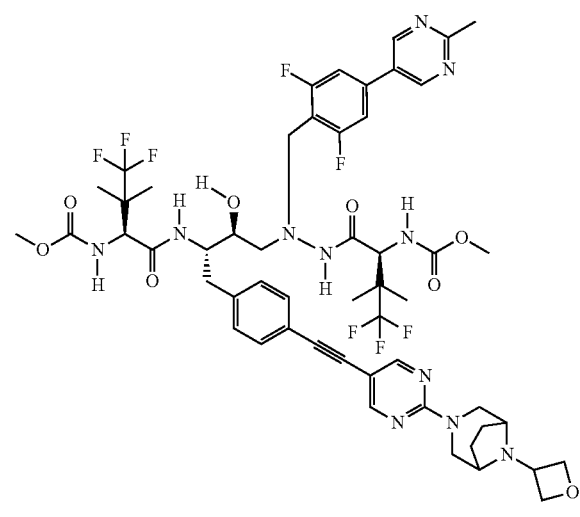 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2cnc(C)nc2)cc1F)NC(=O)[C@@H](NC(=O)OC)C(C)(C)C(F)(F)F)C(C)(C)C(F)(F)F]

EXAMPLE 119

Methyl ((5S,8S,9S,14S)-11-(2,6-difluoro-4-(2-methylpyrimidin-5-yl)benzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (119)

Intermediates: I2, P47, and S7. MS (ESI) m/z 1133.32 [M+H]$^+$. $^1$H NMR (400 MHz, Methanol-d$_4$) δ 8.97 (s, 1H), 8.52 (s, 1H), 8.14 (d, J=9.4 Hz, 1H), 7.34 (dd, J=8.0, 5.0 Hz, 2H), 7.23 (d, J=8.0 Hz, 1H), 7.16 (d, J=10.0 Hz, 2H), 6.79 (d, J=9.9 Hz, 2H), 4.96 (t, J=7.6 Hz, 2H), 4.81-4.73 (m, 6H), 4.44 (d, J=9.9 Hz, 2H), 4.29 (d, J=10.0 Hz, 2H), 4.16 (d, J=14.0 Hz, 2H), 3.96 (d, J=13.2 Hz, 1H), 3.67 (d, J=15.8 Hz, 10H), 3.46 (d, J=14.5 Hz, 1H), 3.20-3.12 (m, 2H), 2.95-2.79 (m, 2H), 2.74 (s, 3H), 2.22 (dd, J=14.5, 8.2 Hz, 1H), 1.99 (d, J=8.8 Hz, 1H), 1.27-1.09 (m, 10H), 1.04 (s, 6H).

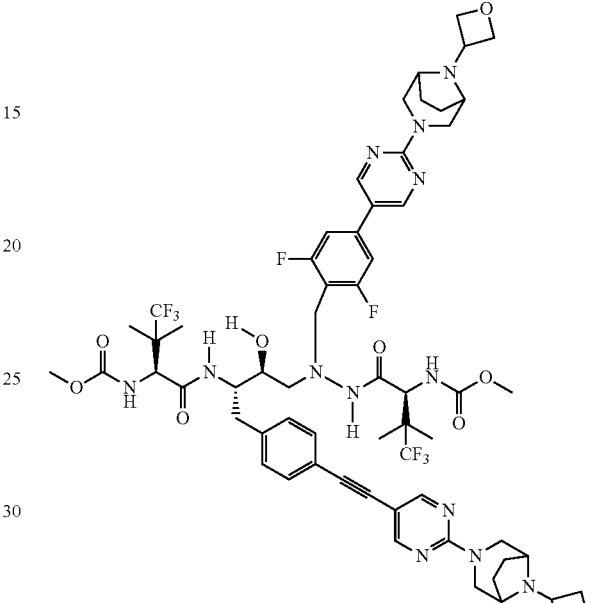

EXAMPLE 120

Methyl ((5S,8S,9S,14S)-11-(2,6-difluoro-4-(2-(8-(oxetan-3-yl)-3,8-diazabicyclo[3.2.1]octan-3-yl)pyrimidin-5-yl)benzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (120)

Intermediates: I2, P20, and S7. MS (ESI) m/z 1284.4 [M+H]$^+$. $^1$H NMR (400 MHz, Methanol-d4) δ 8.73 (s, 2H), 8.53 (s, 2H), 8.19 (d, J=9.4 Hz, 1H), 7.35 (d, J=7.9 Hz, 2H), 7.23 (d, J=8.5 Hz, 5H), 6.84 (d, J=9.8 Hz, 1H), 5.04-4.92 (m, 5H), 4.80 (d, J=4.3 Hz, 2H), 4.44 (d, J=9.9 Hz, 1H), 4.31 (d, J=10.0 Hz, 1H), 4.15 (s, 6H), 3.95 (d, J=13.2 Hz, 1H), 3.74 (s, 1H), 3.69 (s, 3H), 3.66 (s, 3H), 3.47 (dd, J=14.4, 9.6 Hz, 5H), 2.91 (d, J=7.7 Hz, 2H), 2.79 (d, J=9.6 Hz, 1H), 2.21 (s, 4H), 1.99 (t, J=7.3 Hz, 5H), 1.17 (s, 3H), 1.14 (s, 3H), 1.11 (s, 3H), 1.03 (s, 3H).

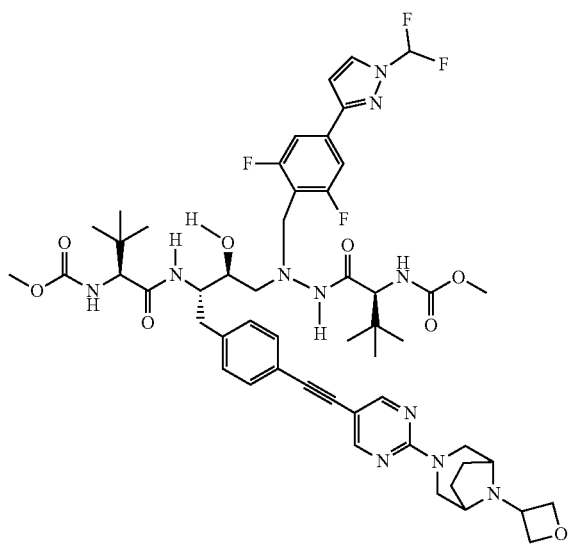 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC)C(C)(C)C)C(C)(C)C]

EXAMPLE 121

Methyl ((5S,8S,9S,14S)-5-(tert-butyl)-11-(4-(1-(difluoromethyl)-1H-pyrazol-3-yl)-2,6-difluorobenzyl)-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-2-oxa-4,7,11,12-tetraazahexadecan-14-yl)carbamate (121)

Intermediates: I1, P4, and S7. MS (ESI) m/z 1048.4 [M+H]⁺. ¹H NMR (400 MHz, Methanol-d4) δ 8.44 (s, 2H), 8.01 (d, J=2.7 Hz, 1H), 7.77 (d, J=9.5 Hz, 1H), 7.44 (t, J=59.7 Hz, 1H), 7.35 (d, J=8.2 Hz, 2H), 7.26 (d, J=8.0 Hz, 2H), 7.15 (d, J=8.0 Hz, 2H), 6.84 (d, J=2.8 Hz, 1H), 4.87 (dd, J=8.1, 7.0 Hz, 2H), 4.71 (dd, J=8.1, 5.1 Hz, 2H), 4.02 (d, J=13.8 Hz, 4H), 3.87 (d, J=13.4 Hz, 1H), 3.80 (s, 1H), 3.72-3.62 (m, 1H), 3.58 (s, 3H), 3.55 (s, 2H), 3.38 (d, J=1.6 Hz, 1H), 3.34 (s, 1H), 2.83 (t, J=7.0 Hz, 1H), 2.72 (s, 2H), 2.11 (s, 2H), 1.89 (d, J=9.1 Hz, 2H), 0.79 (s, 8H), 0.74 (s, 8H).

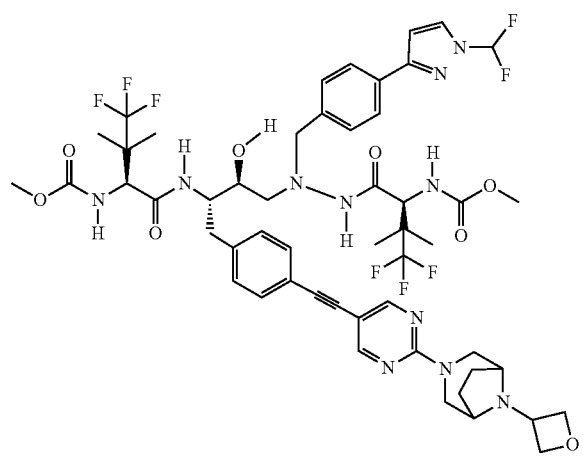 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1ccc(C(=N)/C=C\NC(F)F)cc1)NC(=O)[C@@H](NC(=O)OC)C(C)(C)C(F)(F)F)C(C)(C)C(F)(F)F]

EXAMPLE 122

Methyl ((5S,8S,9S,14S)-11-(4-(1-(difluoromethyl)-1H-pyrazol-3-yl)benzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (122)

Intermediates: I2, P6, and S7. MS (ESI) m/z 1121.0 [M+H]⁺. ¹H NMR (400 MHz, Methanol-d4) δ 8.52 (s, 2H), 8.09 (d, J=9.4 Hz, 1H), 8.04 (d, J=2.7 Hz, 1H), 7.78 (d, J=8.1 Hz, 2H), 7.49 (t, J=60.0 Hz, 1H), 7.44 (d, J=8.1 Hz, 2H), 7.34 (d, J=8.0 Hz, 2H), 7.23 (d, J=8.0 Hz, 2H), 7.09 (d, J=9.8 Hz, 1H), 6.86 (d, J=2.7 Hz, 1H), 6.76 (d, J=9.9 Hz, 1H), 4.95 (t, J=7.6 Hz, 2H), 4.82-4.78 (m, 2H), 4.75 (s, 1H), 4.39 (d, J=9.8 Hz, 1H), 4.24 (d, J=9.8 Hz, 1H), 4.18 (d, J=8.3 Hz, 1H), 4.16-4.08 (m, 2H), 4.00 (d, J=13.1 Hz, 1H), 3.88 (d, J=13.4 Hz, 1H), 3.74 (s, 1H), 3.67 (s, 3H), 3.59 (s, 3H), 3.46 (d, J=14.5 Hz, 2H), 2.96-2.86 (m, 2H), 2.86-2.68 (m, 2H), 2.29-2.13 (m, 2H), 2.04-1.88 (m, 2H), 1.11 (s, 3H), 1.09 (s, 3H), 1.02 (s, 3H), 0.84 (s, 3H).

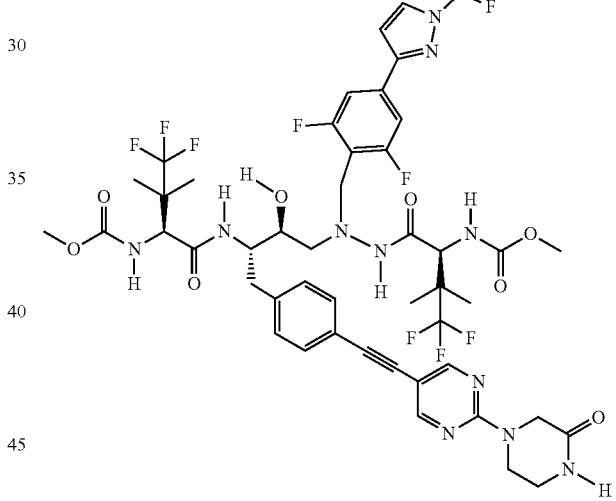

EXAMPLE 123

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-8-(4-((2-(3-oxopiperazin-1-yl)pyrimidin-5-yl)ethynyl)benzyl)-5-(1,1,1-trifluoro-2-methylpropan-2-yl)-2-oxa-4,7,11,12-tetraazahexadecan-14-yl)carbamate (123)

Intermediates: I2, P4, and S58a. MS (ESI) m/z 1088.2 [M+H]⁺. ¹H NMR (400 MHz, Methanol-d4) δ 8.49 (s, 2H), 7.53 (t, J=59.7 Hz, 1H), 7.45 (d, J=8.2 Hz, 2H), 7.34 (d, J=7.8 Hz, 2H), 7.23 (d, J=8.1 Hz, 2H), 7.14 (d, J=10.1 Hz, 1H), 6.94 (d, J=2.8 Hz, 1H), 6.82 (d, J=10.0 Hz, 1H), 4.50-4.39 (m, 1H), 4.38 (s, 2H), 4.34-4.26 (m, 1H), 4.14 (d, J=12.5 Hz, 2H), 4.10-3.99 (m, 2H), 3.94 (d, J=13.1 Hz, 1H), 3.80-3.72 (m, 2H), 3.69 (s, 3H), 3.66 (s, 3H), 3.45-3.38 (m, 2H), 2.94-2.82 (m, 3H), 2.82-2.73 (m, 1H), 1.16 (s, 3H), 1.14 (s, 3H), 1.11 (s, 3H), 1.06-0.99 (m, 3H).

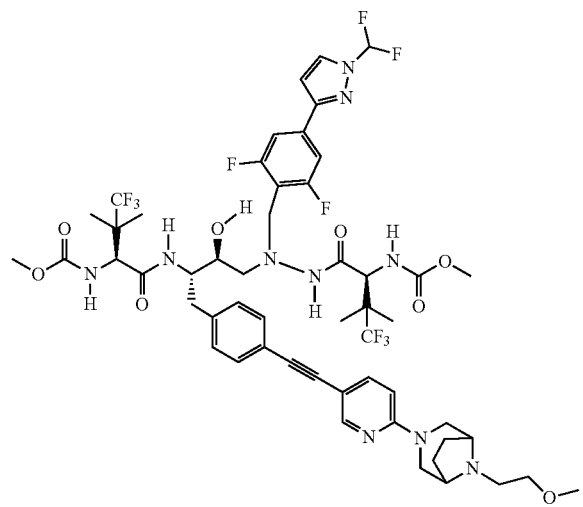

EXAMPLE 124

Methyl ((5S,8S,9S,14S)-11-(4-(1-(difluoromethyl)-1H-pyrazol-3-yl)-2,6-difluorobenzyl)-16,16,16-trifluoro-9-hydroxy-8-(4-((6-(8-(2-methoxyethyl)-3,8-diazabicyclo[3.2.1]octan-3-yl)pyridin-3-yl)ethynyl)benzyl)-15,15-dimethyl-3,6,13-trioxo-5-(1,1,1-trifluoro-2-methylpropan-2-yl)-2-oxa-4,7,11,12-tetraazahexadecan-14-yl)carbamate (124)

Intermediates: I2, P4, and S59. MS (ESI) m/z 1157.3 [M+H]$^+$. $^1$H NMR (400 MHz, Methanol-d4) δ 8.28 (d, J=2.2 Hz, 1H), 8.20-8.07 (m, 1H), 7.74-7.66 (m, 1H), 7.48-7.30 (m, 4H), 7.22 (d, J=8.0 Hz, 2H), 6.93 (d, J=2.8 Hz, 1H), 6.86 (d, J=8.9 Hz, 1H), 4.44 (s, 1H), 4.31 (s, 1H), 4.28 (s, 3H), 4.14 (d, J=12.1 Hz, 2H), 3.94 (d, J=13.1 Hz, 1H), 3.83-3.77 (m, 2H), 3.68 (d, J=12.0 Hz, 7H), 3.44 (s, 4H), 3.35 (s, 3H), 2.94-2.84 (m, 3H), 2.78 (dd, J=12.6, 9.1 Hz, 1H), 2.32-2.24 (m, 2H), 2.06 (d, J=8.6 Hz, 2H), 1.24-1.09 (m, 8H), 1.03 (s, 2H).

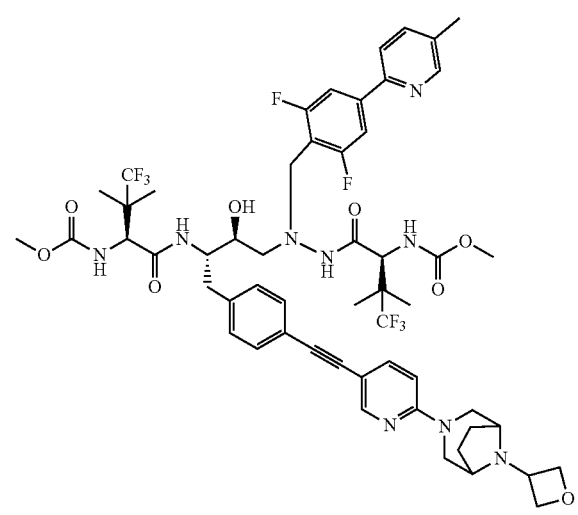 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(C)cn2)cc1F)NC(=O)[C@@H](NC(=O)OC)C(C)(C)C(F)(F)F)C(C)(C)C(F)(F)F]

EXAMPLE 125

Methyl ((5S,8S,9S,14S)-11-(2,6-difluoro-4-(5-methylpyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (125)

Intermediates: I2, P39, and S3. MS (ESI) m/z 1128.8 [M+H]$^+$. $^1$H NMR (400 MHz, Methanol-d$_4$) δ 8.56 (s, 1H), 8.29 (d, J=2.2 Hz, 1H), 8.14 (d, J=9.5 Hz, 1H), 8.01-7.88 (m, 2H), 7.70 (dd, J=8.8, 2.3 Hz, 1H), 7.56 (d, J=8.4 Hz, 2H), 7.33 (d, J=7.9 Hz, 2H), 7.23 (d, J=8.0 Hz, 2H), 6.83 (dd, J=28.9, 9.4 Hz, 2H), 4.96 (t, J=7.6 Hz, 2H), 4.48-4.40 (m, 1H), 4.39-4.27 (m, 3H), 4.22-4.12 (m, 4H), 3.98 (d, J=13.1 Hz, 1H), 3.75 (s, 1H), 3.70 (s, 3H), 3.64 (s, 3H), 3.46-3.37 (m, 2H), 2.95-2.75 (m, 5H), 2.46 (s, 3H), 2.24 (dd, J=9.9, 4.5 Hz, 2H), 2.07 (d, J=8.6 Hz, 2H), 1.34-1.21 (m, 1H), 1.19-1.06 (m, 9H), 1.03 (s, 3H).

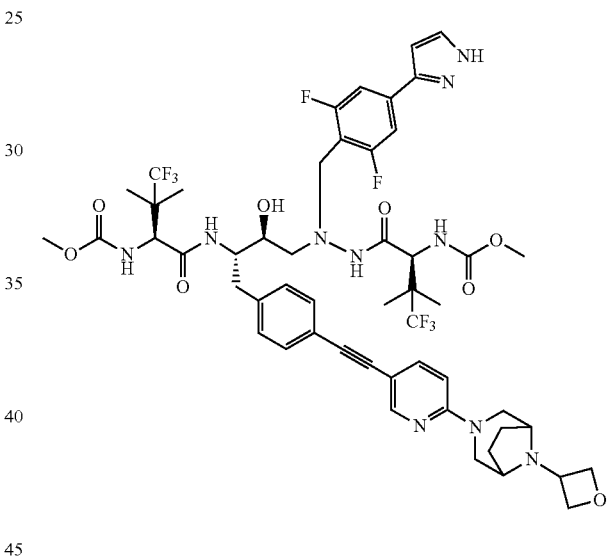

EXAMPLE 126

Methyl ((5S,8S,9S,14S)-11-(2,6-difluoro-4-(1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (126)

Intermediates: I2, P42, and S3. MS (ESI) m/z 1105.3 [M+H]$^+$. $^1$H NMR (400 MHz, Methanol-d$_4$) δ 8.15 (d, J=9.4 Hz, 1H), 7.70 (dd, J=9.4, 2.8 Hz, 2H), 7.35 (dd, J=14.0, 8.3 Hz, 4H), 7.22 (d, J=7.9 Hz, 2H), 6.86 (d, J=8.9 Hz, 1H), 6.81-6.72 (m, 2H), 4.97 (t, J=7.6 Hz, 2H), 4.53 (s, 1H), 4.44 (d, J=9.5 Hz, 1H), 4.34 (t, J=12.5 Hz, 3H), 4.15 (s, 3H), 3.95 (d, J=13.2 Hz, 1H), 3.68 (d, J=14.3 Hz, 10H), 3.39 (d, J=13.9 Hz, 2H), 2.94-2.76 (m, 4H), 2.27-2.19 (m, 2H), 2.08 (d, J=8.5 Hz, 2H), 1.20-1.10 (m, 9H), 1.03 (s, 3H).

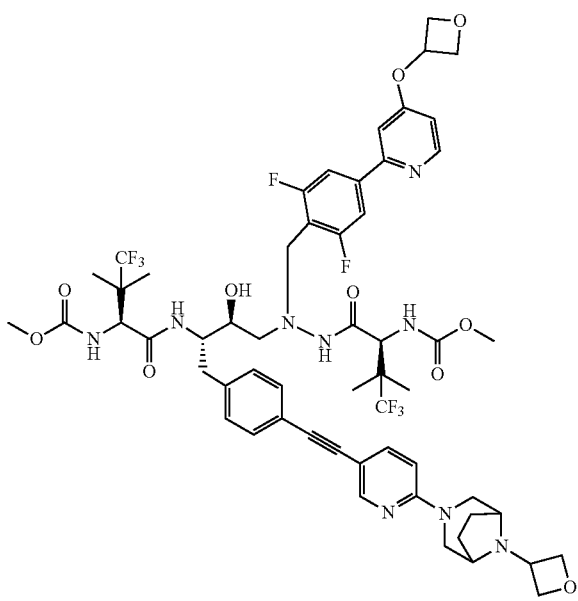 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2cc(OC3COC3)ccn2)cc1F)NC(=O)[C@@H](NC(=O)OC)C(C)(C)C(F)(F)F)C(C)(C)C(F)(F)F]

EXAMPLE 127

Methyl ((5S,8S,9S,14S)-11-(2,6-difluoro-4-(4-(oxetan-3-yloxy)pyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (127)

Intermediates: I2, P43, and S3. MS (ESI) m/z 1188.2 [M+H]⁺. $^1$H NMR (400 MHz, Methanol-d$_4$) δ 8.65 (d, J=6.6 Hz, 1H), 8.32-8.26 (m, 1H), 7.70 (dd, J=8.8, 2.3 Hz, 1H), 7.62-7.52 (m, 2H), 7.34 (d, J=7.9 Hz, 2H), 7.30-7.19 (m, 3H), 6.84 (dd, J=21.8, 9.4 Hz, 1H), 5.76-5.64 (m, 1H), 5.11 (t, J=6.9 Hz, 2H), 4.95 (t, J=7.6 Hz, 2H), 4.90-4.73 (m, 3H), 4.59-4.51 (m, 1H), 4.44 (t, J=5.1 Hz, 1H), 4.32 (td, J=14.6, 5.4 Hz, 3H), 4.25-4.12 (m, 4H), 4.05-3.95 (m, 1H), 3.68 (d, J=17.7 Hz, 5H), 3.48-3.39 (m, 2H), 3.35 (s, 4H), 2.91 (d, J=8.2 Hz, 2H), 2.83 (s, 1H), 2.24 (dd, J=9.7, 4.5 Hz, 2H), 2.07 (d, J=8.6 Hz, 2H), 1.15 (d, J=5.7 Hz, 8H), 1.04 (s, 2H).

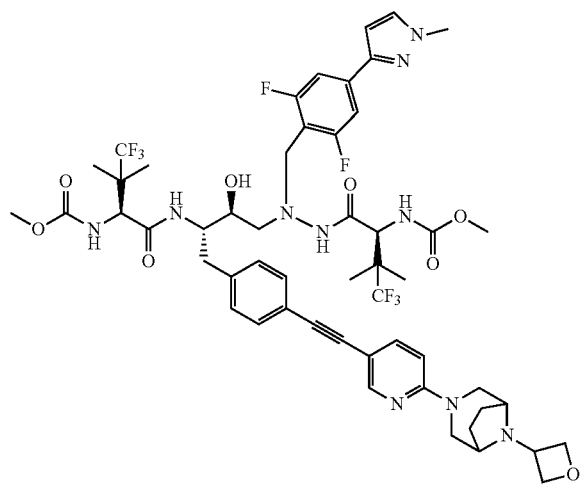 [SMILES: CN/C=C\C(=N)c1cc(F)c(CN(C[C@H](O)[C@H](Cc2ccc(C#Cc3ccc(N4CC5CCC(C4)N5C4COC4)nc3)cc2)NC(=O)[C@@H](NC(=O)OC)C(C)(C)C(F)(F)F)NC(=O)[C@@H](NC(=O)OC)C(C)(C)C(F)(F)F)c(F)c1]

EXAMPLE 128

Methyl ((5S,8S,9S,14S)-11-(2,6-difluoro-4-(1-methyl-1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (128)

Intermediates: I2, P41, and S3. MS (ESI) m/z 1119.9 [M+H]⁺. $^1$H NMR (400 MHz, Methanol-d$_4$) δ 8.29 (d, J=2.2 Hz, 1H), 7.77-7.67 (m, 1H), 7.61 (d, J=2.3 Hz, 1H), 7.33 (d, J=8.2 Hz, 4H), 7.22 (d, J=8.2 Hz, 2H), 6.88 (d, J=8.9 Hz, 1H), 6.65 (d, J=2.3 Hz, 1H), 4.95 (t, J=7.6 Hz, 2H), 4.85 (dd, J=8.2, 5.1 Hz, 2H), 4.55 (p, J=6.2 Hz, 1H), 4.45 (d, J=8.5 Hz, 1H), 4.34 (dd, J=14.5, 2.5 Hz, 3H), 4.19-4.08 (m, 4H), 3.93 (s, 4H), 3.68 (d, J=9.4 Hz, 6H), 3.48-3.39 (m, 2H), 3.35 (s, 1H), 2.99 (s, 1H), 2.94-2.73 (m, 5H), 2.27-2.19 (m, 2H), 2.08 (t, J=6.9 Hz, 2H), 1.35-1.26 (m, 1H), 1.24-1.09 (m, 9H), 1.03 (s, 3H).

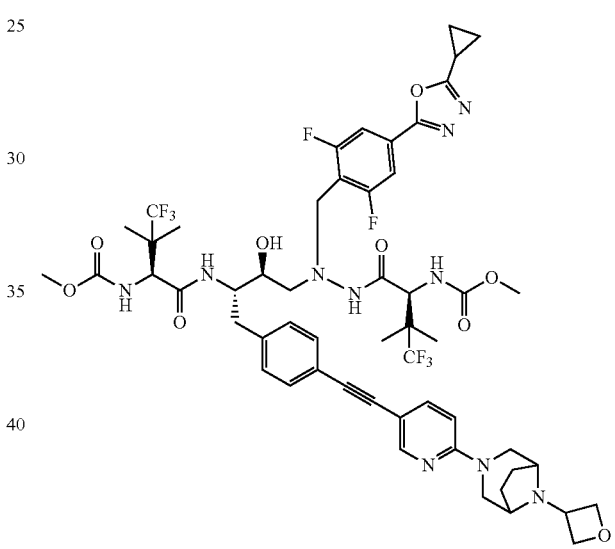

EXAMPLE 129

Methyl ((5S,8S,9S,14S)-11-(4-(5-cyclopropyl-1,3,4-oxadiazol-2-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (129)

Intermediates: I2, P40, and S3. MS (ESI) m/z 1147.4 [M+H]⁺. $^1$H NMR (400 MHz, Methanol-d$_4$) δ 8.33-8.26 (m, 1H), 8.16 (d, J=9.4 Hz, 1H), 7.70 (dt, J=9.1, 2.4 Hz, 1H), 7.54 (d, J=7.3 Hz, 2H), 7.37-7.32 (m, 2H), 7.23 (d, J=8.2 Hz, 2H), 6.91-6.77 (m, 1H), 4.96 (t, J=7.6 Hz, 2H), 4.84 (dd, J=8.2, 5.1 Hz, 2H), 4.59-4.52 (m, 1H), 4.52-4.40 (m, 1H), 4.39-4.24 (m, 3H), 4.22-4.13 (m, 4H), 3.96 (d, J=12.9 Hz, 1H), 3.75 (d, J=9.0 Hz, 1H), 3.72-3.63 (m, 6H), 3.46-3.38 (m, 2H), 2.91 (d, J=8.7 Hz, 2H), 2.88-2.74 (m, 2H), 2.36-

2.20 (m, 3H), 2.08 (d, J=8.6 Hz, 2H), 1.32-1.16 (m, 6H), 1.15 (s, 4H), 1.13 (s, 3H), 1.03 (s, 2H), 0.89 (s, 1H).

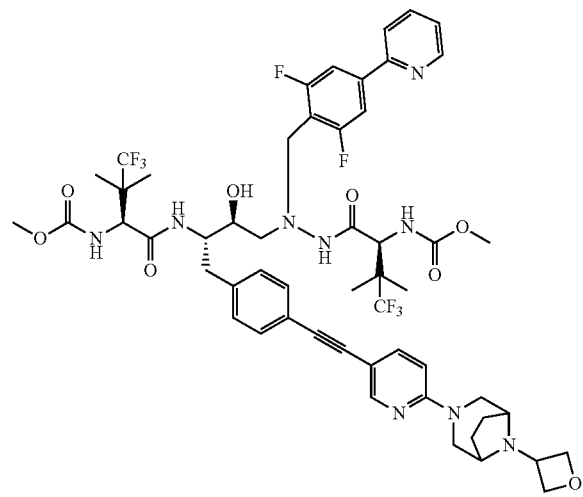 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]

EXAMPLE 130

Methyl ((5S,8S,9S,14S)-11-(2,6-difluoro-4-(pyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (130)

Intermediates: I2, P28, and S3. MS (ESI) m/z 1116.6 [M+H]$^+$. $^1$H NMR (400 MHz, Methanol-d$_4$) δ 8.71 (s, 1H), 8.29 (d, J=2.2 Hz, 1H), 8.17 (d, J=8.5 Hz, 1H), 8.09 (t, J=7.8 Hz, 1H), 8.01 (d, J=7.9 Hz, 1H), 7.70 (dd, J=8.8, 2.3 Hz, 1H), 7.64-7.52 (m, 3H), 7.34 (d, J=7.8 Hz, 2H), 7.23 (d, J=8.0 Hz, 2H), 7.14 (d, J=9.5 Hz, 1H), 6.84 (dd, J=25.9, 9.4 Hz, 2H), 4.96 (t, J=7.6 Hz, 2H), 4.83 (dd, J=8.2, 5.1 Hz, 2H), 4.55 (d, J=7.8 Hz, 1H), 4.48-4.41 (m, 1H), 4.35 (dd, J=14.5, 2.5 Hz, 3H), 4.19-4.13 (m, 4H), 3.99 (d, J=7.6 Hz, 1H), 3.75 (s, 1H), 3.70 (s, 4H), 3.64 (s, 3H), 3.46-3.32 (m, 3H), 2.93 (s, 2H), 2.24 (dd, J=9.6, 4.6 Hz, 2H), 2.07 (d, J=8.6 Hz, 2H), 1.19-1.10 (m, 9H), 1.03 (s, 3H).

EXAMPLE 131

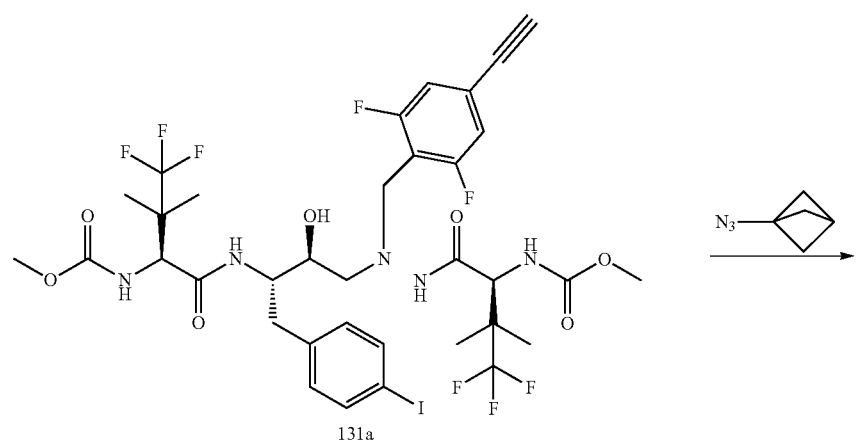

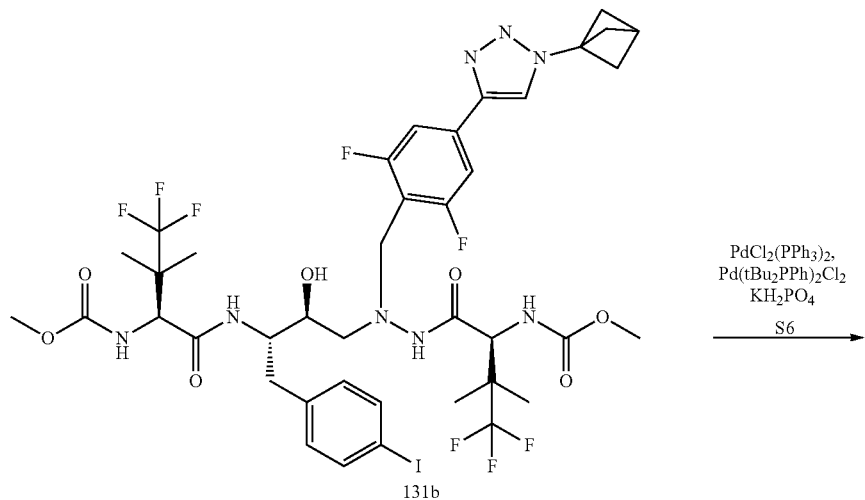

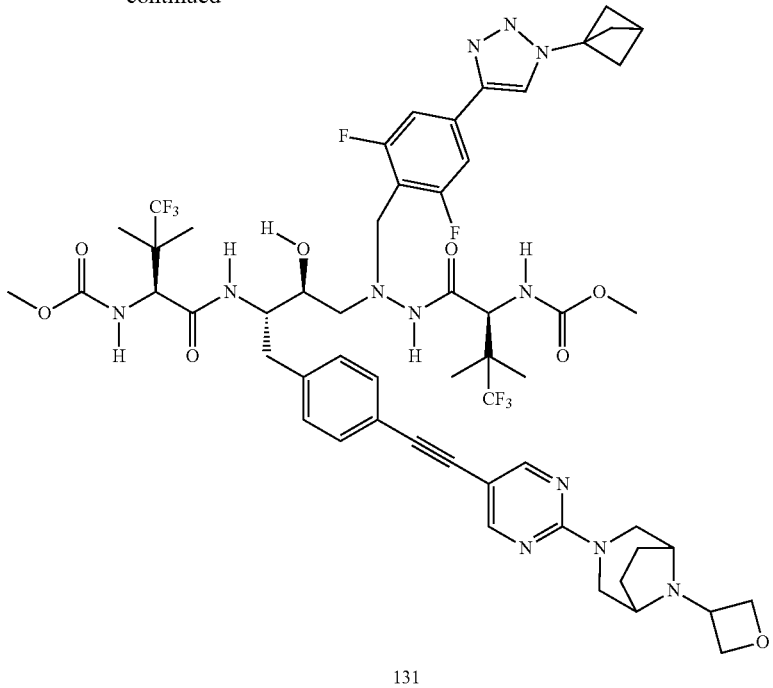

131

Methyl ((5S,10S,11S,14S)-8-(4-ethynyl-2,6-difluorobenzyl)-16,16,16-trifluoro-10-hydroxy-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (131a)

The title compound 131a was prepared according to the method presented for the synthesis of compound 1a but instead utilizing P38. MS (ESI) m/z 924.2 [M+H]$^+$. $^1$H NMR (400 MHz, Methanol-d4) δ 7.52 (d, J=8.0 Hz, 2H), 7.00 (dd, J=11.2, 7.8 Hz, 4H), 4.44 (s, 1H), 4.27 (s, 1H), 4.17-4.01 (m, 2H), 3.90 (d, J=13.2 Hz, 1H), 3.71 (t, J=5.9 Hz, 8H), 2.82 (d, J=7.8 Hz, 2H), 2.77-2.67 (m, 1H), 1.17 (s, 3H), 1.14 (s, 3H), 1.11 (s, 3H), 1.02 (s, 3H).

Methyl ((5S,8S,9S,14S)-11-(4-(1-(bicyclo[1.1.1]pentan-1-yl)-1H-1,2,3-triazol-4-yl)-2,6-difluorobenzyl)-16,16,16-trifluoro-9-hydroxy-8-(4-iodobenzyl)-15,15-dimethyl-3,6,13-trioxo-5-(1,1,1-trifluoro-2-methylpropan-2-yl)-2-oxa-4,7,11,12-tetraazahexadecan-14-yl)carbamate (131b)

To a solution of 131a (62 mg, 0.07 mmol) in THF (2 mL) was added copper (52 mg, 0.818 mmol), 10% CuSO$_4$ (100 uL), and 1-azidobicyclo[1.1.1]pentane in CuSO$_4$ (0.300 ml, 0.082 mmol). After 2h, added more 1-azidobicyclo[1.1.1]pentane in CuSO$_4$ (0.300 ml, 0.082 mmol). Stirred for another 2h, added more 1-azidobicyclo[1.1.1]pentane in CuSO$_4$ (0.300 ml, 0.082 mmol), then stirred for 48h. The reaction was partitioned with EtOAc and brine. The organic extract was washed with NH4Cl solution and dried over Na$_2$SO$_4$ filtered and concentrated under reduced pressure. The residue was purified by silica chromatography (25%-75% EtOAc/hex to yield 131b. MS (ESI) m/z 1032.1 [M+H]$^+$. $^1$H NMR (400 MHz, Methanol-d4) δ 8.50 (s, 1H), 7.52 (d, J=8.0 Hz, 2H), 7.43 (d, J=8.1 Hz, 2H), 6.99 (d, J=8.1 Hz, 2H), 4.44 (s, 1H), 4.30 (s, 1H), 4.17-4.03 (m, 3H), 3.93 (d, J=13.2 Hz, 1H), 3.71 (s, 4H), 3.66 (s, 3H), 2.86-2.67 (m, 5H), 2.45 (s, 7H), 1.16 (s, 4H), 1.14 (s, 3H), 1.11 (s, 3H), 1.02 (s, 3H), 0.89 (d, J=6.7 Hz, 1H).

Methyl ((5S,8S,9S,14S)-11-(4-(1-(bicyclo[1.1.1]pentan-1-yl)-1H-1,2,3-triazol-4-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (131)

The title compound 131 was prepared according to the method presented for the synthesis of compound 1 but instead utilizing 131b and S7. MS (ESI) m/z 1174.1 [M+H]$^+$. $^1$H NMR (400 MHz, Methanol-d4) δ 8.53 (s, 3H), 8.51 (s, 1H), 8.19 (d, J=9.4 Hz, 1H), 7.43 (d, J=8.1 Hz, 3H), 7.34 (d, J=7.8 Hz, 3H), 7.23 (d, J=7.8 Hz, 3H), 7.18 (d, J=9.9 Hz, 1H), 6.83 (d, J=10.1 Hz, 1H), 4.96 (t, J=7.6 Hz, 3H), 4.80 (d, J=7.3 Hz, 6H), 4.44 (d, J=9.6 Hz, 1H), 4.30 (d, J=9.9 Hz, 1H), 4.15 (d, J=6.5 Hz, 5H), 3.94 (d, J=13.1 Hz, 1H), 3.72 (s, 2H), 3.68 (d, J=9.6 Hz, 8H), 3.48 (s, 2H), 3.44 (s, 1H), 2.96-2.81 (m, 3H), 2.79 (d, J=10.1 Hz, 1H), 2.74 (s, 1H), 2.45 (s, 8H), 2.21 (d, J=10.4 Hz, 3H), 1.99 (d, J=9.2 Hz, 3H), 1.16 (s, 5H), 1.14 (s, 8H), 1.11 (s, 4H), 1.02 (s, 4H).

EXAMPLE 132
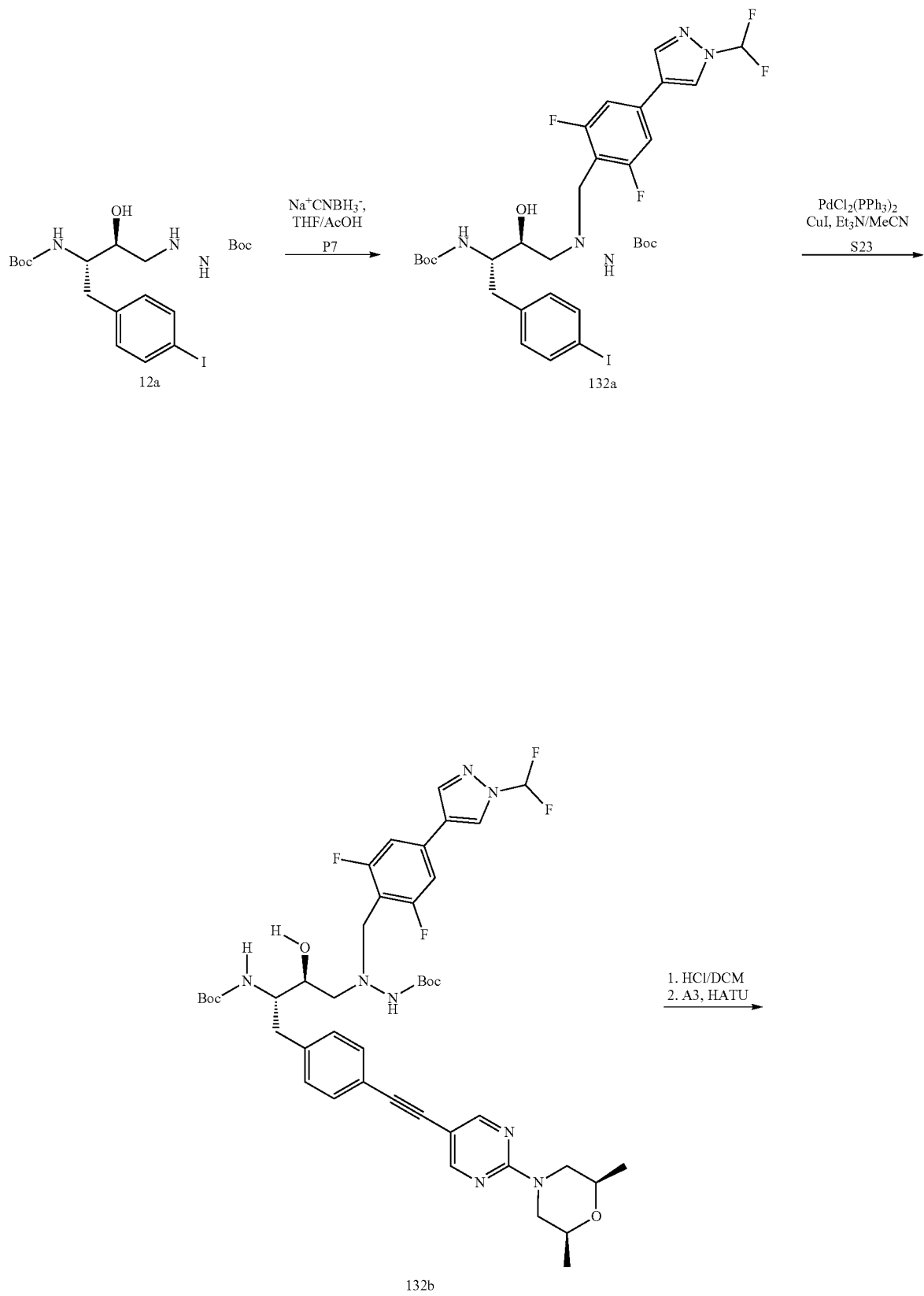

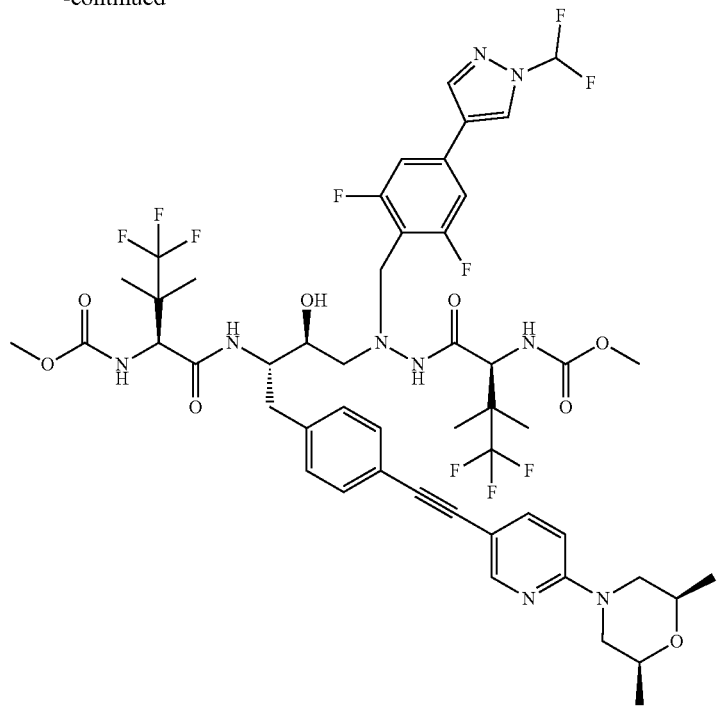

132

Synthesis of tert-butyl 2-((2S,3S)-3-((tert-butoxycarbonyl)amino)-2-hydroxy-4-(4-iodophenyl)butyl)-2-(4-(1-(difluoromethyl)-1H-pyrazol-4-yl)-2,6-difluorobenzyl)hydrazine-1-carboxylate (132a)

The title compound 132a was prepared according to the method presented for the synthesis of compound 1a but instead utilizing I2a and P7. MS (ESI) m/z 764.0 [M+H]⁺.

Synthesis of tert-butyl 2-((2S,3S)-3-((tert-butoxycarbonyl)amino)-4-(4-((6-((2S,6R)-2,6-dimethylmorpholino)pyridin-3-yl)ethynyl)phenyl)-2-hydroxybutyl)-2-(4-(1-(difluoromethyl)-1H-pyrazol-4-yl)-2,6-difluorobenzyl)hydrazine-1-carboxylate (132b)

The title compound 132b was prepared according to the method presented for the synthesis of compound 1 but instead utilizing 132a and S23. MS (ESI) m/z 852.0 [M+H]⁺. ¹H NMR (400 MHz, Methanol-d4) δ 8.53 (s, 1H), 8.19-8.08 (m, 2H), 7.93 (d, J=9.4 Hz, 1H), 7.50 (t, J=59.7 Hz, 1H), 7.40 (d, J=8.2 Hz, 2H), 7.28 (d, J=8.1 Hz, 5H), 4.07 (d, J=12.9 Hz, 2H), 3.74 (ddd, J=10.7, 6.3, 2.5 Hz, 1H), 3.62 (s, 1H), 2.87-2.69 (m, 3H), 1.37 (s, 7H), 1.31 (s, 5H), 1.27 (s, 3H), 1.25 (s, 3H).

Methyl ((5S,8S,9S,14S)-11-(4-(1-(difluoromethyl)-1H-pyrazol-4-yl)-2,6-difluorobenzyl)-8-(4-((6-((2S,6R)-2,6-dimethylmorpholino)pyridin-3-yl)ethynyl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (132)

The title compound 132 was prepared according to the method presented for the synthesis of intermediate I2 but instead utilizing 132b. MS (ESI) m/z 1102.3 [M+H]⁺. 1H NMR (400 MHz, Methanol-d4) δ 8.54 (d, J=0.7 Hz, 1H), 8.25-8.10 (m, 3H), 7.83 (d, J=9.1 Hz, 1H), 7.51 (s, 1H), 7.35 (d, J=7.3 Hz, 2H), 7.24 (t, J=7.7 Hz, 4H), 7.15 (dd, J=20.4, 9.7 Hz, 1H), 6.82 (d, J=10.0 Hz, 1H), 4.44 (d, J=9.8 Hz, 1H), 4.31 (d, J=9.9 Hz, 1H), 4.21-4.03 (m, 4H), 3.93 (d, J=13.2 Hz, 1H), 3.81-3.61 (m, 6H), 2.97-2.80 (m, 2H), 2.80-2.66 (m, 2H), 2.03 (s, 1H), 1.25 (d, J=6.2 Hz, 6H), 1.17 (s, 3H), 1.14 (s, 3H), 1.11 (s, 3H), 1.03 (s, 3H).

EXAMPLE 133
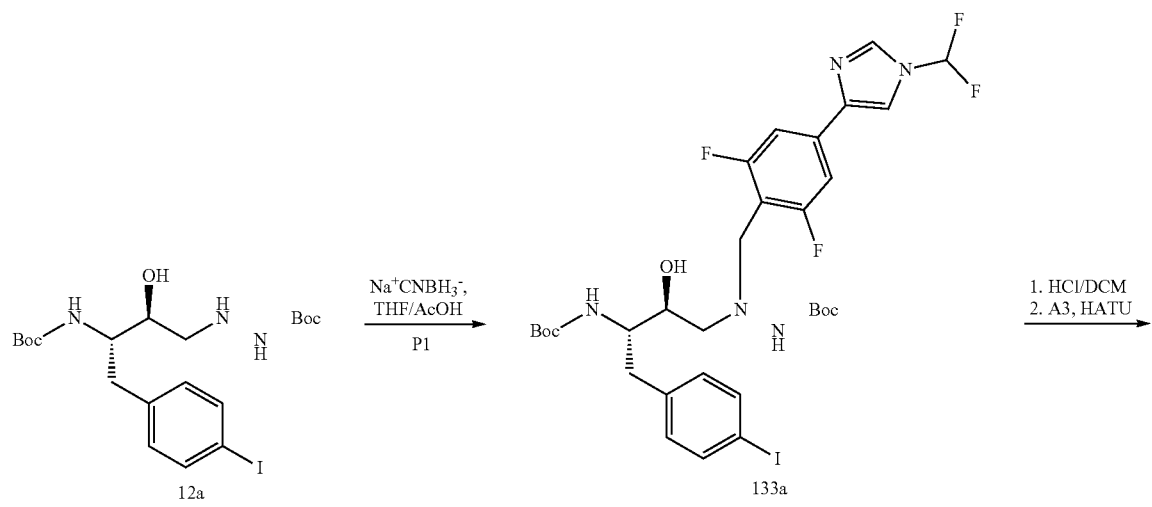
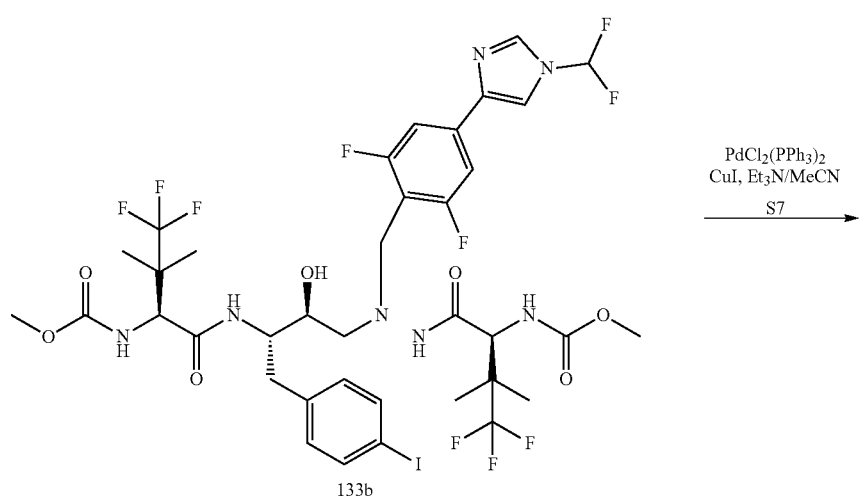

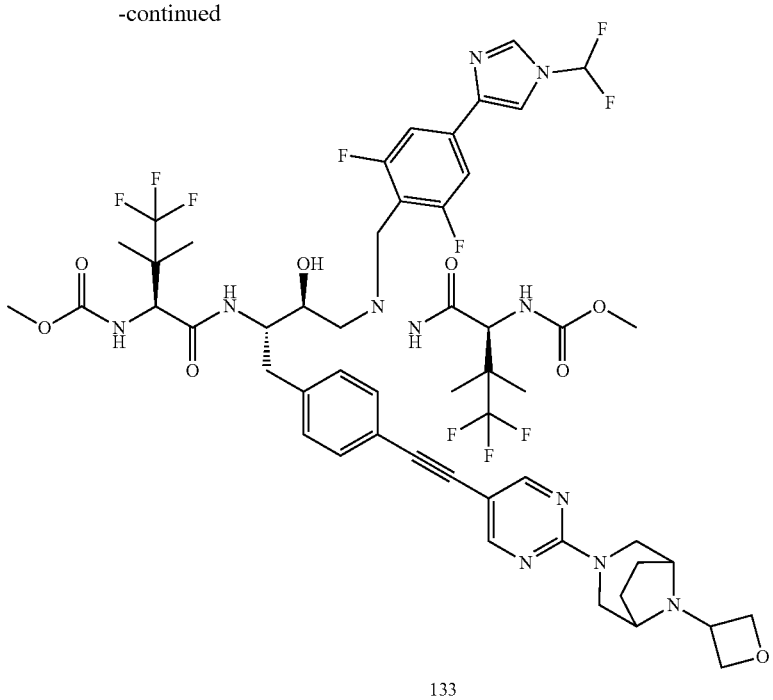

133

Synthesis of tert-butyl 2-((2S,3S)-3-((tert-butoxycarbonyl)amino)-2-hydroxy-4-(4-iodophenyl)butyl)-2-(4-(1-(difluoromethyl)-1H-imidazol-4-yl)-2,6-difluorobenzyl)hydrazine-1-carboxylate (133a)

A mixture of I2a (0.28 g, 0.53 mmol) and P1 (172 mg, 0.67 mmol) were dissolved in a mixture of THF/AcOH (12 mL, 3:1) After stirring at room temperature for 15 min sodium cyanoborohydride (2.49 mmol/gr on resin, 0.44 g, 1.09 mmol) was added. The reaction mixture was stirred overnight, then filtered and the filtered resin was rinsed several times with EtOAc. The combined filtrate was concentrated under reduced pressure; the residue was recrystallized/precipitated from EtOAc/hexanes to afford 133a (351.6 mg, 87.3%). MS (ESI) m/z 764.09 [M+H]+

Synthesis of methyl ((5S,10S,11S,14S)-8-(4-(1-(difluoromethyl)-1H-imidazol-4-yl)-2,6-difluorobenzyl)-16,16,16-trifluoro-10-hydroxy-11-(4-iodobenzyl)-15,15-dimethyl-3,6,13-trioxo-5-(1,1,1-trifluoro-2-methylpropan-2-yl)-2-oxa-4,7,8,12-tetraazahexadecan-14-yl)carbamate (133b)

133a (75%, 0.3 g, 0.29 mmol) was dissolved in DCM (10 mL) and HCl (4.0M in dioxane, 2.6 mL). The reaction was stirred for 3h then concentrated under reduce pressure the crude material was dissolved in DCM (10 mL) and HATU (0.24 g, 0.64 mmol), N, N-diisopropylethylamine (0.6 ml, 0 mol) was added followed by A3 (0.21 g, 0.86 mmol). The reaction was stirred at stirred at room temperature overnight. The reaction mixture was diluted with 5 mL of MeOH and concentrated. The crude residue was diluted with EtOAc and washed with 5% LiCl, saturated NaHCO3, and brine then dried over Na2SO4, filtered and concentrated under reduced pressure. The crude residue was purified by silica column chromatography (30% to 70% EtOAc/Hex) to afford 133b (296 mg, 67%). MS (ESI) m/z 1014.6 [M+H]+. 1H NMR (400 MHz, Methanol-d4) δ 8.15 (d, J=1.2 Hz, 1H), 8.01 (d, J=1.3 Hz, 1H), 7.58 (t, J=59.9 Hz, 1H), 7.52 (d, J=7.9 Hz, 2H), 7.38 (d, J=8.4 Hz, 2H), 6.99 (d, J=8.2 Hz, 2H), 4.45 (s, 1H), 4.30 (s, 1H), 4.14 (s, 0H), 3.93 (d, J=13.2 Hz, 1H), 3.71 (s, 3H), 3.66 (s, 3H), 2.92-2.67 (m, 4H), 1.16 (s, 3H), 1.14 (s, 3H), 1.11 (s, 3H), 1.02 (s, 3H).

Methyl ((5S,10S,11S,14S)-8-(4-(1-(difluoromethyl)-1H-imidazol-4-yl)-2,6-difluorobenzyl)-16,16,16-trifluoro-10-hydroxy-15,15-dimethyl-11-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (133)

In a vial, a solution of 133b (50 mg, 0.05 mmol), S7 (17 mg, 0.06 mmol), copper (I) iodide (4.0 mg, 0.02 mmol), trans-Dichlorobis(triphenylphosphine)palladium (II) (99%, 11.1 mg, 0.02 mmol) in a mixture of and MeCN:Et3N 3:1 (1 mL) was degassed and then stirred at room temperature overnight. Concentrated under reduced pressure. Purification by HPLC and Lyophilized to give 133. MS (ESI) m/z 1156.4 [M+H]+. 1H NMR (400 MHz, Methanol-d4) δ 8.44 (s, 2H), 8.09 (d, J=17.5 Hz, 2H), 7.93 (s, 1H), 7.49 (t, J=60.0 Hz, 1H), 7.27 (dd, J=18.4, 8.1 Hz, 3H), 7.14 (d, J=8.0 Hz, 2H), 6.73 (d, J=9.9 Hz, 1H), 4.86 (d, J=7.6 Hz, 2H), 4.72 (dd, J=8.2, 5.0 Hz, 2H), 4.35 (d, J=8.7 Hz, 1H), 4.22 (d, J=9.8 Hz, 1H), 4.03 (d, J=12.8 Hz, 4H), 3.84 (d, J=13.2 Hz, 1H), 3.58 (d, J=8.6 Hz, 5H), 3.37 (d, J=14.4 Hz, 2H), 2.90-2.62 (m, 4H), 2.56 (s, 1H), 2.12 (d, J=11.1 Hz, 2H), 1.90 (d, J=9.0 Hz, 2H), 1.07 (s, 3H), 1.05 (s, 3H), 1.01 (s, 3H), 0.93 (s, 3H).

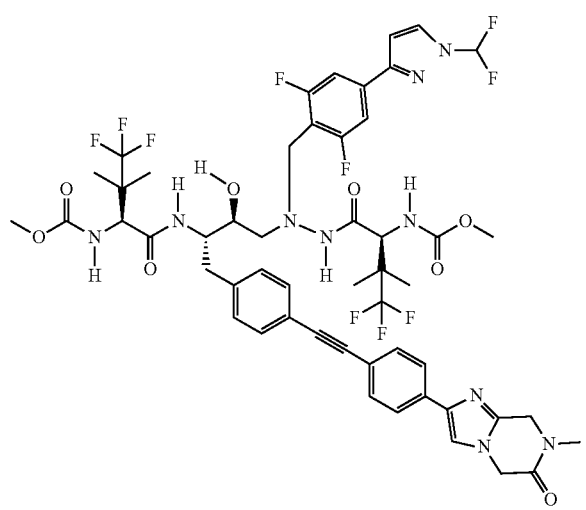

EXAMPLE 134

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((4-(7-methyl-6-oxo-5,6,7,8-tetrahydroimidazo[1,2-a]pyrazin-2-yl)phenyl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: P4, A3, and S5. MS (ESI) m/z 1137.1 [M+H]+. 1H NMR (400 MHz, Methanol-d4) δ 8.11 (d, J=9.4 Hz, 1H), 8.01 (d, J=2.7 Hz, 1H), 7.75-7.50 (m, 6H), 7.46 (d, J=16.5 Hz, 2H), 7.36 (d, J=8.2 Hz, 2H), 7.28 (d, J=9.5 Hz, 3H), 7.15 (d, J=8.0 Hz, 3H), 6.85 (d, J=2.7 Hz, 1H), 6.73 (d, J=10.0 Hz, 1H), 4.79-4.71 (m, 5H), 4.35 (d, J=9.9 Hz, 1H), 4.22 (d, J=10.0 Hz, 1H), 4.06 (d, J=13.5 Hz, 3H), 3.85 (d, J=13.0 Hz, 1H), 3.65 (s, 2H), 3.61 (s, 3H), 3.57 (s, 3H), 3.08 (s, 4H), 2.83 (d, J=8.0 Hz, 2H), 2.73-2.62 (m, 1H), 1.07 (s, 4H), 1.05 (s, 3H), 1.02 (s, 4H), 0.94 (s, 3H).

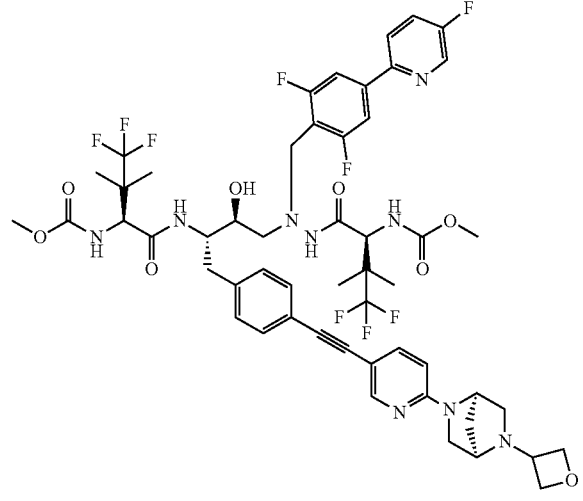

EXAMPLE 135

Methyl ((5S,10S,11S,14S)-8-(2,6-difluoro-4-(5-fluoropyridin-2-yl)benzyl)-16,16,16-trifluoro-10-hydroxy-15,15-dimethyl-11-(4-((6-((1R,4R)-5-(oxetan-3-yl)-2,5 diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (135)

Intermediates: P14, A3, and S6. MS (ESI) m/z 1120.2 [M+H]+. 1H NMR (400 MHz, Methanol-d4) δ 8.46 (d, J=2.9 Hz, 1H), 8.16 (d, J=2.1 Hz, 1H), 8.11 (d, J=9.2 Hz, 1H), 7.87 (dd, J=8.8, 4.3 Hz, 1H), 7.65-7.55 (m, 2H), 7.51 (d, J=8.7 Hz, 2H), 7.23 (d, J=7.9 Hz, 2H), 7.13 (d, J=8.1 Hz, 3H), 6.74 (d, J=10.0 Hz, 1H), 6.57 (d, J=8.8 Hz, 1H), 4.95 (s, 1H), 4.86 (dd, J=8.4, 6.3 Hz, 1H), 4.61 (s, 1H), 4.49 (dq, J=11.2, 6.0, 5.5 Hz, 2H), 4.41 (s, 1H), 4.35 (d, J=9.7 Hz, 1H), 4.21 (d, J=10.0 Hz, 1H), 4.07 (d, J=13.3 Hz, 2H), 3.87 (d, J=13.1 Hz, 1H), 3.74-3.62 (m, 2H), 3.60 (s, 3H), 3.55 (s, 3H), 2.87-2.73 (m, 3H), 2.73-2.65 (m, 1H), 2.23 (s, 2H), 1.06 (d, J=5.4 Hz, 6H), 1.02 (s, 3H), 0.93 (s, 3H).

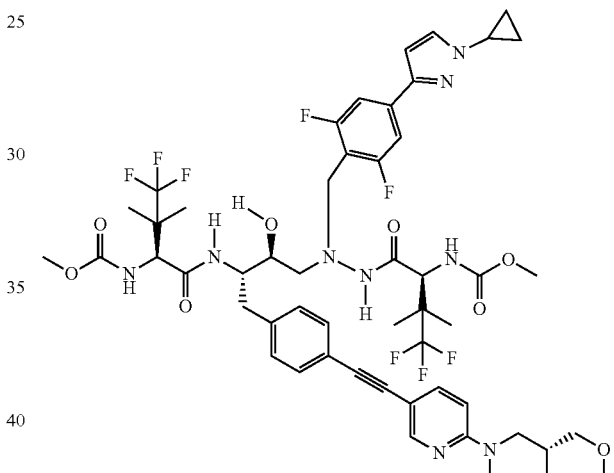

EXAMPLE 136 methyl ((5S,8S,9S,14S)-11-(4-(1-cyclopropyl-1H-pyrazol-3-yl)-2,6-difluorobenzyl)-16,16,16-trifluoro-8-(4-((6-((R)-hexahydropyrazino[2,1-c][1,4]oxazin-8(1H)-yl)pyridin-3-yl)ethynyl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (136)

Intermediates: P13, A3, and S8. MS (ESI) m/z 1118.6 [M+H]+. 1H NMR (400 MHz, Methanol-d4) δ 8.22 (d, J=2.3 Hz, 1H), 8.10 (d, J=9.4 Hz, 1H), 7.61 (dt, J=5.4, 2.6 Hz, 2H), 7.59-7.50 (m, 1H), 7.47 (dt, J=7.7, 4.1 Hz, 1H), 7.30-7.19 (m, 4H), 7.13 (d, J=8.1 Hz, 2H), 7.06 (s, 0H), 6.86 (d, J=8.9 Hz, 1H), 6.72 (d, J=9.9 Hz, 1H), 6.55 (d, J=2.5 Hz, 1H), 4.53 (dd, J=22.7, 13.2 Hz, 2H), 4.42-4.30 (m, 1H), 4.26-4.18 (m, 1H), 4.03 (d, J=13.2 Hz, 4H), 3.84 (d, J=13.1 Hz, 1H), 3.76 (t, J=12.7 Hz, 1H), 3.59 (d, J=9.3 Hz, 6H), 3.49 (d, J=11.0 Hz, 1H), 3.44-3.35 (m, 0H), 2.81 (d, J=7.3 Hz, 3H), 2.72-2.63 (m, 1H), 1.08 (s, 3H), 1.05 (s, 4H), 1.04 (d, J=2.8 Hz, 0H), 1.02 (s, 2H), 1.00-0.95 (m, 1H), 0.94 (s, 3H).

309

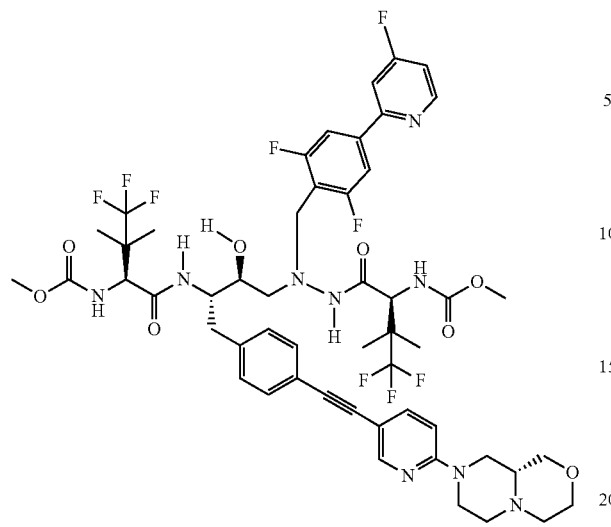

EXAMPLE 137

Methyl ((5S,8S,9S,14S)-11-(2,6-difluoro-4-(4-fluoropyridin-2-yl)benzyl)-16,16,16-trifluoro-8-(4-((6-((R)-hexahydropyrazino[2,1-c][1,4]oxazin-8(1H)-yl)pyridin-3-yl)ethynyl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (137)

Intermediates: P15, A3, and S8. MS (ESI) m/z 1118.6 [M+H]+. $^1$H NMR (400 MHz, Methanol-d4) δ 8.56 (dd, J=8.6, 5.6 Hz, 1H), 8.21 (d, J=2.2 Hz, 1H), 8.11 (d, J=9.3 Hz, 1H), 7.67 (dd, J=10.3, 2.4 Hz, 1H), 7.61 (dd, J=8.9, 2.2 Hz, 1H), 7.56 (d, J=8.5 Hz, 2H), 7.24 (d, J=7.9 Hz, 2H), 7.16-7.08 (m, 3H), 6.86 (d, J=8.9 Hz, 1H), 6.74 (d, J=10.0 Hz, 1H), 4.52 (dd, J=23.4, 12.6 Hz, 2H), 4.35 (d, J=10.0 Hz, 1H), 4.21 (d, J=9.9 Hz, 1H), 4.07 (t, J=10.4 Hz, 4H), 3.87 (d, J=13.2 Hz, 1H), 3.75 (t, J=12.6 Hz, 1H), 3.64 (s, 1H), 3.60 (s, 3H), 3.55 (s, 2H), 3.48 (d, J=10.7 Hz, 1H), 3.39 (t, J=10.4 Hz, 1H), 2.88-2.73 (m, 4H), 2.73-2.64 (m, 1H), 1.06 (d, J=5.6 Hz, 6H), 1.02 (s, 3H), 0.93 (s, 3H).

310

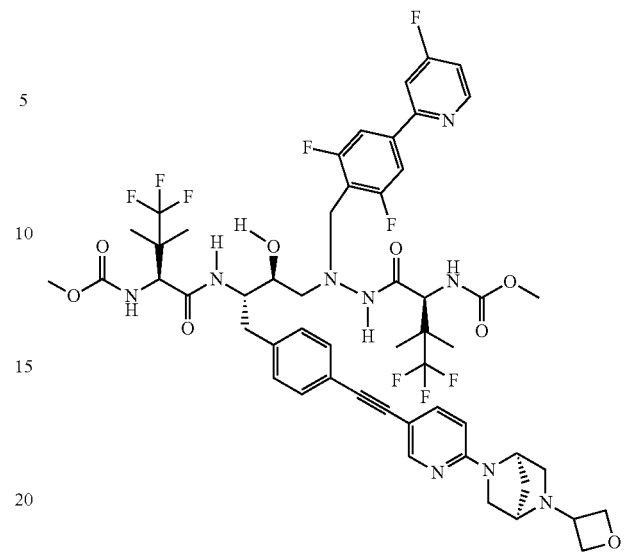

EXAMPLE 138

Methyl ((5S,8S,9S,14S)-11-(2,6-difluoro-4-(4-fluoropyridin-2-yl)benzyl)-16,16,16-trifluoro-9-hydroxy-15,15-dimethyl-8-(4-((6-(((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (138)

Intermediates: P15, A3, and S6. MS (ESI) m/z 1120.6 [M+H]+. $^1$H NMR (400 MHz, Methanol-d4) δ 8.56 (dd, J=8.6, 5.6 Hz, 1H), 8.16 (s, 1H), 8.11 (d, J=9.5 Hz, 1H), 7.68 (d, J=9.4 Hz, 1H), 7.58 (dd, J=14.3, 8.7 Hz, 3H), 7.23 (d, J=7.9 Hz, 2H), 7.13 (d, J=8.0 Hz, 4H), 6.74 (d, J=10.2 Hz, 1H), 6.57 (d, J=8.8 Hz, 1H), 4.95 (s, 1H), 4.61 (s, 1H), 4.49 (dd, J=11.6, 6.4 Hz, 1H), 4.41 (s, 1H), 4.35 (d, J=10.0 Hz, 1H), 4.21 (d, J=9.9 Hz, 1H), 4.08 (d, J=12.8 Hz, 2H), 3.87 (d, J=13.0 Hz, 1H), 3.66 (d, J=16.3 Hz, 2H), 3.60 (d, J=1.1 Hz, 3H), 3.55 (s, 3H), 2.81 (d, J=7.8 Hz, 2H), 2.71 (d, J=9.5 Hz, 1H), 2.23 (s, 2H), 1.06 (d, J=4.6 Hz, 6H), 1.02 (s, 3H), 0.93 (s, 3H).

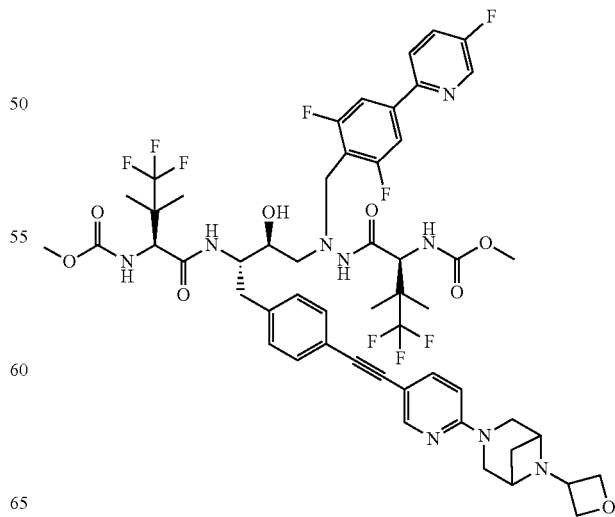

EXAMPLE 139

Methyl ((5S,10S,11S,14S)-8-(2,6-difluoro-4-(5-fluoropyridin-2-yl)benzyl)-16,16,16-trifluoro-10-hydroxy-15,15-dimethyl-11-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamateate (139)

Intermediates: P14, A3, and S4. MS (ESI) m/z 1120.2 [M+H]+. ¹H NMR (400 MHz, Methanol-d4) δ 8.46 (d, J=2.9 Hz, 1H), 8.24 (d, J=2.3 Hz, 1H), 8.10 (d, J=9.3 Hz, 1H), 7.96-7.86 (m, 1H), 7.65 (dd, J=8.8, 2.3 Hz, 1H), 7.59 (td, J=8.5, 3.0 Hz, 1H), 7.51 (d, J=8.6 Hz, 2H), 7.24 (d, J=7.9 Hz, 2H), 7.13 (d, J=8.0 Hz, 2H), 7.08 (d, J=9.9 Hz, 1H), 6.73 (d, J=10.6 Hz, 1H), 6.69 (d, J=8.9 Hz, 1H), 4.96-4.83 (m, 4H), 4.59-4.47 (m, 2H), 4.42-4.31 (m, 1H), 4.31-4.19 (m, 1H), 4.07 (d, J=13.4 Hz, 4H), 3.87 (d, J=13.2 Hz, 1H), 3.64 (s, 2H), 3.60 (s, 3H), 3.56 (s, 3H), 2.82 (d, J=8.4 Hz, 2H), 2.74-2.65 (m, 1H), 2.02 (d, J=11.0 Hz, 1H), 1.07 (s, 4H), 1.06 (s, 3H), 1.02 (s, 3H), 0.93 (s, 3H).

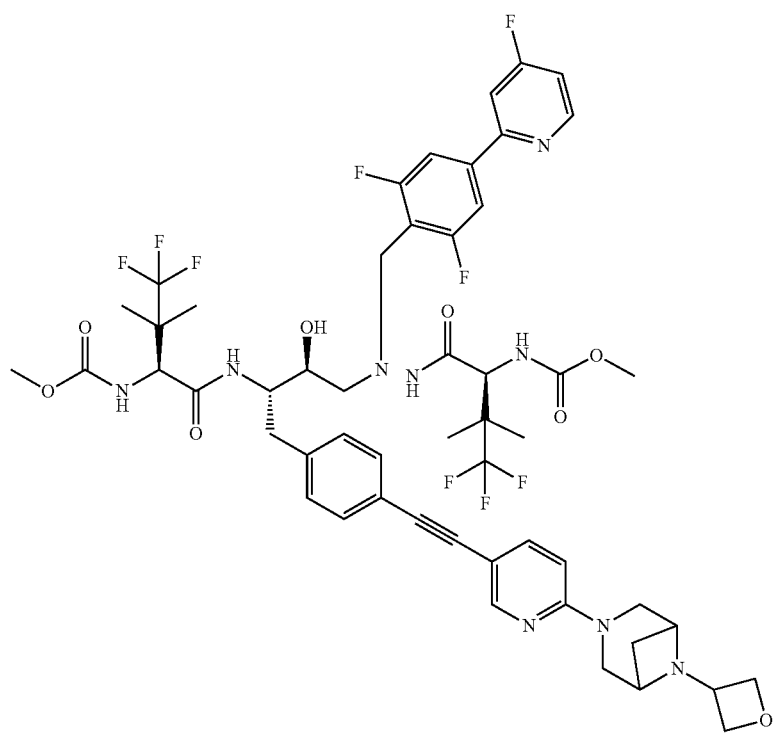

EXAMPLE 140

Methyl ((5S,10S,11S,14S)-8-(2,6-difluoro-4-(4-fluoropyridin-2-yl)benzyl)-16,16,16-trifluoro-10-hydroxy-15,15-dimethyl-11-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,8,12-tetraazahexadecan-14-yl)carbamate (140)

Intermediates: P15, A3, and S4. MS (ESI) m/z 1120.2 [M+H]+. $^1$H NMR (400 MHz, Methanol-d4) δ 8.66 (dd, J=8.6, 5.6 Hz, 1H), 8.33 (s, 1H), 8.21 (d, J=9.3 Hz, 1H), 7.76 (t, J=9.9 Hz, 2H), 7.66 (d, J=8.5 Hz, 2H), 7.34 (d, J=7.8 Hz, 2H), 7.23 (d, J=7.7 Hz, 3H), 6.84 (d, J=10.1 Hz, 0H), 6.78 (d, J=8.9 Hz, 1H), 4.61 (dd, J=8.2, 4.0 Hz, 2H), 4.45 (d, J=10.0 Hz, 1H), 4.31 (d, J=10.0 Hz, 1H), 4.18 (d, J=12.4 Hz, 2H), 3.99 (s, 0H), 3.74 (s, 2H), 3.70 (s, 3H), 3.65 (s, 2H), 2.91 (d, J=8.1 Hz, 2H), 2.80 (d, J=9.8 Hz, 1H), 2.11 (d, J=10.9 Hz, 1H), 1.33-1.23 (m, 1H), 1.16 (s, 4H), 1.15 (s, 3H), 1.12 (s, 2H), 1.03 (s, 3H).

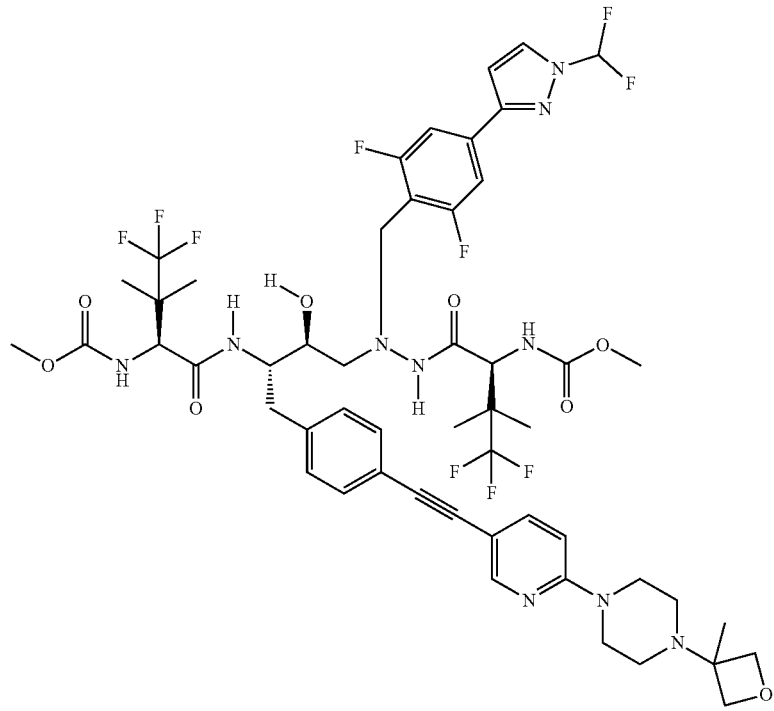 [SMILES: COC(=O)N[C@H](C(=O)N[C@@H](Cc1ccc(C#Cc2ccc(N3CCN(C4(C)COC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 141 methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(((6-(4-(3-methyloxetan-3-yl)piperazin-1-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (141)

Intermediates: P4, A3, and S10. MS (ESI) m/z 1143 [M+H]+. $^1$H NMR (400 MHz, Methanol-d4) δ 8.12 (d, J=2.3 Hz, 1H), 8.08 (d, J=9.4 Hz, 1H), 8.01 (d, J=2.7 Hz, 1H), 7.62-7.42 (m, 3H), 7.36 (d, J=8.2 Hz, 2H), 7.22 (d, J=7.9 Hz, 2H), 7.11 (d, J=8.1 Hz, 2H), 7.06 (d, J=9.9 Hz, 1H), 6.85 (d, J=2.8 Hz, 1H), 6.72 (dd, J=9.5, 5.4 Hz, 2H), 4.56 (d, J=5.9 Hz, 2H), 4.34 (d, J=9.9 Hz, 1H), 4.27-4.15 (m, 3H), 4.05 (d, J=12.1 Hz, 2H), 3.85 (d, J=13.1 Hz, 1H), 3.64 (s, 2H), 3.60 (s, 3H), 3.56 (d, J=8.7 Hz, 7H), 2.75 (dd, J=44.1, 8.8 Hz, 4H), 2.46 (t, J=5.0 Hz, 4H), 1.32 (s, 3H), 1.07 (s, 3H), 1.05 (s, 3H), 1.02 (s, 3H), 0.94 (s, 3H).

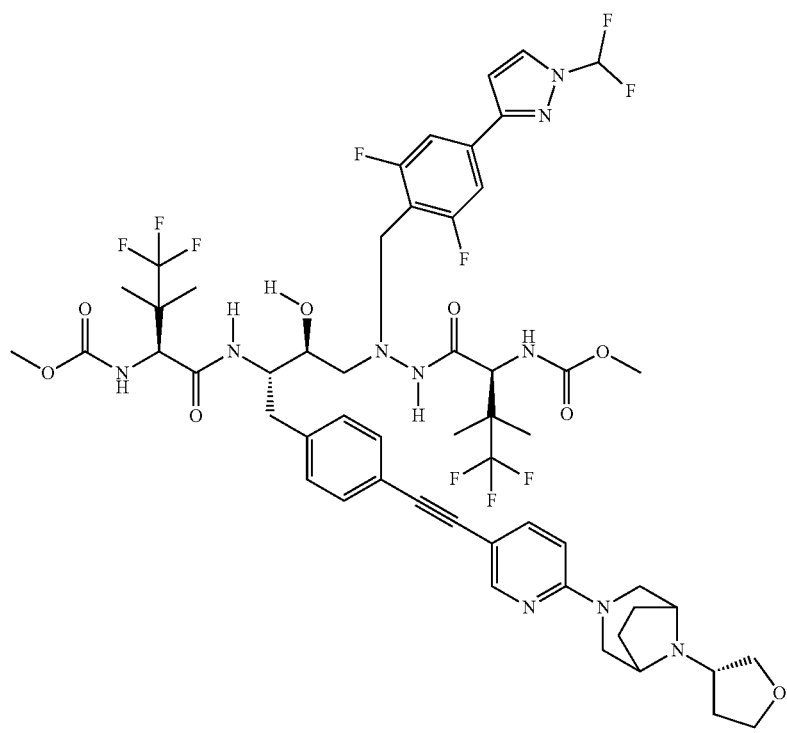 [SMILES: COC(=O)N[C@H](C(=O)N[C@@H](Cc1ccc(C#Cc2ccc(N3CC4CCC(C3)N4[C@H]3CCOC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 142

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-8-(4-((6-(8-((S)-tetrahydrofuran-3-yl)-3,8-diazabicyclo[3.2.1]octan-3-yl)pyridin-3-yl)ethynyl)benzyl)-5-(1,1,1-trifluoro-2-methylpropan-2-yl)-2-oxa-4,7,11,12-tetraazahexadecan-14-yl)carbamate (142)

Intermediates: P4, A3, and S11. MS (ESI) m/z 1170.2 [M+H]+. 1H NMR (400 MHz, Methanol-d4) δ 8.29 (d, J=2.3 Hz, 1H), 8.17 (d, J=9.4 Hz, 1H), 8.10 (d, J=2.7 Hz, 1H), 7.76-7.60 (m, 2H), 7.60-7.52 (m, 1H), 7.45 (d, J=8.2 Hz, 2H), 7.33 (d, J=7.8 Hz, 2H), 7.22 (d, J=8.0 Hz, 2H), 7.13 (d, J=9.8 Hz, 1H), 6.94 (d, J=2.7 Hz, 1H), 6.84 (d, J=8.9 Hz, 1H), 6.79 (d, J=10.0 Hz, 1H), 4.45 (s, 0H), 4.42-4.27 (m, 2H), 4.23 (s, 1H), 4.20-4.05 (m, 2H), 4.05-3.89 (m, 3H), 3.88-3.56 (m, 8H), 3.06-2.85 (m, 3H), 2.85-2.69 (m, 1H), 2.50 (d, J=12.5 Hz, 1H), 2.32 (s, 2H), 2.22-2.00 (m, 3H), 1.16 (s, 4H), 1.14 (s, 3H), 1.11 (s, 3H), 1.03 (s, 3H).

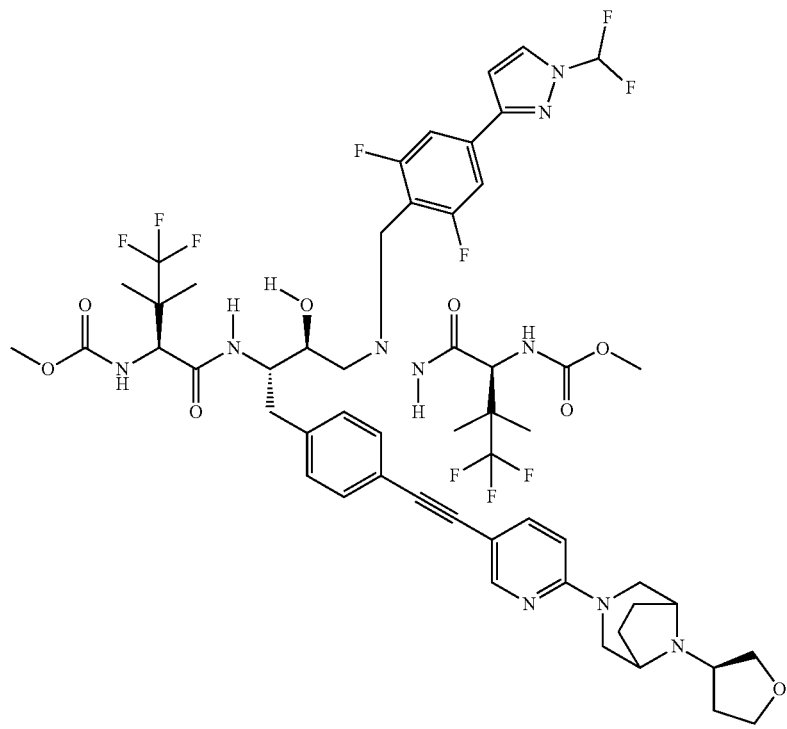

EXAMPLE 143

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-8-(4-((6-(8-((R)-tetrahydrofuran-3-yl)-3,8-diazabicyclo[3.2.1]octan-3-yl)pyridin-3-yl)ethynyl)benzyl)-5-(1,1,1-trifluoro-2-methylpropan-2-yl)-2-oxa-4,7,11,12-tetraazahexadecan-14-yl)carbamate (143)

Intermediates: P4, A3, and S12. MS (ESI) m/z 1170.1 [M+H]+. $^1$H NMR (400 MHz, Methanol-d4) δ 8.29 (d, J=2.2 Hz, 1H), 8.17 (d, J=9.3 Hz, 1H), 8.10 (d, J=2.7 Hz, 1H), 7.74-7.60 (m, 2H), 7.59-7.50 (m, 1H), 7.45 (d, J=8.2 Hz, 2H), 7.33 (d, J=7.8 Hz, 2H), 7.22 (d, J=8.0 Hz, 2H), 7.13 (d, J=9.7 Hz, 1H), 6.94 (d, J=2.7 Hz, 1H), 6.84 (d, J=8.9 Hz, 1H), 6.79 (d, J=9.9 Hz, 1H), 4.44 (d, J=10.1 Hz, 1H), 4.30 (d, J=9.9 Hz, 1H), 4.23 (s, 1H), 4.14 (d, J=12.3 Hz, 2H), 3.97 (t, J=14.4 Hz, 1H), 3.86-3.57 (m, 8H), 2.97-2.84 (m, 3H), 2.84-2.68 (m, 1H), 2.49 (s, 1H), 2.32 (s, 2H), 2.22-2.04 (m, 3H), 1.16 (s, 4H), 1.14 (s, 3H), 1.11 (s, 3H), 1.03 (s, 3H).

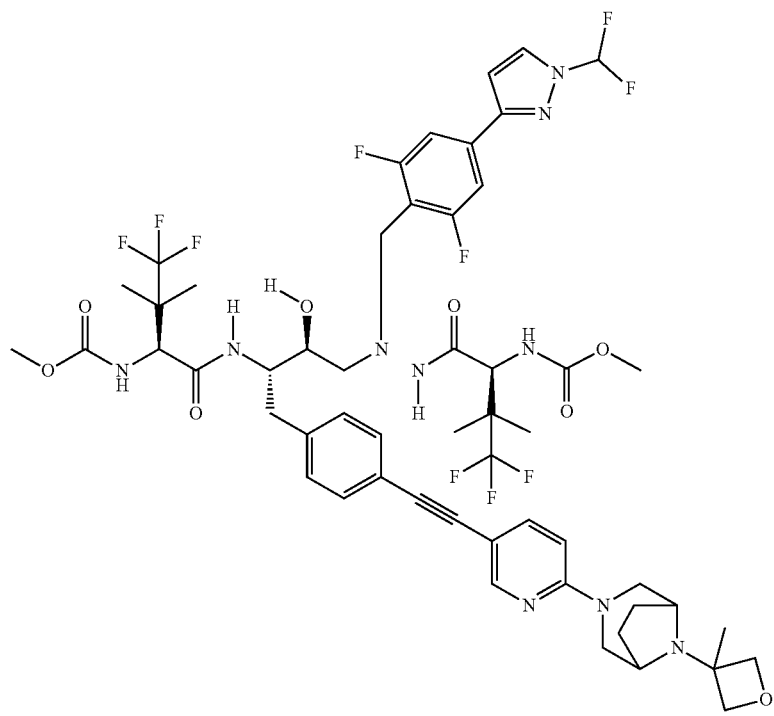

EXAMPLE 144

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(8-(3-methyloxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (144)

Intermediates: P4, A3, and S13. MS (ESI) m/z 1170.9 [M+H]+. $^1$H NMR (400 MHz, Methanol-d4) δ 8.23-8.13 (m, 1H), 8.10 (d, J=2.8 Hz, 1H), 7.57 (dd, J=8.9, 2.4 Hz, 1H), 7.53 (t, J=59.8 Hz, 1H), 7.45 (d, J=8.2 Hz, 2H), 7.31 (d, J=7.9 Hz, 2H), 7.20 (d, J=8.1 Hz, 2H), 6.94 (d, J=2.7 Hz, 1H), 6.69 (d, J=9.0 Hz, 1H), 4.43 (s, 1H), 4.30 (s, 1H), 4.14 (d, J=12.1 Hz, 2H), 3.95 (d, J=13.2 Hz, 1H), 3.84 (dt, J=8.2, 4.5 Hz, 2H), 3.69 (s, 3H), 3.66 (s, 3H), 3.49 (d, J=7.1 Hz, 1H), 3.39 (s, 1H), 3.11 (dt, J=11.9, 2.1 Hz, 2H), 2.90 (d, J=8.0 Hz, 2H), 2.83-2.76 (m, 1H), 2.73 (d, J=5.0 Hz, 1H), 2.69 (s, 0H), 2.62 (d, J=4.9 Hz, 1H), 2.46 (d, J=13.4 Hz, 1H), 1.97 (s, 2H), 1.67 (d, J=9.0 Hz, 2H), 1.43 (s, 3H), 1.16 (s, 3H), 1.14 (s, 3H), 1.11 (s, 3H), 1.03 (s, 3H).

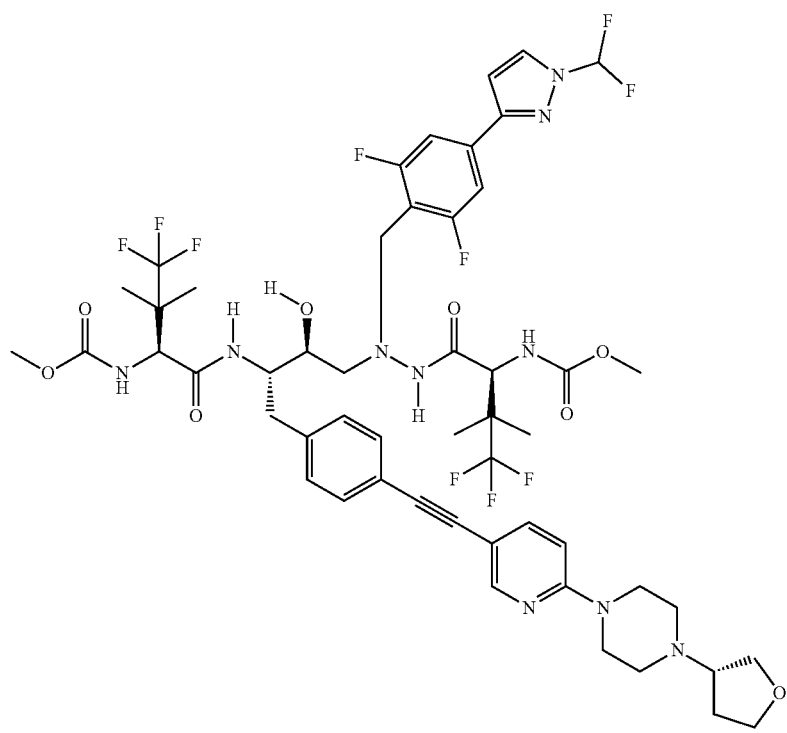 [SMILES: COC(=O)N[C@H](C(=O)N[C@@H](Cc1ccc(C#Cc2ccc(N3CCN([C@H]4CCOC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 145

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-8-(4-((6-(4-((S)-tetrahydrofuran-3-yl)piperazin-1-yl)pyridin-3-yl)ethynyl)benzyl)-5-(1,1,1-trifluoro-2-methylpropan-2-yl)-2-oxa-4,7,11,12-tetraazahexadecan-14-yl)carbamate (145)

Intermediates: P4, A3, and S15. MS (ESI) m/z 1143.5 [M+H]+. $^1$H NMR (400 MHz, Methanol-d4) δ 8.36-8.26 (m, 1H), 8.19 (d, J=9.2 Hz, 1H), 8.11 (d, J=2.7 Hz, 1H), 7.71 (d, J=2.3 Hz, 1H), 7.69 (d, J=2.1 Hz, 1H), 7.67-7.61 (m, 0H), 7.57 (dd, J=7.3, 3.3 Hz, 1H), 7.54 (s, 1H), 7.45 (d, J=8.2 Hz, 2H), 7.33 (d, J=7.9 Hz, 2H), 7.22 (d, J=8.0 Hz, 2H), 7.15 (s, 1H), 6.99-6.86 (m, 2H), 6.81 (d, J=10.1 Hz, 1H), 4.45 (s, 0H), 4.31 (d, J=10.0 Hz, 1H), 4.26-4.02 (m, 5H), 4.00-3.82 (m, 3H), 3.75 (d, J=8.4 Hz, 1H), 3.68 (d, J=10.9 Hz, 6H), 2.97-2.85 (m, 3H), 2.55-2.35 (m, 1H), 2.28-2.16 (m, 1H), 1.16 (s, 4H), 1.15 (s, 3H), 1.12 (s, 3H), 1.03 (s, 3H).

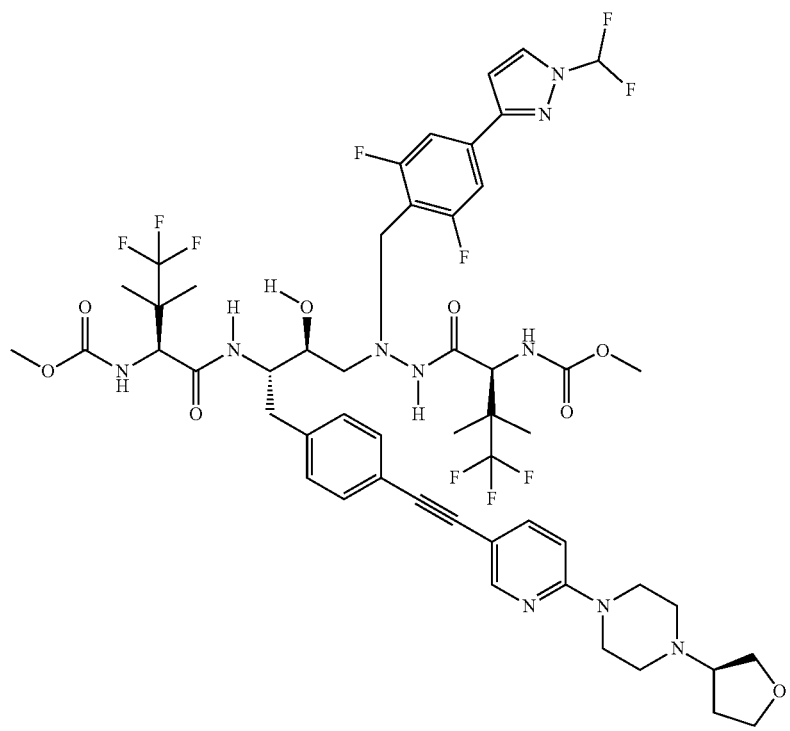 [SMILES: COC(=O)N[C@H](C(=O)N[C@@H](Cc1ccc(C#Cc2ccc(N3CCN([C@@H]4CCOC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 146

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-8-(4-((6-(4-((R)-tetrahydrofuran-3-yl)piperazin-1-yl)pyridin-3-yl)ethynyl)benzyl)-5-(1,1,1-trifluoro-2-methylpropan-2-yl)-2-oxa-4,7,11,12-tetraazahexadecan-14-yl)carbamate (146)

Intermediates: P4, A3, and S14. MS (ESI) m/z 1143.5 [M+H]+. $^1$H NMR (400 MHz, Methanol-d4) δ 8.30 (d, J=2.3 Hz, 1H), 8.19 (d, J=9.1 Hz, 1H), 8.11 (d, J=2.8 Hz, 1H), 7.71 (d, J=2.4 Hz, 0H), 7.69 (s, 1H), 7.68-7.61 (m, 1H), 7.60-7.55 (m, 1H), 7.54 (s, 1H), 7.45 (d, J=8.2 Hz, 2H), 7.33 (d, J=7.8 Hz, 2H), 7.23 (d, J=8.1 Hz, 3H), 6.96-6.85 (m, 2H), 6.81 (d, J=9.9 Hz, 1H), 4.44 (d, J=9.8 Hz, 1H), 4.31 (d, J=10.0 Hz, 1H), 4.23-4.07 (m, 4H), 3.95 (d, J=13.3 Hz, 1H), 3.92-3.86 (m, 1H), 3.75 (d, J=8.2 Hz, 2H), 3.69 (s, 4H), 3.66 (s, 3H), 3.00-2.82 (m, 3H), 2.79 (d, J=10.0 Hz, 1H), 2.42 (s, 0H), 2.21 (d, J=8.5 Hz, 0H), 1.16 (s, 5H), 1.15 (s, 3H), 1.12 (s, 3H), 1.03 (s, 3H).

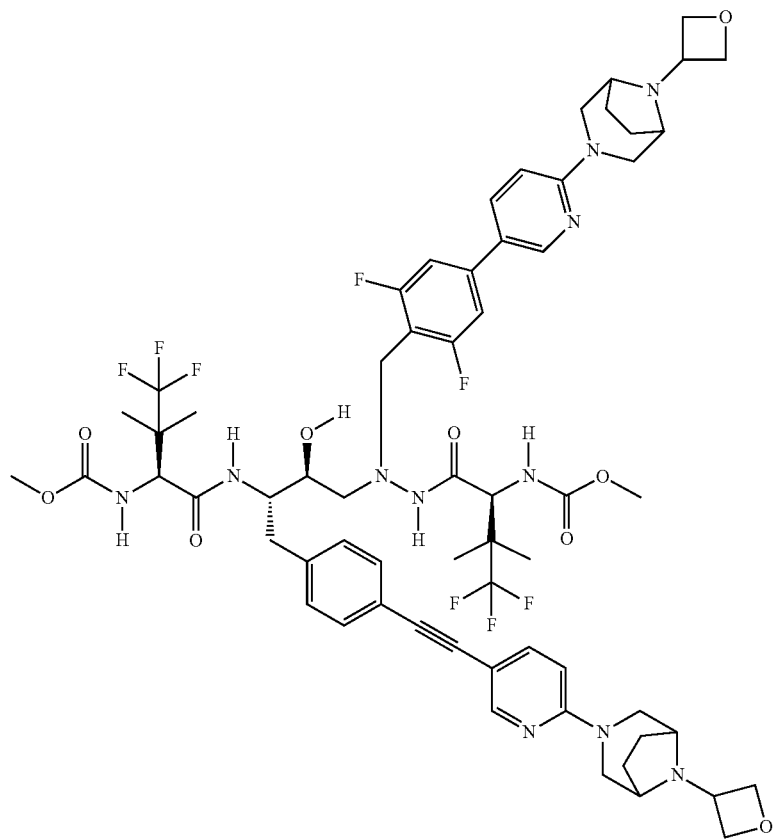 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(N3CC4CCC(C3)N4C3COC3)nc2)cc1F)NC(=O)[C@@H](NC(=O)OC)C(C)(C)C(F)(F)F)C(C)(C)C(F)(F)F]

EXAMPLE 147

Methyl ((5S,8S,9S,14S)-11-(2,6-difluoro-4-(6-(8-(oxetan-3-yl)-3,8-diazabicyclo[3.2.1]octan-3-yl)pyridin-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (147)

Intermediates: P22, A3, and S3. MS (ESI) m/z 1282.4 [M+H]+. $^1$H NMR (400 MHz, Methanol-d4) δ 8.43-8.31 (m, 1H), 8.20 (d, J=2.3 Hz, 1H), 7.84 (d, J=9.0 Hz, 1H), 7.60 (dd, J=8.8, 2.3 Hz, 1H), 7.24 (d, J=7.9 Hz, 2H), 7.17-7.04 (m, 4H), 6.86 (d, J=9.0 Hz, 1H), 6.77 (d, J=8.9 Hz, 1H), 6.71 (d, J=10.0 Hz, 1H), 4.87 (t, J=7.7 Hz, 4H), 4.74-4.68 (m, 4H), 4.37-4.17 (m, 6H), 4.10-3.99 (m, 6H), 3.86 (d, J=13.1 Hz, 1H), 3.67-3.62 (m, 1H), 3.60 (s, 3H), 3.56 (s, 3H), 3.34-3.25 (m, 5H), 2.81 (d, J=7.7 Hz, 2H), 2.74-2.65 (m, 1H), 2.19-2.10 (m, 4H), 2.03-1.93 (m, 4H), 1.07 (s, 3H), 1.05 (s, 3H), 1.02 (s, 3H), 0.93 (s, 3H).

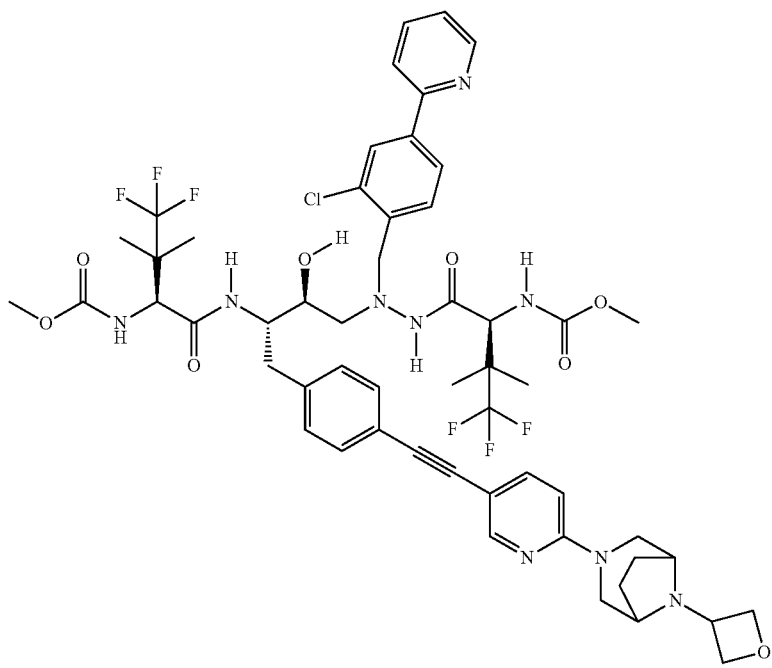 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(-c2ccccn2)cc1Cl)NC(=O)[C@@H](NC(=O)OC)C(C)(C)C(F)(F)F)C(C)(C)C(F)(F)F]

EXAMPLE 148

Methyl ((5S,8S,9S,14S)-11-(2-chloro-4-(pyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (148)

Intermediates: P25, A3, and S3. MS (ESI) m/z 1114.7 [M+H]+. $^1$H NMR (400 MHz, Methanol-d4) δ 8.55 (d, J=5.0 Hz, 1H), 8.20 (d, J=2.1 Hz, 1H), 8.04 (d, J=9.5 Hz, 1H), 7.94-7.85 (m, 1H), 7.82 (d, J=8.1 Hz, 1H), 7.77-7.70 (m, 1H), 7.65 (d, J=8.1 Hz, 1H), 7.60 (dd, J=8.8, 2.3 Hz, 1H), 7.42-7.32 (m, 1H), 7.24 (d, J=7.9 Hz, 2H), 7.13 (d, J=8.0 Hz, 2H), 6.77 (d, J=8.8 Hz, 1H), 6.71 (d, J=10.3 Hz, 1H), 4.87 (t, J=7.6 Hz, 2H), 4.73-4.66 (m, 2H), 4.31 (d, J=10.0 Hz, 1H), 4.18 (d, J=9.7 Hz, 1H), 4.14-4.03 (m, 3H), 3.99 (d, J=14.2 Hz, 1H), 3.74-3.66 (m, 1H), 3.58 (s, 3H), 3.48 (s, 3H), 3.29 (s, 1H), 2.87-2.68 (m, 2H), 2.21-2.07 (m, 1H), 2.03-1.93 (m, 2H), 1.05 (s, 3H), 1.02 (s, 3H), 0.96 (s, 3H), 0.84 (s, 3H).

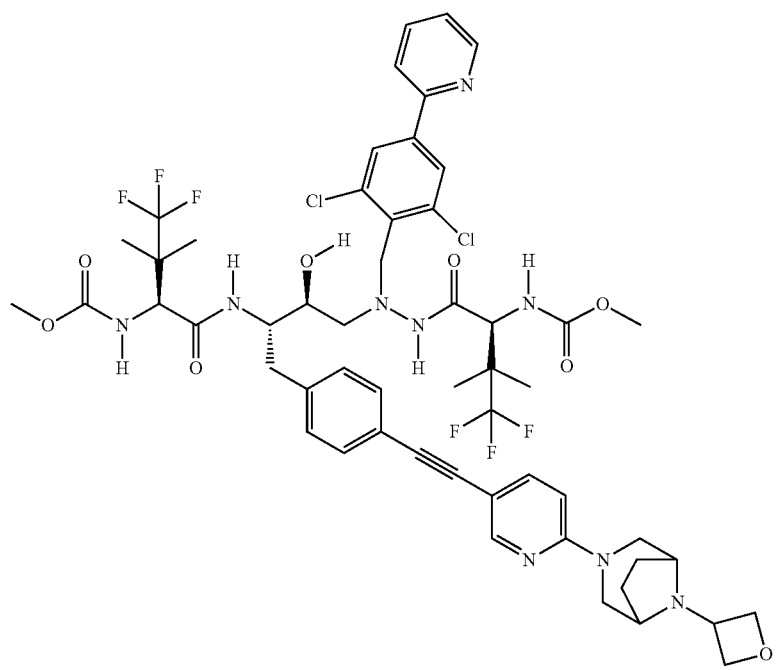 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(Cl)cc(-c2ccccn2)cc1Cl)NC(=O)[C@@H](NC(=O)OC)C(C)(C)C(F)(F)F)C(C)(C)C(F)(F)F]

EXAMPLE 149

Methyl ((5S,8S,9S,14S)-11-(2,6-dichloro-4-(pyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (149)

Intermediates: P24, A3, and S3. MS (ESI) m/z 1148.5 [M+H]+. $^1$H NMR (400 MHz, Methanol-d4) δ 8.56 (d, J=5.0 Hz, 1H), 8.20 (d, J=2.2 Hz, 1H), 8.04 (d, J=9.4 Hz, 1H), 7.88 (s, 2H), 7.83 (d, J=7.8 Hz, 2H), 7.64-7.54 (m, 1H), 7.33 (t, J=5.7 Hz, 1H), 7.23 (d, J=7.7 Hz, 2H), 7.12 (d, J=8.0 Hz, 2H), 6.77 (d, J=8.9 Hz, 1H), 6.71 (d, J=10.1 Hz, 1H), 4.87 (t, J=7.5 Hz, 2H), 4.71 (dd, J=8.2, 4.9 Hz, 2H), 4.36-4.23 (m, 2H), 4.20 (d, J=9.9 Hz, 1H), 4.12-3.98 (m, 4H), 3.69-3.62 (m, 1H), 3.59 (s, 3H), 3.54 (s, 3H), 3.29 (s, 1H), 2.83-2.75 (m, 2H), 2.72-2.62 (m, 1H), 2.17-2.08 (m, 1H), 2.03-1.93 (m, 2H), 1.05 (s, 6H), 0.99 (s, 3H), 0.89 (s, 3H).

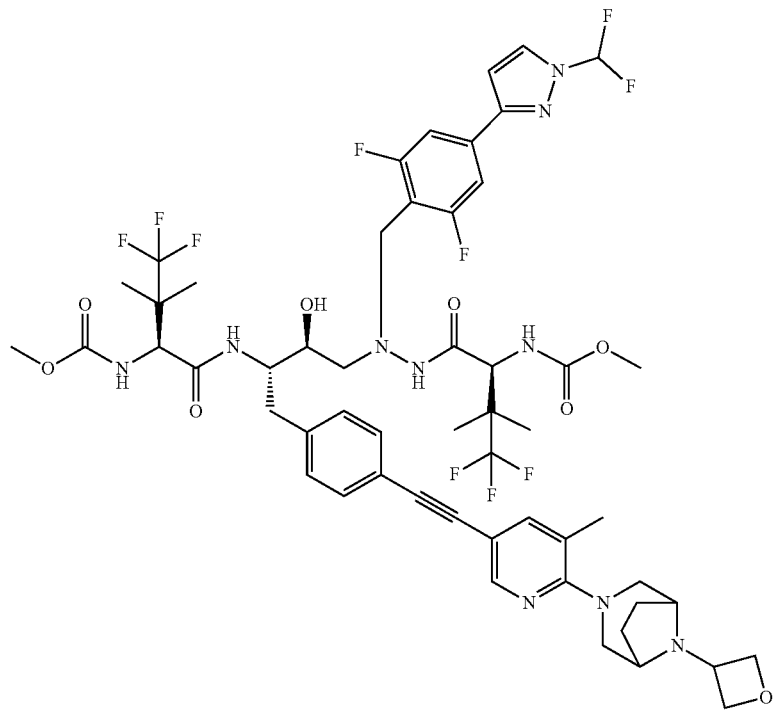 [SMILES: COC(=O)N[C@H](C(=O)N[C@@H](Cc1ccc(C#Cc2cnc(N3CC4CCC(C3)N4C3COC3)c(C)c2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 150

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((5-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (150)

Intermediates: P4, A3, and S44. MS (ESI) m/z 1171.1 [M+H]$^+$. $^1$H NMR (400 MHz, Methanol-d4) δ 8.17 (d, J=2.2 Hz, 1H), 8.07 (d, J=9.4 Hz, 1H), 8.01 (d, J=2.7 Hz, 1H), 7.61-7.55 (m, 3H), 7.44 (s, 1H), 7.35 (d, J=8.3 Hz, 2H), 7.30-7.22 (m, 2H), 7.14 (d, J=8.0 Hz, 2H), 7.02 (d, J=9.9 Hz, 1H), 6.84 (d, J=2.8 Hz, 1H), 6.69 (d, J=9.9 Hz, 1H), 4.88-4.80 (m, 2H), 4.73-4.68 (m, 2H), 4.41 (s, 1H), 4.34 (d, J=9.9 Hz, 1H), 4.21 (d, J=10.0 Hz, 1H), 4.10-3.98 (m, 4H), 3.85 (d, J=13.2 Hz, 1H), 3.64 (s, 1H), 3.59 (s, 3H), 3.57 (s, 3H), 3.48 (d, J=13.5 Hz, 2H), 3.38 (d, J=1.7 Hz, 1H), 3.35 (s, 1H), 3.25 (s, 1H), 2.85-2.74 (m, 3H), 2.72-2.65 (m, 1H), 2.27 (s, 5H), 2.17-2.11 (m, 2H), 1.06 (d, J=6.7 Hz, 6H), 1.02 (s, 3H), 0.93 (s, 3H). $^{19}$F NMR (377 MHz, Methanol-d4) δ −77.38, −77.71, −77.88, −96.97 (dd, J=59.8, 18.8 Hz), −114.92.

EXAMPLE 151

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((4-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (151)

Intermediates: P4, A3, and S46. MS (ESI) m/z 1171.3 [M+H]$^+$. $^1$H NMR (400 MHz, Methanol-d4) δ 8.20 (s, 1H), 8.17 (d, J=9.3 Hz, 1H), 8.10 (d, J=2.7 Hz, 1H), 7.68 (s, 0H), 7.53 (s, 1H), 7.45 (d, J=8.2 Hz, 2H), 7.38 (s, 0H), 7.34 (d, J=7.8 Hz, 2H), 7.23 (d, J=8.1 Hz, 2H), 7.11 (d, J=9.8 Hz, 1H), 6.94 (d, J=2.8 Hz, 1H), 6.82 (s, 0H), 6.79 (s, 1H), 4.99-4.89 (m, 2H), 4.83-4.77 (m, 2H), 4.51 (s, 1H), 4.47-4.42 (m, 1H), 4.35 (s, 1H), 4.31 (s, 1H), 4.29 (s, 0H), 4.16 (s, 1H), 4.13 (s, 3H), 3.95 (d, J=13.2 Hz, 1H), 3.74 (s, 1H), 3.68 (s, 3H), 3.66 (s, 3H), 3.38 (s, 1H), 3.34 (s, 3H), 2.94-2.84 (m, 3H), 2.78 (dd, J=12.5, 9.0 Hz, 1H), 2.44 (s, 3H), 2.25-2.18 (m, 2H), 2.10-2.04 (m, 2H), 1.16 (s, 4H), 1.13 (d, J=12.7 Hz, 7H), 1.02 (s, 3H). $^{19}$F NMR (377 MHz, Methanol-d4) δ −77.38, −77.71, −77.82, −96.97 (dd, J=59.8, 18.6 Hz), −114.92

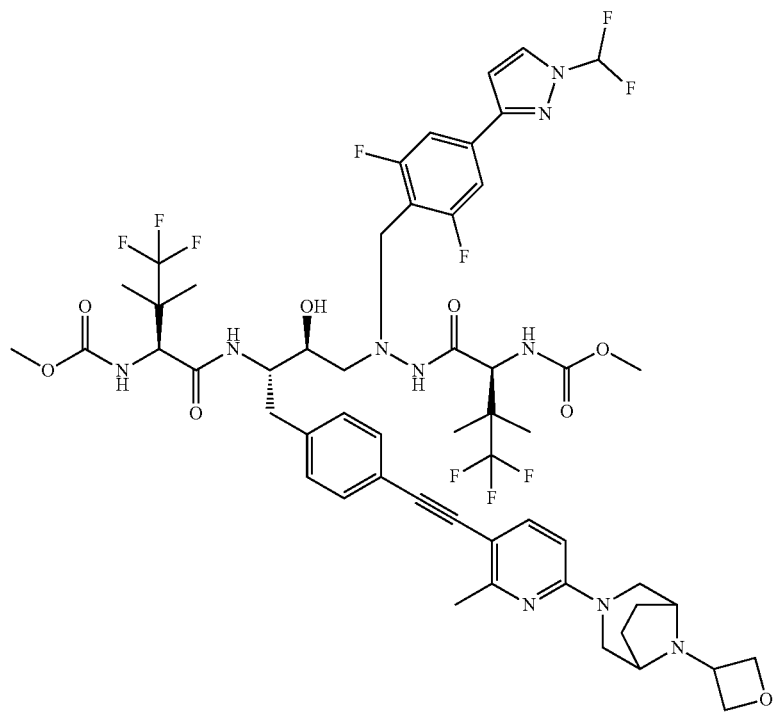 [SMILES: COC(=O)N[C@H](C(=O)N[C@@H](Cc1ccc(C#Cc2cnc(N3CC4CCC(C3)N4C3COC3)cc2C)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 152

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (152)

Intermediates: P4, A3, and S45. MS (ESI) m/z 1170.6 [M+H]+. $^1$H NMR (400 MHz, Methanol-d4) δ 8.17 (d, J=9.3 Hz, 1H), 8.10 (d, J=2.7 Hz, 1H), 7.68 (s, 0H), 7.62 (d, J=8.7 Hz, 1H), 7.53 (s, 1H), 7.45 (d, J=8.2 Hz, 2H), 7.38 (s, 0H), 7.32 (d, J=8.0 Hz, 2H), 7.22 (d, J=8.1 Hz, 2H), 7.11 (d, J=9.9 Hz, 1H), 6.93 (d, J=2.8 Hz, 1H), 6.80 (d, J=9.8 Hz, 1H), 6.67 (d, J=8.8 Hz, 1H), 4.96 (dd, J=8.2, 7.0 Hz, 2H), 4.81 (dd, J=8.2, 5.1 Hz, 2H), 4.51 (s, 1H), 4.47-4.43 (m, 1H), 4.38 (d, J=13.8 Hz, 2H), 4.32-4.27 (m, 1H), 4.15 (d, J=12.2 Hz, 4H), 3.95 (d, J=13.1 Hz, 1H), 3.73 (s, 1H), 3.68 (s, 3H), 3.66 (s, 3H), 3.38-3.35 (m, 1H), 3.34-3.32 (m, 1H), 2.88 (dd, J=18.8, 5.2 Hz, 3H), 2.78 (dd, J=12.5, 9.0 Hz, 1H), 2.56 (s, 3H), 2.25-2.18 (m, 2H), 2.08 (t, J=6.8 Hz, 2H), 1.16 (s, 5H), 1.13 (d, J=13.1 Hz, 7H), 1.02 (s, 3H). $^{19}$F NMR (377 MHz, Methanol-d4) δ −77.39, −77.71, −77.86, −96.97 (dd, J=59.9, 18.5 Hz), −114.92

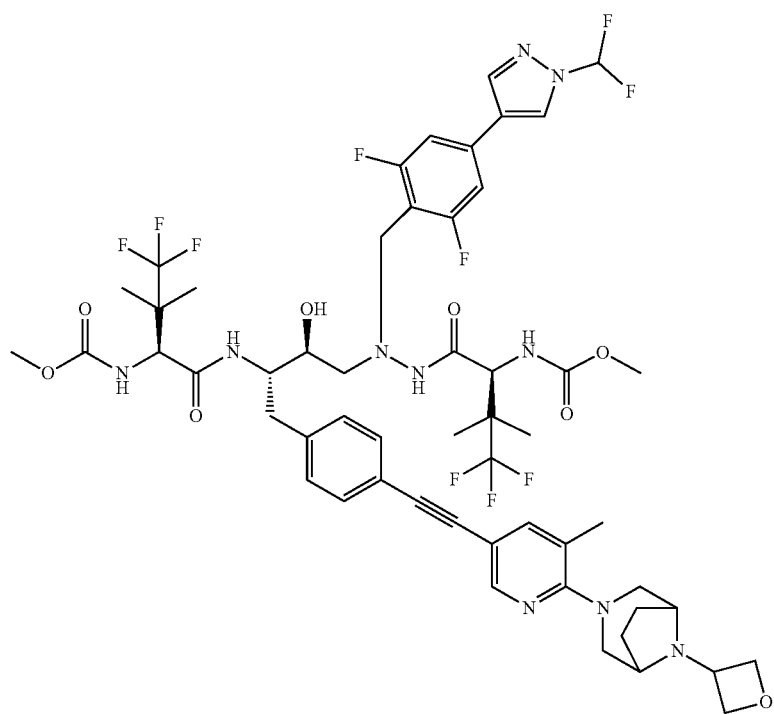 [SMILES: COC(=O)N[C@H](C(=O)N[C@@H](Cc1ccc(C#Cc2cnc(N3CC4CCC(C3)N4C3COC3)c(C)c2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

EXAMPLE 153

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((5-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (153)

Intermediates: P7, A3, and S44. MS (ESI) m/z 1170.6 [M+H]+. $^1$H NMR (400 MHz, Methanol-d4) δ 8.53 (s, 1H), 8.29-8.25 (m, 1H), 8.16 (d, J=9.2 Hz, 1H), 8.12 (s, 1H), 7.70-7.60 (m, 2H), 7.55 (td, J=7.4, 3.1 Hz, 1H), 7.50 (s, 1H), 7.36 (d, J=2.1 Hz, 1H), 7.34 (s, 1H), 7.24 (dd, J=8.2, 6.7 Hz, 4H), 7.16 (d, J=10.0 Hz, 1H), 6.79 (d, J=9.9 Hz, 1H), 4.94 (t, J=7.6 Hz, 2H), 4.79 (dd, J=8.2, 5.2 Hz, 3H), 4.49 (s, 1H), 4.47-4.41 (m, 1H), 4.34-4.27 (m, 1H), 4.15 (d, J=8.8 Hz, 1H), 4.09 (d, J=7.1 Hz, 3H), 3.93 (d, J=13.2 Hz, 1H), 3.69 (s, 3H), 3.66 (s, 3H), 3.57 (d, J=13.5 Hz, 2H), 3.51 (s, 0H), 3.47 (dt, J=3.3, 1.7 Hz, 2H), 3.43 (s, 1H), 2.99 (s, 0H), 2.91 (d, J=7.8 Hz, 2H), 2.87-2.82 (m, 1H), 2.81-2.73 (m, 1H), 2.36 (s, 4H), 2.34 (s, 0H), 2.24 (s, 2H), 2.04-1.91 (m, 0H), 1.33-1.26 (m, 1H), 1.17 (s, 3H), 1.14 (s, 3H), 1.11 (s, 3H), 1.03 (s, 3H). $^{19}$F NMR (377 MHz, Methanol-d4) δ −77.39, −77.51, −77.71, −96.88 (d, J=59.6 Hz), −115.03, −130.01.

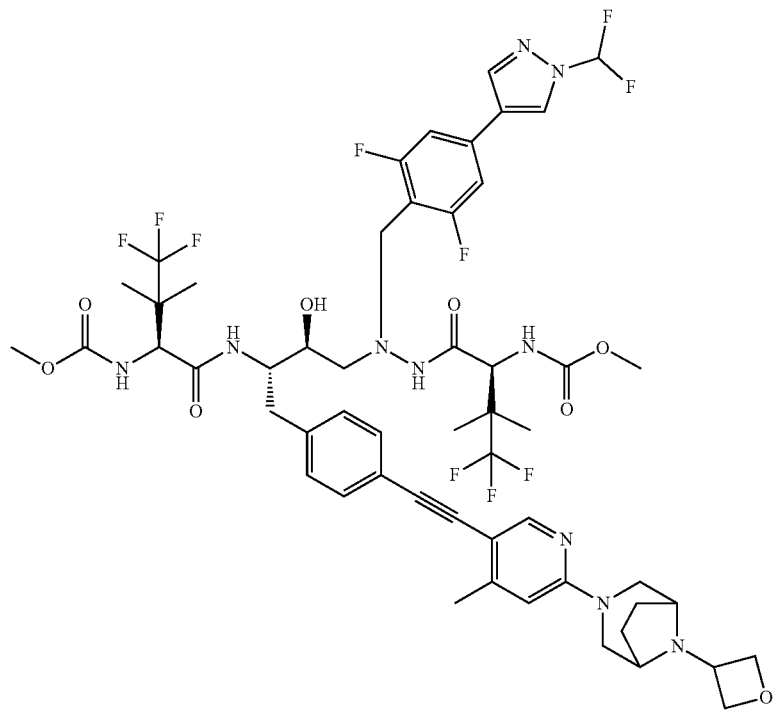 [SMILES: COC(=O)N[C@H](C(=O)N[C@@H](Cc1ccc(C#Cc2cnc(N3CC4CCC(C3)N4C3COC3)cc2C)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

EXAMPLE 154

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((4-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (154)

Intermediates: P7, A3, and S46. MS (ESI) m/z 1169.5 [M+H]+. 1H NMR (400 MHz, Methanol-d4) δ 8.52 (s, 1H), 8.20 (s, 1H), 8.14 (s, 1H), 8.11 (s, 1H), 7.64 (s, 0H), 7.50 (s, 1H), 7.34 (d, J=7.3 Hz, 2H), 7.24 (t, J=7.8 Hz, 4H), 7.11 (d, J=9.9 Hz, 1H), 6.78 (s, 1H), 6.77 (s, 0H), 4.96 (t, J=7.6 Hz, 2H), 4.50 (s, 1H), 4.44 (d, J=9.7 Hz, 1H), 4.36-4.27 (m, 3H), 4.12 (d, J=10.0 Hz, 4H), 3.94 (d, J=13.2 Hz, 1H), 3.70 (s, 2H), 3.68 (s, 3H), 3.66 (s, 3H), 3.38 (s, 1H), 3.34 (s, 3H), 2.94-2.73 (m, 4H), 2.44 (s, 3H), 2.27-2.17 (m, 2H), 2.07 (d, J=8.6 Hz, 2H), 1.29 (t, J=7.4 Hz, 0H), 1.20-1.10 (m, 10H), 1.03 (s, 3H). 19F NMR (376 MHz, Methanol-d4) δ −77.35, −77.62, −77.67, −96.90 (d, J=59.9 Hz), −115.01.

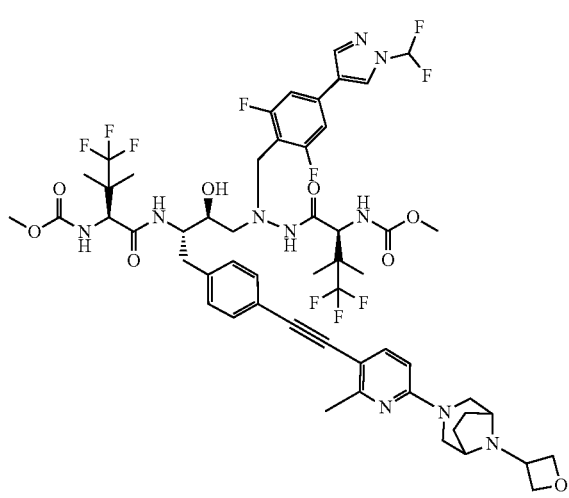 [SMILES: COC(=O)N[C@H](C(=O)N[C@@H](Cc1ccc(C#Cc2ccc(N3CC4CCC(C3)N4C3COC3)nc2C)cc1)[C@@H](O)CN(CCc1c(F)cc(/C(C=N)=C/NC(F)F)cc1F)NC(=O)[C@@H](NC(=O)OC)C(C)(C)C(F)(F)F)C(C)(C)C(F)(F)F]

EXAMPLE 155

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((2-methyl-6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (155)

Intermediates: P7, A3, and S45. MS (ESI) m/z 1169.7 [M+H]+. 1H NMR (400 MHz, Methanol-d4) δ 8.52 (s, 1H), 8.12 (s, 2H), 7.64 (s, 0H), 7.53 (d, J=8.6 Hz, 1H), 7.49 (s, 1H), 7.37-7.28 (m, 3H), 7.23 (dd, J=15.6, 8.1 Hz, 5H), 4.44 (s, 1H), 4.30 (s, 2H), 4.12 (d, J=12.6 Hz, 3H), 3.94 (d, J=13.1 Hz, 1H), 3.68 (s, 4H), 3.66 (s, 4H), 2.90 (d, J=8.2 Hz, 2H), 2.79 (d, J=9.9 Hz, 1H), 2.53 (s, 4H), 2.03 (s, 0H), 1.98 (s, 1H), 1.28 (d, J=7.2 Hz, 3H), 1.17 (s, 5H), 1.15 (s, 4H), 1.12 (s, 4H), 1.03 (s, 4H). 19F NMR (376 MHz, Methanol-d4) δ −77.36, −77.48, −77.68, −96.91 (d, J=59.7 Hz).

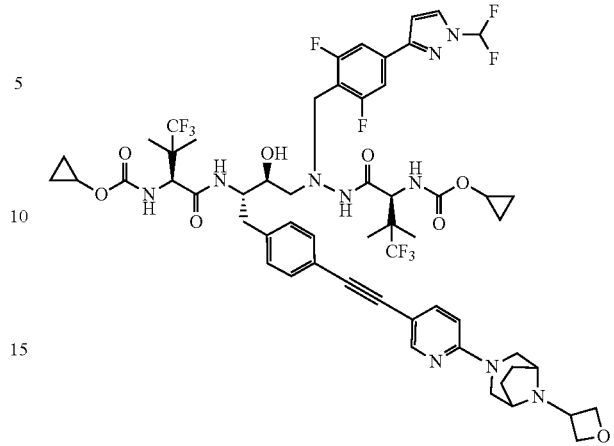

EXAMPLE 156

Cyclopropyl ((2S)-1-(2-((2S,3S)-3-((S)-2-((cyclopropoxycarbonyl)amino)-4,4,4-trifluoro-3,3-dimethylbutanamido)-2-hydroxy-4-(4-((6-(8-(oxetan-3-yl)-3,8-diazabicyclo[3.2.1]octan-3-yl)pyridin-3-yl)ethynyl)phenyl)butyl)-2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate (156)

Intermediates: P4, A6, and S3. MS (ESI) m/z 1208.0 [M+H]+. 1H NMR (400 MHz, Methanol-d4) δ 8.30 (dd, J=2.3, 0.7 Hz, 1H), 8.21 (d, J=9.4 Hz, 1H), 8.11 (d, J=2.7 Hz, 1H), 7.81-7.63 (m, 1H), 7.53 (s, 1H), 7.46 (d, J=8.3 Hz, 2H), 7.42-7.29 (m, 3H), 7.23 (d, J=8.0 Hz, 3H), 6.94 (d, J=2.8 Hz, 1H), 6.85 (t, J=8.7 Hz, 2H), 5.05-4.90 (m, 3H), 4.48 (d, J=10.0 Hz, 1H), 4.34 (t, J=12.0 Hz, 3H), 4.24-3.84 (m, 7H), 3.75 (s, 1H), 3.01-2.66 (m, 5H), 2.22 (dd, J=12.2, 6.4 Hz, 2H), 2.03 (s, 32H), 1.29 (s, 1H), 1.19-1.07 (m, 10H), 1.03 (s, 3H), 1.00-0.50 (m, 8H).

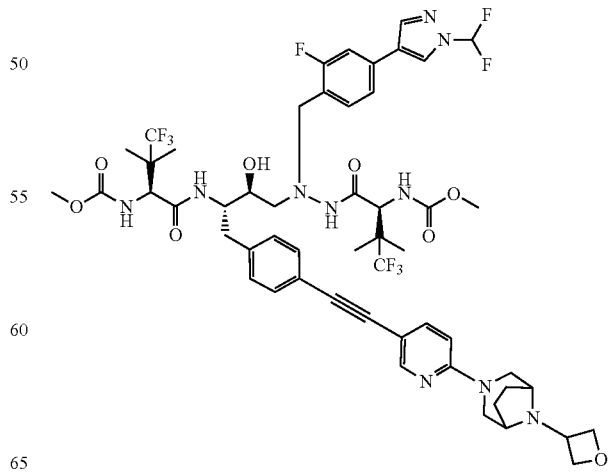

EXAMPLE 157

Methyl ((5S,8S,9S,14S)-11-(4-(1-(difluoromethyl)-1H-pyrazol-4-yl)-2-fluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (157)

Intermediates: P8, A3, and S3. MS (ESI) m/z 1138.1 [M+H]+. 1H NMR (400 MHz, Methanol-d4) δ 8.43 (s, 1H), 8.28-8.25 (m, 1H), 8.07 (s, 1H), 7.68 (dd, J=8.9, 2.3 Hz, 1H), 7.66-7.57 (m, 1H), 7.57-7.45 (m, 1H), 7.41-7.27 (m, 6H), 7.20 (d, J=8.2 Hz, 2H), 6.90-6.81 (m, 1H), 4.94 (dd, J=8.1, 7.0 Hz, 3H), 4.81 (dd, J=8.1, 4.9 Hz, 3H), 4.53 (d, J=6.3 Hz, 1H), 4.45-4.21 (m, 5H), 4.14 (dd, J=4.7, 2.4 Hz, 4H), 4.08-3.83 (m, 3H), 3.70 (d, J=24.6 Hz, 2H), 3.60 (s, 3H), 3.38 (dd, J=14.1, 1.7 Hz, 3H), 3.29 (p, J=1.6 Hz, 6H), 2.93-2.66 (m, 5H), 2.28-2.02 (m, 3H), 1.11 (d, J=14.3 Hz, 7H), 1.04 (s, 4H), 0.93 (s, 4H).

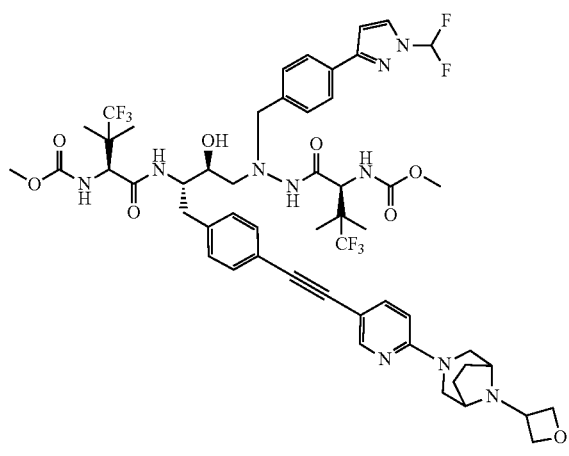 [SMILES: COC(=O)N[C@H](C(=O)N[C@@H](Cc1ccc(C#Cc2ccc(N3CC4CCC(C3)N4C3COC3)nc2)cc1)[C@@H](O)CN(CCc1ccc(C(=N)/C=C\NC(F)F)cc1)NC(=O)[C@@H](NC(=O)OC)C(C)(C)C(F)(F)F)C(C)(C)C(F)(F)F]

EXAMPLE 158

Methyl ((5S,8S,9S,14S)-11-(4-(1-(difluoromethyl)-1H-pyrazol-3-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (158)

Intermediates: P6, A3, and S3. MS (ESI) m/z 1120.2 [M+H]+. 1H NMR (400 MHz, Methanol-d4) δ 8.20 (dd, J=2.3, 0.7 Hz, 1H), 8.16-7.99 (m, 2H), 7.84-7.73 (m, 2H), 7.71-7.37 (m, 4H), 7.37-7.26 (m, 3H), 7.26-7.10 (m, 2H), 6.86 (d, J=2.7 Hz, 1H), 6.69 (dd, J=9.0, 0.8 Hz, 1H), 4.76 (t, J=6.4 Hz, 2H), 4.58 (t, J=5.8 Hz, 3H), 4.39 (s, 1H), 4.25 (s, 1H), 4.01 (d, J=13.1 Hz, 1H), 3.89 (dt, J=13.1, 4.1 Hz, 4H), 3.85-3.74 (m, 1H), 3.60 (s, 3H), 3.12 (dd, J=12.0, 2.2 Hz, 3H), 2.98-2.60 (m, 4H), 1.96-1.86 (m, 3H), 1.69 (d, J=7.8 Hz, 2H), 1.11 (d, J=9.3 Hz, 7H), 1.02 (s, 3H), 1.00-0.76 (m, 4H).

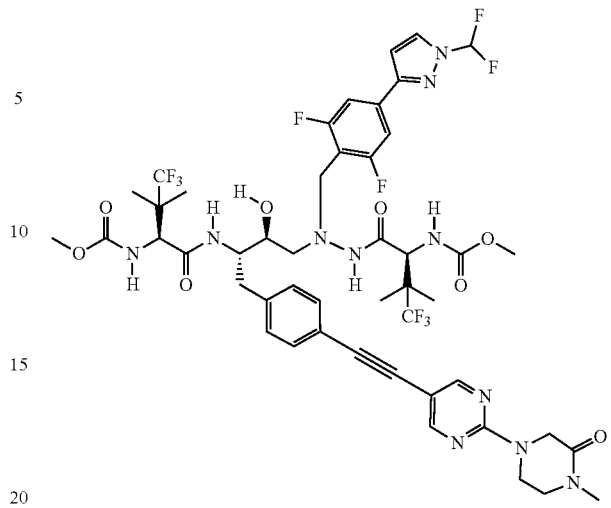

EXAMPLE 159 methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(4-methyl-3-oxopiperazin-1-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (159)

Intermediates: P4, A3, and S58. MS (ESI) m/z 1102.2 [M+H]+. 1H NMR (400 MHz, Methanol-d4) δ 8.50 (s, 2H), 8.20 (d, J=9.5 Hz, 1H), 8.12 (s, 1H), 7.55 (t, J=61.0 Hz, 1H), 7.46 (d, J=8.6 Hz, 2H), 7.35 (d, J=7.7 Hz, 2H), 7.24 (d, J=8.3 Hz, 2H), 6.95 (s, 1H), 4.44 (s, 1H), 4.40 (s, 2H), 4.31 (s, 1H), 4.15 (d, J=15.7 Hz, 4H), 3.95 (d, J=12.9 Hz, 1H), 3.75 (s, 2H), 3.70 (s, 3H), 3.67 (s, 3H), 3.50 (s, 2H), 3.03 (d, J=2.8 Hz, 3H), 2.90 (t, J=12.3 Hz, 2H), 2.80 (d, J=10.7 Hz, 1H), 1.17 (s, 3H), 1.15 (s, 3H), 1.12 (s, 3H), 1.04 (s, 3H).

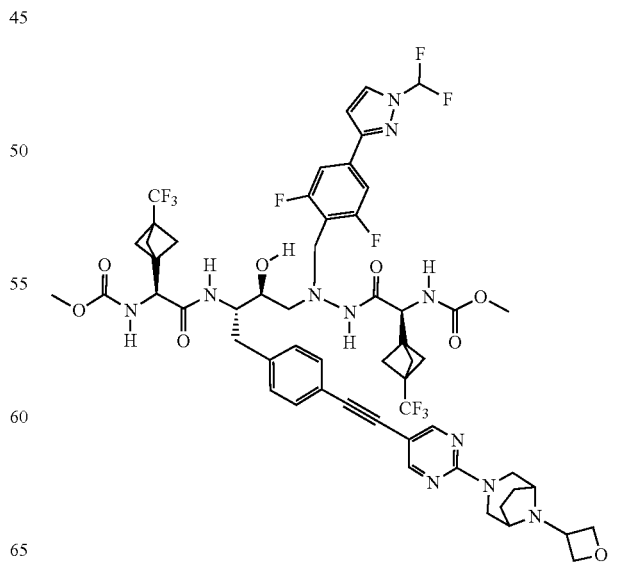

EXAMPLE 160

Methyl ((5S,8S,9S,14S)-11-(4-(1-(difluoromethyl)-1H-pyrazol-3-yl)-2,6-difluorobenzyl)-9-hydroxy-8-(4-((2-(8-(oxetan-3-yl)-3,8-diazabicyclo[3.2.1]octan-3-yl)pyrimidin-5-yl)ethynyl)benzyl)-3,6,13-trioxo-5,14-bis(3-(trifluoromethyl)bicyclo[1.1.1]pentan-1-yl)-2-oxa-4,7,11,12-tetraazatetradecan-14-yl)carbamate (160)

Intermediates: P4, A8, and S7. MS (ESI) m/z 1205.1 [M+H]+. $^1$H NMR (400 MHz, Methanol-d4) δ 8.51 (s, 2H), 8.09 (d, J=2.7 Hz, 1H), 7.52 (t, J=60.0, 59.5 Hz, 1H), 7.48 (d, J=8.3 Hz, 2H), 7.39 (d, J=8.0 Hz, 2H), 7.28 (d, J=8.0 Hz, 2H), 6.91 (d, J=2.7 Hz, 1H), 4.96 (t, J=7.6 Hz, 2H), 4.81 (dd, J=8.3, 5.1 Hz, 2H), 4.76 (s, 1H), 4.33-4.23 (m, 1H), 4.18-4.12 (m, 3H), 4.08 (d, J=18.2 Hz, 2H), 4.03 (d, J=13.5 Hz, 1H), 3.75 (d, J=9.3 Hz, 1H), 3.66 (s, 3H), 3.64 (s, 3H), 3.46 (d, J=14.4 Hz, 2H), 3.04-2.85 (m, 3H), 2.79 (d, J=12.7 Hz, 1H), 2.20 (dd, J=8.9, 3.9 Hz, 2H), 2.01 (dd, J=12.2, 6.9 Hz, 2H), 1.86-1.65 (m, 12H).

EXAMPLE 161

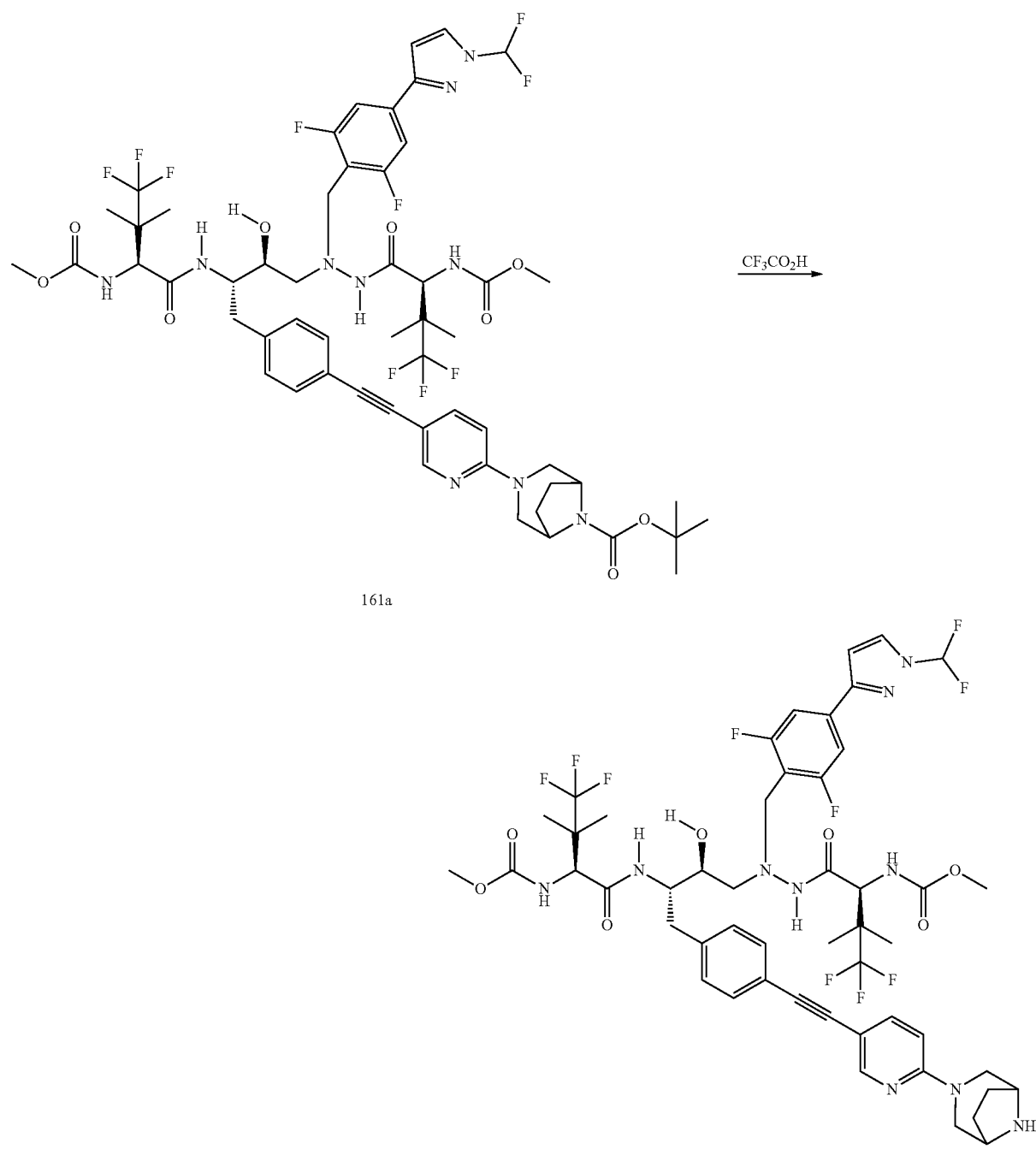

347 tert-butyl 3-(5-((4-((2S,3S)-4-(1-(4-(1-(difluoromethyl)-1H-pyrazol-3-yl)-2,6-difluorobenzyl)-2-((S)-4,4,4-trifluoro-2-((methoxycarbonyl)amino)-3,3-dimethylbutanoyl) hydrazinyl)-3-hydroxy-2-((S)-4,4,4-trifluoro-2-((methoxycarbonyl) amino)-3,3-dimethylbutanamido)butyl)phenyl)ethynyl)pyridin-2-yl)-3,8-diazabicyclo[3.2.1] octane-8-carboxylate (161a)

MS (ESI) m/z 1200.0 [M+H]+. $^1$H NMR (400 MHz, Methanol-d4) δ 8.27-8.14 (m, 2H), 8.11 (d, J=2.7 Hz, 1H), 7.84 (d, J=9.0 Hz, 1H), 7.53 (t, J=59.7 Hz, 2H), 7.45 (d, J=8.2 Hz, 3H), 7.35 (d, J=7.9 Hz, 3H), 7.24 (d, J=8.0 Hz, 3H), 7.15 (d, J=9.5 Hz, 1H), 7.08 (d, J=9.3 Hz, 1H), 6.94 (d, J=2.8 Hz, 1H), 6.82 (d, J=10.0 Hz, 1H), 4.44 (d, J=11.9 Hz, 4H), 4.30 (d, J=10.0 Hz, 1H), 4.14 (d, J=13.3 Hz, 3H), 4.02-3.87 (m, 4H), 3.67 (d, J=10.7 Hz, 10H), 3.28-3.18 (m, 3H), 3.03-2.85 (m, 4H), 2.82-2.69 (m, 1H), 2.00 (dd, J=9.0, 4.0 Hz, 3H), 1.81 (d, J=7.7 Hz, 3H), 1.49 (s, 9H), 1.16 (s, 3H), 1.14 (s, 3H), 1.11 (s, 3H), 1.03 (s, 3H).

348

Methyl ((5S,8S,9S,14S)-8-(4-((6-(3,8-diazabicyclo [3.2.1]octan-3-yl)pyridin-3-yl)ethynyl)benzyl)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate 2,2,2-trifluoroacetate (161)

A solution of 161a (57.8 mg, 0.040 mmol) and trifluoroacetic acid (0.150 ml, 1.96 mmol) in DCM (2 mL) was stirred at room temperature. After 3 h, the reaction mixture was concentrated under reduced pressure and the residue was purified by HPLC and the product lyophilized to afford 161. MS (ESI) m/z 1200.0 [M+H]+. $^1$H NMR (400 MHz, Methanol-d4) δ 8.32-8.26 (m, 1H), 8.18 (d, J=9.4 Hz, 1H), 8.11 (d, J=2.7 Hz, 1H), 7.71-7.64 (m, 1H), 7.71-7.36 (m, 1H), 7.45 (d, J=8.1 Hz, 2H), 7.32 (d, J=7.9 Hz, 2H), 7.22 (d, J=8.1 Hz, 2H), 7.15 (d, J=10.0 Hz, 1H), 6.94 (d, J=2.8 Hz, 1H), 6.82 (t, J=9.9 Hz, 2H), 4.44 (d, J=9.9 Hz, 1H), 4.36-4.22 (m, 4H), 4.16 (d, J=28.1 Hz, 4H), 3.94 (d, J=13.2 Hz, 1H), 3.67 (d, J=11.1 Hz, 8H), 3.26-3.17 (m, 3H), 2.99-2.69 (m, 5H), 2.19-1.96 (m, 5H), 1.16 (s, 3H), 1.14 (s, 3H), 1.11 (s, 3H), 1.02 (s, 3H).

EXAMPLE 162

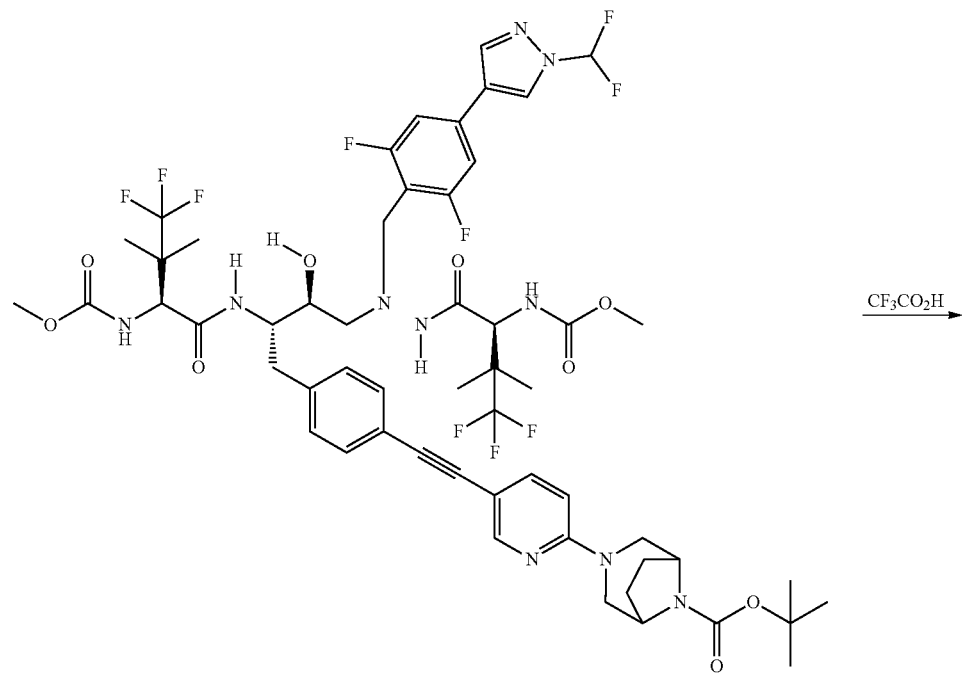

162a

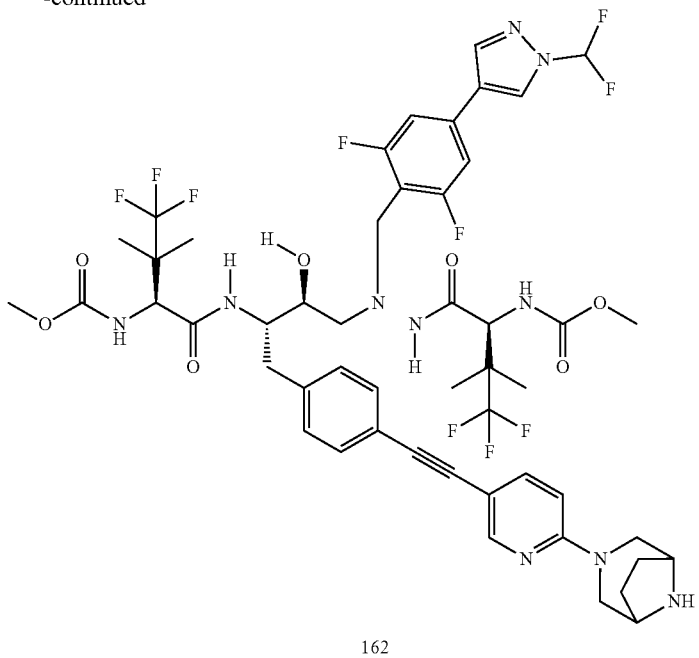

162

Synthesis of tert-butyl 3-(5-((4-((2S,3S)-4-(1-(4-(1-(difluoromethyl)-1H-pyrazol-4-yl)-2,6-difluorobenzyl)-2-((S)-4,4,4-trifluoro-2-((methoxycarbonyl)amino)-3,3-dimethylbutanoyl)hydrazinyl)-3-hydroxy-2-((S)-4,4,4-trifluoro-2-((methoxycarbonyl)amino)-3,3-dimethylbutanamido)butyl)phenyl)ethynyl)pyridin-2-yl)-3,8-diazabicyclo[3.2.1]octane-8-carboxylate (162a)

Intermediates: P7, A3, and S16. MS (ESI) m/z 1199.4 [M+H]+. $^1$H NMR (400 MHz, Methanol-d4) δ 8.53 (d, J=0.7 Hz, 1H), 8.21-8.09 (m, 3H), 7.89 (dd, J=9.4, 2.2 Hz, 1H), 7.69-7.32 (m, 2H), 7.35 (s, 1H), 7.24 (dd, J=8.4, 2.4 Hz, 4H), 7.14 (d, J=9.4 Hz, 2H), 4.43 (d, J=4.2 Hz, 3H), 4.36-4.23 (m, 1H), 4.23-4.00 (m, 2H), 3.97-3.82 (m, 3H), 3.67 (d, J=9.7 Hz, 5H), 3.28 (d, J=9.6 Hz, 2H), 3.00-2.70 (m, 4H), 2.08-1.91 (m, 2H), 1.82 (t, J=6.9 Hz, 2H), 1.49 (s, 9H), 1.23-1.08 (m, 9H), 1.03 (s, 3H).

Methyl ((5S,8S,9S,14S)-8-(4-((6-(3,8-diazabicyclo[3.2.1]octan-3-yl)pyridin-3-yl)ethynyl)benzyl)-11-(4-(1-(difluoromethyl)-1H-pyrazol-4-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate The title compound 162 was prepared according to the method presented for the synthesis of compound 161 but instead utilizing 162a. MS (ESI) m/z 1099.2 [M+H]+. $^1$H NMR (400 MHz, Methanol-d4) δ 8.45 (s, 1H), 8.18 (d, J=2.3 Hz, 1H), 8.08 (d, J=9.4 Hz, 1H), 8.03 (s, 1H), 7.63-7.55 (m, 1H), 7.41 (s, 1H), 7.29-7.20 (m, 2H), 7.14 (dd, J=14.9, 8.2 Hz, 4H), 6.73 (t, J=9.6 Hz, 2H), 4.34 (d, J=9.7 Hz, 1H), 4.28-4.13 (m, 4H), 4.13-3.91 (m, 4H), 3.83 (d, J=13.1 Hz, 1H), 3.58 (d, J=10.5 Hz, 7H), 3.14 (d, J=13.5 Hz, 2H), 2.75 (dd, J=47.8, 9.1 Hz, 4H), 2.12-1.85 (m, 3H), 1.16-0.97 (m, 9H), 0.94 (s, 3H).

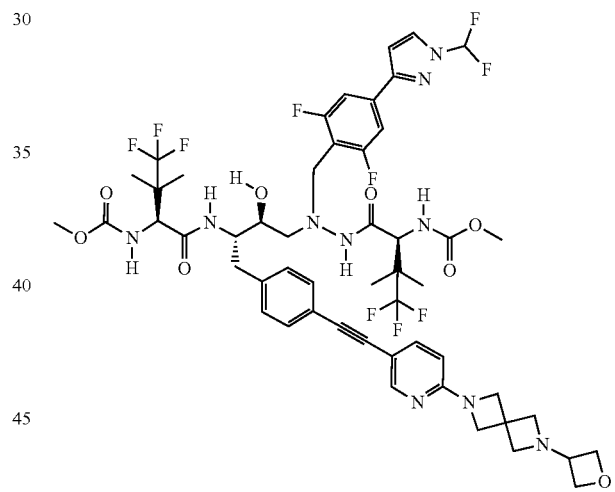

EXAMPLE 163

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(6-(oxetan-3-yl)-2,6-diazaspiro[3.3]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (163)

Intermediates: P4, A3, and S17. MS (ESI) m/z 1141.7 [M+H]+. $^1$H NMR (400 MHz, Methanol-d4) δ 8.17-8.03 (m, 2H), 8.01 (d, J=2.7 Hz, 1H), 7.66 (d, J=8.9 Hz, 1H), 7.44 (t, J=59.8 Hz, 1H), 7.36 (d, J=8.2 Hz, 2H), 7.24 (d, J=7.8 Hz, 2H), 7.13 (d, J=8.0 Hz, 2H), 7.06 (d, J=9.8 Hz, 1H), 6.85 (d, J=2.8 Hz, 1H), 6.72 (d, J=9.9 Hz, 1H), 6.50 (d, J=8.9 Hz, 1H), 4.90-4.82 (m, 1H), 4.49-4.34 (m, 6H), 4.28 (s, 4H), 4.21 (d, J=10.0 Hz, 1H), 4.05 (d, J=13.0 Hz, 2H), 3.85 (d, J=13.2 Hz, 1H), 3.64 (s, 2H), 3.59 (s, 3H), 3.57 (s, 3H), 2.88-2.74 (m, 3H), 2.74-2.63 (m, 1H), 1.06 (s, 3H), 1.05 (s, 3H), 1.02 (s, 3H), 0.93 (s, 3H).

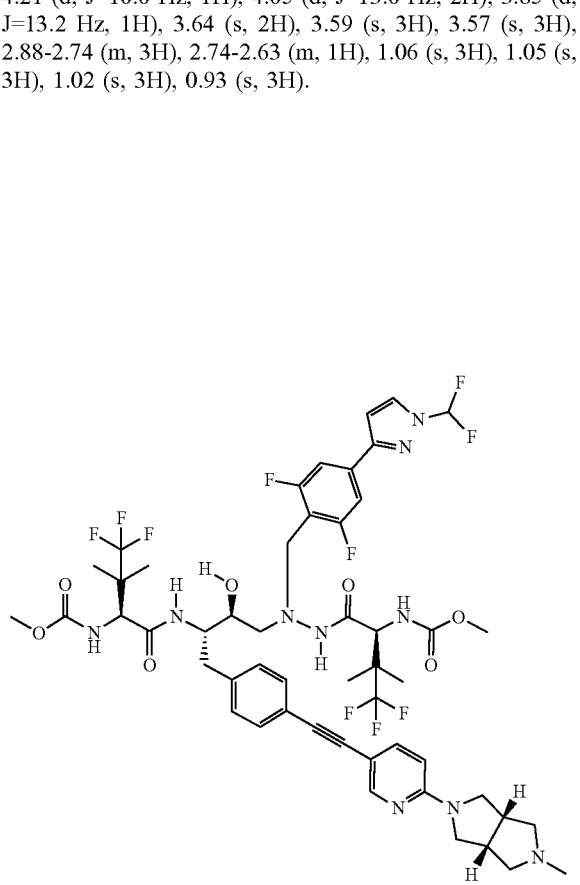

EXAMPLE 164

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-((3aR,6aS)-5-methylhexahydropyrrolo[3,4-c]pyrrol-2(1H)-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (164)

Intermediates: P4, A3, and S18. MS (ESI) m/z 1114.3 [M+H]+. ¹H NMR (400 MHz, Methanol-d4) δ 8.19-8.05 (m, 2H), 8.01 (d, J=2.7 Hz, 1H), 7.61 (dd, J=8.9, 2.2 Hz, 1H), 7.44 (t, J=59.8 Hz, 1H), 7.36 (d, J=8.2 Hz, 2H), 7.24 (d, J=7.9 Hz, 2H), 7.13 (d, J=8.0 Hz, 2H), 7.05 (d, J=9.9 Hz, 1H), 6.85 (d, J=2.7 Hz, 1H), 6.72 (d, J=10.0 Hz, 1H), 6.64 (d, J=8.9 Hz, 1H), 4.35 (d, J=9.8 Hz, 1H), 4.21 (d, J=10.0 Hz, 1H), 4.05 (d, J=12.6 Hz, 2H), 3.85 (d, J=13.1 Hz, 2H), 3.65 (s, 1H), 3.58 (d, J=10.7 Hz, 6H), 3.36 (d, J=14.9 Hz, 2H), 2.84 (dd, J=18.9, 9.2 Hz, 5H), 2.70 (d, J=10.2 Hz, 1H), 1.06 (d, J=6.3 Hz, 6H), 1.02 (s, 3H), 0.93 (s, 3H).

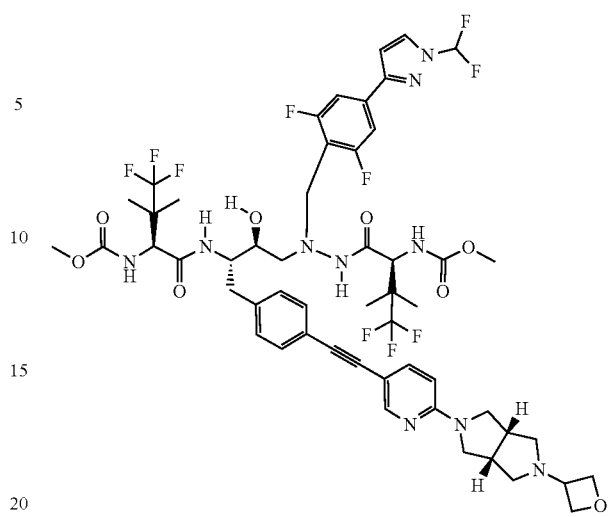

EXAMPLE 165

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-((3aR,6aS)-5-(oxetan-3-yl)hexahydropyrrolo[3,4-c]pyrrol-2(1H)-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (165)

Intermediates: P4, A3, and S19. MS (ESI) m/z 1156.2 [M+H]+. ¹H NMR (400 MHz, Methanol-d4) δ 8.09 (d, J=2.3 Hz, 2H), 8.01 (d, J=2.7 Hz, 1H), 7.72 (dd, J=8.9, 2.2 Hz, 1H), 7.44 (t, J=59.8 Hz, 1H), 7.36 (d, J=8.2 Hz, 2H), 7.25 (d, J=7.9 Hz, 2H), 7.14 (d, J=8.0 Hz, 2H), 7.05 (d, J=9.9 Hz, 1H), 6.85 (d, J=2.7 Hz, 1H), 6.81-6.67 (m, 2H), 4.63 (dd, J=8.3, 5.1 Hz, 2H), 4.46-4.30 (m, 2H), 4.21 (d, J=10.0 Hz, 1H), 4.05 (d, J=13.3 Hz, 2H), 3.85 (d, J=13.2 Hz, 1H), 3.64 (d, J=4.3 Hz, 6H), 3.59 (s, 3H), 3.57 (s, 3H), 3.32 (s, 3H), 2.87-2.62 (m, 4H), 1.06 (d, J=6.2 Hz, 6H), 1.02 (s, 3H), 0.93 (s, 3H).

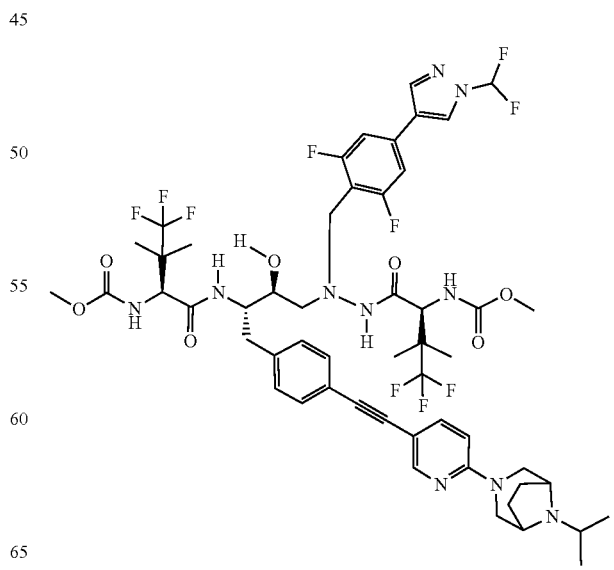

EXAMPLE 166

Methyl ((5S,8S,9S,14S)-11-(4-(1-(difluoromethyl)-1H-pyrazol-4-yl)-2,6-difluorobenzyl)-16,16,16-trifluoro-9-hydroxy-8-(4-((6-(8-isopropyl-3,8-diazabicyclo[3.2.1]octan-3-yl)pyridin-3-yl)ethynyl)benzyl)-15,15-dimethyl-3,6,13-trioxo-5-(1,1,1-trifluoro-2-methylpropan-2-yl)-2-oxa-4,7,11,12-tetraazahexadecan-14-yl)carbamate (166)

Intermediates: P7, A3, and S22. MS (ESI) m/z 1142.5 [M+H]+. $^1$H NMR (400 MHz, Methanol-d4) δ 8.44 (d, J=0.7 Hz, 1H), 8.20 (s, 1H), 8.07 (d, J=9.5 Hz, 1H), 8.06-8.02 (m, 1H), 7.67-7.50 (m, 1H), 7.50-7.43 (m, 0H), 7.41 (s, 0H), 7.29-7.20 (m, 2H), 7.14 (dd, J=13.7, 8.3 Hz, 3H), 6.73 (dd, J=18.5, 9.6 Hz, 1H), 4.34 (t, J=5.2 Hz, 3H), 4.30-4.15 (m, 3H), 4.13-3.94 (m, 3H), 3.84 (d, J=13.2 Hz, 1H), 3.58 (d, J=10.5 Hz, 6H), 3.17 (d, J=2.4 Hz, 1H), 2.91-2.64 (m, 3H), 2.14 (d, J=11.4 Hz, 2H), 1.95 (d, J=8.6 Hz, 1H), 1.37 (d, J=6.4 Hz, 6H), 1.12-0.97 (m, 9H), 0.94 (s, 3H).

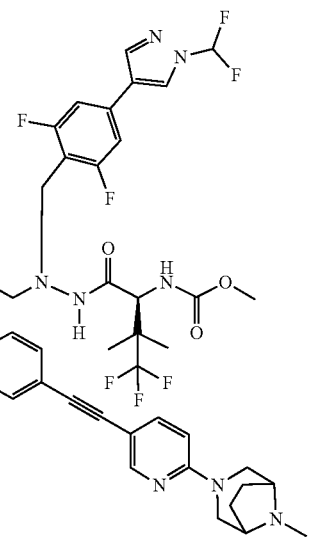

EXAMPLE 167

Methyl ((5S,8S,9S,14S)-11-(4-(1-(difluoromethyl)-1H-pyrazol-4-yl)-2,6-difluorobenzyl)-8-(4-((6-(8-ethyl-3,8-diazabicyclo[3.2.1]octan-3-yl)pyridin-3-yl)ethynyl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (167)

Intermediates: P7, A3, and S21. MS (ESI) m/z 1128.6 [M+H]+. $^1$H NMR (400 MHz, Methanol-d4) δ 8.44 (d, J=0.7 Hz, 1H), 8.19 (d, J=2.2 Hz, 1H), 8.06 (d, J=21.7 Hz, 2H), 7.63-7.53 (m, 2H), 7.41 (s, 1H), 7.28-7.21 (m, 2H), 7.14 (dd, J=13.9, 8.2 Hz, 4H), 6.73 (dd, J=18.8, 9.5 Hz, 2H), 4.42-4.30 (m, 1H), 4.30-4.18 (m, 3H), 4.13 (d, J=4.3 Hz, 1H), 4.02 (d, J=12.6 Hz, 2H), 3.84 (d, J=13.2 Hz, 1H), 3.58 (d, J=10.5 Hz, 7H), 3.09 (q, J=7.3 Hz, 2H), 2.92-2.72 (m, 3H), 2.72-2.61 (m, 1H), 2.24-2.13 (m, 2H), 1.96 (d, J=8.7 Hz, 2H), 1.32 (t, J=7.3 Hz, 3H), 1.11-0.98 (m, 9H), 0.94 (s, 3H).

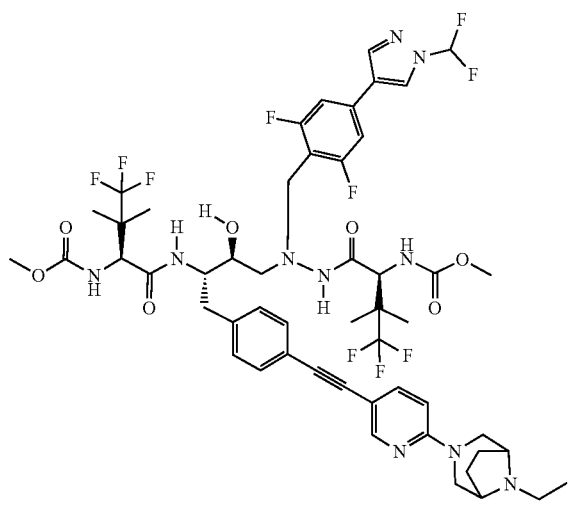

EXAMPLE 168

Methyl ((5S,8S,9S,14S)-11-(4-(1-(difluoromethyl)-1H-pyrazol-4-yl)-2,6-difluorobenzyl)-16,16,16-trifluoro-9-hydroxy-15,15-dimethyl-8-(4-((6-(8-methyl-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (168)

Intermediates: P7, A3, and S20. MS (ESI) m/z 1113.4 [M+H]+. $^1$H NMR (400 MHz, Methanol-d4) δ 8.45 (d, J=0.7 Hz, 1H), 8.24-8.16 (m, 1H), 8.08 (d, J=9.3 Hz, 1H), 8.03 (s, 1H), 7.63-7.54 (m, 1H), 7.41 (s, 1H), 7.28-7.21 (m, 2H), 7.14 (dd, J=14.5, 8.2 Hz, 5H), 6.74 (dd, J=15.5, 9.4 Hz, 2H), 4.34 (d, J=9.9 Hz, 1H), 4.24 (dd, J=17.7, 11.9 Hz, 3H), 4.02 (d, J=13.4 Hz, 4H), 3.83 (d, J=13.2 Hz, 1H), 3.58 (d, J=10.4 Hz, 7H), 3.16 (s, 1H), 3.06-2.96 (m, 0H), 2.85-2.58 (m, 6H), 2.31-2.13 (m, 2H), 2.05-1.89 (m, 2H), 1.13-0.96 (m, 9H), 0.94 (s, 3H).

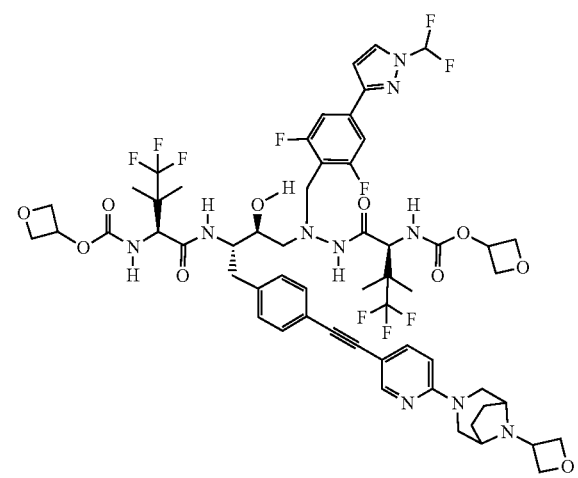 [SMILES: CC(C)([C@H](NC(=O)OC1COC1)C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC1COC1)C(C)(C)C(F)(F)F)C(F)(F)F]

EXAMPLE 169 oxetan-3-yl ((2S)-1-(2-(4-(1-(difluoromethyl)-1H-pyrazol-3-yl)-2,6-difluorobenzyl)-2-((2S,3S)-2-hydroxy-4-(4-((6-(8-(oxetan-3-yl)-3,8-diazabicyclo[3.2.1]octan-3-yl)pyridin-3-yl)ethynyl)phenyl)-3-((S)-4,4,4-trifluoro-3,3-dimethyl-2-(((oxetan-3-yloxy)carbonyl)amino)butanamido)butyl)hydrazinyl)-4,4,4-trifluoro-3,3-dimethyl-1-oxobutan-2-yl)carbamate (169)

Intermediates: P4, A4, and S3. MS (ESI) m/z 1239.3 [M+H]+. ¹H NMR (400 MHz, Methanol-d4) δ 8.13 (d, J=2.3 Hz, 1H), 8.09 (d, J=9.4 Hz, 1H), 8.02 (d, J=2.8 Hz, 1H), 7.52 (dd, J=8.9, 2.4 Hz, 1H), 7.45 (t, J=59.9 Hz, 1H), 7.37 (d, J=8.2 Hz, 2H), 7.21 (d, J=7.9 Hz, 2H), 7.12 (d, J=7.9 Hz, 2H), 6.85 (d, J=2.8 Hz, 1H), 6.61 (d, J=9.0 Hz, 1H), 5.29 (dp, J=17.2, 5.7 Hz, 2H), 4.76-4.73 (m, 4H), 4.67 (t, J=6.4 Hz, 2H), 4.56 (ddd, J=10.3, 7.3, 5.4 Hz, 2H), 4.52-4.42 (m, 4H), 4.32 (s, 1H), 4.20 (s, 1H), 4.11-4.00 (m, 2H), 3.90-3.76 (m, 3H), 3.77-3.60 (m, 2H), 3.08-2.97 (m, 2H), 2.89-2.75 (m, 3H), 2.73-2.63 (m, 1H), 1.90-1.81 (m, 2H), 1.68-1.56 (m, 2H), 1.09 (s, 3H), 1.07 (s, 3H), 1.03 (s, 3H), 0.95 (s, 3H).

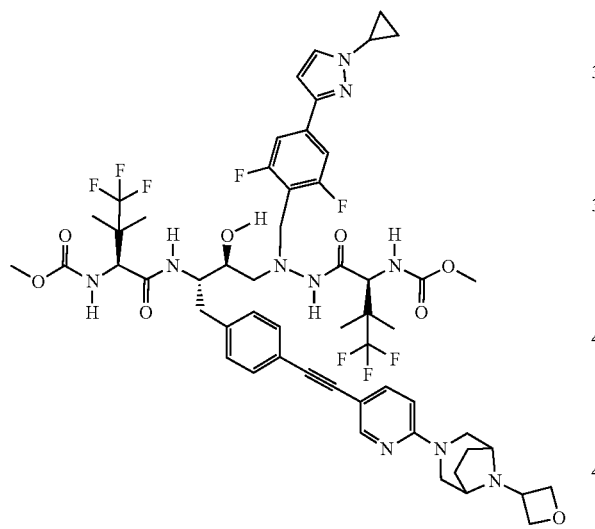

EXAMPLE 170

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (170)

Intermediates: P13, A3, and S3. MS (ESI) m/z 1146.0 [M+H]+. ¹H NMR (400 MHz, Methanol-d4) δ 8.29 (dd, J=2.3, 0.8 Hz, 1H), 8.18 (d, J=9.2 Hz, 1H), 7.70 (td, J=4.9, 4.4, 2.3 Hz, 2H), 7.39-7.27 (m, 4H), 7.22 (d, J=8.1 Hz, 2H), 7.16 (d, J=9.9 Hz, 1H), 6.86 (d, J=8.9 Hz, 1H), 6.80 (d, J=9.9 Hz, 1H), 6.64 (d, J=2.4 Hz, 1H), 4.96 (dd, J=8.2, 7.0 Hz, 2H), 4.81 (dd, J=8.3, 5.1 Hz, 2H), 4.46-4.41 (m, 1H), 4.39-4.33 (m, 1H), 4.31 (d, J=10.0 Hz, 1H), 4.19-4.07 (m, 4H), 3.93 (d, J=13.2 Hz, 1H), 3.76-3.70 (m, 1H), 3.69 (s, 3H), 3.66 (s, 3H), 3.40-3.34 (m, 2H), 2.95-2.70 (m, 4H), 2.30-2.18 (m, 2H), 2.12-2.01 (m, 2H), 1.22-1.04 (m, 13H), 1.02 (s, 3H).

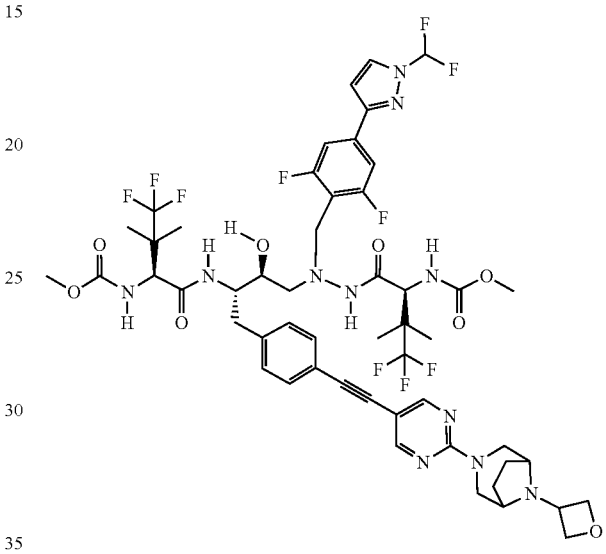

EXAMPLE 171

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (171)

Intermediates: P4, A3, and S7. MS (ESI) m/z 1156.4 [M+H]+. 1H NMR (400 MHz, Methanol-d4) δ 8.43 (s, 2H), 8.08 (d, J=9.4 Hz, 1H), 8.01 (d, J=2.8 Hz, 1H), 7.44 (d, J=59.8 Hz, 1H), 7.35 (d, J=8.2 Hz, 2H), 7.25 (d, J=7.9 Hz, 2H), 7.14 (d, J=8.1 Hz, 2H), 7.03 (d, J=9.9 Hz, 1H), 6.84 (d, J=2.7 Hz, 1H), 6.71 (d, J=9.9 Hz, 1H), 4.87 (t, J=7.6 Hz, 2H), 4.72 (dd, J=8.2, 4.9 Hz, 2H), 4.67 (s, 1H), 4.42-4.29 (m, 1H), 4.25-4.18 (m, 1H), 4.11-3.98 (m, 4H), 3.85 (d, J=13.1 Hz, 1H), 3.69-3.62 (m, 2H), 3.59 (s, 3H), 3.57 (s, 3H), 3.41-3.28 (m, 2H), 2.87-2.75 (m, 3H), 2.68 (dd, J=12.6, 9.1 Hz, 1H), 2.18-2.06 (m, 2H), 1.95-1.83 (m, 2H), 1.07 (s, 3H), 1.05 (s, 3H), 1.02 (s, 3H), 0.93 (s, 3H).

357

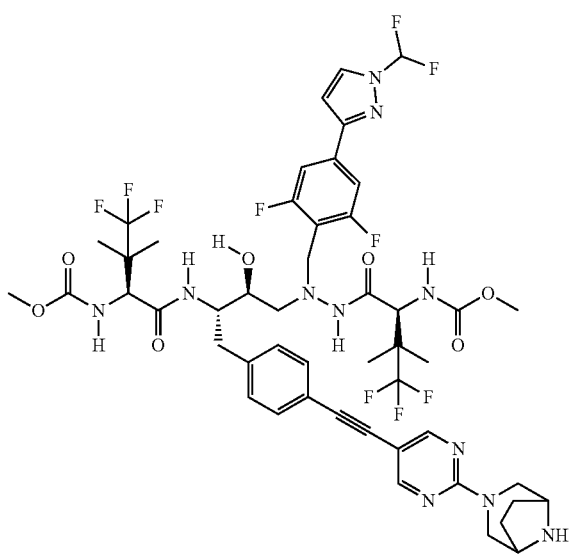 [SMILES: COC(=O)N[C@H](C(=O)N[C@@H](Cc1ccc(C#Cc2cnc(N3CC4CCC(C3)N4)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

358

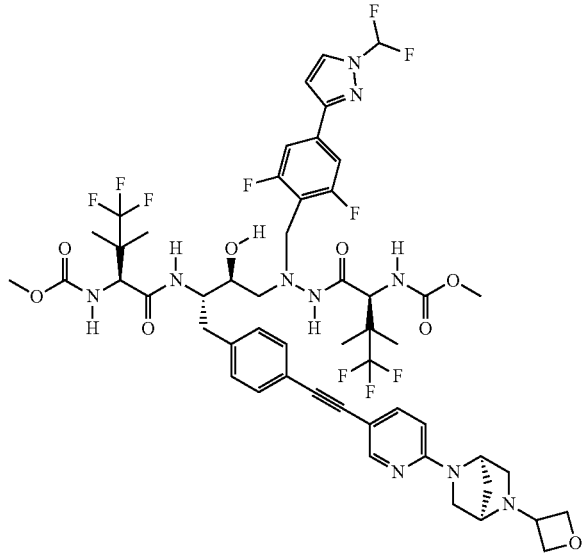 [SMILES: COC(=O)N[C@H](C(=O)N[C@@H](Cc1ccc(C#Cc2ccc(N3C[C@H]4C[C@@H]3CN4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 172

Methyl ((5S,8S,9S,14S)-8-(4-((2-(3,8-diazabicyclo[3.2.1]octan-3-yl)pyrimidin-5-yl)ethynyl)benzyl)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (172)

Intermediates: P4, A3, and S36. MS (ESI) m/z 1100.4 [M+H]+. 1H NMR (400 MHz, Methanol-d4) δ 8.41 (s, 2H), 8.08 (d, J=9.2 Hz, 1H), 8.01 (d, J=2.7 Hz, 1H), 7.44 (d, J=59.8 Hz, 1H), 7.36 (d, J=8.2 Hz, 2H), 7.25 (d, J=7.9 Hz, 2H), 7.14 (d, J=8.1 Hz, 2H), 7.03 (d, J=8.5 Hz, 1H), 6.84 (d, J=2.8 Hz, 1H), 6.70 (d, J=10.2 Hz, 1H), 4.66-4.57 (m, 2H), 4.35 (d, J=9.6 Hz, 1H), 4.26-4.17 (m, 1H), 4.12-3.96 (m, 5H), 3.85 (d, J=13.2 Hz, 1H), 3.69-3.62 (m, 2H), 3.59 (s, 3H), 3.57 (s, 3H), 3.25 (s, 1H), 2.87-2.61 (m, 4H), 2.05-1.96 (m, 2H), 1.90-1.82 (m, 2H), 1.07 (s, 3H), 1.05 (s, 3H), 1.02 (s, 3H), 0.94 (s, 3H).

EXAMPLE 173

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-((1R,4R)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (173)

Intermediates: P4, A3, and S6. MS (ESI) m/z 1141.5 [M+H]+. 1H NMR (400 MHz, Methanol-d4) δ 8.29-8.23 (m, 1H), 8.17 (d, J=9.4 Hz, 1H), 8.10 (d, J=2.7 Hz, 1H), 7.69 (dd, J=8.6, 2.1 Hz, 1H), 7.53 (t, J=59.7 Hz, 1H), 7.45 (d, J=8.2 Hz, 2H), 7.32 (d, J=7.9 Hz, 2H), 7.22 (d, J=8.1 Hz, 2H), 7.13 (d, J=9.8 Hz, 1H), 6.94 (d, J=2.7 Hz, 1H), 6.80 (d, J=10.2 Hz, 1H), 6.71-6.63 (m, 1H), 5.07-5.01 (m, 1H), 4.72-4.68 (m, 1H), 4.64-4.54 (m, 2H), 4.52-4.49 (m, 1H), 4.47-4.41 (m, 1H), 4.30 (d, J=10.0 Hz, 1H), 4.20-4.08 (m, 2H), 3.94 (d, J=13.1 Hz, 1H), 3.79 (d, J=11.0 Hz, 1H), 3.72 (d, J=11.7 Hz, 1H), 3.69 (s, 3H), 3.66 (s, 3H), 2.93-2.82 (m, 3H), 2.81-2.73 (m, 1H), 2.33 (s, 2H), 1.16 (s, 3H), 1.15 (s, 3H), 1.11 (s, 3H), 1.02 (s, 3H).

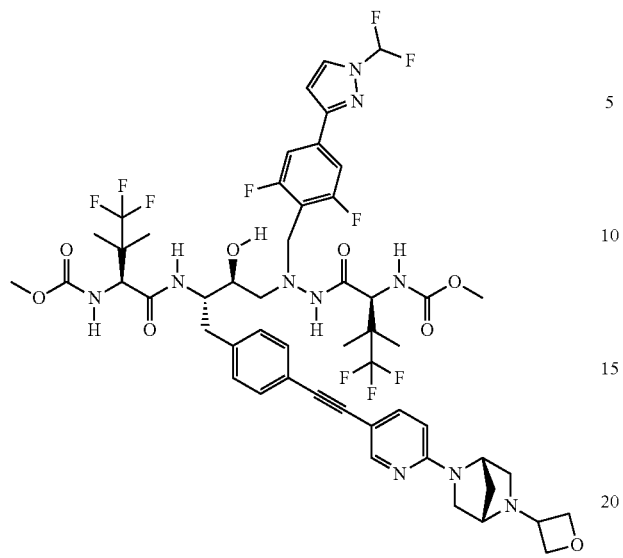

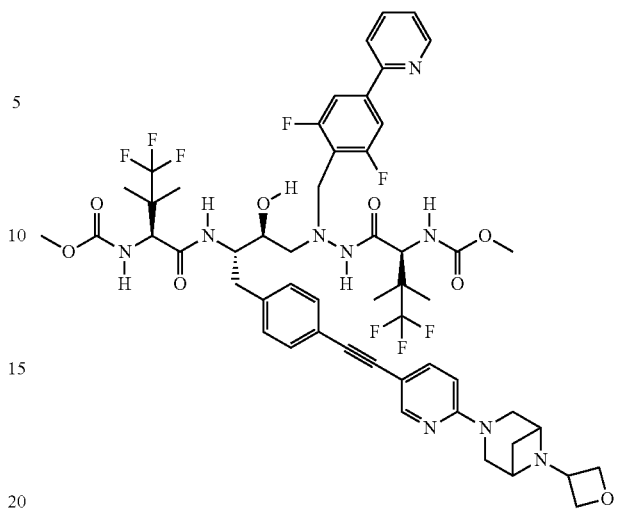

EXAMPLE 174

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(((1S,4S)-5-(oxetan-3-yl)-2,5-diazabicyclo[2.2.1]heptan-2-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (174)

Intermediates: P4, A3, and S30. MS (ESI) m/z 1141.6 [M+H]+. $^1$H NMR (400 MHz, Methanol-d4) δ 8.25 (dd, J=2.2, 0.8 Hz, 1H), 8.17 (d, J=9.4 Hz, 1H), 8.10 (d, J=2.7 Hz, 1H), 7.74-7.68 (m, 1H), 7.53 (t, J=59.6 Hz, 1H), 7.45 (d, J=8.2 Hz, 2H), 7.32 (d, J=7.9 Hz, 2H), 7.22 (d, J=8.1 Hz, 2H), 7.13 (d, J=9.9 Hz, 1H), 6.94 (d, J=2.8 Hz, 1H), 6.80 (d, J=9.9 Hz, 1H), 6.71-6.61 (m, 1H), 5.05 (s, 1H), 4.99-4.93 (m, 1H), 4.70 (dd, J=8.4, 4.5 Hz, 1H), 4.64-4.53 (m, 2H), 4.51 (s, 1H), 4.44 (d, J=9.8 Hz, 1H), 4.30 (d, J=10.0 Hz, 1H), 4.18-4.10 (m, 2H), 3.94 (d, J=13.1 Hz, 1H), 3.79 (dd, J=11.9, 2.2 Hz, 1H), 3.76-3.70 (m, 1H), 3.69 (s, 3H), 3.66 (s, 3H), 2.94-2.73 (m, 4H), 2.33 (s, 2H), 1.16 (s, 3H), 1.14 (s, 3H), 1.11 (s, 3H), 1.02 (s, 3H).

EXAMPLE 175

Methyl ((5S,8S,9S,14S)-11-(2,6-difluoro-4-(pyridin-2-yl)benzyl)-16,16,16-trifluoro-9-hydroxy-15,15-dimethyl-8-(4-(((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (175)

Intermediates: P28, A3, and S4. MS (ESI) m/z 1102.4 [M+H]+. $^1$H NMR (400 MHz, Methanol-d4) δ 8.66 (d, J=5.0 Hz, 1H), 8.33 (d, J=2.2 Hz, 1H), 8.14 (d, J=9.4 Hz, 1H), 8.03-7.88 (m, 2H), 7.74 (dd, J=8.7, 2.3 Hz, 1H), 7.60 (d, J=8.5 Hz, 2H), 7.46 (t, J=6.1 Hz, 1H), 7.34 (d, J=7.8 Hz, 2H), 7.23 (d, J=7.9 Hz, 2H), 7.11 (d, J=9.4 Hz, 1H), 6.78 (d, J=8.8 Hz, 2H), 4.97 (s, 3H), 4.62 (dd, J=8.1, 4.1 Hz, 2H), 4.44 (d, J=8.2 Hz, 1H), 4.34-4.26 (m, 1H), 4.26-4.07 (m, 4H), 3.98 (d, J=13.1 Hz, 2H), 3.79-3.71 (m, 1H), 3.70 (s, 3H), 3.64 (s, 3H), 2.99-2.85 (m, 3H), 2.84-2.74 (m, 1H), 2.11 (d, J=11.2 Hz, 1H), 1.16 (s, 3H), 1.15 (s, 3H), 1.13 (s, 3H), 1.03 (s, 3H).

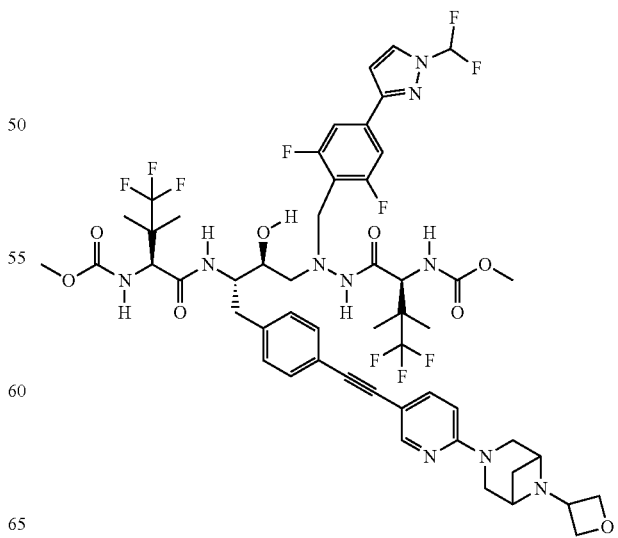

EXAMPLE 176

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(6-(oxetan-3-yl)-3,6-diazabicyclo[3.1.1]heptan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (176)

Intermediates: P4, A3, and S4. MS (ESI) m/z 1141.8 [M+H]+. ¹H NMR (400 MHz, Methanol-d4) δ 8.33 (d, J=2.1 Hz, 1H), 8.14 (d, J=9.3 Hz, 1H), 8.10 (d, J=2.8 Hz, 1H), 7.74 (dd, J=8.8, 2.2 Hz, 1H), 7.53 (t, J=59.8 Hz, 1H), 7.45 (d, J=8.2 Hz, 2H), 7.34 (d, J=7.9 Hz, 2H), 7.22 (d, J=8.0 Hz, 2H), 7.09 (d, J=10.3 Hz, 1H), 6.93 (d, J=2.8 Hz, 1H), 6.78 (d, J=8.8 Hz, 2H), 5.07-4.91 (m, 3H), 4.61 (dd, J=8.2, 4.1 Hz, 2H), 4.44 (d, J=9.9 Hz, 1H), 4.31 (d, J=10.0 Hz, 1H), 4.23-4.06 (m, 3H), 3.95 (d, J=13.3 Hz, 1H), 3.70 (s, 3H), 3.66 (s, 3H), 2.95-2.70 (m, 4H), 2.10 (d, J=11.1 Hz, 1H), 1.16 (s, 3H), 1.15 (s, 3H), 1.12 (s, 3H), 1.03 (s, 3H).

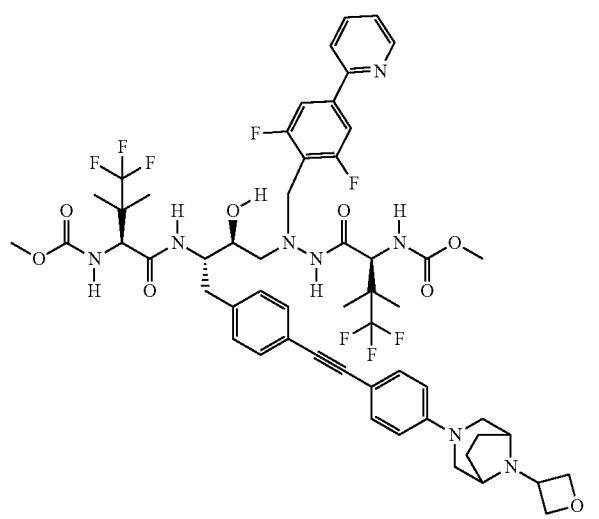 [SMILES: COC(=O)N[C@H](C(=O)N[C@@H](Cc1ccc(C#Cc2ccc(N3CC4CCC(C3)N4C3COC3)cc2)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]

EXAMPLE 177

Methyl ((5S,8S,9S,14S)-11-(2,6-difluoro-4-(pyridin-2-yl)benzyl)-16,16,16-trifluoro-9-hydroxy-15,15-dimethyl-8-(4-((4-(8-(oxetan-3-yl)-3,8-diazabicyclo[3.2.1]octan-3-yl)phenyl)ethynyl)benzyl)-3,6,13-trioxo-5-(1,1,1-trifluoro-2-methylpropan-2-yl)-2-oxa-4,7,11,12-tetraazahexadecan-14-yl)carbamate (177)

Intermediates: P28, A3, and S3. MS (ESI) m/z 1115.9 [M+H]+. ¹H NMR (400 MHz, Methanol-d4) δ 8.69-8.60 (m, 1H), 8.18 (d, J=9.3 Hz, 1H), 7.94 (q, J=7.9 Hz, 2H), 7.60 (d, J=8.6 Hz, 2H), 7.44 (t, J=5.7 Hz, 1H), 7.39 (d, J=8.8 Hz, 2H), 7.31 (d, J=7.9 Hz, 2H), 7.21 (d, J=8.1 Hz, 2H), 7.17 (d, J=10.7 Hz, 1H), 6.96 (d, J=8.8 Hz, 2H), 6.79 (d, J=10.0 Hz, 1H), 5.01-4.92 (m, 3H), 4.84-4.76 (m, 2H), 4.44 (d, J=9.9 Hz, 1H), 4.31 (d, J=10.0 Hz, 1H), 4.23-4.10 (m, 4H), 3.97 (d, J=13.1 Hz, 1H), 3.85 (d, J=13.0 Hz, 2H), 3.79-3.72 (m, 1H), 3.69 (s, 3H), 3.63 (s, 3H), 2.93-2.84 (m, 3H), 2.83-2.75 (m, 1H), 2.21 (q, J=11.1, 10.5 Hz, 4H), 1.27 (d, J=5.7 Hz, 1H), 1.16 (s, 3H), 1.14 (s, 3H), 1.12 (s, 3H), 1.03 (s, 3H). ¹⁹F NMR (377 MHz, Methanol-d4) δ −77.39, −77.73, −77.85, −114.65.

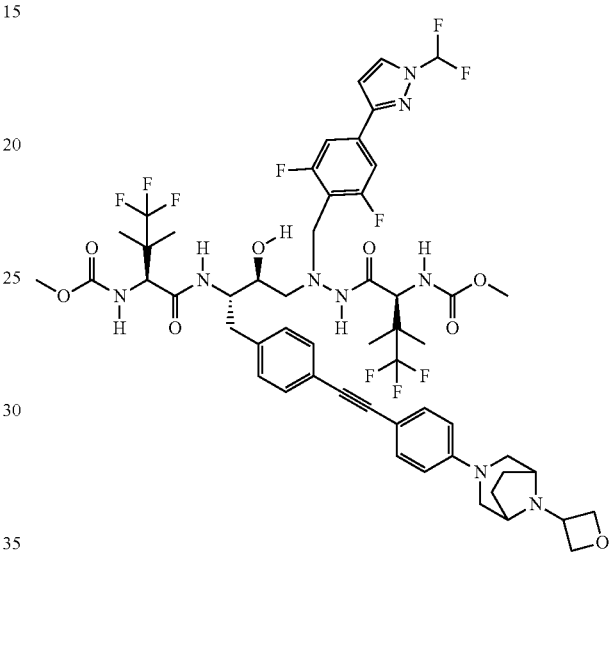

EXAMPLE 178

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((4-(8-(oxetan-3-yl)-3,8-diazabicyclo[3.2.1]octan-3-yl)phenyl)ethynyl)benzyl)-3,6,13-trioxo-5-(1,1,1-trifluoro-2-methylpropan-2-yl)-2-oxa-4,7,11,12-tetraazahexadecan-14-yl)carbamate (178)

Intermediates: P4, A3, and S3. MS (ESI) m/z 1154.4 [M+H]+. ¹H NMR (400 MHz, Methanol-d4) δ 8.07 (d, J=9.4 Hz, 1H), 8.01 (d, J=2.7 Hz, 1H), 7.44 (t, 1H), 7.36 (d, J=8.2 Hz, 2H), 7.30 (d, J=8.5 Hz, 2H), 7.21 (d, J=7.9 Hz, 2H), 7.11 (d, J=8.1 Hz, 2H), 6.89-6.82 (m, 3H), 4.86 (t, J=7.5 Hz, 2H), 4.72-4.64 (m, 2H), 4.35 (d, J=6.4 Hz, 1H), 4.25-4.16 (m, 1H), 4.11-3.95 (m, 3H), 3.85 (d, J=12.5 Hz, 1H), 3.80-3.70 (m, 1H), 3.68-3.62 (m, 1H), 3.60 (s, 3H), 3.57 (s, 3H), 2.85-2.63 (m, 4H), 2.18-1.99 (m, 4H), 1.22-1.18 (m, 2H), 1.07 (s, 3H), 1.05 (s, 3H), 1.02 (s, 3H), 0.93 (s, 3H). ¹⁹F NMR (377 MHz, Methanol-d4) δ −77.40, −77.49, −77.73, −96.96 (dd, J=60.0, 18.7 Hz), −114.92.

363 364

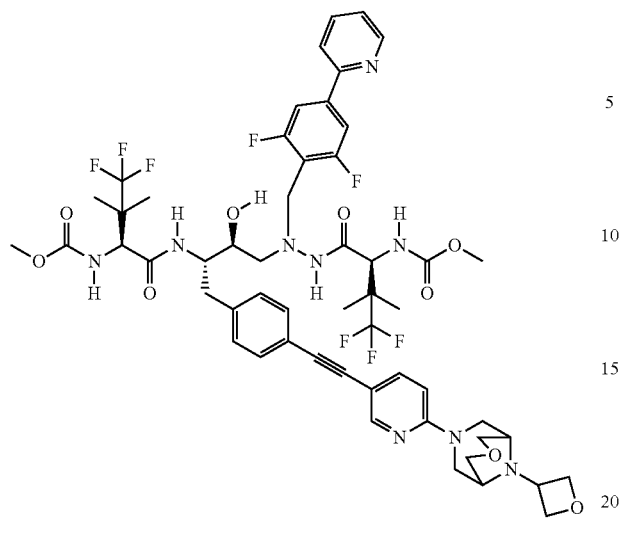

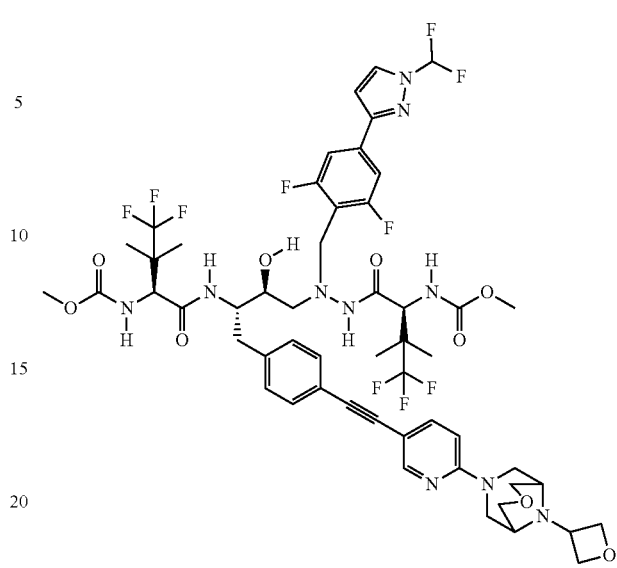

EXAMPLE 179

Methyl ((5S,8S,9S,14S)-11-(2,6-difluoro-4-(pyridin-2-yl)benzyl)-16,16,16-trifluoro-9-hydroxy-15,15-dimethyl-8-(4-((6-(9-(oxetan-3-yl)-3-oxa-7,9-diazabicyclo[3.3.1]nonan-7-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (179)

Intermediates: P28, A3, and S1. MS (ESI) m/z 1133.1 [M+H]+. $^1$H NMR (400 MHz, Methanol-d4) δ 8.66 (d, J=4.8 Hz, 1H), 8.21-8.10 (m, 2H), 8.02-7.82 (m, 3H), 7.60 (d, J=8.6 Hz, 2H), 7.46 (t, J=6.3 Hz, 1H), 7.36 (d, J=7.9 Hz, 2H), 7.25 (d, J=8.1 Hz, 2H), 7.19 (d, J=9.4 Hz, 1H), 4.82-4.76 (m, 2H), 4.66-4.58 (m, 2H), 4.51-4.41 (m, 1H), 4.35-4.27 (m, 1H), 4.23-4.13 (m, 2H), 4.13-3.89 (m, 7H), 3.78-3.72 (m, 2H), 3.69 (s, 3H), 3.68-3.65 (m, 3H), 3.63 (s, 3H), 3.18-3.08 (m, 2H), 3.00-2.84 (m, 3H), 2.84-2.74 (m, 1H), 1.16 (s, 3H), 1.15 (s, 3H), 1.12 (s, 3H), 1.03 (s, 3H). $^{19}$F NMR (377 MHz, Methanol-d4) δ −77.37, −77.71, −77.99, −114.58.

EXAMPLE 180

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-((6-(9-(oxetan-3-yl)-3-oxa-7,9-diazabicyclo[3.3.1]nonan-7-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (180)

Intermediates: P4, A3, and S1. MS (ESI) m/z 1171.8 [M+H]+. $^1$H NMR (400 MHz, Methanol-d4) δ 8.20-8.13 (m, 2H), 8.10 (d, J=2.7 Hz, 1H), 7.87 (d, J=8.7 Hz, 1H), 7.60 (t, J=59.8 Hz, 1H), 7.45 (d, J=8.2 Hz, 2H), 7.36 (d, J=8.0 Hz, 2H), 7.24 (d, J=8.1 Hz, 2H), 7.15 (d, J=9.5 Hz, 1H), 6.93 (d, J=2.7 Hz, 1H), 4.80-4.75 (m, 1H), 4.74-4.67 (m, 1H), 4.62 (t, J=5.7 Hz, 2H), 4.46-4.40 (m, 1H), 4.32-4.25 (m, 1H), 4.21-4.00 (m, 6H), 3.99-3.89 (m, 3H), 3.78-3.71 (m, 1H), 3.69 (s, 3H), 3.66 (s, 3H), 3.12 (d, J=4.9 Hz, 2H), 2.98-2.72 (m, 4H), 1.16 (s, 3H), 1.14 (s, 3H), 1.11 (s, 3H), 1.03 (s, 3H). $^{19}$F NMR (377 MHz, Methanol-d4) δ −77.38, −77.71, −77.85, −96.97 (dd, J=59.7, 19.1 Hz), −114.93.

EXAMPLE 181
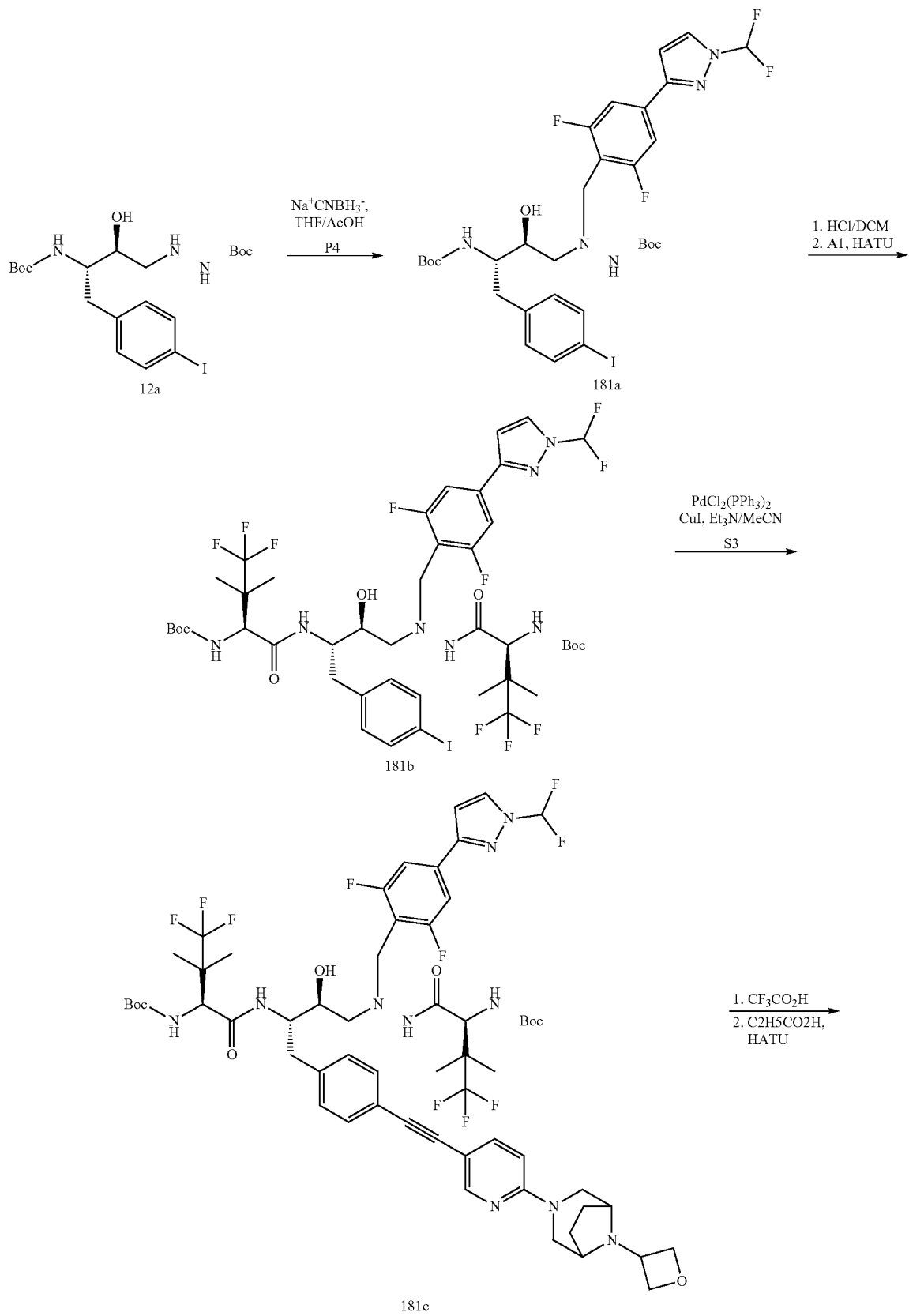

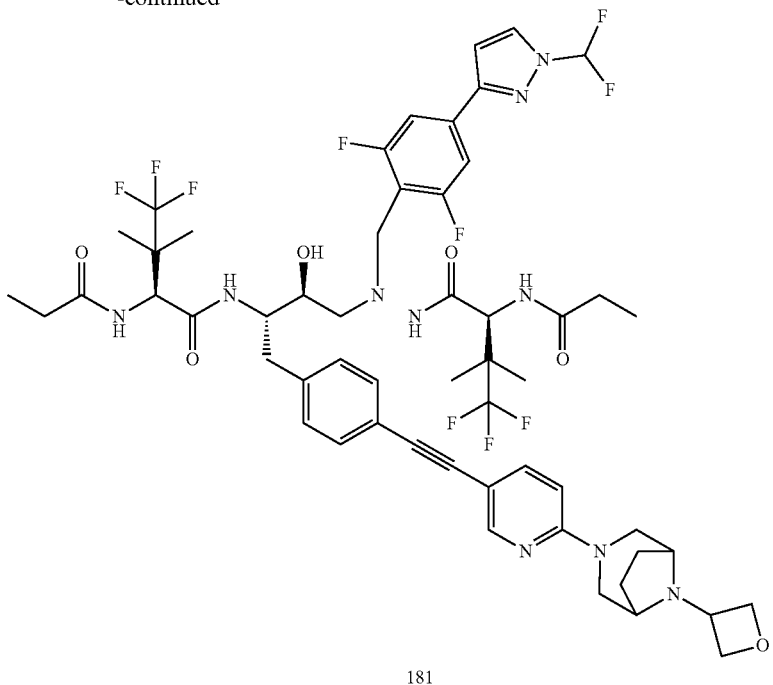

181

Synthesis of tert-butyl 2-((2S,3S)-3-((tert-butoxy-carbonyl)amino)-2-hydroxy-4-(4-iodophenyl)butyl)-2-(4-(1-(difluoromethyl)-1H-pyrazol-3-yl)-2,6-difluorobenzyl)hydrazine-1-carboxylate (181a)

The title compound 181a was prepared according to the method presented for the synthesis of compound 1a but instead utilizing I2a and P4. MS (ESI) m/z 764.1 [M+H]$^+$. $^1$H NMR (400 MHz, Methanol-d4) δ 8.09 (d, J=2.7 Hz, 1H), 7.56 (d, J=8.1 Hz, 2H), 7.53 (t, J=59.8 Hz, 1H), 7.51-7.35 (m, 2H), 7.02 (d, J=8.0 Hz, 2H), 6.93 (d, J=2.7 Hz, 1H), 4.03 (d, J=26.8 Hz, 2H), 3.70 (d, J=8.2 Hz, 1H), 3.57 (d, J=9.0 Hz, 1H), 2.79 (tdd, J=20.0, 11.2, 6.9 Hz, 2H), 1.37 (s, 8H), 1.31 (s, 7H). $^{19}$F NMR (377 MHz, Methanol-d4) δ −96.90 (d, J=59.8 Hz), −115.32

Synthesis of tert-butyl ((6S,11S,12S,15S)-9-(4-(1-(difluoromethyl)-1H-pyrazol-3-yl)-2,6-difluorobenzyl)-17,17,17-trifluoro-11-hydroxy-12-(4-iodobenzyl)-2,2,16,16-tetramethyl-4,7,14-trioxo-6-(1,1,1-trifluoro-2-methylpropan-2-yl)-3-oxa-5,8,9,13-tetraazaheptadecan-15-yl)carbamate (181b)

The title compound 181b was prepared according to the method presented for the synthesis of intermediate I2 but instead utilizing 181a and A1. MS (ESI) m/z 1098.6 [M+H]$^+$.

Synthesis of tert-butyl ((6S,11S,12S,15S)-9-(4-(1-(difluoromethyl)-1H-pyrazol-3-yl)-2,6-difluorobenzyl)-17,17,17-trifluoro-11-hydroxy-2,2,16,16-tetramethyl-12-(4-((6-(8-(oxetan-3-yl)-3,8-diazabicyclo[3.2.1]octan-3-yl)pyridin-3-yl)ethynyl)benzyl)-4,7,14-trioxo-6-(1,1,1-trifluoro-2-methylpropan-2-yl)-3-oxa-5,8,9,13-tetraazaheptadecan-15-yl)carbamate (181c)

The title compound 181c was prepared according to the method presented for the synthesis of compound 133 but instead utilizing 181b and S3. MS (ESI) m/z 1239.9 [M+H]$^+$.

(2S)—N-((2S,3S)-4-(1-(4-(1-(difluoromethyl)-1H-pyrazol-3-yl)-2,6-difluorobenzyl)-2-((S)-4,4,4-trifluoro-3,3-dimethyl-2-propionamidobutanoyl)hydrazinyl)-3-hydroxy-1-(4-((2-(8-(oxetan-3-yl)-3,8-diazabicyclo[3.2.1]octan-3-yl)pyrimidin-5-yl)ethynyl)phenyl)butan-2-yl)-4,4,4-trifluoro-3,3-dimethyl-2-propionamidobutanamide (181)

To a solution of 181c (355 mg, 0.29 mmol) in DCM (10 mL) was added trifluoroacetic acid (2 mL), the mixture was stirred and after 18 h, the reaction mixture was concentrated under reduced pressure and the crude material was dissolved in DMF (3 mL) and HATU (35.28 mg, 0.16 mmol), N,N-diisopropylethylamine (0.13 ml, 0.74 mmol) was added followed by propionic acid (0.01 ml, 0.16 mmol). The reaction was stirred at stirred at room temperature overnight. The reaction mixture was purified by HPLC to afford 181. MS (ESI) m/z 1152.1 [M+H]$^+$. $^1$H NMR (400 MHz, Methanol-d4) δ 8.20 (dd, J=2.3, 0.7 Hz, 1H), 8.11 (d, J=2.7 Hz, 1H), 7.74-7.37 (m, 4H), 7.37-7.23 (m, 2H), 7.23-7.12 (m, 2H), 6.95 (d, J=2.8 Hz, 1H), 6.70 (dd, J=9.1, 0.8 Hz, 1H), 4.83-4.71 (m, 3H), 4.66 (s, 1H), 4.59 (dd, J=6.3, 5.4 Hz, 3H), 4.23-4.13 (m, 2H), 4.00-3.84 (m, 4H), 3.84-3.70 (m, 1H), 3.13 (dd, J=12.0, 2.2 Hz, 3H), 2.95-2.71 (m, 4H), 2.21 (ttd, J=7.5, 5.0, 2.3 Hz, 4H), 1.97-1.90 (m, 2H), 1.70 (d, J=7.8 Hz, 2H), 1.18 (d, J=9.3 Hz, 7H), 1.16-1.00 (m, 13H).

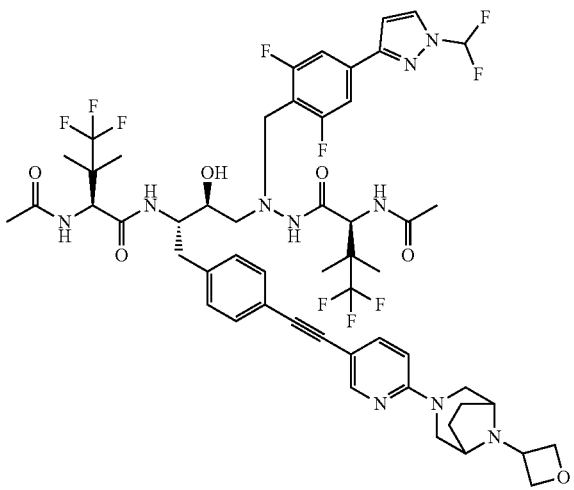 [SMILES: CC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(C)=O)C(C)(C)C(F)(F)F)C(C)(C)C(F)(F)F]

EXAMPLE 182

(2S)-2-acetamido-N-((2S,3S)-4-(2-((S)-2-acetamido-4,4,4-trifluoro-3,3-dimethylbutanoyl)-1-(4-(1-(difluoromethyl)-1H-pyrazol-3-yl)-2,6-difluorobenzyl)hydrazinyl)-3-hydroxy-1-(4-((6-(8-(oxetan-3-yl)-3,8-diazabicyclo[3.2.1]octan-3-yl)pyridin-3-yl)ethynyl)phenyl)butan-2-yl)-4,4,4-trifluoro-3,3-dimethylbutanamide (182)

The title compound 182 was prepared according to the method presented for the synthesis of compound 181 but instead utilizing Intermediates: P4, A1, S3 and acetic acid. MS (ESI) m/z 1123.9 [M+H]$^+$. $^1$H NMR (400 MHz, Methanol-d4) δ 8.18 (dd, J=2.3, 0.7 Hz, 1H), 8.09 (d, J=2.7 Hz, 1H), 7.72-7.35 (m, 4H), 7.35-7.24 (m, 2H), 7.20-7.11 (m, 2H), 6.94 (d, J=2.8 Hz, 1H), 6.69 (dd, J=9.0, 0.8 Hz, 1H), 4.76 (dd, J=12.8, 6.4 Hz, 3H), 4.63 (d, J=1.4 Hz, 1H), 4.57 (dd, J=6.3, 5.4 Hz, 3H), 4.15 (d, J=13.4 Hz, 2H), 3.98-3.65 (m, 5H), 3.11 (dd, J=12.0, 2.2 Hz, 3H), 2.98-2.67 (m, 4H), 2.13 (d, J=10.3 Hz, 0H), 1.98-1.83 (m, 9H), 1.68 (d, J=7.8 Hz, 2H), 1.17 (d, J=6.2 Hz, 6H), 1.12 (s, 3H), 1.04 (s, 3H), 0.88 (d, J=6.7 Hz, 0H).

EXAMPLE 183

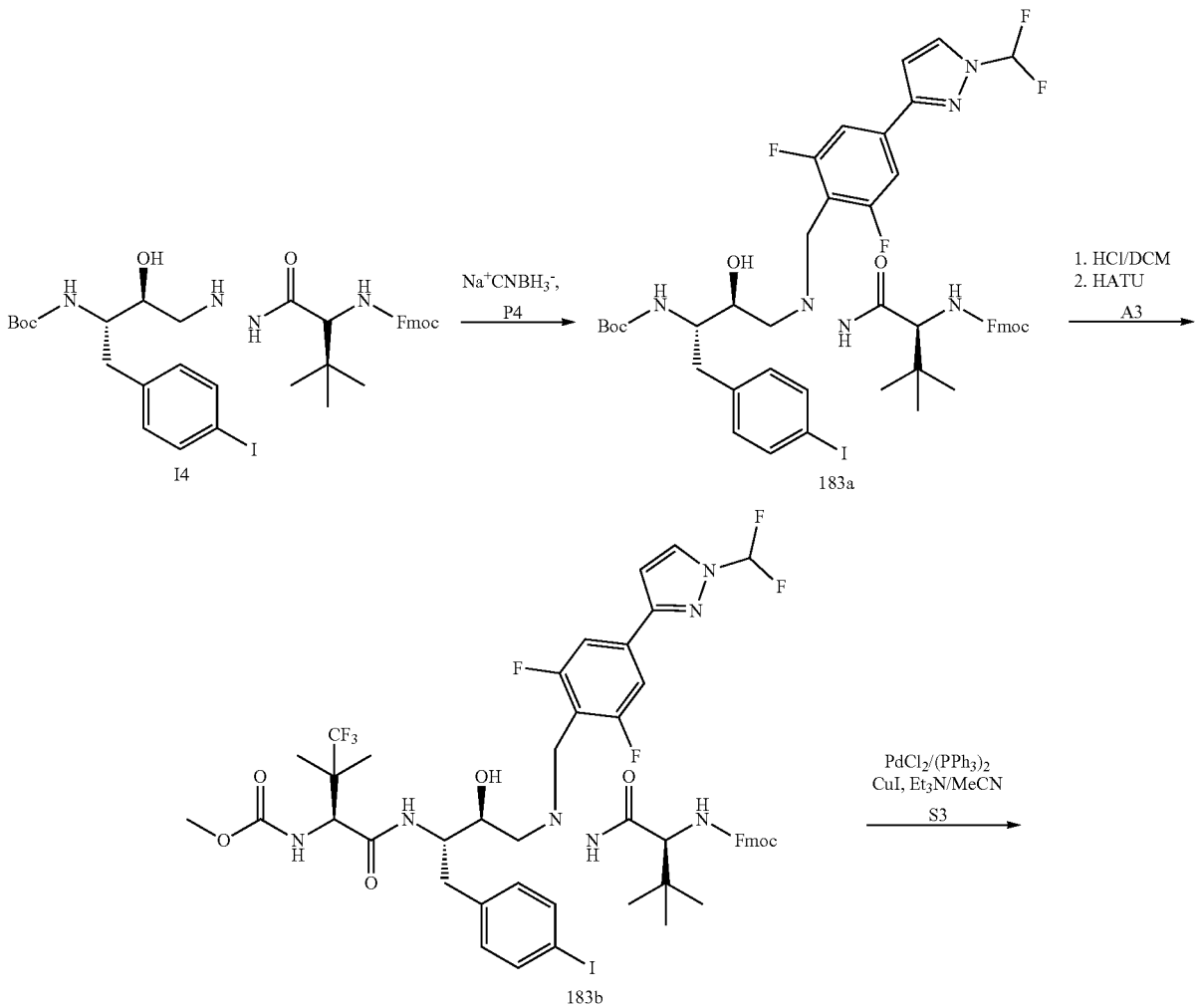

-continued

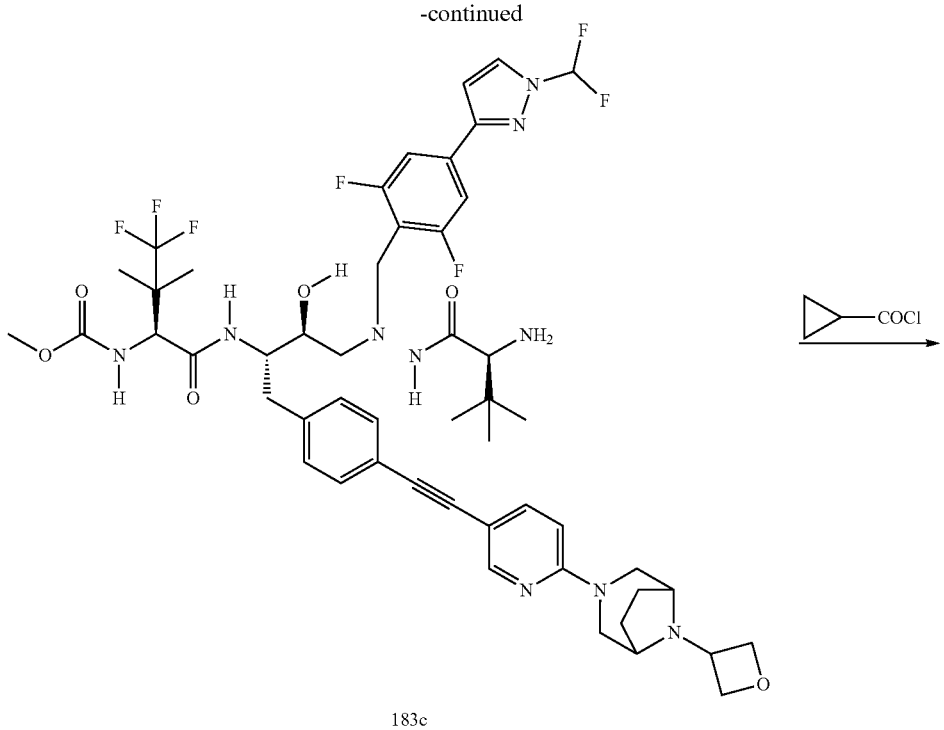

183c

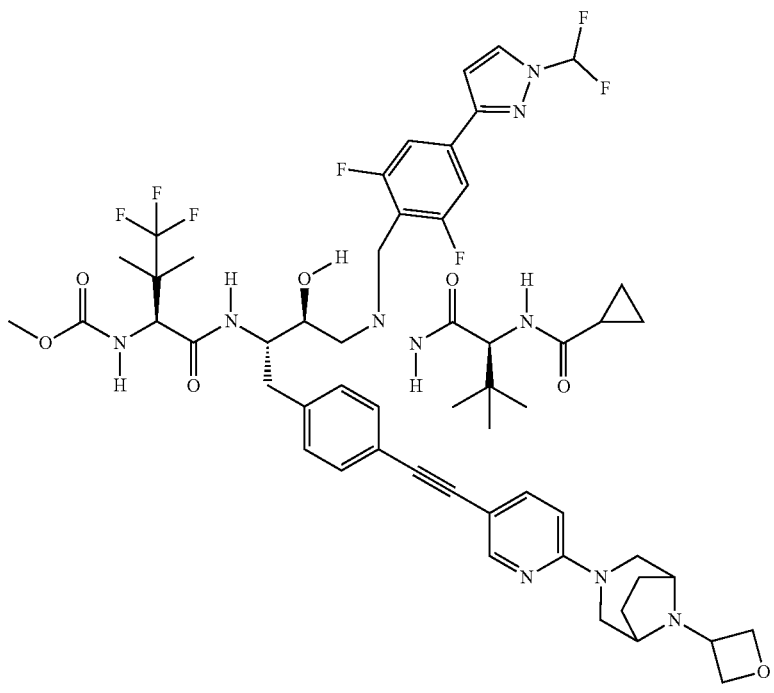

183

Synthesis of (9H-fluoren-9-yl)methyl ((S)-1-(2-((2S, 3S)-3-((tert-butoxycarbonyl)amino)-2-hydroxy-4-(4-iodophenyl)butyl)-2-(4-(1-(difluoromethyl)-1H-pyrazol-3-yl)-2,6-difluorobenzyl)hydrazinyl)-3,3-dimethyl-1-oxobutan-2-yl)carbamate (183a)

The title compound 183a was prepared according to the method presented for the synthesis of compound 133a but instead utilizing I4 and P4. MS (ESI) m/z 999.3 [M+H]$^+$.

Synthesis of (9H-fluoren-9-yl)methyl ((5S,8S,9S, 14S)-11-(4-(1-(difluoromethyl)-1H-pyrazol-3-yl)-2, 6-difluorobenzyl)-9-hydroxy-8-(4-iodobenzyl)-15, 15-dimethyl-3,6,13-trioxo-5-(1,1,1-trifluoro-2-methylpropan-2-yl)-2-oxa-4,7,11,12-tetraazahexadecan-14-yl)carbamate (183b)

The title compound 183b was prepared according to the method presented for the synthesis of compound 133b but instead utilizing 4a and A3. MS (ESI) m/z 1124.6 [M+H]$^+$.

Synthesis of methyl ((2S)-1-(((2S,3S)-4-(2-((S)-2-amino-3,3-dimethylbutanoyl)-1-(4-(1-(difluoromethyl)-1H-pyrazol-3-yl)-2,6-difluorobenzyl)hydrazinyl)-3-hydroxy-1-(4-((6-(8-(oxetan-3-yl)-3,8-diazabicyclo[3.2.1]octan-3-yl)pyridin-3-yl)ethynyl)phenyl)butan-2-yl)amino)-4,4,4-trifluoro-3,3-dimethyl-1-oxobutan-2-yl)carbamate (183c)

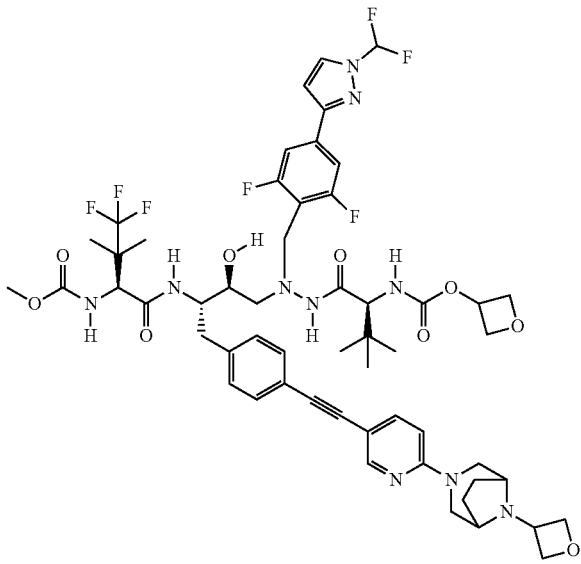 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC1COC1)C(C)(C)C)C(C)(C)C(F)(F)F]

The title compound 183c was prepared according to the method presented for the synthesis of compound 133 but instead utilizing 183b and S3. MS (ESI) m/z 1043.5 [M+H]⁺. ¹H NMR (400 MHz, Methanol-d4) δ 8.29 (dd, J=2.3, 0.7 Hz, 1H), 8.14-8.07 (m, 2H), 7.75-7.65 (m, 1H), 7.53 (d, J=59.8 Hz, 1H), 7.50 (d, J=8.4 Hz, 2H), 7.32 (d, J=8.1 Hz, 2H), 7.25-7.18 (m, 2H), 6.94 (d, J=2.8 Hz, 1H), 6.86 (dd, J=9.0, 0.9 Hz, 1H), 6.78 (d, J=9.9 Hz, 1H), 4.99-4.93 (m, 3H), 4.84 (d, J=5.2 Hz, 1H), 4.82 (d, J=5.0 Hz, 1H), 4.54 (s, 1H), 4.42-4.30 (m, 3H), 4.26-4.06 (m, 5H), 3.81 (t, J=6.6 Hz, 1H), 3.65 (s, 1H), 3.45-3.36 (m, 3H), 2.97-2.76 (m, 4H), 2.28-2.19 (m, 2H), 2.11-2.03 (m, 2H), 1.09 (s, 3H), 1.06 (s, 3H), 0.97 (s, 9H).

Synthesis of methyl ((2S)-1-(((2S,3S)-4-(2-((S)-2-(cyclopropanecarboxamido)-3,3-dimethylbutanoyl)-1-(4-(1-(difluoromethyl)-1H-pyrazol-3-yl)-2,6-difluorobenzyl)hydrazinyl)-3-hydroxy-1-(4-((6-(8-(oxetan-3-yl)-3,8-diazabicyclo[3.2.1]octan-3-yl)pyridin-3-yl)ethynyl)phenyl)butan-2-yl)amino)-4,4,4-trifluoro-3,3-dimethyl-1-oxobutan-2-yl)carbamate (183)

To a solution of 183c (45 mg, 0.33 mmol) in DCM (1 mL) was added Et₃N (0.03 ml, 0.23 mmol) at 5° C., cyclopropanecarbonyl chloride (3.54 μl, 0.39 mmol) was added and the mixture was stirred for 10 min, then diluted with MeOH, concentrated under reduced pressure and the residue was purified by HPLC to afford 183. MS (ESI) m/z 1111.5 [M+H]⁺. ¹H NMR (400 MHz, Methanol-d4) δ 8.35-8.26 (m, 1H), 8.18 (d, J=9.4 Hz, 1H), 8.11 (d, J=2.7 Hz, 1H), 7.91 (d, J=8.9 Hz, 1H), 7.71 (dd, J=8.8, 2.3 Hz, 1H), 7.53 (t, J=59.7 Hz, 1H), 7.46 (d, J=8.3 Hz, 2H), 7.33 (d, J=8.0 Hz, 2H), 7.22 (d, J=8.1 Hz, 2H), 6.94 (d, J=2.8 Hz, 1H), 6.87 (d, J=8.9 Hz, 1H), 6.78 (d, J=9.9 Hz, 1H), 5.03-4.94 (m, 2H), 4.84-4.77 (m, 3H), 4.44 (d, J=9.9 Hz, 1H), 4.41-4.31 (m, 1H), 4.21-4.06 (m, 5H), 3.96 (d, J=13.1 Hz, 1H), 3.81-3.72 (m, 1H), 3.70 (s, 3H), 3.39 (s, 1H), 2.91 (d, J=7.7 Hz, 2H), 2.88-2.73 (m, 2H), 2.29-2.19 (m, 2H), 2.15-2.04 (m, 2H), 1.74-1.67 (m, 1H), 1.31 (t, J=7.5 Hz, 1H), 1.14 (s, 3H), 1.10 (s, 3H), 0.89 (s, 9H), 0.75 (dd, J=8.2, 3.6 Hz, 2H).

EXAMPLE 184 methyl ((2S)-1-(((2S,3S)-4-(1-(4-(1-(difluoromethyl)-1H-pyrazol-3-yl)-2,6-difluorobenzyl)-2-((S)-3,3-dimethyl-2-(((oxetan-3-yloxy)carbonyl)amino)butanoyl)hydrazinyl)-3-hydroxy-1-(4-((6-(8-(oxetan-3-yl)-3,8-diazabicyclo[3.2.1]octan-3-yl)pyridin-3-yl)ethynyl)phenyl)butan-2-yl)amino)-4,4,4-trifluoro-3,3-dimethyl-1-oxobutan-2-yl)carbamate Intermediates: P4, A3, S3 and 4-nitrophenyl oxetan-3-yl carbonate. MS (ESI) m/z 1143.6 [M+H]⁺. ¹H NMR (400 MHz, Methanol-d4) δ 8.25-8.19 (m, 1H), 8.09 (d, J=9.3 Hz, 1H), 8.01 (d, J=2.7 Hz, 1H), 7.65-7.59 (m, 1H), 7.44 (t, J=59.7 Hz, 1H), 7.36 (d, J=8.1 Hz, 2H), 7.23 (d, J=7.9 Hz, 3H), 7.13 (d, J=8.0 Hz, 3H), 6.85 (d, J=2.7 Hz, 1H), 6.77 (d, J=8.9 Hz, 1H), 6.71 (d, J=9.6 Hz, 1H), 4.87 (t, J=7.6 Hz, 3H), 4.76-4.68 (m, 2H), 4.51 (dt, J=23.0, 6.4 Hz, 2H), 4.31-4.22 (m, 2H), 4.12-3.99 (m, 5H), 3.87 (d, J=13.1 Hz, 1H), 3.70-3.62 (m, 2H), 3.59 (s, 3H), 3.30 (s, 1H), 2.89-2.60 (m, 5H), 2.18-2.10 (m, 2H), 2.03-1.95 (m, 2H), 1.24-1.17 (m, 2H), 1.05 (s, 3H), 1.01 (s, 3H), 0.78 (s, 9H).

3H), 3.31-3.24 (m, 2H), 2.84-2.64 (m, 3H), 2.18-2.07 (m, 2H), 2.03-1.94 (m, 2H), 1.04 (s, 3H), 1.03-0.97 (m, 6H), 0.77 (s, 9H).

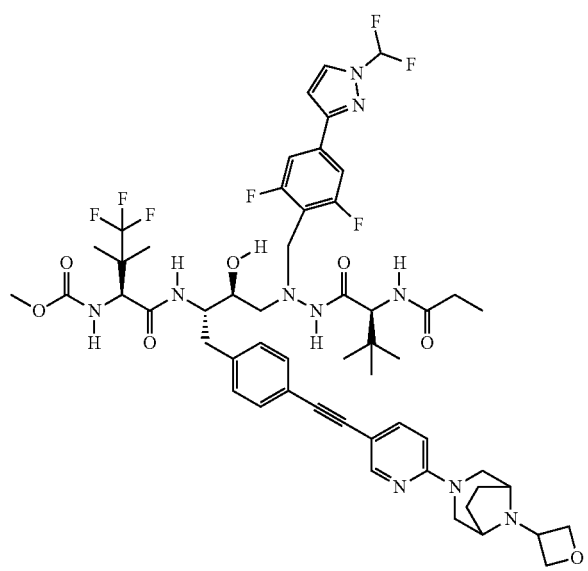 [SMILES: CCC(=O)N[C@H](C(=O)NN(Cc1c(F)cc(-c2ccn(C(F)F)n2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]

EXAMPLE 185

Methyl ((2S)-1-(((2S,3S)-4-(1-(4-(1-(difluoromethyl)-1H-pyrazol-3-yl)-2,6-difluorobenzyl)-2-((S)-3,3-dimethyl-2-propionamidobutanoyl)hydrazinyl)-3-hydroxy-1-(4-((6-(8-(oxetan-3-yl)-3,8-diazabicyclo[3.2.1]octan-3-yl)pyridin-3-yl)ethynyl)phenyl)butan-2-yl)amino)-4,4,4-trifluoro-3,3-dimethyl-1-oxobutan-2-yl)carbamate Intermediates: P4, A3, S3 and propionyl chloride MS (ESI) m/z 1099.6 M+H]+. 1H NMR (400 MHz, Methanol-d4) δ 8.22-8.18 (m, 1H), 8.08 (d, J=9.2 Hz, 1H), 8.01 (d, J=2.7 Hz, 1H), 7.61 (dd, J=8.9, 2.3 Hz, 1H), 7.56 (d, J=9.2 Hz, 1H), 7.43 (d, J=59.9 Hz, 1H), 7.36 (d, J=8.2 Hz, 2H), 7.23 (d, J=8.0 Hz, 2H), 7.12 (d, J=8.1 Hz, 2H), 6.84 (d, J=2.8 Hz, 1H), 6.77 (d, J=8.9 Hz, 1H), 6.69 (d, J=9.9 Hz, 1H), 4.87 (dd, J=8.1, 6.9 Hz, 2H), 4.73-4.69 (m, 2H), 4.36-4.31 (m, 1H), 4.30-4.19 (m, 3H), 4.09-4.02 (m, 4H), 4.01-3.96 (m, 1H), 3.86 (d, J=13.2 Hz, 1H), 3.68-3.62 (m, 1H), 3.59 (s,

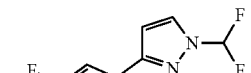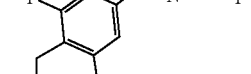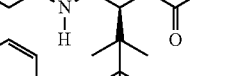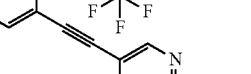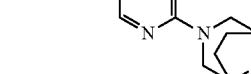

EXAMPLE 186

Methyl ((2S)-1-(((2S,3S)-4-(2-((S)-2-(cyclopropanecarboxamido)-4,4,4-trifluoro-3,3-dimethylbutanoyl)-1-(4-(1-(difluoromethyl)-1H-pyrazol-3-yl)-2,6-difluorobenzyl) hydrazinyl)-3-hydroxy-1-(4-((2-(8-(oxetan-3-yl)-3,8-diazabicyclo[3.2.1]octan-3-yl)pyrimidin-5-yl)ethynyl)phenyl)butan-2-yl)amino)-4,4,4-trifluoro-3,3-dimethyl-1-oxobutan-2-yl) carbamate (186)

Intermediates: P4, A3, S7 and cyclopropanecarboxylic acid. MS (ESI) m/z 1167.0 M+H]+. 1H NMR (400 MHz, Methanol-d4) δ 8.52 (s, 2H), 8.22 (d, J=9.6 Hz, 1H), 8.14 (d, J=9.4 Hz, 1H), 8.09 (d, J=2.7 Hz, 1H), 7.52 (t, J=59.9 Hz, 1H), 7.45 (d, J=8.2 Hz, 2H), 7.34 (d, J=7.9 Hz, 2H), 7.23 (d, J=8.0 Hz, 2H), 6.92 (d, J=2.8 Hz, 1H), 6.75 (d, J=9.9 Hz, 1H), 4.96 (t, J=7.6 Hz, 2H), 4.82-4.77 (m, 2H), 4.75 (s, 1H), 4.65 (d, J=9.7 Hz, 1H), 4.43 (d, J=9.9 Hz, 1H), 4.23-4.07 (m, 4H), 3.92 (d, J=13.0 Hz, 1H), 3.74 (d, J=8.6 Hz, 1H), 3.69 (s, 3H), 3.45 (d, J=14.5 Hz, 2H), 2.97-2.82 (m, 3H), 2.81-2.69 (m, 1H), 2.27-2.10 (m, 2H), 2.03-1.89 (m, 2H), 1.74-1.63 (m, 1H), 1.19 (s, 3H), 1.13 (s, 3H), 1.10 (s, 3H), 1.06 (s, 3H), 0.97-0.88 (m, 1H), 0.87-0.70 (m, 3H).

EXAMPLE 187

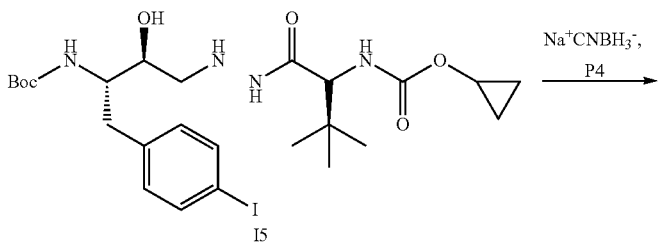

-continued
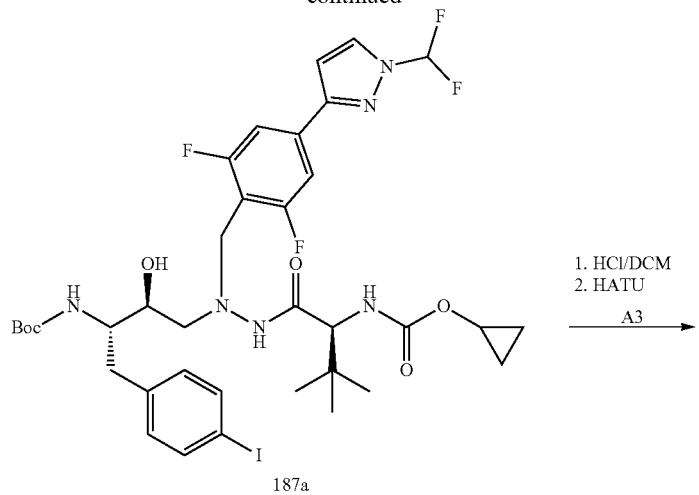
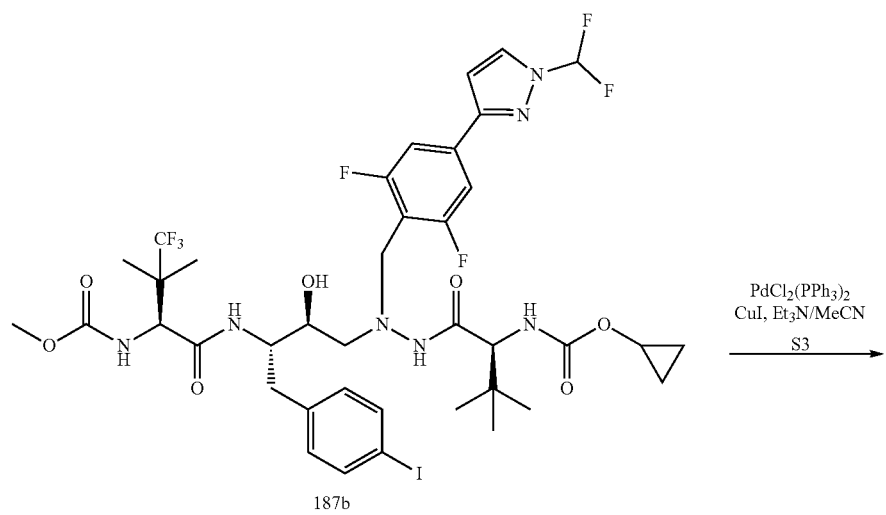

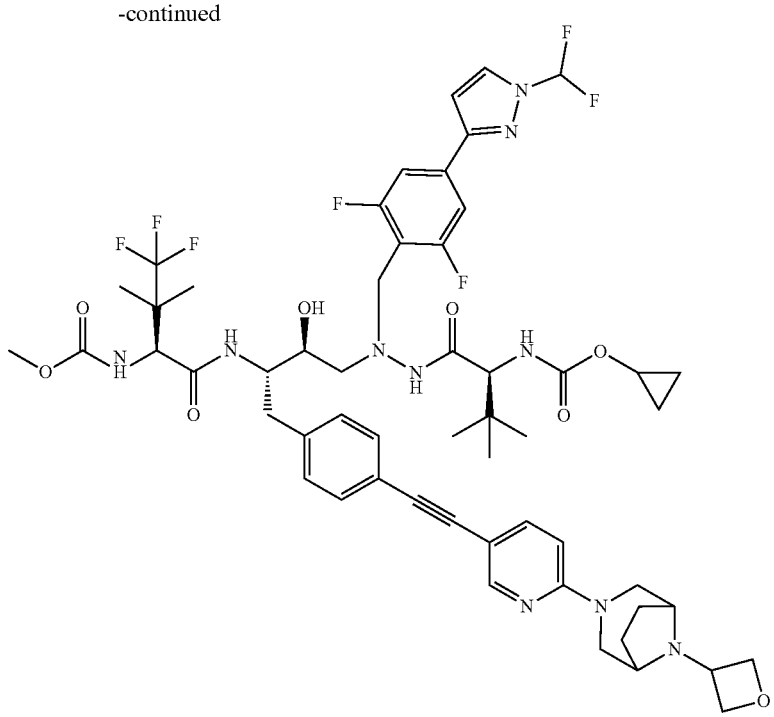

187

Synthesis of cyclopropyl ((S)-1-(2-((2S,3S)-3-((tert-butoxycarbonyl)amino)-2-hydroxy-4-(4-iodophenyl)butyl)-2-(4-(1-(difluoromethyl)-1H-pyrazol-3-yl)-2,6-difluorobenzyl)hydrazinyl)-3,3-dimethyl-1-oxobutan-2-yl)carbamate (187a)

The title compound 187a was prepared according to the method presented for the synthesis of compound 133a but instead utilizing I5 and P4. MS (ESI) m/z 861.1[M+H]+.

Synthesis of cyclopropyl ((5S,8S,9S,14S)-11-(4-(1-(difluoromethyl)-1H-pyrazol-3-yl)-2,6-difluorobenzyl)-9-hydroxy-8-(4-iodobenzyl)-15,15-dimethyl-3,6,13-trioxo-5-(1,1,1-trifluoro-2-methylpropan-2-yl)-2-oxa-4,7,11,12-tetraazahexadecan-14-yl)carbamate (187b)

The title compound 187b was prepared according to the method presented for the synthesis of compound 133b but instead utilizing 5a. MS (ESI) m/z 986.5 [M+H]+.

Synthesis of cyclopropyl ((5S,8S,9S,14S)-11-(4-(1-(difluoromethyl)-1H-pyrazol-3-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (187)

The title compound 187 was prepared according to the method presented for the synthesis of compound 133 but instead utilizing 187b and S3. MS (ESI) m/z 1127.4 [M+H]+. $^1$H NMR (400 MHz, Methanol-d4) δ 8.33-8.25 (m, 1H), 8.18 (d, J=9.3 Hz, 1H), 8.10 (d, J=2.7 Hz, 1H), 7.74-7.66 (m, 1H), 7.53 (d, J=59.7 Hz, 1H), 7.46 (d, J=8.3 Hz, 2H), 7.32 (d, J=8.0 Hz, 2H), 7.22 (d, J=8.1 Hz, 2H), 6.93 (d, J=2.7 Hz, 1H), 6.86 (d, J=8.9 Hz, 1H), 6.80 (d, J=9.9 Hz, 1H), 4.96 (t, J=7.5 Hz, 2H), 4.81 (dd, J=8.2, 5.2 Hz, 2H), 4.44 (d, J=10.0 Hz, 1H), 4.35 (d, J=13.6 Hz, 2H), 4.23-4.06 (m, 4H), 4.03-3.92 (m, 2H), 3.82-3.74 (m, 1H), 3.69 (s, 3H), 3.40-3.33 (m, 2H), 2.97-2.73 (m, 3H), 2.31-2.18 (m, 2H), 2.11-2.04 (m, 2H), 1.16-1.12 (m, 3H), 1.10 (s, 3H), 0.85 (s, 9H), 0.68-0.58 (m, 4H).

EXAMPLE 188
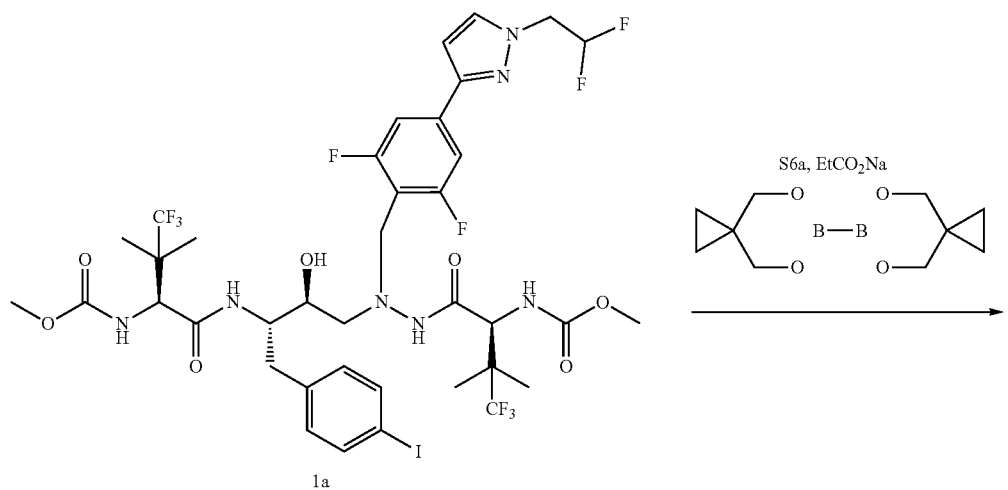

Synthesis of methyl ((5S,8S,9S,14S)-11-(4-(1-(2,2-difluoroethyl)-1H-pyrazol-3-yl)-2,6-difluorobenzyl)-16,16,16-trifluoro-9-hydroxy-15,15-dimethyl-8-(4-(6-((1R,4R)-5-(oxetan-3-yl)-2,5-diazabicyclo[2.2.1]heptan-2-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (188)

A suspension of S6a (59.8 mg, 0.167 mmol), bis(neopentylglycoloato)diboron (38 mg, 0.168 mmol), potassium propionate (44.5 mg, 0.397 mmol) and Pd(PPh₃)₂Cl₂ (2.8 mg, 0.004 mmol) in 2-MeTHF (1 mL) was degassed with argon for 15 min, then heated at 90° C. overnight. Cooled to room temperature, then added 1M Potassium Phosphate in H₂O (0.39 ml) and degassed for 5 min. Added Pd(tBu₂PPh)₂Cl₂ (4.5 mg, 0.007 mmol) and 1a (100 mg, 0.1 mmol) in 2-MeTHF (1 mL) and degassed an additional 5 min. Heated at 65° C. The reaction mixture was cooled to room temperature. Diluted with EtOAc and washed with brine. The separated organic layer was dried over Na₂SO₄ and concentrated under vacuum, the residue was purified by HPLC and the product was lyophilized to afford 188. MS (ESI) m/z 1131.2 [M+H]⁺. ¹H NMR (400 MHz, Methanol-d4) δ 8.19 (s, 1H), 8.10 (d, J=9.3 Hz, 1H), 7.92 (d, J=8.8 Hz, 1H), 7.64 (d, J=2.5 Hz, 1H), 7.28 (d, J=8.4 Hz, 2H), 7.22 (d, J=7.9 Hz, 2H), 7.05 (d, J=9.9 Hz, 1H), 6.82 (d, J=9.0 Hz, 1H), 6.76 (d, J=9.8 Hz, 1H), 6.65 (d, J=2.5 Hz, 1H), 6.32-5.96 (m, 1H), 4.96 (s, 1H), 4.61 (dd, J=8.2, 4.7 Hz, 1H), 4.58-4.49 (m, 3H), 4.45 (dd, J=14.2, 4.8 Hz, 1H), 4.37 (s, 1H), 4.21 (d, J=9.9 Hz, 1H), 4.04 (d, J=13.0 Hz, 2H), 3.84 (d, J=13.2 Hz, 1H), 3.74 (d, J=11.9 Hz, 1H), 3.67 (d, J=11.5 Hz, 2H), 3.54 (s, 4H), 3.47 (s, 3H), 2.92-2.73 (m, 4H), 2.73-2.62 (m, 1H), 2.24 (s, 2H), 1.05 (d, J=4.5 Hz, 7H), 1.01 (s, 3H), 0.92 (s, 3H).

EXAMPLE 189

Methyl ((5S,8S,9S,14S)-11-(4-(1-(difluoromethyl)-1H-imidazol-4-yl)-2,6-difluorobenzyl)-16,16,16-trifluoro-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (189)

Intermediates: I2, P1 and S7a. MS (ESI) m/z 1132.9 [M+H]⁺. ¹H NMR (400 MHz, Methanol-d4) δ 8.65 (s, 2H), 8.19 (d, J=7.9 Hz, 2H), 8.02 (s, 1H), 7.59 (t, J=60.2 Hz, 1H), 7.32 (d, J=7.8 Hz, 2H), 7.17 (d, J=10.0 Hz, 1H), 6.88 (d, J=9.9 Hz, 0H), 4.96 (t, J=7.6 Hz, 2H), 4.83 (dd, J=8.3, 5.3 Hz, 2H), 4.47 (d, J=7.2 Hz, 2H), 4.39-4.23 (m, 1H), 4.13 (d, J=13.3 Hz, 5H), 3.93 (d, J=13.3 Hz, 1H), 3.75 (s, 1H), 3.65 (s, 3H), 3.56 (s, 3H), 3.47 (d, J=14.5 Hz, 2H), 3.03-2.73 (m, 4H), 2.29-2.11 (m, 2H), 2.01 (d, J=9.1 Hz, 2H), 1.14 (d, J=5.2 Hz, 6H), 1.10 (s, 3H), 1.02 (s, 3H).

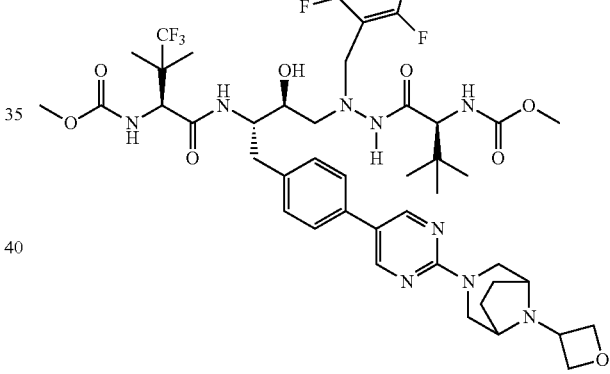

EXAMPLE 190 methyl ((5S,8S,9S,14S)-11-(4-(1-(difluoromethyl)-1H-imidazol-4-yl)-2,6-difluorobenzyl)-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (190)

Intermediates: I3, P1 and S7a. MS (ESI) m/z 1079.3 [M+H]⁺. ¹H NMR (400 MHz, Methanol-d4) δ 8.56 (s, 2H), 8.20-8.03 (m, 2H), 7.92 (d, J=1.3 Hz, 1H), 7.49 (t, J=59.9 Hz, 1H), 7.31 (dd, J=9.9, 8.2 Hz, 4H), 7.22 (d, J=7.8 Hz, 2H), 6.79 (d, J=10.0 Hz, 0H), 4.87 (t, J=7.6 Hz, 2H), 4.75-4.63 (m, 2H), 4.54-4.34 (m, 1H), 4.11-3.95 (m, 3H), 3.86 (d, J=13.2 Hz, 1H), 3.66 (s, 1H), 3.54 (s, 3H), 3.47 (s, 2H), 3.37 (d, J=14.4 Hz, 2H), 2.83 (t, J=8.0 Hz, 2H), 2.71 (d, J=8.8 Hz, 2H), 2.20-2.07 (m, 2H), 1.92 (d, J=8.9 Hz, 2H), 1.04 (s, 3H), 1.00 (s, 3H), 0.75 (s, 8H).

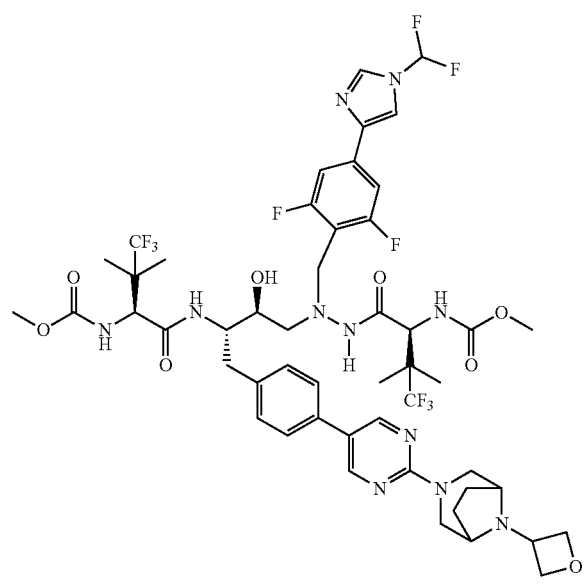 [SMILES: COC(=O)N[C@H](C(=O)N[C@@H](Cc1ccc(-c2cnc(N3CC4CCC(C3)N4C3COC3)nc2)cc1)[C@@H](O)CN(Cc1c(F)cc(-c2cn(C(F)F)cn2)cc1F)NC(=O)[C@@H](NC(=O)OC)C(C)(C)C(F)(F)F)C(C)(C)C(F)(F)F]

385

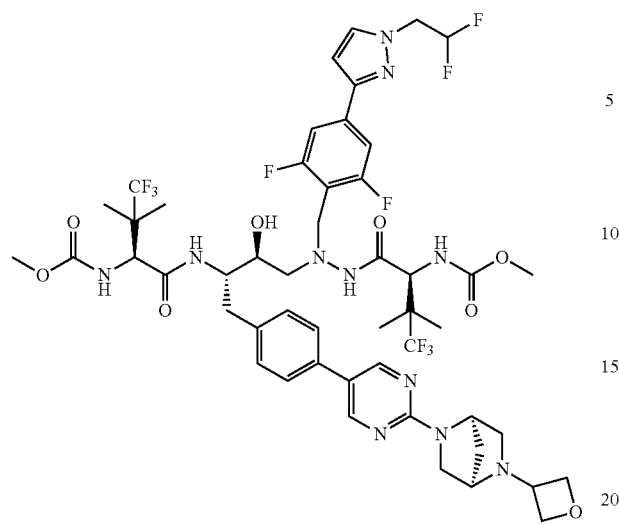

EXAMPLE 191

Methyl ((5S,8S,9S,14S)-11-(4-(1-(2,2-difluoro-ethyl)-1H-pyrazol-3-yl)-2,6-difluorobenzyl)-16,16,16-trifluoro-9-hydroxy-15,15-dimethyl-8-(4-(2-((1R,4R)-5-(oxetan-3-yl)-2,5-diazabicyclo[2.2.1]heptan-2-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate. (191)

Intermediates: I2, P10 and S6a. MS (ESI) m/z 1132.8 [M+H]$^+$. $^1$H NMR (400 MHz, Methanol-d4) δ 8.64 (s, 2H), 8.14 (d, J=9.4 Hz, 1H), 7.87 (d, J=8.6 Hz, 0H), 7.73 (d, J=2.4 Hz, 1H), 7.55 (dt, J=15.4, 7.4 Hz, 1H), 7.50-7.21 (m, 6H), 7.09 (d, J=9.9 Hz, 1H), 6.83 (d, J=9.8 Hz, 1H), 6.73 (d, J=2.4 Hz, 1H), 6.21 (tt, J=55.3, 3.9 Hz, 1H), 5.18 (s, 1H), 5.02-4.89 (m, 2H), 4.73 (d, J=5.1 Hz, 1H), 4.59 (td, J=14.1, 13.7, 6.4 Hz, 3H), 4.52 (s, 1H), 4.46 (d, J=9.7 Hz, 1H), 4.30 (d, J=9.9 Hz, 1H), 4.13 (d, J=13.1 Hz, 2H), 3.99-3.87 (m, 2H), 3.87-3.69 (m, 3H), 3.64 (s, 3H), 3.57 (s, 2H), 2.97-2.84 (m, 3H), 2.84-2.73 (m, 1H), 2.34 (s, 2H), 1.44 (d, J=16.1 Hz, 1H), 1.29 (s, 2H), 1.26 (s, 2H), 1.14 (d, J=4.9 Hz, 6H), 1.10 (s, 3H), 1.02 (s, 3H).

386

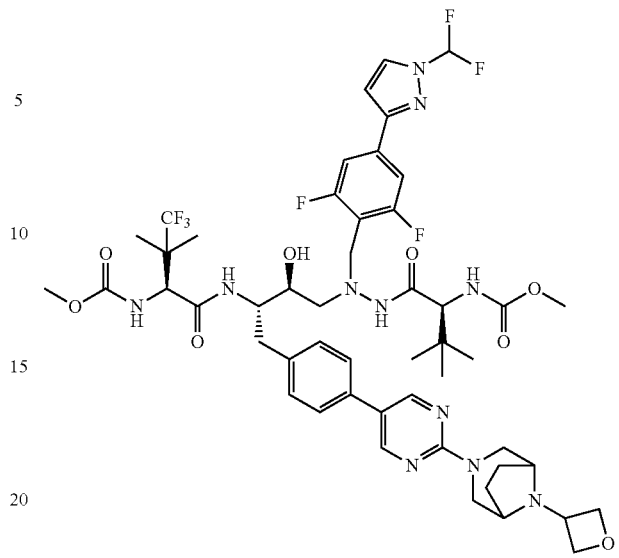

EXAMPLE 192 methyl ((5S,8S,9S,14S)-11-(4-(1-(difluoromethyl)-1H-pyrazol-3-yl)-2,6-difluorobenzyl)-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (192)

Intermediates: I3, P4 and S7a. MS (ESI) m/z 1078.1 [M+H]$^+$. $^1$H NMR (400 MHz, Methanol-d4) δ 8.65 (s, 3H), 8.14 (d, J=9.1 Hz, 1H), 8.09 (d, J=2.8 Hz, 2H), 7.52 (t, J=59.8 Hz, 2H), 7.43 (dd, J=12.4, 8.0 Hz, 6H), 7.31 (d, J=7.8 Hz, 3H), 6.92 (d, J=2.8 Hz, 2H), 6.83 (d, J=9.8 Hz, 1H), 4.96 (t, J=7.6 Hz, 3H), 4.46 (d, J=9.6 Hz, 2H), 4.13 (d, J=13.6 Hz, 7H), 3.97 (d, J=13.1 Hz, 2H), 3.75 (s, 2H), 3.62 (s, 5H), 3.56 (s, 4H), 3.46 (d, J=14.3 Hz, 4H), 2.92 (t, J=8.5 Hz, 2H), 2.81 (d, J=10.7 Hz, 3H), 2.21 (d, J=11.4 Hz, 3H), 2.01 (d, J=9.0 Hz, 3H), 1.27 (d, J=13.9 Hz, 1H), 1.13 (s, 6H), 1.10 (s, 5H), 0.84 (s, 14H).

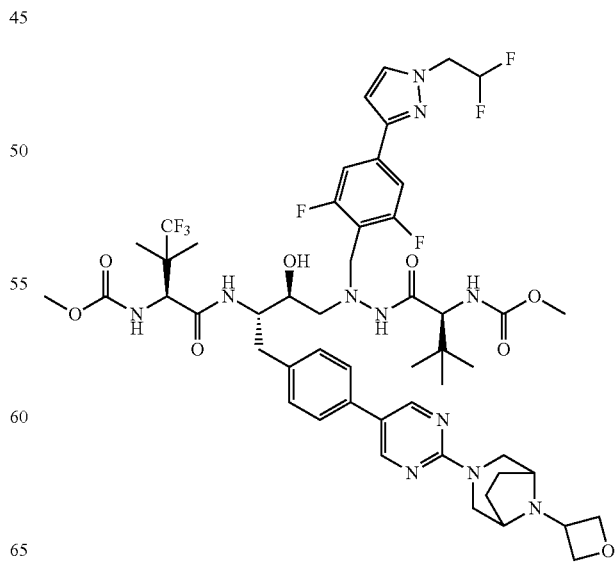

EXAMPLE 193

Methyl ((5S,8S,9S,14S)-11-(4-(1-(2,2-difluoro-ethyl)-1H-pyrazol-3-yl)-2,6-difluorobenzyl)-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (193)

Intermediates: I3, P10 and S7a. MS (ESI) m/z 1092.3 [M+H]⁺. ¹H NMR (400 MHz, Methanol-d4) δ 8.65 (s, 2H), 8.14 (d, J=9.2 Hz, 1H), 7.72 (d, J=2.4 Hz, 1H), 7.39 (dd, J=17.0, 8.2 Hz, 4H), 7.31 (d, J=7.8 Hz, 2H), 6.83 (d, J=9.8 Hz, 1H), 6.73 (d, J=2.4 Hz, 1H), 6.21 (tt, J=55.4, 3.9 Hz, 1H), 4.96 (t, J=7.6 Hz, 2H), 4.76 (s, 1H), 4.59 (td, J=14.3, 4.0 Hz, 2H), 4.49-4.41 (m, 1H), 4.12 (d, J=20.4 Hz, 4H), 3.96 (d, J=13.1 Hz, 1H), 3.76 (s, 2H), 3.62 (s, 3H), 3.56 (s, 3H), 3.47 (d, J=14.5 Hz, 2H), 2.92 (t, J=8.4 Hz, 2H), 2.80 (d, J=9.5 Hz, 2H), 2.26-2.10 (m, 2H), 2.01 (d, J=9.2 Hz, 2H), 1.13 (s, 3H), 1.09 (s, 3H), 0.85 (s, 9H).

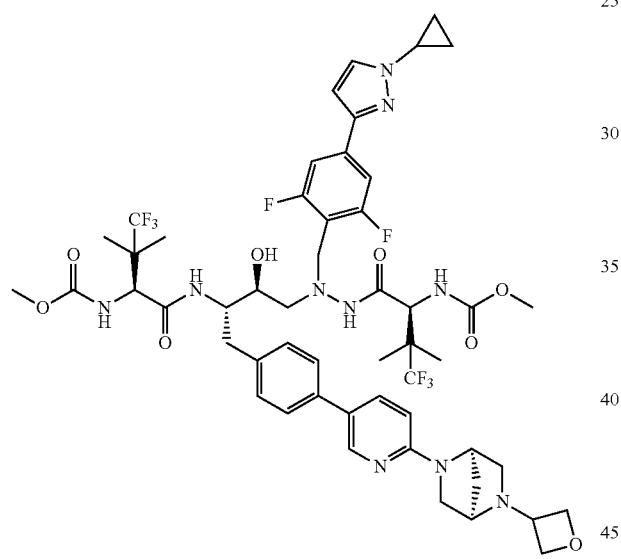

EXAMPLE 194

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-(6-((1R,4R)-5-(oxetan-3-yl)-2,5-diazabicyclo[2.2.1]heptan-2-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (194)

Intermediates: I2, P13 and S6a. MS (ESI) m/z 1092.3 [M+H]⁺. ¹H NMR (400 MHz, Methanol-d4) δ 8.20 (s, 1H), 8.10 (d, J=9.2 Hz, 1H), 7.87 (d, J=9.0 Hz, 1H), 7.60 (d, J=2.4 Hz, 1H), 7.32 (d, J=7.9 Hz, 2H), 7.23 (dd, J=14.4, 8.2 Hz, 4H), 6.76 (d, J=9.4 Hz, 2H), 6.54 (d, J=2.4 Hz, 1H), 4.93 (s, 1H), 4.61-4.53 (m, 1H), 4.52-4.46 (m, 1H), 4.45-4.27 (m, 2H), 4.21 (d, J=9.9 Hz, 1H), 4.03 (d, J=13.0 Hz, 2H), 3.83 (d, J=13.0 Hz, 1H), 3.72 (d, J=9.6 Hz, 1H), 3.66-3.56 (m, 1H), 3.55 (s, 3H), 3.46 (s, 3H), 2.82 (d, J=7.2 Hz, 0H), 2.70 (d, J=9.8 Hz, 1H), 2.22 (s, 2H), 1.05 (d, J=5.1 Hz, 8H), 0.98 (d, J=16.3 Hz, 3H), 0.92 (s, 2H).

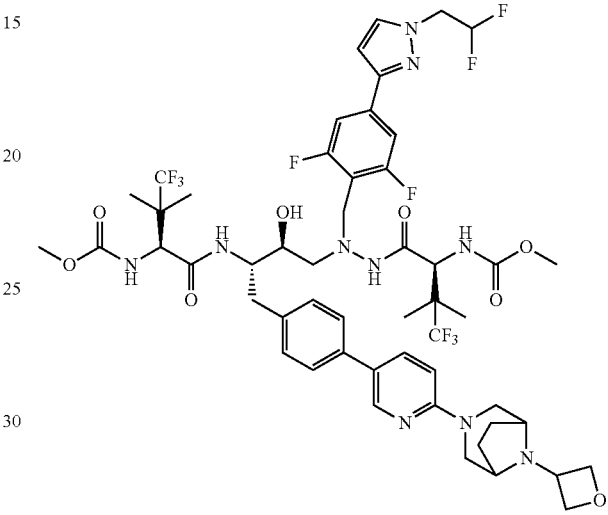

EXAMPLE 195 methyl ((5S,8S,9S,14S)-11-(4-(1-(2,2-difluoro-ethyl)-1H-pyrazol-3-yl)-2,6-difluorobenzyl)-16,16,16-trifluoro-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (195)

Intermediates: I2, P10 and S3c. MS (ESI) m/z 1146.1 [M+H]⁺. ¹H NMR (400 MHz, Methanol-d4) δ 8.29 (s, 1H), 8.07 (d, J=9.3 Hz, 1H), 7.83 (d, J=9.0 Hz, 1H), 7.64 (d, J=2.4 Hz, 1H), 7.33 (d, J=8.1 Hz, 2H), 7.28 (d, J=8.4 Hz, 1H), 7.20 (d, J=8.0 Hz, 2H), 7.02 (d, J=9.8 Hz, 1H), 6.89 (d, J=8.9 Hz, 1H), 6.74 (d, J=9.8 Hz, 1H), 6.64 (d, J=2.5 Hz, 1H), 6.12 (tt, J=55.3, 3.9 Hz, 1H), 4.86 (t, J=7.6 Hz, 2H), 4.74-4.66 (m, 2H), 4.51 (td, J=14.3, 3.9 Hz, 2H), 4.45-4.33 (m, 2H), 4.26-4.09 (m, 3H), 4.03 (d, J=8.7 Hz, 4H), 3.84 (d, J=13.2 Hz, 1H), 3.67 (s, 1H), 3.54 (s, 3H), 3.46 (s, 2H), 3.32 (s, 1H), 3.29 (d, J=1.7 Hz, 1H), 2.91-2.73 (m, 2H), 2.70 (d, J=9.4 Hz, 1H), 2.14 (t, J=6.4 Hz, 2H), 2.01 (d, J=8.5 Hz, 2H), 1.05 (d, J=3.7 Hz, 6H), 1.01 (s, 3H), 0.92 (s, 2H).

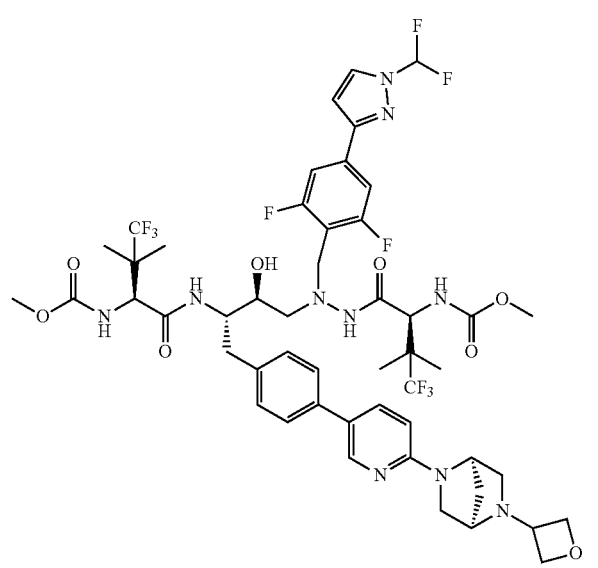 [SMILES: COC(=O)N[C@H](C(=O)N[C@@H](Cc1ccc(-c2ccc(N3C[C@H]4C[C@@H]3CN4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

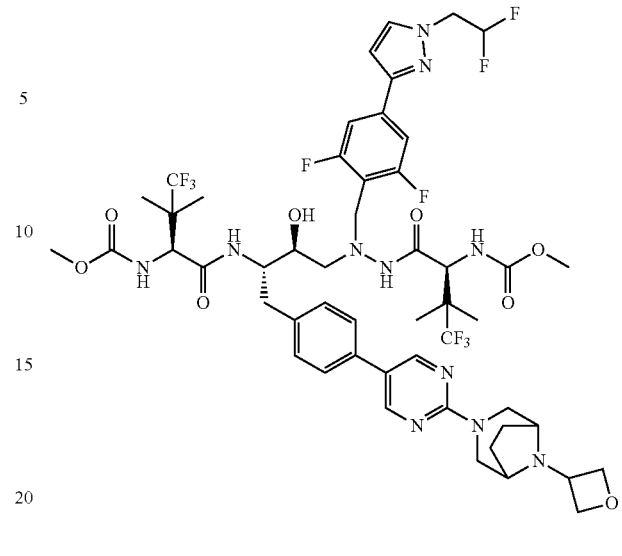

EXAMPLE 196

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(6-((1R,4R)-5-(oxetan-3-yl)-2,5-diazabicyclo[2.2.1]heptan-2-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (196)

Intermediates: I2, P4 and S6a. MS (ESI) m/z 1117.2 [M+H]+. 1H NMR (400 MHz, Methanol-d4) δ 8.20 (s, 1H), 8.07 (d, J=9.2 Hz, 1H), 8.01 (d, J=2.7 Hz, 1H), 7.88 (d, J=8.9 Hz, 1H), 7.44 (t, J=59.8 Hz, 1H), 7.34 (dd, J=11.9, 8.1 Hz, 3H), 7.21 (d, J=7.9 Hz, 2H), 7.02 (d, J=10.0 Hz, 1H), 6.84 (d, J=2.7 Hz, 1H), 6.75 (t, J=10.2 Hz, 1H), 5.01-4.89 (m, 1H), 4.59 (dd, J=8.3, 4.8 Hz, 1H), 4.51 (dd, J=8.0, 5.0 Hz, 1H), 4.37 (dd, J=19.9, 10.1 Hz, 3H), 4.20 (d, J=10.0 Hz, 1H), 4.06 (d, J=13.2 Hz, 2H), 3.85 (d, J=13.2 Hz, 1H), 3.81-3.61 (m, 2H), 3.56 (d, J=4.6 Hz, 3H), 3.53-3.43 (m, 2H), 2.82 (d, J=9.0 Hz, 2H), 2.75-2.61 (m, 1H), 2.22 (s, 2H), 1.05 (s, 6H), 1.01 (s, 3H), 0.92 (s, 3H).

EXAMPLE 197

Methyl ((5S,8S,9S,14S)-11-(4-(1-(2,2-difluoroethyl)-1H-pyrazol-3-yl)-2,6-difluorobenzyl)-16,16,16-trifluoro-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (197)

Intermediates: I2, P10 and S7a. MS (ESI) m/z 1146.4 [M+H] 1H NMR (400 MHz, Methanol-d4) δ 8.65 (s, 2H), 8.15 (d, J=9.4 Hz, 1H), 7.73 (d, J=2.4 Hz, 1H), 7.41 (d, J=8.0 Hz, 2H), 7.37 (d, J=8.4 Hz, 2H), 7.31 (d, J=7.9 Hz, 2H), 7.10 (d, J=9.9 Hz, 1H), 6.84 (d, J=9.7 Hz, 1H), 6.73 (d, J=2.4 Hz, 1H), 6.21 (tt, J=55.3, 4.0 Hz, 1H), 4.96 (t, J=7.6 Hz, 2H), 4.84-4.73 (m, 4H), 4.60 (td, J=14.3, 3.9 Hz, 2H), 4.49-4.42 (m, 1H), 4.33-4.26 (m, 1H), 4.21-4.08 (m, 4H), 3.94 (d, J=13.2 Hz, 1H), 3.81-3.71 (m, 1H), 3.63 (s, 3H), 3.56 (s, 3H), 3.47 (d, J=14.4 Hz, 2H), 2.99-2.74 (m, 4H), 2.28-2.12 (m, 2H), 2.05-1.91 (m, 2H), 1.15 (s, 3H), 1.14 (s, 3H), 1.10 (s, 3H), 1.02 (s, 3H). 19F NMR (376 MHz, Methanol-d4) δ −77.37, −77.69, −77.80, −115.42, −125.27 (dt, J=55.2, 14.3 Hz).

391

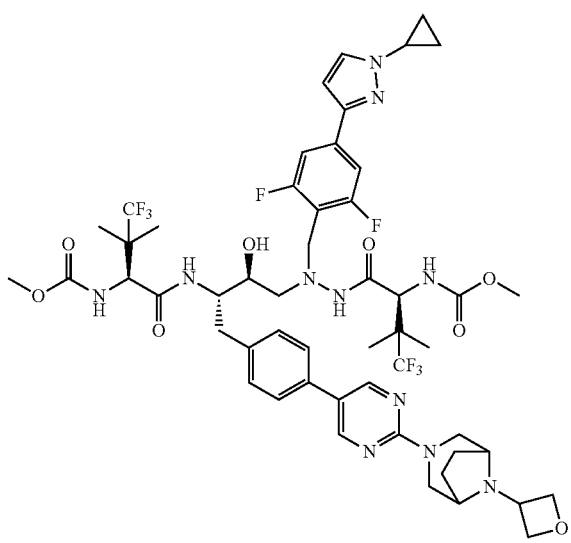 [SMILES: COC(=O)N[C@H](C(=O)N[C@@H](Cc1ccc(-c2cnc(N3CC4CCC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

392

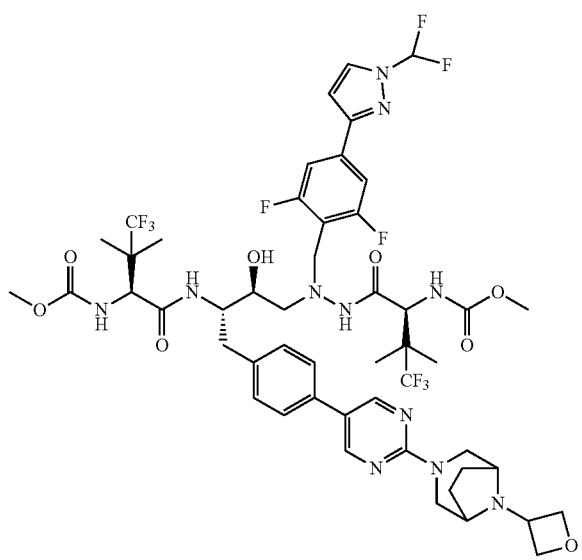 [SMILES: COC(=O)N[C@H](C(=O)N[C@@H](Cc1ccc(-c2cnc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 198 methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (198)

Intermediates: I2, P13 and S7a. MS (ESI) m/z 1122.5 [M+H]$^+$. $^1$H NMR (400 MHz, Methanol-d4) δ 8.56 (s, 2H), 8.07 (d, J=9.3 Hz, 1H), 7.60 (d, J=2.4 Hz, 1H), 7.32 (d, J=7.9 Hz, 2H), 7.28-7.16 (m, 4H), 7.03 (d, J=10.0 Hz, 1H), 6.75 (d, J=9.8 Hz, 1H), 6.54 (d, J=2.4 Hz, 1H), 4.87 (t, J=7.6 Hz, 2H), 4.76-4.70 (m, 2H), 4.67 (s, 1H), 4.37 (d, J=9.9 Hz, 1H), 4.21 (d, J=10.0 Hz, 1H), 4.12-3.99 (m, 4H), 3.84 (d, J=13.2 Hz, 1H), 3.66 (s, 1H), 3.60 (tt, J=7.3, 3.9 Hz, 1H), 3.55 (s, 3H), 3.47 (s, 3H), 3.38 (d, J=14.3 Hz, 2H), 2.89-2.62 (m, 4H), 2.18-2.06 (m, 2H), 1.96-1.85 (m, 2H), 1.12-0.93 (m, 13H), 0.93 (s, 3H).

EXAMPLE 199

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (199)

Intermediates: I2, P4 and S7a. MS (ESI) m/z 1132.9 [M+H]$^+$. 1H NMR (400 MHz, Methanol-d4) δ 8.56 (s, 2H), 8.08 (d, J=9.4 Hz, 1H), 8.01 (d, J=2.7 Hz, 1H), 7.44 (t, J=59.9, 59.5 Hz, 1H), 7.35 (d, J=8.4 Hz, 2H), 7.33 (d, J=8.1 Hz, 2H), 7.23 (d, J=8.0 Hz, 2H), 7.04 (d, J=9.9 Hz, 1H), 6.84 (d, J=2.7 Hz, 1H), 6.77 (d, J=9.9 Hz, 1H), 4.87 (t, J=7.6 Hz, 2H), 4.72 (dd, J=8.3, 5.0 Hz, 2H), 4.69 (s, 2H), 4.37 (d, J=9.8 Hz, 1H), 4.20 (d, J=10.0 Hz, 1H), 4.12-3.96 (m, 4H), 3.85 (d, J=13.1 Hz, 1H), 3.67 (s, 1H), 3.55 (s, 3H), 3.47 (s, 3H), 3.37 (d, J=14.3 Hz, 2H), 2.87-2.75 (m, 3H), 2.75-2.66 (m, 1H), 1.92 (d, J=9.2 Hz, 2H), 1.05 (s, 6H), 1.01 (s, 3H), 0.93 (s, 3H).

393

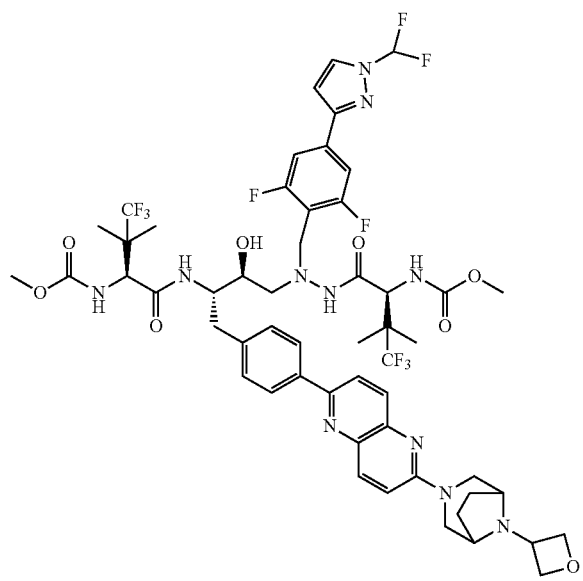 [SMILES: COC(=O)N[C@H](C(=O)N[C@@H](Cc1ccc(-c2ccc3nc(N4CC5CCC(C4)N5C4COC4)ccc3n2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 200

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(6-(8-(oxetan-3-yl)-3,8-diazabicyclo[3.2.1]octan-3-yl)-1,5-naphthyridin-2-yl)benzyl)-3,6,13-trioxo-5-(1,1,1-trifluoro-2-methylpropan-2-yl)-2-oxa-4,7,11,12-tetraazahexadecan-14-yl)carbamate (200)

Intermediates: I2, P4 and S31b. MS (ESI) m/z 1182.3 [M+H]$^+$. $^1$H NMR (400 MHz, Methanol-d4) δ 8.22-8.04 (m, 3H), 8.01 (d, J=2.7 Hz, 2H), 7.85 (d, J=7.9 Hz, 2H), 7.44 (t, J=59.7 Hz, 1H), 7.41 (d, J=9.5 Hz, 1H), 7.36 (d, J=8.2 Hz, 2H), 7.30 (d, J=8.5 Hz, 2H), 6.84 (d, J=2.8 Hz, 1H), 4.89 (t, J=7.6 Hz, 2H), 4.74 (dd, J=8.2, 5.1 Hz, 2H), 4.53 (d, J=14.1 Hz, 2H), 4.37 (s, 1H), 4.21 (s, 1H), 4.16-4.01 (m, 4H), 3.86 (d, J=13.1 Hz, 1H), 3.71 (s, 1H), 3.54 (s, 3H), 3.44 (d, J=13.8 Hz, 2H), 3.41-3.33 (m, 3H), 2.95-2.63 (m, 5H), 2.22-2.10 (m, 2H), 2.11-1.96 (m, 2H), 1.25-1.16 (m, 1H), 1.05 (s, 6H), 1.02 (s, 3H), 0.93 (s, 3H).

394

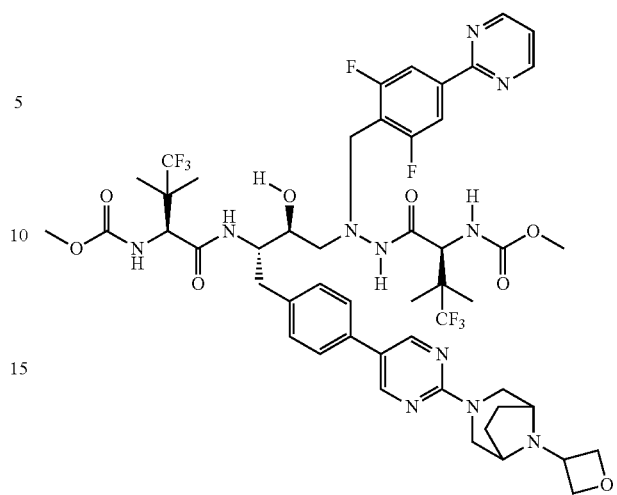

EXAMPLE 201

Methyl ((5S,8S,9S,14S)-11-(2,6-difluoro-4-(pyrimidin-2-yl)benzyl)-16,16,16-trifluoro-9-hydroxy-15,15-dimethyl-8-(4-(2-(8-(oxetan-3-yl)-3,8-diazabicyclo[3.2.1]octan-3-yl)pyrimidin-5-yl)benzyl)-3,6,13-trioxo-5-(1,1,1-trifluoro-2-methylpropan-2-yl)-2-oxa-4,7,11,12-tetraazahexadecan-14-yl)carbamate (201)

Intermediates: I2, P16 and S7a. MS (ESI) m/z 1094.8 [M+H]$^+$. $^1$H NMR (400 MHz, Methanol-d4) δ 8.86 (d, J=4.9 Hz, 1H), 8.65 (s, 1H), 8.14 (d, J=9.4 Hz, 0H), 7.96 (d, J=8.6 Hz, 1H), 7.48-7.37 (m, 2H), 7.32 (d, J=7.9 Hz, 1H), 7.08 (d, J=10.0 Hz, 0H), 6.83 (d, J=9.9 Hz, 0H), 4.96 (t, J=7.6 Hz, 1H), 4.83 (s, 8H), 4.53-4.41 (m, 0H), 4.37-4.25 (m, 1H), 4.23-4.07 (m, 2H), 3.98 (d, J=13.1 Hz, 1H), 3.78 (s, 0H), 3.65 (s, 2H), 3.56 (s, 1H), 3.52-3.39 (m, 1H), 3.00-2.75 (m, 2H), 2.26-2.14 (m, 1H), 2.02 (t, J=7.0 Hz, 1H), 1.12 (d, J=13.2 Hz, 5H), 1.02 (s, 1H).

EXAMPLE 202
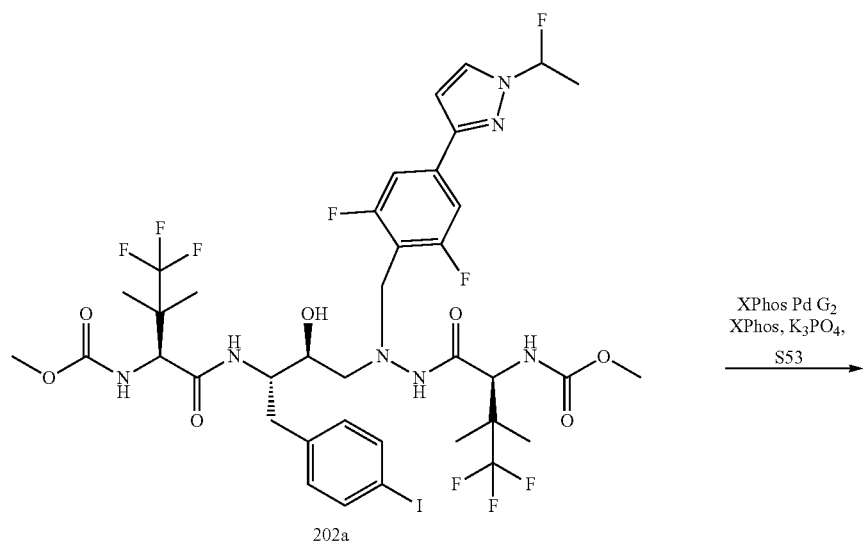
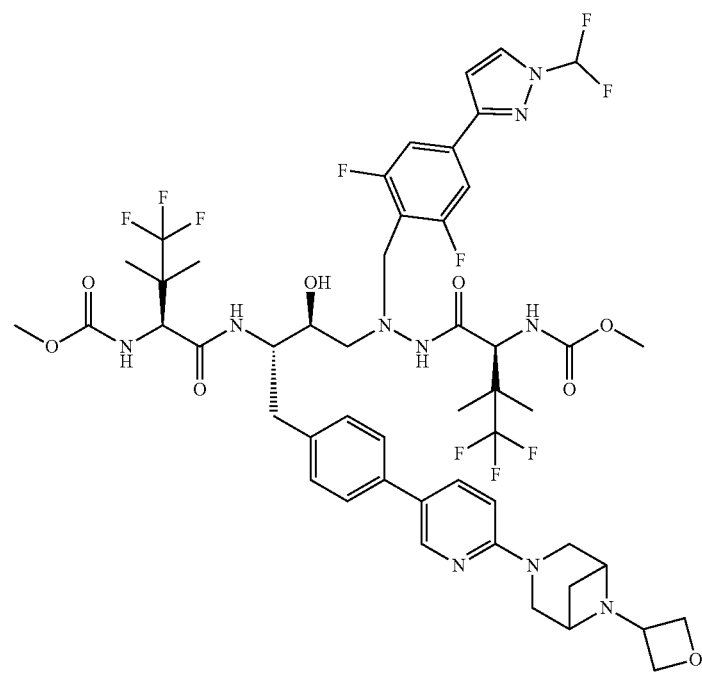

Methyl ((5S,8S,9S,14S)-11-(4-(1-(difluoromethyl)-1H-pyrazol-3-yl)-2,6-difluorobenzyl)-16,16,16-trifluoro-9-hydroxy-8-(4-iodobenzyl)-15,15-dimethyl-3,6,13-trioxo-5-(1,1,1-trifluoro-2-methylpropan-2-yl)-2-oxa-4,7,11,12-tetraazahexadecan-14-yl)carbamate (202a)

The title compound 202a was prepared according to the method presented for the synthesis of compound 1a but instead utilizing P4. MS (ESI) m/z 1014.4 [M+H]+.

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(6-(6-(oxetan-3-yl)-3,6-diazabicyclo[3.1.1]heptan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (202)

In a 20 mL vial, a solution of 202a (50 mg, 0.05 mmol), S53 (38.1 mg, 0.08 mmol), XPhos Pd G2 (16.4 mg, 0.01 mmol), 2-(Dicyclohexylphosphino)-2',4',6'-triisopropylbiphenyl (5.6 mg, 0.01 mmol) and Potassium phosphate tribasic (106 mg, 0.5 mmol) in dioxane (3 mL) and water (1 mL) was degassed for 10 min with argon. The mixture was heated to 100° C. for 1 h. The reaction was cooled to room temperature, diluted with MeOH, filtered through Celite, and the filtrate was concentrated under vacuum. The residue was purified by HPLC and the product was lyophilized to afford 202 MS (ESI) m/z 1117.5 [M+H]+. $^1$H NMR (400 MHz, Methanol-d4) δ 8.31 (s, 1H), 8.11 (d, J=9.3 Hz, 1H), 8.02 (d, J=2.7 Hz, 1H), 7.90 (d, J=8.8 Hz, 1H), 7.44 (t, J=59.8 Hz, 1H), 7.35 (dd, J=8.1, 3.9 Hz, 4H), 7.22 (d, J=7.9 Hz, 2H), 7.05 (d, J=10.0 Hz, 1H), 6.90-6.80 (m, 2H), 6.78 (d, J=9.8 Hz, 0H), 4.88 (t, J=7.3 Hz, 2H), 4.52 (dd, J=8.1, 4.3 Hz, 4H), 4.38 (d, J=9.5 Hz, 1H), 4.21 (d, J=9.9 Hz, 1H), 4.06 (d, J=12.5 Hz, 4H), 3.87 (t, J=14.4 Hz, 3H), 3.68 (s, 1H), 3.55 (s, 3H), 3.46 (s, 2H), 2.94-2.76 (m, 3H), 2.76-2.64 (m, 1H), 2.03 (d, J=11.1 Hz, 1H), 1.05 (s, 6H), 1.01 (s, 3H), 0.91 (s, 3H).

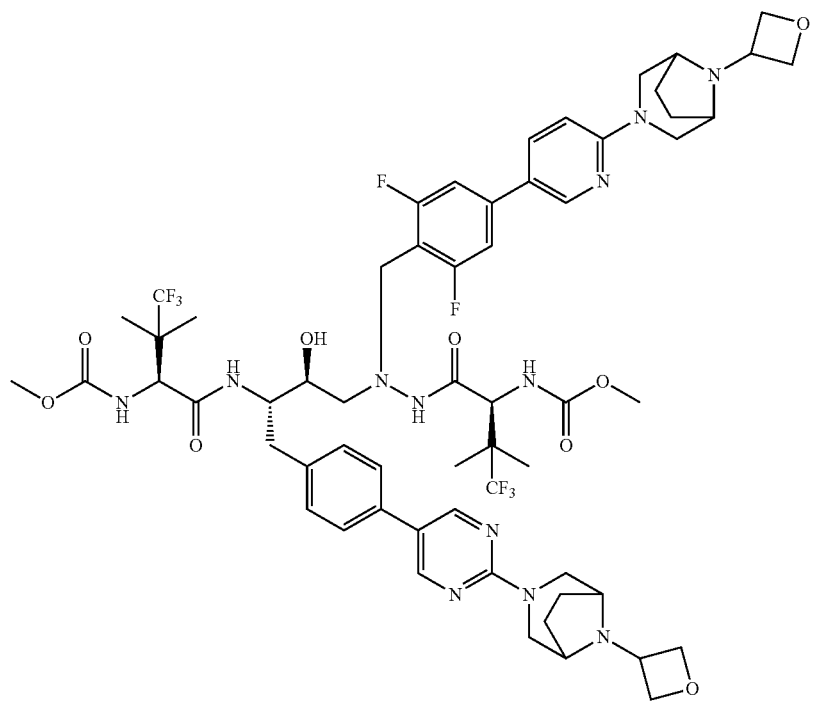 [SMILES: COC(=O)N[C@H](C(=O)N[C@@H](Cc1ccc(-c2cnc(N3CC4CCC(C3)N4C3COC3)nc2)cc1)[C@@H](O)CN(Cc1c(F)cc(-c2ccc(N3CC4CCC(C3)N4C3COC3)nc2)cc1F)NC(=O)[C@@H](NC(=O)OC)C(C)(C)C(F)(F)F)C(C)(C)C(F)(F)F]

EXAMPLE 203

Methyl ((5S,8S,9S,14S)-11-(2,6-difluoro-4-(6-(8-(oxetan-3-yl)-3,8-diazabicyclo[3.2.1]octan-3-yl)pyridin-3-yl)benzyl)-16,16,16-trifluoro-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl) carbamate (203)

Intermediates: I2, P22 and S60. MS (ESI) m/z 1259.4 [M+H]+. 1H NMR (400 MHz, Methanol-d4) δ 8.47 (s, 1H), 8.37 (s, 1H), 8.18 (s, 1H), 7.94 (s, 2H), 7.42 (d, J=7.9 Hz, 2H), 7.30 (d, J=7.9 Hz, 2H), 7.19 (d, J=8.4 Hz, 2H), 6.99 (dd, J=19.7, 9.0 Hz, 2H), 4.95 (dd, J=7.5, 2.8 Hz, 4H), 4.85-4.72 (m, 5H), 4.61-4.24 (m, 7H), 4.16 (s, 6H), 3.73-3.44 (m, 6H), 3.44-3.34 (m, 3H), 2.99-2.73 (m, 2H), 2.35-2.21 (m, 3H), 1.29 (s, 18H), 1.19-0.96 (m, 10H).

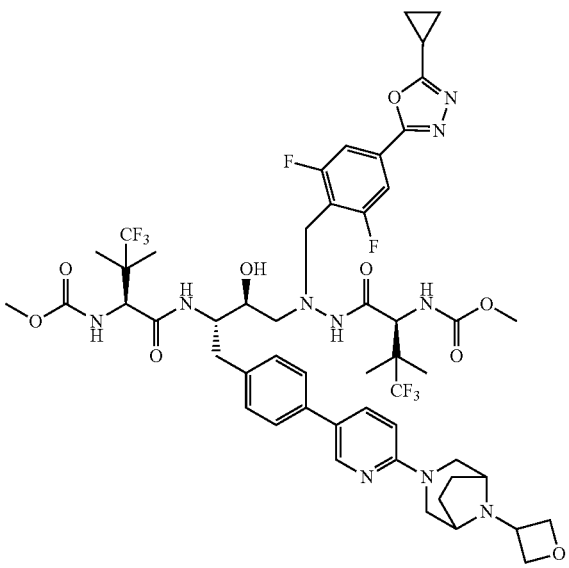

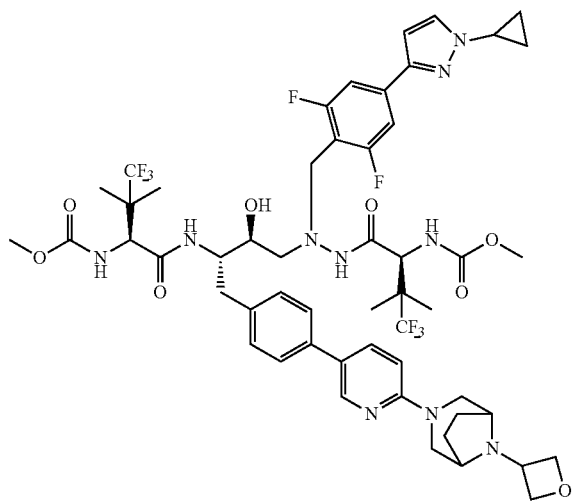 [SMILES: COC(=O)N[C@H](C(=O)N[C@@H](Cc1ccc(-c2ccc(N3CC4CCC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]

EXAMPLE 204

Methyl ((5S,8S,9S,14S)-11-(4-(1-cyclopropyl-1H-pyrazol-3-yl)-2,6-difluorobenzyl)-16,16,16-trifluoro-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (204)

Intermediates: I2, P13 and S60. MS (ESI) m/z 1121.2 [M+H]+. 1H NMR (400 MHz, Methanol-d4) δ 8.37 (s, 1H), 8.19 (s, 0H), 7.69 (d, J=2.5 Hz, 1H), 7.53-7.22 (m, 7H), 6.98 (d, J=8.8 Hz, 1H), 6.63 (d, J=2.5 Hz, 1H), 4.54 (d, J=59.0 Hz, 0H), 4.38-4.24 (m, 4H), 4.24-3.93 (m, 6H), 3.64 (d, J=6.0 Hz, 5H), 3.56-3.39 (m, 6H), 2.09 (d, J=8.5 Hz, 2H), 1.42-0.62 (m, 16H).

EXAMPLE 205

Methyl ((5S,8S,9S,14S)-11-(4-(5-cyclopropyl-1,3,4-oxadiazol-2-yl)-2,6-difluorobenzyl)-16,16,16-trifluoro-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (205)

Intermediates: I3, P40 and S60. MS (ESI) m/z 1123.3 [M+H]+. 1H NMR (400 MHz, Methanol-d4) δ 8.39-8.33 (m, 1H), 8.10 (dd, J=19.9, 9.2 Hz, 2H), 7.53 (d, J=7.3 Hz, 3H), 7.45 (d, J=7.9 Hz, 3H), 7.32 (d, J=7.9 Hz, 3H), 7.13 (dd, J=21.7, 9.5 Hz, 2H), 4.99-4.83 (m, 4H), 4.61-4.50 (m, 2H), 4.50-4.43 (m, 1H), 4.35-4.24 (m, 5H), 4.18 (d, J=11.8 Hz, 5H), 3.78 (s, 1H), 3.67 (s, 4H), 3.59 (d, J=13.0 Hz, 7H), 3.01-2.76 (m, 5H), 2.35-2.23 (m, 4H), 2.14 (t, J=6.9 Hz, 3H), 1.32-1.10 (m, 19H), 1.10-0.95 (m, 5H).

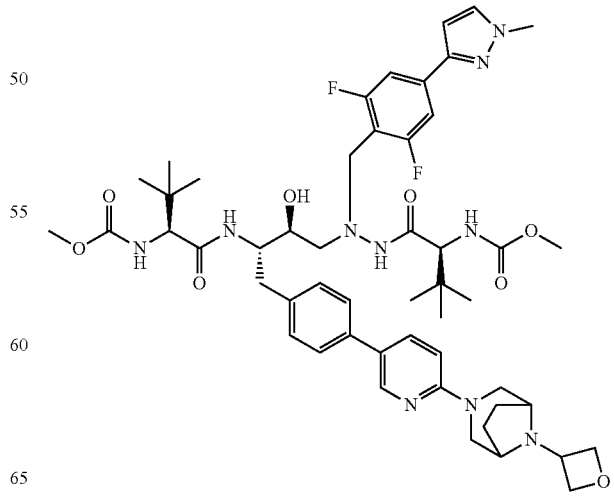

EXAMPLE 206

Methyl ((5S,8S,9S,14S)-5-(tert-butyl)-11-(2,6-difluoro-4-(1-methyl-1H-pyrazol-3-yl)benzyl)-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-2-oxa-4,7,11,12-tetraazahexadecan-14-yl)carbamate (206)

Intermediates: I1, P41 and S60. MS (ESI) m/z 987.6 [M+H]+. 1H NMR (400 MHz, Methanol-d4) δ 8.36 (d, J=2.4 Hz, 1H), 7.61 (d, J=2.3 Hz, 1H), 7.44 (d, J=7.9 Hz, 2H), 7.36-7.28 (m, 4H), 7.07 (d, J=9.0 Hz, 1H), 6.64 (d, J=2.3 Hz, 1H), 4.95 (t, J=7.5 Hz, 2H), 4.83 (dd, J=8.0, 5.1 Hz, 2H), 4.53 (dq, J=12.1, 6.2, 5.7 Hz, 1H), 4.28 (dd, J=14.1, 2.4 Hz, 2H), 4.19-4.06 (m, 4H), 4.00-3.89 (m, 5H), 3.75 (s, 2H), 3.60 (d, J=16.6 Hz, 6H), 3.49 (d, J=13.6 Hz, 2H), 2.95 (td, J=12.3, 11.7, 7.2 Hz, 2H), 2.87-2.79 (m, 2H), 2.29-2.21 (m, 2H), 2.20-2.08 (m, 2H), 0.88 (s, 9H), 0.82 (s, 9H).

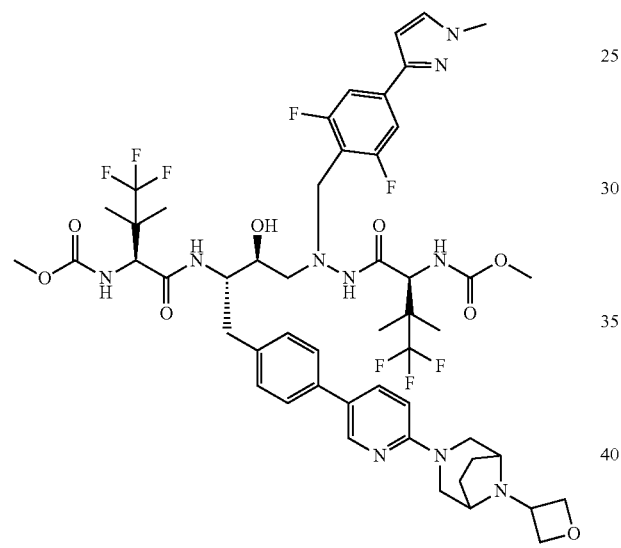

EXAMPLE 207

Methyl ((5S,8S,9S,14S)-11-(2,6-difluoro-4-(1-methyl-1H-pyrazol-3-yl)benzyl)-16,16,16-trifluoro-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (207)

Intermediates: I2, P41 and S60. MS (ESI) m/z 1095.3 [M+H]+. 1H NMR (400 MHz, Methanol-d4) δ 8.36 (d, J=2.3 Hz, 1H), 8.15 (d, J=9.3 Hz, 1H), 7.62 (d, J=2.3 Hz, 1H), 7.45 (d, J=8.0 Hz, 2H), 7.33 (dd, J=8.2, 5.3 Hz, 4H), 7.12 (dd, J=19.4, 9.5 Hz, 1H), 6.65 (d, J=2.3 Hz, 1H), 4.95 (t, J=7.5 Hz, 2H), 4.85 (dd, J=8.1, 5.1 Hz, 2H), 4.58-4.44 (m, 2H), 4.35-4.23 (m, 3H), 4.22-4.09 (m, 4H), 3.93 (s, 4H), 3.65 (s, 3H), 3.60-3.52 (m, 4H), 3.01-2.89 (m, 2H), 2.88-2.74 (m, 2H), 2.30-2.23 (m, 2H), 2.14 (t, J=6.9 Hz, 2H), 1.18-1.08 (m, 8H), 1.02 (s, 3H).

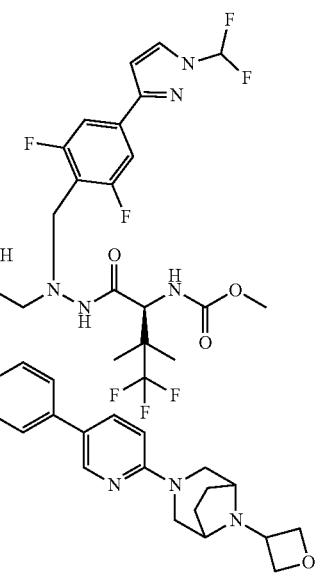

EXAMPLE 208

Methyl ((5S,8S,9S,14S)-11-(4-(1-(difluoromethyl)-1H-pyrazol-3-yl)-2,6-difluorobenzyl)-16,16,16-trifluoro-9-hydroxy-15,15-dimethyl-8-(4-(6-(8-(oxetan-3-yl)-3,8-diazabicyclo[3.2.1]octan-3-yl)pyridin-3-yl)benzyl)-3,6,13-trioxo-5-(1,1,1-trifluoro-2-methylpropan-2-yl)-2-oxa-4,7,11,12-tetraazahexadecan-14-yl)carbamate (208)

Intermediates: I2, P4 and S60. MS (ESI) m/z 1131.4 [M+H]+. 1H NMR (400 MHz, Methanol-d4) δ 8.36 (d, J=2.3 Hz, 1H), 8.16-8.02 (m, 2H), 7.44 (h, J=4.1, 3.5 Hz, 3H), 7.40-7.29 (m, 2H), 7.14 (d, J=9.1 Hz, 1H), 6.93 (d, J=2.7 Hz, 1H), 4.95 (t, J=7.5 Hz, 2H), 4.58-4.43 (m, 2H), 4.34-4.23 (m, 3H), 4.21-4.11 (m, 3H), 4.00-3.91 (m, 1H), 3.77 (s, 1H), 3.67-3.52 (m, 6H), 3.01-2.86 (m, 3H), 2.80 (dd, J=12.6, 9.1 Hz, 1H), 2.31-2.23 (m, 2H), 2.22-2.08 (m, 2H), 1.13 (d, J=14.1 Hz, 7H), 1.03 (s, 2H).

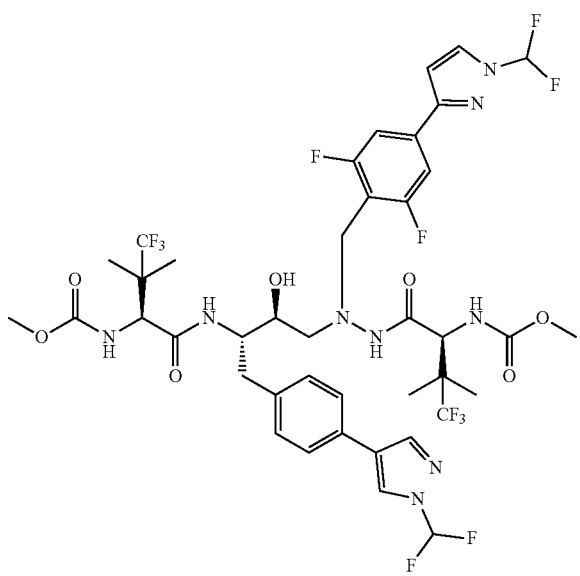

EXAMPLE 209

Methyl ((5S,8S,9S,14S)-11-(4-(1-(difluoromethyl)-1H-pyrazol-3-yl)-2,6-difluorobenzyl)-8-(4-(1-(difluoromethyl)-1H-pyrazol-4-yl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (209)

Intermediates: I2, P4 and 1-(difluoromethyl)-4-(4,4,5,5-tetramethyl-1,3,2-dioxaborolan-2-yl)-1H-pyrazole. MS (ESI) m/z 1004.5 [M+H]$^+$. $^1$H NMR (400 MHz, Methanol-d$_4$) δ 8.32 (s, 2H), 8.09 (d, J=2.7 Hz, 2H), 8.02 (s, 2H), 7.66 (d, J=19.3 Hz, 1H), 7.56-7.31 (m, 13H), 7.24 (d, J=8.0 Hz, 5H), 6.91 (d, J=2.7 Hz, 2H), 4.46 (s, 2H), 4.31 (s, 2H), 4.20-4.07 (m, 5H), 3.93 (d, J=13.1 Hz, 2H), 3.76 (s, 2H), 3.64 (s, 6H), 3.56 (s, 6H), 3.35 (s, 1H), 2.95-2.84 (m, 7H), 2.79 (dd, J=12.6, 9.2 Hz, 3H), 1.24-1.09 (m, 28H), 1.02 (s, 6H).

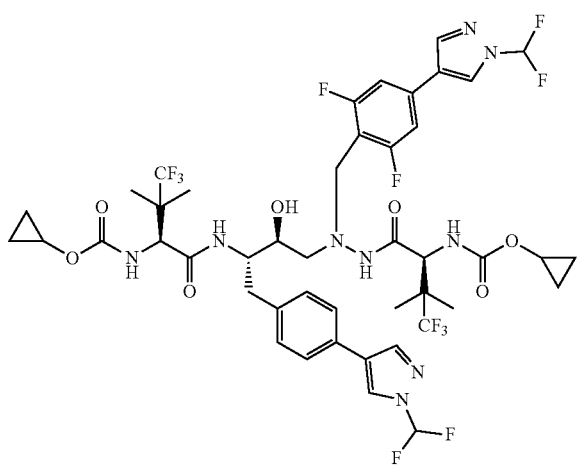 [SMILES: CC(C)([C@H](NC(=O)OC1CC1)C(=O)N[C@@H](Cc1ccc(/C(C=N)=C/NC(F)F)cc1)[C@@H](O)CN(Cc1c(F)cc(/C(C=N)=C/NC(F)F)cc1F)NC(=O)[C@@H](NC(=O)OC1CC1)C(C)(C)C(F)(F)F)C(F)(F)F]

EXAMPLE 210

Cyclopropyl ((S)-1-(2-((2S,3S)-3-((S)-2-((cyclopropoxycarbonyl)amino)-4,4,4-trifluoro-3,3-dimethylbutanamido)-4-(4-(1-(difluoromethyl)-1H-pyrazol-4-yl)phenyl)-2-hydroxybutyl)-2-(4-(1-(difluoromethyl)-1H-pyrazol-4-yl)-2,6-difluorobenzyl)hydrazinyl)-4,4,4-trifluoro-3,3-dimethyl-1-oxobutan-2-yl)carbamate (210)

Intermediates: I2a, A4, P7 and 1-(difluoromethyl)-4-(4,4,5,5-tetramethyl-1,3,2-dioxaborolan-2-yl)-1H-pyrazole MS (ESI) m/z 1056.6 [M+H]$^+$. $^1$H NMR (400 MHz, Methanol-d$_4$) δ 8.53 (d, J=0.8 Hz, 1H), 8.33 (s, 1H), 8.12 (s, 1H), 8.03 (s, 1H), 7.52-7.45 (m, 4H), 7.25 (d, J=8.2 Hz, 4H), 4.47 (s, 1H), 4.32 (s, 1H), 4.14 (s, 1H), 4.01 (td, J=5.6, 3.0 Hz, 1H), 3.93 (d, J=12.1 Hz, 2H), 3.76 (d, J=8.5 Hz, 1H), 2.94-2.73 (m, 5H), 2.01 (s, 2H), 1.23 (t, J=7.1 Hz, 2H), 1.17-1.09 (m, 10H), 1.02 (s, 3H), 0.69-0.51 (m, 8H).

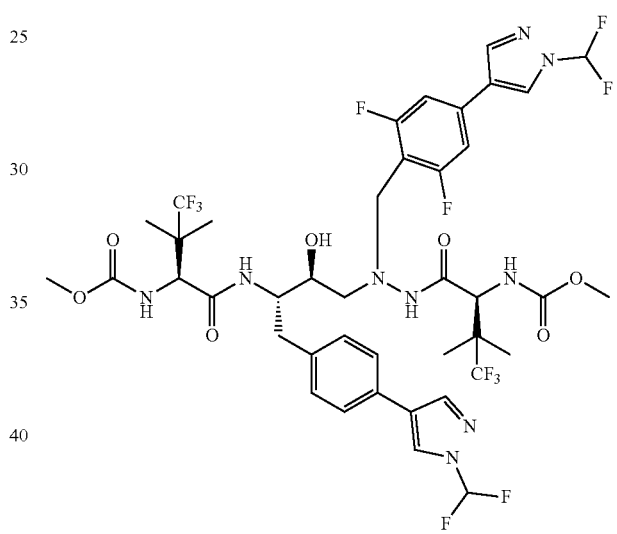

EXAMPLE 211

Methyl ((5S,8S,9S,14S)-11-(4-(1-(difluoromethyl)-1H-pyrazol-4-yl)-2,6-difluorobenzyl)-8-(4-(1-(difluoromethyl)-1H-pyrazol-4-yl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (211)

Intermediates: I2, P7 and 1-(difluoromethyl)-4-(4,4,5,5-tetramethyl-1,3,2-dioxaborolan-2-yl)-1H-pyrazole MS (ESI) m/z 1004.2 [M+H]$^+$. $^1$H NMR (400 MHz, Methanol-d$_4$) δ 8.44 (d, J=0.7 Hz, 1H), 8.24 (s, 1H), 8.03 (s, 1H), 7.93 (s, 1H), 7.41 (s, 1H), 7.39-7.35 (m, 3H), 7.25 (d, J=10.6 Hz, 1H), 7.15 (d, J=8.1 Hz, 4H), 4.35 (s, 1H), 4.20 (s, 1H), 4.05-3.98 (m, 3H), 3.85 (s, 1H), 3.54 (s, 4H), 3.46 (s, 3H), 2.82-2.65 (m, 4H), 1.91 (s, 1H), 1.08-0.99 (m, 9H), 0.92 (s, 3H). $^{19}$F NMR (377 MHz, Methanol-d$_4$) δ −76.33−−79.41 (m), −96.67 (dd, J=145.1, 59.7 Hz).

EXAMPLE 212
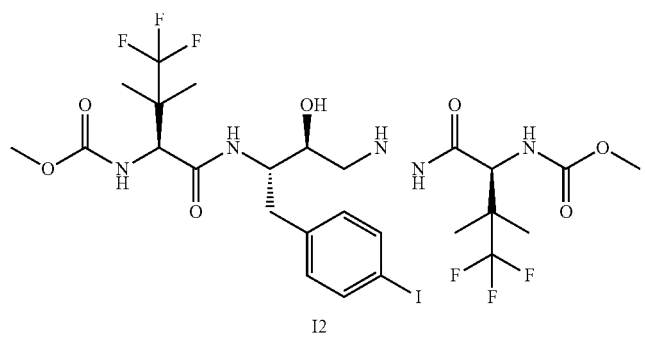
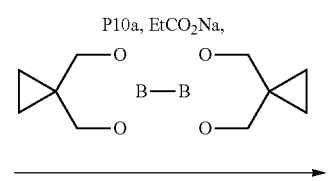
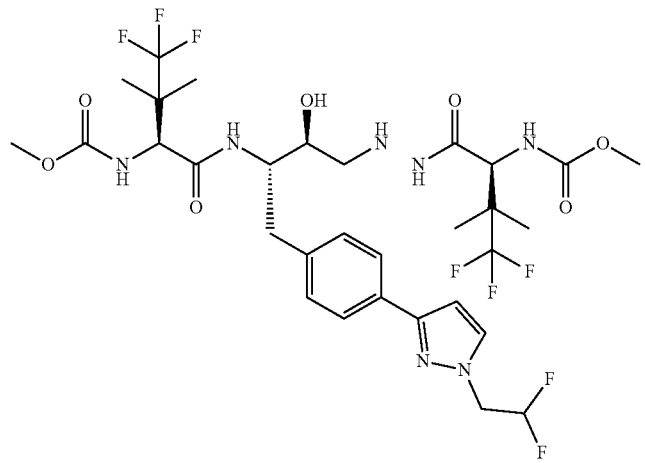
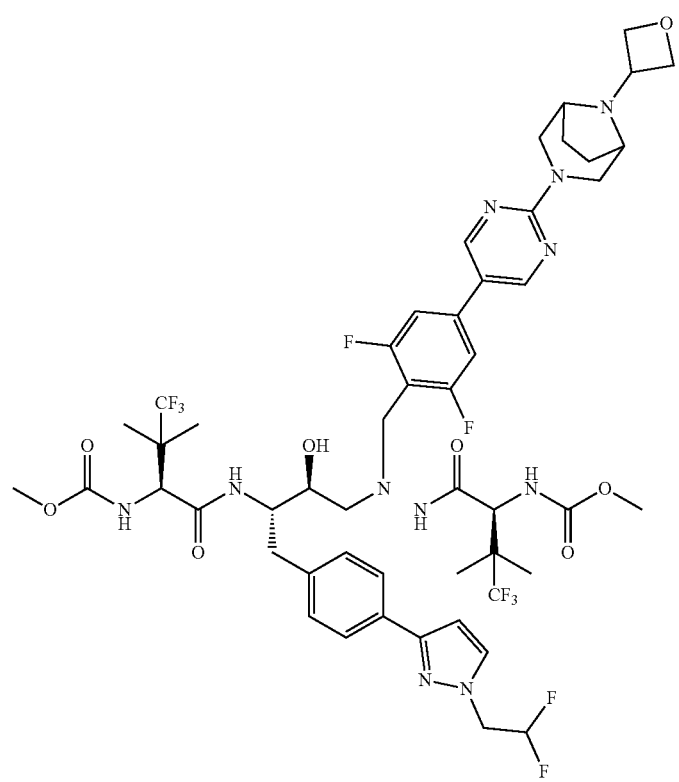

Synthesis of methyl ((5S,10S,11S,14S)-11-(4-(1-(2,2-difluoroethyl)-1H-pyrazol-3-yl)benzyl)-16,16,16-trifluoro-10-hydroxy-15,15-dimethyl-3,6,13-trioxo-5-(1,1,1-trifluoro-2-methylpropan-2-yl)-2-oxa-4,7,8,12-tetraazahexadecan-14-yl)carbamate (212a)

The title compound 212a was prepared according to the method presented for the synthesis of compound 188 but instead utilizing I2 and P10a. MS (ESI) m/z 776.3 [M+H]⁺.

Methyl ((5S,8S,9S,14S)-11-(2,6-difluoro-4-(2-(8-(oxetan-3-yl)-3,8-diazabicyclo[3.2.1]octan-3-yl)pyrimidin-5-yl)benzyl)-8-(4-(1-(2,2-difluoroethyl)-1H-pyrazol-3-yl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (212)

The title compound 212 was prepared according to the method presented for the synthesis of compound 1a but instead utilizing 212a and P20. MS (ESI) m/z 1146.3 [M+H]⁺. ¹H NMR (400 MHz, Methanol-d4) δ 8.71 (s, 2H), 8.11 (d, J=9.7 Hz, 1H), 7.68 (d, J=2.4 Hz, 1H), 7.64 (d, J=7.9 Hz, 2H), 7.25 (s, 1H), 7.21 (d, J=8.3 Hz, 1H), 7.13 (d, J=10.1 Hz, 1H), 6.78 (d, J=10.1 Hz, 1H), 6.63 (d, J=2.4 Hz, 1H), 6.19 (tt, J=55.6, 3.9 Hz, 1H), 4.96 (t, J=7.5 Hz, 2H), 4.56 (td, J=14.3, 3.9 Hz, 2H), 4.43 (d, J=9.7 Hz, 1H), 4.29 (d, J=10.0 Hz, 1H), 4.23-4.08 (m, 4H), 3.95 (d, J=13.5 Hz, 1H), 3.73 (s, 1H), 3.63 (s, 3H), 3.55 (s, 3H), 3.52-3.43 (m, 2H), 2.93-2.73 (m, 3H), 2.25-2.17 (m, 2H), 2.06-1.94 (m, 2H), 1.15-1.12 (m, 6H), 1.11 (s, 3H), 1.01 (s, 3H).

EXAMPLE 213

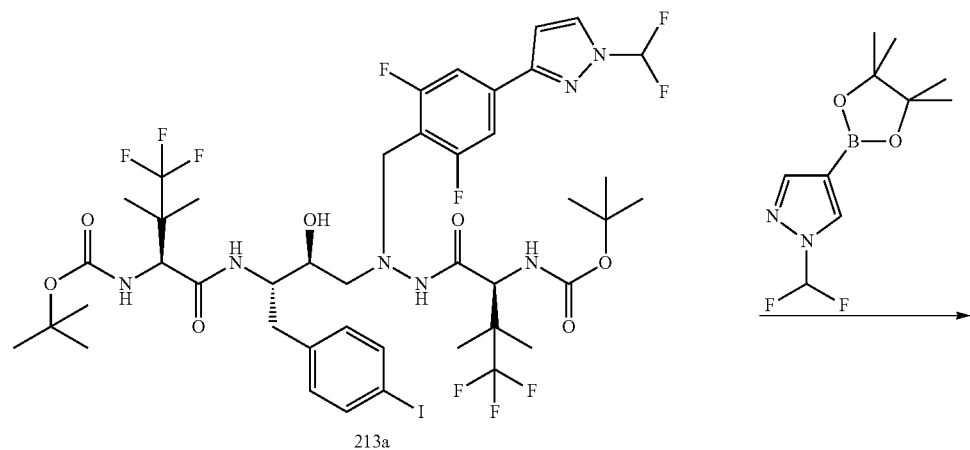

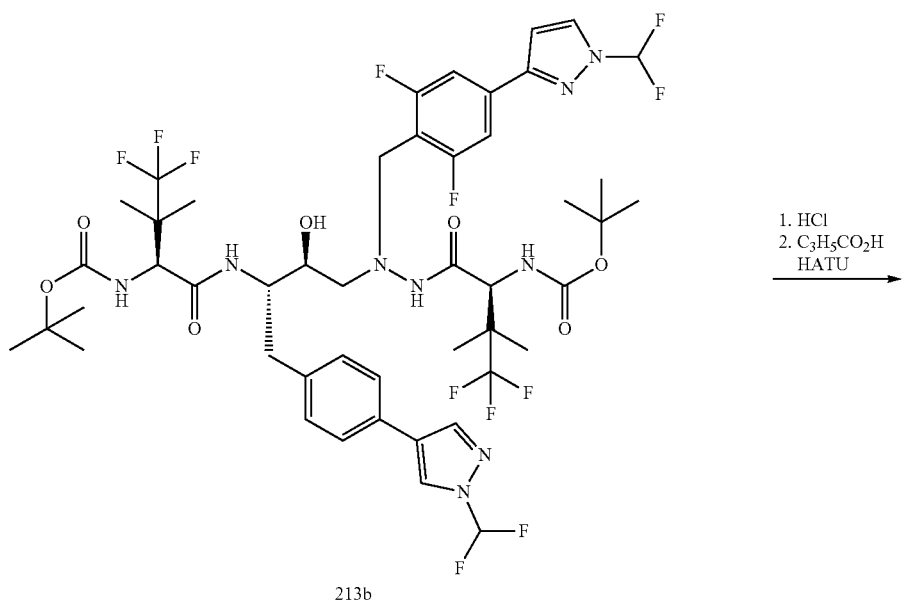

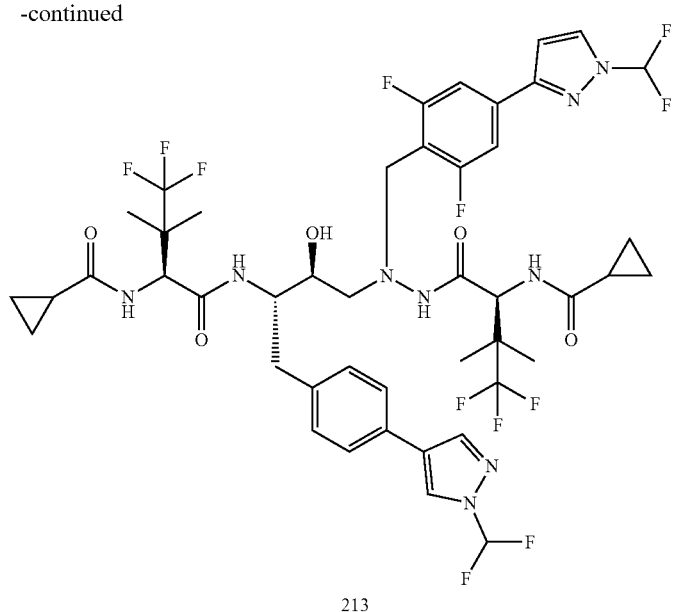

213

Synthesis of tert-butyl ((6S,9S,10S,15S)-12-(4-(1-(difluoromethyl)-1H-pyrazol-3-yl)-2,6-difluorobenzyl)-17,17,17-trifluoro-10-hydroxy-9-(4-iodobenzyl)-2,2,16,16-tetramethyl-4,7,14-trioxo-6-(1,1,1-trifluoro-2-methylpropan-2-yl)-3-oxa-5,8,12,13-tetraazaheptadecan-15-yl)carbamate (213a). The title compound 213a was prepared according to the method presented for the synthesis of compound 188 but instead utilizing I2a, A1, and P4.

Synthesis of tert-butyl ((6S,9S,10S,15S)-12-(4-(1-(difluoromethyl)-1H-pyrazol-3-yl)-2,6-difluorobenzyl)-9-(4-(1-(difluoromethyl)-1H-pyrazol-4-yl)benzyl)-17,17,17-trifluoro-10-hydroxy-2,2,16,16-tetramethyl-4,7,14-trioxo-6-(1,1,1-trifluoro-2-methylpropan-2-yl)-3-oxa-5,8,12,13-tetraazaheptadecan-15-yl)carbamate (213b)

The title compound 213b was prepared according to the method presented for the synthesis of compound 218 but instead utilizing 213a and 1-(difluoromethyl)-4-(4,4,5,5-tetramethyl-1,3,2-dioxaborolan-2-yl)-1H-pyrazole. MS (ESI) m/z 1088.5 [M+H]+.

Synthesis of N—((S)-1-(2-((2S,3S)-3-((S)-2-(cyclopropanecarboxamido)-4,4,4-trifluoro-3,3-dimethylbutanamido)-4-(4-(1-(difluoromethyl)-1H-pyrazol-4-yl)phenyl)-2-hydroxybutyl)-2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)cyclopropanecarboxamide (213)

To a solution of 213a (255 mg, 0.23 mmol) in CH₂Cl₂ (5 mL) at room temperature was added 4 M hydrochloric acid (0.8 mL). After stirring for 18h the reaction and the mixture was concentrated in vacuo. To this crude residue dissolved in DMF (3 mL) was added cyclopropanecarboxylic acid (29.97 µl, 0.4 mmol), HATU (93.32 mg, 0.4 mmol) and DIPEA (0.34 ml, 1.96 mmol). The mixture was stirred for 48h then purified by HPLC HPLC and Lyophilized to give 212. MS (ESI) m/z 1146.3 [M+H]+. ¹H NMR (400 MHz, Methanol-d4) δ 8.34 (d, J=0.7 Hz, 1H), 8.25 (d, J=9.8 Hz, 1H), 8.20-8.06 (m, 2H), 8.06-7.95 (m, 2H), 7.56-7.45 (m, 4H), 7.48-7.31 (m, 2H), 7.24 (d, J=8.1 Hz, 1H), 6.93 (dd, J=5.4, 2.7 Hz, 1H), 4.73-4.61 (m, 1H), 4.16 (d, J=13.2 Hz, 2H), 3.93 (d, J=13.2 Hz, 1H), 3.77 (s, 1H), 2.93-2.74 (m, 4H), 1.69 (dd, J=8.5, 4.1 Hz, 1H), 1.58 (tt, J=8.2, 4.6 Hz, 1H), 1.36-1.20 (m, 1H), 1.17 (d, J=13.5 Hz, 9H), 1.07 (s, 3H), 0.91 (q, J=10.2, 9.5 Hz, 1H), 0.89-0.66 (m, 1H), 0.65-0.54 (m, 1H).

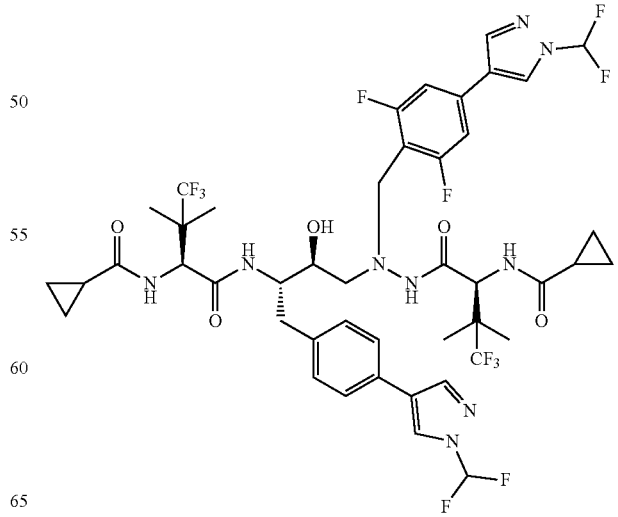

EXAMPLE 214

N—((S)-1-(2-((2S,3S)-3-((S)-2-(cyclopropanecarboxamido)-4,4,4-trifluoro-3,3-dimethylbutanamido)-4-(4-(1-(difluoromethyl)-1H-pyrazol-4-yl)phenyl)-2-hydroxybutyl)-2-(4-(1-(difluoromethyl)-1H-pyrazol-4-yl)-2,6-difluorobenzyl)hydrazinyl)-4,4,4-trifluoro-3,3-dimethyl-1-oxobutan-2-yl)cyclopropanecarboxamide (214)

The title compound 214 was prepared according to the method presented for the synthesis of compound 213 but instead utilizing P7. MS (ESI) m/z 1024.5 [M+H]+. 1H NMR (400 MHz, Methanol-d4) δ 8.53 (s, 1H), 8.33 (d, J=0.7 Hz, 1H), 8.27 (d, J=9.8 Hz, 1H), 8.13-8.09 (m, 2H), 8.03-7.96 (m, 2H), 7.64 (d, J=10.5 Hz, 1H), 7.52-7.45 (m, 3H), 7.34 (d, J=10.7 Hz, 1H), 7.24 (t, J=8.5 Hz, 4H), 4.81-4.78 (m, 1H), 4.69-4.64 (m, 1H), 4.12 (d, J=12.4 Hz, 2H), 3.91 (d, J=13.2 Hz, 1H), 3.74 (d, J=8.9 Hz, 1H), 2.88 (d, J=7.6 Hz, 3H), 2.77 (dd, J=12.5, 9.3 Hz, 1H), 1.69 (dt, J=8.0, 3.7 Hz, 1H), 1.57 (tt, J=8.3, 4.6 Hz, 1H), 1.29 (d, J=0.6 Hz, 1H), 1.24 (d, J=7.7 Hz, 1H), 1.21-1.12 (m, 9H), 1.06 (s, 2H), 0.94-0.68 (m, 7H), 0.59 (d, J=8.0 Hz, 1H).

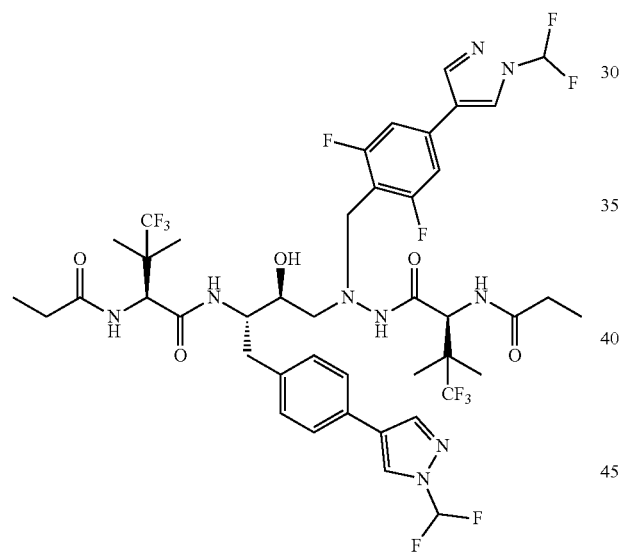

EXAMPLE 215

(S)—N-((2S,3S)-4-(1-(4-(1-(difluoromethyl)-1H-pyrazol-4-yl)-2,6-difluorobenzyl)-2-((S)-4,4,4-trifluoro-3,3-dimethyl-2-propionamidobutanoyl)hydrazinyl)-1-(4-(1-(difluoromethyl)-1H-pyrazol-4-yl)phenyl)-3-hydroxybutan-2-yl)-4,4,4-trifluoro-3,3-dimethyl-2-propionamidobutanamide (215)

The title compound 215 was prepared according to the method presented for the synthesis of compound 213 but instead utilizing P7 and propionic acid. MS (ESI) m/z 1000.5 [M+H]+. 1H NMR (400 MHz, Methanol-d4) δ 8.54 (d, J=0.7 Hz, 1H), 8.35 (d, J=0.7 Hz, 1H), 8.14-8.00 (m, 5H), 7.71 (d, J=9.8 Hz, 1H), 7.64 (d, J=10.9 Hz, 1H), 7.52-7.44 (m, 4H), 7.25 (t, J=8.6 Hz, 5H), 4.78-4.74 (m, 1H), 4.67-4.63 (m, 1H), 4.14 (d, J=13.2 Hz, 2H), 3.92 (d, J=13.2 Hz, 1H), 3.73 (d, J=8.7 Hz, 1H), 2.88 (d, J=8.7 Hz, 4H), 2.76 (dd, J=12.7, 9.3 Hz, 1H), 2.25-1.99 (m, 6H), 1.25-0.95 (m, 24H).

EXAMPLE 216

N—((S)-1-(2-(4-(1-(difluoromethyl)-1H-pyrazol-4-yl)-2,6-difluorobenzyl)-2-((2S,3S)-4-(4-(1-(difluoromethyl)-1H-pyrazol-4-yl)phenyl)-2-hydroxy-3-((S)-4,4,4-trifluoro-3,3-dimethyl-2-(1-methylcyclopropane-1-carboxamido)butanamido)butyl)hydrazinyl)-4,4,4-trifluoro-3,3-dimethyl-1-oxobutan-2-yl)-1-methylcyclopropane-1-carboxamide (216)

The title compound 216 was prepared according to the method presented for the synthesis of compound 213 but instead utilizing P7 and 1-Methylcyclopropanecarboxylic acid. MS (ESI) m/z 1052.7 [M+H]+. 1H NMR (400 MHz, Methanol-d4) δ 8.17 (s, 1H), 7.97 (s, 1H), 7.87 (d, J=9.5 Hz, 1H), 7.75 (s, 1H), 7.65 (s, 1H), 7.15-7.07 (m, 4H), 6.87 (t, J=8.2 Hz, 4H), 6.42 (d, J=9.6 Hz, 1H), 6.17 (d, J=9.6 Hz, 1H), 4.38 (d, J=9.5 Hz, 1H), 4.27 (d, J=9.5 Hz, 1H), 3.89-3.73 (m, 2H), 3.58-3.48 (m, 1H), 3.39 (s, 1H), 2.50 (t, J=7.6 Hz, 3H), 2.41 (dd, J=12.6, 9.0 Hz, 1H), 0.95-0.54 (m, 25H), 0.22 (d, J=3.8 Hz, 2H), 0.13 (ddd, J=9.8, 6.4, 3.6 Hz, 1H).

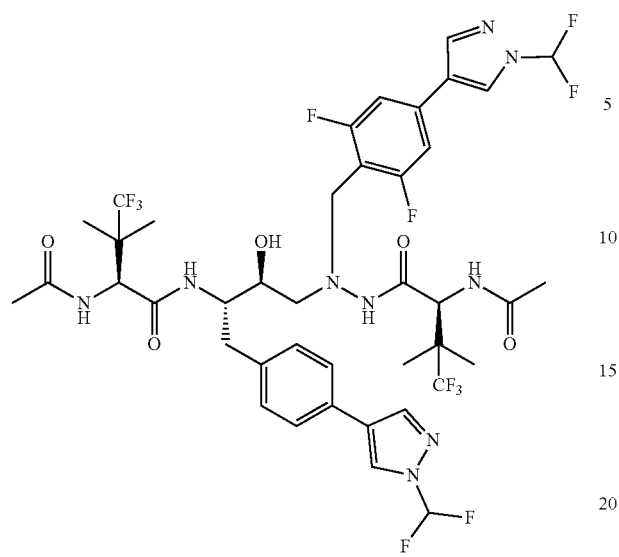

EXAMPLE 217

(S)-2-acetamido-N-((2S,3S)-4-(2-((S)-2-acetamido-4,4,4-trifluoro-3,3-dimethylbutanoyl)-1-(4-(1-(difluoromethyl)-1H-pyrazol-4-yl)-2,6-difluorobenzyl)hydrazinyl)-1-(4-(1-(difluoromethyl)-1H-pyrazol-4-yl)phenyl)-3-hydroxybutan-2-yl)-4,4,4-trifluoro-3,3-dimethylbutanamide (217)

The title compound 217 was prepared according to the method presented for the synthesis of compound 213 but instead utilizing P7 and Acetic anhydride. MS (ESI) m/z 972.5 [M+H]$^+$. $^1$H NMR (400 MHz, Methanol-$d_4$) δ 8.55 (s, 1H), 8.36 (s, 1H), 8.16 (d, J=21.4 Hz, 2H), 8.07 (d, J=20.2 Hz, 2H), 7.52-7.46 (m, 3H), 7.25 (t, J=8.3 Hz, 4H), 5.48 (d, J=0.6 Hz, 2H), 4.78-4.73 (m, 1H), 4.66-4.61 (m, 1H), 4.16 (s, 1H), 3.95-3.88 (m, 1H), 3.74 (d, J=8.5 Hz, 1H), 2.91-2.84 (m, 3H), 2.77 (dd, J=12.7, 9.2 Hz, 1H), 2.15 (s, 1H), 2.03 (d, J=0.5 Hz, 15H), 1.93 (s, 2H), 1.81 (s, 2H). $^{19}$F NMR (377 MHz, Methanol-$d_4$) δ −76.14−−79.22 (m), −96.72 (dd, J=133.4, 59.8 Hz).

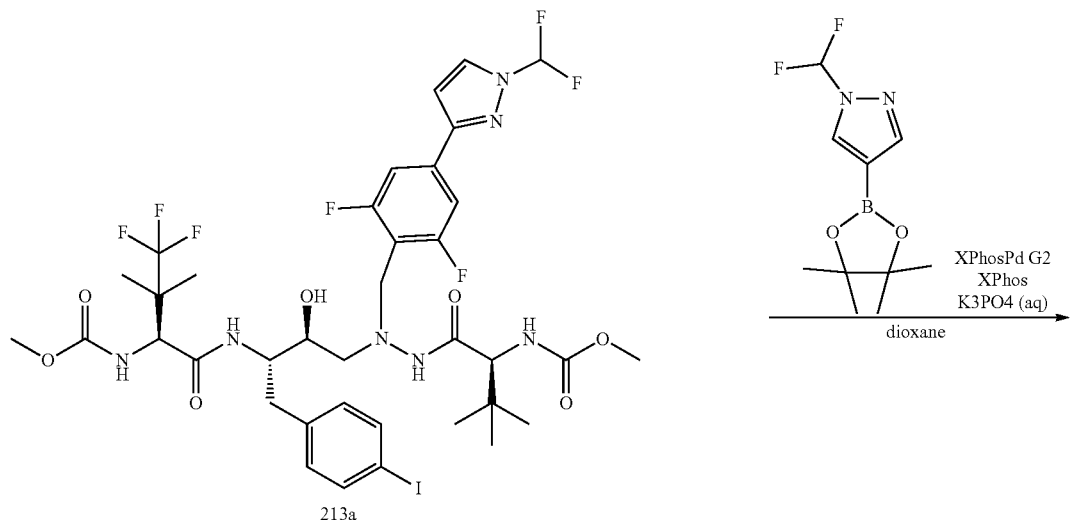

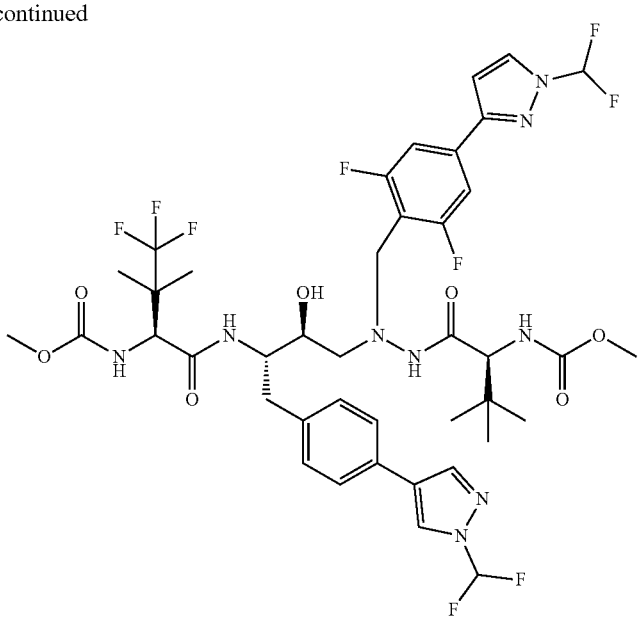

EXAMPLE 218

Methyl ((5S,8S,9S,14S)-11-(4-(1-(difluoromethyl)-1H-pyrazol-3-yl)-2,6-difluorobenzyl)-8-(4-(1-(difluoromethyl)-1H-pyrazol-4-yl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate (218)

To a solution of methyl ((5S,8S,9S,14S)-11-(4-(1-(difluoromethyl)-1H-pyrazol-3-yl)-2,6-difluorobenzyl)-9-hydroxy-8-(4-iodobenzyl)-15,15-dimethyl-3,6,13-trioxo-5-(1,1,1-trifluoro-2-methylpropan-2-yl)-2-oxa-4,7,11,12-tetraazahexadecan-14-yl)carbamate (0.02g, 0.02 mmol) in 1,4-dioxane (0.3 mL) was added 1-(Difluoromethyl)-4-(4,4,5,5-tetramethyl-1,3,2-dioxaborolan-2-yl)-1H-pyrazole (0.01 g, 0.04 mmol), XPhos Pd G2 (0.005 g, 0.003 mmol), XPhos (0.001g, 0.003 mmol) and Potassium phosphate tribasic (0.01 ml) as an aqueous solution in water (0.01 mL). The resulting suspension was sparged with argon for 5 minutes and subsequently placed in a 100° C. aluminum heating block and let stir, heating, overnight under an atmosphere of argon. Upon completion, the residue was purified by reverse phase high pressure liquid chromatography (20-83% acetonitrile in water, 0.1% TFA buffer). The collected product fractions were quenched with sodium bicarbonate (aqueous, saturated), extracted with ethyl acetate and further purified by normal phase silica gel chromatography (0-8% methanol in dichloromethane) to give methyl ((5S,8S,9S,14S)-11-(4-(1-(difluoromethyl)-1H-pyrazol-3-yl)-2,6-difluorobenzyl)-8-(4-(1-(difluoromethyl)-1H-pyrazol-4-yl)benzyl)-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate. ES/MS m/z 950.542 [M+H]$^+$.

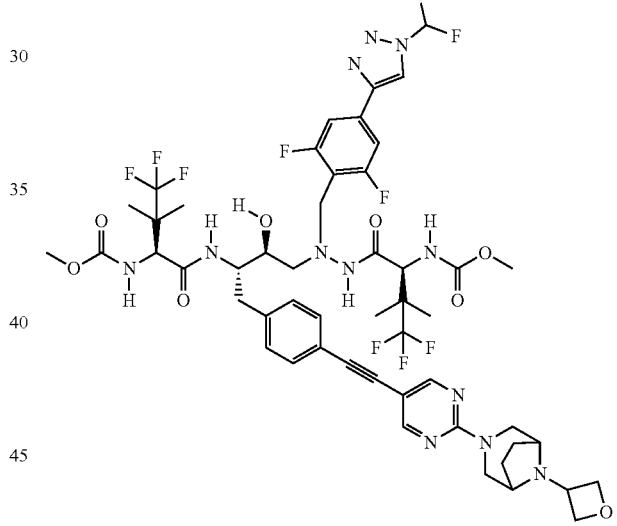

EXAMPLE 219

Methyl ((5S,8S,9S,14S)-11-(4-(1-(difluoromethyl)-1H-1,2,3-triazol-4-yl)-2,6-difluorobenzyl)-16,16,16-trifluoro-9-hydroxy-15,15-dimethyl-8-(4-((2-(8-(oxetan-3-yl)-3,8-diazabicyclo[3.2.1]octan-3-yl)pyrimidin-5-yl)ethynyl)benzyl)-3,6,13-trioxo-5-(1,1,1-trifluoro-2-methylpropan-2-yl)-2-oxa-4,7,11,12-tetraazahexadecan-14-yl)carbamate (219)

Intermediates: P44, A3, and S7. MS (ESI) m/z 1157.9 [M+H]+. 1H NMR (400 MHz, Methanol-d4) δ 8.97 (s, 1H), 8.53 (s, 2H), 8.17 (d, J=9.8 Hz, 1H), 8.00 (t, J=58.6 Hz, 1H), 7.53 (d, J=8.0 Hz, 2H), 7.35 (d, J=7.9 Hz, 2H), 7.24 (d, J=8.1 Hz, 2H), 7.14 (d, J=9.9 Hz, 1H), 6.81 (d, J=9.9 Hz, 1H), 4.96 (dd, J=8.2, 7.1 Hz, 2H), 4.83-4.78 (m, 3H), 4.50-4.41 (m, 1H), 4.30 (d, J=10.0 Hz, 1H), 4.21-4.08 (m, 4H), 3.96 (d, J=13.2 Hz, 1H), 3.74 (d, J=8.8 Hz, 1H), 3.69 (s, 3H), 3.67 (s, 3H), 3.47 (d, J=14.5 Hz, 2H), 2.98-2.84 (m, 3H), 2.82-2.74 (m, 1H), 2.29-2.17 (m, 2H), 2.02-1.94 (m, 2H), 1.16 (s, 3H), 1.15 (s, 3H), 1.12 (s, 3H), 1.03 (s, 3H). 19F NMR (377 MHz, Methanol-d4) δ −77.37, −77.70, −77.82, −98.78 (d, J=58.6 Hz), −114.26.

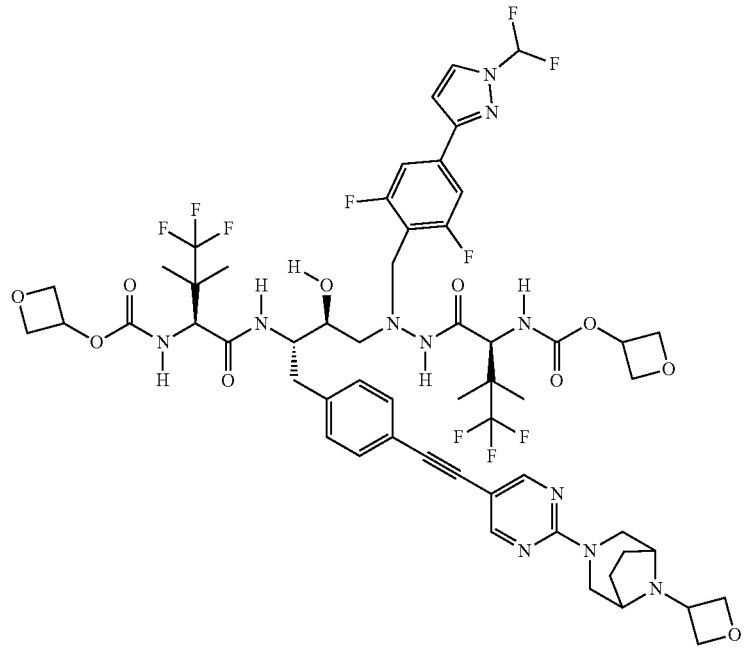 [SMILES: CC(C)([C@H](NC(=O)OC1COC1)C(=O)N[C@@H](Cc1ccc(C#Cc2cnc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC1COC1)C(C)(C)C(F)(F)F)C(F)(F)F]

EXAMPLE 220

Oxetan-3-yl ((2S)-1-(2-(4-(1-(difluoromethyl)-1H-pyrazol-3-yl)-2,6-difluorobenzyl)-2-((2S,3S)-2-hydroxy-4-((2-(8-(oxetan-3-yl)-3,8-diazabicyclo [3.2.1]octan-3-yl)pyrimidin-5-yl)ethynyl)phenyl)-3-((S)-4,4,4-trifluoro-3,3-dimethyl-2-(((oxetan-3-yloxy)carbonyl)amino)butanamido)butyl) hydrazinyl)-4,4,4-trifluoro-3,3-dimethyl-1-oxobutan-2-yl)carbamate (220)

Intermediates: P4, A4, and S7. MS (ESI) m/z 1240.3 [M+H]+. 1H NMR (400 MHz, Methanol-d4) δ 8.45 (s, 2H), 8.12 (d, J=9.3 Hz, 1H), 8.02 (d, J=2.7 Hz, 1H), 7.45 (t, J=59.8 Hz, 1H), 7.37 (d, J=8.2 Hz, 2H), 7.25 (d, J=8.0 Hz, 2H), 7.15 (d, J=8.0 Hz, 3H), 7.07 (d, J=10.0 Hz, 1H), 6.85 (d, J=2.8 Hz, 1H), 5.37-5.21 (m, 2H), 4.92-4.83 (m, 2H), 4.73-4.69 (m, 2H), 4.56 (ddd, J=12.4, 7.3, 5.2 Hz, 2H), 4.50-4.44 (m, 2H), 4.33 (d, J=10.0 Hz, 1H), 4.20 (d, J=9.9 Hz, 1H), 4.13-3.98 (m, 4H), 3.85 (d, J=13.1 Hz, 1H), 3.67 (s, 1H), 3.39-3.32 (m, 3H), 2.86-2.78 (m, 3H), 2.68 (dd, J=12.6, 8.9 Hz, 1H), 2.14-2.08 (m, 2H), 1.92-1.83 (m, 2H), 1.09 (s, 3H), 1.07 (s, 3H), 1.05-0.99 (m, 3H), 0.99-0.93 (m, 3H). 19F NMR (377 MHz, Methanol-d4) δ −77.46, −77.56, −77.78, −96.92 (d, J=59.7 Hz), −114.94.

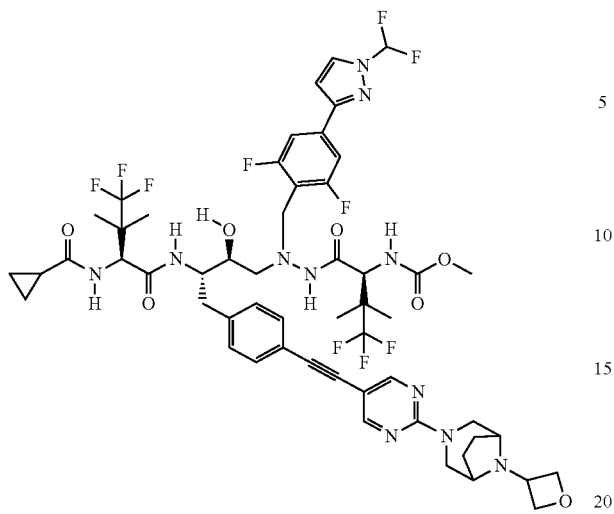

EXAMPLE 221

Methyl ((2S)-1-(2-((2S,3S)-3-((S)-2-(cyclopropan-ecarboxamido)-4,4,4-trifluoro-3,3-dimethylbutana-mido)-2-hydroxy-4-(4-((2-(8-(oxetan-3-yl)-3,8-diaz-abicyclo[3.2.1]octan-3-yl)pyrimidin-5-yl)ethynyl)phenyl)butyl)-2-(4-(1-(difluoromethyl)-1H-pyrazol-3-yl)-2,6-difluorobenzyl)hydrazinyl)-4,4,4-trifluoro-3,3-dimethyl-1-oxobutan-2-yl)carbamate (221)

Intermediate I9 was acylated with cyclopropyl carbonyl chloride in the presence of aqueous 2M NaOH, followed by coupling with S7 analogously to the procedure provided for example 1. MS (ESI) m/z 1166.9 [M+H]+. 1H NMR (400 MHz, Methanol-d4) δ 8.42 (s, 2H), 8.07 (d, J=9.4 Hz, 1H), 8.01 (d, J=2.7 Hz, 1H), 7.89 (d, J=9.7 Hz, 1H), 7.44 (t, J=59.7 Hz, 1H), 7.36 (d, J=8.3 Hz, 2H), 7.26 (d, J=8.1 Hz, 2H), 7.12 (d, J=8.1 Hz, 2H), 7.06 (d, J=9.7 Hz, 1H), 6.85 (d, J=2.7 Hz, 1H), 4.90-4.83 (m, 2H), 4.74-4.68 (m, 3H), 4.21 (d, J=10.0 Hz, 1H), 4.11-3.98 (m, 4H), 3.85 (d, J=13.0 Hz, 1H), 3.57 (s, 3H), 3.41-3.31 (m, 2H), 2.86-2.75 (m, 3H), 2.73-2.61 (m, 1H), 2.19-2.01 (m, 2H), 1.93-1.82 (m, 2H), 1.64-1.51 (m, 1H), 1.10 (s, 3H), 1.07 (s, 3H), 1.07 (s, 3H), 0.94 (s, 3H), 0.90-0.83 (m, 1H), 0.79-0.62 (m, 2H). 19F NMR (377 MHz, Methanol-d4) δ −77.41, −77.71, −77.73, −96.95 (dd, J=59.9, 20.5 Hz), −114.88.

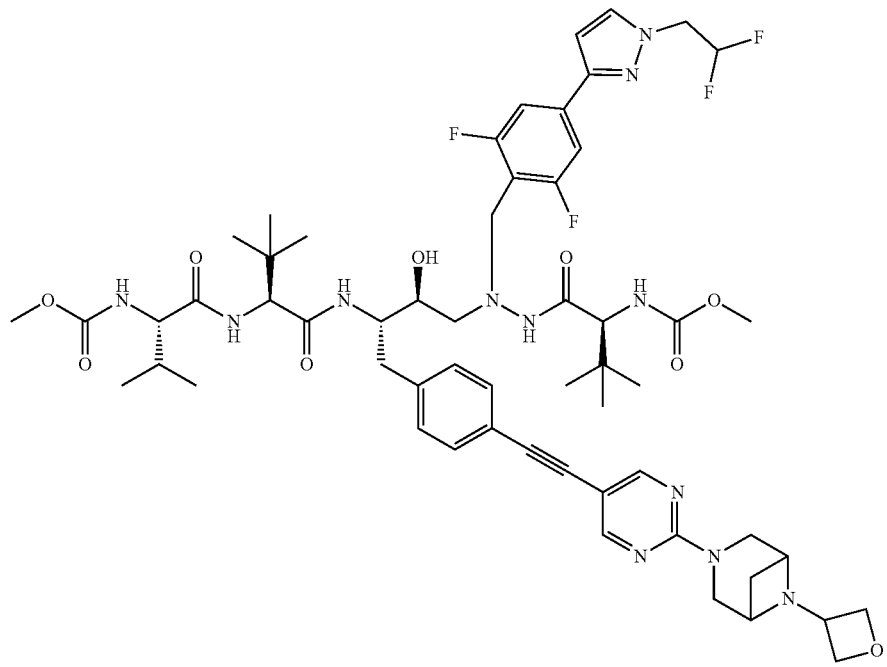 [SMILES: COC(=O)N[C@H](C(=O)N[C@H](C(=O)N[C@@H](Cc1ccc(C#Cc2cnc(N3CC4CC(C3)N4C3COC3)nc2)cc1)[C@@H](O)CN(Cc1c(F)cc(-c2ccn(CC(F)F)n2)cc1F)NC(=O)[C@@H](NC(=O)OC)C(C)(C)C)C(C)(C)C)C(C)C]

EXAMPLE 222

Methyl ((5S,8S,11S,12S,17S)-8-(tert-butyl)-14-(4-(1-(2,2-difluoroethyl)-1H-pyrazol-3-yl)-2,6-difluorobenzyl)-12-hydroxy-5-isopropyl-18,18-dimethyl-11-(4-((2-(6-(oxetan-3-yl)-3,6-diazabicyclo[3.1.1]heptan-3-yl)pyrimidin-5-yl)ethynyl)benzyl)-3,6,9,16-tetraoxo-2-oxa-4,7,10,14,15-pentaazanonadecan-17-yl)carbamate (222)

MS (ESI) m/z 1147.4 [M+H]+. 1H NMR (400 MHz, Methanol-d4) δ 8.50 (s, 2H), 7.87 (d, J=9.2 Hz, 1H), 7.64 (d, J=2.4 Hz, 1H), 7.50 (d, J=9.4 Hz, 1H), 7.35-7.24 (m, 4H), 7.16 (d, J=8.0 Hz, 2H), 6.65 (d, J=2.5 Hz, 1H), 6.13 (tt, J=55.3, 3.9 Hz, 1H), 4.58-4.44 (m, 4H), 4.39 (s, 0H), 4.16 (d, J=9.2 Hz, 1H), 4.07-3.92 (m, 2H), 3.90-3.77 (m, 2H), 3.67 (s, 1H), 3.59 (s, 1H), 3.55 (s, 3H), 3.55 (s, 3H), 2.90-2.66 (m, 3H), 2.06-1.86 (m, 2H), 0.85 (s, 9H), 0.79 (d, J=6.8 Hz, 3H), 0.76 (s, 9H), 0.72 (d, J=6.8 Hz, 3H). 19F NMR (377 MHz, Methanol-d4) δ −77.64, −115.17, −125.29 (dt, J=55.2, 14.2 Hz).

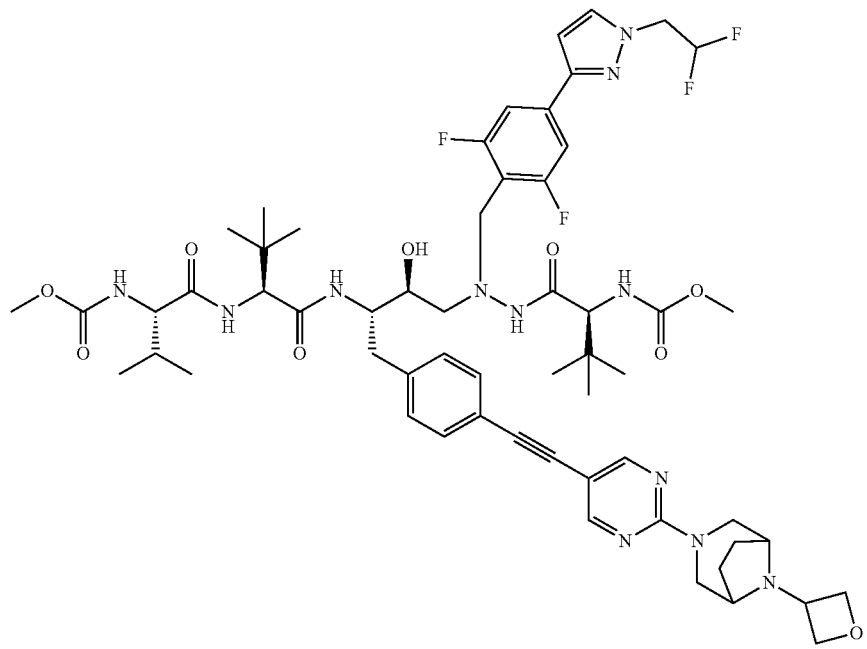 [SMILES: COC(=O)N[C@H](C(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ccn(CC(F)F)n2)cc1F)NC(=O)[C@@H](NC(=O)OC)C(C)(C)C)C(C)(C)C)C(C)C]

EXAMPLE 223

Methyl ((5S,8S,11S,12S,17S)-5,8-di-tert-butyl-14-(4-(1-(2,2-difluoroethyl)-1H-pyrazol-3-yl)-2,6-difluorobenzyl)-12-hydroxy-18,18-dimethyl-11-(4-((2-(6-(oxetan-3-yl)-3,6-diazabicyclo[3.1.1]heptan-3-yl)pyrimidin-5-yl)ethynyl)benzyl)-3,6,9,16-tetraoxo-2-oxa-4,7,10,14,15-pentaazanonadecan-17-yl)carbamate (223)

MS (ESI) m/z 1174.4 [M+H]+. 1H NMR (400 MHz, Methanol-d4) δ 8.21 (d, J=2.3 Hz, 1H), 7.87 (d, J=9.0 Hz, 1H), 7.64 (d, J=2.4 Hz, 1H), 7.61 (dd, J=8.8, 2.3 Hz, 1H), 7.53 (d, J=9.2 Hz, 1H), 7.28 (d, J=8.4 Hz, 2H), 7.24 (d, J=8.1 Hz, 1H), 7.15 (d, J=8.1 Hz, 2H), 6.77 (d, J=8.9 Hz, 1H), 6.65 (d, J=2.4 Hz, 1H), 6.13 (tt, J=55.3, 3.9 Hz, 1H), 4.92-4.83 (m, 2H), 4.74-4.68 (m, 2H), 4.51 (td, J=14.3, 3.9 Hz, 2H), 4.26 (d, J=13.7 Hz, 2H), 4.16 (d, J=9.3 Hz, 1H), 4.09-3.94 (m, 3H), 3.91 (s, 1H), 3.85 (d, J=13.1 Hz, 1H), 3.70-3.64 (m, 1H), 3.63-3.57 (m, 2H), 3.55 (s, 3H), 3.54 (s, 3H), 3.28 (d, J=13.9 Hz, 2H), 2.89-2.66 (m, 4H), 2.17-2.08 (m, 2H), 2.02-1.95 (m, 2H), 0.85 (s, 9H), 0.80 (s, 9H), 0.75 (s, 9H).

19F NMR (377 MHz, Methanol-d4) δ −77.71, −115.18, −125.29 (dt, J=55.3, 14.2 Hz).

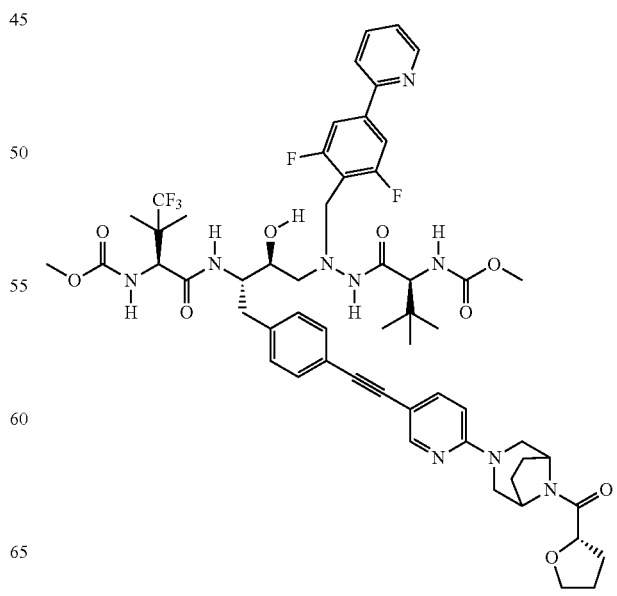

EXAMPLE 224

Methyl ((5S,8S,9S,14S)-11-(2,6-difluoro-4-(pyridin-2-yl)benzyl)-9-hydroxy-15,15-dimethyl-3,6,13-trioxo-8-(4-((6-(8-((S)-tetrahydrofuran-2-carbonyl)-3,8-diazabicyclo[3.2.1]octan-3-yl)pyridin-3-yl)ethynyl)benzyl)-5-(1,1,1-trifluoro-2-methylpropan-2-yl)-2-oxa-4,7,11,12-tetraazahexadecan-14-yl)carbamate (224)

Intermediates: P28, I3, and S25. MS (ESI) m/z 1104.4 [M+H]+. 1H NMR (400 MHz, Methanol-d4) δ 8.58 (d, J=5.0 Hz, 1H), 8.14-8.01 (m, 2H), 7.93 (t, J=7.7 Hz, 1H), 7.86 (d, J=7.9 Hz, 1H), 7.72 (t, J=8.7 Hz, 1H), 7.50 (d, J=8.5 Hz, 2H), 7.43-7.35 (m, 1H), 7.25 (d, J=7.8 Hz, 2H), 7.14 (d, J=8.0 Hz, 2H), 6.72 (d, J=9.8 Hz, 1H), 4.63-4.54 (m, 1H), 4.39-4.29 (m, 1H), 4.11-3.73 (m, 8H), 3.66 (s, 1H), 3.59 (s, 3H), 3.53 (s, 3H), 3.13 (d, J=12.1 Hz, 1H), 2.90-2.64 (m, 4H), 2.20-1.67 (m, 10H), 1.05 (s, 4H), 1.02 (s, 3H), 0.76 (s, 9H). 19F NMR (377 MHz, Methanol-d4) δ −77.33, −78.06, −114.28.

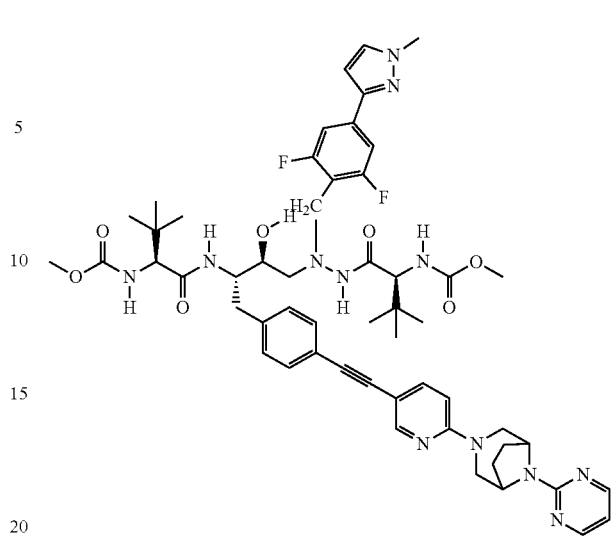

EXAMPLE 226 methyl ((5S,8S,9S,14S)-5-(tert-butyl)-11-(2,6-difluoro-4-(1-methyl-1H-pyrazol-3-yl)benzyl)-9-hydroxy-15,15-dimethyl-3,6,13-trioxo-8-(4-((6-(8-(pyrimidin-2-yl)-3,8-diazabicyclo[3.2.1]octan-3-yl)pyridin-3-yl)ethynyl)benzyl)-2-oxa-4,7,11,12-tetraazahexadecan-14-yl)carbamate (226)

Intermediates: I1, P41 and S61. MS (ESI) m/z 1033.4 [M+H]+. 1H NMR (400 MHz, Methanol-d4) δ 8.31 (d, J=4.9 Hz, 2H), 8.07 (d, J=2.1 Hz, 1H), 7.76 (d, J=9.3 Hz, 1H), 7.68 (d, J=9.1 Hz, 1H), 7.52 (d, J=2.3 Hz, 1H), 7.29-7.19 (m, 4H), 7.14 (d, J=8.1 Hz, 2H), 6.90 (d, J=9.3 Hz, 1H), 6.61 (t, J=4.9 Hz, 1H), 6.56 (d, J=2.4 Hz, 1H), 4.92-4.84 (m, 2H), 4.08-3.97 (m, 2H), 3.89 (d, J=13.0 Hz, 2H), 3.84 (s, 3H), 3.80 (s, 1H), 3.66 (s, 1H), 3.64-3.59 (m, 1H), 3.58 (s, 3H), 3.56 (s, 3H), 2.87-2.62 (m, 3H), 2.06-1.95 (m, 2H), 1.84 (q, J=7.2, 6.6 Hz, 2H), 0.79 (s, 9H), 0.74 (s, 9H). 19F NMR (377 MHz, Methanol-d4) δ −77.75, −115.32.

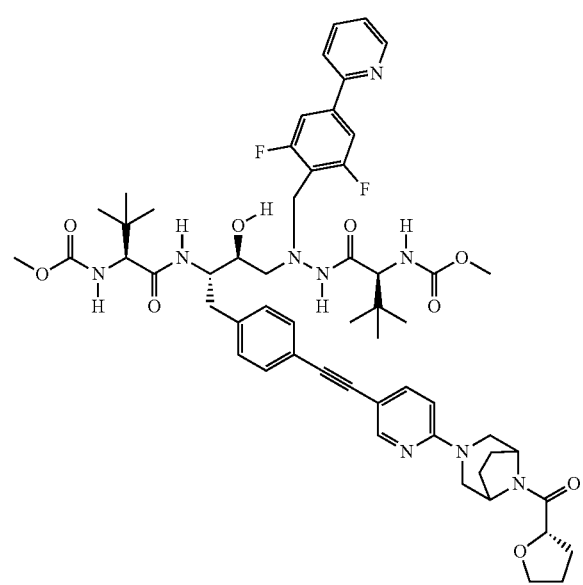 [SMILES: COC(=O)N[C@H](C(=O)N[C@@H](Cc1ccc(C#Cc2ccc(N3CC4CCC(C3)N4C(=O)[C@@H]3CCCO3)nc2)cc1)[C@@H](O)CN(Cc1c(F)cc(-c2ccccn2)cc1F)NC(=O)[C@@H](NC(=O)OC)C(C)(C)C)C(C)(C)C]

EXAMPLE 225

Methyl ((5S,8S,9S,14S)-5-(tert-butyl)-11-(2,6-difluoro-4-(pyridin-2-yl)benzyl)-9-hydroxy-15,15-dimethyl-3,6,13-trioxo-8-(4-((6-(8-((S)-tetrahydrofuran-2-carbonyl)-3,8-diazabicyclo[3.2.1]octan-3-yl)pyridin-3-yl)ethynyl)benzyl)-2-oxa-4,7,11,12-tetraazahexadecan-14-yl)carbamate (225)

Intermediates: P28, I1, and S25. MS (ESI) m/z 1050.4 [M+H]+. 1H NMR (400 MHz, Methanol-d4) δ 8.67 (dt, J=4.9, 1.4 Hz, 1H), 8.19 (d, J=2.8 Hz, 1H), 8.00 (t, J=7.7 Hz, 1H), 7.94 (d, J=8.0 Hz, 1H), 7.89-7.74 (m, 2H), 7.59 (d, J=8.5 Hz, 2H), 7.48 (t, J=6.2 Hz, 1H), 7.35 (d, J=7.9 Hz, 2H), 7.25 (d, J=7.8 Hz, 2H), 7.08-6.89 (m, 1H), 4.73-4.64 (m, 1H), 4.23-3.81 (m, 8H), 3.75 (s, 1H), 3.73-3.69 (m, 1H), 3.68 (s, 3H), 3.63 (s, 3H), 3.24-3.14 (m, 1H), 2.99-2.79 (m, 4H), 2.32-1.75 (m, 9H), 0.90 (s, 9H), 0.84 (s, 9H). 19F NMR (377 MHz, Methanol-d4) δ −78.01, −114.33.

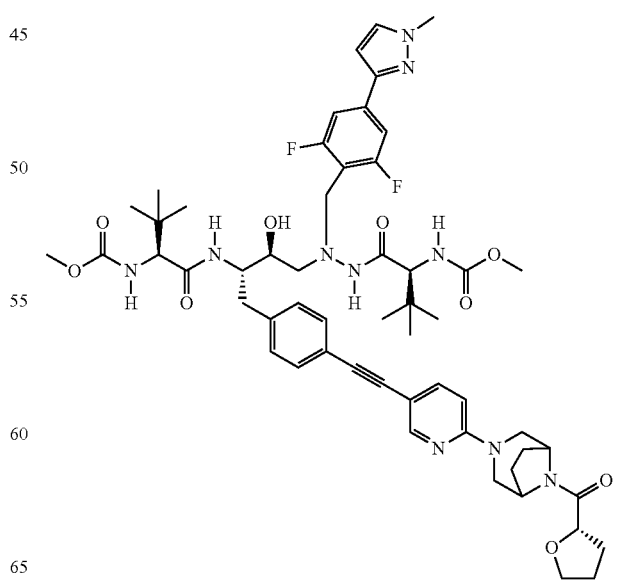

EXAMPLE 227

Methyl ((5S,8S,9S,14S)-5-(tert-butyl)-11-(2,6-difluoro-4-(1-methyl-1H-pyrazol-3-yl)benzyl)-9-hydroxy-15,15-dimethyl-3,6,13-trioxo-8-(4-(((6-(8-((S)-tetrahydrofuran-2-carbonyl)-3,8-diazabicyclo[3.2.1]octan-3-yl)pyridin-3-yl)ethynyl)benzyl)-2-oxa-4,7,11,12-tetraazahexadecan-14-yl)carbamate (227)

Intermediates: I1, P41 and S25. MS (ESI) m/z 1053.3 [M+H]+. 1H NMR (400 MHz, Methanol-d4) δ 8.10 (s, 1H), 7.79-7.64 (m, 2H), 7.52 (d, J=2.3 Hz, 1H), 7.28-7.19 (m, 4H), 7.14 (d, J=8.0 Hz, 2H), 6.89 (t, J=10.6 Hz, 1H), 6.56 (d, J=2.4 Hz, 1H), 4.63-4.55 (m, 1H), 4.09-3.89 (m, 3H), 3.84 (s, 3H), 3.81-3.73 (m, 2H), 3.66 (s, 1H), 3.64-3.60 (m, 1H), 3.58 (s, 3H), 3.56 (s, 3H), 3.10 (d, J=12.2 Hz, 1H), 2.90-2.61 (m, 4H), 2.18-1.67 (m, 7H), 0.80 (s, 9H), 0.75 (s, 9H). 19F NMR (377 MHz, Methanol-d4) δ −77.94, −115.33.

EXAMPLE 228

Methyl ((5S,8S,9S,14S)-8-(4-(((6-(4-acetylpiperazin-1-yl)pyridin-3-yl)ethynyl)benzyl)-5-(tert-butyl)-11-(2,6-difluoro-4-(1-methyl-1H-pyrazol-3-yl)benzyl)-9-hydroxy-15,15-dimethyl-3,6,13-trioxo-2-oxa-4,7,11,12-tetraazahexadecan-14-yl)carbamate (228)

Intermediates: I1, and P41. MS (ESI) m/z 971.3 [M+H]+. 1H NMR (400 MHz, Methanol-d4) δ 8.12 (dd, J=2.2, 0.7 Hz, 1H), 7.73 (d, J=9.4 Hz, 1H), 7.65 (dd, J=9.0, 2.3 Hz, 1H), 7.52 (d, J=2.3 Hz, 1H), 7.32-7.18 (m, 4H), 7.14 (d, J=8.1 Hz, 2H), 6.88 (d, J=9.2 Hz, 1H), 4.10-3.97 (m, 2H), 3.90-3.76 (m, 5H), 3.70-3.50 (m, 15H), 2.90-2.78 (m, 2H), 2.72 (d, J=7.9 Hz, 2H), 2.06 (s, 3H), 0.80 (s, 9H), 0.75 (s, 9H). 19F NMR (377 MHz, Methanol-d4) δ −77.88, −115.32.

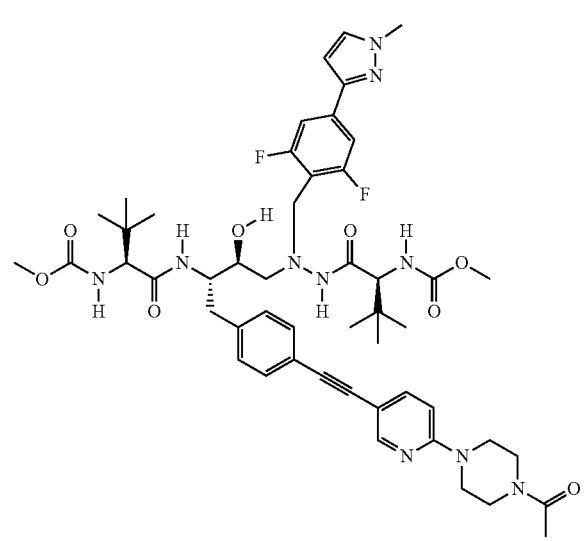 [SMILES: COC(=O)N[C@H](C(=O)N[C@@H](Cc1ccc(C#Cc2ccc(N3CCN(C(C)=O)CC3)nc2)cc1)[C@@H](O)CN(Cc1c(F)cc(-c2ccn(C)n2)cc1F)NC(=O)[C@@H](NC(=O)OC)C(C)(C)C)C(C)(C)C]

EXAMPLE 229

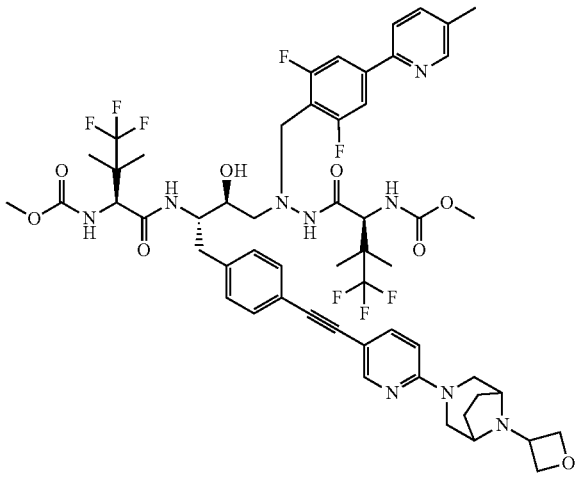 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(C)cn2)cc1F)NC(=O)[C@@H](NC(=O)OC)C(C)(C)C(F)(F)F)C(C)(C)C(F)(F)F]

Methyl ((5S,8S,9S,14S)-11-(2,6-difluoro-4-(5-methylpyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I2, P39, S3. MS (ESI) m/z 1030.2 [M+H]+. ¹H NMR (400 MHz, Methanol-d₄) δ 8.55 (s, 1H), 8.29 (d, J=2.2 Hz, 1H), 8.13 (d, J=9.4 Hz, 1H), 8.01-7.87 (m, 2H), 7.69 (dd, J=8.8, 2.3 Hz, 1H), 7.55 (d, J=8.4 Hz, 2H), 7.33 (d, J=7.9 Hz, 2H), 7.22 (d, J=8.0 Hz, 2H), 7.12 (d, J=9.9 Hz, 1H), 6.86 (d, J=8.9 Hz, 1H), 6.79 (d, J=9.9 Hz, 1H), 4.95 (t, J=7.6 Hz, 2H), 4.85-4.78 (m, 2H), 4.58-4.49 (m, 1H), 4.48-4.40 (m, 1H), 4.40-4.26 (m, 3H), 4.23-4.09 (m, 4H), 3.98 (d, J=13.1 Hz, 1H), 3.79-3.71 (m, 1H), 3.69 (s, 3H), 3.64 (s, 3H), 3.46-3.35 (m, 2H), 2.94-2.87 (m, 3H), 2.80 (t, J=10.9 Hz, 1H), 2.45 (s, 3H), 2.30-2.19 (m, 2H), 2.12-2.00 (m, 2H), 1.16 (s, 3H), 1.15 (s, 3H), 1.12 (s, 3H), 1.03 (s, 3H).

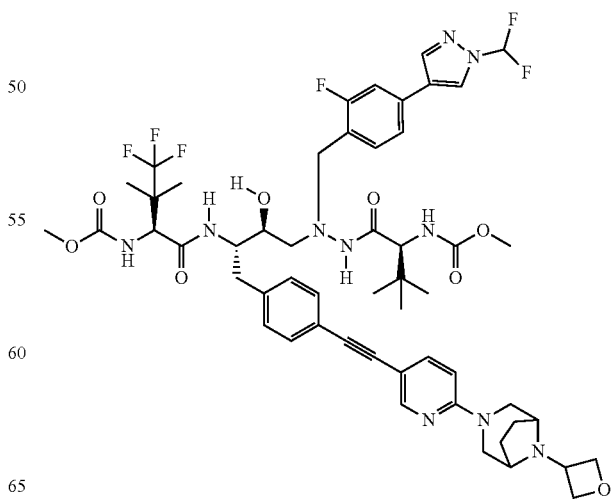

EXAMPLE 230 methyl ((5S,8S,9S,14S)-11-(4-(1-(difluoromethyl)-1H-pyrazol-4-yl)-2-fluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I3, P8, and S3. MS (ESI) m/z 1083.8 [M+H]+. 1H NMR (400 MHz, Methanol-d4) δ 8.11 (d, J=21.6 Hz, 4H), 7.72-7.55 (m, 3H), 7.42-7.29 (m, 5H), 7.22 (d, J=8.1 Hz, 2H), 6.88-6.77 (m, 1H), 4.96 (t, J=7.6 Hz, 2H), 4.81 (dd, J=8.2, 5.0 Hz, 2H), 4.54 (s, 1H), 4.42-4.32 (m, 3H), 4.16 (s, 3H), 4.08-3.91 (m, 2H), 3.81-3.60 (m, 9H), 3.42-3.34 (m, 2H), 2.98-2.70 (m, 4H), 2.27-2.20 (m, 2H), 2.11-2.03 (m, 2H), 1.08 (d, J=22.3 Hz, 6H), 0.80 (s, 10H).

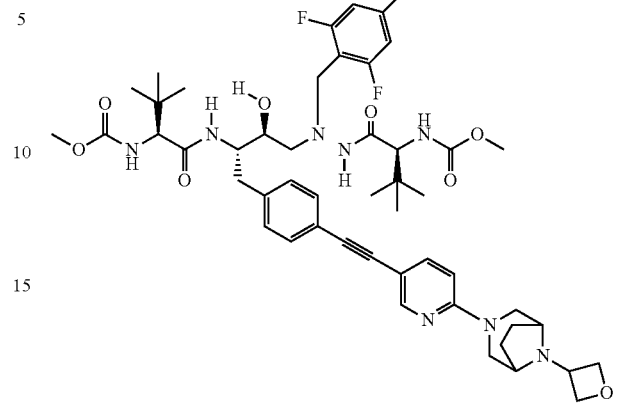

EXAMPLE 231 methyl ((5S,8S,9S,14S)-11-(4-(1-(difluoromethyl)-1H-pyrazol-4-yl)-2-fluorobenzyl)-16-fluoro-5-(1-fluoro-2-methylpropan-2-yl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate Intermediates: I1a, A7, P8, and S3. MS (ESI) m/z 1083.8 [M+H]+. 1H NMR (400 MHz, Methanol-d4) δ 8.48-8.06 (m, 3H), 7.70 (dd, J=8.9, 2.3 Hz, 2H), 7.66-7.55 (m, 1H), 7.43-7.30 (m, 5H), 7.24 (d, J=8.1 Hz, 3H), 4.96 (t, J=7.6 Hz, 2H), 4.82 (dd, J=8.3, 5.1 Hz, 3H), 4.54 (s, 1H), 4.35 (d, J=13.4 Hz, 2H), 4.24-3.89 (m, 12H), 3.83-3.59 (m, 8H), 3.39 (d, J=13.8 Hz, 2H), 3.00-2.72 (m, 4H), 2.28-2.19 (m, 2H), 2.12-2.00 (m, 2H), 0.92-0.75 (m, 13H).

EXAMPLE 232 methyl ((5S,8S,9S,14S)-5-(tert-butyl)-11-(4-(1-(difluoromethyl)-1H-pyrazol-3-yl)-2,6-difluorobenzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate Intermediates: I1, P4, and S3. MS (ESI) m/z 1047.5 [M+H]+. 1H 1H NMR (400 MHz, Methanol-d4) δ 8.30-8.26 (m, 1H), 8.09 (d, J=2.7 Hz, 1H), 7.80 (d, J=9.4 Hz, 1H), 7.68 (dd, J=9.0, 2.5 Hz, 2H), 7.48-7.31 (m, 5H), 7.23 (d, J=8.0 Hz, 2H), 6.93 (d, J=2.8 Hz, 1H), 6.84 (d, J=8.8 Hz, 1H), 4.94 (t, J=7.5 Hz, 2H), 4.46 (s, 1H), 4.30 (d, J=13.8 Hz, 2H), 4.18-4.02 (m, 5H), 4.02-3.88 (m, 3H), 3.79-3.63 (m, 9H), 3.35 (d, J=13.7 Hz, 2H), 2.98-2.77 (m, 5H), 2.24-2.16 (m, 2H), 2.04 (d, J=8.4 Hz, 2H), 0.87 (d, J=21.8 Hz, 19H).

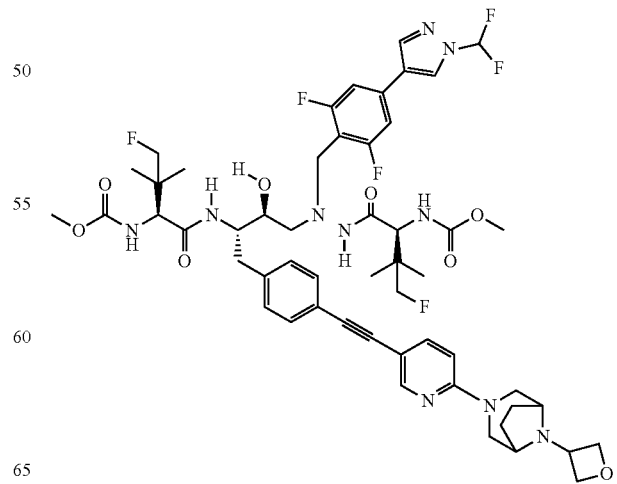

EXAMPLE 233 methyl ((5S,8S,9S,14S)-11-(4-(1-(difluoromethyl)-1H-pyrazol-4-yl)-2,6-difluorobenzyl)-16-fluoro-5-(1-fluoro-2-methylpropan-2-yl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate Intermediates: I1a, A7, P7, and S3. MS (ESI) m/z 1084.0 [M+H]+. 1H NMR (400 MHz, Methanol-d4) δ 8.31-8.28 (m, 1H), 8.12 (s, 1H), 7.88 (d, J=9.4 Hz, 1H), 7.70 (dd, J=8.8, 2.3 Hz, 1H), 7.37-7.21 (m, 7H), 6.86 (d, J=8.9 Hz, 1H), 4.96 (t, J=7.6 Hz, 2H), 4.81 (dd, J=8.0, 5.2 Hz, 3H), 4.52 (s, 1H), 4.35 (d, J=14.0 Hz, 2H), 4.25-3.89 (m, 13H), 3.67 (d, J=8.3 Hz, 8H), 3.37 (d, J=13.8 Hz, 2H), 2.95-2.78 (m, 4H), 2.26-2.19 (m, 2H), 2.07 (d, J=8.6 Hz, 2H), 0.95-0.83 (m, 13H).

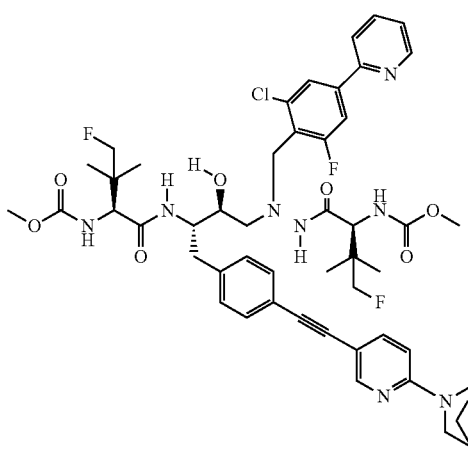

EXAMPLE 234 methyl ((5S,8S,9S,14S)-11-(2-chloro-6-fluoro-4-(pyridin-2-yl)benzyl)-16-fluoro-5-(1-fluoro-2-methylpropan-2-yl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-2-oxa-4,7,11,12-tetraazahexadecan-14-yl)carbamate Intermediates: I1a, A7, P26, and S3. MS (ESI) m/z 1060.3 [M+H]+. 1H NMR (400 MHz, Methanol-d4) δ 8.65 (d, J=4.8 Hz, 1H), 8.31-8.28 (m, 1H), 7.91 (q, J=13.2, 11.5 Hz, 4H), 7.73-7.65 (m, 2H), 7.34 (d, J=7.9 Hz, 2H), 7.24 (d, J=8.0 Hz, 2H), 4.96 (t, J=7.6 Hz, 2H), 4.81 (dd, J=8.3, 5.0 Hz, 3H), 4.52 (s, 1H), 4.35 (d, J=14.1 Hz, 2H), 4.30-3.96 (m, 12H), 3.73 (s, 1H), 3.66 (d, J=16.2 Hz, 6H), 3.38 (d, J=13.8 Hz, 2H), 2.99-2.78 (m, 5H), 2.23 (d, J=10.7 Hz, 2H), 2.07 (d, J=8.7 Hz, 2H), 0.93-0.81 (m, 13H).

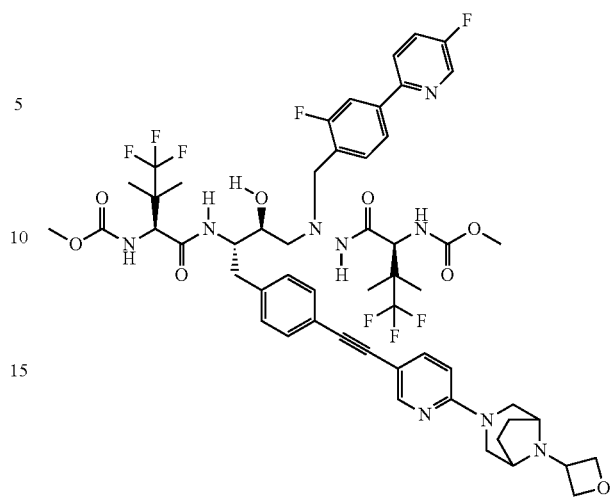

EXAMPLE 235 methyl ((5S,8S,9S,14S)-16,16,16-trifluoro-11-(2-fluoro-4-(5-fluoropyridin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I2, P14, and S3. MS (ESI) m/z 1116.4 [M+H]+.

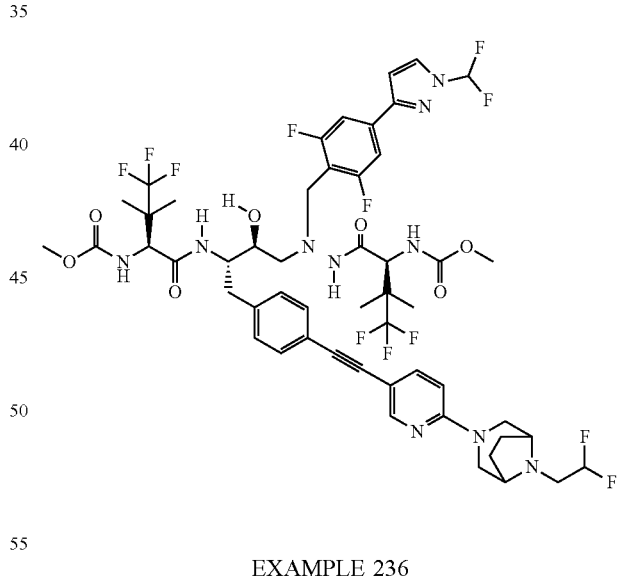

EXAMPLE 236 methyl ((5S,8S,9S,14S)-8-(4-((6-(8-(2,2-difluoroethyl)-3,8-diazabicyclo[3.2.1]octan-3-yl)pyridin-3-yl)ethynyl)benzyl)-11-(4-(1-(difluoromethyl)-1H-pyrazol-3-yl)-2,6-difluorobenzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate Intermediates: P4, A3, and S63. MS (ESI) m/z 1078.4 [M+H]+. 1H NMR (400 MHz, Methanol-d4) δ 8.29-8.24 (m, 1H), 8.18-8.08 (m, 2H), 7.74-7.61 (m, 3H), 7.59-7.51 (m, 2H), 7.45 (d, J=8.2 Hz, 2H), 7.39-7.31 (m, 2H), 7.22 (d, J=8.0 Hz, 2H), 6.93 (d, J=2.7 Hz, 1H), 6.88 (d, J=8.9 Hz, 1H), 4.33-4.28 (m, 1H), 4.27-4.10 (m, 7H), 3.95 (d, J=13.2 Hz, 1H), 3.68 (d, J=10.7 Hz, 10H), 3.42 (d, J=13.5 Hz, 2H), 2.95-2.73 (m, 4H), 2.29 (d, J=10.5 Hz, 2H), 2.08 (d, J=8.6 Hz, 2H), 1.20-1.08 (m, 10H), 1.03 (s, 3H).

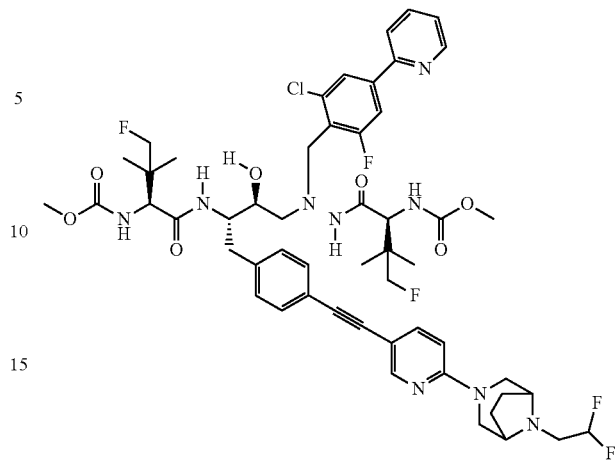

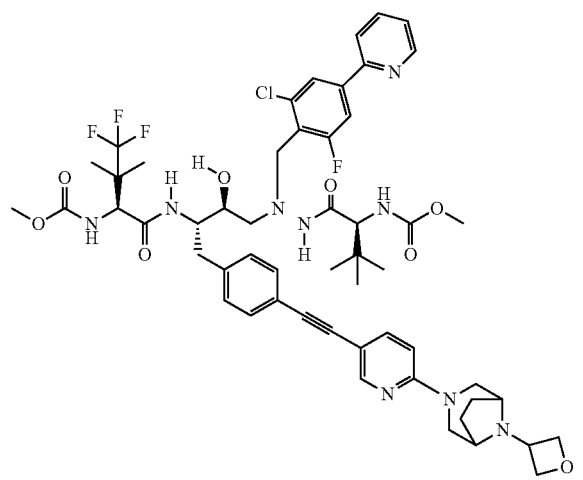

EXAMPLE 237 methyl ((5S,8S,9S,14S)-11-(2-chloro-6-fluoro-4-(pyridin-2-yl)benzyl)-9-hydroxy-15,15-dimethyl-8-(4-(((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I3, P26, and S3. MS (ESI) m/z 1060.3 [M+H]+. 1H NMR (400 MHz, Methanol-d4) δ 8.65 (d, J=4.8 Hz, 1H), 8.12 (d, J=9.4 Hz, 1H), 7.92 (dd, J=18.0, 8.2 Hz, 3H), 7.73-7.65 (m, 2H), 7.42 (t, J=5.5 Hz, 1H), 7.33 (d, J=7.9 Hz, 2H), 7.22 (d, J=8.0 Hz, 2H), 6.86 (d, J=8.9 Hz, 1H), 4.96 (t, J=7.6 Hz, 2H), 4.81-4.76 (m, 3H), 4.46-4.23 (m, 5H), 4.18-4.03 (m, 5H), 3.68 (s, 5H), 3.62 (s, 3H), 3.37 (d, J=14.0 Hz, 3H), 2.96-2.75 (m, 4H), 2.23 (d, J=10.2 Hz, 2H), 2.08 (d, J=8.7 Hz, 2H), 1.12 (d, J=16.0 Hz, 7H), 0.84 (s, 10H).

EXAMPLE 238 methyl ((5S,8S,9S,14S)-11-(2-chloro-6-fluoro-4-(pyridin-2-yl)benzyl)-8-(4-(((6-(8-(2,2-difluoroethyl)-3,8-diazabicyclo[3.2.1]octan-3-yl)pyridin-3-yl)ethynyl)benzyl)-16-fluoro-5-(1-fluoro-2-methylpropan-2-yl)-9-hydroxy-15,15-dimethyl-3,6,13-trioxo-2-oxa-4,7,11,12-tetraazahexadecan-14-yl)carbamate Intermediates: I1a, A7, P26, and S63. MS (ESI) m/z 1068.6 [M+H]+. 1H NMR (400 MHz, Methanol-d4) δ 8.65 (d, J=4.9 Hz, 1H), 8.28-8.24 (m, 1H), 8.00-7.82 (m, 4H), 7.75-7.65 (m, 2H), 7.47-7.41 (m, 1H), 7.34 (d, J=7.9 Hz, 2H), 7.24 (d, J=8.0 Hz, 2H), 6.88 (d, J=8.9 Hz, 1H), 4.31-3.95 (m, 15H), 3.66 (d, J=15.6 Hz, 10H), 3.43 (d, J=13.4 Hz, 2H), 2.99-2.79 (m, 4H), 2.34-2.24 (m, 2H), 2.08 (t, J=7.0 Hz, 2H), 0.96-0.80 (m, 14H).

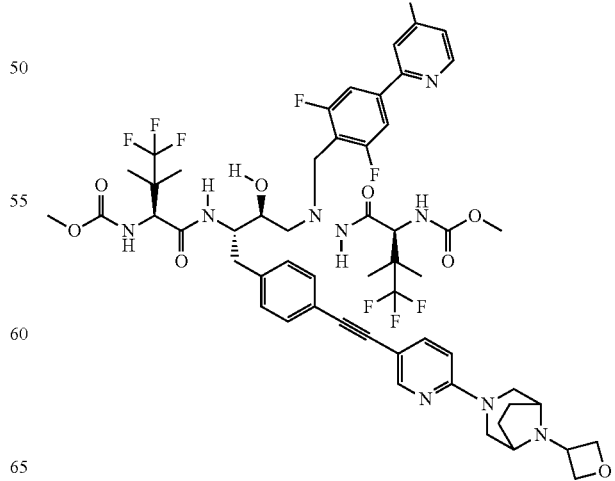

EXAMPLE 239 methyl ((5S,8S,9S,14S)-11-(2,6-difluoro-4-(4-fluoropyridin-2-yl)benzyl)-16,16,16-trifluoro-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I2, P15, and S3. MS (ESI) m/z 1134.4 [M+H]+. 1H NMR (400 MHz, Methanol-d4) δ 8.65 (dd, J=8.6, 5.6 Hz, 1H), 8.29 (d, J=2.2 Hz, 1H), 8.12 (d, J=9.5 Hz, 1H), 7.78-7.61 (m, 5H), 7.33 (d, J=7.8 Hz, 2H), 7.25-7.18 (m, 3H), 6.85 (d, J=8.9 Hz, 1H), 4.96 (t, J=7.6 Hz, 2H), 4.53 (s, 1H), 4.44 (d, J=9.7 Hz, 1H), 4.33 (dd, J=19.5, 12.0 Hz, 4H), 4.17 (d, J=14.3 Hz, 5H), 3.98 (d, J=13.1 Hz, 1H), 3.67 (d, J=16.2 Hz, 8H), 3.38 (d, J=13.8 Hz, 2H), 2.96-2.75 (m, 5H), 2.23 (d, J=11.2 Hz, 2H), 2.08 (d, J=8.6 Hz, 2H), 1.18-1.10 (m, 10H), 1.03 (s, 3H).

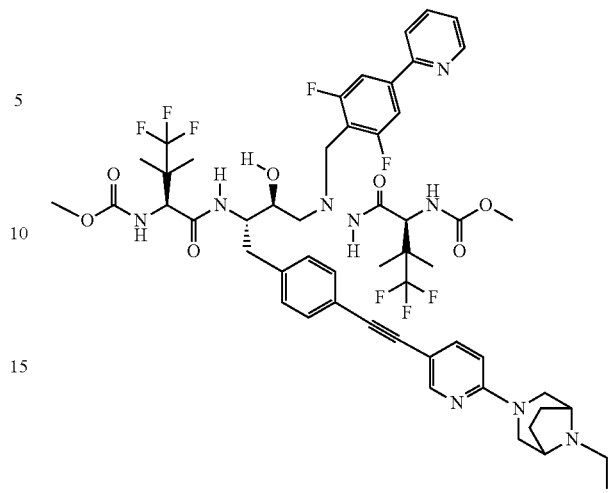

EXAMPLE 241 methyl ((5S,8S,9S,14S)-11-(2,6-difluoro-4-(pyridin-2-yl)benzyl)-8-(4-((6-(8-ethyl-3,8-diazabicyclo[3.2.1]octan-3-yl)pyridin-3-yl)ethynyl)benzyl)-16,16,16-trifluoro-9-hydroxy-15,15-dimethyl-3,6,13-trioxo-5-(1,1,1-trifluoro-2-methylpropan-2-yl)-2-oxa-4,7,11,12-tetraazahexadecan-14-yl)carbamate Intermediates: I2, P28, and S21. MS (ESI) m/z 1088.1 [M+H]+.

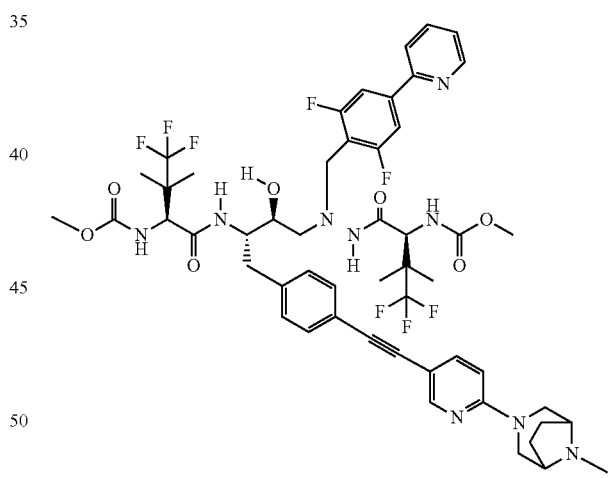

EXAMPLE 240 methyl ((5S,8S,9S,14S)-11-(2,6-difluoro-4-(pyridin-2-yl)benzyl)-16,16,16-trifluoro-9-hydroxy-8-(4-((6-(8-isopropyl-3,8-diazabicyclo[3.2.1]octan-3-yl)pyridin-3-yl)ethynyl)benzyl)-15,15-dimethyl-3,6,13-trioxo-5-(1,1,1-trifluoro-2-methylpropan-2-yl)-2-oxa-4,7,11,12-tetraazahexadecan-14-yl)carbamate Intermediates: I2, P28, and S22. MS (ESI) m/z 1102.1 [M+H]+.

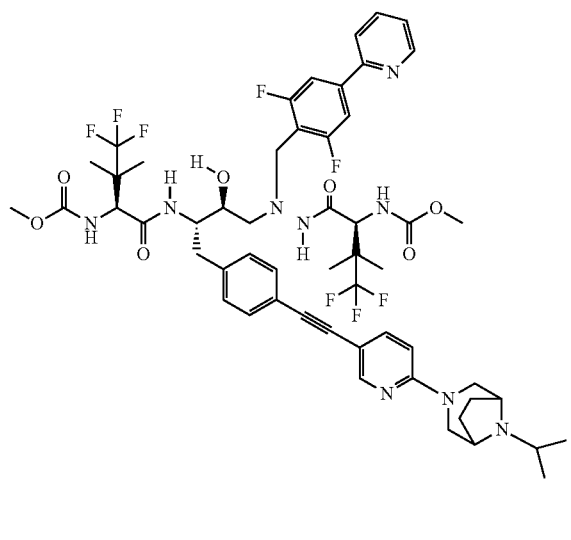

EXAMPLE 242 methyl ((5S,8S,9S,14S)-11-(2,6-difluoro-4-(pyridin-2-yl)benzyl)-16,16,16-trifluoro-9-hydroxy-15,15-dimethyl-8-(4-((6-(8-methyl-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I2, P28, and S20. MS (ESI) m/z 1074.4 [M+H]+. 1H NMR (400 MHz, Methanol-d4) δ 8.65 (d, J=5.1 Hz, 1H), 8.29 (s, 1H), 7.92 (d, J=8.1 Hz, 2H), 7.68 (d, J=9.0 Hz, 1H), 7.60 (d, J=8.6 Hz, 2H), 7.33 (d, J=7.9 Hz, 2H), 7.22

(d, J=8.0 Hz, 2H), 6.84 (d, J=8.9 Hz, 1H), 4.44 (d, J=9.7 Hz, 1H), 4.33 (dd, J=19.0, 11.6 Hz, 3H), 4.20-4.06 (m, 5H), 3.98 (d, J=13.0 Hz, 1H), 3.66 (d, J=21.3 Hz, 8H), 3.26 (s, 1H), 2.91 (d, J=7.9 Hz, 7H), 2.31 (s, 2H), 2.07 (d, J=8.8 Hz, 2H), 1.19-1.10 (m, 11H), 1.03 (s, 3H).

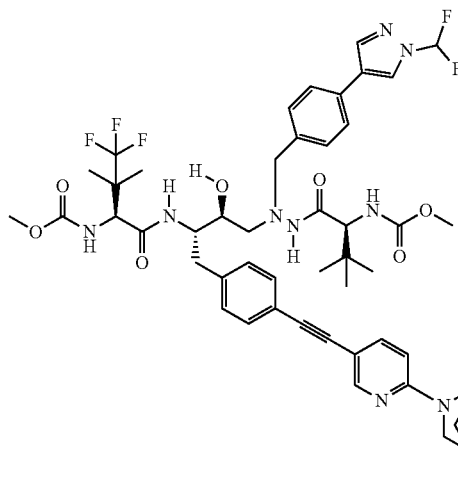

EXAMPLE 243 methyl ((5S,8S,9S,14S)-11-(4-(1-(difluoromethyl)-1H-pyrazol-4-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamat Intermediates: I3, P9, and S3. MS (ESI) m/z 1065.6 [M+H]⁺. ¹H NMR (400 MHz, Methanol-d4) δ 8.39-8.28 (m, 2H), 8.08 (d, J=26.3 Hz, 2H), 7.70 (dd, J=8.8, 2.3 Hz, 1H), 7.54 (d, J=8.0 Hz, 2H), 7.48 (s, 1H), 7.43 (d, J=8.1 Hz, 2H), 7.32 (d, J=8.0 Hz, 2H), 7.21 (d, J=8.0 Hz, 2H), 6.88-6.73 (m, 2H), 4.96 (t, J=7.6 Hz, 2H), 4.81 (dd, J=8.2, 5.0 Hz, 2H), 4.52 (s, 1H), 4.37 (t, J=13.2 Hz, 3H), 4.15 (s, 3H), 3.95 (t, J=10.7 Hz, 2H), 3.78 (d, J=9.5 Hz, 1H), 3.69 (d, J=10.5 Hz, 5H), 3.62 (s, 3H), 3.38 (d, J=13.9 Hz, 2H), 2.90 (t, J=7.0 Hz, 2H), 2.79 (t, J=11.1 Hz, 2H), 2.23 (d, J=11.0 Hz, 2H), 2.07 (d, J=8.6 Hz, 2H), 1.09 (s, 3H), 1.01 (s, 3H), 0.76 (s, 10H).

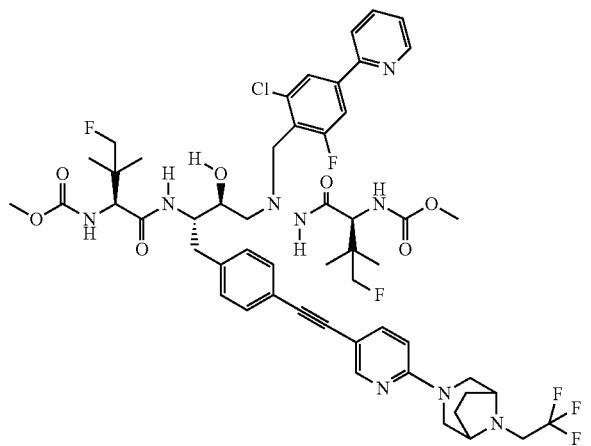

EXAMPLE 244 methyl ((5S,8S,9S,14S)-11-(2-chloro-6-fluoro-4-(pyridin-2-yl)benzyl)-16-fluoro-5-(1-fluoro-2-methylpropan-2-yl)-9-hydroxy-15,15-dimethyl-3,6,13-trioxo-8-(4-((6-(8-(2,2,2-trifluoroethyl)-3,8-diazabicyclo[3.2.1]octan-3-yl)pyridin-3-yl)ethynyl)benzyl)-2-oxa-4,7,11,12-tetraazahexadecan-14-yl) carbamate Intermediates: I1a, A7, P26, and S62. MS (ESI) m/z 1086.4 [M+H]⁺. ¹H 1H NMR (400 MHz, Methanol-d4) δ 8.67-8.62 (m, 1H), 7.99-7.80 (m, 5H), 7.71-7.61 (m, 2H), 7.59-7.51 (m, 1H), 7.44 (dd, J=7.1, 5.1 Hz, 1H), 7.36 (d, J=7.9 Hz, 2H), 7.25 (d, J=8.0 Hz, 2H), 4.30-3.96 (m, 10H), 3.90 (d, J=9.1 Hz, 1H), 3.84 (d, J=11.5 Hz, 2H), 3.77-3.46 (m, 10H), 3.23-3.11 (m, 3H), 2.99-2.80 (m, 5H), 2.08-1.98 (m, 3H), 1.78 (t, J=7.1 Hz, 2H), 0.95-0.80 (m, 12H).

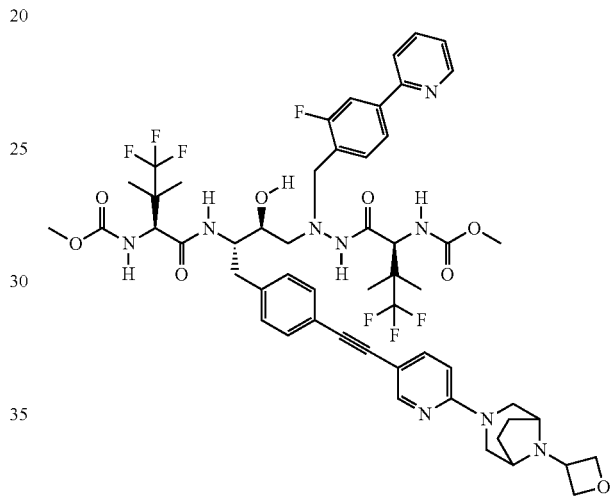

EXAMPLE 245

Methyl ((5S,8S,9S,14S)-16,16,16-trifluoro-11-(2-fluoro-4-(pyridin-2-yl)benzyl)-9-hydroxy-15,15-dimethyl-8-(4-((6-(8-(oxetan-3-yl)-3,8-diazabicyclo[3.2.1]octan-3-yl)pyridin-3-yl)ethynyl)benzyl)-3,6,13-trioxo-5-(1,1,1-trifluoro-2-methylpropan-2-yl)-2-oxa-4,7,11,12-tetraazahexadecan-14-yl)carbamate Intermediates: I2, P29, and S3. MS (ESI) m/z 1098.7 [M+H]⁺. ¹H NMR (400 MHz, Methanol-d4) δ 8.65-8.61 (m, 1H), 8.29 (d, J=2.3 Hz, 1H), 8.11 (d, J=9.1 Hz, 1H), 7.92 (dd, J=18.5, 7.8 Hz, 2H), 7.75-7.62 (m, 4H), 7.33 (d, J=7.8 Hz, 2H), 7.22 (d, J=8.0 Hz, 2H), 7.15 (d, J=9.9 Hz, 1H), 6.85 (d, J=8.9 Hz, 1H), 4.96 (t, J=7.6 Hz, 3H), 4.82-4.76 (m, 2H), 4.53-4.12 (m, 10H), 3.99 (d, J=13.7 Hz, 3H), 3.76 (s, 1H), 3.68 (s, 3H), 3.58 (s, 3H), 3.37 (d, J=14.0 Hz, 2H), 2.86 (dd, J=31.3, 7.8 Hz, 4H), 2.22 (d, J=10.8 Hz, 2H), 2.07 (d, J=8.8 Hz, 2H), 1.18-1.05 (m, 9H), 0.94 (s, 3H).

4. Biological Assays

MT-4 HIV Assay.

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Agilent ECHO acoustic dispenser. Each plate contained up to 8 test compounds, with negative (No Drug Control) and 5 uM AZT positive controls. MT-4 cells were pre-infected with 10 uL of either RPMI (mock-infected) or a fresh 1:250 dilution of an HIV-1 (IIIB) concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates to quantify the amount of luciferase. $EC_{50}$ and $CC_{50}$ values were defined as the compound concentration that causes a 50% decrease in luminescence signal, and were calculated using a sigmoidal dose-response model to generate curve fits. Data for certain compounds is reported in Table 1 below.

MT-4 HIV High Resolution Antiviral Assay

Assay protocol is identical to that described for the MT-4 antiviral assay with the following changes: Each drug is run in 2 series of quadruplicates with different starting concentrations for each series and 19 1.5 fold dilutions performed across the plate. This results in an inhibition curve with 40 data points for each compound. Data is analyzed and Hill coefficients determined in Graph Pad Prism (San Diego, Calif.). $EC_{95}$s were determined by the formula $EC_{95}=(19)^{1/hill\ coefficient} \times EC_{50}$. HD values were determined for certain compounds and reported in Table 5 below as an illustrative example.

Liver Microsomal Stability Protocol

Test compounds and one control compound (verapamil) were tested in 3 different species in duplicate sets.

General Conditions:

Test compound concentration: 1 uM; Protein concentration: 0.5 mg/mL (for dog, rat, and human liver microsomes); Cofactor: NADPH-Regenerating system (NRS) solution; Time-points: 2, 12, 25, 45, and 65 minutes.

Reaction composition (in each incubation well) contains:

| | |
|---|---|
| 5 uL | compound (50 uM stock solution, 50:50 ACN:H2O) |
| 25 uL | NRS solution |
| 6.25 uL | 20 mg/mL liver microsomes |
| 213.75 uL | 100 mM KPO4, pH 7.4 |
| 250 uL | total volume |

At an incubation temperature of 37° C., the reaction was started with addition of NADPH Regeneration System, at each time point, 25 uL of the reaction mixture was removed and added to a plate with 225 uL quenching solution (50% MeOH, 25% ACN, 25% H2O, and 200 nM labetalol as internal standard). After plates were vortexed, they were centrifuged for 30 minutes to remove proteins. About 100 μL supernatant was removed to a new plate and diluted with 150 μL water. About 20 μL of the mixture was injected into LC/MS/MS system to monitor the compound's response. In vitro measured t1/2 was used to calculate Clint values. Data is presented in Table 1 below and FIG. 1.

TABLE 1

| Cmpd | $EC_{50}$ (nM) | Rat. Pred. Cl. (L/H/kg) | Dog. Pred. Cl. (L/H/kg) | Human Pred Cl. (L/H/kg) |
|---|---|---|---|---|
| 1 | — | — | | — |
| 2 | 2.64 | | | |
| 3 | 6.95 | | | |
| 4 | 2.82 | | | |
| 5 | 4.37 | | | |
| 6 | 3.56 | 0.22 | | <0.11 |
| 7 | 3.61 | 0.21 | | <0.11 |
| 8 | 2.46 | | | |
| 9 | 10.13 | | | |
| 10 | 3.46 | | | |
| 11 | 3.72 | 0.18 | | 0.18 |
| 12 | 3.11 | | | |
| 13 | 6.3 | | | |
| 14 | 4.39 | 1.13 | | 0.66 |
| 15 | 4.22 | | | |
| 16 | 4.64 | 0.45 | | <0.11 |
| 17 | 7.24 | | | |
| 18 | 5 | 1.03 | | 0.13 |
| 19 | 8.43 | 0.29 | | <0.11 |
| 20 | 4.39 | 0.18 | | 0.34 |
| 21 | 2.32 | | | |
| 22 | 3.24 | | | |
| 23 | 4.82 | 0.22 | 0.21 | <0.11 |
| 24 | 3.82 | | | |
| 25 | 3.19 | 1.41 | | 0.16 |
| 26 | 4.24 | 1.6 | | <0.11 |
| 27 | 3.5 | | | |
| 28 | 4.56 | | | |
| 29 | 4.02 | | | |
| 30 | 4.44 | | | |
| 31 | 3.06 | 0.75 | | <0.11 |
| 32 | 2.65 | 0.59 | | <0.11 |
| 33 | 4.71 | | | |
| 34 | 5.26 | | | |
| 35 | 3.54 | 2.1 | 1.74 | <0.11 |
| 36 | 3.68 | 0.27 | | <0.11 |
| 37 | 6.75 | 0.32 | | <0.11 |
| 38 | 6.13 | | | |
| 39 | 2.57 | 0.54 | | 0.15 |
| 40 | 3.89 | 0.5 | | 0.13 |
| 41 | 3.58 | | | |
| 42 | 3.18 | | | |
| 43 | 2.87 | 1.01 | 1.66 | 0.16 |
| 44 | 3.97 | 2.54 | | 0.13 |
| 45 | 2.56 | 0.92 | | <0.11 |
| 46 | 4.34 | 0.19 | 1.64 | <0.11 |
| 47 | 7.18 | | | |
| 48 | 114.29 | 0.18 | | <0.11 |
| 49 | 37.3 | | | |
| 50 | 4.31 | <0.18 | | <0.11 |
| 51 | 2.8 | | | <0.11 |
| 52 | 8.15 | <0.18 | | 0.14 |
| 53 | 2.98 | 0.2 | | 0.51 |
| 54 | 8.47 | | | |
| 55 | 4.44 | | | |
| 56 | 3.59 | 0.19 | 1.47 | 0.17 |
| 57 | 2.91 | <0.18 | | <0.11 |
| 58 | 4.79 | 0.24 | | <0.11 |
| 59 | 3.38 | 0.83 | | 0.6 |
| 60 | 3.42 | 0.65 | | 0.12 |
| 61 | 4.11 | <0.18 | | <0.11 |
| 62 | 8.83 | | | |
| 63 | 4.25 | 0.2 | 0.86 | <0.11 |
| 64 | 5.4 | | | |
| 65 | 7.7 | | | |
| 66 | 14.52 | | | |
| 67 | 6.25 | 1.43 | | 0.41 |
| 68 | 7.25 | 0.61 | | <0.11 |
| 69 | 3.24 | <0.18 | | <0.11 |
| 70 | 4.79 | <0.18 | | <0.11 |
| 71 | 3.37 | <0.18 | 0.47 | <0.11 |
| 72 | 5.19 | <0.18 | | 0.14 |
| 73 | 4.72 | <0.18 | | 0.13 |
| 74 | 6.79 | 0.2 | 1.53 | 0.17 |
| 75 | 3.41 | 0.21 | | <0.11 |
| 76 | 3.53 | | | |
| 77 | 2.49 | 0.25 | | <0.11 |
| 78 | 6.27 | <0.18 | | <0.11 |
| 79 | 3.53 | <0.18 | | <0.11 |
| 80 | 3.13 | | | |

TABLE 1-continued

| Cmpd | EC$_{50}$ (nM) | Rat. Pred. Cl. (L/H/kg) | Dog. Pred. Cl. (L/H/kg) | Human Pred Cl. (L/H/kg) |
|---|---|---|---|---|
| 81 | 4.39 | 0.39 | | <0.11 |
| 82 | 4.4 | 0.44 | | 0.82 |
| 83 | 17.25 | | | |
| 84 | 3.23 | | | |
| 85 | 3.78 | 0.19 | | 0.13 |
| 86 | 2.61 | <0.18 | | <0.11 |
| 87 | 4.26 | 0.23 | | 0.13 |
| 88 | 4.57 | <0.18 | 1.63 | <0.11 |
| 89 | 3.32 | <0.18 | 1.67 | <0.11 |
| 90 | 3.45 | 0.67 | | 0.14 |
| 91 | 3.69 | | | |
| 92 | 3.72 | | | |
| 93 | 2.49 | 1.13 | | 0.19 |
| 94 | 2.57 | | | |
| 95 | 2.44 | 1.39 | | 0.38 |
| 96 | 2.33 | | | |
| 97 | 4.54 | 0.31 | | 0.46 |
| 98 | 4.97 | 0.65 | | 0.26 |
| 99 | 7.96 | 0.26 | | <0.11 |
| 100 | 7.96 | | | |
| 101 | 4.22 | | | <0.11 |
| 102 | 5.68 | <0.18 | | 0.18 |
| 103 | 4.84 | 0.32 | | 0.16 |
| 104 | 4.97 | | | |
| 105 | 3.16 | | | 0.39 |
| 106 | 4.04 | | | |
| 107 | 2.23 | | | 1.1 |
| 108 | 7.23 | | | |
| 109 | 59.71 | | | |
| 110 | 30.8 | | | |
| 111 | 7.22 | | | |
| 112 | 4.45 | 0.32 | | <0.11 |
| 113 | 6.01 | | | |
| 114 | 5.1 | 0.28 | | <0.11 |
| 115 | 3.19 | <0.18 | | 0.12 |
| 116 | 2.79 | 0.39 | | 0.19 |
| 117 | 4.15 | | | |
| 118 | 10.61 | | | |
| 119 | 3.66 | 0.27 | 1.35 | <0.11 |
| 120 | 5.36 | 0.53 | | 0.14 |
| 121 | 3.31 | <0.18 | | <0.11 |
| 122 | 4.57 | | | <0.11 |
| 123 | 4.16 | <0.18 | | <0.11 |
| 124 | 6.32 | 0.5 | | <0.11 |
| 125 | | | | |
| 126 | 4.13 | <0.18 | | 0.45 |
| 127 | 4.19 | 1.3 | | 0.54 |
| 128 | 3.16 | 0.37 | | 0.15 |
| 129 | 3.62 | | | <0.11 |
| 130 | 3.41 | <0.18 | | 0.32 |
| 131 | 5.24 | | | <0.11 |
| 132 | 18.24 | | | |
| 133 | 3.44 | <0.18 | | <0.11 |
| 134 | 5.52 | <0.18 | | <0.11 |
| 135 | 3.64 | | | |
| 136 | 3.85 | | | |
| 137 | 3.31 | | | |
| 138 | 2.32 | 0.95 | | 0.17 |
| 139 | 3.92 | | | |
| 140 | 5.09 | | | |
| 141 | 6.68 | | | |
| 142 | 8.78 | | | |
| 143 | 7.79 | | | |
| 144 | 5.12 | | | 0.95 |
| 145 | 5.06 | | | <0.11 |
| 146 | 8.17 | | | <0.11 |
| 147 | 6.79 | | | <0.11 |
| 148 | 6.95 | | | |
| 149 | 8.3 | | | |
| 150 | 5.86 | | | |
| 151 | 4.82 | | | |
| 152 | 6.16 | | | |
| 153 | | | | |
| 154 | 4.81 | <0.18 | | <0.11 |
| 155 | 8.95 | | | |
| 156 | 17.04 | | | |
| 157 | 4.53 | | | |
| 158 | 4.37 | 0.22 | | <0.11 |
| 159 | 3.83 | | | <0.11 |
| 160 | 5700 | | | |
| 161 | 14 | | | <0.11 |
| 162 | 12.25 | | | |
| 163 | 2.32 | | | <0.11 |
| 164 | 7.89 | | | |
| 165 | 4.05 | 3.2 | | 0.56 |
| 166 | 7.06 | | | |
| 167 | 4.97 | | | <0.11 |
| 168 | 5.48 | 2.42 | | 0.19 |
| 169 | 6.76 | | | |
| 170 | 4.13 | <0.18 | | <0.11 |
| 171 | 4.59 | 0.215 | 0.27 | <0.11 |
| 172 | 5.86 | | | |
| 173 | 2.55 | 1.2 | | <0.11 |
| 174 | 2.33 | 0.69 | | 0.18 |
| 175 | 2.17 | 0.7 | | 0.67 |
| 176 | 3.36 | 0.75 | | <0.11 |
| 177 | 8.12 | | | |
| 178 | 10.32 | | | |
| 179 | 3.55 | 0.27 | | 0.33 |
| 180 | 3.69 | <0.18 | | <0.11 |
| 181 | 8.5 | | | |
| 182 | 8.82 | | | |
| 183 | | — | | — |
| 184 | 3.66 | <0.18 | | <0.11 |
| 185 | 2.58 | 0.31 | | 0.32 |
| 186 | 4.74 | | | <0.11 |
| 187 | 4.7 | | | |
| 188 | 9 | | | |
| 189 | 5.47 | | | |
| 190 | 7.06 | | | |
| 191 | 17.42 | | | |
| 192 | 2.89 | 0.36 | 1.04 | 0.22 |
| 193 | 2.78 | | | |
| 194 | 7.2 | | | |
| 195 | 2.76 | 0.52 | | 0.12 |
| 196 | 10.54 | | | |
| 197 | 2.61 | 0.32 | | <0.11 |
| 198 | 2.19 | 0.33 | | <0.11 |
| 199 | 2.72 | 0.48 | 0.91 | <0.11 |
| 200 | 4.36 | 0.19 | | <0.11 |
| 201 | 2.67 | 0.49 | | 0.27 |
| 202 | 9.67 | | | |
| 203 | 5.02 | 1.09 | | 0.32 |
| 204 | 3.18 | 0.48 | | 0.19 |
| 205 | 5.25 | | | |
| 206 | 3.7 | 1.03 | | 0.41 |
| 207 | 2.46 | 0.92 | | 0.25 |
| 208 | 2.51 | 0.74 | | 0.16 |
| 209 | 3.19 | 1.21 | | 1.12 |
| 210 | 14.98 | <0.18 | | 0.18 |
| 211 | 5.75 | | | |
| 212 | 4.97 | 0.33 | | 0.33 |
| 213 | 4.86 | | | |
| 214 | 12.33 | <0.18 | | <0.11 |
| 215 | 18.21 | | | |
| 216 | 114.29 | | | |
| 217 | 113.31 | | | |
| 218 | 2.99 | 0.45 | | 0.92 |
| 219 | 4.1 | 0.24 | 0.19 | <0.11 |
| 220 | 7.66 | 0.34 | 0.46 | <0.11 |
| 221 | 4.49 | 0.28 | 0.14 | <0.11 |
| 222 | 12.93 | | | |
| 223 | 12.88 | | | |
| 224 | 4.12 | | | |
| 225 | 4.26 | | | |
| 226 | 14.93 | | | |
| 227 | 2.9 | | | |
| 228 | 1.66 | | | |
| 229 | 7.86 | 0.26 | | <0.11 |
| 230 | 3.97 | | | |
| 231 | 2.77 | | | |
| 232 | 2.47 | | | |
| 233 | 2.71 | <0.18 | | <0.11 |
| 234 | 2.54 | | | |

TABLE 1-continued

| Cmpd | EC$_{50}$ (nM) | Rat. Pred. Cl. (L/H/kg) | Dog. Pred. Cl. (L/H/kg) | Human Pred Cl. (L/H/kg) |
|---|---|---|---|---|
| 235 | 16.74 | | | |
| 236 | 37.03 | | | |
| 237 | 4.89 | | | |
| 238 | 12.3 | | | |
| 239 | 4.45 | <0.18 | | <0.11 |
| 240 | 5.62 | | | |
| 241 | 6.57 | | | |
| 242 | 3.45 | | | |
| 243 | 5.32 | | | |
| 244 | 19.53 | | | |
| 245 | 3.59 | | | |
| DRV | | 2.8 | 1.2 | 1.2 |
| ATV | | 3.7 | 1.4 | 1.07 |

3H Human Predicted Clearance Assay:

For certain compounds, tritiated analogs (H$^3$) were prepared to further determined their human predicted clearance with increased resolution. Those studies were performed as described above using the tritiated analogs. Data from those compounds is found in Table 2 below and reported in FIG. 1 (note ATV and DRV were not tritiated).

TABLE 2

| Compound | 3H Human Predicted Cl. |
|---|---|
| 23 | 0.07 |
| 36 | 0.1 |
| 46 | 0.04 |
| 51 | 0.11 |
| 58 | 0.05 |
| 88 | 0.08 |
| 73 | 0.09 |
| 75 | 0.11 |
| 89 | 0.08 |
| 101 | 0.08 |
| 112 | 0.11 |
| 153 | 0.43 |
| 170 | 0.05 |
| 171 | 0.02 |
| 173 | 0.14 |
| 176 | 0.09 |
| 199 | 0.15 |
| 208 | 0.11 |
| 239 | 0.13 |

Pharmacokinetic Profiling
Dog PK

Test compound was formulated in 5% EtOH, 55% PEG 300 and 40% Water (pH 2, HCl) for IV infusion administration and was formulated in 5% Ethanol, 55% PEG 300, 1% Tween 80 and 39% water (pH 2) for oral dosing. Each dosing group consisted of three non-naïve male beagle dogs. At dosing, the animals weighed between 9 to 12 kg. The animals were fasted overnight prior to dose administration and up to four hours after dosing. The test article was administered by intravenous infusion over 30-minutes. The rate of infusion was adjusted according to the body weight of each animal to deliver a dose of 0.5 or 1.0 mg/kg. For the oral dosing group, the test article was administered by oral gavage at a dose volume of 2 mL/kg.

Figure 2:
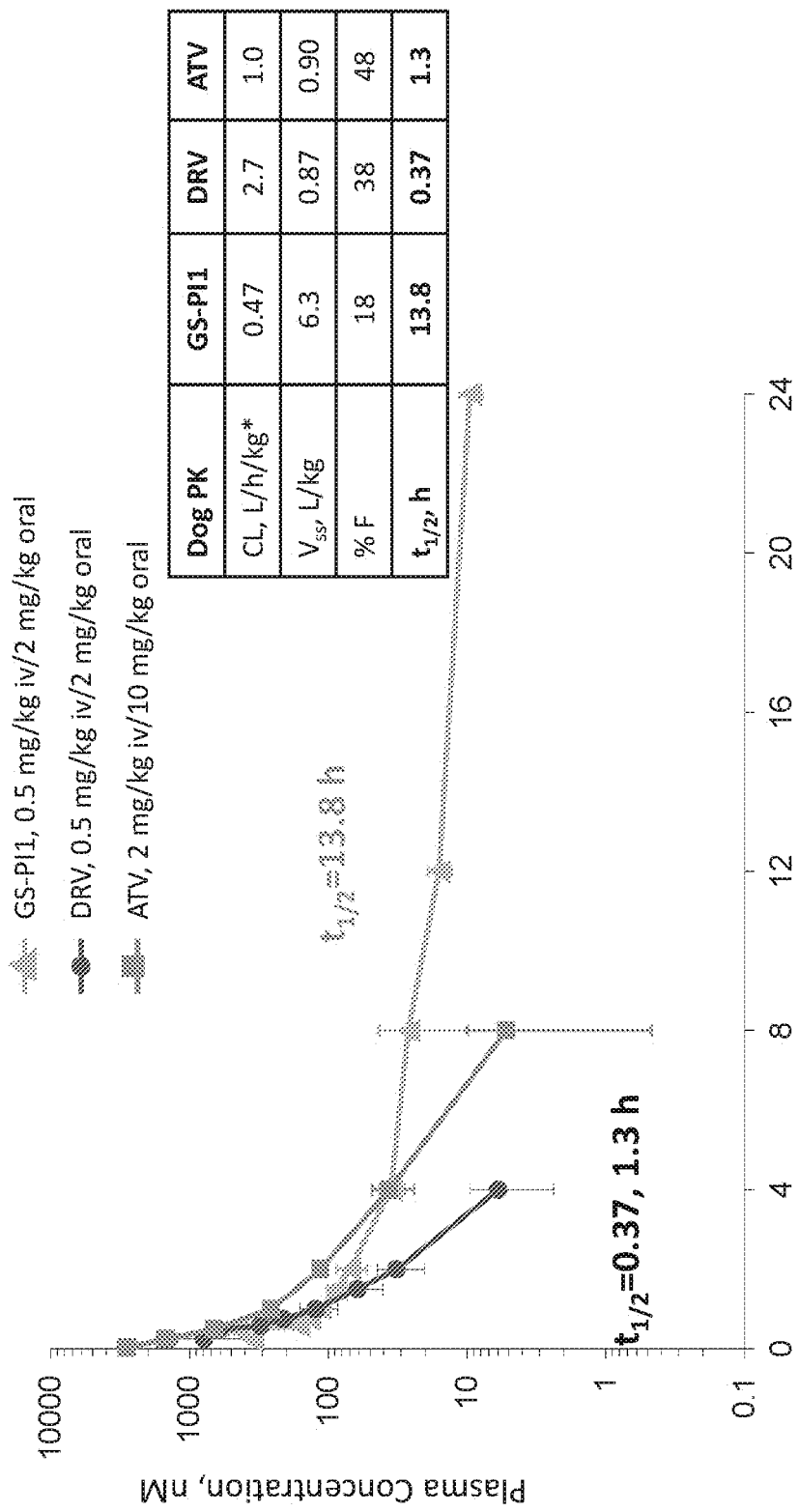
FIG. 2 describes a graph of the IV dog pharmacokinetic studies for certain compounds and reference compounds and table summarizing IV and oral PK data for those compounds as more fully described in the examples herein.

Serial venous blood samples (approximately 1.0 mL each) were collected at predose and 0.25, 0.48, 0.58, 0.75, 1.0, 1.5, 2, 4, 8, 12 and 24 hours post dose from each animal for the IV dosing group; blood samples were collected at predose, 0.25, 0.50, 1, 2 4, 6, 8, 12 and 24 hours post dose for the oral dosing group. The blood samples were collected into Vacutainer™ tubes containing EDTA-K2 as the anti-coagulant and were immediately placed on wet ice pending centrifugation for plasma. An LC/MS/MS method was used to measure the concentration of test compound in plasma. Non-compartmental pharmacokinetic analysis was performed on the plasma concentration-time data. Data for certain compounds are reported in FIG. 2 and Table 3 below. VSS=apparent volume of distribution, t1/2=half life, F=oral bioavailability.

TABLE 3

| Compound | DOG IV CL (L/HR/KG) | DOG IV VSS (L/KG) | DOG IV T1/2 (HR) | DOG PO F (%) | DOG PO DOSE (mg/kg) |
|---|---|---|---|---|---|
| 58 | 0.47 | 6.34 | 13.8 | 18 | 2 |
| 63 | 0.28 | 2.4 | 8.16 | | |
| 170 | 1.39 | 4.35 | 7.62 | 2.45 | 2 |
| 171 | 0.26 | 3.12 | 13.4 | 23 | 2 |
| DRV | 2.7 | 0.87 | 0.37 | 38 | 2 |
| ATV | 1.0 | 0.90 | 1.3 | 48 | 10 |

Rat PK:

Test article was formulated in 5% Ethanol, 55% PEG 300 and 40% Water (pH 2) for IV infusion administration and was formulated in 5% Ethanol, 55% PEG 300, 1% Tween 80 and 39% water (pH 2) for oral administration. Each dosing group consisted of 3 male naïve SD Rats. At dosing, the animals weighed between 0.27 to 0.32 kg. The animals were fasted overnight prior to dose administration. The test article was administered by intravenous infusion over 30 min. The rate of infusion was adjusted according to the body weight of each animal to deliver a dose of 0.5 or 1.0 mg/kg. For the oral dosing group, the test article was administered to animals by oral gavage administration. Serial venous blood samples (approximately 0.30 mL each) were taken at predose and 0.25, 0.48, 0.58, 0.75, 1.5, 3, 6, 8, 12 and 24 hours post dose for the IV dosing group animals. Blood samples were taken at predose, 0.25, 0.50, 1, 2, 4, 6, 8, 12 and 24 hours post dose for the oral group animals. The blood samples were collected into Vacutainer™ tubes containing EDTA-K2 as the anti-coagulant and were immediately placed on wet ice pending centrifugation for plasma. An LC/MS/MS method was used to measure the concentration of test compound in plasma. Non-compartmental pharmacokinetic analysis was performed on the plasma concentration-time data.

Figure 3:
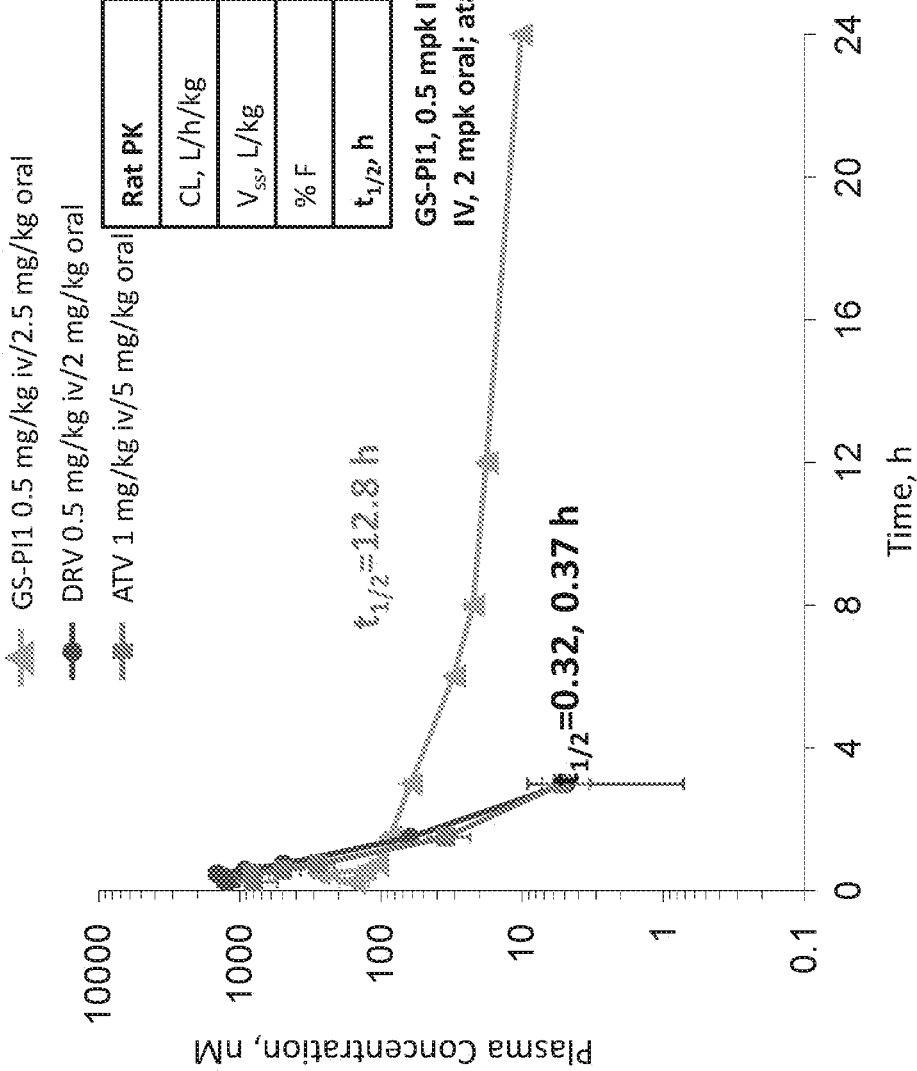
FIG. 3 describes a graph of the IV rat pharmacokinetic studies for certain compounds and reference compounds and table summarizing IV and oral PK data for those compounds as more fully described in the examples herein.

Data for certain compounds are reported in Table 4 and FIG. 3 accordingly.

TABLE 4

| Compound | RAT IV CL (L/HR/KG) | RAT IV VSS (L/KG) | RAT IV T1/2 (HR) | RAT PO F (%) | RAT PO DOSE (mg/kg) |
|---|---|---|---|---|---|
| 36 | 0.32 | 5.99 | 15.7 | 16.4 | 2.5 |
| 46 | 0.45 | 4.22 | 9.22 | 13 | 2.5 |
| 56 | 0.85 | 7.44 | 8.77 | 34.1 | 2.5 |
| 57 | 0.36 | 2.45 | 6.28 | 23.2 | 2.5 |
| 58 | 0.48 | 6.68 | 12.8 | 37.2 | 2.5 |
| 61 | 0.43 | 6.5 | 12.9 | 18.5 | 2.5 |
| 63 | 0.42 | 5.46 | 11.9 | 19 | 2.5 |
| 71 | 0.9 | 7.26 | 9.27 | 24.6 | 2.5 |
| 73 | 0.32 | 3.34 | 9.43 | 35 | 2.5 |
| 74 | 0.39 | 5.07 | 11.6 | 35.8 | 2.5 |
| 79 | 0.77 | 4.07 | 5.13 | 13.1 | 2.5 |
| 89 | 0.3 | 3.53 | 10.2 | 44.2 | 2.5 |
| 101 | 0.48 | 6.07 | 10 | 38.4 | 2.5 |
| 130 | 0.39 | 5.27 | 11.5 | 55.7 | 2.5 |
| 170 | 0.35 | 3.32 | 9.38 | 36.6 | 2.5 |
| 171 | 0.32 | 8.11 | 22.5 | 39 | 2.5 |

TABLE 4-continued

| Compound | RAT IV CL (L/HR/KG) | RAT IV VSS (L/KG) | RAT IV T1/2 (HR) | RAT PO F (%) | RAT PO DOSE (mg/kg) |
|---|---|---|---|---|---|
| 180 | 0.39 | 0.52 | 2.81 | 4.29 | 2.5 |
| 199 | 0.46 | 1.07 | 2.09 | 14.7 | 2.5 |
| 221 | 0.32 | 4.41 | 11.5 | 19.9 | 2.5 |
| 239 | 0.4 | 5.49 | 12.9 | 26.3 | 2.5 |
| DRV | 2.2 | 0.73 | 0.32 | 24 | 2.0 |
| ATV | 2.7 | 0.87 | 0.37 | 38 | 5.0 |

Protease Resistance Screening.

Figure 4:
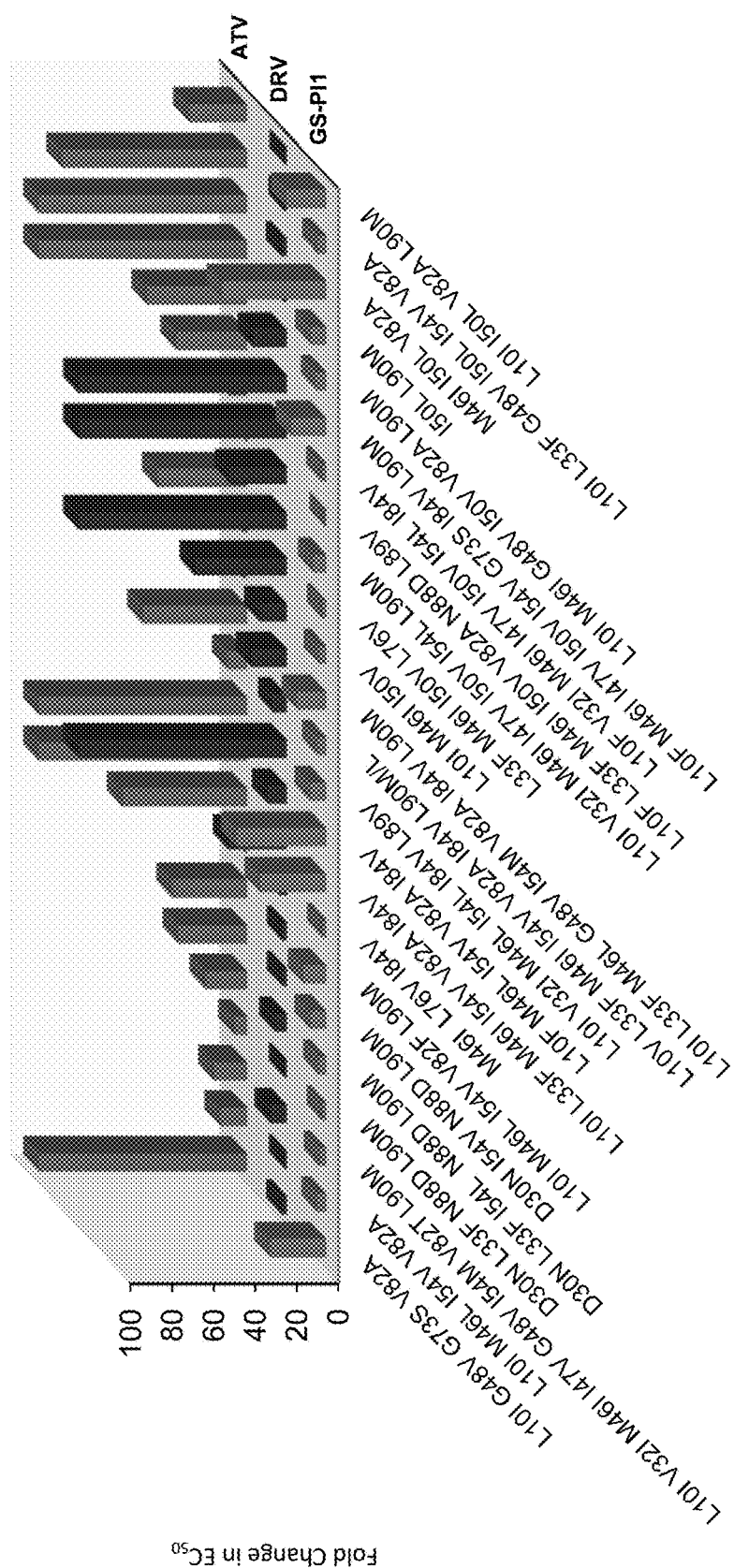
FIG. 4 describes the fold change vs. wild type for certain clinical isolate resistance mutations for certain compounds and reference compounds as more fully described in the examples herein.

Drug $EC_{50}$ values versus PI resistant mutant viruses for certain compounds were determined in a 5-day multi-cycle cell viability assay measuring protection from cytopathic effect (CPE). Briefly, MT-2 cells were bulk infected at a density of $2\times10^6$ cells/mL with WT or mutant viruses at a multiplicity of infection (MOI) of 0.01 by gently rocking the culture for 3 hours at 37° C. and then added in triplicate to 96-well plates (Corning Life Sciences, Tewksbury, Mass., USA). Cells were incubated in complete RPMI medium containing a 10-point, 3-fold serial drug dilution (0.5% final DMSO concentration) for five days at 37° C. in 5% $CO_2$. After this time, 100 µL of CellTiter-Glo reagent (Promega, Madison, Wis., USA) was added to each well and the luminescence signals quantified on an EnVision plate reader (Perkin-Elmer, Inc., Waltham, Mass., USA). $EC_{50}$ values, defined as the drug concentration inducing a 50% protection from HIV-induced cell killing, were calculated from a minimum of three independent experiments performed in quadruplicate using XLFit™ software (IDBS, Ltd., Guildford, Surrey, UK) and nonlinear regression analysis. As an illustrative example, data associated with the compound of Example 58 (GSPI1) is presented in FIG. 4 below as compared to other HIV protease inibitors (atazanavir and darunavir).

MT-2 Cell Viral Breakthrough Assay.

Figure 5:
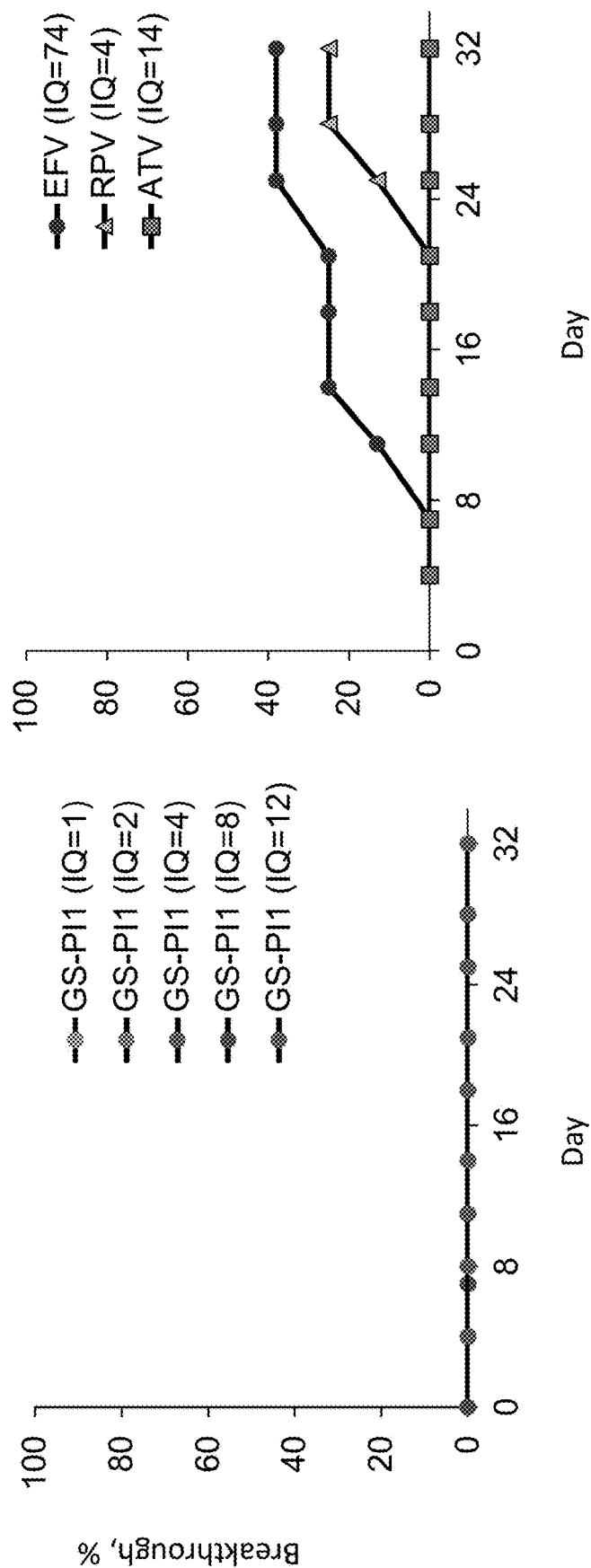
FIG. 5 describes the resistance breakthrough for certain compounds and reference compounds as more fully described in the examples herein.

MT-2 cells were infected with HIV-$1_{IIIB}$ (Advanced Biotechnologies, Eldersburg, Md., USA) at a relatively high multiplicity of infection (MOI=0.05) for 3 hours and plated in 24-well plates at $2\times10^5$ cells per well. Drugs were added 16 hours later to a minimum of quadruplicate wells at fixed multiples of their $EC_{50}$ values. Every 3-4 days, cells were diluted (1:5) into freshly prepared cell culture media containing drug concentrations at the same multiple of $EC_{50}$ values and monitored for virus-induced cytopathic effects (CPE) over a period of 32 days. Cell-free viral supernatants were harvested from wells showing >80% CPE and kept frozen at −80° C. until further analyzed. As an illustrative example, data associated with the compound of Example 58 (GSPI1) is presented in FIG. 5 below as compared to other HIV protease inhibitors (atazanavir, rilpivirine) and efavirenz.

Genotypic Analysis of Breakthrough Viruses.

Total RNA was purified from the cell-free supernatants obtained from each CPE-positive and p24-positive well using the Qiagen Viral RNA Isolation kit (Qiagen, Valencia, Calif., USA). The coding regions targeted by each drug were amplified by One-Step RT-PCR (Qiagen) and the products subjected to DNA sequencing. Sequence changes were identified by alignment with input virus sequences using Sequencher (Gene Codes Corp., Ann Arbor, Mich., USA) and amino acid substitutions determined.

Equilibrium Dialysis Assay

Pooled plasma (from at least 3 males and 3 females) was from Bioreclamation IVT. Sodium EDTA was used as the anticoagulant. 10% plasma was diluted in in 0.133M phosphate buffer consisted of 1.5% (w/v) Sodium EDTA.

RPMI cell culture media consisted 10% FBS was provided by biology department, Gilead Sciences, Inc.

Plasma Protein Binding Assay:

Studies were conducted in duplicate or triplicate using a Dianorm Equilibrium Dialyser (Harvard Apparatus, Holliston Mass.) with each cell consisting of a semipermeable membrane (2.4 cm working diameter) separating two 1 mL PTFE half-cells (Weder H G, Schildknecht J, Kesselring P. A new equilibrium dialyzing system. *American Laboratory.* 1971; 10: 15-21). Prior to the study, the dialysis membrane was soaked for approximately one hour in 0.133 M phosphate buffer, pH 7.4. 10% plasma and cell culture media spiked with 1 µM compound (1 mL) were placed into opposite sides of the assembled dialysis cells and the dialysis cells were then rotated slowly in a 37° C. water bath. After the equilibration period, matrix-containing samples from both sides were drained into pre-weighed polypropylene tubes. Post-dialysis 10% plasma samples were transferred into centrifuge tubes containing 1 mL of blank cell culture media. Post-dialysis cell culture media samples were transferred into centrifuge tubes containing 1 mL of blank 10% plasma. All samples weights were measured and recorded for calculations of volume shift and recovery.

Samples were deproteinated by treatment with four volumes of 90% (v/v) acetonitrile, 10% (v/v) methanol containing the LC-MS internal standard. Samples were centrifuged 15,000 rpm at 4° C. for 15 min and 200 µL aliquots of the supernatants removed and mixed with an equal volume of water. Samples were vortexed for 2 min, and then aliquots (10 µL) subject to LC-MS/MS analysis.

Data Analysis

The binding ratio for an analyte in plasma vs. cell culture media was calculated using the following equations:

$$\text{Ratio} = C_{10\%\ plasma} / C_{CCM}$$

where $C_{10\%\ plasma}$ is the post-dialysis 10% plasma concentration (determined by PAR), and $C_{CCM}$ is the post-dialysis cell culture media concentration (determined by PAR), respectively. Each concentration was corrected gravimetrically for changes in liquid volume in the dialysis cells occurring during dialysis.

Protease Ki Assay

Inhibitor potency was measured using an enzymatic assay with a fluorogenic readout. To a reaction buffer containing 100 mM ammonium acetate at pH 5.3, 100 mM NaCl, 1 mM EDTA, 1 mM DTT, 0.25 mg/mL BSA and 1% DMSO were added 2.5 nM of recombinant HIV protease and test compound at one of various concentrations. After a 20-minute pre-incubation, the enzymatic reaction was initiated by the addition of the fluorogenic substrate (2-aminobenzoyl)Thr-Ile-Nle-(p-nitro)Phe-Gln-Arg (Bachem) to a final concentration of 40 µM. The total volume of the assay solution was 100 µL. The reaction was measured over 20 minutes on a Tecan Infinite M1000 plate reader using an excitation wavelength of 320 nm and a detection wavelength of 420 nm. The slopes of the progress curves were the measure of reaction rates. Reaction rates were plotted as a function of inhibitor concentration, and the data were fit using the tight-binding equation described by Morrison (Biochim. Biophys. Acta 1969, 185, 269-286) to yield $K_i$ values.

447

TABLE 5

| Potency of Compound 58, DRV, and ATV | | | |
|---|---|---|---|
|  | Compound 58 | darunavir | atazanavir |
| Ki (nM) | 0.060 | <0.030 | 0.035 |
| EC$_{50}$ (nM) | 6.8 | 7.2 | 9.7 |
| Hill-coefficient | 5.8 | 2.9 | 3.1 |
| EC$_{95}$ (nM) | 11.4 | 19.9 | 25 |
| Protein Adjusted EC$_{95}$ (nM) | 353 | 42 | 75 |

What is claimed is:

1. A pharmaceutical composition comprising a compound of Formula (I):

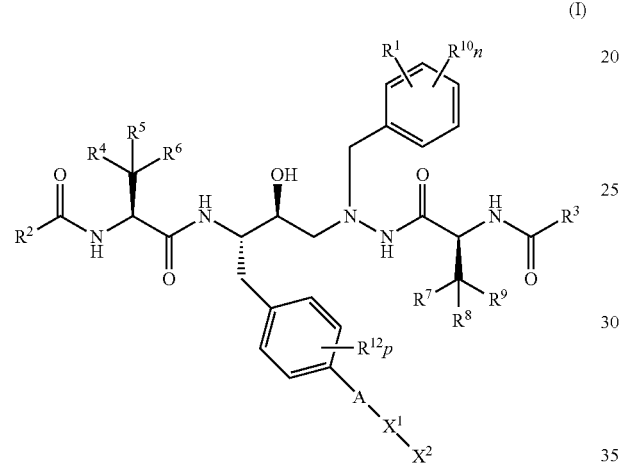

or a pharmaceutically acceptable salt thereof, wherein:
$R^1$ is a 5 to 10-membered heterocycle having 1 to 5 heteroatoms selected from N, O, and S, or a 5 to 10-membered heteroaryl having 1 to 5 heteroatoms selected from N, O, and S, wherein the 5 to 10-membered heterocycle or 5 to 10-membered heteroaryl is optionally substituted with 1 to 5 $R^a$ groups;
$R^2$ and $R^3$ are each independently $C_{1-4}$alkyl, $C_{3-6}$cycloalkyl, O—$R^{2A}$, $C_{1-2}$alkyl-O—$R^{2A}$, N—$(R^{3A})_2$, or $C_{1-2}$alkyl-N—$(R^{3A})_2$,
wherein each $R^{2A}$ is independently $C_{1-4}$alkyl, $C_{3-6}$cycloalkyl, or a 4 to 10-membered heterocyclyl having 1 to 5 heteroatoms selected from N, O, and S, wherein each $R^{3A}$ is independently hydrogen, $C_{1-4}$alkyl, $C_{3-6}$cycloalkyl, or COO($R^e$),
and wherein each $C_{3-6}$cycloalkyl or 4 to 10-membered heterocyclyl is optionally substituted by 1 to 3 $R^f$ groups, wherein each $R^f$ is independently $C_{1-2}$alkyl or halogen;
$R^4$ is hydrogen, halo, $C_{1-4}$alkyl, $C_{1-4}$haloalkyl, $C_{3-6}$cycloalkyl, $C_{1-4}$alkoxy, or $C_{1-4}$haloalkoxy;
$R^7$ is hydrogen, halo, $C_{1-4}$alkyl, $C_{1-4}$haloalkyl, $C_{3-6}$cycloalkyl, $C_{1-4}$alkoxy, or $C_{1-4}$haloalkoxy;
$R^5$, $R^6$, $R^8$, and $R^9$ are each independently hydrogen, halo, $C_{1-2}$alkyl, $C_{1-2}$haloalkyl, or $C_{3-6}$cycloalkyl;
and wherein two or more of $R^4$, $R^5$ and $R^6$ or two or more of $R^7$, $R^8$, and $R^9$ optionally join together to form one or more $C_{3-6}$cycloalkyl groups that are

448 optionally substituted with 1 to 4 groups selected from halogen, $C_{1-2}$alkyl, and $C_{1-2}$haloalkyl;
each $R^{10}$ is independently halogen, cyano, $C_{1-4}$alkoxy, $C_{1-6}$alkyl, or $C_{3-6}$cycloalkyl;
n is 0 to 4;
each $R^a$ is independently halogen, $C_{1-4}$alkyl, $C_{1-4}$alkyl substituted with 1 to 2 groups selected from hydroxyl and $C_{1-4}$ alkoxy, $C_{1-4}$ haloalkyl, $C_{1-4}$alkoxy, $C_{3-6}$ cycloalkyl, 4 to 10-membered heterocyclyl having 1 to 5 heteroatoms selected from N, O, and S which is optionally substituted with $R^{a1}$, or O—$R^{3B}$,
wherein $R^{3B}$ is $C_{3-6}$cycloalkyl optionally substituted with $R^{a1}$ or a 4 to 10-membered heterocyclyl having 1 to 5 heteroatoms selected from N, O, and S optionally substituted with $R^{a1}$,
wherein each $R^{a1}$ is independently $C_{1-4}$alkyl, $C_{3-6}$cycloalkyl, $C_{1-4}$haloalkyl, or 4 to 8-membered heterocyclyl having 1 to 3 heteroatoms selected from N, O, and S;
A is ethynyl;
$X^1$ is a 6 to 10-membered aryl or a 5 to 10-membered heteroaryl having 1 to 3 heteroatoms selected from N, O, and S, wherein each 6 to 10-membered aryl or 5 to 10-membered heteroaryl is optionally substituted with 1 to 4 $R^b$ groups;
$X^2$ is hydrogen or a 4 to 10-membered heterocyclyl having 1 to 5 heteroatoms selected from N, O, and S, wherein the 4 to 10-membered heterocyclyl is optionally substituted with one $R^{11}$ and optionally substituted with 1 to 5 $R^b$ groups;
$R^{11}$ is C═O($R^c$), $CH_2(R^d)$, $S(O)_{1-2}(C_{1-4}$alkyl), $S(O)_{1-2}C_{3-6}$cycloalkyl, a 4 to 10-membered heterocyclyl having 1 to 5 heteroatoms selected from N, O, and S, or a 5 to 9-membered heteroaryl having 1 to 5 heteroatoms selected from N, O, and S, wherein each 4 to 10-membered heterocyclyl or 5 to 9-membered heteroaryl is optionally substituted with 1 to 5 $R^b$ groups;
each $R^b$ is independently halogen, oxo, $C_{1-4}$alkyl, $C_{1-4}$alkyl substituted with 1 to 2 groups selected from hydroxyl and $C_{1-4}$ alkoxy, $C_{1-4}$ haloalkyl, $C_{1-4}$ alkoxy, or COO($R^e$);
$R^c$ is $C_{1-4}$alkyl, $C_{1-4}$ haloalkyl, $C_{1-4}$alkoxy, $N(R^e)_2$, $C_{3-6}$cycloalkyl, or a 4 to 6-membered heterocyclyl having 1 to 3 heteroatoms selected from N, O, and S, wherein the $C_{3-6}$ cycloalkyl and the 4 to 6-membered heterocyclyl are optionally substituted by 1 to 5 $R^b$ groups;
$R^d$ is COO($R^e$), $N(R^e)_2$, $C_{3-6}$ cycloalkyl, or a 4 to 6-membered heterocyclyl having 1 to 3 heteroatoms selected from N, O, and S, wherein the $C_{3-6}$ cycloalkyl and the 4 to 6-membered heterocyclyl is optionally substituted by 1 to 5 $R^b$ groups;
each $R^{12}$ is $C_{1-2}$alkyl, halo, —O$C_{1-2}$alkyl, or cyano;
each p is 0 to 4;
and each $R^e$ is independently hydrogen or $C_{1-4}$alkyl;
and one or more additional therapeutic agents selected from the group consisting of combination drugs for HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, gp41 inhibitors, CXCR4 inhibitors, gp120 inhibitors, CCR5 inhibitors, capsid polymerization inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof.

2. The pharmaceutical composition of claim 1, wherein the composition comprises one, two, three, or four additional therapeutic agents.

3. The pharmaceutical composition of claim 1, wherein the additional therapeutic agents are selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and pharmacokinetic enhancers, or any combinations thereof.

4. The pharmaceutical composition of claim 1, wherein the HIV nucleoside or nucleotide inhibitors of reverse transcriptase are selected from the group consisting of abacavir sulfate, tenofovir, tenofovir disoproxil, tenofovir disoproxil fumarate, tenofovir disoproxil hemifumarate, tenofovir alafenamide, tenofovir alafenamide fumarate and tenofovir alafenamide hemifumarate.

5. The pharmaceutical composition of claim 1, wherein the integrase inhibitors are selected from the group consisting of bictegravir, cabotegravir and dolutegravir.

6. The pharmaceutical composition of claim 1, wherein the HIV nucleoside or nucleotide inhibitors of reverse transcriptase are selected from the group consisting of tenofovir alafenamide, tenofovir alafenamide fumarate and tenofovir alafenamide hemifumarate.

7. The pharmaceutical composition of claim 1, wherein $R^2$ and $R^3$ are each methoxy.

8. The pharmaceutical composition of claim 1, wherein $R^4$ is $CF_3$.

9. The pharmaceutical composition of claim 1, wherein $R^7$ is $CF_3$.

10. The pharmaceutical composition of claim 1, wherein $R^5$ and $R^6$ are methyl.

11. The pharmaceutical composition of claim 1, wherein $R^8$ and $R^9$ are methyl.

12. The pharmaceutical composition of claim 1, wherein n is 2.

13. The pharmaceutical composition of claim 1, wherein each $R^{10}$ is fluoro.

14. The pharmaceutical composition of claim 1, wherein $R^1$ is:

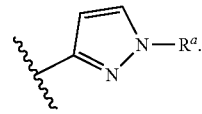

15. The pharmaceutical composition of claim 1, wherein $R^a$ is:

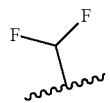

16. The pharmaceutical composition of claim 1, wherein $X^1$ is:

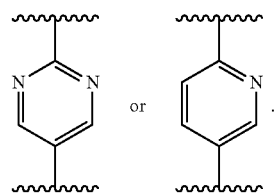 [SMILES: *c1cnc(*)nc1 ; *c1ccc(*)nc1]

17. The pharmaceutical composition of claim 1, wherein $X^2$ is:

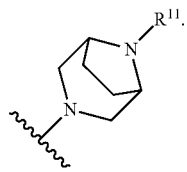

18. The pharmaceutical composition of claim 17, wherein $R^{11}$ is oxetan-3-yl, tetrahydrofuran-3-yl, or tetrahydropyran-4-yl.

19. The pharmaceutical composition of claim 1, wherein p is 0.

20. A pharmaceutical composition comprising a compound selected from:
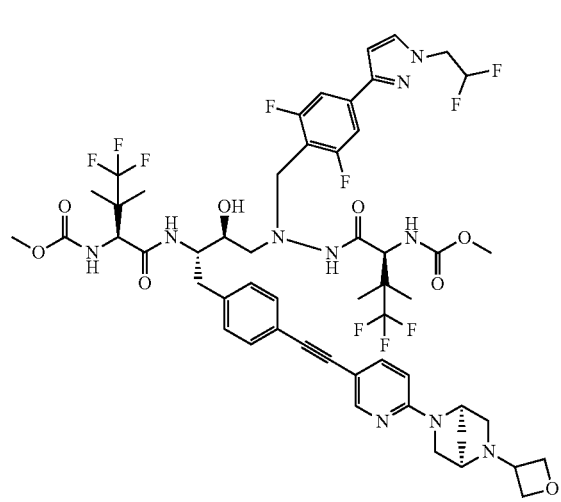
EXAMPLE 1
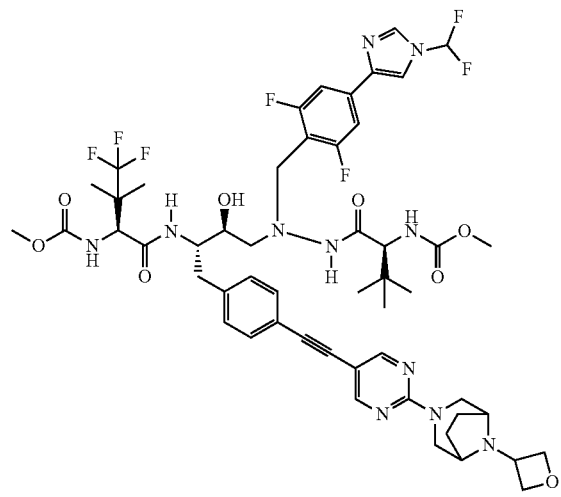 [SMILES: COC(=O)N[C@H](C(=O)NN(Cc1c(F)cc(-c2cn(C(F)F)cn2)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C]
EXAMPLE 2
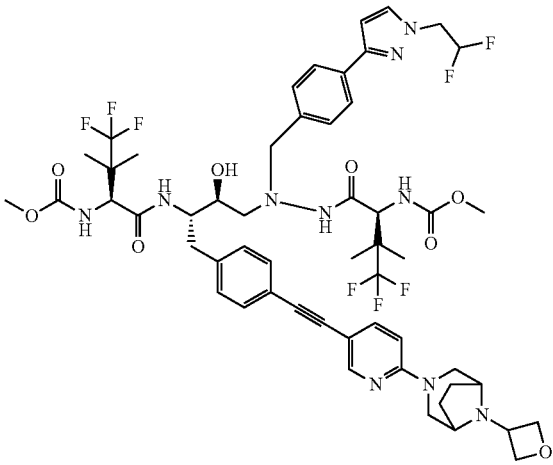 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(C(=N)/C=C\NCC(F)F)cc1)NC(=O)[C@@H](NC(=O)OC)C(C)(C)C(F)(F)F)C(C)(C)C(F)(F)F]
EXAMPLE 3
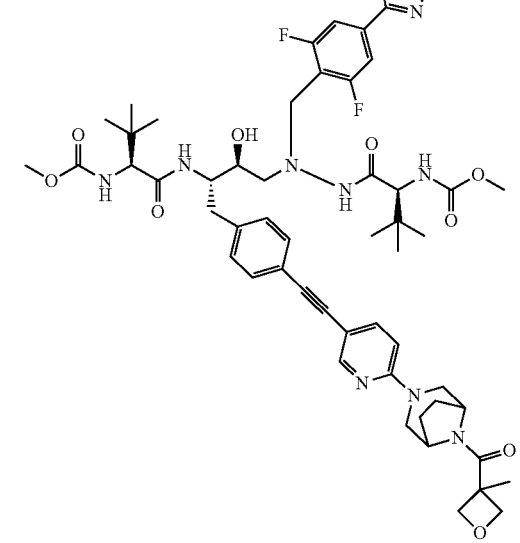

EXAMPLE 4
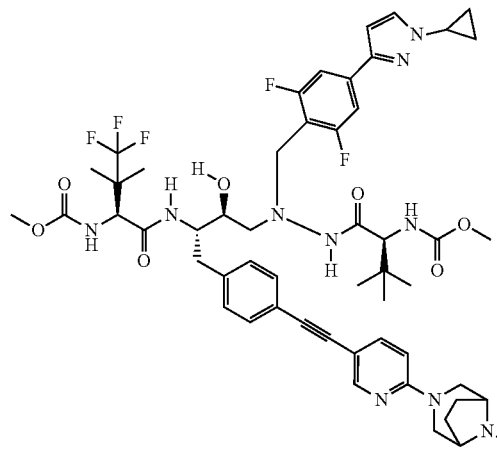
EXAMPLE 5
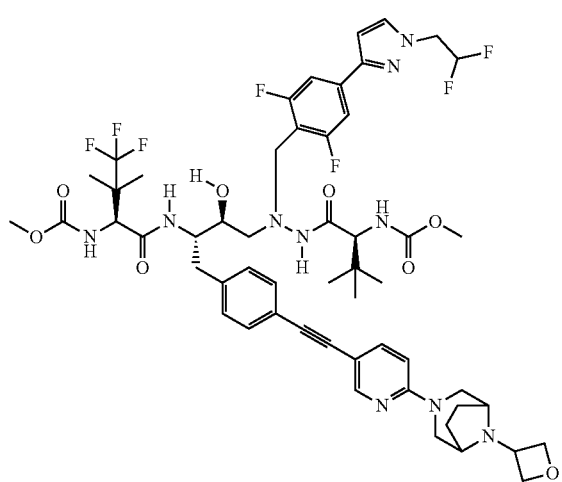 [SMILES: COC(=O)N[C@H](C(=O)NN(Cc1c(F)cc(C(=N)/C=C\NCC(F)F)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]
EXAMPLE 6
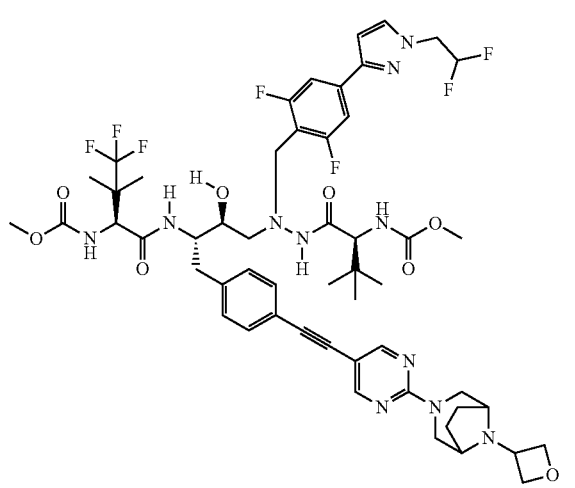 [SMILES: COC(=O)N[C@H](C(=O)NN(Cc1c(F)cc(C(=N)/C=C\NCC(F)F)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C]
EXAMPLE 7
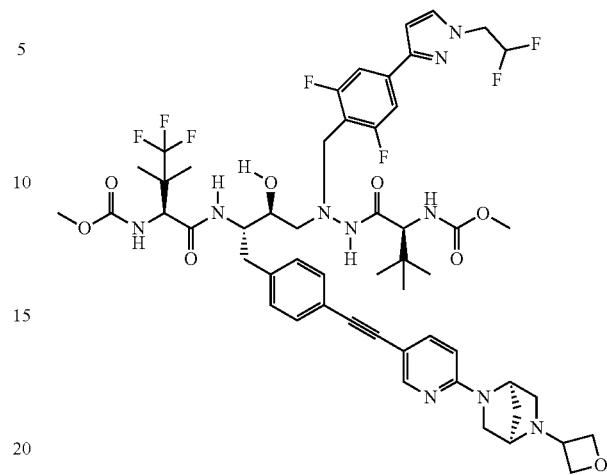
EXAMPLE 8
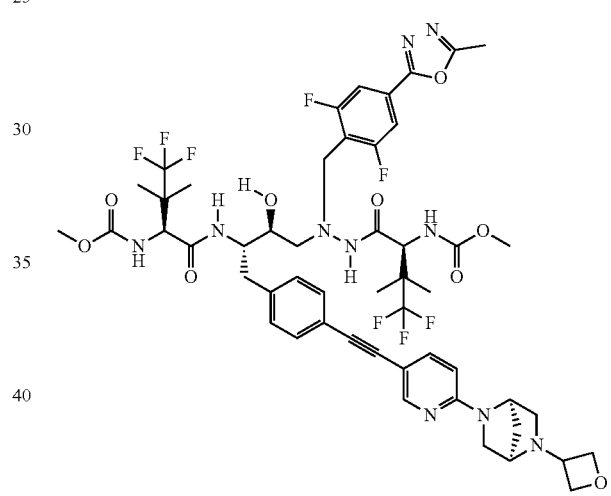
EXAMPLE 9
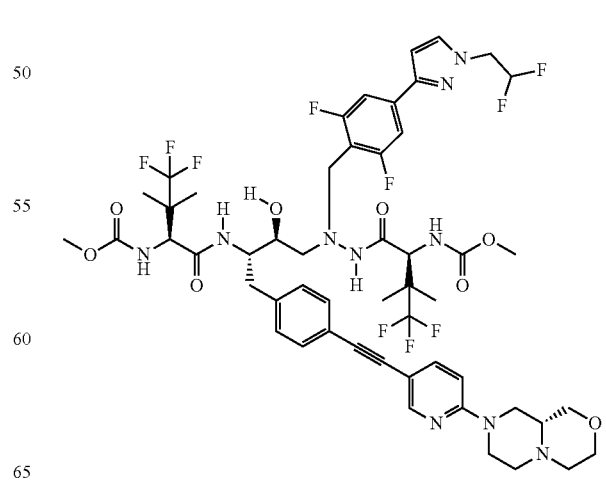

EXAMPLE 10
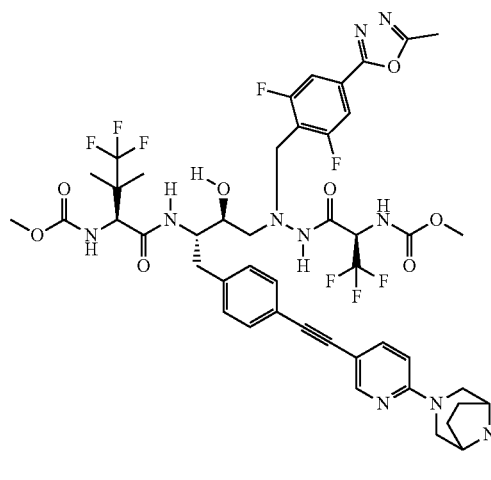
EXAMPLE 12
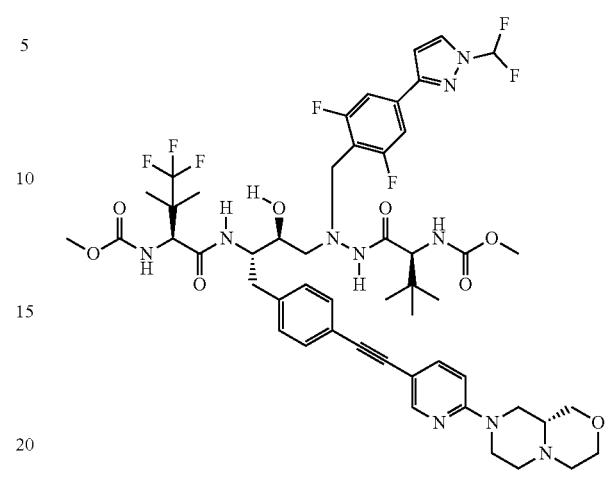
EXAMPLE 13
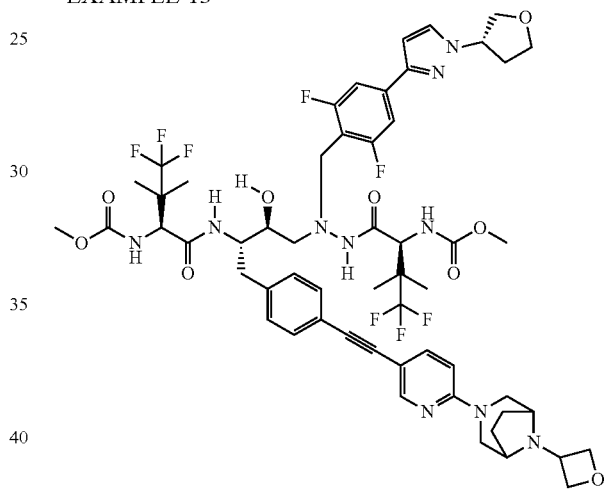
EXAMPLE 11
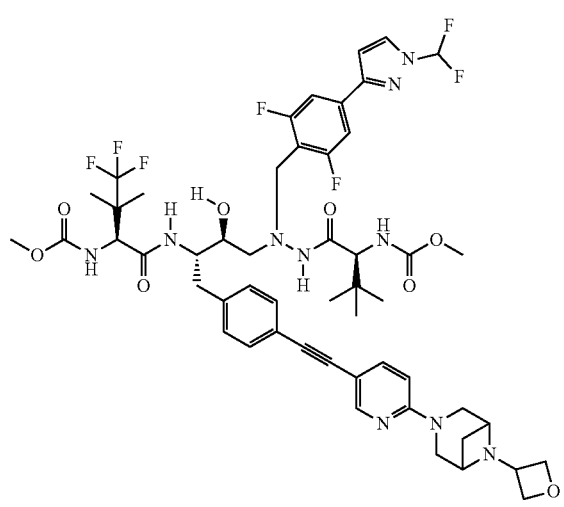 [SMILES: COC(=O)N[C@H](C(=O)NN(Cc1c(F)cc(C(=N)/C=C\NC(F)F)cc1F)C[C@H](O)[C@H](Cc1ccc(C#Cc2ccc(N3CC4CC(C3)N4C3COC3)nc2)cc1)NC(=O)[C@@H](NC(=O)OC)C(C)(C)C(F)(F)F)C(C)(C)C]
EXAMPLE 14

EXAMPLE 15
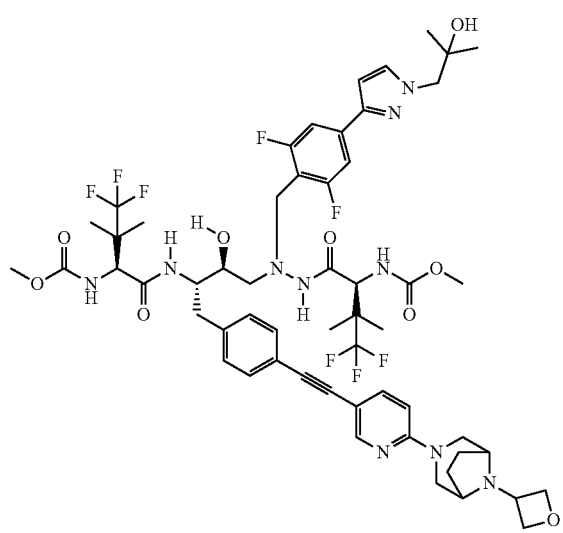 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(C(=N)/C=C\NCC(C)(C)O)cc1F)NC(=O)[C@@H](NC(=O)OC)C(C)(C)C(F)(F)F)C(C)(C)C(F)(F)F]
EXAMPLE 16
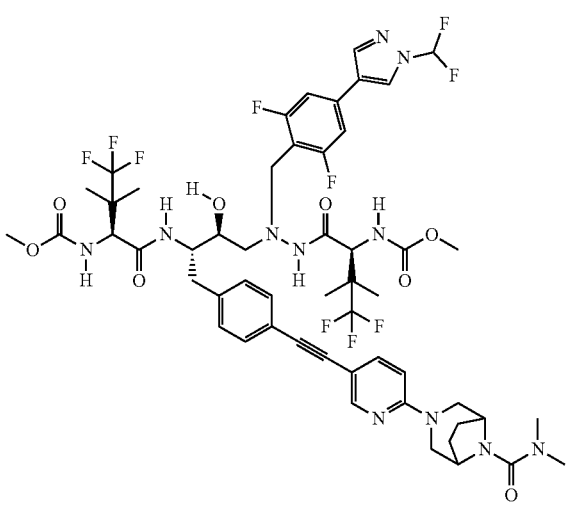
EXAMPLE 17
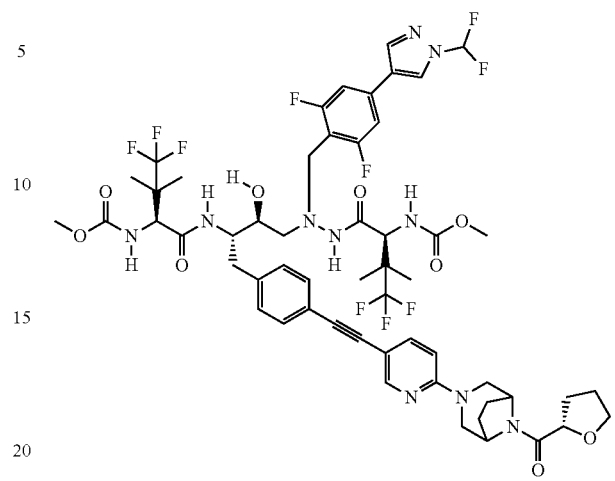
EXAMPLE 18
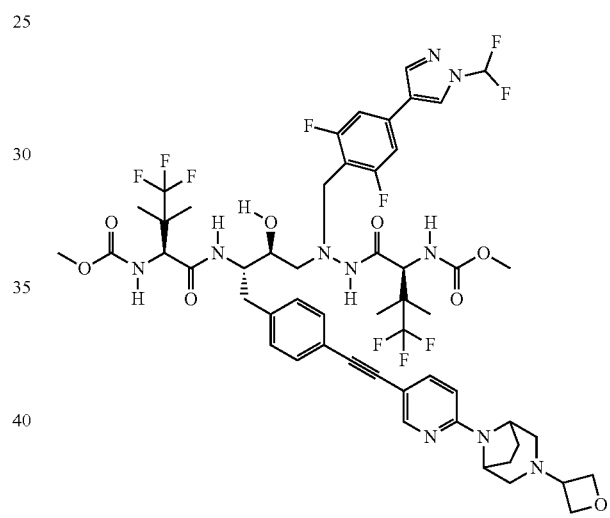
EXAMPLE 19
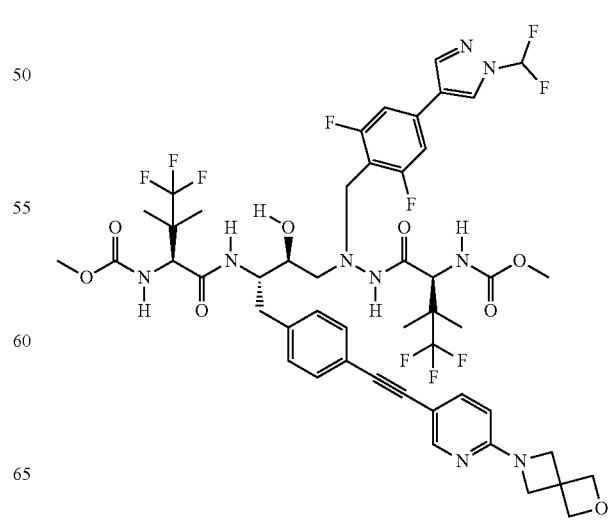

459
EXAMPLE 20
460
EXAMPLE 22
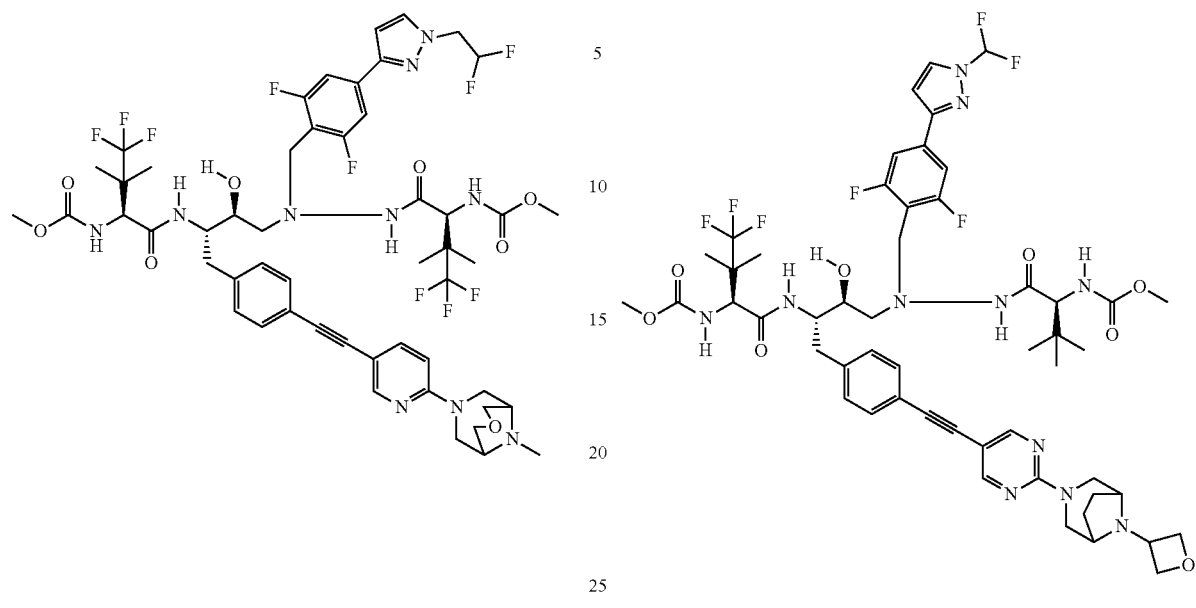
EXAMPLE 21
EXAMPLE 23
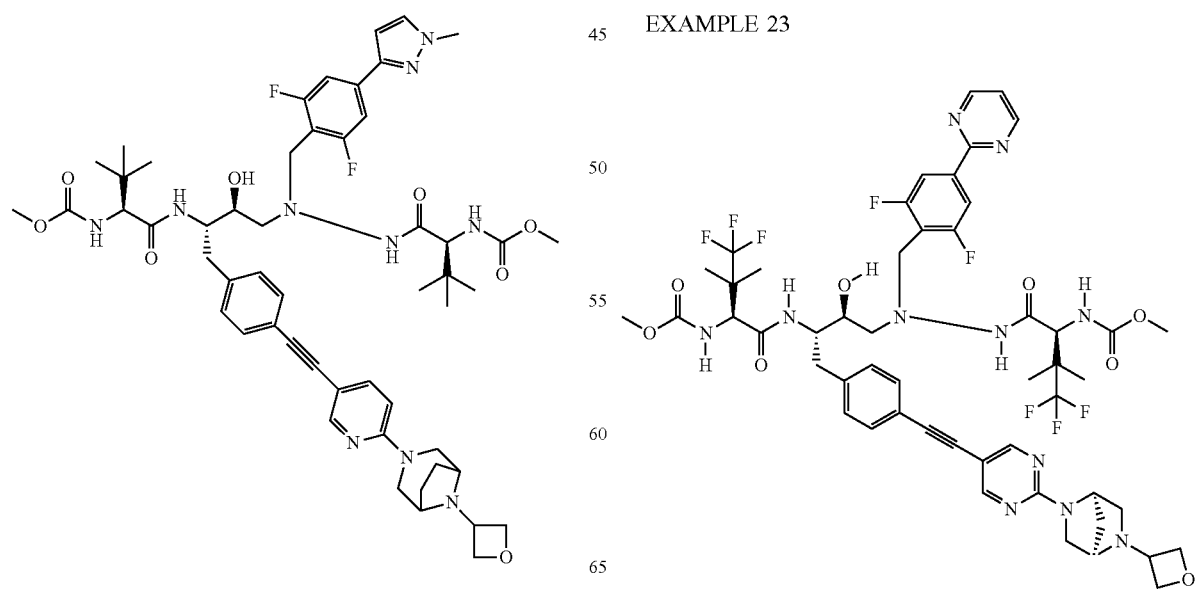

EXAMPLE 24
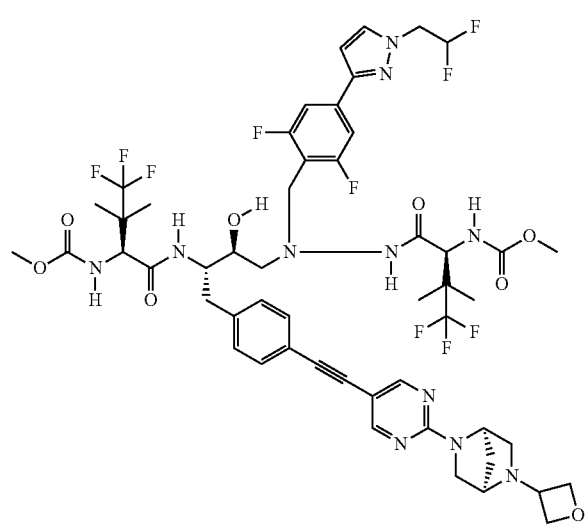 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1c(F)cc(-c2ccn(CC(F)F)n2)cc1F)NC(=O)[C@@H](NC(=O)OC)C(C)(C)C(F)(F)F)C(C)(C)C(F)(F)F]
EXAMPLE 26
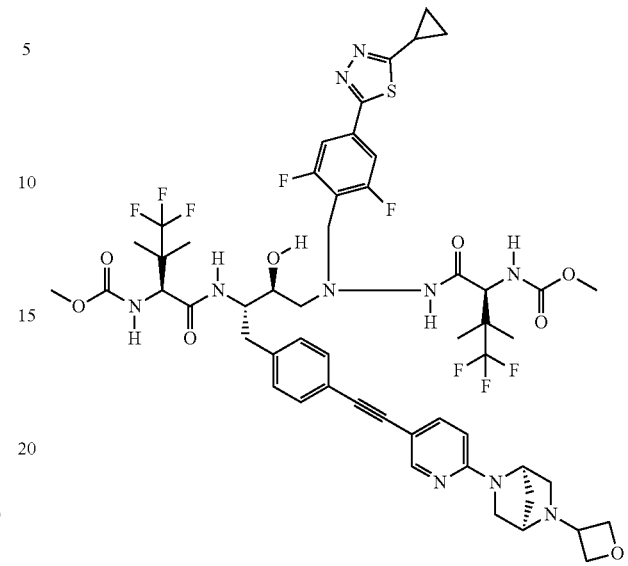
EXAMPLE 27
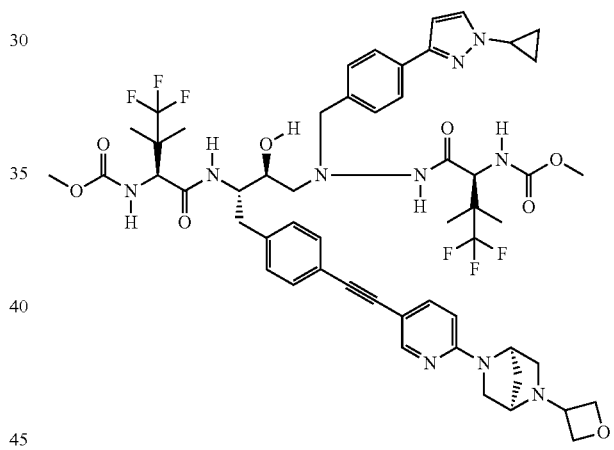
EXAMPLE 25
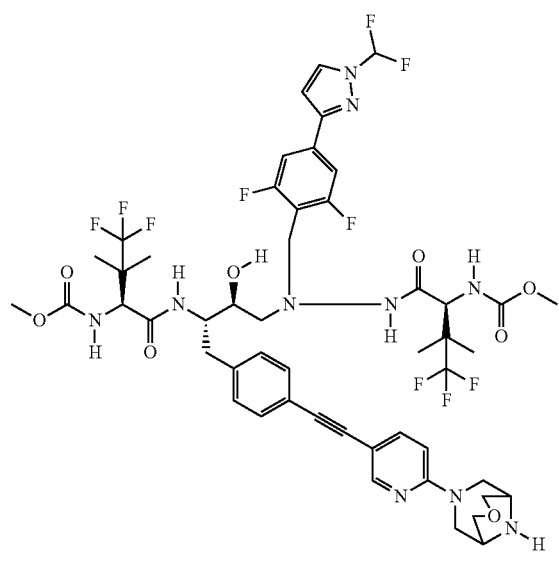
EXAMPLE 28
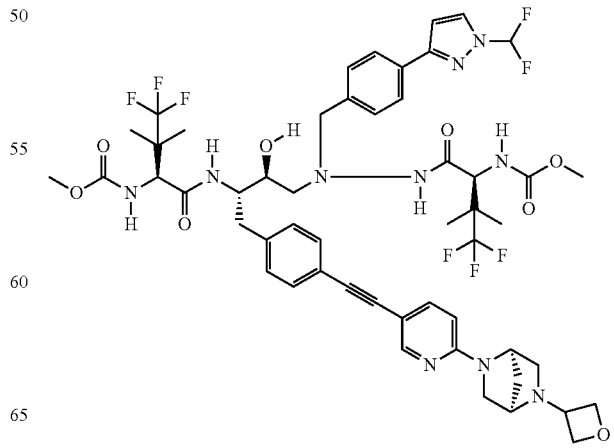

EXAMPLE 29
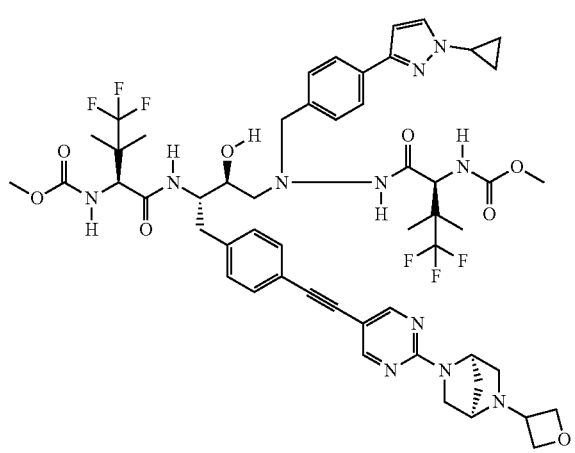 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1ccc(-c2ccn(C3CC3)n2)cc1)NC(=O)[C@@H](NC(=O)OC)C(C)(C)C(F)(F)F)C(C)(C)C(F)(F)F]
EXAMPLE 30
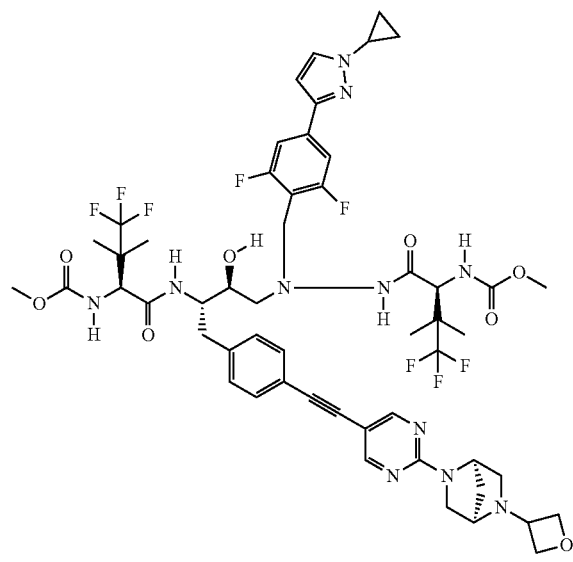 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]
EXAMPLE 31
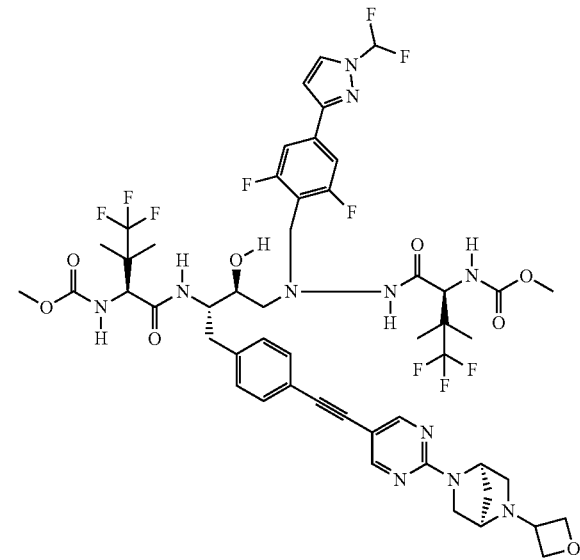 [SMILES: COC(=O)N[C@H](C(=O)N[C@@H](Cc1ccc(C#Cc2cnc(N3C[C@H]4C[C@@H]3CN4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 32
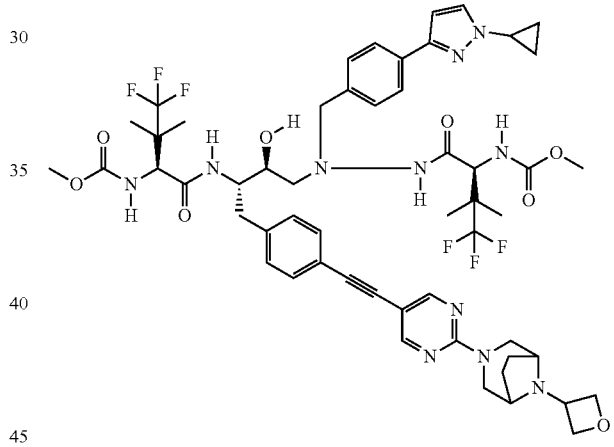
EXAMPLE 33
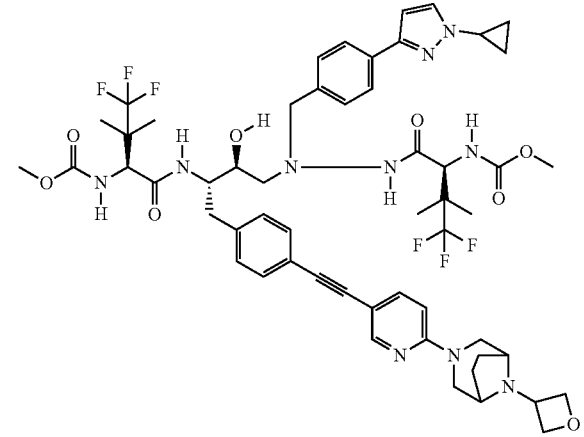 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(-c2ccn(C3CC3)n2)cc1)NC(=O)[C@@H](NC(=O)OC)C(C)(C)C(F)(F)F)C(C)(C)C(F)(F)F]

EXAMPLE 34
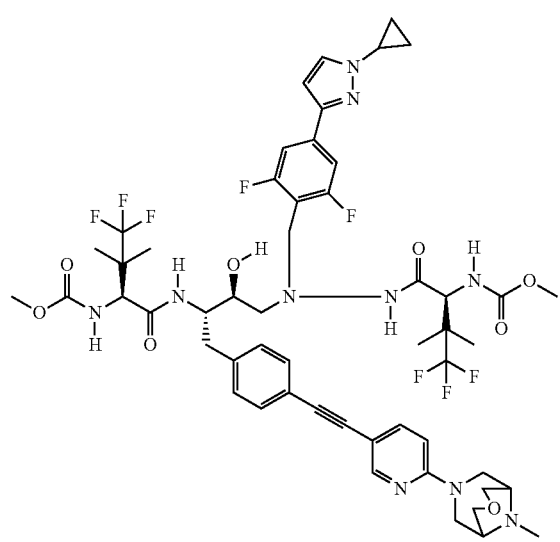
EXAMPLE 36
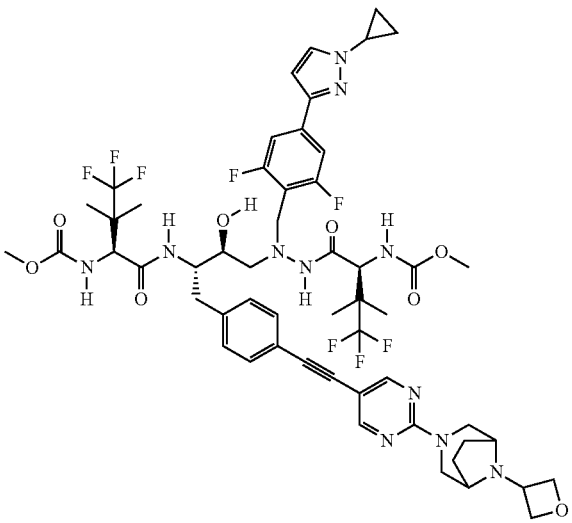 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]
EXAMPLE 35
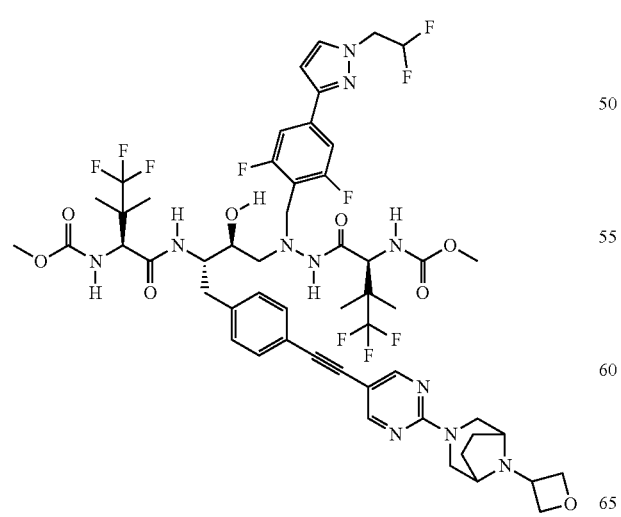
EXAMPLE 37
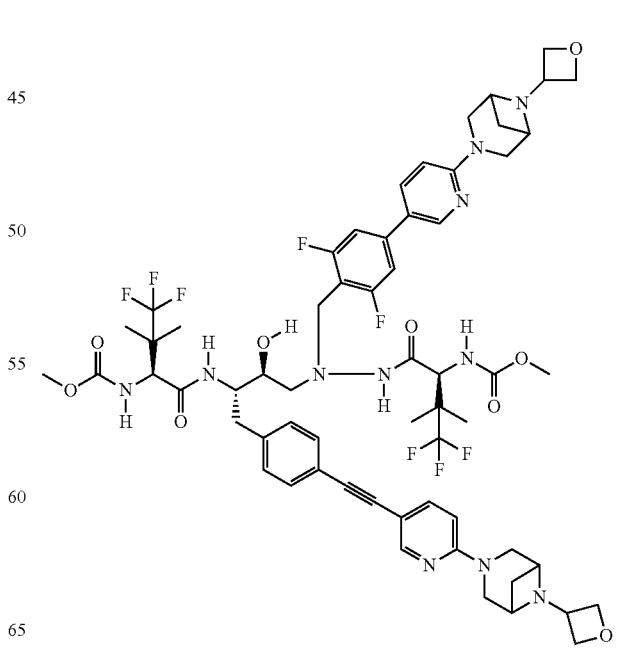

EXAMPLE 38
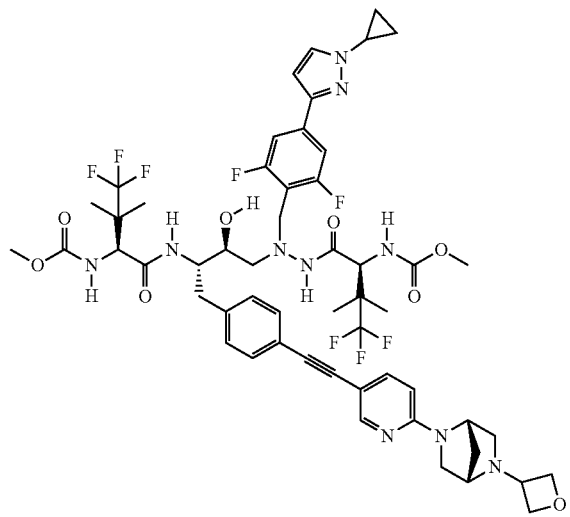 [SMILES: COC(=O)N[C@H](C(=O)N[C@@H](Cc1ccc(C#Cc2ccc(N3C[C@@H]4C[C@H]3CN4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]
EXAMPLE 40
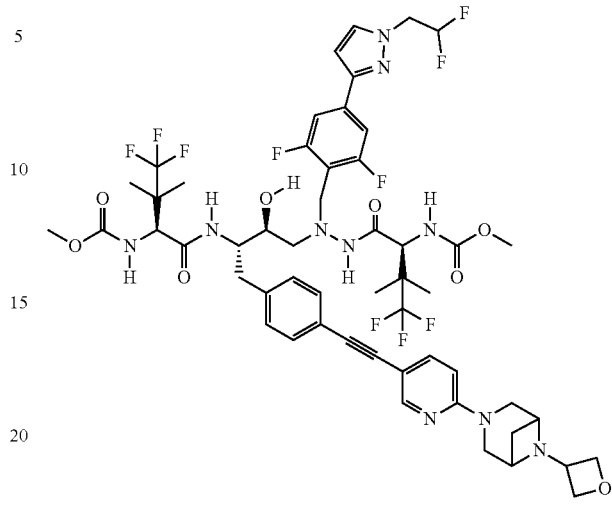
EXAMPLE 39
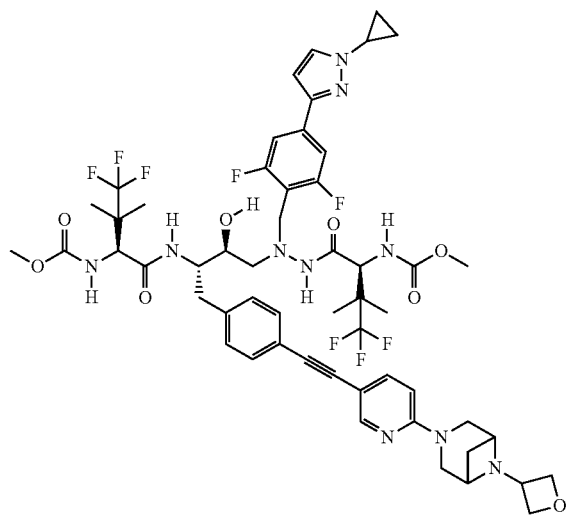 [SMILES: COC(=O)N[C@H](C(=O)N[C@@H](Cc1ccc(C#Cc2ccc(N3CC4CC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]
EXAMPLE 41

EXAMPLE 42
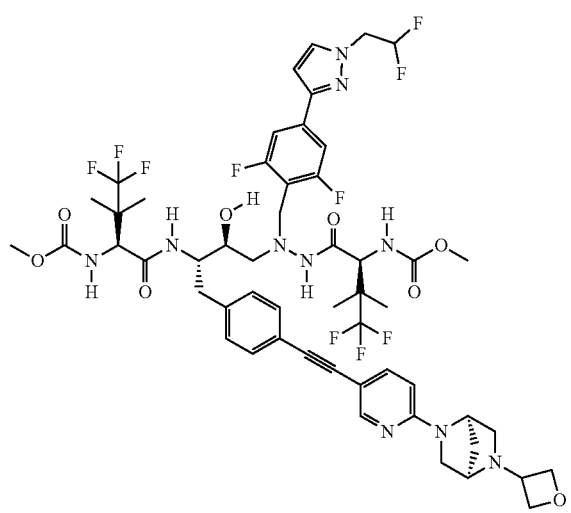 [SMILES: COC(=O)N[C@H](C(=O)N[C@@H](Cc1ccc(C#Cc2ccc(N3C[C@H]4C[C@@H]3CN4C3COC3)nc2)cc1)[C@@H](O)CN(Cc1c(F)cc(-c2ccn(CC(F)F)n2)cc1F)NC(=O)[C@@H](NC(=O)OC)C(C)(C)C(F)(F)F)C(C)(C)C(F)(F)F]
EXAMPLE 44
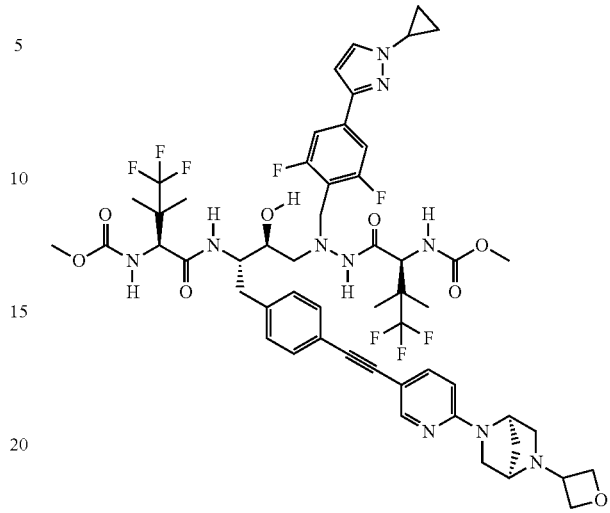
EXAMPLE 43
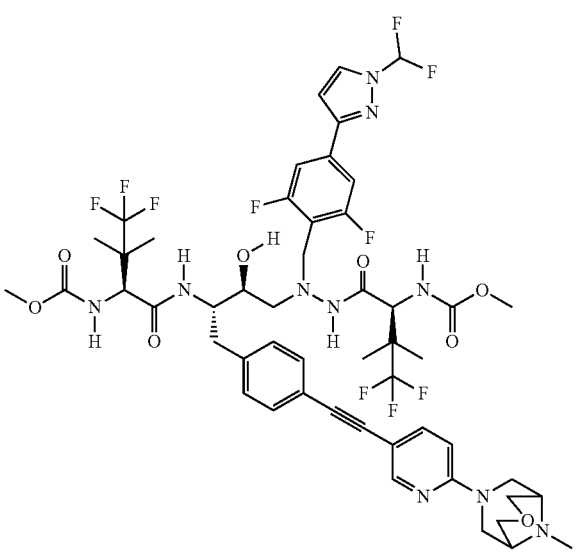
EXAMPLE 45
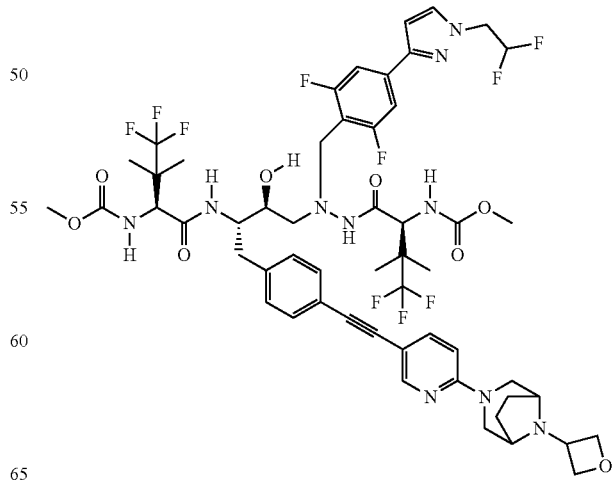

EXAMPLE 46
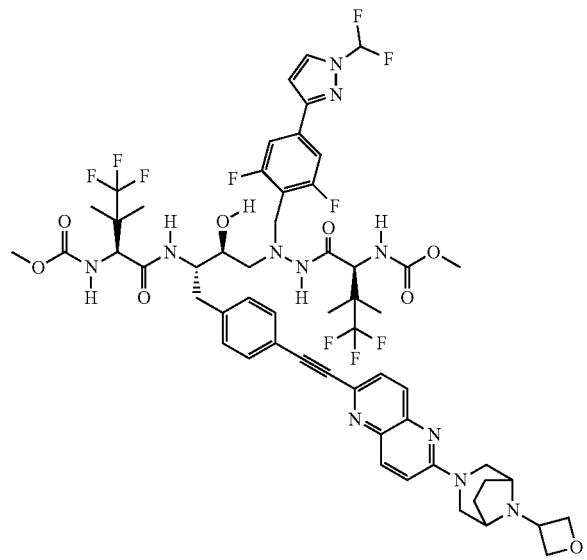 [SMILES: COC(=O)N[C@H](C(=O)N[C@@H](Cc1ccc(C#Cc2ccc3nc(N4CC5CCC(C4)N5C4COC4)ccc3n2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 48
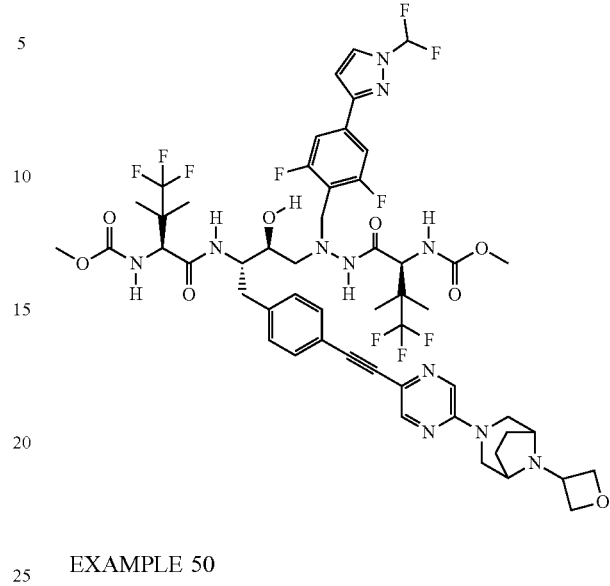
EXAMPLE 50
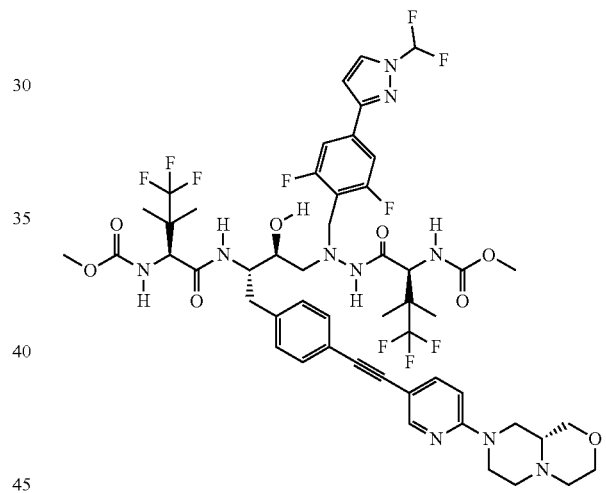
EXAMPLE 47
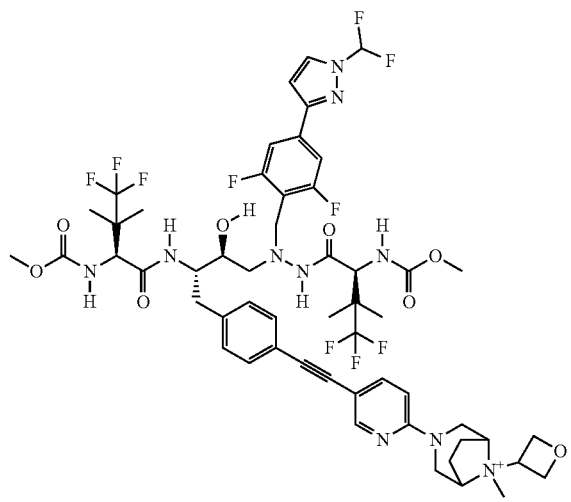 [SMILES: COC(=O)N[C@H](C(=O)N[C@@H](Cc1ccc(C#Cc2ccc(N3CC4CCC(C3)[N+]4(C)C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 51
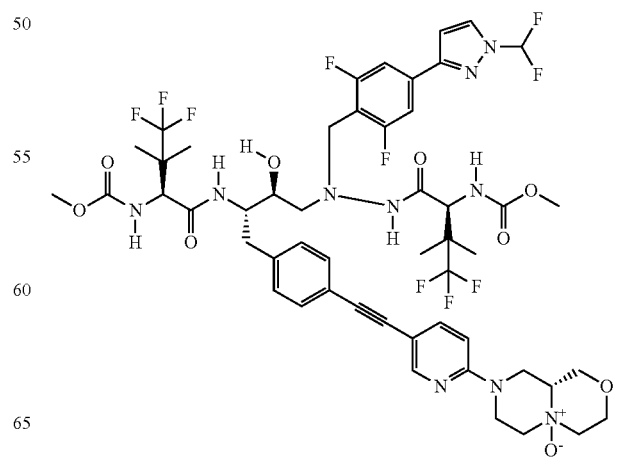

EXAMPLE 52
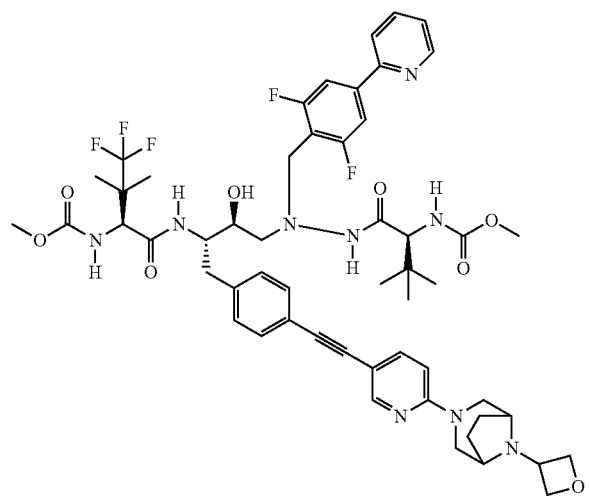 [SMILES: COC(=O)N[C@H](C(=O)NN(Cc1c(F)cc(-c2ccccn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]
EXAMPLE 54
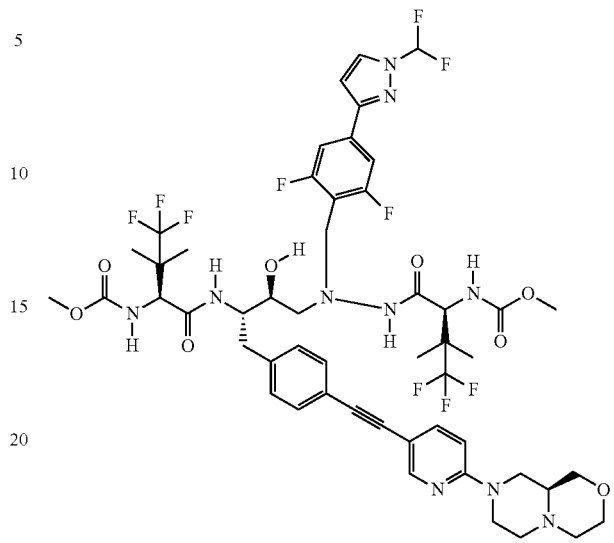
EXAMPLE 53
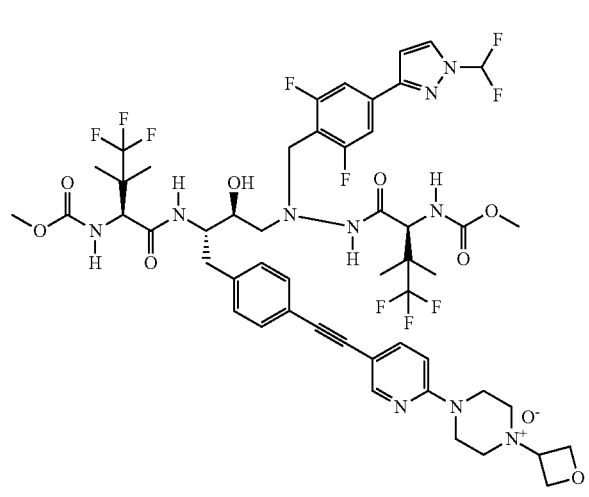
EXAMPLE 55

EXAMPLE 56
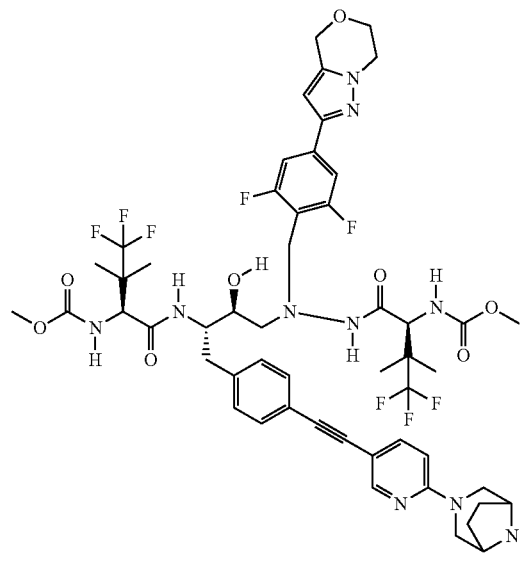
EXAMPLE 58
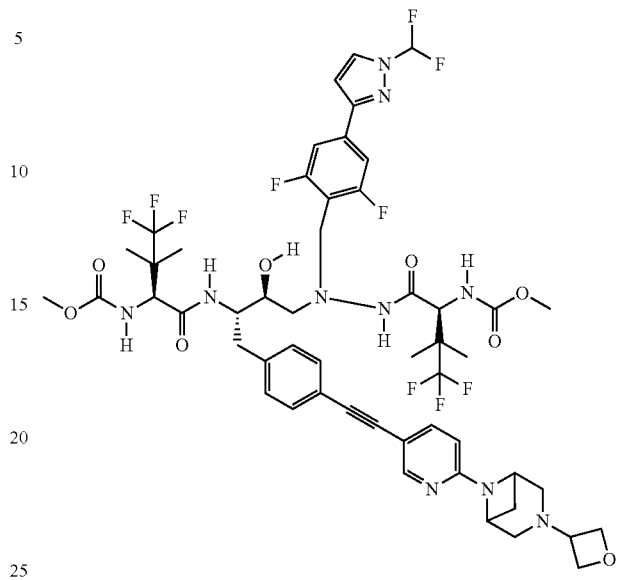
EXAMPLE 57
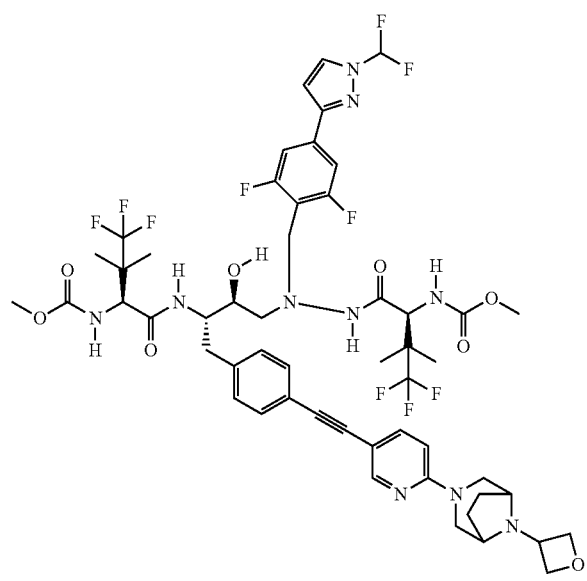 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 59
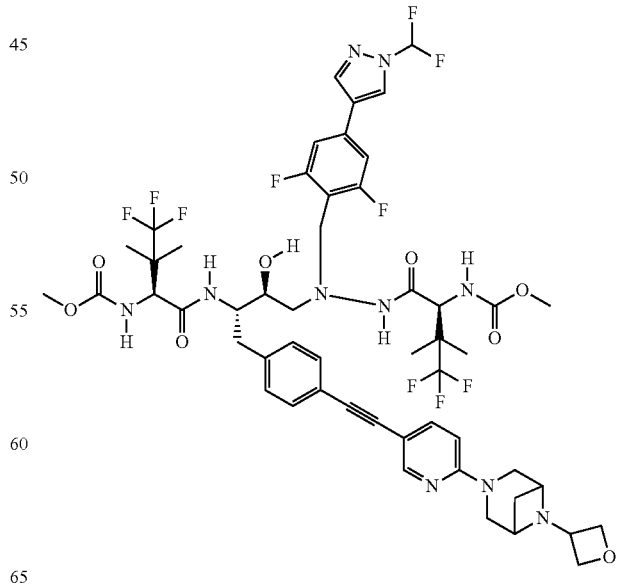

EXAMPLE 60
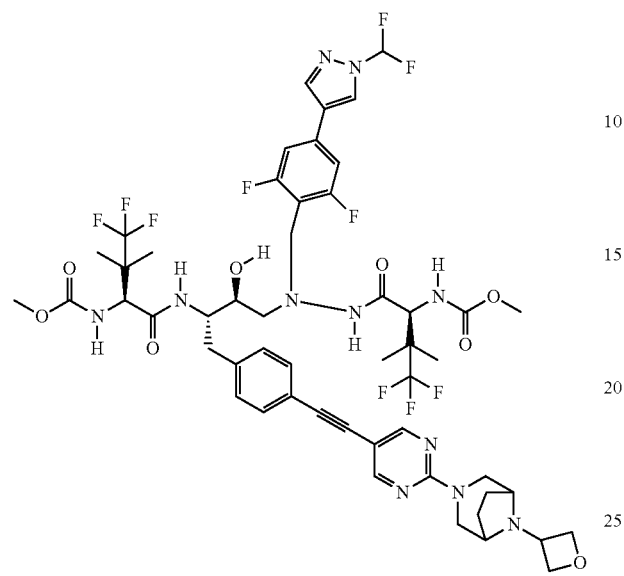
EXAMPLE 61
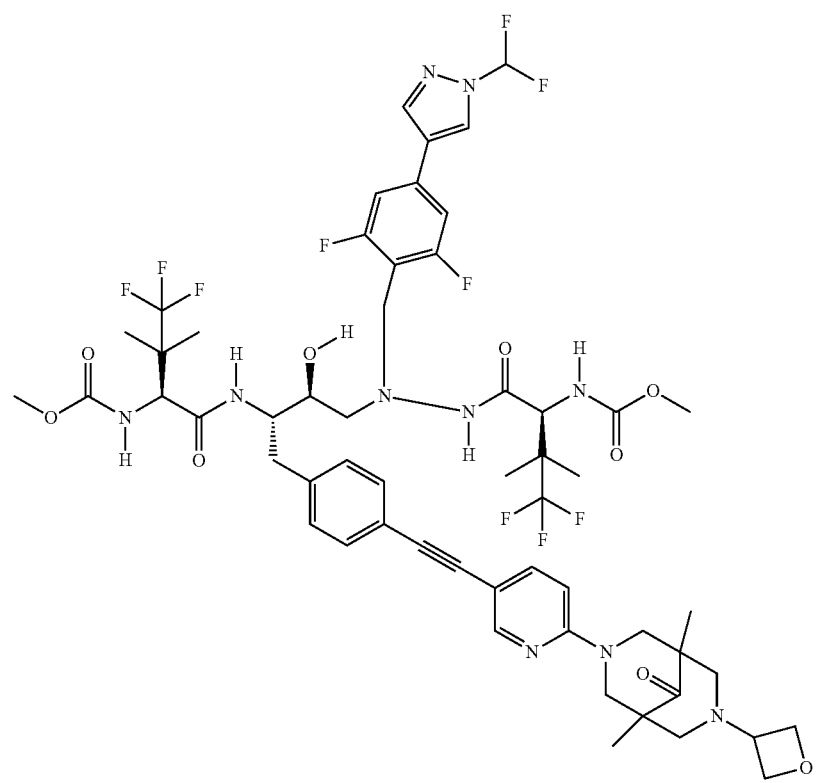 [SMILES: COC(=O)N[C@H](C(=O)N[C@@H](Cc1ccc(C#Cc2ccc(N3CC4(C)CN(C5COC5)CC(C)(C3)C4=O)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

EXAMPLE 62
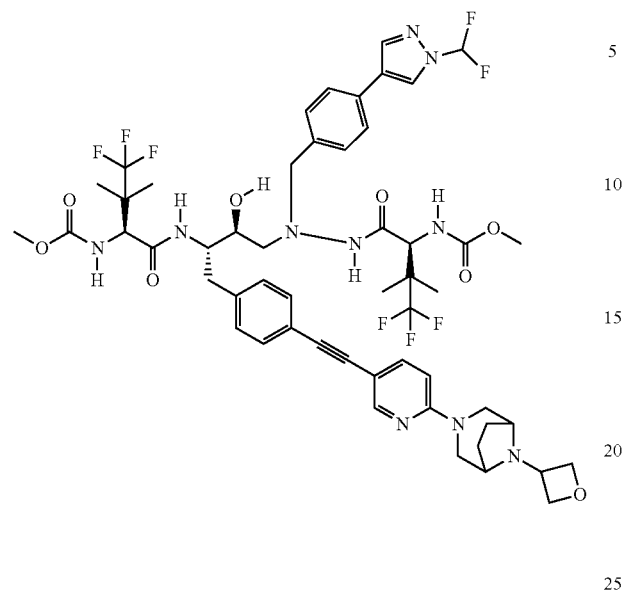
EXAMPLE 63
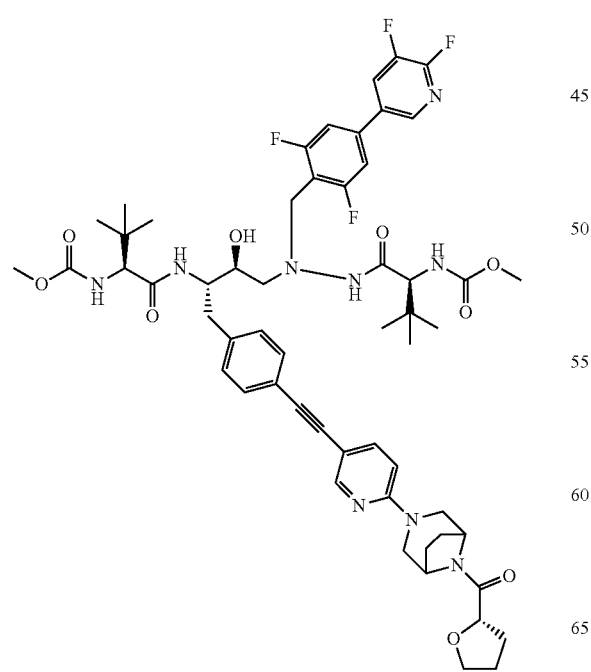

EXAMPLE 64
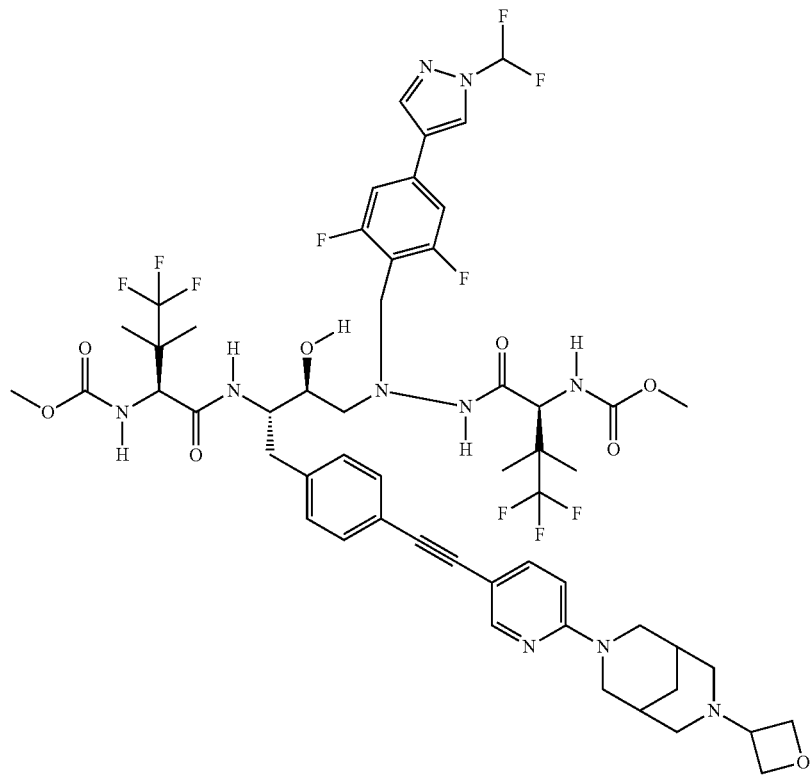 [SMILES: COC(=O)N[C@H](C(=O)N[C@@H](Cc1ccc(C#Cc2ccc(N3CC4CC(C3)CN(C3COC3)C4)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]
EXAMPLE 65
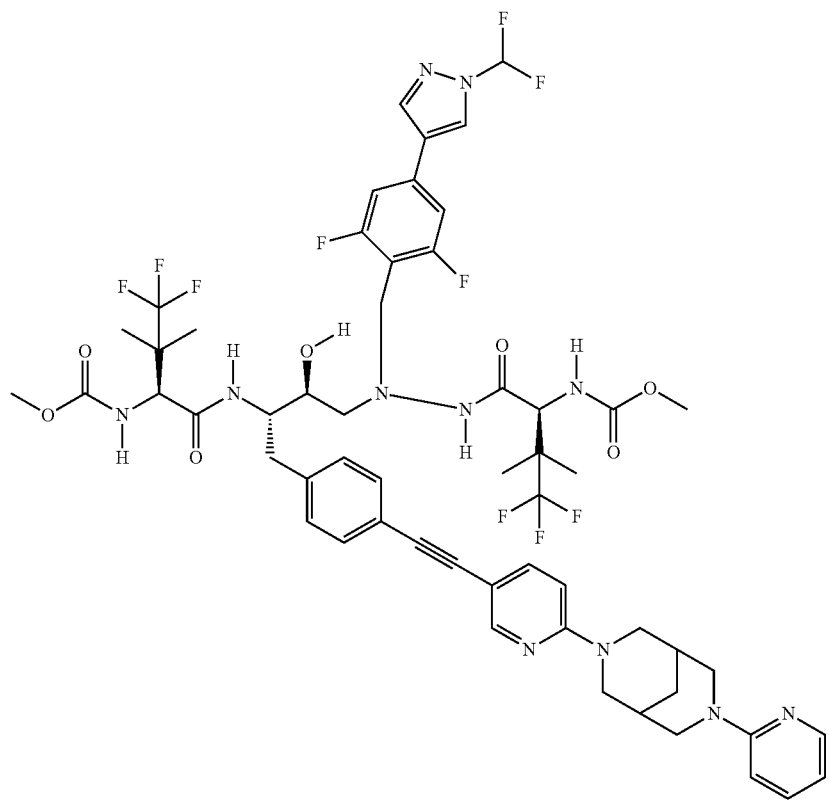 [SMILES: COC(=O)N[C@H](C(=O)N[C@@H](Cc1ccc(C#Cc2ccc(N3CC4CC(CN(c5ccccn5)C4)C3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

483 484
EXAMPLE 66
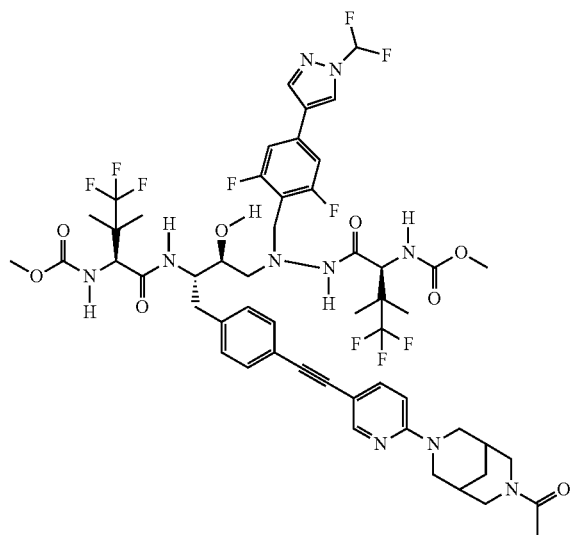 [SMILES: COC(=O)N[C@H](C(=O)N[C@@H](Cc1ccc(C#Cc2ccc(N3CC4CC(CN(C(C)=O)C4)C3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]
EXAMPLE 68
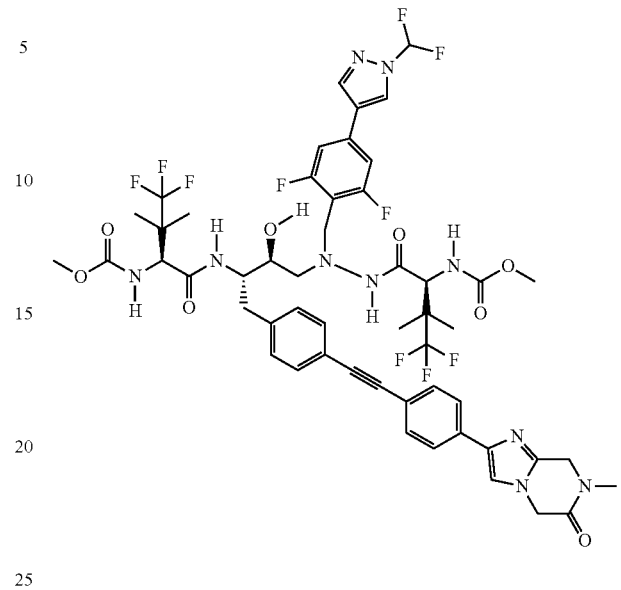
EXAMPLE 67
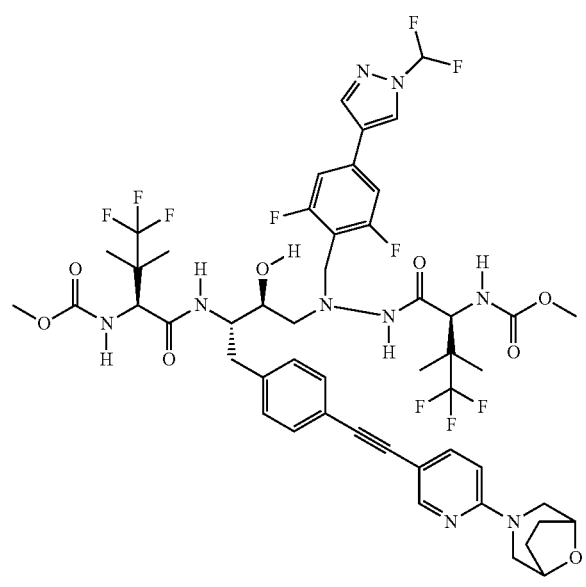
EXAMPLE 69
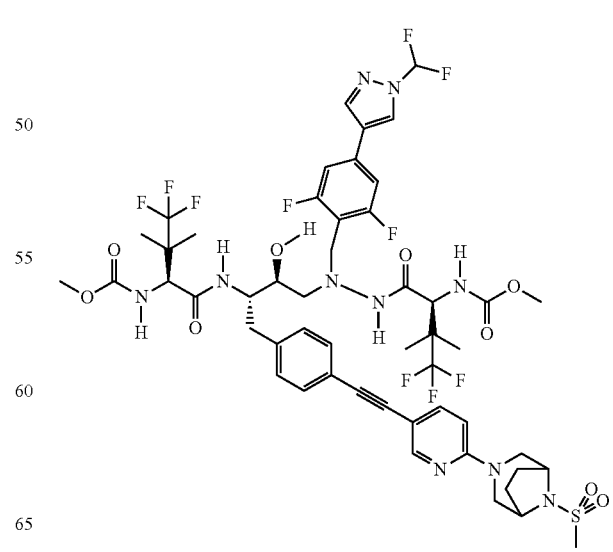

EXAMPLE 70
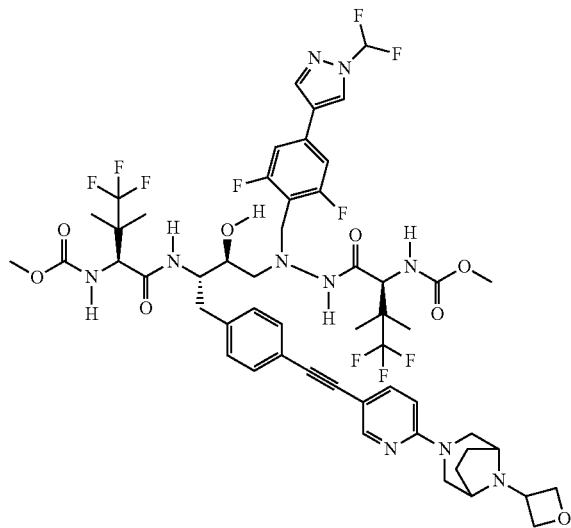 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]
EXAMPLE 72
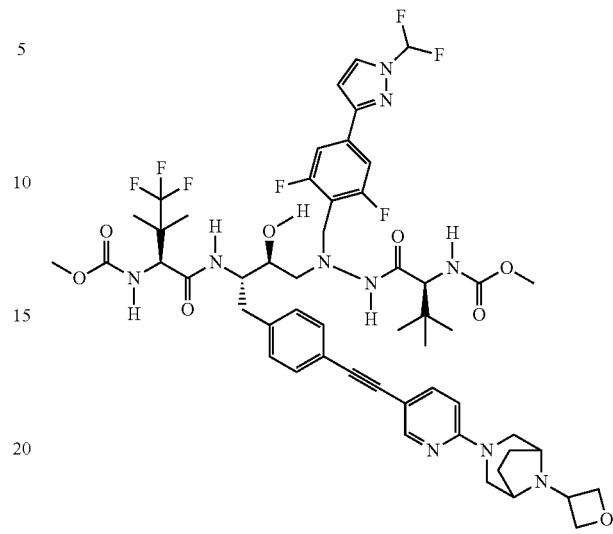
EXAMPLE 73
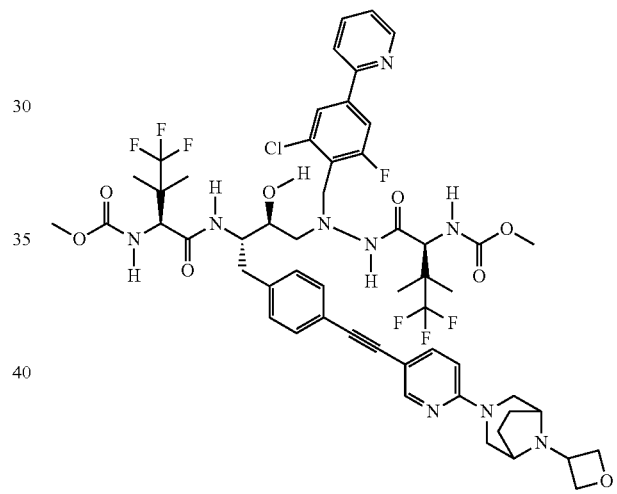
EXAMPLE 71
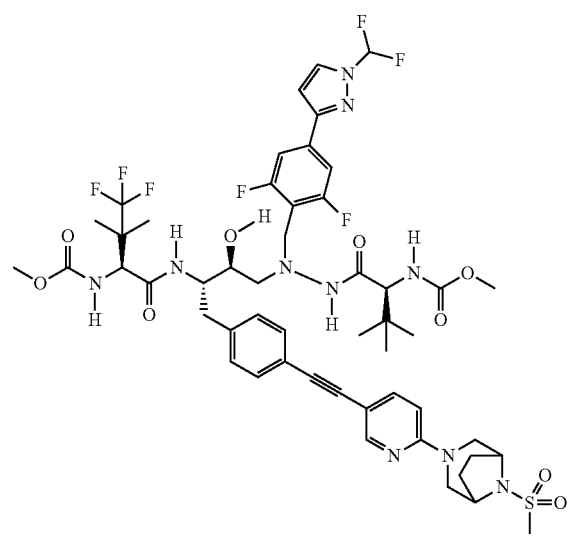 [SMILES: COC(=O)N[C@H](C(=O)NN(Cc1c(F)cc(-c2ccn(C(F)F)n2)cc1F)C[C@H](O)[C@H](Cc1ccc(C#Cc2ccc(N3CC4CCC(C3)N4S(C)(=O)=O)nc2)cc1)NC(=O)[C@@H](NC(=O)OC)C(C)(C)C(F)(F)F)C(C)(C)C]
EXAMPLE 74
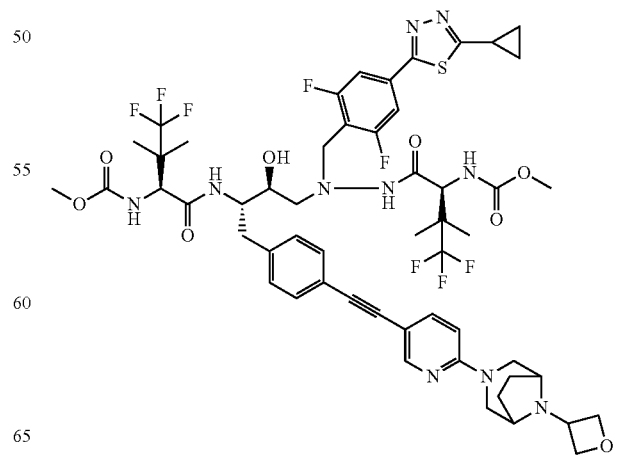

EXAMPLE 75
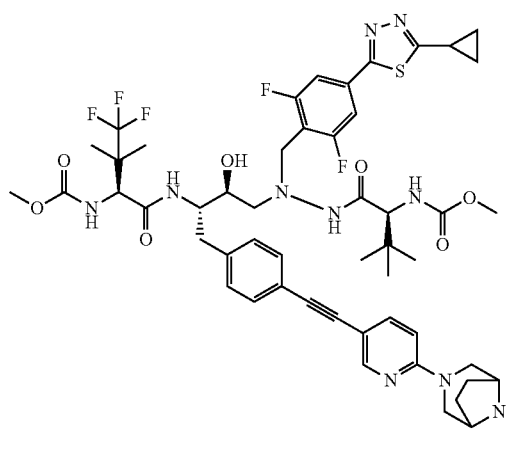
EXAMPLE 78
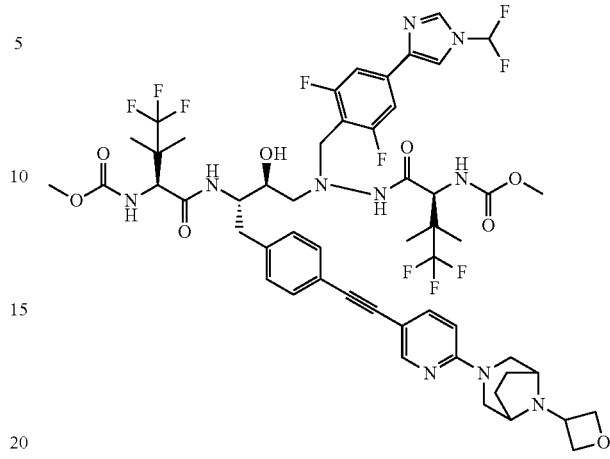
EXAMPLE 76
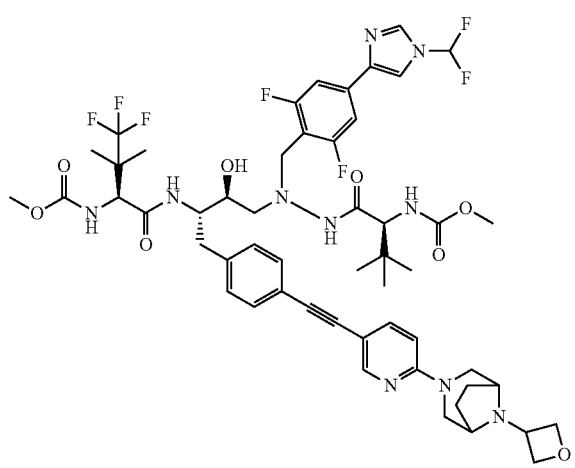 [SMILES: COC(=O)N[C@H](C(=O)NN(Cc1c(F)cc(-c2cn(C(F)F)cn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]
EXAMPLE 79
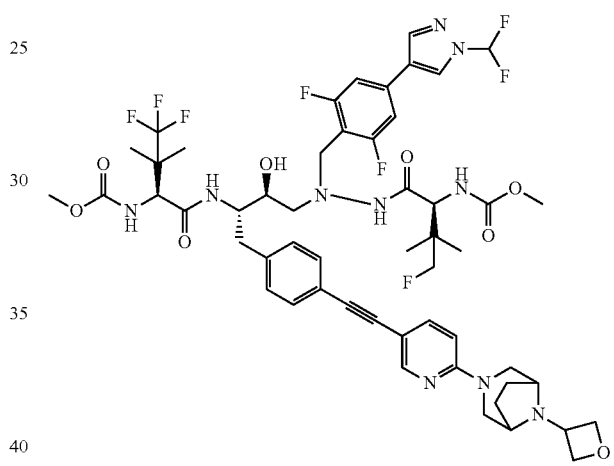
EXAMPLE 77
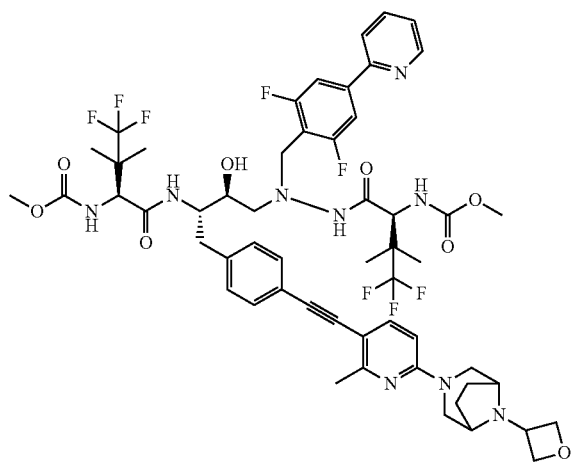 [SMILES: COC(=O)N[C@H](C(=O)N[C@@H](Cc1ccc(C#Cc2ccc(N3CC4CCC(C3)N4C3COC3)nc2C)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]
EXAMPLE 80
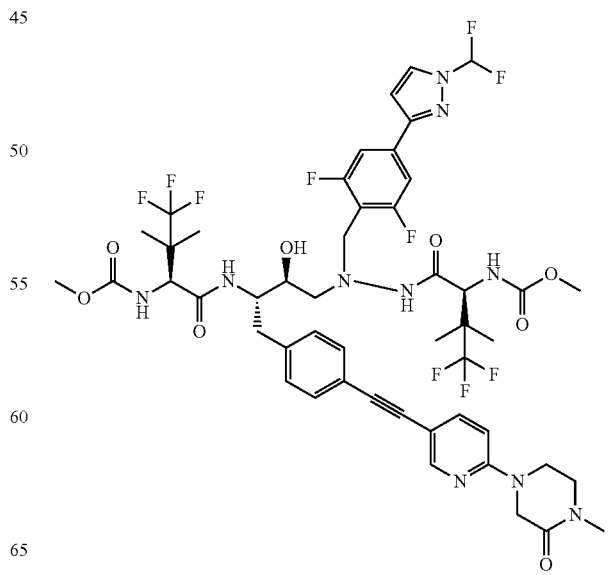

EXAMPLE 81
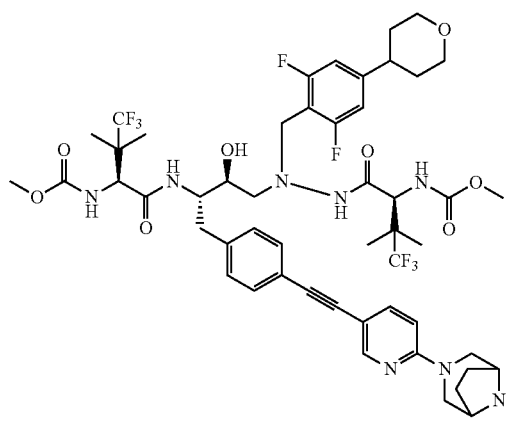
EXAMPLE 84
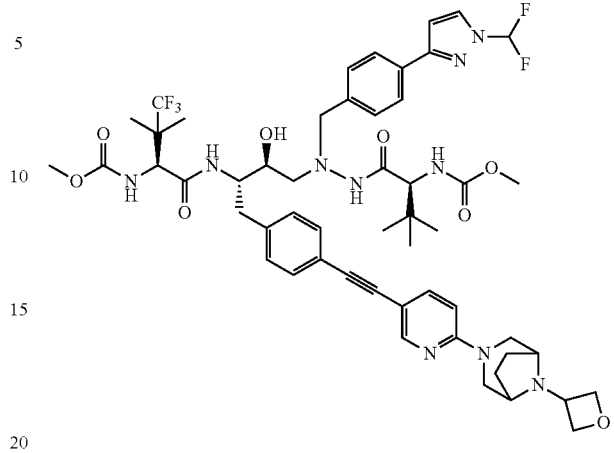
EXAMPLE 85
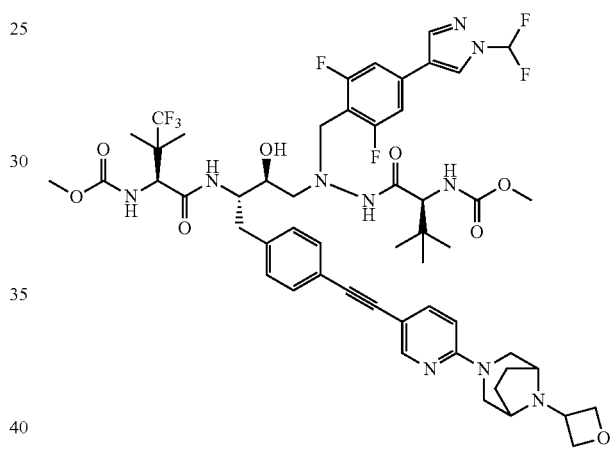
EXAMPLE 82
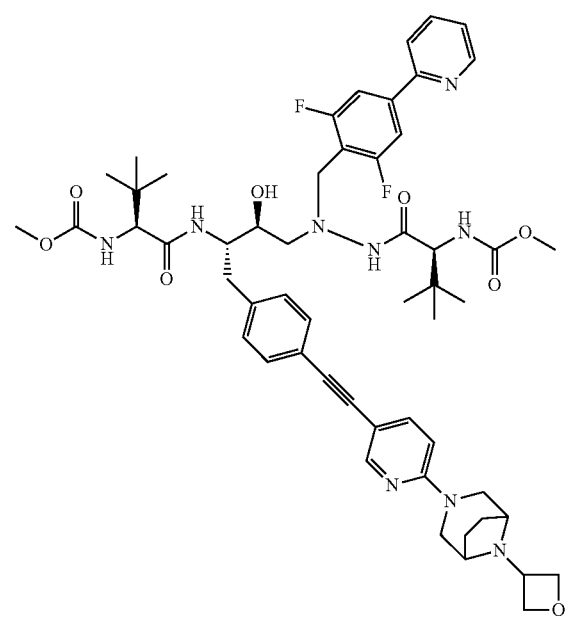 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccccn2)cc1F)NC(=O)[C@@H](NC(=O)OC)C(C)(C)C)C(C)(C)C]
EXAMPLE 86
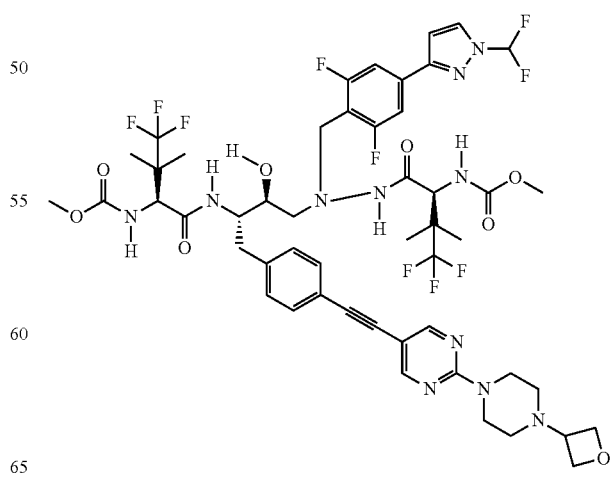

EXAMPLE 87
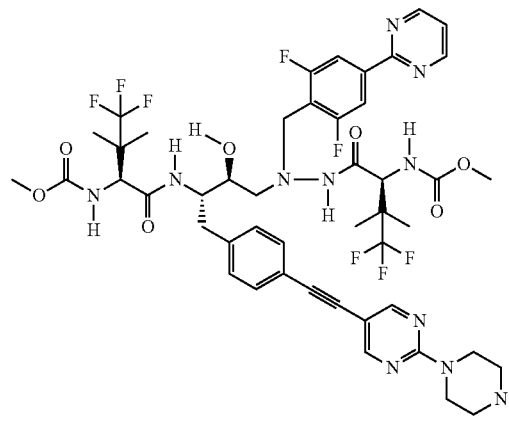
EXAMPLE 90
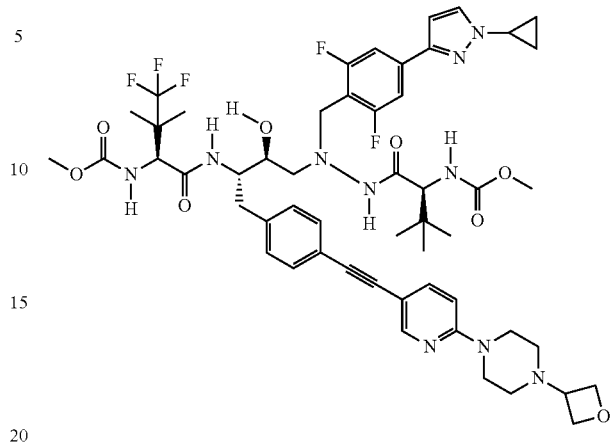
EXAMPLE 88
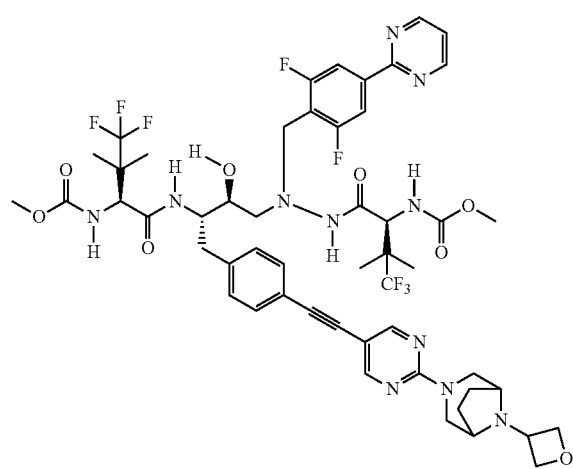 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ncccn2)cc1F)NC(=O)[C@@H](NC(=O)OC)C(C)(C)C(F)(F)F)C(C)(C)C(F)(F)F]
EXAMPLE 91
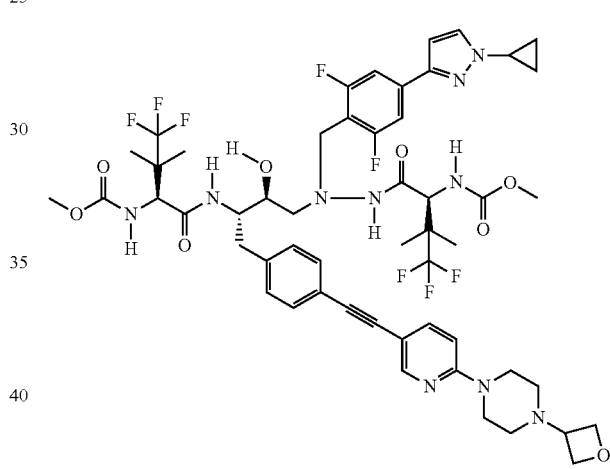
EXAMPLE 89
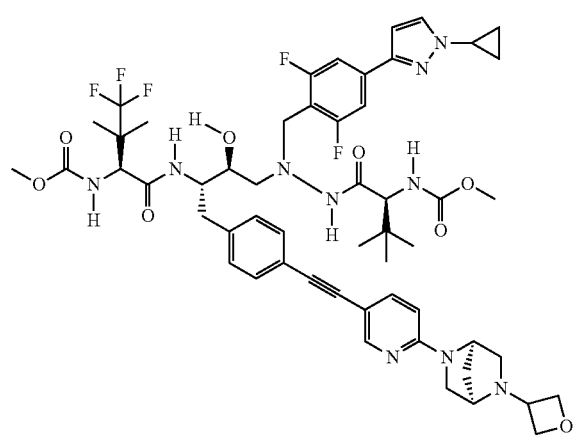 [SMILES: COC(=O)N[C@H](C(=O)NN(Cc1c(F)cc(-c2ccn(C3CC3)n2)cc1F)C[C@H](O)[C@H](Cc1ccc(C#Cc2ccc(N3C[C@H]4C[C@@H]3CN4C3COC3)nc2)cc1)NC(=O)[C@@H](NC(=O)OC)C(C)(C)C(F)(F)F)C(C)(C)C]
EXAMPLE 92
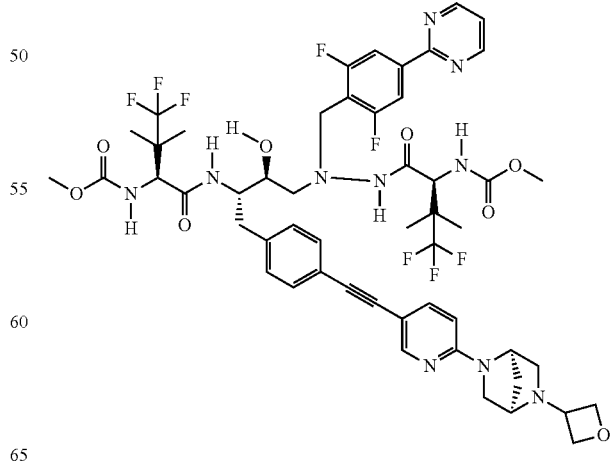

EXAMPLE 93
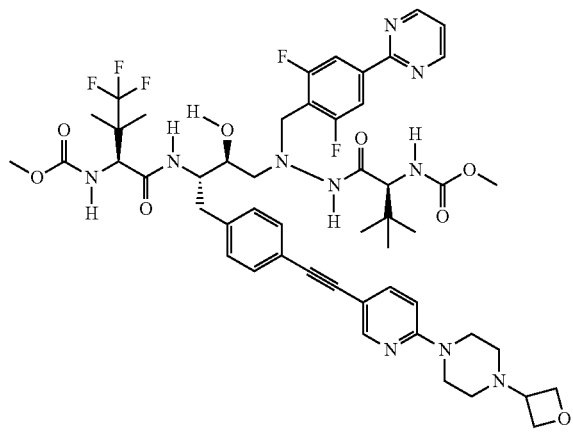 [SMILES: COC(=O)N[C@H](C(=O)NN(Cc1c(F)cc(-c2ncccn2)cc1F)C[C@H](O)[C@H](Cc1ccc(C#Cc2ccc(N3CCN(C4COC4)CC3)nc2)cc1)NC(=O)[C@@H](NC(=O)OC)C(C)(C)C(F)(F)F)C(C)(C)C]
EXAMPLE 94
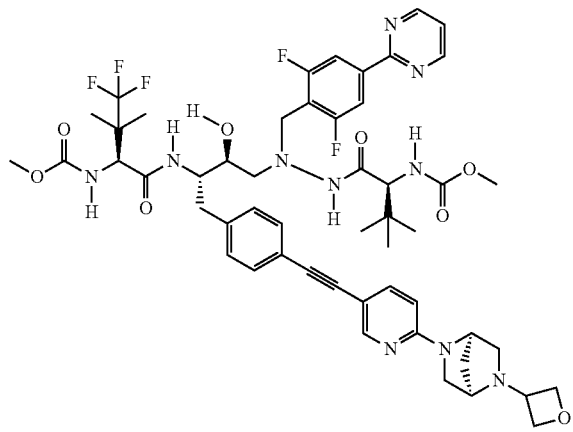 [SMILES: COC(=O)N[C@H](C(=O)NN(Cc1c(F)cc(-c2ncccn2)cc1F)C[C@H](O)[C@H](Cc1ccc(C#Cc2ccc(N3C[C@H]4C[C@@H]3CN4C3COC3)nc2)cc1)NC(=O)[C@@H](NC(=O)OC)C(C)(C)C(F)(F)F)C(C)(C)C]
EXAMPLE 95
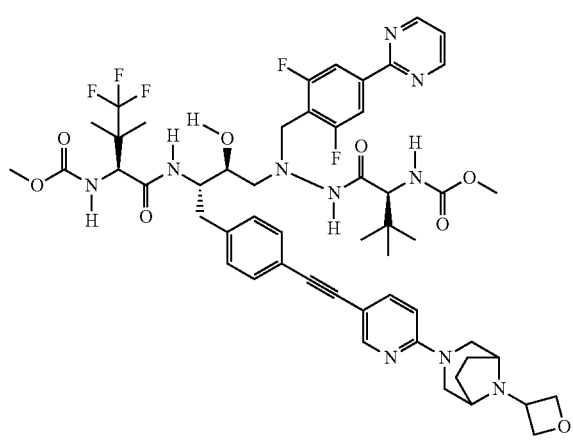 [SMILES: COC(=O)N[C@H](C(=O)NN(Cc1c(F)cc(-c2ncccn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]
EXAMPLE 96
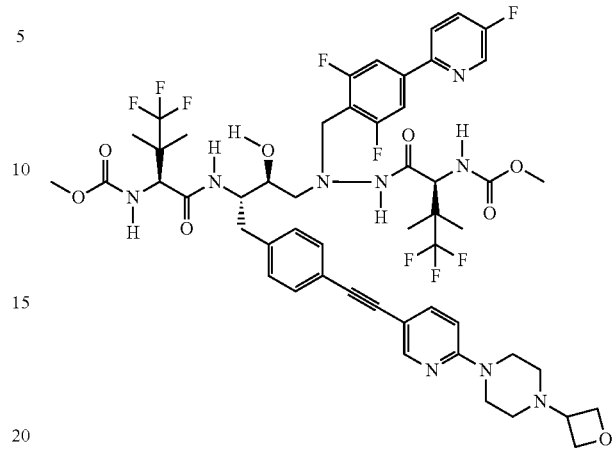
EXAMPLE 97
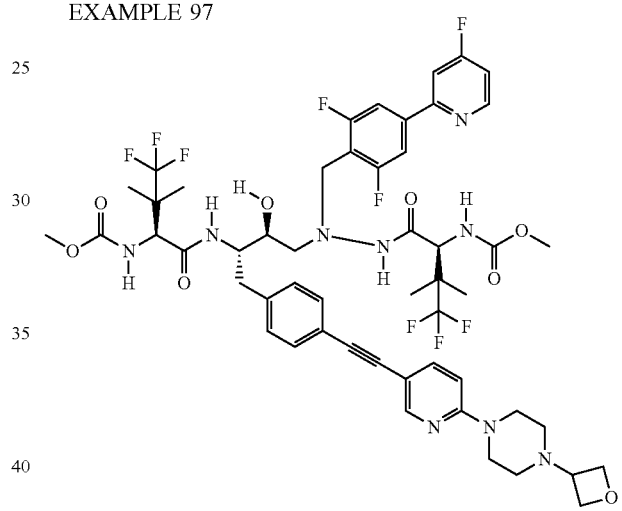
EXAMPLE 98
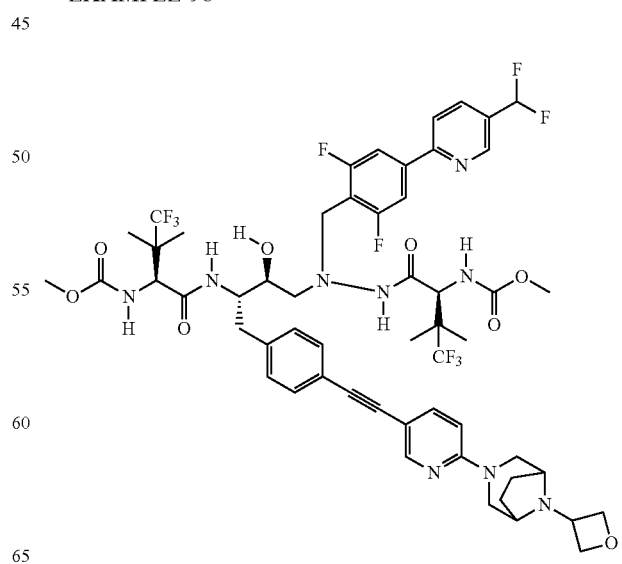

EXAMPLE 99
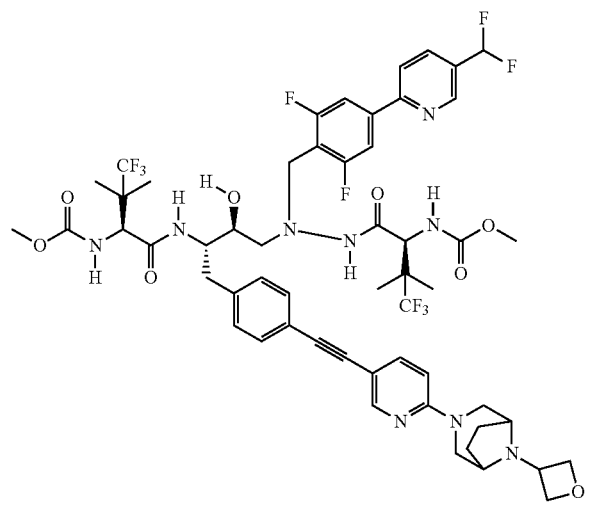 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(C(F)F)cn2)cc1F)NC(=O)[C@@H](NC(=O)OC)C(C)(C)C(F)(F)F)C(C)(C)C(F)(F)F]
EXAMPLE 101
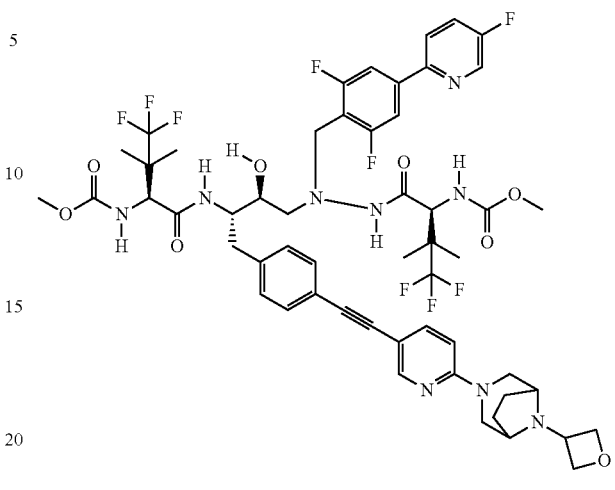
EXAMPLE 100
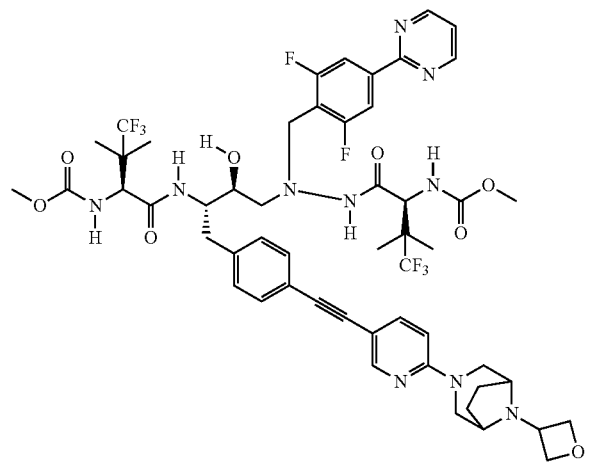 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ncccn2)cc1F)NC(=O)[C@@H](NC(=O)OC)C(C)(C)C(F)(F)F)C(C)(C)C(F)(F)F]
EXAMPLE 102
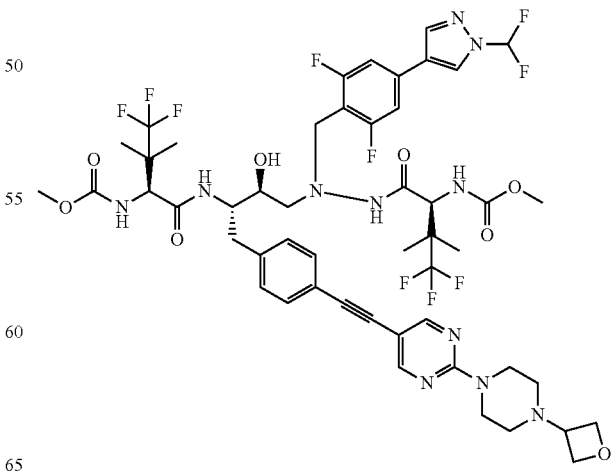

EXAMPLE 103
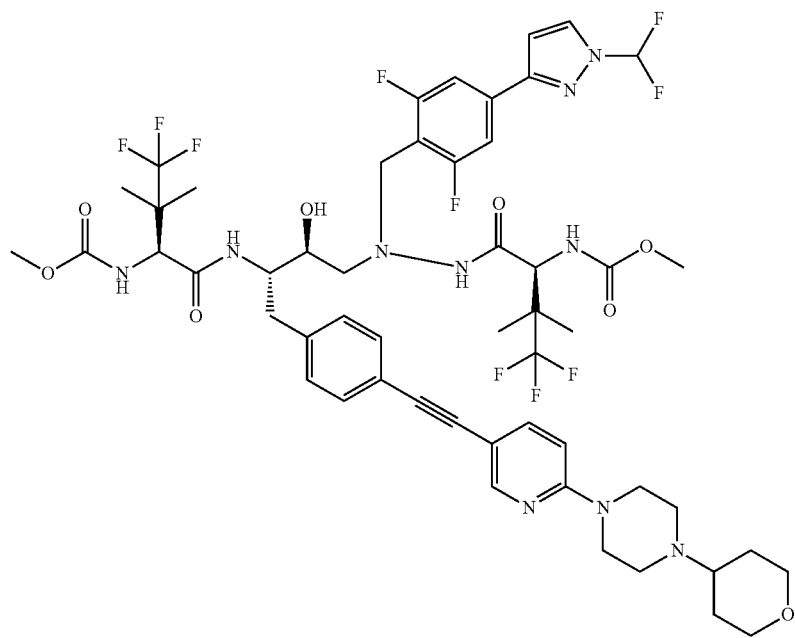 [SMILES: COC(=O)N[C@H](C(=O)N[C@@H](Cc1ccc(C#Cc2ccc(N3CCN(C4CCOCC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 104
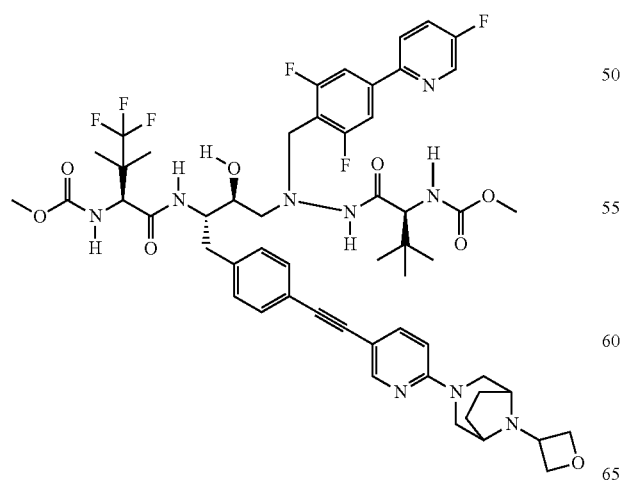

EXAMPLE 105
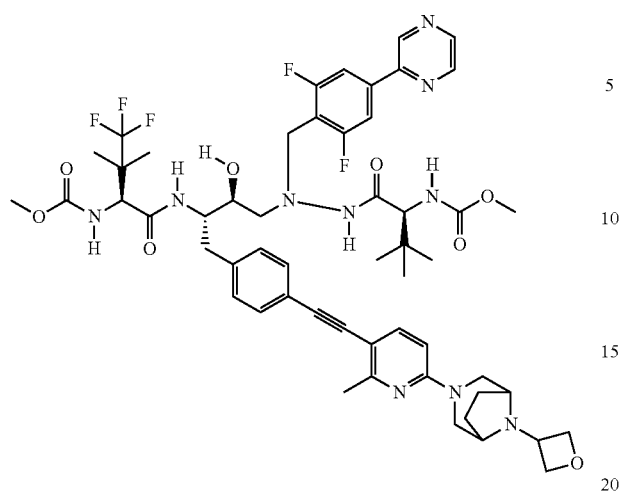
EXAMPLE 106
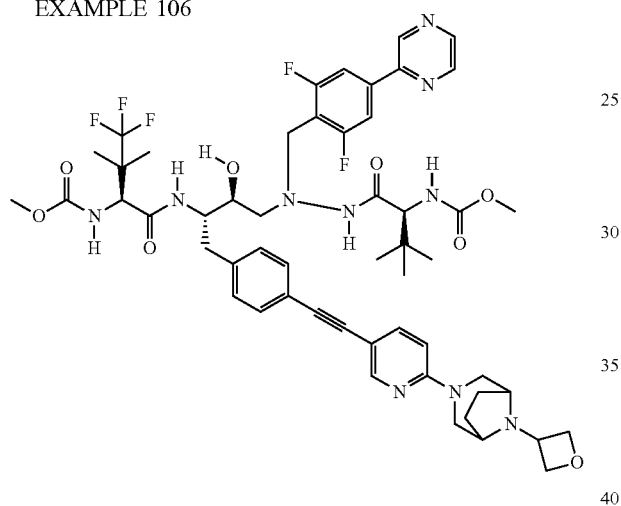
EXAMPLE 107
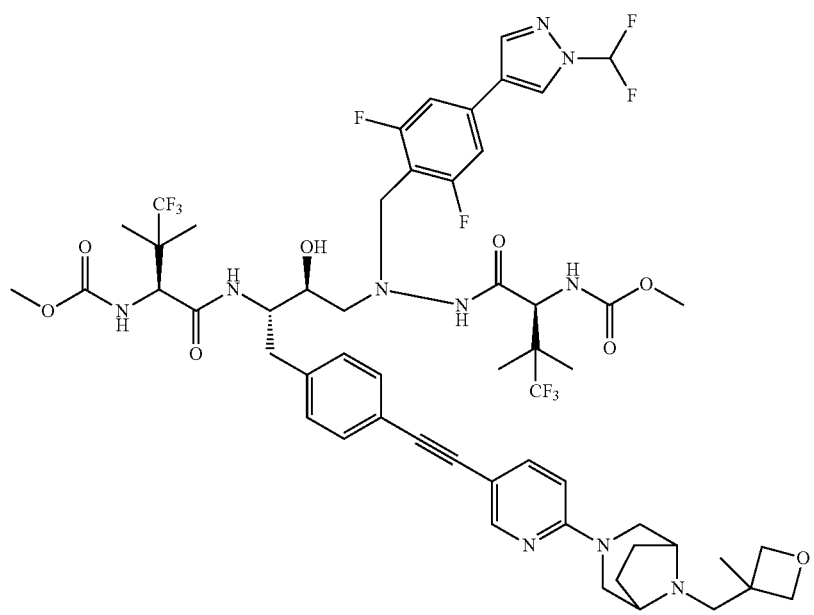 [SMILES: COC(=O)N[C@H](C(=O)N[C@@H](Cc1ccc(C#Cc2ccc(N3CC4CCC(C3)N4CC3(C)COC3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

EXAMPLE 108
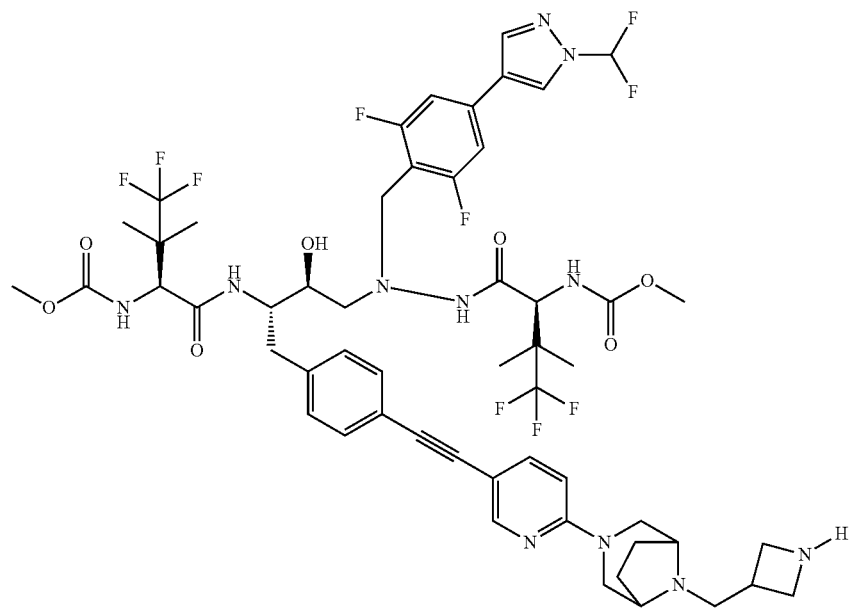 [SMILES: COC(=O)N[C@H](C(=O)N[C@@H](Cc1ccc(C#Cc2ccc(N3CC4CCC(C3)N4CC3CNC3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]
EXAMPLE 109
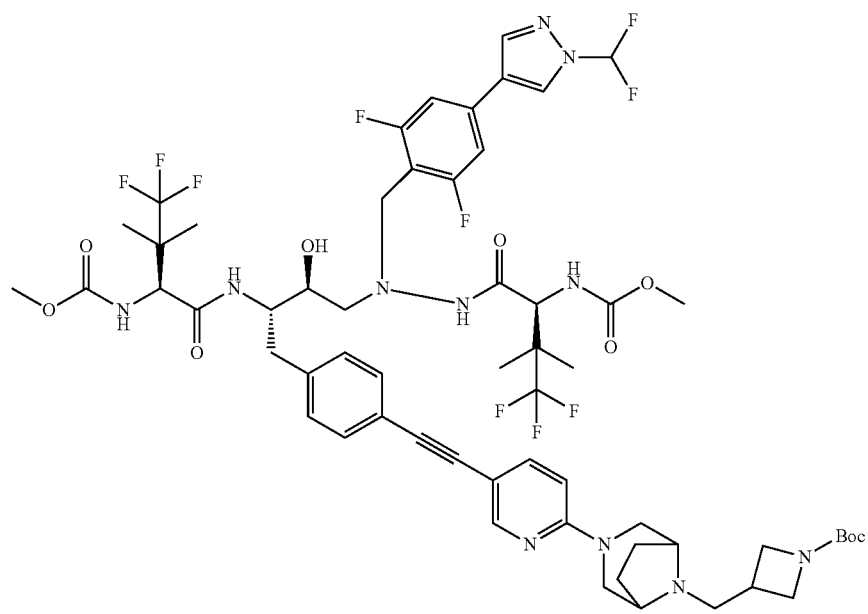 [SMILES: COC(=O)N[C@H](C(=O)N[C@@H](Cc1ccc(C#Cc2ccc(N3CC4CCC(C3)N4CC3CN(C(=O)OC(C)(C)C)C3)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]

EXAMPLE 110
EXAMPLE 112
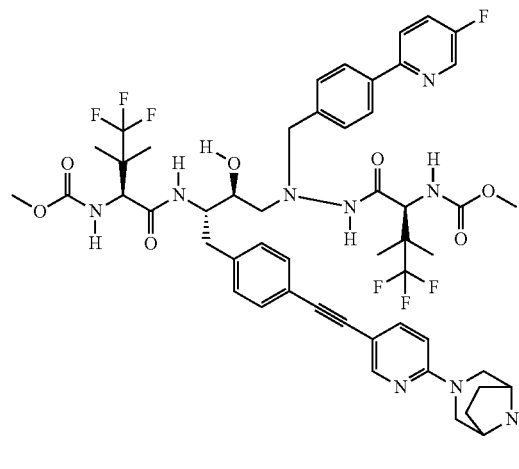
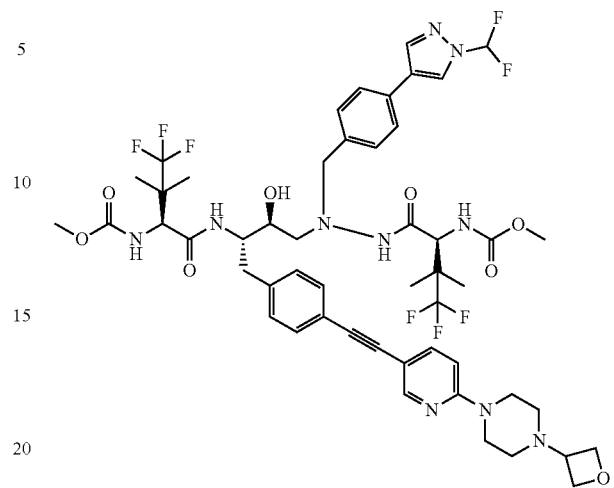
EXAMPLE 113
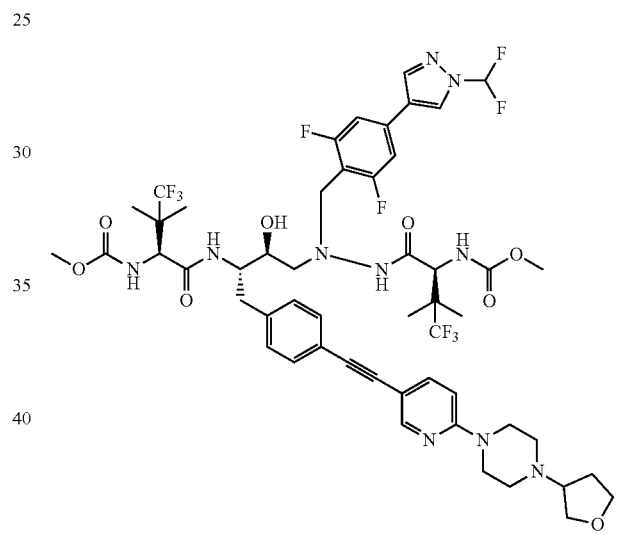
EXAMPLE 111
EXAMPLE 114
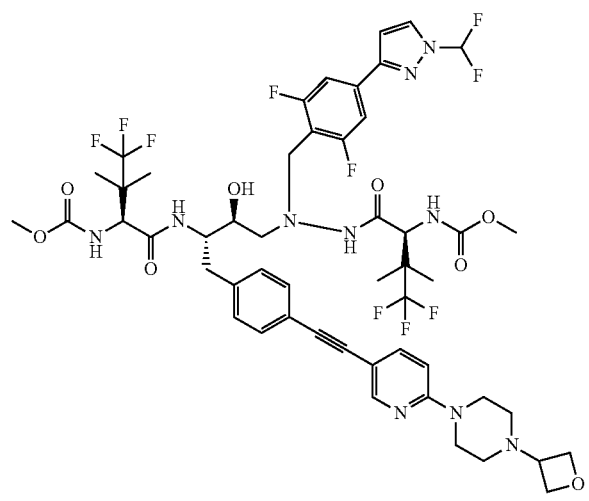 [SMILES: COC(=O)N[C@H](C(=O)N[C@@H](Cc1ccc(C#Cc2ccc(N3CCN(C4COC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
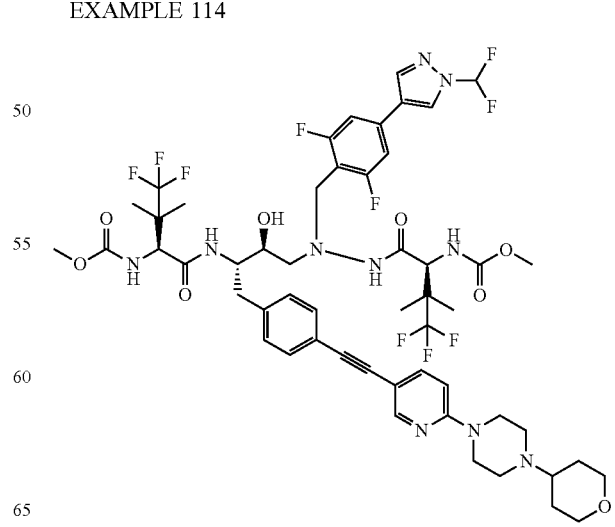

EXAMPLE 115
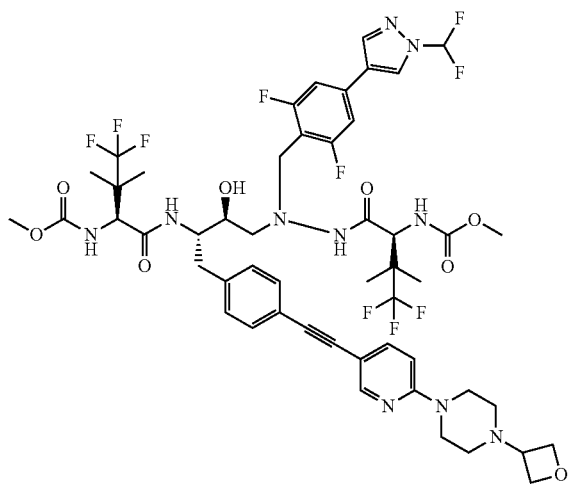 [SMILES: COC(=O)N[C@H](C(=O)NCN(CCc1c(F)cc(-c2cnn(C(F)F)c2)cc1F)C[C@H](O)[C@H](Cc1ccc(C#Cc2ccc(N3CCN(C4COC4)CC3)nc2)cc1)NC(=O)[C@@H](NC(=O)OC)C(C)(C)C(F)(F)F)C(C)(C)C(F)(F)F]
EXAMPLE 116
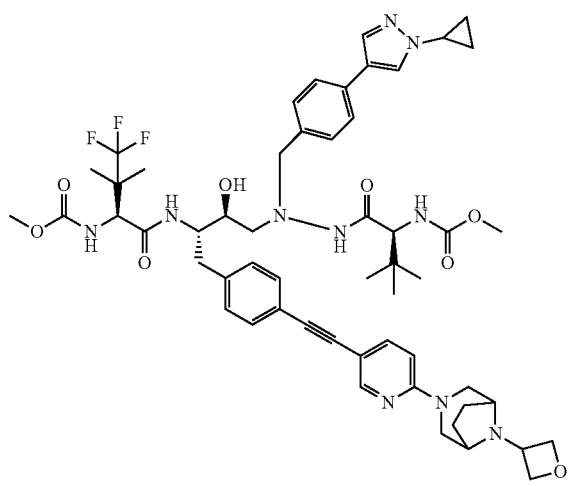 [SMILES: COC(=O)N[C@H](C(=O)NCN(CCc1ccc(-c2cnn(C3CC3)c2)cc1)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C]
EXAMPLE 117
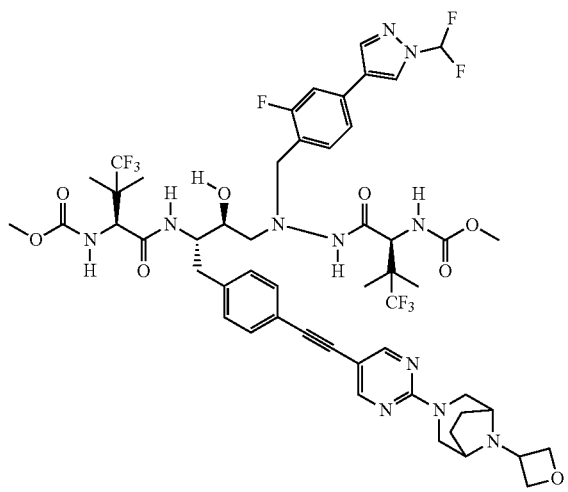 [SMILES: COC(=O)N[C@H](C(=O)NCN(CCc1ccc(-c2cnn(C(F)F)c2)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C(F)(F)F]
EXAMPLE 118
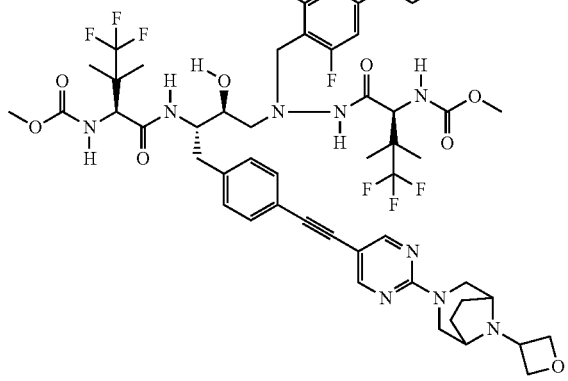

EXAMPLE 119
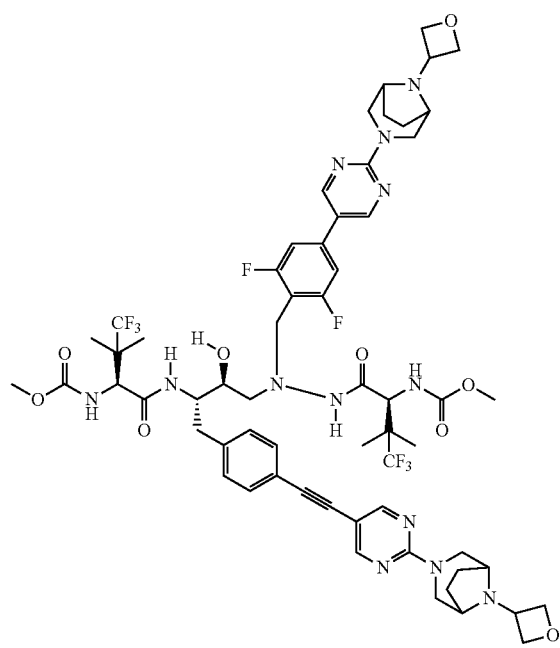 [SMILES: COC(=O)N[C@H](C(=O)NCN(CCc1c(F)cc(-c2cnc(N3CC4CCC(C3)N4C3COC3)nc2)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C(F)(F)F]
EXAMPLE 121
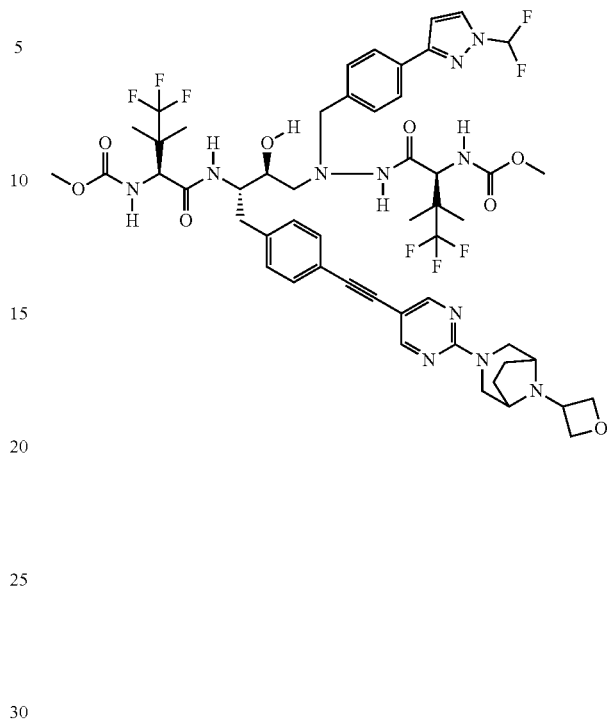
EXAMPLE 120
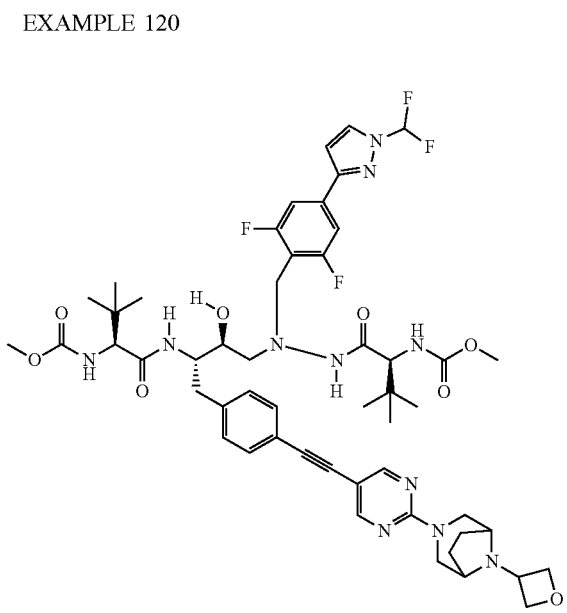
EXAMPLE 122
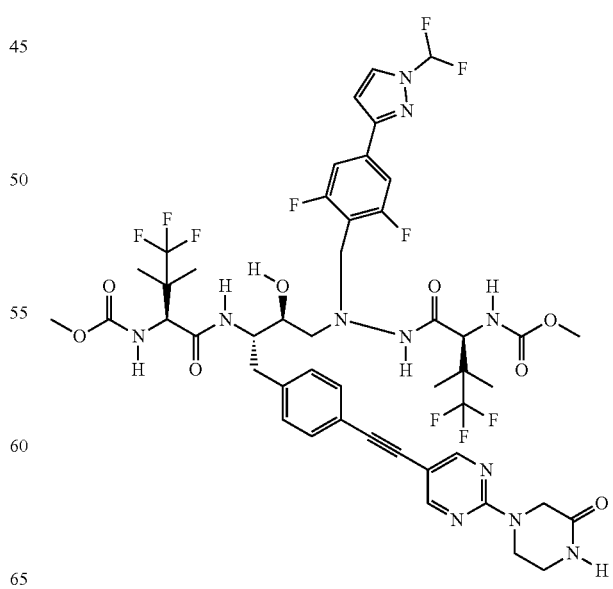

EXAMPLE 123
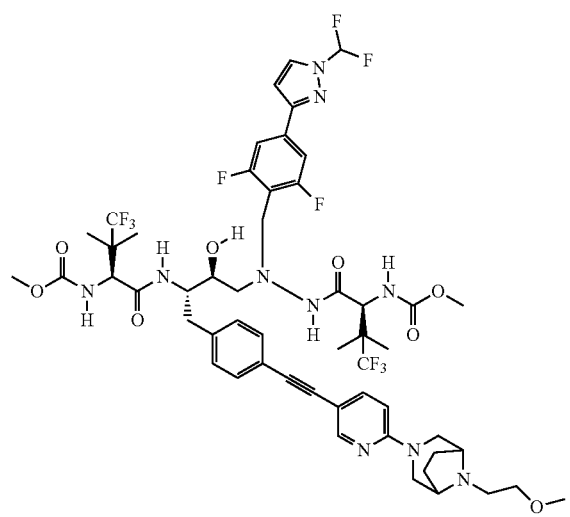
EXAMPLE 125
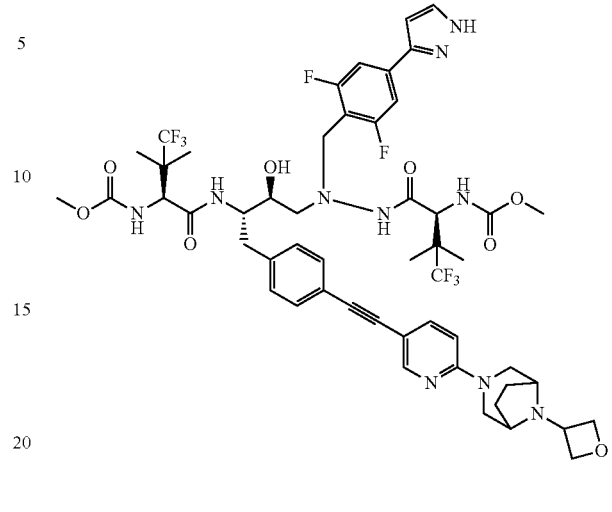
EXAMPLE 124
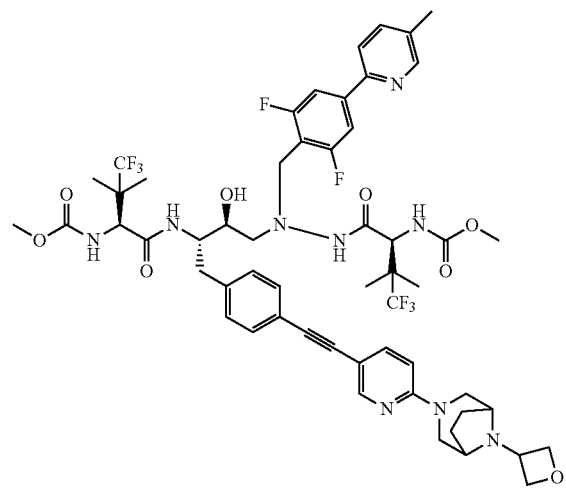 [SMILES: COC(=O)N[C@H](C(=O)NCN(CCc1c(F)cc(-c2ccc(C)cn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C(F)(F)F]
EXAMPLE 126
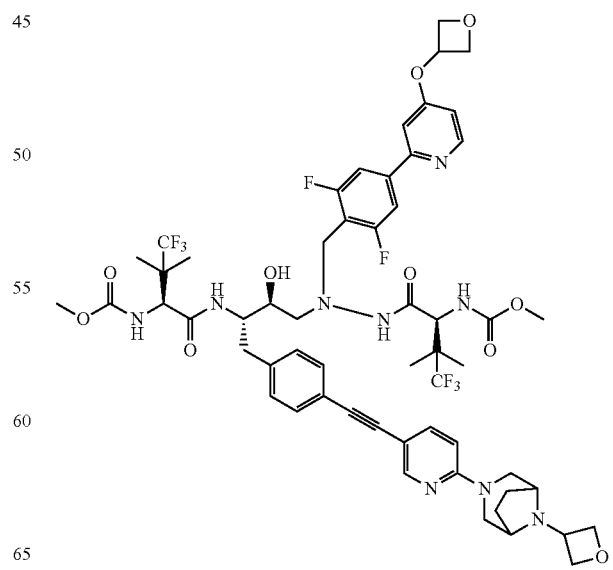

EXAMPLE 127
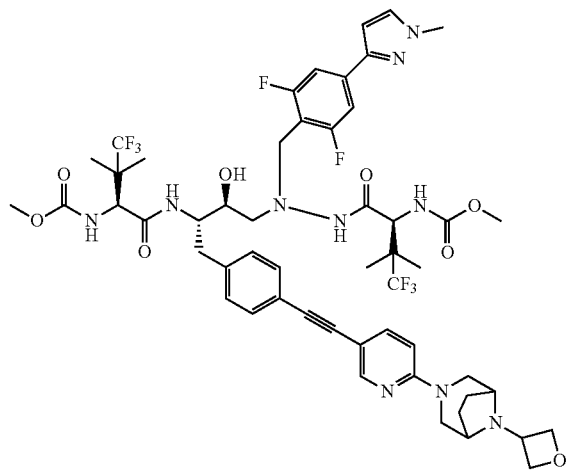 [SMILES: COC(=O)N[C@H](C(=O)NCN(CCc1c(F)cc(C(=N)/C=C\N)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(C)(C)C(F)(F)F]
EXAMPLE 129
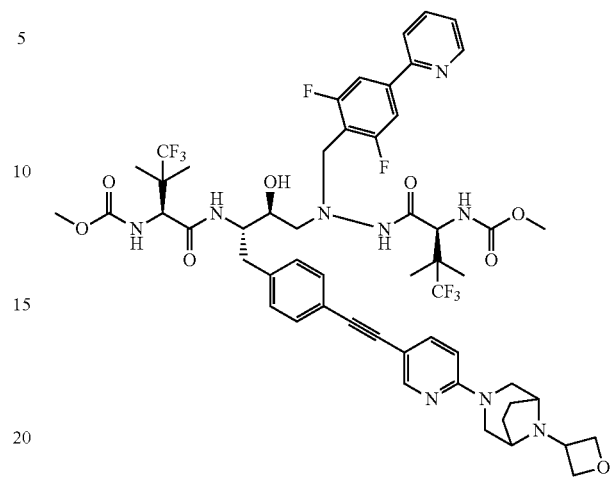
EXAMPLE 128
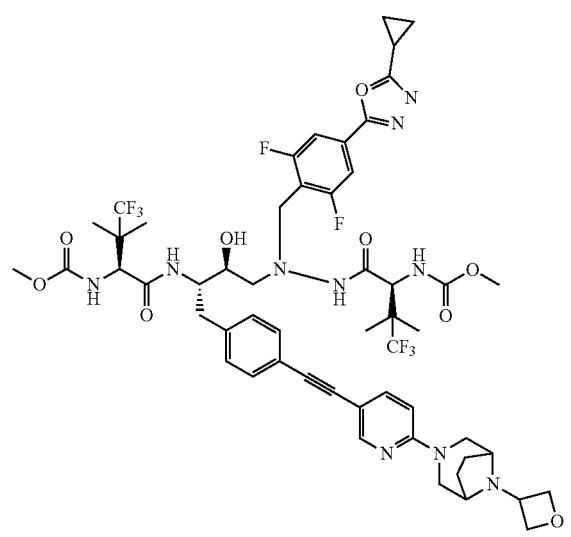
EXAMPLE 130
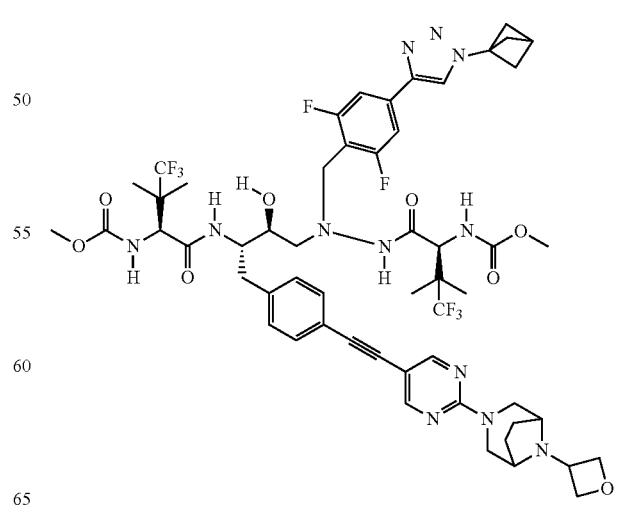

EXAMPLE 131
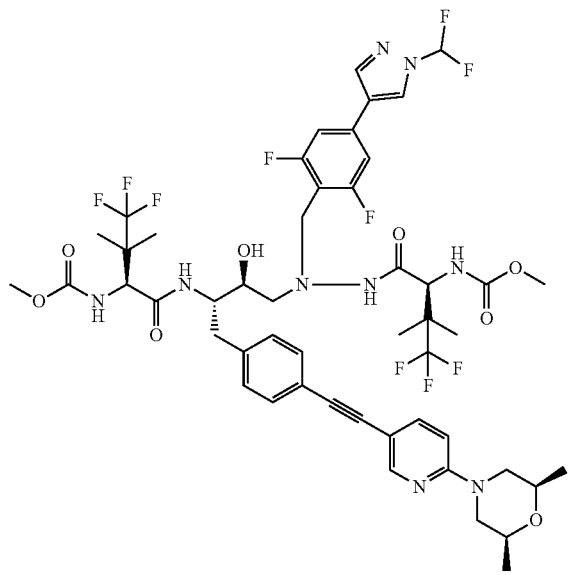
EXAMPLE 132
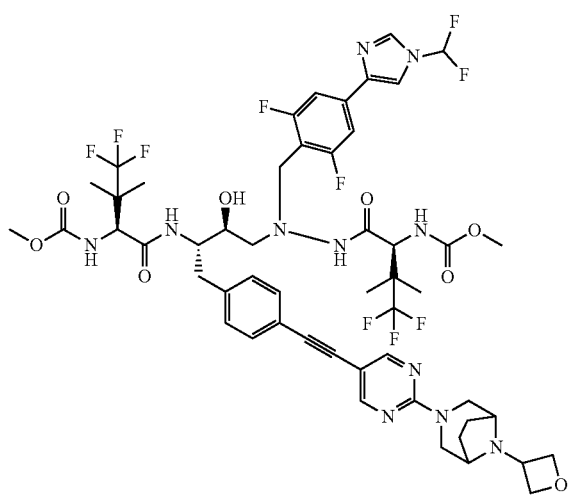 [SMILES: COC(=O)N[C@H](C(=O)NCN(CCc1c(F)cc(-c2cn(C(F)F)cn2)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C(F)(F)F]
EXAMPLE 133
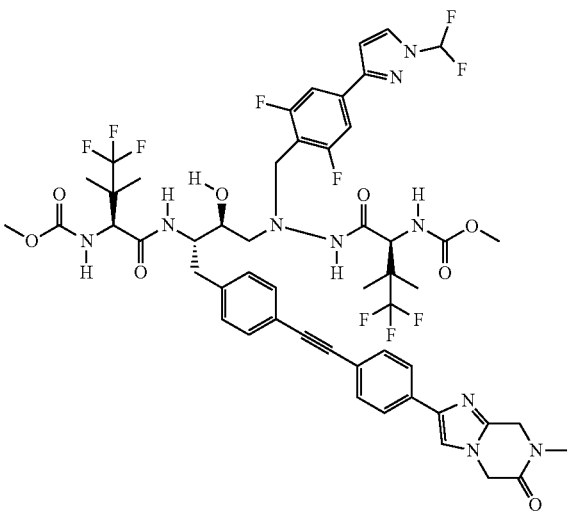
EXAMPLE 134
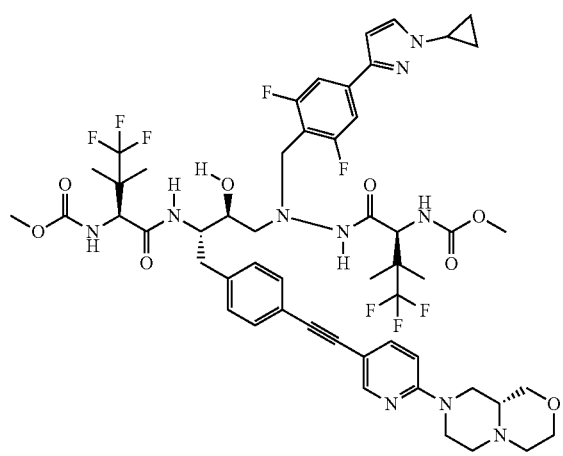 [SMILES: COC(=O)N[C@H](C(=O)NCN(CCc1c(F)cc(C(=N)/C=C\NC2CC2)cc1F)C[C@H](O)[C@H](Cc1ccc(C#Cc2ccc(N3CCN4CCOC[C@H]4C3)nc2)cc1)NC(=O)[C@@H](NC(=O)OC)C(C)(C)C(F)(F)F)C(C)(C)C(F)(F)F]
EXAMPLE 135

EXAMPLE 136
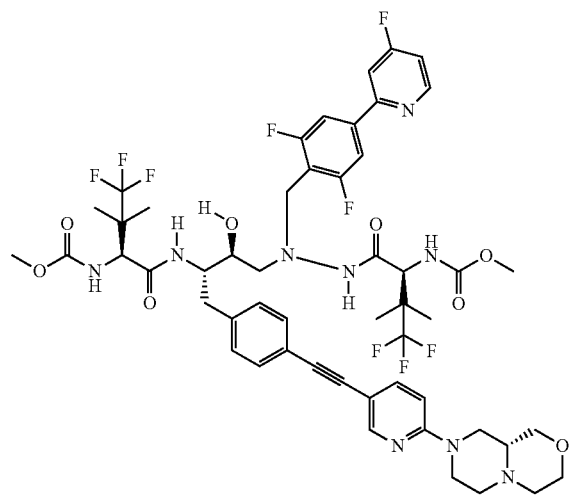 [SMILES: COC(=O)N[C@H](C(=O)NCN(CCc1c(F)cc(-c2cc(F)ccn2)cc1F)C[C@H](O)[C@H](Cc1ccc(C#Cc2ccc(N3CCN4CCOC[C@H]4C3)nc2)cc1)NC(=O)[C@@H](NC(=O)OC)C(C)(C)C(F)(F)F)C(C)(C)C(F)(F)F]
EXAMPLE 138
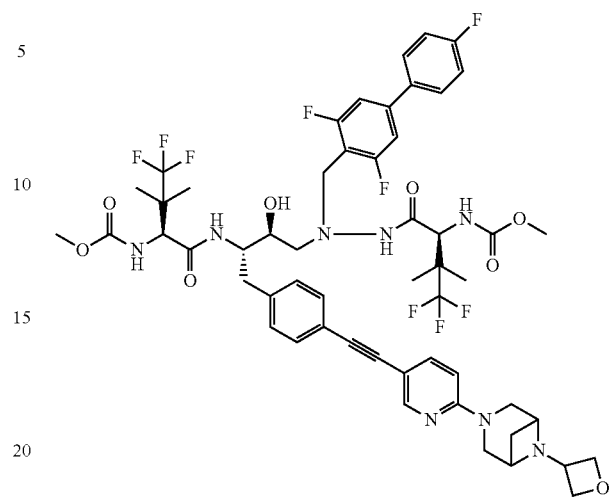
EXAMPLE 137
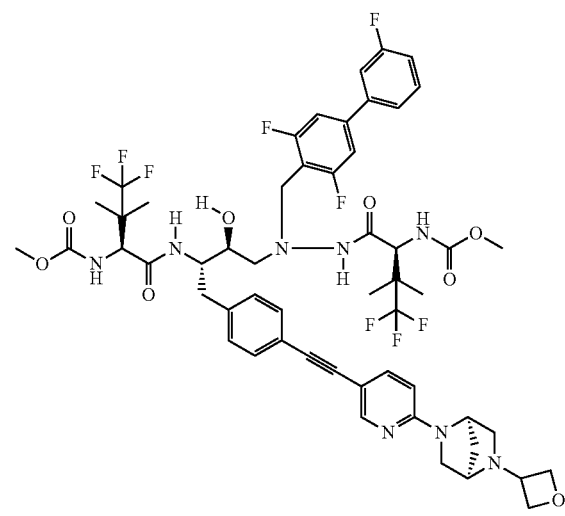 [SMILES: COC(=O)N[C@H](C(=O)NCN(CCc1c(F)cc(-c2cccc(F)c2)cc1F)C[C@H](O)[C@H](Cc1ccc(C#Cc2ccc(N3C[C@H]4C[C@@H]3CN4C3COC3)nc2)cc1)NC(=O)[C@@H](NC(=O)OC)C(C)(C)C(F)(F)F)C(C)(C)C(F)(F)F]
EXAMPLE 139
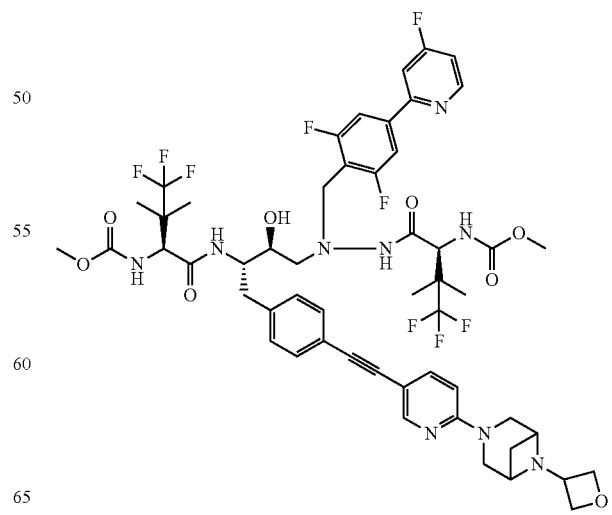

EXAMPLE 140
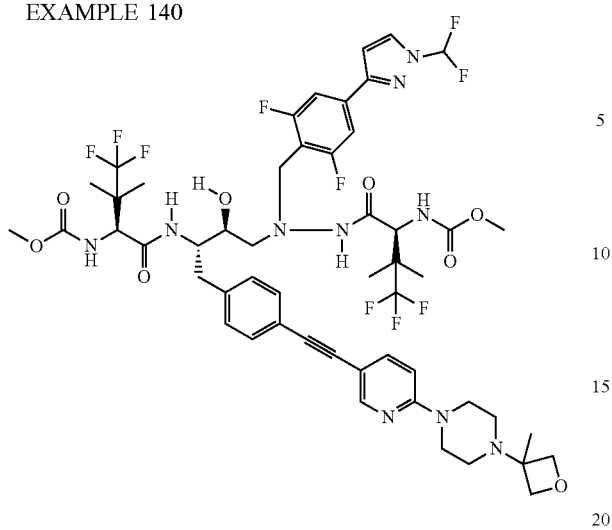
EXAMPLE 141
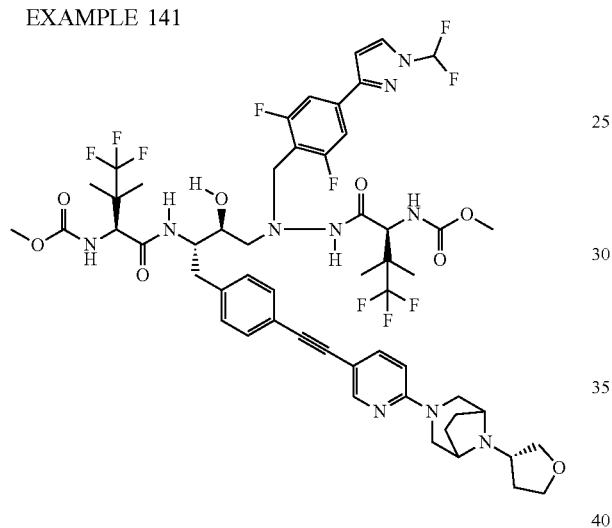
EXAMPLE 142
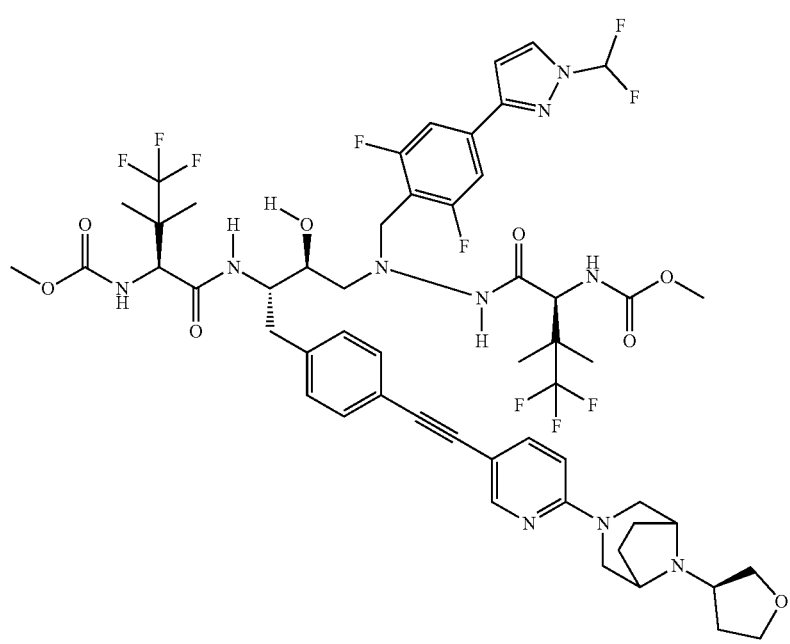 [SMILES: COC(=O)N[C@H](C(=O)N[C@@H](Cc1ccc(C#Cc2ccc(N3CC4CCC(C3)N4[C@@H]3CCOC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 143
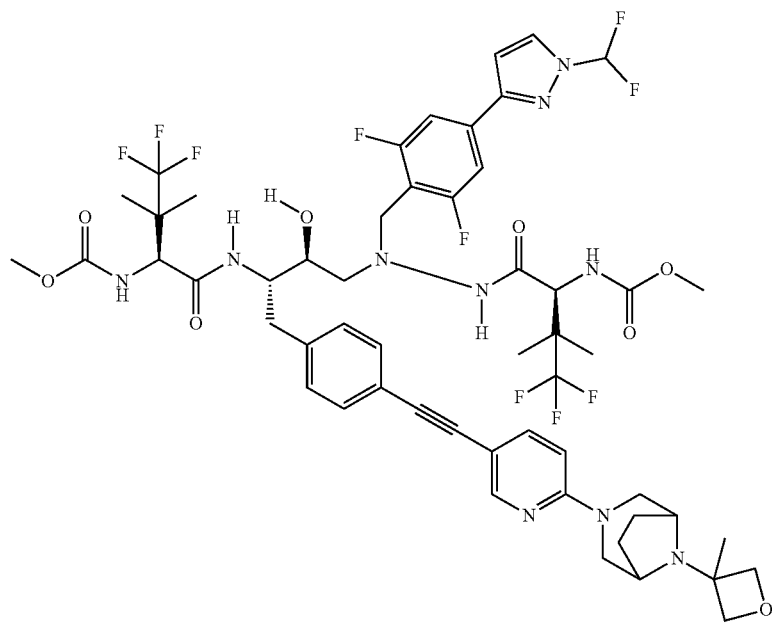 [SMILES: COC(=O)N[C@H](C(=O)N[C@@H](Cc1ccc(C#Cc2ccc(N3CC4CCC(C3)N4C3(C)COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 144
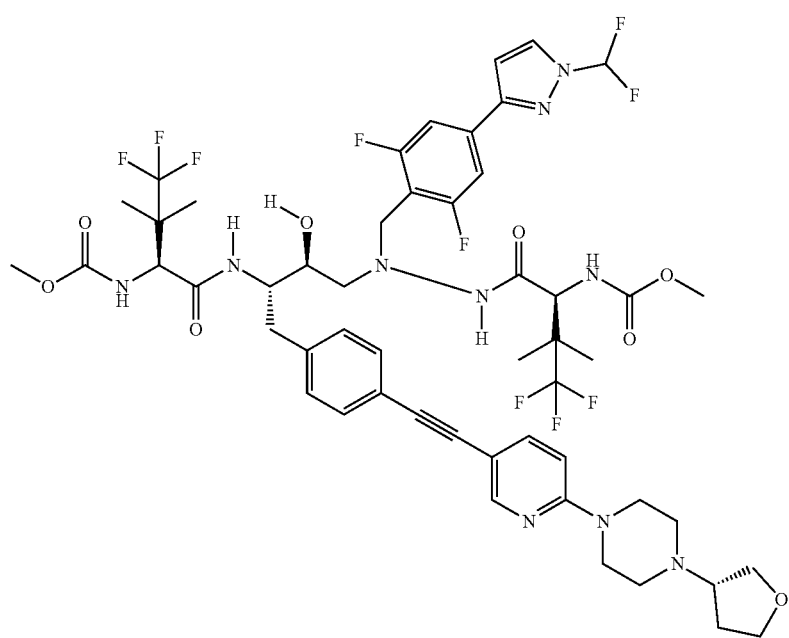 [SMILES: COC(=O)N[C@H](C(=O)N[C@@H](Cc1ccc(C#Cc2ccc(N3CCN([C@H]4CCOC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 145
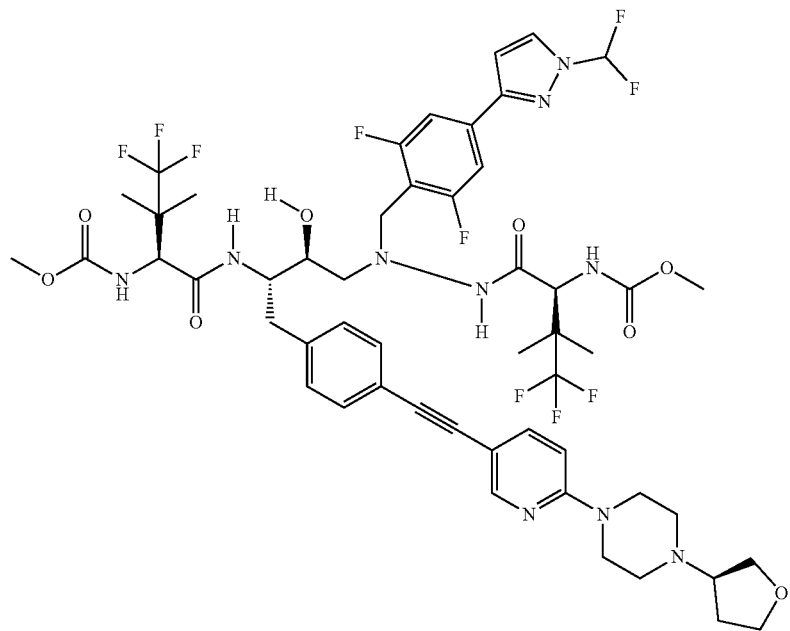 [SMILES: COC(=O)N[C@H](C(=O)N[C@@H](Cc1ccc(C#Cc2ccc(N3CCN([C@@H]4CCOC4)CC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 146
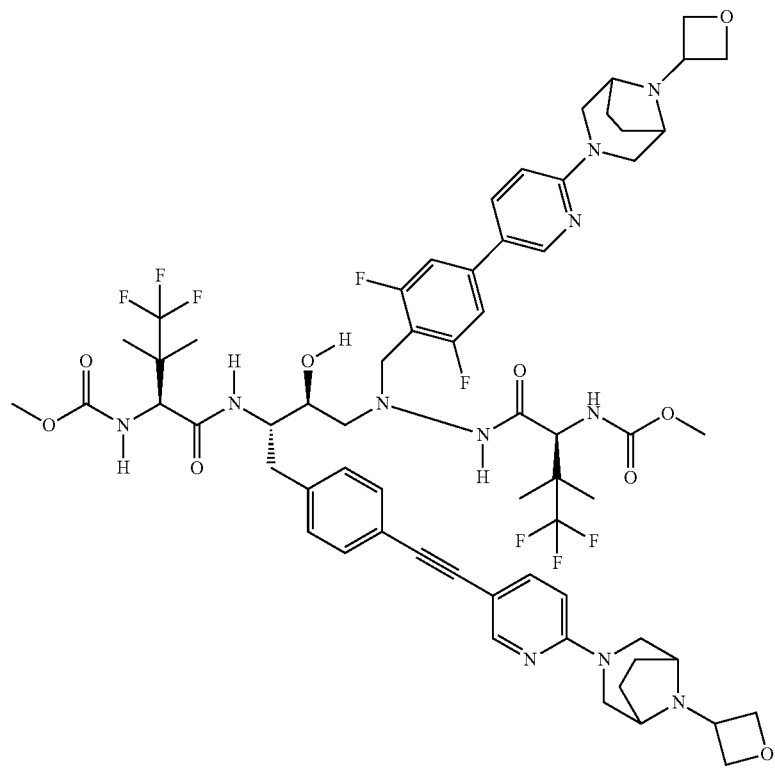 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccc(N3CC4CCC(C3)N4C3COC3)nc2)cc1F)NC(=O)[C@@H](NC(=O)OC)C(C)(C)C(F)(F)F)C(C)(C)C(F)(F)F]

EXAMPLE 147
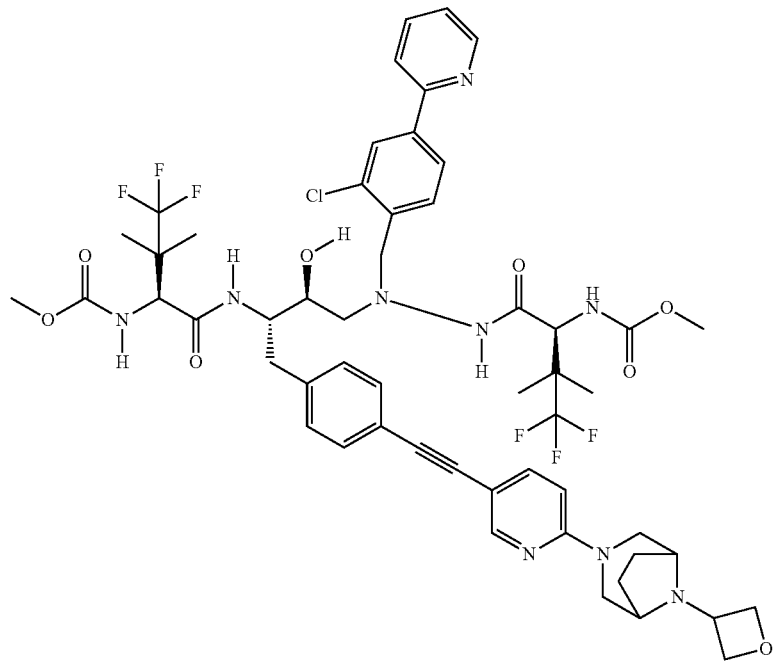 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(-c2ccccn2)cc1Cl)NC(=O)[C@@H](NC(=O)OC)C(C)(C)C(F)(F)F)C(C)(C)C(F)(F)F]
EXAMPLE 148
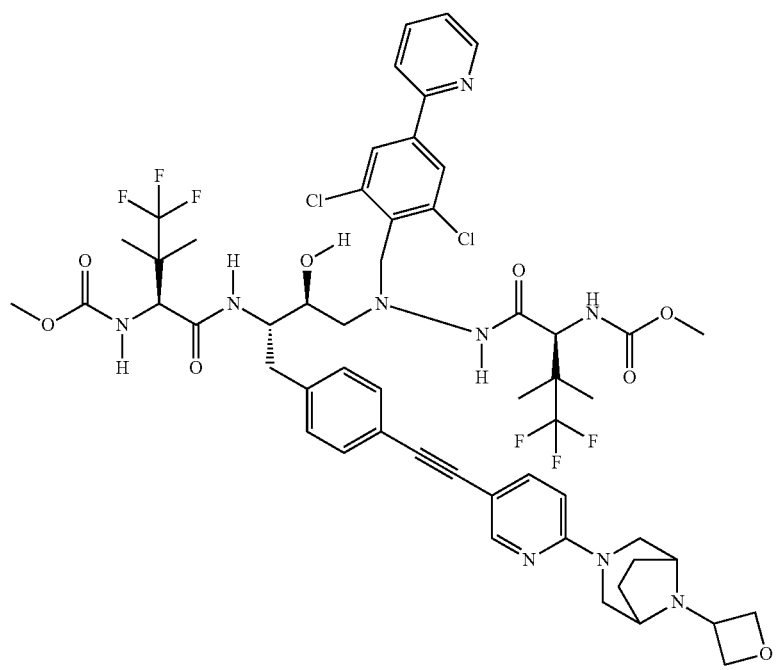 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(Cl)cc(-c2ccccn2)cc1Cl)NC(=O)[C@@H](NC(=O)OC)C(C)(C)C(F)(F)F)C(C)(C)C(F)(F)F]

EXAMPLE 149
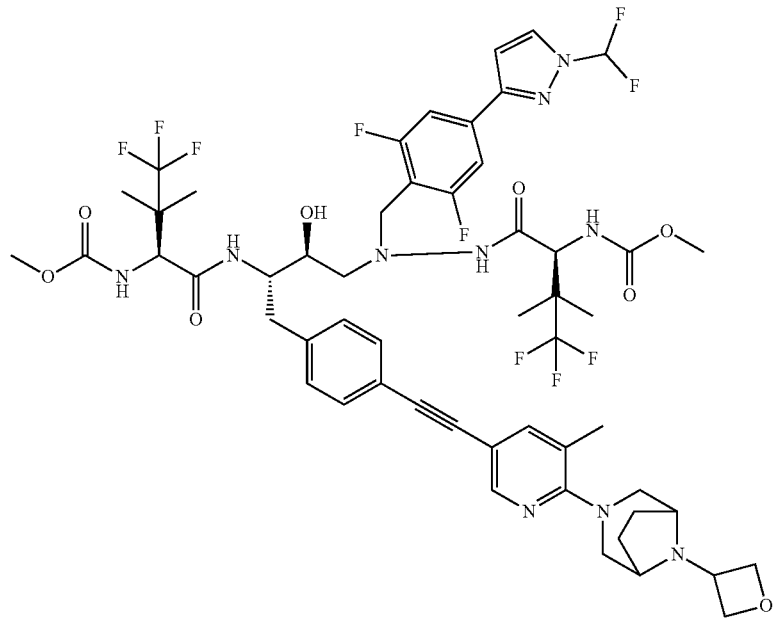 [SMILES: COC(=O)N[C@H](C(=O)N[C@@H](Cc1ccc(C#Cc2cnc(N3CC4CCC(C3)N4C3COC3)c(C)c2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 150
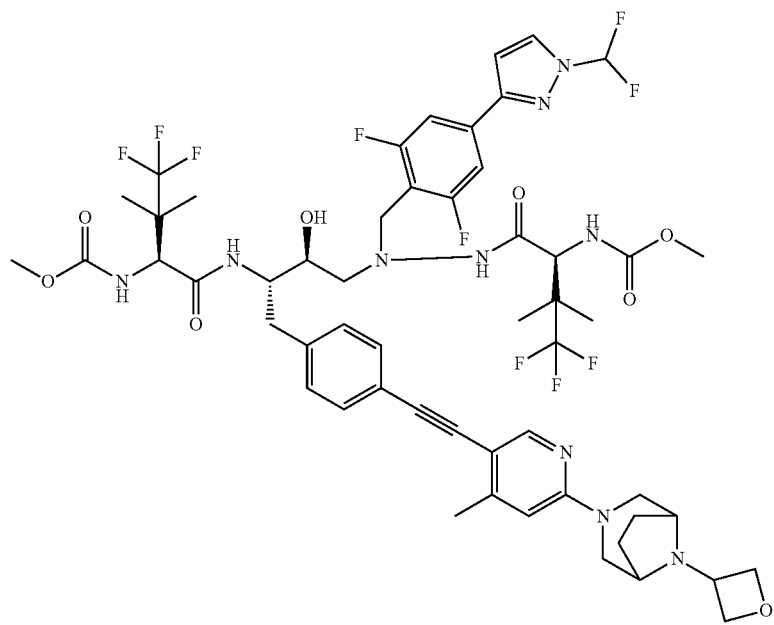 [SMILES: COC(=O)N[C@H](C(=O)N[C@@H](Cc1ccc(C#Cc2ccc(N3CC4CCC(C3)N4C3COC3)nc2C)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 151
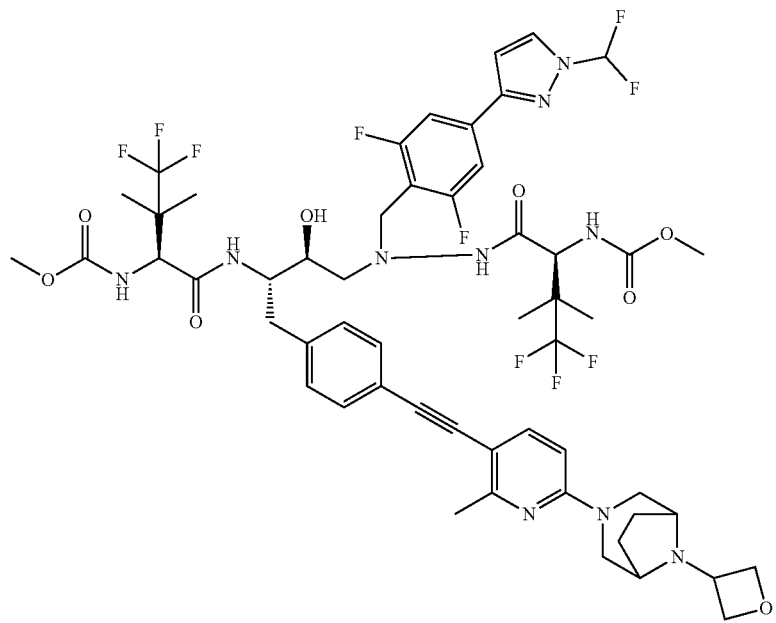
EXAMPLE 152
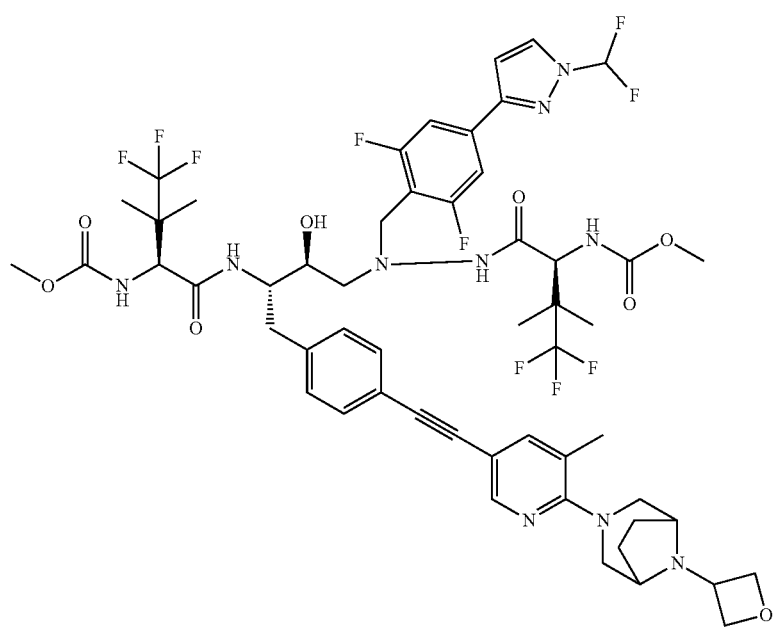 [SMILES: COC(=O)N[C@H](C(=O)N[C@@H](Cc1ccc(C#Cc2cnc(N3CC4CCC(C3)N4C3COC3)c(C)c2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 153
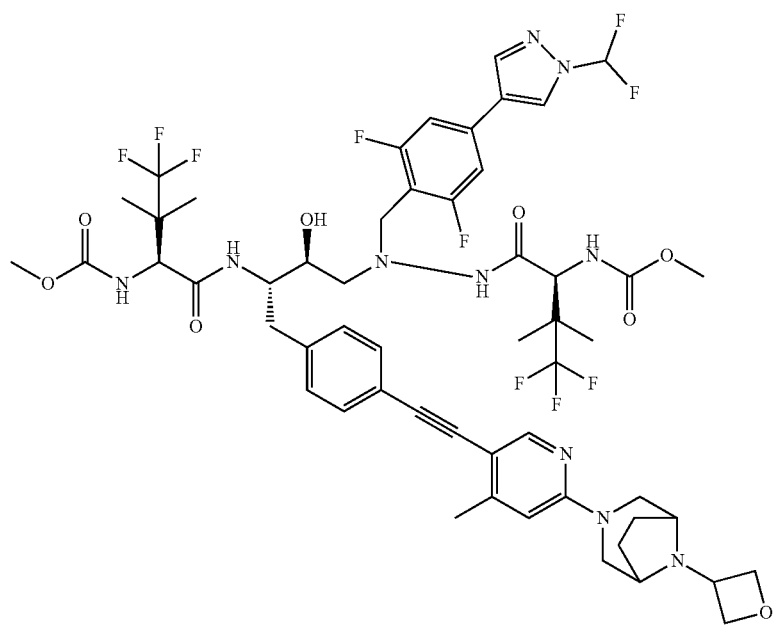 [SMILES: COC(=O)N[C@H](C(=O)N[C@@H](Cc1ccc(C#Cc2cnc(N3CC4CCC(C3)N4C3COC3)cc2C)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]
EXAMPLE 154
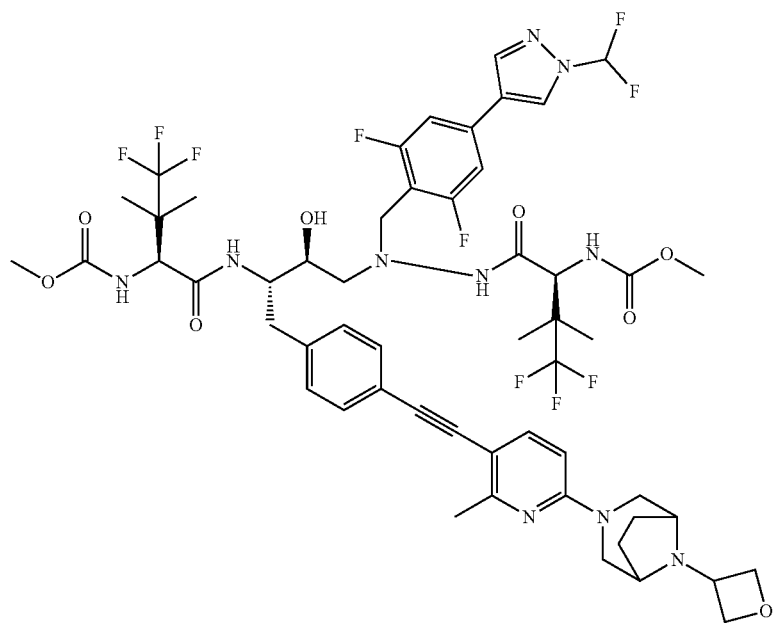

EXAMPLE 155
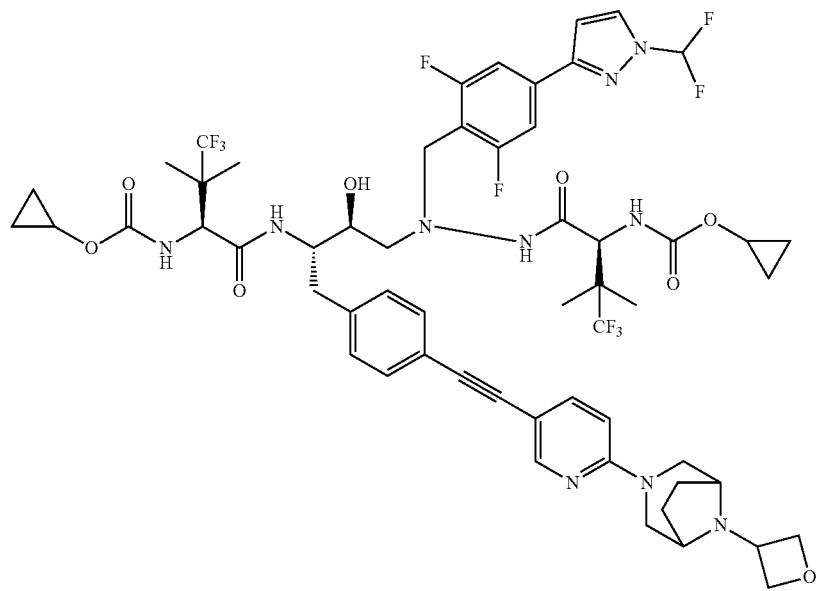 [SMILES: CC(C)([C@H](NC(=O)OC1CC1)C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC1CC1)C(C)(C)C(F)(F)F)C(F)(F)F]
EXAMPLE 156
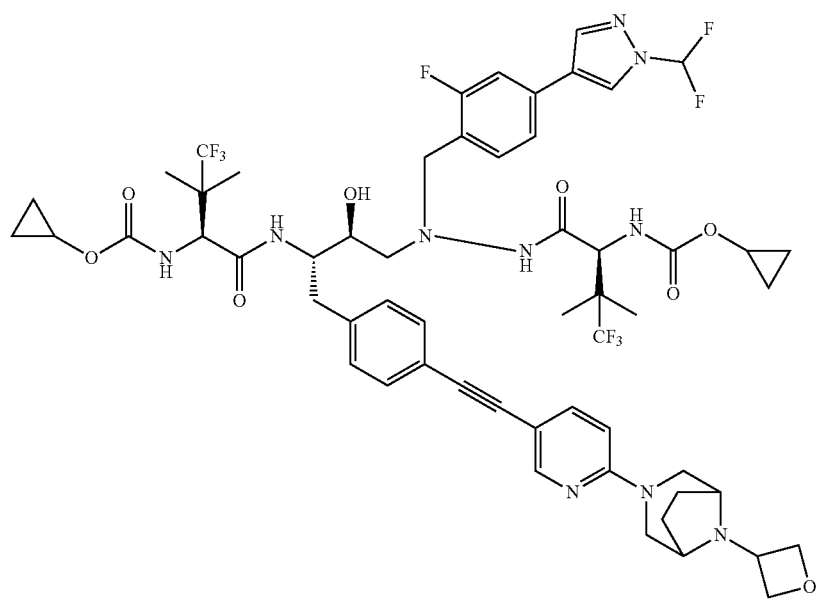 [SMILES: CC(C)([C@H](NC(=O)OC1CC1)C(=O)N[C@@H](Cc1ccc(C#Cc2ccc(N3CC4CCC(C3)N4C3COC3)nc2)cc1)[C@@H](O)CN(Cc1ccc(-c2cnn(C(F)F)c2)cc1F)NC(=O)[C@@H](NC(=O)OC1CC1)C(C)(C)C(F)(F)F)C(F)(F)F]

EXAMPLE 157
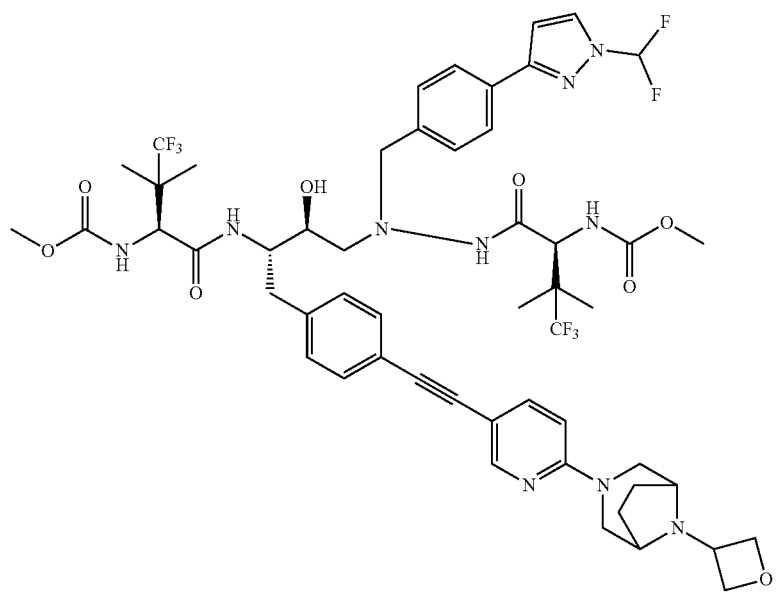 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(-c2ccn(C(F)F)n2)cc1)NC(=O)[C@@H](NC(=O)OC)C(C)(C)C(F)(F)F)C(C)(C)C(F)(F)F]
EXAMPLE 158
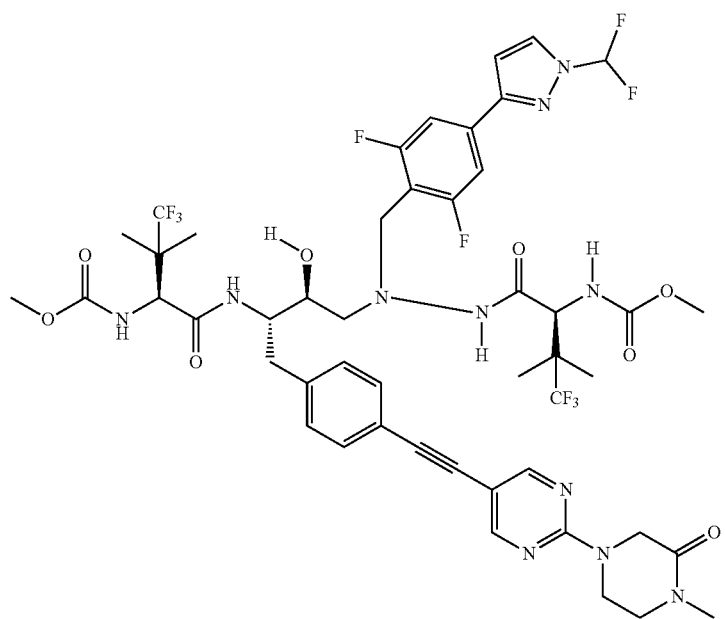 [SMILES: COC(=O)N[C@H](C(=O)N[C@@H](Cc1ccc(C#Cc2cnc(N3CCN(C)C(=O)C3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 159
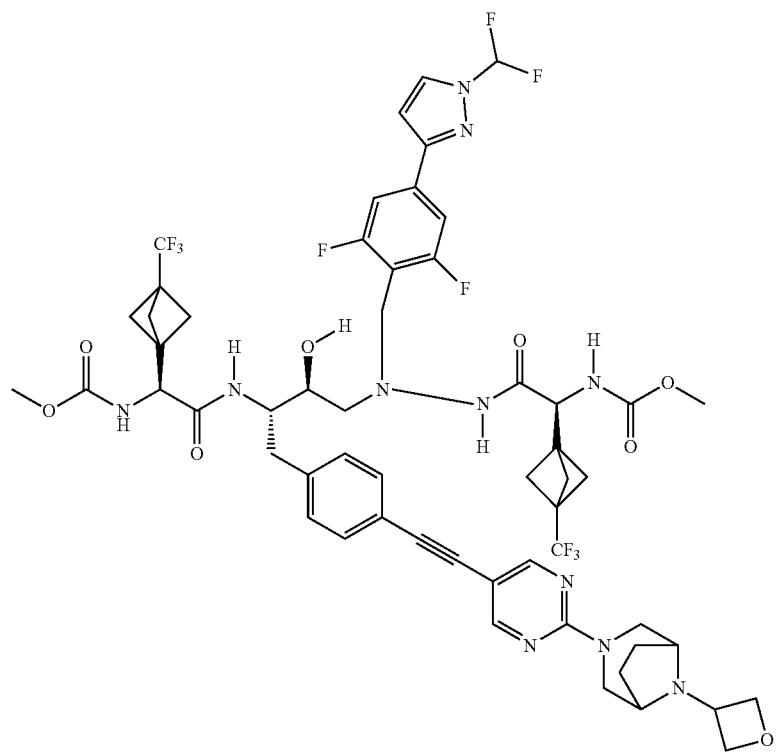 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC)C12CC(C(F)(F)F)(C1)C2)C12CC(C(F)(F)F)(C1)C2]
EXAMPLE 160
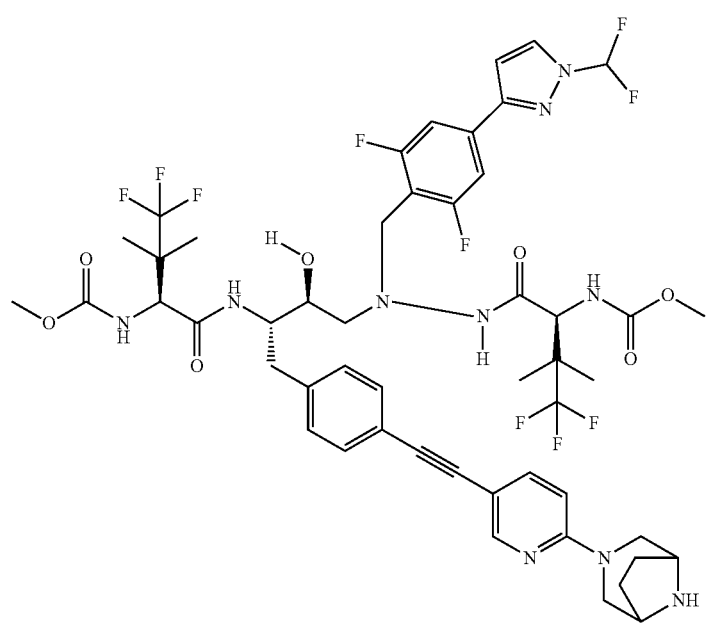

EXAMPLE 161
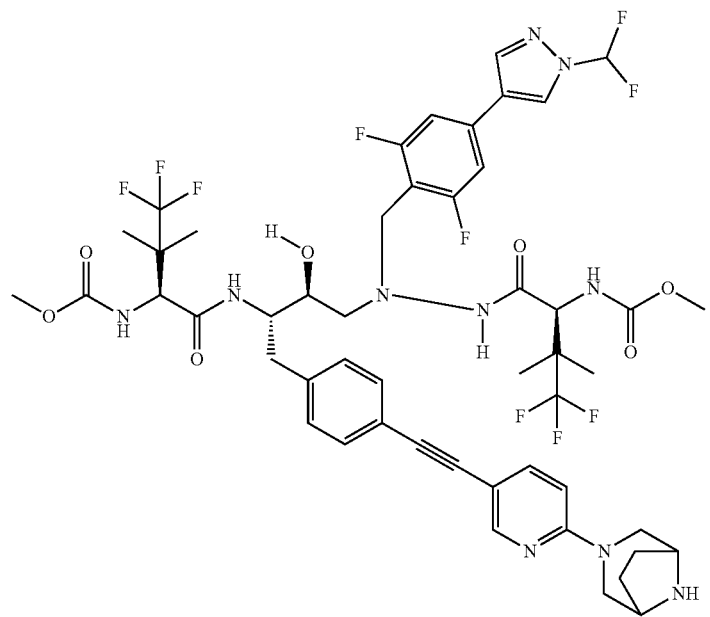
EXAMPLE 162
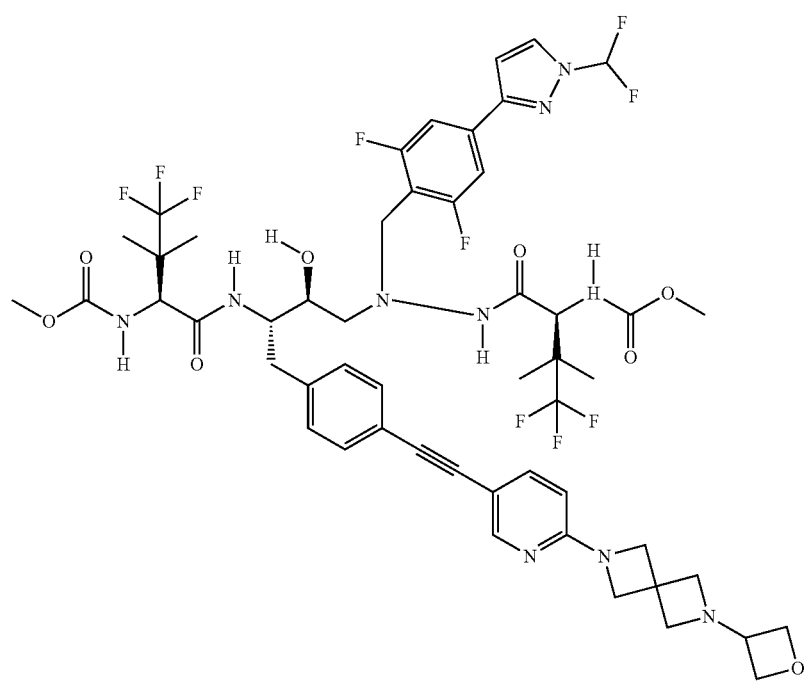

EXAMPLE 163
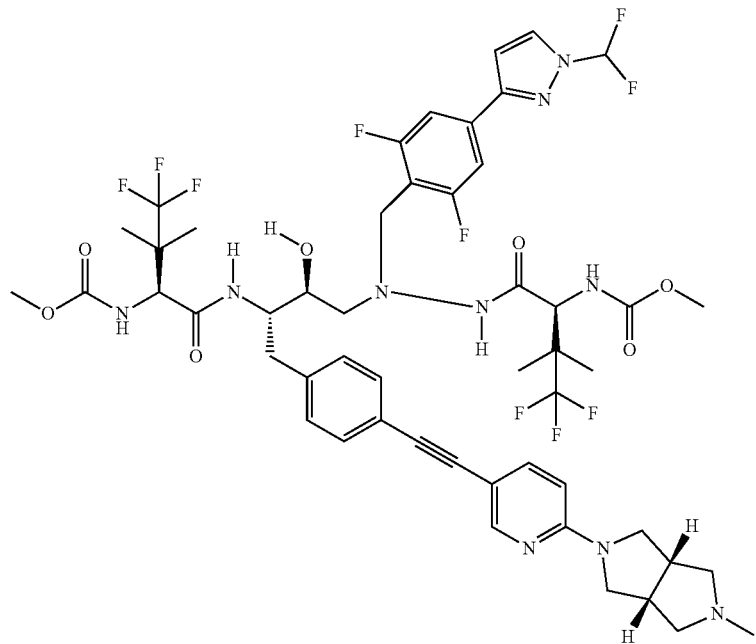
EXAMPLE 164
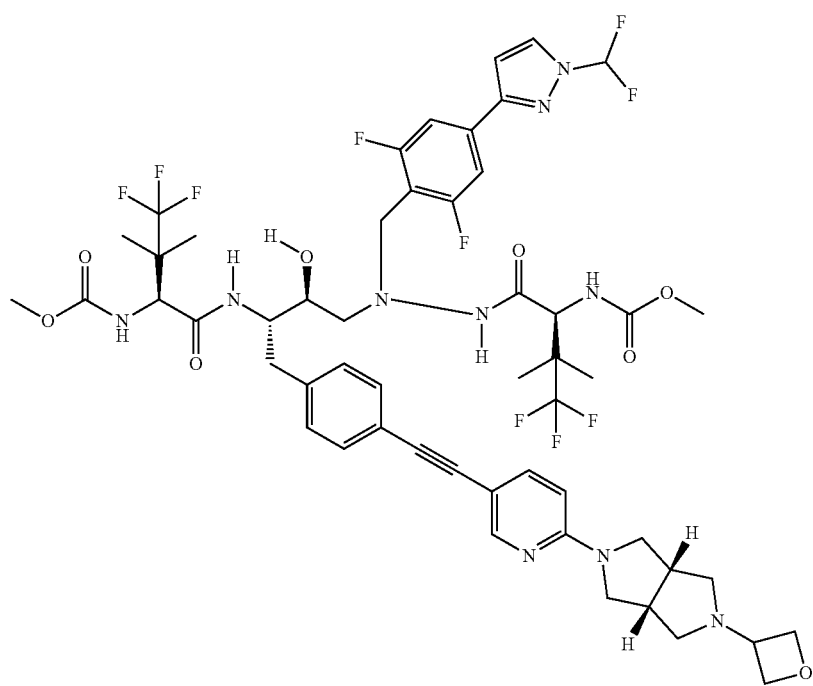 [SMILES: COC(=O)N[C@H](C(=O)N[C@@H](Cc1ccc(C#Cc2ccc(N3C[C@@H]4CN(C5COC5)C[C@@H]4C3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 165
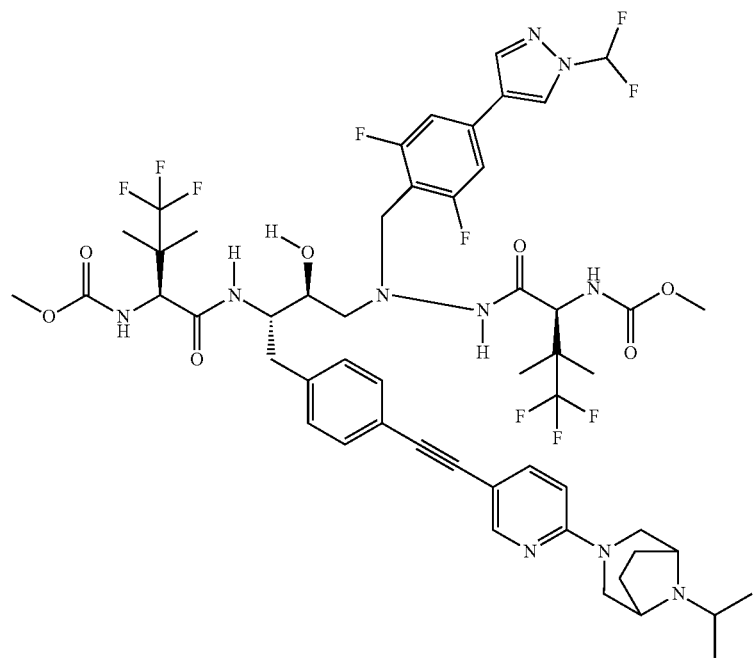 [SMILES: COC(=O)N[C@H](C(=O)N[C@@H](Cc1ccc(C#Cc2ccc(N3CC4CCC(C3)N4C(C)C)nc2)cc1)[C@@H](O)CN(Cc1c(F)cc(-c2cnn(C(F)F)c2)cc1F)NC(=O)[C@@H](NC(=O)OC)C(C)(C)C(F)(F)F)C(C)(C)C(F)(F)F]
EXAMPLE 166
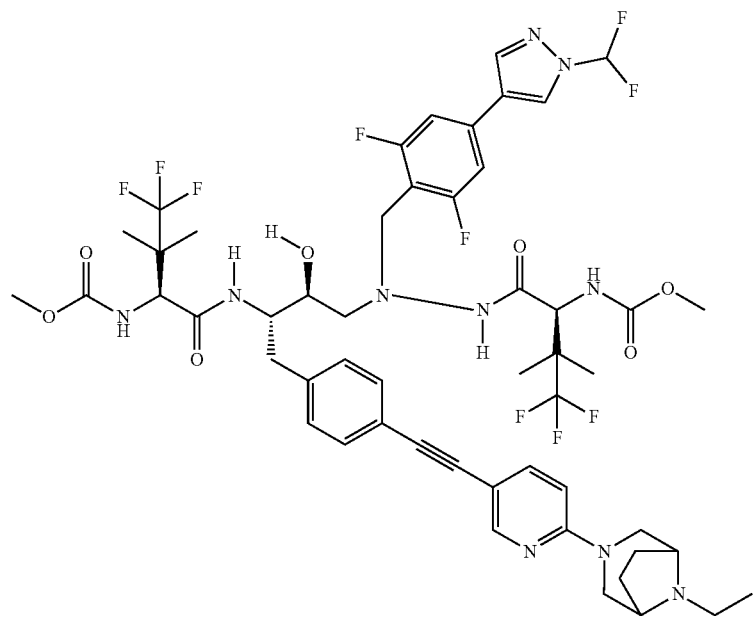 [SMILES: CCN1C2CCC1CN(c1ccc(C#Cc3ccc(C[C@H](NC(=O)[C@@H](NC(=O)OC)C(C)(C)C(F)(F)F)[C@@H](O)CN(Cc4c(F)cc(-c5cnn(C(F)F)c5)cc4F)NC(=O)[C@@H](NC(=O)OC)C(C)(C)C(F)(F)F)cc3)cn1)C2]

EXAMPLE 167
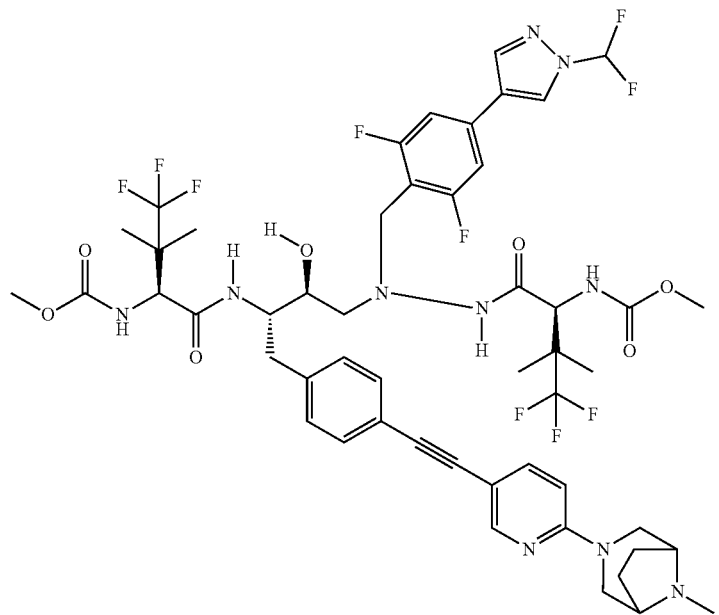
EXAMPLE 168
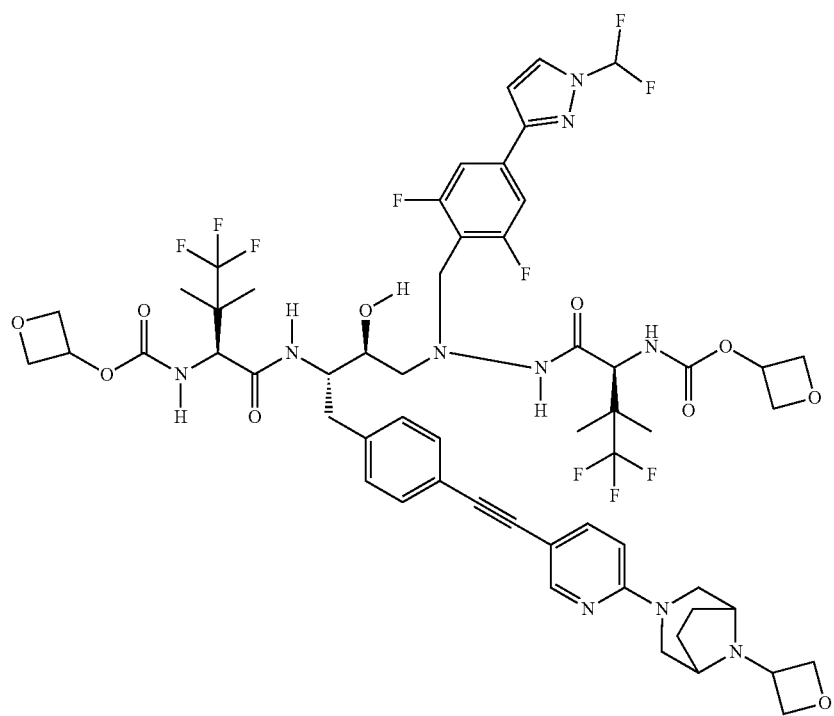 [SMILES: CC(C)([C@H](NC(=O)OC1COC1)C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC1COC1)C(C)(C)C(F)(F)F)C(F)(F)F]

EXAMPLE 169
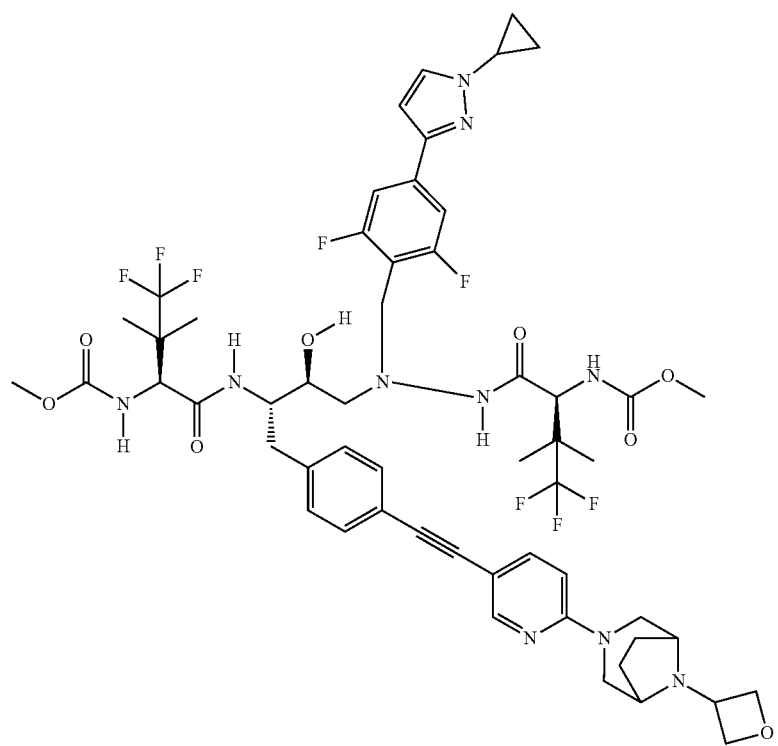 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccn(C3CC3)n2)cc1F)NC(=O)[C@@H](NC(=O)OC)C(C)(C)C(F)(F)F)C(C)(C)C(F)(F)F]
EXAMPLE 170
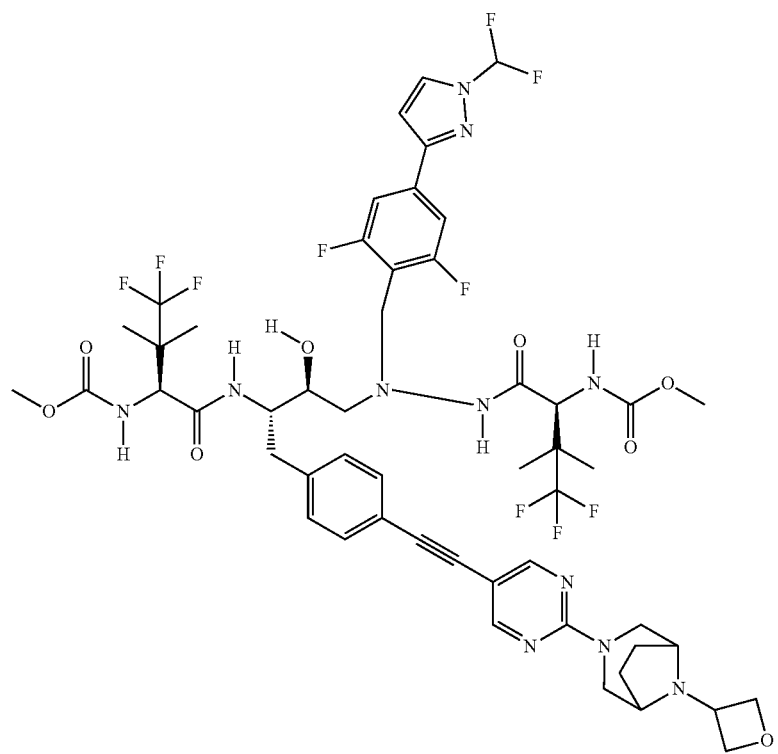 [SMILES: COC(=O)N[C@H](C(=O)N[C@@H](Cc1ccc(C#Cc2cnc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]

EXAMPLE 171
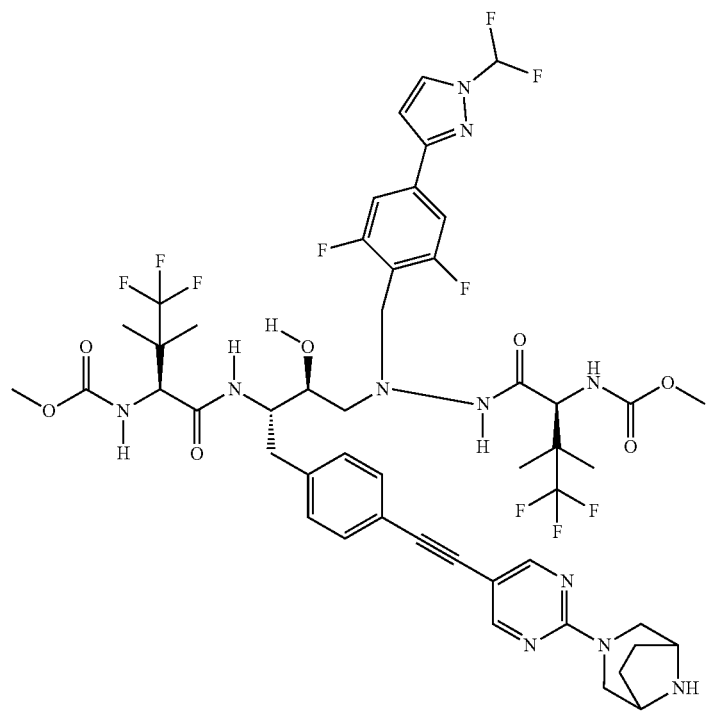
EXAMPLE 172
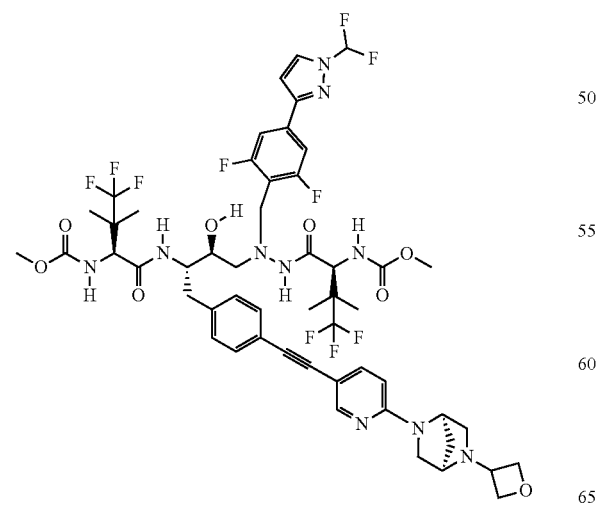

EXAMPLE 173
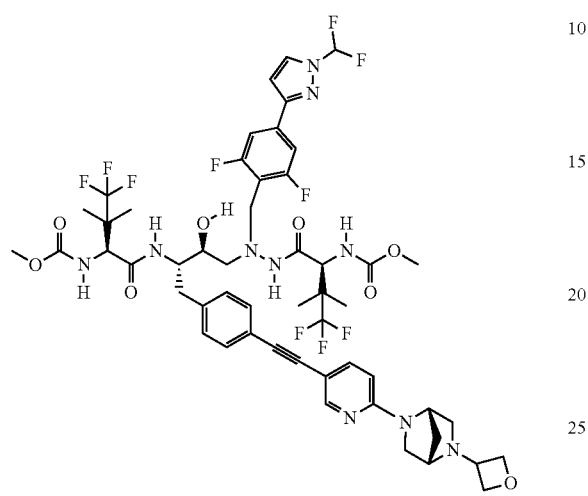
EXAMPLE 174
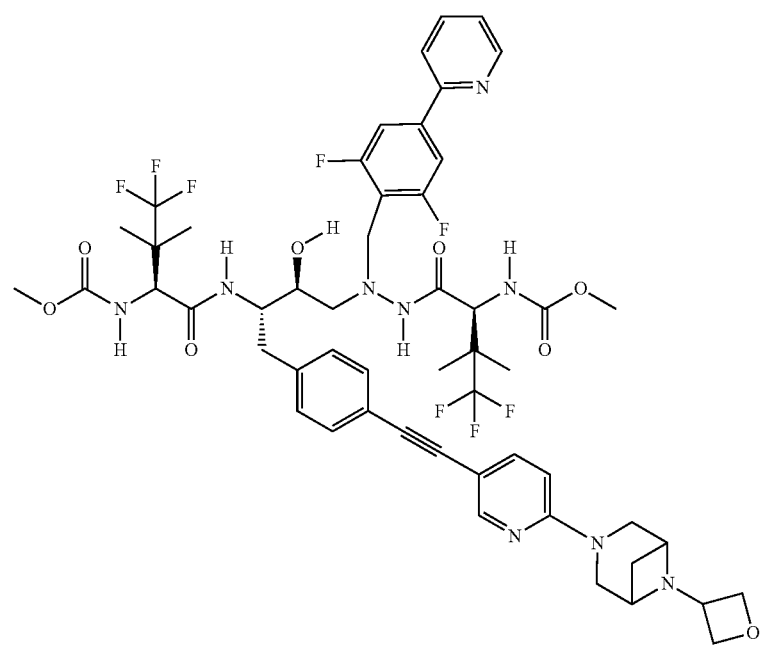 [SMILES: COC(=O)N[C@H](C(=O)N[C@@H](Cc1ccc(C#Cc2ccc(N3CC4CC(C3)N4C3COC3)nc2)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]

EXAMPLE 175
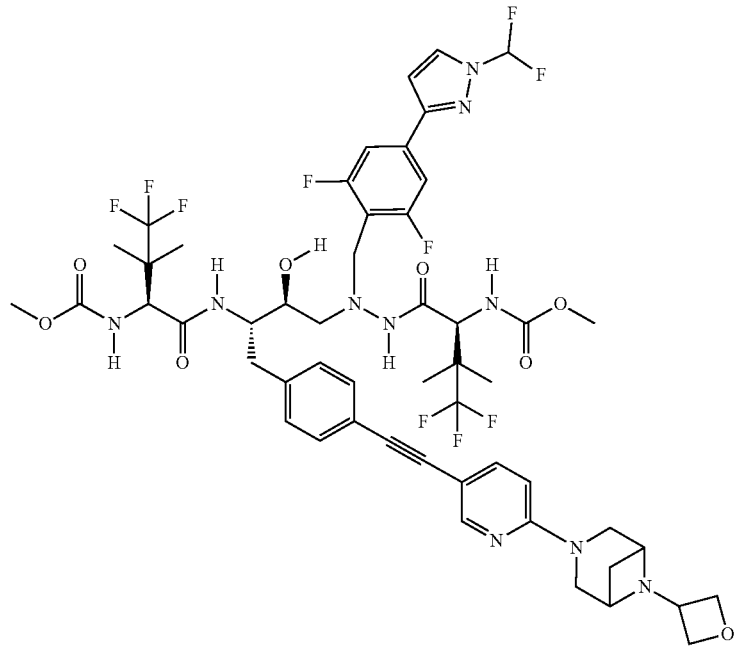 [SMILES: COC(=O)N[C@H](C(=O)N[C@@H](Cc1ccc(C#Cc2ccc(N3CC4CC(C3)N4C3COC3)nc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 176
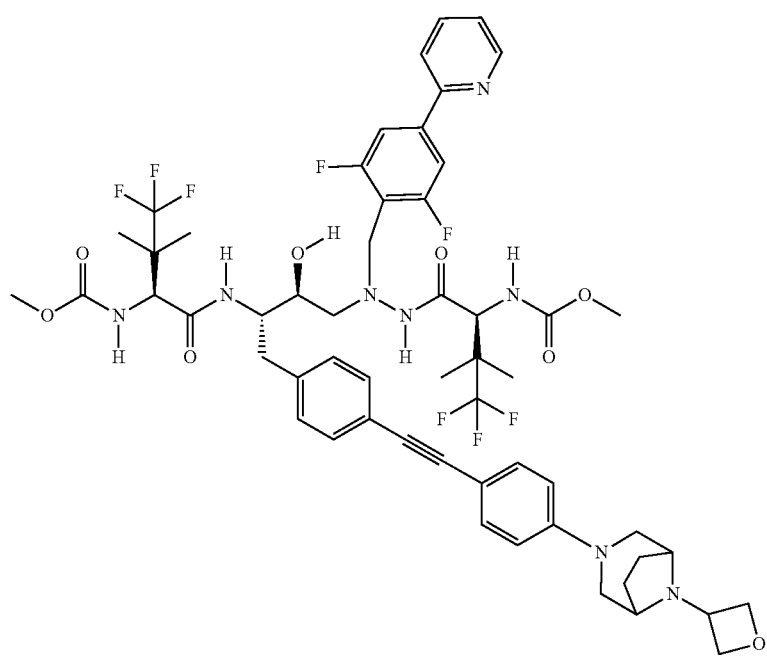 [SMILES: COC(=O)N[C@H](C(=O)N[C@@H](Cc1ccc(C#Cc2ccc(N3CC4CCC(C3)N4C3COC3)cc2)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]

EXAMPLE 177
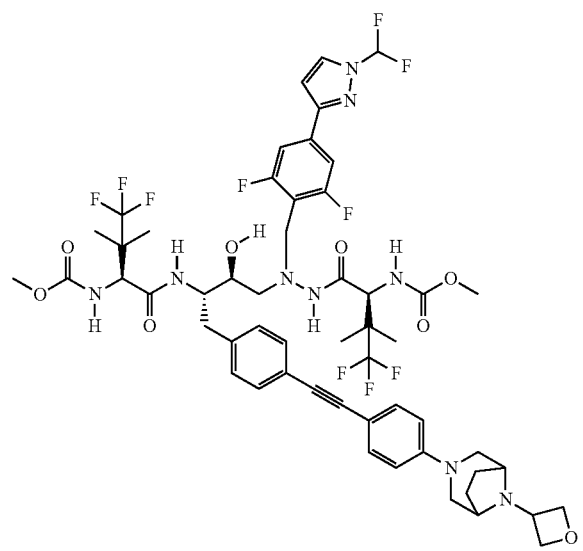 [SMILES: COC(=O)N[C@H](C(=O)N[C@@H](Cc1ccc(C#Cc2ccc(N3CC4CCC(C3)N4C3COC3)cc2)cc1)[C@@H](O)CN(Cc1c(F)cc(-c2ccn(C(F)F)n2)cc1F)NC(=O)[C@@H](NC(=O)OC)C(C)(C)C(F)(F)F)C(C)(C)C(F)(F)F]
EXAMPLE 179
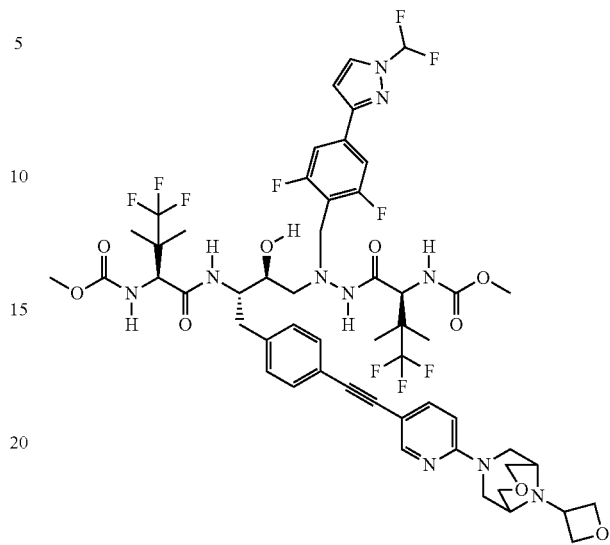
EXAMPLE 178
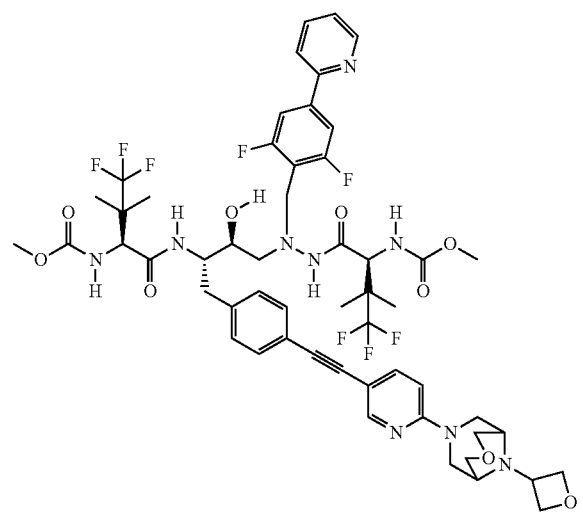 [SMILES: COC(=O)N[C@H](C(=O)N[C@@H](Cc1ccc(C#Cc2ccc(N3CC4COCC(C3)N4C3COC3)nc2)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]
EXAMPLE 180
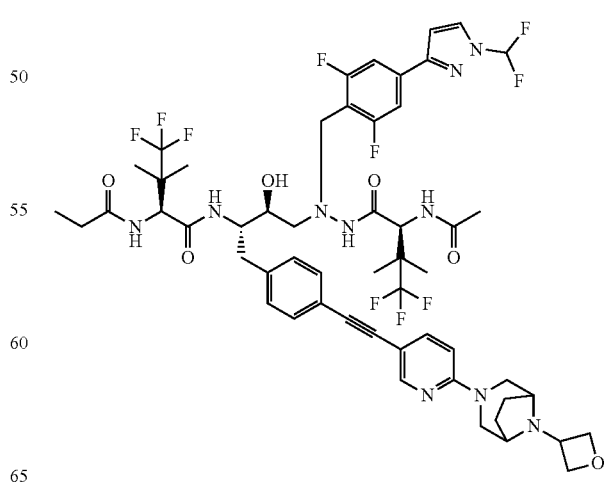

EXAMPLE 181
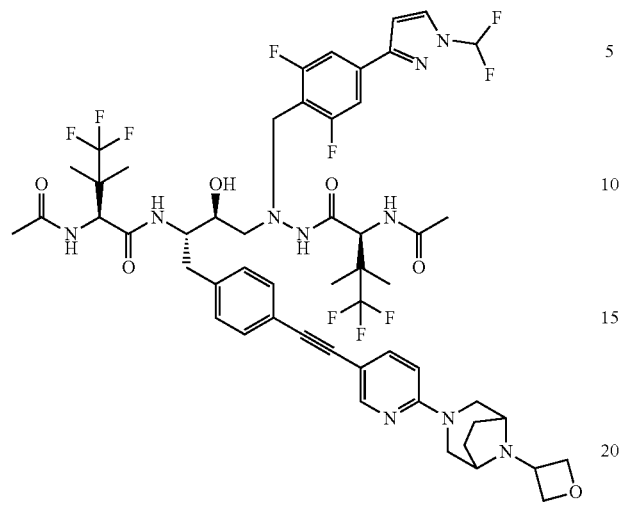
EXAMPLE 183
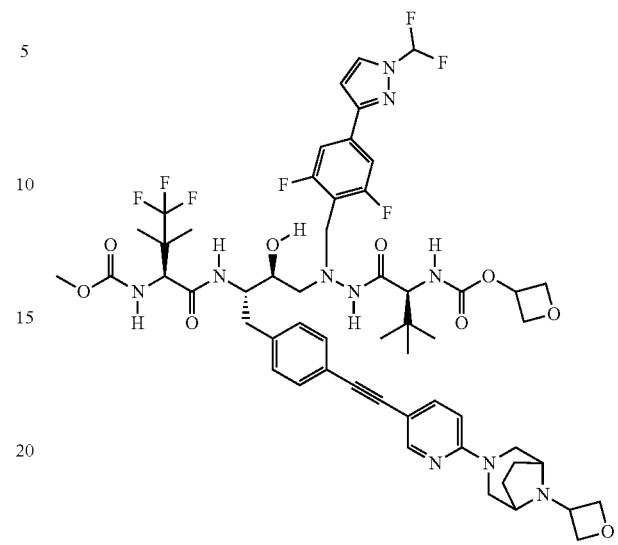
EXAMPLE 182
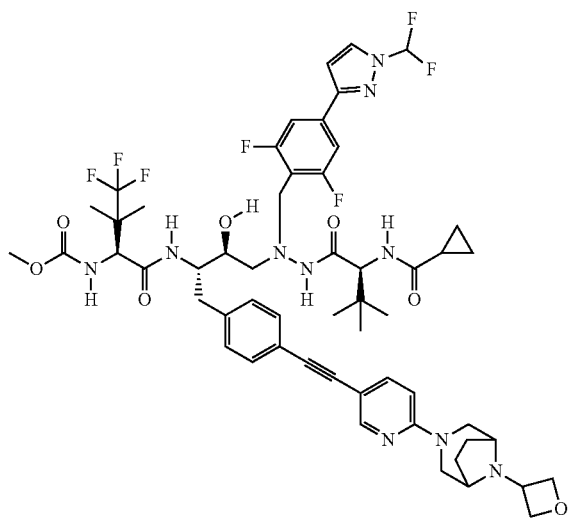 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)C1CC1)C(C)(C)C)C(C)(C)C(F)(F)F]
EXAMPLE 184
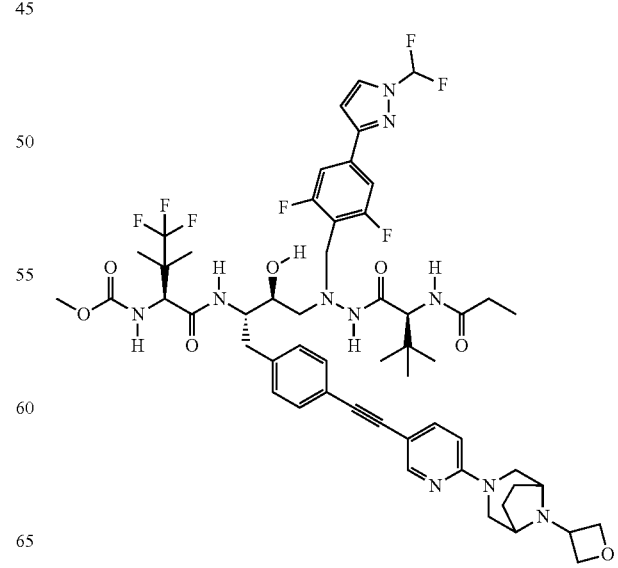

EXAMPLE 185
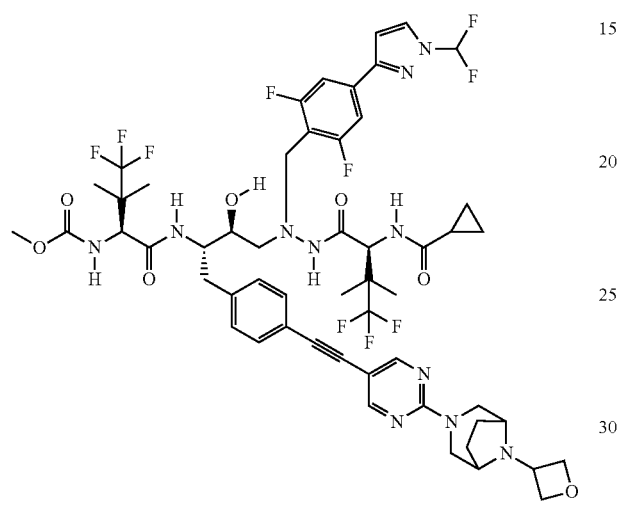
EXAMPLE 186
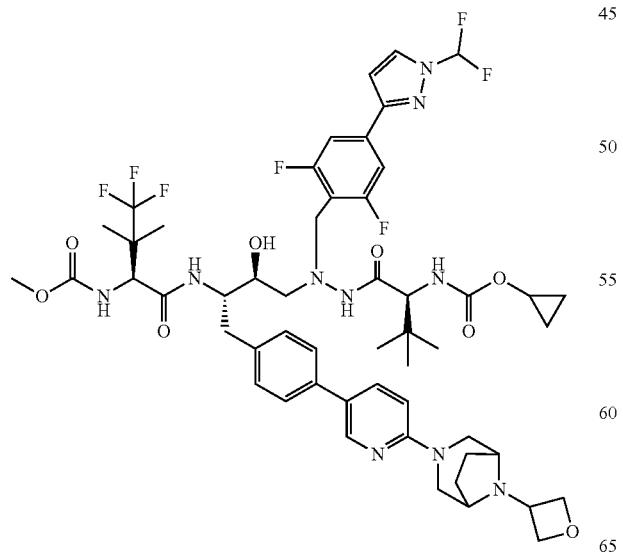

EXAMPLE 187
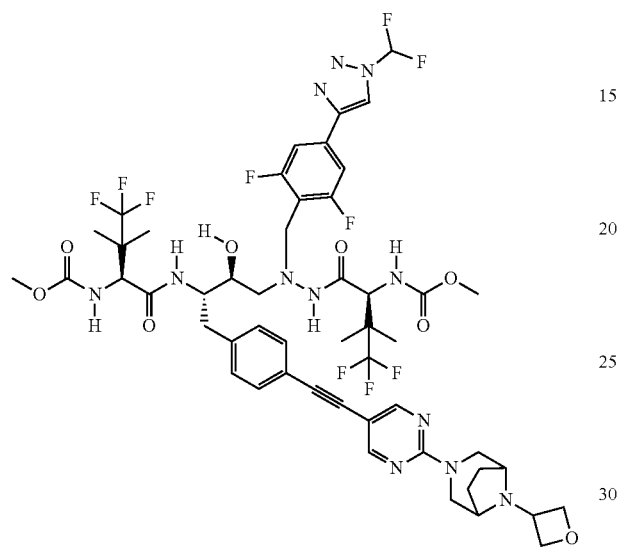
EXAMPLE 219
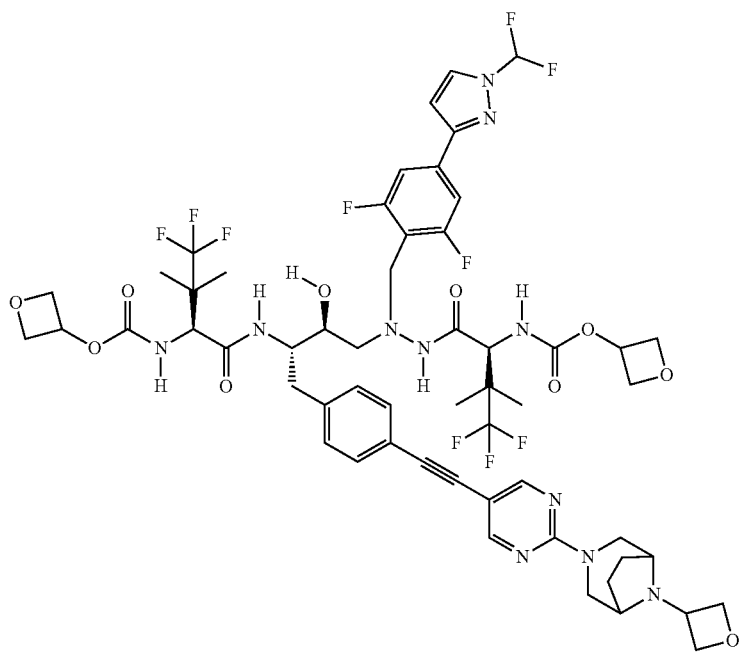 [SMILES: CC(C)([C@H](NC(=O)OC1COC1)C(=O)N[C@@H](Cc1ccc(C#Cc2cnc(N3CC4CCC(C3)N4C3COC3)nc2)cc1)[C@@H](O)CN(Cc1c(F)cc(-c2ccn(C(F)F)n2)cc1F)NC(=O)[C@@H](NC(=O)OC1COC1)C(C)(C)C(F)(F)F)C(F)(F)F]

EXAMPLE 220
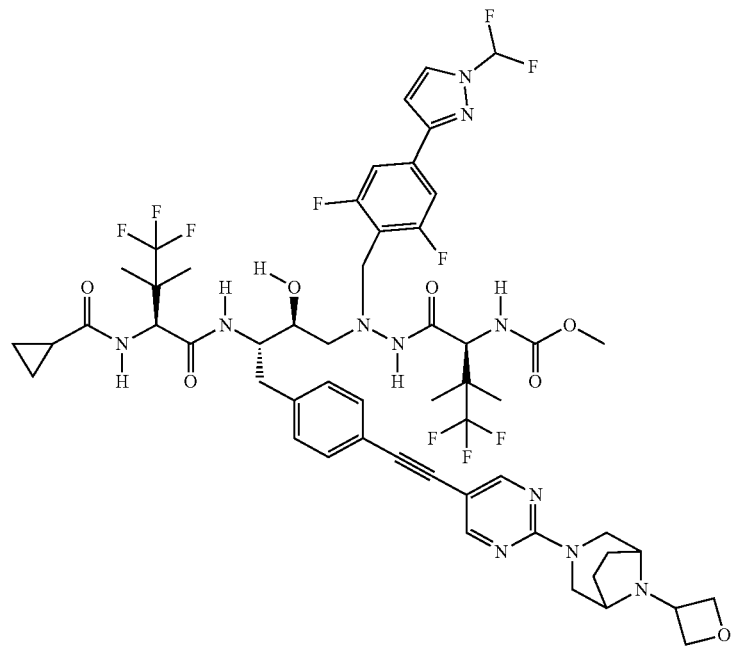 [SMILES: COC(=O)N[C@H](C(=O)NN(Cc1c(F)cc(-c2ccn(C(F)F)n2)cc1F)C[C@H](O)[C@H](Cc1ccc(C#Cc2cnc(N3CC4CCC(C3)N4C3COC3)nc2)cc1)NC(=O)[C@@H](NC(=O)C1CC1)C(C)(C)C(F)(F)F)C(C)(C)C(F)(F)F]
EXAMPLE 221
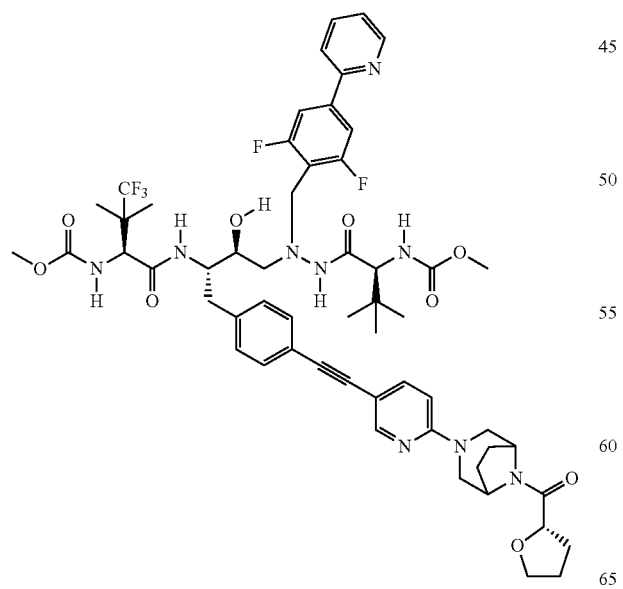

EXAMPLE 224
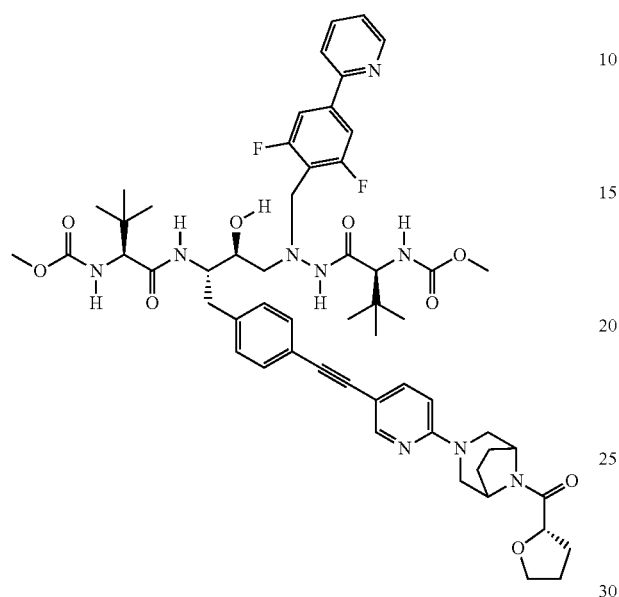
EXAMPLE 225
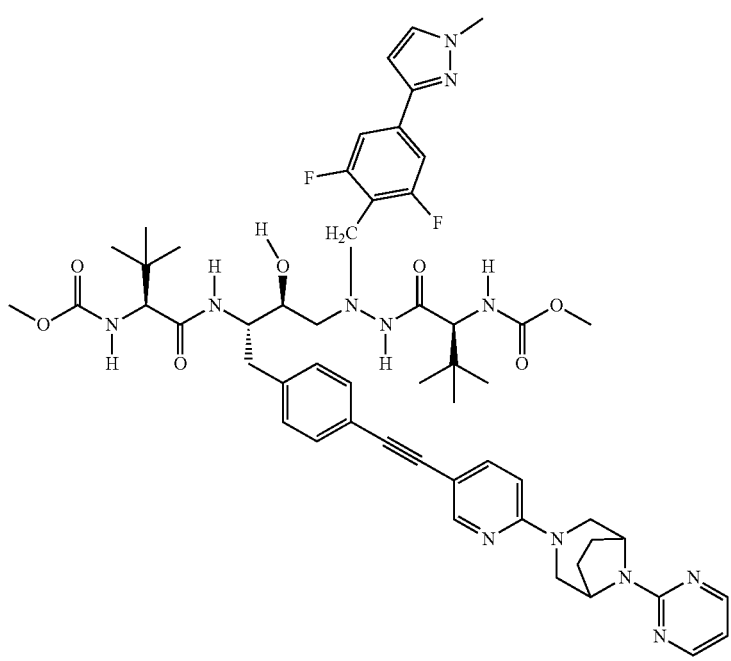 [SMILES: COC(=O)N[C@H](C(=O)N[C@@H](Cc1ccc(C#Cc2ccc(N3CC4CCC(C3)N4c3ncccn3)nc2)cc1)[C@@H](O)CN(Cc1c(F)cc(-c2ccn(C)n2)cc1F)NC(=O)[C@@H](NC(=O)OC)C(C)(C)C)C(C)(C)C]

EXAMPLE 226
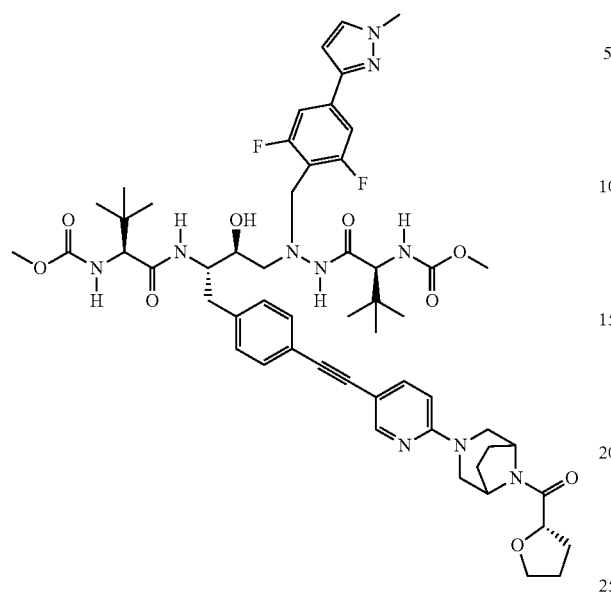
EXAMPLE 228
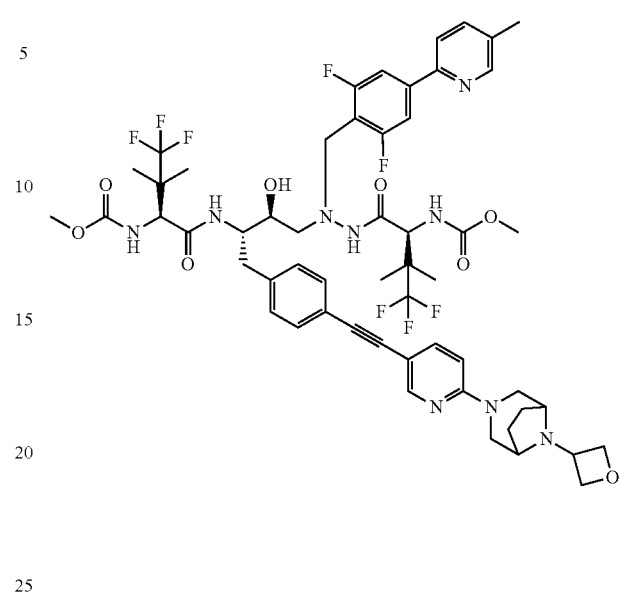
EXAMPLE 227
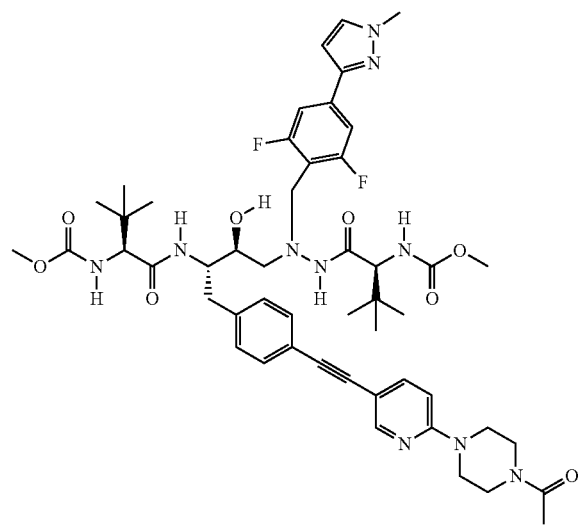 [SMILES: COC(=O)N[C@H](C(=O)N[C@@H](Cc1ccc(C#Cc2ccc(N3CCN(C(C)=O)CC3)nc2)cc1)[C@@H](O)CN(Cc1c(F)cc(-c2ccn(C)n2)cc1F)NC(=O)[C@@H](NC(=O)OC)C(C)(C)C)C(C)(C)C]
EXAMPLE 229
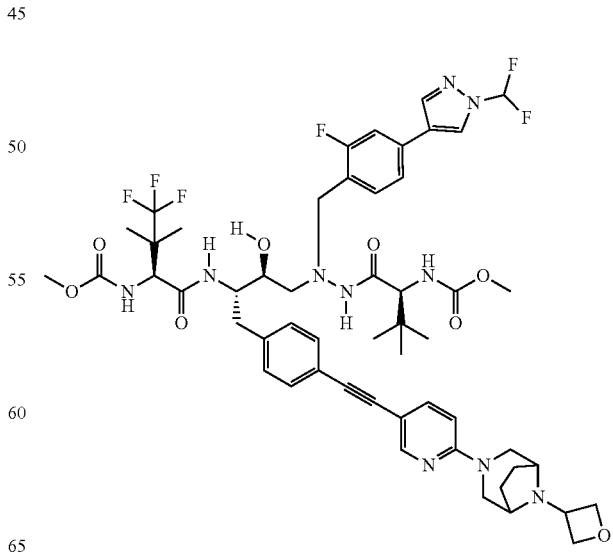

EXAMPLE 230
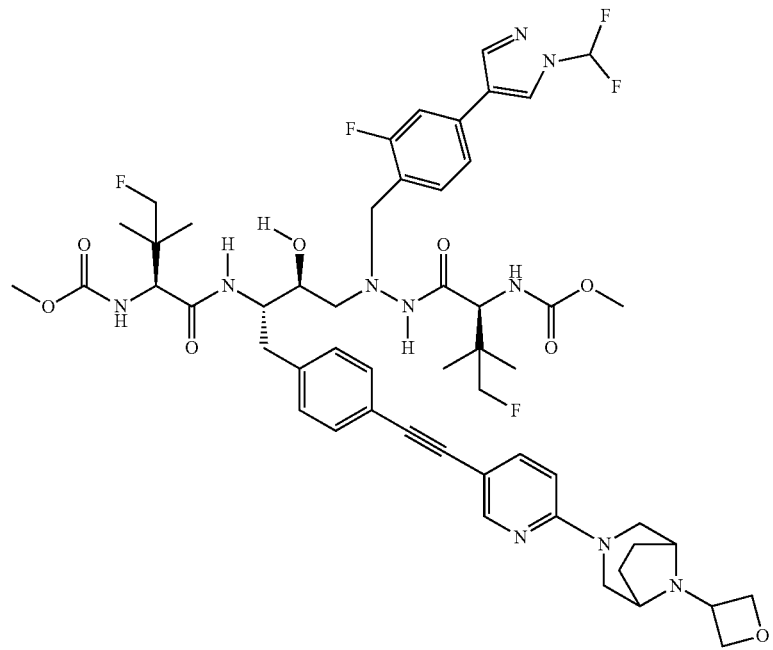 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(/C(C=N)=C/NC(F)F)cc1F)NC(=O)[C@@H](NC(=O)OC)C(C)(C)CF)C(C)(C)CF]
EXAMPLE 231
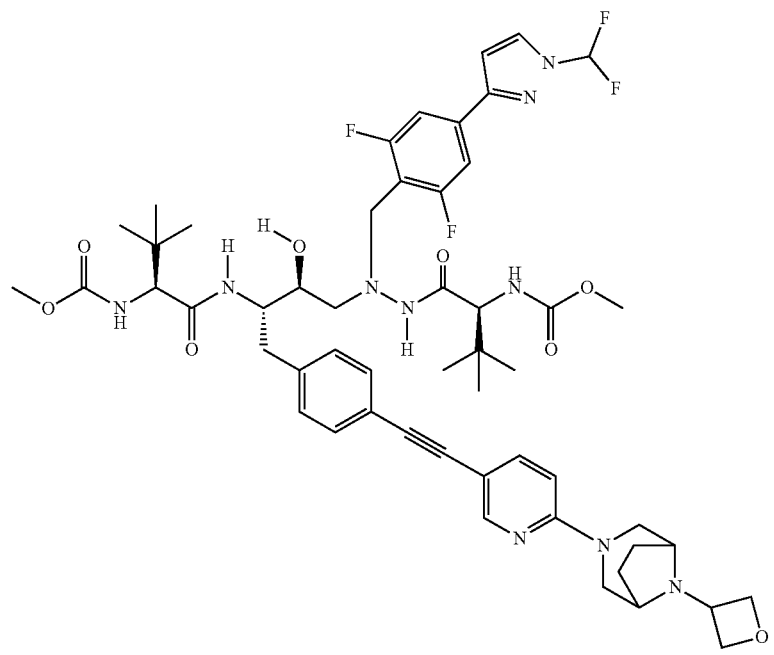 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(C(=N)/C=C\NC(F)F)cc1F)NC(=O)[C@@H](NC(=O)OC)C(C)(C)C)C(C)(C)C]

EXAMPLE 232
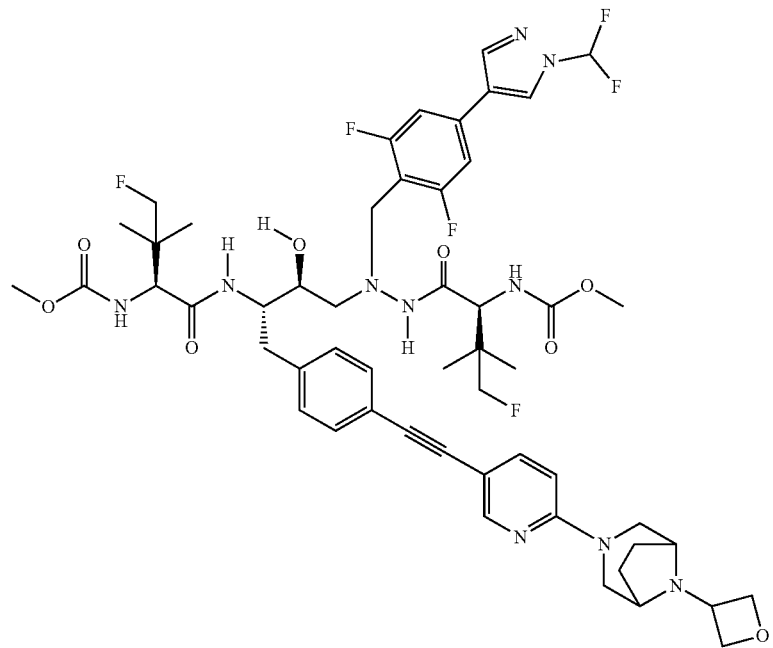 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(/C(C=N)=C/NC(F)F)cc1F)NC(=O)[C@@H](NC(=O)OC)C(C)(C)CF)C(C)(C)CF]
EXAMPLE 233
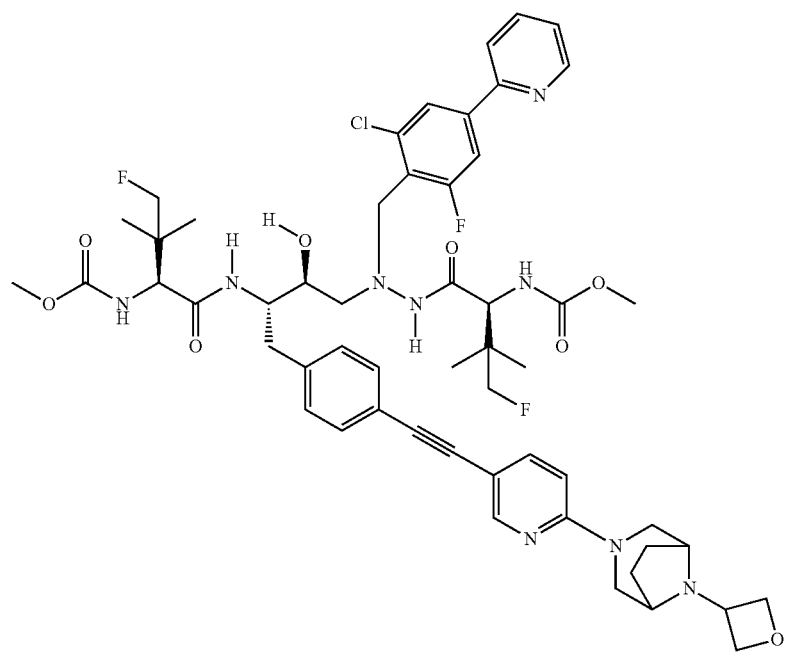 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2ccccn2)cc1Cl)NC(=O)[C@@H](NC(=O)OC)C(C)(C)CF)C(C)(C)CF]

EXAMPLE 234
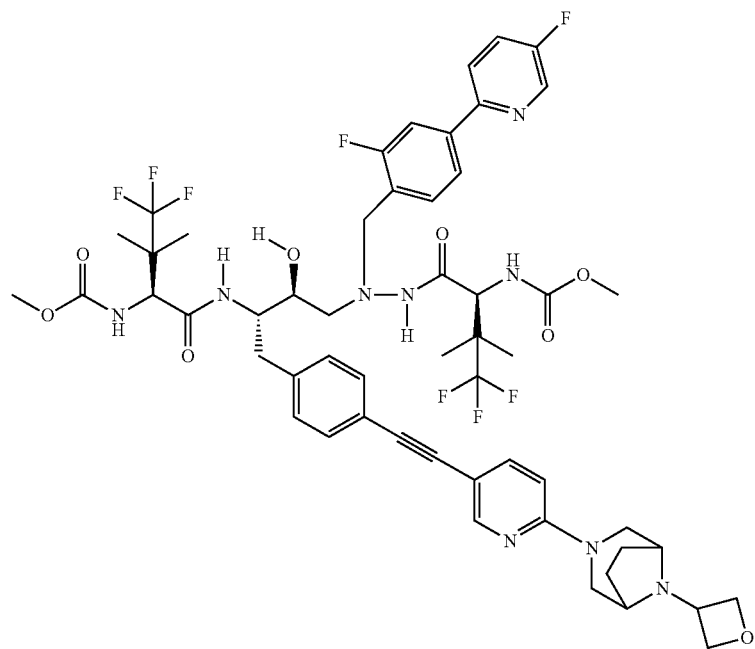 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1ccc(-c2ccc(F)cn2)cc1F)NC(=O)[C@@H](NC(=O)OC)C(C)(C)C(F)(F)F)C(C)(C)C(F)(F)F]
EXAMPLE 235
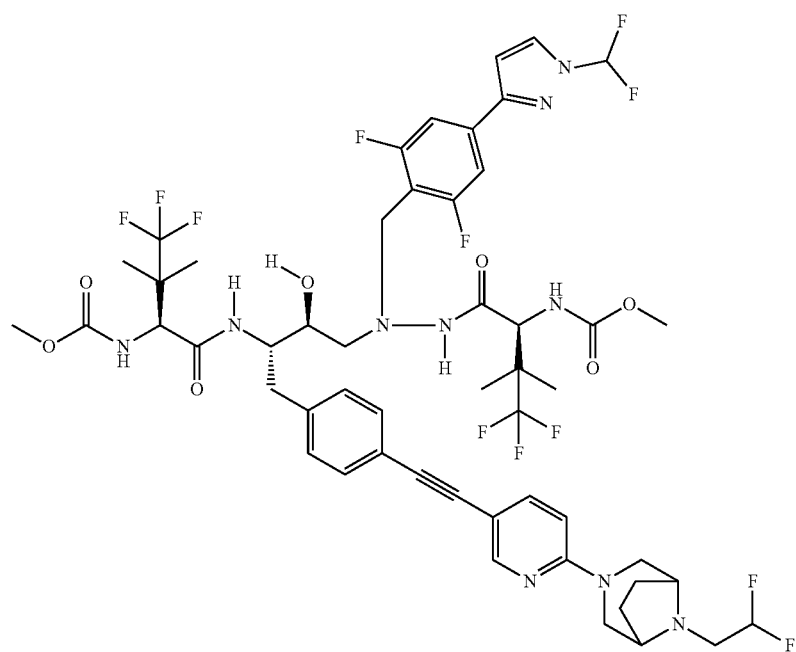 [SMILES: COC(=O)N[C@H](C(=O)N[C@@H](Cc1ccc(C#Cc2ccc(N3CC4CCC(C3)N4CC(F)F)nc2)cc1)[C@@H](O)CN(Cc1c(F)cc(C(=N)/C=C\NC(F)F)cc1F)NC(=O)[C@@H](NC(=O)OC)C(C)(C)C(F)(F)F)C(C)(C)C(F)(F)F]

EXAMPLE 236
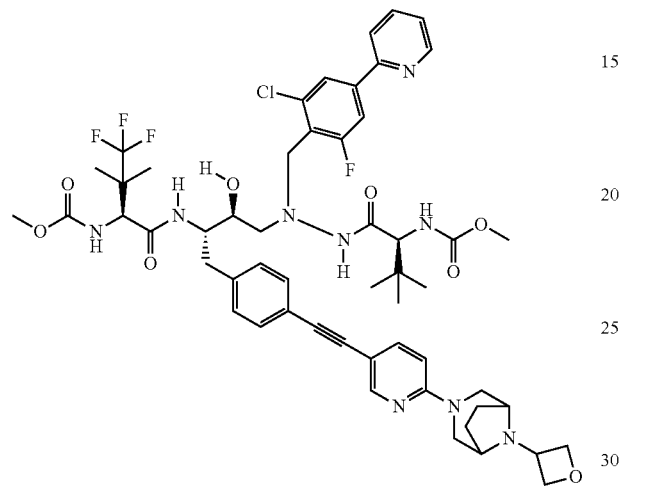
EXAMPLE 237
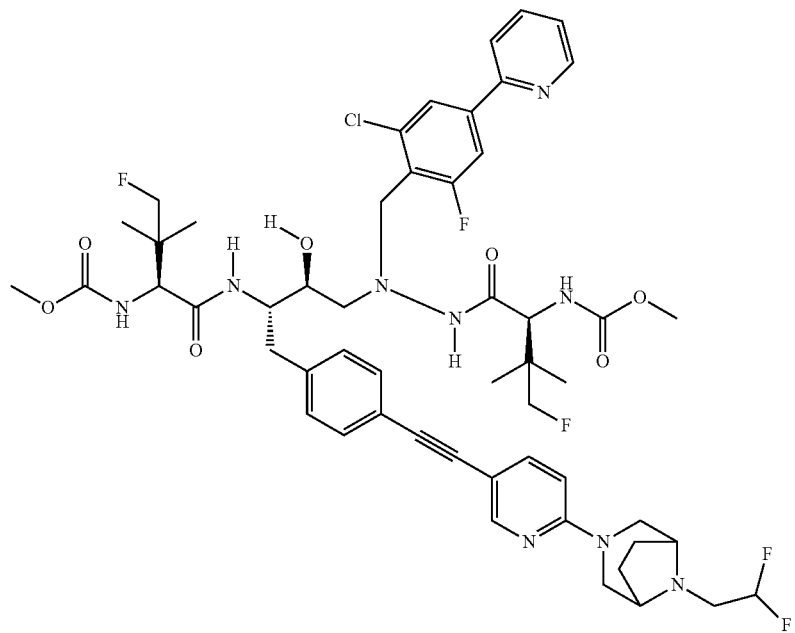 [SMILES: COC(=O)N[C@H](C(=O)N[C@@H](Cc1ccc(C#Cc2ccc(N3CC4CCC(C3)N4CC(F)F)nc2)cc1)[C@@H](O)CN(Cc1c(F)cc(-c2ccccn2)cc1Cl)NC(=O)[C@@H](NC(=O)OC)C(C)(C)CF)C(C)(C)CF]

EXAMPLE 238
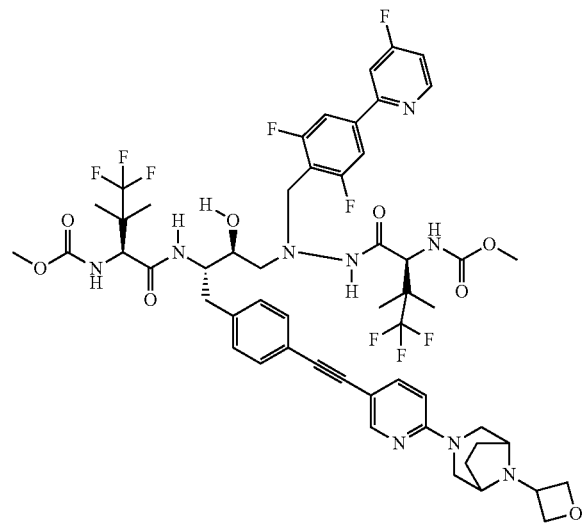 [SMILES: COC(=O)N[C@H](C(=O)N[C@@H](Cc1ccc(C#Cc2ccc(N3CC4CCC(C3)N4C3COC3)nc2)cc1)[C@@H](O)CN(Cc1c(F)cc(-c2cc(F)ccn2)cc1F)NC(=O)[C@@H](NC(=O)OC)C(C)(C)C(F)(F)F)C(C)(C)C(F)(F)F]
EXAMPLE 240
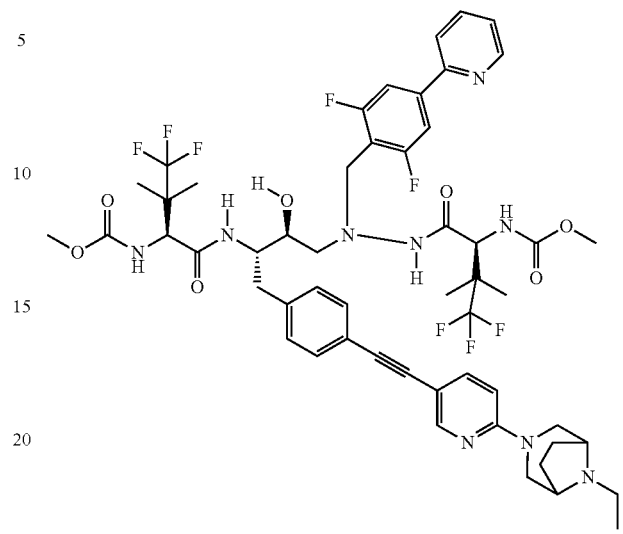
EXAMPLE 239
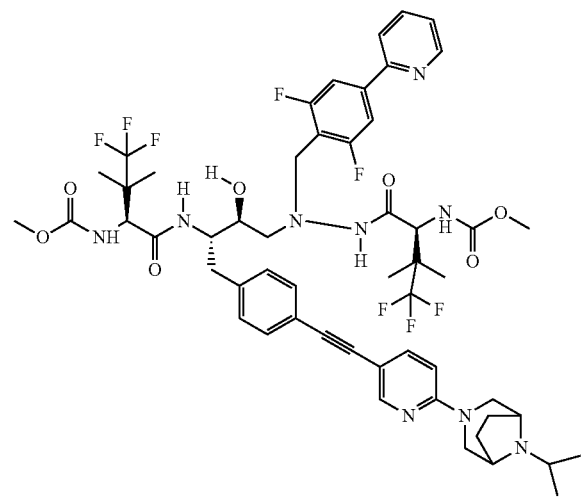 [SMILES: COC(=O)N[C@H](C(=O)N[C@@H](Cc1ccc(C#Cc2ccc(N3CC4CCC(C3)N4C(C)C)nc2)cc1)[C@@H](O)CN(Cc1c(F)cc(-c2ccccn2)cc1F)NC(=O)[C@@H](NC(=O)OC)C(C)(C)C(F)(F)F)C(C)(C)C(F)(F)F]
EXAMPLE 241
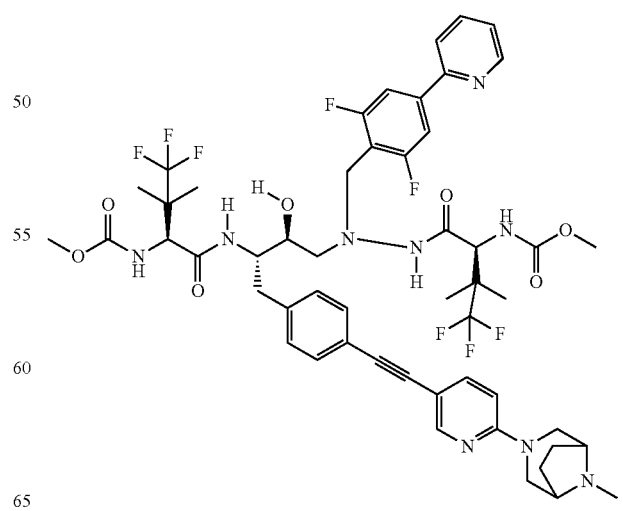

EXAMPLE 242
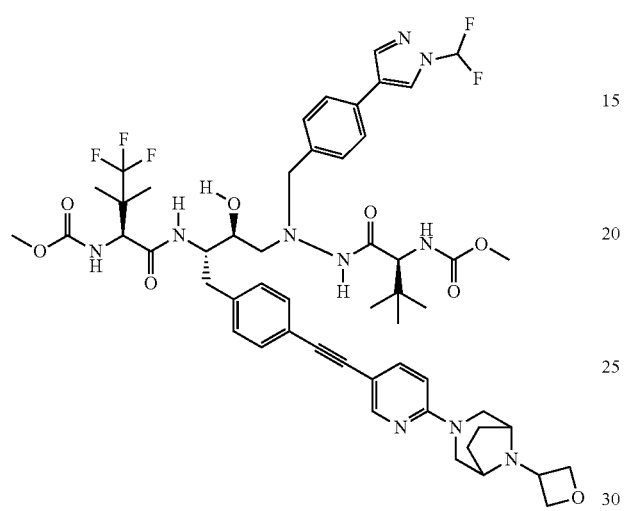
EXAMPLE 243
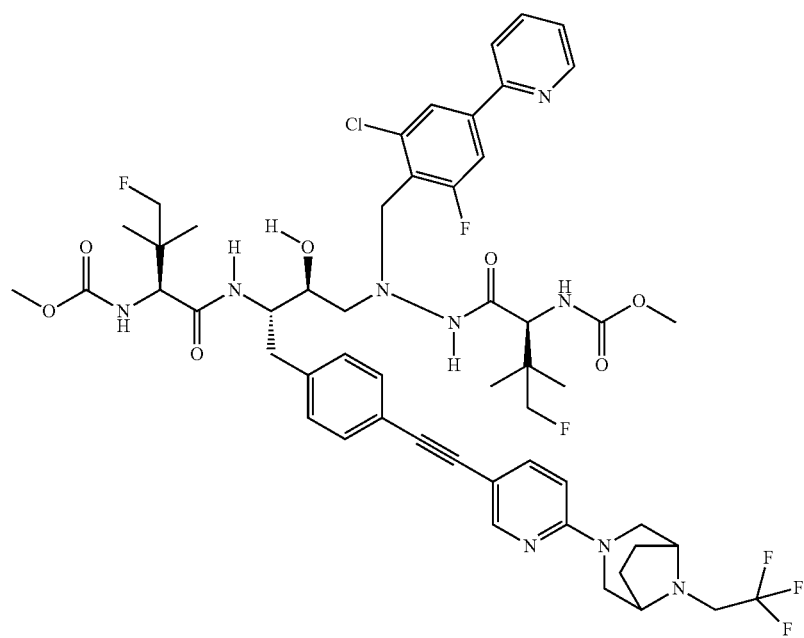 [SMILES: COC(=O)N[C@H](C(=O)N[C@@H](Cc1ccc(C#Cc2ccc(N3CC4CCC(C3)N4CC(F)(F)F)nc2)cc1)[C@@H](O)CN(Cc1c(F)cc(-c2ccccn2)cc1Cl)NC(=O)[C@@H](NC(=O)OC)C(C)(C)CF)C(C)(C)CF]

EXAMPLE 244, AND

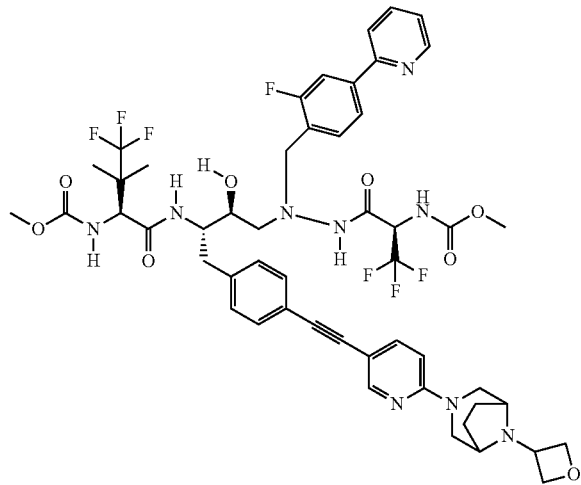 [SMILES: COC(=O)N[C@H](C(=O)NN(Cc1ccc(-c2ccccn2)cc1F)C[C@H](O)[C@H](Cc1ccc(C#Cc2ccc(N3CC4CCC(C3)N4C3COC3)nc2)cc1)NC(=O)[C@@H](NC(=O)OC)C(C)(C)C(F)(F)F)C(F)(F)F]

EXAMPLE 245 or a pharmaceutically acceptable salt thereof,
and one or more additional therapeutic agents selected from the group consisting of combination drugs for HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, gp41 inhibitors, CXCR4 inhibitors, gp120 inhibitors, CCR5 inhibitors, capsid polymerization inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof.

21. The pharmaceutical composition of claim 1, wherein the compound of Formula (I) is selected from:

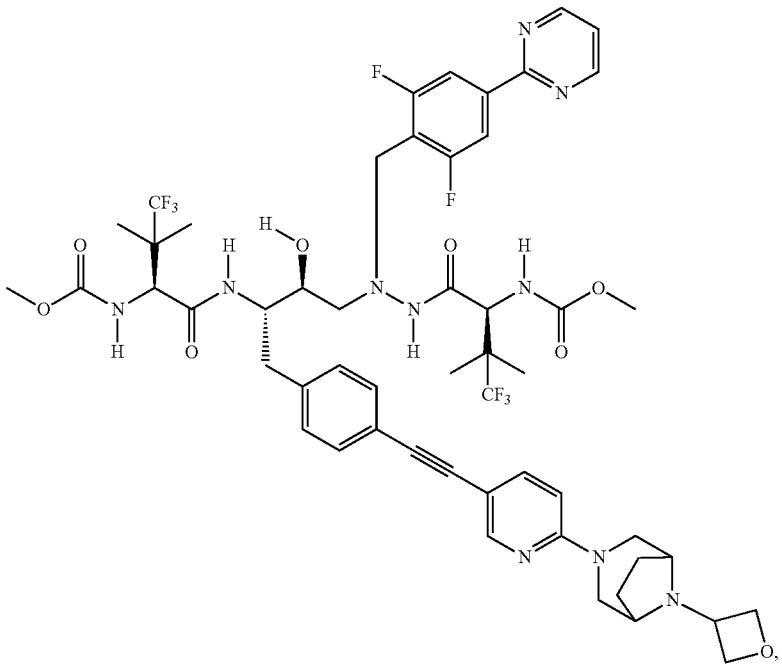

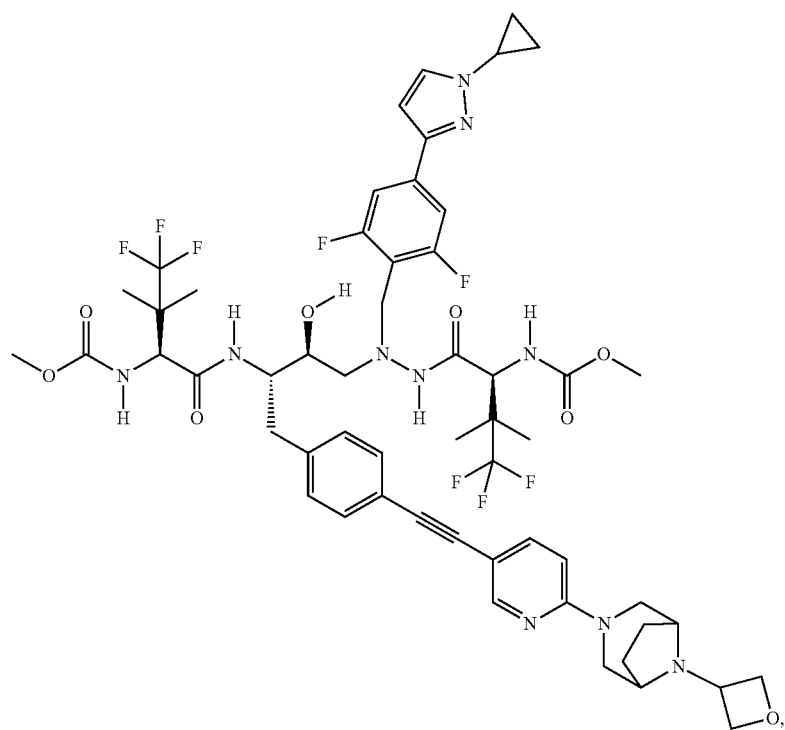
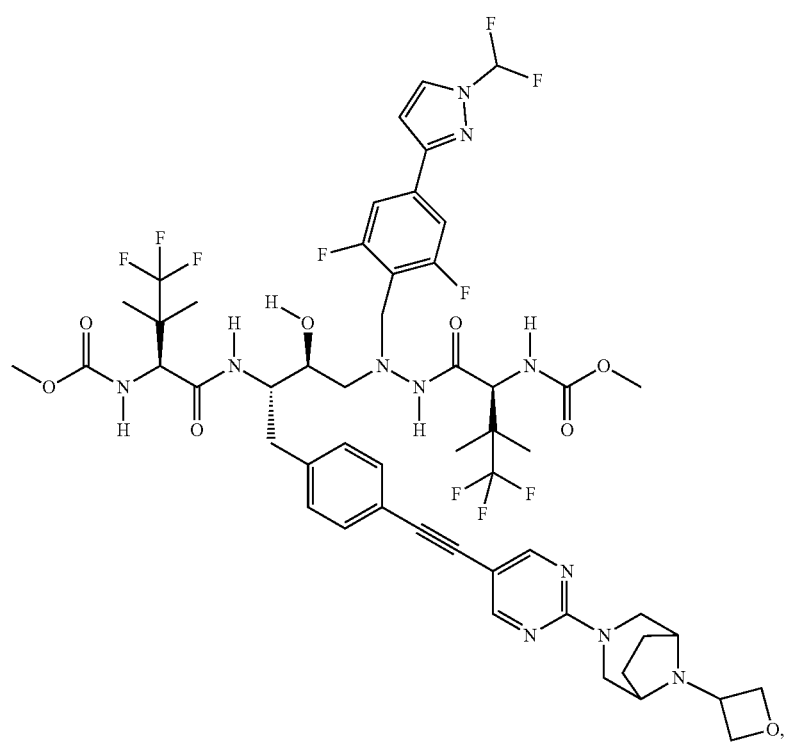

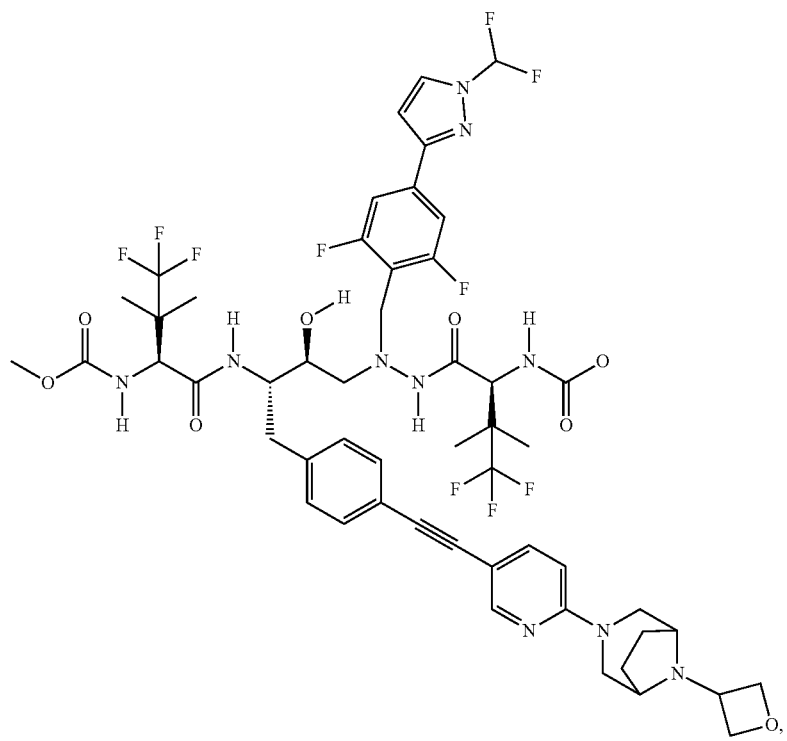
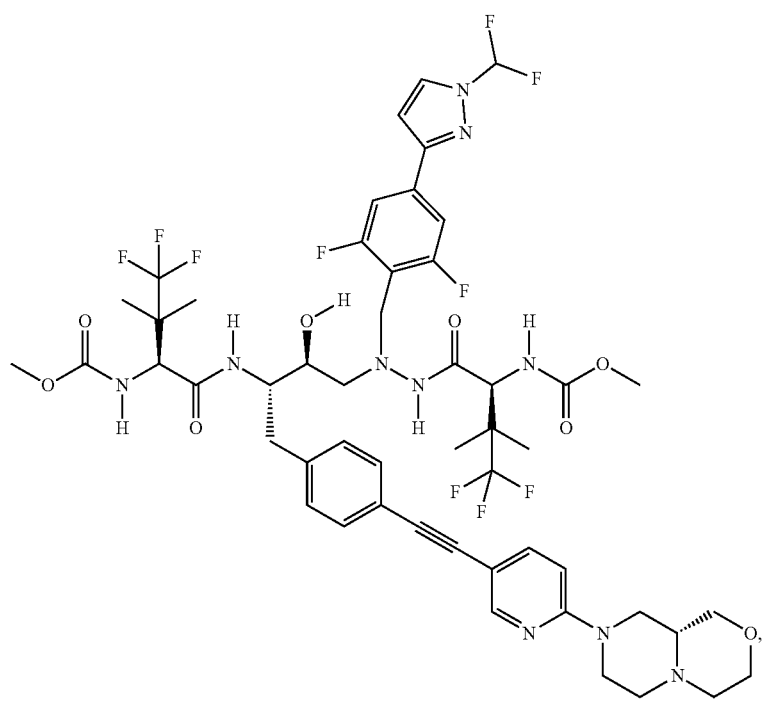

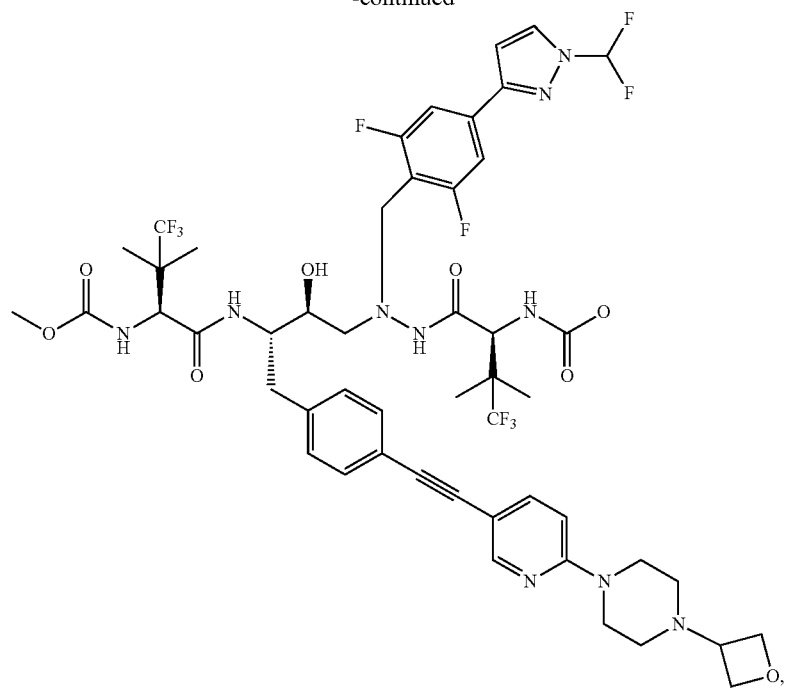
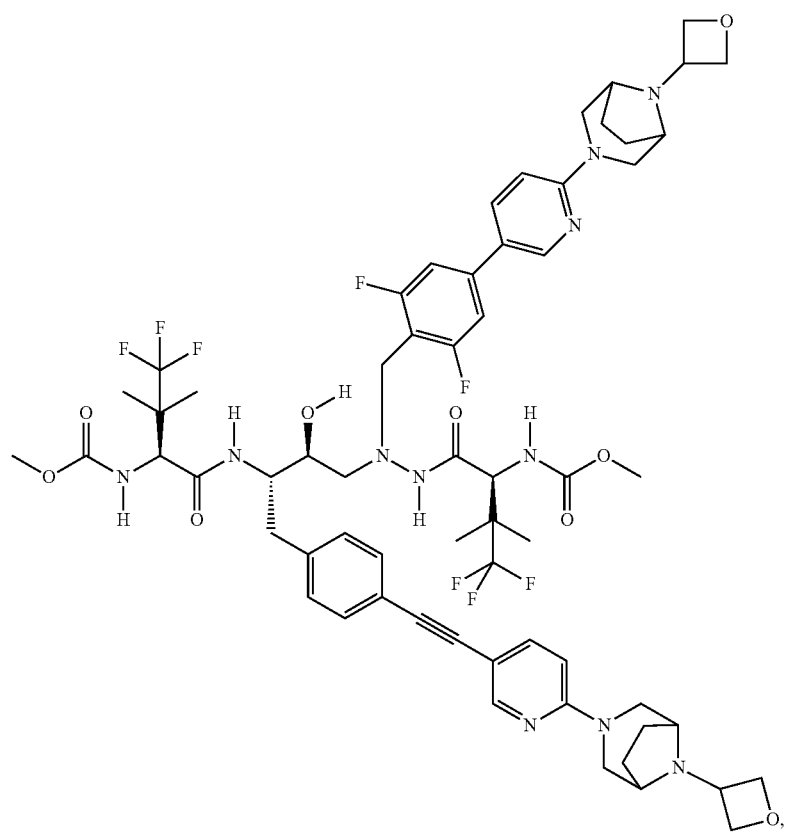

-continued
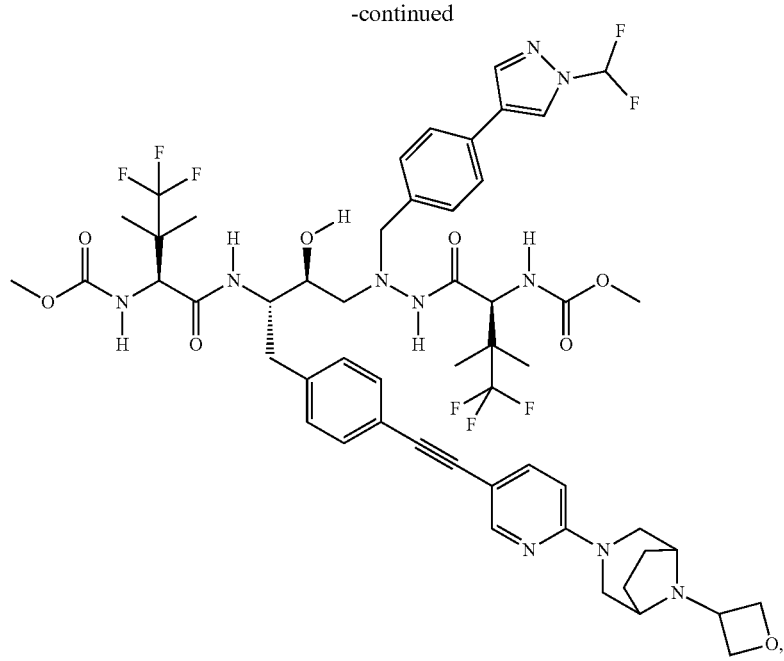
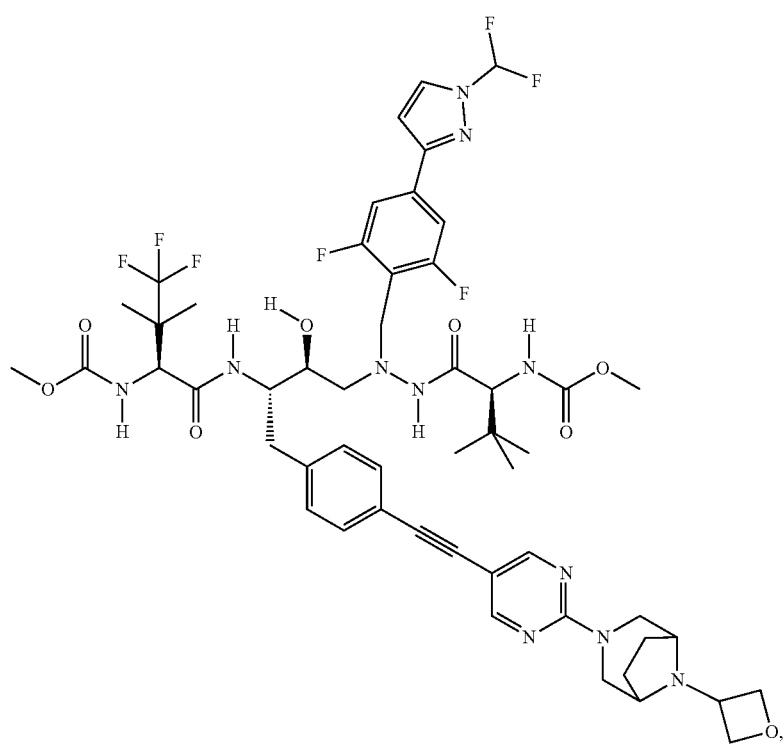 [SMILES: COC(=O)N[C@H](C(=O)NN(Cc1c(F)cc(-c2ccn(C(F)F)n2)cc1F)C[C@H](O)[C@H](Cc1ccc(C#Cc2cnc(N3CC4CCC(C3)N4C3COC3)nc2)cc1)NC(=O)[C@@H](NC(=O)OC)C(C)(C)C(F)(F)F)C(C)(C)C]

and
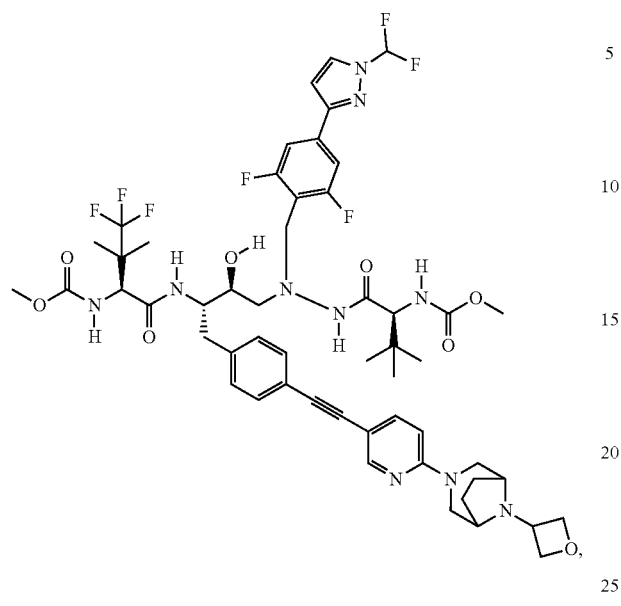
or a pharmaceutically acceptable salt thereof.
22. A method of treating a human immunodeficiency virus (HIV) infection comprising administering a therapeutically effective amount of a pharmaceutical composition of claim 1 to a subject in need thereof.
23. A pharmaceutical composition comprising a compound selected from:
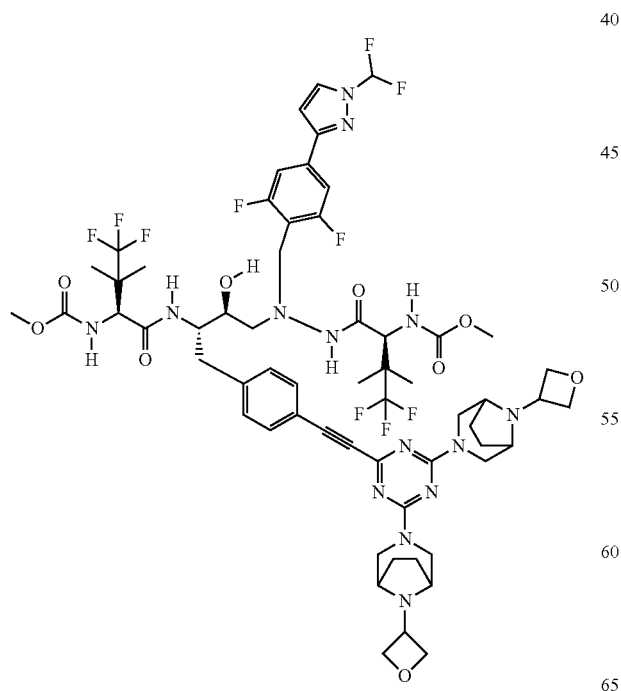

EXAMPLE 49
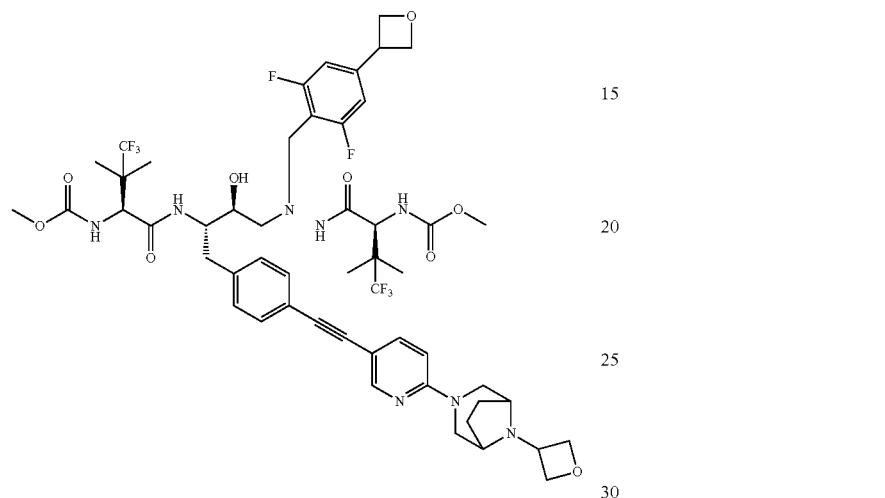
EXAMPLE 83
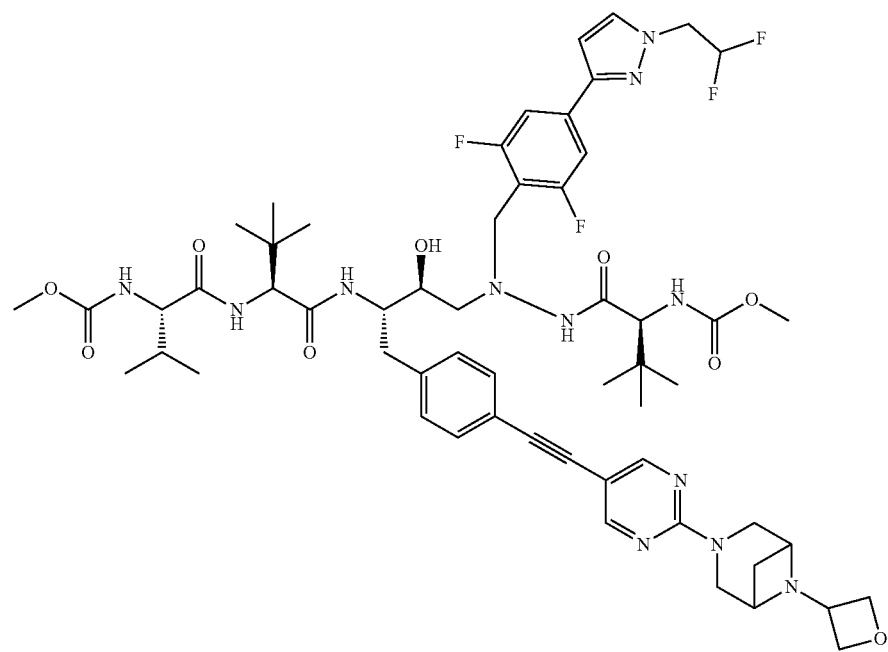 [SMILES: COC(=O)N[C@H](C(=O)N[C@H](C(=O)N[C@@H](Cc1ccc(C#Cc2cnc(N3CC4CC(C3)N4C3COC3)nc2)cc1)[C@@H](O)CN(Cc1c(F)cc(-c2ccn(CC(F)F)n2)cc1F)NC(=O)[C@@H](NC(=O)OC)C(C)(C)C)C(C)(C)C)C(C)C]

EXAMPLE 222, AND

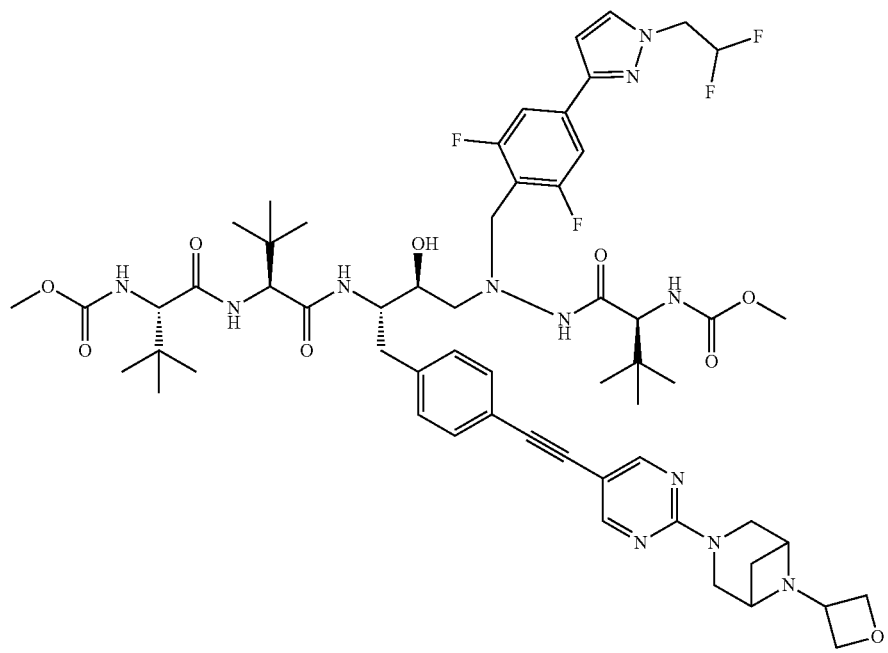 [SMILES: COC(=O)N[C@H](C(=O)N[C@H](C(=O)N[C@@H](Cc1ccc(C#Cc2cnc(N3CC4CC(C3)N4C3COC3)nc2)cc1)[C@@H](O)CN(Cc1c(F)cc(-c2ccn(CC(F)F)n2)cc1F)NC(=O)[C@@H](NC(=O)OC)C(C)(C)C)C(C)(C)C)C(C)(C)C]

EXAMPLE 223 or a pharmaceutically acceptable salt thereof, and one or more additional therapeutic agents selected from the group consisting of combination drugs for HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, gp41 inhibitors, CXCR4 inhibitors, gp120 inhibitors, CCR5 inhibitors, capsid polymerization inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or any combinations thereof.

* * * * *

UNITED STATES PATENT AND TRADEMARK OFFICE
CERTIFICATE OF CORRECTION

PATENT NO. : 11,078,208 B1  Page 1 of 97
APPLICATION NO. : 16/805933
DATED : August 3, 2021
INVENTOR(S) : Elizabeth M. Bacon et al.

It is certified that error appears in the above-identified patent and that said Letters Patent is hereby corrected as shown below:

In the Specification

Column 18, Line 45, delete " 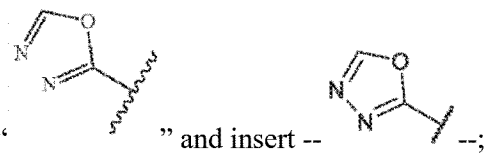 " and insert -- --;

Column 18, Line 55, delete " 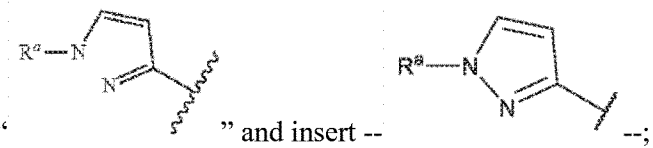 " and insert -- --;

Column 18, Line 60, delete " 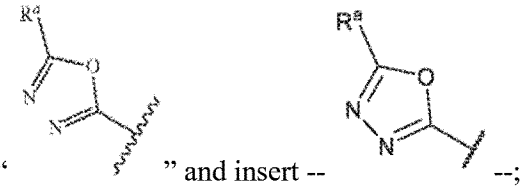 " and insert -- --;

Column 19, Line 1, delete " 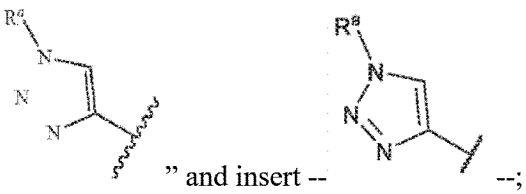 " and insert -- --;

Signed and Sealed this
Thirteenth Day of September, 2022

Katherine Kelly Vidal
*Director of the United States Patent and Trademark Office*

Column 27, second structure, delete " 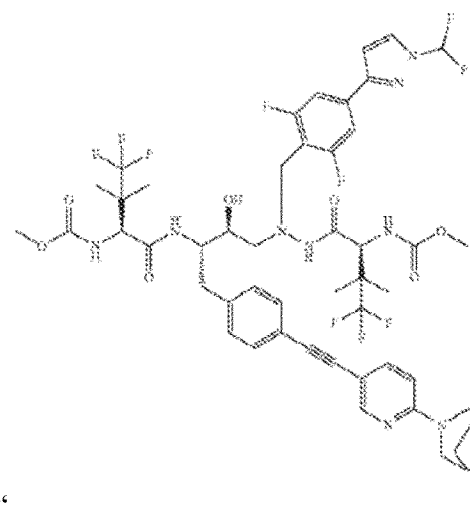 " and insert
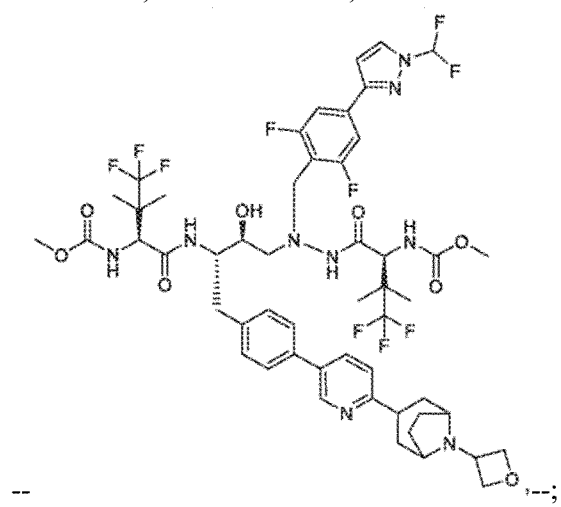 --;
Column 37, Lines 45-65, delete " 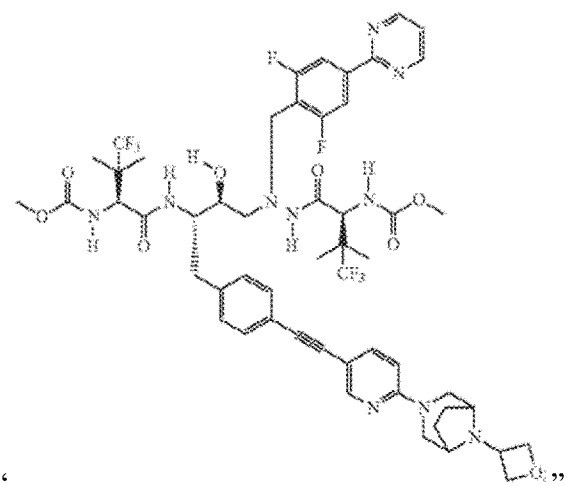 "

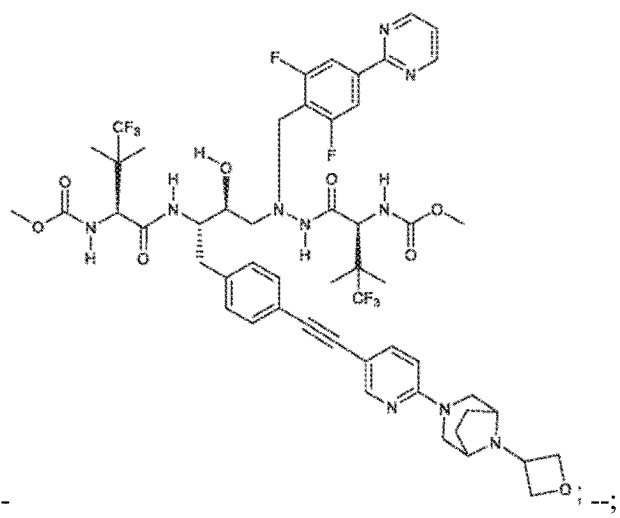
and insert --
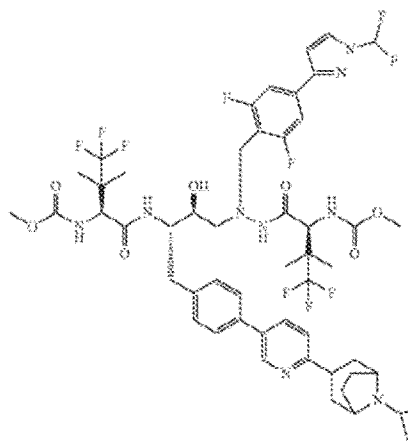
Column 38, Lines 3-25, delete "  " and insert
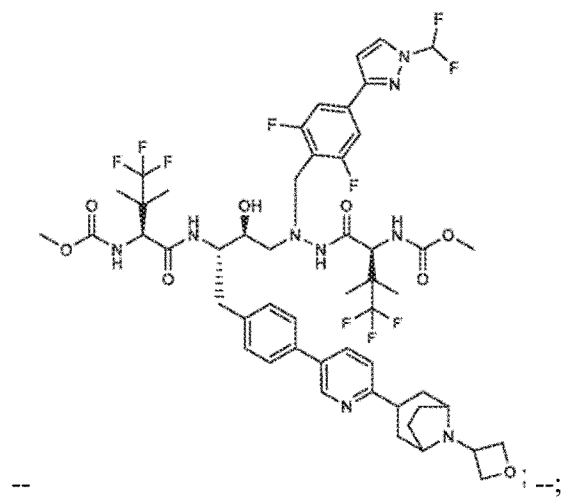
--

Column 39, Lines 4-24, delete " 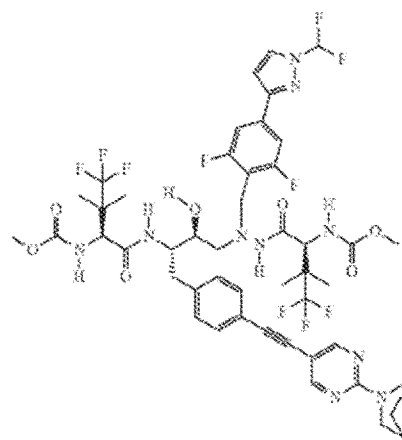 " and insert
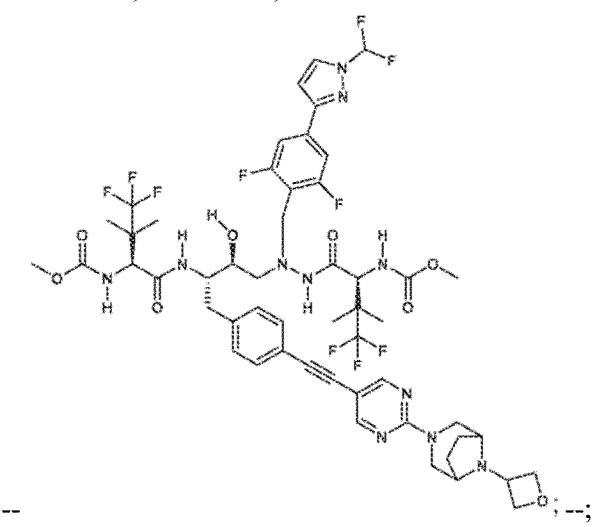 --;
Column 39, Lines 45-65, delete " 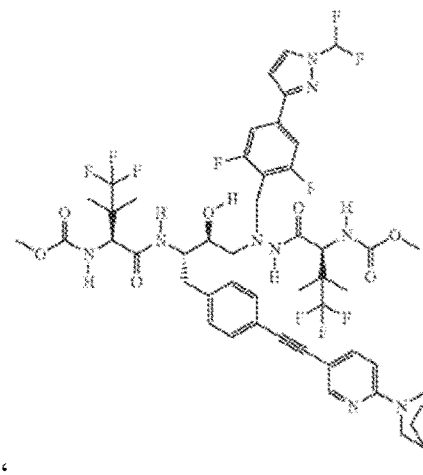 " and insert 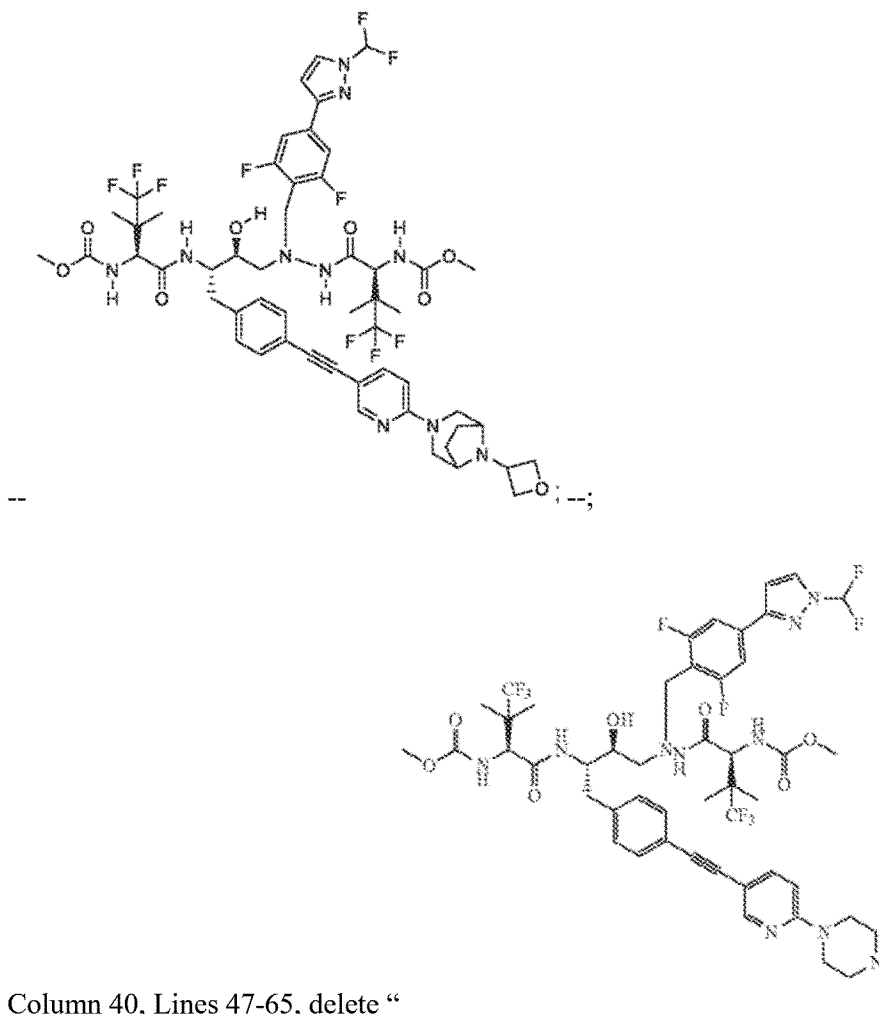
Column 40, Lines 47-65, delete " 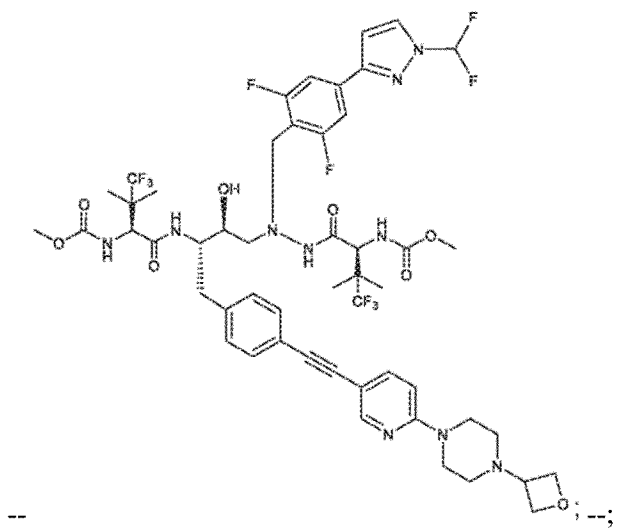 " and insert
--- …;--

Column 41, Lines 45-65, delete " 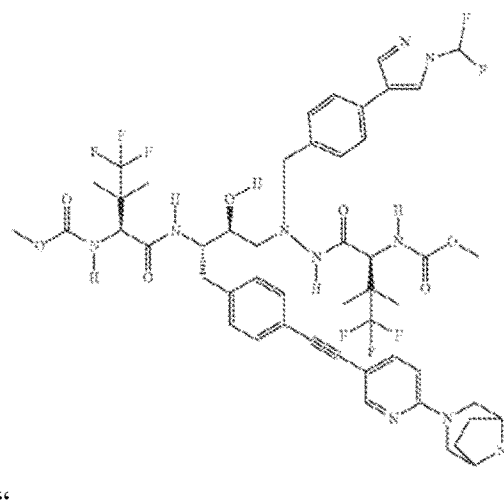 " and insert
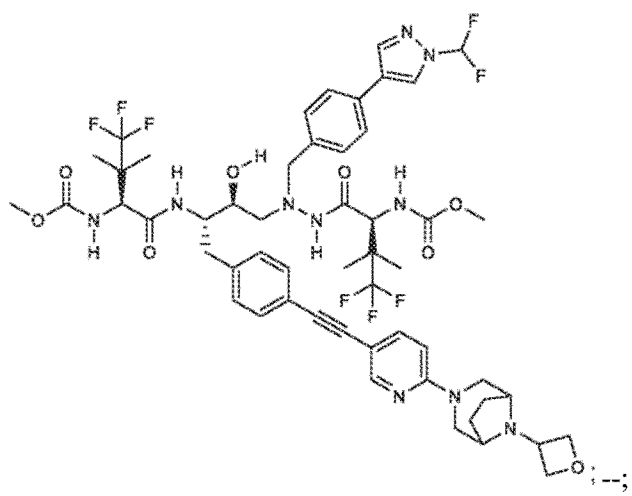
--;
Column 75-76, Scheme 1.4, delete " 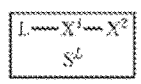 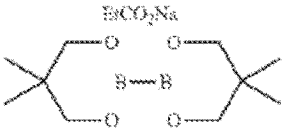 " and insert -- 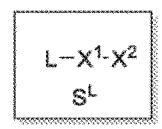  --;
Column 78, Scheme 1.6, delete " 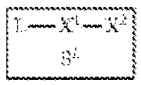 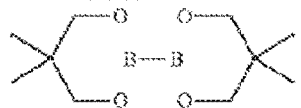 " and insert -- 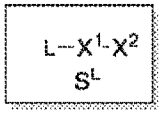 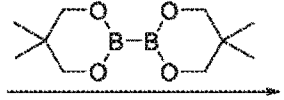 --;

Column 79, Scheme 1.7, delete " 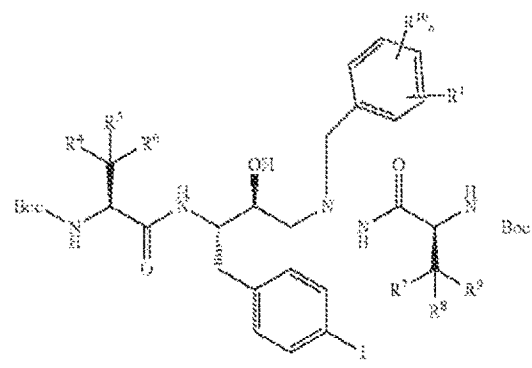 " and insert
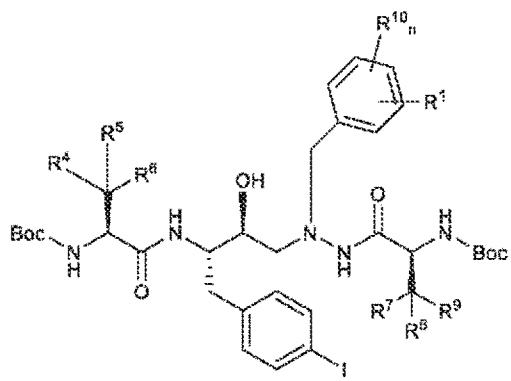 --;
Column 79-80, Scheme 1.7, above the arrow, delete " 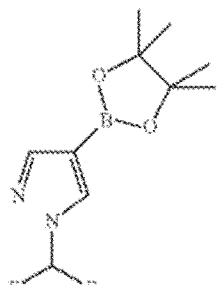 " and insert
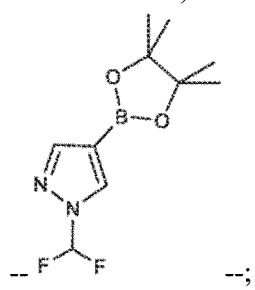 --;

Column 79-80, Scheme 1.7, delete " 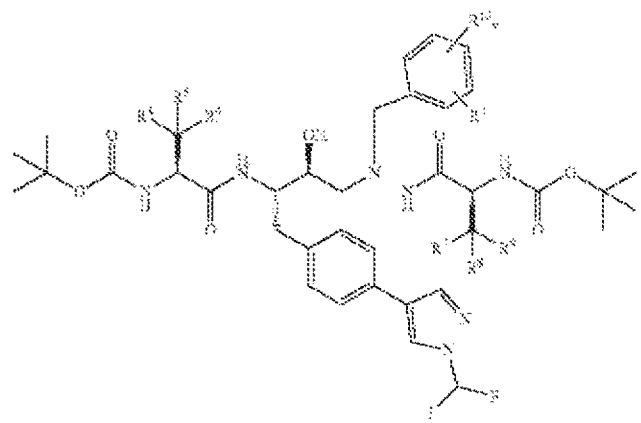 " and
insert -- 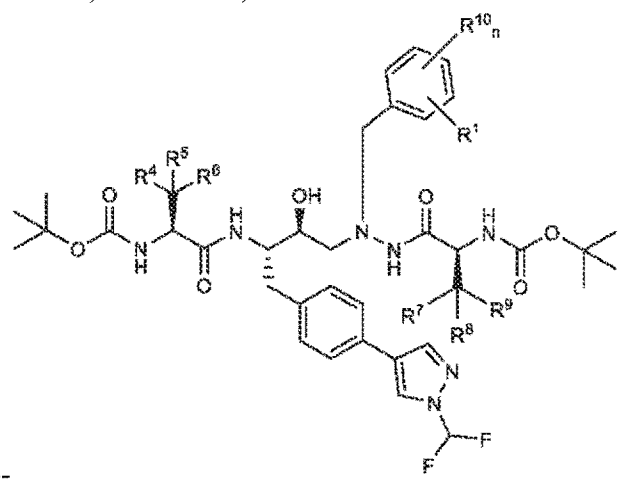 --;
Column 79-80, last structure on page, delete " 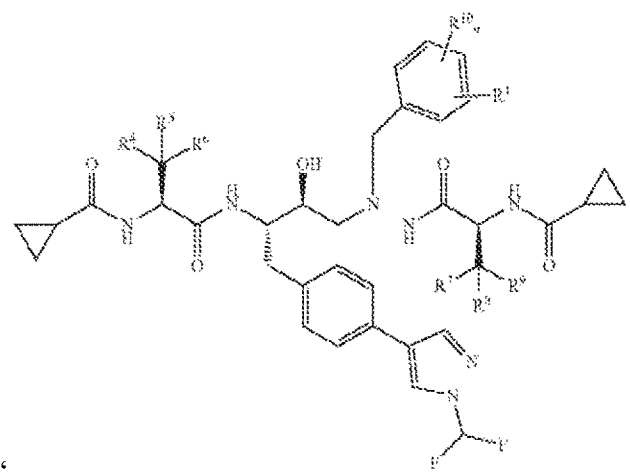 "

CERTIFICATE OF CORRECTION (continued)
U.S. Pat. No. 11,078,208 B1

Page 9 of 97 and insert --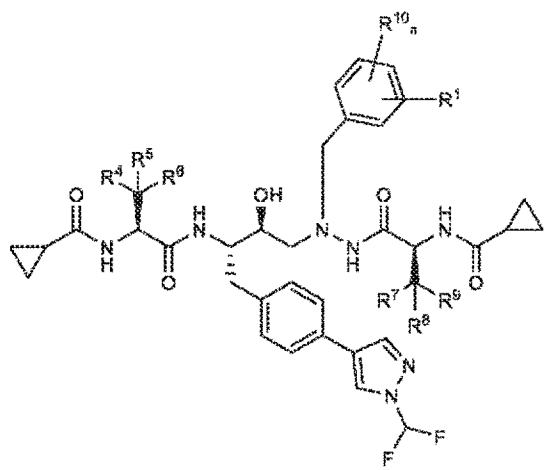--;

Column 87, Lines 25-30, delete "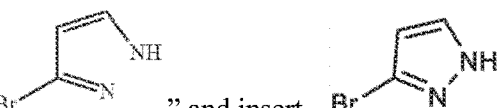" and insert --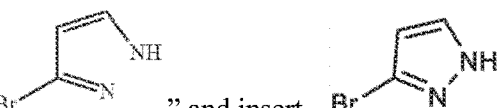--;

Column 87, Lines 35-45, delete "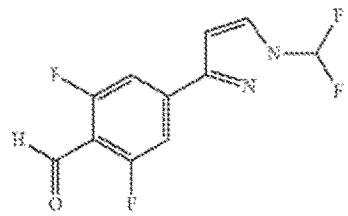" and insert --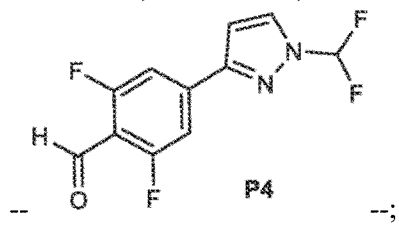--;

Column 90, Lines 35-40, delete "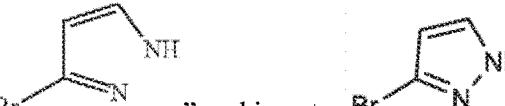" and insert --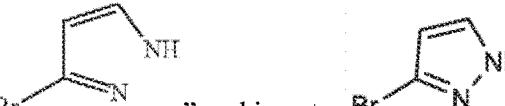--;

Column 90, Lines 48-58, delete "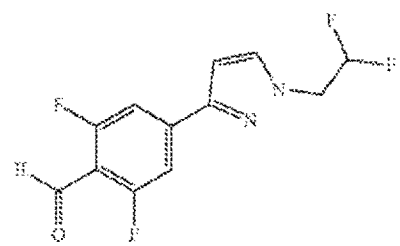" and insert

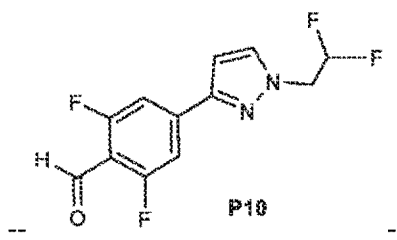
Column 91, Lines 37-43, delete "  " and insert --  --;
Column 91, Lines 44-55, delete " 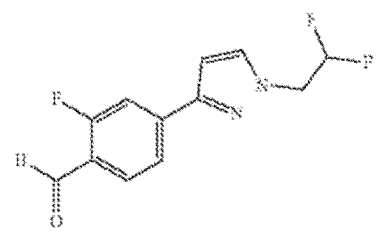 " and insert
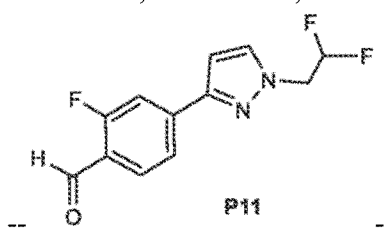 --;
Column 92, Lines 1-5, delete "  " and insert --  --;
Column 92, Lines 7-17, delete " 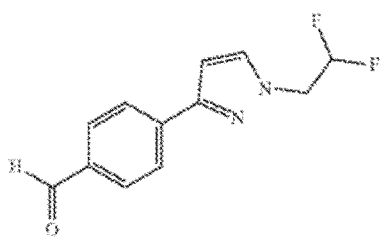 " and insert
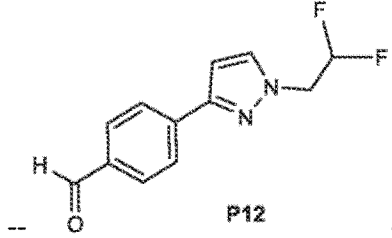 --;

Column 92, Lines 32-36, delete " 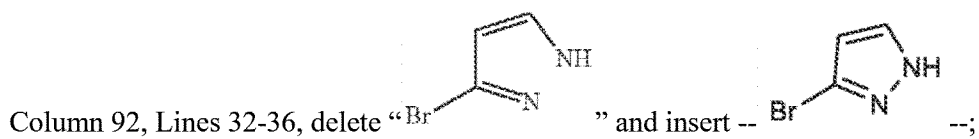 " and insert -- ;
Column 92, Lines 39-48, delete " 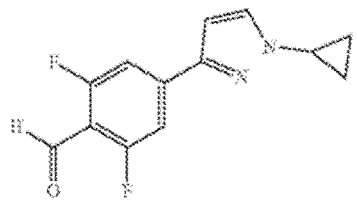 " and insert 
-- 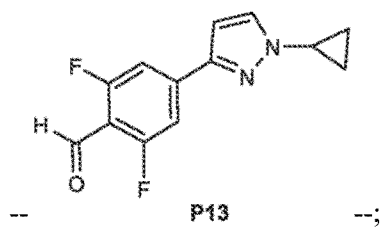 --;
Column 95, Lines 5-10, delete " 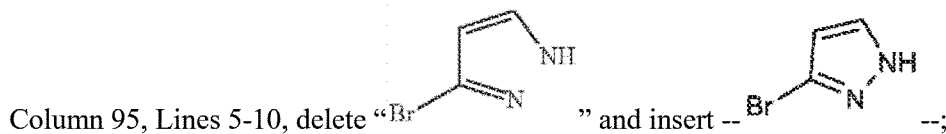 " and insert -- ;
Column 95, Lines 17-26, delete " 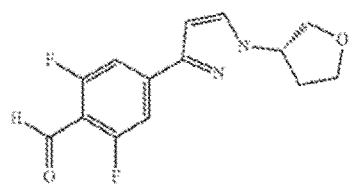 " and insert 
-- 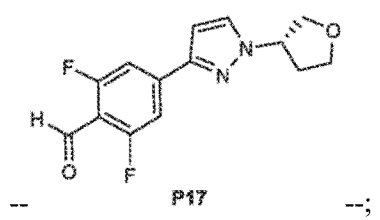 --;
Column 96, Lines 3-7, delete " 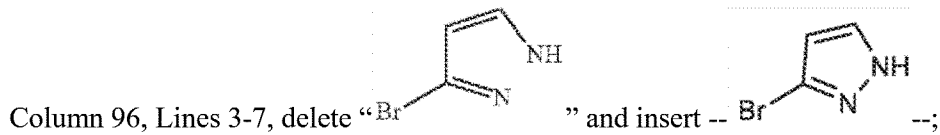 " and insert -- ;

CERTIFICATE OF CORRECTION (continued)
U.S. Pat. No. 11,078,208 B1

Column 96, Lines 11-19, delete " 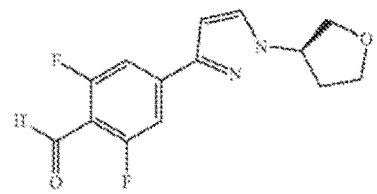 " and insert

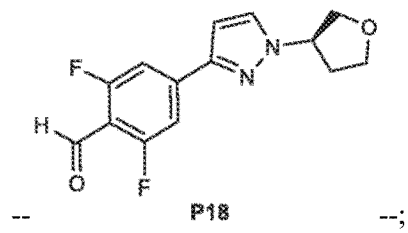

-- -- ;

Column 96, Lines 38-43, delete " 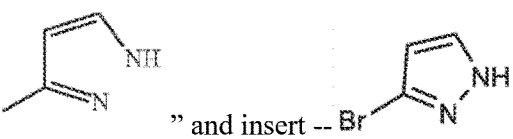 " and insert -- -- ;

Column 96, Lines 47-57, delete " 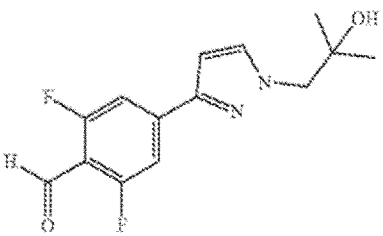 " and insert

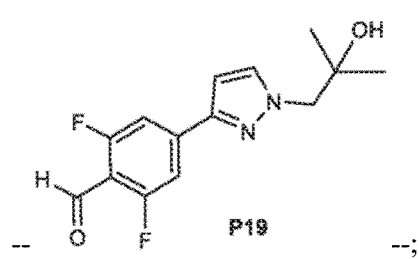

-- -- ;

Column 97, Lines 50-55, delete " 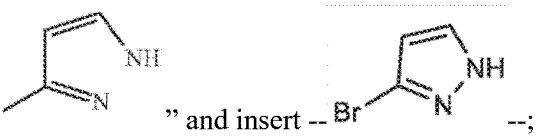 " and insert -- -- ;

Column 97, Lines 55-65, delete " 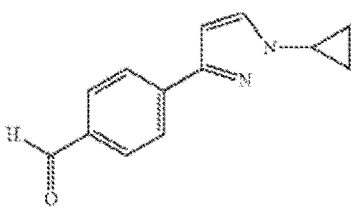 " and insert

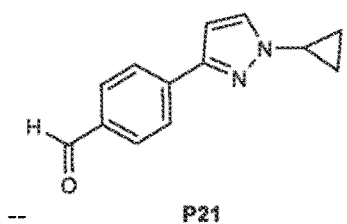
-- P21 --;
Column 101, Lines 44-54, delete " 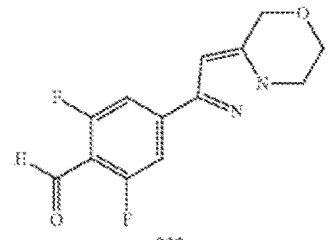 " and insert -- 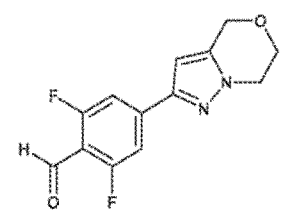 --;
Column 105, Lines 32-36, delete " " and insert -- --;
Column 105, Lines 37-46, delete " 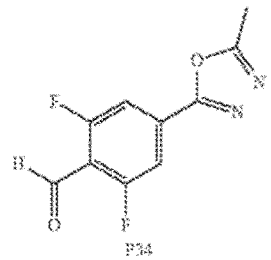 " and insert -- 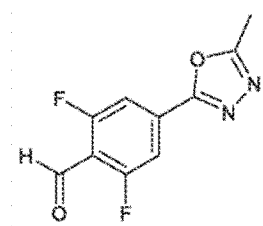 --;
Column 108, Lines 22-28, delete " " and insert -- --;

Column 108, Lines 28-39, delete " 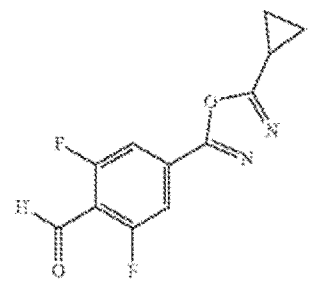 " and insert -- 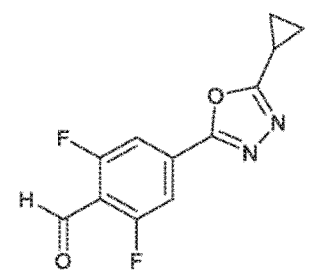 --;
Column 108, Lines 58-65, delete " 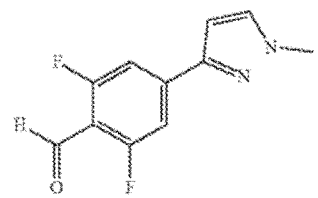 " and insert -- 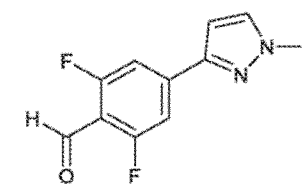 --;
Column 109, Lines 35-45, delete " 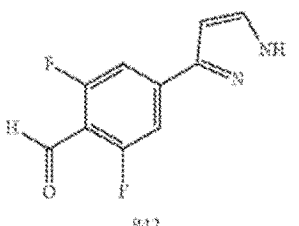 " and insert -- 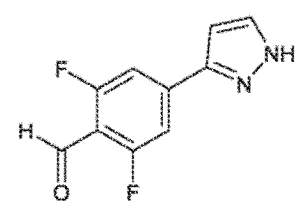 --;
Column 112, Lines 8-11, delete " 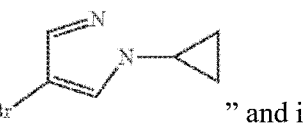 " and insert --  --;
Column 112, Lines 15-25, delete " 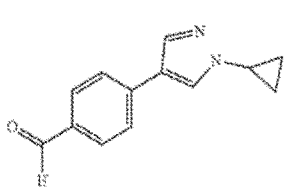 " and insert -- 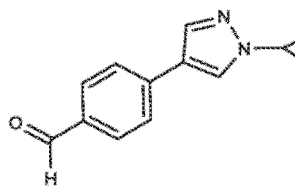 --;
Column 174, Lines 10-20, delete " 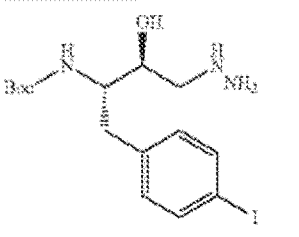 " and insert -- 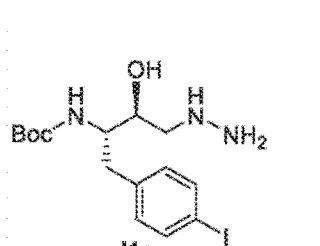 --;

CERTIFICATE OF CORRECTION (continued)
U.S. Pat. No. 11,078,208 B1

Column 174, Lines 20-30, delete " 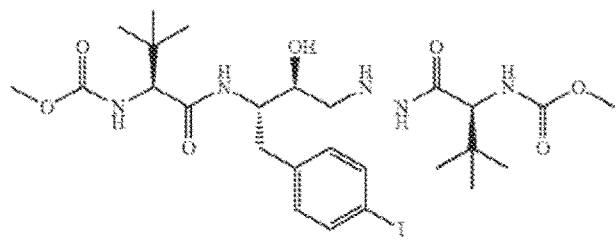 " and insert

-- 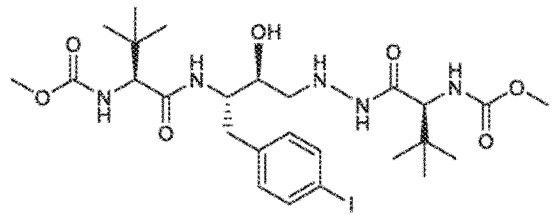 --;

Column 175, Lines 17-25, delete " 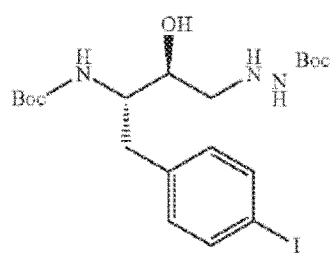 " and insert

-- 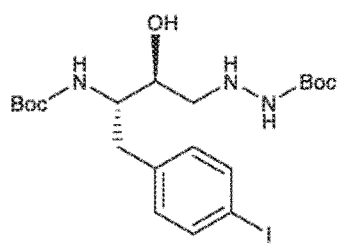 --;

Column 175, Lines 25-37, delete " 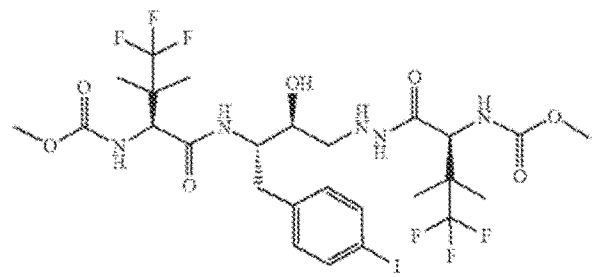 " and insert -- 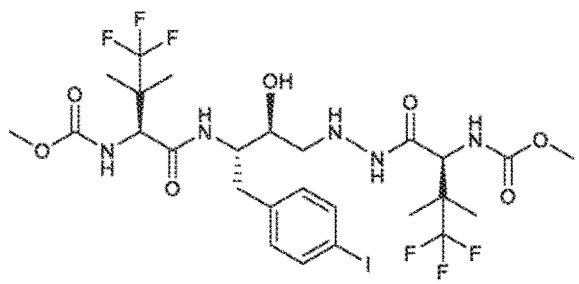 --;
Column 176, Lines 20-25, delete " 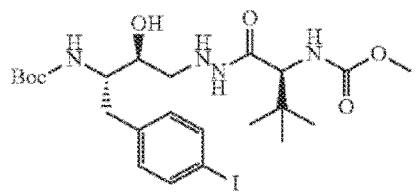 " and insert
-- 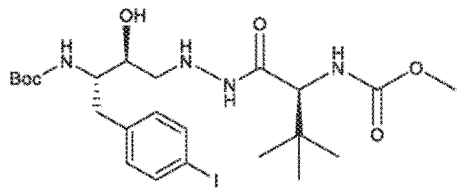 --;
Column 176, Lines 26-37, delete " 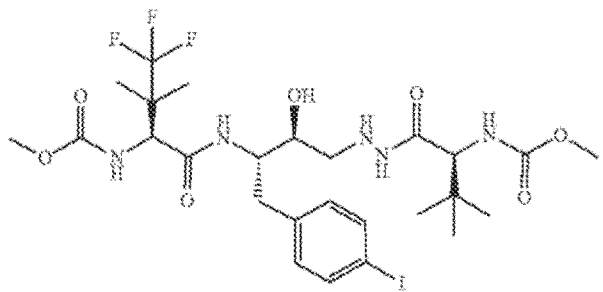 " and insert
-- 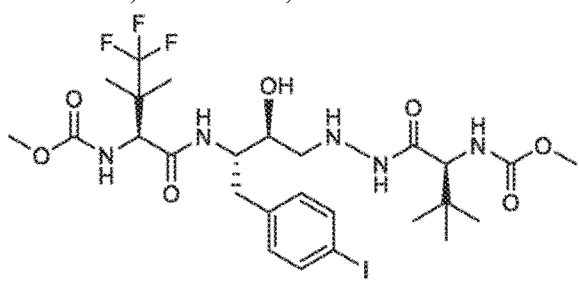 --;

Column 177, Lines 10-20, delete " 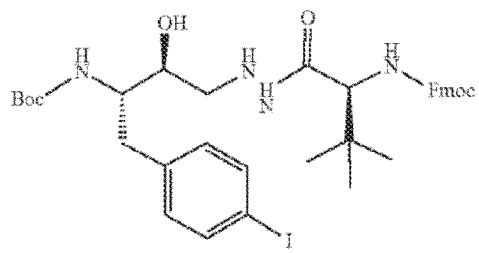 " and insert -- 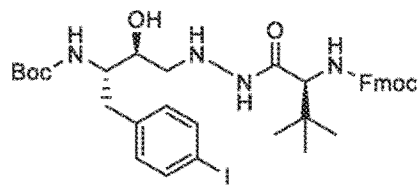 --;
Column 177, Lines 58-67, delete " 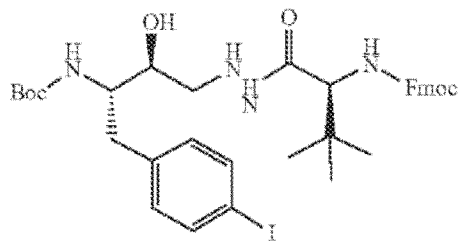 " and insert -- 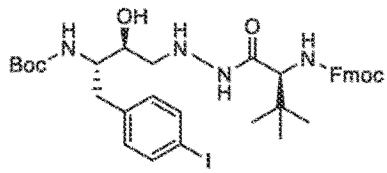 --;
Column 178, Lines 1-12, delete " 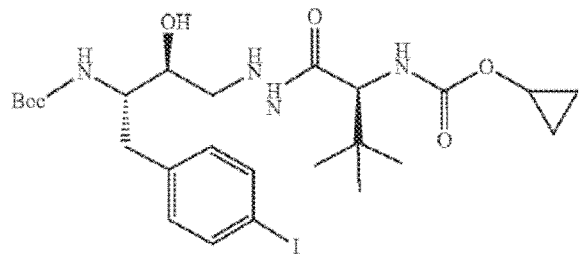 " and insert

CERTIFICATE OF CORRECTION (continued)
U.S. Pat. No. 11,078,208 B1

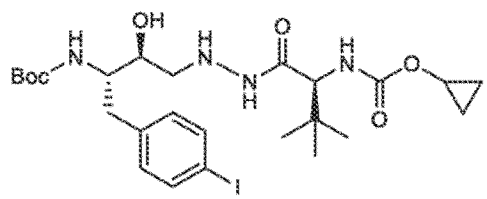

-- I5 --;

Column 178, Lines 30-38, delete " 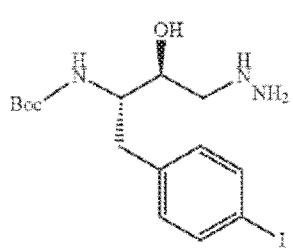 " and insert -- 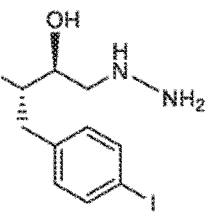 --;

Column 178, Lines 47-57, delete " 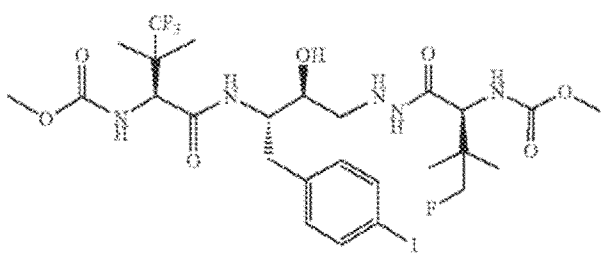 " and insert

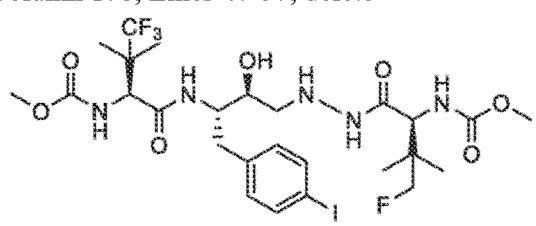

-- I6 --;

Column 185-186, Example 1 first structure, delete

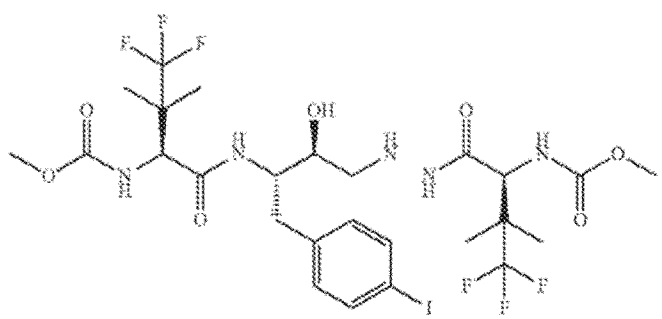

" " and insert

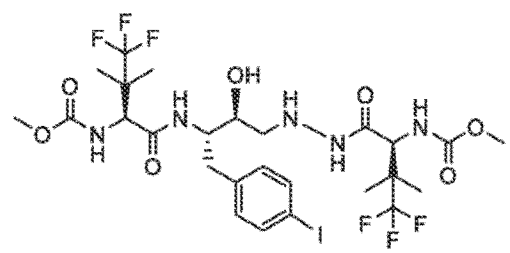
-- 12 --;
Column 185-186, Example 1 second structure, delete
" 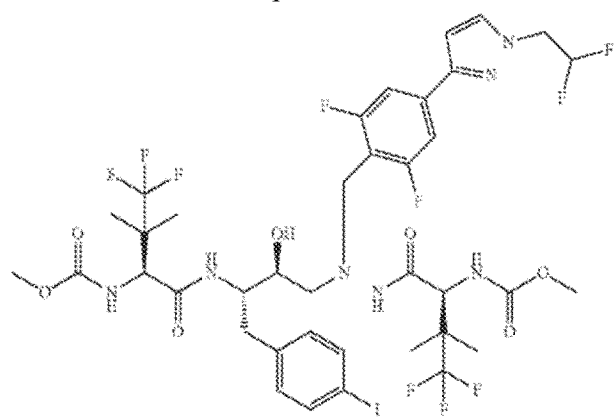 " and insert
-- 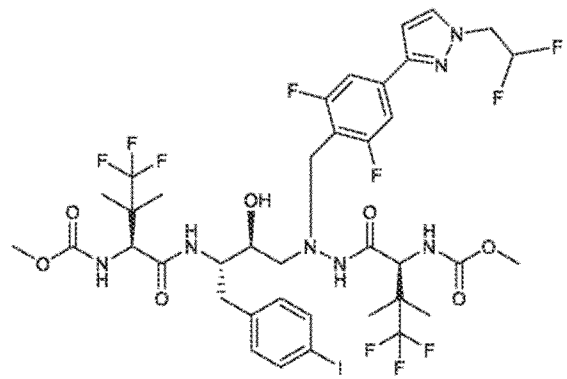 --;

CERTIFICATE OF CORRECTION (continued)
U.S. Pat. No. 11,078,208 B1

Column 185-186, Example 1 third structure, delete " 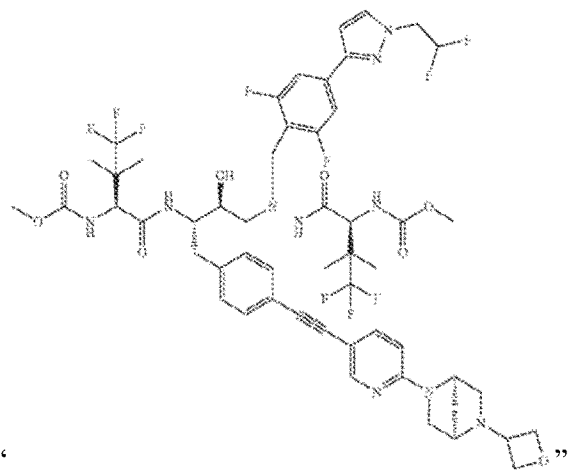 "

and insert -- 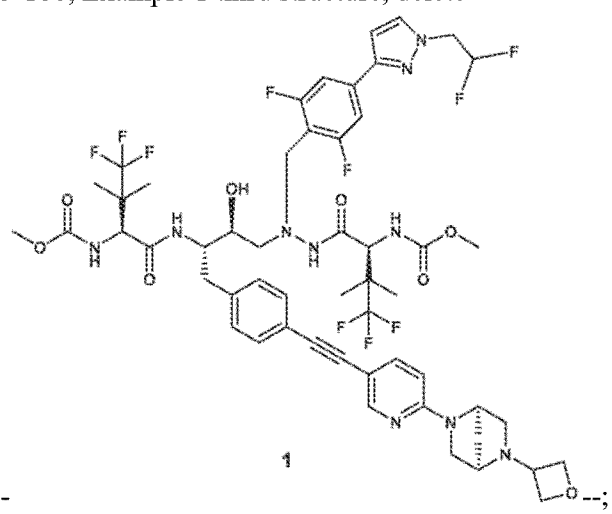 --;

Column 187, Example 2, Lines 46-66, delete " 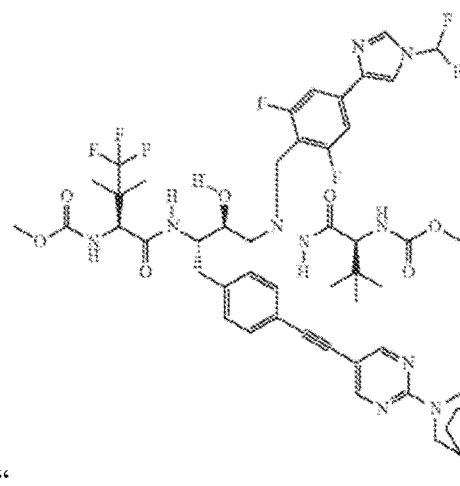 " and

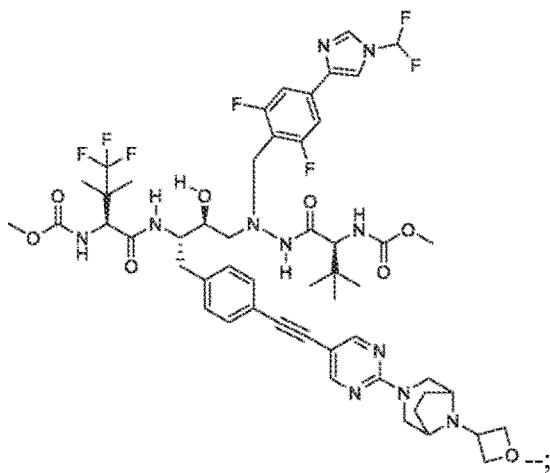
insert --
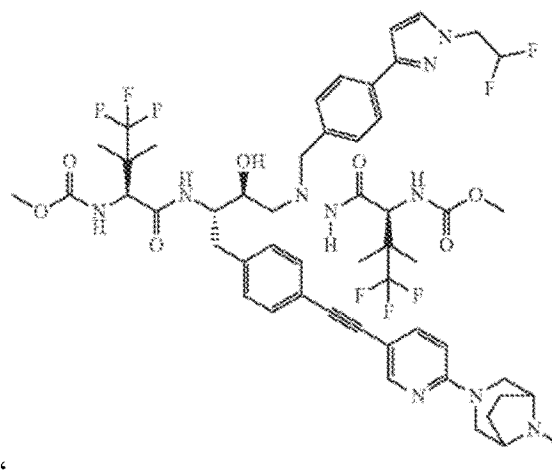
Column 188, Example 3, Lines 25-43, delete "
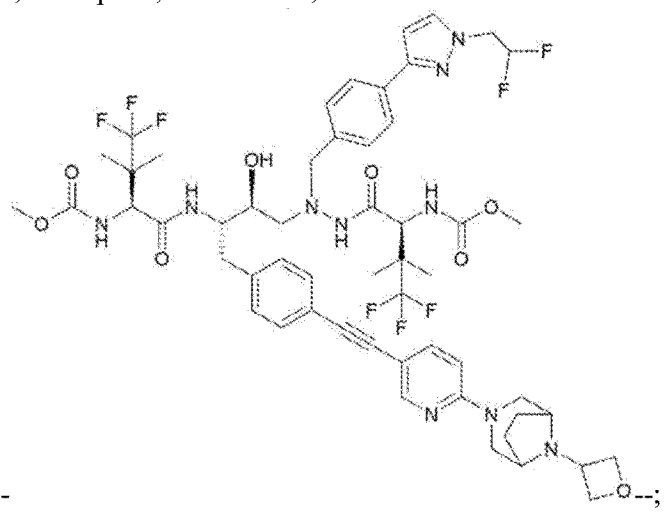
and insert --

Column 189, Example 5, Lines 45-65, delete " 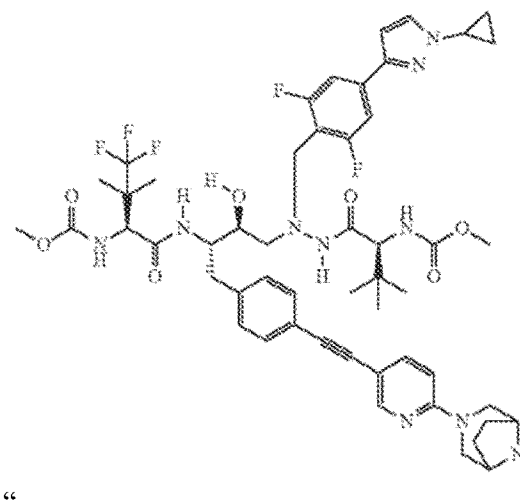 " and
insert --  --;
Column 190, Example 6, Lines 25-45, delete " 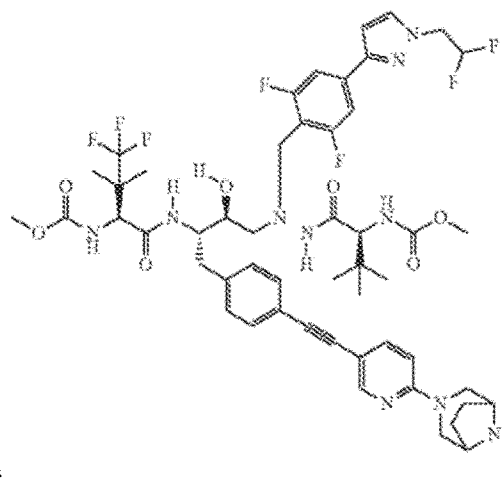 " and

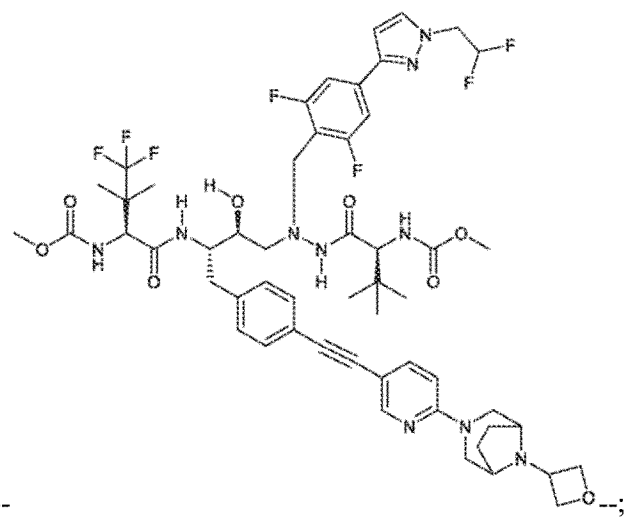
insert --
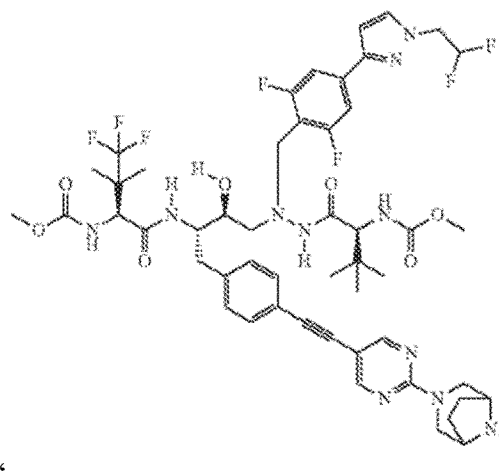 and
Column 191, Example 7, Lines 1-20, delete "
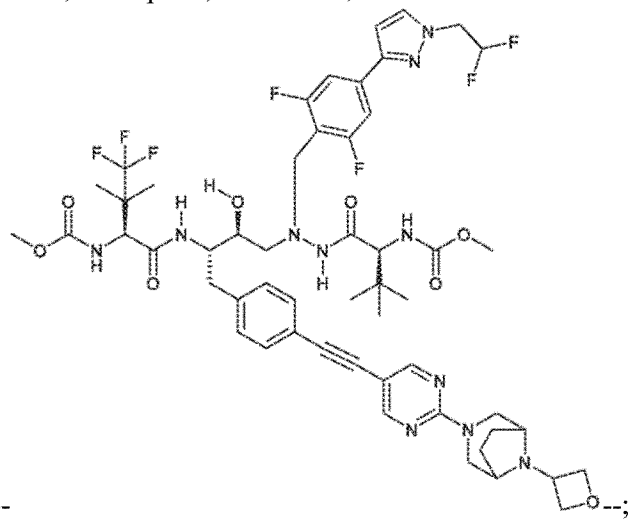
insert --

CERTIFICATE OF CORRECTION (continued)
U.S. Pat. No. 11,078,208 B1

Column 191, Example 8, Lines 47-66, delete " 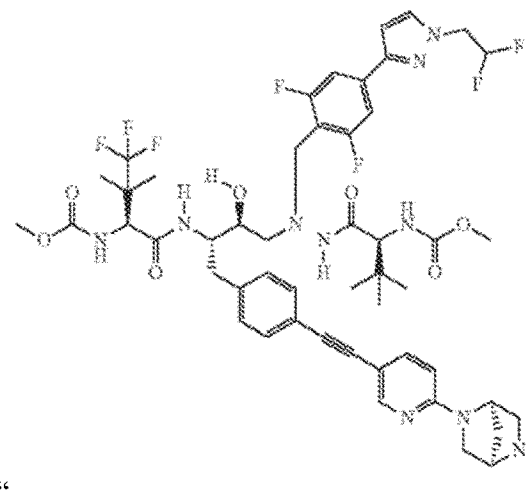" and insert -- 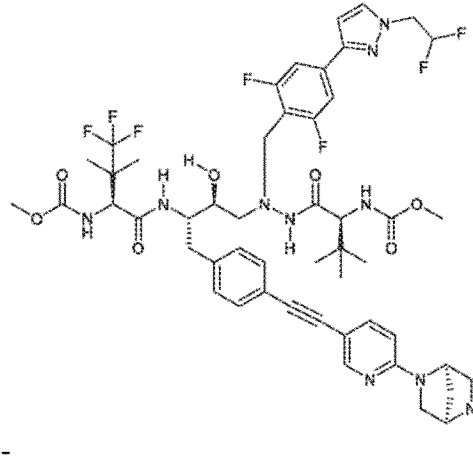--;

Column 192, Example 9, Lines 25-45, delete " 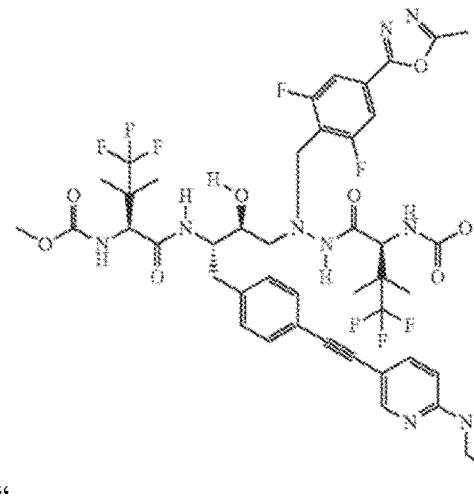" and

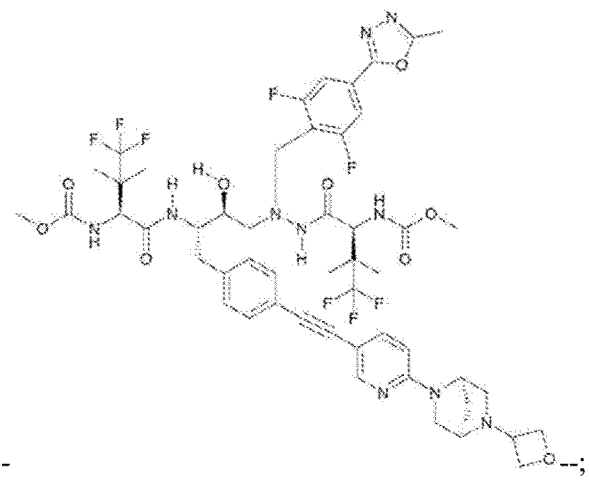
insert --
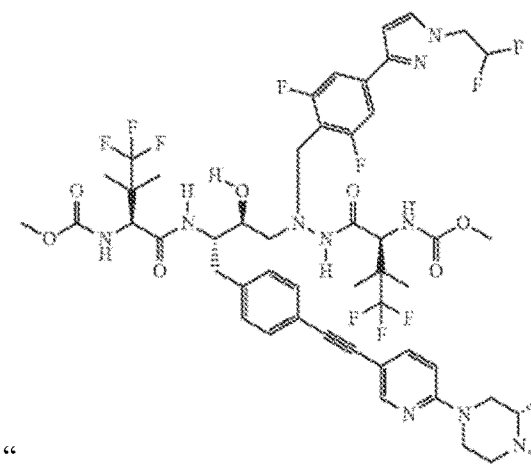
Column 193, Example 10, Lines 1-20, delete " " and
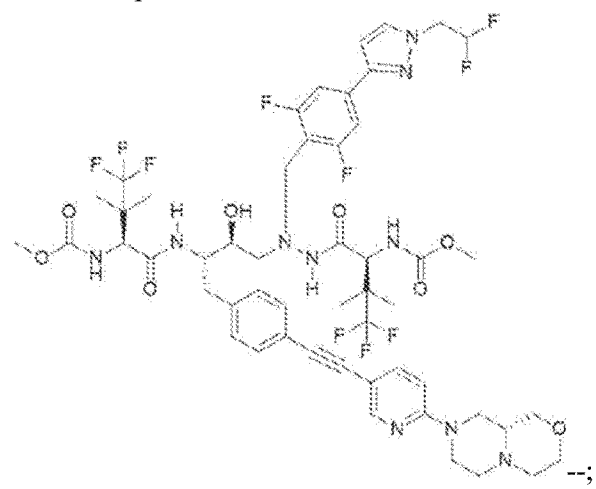
insert -- --;

CERTIFICATE OF CORRECTION (continued)
U.S. Pat. No. 11,078,208 B1

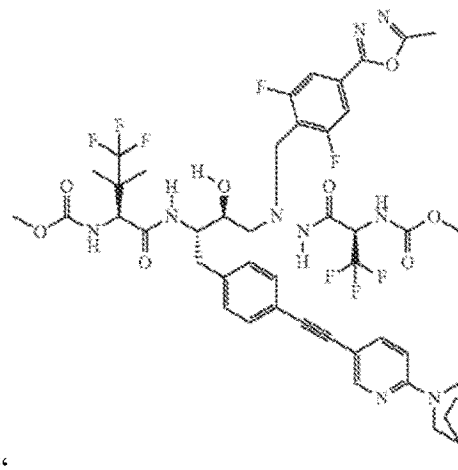

Column 193, Example 11, Lines 47-66, delete "  " and

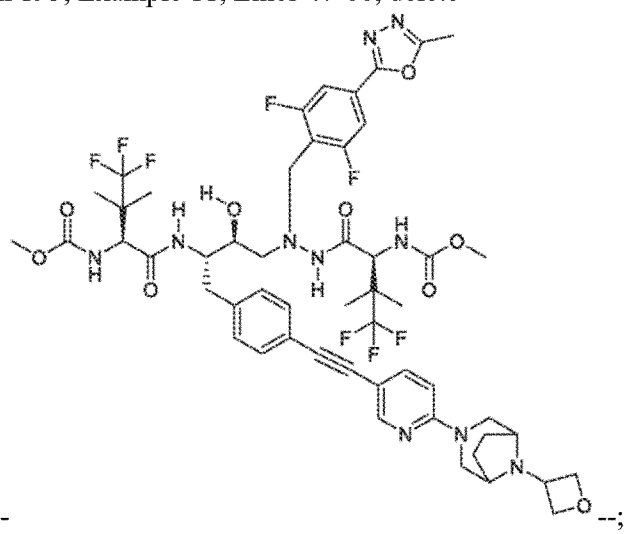

insert -- --;

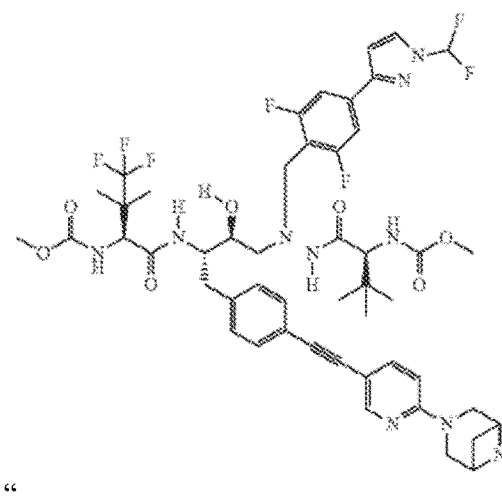

Column 194, Example 12, Lines 25-45, delete " " and

CERTIFICATE OF CORRECTION (continued)
U.S. Pat. No. 11,078,208 B1

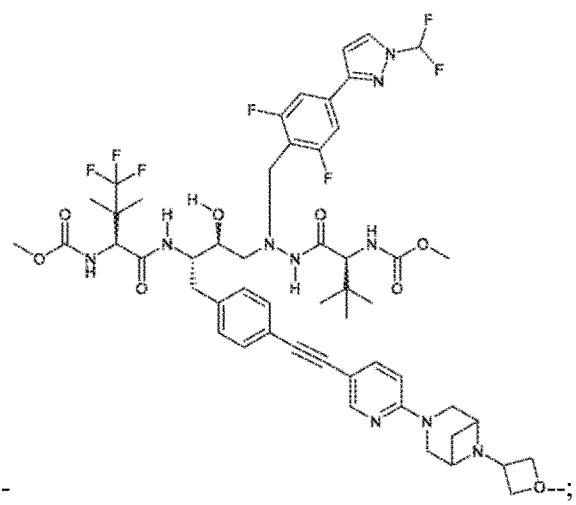

insert --

Column 195, Example 13, Lines 1-20, delete " 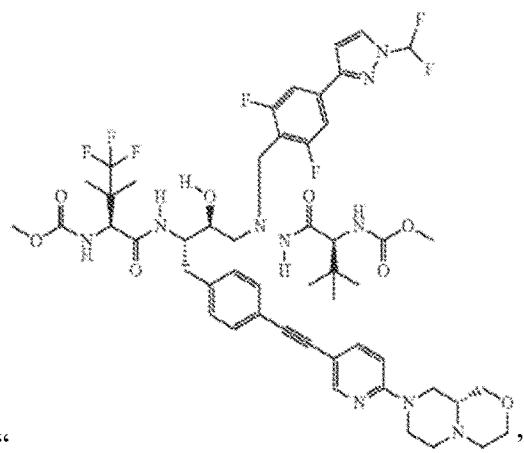 " and insert

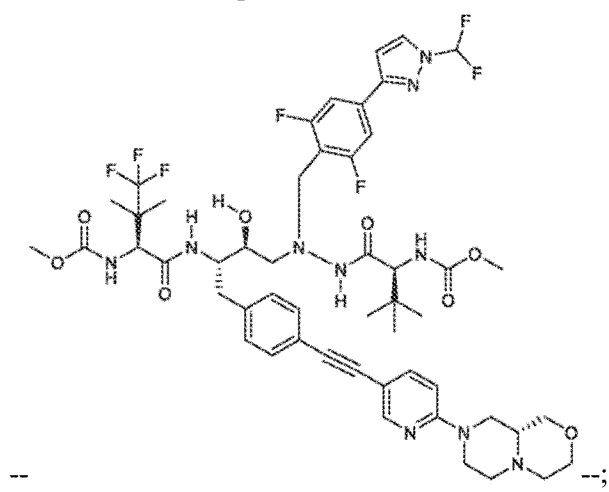

-- --;

CERTIFICATE OF CORRECTION (continued)
U.S. Pat. No. 11,078,208 B1

Column 195, Example 14, Lines 47-66, delete " 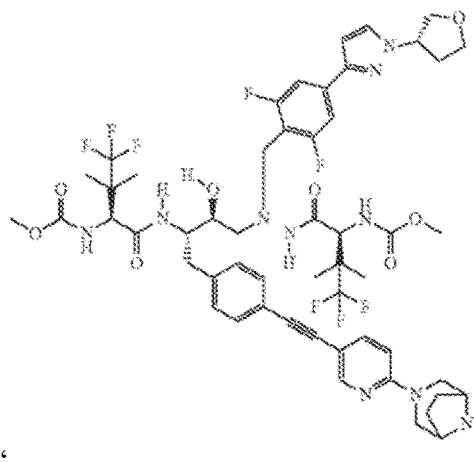 " and insert -- 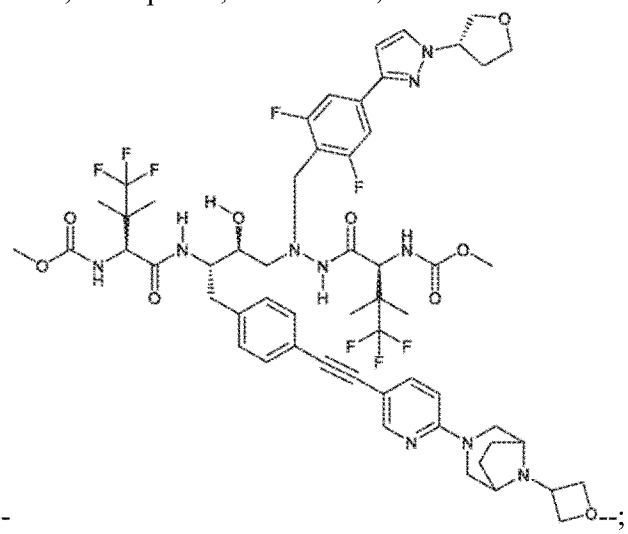 --;

Column 196, Example 15, Lines 25-45, delete " 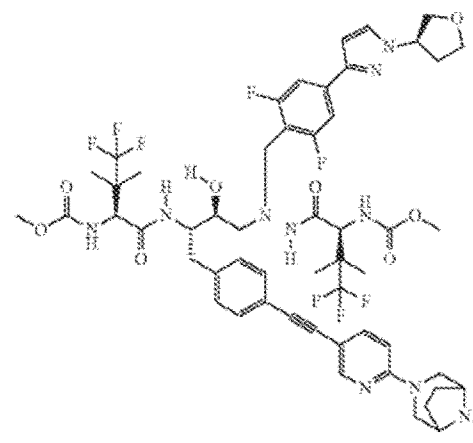 " and insert -- 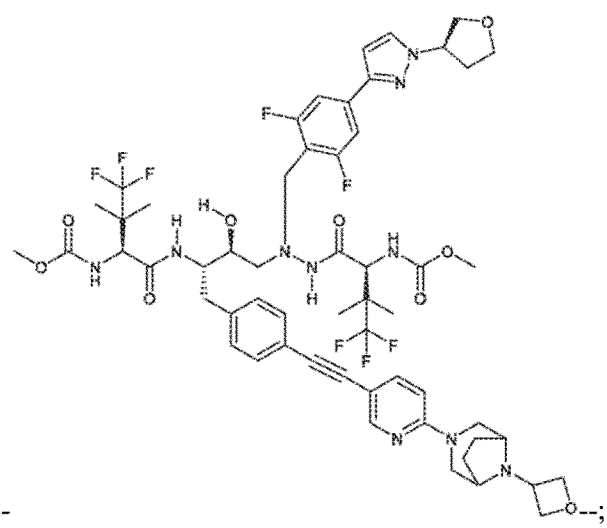 ;
Column 197, Example 16, Lines 1-22, delete " 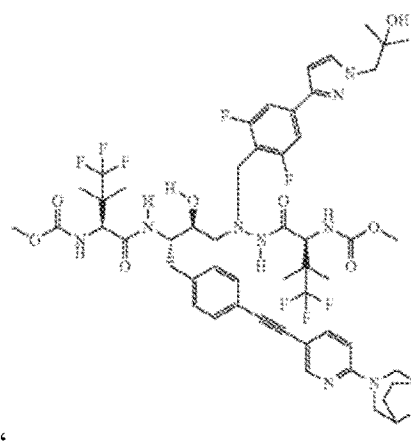 " and insert
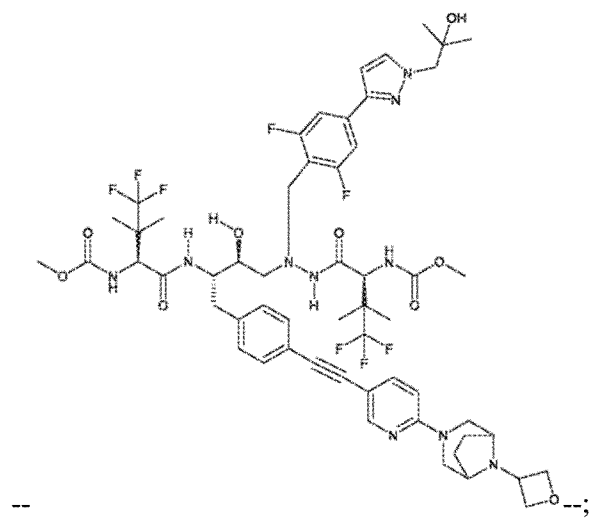 --

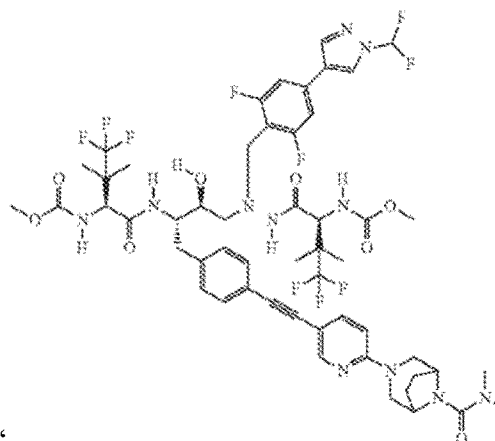
Column 197, Example 17, Lines 47-66, delete " 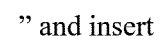 " and insert
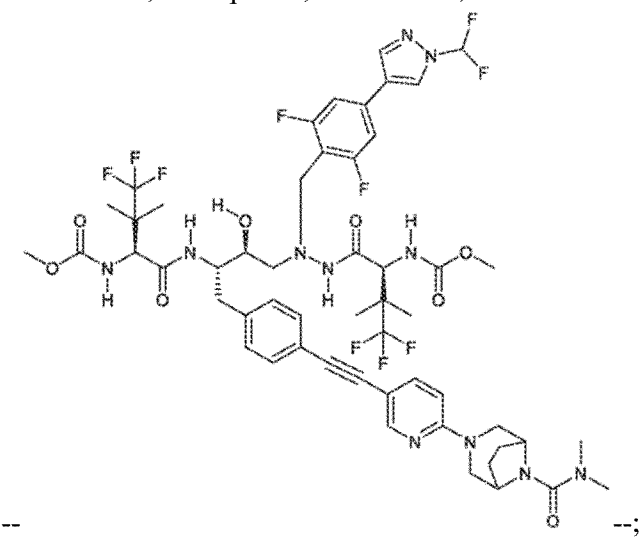
-- --;
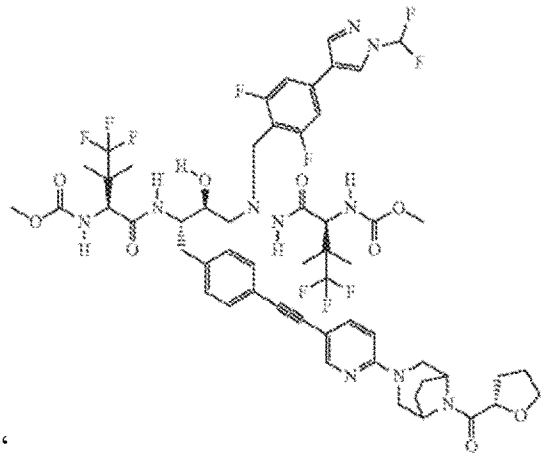
Column 198, Example 18, Lines 25-45, delete "  " and insert -- 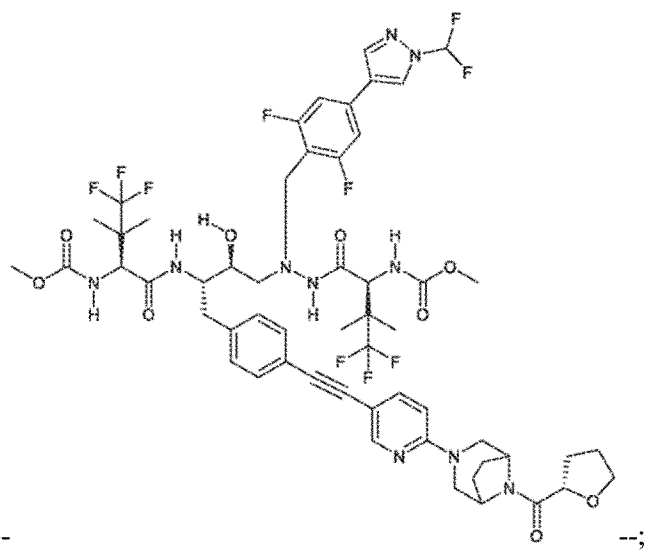 --;
Column 199, Example 19, Lines 1-20, delete " 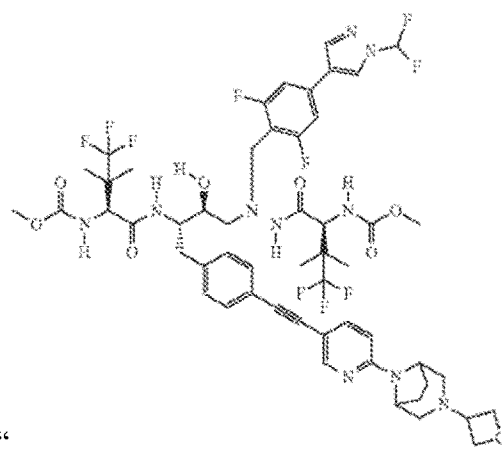 " and insert
-- 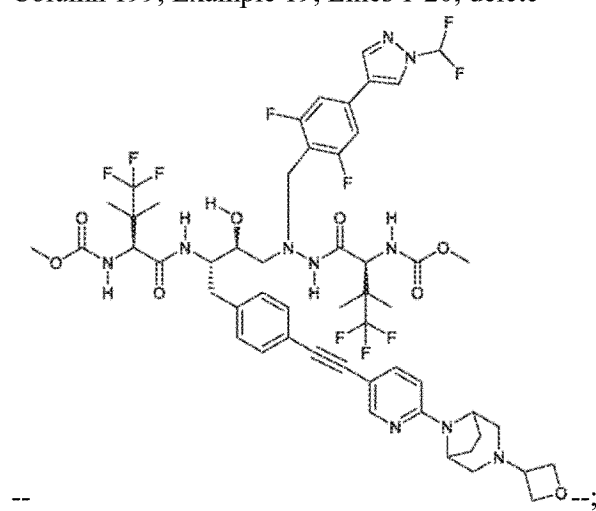 --;

Column 199, Example 20, Lines 47-66, delete " 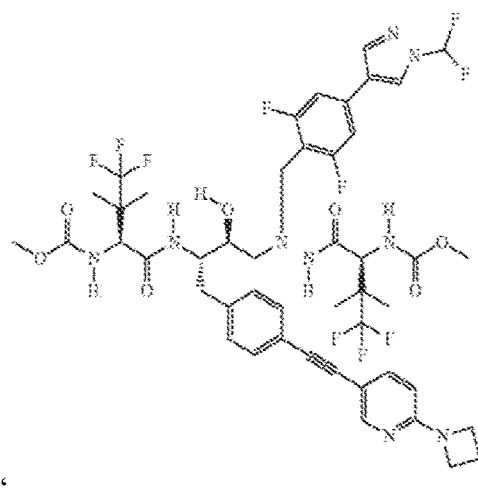 " and
insert -- 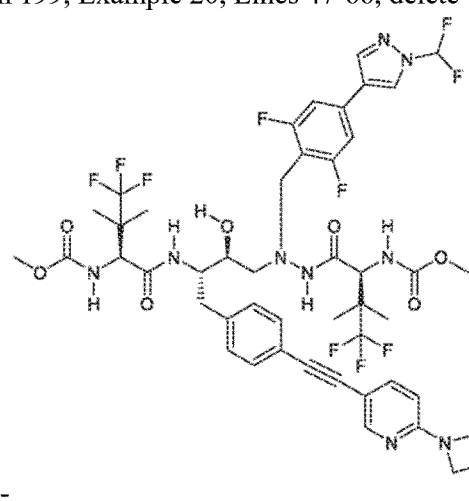 --;
Column 200, Example 21, Lines 25-45, delete " 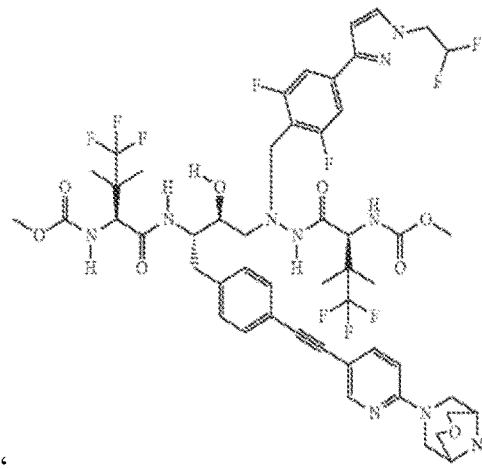 " and

CERTIFICATE OF CORRECTION (continued)
U.S. Pat. No. 11,078,208 B1 insert -- 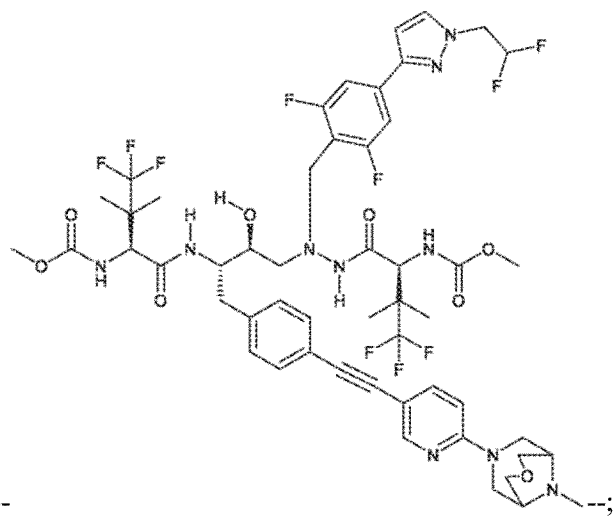 --;

Column 204, Example 26, Lines 1-23, delete " 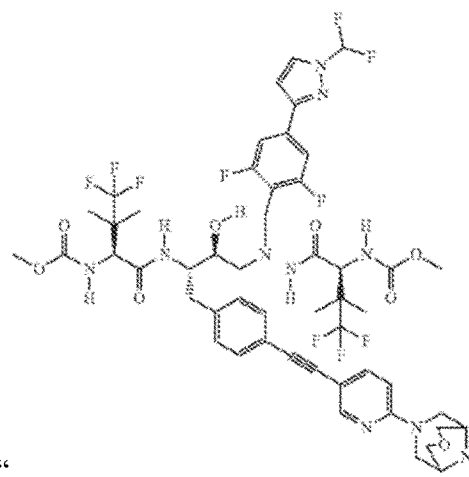 " and insert

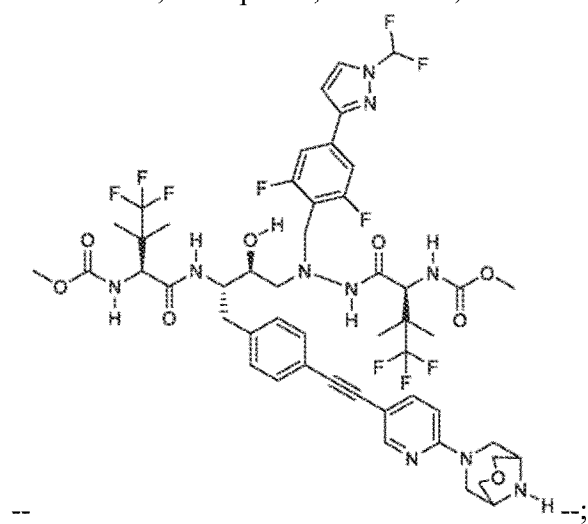 --;

Column 204, Example 27, Lines 45-65, delete " 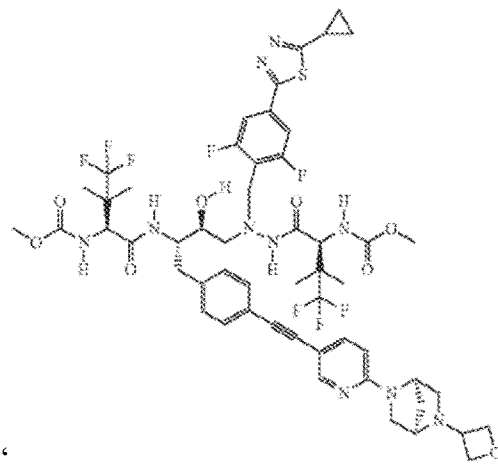 " and insert
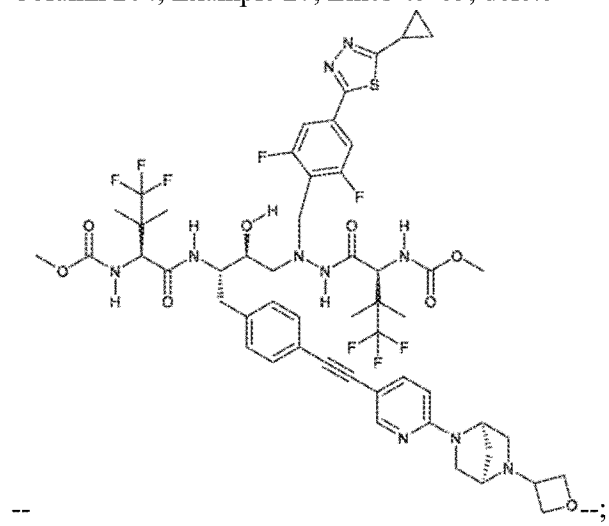
--;
Column 205, Example 28, Lines 25-42, delete " 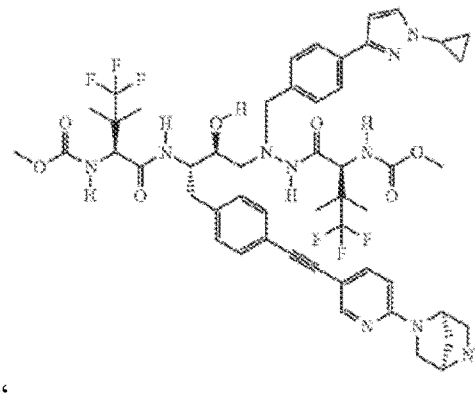 " and insert

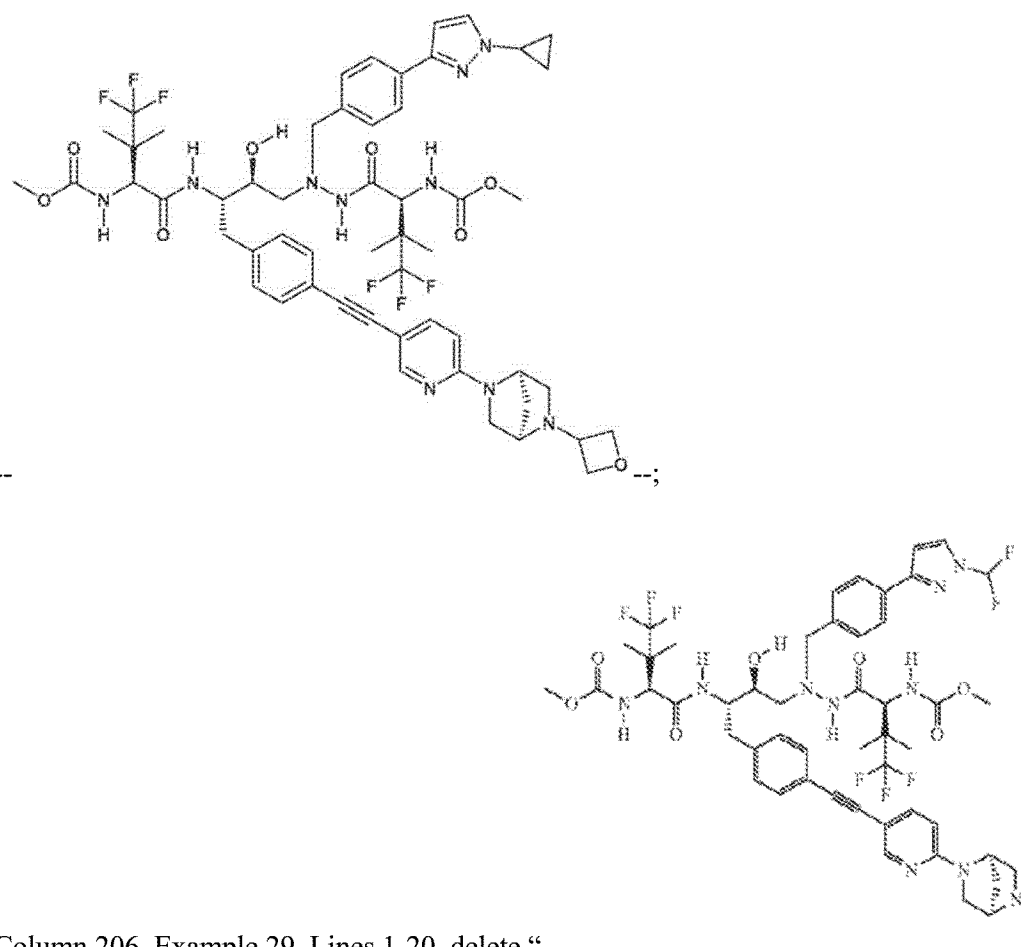
--;
Column 206, Example 29, Lines 1-20, delete " 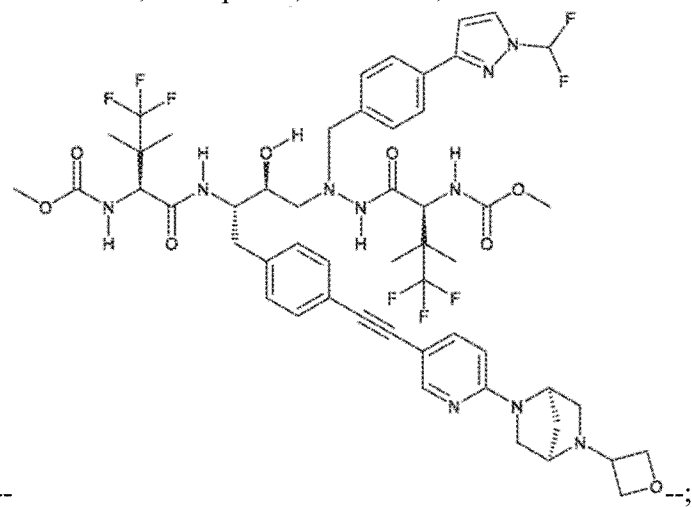 " and insert
--;

Column 206, Example 30, Lines 50-66, delete " 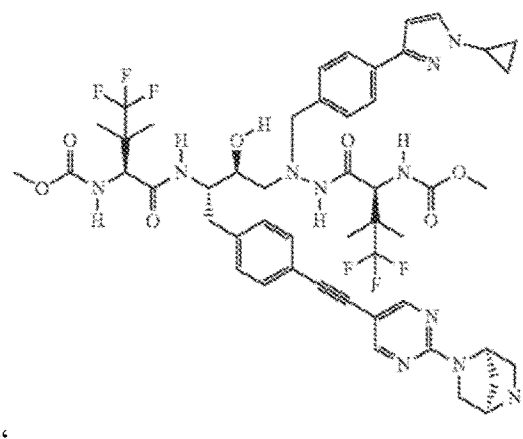 " and
insert -- 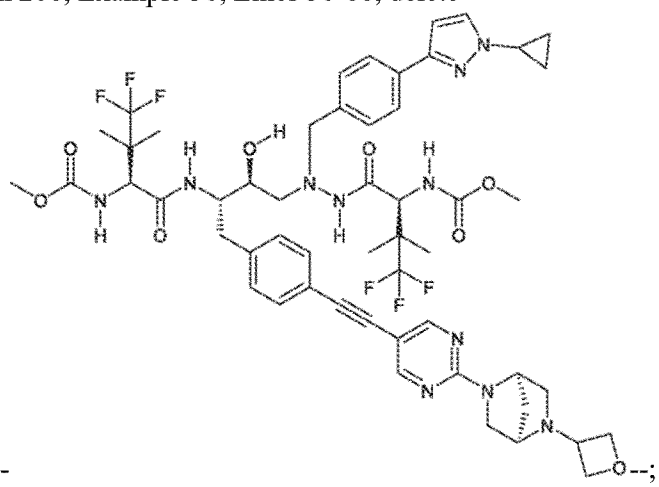 --;
Column 208, Example 33, Lines 50-66, delete " 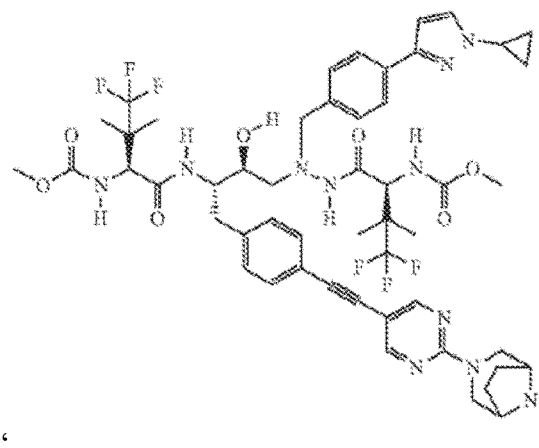 " and

CERTIFICATE OF CORRECTION (continued)
U.S. Pat. No. 11,078,208 B1

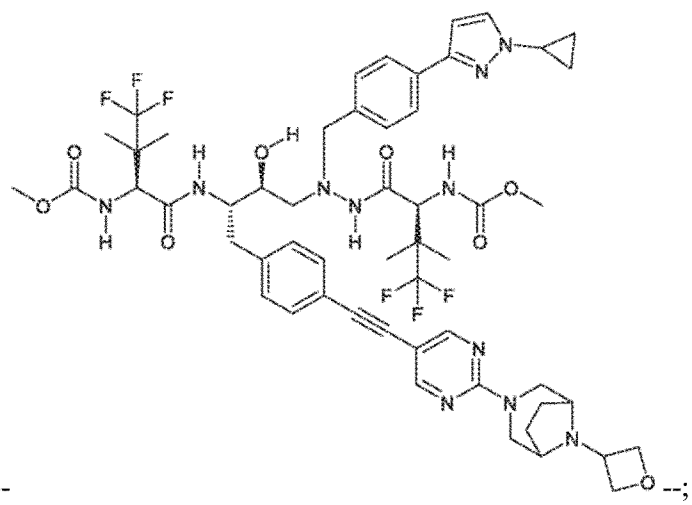

insert --

Column 209, Example 34, Lines 25-43, delete " 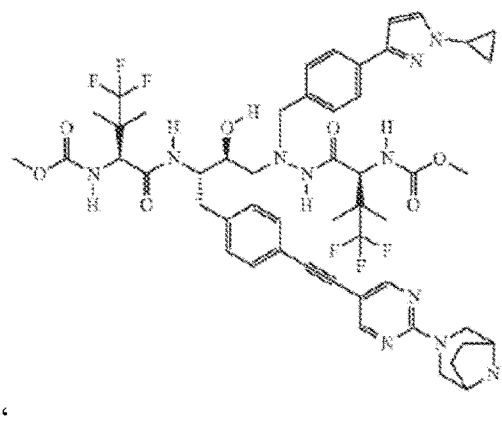 " and insert

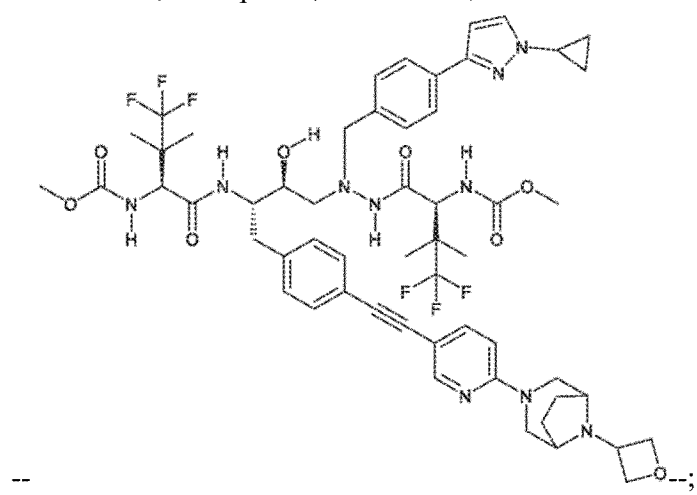

--

Column 212, Example 38, Lines 13-36, delete " 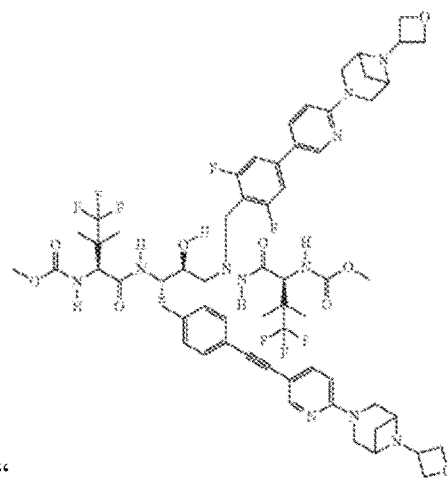 " and insert
 --;
Column 217, Example 46, Lines 47-66, delete " 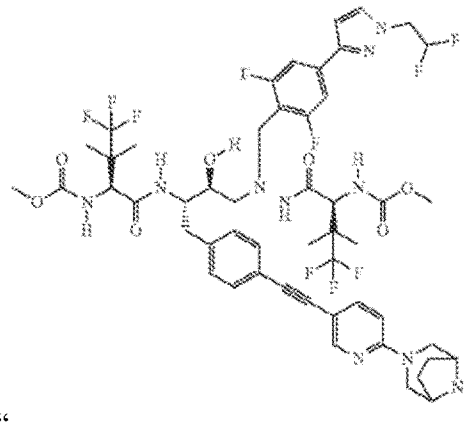 " and insert

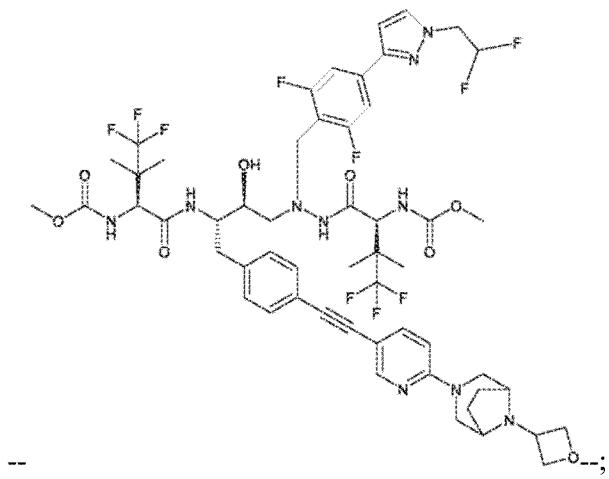
--
Column 226, Example 58, Lines 29-50, delete " 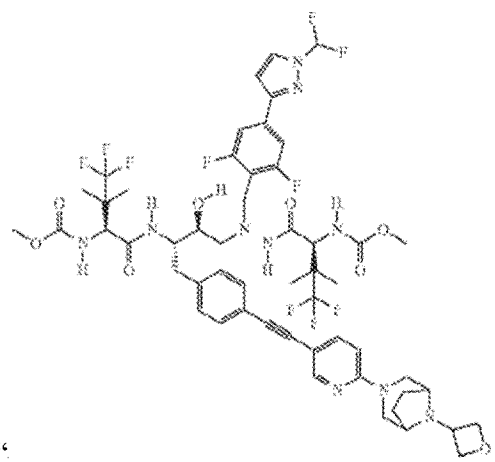 " and insert
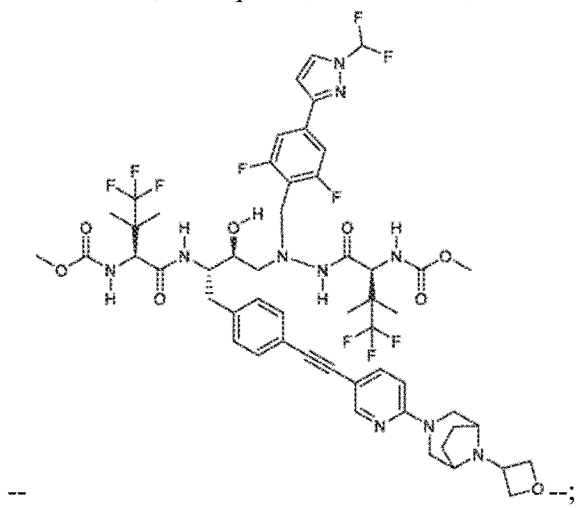
--

Column 244, Example 80, Lines 47-66, delete " 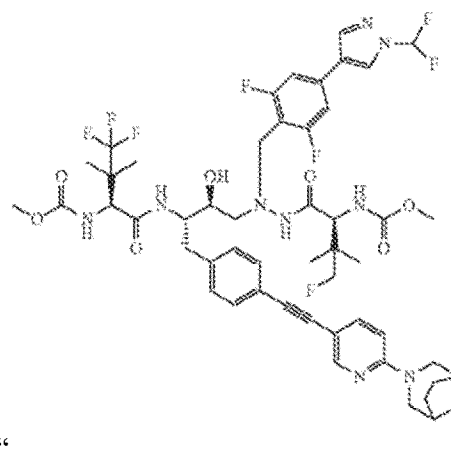 " and insert
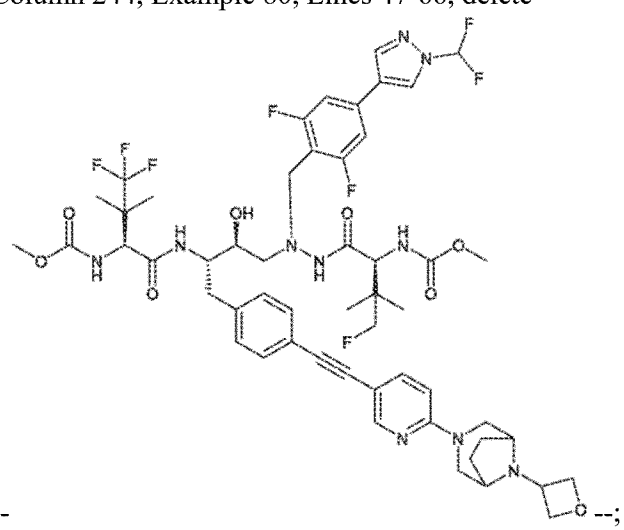
-- ;
Column 247, Example 83, Lines 1-20, delete " 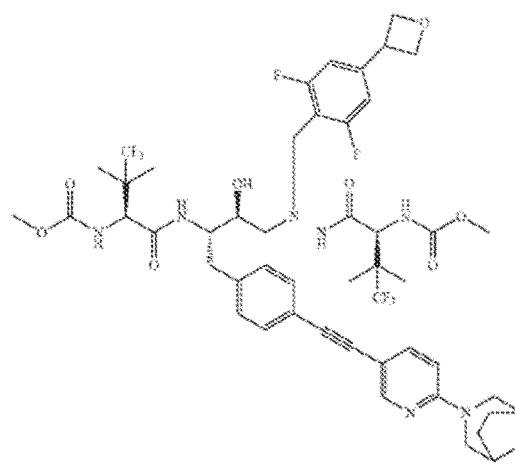 " and insert

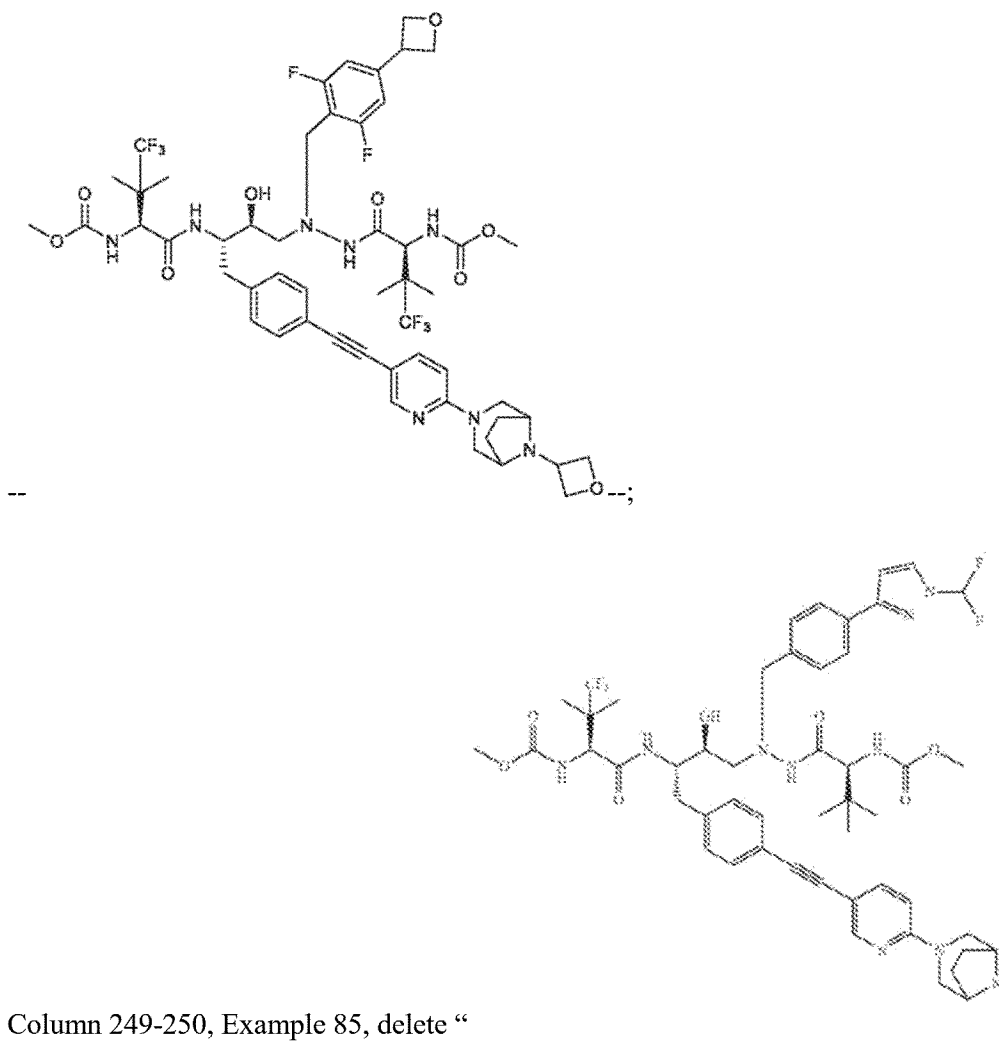
Column 249-250, Example 85, delete " 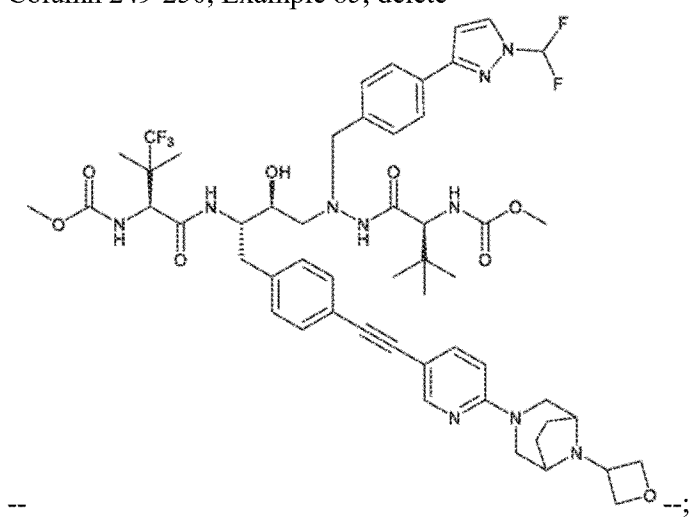 " and insert

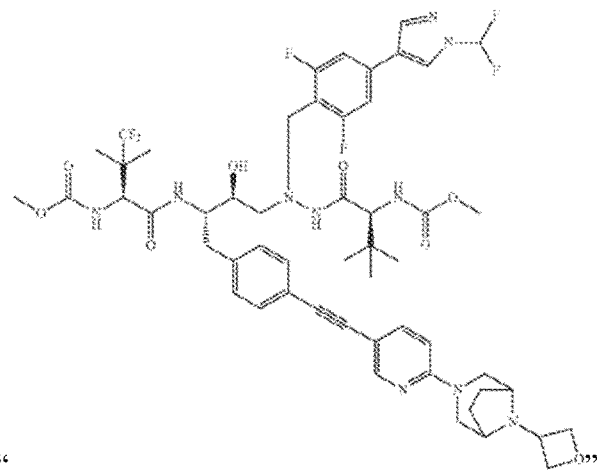
Column 251-252, Example 86, Lines 1-25, delete "
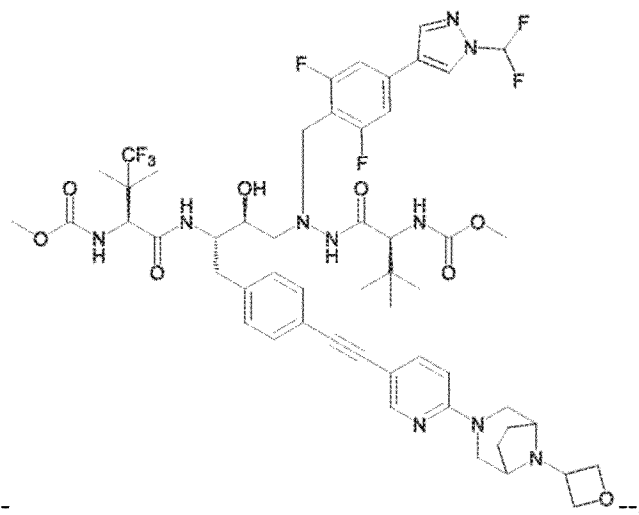
and insert --
--;
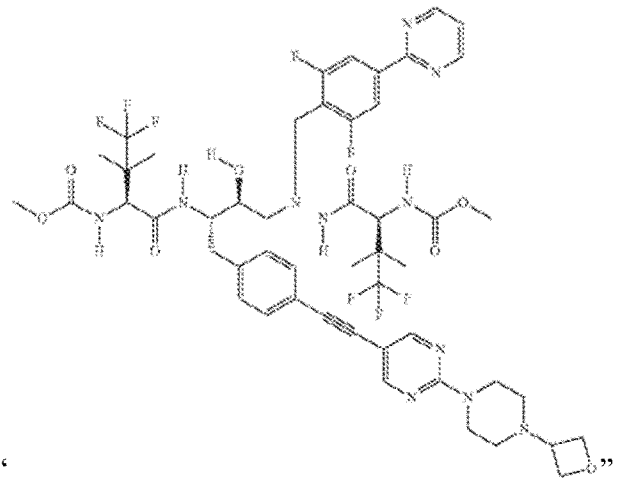
Column 253-254, Example 88, Lines 20-45, delete "

CERTIFICATE OF CORRECTION (continued)
U.S. Pat. No. 11,078,208 B1

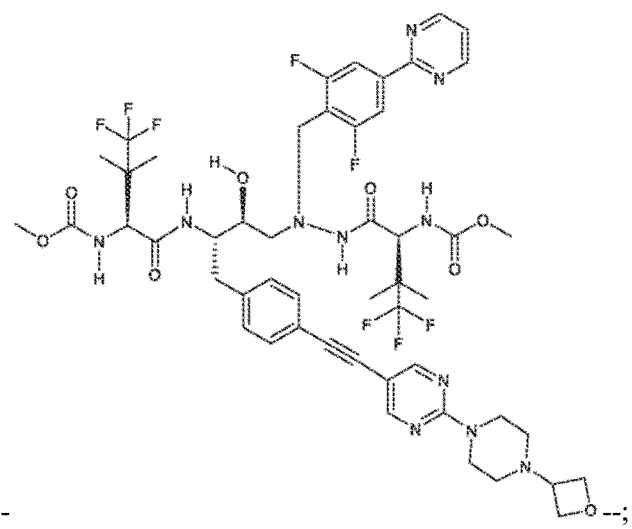

and insert --

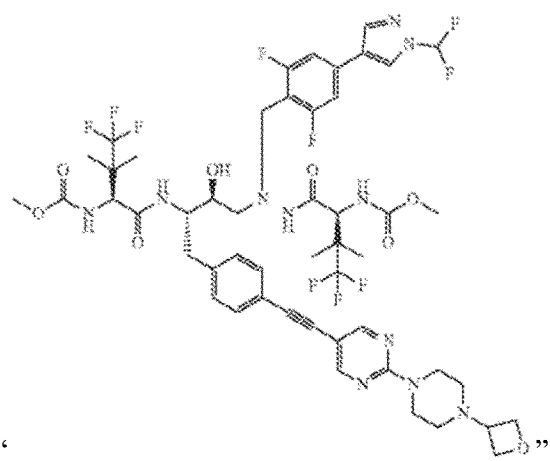

Column 275, Example 103, Lines 23-42, delete "

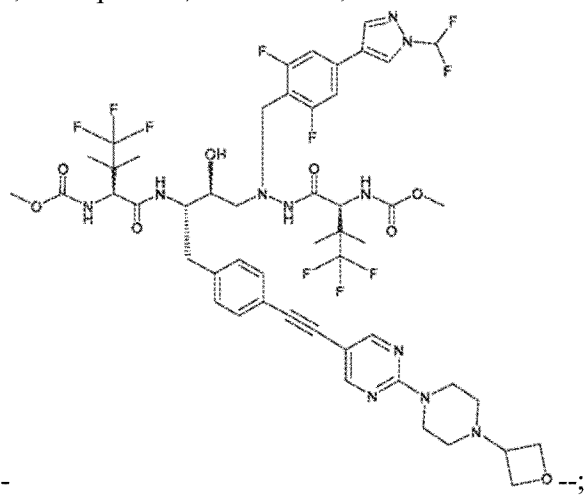

and insert --

Column 276, Example 104, Lines 1-22, delete " 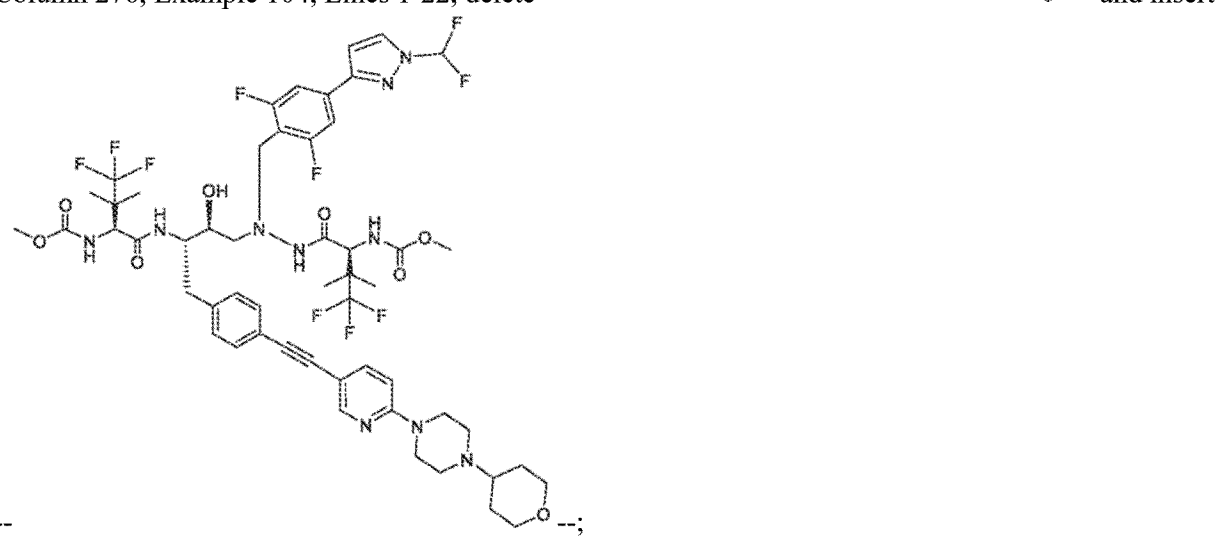 " and insert 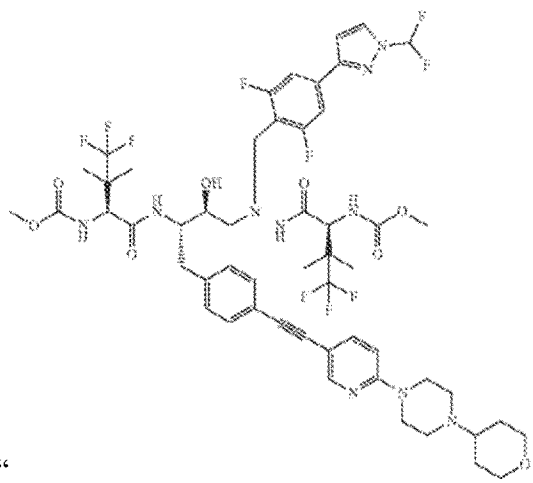 --;
Column 278, Example 108, Lines 49-66, delete " 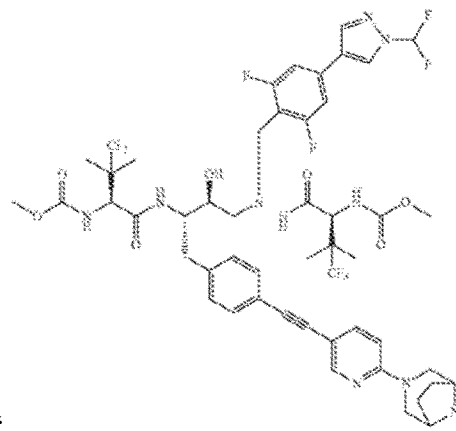 " and insert

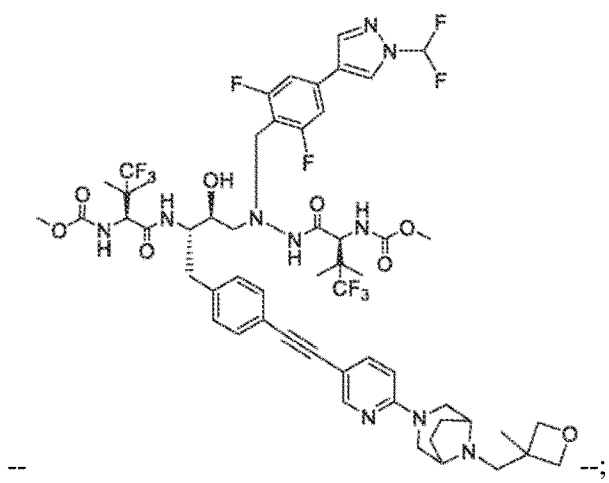
Column 279-280, Example 109, Lines 22-45, delete " 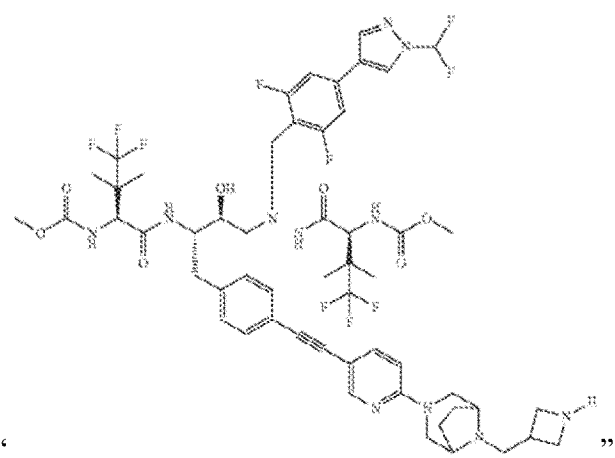 "
and insert -- 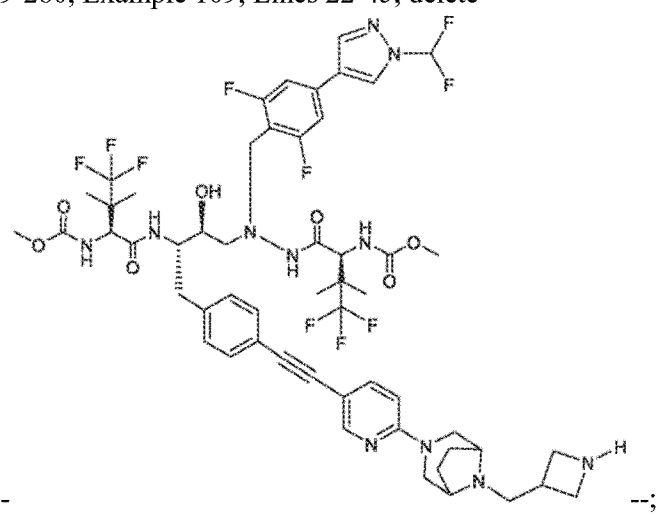 --;

Column 281-282, Example 110, Lines 1-25, delete " 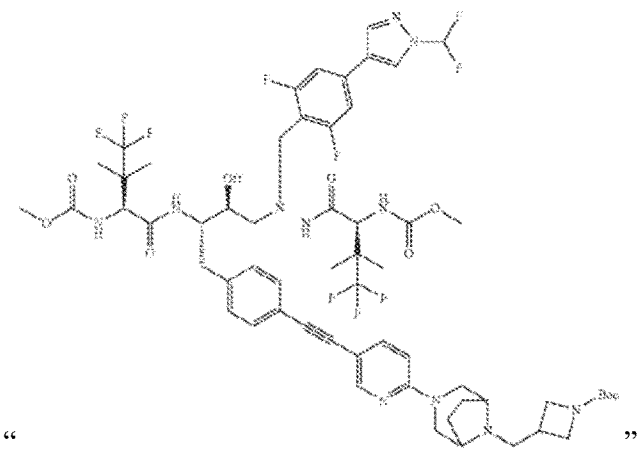 "
and insert -- 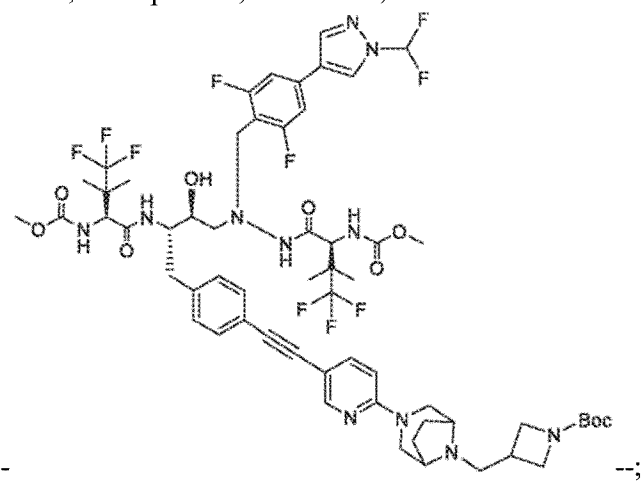 --;
Column 282, Example 112, Lines 47-66, delete " 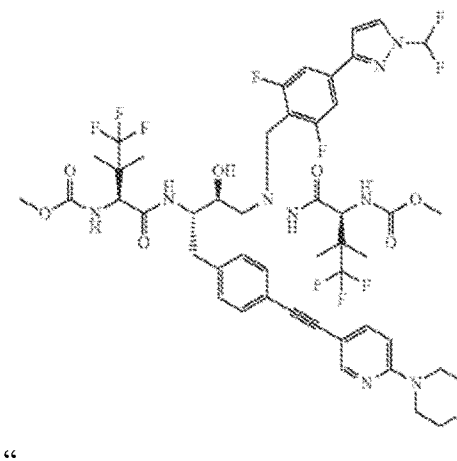 " and insert

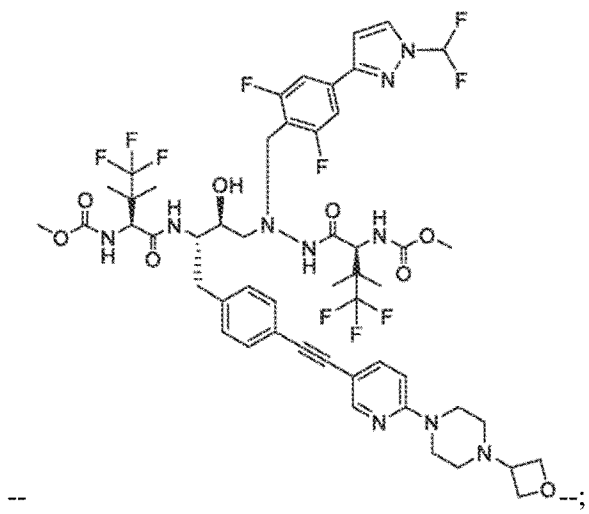
Column 284, Example 114, Lines 1-20, delete " 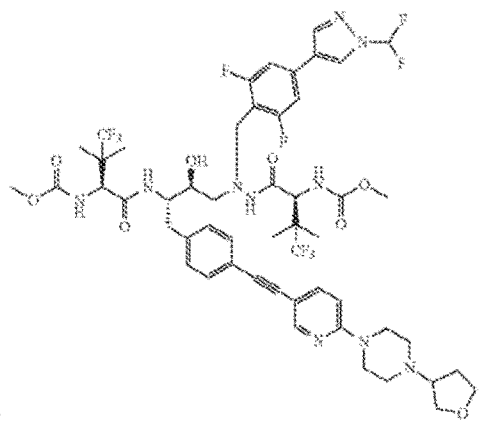 " and insert
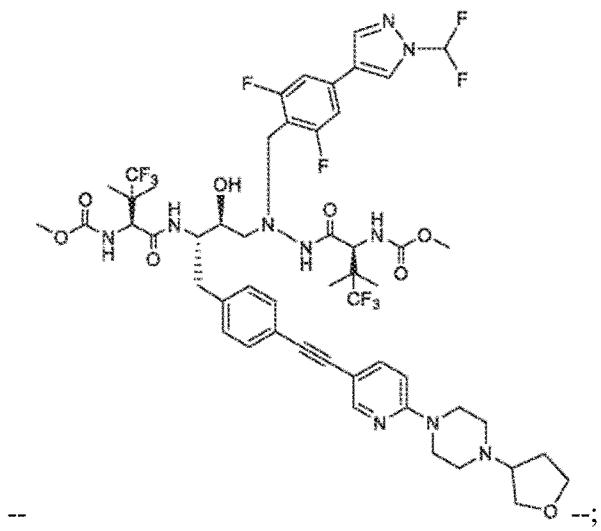

Column 284, Example 115, Lines 47-66, delete " 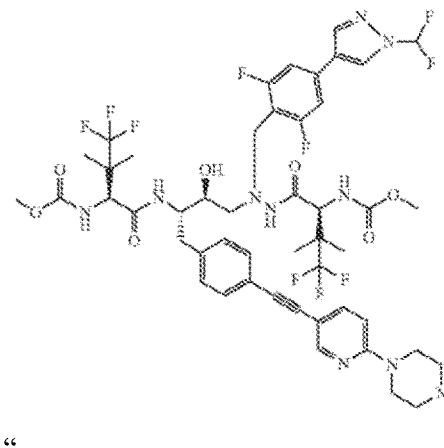" and insert
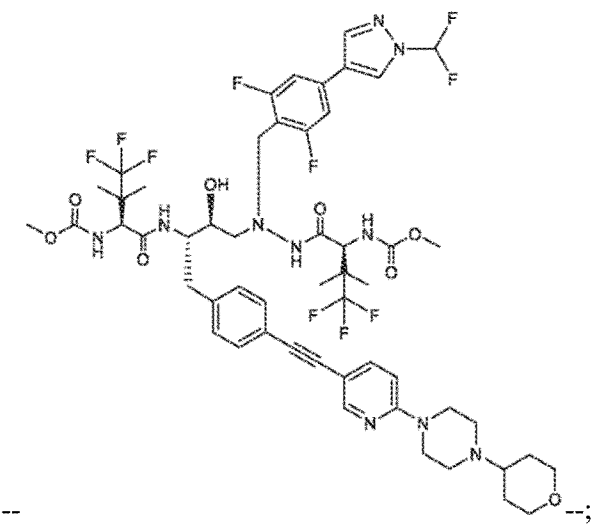
--;
Column 285, Example 116, Lines 25-45, delete " 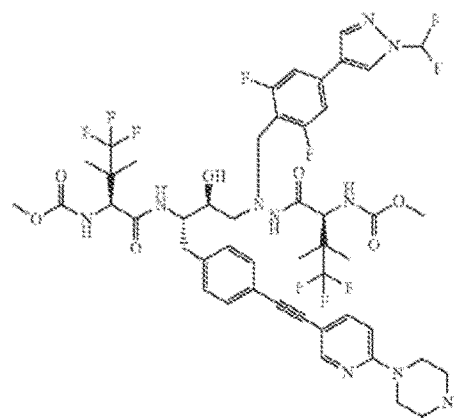" and insert

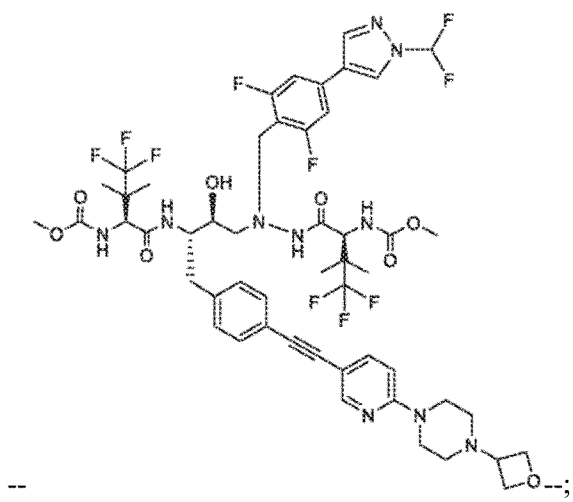
--;
Column 286, Example 117, Lines 1-21, delete " 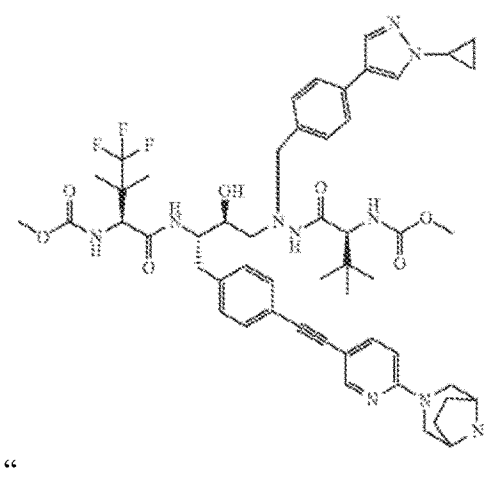 " and insert
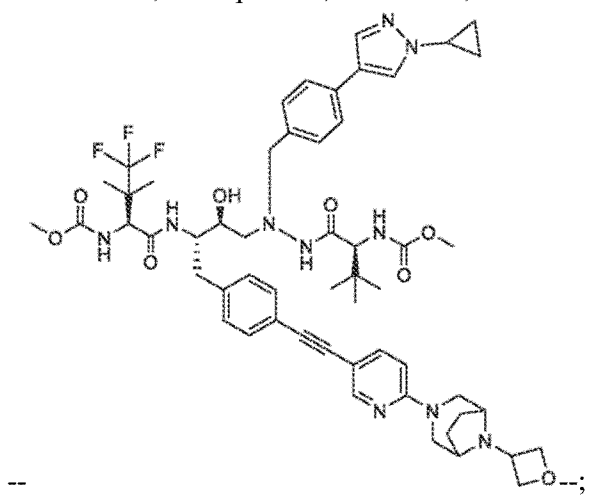
--;

Column 286, Example 118, Lines 47-66, delete " 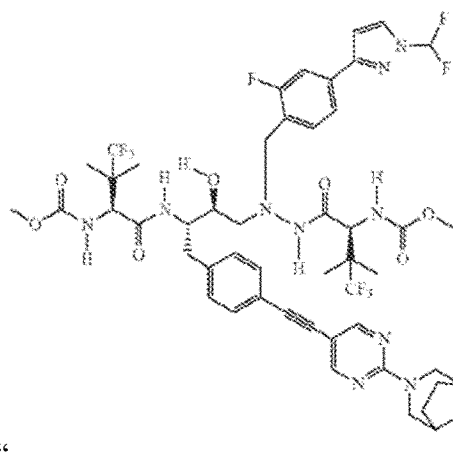" and insert
--;
Column 289, Example 122, Lines 48-66, delete " 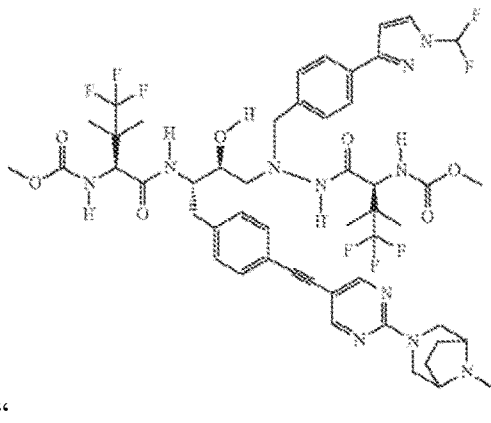" and insert

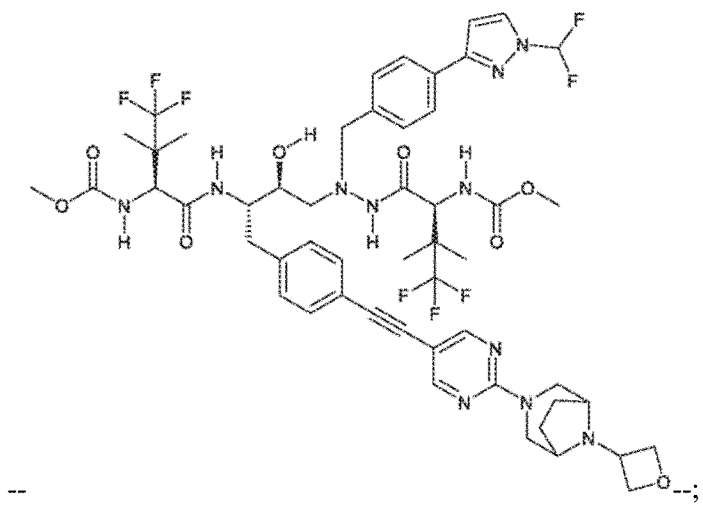
--
Column 290, Example 303-304, Compound 133a, delete " 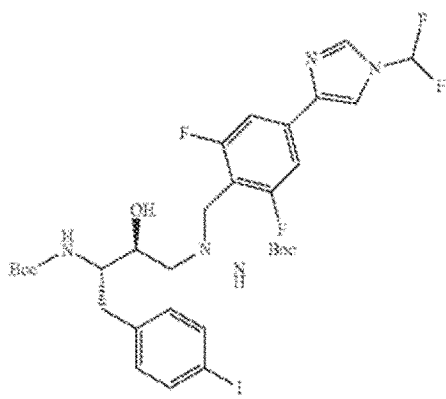 " and
insert -- 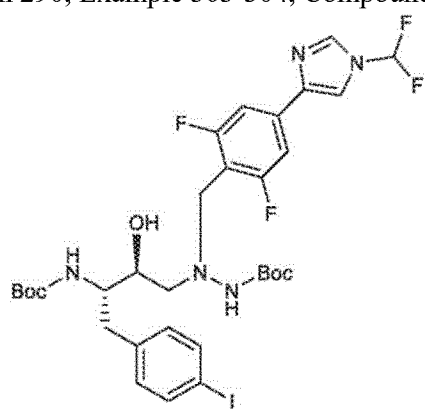 --;

Column 292, Example 126, Lines 25-45, delete " 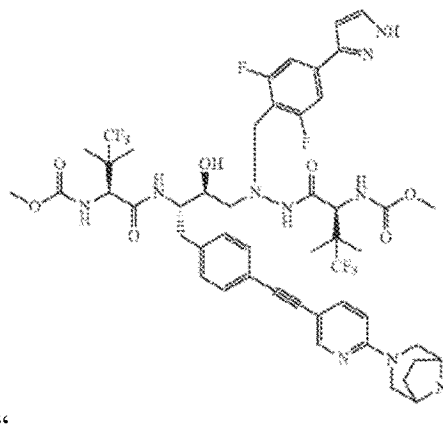" and insert
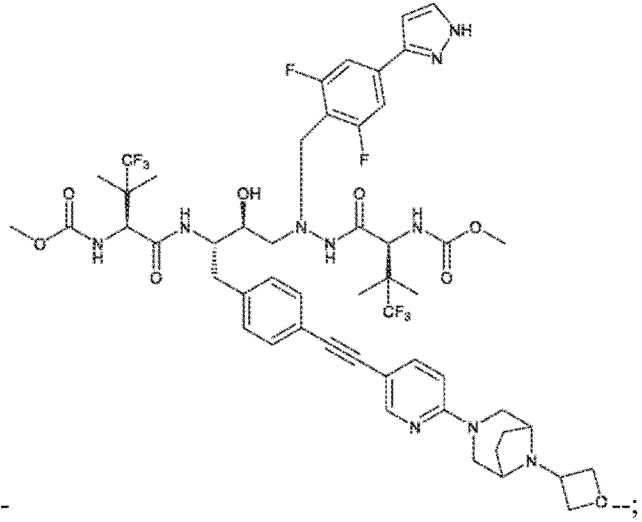
--;
Column 293, Example 128, Lines 47-66, delete " 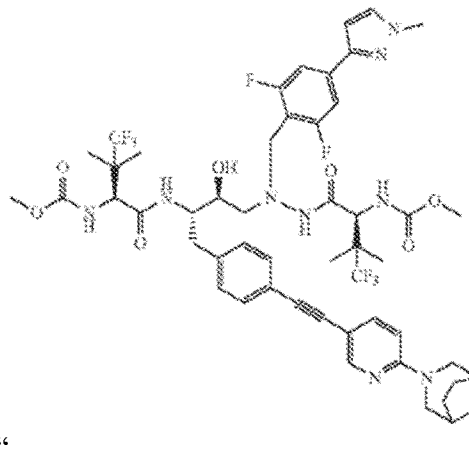" and insert Column 294, Example 129, Lines 25-45, delete " " and insert
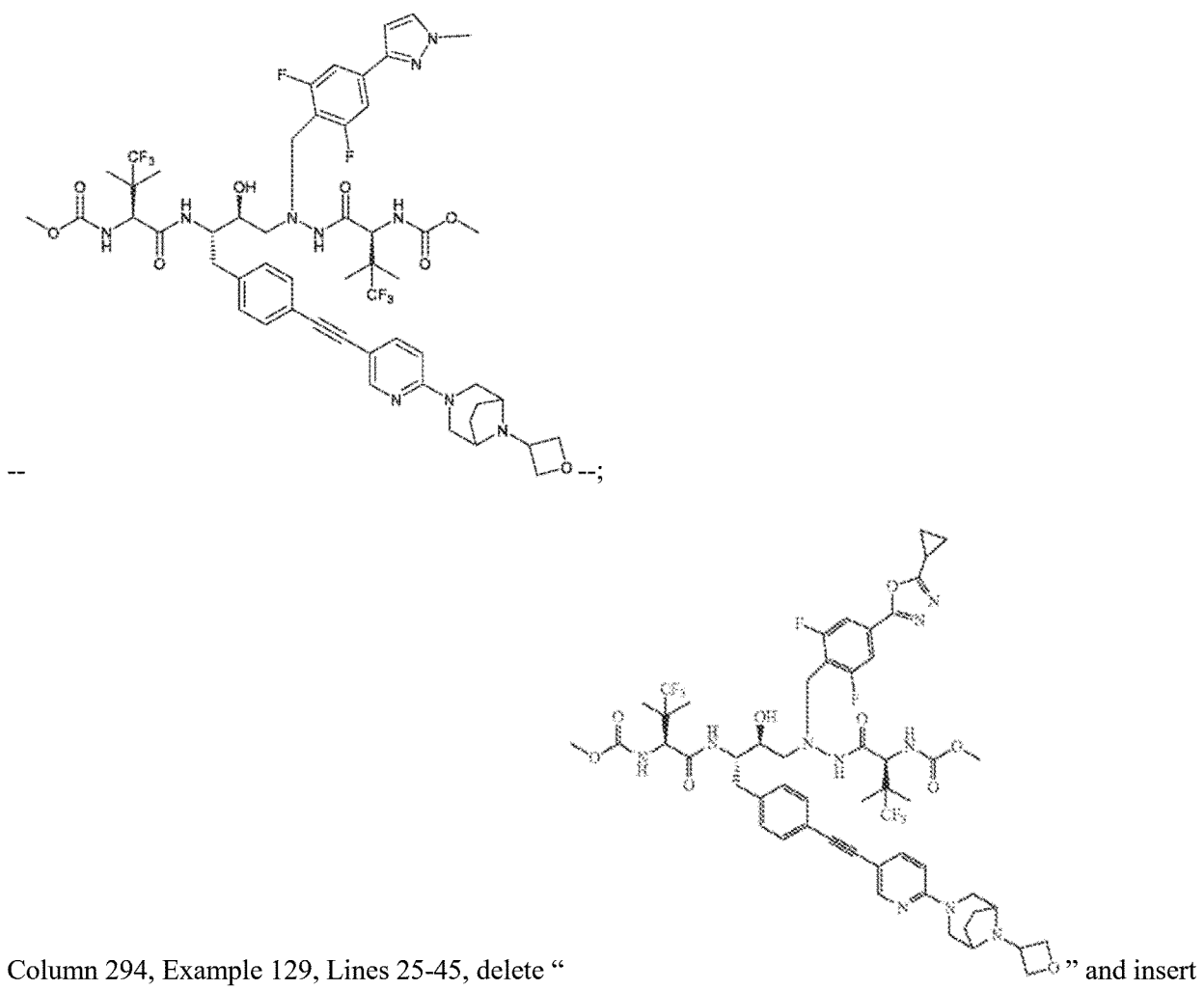

Column 295-296, Compound 131a, middle structure, delete " 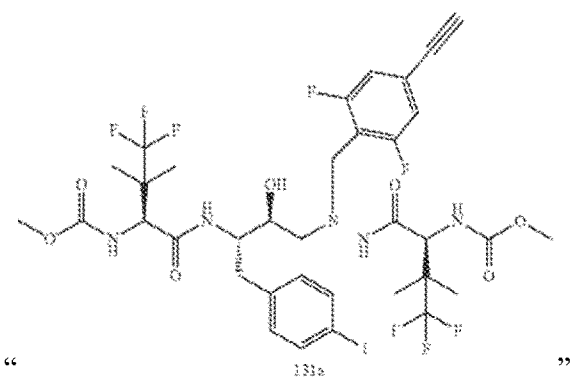 "
and insert -- 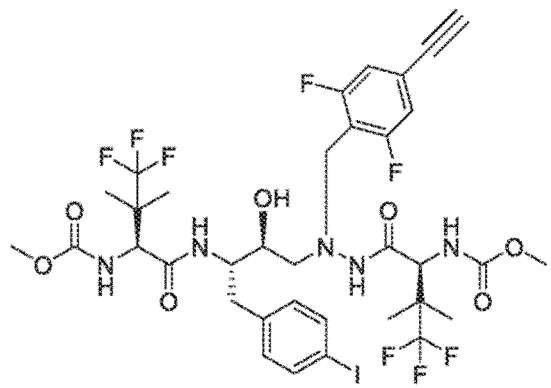 --;
Column 295-296, Compound 131b, bottom structure, delete " 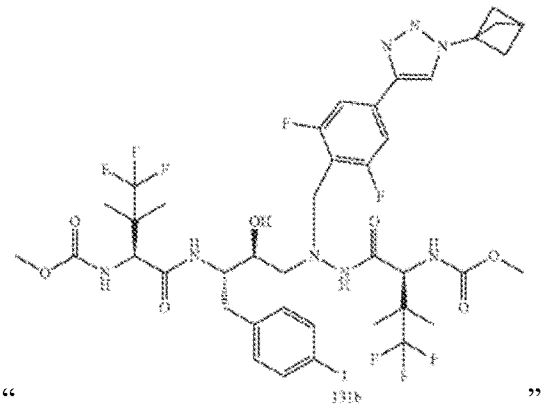 "

and insert -- 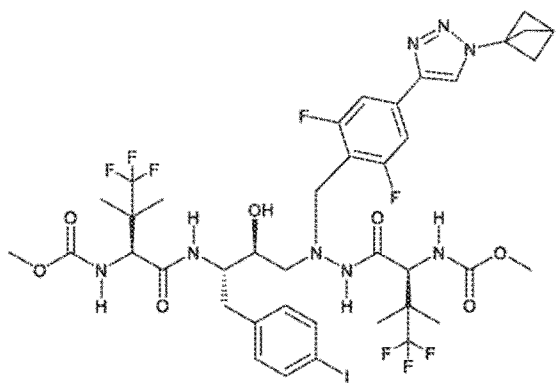 --;
Column 297-298, Compound 131, delete " 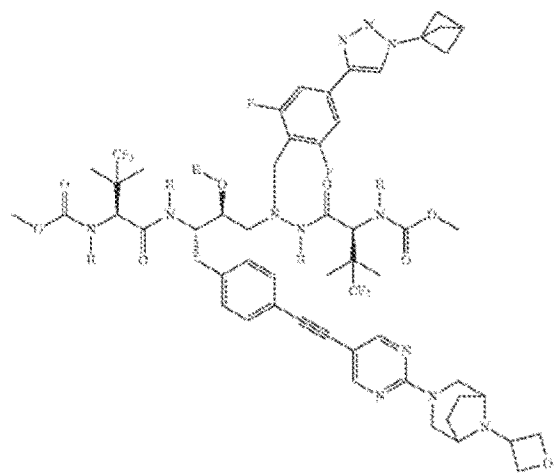 " and insert
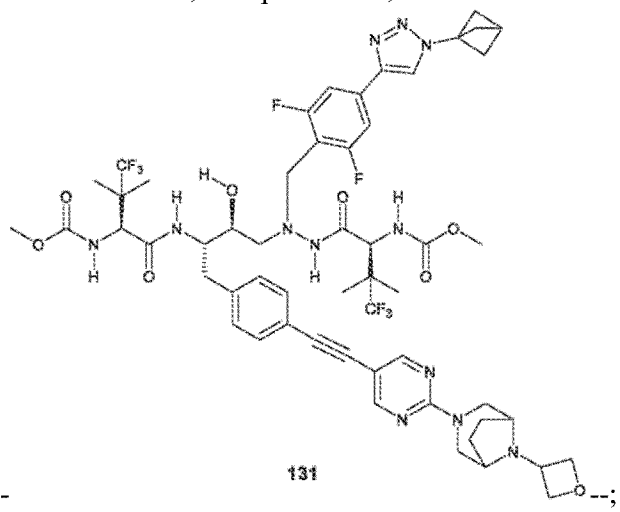 --;

Column 299, Compound I2a, delete " 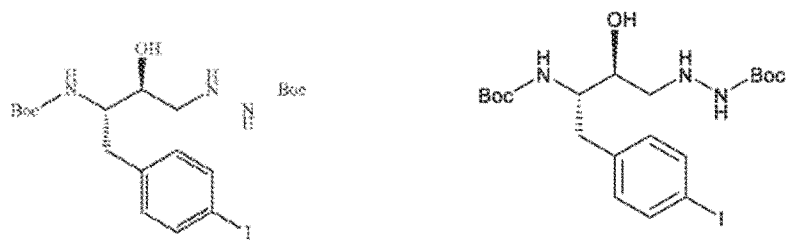 " and insert -- ... --;
Column 299-300, Compound 132a, delete " 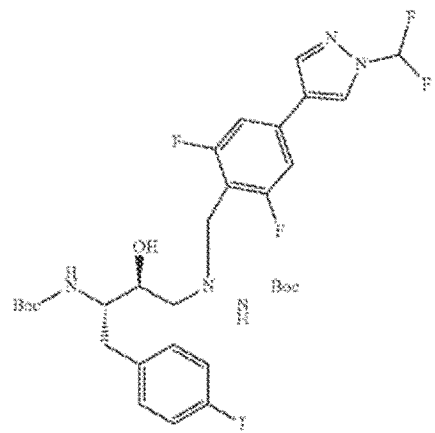 " and insert -- 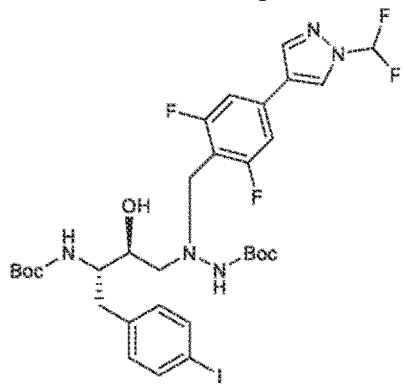 --;
Column 303, Example 133, Compound I2a, delete " 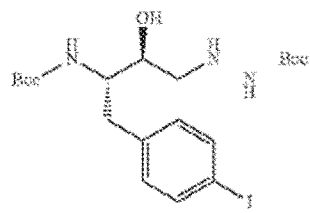 " and insert

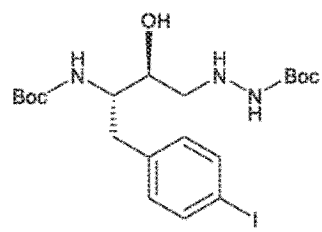
-- I2a --;
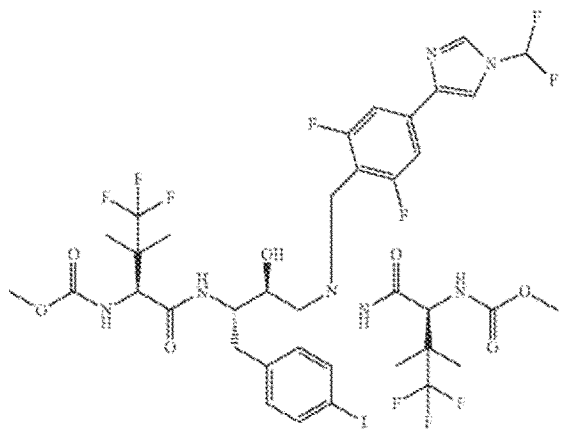
Column 303-304, Example 133, Compound 133b, delete "                                                                                                                                        "
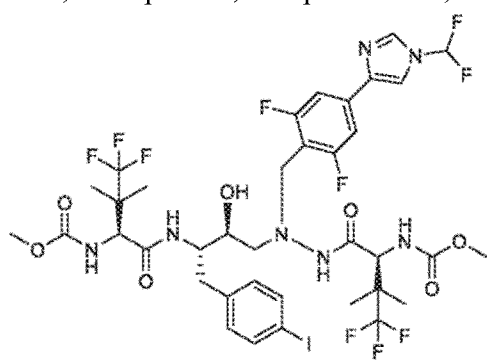
and insert -- 133b --;

Column 305-306, Example 133, delete " 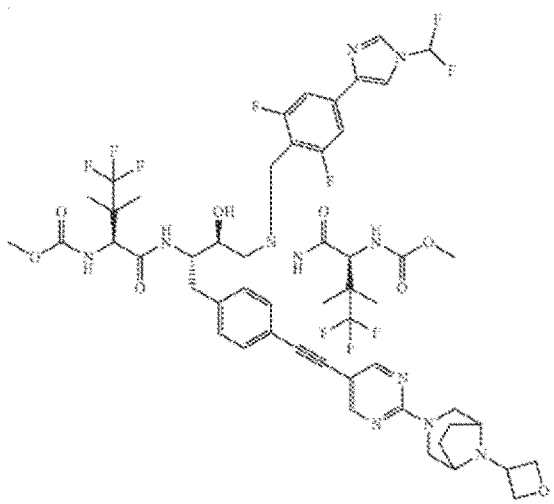 " and insert
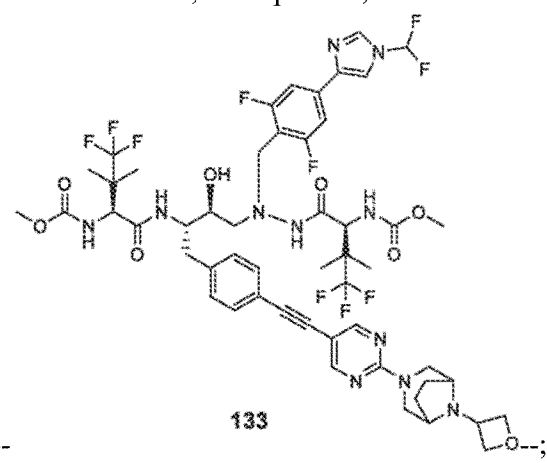
-- ;
Column 307, Example 134, Lines 1-20, delete " 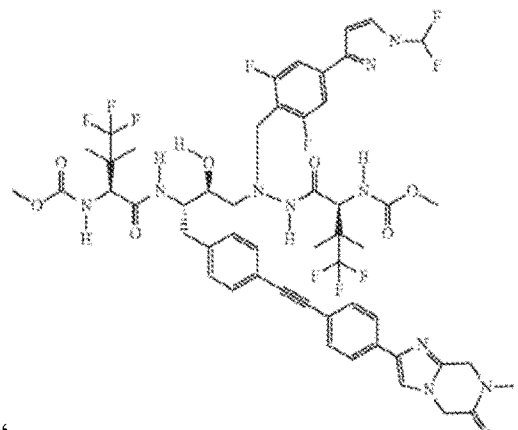 " and insert

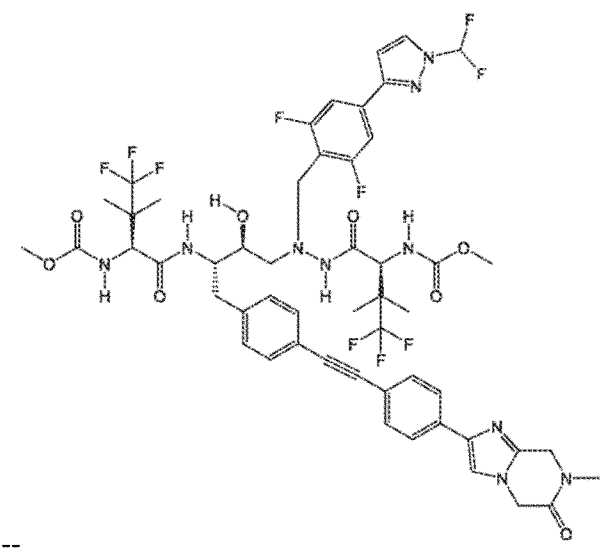
--;
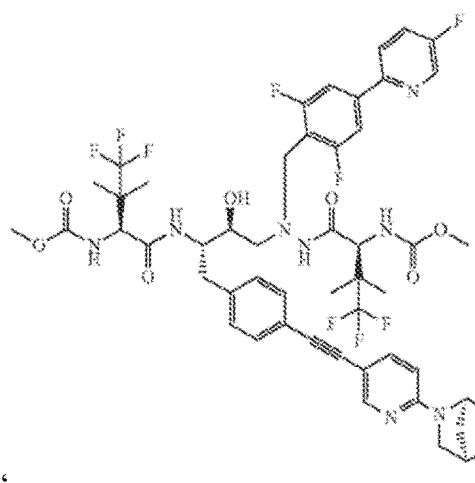
Column 307, Example 135, Lines 47-66, delete " " and insert
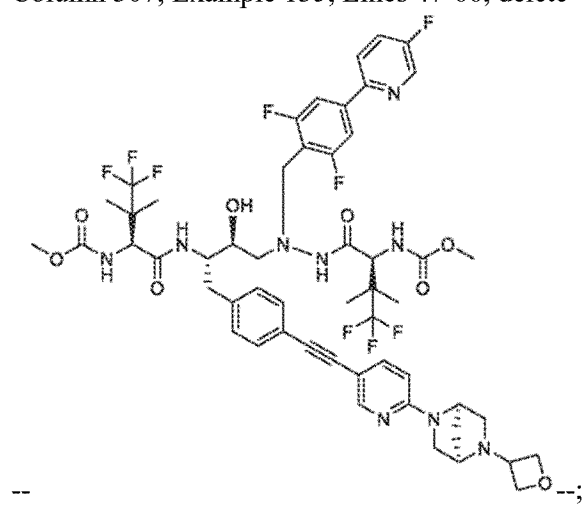
--;

Column 308, Example 136, Lines 25-45, delete " 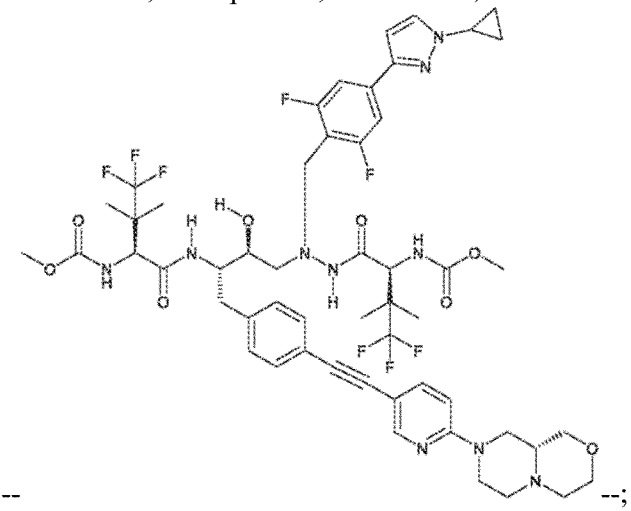 " and insert -- 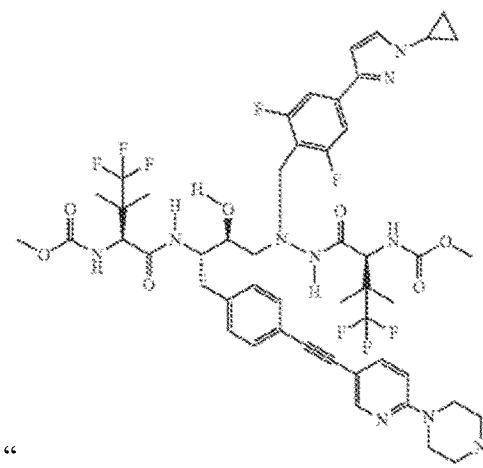 --;
Column 310, Example 139, Lines 47-66, delete " 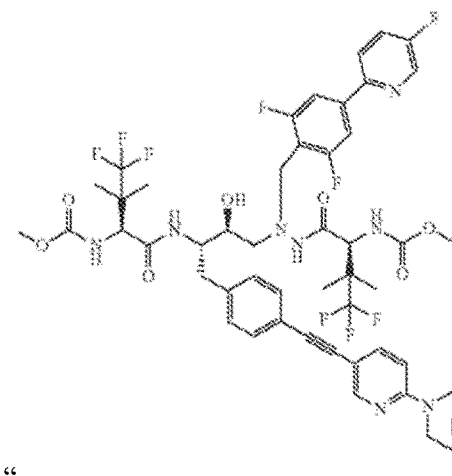 " and insert

CERTIFICATE OF CORRECTION (continued)
U.S. Pat. No. 11,078,208 B1

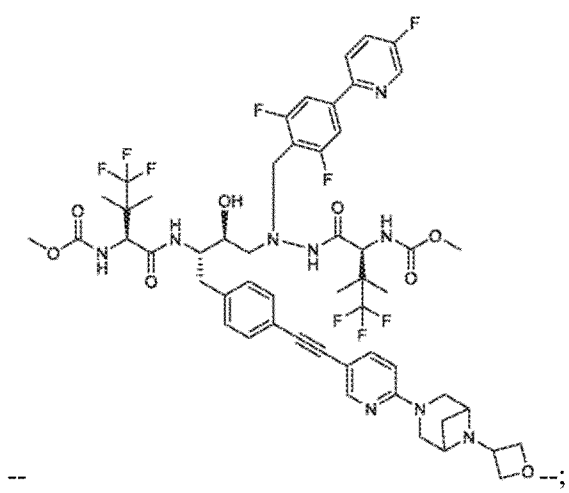

-- ;

Column 311-312, Example 140, delete " 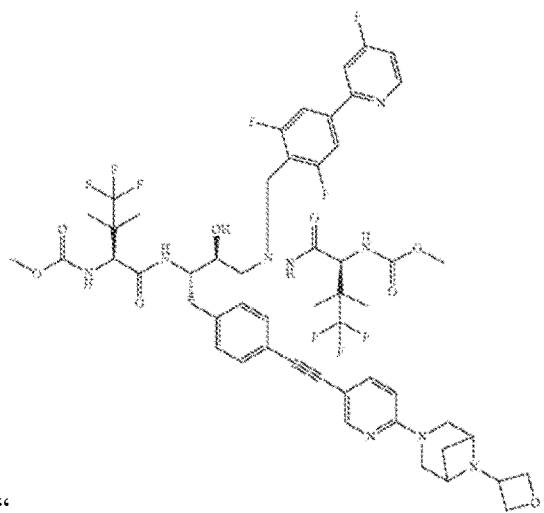 " and insert

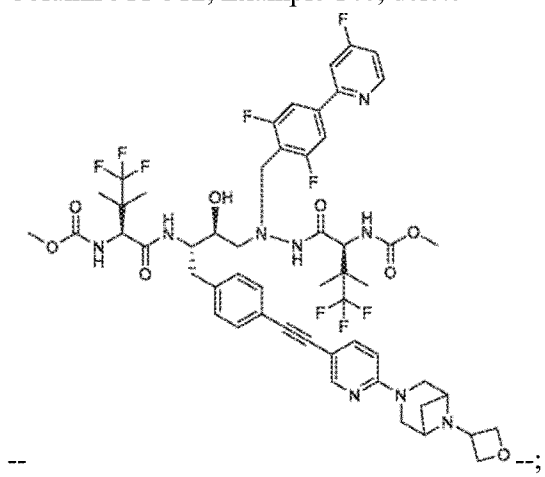

-- ;

Column 317-318, Example 143, delete " 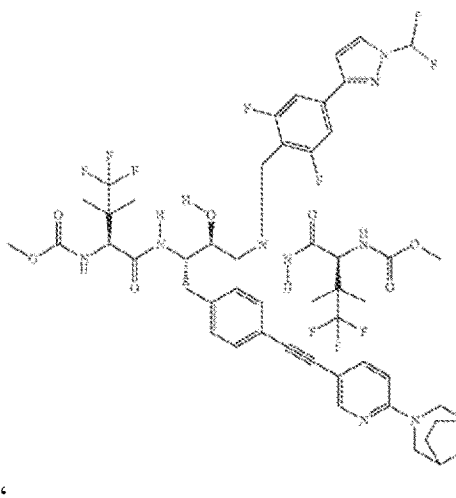 " and insert
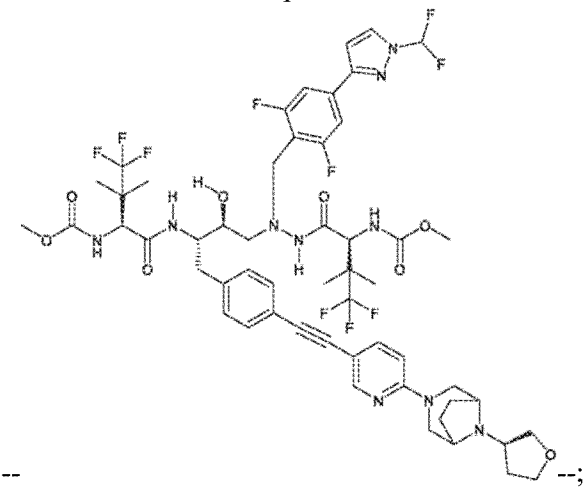 --;
Column 319-320, Example 144, delete " 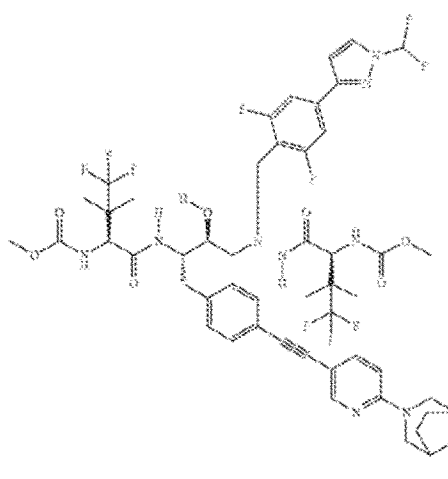 " and insert

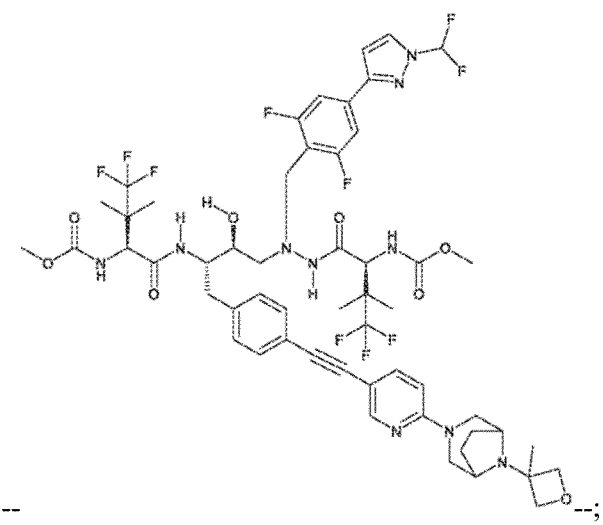
--;
Column 341, Example 155, Lines 25-45, delete " 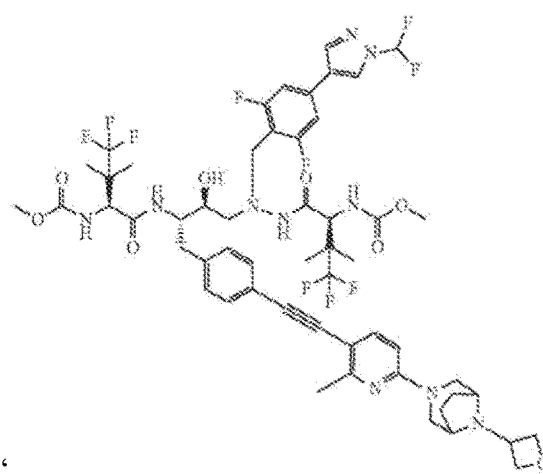 " and insert
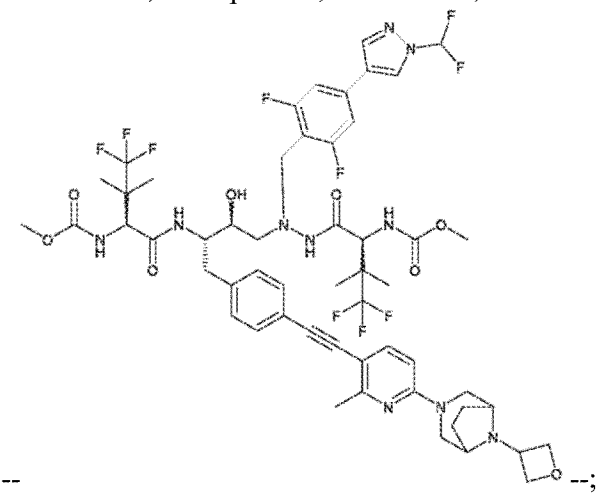
--;

Column 342, Example 156, Lines 1-20, delete " 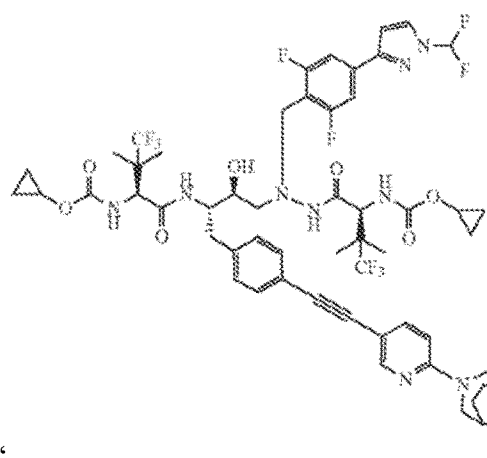 " and
insert -- 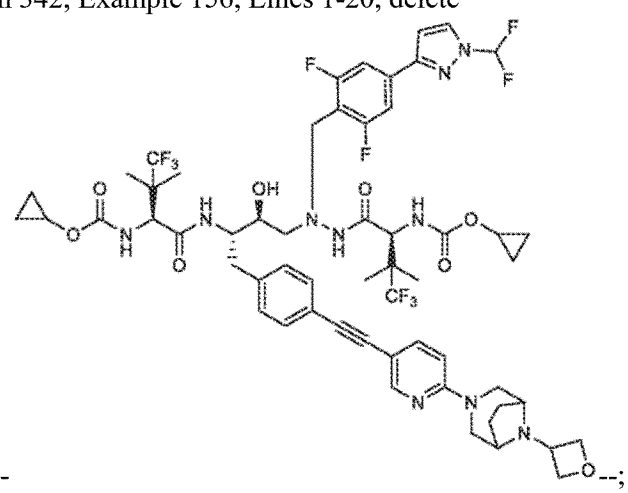 --;
Column 342, Example 157, Lines 50-65, delete " 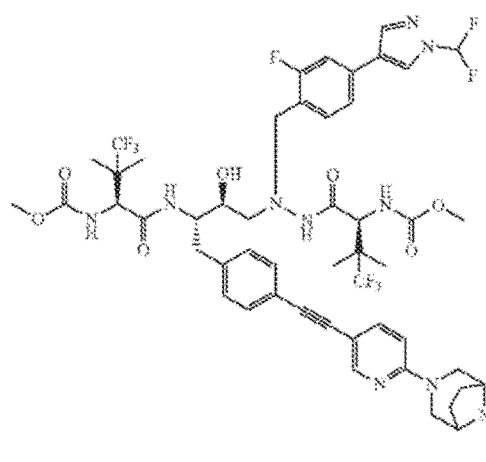 " and

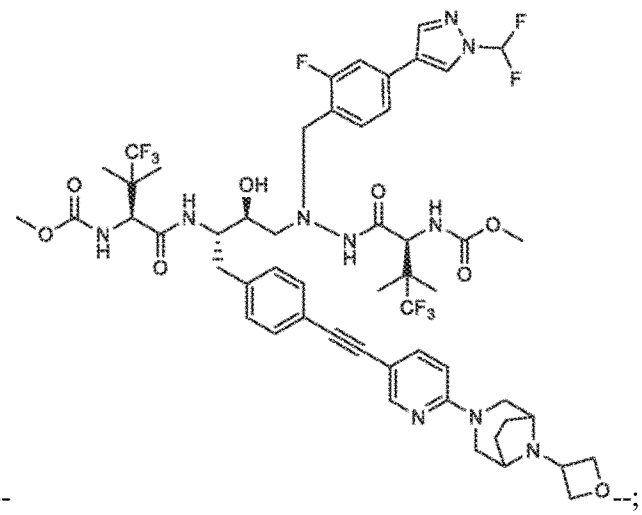
insert --
Column 343, Example 158, Lines 50-65, delete " 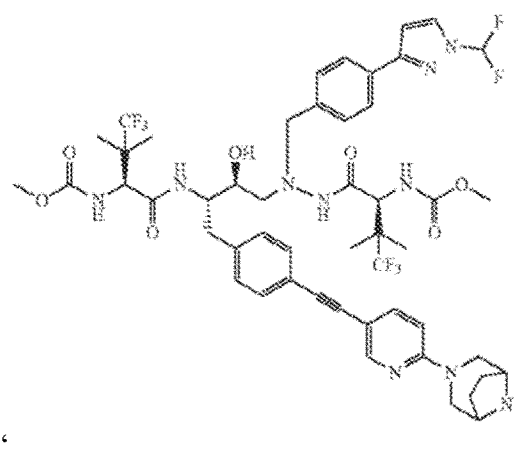 " and
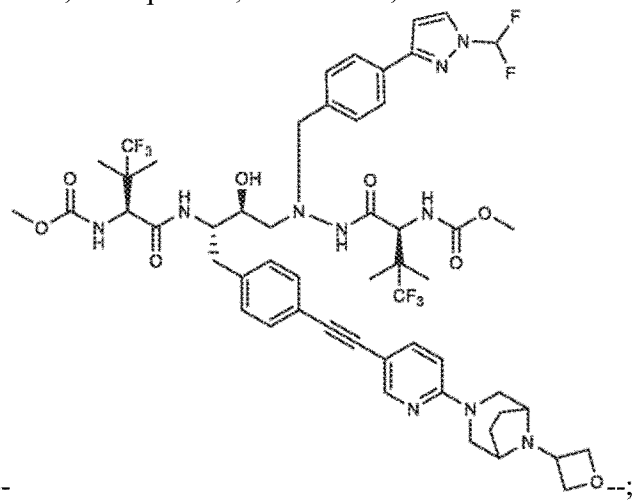
insert --

Column 345-346, Example 161, Compound 161a, delete " 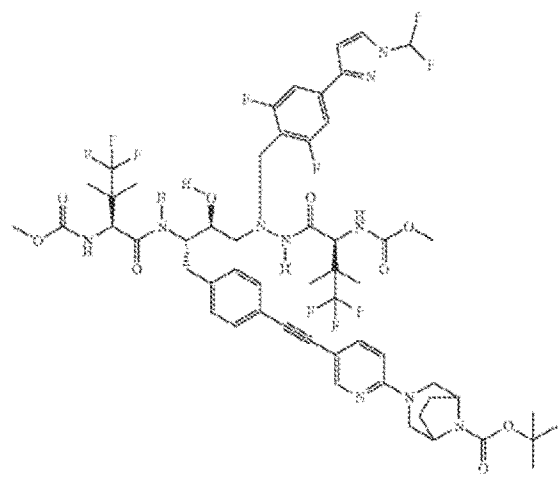 "
and insert -- 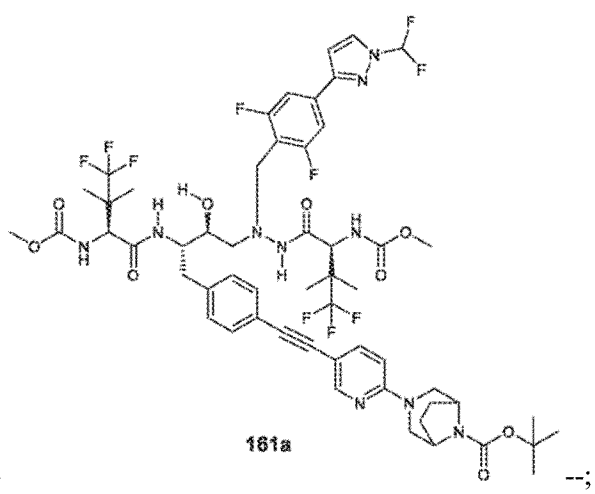 --;
Column 345-346, Example 161, Compound 161, delete " 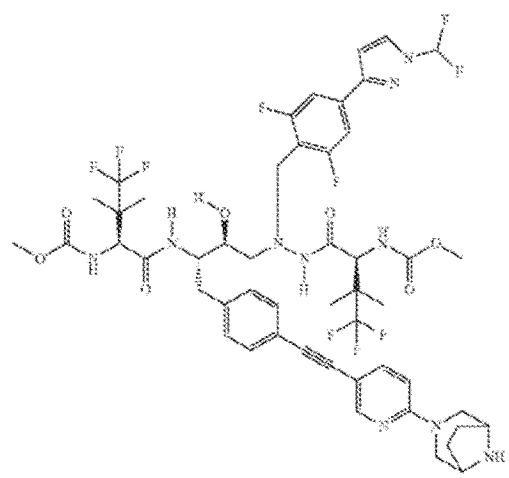 " and insert -- 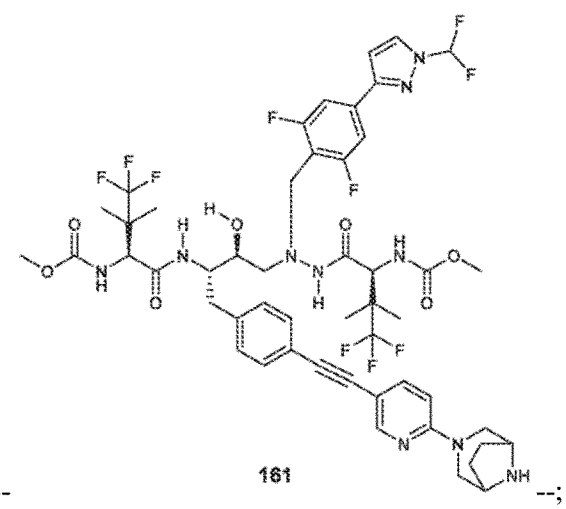 --;
Column 347-348, Example 162, delete " 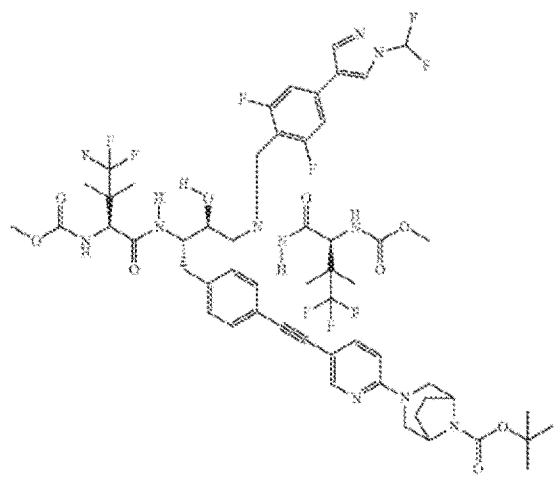 " and insert
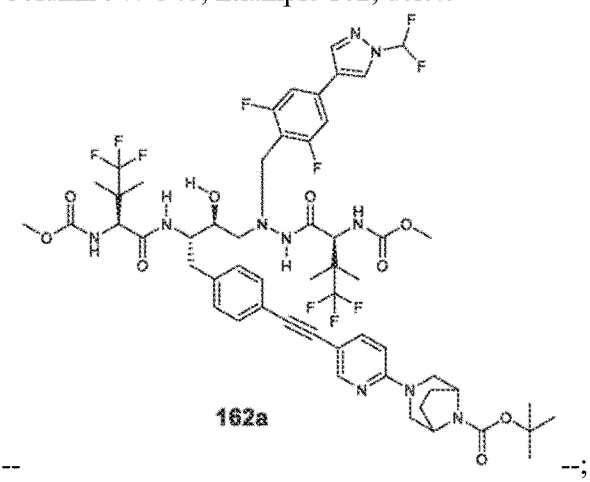
-- --;

CERTIFICATE OF CORRECTION (continued)
U.S. Pat. No. 11,078,208 B1

Column 349-350, Example 162, delete " 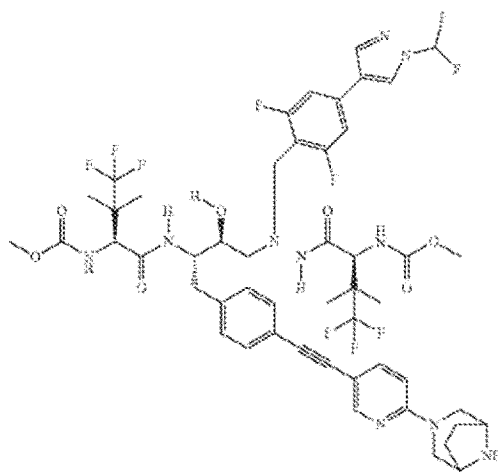 " and insert

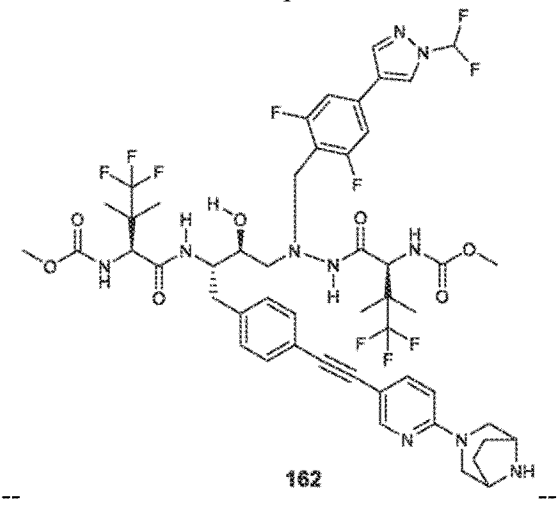

-- --;

Column 350, Example 163, Lines 30-48, delete " 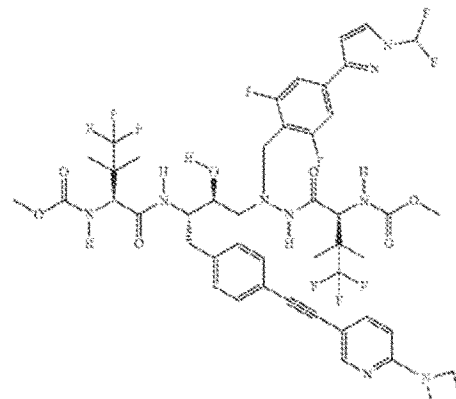 " and insert

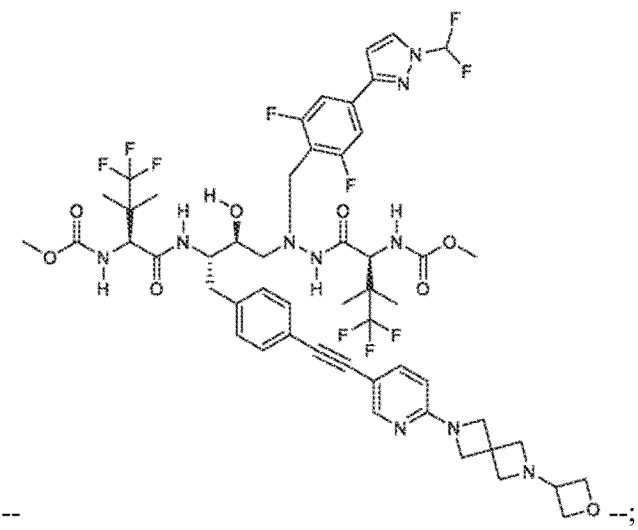
Column 351, Example 164, Lines 15-35, delete " 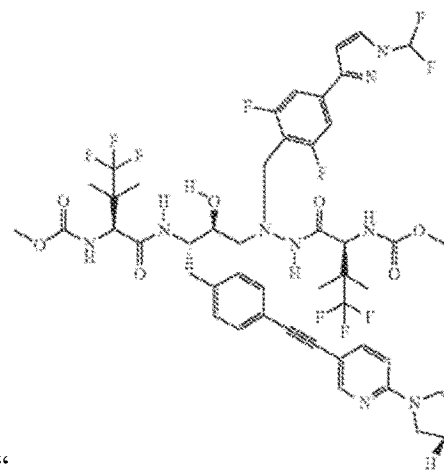 " and insert
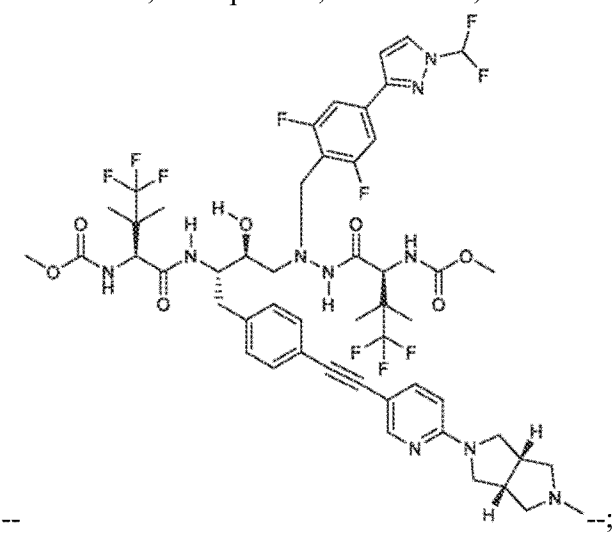

Column 352, Example 165, Lines 1-22, delete " 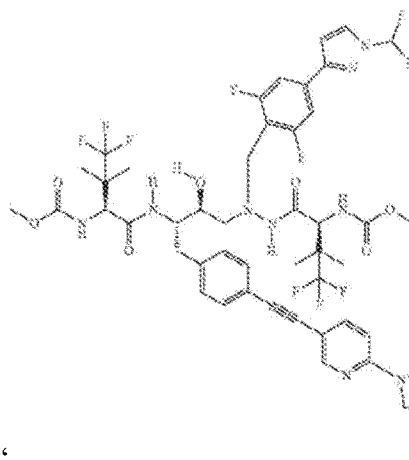 " and insert
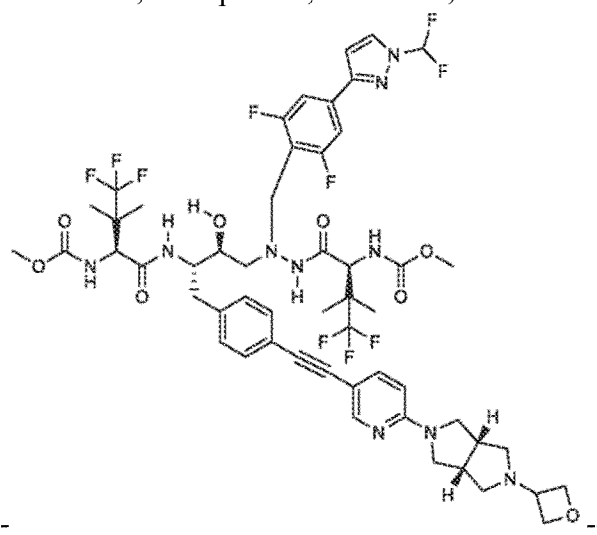
--;
Column 352, Example 166, Lines 45-67, delete " 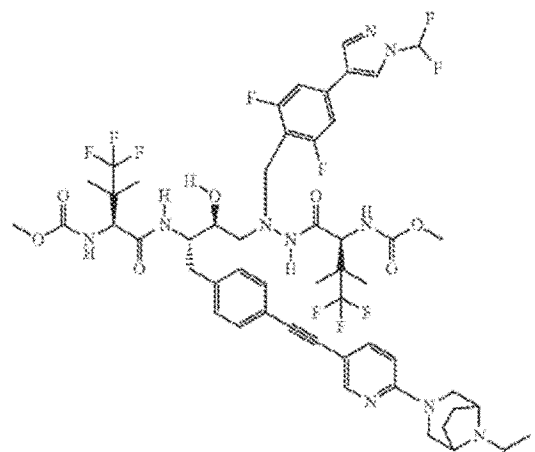 " and insert

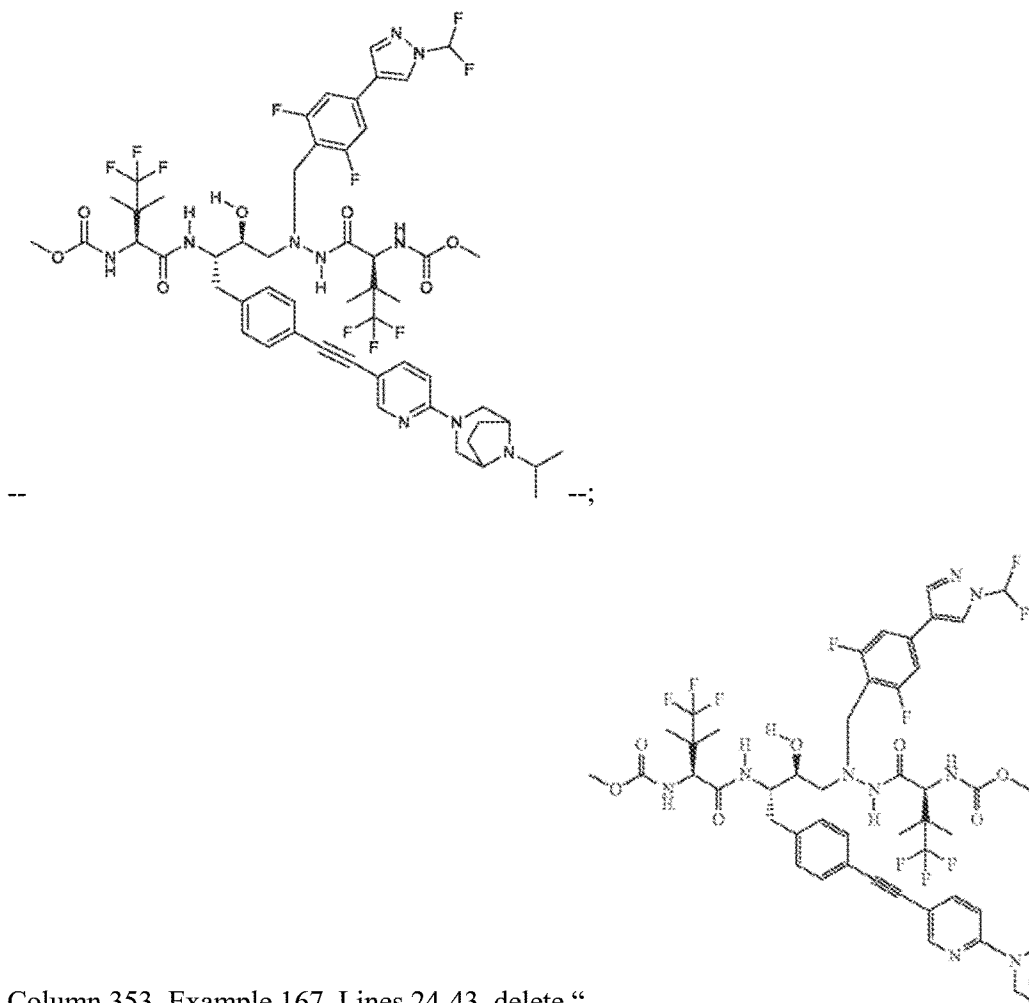
Column 353, Example 167, Lines 24-43, delete "  " and insert
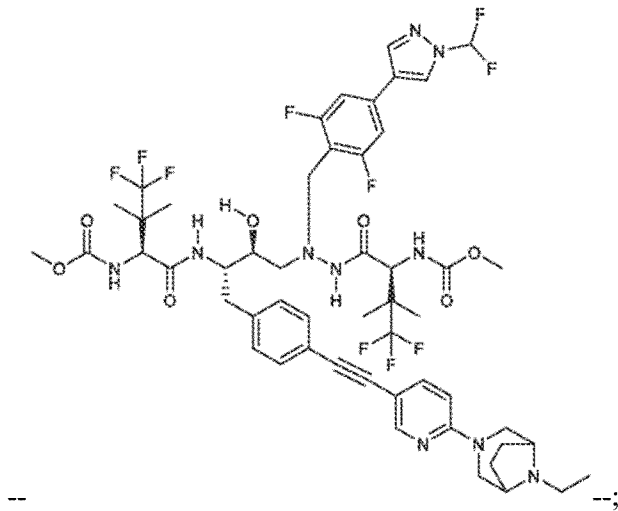

CERTIFICATE OF CORRECTION (continued)
U.S. Pat. No. 11,078,208 B1

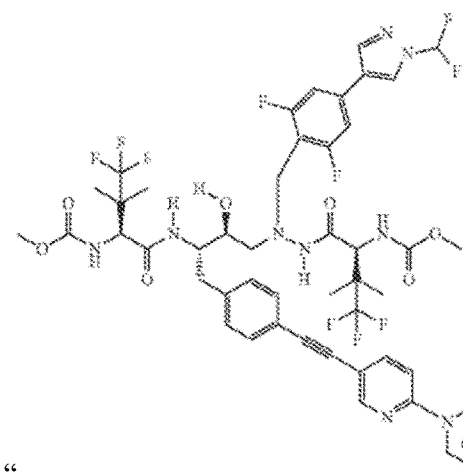

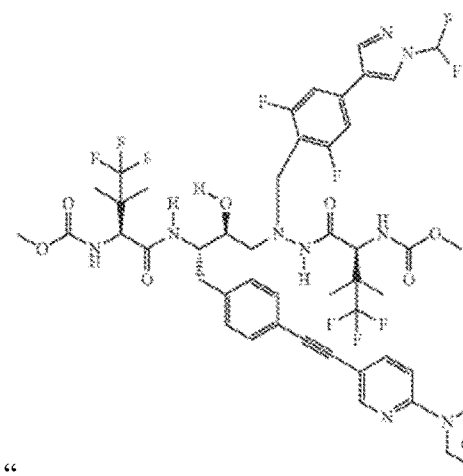

Column 354, Example 168, Lines 1-23, delete " " and insert

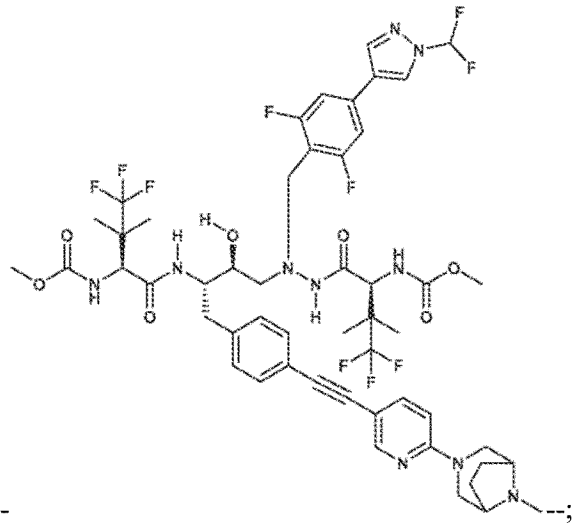

--;

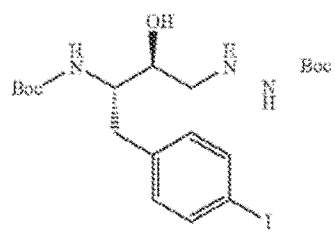

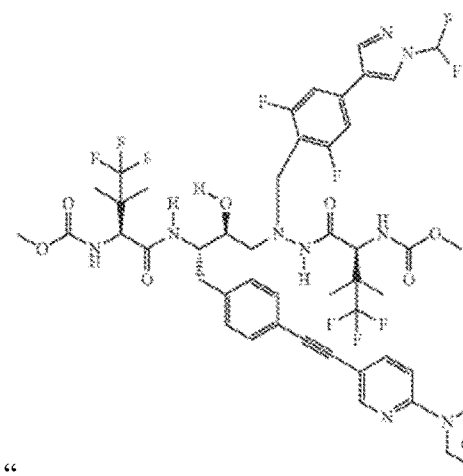

Column 365, Example 181, Compound I2a, delete " " and insert

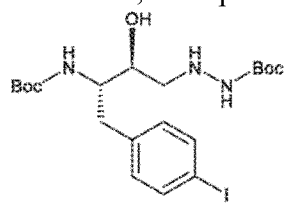

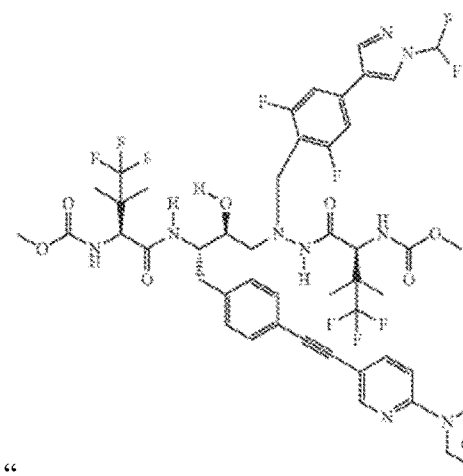

--;

Column 365-366, Example 181, Compound 181a, delete " 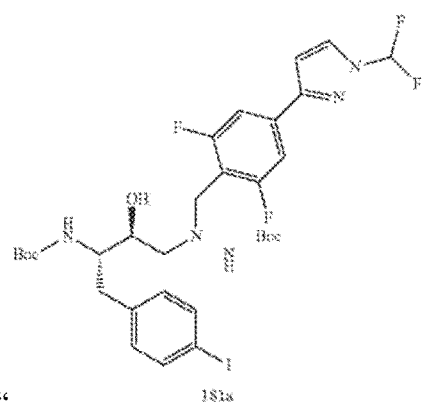 " and insert
-- 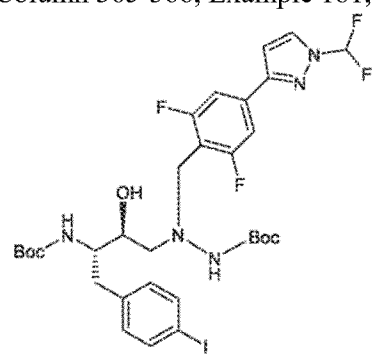 --;
Column 365-366, Example 181, Compound 181b, delete " 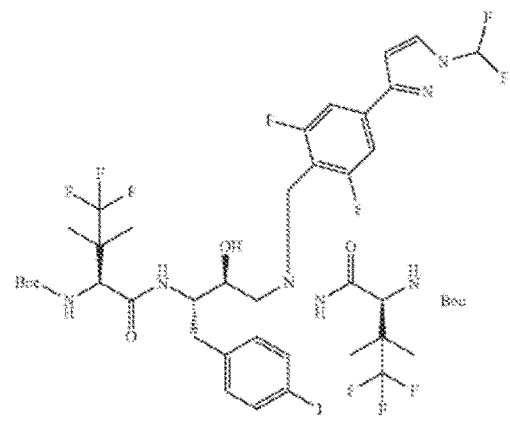 " and insert -- 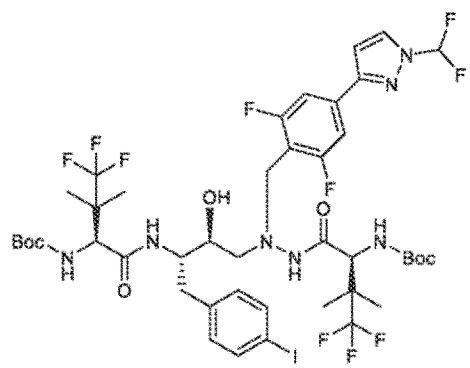 --;
Column 365-366, Example 181, Compound 181c, delete " 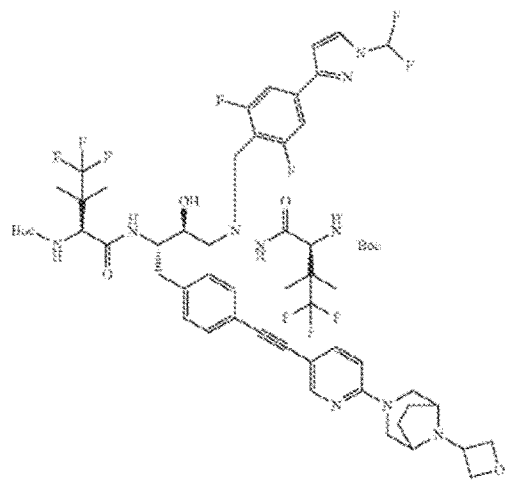 " and
insert -- 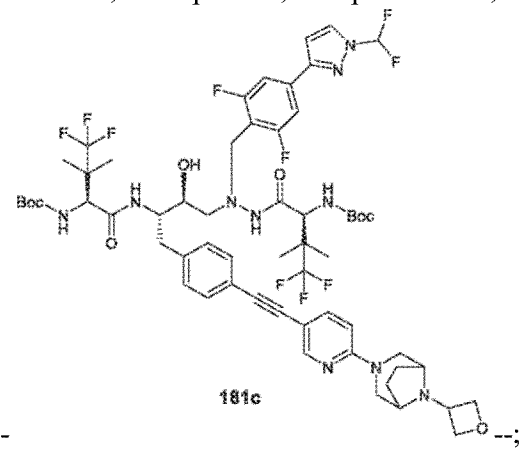 --;

Column 367-368, Example 181, delete " 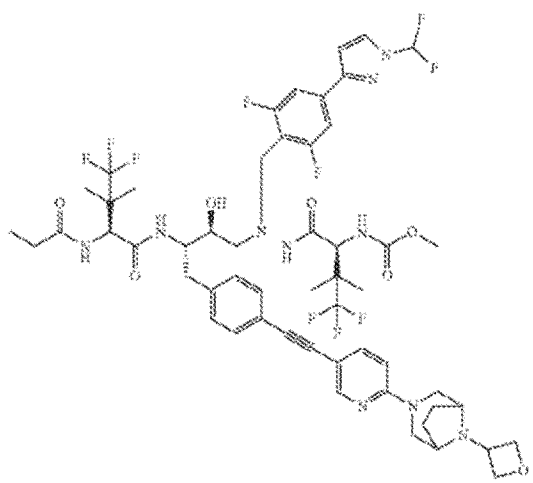 " and insert
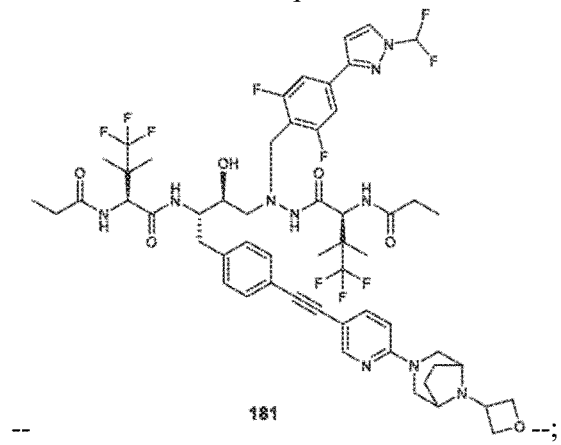 --;
Column 369, Example 183, Compound I4, delete " 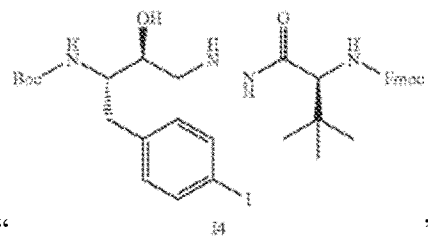 " and insert
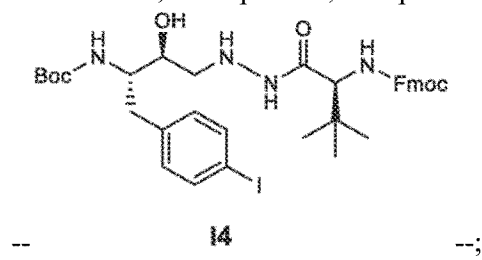 --;

Column 369-370, Compound 183a, delete " 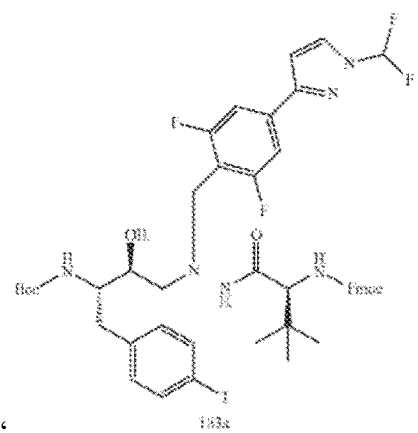 " and insert
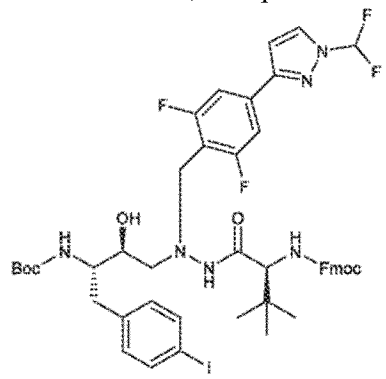
-- ;
Column 369-370, Compound 183b, delete " 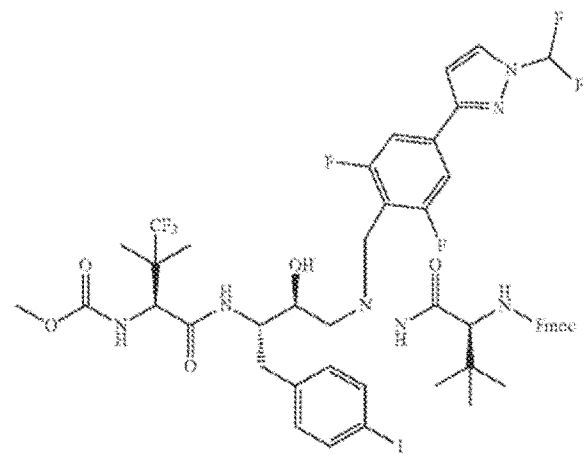 " and insert

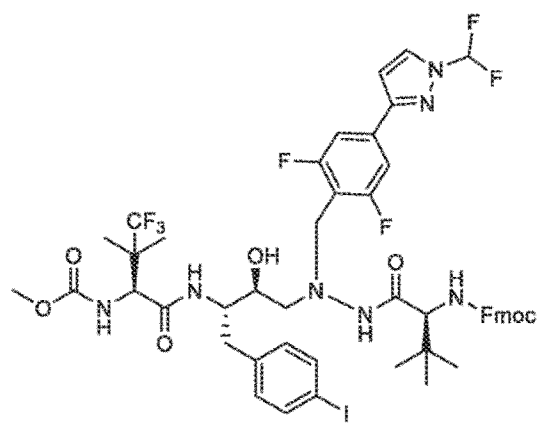
— 183b —;
Column 371-372, Compound 183c, delete " 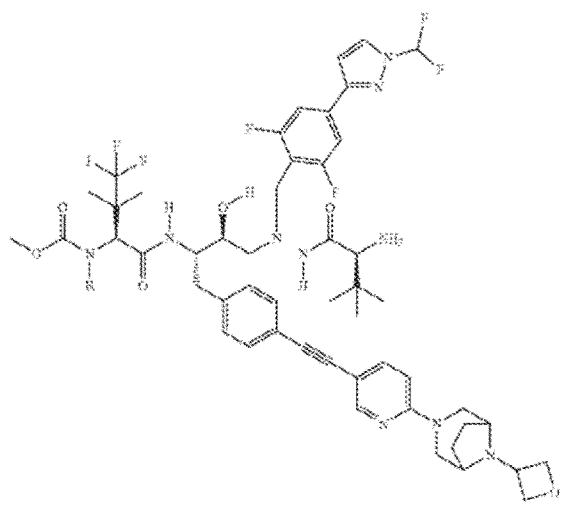 " and insert
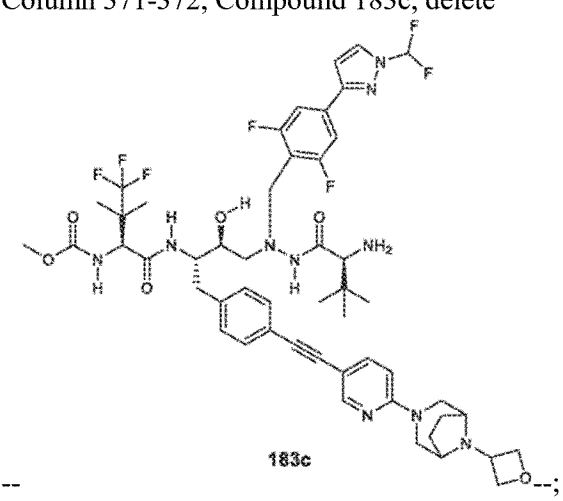
— 183c —;

Column 371-372, Example 183, delete " 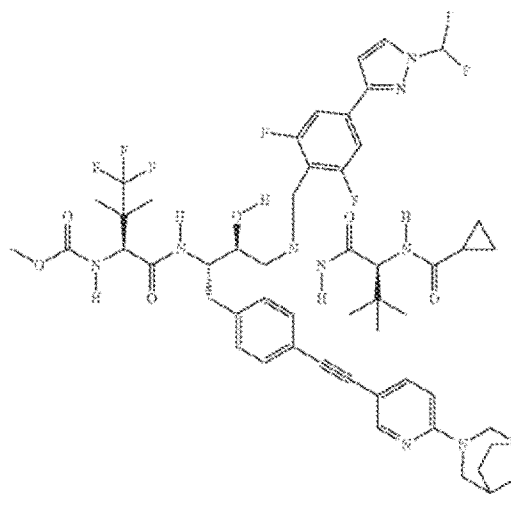 " and insert
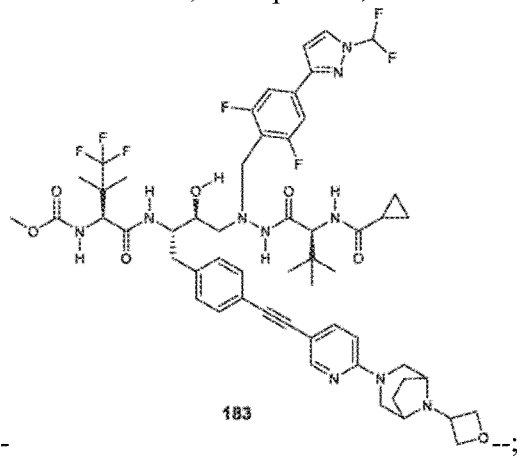
--;
Column 375, Compound I5, delete " 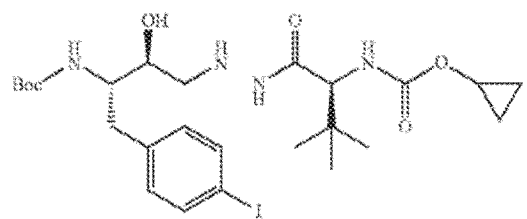 " and insert
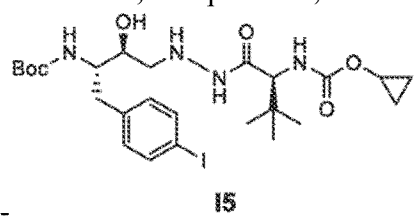
--;

Column 382, Example 188, above reaction arrow, delete " 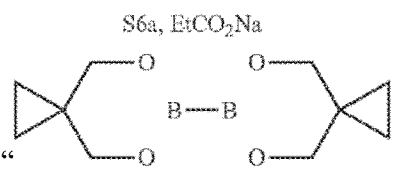 " and insert
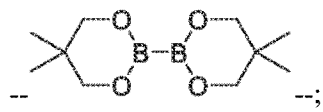 --;
Column 401, Example 207, Lines 23-43, delete " 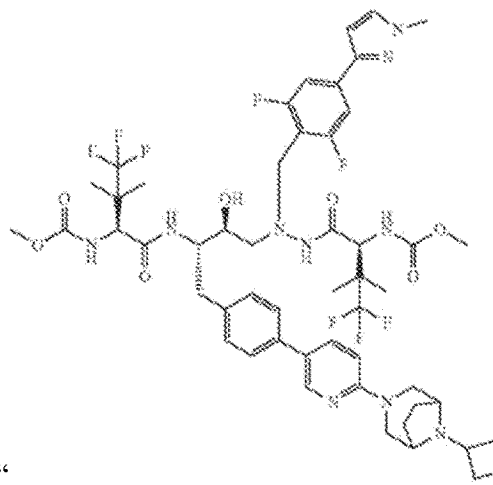 " and insert
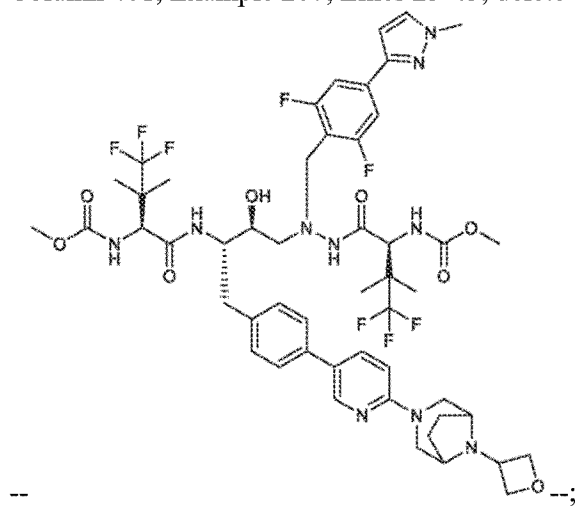 --;

Column 402, Example 208, Lines 1-25, delete " 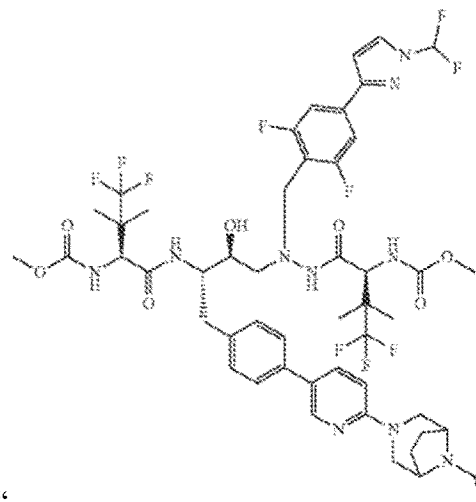 " and insert
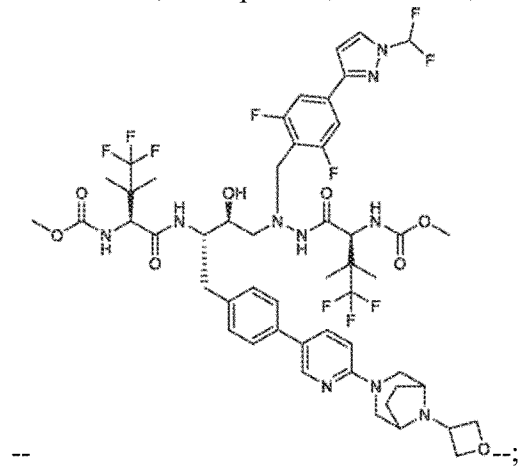
-- ;
Column 403, Example 209, Lines 1-25, delete " 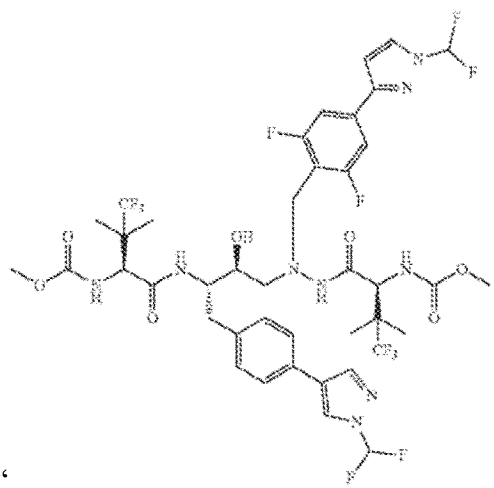 " and insert

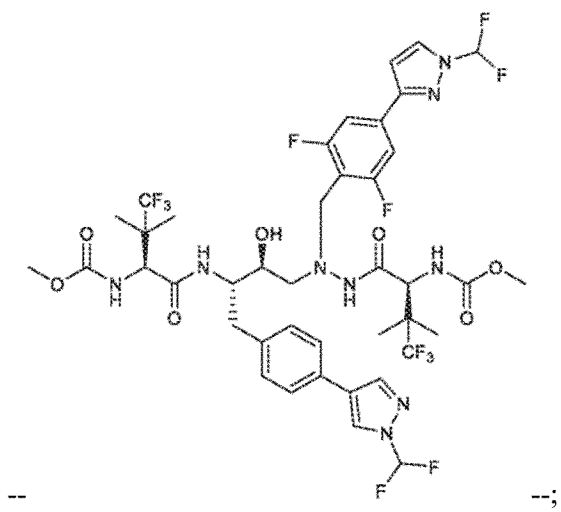
Column 403, Example 210, Lines 48-66, delete " 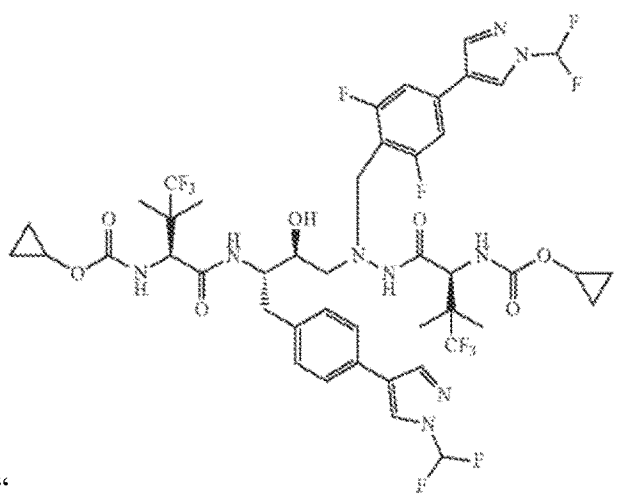 " and
insert -- 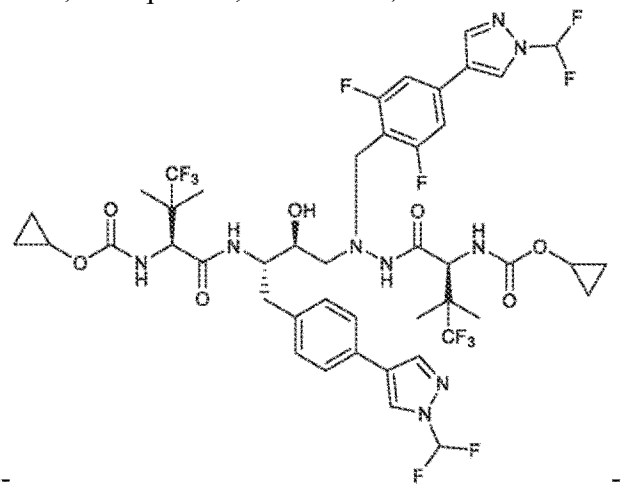 --;

Column 404, Example 211, Lines 24-44, delete " 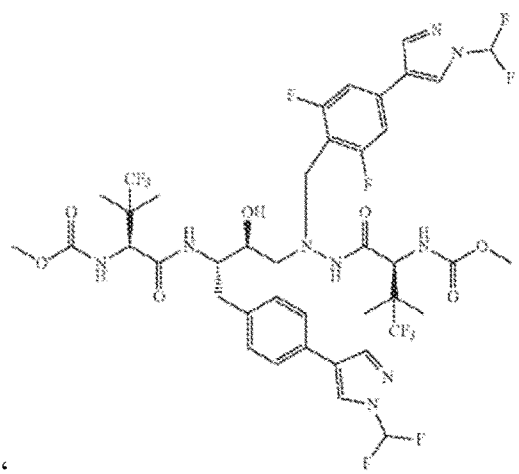 " and insert
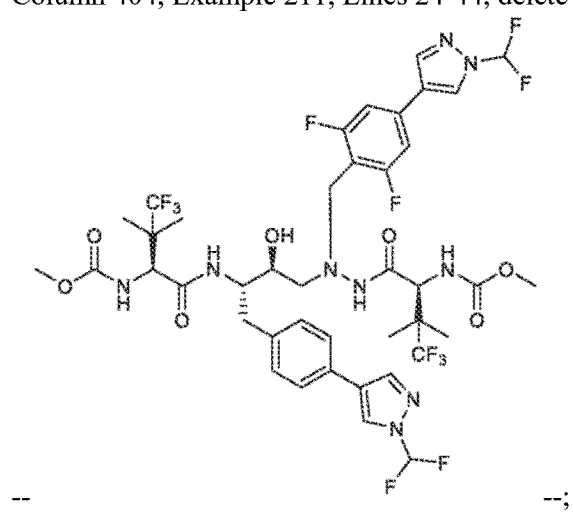
-- -- ;
Column 405, Example 212, Compound I2, delete " 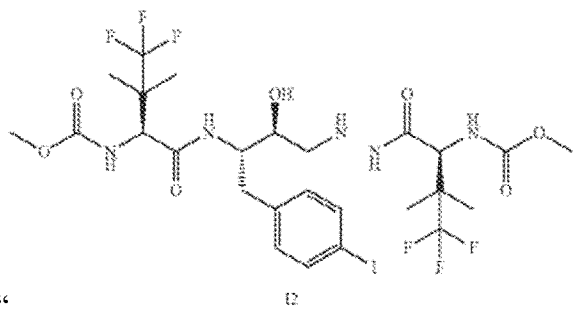 " and insert
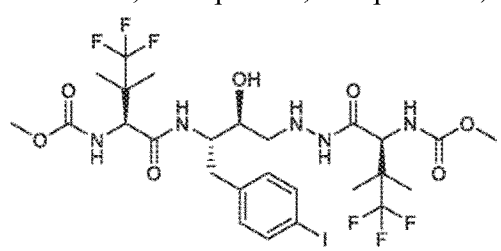
-- I2 -- ;

Column 406, Example 212, above reaction arrow, delete " 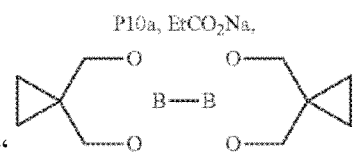 " and insert
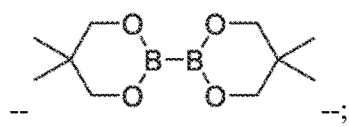 --;
Column 405-406, Example 212, Compound 212a, delete " 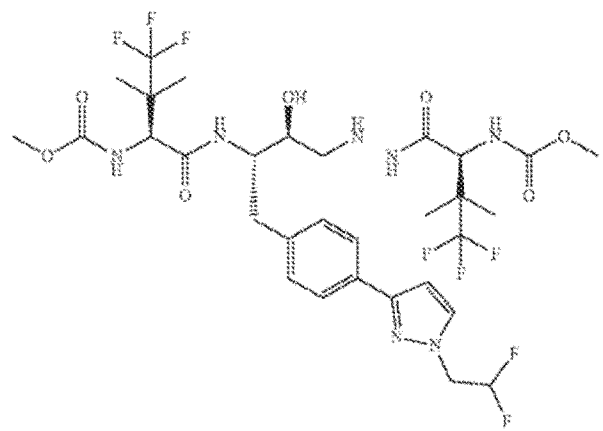 "
and insert -- 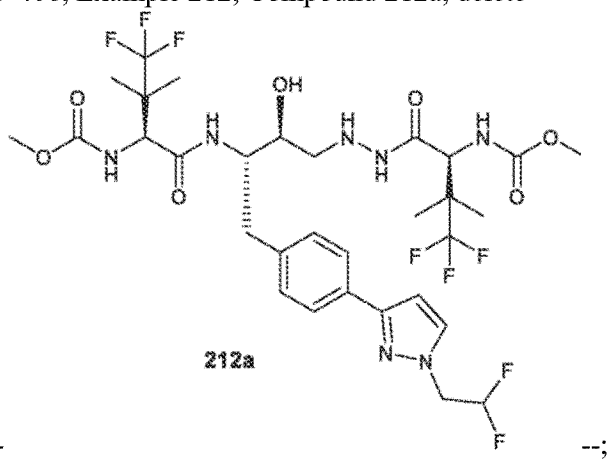 --;

Column 405-406, Example 212, Compound 212, delete " 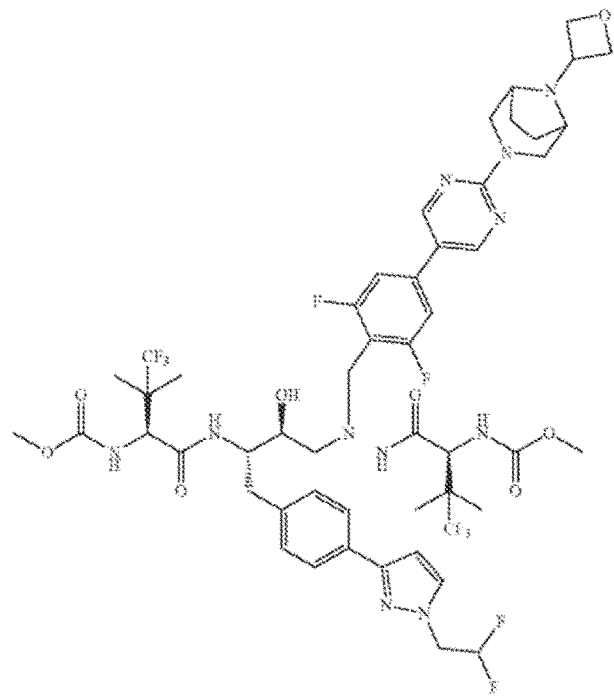 "
and insert -- 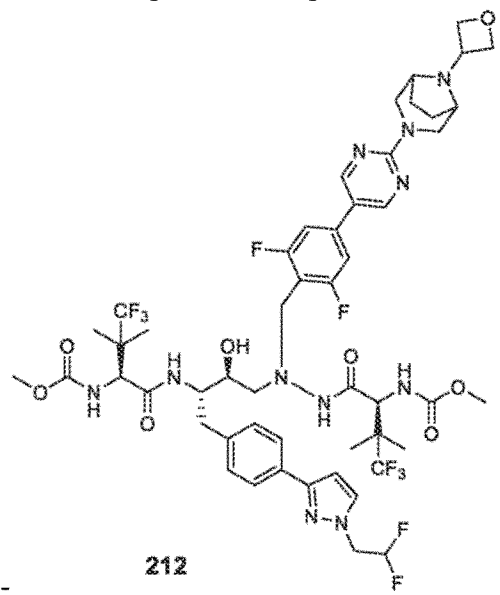 --;

CERTIFICATE OF CORRECTION (continued)
U.S. Pat. No. 11,078,208 B1

Column 410, Example 214, Lines 46-66, delete " 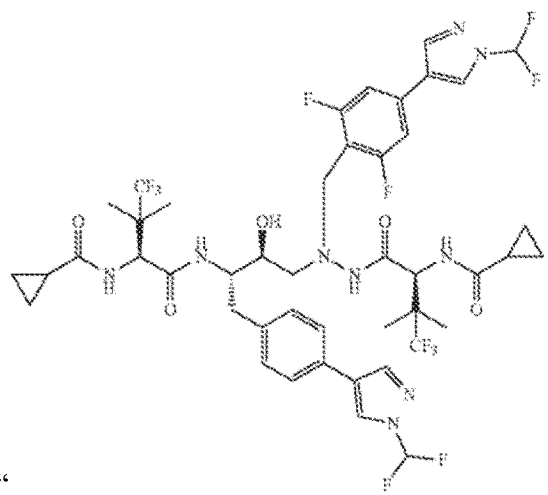 " and insert

-- 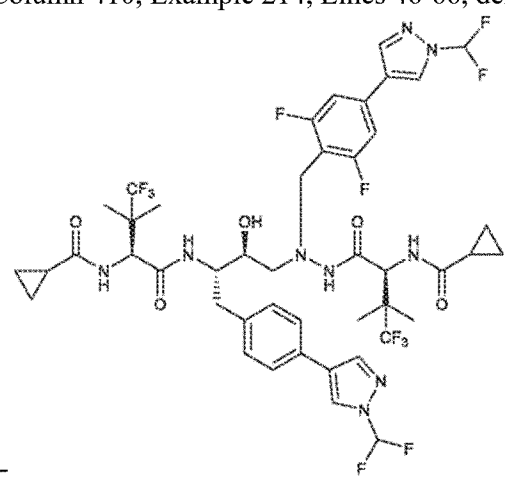 --;

Column 411, Example 215, Lines 28-48, delete " 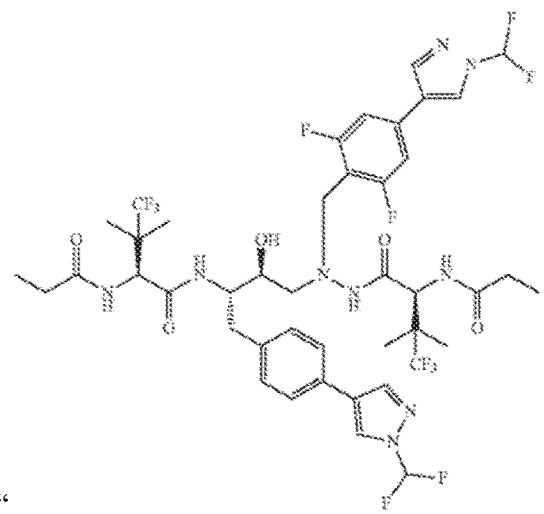 " and insert

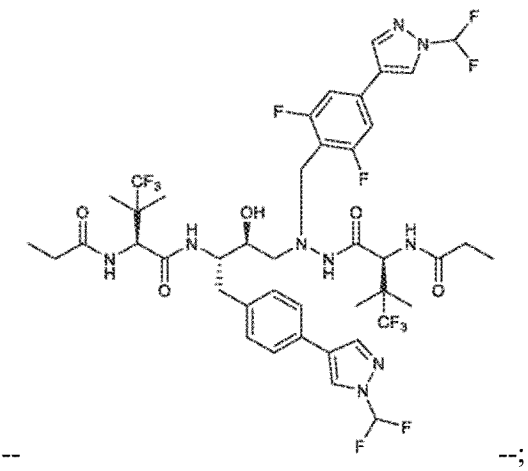
Column 412, Example 216, Lines 13-32, delete " 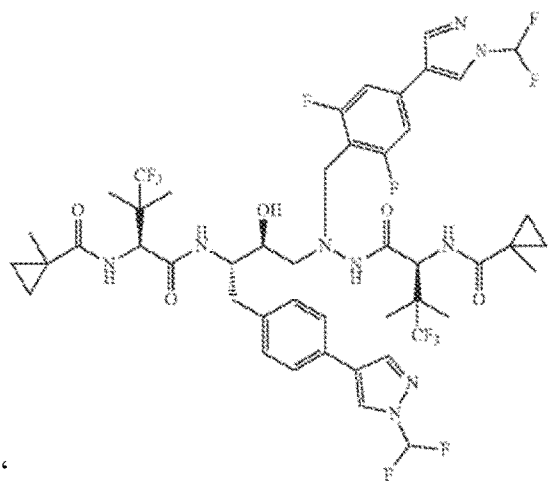 " and insert
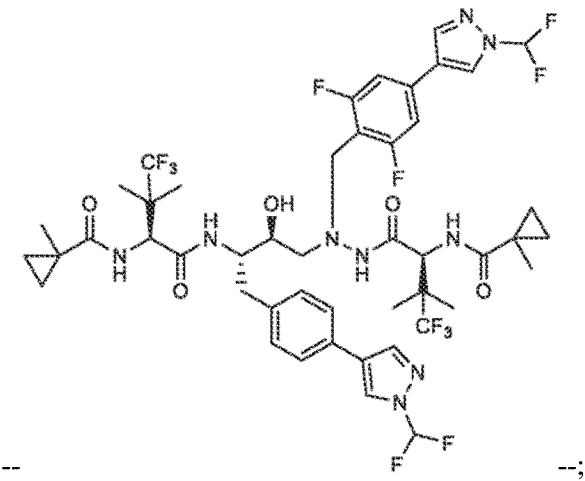

Column 413, Example 217, Lines 1-23, delete " 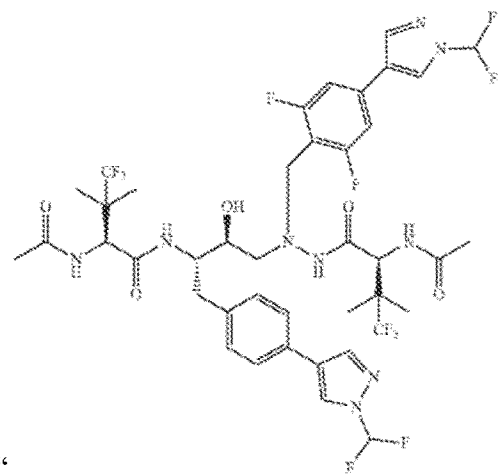 " and insert
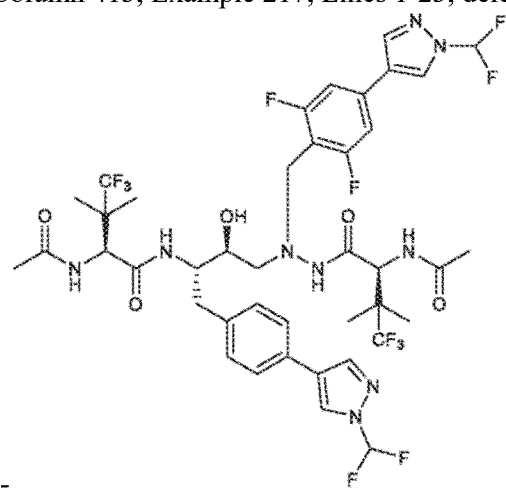
-- --;
Column 416, Example 219, Lines 28-48, delete " 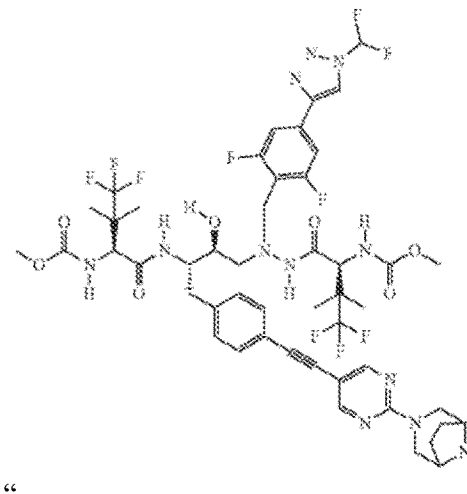 " and insert

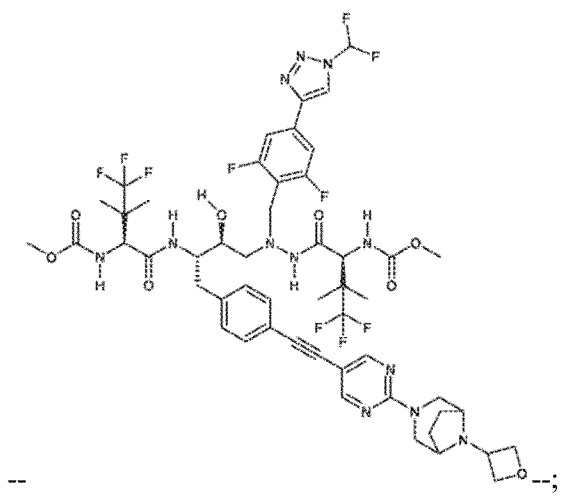
Column 429, Example 231, Lines 20-40, delete " 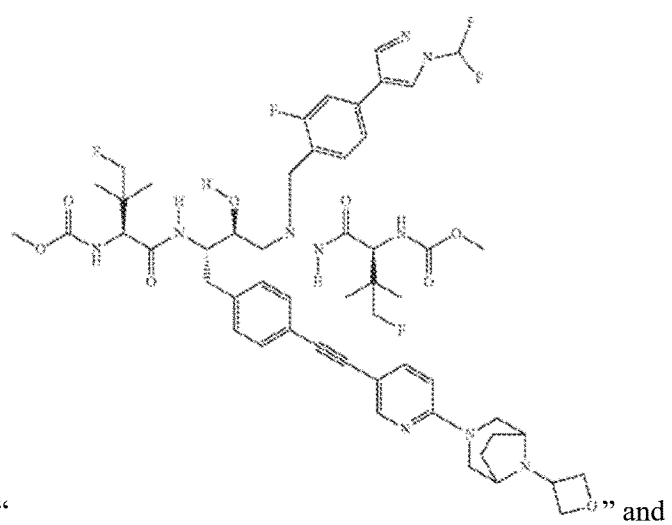 " and
insert -- 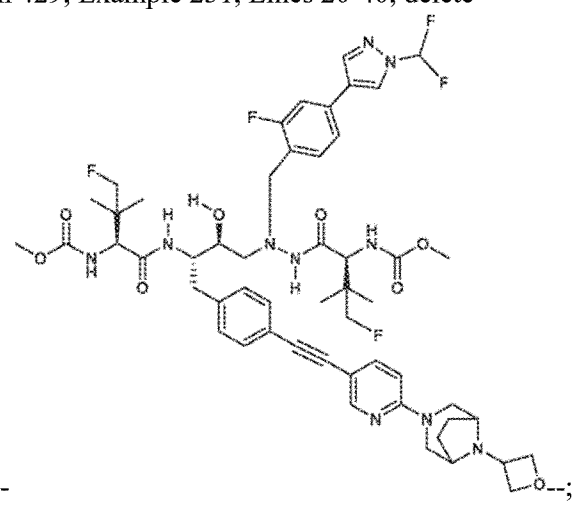 --;

Column 430, Example 232, delete " 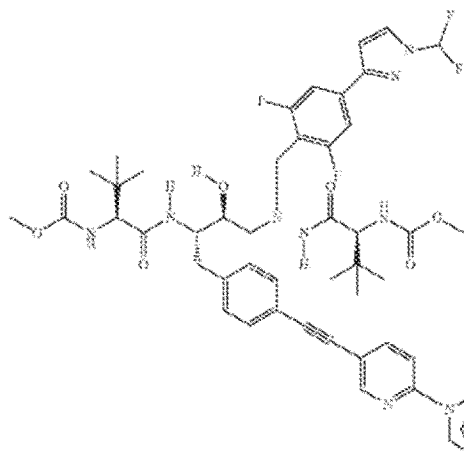 " and insert
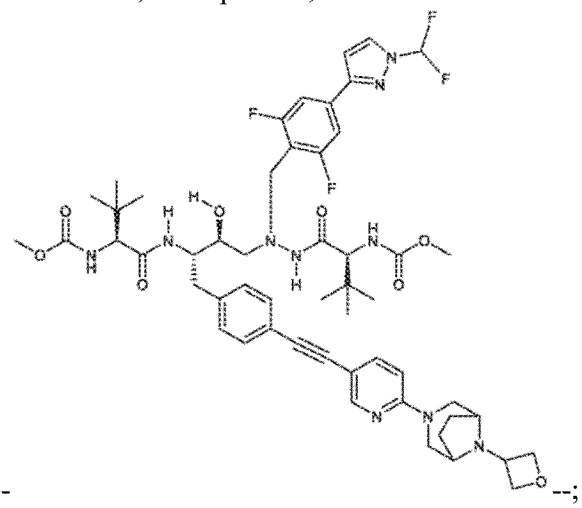 --;
Column 430, Example 233, Lines 48-67, delete " 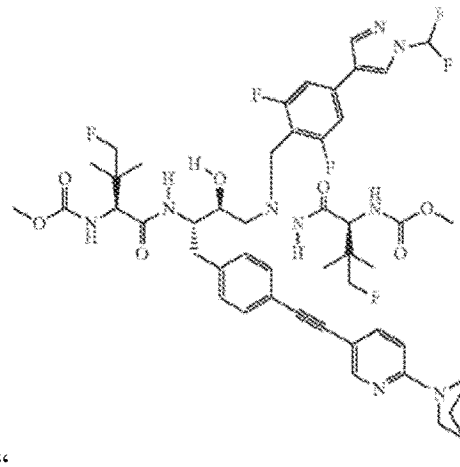 " and insert

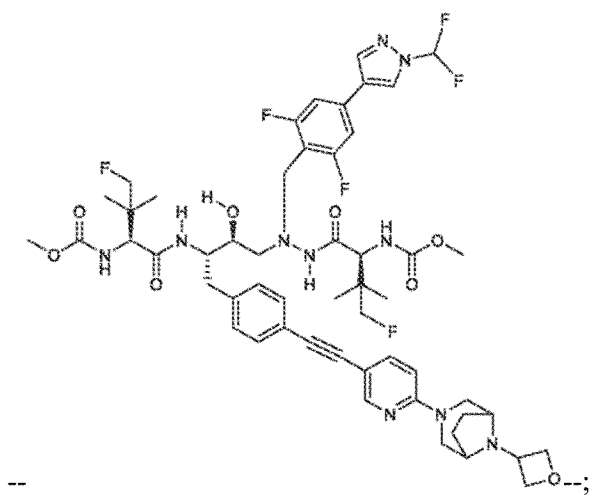
Column 431, Example 234, Lines 23-42, delete " 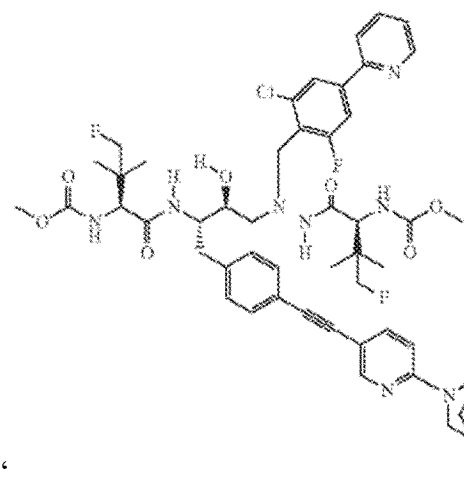 " and insert -
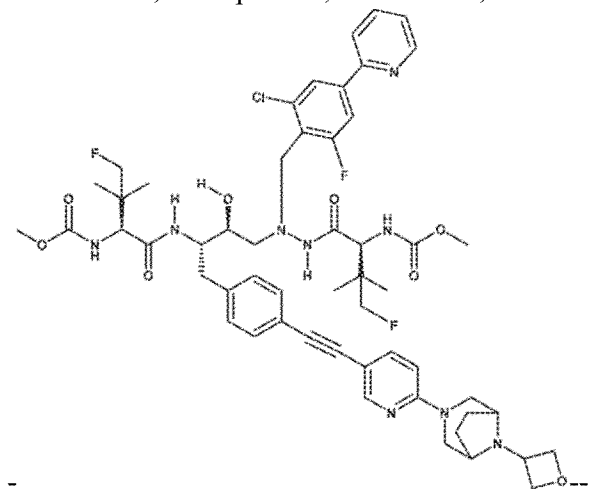

CERTIFICATE OF CORRECTION (continued)
U.S. Pat. No. 11,078,208 B1

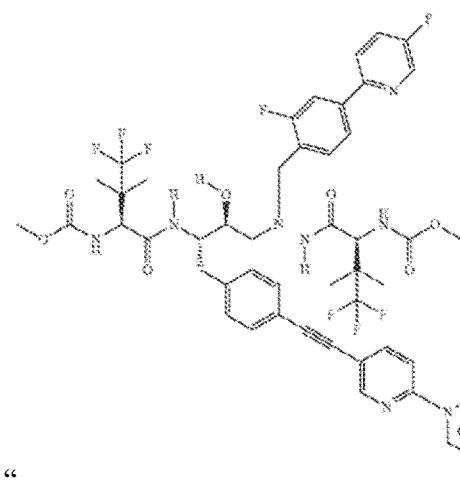

Column 432, Example 235, Lines 1-21, delete " 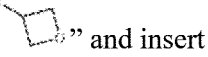 " and insert

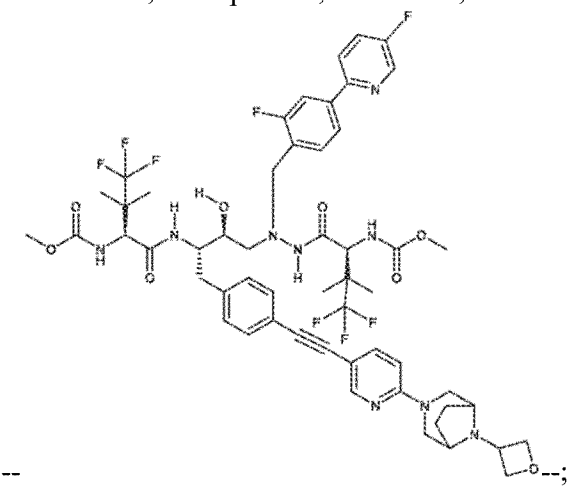

--

Column 432, Example 236, Lines 37-54, delete " 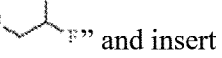 " and insert

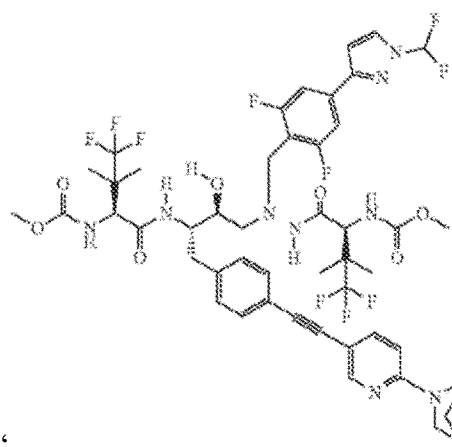

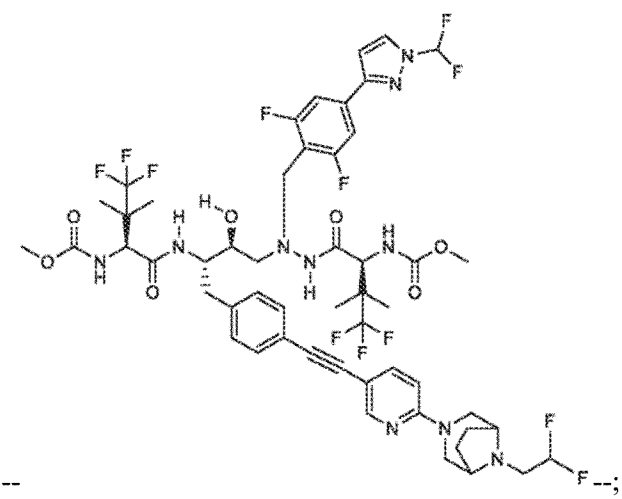
--;
Column 433, Example 237, Lines 18-36, delete " 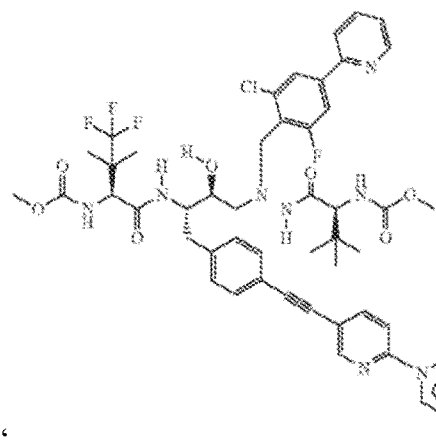 " and insert
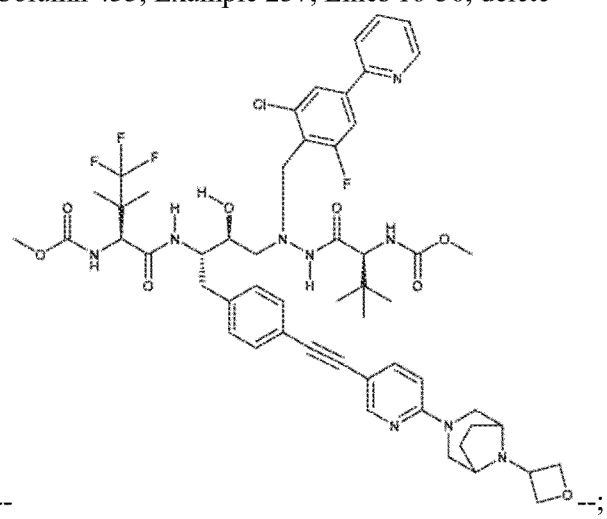
--;

Column 434, Example 238, Lines 1-20, delete " 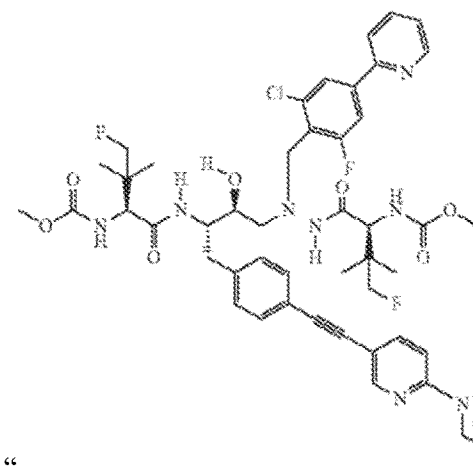" and insert -
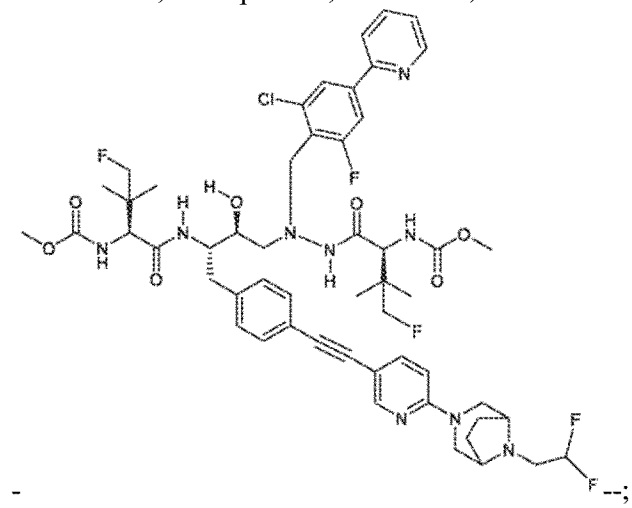 - ;
Column 434, Example 239, Lines 47-66, delete " 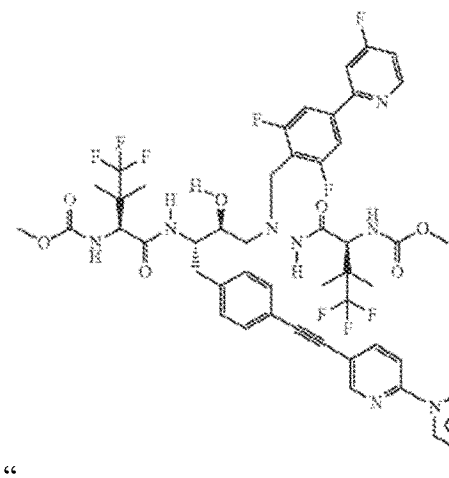" and insert

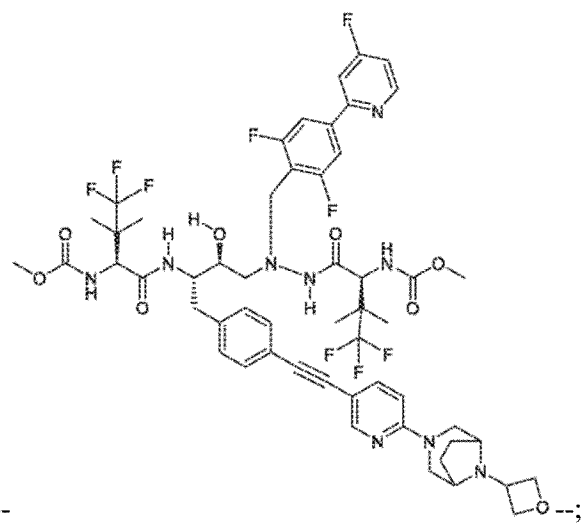
Column 435, Example 240, Lines 30-50, delete " 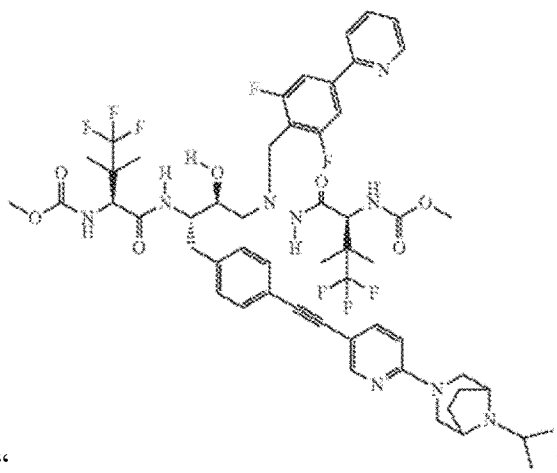 " and insert
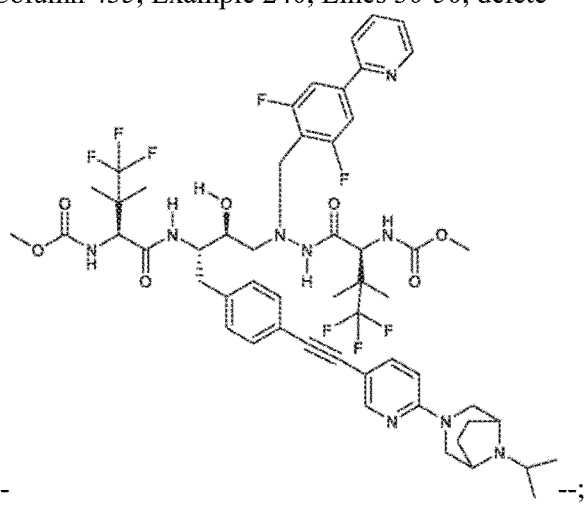

CERTIFICATE OF CORRECTION (continued)
U.S. Pat. No. 11,078,208 B1

Column 436, Example 241, Lines 1-20, delete " 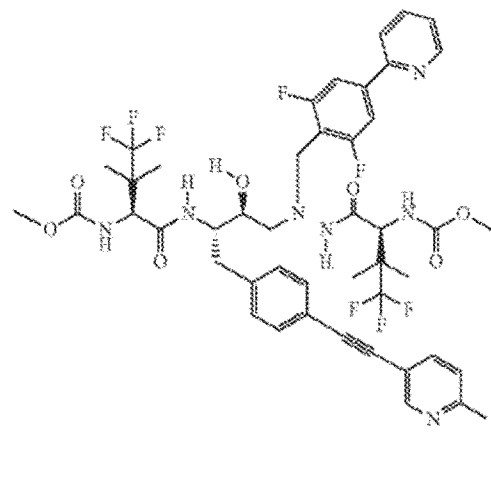 " and insert -

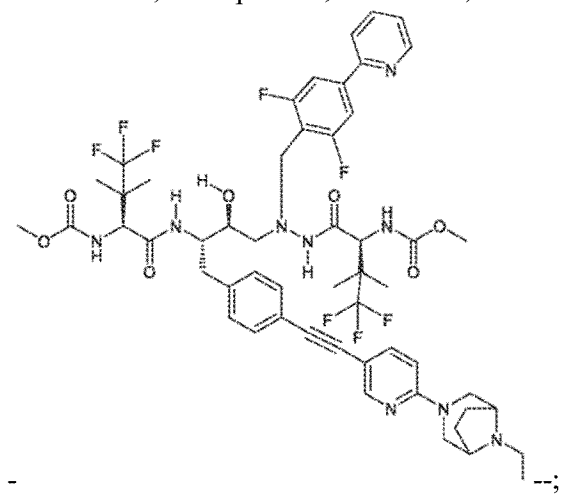

- ;

Column 436, Example 242, Lines 35-53, delete " 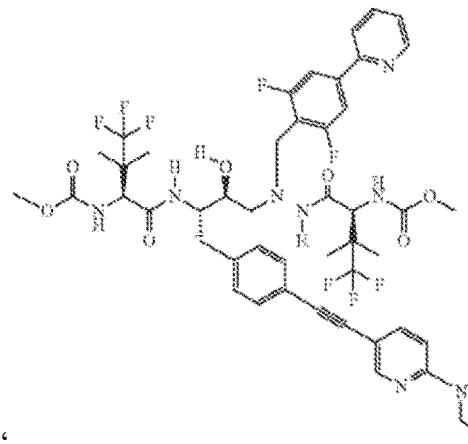 " and insert

CERTIFICATE OF CORRECTION (continued)
U.S. Pat. No. 11,078,208 B1

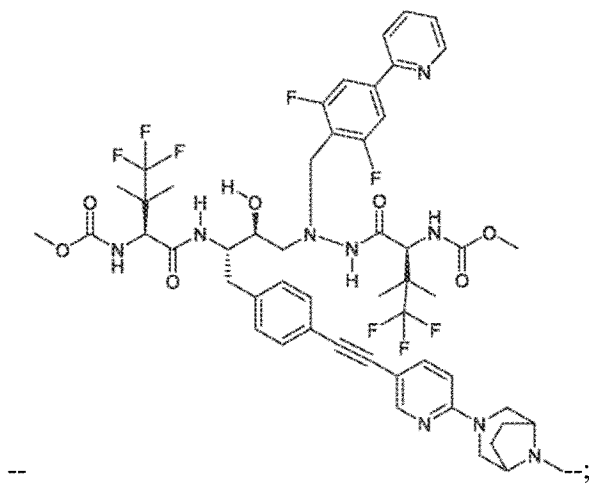

--

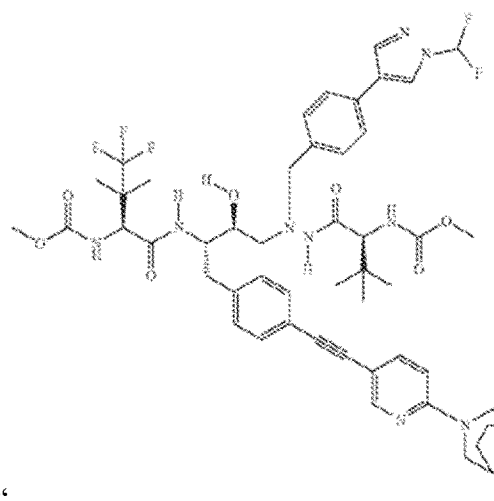

Column 437, Example 243, Lines 7-25, delete " " and

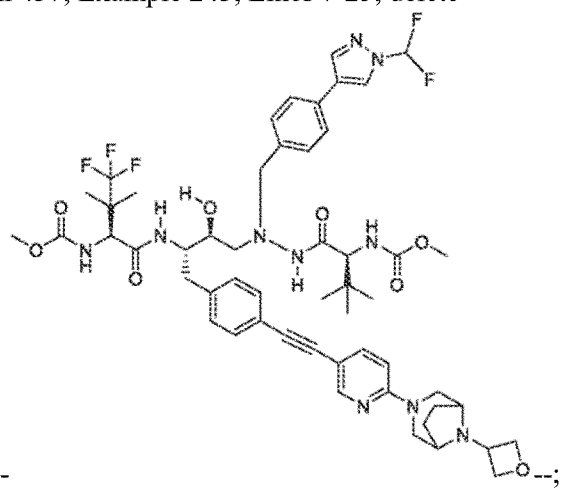

insert -- --;

CERTIFICATE OF CORRECTION (continued)
U.S. Pat. No. 11,078,208 B1

Column 437, Example 244, Lines 48-66, delete " 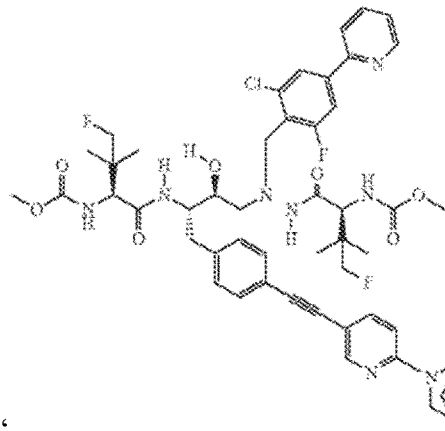 " and insert -- 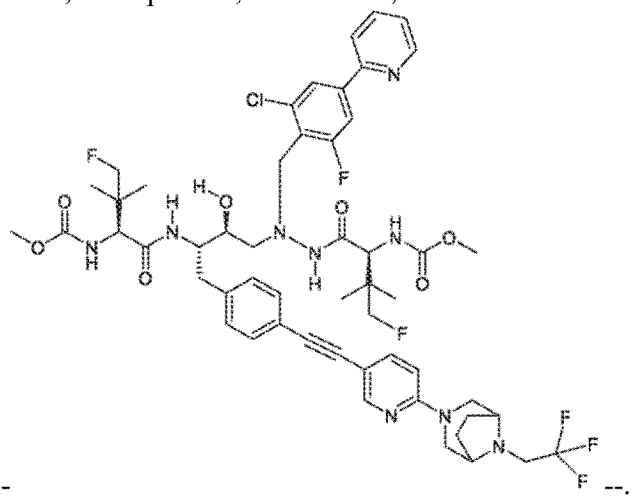 --.